(12) United States Patent
Maizels et al.

(10) Patent No.: US 12,105,785 B2
(45) Date of Patent: Oct. 1, 2024

(54) INTERPRETING WORDS PRIOR TO VOCALIZATION

(71) Applicant: Q (CUE) LTD., Ramat Gan (IL)

(72) Inventors: Aviad Maizels, Ramat Hasharon (IL); Yonatan Wexler, Jerusalem (IL); Avi Barliya, Tel Aviv (IL)

(73) Assignee: Q (Cue) Ltd., Ramat Gan (IL)

( * ) Notice: Subject to any disclaimer, the term of this patent is extended or adjusted under 35 U.S.C. 154(b) by 0 days.

(21) Appl. No.: 18/509,976

(22) Filed: Nov. 15, 2023

(65) Prior Publication Data

US 2024/0079011 A1 Mar. 7, 2024

Related U.S. Application Data

(63) Continuation of application No. PCT/IB2023/057369, filed on Jul. 19, 2023, which is
(Continued)

(51) Int. Cl.
*G10L 15/25* (2013.01)
*A61B 5/1171* (2016.01)
(Continued)

(52) U.S. Cl.
CPC ............ *G06F 21/32* (2013.01); *A61B 5/1176* (2013.01); *G06F 16/532* (2019.01); *G06F 40/40* (2020.01);
(Continued)

(58) Field of Classification Search
CPC .................................. G10L 15/25; G06F 40/40
(Continued)

(56) References Cited

U.S. PATENT DOCUMENTS 5,826,234 A 10/1998 Lyberg
5,943,171 A 8/1999 Budd et al.
(Continued)

FOREIGN PATENT DOCUMENTS

| CN | 105488524 A | 4/2016 |
|----|-------------|--------|
| EP | 3745303 | 2/2020 |
| WO | 2002077972 A1 | 10/2002 |
| WO | 2009013738 A1 | 1/2009 |
| WO | 2019017841 A1 | 1/2019 |

(Continued)

OTHER PUBLICATIONS

Chandrashekhar, V., "The Classification of EMG Signals Using Machine Learning for the Construction of a Silent Speech Interface," The Young Researcher—RSGC Royal St. George's College, 2021, vol. 5, Issue 1, pp. 266-283.
(Continued)

*Primary Examiner* — Michael N Opsasnick
(74) *Attorney, Agent, or Firm* — Finnegan, Henderson, Farabow, Garrett & Dunner LLP

(57) ABSTRACT

Systems, methods, and computer program products are disclosed for initiating content interpretation operations prior to vocalization of content to be interpreted. Initiating content interpretation operations prior to vocalization of content to be interpreted includes receiving signals representing facial skin micromovements; determining from the signals at least one word to be spoken prior to vocalization of the at least one word in an origin language; prior to the vocalization of the at least one word, instituting an interpretation of the at least one word; and causing the interpretation of the at least one word to be presented as the at least one word is spoken.

20 Claims, 114 Drawing Sheets

Related U.S. Application Data a continuation-in-part of application No. PCT/IB2022/056418, filed on Jul. 12, 2022, which is a continuation-in-part of application No. PCT/IB2022/054527, filed on May 16, 2022.

(60) Provisional application No. 63/487,299, filed on Feb. 28, 2023, provisional application No. 63/441,183, filed on Jan. 26, 2023, provisional application No. 63/438,061, filed on Jan. 10, 2023, provisional application No. 63/394,329, filed on Aug. 2, 2022, provisional application No. 63/390,653, filed on Jul. 20, 2022, provisional application No. 63/229,091, filed on Aug. 4, 2021.

(51) Int. Cl.
| | |
|---|---|
| *G06F 16/532* | (2019.01) |
| *G06F 21/32* | (2013.01) |
| *G06F 40/40* | (2020.01) |
| *G06V 20/50* | (2022.01) |
| *G06V 40/16* | (2022.01) |
| *G10L 13/02* | (2013.01) |
| *G10L 15/08* | (2006.01) |
| *G10L 15/20* | (2006.01) |
| *G10L 15/22* | (2006.01) |
| *H04R 1/02* | (2006.01) |
| *H04R 1/10* | (2006.01) |

(52) U.S. Cl.
CPC ............ *G06V 20/50* (2022.01); *G06V 40/166* (2022.01); *G06V 40/171* (2022.01); *G06V 40/172* (2022.01); *G06V 40/176* (2022.01); *G10L 13/02* (2013.01); *G10L 15/08* (2013.01); *G10L 15/20* (2013.01); *G10L 15/22* (2013.01); *G10L 15/25* (2013.01); *H04R 1/028* (2013.01); *H04R 1/10* (2013.01); *G10L 2015/088* (2013.01); *G10L 2015/223* (2013.01)

(58) Field of Classification Search
USPC ........................................................ 704/231
See application file for complete search history.

(56) References Cited

U.S. PATENT DOCUMENTS

| | | |
|---|---|---|
| 5,995,856 A | 11/1999 | Mannheimer et al. |
| 6,219,640 B1 | 4/2001 | Basu |
| 6,272,466 B1 | 8/2001 | Harada et al. |
| 6,598,006 B1 | 7/2003 | Honda et al. |
| 7,222,360 B1 | 5/2007 | Miller |
| 7,859,654 B2 | 12/2010 | Hartog |
| 8,082,149 B2 | 12/2011 | Schultz et al. |
| 8,200,486 B1 | 6/2012 | Jorgensen et al. |
| 8,638,991 B2 | 1/2014 | Zalevsky et al. |
| 8,792,159 B2 | 7/2014 | Zalevsky et al. |
| 8,860,948 B2 | 10/2014 | Abdulhalim et al. |
| 8,897,500 B2 | 11/2014 | Syrdal et al. |
| 8,970,348 B1 | 3/2015 | Evan et al. |
| 9,129,595 B2 | 9/2015 | Russell et al. |
| 9,199,081 B2 | 12/2015 | Zalevsky et al. |
| 9,263,044 B1 | 2/2016 | Cassidy et al. |
| 9,288,045 B2 | 3/2016 | Sadot et al. |
| 9,668,672 B2 | 6/2017 | Zalevsky et al. |
| 9,680,983 B1 | 6/2017 | Schuster et al. |
| 9,916,433 B2 | 3/2018 | Schwarz et al. |
| 10,299,008 B1 | 5/2019 | Catalano et al. |
| 10,335,041 B2 | 7/2019 | Fixler et al. |
| 10,398,314 B2 | 9/2019 | Zalevsky et al. |
| 10,489,636 B2 | 11/2019 | Chen et al. |
| 10,529,355 B2 | 1/2020 | Rakshit et al. |
| 10,592,734 B2 | 3/2020 | Klett |
| 10,614,295 B2 | 4/2020 | Kim et al. |
| 10,679,644 B2 | 6/2020 | Rakshit et al. |
| 10,838,139 B2 | 11/2020 | Zalevsky et al. |
| 10,867,460 B1 | 12/2020 | Miller et al. |
| 10,878,818 B2 | 12/2020 | Kapur et al. |
| 10,931,881 B2 | 2/2021 | Zalevsky et al. |
| 11,114,101 B2 | 9/2021 | Mossinkoff et al. |
| 11,169,176 B2 | 11/2021 | Zalevsky et al. |
| 11,257,493 B2 | 2/2022 | Vasconcelos et al. |
| 11,341,222 B1 | 5/2022 | Caffey |
| 11,343,596 B2 | 5/2022 | Chappell, III et al. |
| 11,467,659 B2 | 10/2022 | Bikumandla et al. |
| 11,538,279 B2 | 12/2022 | Nduka |
| 11,605,376 B1 | 3/2023 | Hoover |
| 11,609,633 B2 | 3/2023 | Alcaide et al. |
| 11,682,398 B2 | 6/2023 | Im et al. |
| 11,709,548 B2 | 7/2023 | Tadi et al. |
| 11,744,376 B2 | 9/2023 | Schmidt et al. |
| 11,893,098 B2 | 2/2024 | Lawrenson et al. |
| 2003/0123712 A1 | 7/2003 | Dimitrova et al. |
| 2004/0240712 A1 | 12/2004 | Rowe et al. |
| 2004/0243416 A1 | 12/2004 | Gardos |
| 2004/0249510 A1 | 12/2004 | Hanson |
| 2006/0287608 A1 | 12/2006 | Dellacorna |
| 2007/0047768 A1 | 3/2007 | Gardu et al. |
| 2008/0043025 A1 | 2/2008 | Isabelle et al. |
| 2008/0103769 A1 | 5/2008 | Schultz et al. |
| 2008/0177994 A1 | 7/2008 | Mayer |
| 2008/0216171 A1 | 9/2008 | Sano |
| 2009/0082642 A1 | 3/2009 | Fine |
| 2009/0233072 A1 | 9/2009 | Harvey et al. |
| 2010/0141663 A1 | 6/2010 | Becker et al. |
| 2010/0328433 A1 | 12/2010 | Li |
| 2011/0307241 A1 | 12/2011 | Waibel et al. |
| 2012/0040747 A1 | 2/2012 | Auterio et al. |
| 2012/0209603 A1 | 8/2012 | Jing |
| 2012/0284022 A1 | 11/2012 | Konchitsky |
| 2013/0300573 A1 | 11/2013 | Brown et al. |
| 2013/0314781 A1 | 11/2013 | Jang et al. |
| 2014/0126743 A1 | 5/2014 | Petit et al. |
| 2014/0375571 A1 | 12/2014 | Hirata |
| 2015/0253502 A1 | 9/2015 | Fish et al. |
| 2015/0356981 A1 | 12/2015 | Johnson et al. |
| 2016/0004059 A1 | 1/2016 | Menon et al. |
| 2016/0011063 A1 | 1/2016 | Zhang et al. |
| 2016/0027441 A1* | 1/2016 | Liu .................. G10L 15/08 |
| | | 704/255 |
| 2016/0034252 A1 | 2/2016 | Chabrol |
| 2016/0086021 A1 | 3/2016 | Grohman et al. |
| 2016/0093284 A1 | 3/2016 | Begum et al. |
| 2016/0100787 A1 | 4/2016 | Leung et al. |
| 2016/0116356 A1 | 4/2016 | Goldstein |
| 2016/0150978 A1 | 6/2016 | Yuen et al. |
| 2016/0374577 A1 | 12/2016 | Baxi et al. |
| 2016/0379638 A1 | 12/2016 | Basye et al. |
| 2016/0379683 A1 | 12/2016 | Sandrew et al. |
| 2017/0068839 A1 | 3/2017 | Fukuda |
| 2017/0084266 A1 | 3/2017 | Bronakowski et al. |
| 2017/0209047 A1 | 7/2017 | Zalevsky et al. |
| 2017/0222729 A1 | 8/2017 | Sadot et al. |
| 2017/0231513 A1 | 8/2017 | Presura et al. |
| 2017/0245796 A1 | 8/2017 | Zalevsky et al. |
| 2017/0263237 A1 | 9/2017 | Green et al. |
| 2017/0374074 A1 | 12/2017 | Stuntebeck |
| 2018/0020285 A1 | 1/2018 | Zass |
| 2018/0025750 A1 | 1/2018 | Smith et al. |
| 2018/0070839 A1 | 3/2018 | Ritscher et al. |
| 2018/0107275 A1 | 4/2018 | Chen et al. |
| 2018/0132766 A1 | 5/2018 | Lee et al. |
| 2018/0149448 A1 | 5/2018 | Stolov |
| 2018/0232511 A1 | 8/2018 | Bakish |
| 2018/0292523 A1 | 10/2018 | Orenstein et al. |
| 2018/0306568 A1 | 10/2018 | Holman et al. |
| 2018/0333053 A1 | 11/2018 | Verkruijsse et al. |
| 2019/0012528 A1 | 1/2019 | Wilson et al. |
| 2019/0029528 A1 | 1/2019 | Tzvieli et al. |
| 2019/0074012 A1 | 3/2019 | Kapur et al. |
| 2019/0074028 A1 | 3/2019 | Howard |
| 2019/0080153 A1 | 3/2019 | Kalscheur |

(56) References Cited

U.S. PATENT DOCUMENTS

| | | | |
|---|---|---|---|
| 2019/0096147 | A1 | 3/2019 | Park et al. |
| 2019/0189145 | A1 | 6/2019 | Rakshit et al. |
| 2019/0197224 | A1 | 6/2019 | Smits |
| 2019/0198022 | A1 | 6/2019 | Varner et al. |
| 2019/0277694 | A1 | 9/2019 | Sadot et al. |
| 2019/0340421 | A1 | 11/2019 | Boenapalli et al. |
| 2019/0348041 | A1 | 11/2019 | Cella et al. |
| 2020/0013407 | A1 | 1/2020 | Chae |
| 2020/0020352 | A1 | 1/2020 | Ito et al. |
| 2020/0034608 | A1 | 1/2020 | Nduka et al. |
| 2020/0075007 | A1 | 3/2020 | Kawahara et al. |
| 2020/0081530 | A1 | 3/2020 | Greenberg |
| 2020/0126283 | A1 | 4/2020 | van Vuuren et al. |
| 2020/0205707 | A1 | 7/2020 | Sanyal et al. |
| 2020/0237290 | A1 | 7/2020 | Einfalt et al. |
| 2020/0257785 | A1 | 8/2020 | Li et al. |
| 2020/0300970 | A1 | 9/2020 | Nguyen et al. |
| 2020/0319301 | A1 | 10/2020 | Qiu et al. |
| 2020/0370879 | A1 | 11/2020 | Mutlu et al. |
| 2020/0383628 | A1 | 12/2020 | Borremans et al. |
| 2021/0027154 | A1 | 1/2021 | Zalevsky et al. |
| 2021/0035585 | A1 | 2/2021 | Gupta |
| 2021/0052368 | A1 | 2/2021 | Smadja et al. |
| 2021/0063563 | A1 | 3/2021 | Zalevsky et al. |
| 2021/0072153 | A1 | 3/2021 | Zalevsky et al. |
| 2021/0169333 | A1 | 6/2021 | Zalevsky et al. |
| 2021/0172883 | A1 | 6/2021 | Zalevsky et al. |
| 2021/0195142 | A1 | 6/2021 | Mireles et al. |
| 2021/0209388 | A1 | 7/2021 | Ciftci et al. |
| 2021/0235202 | A1 | 7/2021 | Wexler et al. |
| 2021/0255488 | A1 | 8/2021 | Piestun et al. |
| 2021/0256246 | A1 | 8/2021 | Dagdeviren et al. |
| 2021/0271861 | A1 | 9/2021 | Nduka et al. |
| 2021/0365533 | A1 | 11/2021 | Kaplan et al. |
| 2021/0386409 | A1 | 12/2021 | Clouse et al. |
| 2022/0060230 | A1 | 2/2022 | Na et al. |
| 2022/0065617 | A1 | 3/2022 | Goodwin et al. |
| 2022/0067134 | A1 | 3/2022 | Wan |
| 2022/0078369 | A1 | 3/2022 | Bartha et al. |
| 2022/0084196 | A1 | 3/2022 | Ogawa et al. |
| 2022/0084529 | A1 | 3/2022 | He et al. |
| 2022/0099431 | A1 | 3/2022 | Chen et al. |
| 2022/0117558 | A1 | 4/2022 | Nicolae et al. |
| 2022/0125286 | A1 | 4/2022 | Zalevsky et al. |
| 2022/0132217 | A1 | 4/2022 | Aher et al. |
| 2022/0156485 | A1 | 5/2022 | Tzvieli et al. |
| 2022/0163444 | A1 | 5/2022 | Zalevsky |
| 2022/0189131 | A1 | 6/2022 | Nouri et al. |
| 2022/0161465 | A1 | 8/2022 | Levitoy |
| 2022/0309837 | A1 | 9/2022 | Boic et al. |
| 2022/0310109 | A1 | 9/2022 | Donsbach et al. |
| 2022/0391170 | A1 | 12/2022 | Kim et al. |
| 2023/0215437 | A1* | 7/2023 | Maizels .................. G10L 15/26 704/235 |
| 2023/0230574 | A1 | 7/2023 | Maizels et al. |
| 2023/0230575 | A1* | 7/2023 | Maizels .................. G06V 10/60 704/260 |
| 2023/0230594 | A1 | 7/2023 | Maizels et al. |
| 2023/0267914 | A1* | 8/2023 | Maizels ................ G10L 13/027 704/260 |
| 2023/0293084 | A1 | 9/2023 | Argyropoulos et al. |

FOREIGN PATENT DOCUMENTS

| | | | |
|---|---|---|---|
| WO | 2021040747 | A1 | 3/2021 |
| WO | 2023012527 | A1 | 2/2023 |
| WO | 2023012546 | A1 | 2/2023 |

OTHER PUBLICATIONS

International Search Report and Written Opinion from International Application No. PCT/IB2022/054527 dated Aug. 30, 2022 (7 pages).

International Search Report and Written Opinion from International Application No. PCT/IB2022/056418 dated Oct. 31, 2022 (11 pages).

Guzelsu et al., Measurement of skin stretchy via light reflection, Jan. 2003, Journal of Biomedical Optics, 8(1), pp. 80-86.

Zhang et al., "SpeeChin: A Smart Necklace for Silent Speech Recognition," Proceedings of the ACM on Interactive, Mobile, Wearable and Ubiquitous Technologies (IMWUT), vol. 5, No. 4, article No. 192, pp. 1-23, Dec. 2021.

Fleischman, "Smart necklace recognizes English, Mandarin commands," Cornell Chronicle, pp. 1-3, Feb. 14, 2022.

Kalyuzhner et al., "Remote photonic detection of human senses using secondary speckle patterns," Nature Portfolio, Scientific Reports, vol. 12, pp. 1-9, year 2022.

International Application # PCT/IB2022/054527 Search Report dated Aug. 30, 2022.

Makin et al., "Machine translation of cortical activity to text with an encoder-decoder framework," Nature Neuroscience, vol. 23, No. 4, pp. 575-582, year 2020.

Gaddy et al., "Digital voicing of silent speech," Proceedings of the 2020 Conference on Empirical Methods in Natural Language Processing, Association for Computational Linguistics, pp. 5521-5530, year 2020.

Wigdahl, "The Road Ahead for Speech Recognition Technology," Coruzant Technologies, pp. 1-5, Aug. 2, 2021, as downloaded from https://coruzant.com/ai/the-road-ahead-for-speech-recognition-technology/TWIGDAHLW.

Holst, "Number of digital voice assistants in use worldwide 2019-2024," Statista, pp. 1-1, Jan. 4, 2021.

Spandaslui, "Are You Too Embarrassed To Use Siri, Cortana Or Google Voice Commands In Public?," LifeHacker Australia, pp. 1-6, Jun. 8, 2016, as downloaded from https://www.lifehacker.com.au/2016/06/are-you-embarrassed-to-use-siri-cortana-or-ok-google-in-public/.

Statista Research Department, "Global sales volume for true wireless hearables," pp. 1-1, Jan. 15, 2021.

Cherrayil, "Augmented reality-based devices to replace smartphones in future," Techchannel News, pp. 1-2, Sep. 6, 2021, as downloaded from https://techchannel.news/06/09/2021/ar-based-devices-set-to-replace-smartphones-in-future/.

Dulak et al., "Neuroanatomy, Cranial Nerve 7 (Facial)," NCBI Bookshelf, pp. 1-8, Jul. 24, 2023.

Nelson Longenbaker, "Mader's Understanding Human Anatomy & Physiology", 9th Edition, McGraw Hill Education, pp. 1-513, year 2017.

Learneo, Inc., "Neuromuscular Junctions and Muscle Contractions," Nursing Hero, Anatomy and Physiology I, Module 8: Muscle Tissue, pp. 1-20, year 2024.

Dainty (ed.), "Laser Speckle and Related Phenomena," Topics in Applied Physics, vol. 9, pp. 1-295, year 1975.

Gaddy et al., "An Improved Model for Voicing Silent Speech," Proceedings of the 59th Annual Meeting of the Association for Computational Linguistics and the 11th International Joint Conference on Natural Language Processing (Short Papers), pp. 175-181, Aug. 2021.

Fu et al., "Ultracompact meta-imagers for arbitrary all-optical convolution," Light: Science & Applications, vol. 11, issue 62, pp. 1-13, year 2022.

Mcworther, "The world's most musical languages," The Atlantic, pp. 1-9, Nov. 13, 2015.

Mingxing et al., "Towards optimizing electrode configurations for silent speech recognition based on high-density surface electromyography," Journal of Neural Engineering, vol. 18, pp. 1-15, year 2021.

Cvetkovska, "26 Beard Statistics and Facts You Probably Didn't Know", pp. 1-11, Jan. 1, 2021, as downloaded from https://web.archive.org/web/20210730125541/https://moderngentlemen.net/beard-statistics/.

Gilette, "10 facts on the science of beard growth", pp. 1-5, year 2021, as downloaded from https://gillette.com/en-us/shaving-tips/how-to-shave/beard-growth-science.

Rietzler et al., "The male beard hair and facial skin—challenges for shaving," Symposium presentation at the 23rd World Congress of Dermatology in Vancouver, Canada, pp. 1-19, Jun. 2015.

(56) References Cited

OTHER PUBLICATIONS

Janke et al., "EMG-to-Speech: Direct Generation of Speech From Facial Electromyographic Signals," IEEE/ACM Transactions on Audio, Speech and Language Processing, vol. 25, issue 12, pp. 2375-2385, Dec. 1, 2017.

Mit Media Lab, "Fluid Interfaces—Project AlterEgo," pp. 1-3, Jun. 21, 2021, as downloaded from https://web.archive.org/web/20210621110900/https://www.media.mit.edu/projects/alterego/overview/.

Brigham Young University, "Skeletal muscle: Whole muscle physiology—Motor units," Atonomy & Physiology, pp. 1-7, year 2021.

Krans et al., "The sliding filament theory of muscle contraction," Nature Education, vol. 3, issue 9, article No. 66, pp. 1-11, year 2010.

Warden et al., "Launching the Speech Commands Dataset", pp. 1-3, Aug. 24, 2017, as downloaded from https://research.google/blog/launching-the-speech-commands-dataset/.

O'Neill et al., "SPGISpeech: 5,000 hours of transcribed financial audio for fully formatted end-to-end speech recognition," arXiv:2104.02014v2, pp. 1-5, Apr. 6, 2021.

Jou et al., "Towards Continuous Speech Recognition Using Surface Electromyography," Conference paper, Interspeech 2006—ICSLP—9th International conference on spoken language processing, pp. 1-4, Sep. 2006.

Ko et al., "Audio Augmentation for Speech Recognition," Conference paper, Sixteenth annual conference of the international speech communication association, pp. 1-4, year 2015.

Nalborczyk et al., "Can we decode phonetic features in inner speech using surface electromyography?," Plos One, pp. 1-16, May 27, 2020.

International Application # PCT/IB2022/056418 Search Report dated Oct. 31, 2022.

Nicolo et al., "The importance of respiratory rate monitoring: from health-care to sports and exercise," Sensors, vol. 20, issue 21, article No. 6396, pp. 1-46, Nov. 2020.

Office Action from India Intellectual Property Office in Indian patent application No. 202447014135, mailed Jun. 20, 2024 (7 pages).

* cited by examiner

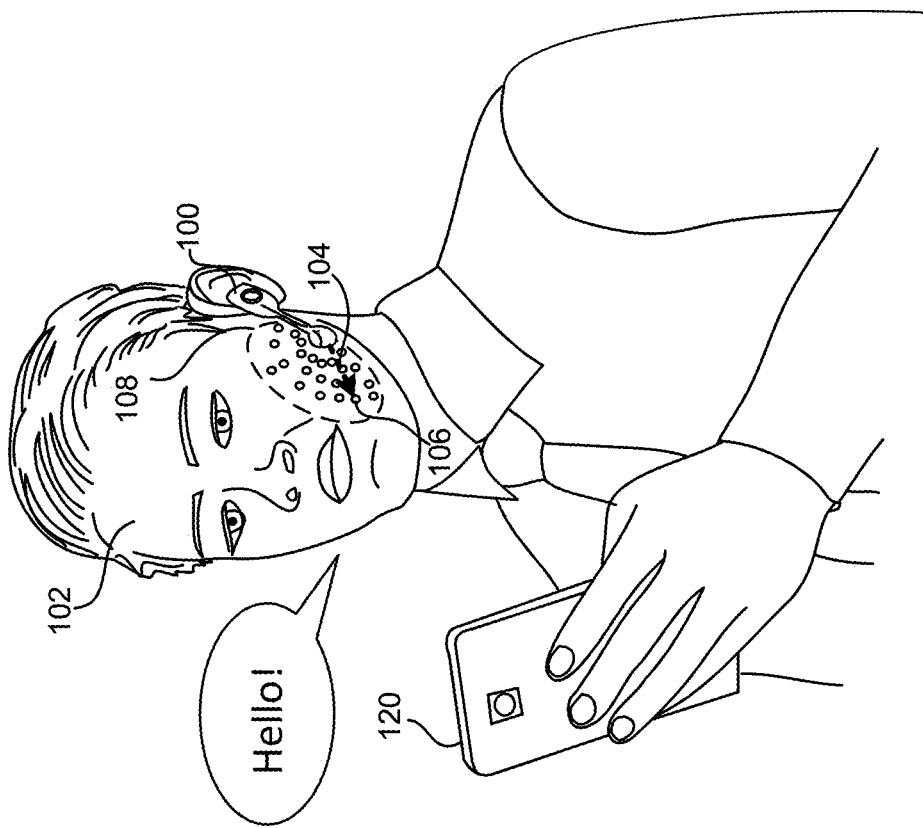
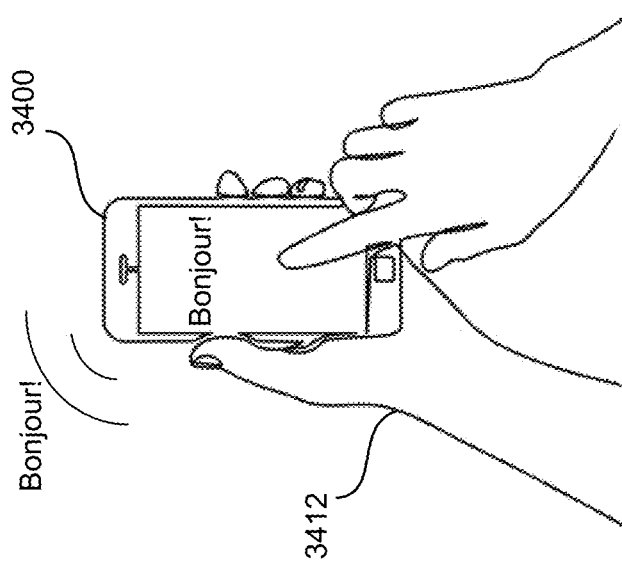
FIG. 34

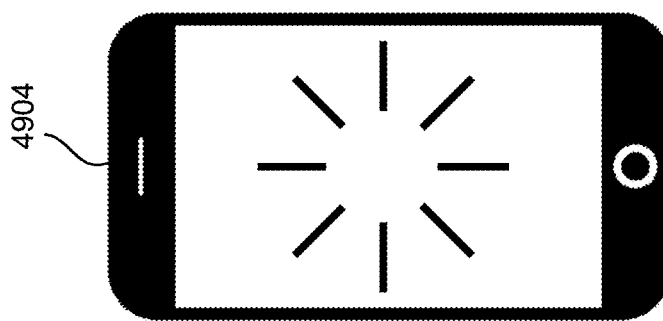
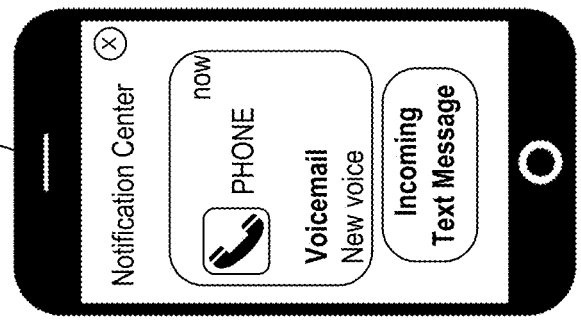
FIG. 49

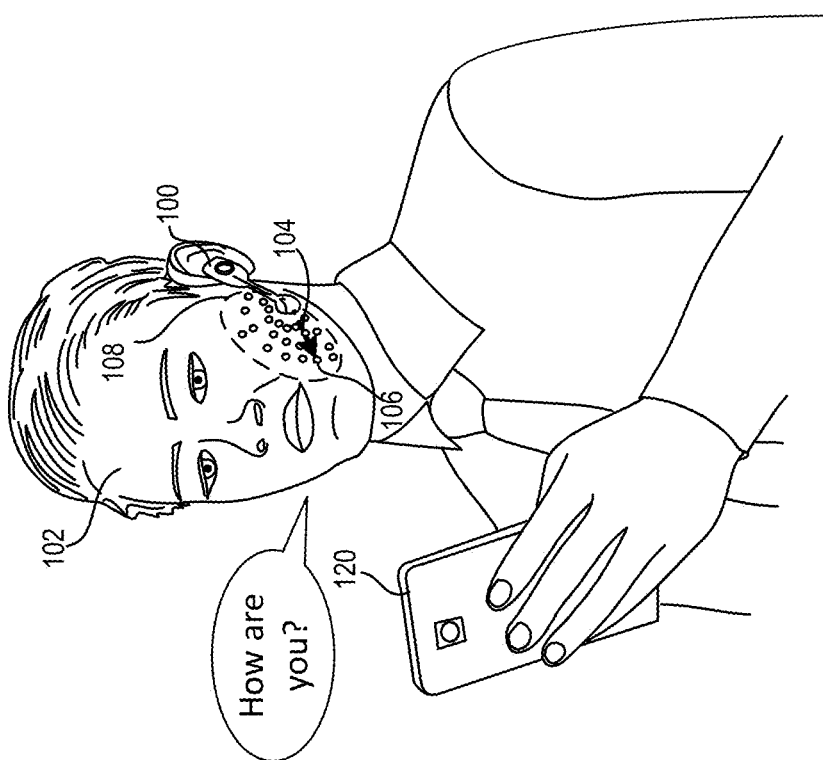
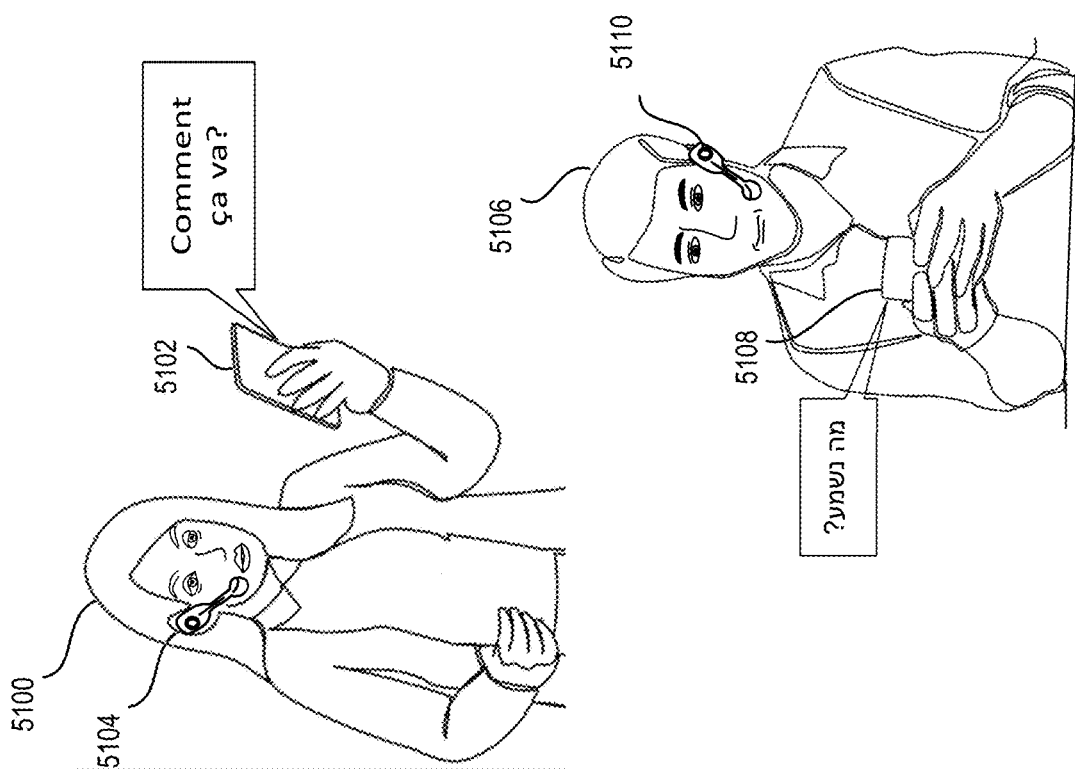
FIG. 51

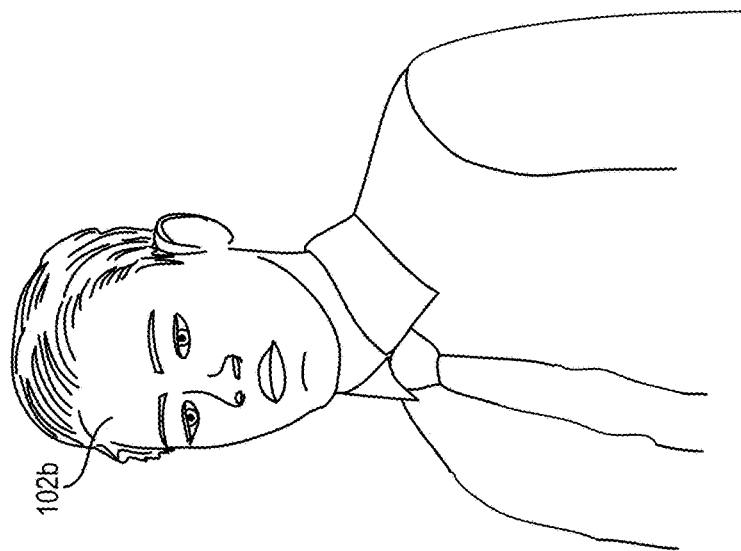
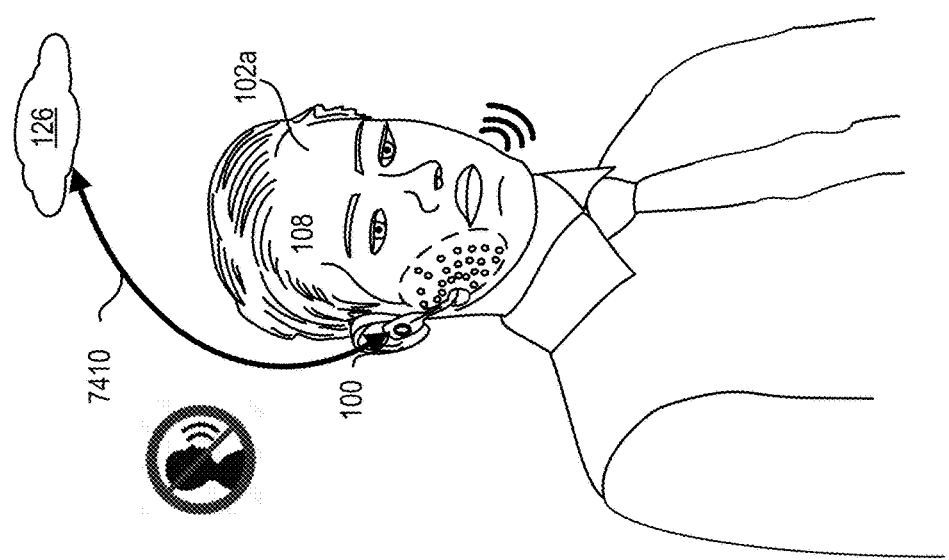
FIG. 74

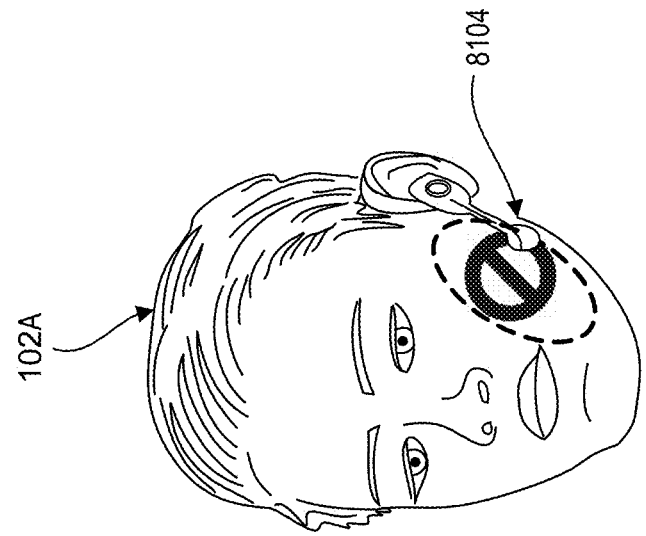
FIG. 81

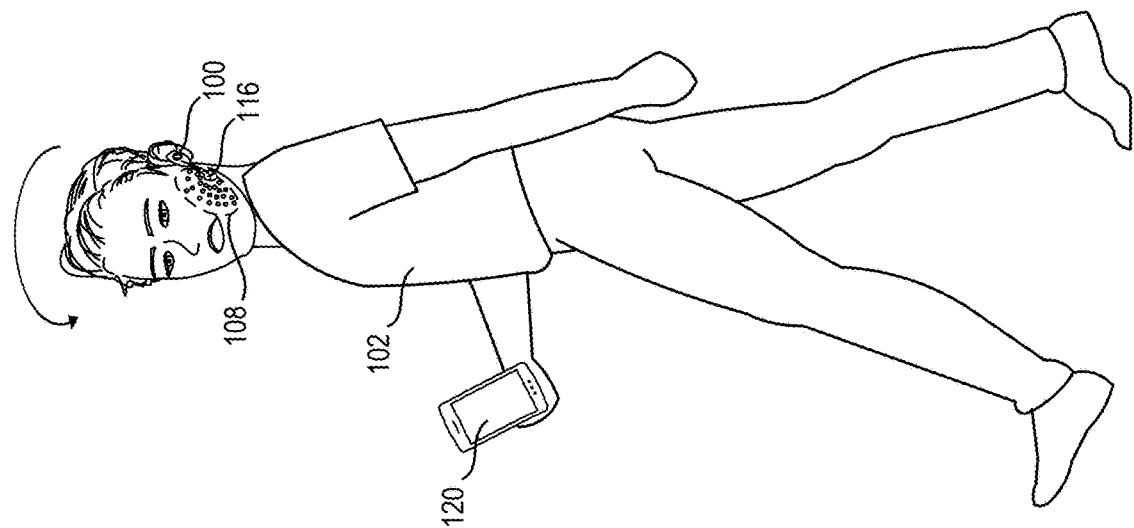
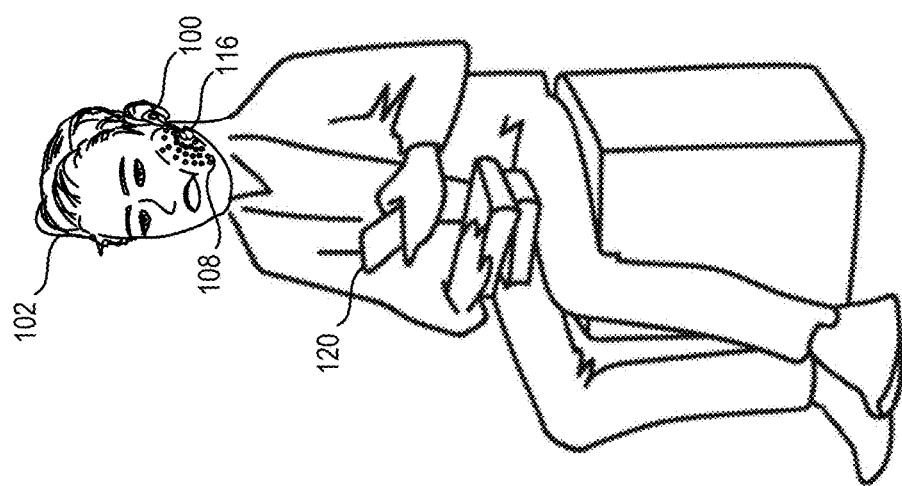
FIG. 103

INTERPRETING WORDS PRIOR TO VOCALIZATION

CROSS REFERENCES TO RELATED APPLICATIONS

This application is a continuation of PCT International Application No. PCT/162023/057369, filed Jul. 19, 2023, which claims the benefit of priority of U.S. Provisional Patent Application No. 63/390,653, filed on Jul. 20, 2022; U.S. Provisional Patent Application No. 63/394,329, filed on Aug. 2, 2022; U.S. Provisional Patent Application No. 63/438,061, filed on Jan. 10, 2023; U.S. Provisional Patent Application No. 63/441,183, filed on Jan. 26, 2023; and U.S. Provisional Patent Application No. 63/487,299, filed on Feb. 28, 2023. This application is also a continuation-in-part of International Application No. PCT/162022/056418, filed on Jul. 12, 2022, which is a continuation-in-part of International Application No. PCT/162022/054527, filed on May 16, 2022, which claims the benefit of U.S. Provisional Application No. 63/229,091, filed on Aug. 4, 2021, all of which are incorporated herein by reference in their entirety.

TECHNICAL FIELD

The present disclosure generally relates to the field of discerning information from neuromuscular activity. One example is to discern communications by detecting facial skin movements that occur during subvocalization. Other examples include enabling control based neuromuscular activity and discerning changes in neuromuscular activity over time.

BACKGROUND

The human brain and neural activity are complex and involve many subsystems. One of those subsystems is the facial region used by humans for communication with others. From birth, humans are trained to activate craniofacial muscles to articulate sounds. Even before full language ability evolves, babies use facial expressions, including micro-expressions, to convey deeper information about themselves. After language abilities are learned, however, speech is the main technique that humans use to communicate.

The normal process of vocalized speech uses multiple groups of muscles and nerves, from the chest and abdomen, through the throat, and up through the mouth and face. To utter a given phoneme, motor neurons activate muscle groups in the face, larynx, and mouth in preparation for propulsion of air flow out of the lungs, and these muscles continue moving during speech to create words and sentences. Without this air flow, no sounds are emitted from the mouth. Silent speech occurs when the air flow from the lungs is absent, while the muscles in the face, larynx, and mouth articulate the desired sounds or move in a manner enabling interpretation.

Some of the disclosed embodiments are directed to providing a new approach for extracting meaning from neuromuscular activity, one that detects facial skin micromovements that occur during subvocalization, such as, silent speech.

SUMMARY

Embodiments consistent with the present disclosure provide systems, methods, and devices for detection and usage of facial movements.

Some disclosed embodiments may include systems, methods, and non-transitory computer readable media for identifying individuals using facial skin micromovements. These embodiments may involve operating a wearable coherent light source configured to project light towards a facial region a head of an individual; operating at least one detector configured to receive coherent light reflections from the facial region and to output associated reflection signals; analyzing the reflection signals to determine specific facial skin micromovements of the individual; accessing memory correlating a plurality of facial skin micromovements with the individual; searching for match between the determined specific facial skin micromovements and at least one of the plurality of facial skin micromovements in the memory; if a match is identified, initiating a first action; and if a match is not identified, initiating a second action different from the first action.

Some disclosed embodiments may include systems, methods, and non-transitory computer readable media for interpreting facial skin movements. These embodiments may involve projecting light on a plurality of facial region areas of an individual, wherein the plurality of areas includes at least a first area and a second area, the first area being closer to at least one of a zygomaticus muscle or a risorius muscle than the second area; receiving reflections from the plurality of areas; detecting first facial skin movements corresponding to reflections from the first area and second facial skin movements corresponding to reflections from the second area; determining, based on differences between the first facial skin movements and the second facial skin movements, that the reflections from the first area closer to the at least one of a zygomaticus muscle or a risorius muscle are a stronger indicator of communication than the reflections from the second area; based on the determination that the reflections from the first area are a stronger indicator of communication, processing the reflections from the first area to ascertain the communication, and ignoring the reflections from the second area.

Some disclosed embodiments may include systems, methods, and non-transitory computer readable media for performing identity verification operations based on facial micromovements. These embodiments may involve receiving in a trusted manner, reference signals for verifying correspondence between a particular individual and an account at an institution, the reference signals being derived based on reference facial micromovements detected using first coherent light reflected from a face of the particular individual; storing in a secure data structure, a correlation between an identity of the particular individual and the reference signals reflecting the facial micromovements; following storing, receiving via the institution, a request to authenticate the particular individual; receiving real-time signals indicative of second coherent light reflections being derived from second facial micromovements of the particular individual; comparing the real-time signals with the reference signals stored in the secure data structure to thereby authenticate the particular individual; and upon authentication, notifying the institution that the particular individual is authenticated.

Some disclosed embodiments may include systems, methods, and non-transitory computer readable media for continuous authentication based on facial skin micromovements. These embodiments may involve receiving during an ongoing electronic transaction, first signals representing coherent light reflections associated with first facial skin micromovements during a first time period; determining, using the first signals, an identity of a specific individual associated with the first facial skin micromovements; receiving during the ongoing electronic transaction second signals representing coherent light reflections associated with second facial skin micromovements, the second signals being received during a second time period following the first time period; determining, using the second signals, that the specific individual is also associated with the second facial skin micromovements; receiving during the ongoing electronic transaction third signals representing coherent light reflections associated with third facial skin micromovements, the third signals being received during a third time period following the second time period; determining, using the third signals, that the third facial skin micromovements are not associated with the specific individual; and initiating an action based on the determination that the third facial skin micromovements are not associated with the specific individual.

Some disclosed embodiments may include systems, methods, and non-transitory computer readable media for performing thresholding operations for interpretation of facial skin micromovements. These embodiments may involve detecting facial micromovements in an absence of perceptible vocalization associated with the facial micromovements; determining an intensity level of the facial micromovements; comparing the determined intensity level with a threshold; when the intensity level is above the threshold, interpreting the facial micromovements; and when the intensity level falls beneath the threshold, disregarding the facial micromovements.

Some disclosed embodiments may include systems, methods, and non-transitory computer readable media for establishing nonvocalized conversations. These embodiments may involve establishing a wireless communication channel for enabling a nonvocalized conversation via a first wearable device and a second wearable device, wherein both the first wearable device and the second wearable device each contain a coherent light source and a light detector configured to detect facial skin micromovements from coherent light reflections; detecting by the first wearable device first facial skin micromovements occurring in an absence of perceptible vocalization; transmitting a first communication via the wireless communication channel from the first wearable device to the second wearable device, wherein the first communication is derived from the first facial skin micromovements and is transmitted for presentation via the second wearable device; receiving a second communication via the wireless communication channel from the second wearable device, wherein the second communication is derived from second facial skin micromovements detected by the second wearable device; and presenting the second communication to a wearer of the first wearable device.

Some disclosed embodiments may include systems, methods, and non-transitory computer readable media for initiating content interpretation operations prior to vocalization of content to be interpreted. These embodiments may involve receiving signals representing facial skin micromovements; determining from the signals at least one word to be spoken prior to vocalization of the at least one word in an origin language; prior to the vocalization of the at least one word, instituting an interpretation of the at least one word; and causing the interpretation of the at least one word to be presented as the at least one word is spoken.

Some disclosed embodiments may include systems, methods, and non-transitory computer readable media for performing private voice assistance operations. These embodiments may involve receiving signals indicative of specific facial skin micromovements reflective of a private request to an assistant, wherein answering the private request requires an identification of a specific individual associated with the specific facial skin micromovements; accessing a data structure maintaining correlations between the specific individual and a plurality of facial skin micromovements associated with the specific individual; searching in the data structure for a match indicative of a correlation between a stored identity of the specific individual and the specific facial skin micromovements; in response to a determination of an existence of the match in the data structure, initiating a first action responsive to the request, wherein the first action involves enabling access to information unique to the specific individual; and if the match is not identified in the data structure, initiating a second action different from the first action.

Some disclosed embodiments may include systems, methods, and non-transitory computer readable media for determining subvocalized phonemes from facial skin micromovements. These embodiments may involve controlling at least one coherent light source in a manner enabling illumination of a first region of a face and a second region of the face; performing first pattern analysis on light reflected from the first region of the face to determine first micromovements of facial skin in the first region of the face; performing second pattern analysis on light reflected from the second region of the face to determine second micromovements of facial skin in the second region of the face; and using the first micromovements of the facial skin in the first region of the face and the second micromovements of the facial skin in the second region of the face to ascertain at least one subvocalized phoneme.

Some disclosed embodiments may include systems, methods, and non-transitory computer readable media for generating synthesized representations of facial expressions. These embodiments may involve controlling at least one coherent light source in a manner enabling illumination of a portion of a face; receiving output signals from a light detector, wherein the output signals correspond to reflections of coherent light from the portion of the face; applying speckle analysis on the output signals to determine speckle analysis-based facial skin micromovements; using the determined speckle analysis-based facial skin micromovements to identify at least one word prevocalized or vocalized during a time period; using the determined speckle analysis-based facial skin micromovements to identify at least one change in a facial expression during the time period; and during the time period, outputting data for causing a virtual representation of the face to mimic the at least one change in the facial expression in conjunction with an audio presentation of the at least one word.

Some disclosed embodiments may include systems, methods, and non-transitory computer readable media for performing operations for attention-associated interactions based on facial skin micromovements. These embodiments may involve determining facial skin micromovements of an individual based on reflections of coherent light from a facial region of the individual; using the facial skin micromovements to determine a specific engagement level of the individual; receiving data associated with a prospective interaction with the individual; accessing a data structure correlating information reflective of alternative engagement levels with differing presentation manners; based on the specific engagement level and the correlating information, determining a specific presentation manner for the prospective interaction; and associating the specific presentation manner with the prospective interaction for subsequent engagement with the individual.

Some disclosed embodiments may include systems, methods, and non-transitory computer readable media for performing voice synthetization operations from detected facial skin micromovements. These embodiments may involve determining particular facial skin micromovements of a first individual speaking with a second individual based on reflections of light from a facial region of the first individual; accessing a data structure correlating facial micromovements with words; performing a lookup in the data structure of particular words associated with the particular facial skin micromovements; obtaining an input associated with a preferred speech consumption characteristic of the second individual; adopting the preferred speech consumption characteristic; and synthesizing, using the adopted preferred speech consumption characteristic, audible output of the particular words.

Some disclosed embodiments may include systems, methods, and non-transitory computer readable media for performing operations for personal presentation of prevocalization. These embodiments may involve receiving reflection signals corresponding to light reflected from a facial region of an individual; using the received reflections signals to determine particular facial skin micromovements of an individual in an absence of perceptible vocalization associated with the particular facial skin micromovements; accessing a data structure correlating facial skin micromovements with words; performing a lookup in the data structure of particular unvocalized words associated with the particular facial skin micromovements; and causing an audible presentation of the particular unvocalized words to the individual prior to vocalization of the particular words by the individual.

Some disclosed embodiments may include systems, methods, and non-transitory computer readable media for interpreting impaired speech based on facial movements. These embodiments may involve receiving signals associated with specific facial skin movements of an individual having a speech impairment that affects a manner in which the individual pronounces a plurality of words; accessing a data structure containing correlations between the plurality of words and a plurality of facial skin movements corresponding to the manner in which the individual pronounces the plurality of words; based on the received signals and the correlations, identifying specific words associated with the specific facial skin movements; and generating an output of the specific words for presentation, wherein the output differs from how the individual pronounces the specific words.

Some disclosed embodiments may include systems, methods, and non-transitory computer readable media for ongoing verification of communication authenticity based on light reflections from facial skin. These embodiments may involve generating a first data stream representing a communication by a subject, the communication having a duration; generating a second data stream for corroborating an identity of the subject from facial skin light reflections captured during the duration of the communication; transmitting the first data stream to a destination; transmitting the second data stream to the destination; and wherein the second data stream is correlated to the first data stream in a manner such that upon receipt at the destination, the second data stream is enabled for use in repeatedly checking during the duration of the communication that the communication originated from the subject.

Some disclosed embodiments may include systems, methods, and non-transitory computer readable media for noise suppression using facial skin micromovements. These embodiments may involve operating a wearable coherent light source configured to project light towards a facial region of a head of a wearer; operating at least one detector configured to receive coherent light reflections from the facial region associated with facial skin micromovements and to output associated reflection signals; analyzing the reflection signals to determine speech timing based on the facial skin micromovements in the facial region; receiving audio signals from at least one microphone, the audio signals containing sounds of words spoken by the wearer together with ambient sounds; correlating, based on the speech timing, the reflection signals with the received audio signals to determine portions of the audio signals associated with the words spoken by the wearer; and outputting the determined portions of the audio signals associated with the words spoken by the wearer, while omitting output of other portions of the audio signals not containing the words spoken by the wearer.

Some disclosed embodiments may include systems, methods, and non-transitory computer readable media for providing private answers to silent questions. These embodiments may involve receiving signals indicative of particular facial micromovements in an absence of perceptible vocalization; accessing a data structure correlating facial micromovements with words; using the received signals to perform a lookup in the data structure of particular words associated with the particular facial micromovements; determining a query from the particular words; accessing at least one data structure to perform a look up for an answer to the query; and generating a discreet output that includes the answer to the query.

Some disclosed embodiments may include systems, methods, and non-transitory computer readable media for performing control commands based on facial skin micromovements. These embodiments may involve operating at least one coherent light source in a manner enabling illumination of a non-lip portion of a face; receiving specific signals representing coherent light reflections associated with specific non-lip facial skin micromovements; accessing a data structure associating a plurality of non-lip facial skin micromovements with control commands; identifying in the data structure a specific control command associated with the specific signals associated with the specific non-lip facial skin micromovements; and executing the specific control command.

Some disclosed embodiments may include systems, methods, and non-transitory computer readable media for detecting changes in neuromuscular activity over time. These embodiments may involve establishing a baseline of neuromuscular activity from coherent light reflections associated with historical skin micromovements; receiving current signals representing coherent light reflections associated with current skin micromovements of an individual; identifying a deviation of the current skin micromovements from the baseline of neuromuscular activity; and outputting an indicator of the deviation.

Some disclosed embodiments may include systems, methods, and non-transitory computer readable media for projecting graphical content and for interpreting non-verbal speech. These embodiments may involve operating a wearable light source configured to project light in a graphical pattern on a facial region of an individual, wherein the graphical pattern is configured to visibly convey information; receiving from a sensor, output signals corresponding with a portion of the light reflected from the facial region; determining from the output signals facial skin micromovements associated with non-verbalization; and processing the output signals to interpret the facial skin micromovements.

Some disclosed embodiments may include systems, methods, and non-transitory computer readable media for interpreting facial skin micromovements. These embodiments may involve receiving coherent light reflections from a facial region associated with facial skin micromovements of an individual; outputting reflection signals associated with the light reflections; capturing sounds produced by the individual; outputting audio signals associated with the captured sounds; and using both the reflection signals and the audio signals to generate output corresponding to words articulated by the individual.

Some disclosed embodiments may include systems, methods, and non-transitory computer readable media for interpreting facial skin micromovements. These embodiments may involve receiving during a first time period first signals representing prevocalization facial skin micromovements; receiving during a second time period succeeding the first time period, second signals representing sounds; analyzing the sounds to identify words spoken during the second time period; correlating the words spoken during the second time period with the prevocalization facial skin micromovements received during the first time period; storing the correlations; receiving during a third time period, third signals representing facial skin micromovements received in an absence of vocalization; using the stored correlations to identify language associated with the third signals; and outputting the language.

Some disclosed embodiments may include systems, methods, and non-transitory computer readable media for operating a multifunctional earpiece. These embodiments may involve operating a speaker integrated with an ear-mountable housing associated with the multifunctional earpiece for presenting sound; operating a light source integrated with the ear-mountable housing for projecting light toward skin of the wearer's face; operating a light detector integrated with the ear-mountable housing and configured to receive reflections from the skin corresponding to facial skin micromovements indicative of prevocalized words of the wearer; and simultaneously presenting the sound through the speaker, projecting the light toward the skin, and detecting the received reflections indicative of the prevocalized words.

Some disclosed embodiments may include a driver for integration with a software program and for enabling a neuromuscular detection device to interface with the software program. The driver comprising: an input handler for receiving non-audible muscle activation signals from the neuromuscular detection device; a lookup component for mapping specific ones of the non-audible activation signals to corresponding commands in the software program; a signal processing module for receiving the non-audible muscle activation signals from the input handler, supplying the specific ones of the non-audible muscle activation signals to the lookup component, and receiving an output as the corresponding commands; and a communications module for conveying the corresponding commands to the software program, to thereby enable control within the software program based on non-audible muscular activity detected by the neuromuscular detection device.

Some disclosed embodiments may include systems, methods, and non-transitory computer readable media for performing context-driven facial micromovement operations. These embodiments may involve receiving during a first time period, first signals representing first coherent light reflections associated with first facial skin micromovements; analyzing the first coherent light reflections to determine a first plurality of words associated with the first facial skin micromovements; receiving first information indicative of a first contextual condition in which the first facial skin micromovements occurred; receiving during a second time period, second signals representing second coherent light reflections associated with second facial skin micromovements; analyzing the second coherent light reflections to determine a second plurality of words associated with the second facial skin micromovements; receiving second information indicative of a second contextual condition in which the second facial skin micromovements occurred; accessing a plurality of control rules correlating a plurality of actions with a plurality of contextual conditions, wherein a first control rule prescribes a form of private presentation based on the first contextual condition, and a second control rule prescribes a form of non-private presentation based on the second contextual condition; upon receipt of the first information, implementing the first control rule to privately output the first plurality of words; and upon receipt of the second information, implementing the second control rule to non-privately output the second plurality of words.

Some disclosed embodiments may include systems, methods, and non-transitory computer readable media for extracting reactions to content based on facial skin micromovements. These embodiments may involve during a time period when an individual is consuming content, determining the facial skin micromovements of the individual based on reflections of coherent light from a facial region of the individual; determining at least one specific micro-expression from the facial skin micromovements; accessing at least one data structure containing correlations between a plurality of micro-expressions and a plurality of non-verbalized perceptions; based on the at least one specific micro-expression and the correlations in the data structure, determining a specific non-verbalized perception of the content consumed by the individual; and initiating an action associated with the specific non-verbalized perception.

Some disclosed embodiments may include systems, methods, and non-transitory computer readable media for removing noise from facial skin micromovement signals. These embodiments may involve during a time period when an individual is involved in at least one non-speech-related physical activity, operating a light source in a manner enabling illumination of a facial skin region of the individual; receiving signals representing light reflections from the facial skin region; analyzing the received signals to identify a first reflection component indicative of prevocalization facial skin micromovements and a second reflection component associated with the at least one non-speech-related physical activity; and filtering out the second reflection component to enable interpretation of words from the first reflection component indicative of the prevocalization facial skin micromovements.

Consistent with other disclosed embodiments, non-transitory computer-readable storage media may store program instructions, which are executed by at least one processing device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 34 is a schematic illustration of an exemplary content interpretation process initiated prior to vocalization of content to be interpreted, consistent with some embodiments of the present disclosure.

FIG. 49 is a schematic illustration of receipt of a prospective interaction via a smartphone, consistent with some embodiments of the present disclosure.

FIG. 51 illustrates a first individual wearing speech detection system while communicating with at least one second individual, consistent with some embodiments of the present disclosure.

FIG. 74 is a schematic illustration of two individuals each using an example speech detection system, consistent with some embodiments of the present disclosure.

FIG. 81 is a schematic illustration of altering a projected graphical pattern consistent with some embodiments of the present disclosure.

FIG. 103 illustrates an individual performing a first non-speech-related activity (e.g., walking) and a second non-speech-related activity (e.g., sitting) while wearing a speech recognition system, consistent with embodiments of the present disclosure.

DETAILED DESCRIPTION

Figure 1:
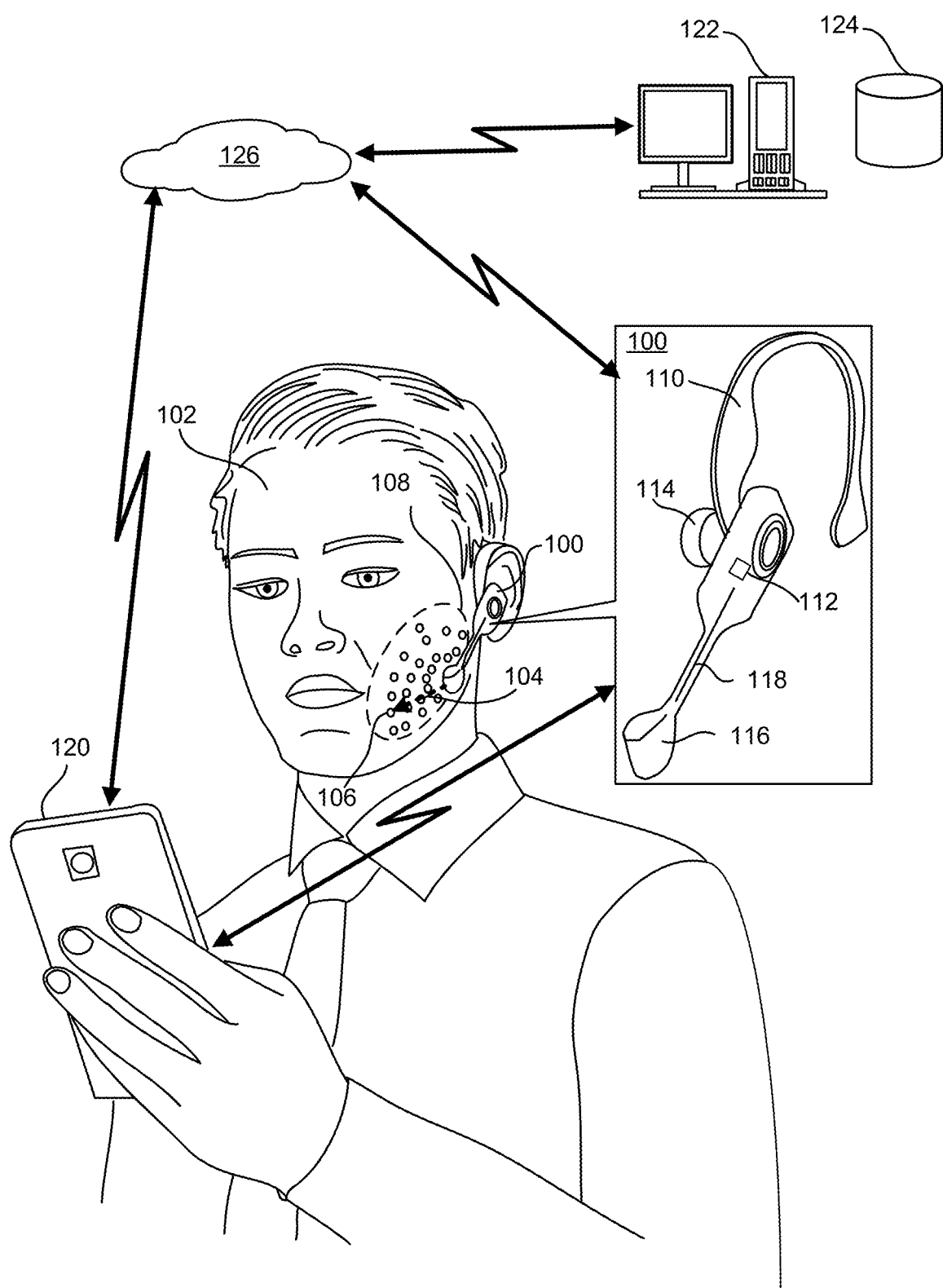
FIG. 1 is a schematic illustration of a user using a first example speech detection system, consistent with some embodiments of the present disclosure.

The following detailed description includes references to the accompanying drawings. Wherever possible, the same reference numbers are used in the drawings and the description to refer to the same or similar parts. While several illustrative embodiments are described herein, modifications, adaptations, and other implementations are possible. For example, substitutions, additions, or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Various terms used in the specification and claims may be defined or summarized differently when discussed in connection with differing disclosed embodiments. It is to be understood that the definitions, summaries and explanations of terminology in each instance apply to all instances, even when not repeated, unless the transitive definition, explanation, or summary would result in inoperability of an embodiment. It is also to be understood that once a term is defined herein, in the absence of an inherent inconsistency, that definition applies to all other uses of the term herein. Moreover, the exemplary embodiments of the figures and their description are not to be considered definitions of claim terms, but rather are non-limiting examples used to illustrate specific embodiments.

Throughout, this disclosure mentions "embodiments" and "disclosed embodiments," which refer to examples of inventive ideas, concepts, and/or manifestations described herein. Many related and unrelated embodiments are described throughout this disclosure. The fact that some "disclosed embodiments" are described as exhibiting a feature or characteristic does not mean that other disclosed embodiments necessarily share that feature or characteristic.

This disclosure employs open-ended permissive language, indicating for example, that some embodiments "may" employ, involve, or include specific features. The use of the term "may," and other open-ended terminology, is intended to indicate that although not every embodiment may employ the specific disclosed feature, at least one embodiment employs the specific disclosed feature.

Differing embodiments of this disclosure may involve systems, methods, and/or computer readable media containing instructions. A system refers to at least two interconnected or interrelated components or parts that work together to achieve a common objective, function, or sub-function. A method refers to at least two steps, actions, or techniques to be followed in order to complete a task or a sub-task, to reach an objective, or to arrive at a next step. Computer-readable media containing instructions refers to any storage mechanism that contains program code instructions, for example to be executed by a computer processor. Examples of computer-readable media are further described elsewhere in this disclosure. Instructions may be written in any type of computer programming language, such as an interpretive language (e.g., scripting languages such as HTML and JavaScript), a procedural or functional language (e.g., C or Pascal that may be compiled for converting to executable code), an object-oriented programming language (e.g., Java or Python), a logical programming language (e.g., Prolog or Answer Set Programming), and/or any other programming language. Instructions executed by at least one processor may include implementing one or more program code instructions in hardware, in software (including in one or more signal processing and/or application specific integrated circuits), in firmware, or in any combination thereof, as described earlier. Causing a processor to perform operations may involve causing the processor to calculate, execute, or otherwise implement one or more arithmetic, mathematic, logic, reasoning, or inference steps.

Some disclosed embodiments may involve detecting facial skin micromovements. The term "facial skin micromovements" broadly refers to skin motions on the face that may be detectable using a sensor, but which might not be readily detectable to the naked eye. The facial skin micromovements include various types of movements, including involuntary movements caused by muscle recruitments and other types of small-scale skin deformations that fall within the range of micrometers to millimeters and fractions of a second to several seconds in duration. In some cases, the facial skin micromovements are part of a larger-scale skin movement visible to the naked eye (e.g., a smile may involve many facial skin micromovements). In other cases, the facial skin micromovements are not part of any larger-scale skin movement visible to the naked eye. While such micromovements may occur over a multi-square millimeter facial area, they may occur in a surface area of the facial skin of less than one square centimeter, less than one square millimeter, less than 0.1 square millimeter, less than 0.01 square millimeter, or an even smaller area. In some embodiments, the facial skin micromovements correspond to one or more muscle recruitments in a facial region of a head of an individual. The facial region may include specific anatomical areas, for example: a part of the cheek above the mouth, a part of the cheek below the mouth, a part of the mid-jaw, a part of the cheek below the eye, a neck, a chin, and other areas associated with specific muscle recruitments that may cause facial skin micromovements. In some embodiments, the specific muscles may be connected to skin tissue and not to any bone. In particular, the specific muscles may be located in a subcutaneous tissue associated with cranial nerve V or cranial nerve VII. As is discussed herein in greater detail, first facial skin micromovement 522A and second facial skin micromovement 522B in FIG. 5A and are non-limiting examples of facial skin micromovements, consistent with the present disclosure.

Figure 5A:
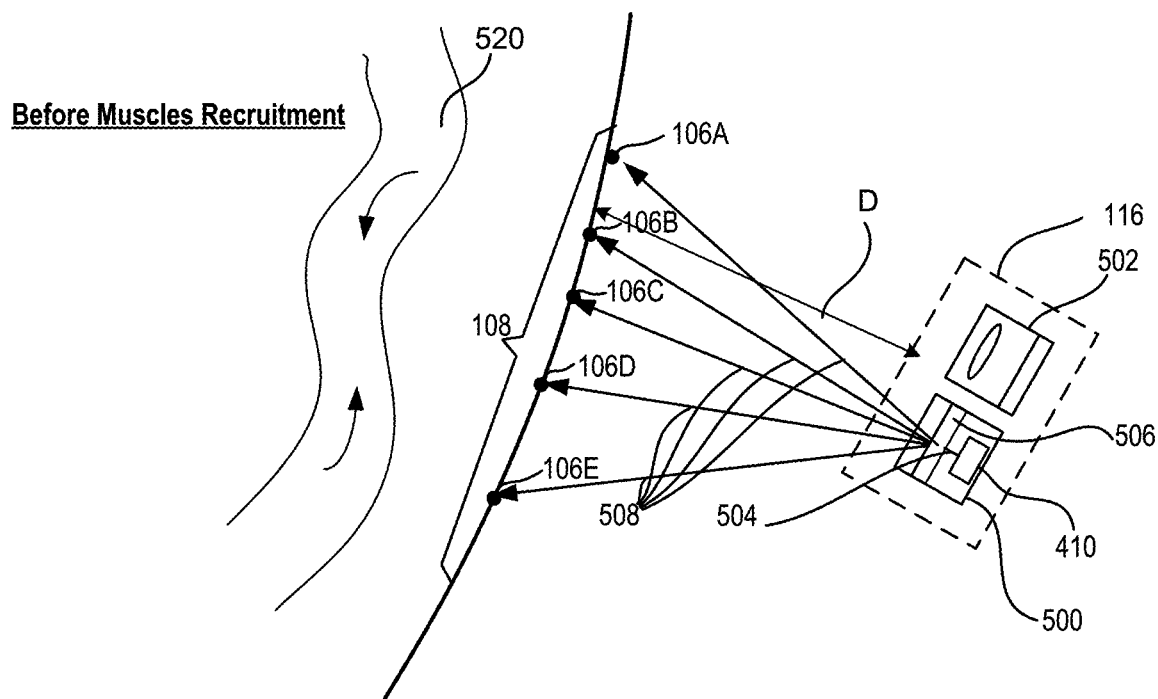
FIGS. 5A and 5B are schematic illustrations of part of the speech detection system as it detects facial skin micromovements, consistent with some embodiments of the present disclosure.
Figure 5B:
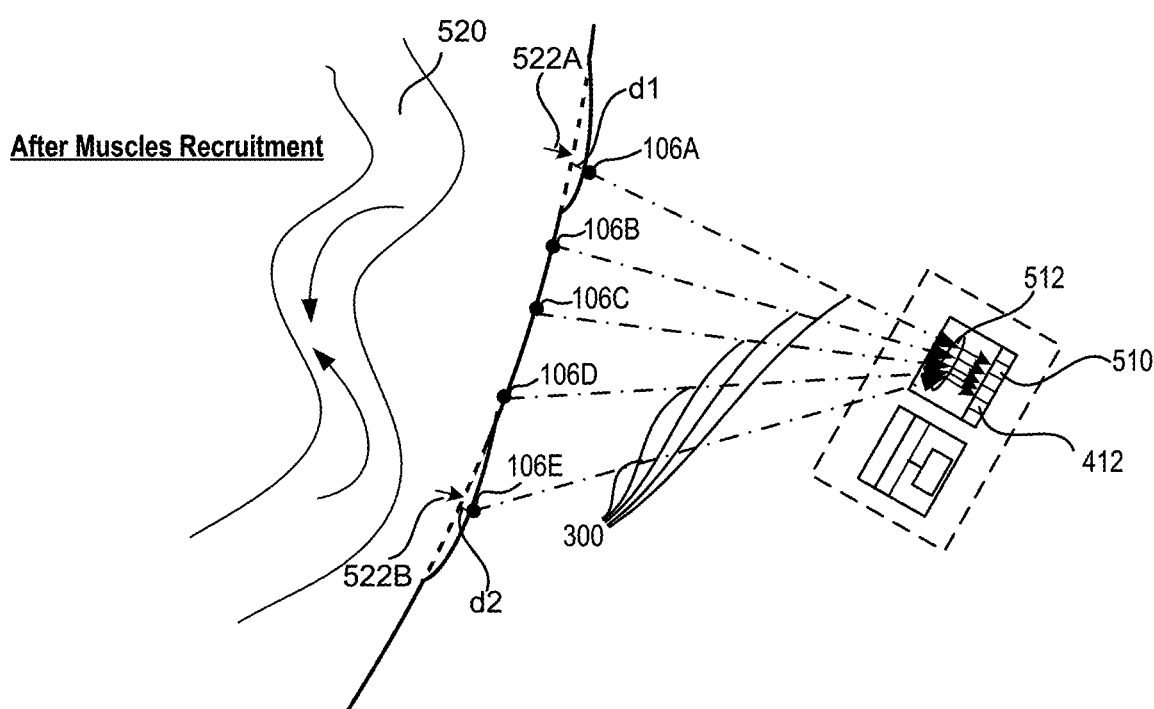

When specific muscles contract, the muscles pull on the facial skin and cause movements of the facial skin. Some of the movements that occur when the specific muscles contract may be micromovements. By way of example, the specific muscles that may cause facial skin micromovements in the context of the present disclosure may broadly be split into four groups: orbital, nasal, oral, and tongue. The orbital group of facial muscles contains two muscles associated with the eye socket. These muscles control the movements of the eyelids, important in protecting the cornea from damage. They are both innervated by cranial nerve VII. The nasal group of facial muscles is associated with movements of the nose and the skin around it. There are three muscles in this group, and they are also all innervated by cranial nerve VII. The oral group is the most important group of the facial expressors: responsible for movements of the mouth and lips. Such movements are required in singing and whistling and add emphasis to vocal communication. The oral group of muscles consists of the orbicularis oris, buccinator, and various smaller muscles. In a specific embodiment, a disclosed system may monitor facial skin micromovements that correspond to recruitment of the buccinator muscle. The buccinator muscle is located between the mandible and maxilla relatively deep compared to other muscles of the face. The tongue group of muscles consists of four intrinsic muscles (e.g., the superior longitudinal muscle, the inferior longitudinal muscle, the vertical muscle, and the transverse muscle) used to change the shape of the tongue; and four extrinsic muscles (e.g., the genioglossus, the hyoglossus, the styloglossus, and the palatoglossus) used to change the position of the tongue. Any of the tongue muscles listed above may cause movements of the tongue that may be detected by analyzing detected facial skin micromovements. As is discussed herein in greater detail, muscle fiber 520 in FIGS. 5A and 5B is a non-limiting example of a facial muscle that causes micromovements of the facial skin, consistent with the present disclosure.

Figure 7:
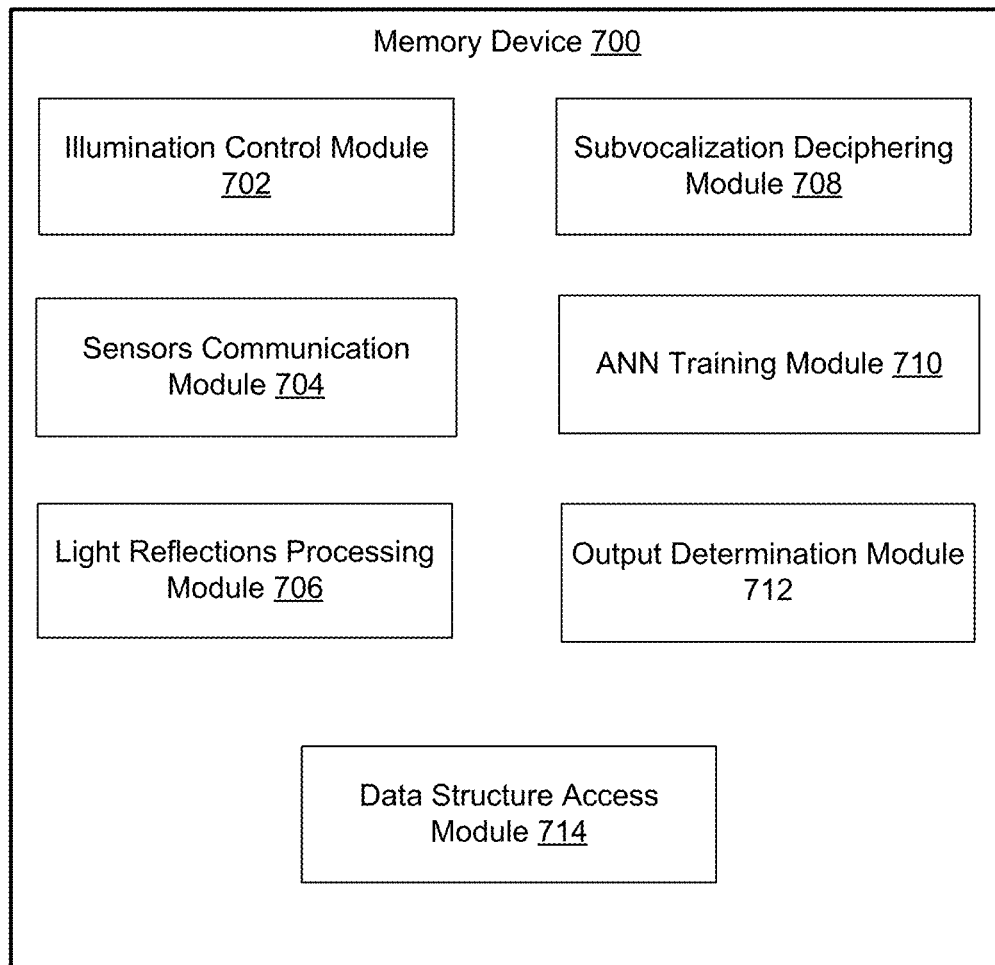
FIG. 7 is a block diagram of a memory consistent with the disclosed embodiments.

Consistent with the present disclosure, facial skin micromovements may be detected during subvocalization. The term "during subvocalization" refers to any speech-related activity that takes place without utterance, before utterance, or preceding an imperceptible utterance. In one embodiment, the speech-related activity may include silent speech (i.e., when air flow from the lungs is absent but the facial muscles articulate the desired sounds). In another embodiment, the speech-related activity may include speaking soundlessly (i.e., when some air flow from the lungs, but words are articulated in a manner that is not perceptible using an audio sensor). In yet another embodiment, the speech-related activity may include prevocalization muscle recruitments (i.e., subvocalization that occurs prior to an onset of vocalization is sometimes referred to herein as prevocalization). In some cases, the prevocalization facial skin micromovements may be triggered by voluntary muscle recruitments that occur when certain craniofacial muscles start to vocalize words. In other cases, the prevocalization facial skin micromovements may be triggered by involuntary facial muscle recruitments that the individual makes when certain craniofacial muscles prepare to vocalize words. By way of example, the involuntary facial muscle recruitments may occur between 0.1 seconds to 0.5 seconds before the actual vocalization. In some cases, a suggested system may use the detected facial skin micromovement occur during subvocalization to identify words that are about to be vocalized. Determining words that the user intends to say before they are actually vocalized may have many benefits because the system does not have to wait for the user to vocally articulate the words to start process the words. In one example, a disclosed system may generate subtitles for live broadcasts without delays. In another example, a disclosed system may translate what the user is saying in real-time to a different language. Additionally, because the disclosed system can detect words before they are vocalized, the actual vocalization of these words is not a requirement. Thus, facial skin micromovements that occur during subvocalization may be detected in an absence of perceptible vocalization. Movement of facial skin or muscles in an absence of vocalization but which nevertheless conveys speech-related information is referred to herein as silent speech. Detecting silent speech may have various usages, including but not limited to enabling silent communicating with other users, initiating a command, or enabling interaction with a virtual personal assistance. As is discussed herein in greater detail, subvocalization deciphering module 708 in FIG. 7 is a non-limiting example of a software module used for deciphering some subvocalization facial skin micromovements.

Figure 2A:
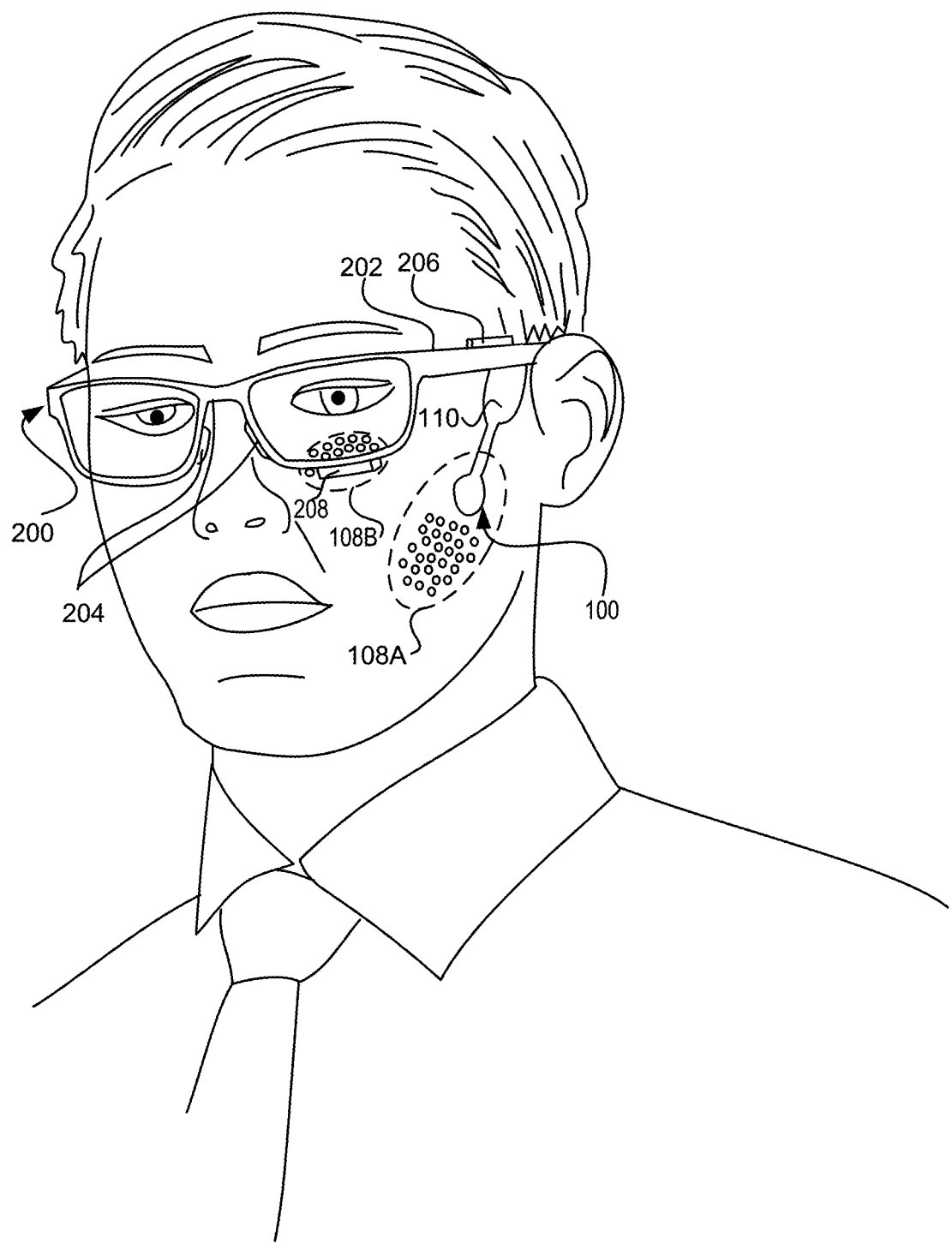
FIG. 2A is a schematic illustration of a user using a second example speech detection system, consistent with some embodiments of the present disclosure.

In some embodiments, the detection of the facial skin micromovements occurs using a speech detection system. While the shorthand "speech detection system" is employed, it is to be understood that the system may alternatively or additionally be configured to detect non-speech commands, expressions, or emotions. The system may also be used for user authentication. The speech detection system may include any device of a group of devices operatively coupled together. As used herein, the term "system" includes any device or a group of devices operatively connected together and configured to perform a function. In some embodiments, the system may include a computer (e.g., a desktop computer, a laptop computer, a server, a smart phone, a portable digital assistant (PDA), or a similar device) or plurality of computers or servers operatively connected together (e.g., using wires or wirelessly) to share information and/or data. The computer(s) may include special purpose computers (e.g., hardwired and coded to perform desired functions) or may include general purpose computers (e.g., using software to perform any desired function). In some embodiments, the system may include a cloud server. As described elsewhere in this disclosure, a cloud server may be a computer platform that provides services via a network, such as the Internet. In one embodiment, the speech detection system may include a wearable housing, a coherent light source or a non-coherent light source, a light detector, and a processor. However, the specific list of components mentioned above is not intended to limit systems covered by the present disclosure. As will be appreciated by a person skilled in the art having the benefit of this disclosure, numerous variations and/or modifications may be made to the example speech detection system. For example, not all components may be essential for the detection of facial skin micromovements in all cases. Moreover, the components may be rearranged into a variety of configurations while providing the functionality of various disclosed embodiments. In some cases, a speech detection system according to some embodiments of the disclosure does not have to be wearable, but could be aimed at a skin from a location not connected to a human body. A wearable or a non-wearable system may project coherent light towards a facial region of a user, analyze reflected light, and determine facial skin micromovements. Alternatively, in other cases, a speech detection system according to some embodiments of the disclosure does not have to include a coherent light source. Specifically, the light detector may be an ultra-high resolution image sensor (e.g., more than 120 megapixel) or any other sensor capable of facial micromovement detection, and the detection of the facial skin micromovements may be accomplished using one or more image processing algorithms. As is discussed herein in greater detail, speech detection systems 100 in FIGS. 1-3 are non-limiting examples of a speech detection system, consistent with the present disclosure. As illustrated in these examples, the system includes a wearable housing 110, a light source 410, a light detector 412, and a processing device 400.

Some disclosed embodiments involve a wearable housing configured to be worn on a head of an individual. The term "wearable housing" broadly includes any structure or enclosure designed for connection to a human head, such as in a manner configured to be worn by a user. Such a wearable housing may be configured to contain or support one or more electronic components or sensors. In one example, the wearable housing is configured for association with a pair of glasses. In another example, the wearable housing is associated with an earbud. The wearable housing may have a cross-section that is button-shaped, P-shaped, square, rectangular, rounded rectangular, or any other regular or irregular shape capable of being worn by a user. Such a structure may permit the wearable housing to be worn on, in, or around a body part associated with a head of the user (e.g., on the ear, in the ear, around the neck). The wearable housing may be made of plastic, metal, composite, a combination of two or more of plastic, metal and composite, or other suitable material. Consistent with disclosure embodiments, the housing may be worn on an ear. There are several ways in which the housing can be attached to the ear: 1. In-the-ear (ITE): the housing may be inserted directly into the ear canal and held in place by the shape of the ear. Examples include earbuds and earplugs. In some cases, the housing may be custom-made to fit the specific shape of an individual's ear and seated in the ear bowl. 2. Behind-the-ear (BTE): the housing may be seated behind the ear and with a small tube that runs to the ear canal. Examples include hearing aids and Bluetooth headsets. 3. Over-the-ear (OTE): the housing may be seated on top of the ear and held in place by a headband or other support. Examples include structures like headphones and earmuffs. 4. Over-the-head (OTH): the housing may be held in place by a headband that goes over the top of the head. In other embodiments, the wearable housing may be attached to a secondary device such as a glasses (sun or corrective vision glasses), a hat, a helmet, a visor, or any other type of head wearable devices. In some cases, the wearable housing may be attached to a secondary device using at least one adaptor. Specifically, the at least one adaptor may be configured to enable the individual to wear the speech detection system in two or more different ways. For example, a single adapter may enable the wearable housing to be attached to glasses and to an earbud. As is discussed herein in greater detail, wearable housings 110 in FIG. 1 and FIG. 2A are non-limiting examples of a wearable housing, consistent with the present disclosure.

Some embodiments involve a coherent light source configured to project light towards a facial region of the user. Other embodiments involve a non-coherent light source configured to project light towards a facial region of the user. As used herein, the term "light source" broadly refers to any device configured to emit light. The term "coherent light" includes light that is highly ordered and exhibits a high degree of spatial and temporal coherence. This may occur, for example, when the light waves are in phase with each other and have a uniform frequency and wavelength, resulting in a beam of light that is highly directional and has restricted outward spread out as it travels. Alternatively, coherent light may include a scenario when light waves have constant phase difference. In some examples, coherent light may be produced by a coherent light source, such as lasers and other types of light sources that have a narrow spectral range and a high degree of monochromaticity (i.e., the light consists of a single wavelength). In contrast, incoherent light may be produced by a non-coherent light source such as incandescent bulbs and natural sunlight, which have a broad spectral range and a low degree of monochromaticity.

By way of example, coherent light may include many waves of the same frequency, having different phases and amplitudes, not necessarily in the same time and locations. To control the interference, light phase information may be required to be recognized in advance. In one embodiment, the coherent light source may be a laser such as a solid-state laser, laser diode, a high-power laser, Quantum-Cascade Laser (QCLs), or an alternative light source such as a light emitting diode (LED)-based light source. In addition, the coherent light source may emit light in differing formats, such as light pulses, continuous wave (CW), quasi-CW, and so on. For example, one type of light source that may be used is a vertical-cavity surface-emitting laser (VCSEL). Another type of light source that may be used is an external cavity diode laser (ECDL). In some examples, the light source may include a laser diode configured to emit light at a wavelength between about 650 nm and 1150 nm. Alternatively, the coherent light source may include a laser diode configured to emit light at a wavelength between about 800 nm and about 1020 nm, between about 850 nm and about 950 nm, or between about 1300 nm and about 1700 nm. Unless indicated otherwise, the terms "about" and "substantially the same," with regard to a numeric value, may include a variance of up to 5% with respect to the stated value. As is discussed herein in greater detail, light source 410 in FIG. 4 and in FIGS. 5A and 5B are non-limiting examples of a light source, consistent with the present disclosure. In the context of this disclosure, it should be recognized that the use of a coherent light source is intended as a non-limiting example implementation in the context of speech detection systems, methods, and computer readable media. Many of the embodiments described herein may be practiced with coherent light or non-coherent light, and the reference to either herein by way of example, is not intended to be limiting. For example, even when not explicitly stated, the described and claimed speech detection systems, methods, and computer program products may be configured to measure non-coherent light reflections for detecting facial skin micromovements.

Some embodiments involve at least one detector configured to receive light reflections from a facial region of the user. The term "light detector," or simply "detector," broadly refers to any device, element, or system capable of measuring one or more properties (e.g., power, frequency, phase, pulse timing, pulse duration, or other characteristics) of electromagnetic waves and to generate an output relating to the measured property or properties. Examples of detectors consistent with this disclosure may include: a light sensitive sensor, an imaging sensor, a phase detector, a MEMS senor, a wavemeter, a spectrometer, a spectrophotometer, a homodyne detector, or a heterodyne detector. In some embodiments, the at least one detector may be configured to detect coherent light reflections. Additionally or alternatively, the at least one detector may be configured to detect non-coherent light reflections. The at least one detector may include a plurality of detectors constructed from a plurality of detecting elements. The at least one detector may include a light detector of different types. The at least one detector may include multiple detectors of the same type which may differ in other characteristics (e.g., sensitivity, size). Combinations of several types of detectors may be used for different reasons. Consistent with some embodiments, the at least one detector may measure any form of reflection and of scattering of light, including secondary speckle patterns, different types of specular reflections, diffuse reflections, speckle interferometry, and any other form of light scattering. In some embodiments, the at least one detector is configured to output associated reflection signals from the detected coherent light reflections. In the context of this disclosure, the term "reflection signals" broadly refers to any form of data retrieved from the at least one light detector in response to the light reflections from the facial region. The reflection signals may be any electronic representation of a property determined from the light reflections, or raw measurement signals detected by the at least one light detector. As is discussed herein in greater detail, light detector 412 in FIG. 4 and in FIGS. 5A and 5B are non-limiting examples of a light detector, consistent with the present disclosure.

Figure 4:
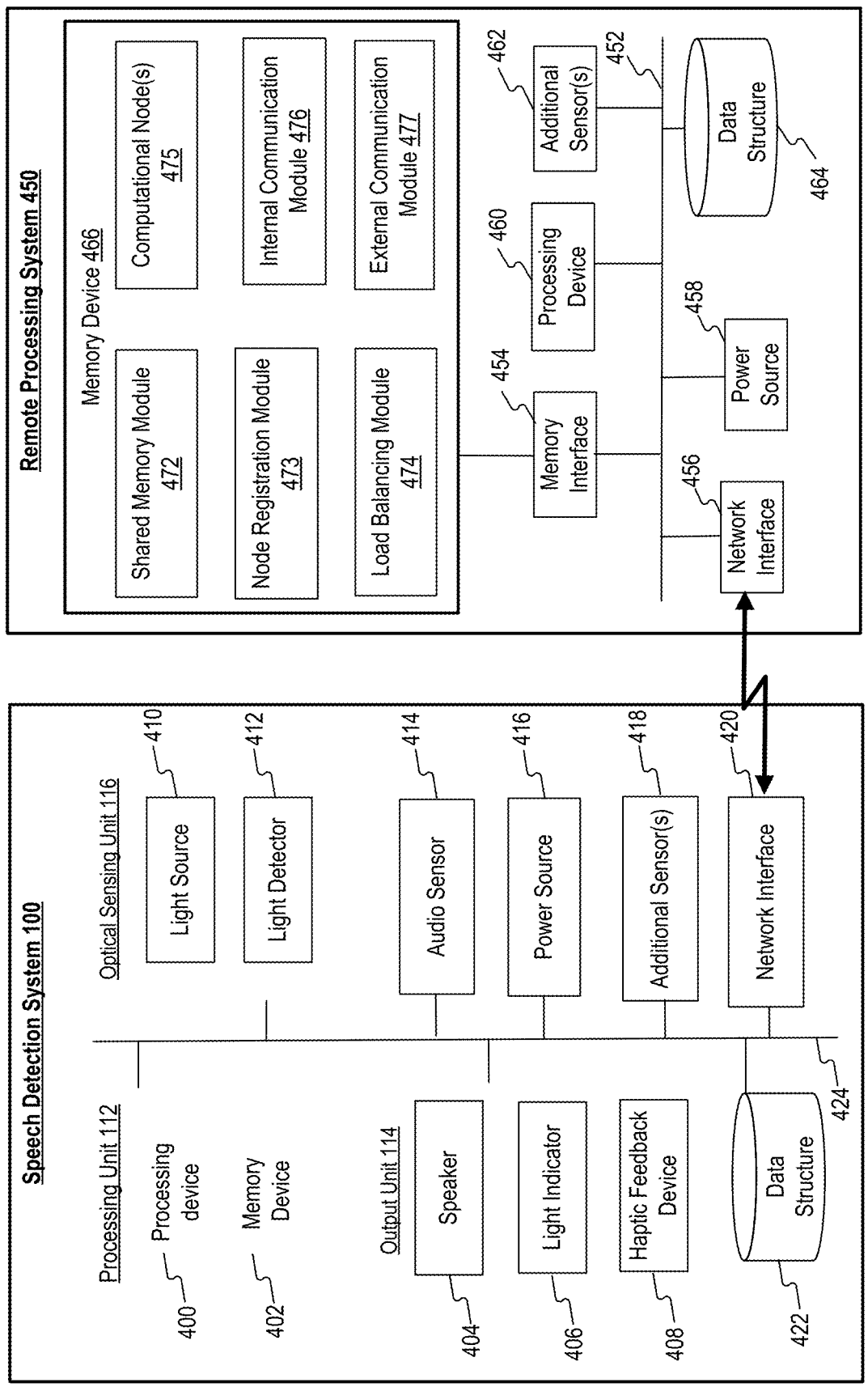
FIG. 4 is a block diagram illustrating some of the components of a speech detection system and a remote processing system, consistent with some embodiments of the present disclosure.

Some embodiments involve at least one processor configured to use the reflection signals from the detector and determine the facial skin micromovements. The term "at least one processor" may involve any physical device or group of devices having electric circuitry that performs a logic operation on an input or inputs. For example, the at least one processor may include one or more integrated circuits (IC), including an application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively and may be co-located or located remotely from each other. The processors may be coupled electrically, magnetically, optically, acoustically, mechanically, or by other means that permit them to interact. As is discussed herein in greater detail, processing unit 112 in FIG. 1 and processing device 400 in FIG. 4 are non-limiting examples of at least one processor, consistent with the present disclosure In some embodiments, the at least one processor may determine the facial skin micromovements by applying a light reflection analysis. The term "light reflection analysis" involves the evaluation of properties of a surface by analyzing patterns of light scattered off the surface. When light strikes a surface (e.g., the facial skin), some of it is absorbed, some is transmitted, and some is reflected. The amount and type of light that is reflected depends on the properties of the surface and the angle at which the light strikes it. In one example, when a non-coherent light source is used, the light reflection analysis may include scattering analysis which involves measuring the scattering of light from the surface (e.g., the facial skin). In another example, when a coherent light source is used, the light reflection analysis may include a speckle analysis or any pattern-based analysis. By way of example, coherent light shining onto a rough, contoured, or textured surface may be reflected or scattered in many different directions, resulting in a pattern of bright and dark areas called "speckles." Such analysis may be performed using a computer (e.g., including a processor) to identify a speckle pattern and derive information about a surface (e.g., facial skin) represented in reflection signals received from at least light detector. A speckle pattern may occur as the result of the interference of coherent light waves added together to give a resultant wave whose intensity varies. The detected speckle pattern or any other detected pattern may then be processed to generate reflection image data. As is discussed herein in greater detail, light reflections processing module 706 depicted in FIG. 7 is a non-limiting example of a software module used for determining facial skin micromovements by applying a light reflection analysis.

Consistent with the present disclosure, the reflection image data may be processed by any image processing algorithms, including classic and/or artificial neural network (ANN) based algorithms such as Convolutional Neural Network (CNN), Recurrent Neural Networks (RNN). In some examples, the reflection image data may be preprocessed by transforming the image data using a transformation function to obtain a transformed speckle image. For example, the transformed reflection image data may include one or more convolutions of the speckle image. The transformation function may include one or more image filters, such as low-pass filters, high-pass filters, band-pass filters, all-pass filters, and so forth. In some examples, the transformation function may comprise a nonlinear function. In some examples, the reflection image data may be preprocessed by smoothing at least parts of the reflection image data, for example using Gaussian convolution, using a median filter, and so forth. In some examples, the reflection image data may be preprocessed to obtain a different representation of the reflection image data. For example, reflection image data may comprise: a representation of at least part of the reflection image data in a frequency domain; a Discrete Fourier Transform of at least part of the reflection image data; a Discrete Wavelet Transform of at least part of the reflection image data; a time/frequency representation of at least part of the reflection image data; a representation of at least part of the reflection image data in a lower dimension; a lossy representation of at least part of the reflection image data; a lossless representation of at least part of the reflection image data; a time-ordered series of any of the above; any combination of the above. In some examples, the reflection image data may be preprocessed to extract edges, and the preprocessed reflection image data may comprise information based on and/or related to the extracted edges. In some examples, the reflection image data may be preprocessed to extract features from the reflection image data. Some examples of such features may comprise information related to: edges, corners, blobs, ridges, Scale Invariant Feature Transform (SIFT) features, temporal features, and more.

In some embodiments, performing light reflection analysis may include evaluating the reflection image data and/or the preprocessed reflection image data using one or more rules, functions, procedures, artificial neural networks, object detection algorithms, visual event detection algorithms, action detection algorithms, motion detection algorithms, background subtraction algorithms, inference models, and so forth. Some non-limiting examples of such inference models may include: an inference model preprogrammed manually; a classification model; a regression model; a result of training algorithms, such as machine learning algorithms and/or deep learning algorithms, on training examples, where the training examples may include examples of data instances, and in some cases, a data instance may be labeled with a corresponding desired label and/or result; and so forth. In some embodiments, performing speckle analysis may comprise analyzing pixels, voxels, point cloud, range data, etc. included in the reflection image data.

Some embodiments may involve analyzing the reflection image data to decipher speech. The process of deciphering the speech from the reflection image data may involve identifying patterns or recognizing signatures in the reflection image data. For example, know data, patterns, or signatures may be associated with certain phenomes, combinations of phonemes, words, combinations of words, or any other speech-related component. By recognizing such information in the reflection image data, speech may be deciphered. Such recognition and/or deciphering may be aided by machine learning. For example, machine learning models or algorithms may be employed to recognize and/or understand speech or commands. Some non-limiting examples of machine learning algorithms that may be used include classification algorithms, data regressions algorithms, image segmentation algorithms, visual detection algorithms (such as object detectors, motion detectors, edge detectors, etc.), visual recognition algorithms (such as object recognition, etc.), speech recognition algorithms, mathematical embedding algorithms, natural language processing algorithms, support vector machines, random forests, nearest neighbors algorithms, deep learning algorithms, artificial neural network algorithms, convolutional neural network algorithms, recursive neural network algorithms, linear machine learning models, non-linear machine learning models, ensemble algorithms, and so forth. For example, a trained machine learning algorithm may include an inference model, such as a predictive model, a classification model, a regression model, a clustering model, a segmentation model, an artificial neural network (such as a deep neural network, a convolutional neural network, a recursive neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. In some examples, engineers, scientists, processes, and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters are set manually by a person or automatically by a process external to the machine learning algorithm (such as a hyper parameter search algorithm), and the parameters of the machine learning algorithm are set by the machine learning algorithm according to the training examples. In some implementations, the hyper-parameters are set according to the training examples and the validation examples, and the parameters are set according to the training examples and the selected hyper-parameters.

Figure 6:
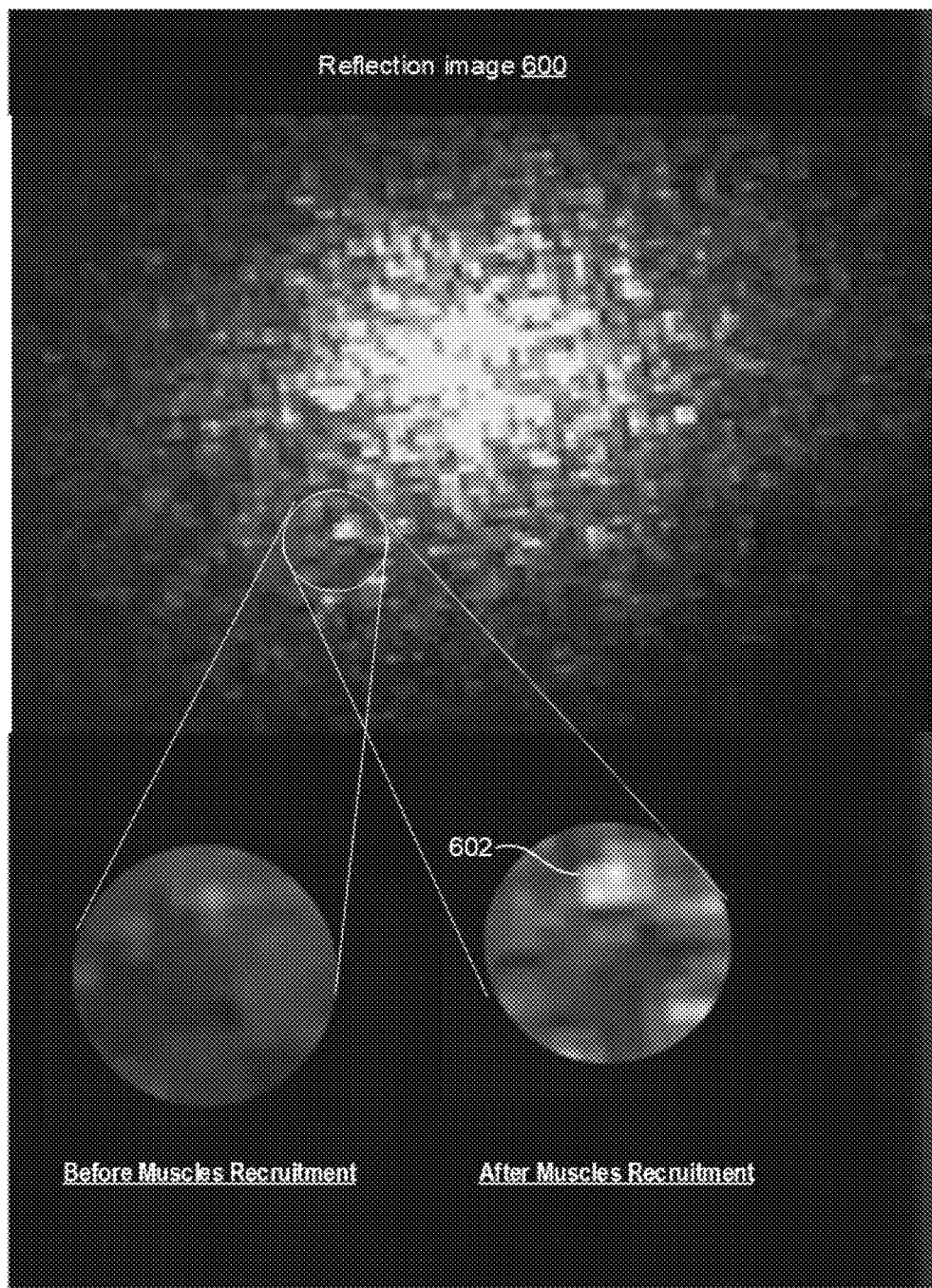
FIG. 6 is a schematic illustration of a reflection image associated with light reflections received from an area of facial region associated with a single spot, consistent with some embodiments of the present disclosure.

In some examples, deciphering the speech from the reflection image data may involve a trained machine learning algorithm that is used as an inference model that when provided with an input generates an inferred output. For example, a trained machine learning algorithm may include a classification algorithm, the input may include a sample, and the inferred output may include a classification of the sample. In another example, a trained machine learning algorithm may include a regression model, the input may include a sample, and the inferred output may include an inferred value for the sample. In yet another example, a trained machine learning algorithm may include a clustering model, the input may include a sample, and the inferred output may include an assignment of the sample to at least one cluster. In an additional example, a trained machine learning algorithm may include a classification algorithm, the input may include an image, and the inferred output may include a classification of an item depicted in the image. In yet another example, a trained machine learning algorithm may include a regression model, the input may include an image, and the inferred output may include an inferred value for an item depicted in the image (such as an estimated facial skin motion, and so forth). In an additional example, a trained machine learning algorithm may include an image segmentation model, the input may include an image, and the inferred output may include a segmentation of the image. In yet another example, a trained machine learning algorithm may include an object detector, the input may include an image, and the inferred output may include one or more detected objects in the image and/or one or more locations of objects within the image. In some examples, the trained machine learning algorithm may include one or more formulas and/or one or more functions and/or one or more rules and/or one or more procedures, the input may be used as input to the formulas and/or functions and/or rules and/or procedures, and the inferred output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth). As is discussed herein in greater detail, reflection image 600 in FIG. 6 is a non-limiting example of a visualization of reflection image data, consistent with the present disclosure.

In some embodiments, artificial neural networks may be configured to analyze inputs and generate corresponding outputs. Some non-limiting examples of such artificial neural networks may include shallow artificial neural networks, deep artificial neural networks, feedback artificial neural networks, feed-forward artificial neural networks, autoencoder artificial neural networks, probabilistic artificial neural networks, time-delay artificial neural networks, convolutional artificial neural networks, recurrent artificial neural networks, long/short term memory artificial neural networks, and so forth. In some examples, an artificial neural network may be configured manually. For example, a structure of the artificial neural network may be selected manually, a type of an artificial neuron of the artificial neural network may be selected manually, a parameter of the artificial neural network (such as a parameter of an artificial neuron of the artificial neural network) may be selected manually, and so forth. In some examples, an artificial neural network may be configured using a machine learning algorithm. For example, a user may select hyper-parameters for the artificial neural network and/or the machine learning algorithm, and the machine learning algorithm may use the hyper-parameters and training examples to determine the parameters of the artificial neural network, for example using back propagation, using gradient descent, using stochastic gradient descent, using mini-batch gradient descent, and so forth. In some examples, an artificial neural network may be created from two or more other artificial neural networks by combining the two or more other artificial neural networks into a single artificial neural network.

Disclosed embodiments may include and/or access a data structure or data. A data structure consistent with the present disclosure may include any collection of data values and relationships among them. By way of example, a data structure may contain correlations of facial micromovements with words or phonemes, and the at least one processor may perform a lookup in the data structure of particular words or phenomes associated with detected facial skin micromovements. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database, or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, servers that may be owned or operated by the same or different entities. Thus, the term "data structure" as used herein in the singular is inclusive of plural data structures. As is discussed herein in greater detail, data structure 124 in FIG. 1 and data structures 422 and 464 in FIG. 4 are non-limiting examples of a data structure, consistent with the present disclosure.

Consistent with the present disclosure, at least one processor may generate output associated with the determined facial skin micromovements. The term "generating an output" broadly refers to emitting a command, emitting data, and/or causing any type of electronic device to initiate an action. In some embodiments, the output may be sound (e.g., delivered via a speaker configured to fit in the ear of the user), and the sound may be an audible presentation of words associated with silent or prevocalized speech. In one example, the audible presentation of words may include an answer to a question that the user silently asked a virtual personal assistance. In another example, the audible presentation of words may include synthesized speech (e.g., artificial production of human speech). According to other disclosed embodiments, the output may be directed to a display (e.g., a visual display such as a computer monitor, television, mobile communications device, VR or XR glasses, or any other device that enables visual perception) and the generated output may include graphics, images, or textual presentations of words associated with prevocalized or vocalized speech (e.g., subtitles). The textual presentation of the words may be presented at the same time words are vocalized. In other embodiments, the output may be directed to a communications device associated with the user and the generated output may be any data exchanged with the communications device. The term "communications device" is intended to include all possible types of devices capable of exchanging data using a network configured to convey data. In some examples, the communications device may include a smartphone, a tablet, a smartwatch, a personal digital assistant, a desktop computer, a laptop computer, an Internet of Things (IoT) device, a dedicated terminal, a wearable communications device, and any other device that enables data communications. As is discussed herein in greater detail, output determination module 712 in FIG. 7 is a non-limiting example of a software module used for generating output associated with the determined facial skin micromovements.

Disclosed embodiments may involve exchanging data (e.g., textual data) using a network. The term "communications network," or simply "network," may include any type of physical or wireless computer networking arrangement used to exchange data. For example, a network may be the Internet, a private data network, a virtual private network using a public network, a Wi-Fi network, a LAN or WAN network, a combination of one or more of the foregoing, and/or other suitable connections that may enable information exchange among various components of the system. In some embodiments, a network may include one or more physical links used to exchange data, such as Ethernet, coaxial cables, twisted pair cables, fiber optics, or any other suitable physical medium for exchanging data. A network may also include a public switched telephone network ("PSTN") and/or a wireless cellular network. A network may be a secured network or an unsecured network. In other embodiments, one or more components of the system may communicate directly through a dedicated communication network. Direct communications may use any suitable technologies, including, for example, BLUETOOTH™, BLUETOOTH LE™ (BLE), Wi-Fi, near-field communications (NFC), or other suitable communication methods that provide a medium for exchanging data and/or information between separate entities. As is discussed herein in greater detail, communications network 126 shown in FIG. 1, is a non-limiting example of a communications network, consistent with the present disclosure.

As used herein, a non-transitory computer-readable storage medium (or similar constructs such as a non-transitory computer-readable media) refers to any type of physical memory on which information or data readable by at least one processor can be stored. Examples include Random Access Memory (RAM), Read-Only Memory (ROM), volatile memory, nonvolatile memory, hard drives, CD ROMs, DVDs, flash drives, disks, any other optical data storage medium, any physical medium with patterns of holes, markers, or other readable elements, a PROM, an EPROM, a FLASH-EPROM or any other flash memory, NVRAM, a cache, a register, any other memory chip or cartridge, and networked versions of the same. The terms "memory" and "computer-readable storage medium" may refer to multiple structures, such as a plurality of memories or computer-readable storage mediums located within a wearable device or at a remote location. Additionally, one or more computer-readable storage mediums can be utilized in implementing a computer-implemented method. Accordingly, the term computer-readable storage medium should be understood to include tangible items and exclude carrier waves and transient signals.

Reference is now made to FIG. 1, which illustrates an individual 102 using a speech detection system consistent with some embodiments of the present disclosure. FIG. 1 is a single exemplary representation, and it is to be understood that some illustrated elements might be omitted, and others may be added within the scope of this disclosure. In the illustrated example implementation, a speech detection system 100 may be mountable on a head of user 102. Specifically, speech detection system 100 (also referred to herein simply as "the system") may have the form and appearance of an over-the-ear clip-on headset. Alternatively, the system may be head-mountable in one of many other ways within the scope of this disclosure, including an in-ear bud, integration into or connectable to a temple of glasses, a head band, or any other mechanism capable of securing the system or a portion thereof to a human head. Speech detection system 100 may be configured to direct projected light 104 (e.g., coherent light) toward respective locations on the face of user 102, thus creating an array of light spots 106 extending over a facial region 108 of the face. Facial region 108 may have an area of at least 1 cm$^2$, at least 2 cm$^2$, at least 4 cm$^2$, at least 6 cm$^2$, or at least 8 cm$^2$. In some embodiments, the size of facial region 108 may be determined to enable sensing the motion of different parts of the facial muscles. In the depicted example, only one beam of projected light 104 is illustrated, however, it is contemplated that that every spot projected towards facial region 108 may be associated with a corresponding light beam or with one or more light beams. In other embodiments, the light source may project light in a manner other than an array of spots. For example, a region of the face may be uniformly or non-uniformly illuminated.

For embodiments that are head-worn, speech detection system 100 may include a wearable housing 110 configured to be worn on a head of user 102. Wearable housing 110 may include or be associated with a processing unit 112 configured to interpret facial skin micromovements; an output unit 114 configured to fit into the user's ear and to present audible and/or vibrational output; and optical sensing unit 116 configured to project light toward a non-lip part of the face of user 102 and to detect reflections of the projected light. In the illustrated example, optical sensing unit 116 may be connected to output unit 114 by an arm 118 and thus may be held in a location in proximity to and/or facing the user's face. According to some disclosed embodiments, optical sensing unit 116 does not contact the user's skin at facial region 108, but rather optical sensing unit 116 may be held at a certain distance from the skin surface of facial region 108. The distance of optical sensing unit 116 from the skin surface may be at least 5 mm, at least 7.5 mm, at least 10 mm, at least 15 mm, or at least 20 mm.

Optical sensing unit 116 may be configured to receive reflections of light 104 from facial region 108 and to output associated reflection signals. Specifically, the reflection signals may be indicative of light patterns (e.g., secondary speckle patterns) that may arise due to reflection of the coherent light from each of spots 106 within a field of view of speech detection system 100. To cover a sufficiently large facial region 108, the detector of speech detection system 100 may have a wide field of view, for example, the field of view may have an angular width of at least 60°, at least 70°, or at least 90°. Within this field of view, speech detection system 100 may sense and process the signals reflective of light patterns in all of spots 106 or only a certain subset of spots 106. For example, processing unit 112 may select a subset of spots 106 determined to give the largest amount of useful and reliable information with respect to the relevant movements of the skin surface of user 102 and may avoid processing data from other spots 106. Additional details of the structure and operation of optical sensing unit 116 are described below with reference to FIG. 5.

Consistent with the present disclosure, speech detection system 100 may be capable of detecting facial skin micromovements of user 102 and extract meaning from the detected movements, even without vocalization of speech or utterance of any other sounds by user 102. The extracted meaning may be an identification of user 102 wearing speech detection system 100, an identification of a subvocalization by a user, such as a word silently spoken by user 102, an identification of a word vocally spoken by user 102, an identification of a phoneme silently spoken by user 102, or an identification of a phoneme vocally spoken by user 102. Similarly, the extract meaning may include an identification of a heart rate of user 102, an identification of a breathing rate of user 102, and/or other characteristics associated with verbal or non-verbal communication by user 102. In one example, speech detection system 100 may generate output signals that include data associated with an identification information, a UI command, synthesized audio signal, a textual transcription, or any combination thereof. In one example, the synthesized audio signal may be played back to user 102 via a speaker in output unit 114. This playback may be useful in giving user 102 feedback with respect to the speech output.

Consistent with the present disclosure, speech detection system 100 may exchange data (e.g., output signals) with a variety of communications devices associated with users, for example, a mobile communications device 120 or a server 122. The term "communications device" is intended to include all possible types of devices capable of exchanging data using a digital communications network, an analog communication network, or any other communications network configured to convey data. In some examples, the communications device may include a wearable communications device, such as a smartphone, a tablet, a smartwatch, a personal digital assistant, a laptop computer, an IoT device, a dedicated terminal, industrial machinery, a vehicle, a smart house, an appliance, or any other electronic device capable of exchanging information or data with another electronic device. In other examples, the communications device may include a non-wearable communications device, such as a desktop computer, a smart home hub, a router, a server, or any other network-connected equipment. In some cases, a processing device of mobile communications device 120 or server 122 may supplement or replace some functions of processing unit 112 of speech detection system 100. In some embodiments, the output signals generated by speech detection system 100 may be transmitted via a communication link to mobile communications device 120 or to a cloud server. The term "cloud server" refers to a computer platform that provides services via a network, such as the Internet. In the example embodiment illustrated in FIG. 1, a server 122 may use one or more virtual machines that may not correspond to individual pieces of hardware. For example, computational and/or storage capabilities may be implemented by allocating appropriate portions of desirable computation/storage power from a scalable repository, such as a data center or a distributed computing environment. In one example configuration, server 122 may be a cloud server that determines neural activity of user 102 based on facial skin micromovements. In one example, server 122 may implement the methods described herein using customized hard-wired logic, one or more Application Specific Integrated Circuits (ASICs), Field Programmable Gate Arrays (FPGAs), firmware, and/or program logic which, in combination with the computer system, cause server 122 to be a special-purpose machine.

In some embodiments, server 122 may access data structure 124 to determine, for example, correlations between words and a plurality of facial movements. Data structure 124 may utilize a volatile or non-volatile, magnetic, semiconductor, tape, optical, removable, non-removable, other type of storage device or tangible or non-transitory computer-readable medium, or any medium or mechanism for storing information. Data structure 124 may be part of server 122 or separate from server 122, as shown. When data structure 124 is not part of server 122, server 122 may exchange data with data structure 124 via a communication link. Data structure 124 may include one or more memory devices that store data and instructions used to perform one or more features of the disclosed methods. In one embodiment, data structure 124 may include any of a plurality of suitable data structures, ranging from small data structures hosted on a workstation to large data structures distributed among data centers. Data structure 124 may also include any combination of one or more data structures controlled by memory controller devices (e.g., servers) or software. Consistent with the present disclosure, speech detection system 100 may communicate with mobile communications device 120 or server 122 using a communications network 126 as defined above.

Reference is now made to FIG. 2A, which illustrates another example implementation of speech detection system 100, in accordance with the present disclosure. In this example, wearable housing 110 may be integrated with or otherwise attached to a pair of glasses 200 having a frame 202. In this example implementation, glasses 200 may include nasal electrodes 204 and temporal electrodes 206 attached to frame 202 and contacting the user's skin surface. Electrodes 204 and 206 may receive body surface electromyogram (sEMG) signals, which provide additional information regarding the activation of the user's facial muscles. Speech detection system 100 may use the electrical activity sensed by electrodes 204 and 206 together with the output of optical sensing unit 116 in generating, for example, the synthesized audio signals. Additionally or alternatively, speech detection system 100 may include one or more additional optical sensing units 208, similar to optical sensing unit 116, for sensing skin movements in other areas of the user's face, such as eye movement. These additional optical sensing units may be used together with or instead of optical sensing unit 116. In the illustrated example, optical sensing unit 116 may illuminate a first facial region 108A and optical sensing unit 208 may illuminate a second facial region 108B. First facial region 108A and second facial region 108B may be nonoverlapping.

In some disclosed embodiments, the speech detection system may be incorporated with, integrated with, or otherwise attached to an extended reality appliance. As used herein, the term "extended reality appliance" may include any type of device or system that enables a user to perceive and/or interact with an extended reality environment. The term "extended reality environment," refers to all types of real-and-virtual combined environments and human-machine interactions at least partially generated by computer technology. One non-limiting example of an extended reality environment may be a Virtual Reality (VR) environment. A virtual reality environment may be an immersive simulated non-physical environment which provides to the user the perception of being present in the virtual environment. Another non-limiting example of an extended reality environment may be an Augmented Reality (AR) environment. An augmented reality environment may involve live direct or indirect views of a physical real-world environment enhanced with virtual computer-generated perceptual information, such as virtual objects with which the user may interact. Another non-limiting example of an extended reality environment is a Mixed Reality (MR) environment. A mixed reality environment may be a hybrid of physical real-world and virtual environments, in which physical and virtual objects may coexist and interact in real time. Examples of the extended reality appliance may include VR headsets, AR headsets, MR headsets, smart glasses, and wearable projection devices.

Figure 2B:
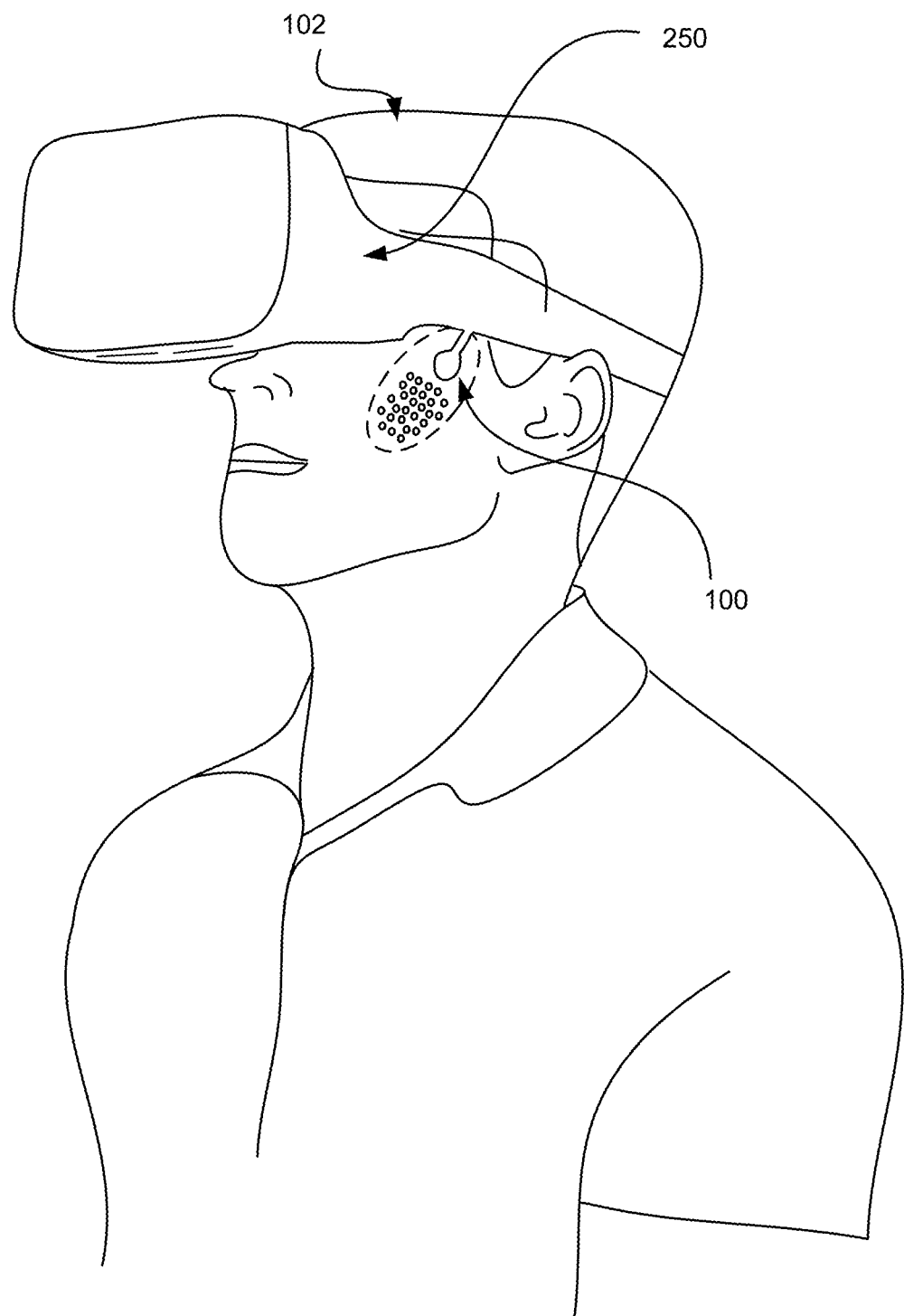
FIG. 2B is a perspective view of a user using a third example speech detection system, consistent with some embodiments of the present disclosure.
Figure 3:
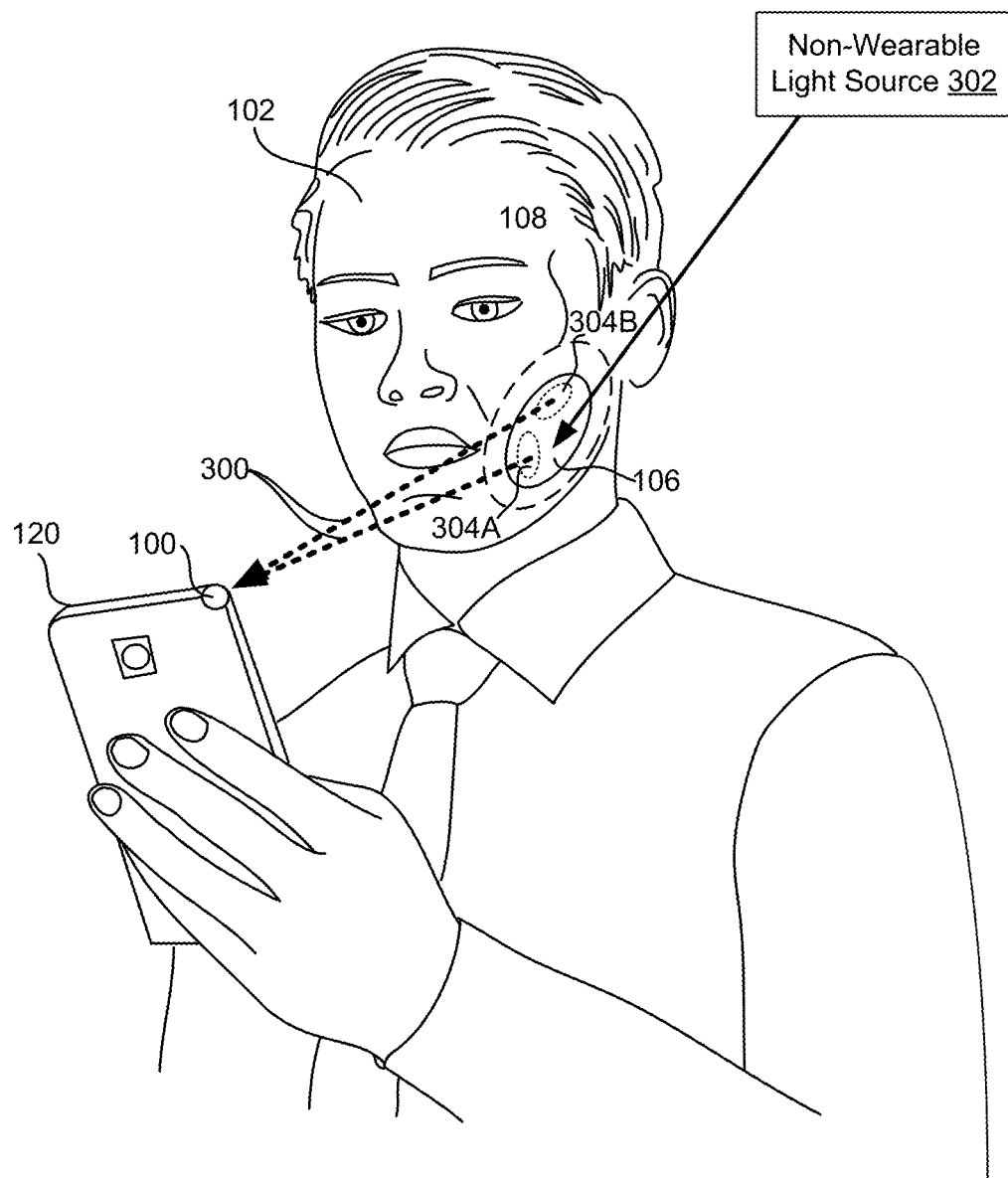
FIG. 3 is a schematic illustration of a user using a fourth example speech detection system, consistent with some embodiments of the present disclosure.

Reference is now made to FIG. 2B, illustrating another example implementation of speech detection system 100, in accordance with some embodiments of the present disclosure. In the depicted example, speech detection system 100 may be part of an extended reality appliance 250. Extended reality appliance 250 may include all the sensors discussed above with reference to glasses 200 and more. For example, extended reality appliance 250 may include one or more of a gyroscope, an accelerometer, a magnetometer, an image sensor, a depth sensors, an infrared sensors, a proximity sensor, and/or any other sensor configured to measure one or more properties associated with the individual wearing extended reality appliance 250 and to generate an output relating to the measured property or properties. In some cases, speech detection system 100 may use the input from any one of the sensors of extended reality appliance 250 to determine the vocalized or subvocalized words that individual 102 articulated. For example, speech detection system 100 may use input from an image sensor of extended reality appliance 250 together with data from optical sensing unit 116 (See FIG. 1) to extract meaning of facial movements. In other cases, extended reality appliance 250 may generate output that includes a visual and/or audible presentation associated with the words detected by the speech detection system 100. For example, individual 102 may interact with extended reality appliance 250 using silent commands.

Reference is now made to FIG. 3, which illustrates another example implementation of speech detection system 100, in accordance with the present disclosure. In the implementation illustrated in FIG. 3, speech detection system 100 may be integrated with mobile communications device 120. Specifically, mobile communications device 120 may include a light detector configured to detect reflections 300 of light from facial region 108. In this example, the light projected to facial region 108 originates from a non-wearable light source 302 that may be a coherent light source or non-coherent light source. In some configurations, non-wearable light source 302 may be included in mobile communications device 120. Alternatively, non-wearable light source 302 may be separated from mobile communications device 120.

Consistent with the present disclosure, and as depicted in FIG. 3, the pattern of the light projected to facial region 108 may be a single spot 106 large enough to illuminate different portions of facial region 108. For example, spot 106 may include a first portion 304A associated with a first facial muscle and a second portion 304B associated with a second facial muscle. Thereafter, a processing device of mobile communications device 120 may apply a light reflection analysis on received reflections 300 to determine facial skin micromovements. In particular, the processing device of mobile communications device 120 may determine first facial skin micromovements of first portion 304A and second facial skin micromovements of second portion 304B. The processing device may use both the first facial skin micromovements and the second facial skin micromovements to extract meaning (e.g., determine speech or a command, or to authenticate user 102) and to generate output. The example implementation of speech detection system 100 illustrated in FIG. 3 may be used when the extracted meaning includes a continuous authentication of user 102. Specifically, speech detection system 100 may provide an authentication service that uses biometrics of facial micromovements for continuous authentication during usage of mobile communications device 120.

FIG. 4 is a block diagram of an exemplary configuration of speech detection system 100 and an exemplary configuration of remote processing system 450. It is to be noted that FIG. 4 is a representation of just one embodiment, and it is to be understood that some illustrated elements might be omitted and others added within the scope of this disclosure. In the depicted embodiment, speech detection system 100 comprises processing unit 112 that includes a processing device 400 and a memory device 402; output unit 114 that includes a speaker 404, a light indicator 406, and a haptic feedback device 408; optical sensing unit 116 that includes at least one light source 410 and at least one light detector 412; an audio sensor 414, a power source 416, one or more additional sensors 418, network interface 420, and data structure 422. Speech detection system 100 may directly or indirectly access a bus 424 (or any other communication mechanism) that interconnects the above-mentioned subsystems and components for transferring information and commands within speech detection system 100. Some of the subsystems and components listed above are referred to herein in the singular but in alternative configurations may be plural. For example, in some configurations speech detection system 100 may include multiple light sources 410 or multiple light detectors 412.

Processing device 400, shown in FIG. 4, may constitute any physical device or group of devices having electric circuitry that performs a logic operation on an input or inputs. The instructions executed by at least one processor may, for example, be pre-loaded into a memory integrated with or embedded into processing device 400, or may be stored in a separate memory (e.g., memory device 402 or data structure 422). As described above, the processing device may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively and may be co-located or located remotely from each other. The processors may be coupled electrically, magnetically, optically, acoustically, mechanically, or by other means that permit them to interact. Consistent with the present disclosure, at least some of the functionalities described below with regard to processing device 400 may be executed by a processing device of remote processing system 450.

Memory device 402, shown in FIG. 4, may include high-speed random-access memory and/or non-volatile memory, such as one or more magnetic disk storage devices, one or more optical storage devices, and/or flash memory (e.g., NAND, NOR). Consistent with the present disclosure, the components of memory device 402 may be distributed in more than one unit of speech detection system 100 and/or in more than one memory device. In particular, memory device 402 may be used to store a software product and/or data stored on a non-transitory computer-readable medium. As described above, the terms "memory" and "computer-readable storage medium" may refer to multiple structures, such as a plurality of memories or computer-readable storage mediums located within speech detection system 100 or at a remote location (e.g., at remote processing system 450). Additionally, one or more computer-readable storage mediums can be utilized in implementing a computer-implemented method. Examples of software modules stored in memory device 402 are described below with reference to FIG. 7.

Output unit 114, shown in FIG. 4, may cause output from a variety of output devices, such as speaker 404, light indicator 406, and a haptic feedback device 408. Examples of speaker 404 may include or may be incorporated with a loudspeaker, earbuds, audio headphones, a hearing aid type device, a bone conduction headphone, and any other device capable of converting an electrical audio signal into a corresponding sound. In some embodiments, speaker 404 may be configured to let only user 102 to listen to the generated audio signals. Alternatively, speaker 404 may be configured to emit sound into the open air for anyone nearby to hear. Light indicator 406 may include one or more light sources, for example, a LED array associated with different colors. Light indicator 406 may be used to indicate the battery status of speech detection system 100 or to indicate its operational mode. Haptic feedback device 408 may include a vibrating motor, linear actuator, vibrational transducer, or any other force feedback device that provide tactile or haptic cues or is capable of converting an electrical signal into corresponding vibrations or force applications.

Optical sensing unit 116, shown in FIG. 4, may include light source 410 and light detector 412. Light source 410 may project coherent light or non-coherent light to facial region 108. As discussed above, light source 410 may be a laser such as a solid-state laser, laser diode, a high-power laser, or an alternative light source such as a light emitting diode (LED)-based light source. In addition, the light source 410, may emit light in differing formats, such as light pulses, continuous wave (CW), quasi-CW, and so on. In one embodiment, light source 410 may be an infrared laser diode configured to emit an input beam of coherent radiation. Light source 410 may be associated with a beam-splitting element, such as a Dammann grating or another suitable type of diffractive optical element (DOE), for splitting an input beam into multiple output beams, which form respective spots 106 at a matrix of locations extending over facial region 108. In another embodiment (not shown in the figures) light source 410 may include multiple laser diodes or other emitters, which generate respective groups of the output beams, covering different respective sub-areas within facial region 108. In one embodiment, processing unit 112 may select and actuate only a subset of the emitters, without actuating all the emitters. For example, to reduce the power consumption of speech detection system 100, processing unit 112 may actuate only one emitter or a subset consisting of two or more emitters that illuminates a specific area on the user's face that has been found to give the most useful information for generating the desired speech output.

Light detector 412, shown in FIG. 4, may be used to detect reflections from facial region 108 indicative of facial skin movements. As discussed above, a light detector may be capable of measuring properties of coherent or non-coherent light, such as power, frequency, phase, pulse timing, pulse duration, and other properties. In some embodiments, light detector 412 may include an array of detecting elements, for example, a set of a charge-coupled device (CCD) sensors and/or a set of complementary metal-oxide semiconductor (CMOS) sensors, with objective optics for imaging facial region 108 onto the array. Due to the small dimensions of optical sensing unit 116 and its proximity to the skin surface, light detector 412 may have a sufficiently wide field of view to detect many of spots 106 at a high angle of at least 60°, at least 70°, or at least 90°. Light detector 412 may be configured to generate an output relating to the measured properties of the detected light. Consistent with the present disclosure, the output of light detector 412 may include any form of data determined in response to the received light reflections from facial region 108. In some embodiments, the output may include reflection signals that include electronic representation of one or more properties determined from the coherent or non-coherent light reflections. In other embodiments, the output may include raw measurements detected by at least one light detector 412.

In some embodiments, light detector 412 may measure one of more optical attributes associated with skin changes. The term "skin changes" refers to any detectable movements, alterations, or modifications that occurred to the skin. Such skin changes may include changes in the epidermis (i.e., the outermost layer of the skin), changes in the dermis (i.e., the middle layer of the skin), changes in the hypodermis (i.e., the deepest layer of the skin), and changes in deeper muscle tissues. The optical attributes may be measured without contacting the skin of individual 102. Examples of one of more optical attributes of the reflected light that may be measured by light detector 412 may include intensity, frequency, reflection, angle, sharpness, bidirectional reflectance distribution function, color, brightness, glossiness, transparency, opacity, surface texture, surface relief, surface movement, and other optical attributes derivable from analysis of light reflections. The output of light detector 412 may be used to determine information associated with skin changes. In some embodiments, the information associated with those skin changes may be derived from changes in a distance from the skin to the detector as the skin moves, and in other embodiments the changes may not be derived from variations in the distance of the skin from light detector 412. For example, the determined speed or angular speed of the changes of the facial skin may be determined by detecting the changes of non-distance measurements (e.g., image sharpness) over time. Thus, in one non-limiting example, optical attributes may be detected from random intensity variations observed when coherent light interacts with a rough or scattering surface, such as human skin. In another non-limiting example, optical attributes may be detected based on the interference of light waves, such as when interference patterns are used to measure the phase difference or amplitude changes between two or more optical paths.

In some embodiments, optical sensing unit 116 may not require reference to parameters of the light source, such as the light source's wavelength, intensity, or coherence, and may not require a reference beam (typically used with a beam-splitter) to measure the one or more optical attributes of the reflected light. For example, optical sensing unit 116 may use a single beam to illuminate the skin and then process the light reflections returned to light detector 412. While some speech detection systems may include a single pixel sensor (e.g., a photo diode), in other embodiments, light detector 412 may include one or more multi-pixel sensors (e.g., each pixel sensor includes more than 4 megapixels, more than 10 megapixels, or more than 10 megapixels) that enables producing an image providing spatial information beyond a single point. For example, a reflection image depicted in FIG. 6 may be produced from the output of light detector 412. As described throughout the disclosure, output of light detector 412 may be analyzed using image processing to determine patterns of light scattered off a surface. For example, features of secondary speckles may be determined.

In some non-limiting examples, optical sensing unit 116 may use a diffractive element to split the outbound beam to multiple beams and may not rely on superposition of coherent light waves to cause interference. In some non-limiting examples, optical sensing unit 116 may be arranged such that light detector 412 may be positioned along a different optical axis from light source 410. In other non-limiting examples, aligning the light source and the sensor along the same optical axis may be used for maintaining coherence, achieving path length matching, ensuring spatial overlap, and preserving the sensitivity and accuracy of the interference patterns. However, since some implementations of light detector 412 detect a reflection image and not a distance to a point, optical sensing unit 116 may include a first optical axis for outbound light and a second optical axis, not aligned with the first optical axis, for inbound light. In some embodiments, light detector 412 is configured to measure both sub-microbic speed and depth changes in the ranges of 5-500 microns. In alternative embodiments, light detector 412 is configured to measure changes that are less than a micron. All of the examples provided in this paragraph are alternatives and may be implement in the many alternative embodiments provided herein, depending on the specifics of implementation.

Audio sensor 414, shown in FIG. 4, may include one or more audio sensors configured to capture audio by converting sounds to digital information. Some examples of audio sensors may include microphones, unidirectional microphones, bidirectional microphones, cardioid microphones, omnidirectional microphones, onboard microphones, wired microphones, wireless microphones, or any combination of the above. Audio sensor 414 may be configured to capture sounds uttered by user 102, thereby enabling user 102 to use speech detection system 100 as a conventional headphone when desired. Additionally or alternatively, audio sensor 414 may be used in conjunction with the silent speech sensing capabilities of speech detection system 100. In one embodiment, the audio signals output by audio sensor 414 can be used in changing the operational state of speech detection system 100. For example, processing unit 112 may generate the speech output only when audio sensor 414 does not detect vocalization of words by user 102. In another embodiment, audio sensor 414 may be used in a calibration procedure, in which optical sensing unit 116 detects micromovements of the skin while user 102 utters certain phonemes or words. Processing unit 112 may compare the reflection signals output by light detector 412 to the sounds sensed by audio sensor 414 to calibrate optical sensing unit 116. This calibration may include prompting user 102 to shift the position of optical sensing unit 116 to align the optical components in the desired position relative to facial region 108. In yet another embodiment, audio sensor 414 enables on-the-fly training of a neural network of speech detection system 100. For example, speech detection system 100 may be configured to correlate facial skin micromovements with words using audio signals concurrently captured with the micromovements. After recognizing recorded words, speech detection system 100 can perform a look-back to identify facial micromovement that preceded articulation of those words, thereby training speech detection system 100. In a similar way, speech detection system can be used to train on expressions, commands, user recognition, and emotions.

Power source 416, shown in FIG. 4, may provide electrical energy to power speech detection system 100. A power source may include any device or system that can store, dispense, or convey electric power, including, but not limited to, one or more batteries (e.g., a lead-acid battery, a lithium-ion battery, a nickel-metal hydride battery, a nickel-cadmium battery), one or more capacitors, one or more connections to external power sources, one or more power convertors, or any combination of the foregoing. With reference to the example illustrated in FIG. 4, power source 416 may be mobile, which means that speech detection system 100 can be wearable. The mobility of the power source enables user 102 to use speech detection system 100 in a variety of situations. In other embodiments, power source 416 may be associated with a connection to an external power source (such as an electrical power grid) that may be used to charge power source 416.

Additional sensors 418, shown in FIG. 4, may include a variety of sensors, for example, image sensors, motion sensors, environmental sensors, Electromyography (EMG) sensors, resistive sensors, ultrasonic sensors, proximity sensors, biometric sensors, or other sensing devices configured to facilitate related functionalities. For example, speech detection system 100 may include one or more image sensors configured to capture visual information from the environment of user 102 by converting light (not emitted from light source 410) to image data. Consistent with the present disclosure, an image sensor may be included in any device or system capable of detecting and converting optical signals in the near-infrared, infrared, visible, and/or ultraviolet spectrums into electrical signals. Examples of image sensors may include digital cameras, semiconductor charge-coupled devices (CCDs), active pixel sensors in complementary metal-oxide semiconductor (CMOS), or N-type metal-oxide-semiconductor (NMOS, Live MOS). The electrical signals may be used to generate image data. Consistent with the present disclosure, the image data may include pixel data streams, digital images, digital video streams, data derived from captured images, and data that may be used to construct one or more 3D images, a sequence of 3D images, 3D videos, or a virtual 3D representation. The image data acquired by the one or more image sensors may be transmitted by wired or wireless transmission to processing unit 112 or to remote processing system 450.

Speech detection system 100 may also include one or more motion sensors configured to measure motion of user 102. Specifically, a motion sensor may perform at least one of the following: detect motion of user 102, measure the velocity of user 102, measure the acceleration of user 102, or measure any other action that involves movement. In some embodiments, the motion sensor may include one or more accelerometers configured to detect changes in acceleration (e.g., proper acceleration) and/or to measure acceleration of speech detection system 100. In some embodiments, the motion sensor may include one or more gyroscopes configured to detect changes in the orientation of speech detection system 100 and/or to measure information related to the orientation of speech detection system 100. In some embodiments, the motion sensors may include one or more using image sensors, LIDAR sensors, radar sensors, or proximity sensors. For example, by analyzing captured images, processing device 400 may determine the motion of speech detection system 100, for example, using ego-motion algorithms. In addition, the processing device may determine the motion of objects in the environment of speech detection system 100, for example, through object tracking.

Speech detection system 100 may also include one or more environmental sensors of different types configured to capture data reflective of the environment of user 102. In some embodiments, the environmental sensor may include one or more chemical sensors configured to perform at least one of the following: measure chemical properties in the environment of user 102, measure changes in the chemical properties in the environment of user 102, detect the present of chemicals in the environment of user 102, and/or measure the concentration of chemicals in the environment of user 102. Examples of measurable chemical properties include: pH level, toxicity, and temperature. Examples of chemicals or phenomena that may be measured include: electrolytes, particular enzymes, particular hormones, particular proteins, smoke, carbon dioxide, carbon monoxide, oxygen, ozone, hydrogen, and hydrogen sulfide. In other embodiments, the environmental sensor may include one or more temperature sensors configured to detect changes in the temperature of the environment of user 102 and/or to measure the temperature of the environment of user 102. In other embodiments, the environmental sensor may include one or more barometers configured to detect changes in the atmospheric pressure in the environment of user 102 and/or to measure the atmospheric pressure in the environment of user 102. In other embodiments, the environmental sensor may include one or more light sensors configured to detect changes in the ambient light in the environment of user 102.

Network interface 420, shown in FIG. 4, may provide two-way data communications to a network, such as communications network 126. In one embodiment, network interface 420 may include an Integrated Services Digital Network (ISDN) card, cellular modem, satellite modem, or a modem to provide a data communication connection over the Internet. As another example, network interface 420 may include a Wireless Local Area Network (WLAN) card. In another embodiment, network interface 420 may include an Ethernet port connected to radio frequency receivers and transmitters and/or optical (e.g., infrared) receivers and transmitters. The specific design and implementation of network interface 420 may depend on the communications network or networks over which speech detection system 100 is intended to operate. For example, in some embodiments, speech detection system 100 may include network interface 420 designed to operate over a GSM network, a GPRS network, an EDGE network, a Wi-Fi or WiMax network, and a Bluetooth network. In any such implementation, network interface 420 may be configured to send and receive electrical, electromagnetic, or optical signals that carry digital data streams or digital signals representing various types of information.

Data structure 422, shown in FIG. 4, may include any hardware, software, firmware, or combination thereof for storing and facilitating the retrieval of information from a database. The term "database" may be understood to include a collection of data that may be distributed or non-distributed. A database may include a database management system that controls the organization, storage and retrieval of data contained within the database. As described above, the data included in the database may be stored linearly, horizontally, hierarchically, relationally, non-relationally, unidimensionally, multidimensionally, operationally, in an ordered manner, in an unordered manner, in an object-oriented manner, in a centralized manner, in a decentralized manner, in a distributed manner, in a custom manner, or in any manner enabling data access. In disclosed embodiments, data structure 422 may include correlations of facial micromovements with words, commands, emotions, expressions, and/or biological conditions. The at least one processor may perform a lookup in the data structure to thereby interpret the detected facial skin micromovements. In accordance with one embodiment, at least some of the data stored in data structure 422 may alternatively or additionally be stored in remote processing system 450.

Consistent with the present disclosure, speech detection system 100 may be configured to communicate with a remote processing system 450 (e.g., mobile communications device 120 or server 122). Remote processing system 450 may directly or indirectly accesses a bus 452 (or other communication mechanism) interconnecting subsystems and components for transferring information within remote processing system 450. For example, bus 452 may interconnect a memory interface 454, a network interface 456, a power source 458, a processing device 460, one or more additional sensors 462, a data structure 464, and memory device 466.

Memory interface 454, shown in FIG. 4, may be used to access a software product and/or data stored on a non-transitory computer-readable medium or on other memory devices, such as memory devices 402, 466, data structure 422, or data structure 464. Memory device 466 may contain software modules to execute processes consistent with the present disclosure. In particular embodiments, memory device 466 may include a shared memory module 472, a node registration module 473, a load balancing module 474, one or more computational nodes 475, an internal communication module 476, an external communication module 477, and a database access module (not shown). Modules 472-477 may contain software instructions for execution by at least one processor (e.g., processing device 460) associated with remote processing system 450. Shared memory module 472, node registration module 473, load balancing module 474, computational module 475, and external communication module 477 may cooperate to perform various operations.

Shared memory module 472 may allow information sharing between remote processing system 450 and other devices related to one or more speech detection systems 100. In some embodiments, shared memory module 472 may be configured to enable processing device 460 to access, retrieve, and store data. For example, using shared memory module 472, processing device 460 may perform at least one of: executing software programs stored on memory devices 402, 466, data structure 422, or data structure 464; storing information in memory devices 402, 466, Data structure 422, or data structure 464; or retrieving information from memory devices 402, 466, data structure 422, or data structure 464.

Node registration module 473 may be configured to track the availability of one or more computational nodes 475. In some examples, node registration module 473 may be implemented as: a software program, such as a software program executed by one or more computational nodes 475, a hardware solution, or a combined software and hardware solution. In some implementations, node registration module 473 may communicate with one or more computational nodes 475, for example, using internal communication module 476. In some examples, one or more computational nodes 475 may notify node registration module 473 of their status, for example, by sending messages: at startup, at shutdown, at constant intervals, at selected times, in response to queries received from node registration module 473, or at any other determined times. In some examples, node registration module 473 may query about the status of one or more computational nodes 475, for example, by sending messages: at startup, at constant intervals, at selected times, or at any other determined times.

Load balancing module 474 may be configured to divide the workload among one or more computational nodes 475. In some examples, load balancing module 474 may be implemented as a software program, such as a software program executed by one or more of the computational nodes 475, a hardware solution, or a combined software and hardware solution. In some implementations, load balancing module 474 may interact with node registration module 473 to obtain information regarding the availability of one or more computational nodes 475. In some implementations, load balancing module 474 may communicate with one or more computational nodes 475, for example, using internal communication module 476. In some examples, one or more computational nodes 475 may notify load balancing module 474 of their status, for example, by sending messages: at startup, at shutdown, at constant intervals, at selected times, in response to queries received from load balancing module 474, or at any other determined times. In some examples, load balancing module 474 may query about the status of one or more computational nodes 475, for example, by sending messages: at startup, at constant intervals, at preselected times, or at any other determined times.

Internal communication module 476 may be configured to receive and/or to transmit information from one or more components of remote processing system 450. For example, control signals and/or synchronization signals may be sent and/or received through internal communication module 476. In one embodiment, input information for computer programs, output information of computer programs, and/or intermediate information of computer programs may be sent and/or received through internal communication module 476. In another embodiment, information received though internal communication module 476 may be stored in memory device 466 or in data structure 464. For example, information retrieved from data structure 464 may be transmitted using internal communication module 476. In another example, reference signals reflecting facial micromovements of user 102 may be stored in data structure 464 and accessed using internal communication module 476.

External communication module 477 may be configured to receive and/or to transmit information from one or more speech detection systems 100. For example, control signals may be sent and/or received through external communication module 477. In one embodiment, information received though external communication module 477 may be stored in memory device 466, in data structure 464, and/or any memory device in the one or more speech detection systems 100. In another embodiment, information retrieved from data structure 464 may be transmitted using external communication module 477 to speech detection system 100 or to any entity with whom user 102 communicates. For example, when user 102 communicate with a financial institution (e.g., a bank) information retrieved from data structure 464 may be transmitted to enable authentication of user 102. In another embodiment, sensor data may be transmitted and/or received using external communication module 477. Examples of such input data may include data received from speech detection system 100, information captured from the environment of user 102 using one or more sensors such as additional sensors 418 and additional sensors 462.

In some embodiments, aspects of modules 472-477 may be implemented in hardware, in software (including in one or more signal processing and/or application specific integrated circuits), in firmware, or in any combination thereof, executable by one or more processors, alone, or in various combinations with each other. Specifically, modules 472-477 may be configured to interact with each other and/or other modules of speech detection system 100 to perform functions consistent with disclosed embodiments. Memory device 466 may include additional modules and instructions or fewer modules and instructions.

Network interface 456, power source 458, processing device 460, additional sensors 462, and data structure 464, shown in FIG. 4, may share similar functionality with the functionality of corresponding elements in speech detection system 100, as described above. The specific design and implementation of the above-mentioned components may vary based on the implementation of remote processing system 450. In addition, remote processing system 450 may include more or fewer components. For example, when remote processing system 450 is a mobile communications device associated with user 102 (e.g., mobile communications device 120) it may include a speaker, a microphone, and additional sensors.

The components and arrangements of speech detection system 100 and remote processing system 450 as illustrated in FIG. 4 are not intended to limit the disclosed embodiments. As will be appreciated by a person skilled in the art having the benefit of this disclosure, numerous variations and/or modifications may be made to the depicted configuration of speech detection system 100 and remote processing system 450. For example, not all components may be essential for the operation of an input unit in all cases. Any component may be located in any appropriate part of speech detection system 100 or remote processing system 450. Moreover, the components may be rearranged into a variety of configurations while providing the functionality of the disclosed embodiments. For example, some speech detection systems may not include all of the elements as shown in speech detection system 100 and in remote processing system 450. Other speech detection systems may include additional components and still fall within the scope of this disclosure.

FIGS. 5A and 5B include two schematic illustrations of optical sensing unit 116 as it detects facial skin micromovements in accordance with some embodiments of the present disclosure. The two schematic illustrations show a simplified scenario before muscle recruitment and after muscle recruitment. As depicted, optical sensing unit 116 may include an illumination module 500, a detection module 502, and, optionally, audio sensor 414. As discussed above and illustrated in FIG. 5, optical sensing unit 116 may be configured not to contact the user's skin at facial region 108, but rather may be held at a distance D from the skin surface of facial region 108. The distance D of optical sensing unit 116 from the skin surface may be at least 5 mm, at least 7.5 mm, at least 10 mm, at least 15 mm, or at least 20 mm.

In the depicted embodiment, illumination module 500 includes light source 410 (e.g., an infrared laser diode) configured to generate an input light beam 504. Illumination module 500 further includes a beam-splitting element 506, such as a Dammann grating or another suitable type of diffractive optical element (DOE), configured to split input beam 504 into multiple output beams 508, which form respective spots 106A-106E at a pattern (e.g., a matrix of locations) extending over facial region 108. In an alternative embodiment (not shown in the figure), illumination module 500 may include multiple light sources 410, which generate respective groups of output beams 508, covering different respective sub-areas within facial region 108. In this alternative embodiment, processing unit 112 may select and actuate only a subset of the multiple light sources, without actuating all of them. For example, to reduce the power consumption of speech detection system 100, processing unit 112 may actuate only one light source or a group of two or more light sources that illuminate a part of facial region 108.

Detection module 502 may include light detector 412, which may include an array 510 of optical sensors (e.g., an array of CMOS image sensors) with objective optics 512 for obtaining reflections 300 of coherent light from facial region 108. Because of the small dimensions of optical sensing unit 116 and its proximity to the skin surface, detection module 502 may be configured to have a wide field of view to acquire reflections from many spots 106 at a high angle. As mentioned above, the field of view of light detector 412 may have an angular width of at least 60°, at least 70°, or at least 90°. Due to the roughness of the skin surface, the light patterns at spots 106 can be detected at these high angles, as well.

Speech detection system 100 may analyze light reflections 300 to determine facial skin micromovements resulting from recruitment of muscle fiber 520. Determining the facial skin micromovements may include determining an amount of the skin movement, determining a direction of the skin movement, and/or determining an acceleration of the skin movement. The determined facial skin micromovements may include voluntary and/or involuntary recruitment of muscle fiber 520. Muscle fiber 520 may be part of: a zygomaticus muscle, an orbicularis oris muscle, a risorius muscle, genioglossus muscle, or a levator labii superioris alaeque nasi muscle. Processing device 400 may be configured to perform a first speckle analysis on light reflected from a first region of face in proximity to spot 106A to determine that the first region moved by a distance d1, i.e., first facial skin micromovement 522A; and perform a second speckle analysis on light reflected from a second region of face in proximity to spot 106E to determine that the second region moved by a distance d2, i.e., second facial skin micromovement 522B. Thereafter, processing device 400 may use the determined movements of the first region and the second region to ascertain at least one spoken word. Consistent with disclosed embodiments, distances d1 and d2 may be less than 1000 micrometers, less than 100 micrometers, less than 10 micrometers, or less.

FIG. 6 is a schematic illustration of a reflection image 600 associated with light reflections 300 received from an area of facial region 108 associated with a single spot 106 (e.g., spot 106A depicted in FIG. 5). In disclosed embodiments, processing device 400 may receive reflection signals indicative of coherent light reflections from facial region 108. The reflection signals may be represented by reflection image 600. Thereafter, processing device 400 may determine the facial skin micromovements by applying a light reflection analysis. When light source 410 is a coherent light source, the light reflection analysis may include a speckle analysis or any pattern-based analysis. Such analysis may be performed by processing device 400 or processing device 460 to identify a speckle pattern and derive thereof movement of a corresponding area of facial region 108.

In the depicted example, a speckle 602 appears in reflection image 600 after recruitment of muscle fiber 520. The detected speckle or any other detected pattern may then be processed to generate reflection image data. With reference to the example discussed above, assuming reflection image 600 reflects spot 106A, the reflection image data may include data indicating that the first region moved by a distance d1. In some cases, the reflection image data may be processed by any image processing algorithms (e.g., CNN and RNN) to determine skin movements of at least two areas within facial region 108. Thereafter, processing device 400 may use one or more machine learning (ML) algorithms and artificial intelligence (AI) algorithms to decipher the reflection image data and to extract meaning from the facial skin micromovement.

As shown in FIG. 7, memory device 700 may contain software modules to execute processes consistent with the present disclosure. In particular, memory device 700 may include an illumination control module 702, a sensors communication module 704, a light reflections processing module 706, an artificial neural network (ANN) training module 710, a subvocalization deciphering module 708, an output determination module 712, and a database structure access module 714. The disclosed embodiments are not limited to any particular configuration of memory 700. Further, processing device 400 and/or processing device 460 may execute the instructions stored in any of modules 702-714 included in memory device 700. It is to be understood that references in the following discussions to a processing device may refer to processing device 400 of speech detection system 100 and processing device 460 of remote processing system 450 individually or collectively. Accordingly, steps of any of the following processes associated with modules 702-714 may be performed by one or more processors associated with speech detection system 100.

Consistent with disclosed embodiments, illumination control module 702, sensors communication module 704, light reflections processing module 706, subvocalization deciphering module 708, ANN training module 710, output determination module 712, and database access module 714 may cooperate to perform various operations. For example, illumination control module 702 may determine light characteristics for illuminating facial region 108. Sensors communication module 704 may receive coherent light reflections from facial region 108 and output associated reflection signals. Light reflections processing module 706 may process the reflection signals to determine facial skin micromovements. Subvocalization deciphering module 708 and database access module 714 may cooperate to extract meaning (e.g., determine silently spoken words) from the facial skin micromovements. In some cases, ANN training module 710 may use the determined silently spoken words and the determined facial skin micromovements to train an artificial network. Output determination module 712 may generate a presentation of the determined words.

Illumination control module 702 may regulate the operation of light source 410 to illuminate facial region 108. In some embodiments, illumination control module 702 may determine values for characteristics of projected light 104 such as light intensity, pulse frequency, duty cycle, illumination pattern, light flux, or any other optical characteristic. In a specific embodiment, as long as user 102 is not speaking, speech detection system 100 may operate in a first illumination mode (e.g., low frame rate) to conserve power of its battery. While speech detection system 100 operates at this first illumination mode, it may process the images to detect at least one trigger in the reflection signals (e.g., a movement of the face) indicative of speech. When such trigger is detected, illumination control module 702 may cause the coherent light source to operate in a second illumination mode (e.g., high frame rate) to enable detection of changes in the coherent light patterns (e.g., speckle) that occur due to silent speech. Illumination control module 702 may also configured to change one or more characteristics of projected light 104 based on various types of triggers. The various types of triggers may be detected by analysis of data from sensors communication module 704.

Sensors communication module 704 may regulate the operation of light detector 412, audio sensor 414, and additional sensors 418 to receive captured measurements from one or more sensors, integrated with, or connected to, speech detection system 100. In one embodiment, sensors communication module 704 may use the signals received from one or more sensors to generate sensor data associated with user 102. In one example, sensors communication module 704 may receive reflection signals from light detector 412 and may generate a first data stream of reflections images from which the facial skin micromovements in the facial region may be determined. In another example, sensors communication module 704 may receive audio signals from audio sensor 414 and may generate a second data stream from which the words vocally spoken by user 102 may be determined. In another example, sensors communication module 704 may receive motion signals from a motion sensor included in additional sensors 418 and generate a third data stream from which an activity that user 102 is engaged with may be determined. Sensors communication module 704 may convey the sensor data to other software modules for processing.

Light reflections processing module 706 may process the sensor data received from sensors communication module 704 in preparation for speech deciphering. In one embodiment, light reflections processing module 706 may receive from sensors communication module 704 reflection signals indicative of coherent light reflections from facial region 108 that originates from light detector 412. The reflection signals may by represented by a reflection image (e.g., reflection image 600) that can be processed by at least one image processing algorithm to extracts the skin motion at a set of pre-selected locations on the face of user 102. The number of locations to inspect may be an input to the image processing algorithm. In some cases, the locations on the skin that are extracted for coherent light processing may be taken from a list of points of interest. The list of points of interest specifies anatomical locations that correspond with the zygomaticus muscle, the orbicularis oris muscle, the risorius muscle, genioglossus muscle, or the levator labii superioris alaeque nasi muscle. In layman's terms, the list of points of interest may include specific points in the cheek above mouth, in the chin, in mid-jaw, in the cheek below mouth, in the high cheek, and in the back of the cheek. Consistent with the present disclosure, the list of points of interest may be dynamically updated with more points on the face that are extracted during a training phase. The entire set of locations may be ordered in descending order such that any subset of the list (in order) minimizes the word error rate (WER) with respect to the chosen number of locations that are inspected. In another embodiment, light reflections processing module 706 may crop each of the coherent light spots that were extracted from the raw image frames around the coherent light spots, and the algorithm process only the cropped images. Typically, the process of coherent light spot processing involves reducing by two the order of magnitude of a size of full frame image pixels (of ~1.5 MP) that are received from sensors communication module 704, with a very short exposure. Exposure may be dynamically set and adapted to be able to capture only coherent light reflections and not skin segments. The cropped images of the coherent light spots may depict coherent light patterns. In other embodiments, light reflections processing module 706 may apply image processing algorithm on the reflection image. For example, light reflections processing module 706 may improve the images' contrast, by removing noise using a threshold to determine black pixels and computing a characteristic metric of the coherent light, such as scalar speckle energy measure, e.g., an average intensity. In addition, light reflections processing module 706 may analyze changes in time in the reflections pattern (e.g., in average speckle intensity). Alternatively, other metrics may be used such as the detection of specific coherent light patterns. Thereafter, light reflections processing module 706 may assign a sequence of values of the characteristic metric of the coherent light, which may be calculated frame-by-frame and aggregated to generate reflection image data indicative of facial skin micromovements. Light reflections processing module 706 may convey the reflection image data indicative of facial skin micromovements to other software modules for processing.

Subvocalization deciphering module 708 may use machine learning (ML) algorithms and artificial intelligence (AI) algorithms to decipher the reflection image data indicative of facial skin micromovements received from light reflections processing module 706. Consistent with the present disclosure, deciphering the reflection image data may include extracting meaning from the detected facial skin micromovements. In one embodiment, subvocalization deciphering module 708 may use a trained ANN to correlate words with the facial skin micromovements. Different types ANNs may be used, such as a classification NN that eventually outputs words, and a sequence-to-sequence NN which outputs a sentence (word sequence). In some embodiments, during normal speech of the user, system 100 may simultaneously sample the voice of user 102 and the facial movements. Automatic speech recognition (ASR) and Natural Language Processing (NLP) algorithms may be applied by subvocalization deciphering module 708 on the actual voice, and the outcome of these algorithms may be used for optimizing the parameters of the algorithms used by subvocalization deciphering module 708. These parameters may include the weights of the various neural networks, as well as the spatial distribution of laser beams for optimal performance. In addition, subvocalization deciphering module 708 may limit the output of the algorithms to a predefined word set may significantly increase the accuracy of word detection in cases of ambiguity, i.e., when two different words result in similar micromovements on the facial skin. The used word set can be personalized over time, adjusting the dictionary to the actual words used by the specific user, with their respective frequency and context. In addition, subvocalization deciphering module 708 may use the context of a conversation between user 102 and a callee. The context may be determined from the input of the words and sentences extraction algorithms to increase the accuracy by eliminating out-of-context options. The context of the conversation may be understood by applying Automatic speech recognition (ASR) and Natural Language Processing (NLP) algorithms on the side of user 102 and on the side of the callee.

ANN training module 710 may be used to train an ANN to perform silent speech deciphering, in accordance with embodiments of the disclosure. To train an ANN such as the one that may be used by subvocalization deciphering module 708 may require several thousands of examples. To achieve this, ANN training module 710 may rely on a large group of persons (e.g., a group of reference human subjects). In one example, subvocalization deciphering module 708 may perform fine adjustments to the ANN such that it is customized to user 102. In this manner, within minutes or less of wearing speech detection system 100, subvocalization deciphering module 708 may be ready for deciphering the facial skin micromovements. ANN training module 710 can be used to train two different ANN types: a classification neural network that eventually outputs words, and a sequence-to-sequence neural network which outputs a sentence (word sequence). To do so, ANN training module 710 may upload from a memory training data, such as silent speech data received from light reflections processing module 706 that was gathered from multiple reference human subjects. The silent speech data may be collected from a wide variety of people (people of varying ages, genders, ethnicities, physical disabilities, etc.). It is to be noted that the number of examples required for learning and generalization may be task-dependent. For word/utterance prediction (within a closed group) at least several thousands of examples may be gathered. Thereafter, ANN training module 710 may augment the image processed training data to get more artificial data for the training process. In particular, the augmented data may include image processed coherent light patterns, with some of the image processing steps described herein. The data augmentation process may include the steps of (i) time dropout, where amplitudes at random time points are replaced by zeros; (ii) frequency dropout, where the signal is transformed into the frequency domain, and random frequency chunks are filtered out; (iii) clipping, where the maximum amplitude of the signal at random time points is clamped. This clipping may add a saturation effect to the data; (iv) noise addition, where Gaussian noise is added to the signal, and speed change, where the signal is resampled to achieve a slightly lower or slightly faster signal.

The augmented dataset may go through a feature extraction process. In this process, ANN training module 710 may compute time domain silent speech features. For this purpose, for example, each signal may be split into low and high frequency components, x_low and x_high, and windowed to create time frames, for example, using a frame length of 27 ms and shift of 10 ms. For each of the frame five time-domain features and the nine frequency domain features, a total of 14 features per signal may be computed. Specifically, the time-domain features may be represented as follows:

$$\left[\frac{1}{n}\sum_i (x_{low}[i])^2, \frac{1}{n}\sum_i x_{low}[i], \frac{1}{n}\sum_i (x_{high}[i])^2, \frac{1}{n}\sum_i |x_{high}[i]|, ZCR(x_{high})\right]$$

where ZCR is the zero-crossing rate. In addition, in this example, the magnitude values used are from a 16-point short Fourier transform, i.e., frequency domain features and all features are normalized to zero mean unit variance.

Thereafter, ANN training module 710 may split the data into training, validation, and test sets. The training set may be the data used to train the model. Hyperparameter tuning may be done using the validation set, and final evaluation may be done using the test set. The model architecture may be task dependent. Two different examples describe training two networks for two conceptually different tasks. A first task may include signal transcription, i.e., translating silent speech to text by generating a word, a phoneme, or a letter. This first task may be addressed by using a sequence-to-sequence model. A second task may include predicting a word or an utterance, i.e., categorizing utterances uttered by users into a single category within a closed group. This second task may be addressed by using a classification model. The disclosed sequence-to-sequence model may be composed of an encoder, which may transform the input signal into high level representations (embeddings), and a decoder, which produces linguistic outputs (i.e., characters or words) from the encoded representations. The input entering the encoder may be a sequence of feature vectors.

In one example, the input may enter the first layer of the encoder, a temporal convolution layer, which may downsample the data to achieve a good performance. The model may use an order of a hundred of such convolution layers.

In some embodiments, the outputs from the temporal convolution layer at each time step may be passed to three layers of bidirectional recurrent neural networks (RNN). ANN training module 710 may employ long short-term memory (LTSM) as units in each RNN layer. Each RNN state may be a concatenation of the state of the forward RNN with the state of the backward RNN. The decoder RNN may be initialized with the final state of the encoder RNN (concatenation of the final state of the forward encoder RNN with the first state of the backward encoder RNN). At each time step, the decoder RNN may receive as input the preceding word, encoded one-hot and embedded in a 150-dimensional space with a fully connected layer. The decoder RNN output may be projected through a matrix into the space of words or phonemes (depending on the training data). The sequence-to-sequence model may condition the next step prediction on the previous prediction. During learning, a log probability may be maximized:

$$\max_{\theta} \sum_{i} \log P(y_i \mid x, y^*_{<i}; \theta)$$

where y<i is the ground truth of the previous prediction. The classification neural network may be composed of the encoder as in the sequence-to-sequence network and an additional fully connected classification layer on top of the encoder output. The output may be projected into the space of closed words and the scores may be translated into probabilities for each word in the dictionary. The results of the above entire procedure may include two types of trained ANNs, expressed in computed coefficients. The coefficients may be stored in a data structure associated with speech detection system 100 (e.g., data structure 422 and data structure 464). In day-to-day use, ANN training module 710 may receive up to date coefficients for the trained ANN. The first ANN task may be the signal transcription, i.e., translating silent speech to text by word/phoneme/letter generation. The second ANN task may be word/utterance prediction, i.e., categorizing utterances uttered by users into a single category within closed group.

Output determination module 712 may regulate the operation of output unit 114 and the operation of network interface 420 to generate output using speaker 404, light indicator 406, haptic feedback device 408, and/or to send data to a remote computing device. In some embodiments, the output generated by output determination module 712 may include various types of output associated with silent speech determined from detected facial skin micromovements. Specifically, output determination module 712 may synthesize vocalization of words determined from the facial skin movements by subvocalization deciphering module 708. The synthesis may emulate a voice of user 102 or emulate a voice of someone other than user 102 (e.g., a voice of a celebrity or preselected template voice). The vocalization of the words may be presented via speaker 404 or transmitted to the remote computing device via network interface 420. Alternatively, output determination module 712 may generate a textual output from the facial skin movements by subvocalization deciphering module 708. The textual output may be transmitted to the remote computing device via network interface 420. According to another embodiment, the output generated by output determination module 712 may relate to the operation of speech detection system 100. In some cases, light indicator 406 may include a light indicator that shows the battery status of speech detection system 100. For example, the light indicator may start to blink when speech detection system 100 has low battery. Additional examples of the types of output that may be generated by output determination module 712 are described throughout the present disclosure.

Database access module 714 may cooperate with data structures 422 and 464 to retrieve stored data. The retrieved data may include, for example, correlations between a plurality of words and a plurality of facial skin movements, correlations between a specific individual and a plurality of facial skin micromovements associated with the specific individual, and more. As described above, subvocalization deciphering module 708 may use a trained ANN to perform silent speech deciphering. The trained ANN may use data stored in data structures 422 and 464 to extract meaning from detected facial skin micromovements. Data structures 422 and 464 may include separate databases, including, for example, a vector database, raster database, tile database, viewport database, and/or a user input database. The data stored in data structures 422 and 464 may be received from modules 702-712 or other components of speech detection system 100. Moreover, the data stored in data structures 422 and 464 may be provided as input using data entry, data transfer, or data uploading.

Modules 702-714 may be implemented in software, hardware, firmware, a mix of any of those, or the like. Processing devices of speech detection system 100 and remote processing system 450 may be configured to execute the instructions of modules 702-714. In some embodiments, aspects of modules 702-714 may be implemented in hardware, in software (including in one or more signal processing and/or application specific integrated circuits), in firmware, or in any combination thereof, executable by one or more processors, alone, or in various combinations with each other. Specifically, modules 702-714 may be configured to interact with each other and/or other modules associated with speech detection system 100 to perform functions consistent with disclosed embodiments.

Nowadays, image-based facial recognition technology is commonly used as a biometric authentication method in many communications devices. It allows users to unlock their devices, make payments, and access apps or accounts using their face as a unique identifier. But image-based facial recognition technology is not always reliable and has limitations that can make it less effective in certain situations. For example, image-based facial recognition systems can be impacted by factors such as poor lighting conditions, low-quality images, and occlusions such as masks or accessories. These factors may lead to inaccurate or incomplete matches. Additionally, image recognition algorithms may exhibit bias, leading to misidentifications based on various factors like race, gender, or age. Moreover, false positives and false negatives are common issues in image-based facial recognition technology; thus, individuals may be misidentified as someone else or not recognized at all. The following disclosure suggests a new and improved technological solution for providing a reliable biometric authentication that may overcome inherent deficiencies of image-based facial recognition technology.

Some disclosed embodiments of the present disclosure may be configured to detect facial skin micromovements of an individual, use the detected facial skin micromovements to identify the individual, and determine an action to initiate based on the identification of the individual.

Figure 8:
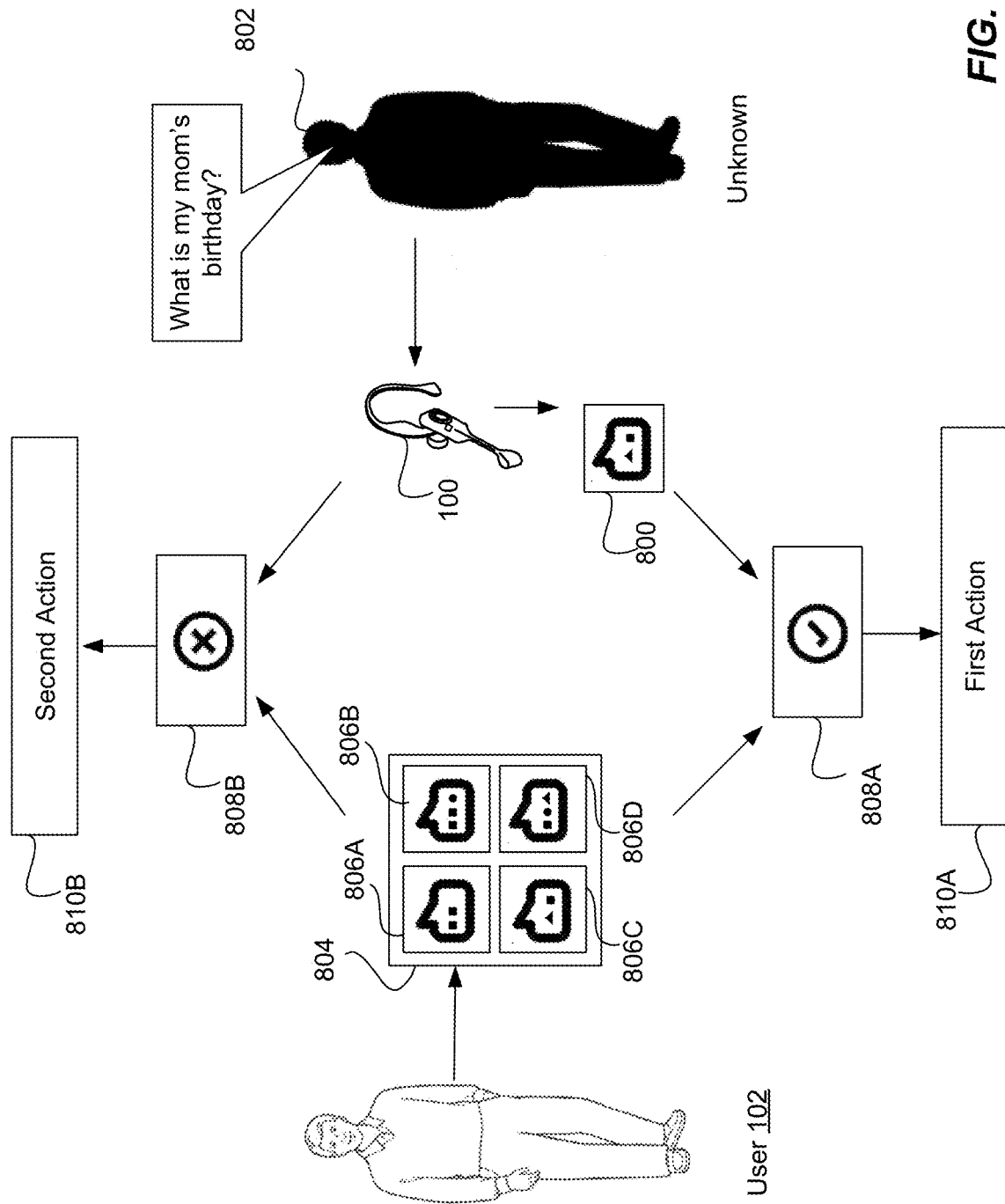
FIG. 8 is an exemplary alternative action speech detection process diagram consistent with some embodiments of the present disclosure.
Figure 9:
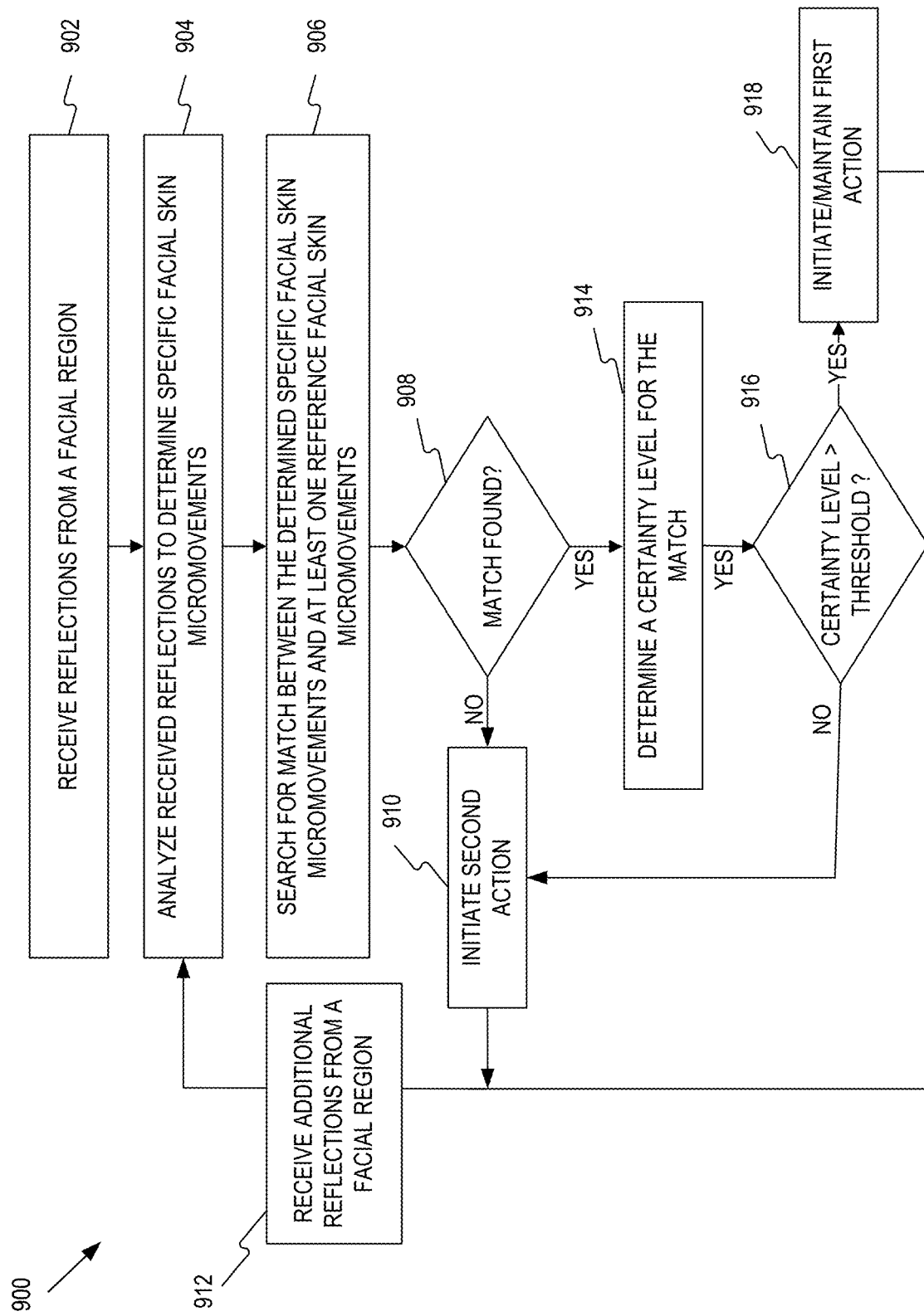
FIG. 9 is a flowchart of an example process for identifying individuals, consistent with some embodiments of the present disclosure.
Figure 10:
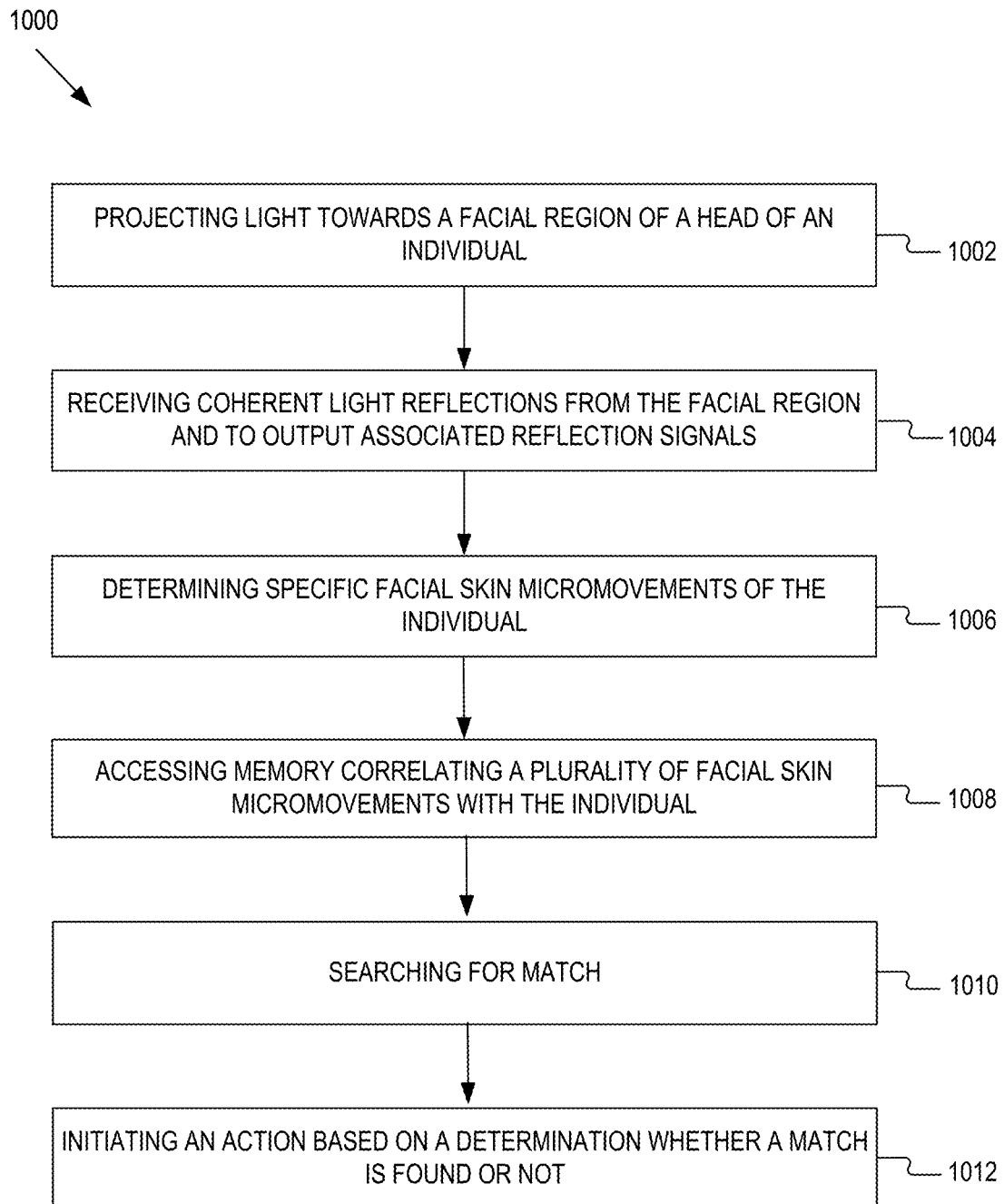
FIG. 10 is a flowchart of an example process for identifying individuals using facial skin micromovements, consistent with some embodiments of the present disclosure.

The description that follows refers to FIGS. 8 to 10 to illustrate exemplary implementations for identifying individuals using facial skin micromovements, consistent with some disclosed embodiments. FIGS. 8 to 10 are intended merely to facilitate conceptualization of exemplary implementations for performing operations for identifying individuals using facial skin micromovements and do not limit the disclosure to any particular implementation.

Some disclosed embodiments involve a head mountable system for identifying individuals using facial skin micromovements. Consistent with this disclosure, a head mountable system may be understood to include any component or combination of components that can be attached to a head, as exemplified and described elsewhere in this disclosure. The term "identifying individuals" refers to a process for determining whether an individual is known to the system. Specifically, the identification process may involve comparing detected characteristics of an individual with known characteristics of that individual to identify, verify, or authenticate that individual. Consistent with the present disclosure, the individual may be identified based on the individual's facial skin micromovements. The term "facial skin micromovements" may be understood as described and exemplified elsewhere in this disclosure. In some cases, the head mountable system may access data indicative of reference facial skin micromovements and use that data to determine whether an individual currently using the head mountable system is the same individual associated with the reference facial skin micromovements. Depending on implementation, the probability that the identification process described below would result in misidentification of an individual based on his/her facial skin micromovements may be less than one in 10,000, less than one in 100,000, or less than one in 1,000,000.

Some disclosed embodiments involve a wearable housing configured to be worn on a head of an individual. The term "wearable housing" may be understood as described and exemplified elsewhere in this disclosure. Consistent with some disclosed embodiments, the head mountable system includes at least one coherent light source associated with the wearable housing. The term "coherent light source" may be understood as described and exemplified elsewhere in this disclosure. The term "associated with the wearable housing" may relate to any component that is linked, incorporated, affiliated with, connected to, or related to the wearable housing. For example, the light source may be mounted to the wearable housing with screws adhesive, clips, heat and pressure, or any other known way to attach two elements. Or, the light source may be partially or fully contained within the housing. In an alternative embodiment, the light source may be associated with the housing through a wired or wireless connection. Light source 410 in FIG. 4 is one example of a coherent light source.

Consistent with some disclosed embodiments, the at least one coherent light source may be configured to project light towards a facial region of the head. Projecting coherent light may include radiating coherent light in a direction toward a portion of the face. The coherent light may be a monochromatic wave having a well-defined phase relationship across its wavefront in a defined direction, such as towards a facial region of the head. A facial region of the head refers to any anatomical part of the human body above the shoulders. The facial region may include at least some of the following: forehead, eyes, cheeks, ears, nose, mouth, chin, and neck. Examples of facial regions are illustrated in FIGS. 1-3 (e.g., facial region 108). For example, as illustrated in FIG. 1 and FIG. 2, coherent light source 410 included in optical sensing unit 116 is attached to wearable housing 110 and may direct light towards the facial region. The head mountable system may also include at least one detector associated with the wearable housing. The terms "detector" and "associated with the wearable housing" may be understood as described and exemplified elsewhere in this disclosure. The at least one detector may be configured to receive coherent light reflections from the facial region and to output associated reflection signals. Receiving coherent light reflections may refer to detecting, acquiring, obtaining, or otherwise measuring electromagnetic waves (e.g., in the visible or invisible spectrum) reflected from the facial region and impinging on the at least one detector. Outputting associated reflection signals may include sending, transmitting, producing, and/or providing information representing or corresponding to the coherent light reflections. For example, projecting coherent light on facial skin that does not move may result in first reflection signals indicative of the coherent light reflections. But even small micromovements of the facial skin may cause the at least one detector to output second reflection signals differing from the first reflection signals. The changes between the first and second reflection signals may be used to determine specific facial skin micromovements. By way of one example, light detector 412 in FIG. 4 is associated with a wearable housing 110 and is employed to determine facial skin micromovements.

Consistent with some disclosed embodiments, the head mountable system includes at least one processor. The term "processor" may be understood as described and exemplified elsewhere in this disclosure. The processor may be employed to provide some or all of the functionality described herein. Processing device 400 in FIG. 4 is one example of at least one processor provided for purposes of achieving at least some of the functionality described herein.

Some disclosed embodiments involve analyzing reflection signals to determine specific facial skin micromovements of an individual. The term "analyzing" refers to examining, investigating, scrutinizing, and/or studying. Reflection signals may be analyzed to determine if they are recognized or whether they correlate with other information. For example, the reflection signals (or a data set derived from the reflection signals, may be analyzed, for example, to determine a correlation, association, pattern, or lack thereof within the data set or with respect to a different data set. Specifically, the reflection signals received from the at least one detector may be analyzed, for example, using one or more processing techniques, such as light pattern analysis (as described and exemplified elsewhere in this disclosure). Other processing techniques may include convolutions, fast Fourier transforms, edge detection, pattern recognition, object detection algorithms, clustering, artificial intelligence, machine and/or deep learning, and any other processing technique for determining specific facial skin micromovements of the individual. In some examples, a machine learning model may be trained using training examples to determine facial skin micromovements based on reference reflection data. An example of such training example may include a sample reflection data stream, together with a label indicating associated facial skin micromovements. The trained machine learning model may be used to analyze the received reflection signals relative to the reference reflection data to determine the facial skin micromovements. In some examples, at least part of the reflection signals may be analyzed to calculate a convolution of the at least part of the reflection signals and thereby obtain a result value of the calculated convolution. Further, in response to the result value of the calculated convolution being a first value, a first facial skin micromovements may be determined, and in response to the result value of the calculated convolution being a second value, a second different facial skin micromovements may be determined. For example, reflection signals received by the at least one detector may be analyzed as described elsewhere in this disclosure, and facial skin micromovements associated with the question "what is my mom's birthday?" may be determined. Additional details and examples on how the at least one processor may analyze the reflection signals to determine specific facial skin micromovements are described herein with reference to light reflections processing module 706.

Consistent with some disclosed embodiments, at least some of the specific facial skin micromovements in the facial region may include micromovements of less than 100 microns or less than 50 microns. In other words, the output of the process of determining the specific facial skin micromovements may be accurate enough to distinguish changes in facial skin in the range of 10 to 100 microns. In some embodiments, these changes may be detected over a time period of 0.01 to 0.1 seconds. In some disclosed embodiments, the determined specific facial skin micromovements may correspond to a facial expression (e.g., smile, scowl, worried) or to a facial muscular action corresponding to a physiological event (e.g., sneeze, laugh, yawn). In other embodiments, the facial skin micromovements may correspond to a phenome, syllable, word, or phrase that is pre-vocalized or vocalized, as described below. In yet other embodiments, the facial skin micromovements may correspond to a biological process such as pulse or respiration rate. In further embodiments, the facial skin micromovements may correspond to a combination of one or more of the foregoing.

Consistent with some disclosed embodiments, the specific facial skin micromovements may correspond to prevocalization muscle recruitments. As described elsewhere herein, prevocalization or subvocalization refers to the effects of facial muscle movement in an absence of audible vocalization or prior to an occurrence of vocalization. Facial skin micromovements correspond to prevocalization muscle recruitment, when the prevocalization muscle recruitments are the direct or indirect cause of the facial skin micromovements. In some case, prevocalization muscle recruitment may cause facial skin micromovements prior to an onset of vocalization. By way of example, the prevocalization muscle recruitments may occur between 0.1 seconds to 0.5 seconds before the actual vocalization. In some cases, the prevocalization muscle recruitment may include voluntary muscle recruitments that occur when an individual start to vocalize words. In other cases, the prevocalization muscle recruitment may include involuntary facial muscle recruitments that occur when certain craniofacial muscles prepare to vocalize words.

Consistent with some disclosed embodiments, the specific facial skin micromovements may correspond to muscle recruitment during pronunciation of at least one word or a portion thereof. For example, the at least one word may correspond to a predefined expression, a password, or a secret passphrase. As discussed above, actual vocalization depends on whether air is emitted from the lungs and into the throat. Without this air flow, no sounds are emitted. Because prevocalization muscle recruitment occurs before and separately from the muscles that convey the air flow, the prevocalization muscle recruitment may occur when there is subsequent vocalization or when there is no subsequent vocalization.

FIG. 8 illustrates an exemplary speech detection process. In the illustrated example, speech detection system 100 may analyze the reflection signals associated with the question "what is my mom's birthday?" to determine specific facial skin micromovements 800 associated with an unknown individual 802.

Some disclosed embodiments involve accessing memory correlating a plurality of facial skin micromovements with the individual. The term "accessing memory" refers to retrieving or examining electronically stored information. This may occur, for example, by communicating with or connecting to electronic devices or components in which data is electronically stored. Such data may be organized, for example, in a data structure for the purpose of reading stored data (e.g., acquiring relevant information) or for the purpose of writing new data (e.g., storing additional information). In some cases, the accessed memory may be part of a speech detection system or part of a remote processing device (e.g., cloud server) that may be accessed by the speech detection system. In some examples, the at least one processor may access the memory, for example, at startup, at shutdown, at constant intervals, at selected times, in response to queries received from the at least one processor, or at any other determined times. The memory may store data that correlates a plurality of facial skin micromovements with the individual. The stored data may be any electronic representation of the facial skin micromovements, any electronic representation of one or more properties determined from the facial skin micromovements, or raw measurement signals detected by the at least one light detector and representing the facial skin micromovements. Correlating a plurality of facial skin micromovements with the individual may include storing relationships between facial skin micromovements and an identifier of the individual in a memory or data structure. This may allow for efficient retrieval and identification of the individual based on these relationships. For example, the memory may be associated with a built-in mechanism for linking or associating facial skin micromovements with an identifier of the individual. In one example, correlations may be stored between specific phenomes, syllables, words, or phrases and associated skin micromovements. Depending on implementation, these correlations may be unique to the individual or specific to a population or subpopulation associated with the individual. (e.g., micromovements associated with certain parts of speech may vary across individuals, countries, dialects, or based on different regional accents.) Correlating a plurality of facial skin micromovements with the individual may occur through any one of the above examples. If the intention is to verify a personal identity of a specific individual, then a comparison may occur to a database of correlations associated with that specific individual (e.g., based on samples previously capture from that individual.) Alternatively, if the intention is to identify the individual as part of a population or subpopulation, then pre-stored data associated with that population or subpopulation may be accessed.

Consistent with the present disclosure, the fact that the plurality of facial skin micromovements correlates with the individual means that the plurality of facial skin micromovements can either uniquely identify the individual or identify the individual as part of a particular population or subpopulation. In one exemplary embodiment for uniquely identifying an individual, the probability that the plurality of facial skin micromovements would be identical for two different individuals may be less than one in 10,000, less than one in 100,000, less than one in 1,000,000, or less than one in 10,000,000, depending on implementation.

Consistent with some disclosed embodiments, the memory may correlate a plurality of facial skin movements with a plurality of individuals. Specifically, the memory may be designed to store relationships between facial skin micromovements with a plurality of identifiers associated with a plurality of individuals. For example, specific correlations may be stored for each of many individuals such that when a current signal is received, it may be compared with the various stored correlations to uniquely identify an individual associated with the stored correlation. In some disclosed embodiments, for each of the plurality of individuals the memory may store at least 10, at least 50, or at least 100 data entries associated with different facial skin micromovements. In some examples, the plurality of individuals may be related, e.g., the plurality of individuals may be family members or part of the same organization. In other examples, the plurality of individuals may be unrelated but include a common attribute, e.g., individuals from the same group age, or individuals associated with a same language dialect.

Consistent with some disclosed embodiments, the at least one processor may be configured to distinguish the plurality of individuals from each other based on reflection signals unique to each of the plurality of individuals. Distinguishing the plurality of individuals from each other means that the at least one processor may be able to determine which individual is responsible for the received reflection signals. For example, the at least one processor may identify that a certain sentence was spoken by a particular individual and not by any other individuals contained in the database. The at least one processor may be configured to distinguish the plurality of individuals from each other by detecting reflection signals unique to each individual. Unique reflection signals means that no two individuals have the same reflection signals. For example, the unique reflection signals may be associated with a distinctive sequence of facial skin micromovements that occurs when the individual vocalizes or prevocalizes one or more phonemes, syllables, words or phrases, such as a passphrase. In one example, the speech detection system may be used by a group of individuals and for each individual the speech detection system may store personal settings. In one embodiment, the at least one processor may detect, during a first time period, first facial skin micromovements of a first individual and at a subsequent second time period, detect second facial skin micromovements of a second individual. Upon identifying the first individual using the first facial skin micromovements, the at least one processor may initiate a first action (e.g., applying personal settings associated with the first individual), and upon identifying the second individual using the second facial skin micromovements, the at least one processor may initiate a second action (e.g., applying personal settings associated with the second individual). Or, if a correlation is identified for a particular individual, access to an application may be provided; while access may be denied if a correlation is not identified.

By way of one example with reference to FIG. 8, memory 804 may store a plurality of reference facial skin micromovements (e.g., 806A, 806B, 806C, and 806D) associated with user 102. In the figure, only four reference facial skin micromovements are illustrated, but as will be appreciated by a person skilled in the art having the benefit of this disclosure, a greater number of reference facial skin micromovements may be stored as reference data to identify individuals. For example, the plurality of reference facial skin micromovements may be for all known phonemes, or for at least 1,000 words. In addition, memory 804 may be designed to store a plurality of reference facial skin micromovements for multiple users, thus enabling the processor to distinguish the plurality of individuals from each other based on reflection signals unique to each of the multiple individuals.

Some disclosed embodiments involve searching for match between the determined specific facial skin micromovements and at least one of the plurality of facial skin micromovements in the memory. The term "searching for a match" may refer to finding one or more records that satisfy a given set of search criteria. Different types of search algorithms may be used to search for the match, such as a linear search, a binary search, tree-based search, and various types of database searches. In addition, an artificial intelligence model may be employed and used to search for a match in a dataset accessible to the AI model, as described in the following paragraph. In some cases, the initiated search may be used for finding which of the plurality of facial skin micromovements was most likely generated by a same individual that generated the specific facial skin micromovements. A likelihood level or a certainty level of a match may be determined to provide an indication of probability or degree of confidence in the determination that the identification hypothesis is correct, i.e., that a reference facial skin micromovements stored in the memory was indeed generated by a same individual that generated the specific facial skin micromovements. In some disclosed embodiments, a match may be considered to be found when the likelihood level or the certainty level is, by way of example only, greater than 90%, greater than 95%, or greater than 99%.

Consistent with the present disclosure, the at least one processor may use an artificial neural network (such as a deep neural network, a convolutional neural network) to identify a match. The artificial neural network may be configured manually, using machine learning methods, or by combining other artificial neural networks. Other ways that the at least one processor may use to identify a match includes comparing the determined specific facial skin micromovements with the plurality of facial skin micromovements in the memory; taking the difference between the determined specific facial skin micromovements with the plurality of facial skin micromovements in the memory and comparing it to a threshold value; calculating at least one statistical value (e.g., mean, variance, or standard deviation) and comparing the at least one statistical value to a threshold; calculating the distance between two vectors in a multi-dimensional space, wherein, if the distance is below a certain threshold, a match is identified; calculating the cosine of the angle between two vectors in a multi-dimensional space, wherein, if the cosine value is above a certain threshold, a match is identified; and any other known way of identifying a match in a database.

By way of one example with reference to FIG. 8, searching for a match may result in a first outcome 808A indicating that match is identified and a second outcome 808B that indicates that match is not identified.

Some disclosed embodiments involve initiating a first action if a match is identified, and initiating a second action different from the first action if a match is not identified. The term "initiating" may refer to carrying out, executing, or implementing one or more operative steps. For example, the at least one processor may initiate execution of a program code instructions or cause a message to be sent to another processing device to achieve a targeted (e.g., deterministic)

outcome or goal. The action may be an initiated response to a determination if a match between the determined specific facial skin micromovements with the plurality of facial skin micromovements is found in the memory. The term "action" may refer to the performance or execution of an activity or task. For example, performing an action may include executing at least one program code instruction to implement a function or procedure. The action may be user-defined or system-defined (e.g., software and/or hardware), or any combination thereof. At least one processor may select which action to initiate (e.g., first action or second action) and may determine to initiate the selected action based on the results of the search for match and based on various criteria. The various criteria may include user experiences (e.g., preferences, such as based on context, location, environmental conditions, use type, user type), user requirements (e.g., context limitations, urgency or priority of the purpose behind the action), device requirements (e.g., computation capacity, computation limitations, presentation limitations, memory capacity, or memory limitations), communication network requirements (e.g., bandwidth, latency). For example, after a match is found, a first action of sending an audio message may be initiated. The artificial voice used to generate the audio message may be selected based on the various criteria listed above. The action may be initiated by at least one processor configured with the speech detection system, a different local processing device (e.g., associated with a device in proximity to the speech detection system), and/or by a remote processing device (e.g., associated with a cloud server), or any combination thereof. Thus, "initiating an action responding to the search results" may include performing or implementing one or more operations in response to the outcome of the search for a match between the determined specific facial skin micromovements and at least one of the plurality of facial skin micromovements in the memory.

Consistent with some disclosed embodiments, the first action institutes at least one predetermined setting associated with the individual. The term "predetermined setting" refers to any configurations or preferences associated with an operation software of a related computing device, or any other software installed on the computing device. Examples of such predetermined settings may include language settings, default actions, preferred output modes, types of notifications, permissions, display brightness, volume levels, default apps, network settings, and any other option selectable by the user. Consistent with the present disclosure, when a match is identified, the at least one processor may institute (i.e., appoint, establish, or set up) a specific setting associated with the identified individual. Stating that a predetermined setting is associated with the individual means that data reflecting the individual's selection of the predetermined setting is stored in a database, a data structure, lookup table, or a linked list. In one example, the predetermined settings may govern what the speech detection system should do upon detecting silent speech. Specifically, after a match is identified, the speech detection system may automatically translate words spoken silently in English to French and synthesize them with an artificial voice that sounds like the identified individual.

Consistent with some disclosed embodiments, the first action (i.e., when the individual is identified) includes unlocking a computing device, and the second action (i.e., when the individual is not identified) includes presentation of a message indicating that the computing device remains locked. The computing device may be any electronic device to which access is restricted. For example, the computing device may be a laptop, PC, tablet, smartphone, wearable electronics, electronic door lock, entry gate, application, system, vehicle, communications device (e.g., mobile communications device 120). In one embodiment, the computing device may be at least a portion of speech detection system 100. The term "unlocking a computing device" generally refers to the process of gaining access to a device that has a security mechanism in place to prevent unauthorized access. For example, upon identifying the individual, the at least one processor may send data to mobile communications device 120 (e.g., a passcode) that causes mobile communications device 120 to unlock. The message indicating that the computing device remains locked may be provided by the computing device or by any other device in any known manner, for example, the message may be provided audible, textually, or virtually. For example, when the individual in not identified, speech detection system 100 may present a message that mobile communications device 120 remains locked.

Consistent with some disclosed embodiments, the first action (i.e., when the individual is identified) provides personal information, and the second action (i.e., when the individual is not identified) provides public information. Personal information includes data that is specific to an individual or information that an entity (e.g., user, person, organization or other data owner) may not wish to share with another entity. For example, it may include any information that, if revealed to a non-authorized entity, may cause harm, loss, or injury to an individual or entity associated therewith. Some examples of personal information (e.g., sensitive data) may include identifying information, location information, genetic data, information related to health, financial, business, personal, family, education, political, religious, and/or legal matters, and/or sexual orientation or gender identification. Public information may include any information other than personal information and may be found in public databases, such as the Internet. For example, following receiving a query from the individual, speech detection system 100 may use the specific facial skin micromovements to generate a response that either includes personal information (when the individual is identified) or includes public information (when the individual is not identified).

Consistent with some disclosed embodiments, the first action (i.e., when the individual is identified) authorizes a transaction, and the second action (i.e., when the individual is not identified) provides information indicating that the transaction is not authorized. Authorizing a transaction refers to the process of granting approval or permission for an activity to occur. In some cases, authorizing a transaction may involve verifying the legitimacy of a transaction request and confirming the identity of an individual by finding a match. Examples of transactions may include financial transactions (e.g., withdrawal or deposit from a bank account, purchase or sale of goods or services using a credit card, transfer of funds between accounts, payment of bills, wire transfer, or electronic funds transfer), non-financial transactions (e.g., booking a flight, making a hotel reservation, ordering products online, renting a car, enrolling in a subscription, updating an address, or phone number), business transactions (e.g., ordering supplies, billing customers for products or services rendered, approving refunds, or processing invoices), and government transactions (e.g., applying for a passport or visa, paying taxes or fines, registering a vehicle, obtaining a driver's license, obtaining permits for business operations). When a match is not found, information may be provided to indicate that the transaction is not authorized. The information may be provided via a speech detection system or via a mobile communications device. For example, when speech detection system 100 is linked to a virtual wallet, upon receiving a request to pay, speech detection system 100 may prompt individual to silently say a password. Thereafter, speech detection system 100 may use the determined specific facial skin micromovements to determine the password and compare the determined password with a previously stored password stored in association with the user. When the determined password matches the stored password, speech detection system 100 may authorize the payment (i.e., when the individual is identified). Alternatively, when the determined password does not match the stored password, speech detection system 100 may not authorize the payment (i.e., when the individual is not identified).

Consistent with some disclosed embodiments, the first action (i.e., when the individual is identified) permits access to an application, and the second action (i.e., when the individual is not identified) prevents access to the application. Permitting access to an application may refer to the process of granting authorization to an individual to use a particular software application or to use electronic hardware. The software application may be installed in a speech detection system or in any computing device associated with the individual (e.g., the individual's smartphone). For example, a calendar application of an individual may be accessed in response to detected query, such as: "What was the name of the person I met with last Wednesday?" from an identified individual. If the individual is not identified, access to the calendar application would be prohibited and therefore the query may not be answered.

Consistent with some disclosed embodiments, a head mountable system includes an integrated audio output, wherein at least one of the first action or at least one of the second action includes outputting audio via the audio output. The term integrated audio output means that the head mountable system includes internal audio hardware configured to generate sounds without the need for an external audio interface. For example, the head mountable system may include an audio chipset that can convert digital audio signals into analog signals and built-in speakers or headphone jack. Additional examples of the integrated audio output may include or may be associated with a loudspeaker, earbuds, audio headphones, a hearing aid type device, and any other device capable of converting an electrical audio signal into a corresponding sound. For example, the first action may be emitting sounds into the open air using an audio output device, such as loudspeaker, for anyone nearby to hear, and the second action may be emitting sounds using an audio output device such as earbuds for letting only the individual listen to the generated audio signals.

By way of one example with reference to FIG. 8, first action 810A may be initiated when a match is found (i.e., that individual 802 is identified as user 102), and second action 810B may be initiated when a match is not found (i.e., that individual 802 is not identified as user 102).

Consistent with some disclosed embodiments, a match may be identified upon determination by the at least one processor of a certainty level. As described elsewhere in this disclosure, the determination of the certainty level provides an indication of the confidence that the identification hypothesis is correct. In other words, and with reference to FIG. 8, the certainty level provides an indication that unknown individual 802 is user 102. Consistent with some disclosed embodiments, when the certainty level is initially not reached, the at least one processor may analyze additional reflection signals to determine additional facial skin micromovements, and arrive at the certainty level based at least in part on analysis of the additional reflection signals. FIG. 9 (as discussed below) depicts an example implementation of these embodiments.

FIG. 9 depicts a flowchart of an example process 900 executed by a processing device of speech detection system 100 (e.g., processing device 400) for identifying individuals above a certainty level. For purposes of illustration, in the following description, reference is made to certain components of speech detection system 100. It will be appreciated, however, that other implementations are possible and that other components may be used to implement example process 900. It will also be readily appreciated that the example process 900 can be altered to modify the order of steps, delete steps, or further include additional steps.

Process 900 begins when the processing device receives reflections from a facial region (block 902), then the processing device analyzes the reflections to determine specific facial skin micromovements (block 904), and searches for match between the determined specific facial skin micromovements and at least one reference facial skin micromovements (block 906). If a match was not found (decision block 908), the processing device may initiate a second action (block 910), and the process continues by receiving additional reflection signals (block 912), analyzing them to determine additional facial skin micromovements, and searching for a match to identify individual 802. If a match was found (decision block 908), the processing device may determine a certainty level for the match (block 914) and compare the determined certainty level to a threshold (decision block 916). If the certainty level is greater than a threshold, the processing device may initiate a first action (block 918) and the process continues for receiving additional reflection signals (block 912), analyzing (block 904), and searching (block 906). But, if the certainty level is less than a threshold, the processing device may initiate the second action (block 910).

Consistent with some disclosed embodiments, at least one processor continuously compares new facial skin micromovements with the plurality of facial skin micromovements in the memory to determine an instantaneous level of certainty. In this context, the term "continuously compares" means constantly or regularly compares new facial skin micromovements with the plurality of facial skin micromovements in the memory over a period of time (e.g., during a phone call). In this context, continuous comparison includes intervals between comparisons such as multiple times a second or multiple times a minute. The term "instantaneous level of certainty" refers to a degree of confidence in an identity of individual associated with the new facial skin micromovements. For example, during a phone call with a banker, the system may regularly compare new facial skin micromovements to make sure that the same authorized individual remains on the line. Consistent with some disclosed embodiments, when the instantaneous certainty level is below a threshold, the at least one processor is configured to initiate an associated action. The fact that the instantaneous certainty level is below a threshold means that there is a risk that someone else—other than the identified individual—is responsible for the new facial skin micromovements. The associated action refers to an action associated with the fact that the instantaneous certainty level is now below a threshold and may include the second action or stopping the first action. Specifically, in some embodiments, after initiating the first action, when the instantaneous certainty level is below a threshold, the at least one processor is configured to stop the first action. For example, the first action may be authorizing a transaction in the bank by speaking with a banker over the phone and providing the banker with ongoing confirmation of the identity of the individual over the phone. But, once the instantaneous certainty level drops below the threshold, which may indicate that someone other than the individual is talking to the banker, the transaction may be stopped. In some cases, the second action may include stopping the first action.

With reference to FIG. 9, after the first action was initiated at block 918, additional reflections are received, and the analyzing step (block 904) and the searching step (block 906) are executed. If the determined instantaneous certainty level associated with the additional reflections is below the threshold, then the first action may be stopped by initiating the second action.

Consistent with some disclosed embodiments, initiating the first action may be associated with an event, and the at least one processor may continuously compare new facial skin micromovements during the event. The term "event" in this context may refer to an occurrence of an action, activity, change of state, or any other type of detectable development or stimulus. The term "during the event" means any time from a time when the event was detected up until a time the event ends. In one example, the event can be a purchase at point of sale (POS) where the user puts on the device to approve the transaction. In another example, the event may be associated with an online activity (e.g., a financial transaction, a wagering session, an account access session, a gaming session, an exam, a lecture, or an educational session). In another example, the event may include maintaining a secured session with access to a resource (e.g., a file, a folder, a database, a computer program, a computer code, or computer settings).

FIG. 10 illustrates a flowchart of an exemplary process 1000 for identifying individuals using facial skin micromovements, consistent with embodiments of the present disclosure. In some disclosed embodiments, process 1000 may be performed by at least one processor (e.g., processing device 400 or processing device 460) to perform operations or functions described herein. In some embodiments, some aspects of process 1000 may be implemented as software (e.g., program codes or instructions) that are stored in a memory (e.g., memory device 402 or memory device 466) or a non-transitory computer readable medium. In some embodiments, some aspects of process 1000 may be implemented as hardware (e.g., a specific-purpose circuit). In some embodiments, process 1000 may be implemented as a combination of software and hardware.

Referring to FIG. 10, process 1000 includes a step 1002 of projecting light towards a facial region of a head of an individual. For example, the at least one processor may operate a wearable coherent light source (e.g., light source 410) to illuminate facial region 108 (e.g., using multiple output beams 508). Process 1000 includes a step 1004 of receiving coherent light reflections from the facial region and to output associated reflection signals. For example, the at least one processor may operate at least one detector (e.g., at least one detector 412) to receive coherent light reflections (e.g., light reflections 300) from facial region 108. Process 1000 includes a step 1006 of analyzing the reflection signals to determine specific facial skin micromovements of the individual. For example, using light reflections processing module 706 and subvocalization deciphering module 708 to determine the specific facial skin micromovements. Process 1000 includes a step 1008 of accessing memory correlating a plurality of facial skin micromovements with the individual. Process 1000 includes a step 1010 of searching for a match between the determined specific facial skin micromovements and at least one of the plurality of facial skin micromovements in the memory. Process 1000 includes a step 1012 of initiating an action based on a determination whether a match is found or not. Specifically, if a match is identified, initiating a first action (e.g., first action 810A), and if a match is not identified, initiating a second action (e.g., second action 810B) different from the first action.

In accordance with one implementation, a speech detection system projects a pattern of light on facial skin (e.g., a cheek) of a user. Thereafter, the speech detection system may detect light reflections from various locations of the facial skin. Notably, reflections associated with specific areas may be more relevant for extracting meaning (e.g., determining communication) than other areas. The specific areas may be those that are located closer to particular facial muscles. Identifying the specific locations may pose challenges because each user has unique facial features, and the position of the light source and/or detector relative to the user's face may change during every usage and even during ongoing operations. The following paragraphs describes systems, methods, and computer program products for identifying the locations of those specific areas, using the light reflections from the specific areas to extract meaning, and ignoring light reflections from other areas to conserve processing resources.

Some disclosed embodiments involve interpreting facial skin movements. The term "interpreting facial skin movements" refers to extracting meaning from detected skin movements, as described elsewhere in this disclosure. In one example, interpreting facial skin movements may include determining one or more vocalized or subvocalized words from the facial skin movements or determining a facial expression (e.g., happy, sad, anger, fear, surprise, disgust, contempt, or other emotion) of the individual. In another example, interpreting facial skin movements may include determining an identity of the individual. These facial skin movements may be detectable as described elsewhere in this disclosure.

Figure 11:
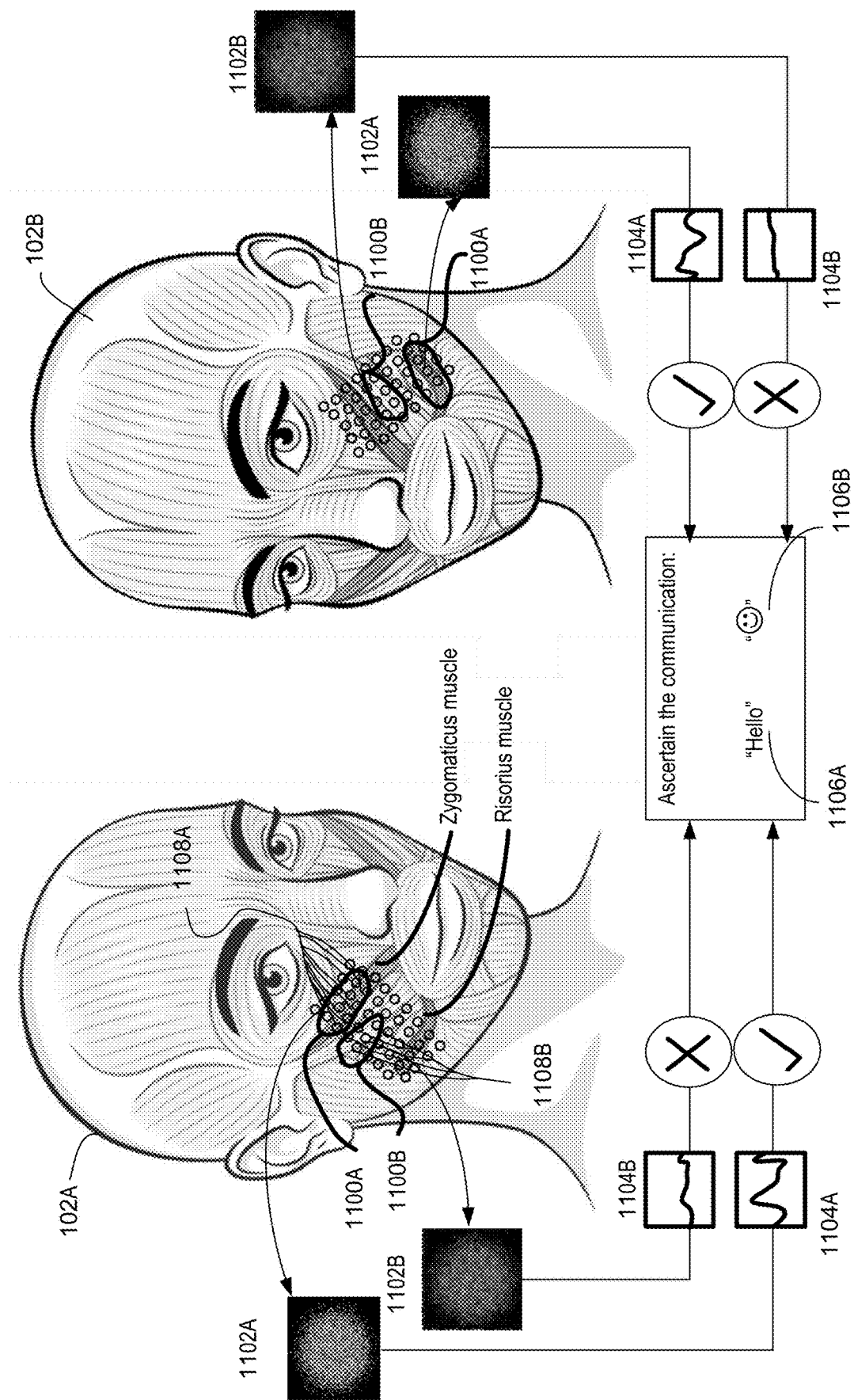
FIG. 11 is an illustration of two example use cases for interpreting facial skin movements from light reflections, consistent with some embodiments of the present disclosure.
Figure 12:
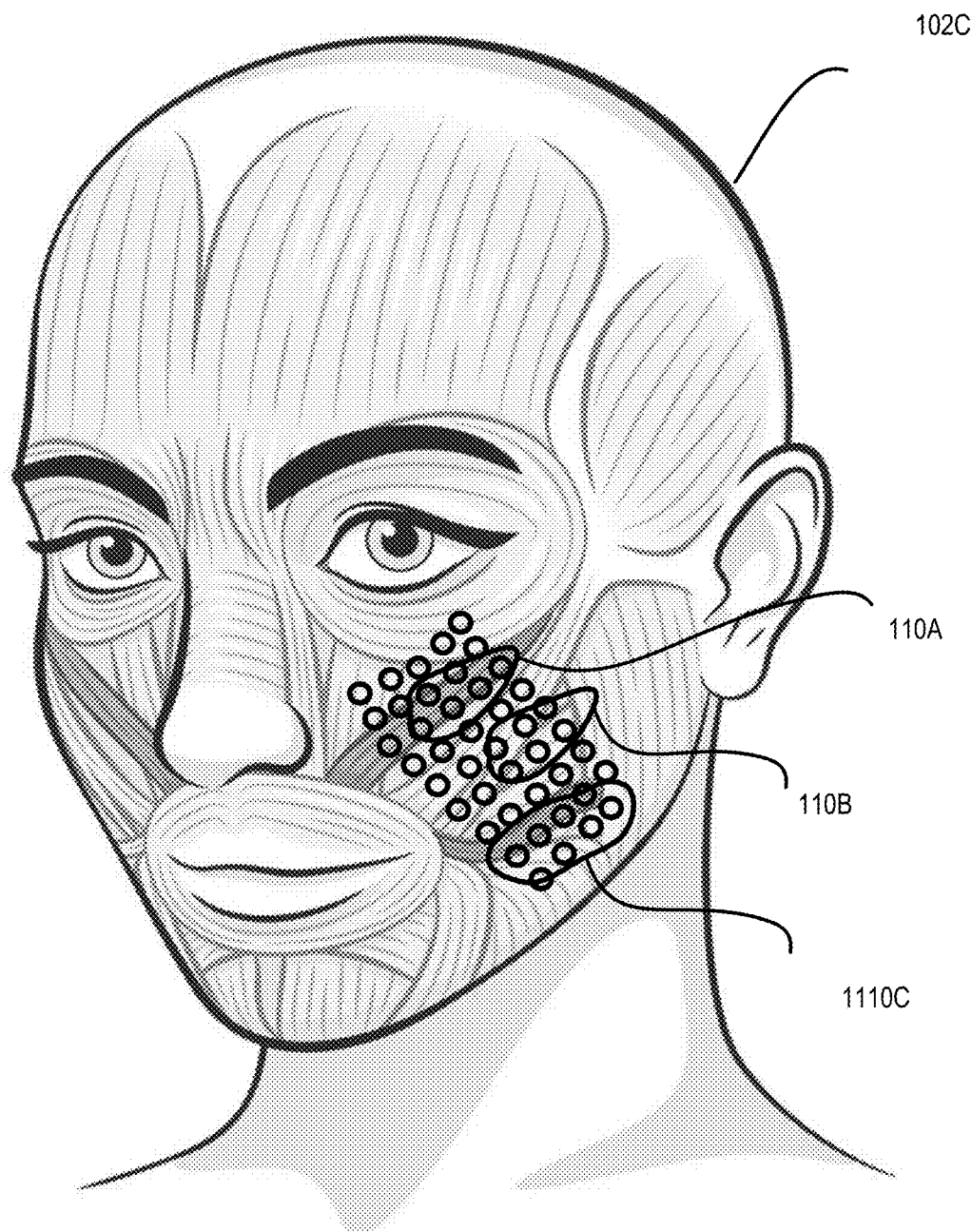
FIG. 12 is an illustration of another example use case for interpreting facial skin movements from light reflections, consistent with some embodiments of the present disclosure.

Some disclosed embodiments involve projecting light on a plurality of facial region areas of an individual, wherein the plurality of areas includes at least a first area and a second area. The term "projecting" includes controlling a light source (e.g., a coherent light source) such that it emits light in a given direction (e.g., toward a portion of the face), as discussed elsewhere in this disclosure. The term "individual" includes a person who uses a speech detection system (or another person to whom the light source is projected), as described elsewhere in this disclosure. The term "facial region area" or simply "area" in the context of the face includes a portion of the face of the individual, as described elsewhere in this disclosure. For example, a facial region area may have a size of at least 1 cm$^2$, at least 2 cm$^2$, at least 4 cm$^2$, at least 6 cm$^2$, or at least 8 cm$^2$. Consistent with some disclosed embodiments, the projected light illuminates a plurality of facial region areas. For example, the plurality of areas includes 4, 8, 16, 32, or any other numbers of areas. In some cases, the projected light may include at least one spot, as described elsewhere in this disclosure. The at least one spot may illuminate more than one facial region area, for example, as illustrated in FIG. 3, a single spot 106 may illuminate different portions of facial region 108. For example, spot 106 may include a first portion 304A associated with a first facial muscle and a second portion 304B associated with a second facial muscle. Alternatively, a single facial region area may be illuminated by multiple light spots. Some of the plurality of areas may be spaced apart from each other while others of the plurality of areas may be overlapping with each other. The term "spaced apart" may refer to being non-overlapping or separated by at least some distance. Thus, spaced apart areas may refer to two or more facial region areas that do not overlap with each other and have even a very small gap in between. For example, stating that a first facial region area is spaced apart from a second facial region area may include distances between the first and second region of at least 5 mm, at least 10 mm, at least 15 mm, or any other desired distance. In some embodiments the distance may be less than 1 mm, or between 1 mm and 5 mm. In some cases, only a portion of a facial region area may be illuminated by the projected light. In other cases, all of the facial region areas may be illuminated by the projected light. By way of example, FIGS. 11 and 12 illustrate illuminating plurality of facial region areas of an individual using a plurality of spots. As illustrated, each of facial areas 1100A and 1100B are illustrated by more than one light spot.

Some disclosed embodiments involve illuminating at least a portion of the first area and at least a portion of the second area with a common light spot. As used herein, the term "at least a portion" and/or grammatical equivalents thereof can refer to any fraction of a whole amount. For example, "at least a portion" can refer to at least about 1%, 5%, 10%, 20%, 40%, 65%, 90%, 95%, 99%, 99.9%, or 100% of a whole amount, or any other fraction. The term "common light spot" means that a single (common) light spot may cover some or all of the first area and the second area. The common light spot may illuminate at least a portion of the first area and the second area. In one example, the common light spot may illuminate 30% of the first area and 10% of the second area. In another example, the common light spot may illuminate 100% of the first area and 100% of the second area. Controlling the at least one coherent light source may include illuminating a continuous area on the face that includes the first area and the second area. By way of one example, as illustrated in FIG. 3 single light spot 106 may illuminate two or more facial areas (e.g., 304A and 304B).

Some disclosed embodiments involve illuminating the first area with a first group of spots and illuminating the second area with a second group of sports distinct from the first group of spots. The term "group of spots" refers to more than one light spot. The number of spots in the group of spots may range from two to 64 or more. For example, the group of spots may include 4 spots, 8 spots, 16 spots, 32 spots, 64 spots, or any number of spots greater than two. There may be variations in illumination characteristics between spots or within the group of spots, as discussed elsewhere in this disclosure. Illuminating an area with a group of spots may refer to illuminating some or all of a facial area region by two or more spots. In one example, the group of spots may illuminate at least 15% of the area, at least 40% of the area, or at least 70% of the area. A first area may be illuminated by a first group of spots and a second area may be illuminated by a second group of spots distinct from the first group of spots. In this context, the term "distinct" means that the first group of spots is distinguishable from the second group of spots. For example, the first group of spots may include at least one spot not included in the second group of spots. By way of example, FIGS. 11 and 12 illustrate a first area facial regions 1100A illuminated by a first group of spots 1108A and a second area 1100B illuminated by a second group of sports 1108B distinct from the first group of spots.

Some disclosed embodiments involve operating a coherent light source (as described elsewhere in this disclosure) located within a wearable housing (as described elsewhere in this disclosure) in a manner enabling illumination of the plurality of facial region areas. Enabling illumination, as used herein, may refer to a process of controlling a light source to generate at least one light beam and directing the at least one light beam toward the plurality of facial region areas. For example, enabling illumination may also include utilizing a beam-splitting element (as described elsewhere in this disclosure) configured to split an input beam into multiple output beams (as described elsewhere in this disclosure) extending over a portion of a face. In an alternative embodiment, enabling illumination may include utilizing multiple light sources which generate respective groups of output beams, covering different respective sub-areas within a portion of a face. FIGS. 1 and 2 illustrate an example implementation of speech detection system (e.g., speech detection system 100) in which at least one facial region area (e.g., facial region 108) is illuminated by a plurality of light spots (e.g., light spots 106). The plurality of light spots may be generated by optical sensing unit 116 that includes at least one light source 410 and at least one light detector 412 and located in a wearable housing 110.

Some disclosed embodiments involve operating a coherent light source (as described elsewhere in this disclosure) located remote from a wearable housing (as described elsewhere in this disclosure) in a manner enabling illumination of the plurality of facial region areas (as described elsewhere in this disclosure). The term "located remote" indicates that two objects are separated from each other and with a physical distance between them such that they do not appear physically as a unified component. For example, the coherent light source may be part of device other than the speech detection system and located more than 1 cm from a wearable housing of the speech detection system. As another example, the coherent light source may be located more than 3 cm from a wearable housing of the speech detection system. It should be understood that the distances 1 cm and 3 cm are exemplary and nonlimiting and other distances may be used. FIG. 3 illustrate an example implementation of speech detection system in which a plurality of facial region areas (e.g., first portion 304A of facial region 108 and second portion 304B of facial region 108) are illuminated by a coherent light source located remote from the wearable housing (e.g., a non-wearable light source 302).

In some disclosed embodiments, the first area is closer to at least one of a zygomaticus muscle or a risorius muscle than the second area. The phrase "a first area is closer to a muscle than a second area" means that a distance of the first area to a specific muscle is less than a distance of the second area to a specific muscle. For example, the distances may be measured from an edge of an area to an edge of specific muscle, from a center of an area to a center of a specific muscle, or any combination thereof. In this context, the center of a shape (i.e., the first area, the second area, or a specific muscle) may be a geometric center, which is the point which corresponds to the mean position of all the points in shape; a circumscribed center, which is the center of the smallest circle that completely encloses the 2D shape; an incenter, which is the center of the inscribed circle that is tangent to all sides of the 2D shape, or any other reference point previously defined. As discussed, the first area is closer to at least one of a zygomaticus muscle or a risorius muscle than a second area. In other words, the disclosed embodiments capture two example use cases, the first example use case is that the first area is closer to the zygomaticus muscle than the second area. The second example use case is that the first area is closer to the risorius muscle than the second area. By way of example, FIG. 11 illustrates one implementation of the first and second example use cases. Specifically, the first use case is illustrated with regards to individual 102A and the second use case is illustrated with regards to individual 102B.

FIG. 11 illustrates two example use cases for interpreting facial skin movements. In both example use cases, a plurality of facial region areas 1100 of individual 102 may be illuminated by at least one light source (e.g., light source 410, not shown). The depicted plurality of areas includes at least a first area 1100A and a second area 1100B. In the first example use case involving individual 102A, first area 1100A is closer to the zygomaticus muscle than second area 1100B, and in the second example use case involving individual 102B, first area 1100A is closer to the risorius muscle than second area 1100B.

Some disclosed embodiments involve receiving reflections from the plurality of areas. The term "receiving" may include obtaining, retrieving, acquiring, or otherwise gaining access to data or signals. In some cases, receiving may include reading data from memory and/or obtaining data from a computing device via a (e.g., wired and/or wireless) communications channel. In other cases, receiving may include detecting electromagnetic waves (e.g., in the visible or invisible spectrum) and generating an output relating to measured properties of the electromagnetic waves. In a first embodiment, at least one processor may receive data indicative of light reflected from the plurality of areas from at least one detector. In a second embodiment, at least one detector may receive light rays reflected from the plurality of areas. The term "reflections" refers to one or more light rays bouncing off a surface (e.g., the individual's face) or data derived from the one or more light rays bouncing off the surface. For example, the reflections may include light detected by a light detector after it was deflected from an object. The light detected by the light detector may be generated by at least one coherent light source of the disclosed speech detection system and/or may be generated from sources other than the disclosed speech detection system. By way of one example, light detector 412 in FIGS. 5A and 5B is employed to receive reflections 300 that originated from light generated by light source 410.

By way of example with reference to the two uses cases depicted in FIG. 11, a reflection image 1102A may represent the reflections received from the first area 1100A, and reflection image 1102B may represent the reflections received from the second area 1100B. As illustrated, in the first example use case, reflection image 1102A represents the reflections received from an area closer to the zygomaticus muscle; and in the second example use case, image 1102A represents the reflections received from an area closer to the risorius muscle.

Some disclosed embodiments involve detecting first facial skin movements corresponding to reflections from the first area and second facial skin movements corresponding to reflections from the second area. The term "detecting" in this context refers to the process of discovering, identifying, or determining the existence of light reflections (or signals associated therewith). In one example, a change in the position of facial skin may be detected. As discussed elsewhere in this disclosure, the detection process may involve using various techniques or technologies to determine the existence of the pattern or the event. In some cases, the process of detecting facial skin movement may involve determining if there is any movement that occurred and to record information representing the detected movement. For example, at least one processor may detect facial skin movements by applying a light reflection analysis on received reflections. In other cases, detecting facial skin movements may include determining times in which facial skin movements occurred. In other cases, detecting facial skin movements may include determining data representing the facial skin movements (e.g., direction, velocity, acceleration). The term "facial skin movements" broadly refers any type of movements prompted by recruitment of underlying facial muscles. The facial skin movements include facial skin micromovements—as described elsewhere in this disclosure—and larger-scale skin movements generally visible and detectable to the naked eye without the need for magnification (e.g., a smile, a yawn, a frown). The term "the facial skin movements corresponding to reflections from a specific area" means that the detected facial skin movements took place in a specific area of the face from which reflections were received. For example, detecting first facial skin movements corresponding to reflections from the first area means that the first facial skin movements may be detected by analyzing reflections received from the first area; and detecting second facial skin movements corresponding to reflections from the second area means that the second facial skin movements may be detected by analyzing reflections received from the second area.

In some disclosed embodiments, detecting the first facial skin movements involves performing a first speckle analysis on light reflected from the first area, and detecting the second facial skin movements involves performing a second speckle analysis on light reflected from the second area. The term "performing" refers to the act of carrying out a task, activity, or function. The term "speckle analysis" may be understood as described elsewhere in this disclosure. Consistent with the present disclosure, performing a speckle analysis may include detecting a speckle pattern, or any other patterns in signals received from a light reflected from a facial region area. For example, performing a speckle analysis may include identifying secondary speckle patterns that arise due to reflection of the coherent light from each area. In other embodiments, detecting facial skin movements may involve performing a pattern-based analysis or an image-based analysis additionally or alternatively from performing a speckle analysis.

Consistent with some disclosed embodiments, the first speckle analysis and the second speckle analysis occur concurrently by the at least one processor. the term "occur concurrently" means that two or more events occur during coincident or overlapping time periods, either where one begins and ends during the duration of the other, or where a later one starts before the completion of the other. In some cases the two or more events may be speckle analyses (or any pattern-based analysis). In order for the first speckle analysis and the second speckle analysis to occur concurrently, the at least one processor may include a plurality of processors or a multi-core processor that allows multiple speckle analyses to be executed simultaneously.

By way of example with reference to the two uses cases depicted in FIG. 11, first facial skin movements 1104A may correspond to reflections from the first area 1100A and second facial skin movements 1104B may correspond to reflections from the second area 1100B. For example, in the first example use case, first facial skin movements 1104A correspond to reflections received from an area closer to the zygomaticus muscle; and in the second example use case, second facial skin movements 1104B correspond to reflections received from an area closer to the risorius muscle.

Some disclosed embodiments involve determining, based on differences between the first facial skin movements and the second facial skin movements, that the reflections from the first area closer to the at least one of a zygomaticus muscle or a risorius muscle are a stronger indicator of communication than the reflections from the second area. Determining refers to ascertaining. For example, from the differences between the first and second facial skin movements, the processor may determine which is closer to the associated muscle. The differences between the first facial skin movements and the second facial skin movements may include any distinctions, variations, or dissimilarities between the first facial skin movements and the second facial skin movements. The differences between the first facial skin movements and the second facial skin movements may be determined using at least one of the following techniques: surface alignment, point-to-point comparison, surface registration, topological analysis, or any other technique for determining differences between two data sets. For example, the differences between the first facial skin movements and the second facial skin movements may include differences in the movement intensity, movement trajectory, the movement speed, and/or various changes in topography the facial skin. Based on the differences, the at least one processor may determine that reflections from a first area are a stronger indicator of communication than the reflections from a second area. The term "communication" refers to the process of conveying information through various mediums, such as spoken language, words, body language, gestures, or signals. For example, the communication may include verbal cues (e.g., words, phrases, and language) and non-verbal cues (e.g., body language, facial expressions, gestures, and eye contact). The term "indicator of communication" refers to a measure or sign reflective of an information conveyed by the individual. For example, the statement that reflections from the first area are a stronger indicator of communication than the reflections from a second area means that it may be easier to determine that the individual intends to convey information and what communication the individual intends to convey from the first facial skin movements than from the second facial skin movements. For example, the reflections from the first area may be a stronger indicator of communication than the reflections from a second area because the facial skin micromovements determined from the reflections from the first area may be associated with a higher velocity, a higher displacement, or a higher other parameter indicating that the individual intents to convey information and/or the content of the information that the individual intends to convey. Consistent with disclosed embodiments, in the first example use case, when the first area is closer to the zygomaticus muscle, the first facial skin movements may reflect movements with a velocity on the order of one to ten μm/ms, and the second facial skin movements may reflect smaller movements, if any. In the second example use case, when the first area is closer to the risorius muscle, the first facial skin movements may reflect movements on the order of 0.5-2 mm, and the second facial skin movements reflect smaller movements, if any.

Consistent with some disclosed embodiments, the differences between the first facial skin movements and the second facial skin movements include differences of less than 100 microns. The term "differences of less than 100 microns" means that the changes between a first parameter that represents the first facial skin movements and a second parameter that represents second facial skin movements is less than 100 microns. In one example, the first parameter may be a magnitude of a first displacement change vector associated with the first facial skin movements and a second parameter may be a magnitude of a second displacement change vector associated with the second facial skin movements. A displacement change is a vector that quantifies the distance and direction changes between two measurements of the facial skin. For example, the differences between the first facial skin movements and the second facial skin movements include differences of less than 50 microns, less than 10 microns, or less than 1 micron. In other embodiments, the differences between the first facial skin movements and the second facial skin movements include differences of less than 1 millimeter. Accordingly, the determination that the reflections from the first area are a stronger indicator of communication than the reflections from the second area is based on the differences of less than 1 millimeter, less than 100 microns, less than 50 microns, less than 10 microns, or less than 1 micron.

Some disclosed embodiments involve, based on the determination that the reflections from the first area are a stronger indicator of communication, processing the reflections from the first area to ascertain the communication. The term "processing" refers to the act of performing operations or transformations on data or information to achieve a desired outcome. For example, processing may include manipulating, analyzing, or altering inputs in a systematic way to produce meaningful outputs. The term "processing reflections" means extracting information from signals representing the received reflections. For example, processing reflections may include actions, such as: filtering, amplifying, modulating, and applying light reflection analysis as described elsewhere in this disclosure. Based on the determination that the reflections from the first area are a stronger indicator of communication, the reflections from the first area are processed to ascertain the communication. The term "ascertain the communication" means determining speech or facial expressions associated with non-verbal communication from facial movements, as described elsewhere in this disclosure. Consistent with the present disclosure, the reflections from the first area may be processed to create images of speckle patterns. Even at fast exposure times, such as 10 ms, the velocity of motion of the skin may be sufficient to make the speckle pattern change during each frame so that the bright pixels are blurred and washed out. The degree of speckle blur of a given spot in a given frame, as manifested by the loss of contrast in the image, for example, may be indicative of the instantaneous velocity of motion of the skin in the small area of the cheek under the spot. Processing the reflections from the first area may also include extracting quantitative image features from the images of speckle patterns. Vectors of these features, extracted from successive image frames, may be input to a neural network in order to ascertain the communication. Details of neural network architectures and training algorithms that may be used for this purpose are described elsewhere in this disclosure. An example feature that may be extracted for the purpose of ascertaining the communication may include speckle contrast. Any suitable measure of contrast may be used for this purpose, for example, the mean square value of the luminance gradient taking over the area of the speckle pattern. High contrast in the speckle pattern of a given spot from the first area may be indicative that the corresponding location of the cheek is stationary, while reduced contrast may be indicative of motion. The contrast decreases with increasing velocity of motion. Contrast features of this sort may be typically extracted from multiple spots distributed over the first area. Additionally, or alternatively, other features may be extracted from the speckle images and input to the neural network. Examples of such features may include total brightness of the speckle pattern and orientation of the speckle pattern, for instance, as computed by a Sobel filter. By way of one example, subvocalization deciphering module 708 in FIG. 7 may be used for processing the reflections from the first area to ascertain the communication.

Consistent with some disclosed embodiments, the communication ascertained from the reflections from the first area includes words articulated by the individual. "Ascertaining words articulated by the individual" refers to understanding words that are either vocalized or subvocalized by the individual. By processing the signals resulting from reflections, words can be ascertained as discussed elsewhere herein. By way of example, the word "Hello" in FIG. 11 represents the words articulated by individual 102A or individual 102B that may be ascertained from the reflections from the first area.

Consistent with some disclosed embodiments, the communication ascertained from the reflections from the first area includes non-verbal cues of the individual. The term "non-verbal cues" refers to the various forms of communication that occur without the use of spoken words. Some examples of non-verbal cues may include facial expressions, body language, gestures, eye contact, tone of voice, postures, and other subtle signals that convey meaning in interpersonal interactions. For example, non-verbal cues, such as facial expressions, may be used to communicate basic emotions like happiness, sadness, anger, fear, surprise, and disgust. As discussed elsewhere in this disclosure, the at least one processor may determine a non-verbal cue by analyzing reflection signals representing facial skin micromovements in the first facial area. By way of example, the emoji in FIG. 11 represents the non-verbal cues that may be ascertained from the reflections from the first area.

Some disclosed embodiments involve, based on the determination that the reflections from the first area are a stronger indicator of communication, ignoring the reflections from the second area. In this context, the term "ignoring the reflections" means that the processing actions on the signals representing the received reflections from the second area are less than the processing actions on the signals representing the received reflections from the first area. In one embodiment, signals representing the received reflections from the second area may be filtered, amplified, and analyzed to determine the second facial skin movements, but some quantitative features may not be extracted because the communication may not be ascertained from signals representing the received reflections from the second area. In another embodiment which also involves "ignoring," during a first time frame, reflections from both the first area and the second area may be processed to determine which area is closer to the zygomaticus muscle or the risorius muscle. Thereafter, during a subsequent second time frame, and upon determining that the first area is closer to the zygomaticus muscle or the risorius muscle, reflections from the second area may be automatically discarded.

According to some disclosed embodiments, ignoring the reflections from the second area includes omitting use of the reflections from the second area to ascertain the communication. The term "omitting use" refers to not using information associated with reflections from the second area when determining the meaning of the communication.

By way of example with reference to the two uses cases depicted in FIG. 11, reflection image 1102A may be processed to ascertain communication 1106 from facial skin movements 1104A associated with the zygomaticus muscle or the risorius muscle, and reflection image 1102B may ignored, e.g., not used or omitted in ascertaining the communication. As depicted, the ascertained communication may include at least one word 1106A (articulated silently or vocally by individual 102A or individual 102B) and/or at least one facial expression 1106B that serves as an example of a non-verbal cue.

Some disclosed embodiments involve determining, based on differences between the first facial skin movements and the second facial skin movements, that the first area is closer than the second area to the subcutaneous tissue associated with cranial nerve V or with cranial nerve VII. The term "subcutaneous tissue" refers to the layer of tissue located beneath the skin and above the underlying muscles and bones. It is composed of fat cells, connective tissue, blood vessels, nerves, and other structures. Cranial nerve V, also known as the trigeminal nerve, is a sensory nerve for the face that control of jaw muscles. Cranial nerve VII controls facial expressions and carries taste sensation from the front of the tongue. Based on differences between the first facial skin movements and the second facial skin movements (as described above), a determination may be made that the first area is closer than the second area to the subcutaneous tissue associated with cranial nerve V or with cranial nerve VII.

Some disclosed embodiments involve operating a coherent light source in a manner enabling bi-mode illumination of the plurality of facial region areas. The term "coherent light source" may be understood as described elsewhere in this disclosure. Operating a coherent light source in this context refers to regulating, supervising, instructing, allowing, and/or enabling the coherent light source to illuminate at least part of a face. For example, the coherent light source may be controlled to illuminate a region of a face in a specific mode of illumination when turned on in response to a trigger. Bi-mode illumination refers to a capability of the coherent light source to illuminate an object using at least two different modes of illumination. The term "mode of illumination" refers to a specific configuration or settings of the coherent light source. Each of the two modes may be associated with different values of illumination parameters, such as light intensity, illumination pattern, pulse frequency, duty cycle, light flux. Light source 410 in FIG. 4 is one example of either a single mode or multi-mode (e.g., bi-mode) light source.

In some disclosed embodiments, a first light intensity of the first mode of illumination differs from a second light intensity of the second mode of illumination. In some disclosed embodiments, a first illumination pattern of the first mode of illumination differs from a second illumination pattern of the second mode of illumination. Light intensity refers to a brightness level of an illumination and an illumination pattern refers to an arrangement, distribution, or sequence of coherent or non-coherent light emitted from a source or reflected off a surface. The light pattern may be created by a specific design, shape, or configuration of light sources to create a particular visual or non-visual effect on the portion of the face. Examples of illumination patterns may include a grid of light spots having the same size, a grid of light spots having the various sizes, a single light spot, or any other pattern.

Some disclosed embodiments involve analyzing reflections associated with a first mode of illumination to identify one or more light spots associated with the first area, and analyzing reflections associated with a second mode of illumination to ascertain the communication. The term "identifying one or more light spots associated with the first area" means determining which of the light spots projected by the coherent light source are located in the first area. For example, identifying the one or more light spots associated with the first area may be implemented by comparing light intensity at a particular location with boundaries of the first area, based on image analysis of the face of the individual, or by any other processing method. In one example, the first mode of illumination may include a first illumination pattern (e.g., 64 light spots) and the second mode of illumination may include a second illumination pattern (e.g., 32 light spots). By way of example, with reference to the first example use case depicted in FIG. 11, the first mode of illumination may be used to identify eight light spots included within first area 1100A associated with the zygomaticus muscle. Thereafter, the second mode of illumination (e.g., 4 light spots) may be used to illuminate first area 1100A in a manner that enables ascertaining the communication from received reflections.

Consistent with some disclosed embodiments, the first area is closer than the second area to the zygomaticus muscle, and the plurality of areas further include a third area closer to the risorius muscle than each of the first area and second area. The terms "plurality of areas" and "closer to" may be understood as described elsewhere in this disclosure. By way of example with reference to FIG. 12, the plurality of facial areas 1100 includes the first area 1100A closer to the zygomaticus muscle than second area 1100B, and a third area 1100C closer to the risorius muscle than each of the first area 1100A and second area 1100B. In some disclosed embodiments, based on a determination that individual 102C is engaged in silent speech, a processing device of the speech detection system may process the reflections from the first area 1100A to ascertain the communication, and ignore the reflections from the second area 1100B and the third area 1100C. In other embodiments, based on a determination that individual 102C is engaged in voiced speech, a processing device of the speech detection system may process the reflections from third area 1100C to ascertain the communication, and ignore the reflections from the second area 1100B and the first area 1100A.

Some disclosed embodiments involve analyzing reflected light from the first area when speech is generated with perceptible vocalization (i.e., voiced speech) and analyzing reflected light from the third area when speech is generated in an absence of perceptible vocalization (i.e., silent speech). In other words, rather than monitoring the entire cheek and processing reflections from a plurality of areas, the speech detection system may process reflections received from a subset of the cheek area (e.g., only a few square millimeters or centimeters) in these two areas to detect both silent and voiced speech. Furthermore, when the plurality of areas are illuminated by multiple light sources (e.g., an array of laser diodes) only the light sources that illuminate these two areas may be actuated, thus reducing power consumption. If a large movement of the speech detection system relative to the skin is detected, a different set of light sources may be actuated. In some disclosed embodiments, different modes of processing may be applied to ascertain silent speech from voiced speech. For example, during silent speech, the first area being closer to the zygomaticus muscle may exhibit movements with a velocity on the order of one to ten μm/ms. Therefore, features of the images of the speckles themselves may change rapidly, and these features may be analyzed to generate an output. But during voiced speech, the third area being closer to the risorius muscle may exhibit movements on the order of 0.5-2 mm. Thus, the locations of the spots on the cheek may shift laterally due to the movement of the cheek. In this case, the lateral movements of the spots may be indicative of changes in the distance of the spots from the speech detection system, which may thus function as a sort of depth sensor. The two processing modes—speckle sensing and depth sensing—may be used individually in detecting silent and voiced speech, respectively. Alternatively, or additionally, these two processing modes may be used together to improve the precision and specificity of measurement, for example, by applying measurements of voiced speech by a given user to learn the patterns of microscopic movement that will occur in silent speech by the same user.

Figure 13:
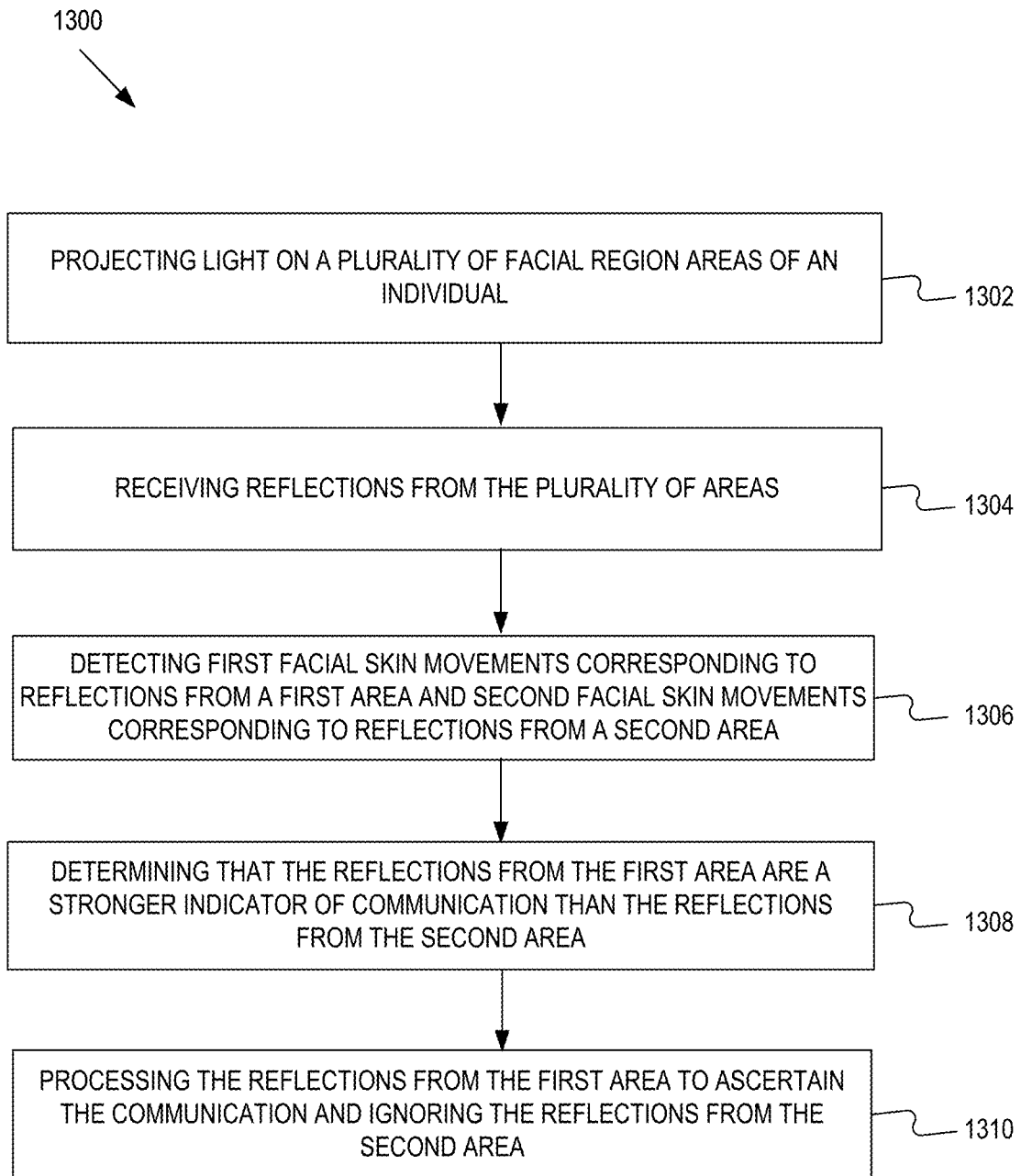
FIG. 13 is a flowchart of an example process for interpreting facial skin movements, consistent with some embodiments of the present disclosure.

FIG. 13 illustrates a flowchart of an exemplary process 1300 for identifying individuals using facial skin micro-movements, consistent with embodiments of the present disclosure. In some disclosed embodiments, process 1300 may be performed by at least one processor (e.g., processing device 400 or processing device 460) to perform operations or functions described herein. In some disclosed embodiments, some aspects of process 1300 may be implemented as software (e.g., program codes or instructions) that are stored in a memory (e.g., memory device 402 or memory device 466) or a non-transitory computer-readable medium. In some disclosed embodiments, some aspects of process 1300 may be implemented as hardware (e.g., a specific-purpose circuit). In some disclosed embodiments, process 1300 may be implemented as a combination of software and hardware.

Referring to FIG. 13, process 1300 includes a step 1302 of projecting light on a plurality of facial region areas of an individual. For example, the at least one processor may operate a wearable coherent light source (e.g., light source 410) to illuminate at least a first area (e.g., first area 1100A) and a second area (e.g., second area 1100A). The first area may be closer to at least one of a zygomaticus muscle or a risorius muscle than the second area. Process 1300 includes a step 1304 of receiving reflections from the plurality of areas. For example, the at least one processor may operate at least one detector (e.g., at least one detector 412) to receive coherent light reflections (e.g., light reflections 300) from the plurality of areas 1100. Process 1300 includes a step 1306 of detecting first facial skin movements corresponding to reflections from a first area and second facial skin movements corresponding to reflections from a second area. For example, the at least one processor may use light reflections processing module 706 to detect the first facial skin movements, the second facial skin movements corresponding to reflections from the second area. Process 1300 includes a step 1308 of determining that the reflections from the first area are a stronger indicator of communication than the reflections from the second area. For example, the determination of step 1308 may be based on differences between the first facial skin movements and the second facial skin movements. Process 1300 includes a step 1310 of processing the reflections from the first area to ascertain the communication and ignoring the reflections from the second area. For example, the determination of step 1310 may be based on the determination that the reflections from the first area are a stronger indicator of communication. At least one word 1106A and at least one facial expression 1106B are examples of the ascertained communication.

The embodiments discussed above for interpreting facial skin movements may be implemented through non-transitory computer-readable medium such as software (e.g., as operations executed through code), as methods (e.g., process 1300 shown in FIG. 13), or as a system (e.g., speech detection system 100 shown in FIGS. 1-3). When the embodiments are implemented as a system, the operations may be executed by at least one processor (e.g., processing device 400 or processing device 460, shown in FIG. 4).

In some embodiments, an authentication or identity verification service provider uses biometrics, such as signals indicative of facial skin micromovements of an individual, for authentication purposes. For example, the authentication service provider may use the individual's facial skin micromovements to verify the identity of the individual. The intensity and order of muscle activation (e.g., muscle fiber recruitment) over the facial region of an individual differs between individuals. Muscle activation or recruitment is the process of activating motor neurons to produce various levels of muscle contraction. Skin micromovements of an individual may be affected by the muscles, the structure of the muscle fibers, characteristics of the skin, characteristics of the sub skin (e.g., blood vessel structure, fat structure, hair structure, etc.), etc. The iris is an example of visible muscles of an individual. The iris is the colored tissue at the front of the eye that contains the pupil in the center and helps control the size of the pupil to let more or less light into the eye. While the iris of every individual is round, the structure of each individual's iris may be unique and may be stable through the life of the individual. This is the same for sub-skin muscles and their activations. Facial skin micromovements may create a unique biometric signature of an individual that may be used to identify an individual. For the sake of brevity, in the discussion below, facial skin micromovements may simply be referred to as facial micromovements. Institutions that require customer identity verification (a/k/a authentication) may subscribe to the authentication service provided by the provider to authenticate individuals (e.g., customers) before providing access to a service or a facility that the institution provides. Such institution may include financial institutions (e.g., banks and brokerage services), subscription services (e.g., that provide media content, research or other information), online gaming sites, other online platforms, government agencies, and other organizations that require user authentication and verification. or any other entity or service that desires customer authentication. Authentication is the process of verifying or validating the identity of an individual.

Some disclosed embodiments involve identity verification of an individual based on the individual's facial micromovements. The verification may occur via a system, computer readable media, or a method. The term "identity verification" is a process of determining who an individual is. It may also refer to a process of confirming or denying whether an individual is who that person claims to be. For example, in some embodiments, systems of the current disclosure may determine who an individual is based on that individual's facial micromovements. And in some embodiments, systems of the current disclosure may determine (e.g., confirm or deny) whether the individual is actually who he/she is purported to be based on the individual's facial micromovements.

Figure 14:
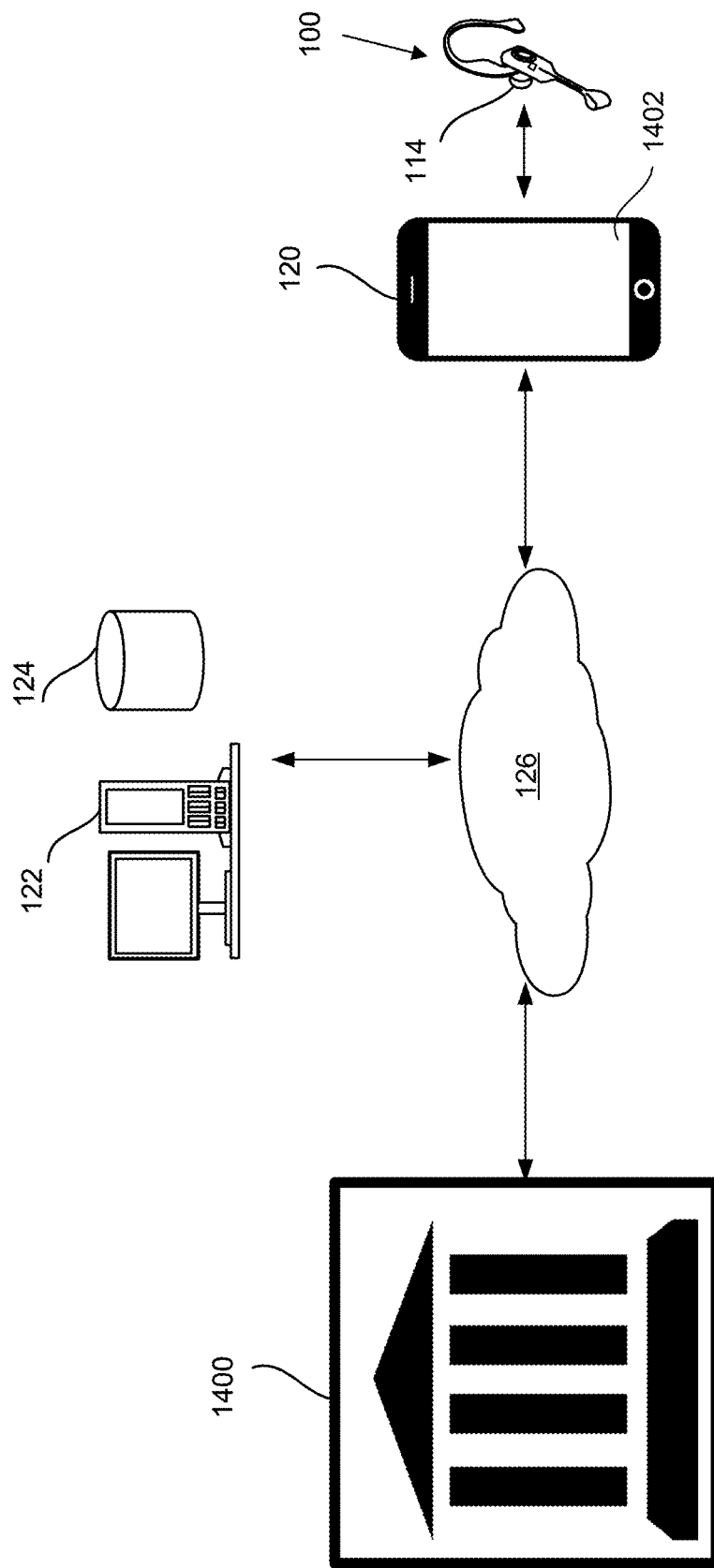
FIG. 14 is a schematic illustration of operation of an exemplary authentication service configured to provide identity verification of an individual based on facial micromovements consistent with some embodiments of the present disclosure.

FIG. 14 is a schematic illustration of one exemplary embodiment that includes a system for providing identity verification of an individual based on the individual's facial micromovements. As illustrated in FIG. 14 (and in FIGS. 1-4), a detection system 100 associated with an individual 102 may detect and communicate, e.g., directly or via mobile communications device 120, signals indicative (or representative) of the individual's facial micromovements to a cloud server 122 using a communications network 126. In some embodiments, as described elsewhere in this disclosure, server 122 may access data structure 124 to determine, for example, correlations between words and facial micromovements of the individual. In some embodiments, cloud server 122 may also be configured to verify the identity of the individual based on the received signals. In some embodiments, an authentication service provider (or an identity verification service provider) may use a system, such as server 122, for providing identity verification of the individual based on the individual's facial micromovements. In some embodiments, as shown in FIG. 14, an institution 1400 and a speech detection system 100 associated with an individual 102 may communicate with each other and cloud server 122 using communications network 126 to request and receive identity verification of the individual.

Figure 15:
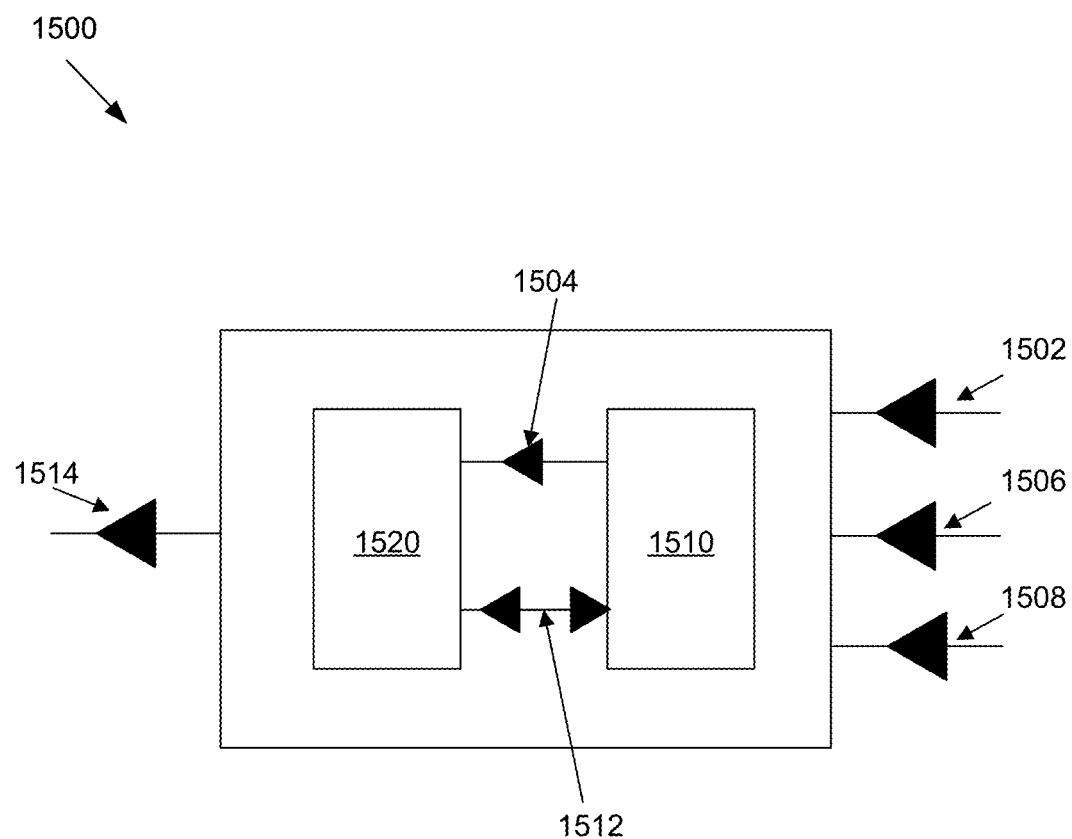
FIGS. 15, 16A and 16B are simplified illustrations of an exemplary system for identity verification of an individual using facial micromovements consistent with some embodiments of the present disclosure.
Figure 16A:
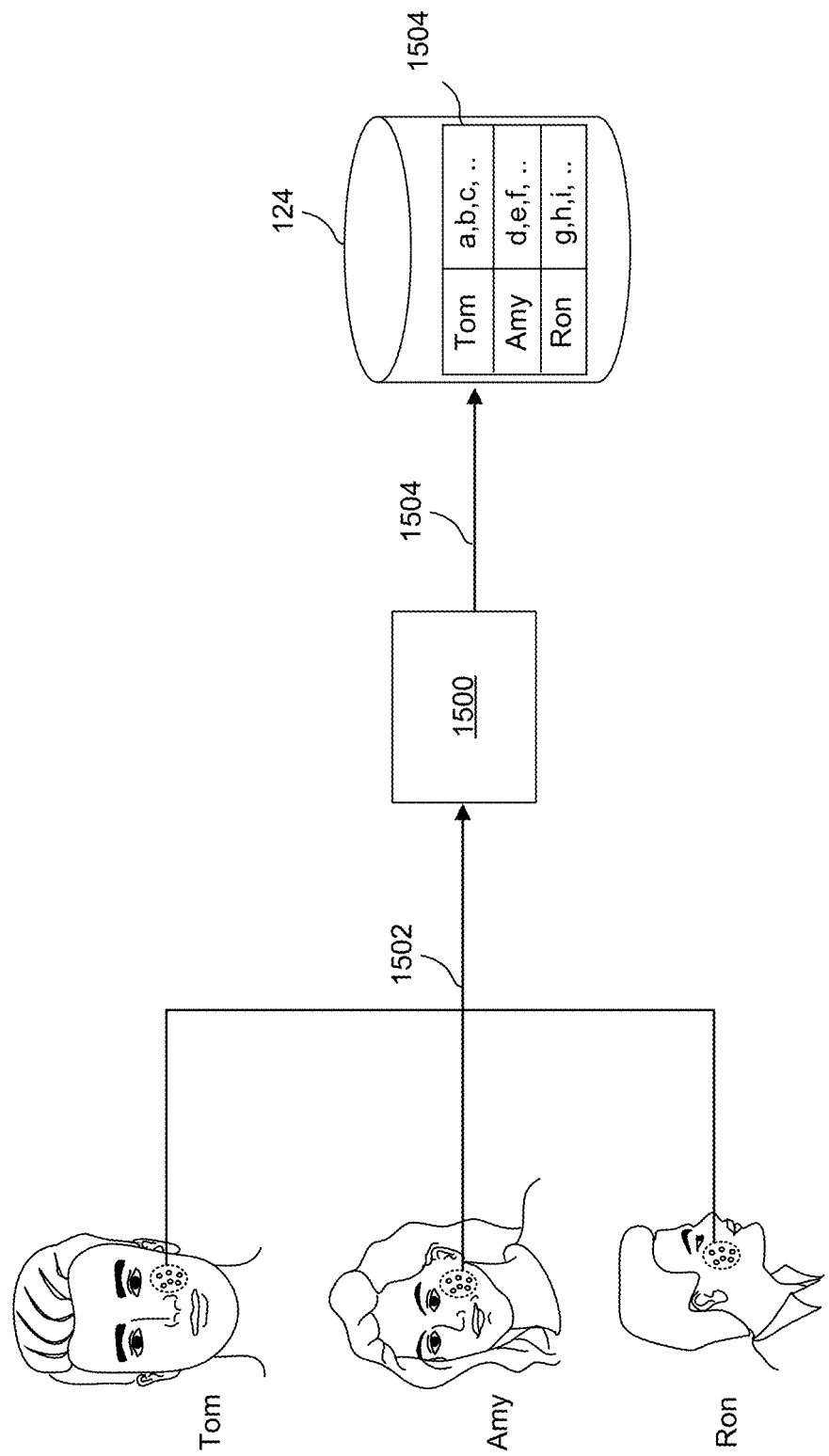
Figure 16B:
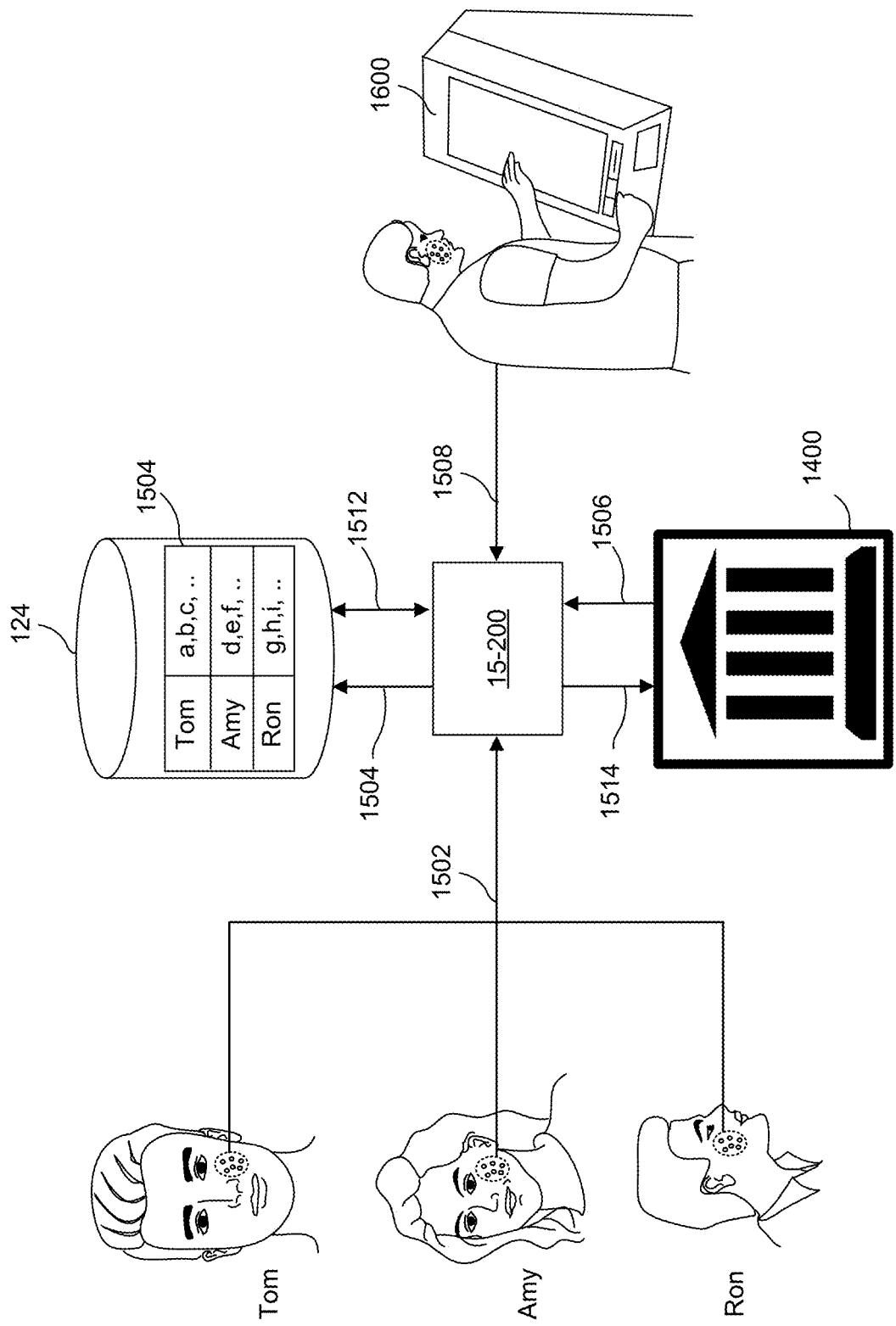

FIGS. 15, 16A, and 16B are simplified block diagrams showing different aspects of an exemplary system 1500 for providing identity verification (or identity authentication) based on facial skin micromovements (or facial micromovements) of an individual. It is to be noted that only elements of authentication system 1500 that are relevant to the discussion below are shown in these figures. Embodiments within the scope of this disclosure may include additional elements or fewer elements. As shown in FIG. 15, system 1500 includes a processor 1510 and a memory 1520. Although only one processor and one memory are illustrated in FIG. 15, in some embodiments, processor 1510 may include more than one processor and memory 220 may include multiple devices. These multiple processors and memories may each be of similar or different constructions and may be electrically connected or disconnected from each other. Although memory 1520 is shown separate from processor 1510 in FIG. 15, in some embodiments, memory 1520 may be integrated with processor 1510. In some embodiments, memory 1520 may be remotely located from system 1500 and may be accessible by system 1500. Memory 1520 may include any device for storing data and/or instructions, such as, for example, a Random Access Memory (RAM), a Read-Only Memory (ROM), a hard disk, an optical disk, a magnetic medium, a flash memory, other permanent, fixed, or volatile memory. In some embodiments, memory 1520 may be non-transitory computer-readable storage medium that stores instructions that when executed by processor 1510 causes processor 1510 to perform identity verification operations based on facial micromovements. In some embodiments, some or all the functionalities of processor 1510 and memory 1520 may be executed by a remote processing device and memory (for example, processing device 400 and memory device 402 of remote processing system 450, see FIG. 4).

Some disclosed embodiments involve receiving in a trusted manner, reference signals for verifying correspondence between a particular individual and an account at an institution. The term "receiving" may include retrieving, acquiring, or otherwise gaining access to, e.g., data. Receiving may include reading data from memory and/or receiving data from a computing device via a (e.g., wired and/or wireless) communications channel. At least one processor may receive data via a synchronous and/or asynchronous communications protocol, for example by polling a memory buffer for data and/or by receiving data as an interrupt event. The term "signals" or "signal" may refer to information encoded for transmission via a physical medium or wirelessly. Examples of signals may include signals in the electromagnetic radiation spectrum (e.g., AM or FM radio, Wi-Fi, Bluetooth, radar, visible light, lidar, IR, Zigbee, Z-wave, and/or GPS signals), sound or ultrasonic signals, electrical signals (e.g., voltage, current, or electrical charge signals), electronic signals (e.g., as digital data), tactile signals (e.g., touch), and/or any other type of information encoded for transmission between two entities via a physical medium or wirelessly (e.g., via a communications network).

In some embodiments, the signals may include, or may be representative of, "speckles," reflection image data, or light reflection analysis data (e.g., speckle analysis, pattern-based analysts, etc.) described elsewhere in this disclosure.

Receiving signals in a "trusted" manner refers to receiving reliable signals. For example, receiving the signals in a manner such that the truth and/or validity of the signals can be relied upon. In some embodiments, when receiving signals in a trusted manner, there may be some level of assurance that the signals are valid or are what they are expected to be. In some embodiments, receiving signals in a trusted manner may indicate that these signals are transmitted in a secure manner such that the signals may not be easily intercepted by and/or deciphered by a third party. In general, signals may be sent and received in a trusted manner using any known secure transmission method. In some embodiments, receiving signals in a trusted manner may refer to receiving encrypted signals. The signals may be encrypted using any now-known or later-developed encryption technology (e.g., Wired Equivalent Privacy (WEP), Wi-Fi Protected Access (WPA), Wi-Fi Protected Access Version 2 (WPA2), Wi-Fi Protected Access Version 3 (WPA3), etc.). In some embodiments, the encrypted signals may include (one or more) keys that may be used to decrypt the encrypted signals by methods known in the art.

As used herein, the term "reference signals" refers to signals that are used as the basis for ascertaining something. For example, the reference signals may be baseline signals used for comparison purposes, e.g., to determine if a characteristic of the signal has changed. In some embodiments, the reference signals may be representative of one or more properties or characteristics of an individual. For example, the reference signals may be representative of one or more properties/characteristics of the facial micromovements of an individual. In some embodiments, the reference signals may be (or may be a representation of) a speckle pattern (e.g., reflection image 600 of FIG. 6) or another light reflection pattern output by speech detection system 100 associated with an individual. In some embodiments, the reference signal may include, or may be representative of, one or more features of the facial micromovements of an individual. In some embodiments, the reference signal may be (or may include) characteristics or features extracted from a light reflection pattern of the individual. In some embodiments, one or more algorithms may be used to extract these characteristics or features of an individual's facial micromovements that are embodied in the reference signals. These extracted features may include fiducial and/or non-fiducial features. Fiducial features may include measurable characteristics of the individual's facial micromovements (e.g., temporal or amplitude onset, peak (minimum or maximum), offset, spacing, time difference between peaks, and other measurable characteristics). On the other hand, non-fiducial features extraction may apply time and/or frequency analysis to obtain statistical features of the individual's facial micromovements. In some embodiments, the reference signals may be representative of multiple biometric signals (e.g., a combination of facial micromovements along with one or more of pulse, cardiac signals, ECG, temperature, pressure, or other biometric signals) of an individual. It is also contemplated that, in some embodiments, the detected facial micromovement signals or the light reflection pattern output by speech detection system 100 may itself be used as the individual's reference signals.

The reference signals may be configured to enable verification of the correspondence between a particular individual and an account at an institution. The term "correspondence" refers to the degree of similarity, connection, equivalence, match, or connection. For example, in some embodiments, the reference signals of a particular individual may be used to determine the equivalence, similarity, match, or connection between that individual and an account (e.g., of a customer) of the institution. The institution may retain in an associative way, biometric or other data of a customer, and that data or related data may be contained within the reference signals. The term "institution" refers to any establishment or organization without limitation. In some embodiments, the institution may be an organization that provides some type of service, for example, to multiple individuals who may each have an account at the institution. In some embodiments, the institution may be a financial organization (e.g., a bank, stock brokerage, mutual fund, etc.) where multiple customers may have accounts (e.g., cash accounts, money market accounts, stock accounts, online accounts, safety deposit boxes, etc.). In some embodiments, the institution may be a company associated with online activity (e.g., gaming activity, betting activity, exam/test provider, education/class provider, etc.), or a university or education institution where multiple students have accounts (to access classes, billing statements, etc.). In some embodiments, the institution may be a health care provider (e.g., hospital, clinic, testing lab, etc.) or an insurance provider (e.g., insurance company) where multiple patients or customers have accounts, a company where multiple employees have accounts, etc. In other embodiments the institution may be a government agency or body. The reference signal may be received from any source (e.g., the individual, the institution, etc.).

In some embodiments, an institution may engage an authentication service provider and/or subscribe to the authentication service to verify the identity of an individual (or customer) in association with providing a service to the individual (for example, before allowing access to an account, etc.). The authentication service provider may use a system (such as system 1500 of FIGS. 15, 16A, and 16B) to verify the identity of the individual using the reference signals. In some embodiments, the system may have access to the reference signals of all the customers of the institution (e.g., all the account holders of a bank, all the students enrolled for a class at a university, etc.). For example, in some embodiments, as illustrated in FIG. 16, reference signals 1502 of all the customers (e.g., account holders) of an institution 1400 (e.g., a bank) may be sent to system 1500 (e.g., during enrollment). System 1500 may securely store correlations 1504 of the reference signals 1502 with the identity of the different customers in a secure data structure (such as data structure 124) accessible by system 1500. In some embodiments, the customer's name and/or other identifying information (account number, or other information that identifies the individual associated with the reference signals) may also be stored and associated with the reference data in the stored correlations 1504. As will be explained in more detail later, system 1500 may use the stored reference signals and correlations to authenticate individuals. For example, as illustrated in FIG. 16B, when an individual engages in a transaction (e.g., attempts to access a customer's account) with the institution 1400, the institution 1400 may request 1506 the authentication service provider (or system 1500) to authenticate the individual (e.g., verify the identity of the individual, confirm that the individual is the customer associated with the account, etc.). System 1500 may receive real-time facial micromovement signals 1508 of the individual when the individual is engaged in the transaction, and the system 1500 may compare 1512 the received real-time signals 1508 with the stored reference signals 1502 or correlations 1504 to determine whether the individual is a customer. For example, system 1500 may compare the two signals to determine if one or more characteristics of the received signals correspond to, or sufficiently match, characteristics of the stored reference signals to determine if the received signals are associated with a customer authorized to access the account.

Consistent with some disclosed embodiments, the reference signals may be derived based on reference facial micromovements detected using first coherent light reflected from a face of the particular individual. The term "reference" in "reference facial micromovements" indicate that these facial micromovements are used to generate the reference signals. As explained elsewhere in this disclosure, "coherent light" includes light that is highly ordered and exhibits a high degree of spatial and temporal coherence. As explained in detail elsewhere in this disclosure, when coherent light strikes the facial skin of an individual, some of it is absorbed, some is transmitted, and some is reflected. The amount and type of light that is reflected depends on the properties of the skin and the angle at which the light strikes it. For example, coherent light shining onto a rough, contoured, or textured skin surface may be reflected or scattered in many different directions, resulting in a pattern of bright and dark areas called "speckles." In some embodiments, when coherent light is reflected from the face of an individual, the light reflection analysis performed on the reflected light may include a speckle analysis or any pattern-based analysis to derive information about the skin (e.g., facial skin micromovements) represented in the reflection signals. In some embodiments, a speckle pattern may occur as the result of the interference of coherent light waves added together to give a resultant wave whose intensity varies. In some embodiments, the detected speckle pattern (or any other detected pattern) may be processed to generate reflection image data from which the reference signals may be generated.

As explained elsewhere in this disclosure with reference to FIGS. 1-6, speech detection system 100 associated with an individual may detect facial micromovements of the individual. For example, with specific reference to FIGS. 5-7, in some embodiments, speech detection system 100 may analyze reflections 300 of coherent light from facial region 108 of the individual to determine facial micromovements (e.g., amount of the skin movement, direction of the skin movement, acceleration of the skin movement, speckle pattern, etc.) resulting from recruitment of muscle fiber 520 and output signals representative of the detected facial micromovements. In some embodiments, the determined facial skin micromovements may correspond to muscle activation.

Consistent with some disclosed embodiments, the reference signals for authentication may correspond to muscle activation during pronunciation of at least one word. The term "authentication" (and other constructions of this term such as authenticate) refers to determining the identity of an individual or to determining whether an individual is, in fact, who the individual purports to be. In some embodiments, authentication is a security process that relies on the unique characteristics of individuals to identify who they are or to verify they are who they claim to be. For example, authentication may be a security measure that matches the biometric features of an individual, for example, looking to access a resource (e.g., a device, a system, a service). As used herein, the term "pronunciation" (or other constructions such as pronounces, pronouncing, etc.) refers to when the individual actually utters (or vocalizes) the at least one word (or a syllable, etc.) or before the individual actually utters the word(s) (e.g., during silent speech or pre-vocalization). As explained elsewhere in this disclosure, speech-related muscle activity occurs prior to vocalization (e.g., when air flow from the lungs is absent but the facial muscles articulate the desired sounds, when some air flows from the lungs but words are articulated in a manner that is not perceptible using an audio sensor, etc.). For example, with reference to FIGS. 15, 16A, and 16B, reference signals 1502 that may be used for verifying correspondence between a particular individual and an account at an institution may correspond to signals caused by muscle activation that occurs during vocalization or prior to vocalization (e.g., during silent speech) of the at least one word. It should be noted that real-time signals 1508 (described below) may also be generated in a similar manner.

Some disclosed embodiments involve muscle activation associated with at least one specific muscle that includes a zygomaticus muscle, an orbicularis oris muscle, a risorius muscle, a genioglossus muscle, or a levator labii superioris alaeque nasi muscle. "Muscle activation" refers to tension, force, and/or movement of a muscle. Such activation may occur when the brain recruits the muscle. In some embodiments, as explained elsewhere in this disclosure, muscle activation or muscle recruitment is the process of activating motor neurons to produce muscle contraction. As also explained elsewhere in this disclosure, facial skin micromovements include various types of voluntary and involuntary movements (for example, that fall within the range of micrometers to millimeters and a time duration of fractions of a second to several seconds) caused by muscle recruitment or muscle activation. Some muscles such as the quadriceps (which is powerful muscle group responsible for displaying force very quickly) have a high ratio of muscle fibers to motor neurons. Other muscles such as the eye muscles, have much lower ratios as they use more precise, refined movement leading to small-scale skin deformations. As explained elsewhere in this disclosure, the zygomaticus muscle, the orbicularis oris muscle, the risorius muscle, the genioglossus muscle, and the levator labii superioris alaeque nasi muscle may articulate specific points in the individual's cheek above mouth, chin, mid-jaw, cheek below mouth, high cheek, and the back of the cheek. In some embodiments, the reference signals for authentication may be based on facial micromovements detected (e.g., based on reflections of coherent light) from the face of the individual when the individual is engaged in normal activity (e.g., speaking normally, silently reading something, etc.). In some embodiments, the reference signals may be generated based on facial skin micromovements when the individual speaks or silently speaks (pronounces, articulates, enunciates, etc.) selected word(s), syllable(s), or phrases.

Consistent with some disclosed embodiments, the identity verification operations may further include presenting the at least one word to the particular individual for pronunciation. As used herein, the term "presenting" refers generally to making something known. For example, in some embodiments, the individual may be presented with a word by visually displaying the word to the individual and the individual may attempt pronounce the displayed word. In some embodiments, the word or words may also be audibly presented to the individual and the individual may repeat or attempt to repeat the word and signals may be generated when the individual vocalizes the presented word(s) or prior to vocalization of the word(s). In some embodiments, one or more figures representing one or more words (e.g., dog, cat) may be presented to the individual for pronunciation.

For example, the individual may be presented with one or more words (a word, a sentence, etc.) to pronounce, and reference signals 1502 (and/or real-time signals 1508) may be generated based on facial micromovements resulting from the individual pronouncing one or more of the presented words or one or more syllables in the word(s). The one or more words may be presented to the individual for pronunciation in any manner and on any device. For example, with reference to FIG. 14, in some embodiments, the word(s) used to generate reference signals 1502 (and/or real-time signals 1508) may be displayed to the individual textually on a display screen 1402 of mobile communications device 120, and reference signals 1502 (and/or real-time signals 1508) may be generated when the user pronounces the displayed word(s). In some embodiments, the at least one word may be graphically presented to the user. For example, an image (e.g., picture, cartoon, etc.) representing a word (e.g., dog, cat, etc.) may be displayed to the individual and reference signal 1502 (and/or real-time signals 1508) may be generated when the individual pronounces the word represented by the image. In general, any word (e.g., a random word) or words may be presented to the individual to pronounce.

Consistent with some disclosed embodiments, presenting the at least one word to the particular individual for pronunciation includes textually presenting the at least one word. For example, presenting the word "dog" may be presented by textually displaying the word "dog." In some embodiments, presenting the word "dog" may occur by graphically showing an image (picture, cartoon, line drawing, or another similar pictorial display) of a dog. For example, the individual may be presented with one or more words (a word, a sentence, etc.) to pronounce, and reference signals 1502 (and/or real-time signals 1508) may be generated based on facial micromovements resulting from individual pronouncing one or more of the presented words or one or more syllables in the word(s). One or more words may be presented to the individual for pronunciation in any manner and on any device. For example, in some embodiments, the word(s) may be displayed to the individual textually on a display screen 1402 of mobile communications device 120, and reference signals 1502 (and/or real-time signals 1508) may be generated when the user pronounces the displayed word(s). In some embodiments, the at least one word may be graphically presented to the user. For example, an image (e.g., picture, cartoon, etc.) representing a word (e.g., dog, cat, etc.) may be displayed to the individual and reference signal 1502 (and/or real-time signals 1508) may be generated when the individual pronounces the word represented by the image. In general, any word (e.g., a random word) or words may be presented to the individual to pronounce.

Consistent with some disclosed embodiments, presenting the at least one word to the particular individual for pronunciation includes audibly presenting the at least one word. For example, one or more word may be presented to an individual by audibly sounding the word(s), for example, on a speaker. For example, with reference to FIG. 16, when an individual is setting up an account at an institution, one or more words may be presented to the individual to pronounce and the reference signals 1502 may be generated based on the resulting facial micromovements. As another example, when engaging in a transaction (e.g., setting up an account or trying to access an account) with institution 1400 using mobile communications device 120, the word(s) used to generate the reference signal 1502 (and/or the real-time signals 1508) may be audibly presented to the individual using a speaker of device 120, the output unit 114 of speech detection system 100, or another speaker. And the speech detection system 100 associated with the individual may generate reference signals 1502 (and/or the real-time signals 1508) based on muscle activation when the user pronounces the word(s) or one or more syllables in the word(s).

It should be noted that although mobile communications device 120 is described as being used to audibly, textually, and/or graphically display the word(s) used to generate reference signals 1502 and/or the real-time signals 1508 to the individual, this is merely exemplary. In general, the word(s) may be presented to the individual on any device. For example, in some embodiments, the words may be visually (e.g., textually, graphically, etc.) presented on a screen 1600 (see FIG. 16B) of any device that the individual has access to (e.g., a visual display of, e.g., a smartphone, a tablet, a smartwatch, a personal digital assistant, a desktop computer, a laptop computer, an Internet of Things (IoT) device, a dedicated terminal, a wearable communications device, VR/XR glasses, etc.). Similarly, the words may be audibly presented to the individual on any device (e.g., a speaker of any one of the devices described above, etc.). It is also contemplated that in some embodiments, instead of presenting the word(s) used to generate the reference and/or real-time signals 1502, 1508 to the user, a question or a prompt that generates the word(s) may be presented (e.g., audibly, textually, graphically, etc.) to the user. For example, a query such as, for example, "what is your password?" "what is the city of your birth?" etc. may be presented to the individual, and reference signals 1502 (and/or real-time signals 1508) may be generated from the response. In some embodiments, both the reference signals 1502 and the real-time signals 1508 may be generated by presenting the same word(s) or syllable(s) to the individual to pronounce.

Consistent with some disclosed embodiments, the presented at least one word may be a password. In general, a "password" may be any word or a string of characters. In some embodiments, the password may be a string of characters, one or more words, or a phrase that must be used to gain admission to something. For example, when an individual sets up an account at an institution, the individual may be asked to pronounce (e.g., vocalize or prevocalize) a password for the account, and reference signals 1502 may be generated based on the resulting facial micromovements. As another example, in an embodiment where the individual is trying to access a customer's account at a financial institution, the individual may be asked to pronounce the password associated with the account, for example, by presenting a query (e.g., "what is your password?"). And, reference signal 1502 and/or real-time signals 1508 may be generated based on reflections of coherent light from the individual's face when the individual pronounces the password.

In some embodiments, the reference signals for authentication may correspond to muscle activation during pronunciation of one or more syllables. For example, the reference signals may be generated when the individual pronounces (vocalizes or pre-vocalizes) a syllable, such as, for example, a vowel or any other syllable. Although not a requirement, in some embodiments, one or more syllables (e.g., vowels or any other characters), or one or more words containing the syllables, may be presented to the individual and the reference signals 1502 (and/or real-time signals 1508) for authentication may be generated by system 1500 based on facial micromovements when the individual pronounces the one or more syllables.

Some disclosed embodiments involve storing, in a secure data structure, a correlation between an identity of the particular individual and the reference signals reflecting the facial micromovements. A "secure data structure" is a location where data or information may be stored securely without being subject to unauthorized access. Unauthorized access may include access by members within an organization (e.g., institution, authentication service provider, etc.) not authorized to access the stored data or access by members outside the organization. A data structure consistent with the present disclosure may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, which may be owned or operated by the same or different entities. Thus, the term "data structure" as used herein in the singular is inclusive of plural data structures.

In some embodiments, the secure data structure may be a secure database. The stored information may be encrypted in the secure data structure. As explained elsewhere in this disclosure, the term "database" may be a collection of data that may be distributed or non-distributed. In some embodiments, the secure data structure may be a secure enclave (also known as Trusted Execution Environment). A secure enclave is a computing environment that provides isolation for code and data from the operating system using either hardware-based isolation or isolating an entire virtual machine by placing the hypervisor within the Trusted Computing Base (TCB). A trusted computing base (TCB) may be a computing system that provides a secure environment for operations. This includes its hardware, firmware, software, operating system, physical locations, built-in security controls, and prescribed security and safety procedures. A hypervisor, also known as a virtual machine monitor or VMM, is software that creates and runs virtual machines (VMs). A hypervisor allows one host computer to support multiple guest VMs by virtually sharing its resources, such as memory and processing. Even users with physical or root access to the machines and operating system may not be able to access the contents of the secure enclave or tamper with the execution of code inside the enclave. A secure enclave provides CPU hardware-level isolation and memory encryption on a server by isolating application code and data and encrypting memory. Secure enclaves are at the core of confidential computing. In some embodiments, sets of security-related instruction codes may be built into the processors to protect the stored data. The data in the security enclave may be protected because the enclave is decrypted on the fly only within the processor, and then only for code and data running within the enclave itself. With suitable software, a secure enclave may enable the encryption of stored data and provide full stack security to the stored data. In some embodiments, secure enclave support may be incorporated into the one or more processors of system 1500 (such as processor 1510). In some embodiments, the secure data structure may include encrypted key/value storage. The secure data structure may, in some embodiments, be on a dedicated chip, in a separate IC circuit, or on part of processor 1510. In some embodiments, the secure data structure may include remote authentication. For example, corresponding authentication keys may be stored locally on system 1500 and on a remote server, and access may be provided to the stored database based on a successful comparison of the two authentication keys.

Consistent with some disclosed embodiments, a correlation between an identity of the particular individual and the reference signals (reflecting the facial micromovements of that individual) may be stored in the secure data structure. "Correlation" refers to a relationship or a connection between the identity of an individual and that individual's reference signals. For example, the correlation is a measure that expresses the extent to which the two are related. In some embodiments, a representation (or a signature) of the received reference signals of the individual may be stored as the correlation. Although not a requirement, in some embodiments, the stored signature may be reduced size version of the received reference signals. In some embodiments, an encrypted version of the signature may be stored in the secure data structure. A "hash" of the received reference signal may be stored as the correlation in some embodiments. As would be recognized a person of ordinary skill in the art, a hash is a unique digital signature generated from an input signal (e.g., the received reference signals reference signals) using, for example, commercially available algorithms. A hashed/encrypted signature of the individual may be stored as the correlation, for example, in a secure data structure to reduce the possibility of unauthorized access to the data. In some embodiments, the correlation may be, or include, features or characteristics of the reference signals extracted, for example, using feature extraction algorithms. In some embodiments, the correlation may include significant information or landmarks (e.g., position and orientation of peaks and/or valleys, spatial and/or temporal gap between peaks and/or valleys) in the reference signals. In some embodiments, encrypted reference signals themselves may be stored as the correlation. Since the stored correlation is a representation of the individual's facial micromovements that are affected by that individual's person traits (e.g., muscle fiber structure, blood vessel structure, tissue structure, etc.), the stored correlation may uniquely identify the individual that the reference signals correspond to. In some embodiments, the correlation may include the identity (e.g., name, account number, or other identifying information) of the individual that the reference signal corresponds to or is associated with. In one exemplary embodiment, as illustrated in FIG. 15, system 1500 stores a correlation 1504 of the reference signals 1502 of an individual in a secure data structure in memory 1520. As illustrated in FIGS. 16A and 16B, in another exemplary embodiment, system 1500 stores correlations 1504 of different individual's (e.g., Tom, Amy, Ron, etc.) reference signals 1502 in a secure data structure in a remote database (e.g., data structure 124).

Some disclosed embodiments involve, following storing, receiving via the institution, a request to authenticate the particular individual. As described earlier, the term "authenticate" refers to determining the identity of an individual or to determining whether an individual is, in fact, who the individual (implicitly or explicitly) purports to be. In some embodiments, authentication is a security process that relies on the unique characteristics of individuals to identify who they are or to verify they are who they claim to be. For example, authentication is a security measure that matches the biometric features of an individual, for example, looking to access a resource (e.g., a device, a system, a service). In some embodiments, access to the resource is granted only when the biometric features of the individual match those stored in the secure data structure for that particular individual. Consistent with its common usage, the term "request" is asking for something. In some embodiments, the request may be an electronic or a digital signal. For example, in some embodiments, as illustrated in FIGS. 15, 16A and 16B, system 1500 may receive a request 1506 for authentication of an individual. In some embodiments, the request 1506 may originate from the institution (e.g., institution 1400) that the individual is engaged in a transaction with. In some embodiments, the individual may send the request 1506 to the institution (e.g., as part of the transaction) and the institution may forward the request to system 1500.

In some embodiments, institution 1400 may send a request 1506 to the authentication service provider to authenticate an individual when it receives (or in response to) a request for a transaction from the individual. Without limitation, the transaction may include any type of interaction between two parties (e.g., the individual and institution 1400). In some embodiments, the transaction between the individual and institution 1400 may include a request from the individual to the institution 1400 to take some sort of action (e.g., request for information, request to access an account, request to transfer funds, etc.).

Consistent with some disclosed embodiments, the authentication is associated with a financial transaction at the institution. As explained elsewhere in this disclosure, the term "transaction" refers to any type of interaction between two parties (e.g., the individual and the institution). For example, an individual may request access to a customer's account in a financial institution (e.g., bank, stock brokerage, etc.), and in response to that request, the institution may request the authentication service to authenticate the individual (e.g., to verify that the individual who requested access is the customer associated with the account) before allowing the individual to access to the account and conduct another transaction. Authentication may be sought by the institution when the individual seeks to conduct any type of transaction. Consistent with some embodiments, the financial transaction includes at least one of: a transfer of funds, a purchase of stocks, a sale of stocks, an access to financial data, or access to an account of the particular individual. For example, an individual may attempt to trade stock from an account at a stock brokerage, transfer funds out of the account, or view financial statements, and the brokerage may send a request for authentication of the individual to system 1500.

Any type of institution may use the disclosed system and authentication service. Consistent with some embodiments, the institution is associated with an online activity, and upon authentication, the particular individual is provided access to perform the online activity. The term "online activity" may refer to any activity performed using the internet or other computer network. For example, when an individual wants to log into and/or trade stock in a customer's account at an online stock brokerage (or other financial institution), the individual may be allowed to continue with the transaction if (only if in some embodiments) the system indicates (in response to the request to authenticate) that the individual is the customer or an individual authorized to operate the account. The institution may be involved in providing any type of online activity to individuals. Consistent with some embodiments, the online activity is at least one of: a financial transaction, a wagering session, an account access session, a gaming session, an exam, a lecture, or an educational session. For example, in some embodiments, the institution involved with the online activity may be an online brokerage that permits multiple individuals to log into their respective online accounts and trade (e.g., buy, sell, etc.) stock. In another embodiments, the institution may be an online betting or a wagering service that allows individuals to log into their respective accounts and place bets (on games, races, etc.). And in some embodiments, the institution may be a university that offers online classes where student can log into their accounts and attend the classes they registered for. In each of these cases, when an individual attempts to log into an account at the institution (e.g., to trade stock, place bets, attend classes, and other do other online transactions), the institution may send a request 1506 to the authentication service or system 1500 to confirm that the individual attempting to log into the account is the person who is associated with the account before allowing the individual to log in.

Consistent with some embodiments, the institution is associated with a resource, and upon authentication, the particular individual is provided access to the resource. As used herein, a "resource" may be anything that may satisfy a need of the of the individual. In some embodiments, resource may be physical or virtual property. For example, a resource may be money in a bank account, stocks in a trading account, documents stored in a computer system, online classes offered by a university, a secure room such as, for example, an access controlled room, or other property. In some embodiments, an individual may seek to access the resource and the institution (maintaining or controlling the resource may send a request 1506 to the authentication service or system 1500 to check whether the individual seeking access is authorized to access the resource. And, if and when the system 1500 authenticates the individual, access may be provided.

Consistent with some embodiments, the resource is at least one of: a file, a folder, a data structure, a computer program, computer code, or computer settings. For example, in some embodiments, an individual may seek to access a resource in the form of a database, a file, a folder, a document, computer code, or a software application stored in a computer system, and the institution that maintains the resource may send a request 1506 to the authentication service or system 1500 to check whether the individual seeking access is authorized to access the resource. In addition to online access (e.g., digital access, computer access, etc.), in some embodiments, the authentication service (and system) may also be used to verify the identity of an individual prior to providing physical access to a resource. For example, an individual may seek access to (e.g., enter, open, etc.), for example, a room, a vault, a storage room, a bank locker, or some other controlled access room, and the institution (associated with the resource) may send a request 1506 to the authentication service or system 1500 to validate the identity of the individual to confirm that the individual is authorized to enter/open the resource before allowing access (e.g., opening a door or window) of the resource. In some embodiments, along with the request 1506 to authenticate an individual, the institution may also send the authentication service or system 1500 identifying information of the individual (e.g., name, account details, or other identifying details provided by the individual when the account was set up).

Some disclosed embodiments involve receiving real-time signals indicative of second coherent light reflections being derived from second facial micromovements of the particular individual. The terms "receiving" and "signals" may have the same meaning described elsewhere in this disclosure. "Real-time" signals refer to signals indicative of events occurring contemporaneous with the receipt of these signals. For example, real-time signals of an event may be received at the same time as the event or with no noticeable delay after the occurrence of the event. As another example, real-time signals indicative of facial micromovements may correspond to the facial micromovements occurring at that period of time (e.g., at the time the event occurs). It should be noted that communication and/or processing latencies may introduce some delays in the time of occurrence of the micromovements and the time when real-time signals indicative of these micromovements are received by the system. However, in general, real-time signals may be received sufficiently quickly such that these signals are indicative of the individual's facial micromovements at that time, even if there is some amount of delay between signal generation and receipt.

The real-time signals may be indicative of coherent light reflections derived from facial micromovements of the individual. For example, these signals may be representative of one or more properties/characteristics of the facial micromovements of an individual. In general, any electronic/electrical signals indicative of the facial micromovements of the individual at that time (e.g., at the time the event, such as, micromovements, occur) may be received by system as the real-time signals. As explained previously with reference to FIGS. 1-6, speech detection system 100 associated with an individual may analyze reflections 300 of coherent light from facial region 108 of the individual to determine facial micromovements (e.g., amount of the skin movement, direction of the skin movement, acceleration of the skin movement, speckle pattern, etc.) of the individual and output signals representative of the detected facial micromovements. As also discussed elsewhere in this disclosure (e.g., with reference to FIGS. 5-7), in some embodiments, at least one processor may determine the individual's facial micromovements by applying a light reflection analysis on the detected reflections. Although not a requirement, in some embodiments, the received real-time signals may be an outcome of the applied light reflection analysis. In some embodiments, the real-time signals of an individual may be similar to, or may have a similar appearance as, the reference signals of the individual. In some embodiments, the real-time signals may be a representation of the speckle pattern, e.g., reflection image 600 of FIG. 6, or another light reflection pattern analyzed by speech detection system 100 associated with an individual. In some embodiments, the real-time signal may be, or include, characteristics or features extracted from a light reflection pattern of the individual. In some embodiments, one or more algorithms may be used to extract these characteristics or features of an individual's facial micromovements that are embodied in the signals. As explained elsewhere in this disclosure with reference to the reference signals, these extracted features may include fiducial and/or non-fiducial features. In some embodiments, the real-time signals may be representative of multiple biometric signals (e.g., a combination of facial micromovements along with one or more of pulse, cardiac signals, ECG, temperature, pressure, or other biometric signals) of an individual occurring at that time.

As illustrated in FIG. 15, in some exemplary embodiments, the exemplary system 1500 receives real-time signals 1508 indicative of facial micromovements of the individual. The real-time signals 1508 may be associated with the request 1506 to authenticate the individual. In general, the real-time signals 1508 may be received before, along with, or subsequent to the request 1506 to authenticate an individual. The real-time facial micromovement signals 1508 may be received by system 1500 from any source. For example, in some embodiments, the real-time signals 1508 may be transmitted from speech detection system 100 associated with the individual 102 (see, e.g., FIGS. 1-3, FIG. 14). In some embodiments, the received real-time signals 1508 may be transmitted by speech detection system 100 to institution 1400 which then retransmits the data to authentication system 1500 along with, for example, the request 1506 to authenticate the individual. It is also contemplated that real-time signals 1508 may be transmitted from remote processing system 450 (see, e.g., FIG. 4) or from memory device 700 (see, e.g., FIG. 7).

Some disclosed embodiments involve comparing the real-time signals with the reference signals stored in the secure data structure to thereby authenticate the particular individual. The term "comparing" refers to contrasting, correlating, measuring, and/or analyzing, e.g., to identify one or more distinguishing and/or similar features between two quantities, measurements and/or objects. In some embodiments, comparing may include looking for the similarities or differences between two things, namely the real-time signals and the reference signals. For example, the real-time signals of the individual may be compared with the stored reference signals of the individual to identify the similarities and/or differences between the two signals. Any known technique may be used to compare the received real-time signals with the stored reference signals. In some embodiments, known algorithms may be used for the comparison. In some embodiments, the algorithms may depend on the computation of matching scores based on the similarity and dissimilarity between the two signals. In some embodiments, during authentication, the determined score may be compared to a predefined threshold, and the claimed identity may be accepted if the score is equal to greater than the threshold value. In general, a "threshold" value or level may include a baseline, a limit (e.g., a maximum or minimum), a tolerance, a starting point, and/or an end point for a measurable quantity. In some embodiments, the threshold value for two signals to be determined to be a match may be user-provided (e.g., provided by institution) and/or predefined, for example, programmed into the system. Known techniques for comparing signals, such as, for example, Euclidean distance, support vector machines (SVMs), dynamic time warping (DTW), and hamming distance, Multilayer Perceptron (MLP), Long short-term memory (LSTM), Dynamic Time Warping (DTW), Radial Basis Function Neural Network (RBFNN), k nearest neighbor (KNN), and other suitable numerical or analytical techniques may be used for the comparison.

In some embodiments, comparing the received real-time signals with the stored reference signals may include determining a relative degree of similarity between the two signals based out of some characteristics (e.g., amplitude, phase, frequency, offset DC bias, etc.) of the two signals. The similarity between the two signals may also be determined using a signal analysis technique such as, for example, signal spectra using FFT techniques, harmonic contents, distortions, cross-correlation (e.g., in MATLAB), kullback-leibler divergence, cross entropy, Jensen-Shannon divergence, Wasserstein distance, Kolmogorov-Smirnov test, Dynamic Time Warping (DTW), etc. Any now-known or future-developed method of comparing two electronic/electrical signals may be used to determine the similarity between the two signals. If the determined similarity between the two signals is greater than or equal to a predefined threshold, the individual may be authenticated. In some embodiments, statistical analysis techniques may be used to compare the two signals to determine or estimate a probability that the real-time signal matches a reference signal. If the determined probability is greater than or equal to a threshold value, the individual may be authenticated.

In some embodiments, the received real-time signals may be compared with all the stored reference signals (e.g., stored reference signals of multiple individuals) to identify a match. For example, to identify the individual that matches the reference signals closest. For example, similar to comparing fingerprints of an individual with a catalog of fingerprints to determine a match, the received real-time signals of an individual's facial micromovements may be compared with the stored reference signals of different individual's to determine the identity of the individual that the real-time signals correspond to. In embodiments, where identifying information of the individual (e.g., name associated with the account that the individual is attempting to access, etc.) is also received in conjunction with the real-time signals, the received real-time signals may be compared with the stored reference signals of the individual corresponding to the identifying information to see if there is a match. For example, the system may select one set of reference signals (from among the multiple sets of stored reference signals) based on the identifying information and compare the received real-time signals with the selected reference signals to determine if they match. Since facial micromovements are unique characteristics of an individual, using facial micromovement signals to verify the identity of the individual may enable accurate validation of the identity of the individual.

As illustrated in FIG. 15, the received real-time signals 1508 of the individual may be compared 1512 with the stored reference signals 1502 to verify the identity of the individual. In some embodiments, during the authentication process, the real-time signals 1508 received by system 1500 may be compared with the database of stored reference signals 1502. In some embodiments, the received real-time signals 1508 may be compared with all the stored reference signals 1502 to identify the individual whose stored reference signal 1502 matches (or most closely matches) the received real-time signals 1508. In embodiments where the name (or other identifying information) of the individual is also received by system 1500, the received real-time signals 1508 may be compared with the stored reference signals 1502 associated with the identifying information to see if there is a match.

Some disclosed embodiments involve, upon authentication, notifying the institution that the particular individual is authenticated. The term "notifying" (and other related constructs such as notify, notification, etc.) refers to informing someone of something. For example, to make someone aware of something. Notification may be done in any manner. For example, in some embodiments, the institution may be notified audibly, textually, graphically, or by any other technique that is likely to inform the institution (e.g., a person at the institution) of the authentication. In some embodiments, the institution may be notified by sending a signal to the institution that indicates that the individual is notified. In some embodiments, the signal may result in an action being taken. For example, in some embodiments, the signal may be configured to enable the individual to continue with the transaction that prompted the institution to send the request to authenticate the individual. For example, when an individual attempts to log into (or do any other transaction) a customer's account at the institution (e.g., a bank, etc.), the bank may send a request to the system to authenticate the individual. And if the authentication process determines that the individual is the customer, the bank (or an official at the bank) may be notified of the match. In some embodiments, a signal that is sent by the system as the notification may authorize the individual to log into the account. In some embodiments, the notification to institution may include a change in the security status of the individual. For example, "user is identified," "user no longer identified," "user changed," "user disconnected the device," or other messages to inform/alert someone. In some embodiments, these secure messages may trigger an action on the institution's server, for example, authorizing the individual's transaction, blocking the transaction, etc. It is also contemplated that, in some embodiments, authorities (e.g., police, security personnel, etc.) may also be notified, for example, of a mismatch. In some embodiments, the notification may include the name and/or other details of the individual that the received real-time signals correspond to. For example, based on the comparison of the real-time signals with the stored reference signals, the individual associated with the received real-time signals may be identified and the institution notified.

As illustrated in FIG. 15, system 1500 may also notify 1514 (e.g., the institution and/or another entity or person) the result of the authentication. For example, when the comparison 1512 indicates that the received real-time signals 1508 of an individual's facial micromovements matches the reference signals 1502 of that particular individual stored in the database, institution 1400 may be notified (e.g., via notification 1514) of the match. Similarly, in some embodiments, when the comparison 1512 indicates that the received real-time signals 1508 of an individual's facial micromovements does not match the reference signals 1502 of that particular individual stored in the database, the institution 1400 may be notified 1514 of the mismatch. In some embodiments, the notification 1514 may be part of an authorization protocol. For example, when the comparison 1512 indicates that the received real-time signals 1508 matches the reference signals 1502, the notification 1514 (e.g., a notification signal) may authorize the individual to conduct the transaction that the individual was engaged in when the real-time signals 1508 were received. Similarly, when the comparison 1512 indicates a mismatch between the real-time signals 1508 and the reference signals 1502, the notification 1514 may block or prevent the individual from conducting the transaction.

An exemplary authorization protocol used for data communications (e.g., reference signals 1502, real-time signals 1508, notification 1514, etc.) between authentication system 1500 and institution 1400 may be, or may be based on, the Transport Layer Security (TLS) protocol. TLS is a widely-used cryptographic protocol designed to provide secure communication over the internet. TLS is commonly used in secure online transactions, such as e-commerce transactions, email communication, and online banking. TLS works by encrypting data (e.g., notification 1514) transmitted between two endpoints (e.g. system 1500 and institution 1400) using a combination of symmetric and asymmetric encryption to provide confidentiality, integrity, and authentication. When one endpoint (e.g., system 1500) initiates a TLS connection with another endpoint (e.g., institution 1400), the two endpoints negotiate a set of cryptographic parameters, such as the encryption algorithm and key length, and exchange digital certificates to authenticate each other's identities. Once the connection is established, data (e.g., notification 1514) transmitted between the endpoints is encrypted and can only be decrypted by the intended recipient. It should be noted that the TLS protocol is only exemplary, and any secure communications protocol may be used for secure communications between system 1500 and institution 1400.

In some disclosed embodiments receiving the real-time signals and comparing the real-time signals occur multiple times during a transaction. The term "multiple" refers to any value (e.g., 2, 3, 4, or any other integer) more than one. For example, in some embodiments, the real-time signals may be received and the individual authenticated continuously when the individual is engaged in a transaction. In some embodiments, after first authenticating the individual (e.g., determining that the rea-time signals received at the onset of a transaction is associated with an individual who is authorized to perform the transaction), the real-time signals indicative of the individual's facial micromovements may be continuously (or periodically) received while the individual is engaged in the transaction. These continuously or periodically received signals may be compared with the stored reference signals to determine that the individual who is engaged in the transaction continues to be the authorized individual. In some embodiments, the individual may be authenticated multiple time before the institution is notified (e.g., of a match or a mismatch). For example, the system may receive real-time signals from an individual multiple times at the onset of a transaction and the system may compare these received signals with the stored reference signals multiple times to confirm that the individual associated with the real-time signals is indeed the authorized individual. In some embodiments, the institution may be notified that the individual is authenticated only if the number of times the signals match exceeds a predetermined threshold.

Figure 17A:
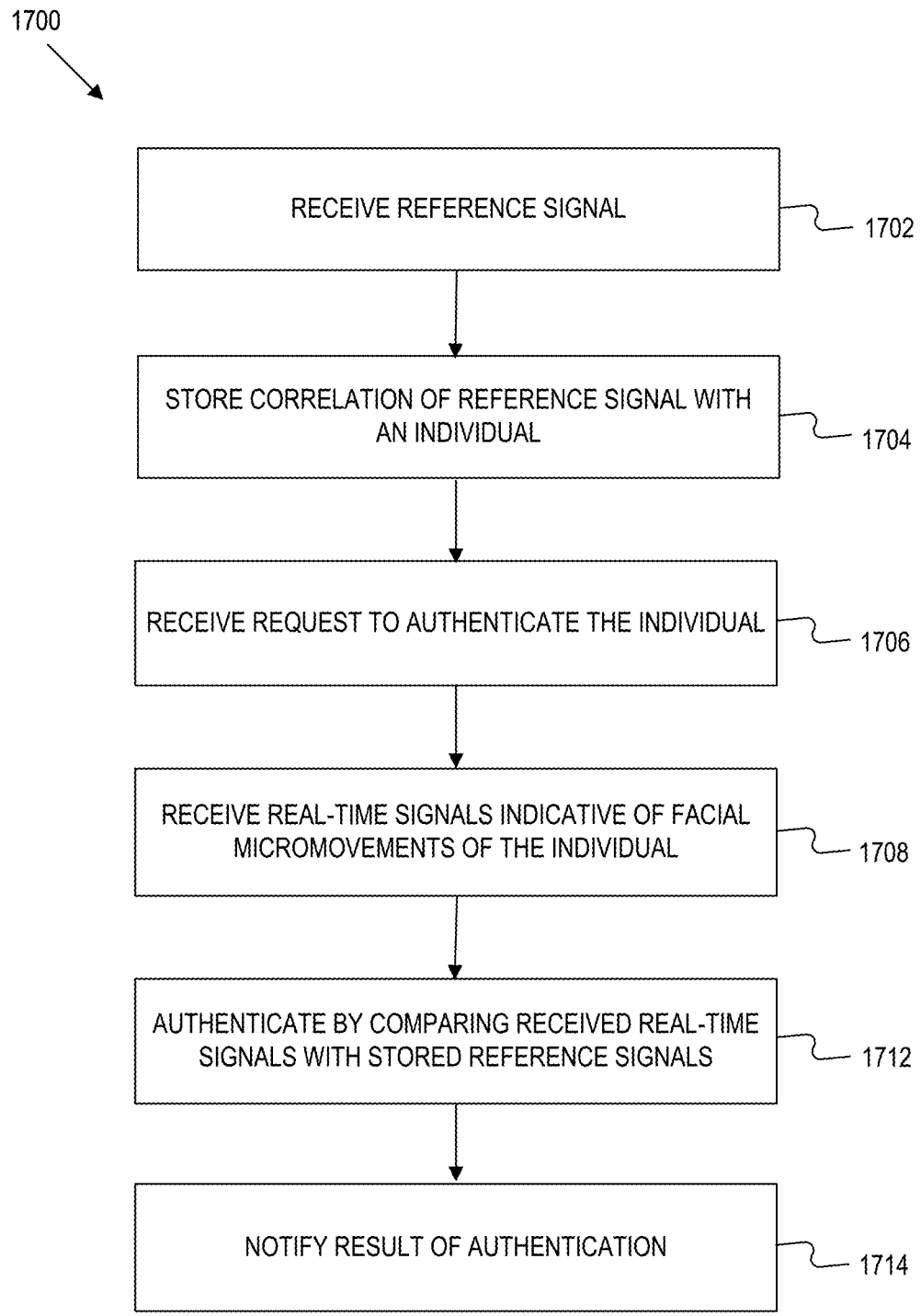
FIG. 17A is a flowchart of an exemplary process for identity verification of an individual using facial micromovements consistent with some embodiments of the present disclosure.

With reference to FIGS. 15 and 17A, in some embodiments, the authentication system 1500 (or service) may authenticate an individual multiple times before notifying 1514 the institution (and/or the authorities) the result of the authentication. For example, when an individual is attempting to access (e.g., log into) an account, after receiving a first set of real-time signals 1508, and comparing 1512 the received first set of real-time signals 1508 with the stored reference signals 1502 to authenticate the individual, system 1500 may receive a second set of real-time signals 1508 and compare 1512 the received second set to the stored reference signals 1502 to confirm the results of the first comparison before notifying 1514 the results of the authentication. In some embodiments, the steps of receiving and comparing may be repeated a preset number of times (10, 20, or any other integer number) before the institution is notified (e.g., via notification 1514) of the results of the comparison. In some embodiments, the institution 1400 may be notified of a successful comparison only if a match between the real-time signals 1508 and a stored reference signal 1502 is detected a preset number or percentage of times (e.g., 100% match, 98% match, etc.). In some embodiments, the institution 1400 may be notified of an authentication failure if a mismatch between the real-time signals 1508 and a stored reference signal 1502 is detected for a preset number or percentage of times (e.g., 1% mismatch, 2% mismatch, etc.).

In some embodiments, authentication system 1500 may continuously authenticate (e.g., authenticate repeatedly, periodically, etc.) the individual by continuously receiving real-time signals 1508 (or sets of real-time signals) of the individual and comparing 1512 each set of received real-time signals 1508 with the stored reference signals 1502 to continuously validate the identity of the individual during the transaction. For example, when an individual first attempts to access a customer account at an institution, system 1500 may receive a request 1506 to authenticate the individual. The institution may provide the individual access to the account upon receiving a notification 1514 that the individual is indeed the customer. In some embodiments, system 1500 may continue to receive real-time signals 1508 of the individual's facial micromovements and compare 1512 the received real-time signals 1508 with the stored reference signals 1502 to confirm that the individual is the customer while the individual is conducting a transaction on the account.

Some disclosed embodiments involve reporting a mismatch if a subsequent difference is detected following the notifying. A "mismatch" refers to a failure to correspond to a match. For example, in some embodiments, if the two signals (real-time signal and reference signal) are not sufficiently similar, a mismatch may be indicated. As explained elsewhere in this disclosure, in some exemplary embodiments, a matching score or a probability (of match) may be determined based on the comparison between the received real-time signal and a stored reference signal. In some such embodiments, the determined matching score or probability may be compared to a predefined threshold. If the determined score or probability is equal to greater than the threshold value a match may be indicated and if it is below the threshold value, a mismatch may be indicated and reported.

With reference to FIGS. 15, if after notifying 1514 the institution of the successful authentication of the individual, system 1500 detects that the real-time signals 1508 received at a subsequent time does not match the stored reference signals 1502 of the individual, system 1500 may report the mismatch to institution 1400 (and/or other authorities). The institution (and/or authentication system 1500) may terminate the individual's access to the account and/or take other protective measures based on the reporting of the mismatch.

Some disclosed embodiments further include determining a certainty level that an individual associated with the real-time signals is the particular individual. Certainty level may be any measure (number, percentage, high/medium/low, etc.) of a degree of confidence. For example, when a real-time signal is compared with a reference signal, the certainty level may be a measure of confidence that the individual associated with the received real-time signals is an individual associated with a stored reference signal. In some embodiments, the signal analysis technique employed to compare the two signals may indicate the certainty level of the degree of match between the two signals (see, e.g., https://brianmcfee.net/dstbook-site/content/ch05-fourier/Similarity.html). As explained elsewhere in this disclosure, in some embodiments, a signal comparison algorithm may be used to compare the two signals (real-time signal and reference signal) and determine a matching score or a probability (e.g., a certainty level) that the two signals match. In some embodiments, the system may allow a predefined number of differences between the two signals and still consider the two signals to be a match. In some embodiments, the system may store several reference signals (e.g., encrypted facial micromovement signatures) associated with a same individual and determine the acceptable number (and/or level) of differences between the two signals based on variations in the stored signatures.

With reference to FIGS. 15 and 17A, in some embodiments multiple reference signals for the same individual may be stored (e.g., updated over time, taken every month, year, etc.). System 1500 may compare 1512 the received real-time signals 1508 of an individual with all the stored reference signals 1502 of the individual. And a match may be indicated if the real-time signals match a predefined number of reference signals for the same individual. In some embodiments, when the real-time signals 1508 are compared with stored reference signals 1502 multiple times during a transaction, the number of times the two signals are determined to match may indicate the certainty level. For example, if the two signals are compared 100 times during a transaction and the two signals are determined to match 95 times (i.e., 95%), the certainty level may be determined to be 95% (or 0.95). In general, the threshold level (for the two signals to be determined to be a match) may include a baseline, a limit (e.g., a maximum or minimum), a tolerance, a starting point, and/or an end point for a measurable quantity of the signals. In some embodiments, the threshold level for the two signals to be determined to be a match may be user-provided (e.g., provided by institution) and/or predefined, for example, programmed into system 1500.

Consistent with some disclosed embodiments, when the certainty level is below a threshold, the operations further include terminating the transaction. As explained elsewhere in this disclosure, the term "threshold" is used to indicate a boundary or a limit. For example, if a quantity is below a threshold (or a threshold value), one condition may be indicated and if the quantity is above the threshold, another condition may be indicated. In general, the threshold may include a baseline, a limit (e.g., a maximum or minimum), a tolerance, a starting point, and/or an end point. In some embodiments, the threshold level for the two signals to be determined to be a match may be a predefined or user-provided (e.g., provided by institution) and/or predefined, for example, programmed into system. For example, in some embodiments, when the individual's real-time signals are compared with stored reference signals multiple times during a transaction and the certainty level of the match is below a threshold (e.g., 90%, 97%, or any other predefined value), the institution may be notified of the mismatch and the transaction that the individual is engaged in at that time may be terminated. In some embodiments, the authentication system (e.g., system 1500) or service may directly terminate the transaction prior to, or contemporaneous with, notifying the institution. With reference to FIGS. 15 and 17A, when the real-time signals 1508 are compared 1512 with stored reference signals 1502 multiple times during a transaction, when the two signal are determined to not match a threshold number of times (e.g., twice, thrice, or any other integer value), the transaction may be terminated. The threshold below which the transaction is terminated may be user-provided and/or a predefined or user-provided value.

Consistent with some disclosed embodiments, when the transaction is a financial transaction that includes providing access to the particular individual's account, and when a certainty level is below a threshold, the operations further include blocking the individual associated with the real-times signals from the particular individual's account. "Blocking" refers to stopping or preventing. For example, when an individual attempts to transfer funds from a customer's account in a bank, and the real-time signals of the individual do not match the stored reference signals of the customer, the institution (and/or the system) may stop or prevent the individual from conducting any more transactions in the account (or in some cases accessing the account) for example, until the reason for the mismatch is determined.

FIG. 17A is a flowchart of an exemplary process 1700 for identity verification of an individual using facial micromovements consistent with some embodiments of the present disclosure. Process 1700 may be used by system 1500 for verifying the identity of (or authenticating) an individual using the individual's facial micromovements. Process 1700 may be performed by at least one processor (e.g., processor 1510 of FIG. 15, processing device 460 of FIG. 4, etc.) to perform operations or functions described herein. In some embodiments, some aspects of process 1700 may be implemented as software (e.g., program codes or instructions) that are stored in a memory (e.g., memory 1520 of FIG. 15, memory device 402 of FIG. 4, etc.) or a non-transitory computer readable medium. In some embodiments, some aspects of process 1700 may be implemented as hardware (e.g., a specific-purpose circuit). In some embodiments, process 1700 may be implemented as a combination of software and hardware. In the discussion below, reference will also be made to FIGS. 15, 16A, and 16B.

Process 1700 may include receiving one or more reference signals 1502 (step 1702). As explained elsewhere in this disclosure, the reference signals 1502 may be a representation of one or more properties, features, or characteristics of the facial micromovements of an individual. These reference signals 1502 may be used for verifying the correspondence between that individual and an account at an institution. For example, reference signals 1502 of any particular individual may be used to determine the equivalence, similarity, match, or connection between that individual and an individual (e.g., customer) who is associated with the account. In some embodiments, system 1500 may receive the reference signals 1502 wirelessly, for example, via communications network 126 (see FIG. 14). The reference signals 1502 received by system 1500 may be transmitted from any source. For example, in some embodiments, the signals may be transmitted from a speech detection system 100 associated with an individual 102 (see, e.g., FIGS. 1-3, FIG. 14). In some embodiments, the received reference signals 1502 may be transmitted to system 1500 by institution 1400 that, for example, subscribes to the authentication service to authenticate customers. For example, reference signals 1502 may be transmitted by an individual to institution 1400, and the institution may in turn transmit the reference signals to system 1500 to verify the identity of the individual. In some embodiments, reference signals 1502 may be transmitted from remote processing system 450 (see, e.g., FIG. 4) or from memory device 700 (see, e.g., FIG. 7).

The received reference signals 1502 in step 1702 may be indicative of the facial micromovements occurring as a result of any facial expression (e.g., smile, frown, grimace, speech, silent speech, or any other facial expression or activity that causes facial skin micromovements) of the individual. For example, in some embodiments, as illustrated in exemplary process 1750 of FIG. 17B, at least one word or syllable (a syllable, a word, a sentence, etc.) may be presented to the individual for pronunciation (step 1752). And reference signals 1502 may be generated based on facial micromovements that occur as a result of the individual pronouncing the presented word(s) or syllable(s) (step 1754). The word(s) may be presented to the individual for pronunciation in step 1752 in any manner on any device. For example, the text of the word(s) may be displayed to the individual on display screen 1402 of mobile communications device 120. In some embodiments, a picture or an image representing the word(s) may be graphically presented to the user in step 1752. For example, presenting the word "dog" may be done by textually displaying the word "dog," or by showing an image (picture, cartoon, line drawing, or another similar pictorial display) of a dog. In some embodiments, the word(s) may be audibly presented in step 1752 and reference signals generated when the individual repeats (e.g., vocalizes or pre-vocalizes) the word (s). In general, any word (e.g., a random word) or words may be presented to the individual to pronounce in step 1752.

Process 1700 may also include storing a correlation of the reference signal with an individual (step 1704). As explained elsewhere in this disclosure, in some embodiments, the stored correlation may include a reduced size and/or an encrypted version and/or a hash of the received reference signals. In some embodiments, the correlation may include extracted features of the reference signals using, for example, using feature extraction algorithms. The correlation may also include the identity (e.g., name, account number, or other identifying information) of the individual that the reference signal is associated with. For example, in one exemplary embodiment, as illustrated in FIGS. 16, system 1500 stores correlations 1504 of different individual's (e.g., Tom, Amy, Ron, etc.) reference signals 1502 in a secure database in a remote data structure 124.

Process 1700 may also include receiving a request to authenticate the individual (step 1706). Request 1506 may be received from the institution 1400 (directly or indirectly). For example, in some embodiments, institution 1400 may send a request 1506 to the authentication service provider to authenticate an individual when it receives (or in response to) a request for a transaction from the individual. For example, an individual may request some service (e.g., access to an online document, access to an online account, access to a secure physical room such as a bank locker) from an institution, and the institution may send a request to system 1500 to validate the identity of the individual as part of providing the service.

Process 1700 may also include receiving real-time signals 1508 indicative of facial micromovements of the individual (step 1708). The real-time signals 1508 may be associated with the request 1506 to authenticate the individual. The real-time facial micromovement signals 1508 may be received by system 1500 from any source. For example, in some embodiments, the real-time signals 1508 may be transmitted from speech detection system 100 associated with the individual 102 (see, e.g., FIGS. 1-3, FIG. 14). In some embodiments, the received real-time signals 1508 may be transmitted by speech detection system 100 to institution 1400 which then retransmits the data to authentication system 1500 along with, for example, the request 1506 to authenticate the individual. In some embodiments, the real-time signals 1508 may also be generated following a process similar to process 1750 of FIG. 17B. For example, at least one word or syllable may be presented to the individual to pronounce (step 1752), and the real-time signals may be generated based on the facial micromovements that occurs when the individual pronounces the presented word(s). As described elsewhere in this disclosure, the word(s) may be presented in any manner on any device. For example, in an embodiment where an individual is attempting to use an ATM (see FIG. 17), the word(s) may be presented to the individual on a screen 1600 of the ATM. In some embodiments, the word(s) presented to generate the reference signals 1502 may be the same as (or include similar syllables) as the word(s) displayed to generate the real-time signals 1508.

Process 1700 may include authenticating the individual by comparing the received real-time signals with the stored reference signals (step 1712). As illustrated in FIG. 15 to FIG. 2C, the received real-time signals 1508 of the individual may be compared 1512 with the stored reference signals 1502 to verify the identity of the individual. In some embodiments, during step 1712, the real-time signals 1508 may be compared with the database of stored reference signals 1502. In some embodiments, the real-time signals 1508 may be compared with all the stored reference signals 1502 to identify the individual whose stored reference signal 1502 matches (or most closely matches) the real-time signals 1508. In embodiments where the name (or other identifying information) of the individual is also received by system 1500 (e.g., in steps 1706, 1708, etc.), the real-time signals 1508 may be compared with the stored reference signals 1502 associated with the identifying information to see if there is a match.

Process 1700 may also include notifying 1514 (e.g., the institution and/or another entity or person) the result of the authentication (step 1714). For example, when the comparison 1512 of step 1712 indicates that the received real-time signals 1508 of an individual's facial micromovements matches the reference signals 1502 of that particular individual stored in the database, institution 1400 may be notified (e.g., via notification 1514) of the match. Similarly, in some embodiments, when the comparison 1512 indicates that the received real-time signals 1508 of an individual's facial micromovements does not match the reference signals 1502 of that particular individual stored in the database, the institution 1400 may be notified 1514 of the mismatch.

Figure 17B:
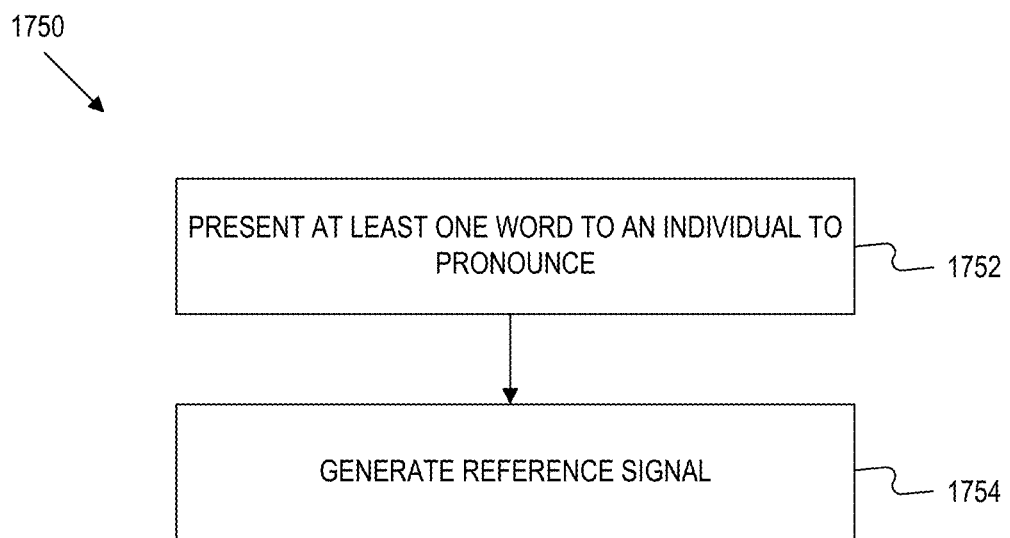
FIG. 17B is a flowchart of an exemplary process for generating a reference signal for identity verification of an individual consistent with some embodiments of the present disclosure.

It should be noted that the order of the steps of processes 1700 and 1750 illustrated in FIGS. 17A and 17B are only exemplary and the steps may be performed in other orders. For example, in some embodiments, the request to authenticate an individual (step 1706) may be received after receiving real-time signals of an individual (step 1708), etc. It should also be noted that the authentication processes 1700 and 1750 are only exemplary. For example, in some exemplary embodiments, the disclosed processes may include additional steps (e.g., receive a request for the certainty level of a comparison, etc.). In some embodiments, some of the illustrated steps of FIG. 17A may be eliminated or combined. For example, steps 1706 and 1708 may be combined, etc. Moreover, in some embodiments, process 1700 of FIG. 17A may be incorporated in another process or may be part of a larger process.

In some embodiments, an authentication or identity verification system (or service) may use facial skin micromovements of an individual to provide continuous authentication of the individual. In contrast with conventional facial or retinal identification technology that verifies an individual's identity at a single moment in time (e.g., a snapshot in time), identity verification systems of the current disclosure may provide identity verification of the individual continuously for an extended period of time (e.g., for the period of time that an individual may be engaged in a transaction). For example, some disclosed embodiments may involve confirming an individual's (e.g., a bank customer) identity in real time when the individual engages in a transaction (e.g., banking). Continuous authentication may happen when the customer engages in any type of transaction with the bank (e.g., when the customer is using a mobile phone or desktop to transact with the bank, using an ATM, when the customer is physically at a bank, or any other interaction). In some embodiments, continuous authentication of the customer may extend for the entire banking session from beginning to end, or from login to logout. In some embodiments, continuous authentication may extend for multiple periods of time (e.g., multiple spaced-apart periods of time) during a transaction. In some embodiments, continuous authentication may rely on continuous facial skin micromovement signals of the customer being processed by the authentication system during the entire session. Continuous authentication may make it possible for the bank to continuously confirm that a legitimate bank account owner is in fact the person transacting on the account—and not a fraudster. Continuous authentication may happen throughout all events, such as checking a balance, making a wire transfer, or adding a payee, as the customer progresses through their banking session.

It should be noted that although an exemplary application of continuous authentication of a customer at a bank is described above, continuous authentication can be used to validate an individual during any transaction by any institution or person. For example, a phone conversant may use the disclosed continuous authentication techniques to continuously know the identity of the person on the other end of the line. Similarly, any institution (e.g., bank, online brokerage, online gaming company, company, university) may verify that an individual who is engaged in a transaction (e.g., withdrawing money transferring funds, trading stock, reviewing a file, attending a class, etc.) with it is an authorized individual for a length of time (the entire length of time or for selected periods of time) that the individual is engaged in the transaction.

The authentication systems of the current disclosure may use the individual's facial skin micromovements (alone or in combination with other biometric data) to continuously authenticate or verify the identity of the individual. Facial skin micromovements of an individual may be affected by the muscles, the structure of the muscle fibers, characteristics of the skin, characteristics of the sub skin (e.g., blood vessel structure, fat structure, hair structure). As explained elsewhere in this disclosure, characteristics of skin micromovements (e.g., the intensity and order of muscle activation) over the facial region of an individual are different between different individuals, and therefore, facial skin micromovements create a unique biometric signature of an individual that may be used to identify the individual.

Figure 18:
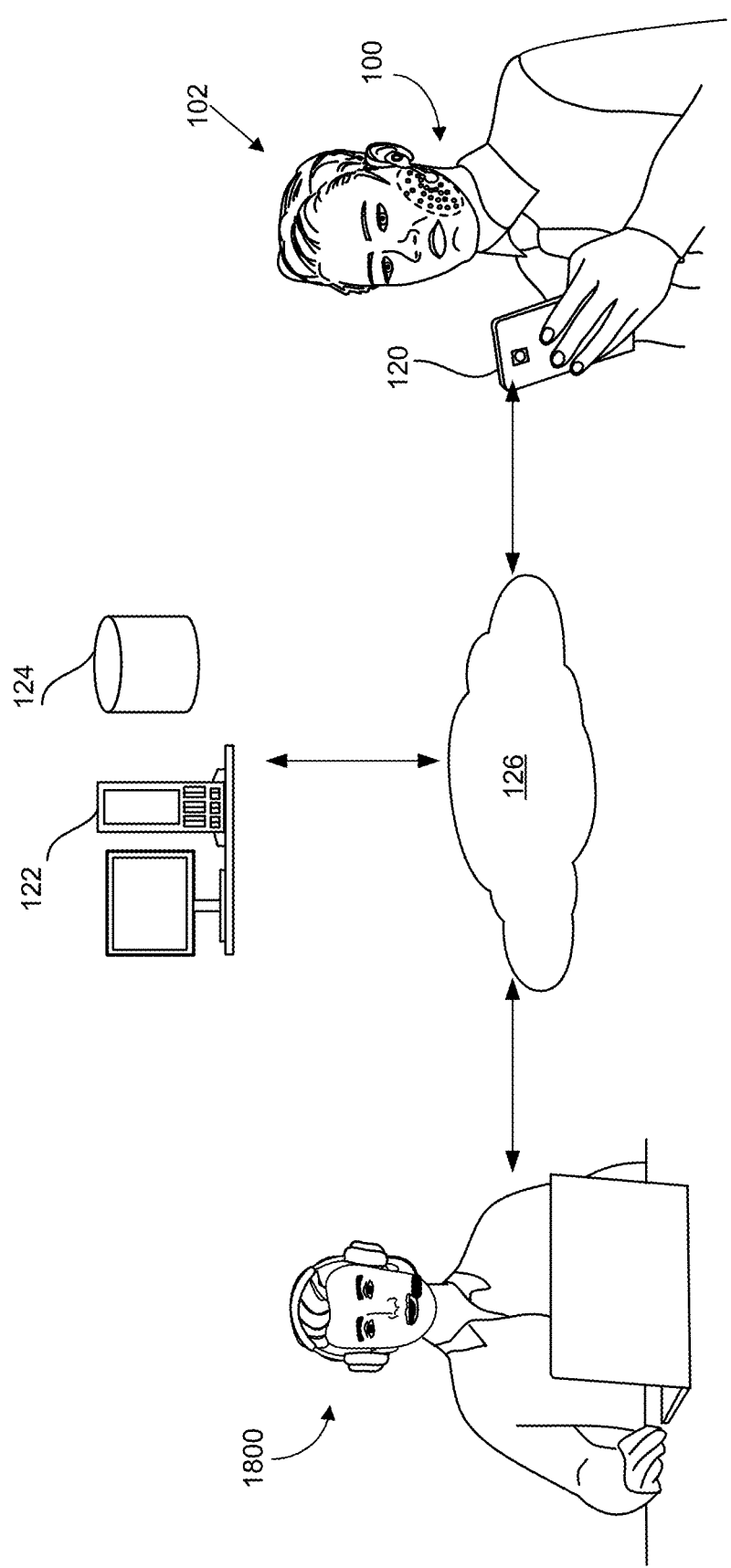
FIG. 18 is a schematic illustration of an exemplary authentication system and service configured to provide continuous authentication of an individual based on facial skin micromovements consistent with some embodiments of the present disclosure.

Some disclosed embodiments involve a system for providing identity verification based on the individual's facial micromovements. The term system may be interpreted consistent with the previous descriptions of this term. The system may be configured to provide identity verification of an individual. "Identity verification" may be a process of determining who an individual is. It may also refer to a process of confirming or denying whether an individual is who that person claims to be. For example, in some embodiments, systems of the current disclosure may determine who an individual is based on that individual's facial micromovements. And in some embodiments, systems of the current disclosure may determine (e.g., confirm or deny) whether the individual is actually who he/she is purported to be based on the individual's facial micromovements. FIG. 18 is a schematic illustration of an exemplary embodiment of an identity verification (or authentication) system of the current disclosure. The system may be configured to provide continuous identity verification (or authentication) of an individual based on the individual's facial skin micromovements. As used herein, the term "continuous" includes verification multiple times a second, verification multiple times a minute, or verification at sufficient intervals during a transaction or portion thereof to ensure that an important juncture is not passed without identity verification. As described elsewhere in this disclosure (e.g., with reference to FIGS. 1-6), speech detection system 100 associated with an individual 102 may detect light reflections indicative of the individual's facial skin micromovements and communicate representative signals to a cloud server 122, for example, via a mobile communications device 120 and a communications network 126. As also described elsewhere in this disclosure (e.g., with reference to FIGS. 15-17), cloud server 122 (or another system) may compare the received signals with reference signals (e.g., encrypted digital signatures that represent characteristics of the facial skin micromovements of different individuals) stored in a memory (e.g., a secure data structure such as, for example, data structure 124, etc.) to identify the particular individual associated with the received signals. In some embodiments, cloud server 122 may compare the received signals to the stored reference signals based on a request received from an institution 1800 (e.g., a bank, university, online trading company, online gambling/gaming company, etc.). For example, when an individual is engaged in an electronic transaction (e.g., logging into an account, transferring funds, trading stock, engaged in a phone conversation, attending a class, reading a folder/file, attempting to enter a secure room, etc.) with the institution, the institution may send a request to server 122 to authenticate the individual. In some embodiments, cloud server 122 may also notify the institution and/or another person/entity the results of the comparison. In some embodiments, an authentication service provider may use an authentication system, such as cloud server 122, for providing identity verification of the individual based on the individual's facial micromovements.

Some disclosed embodiments involve a non-transitory computer readable medium containing instructions that when executed by at least one processor cause the at least one processor to perform operations for continuous authentication based on facial skin micromovements. The terms "non-transitory computer readable medium," "at least one processor," and "instructions" may be interpreted consistent with the previous descriptions of these terms. The term "authentication" (and other constructions of this term such as authenticate, authenticating, etc.) refers to determining the identity of an individual or to determining whether an individual is, in fact, who the individual purports to be. In some embodiments, authentication may be a security process that relies on the unique characteristics of individuals to identify who they are or to verify they are who they claim to be. For example, authentication may be a security measure that matches the biometric features of an individual, for example, looking to access a resource (e.g., a device, a system, a service). "Continuous authentication" refers to authentication for more than a single instant in time. For example, continuous authentication may be provided by uninterrupted authentication for a contiguous length of time or time period. The time period may be any amount of time (e.g., seconds, minutes, hours, days, or any other extent of time depending on the specific implementation). As another example, continuous authentication may be provided by authentication for multiple spaced-apart time periods. The multiple time periods may be spaced apart by any amount of time. In some embodiments, continuous authentication may also be provided by repeated authentication at discrete times within a time period. The spacing between the discrete times may be of any duration and the spacing may be constant or variable.

Figure 19:
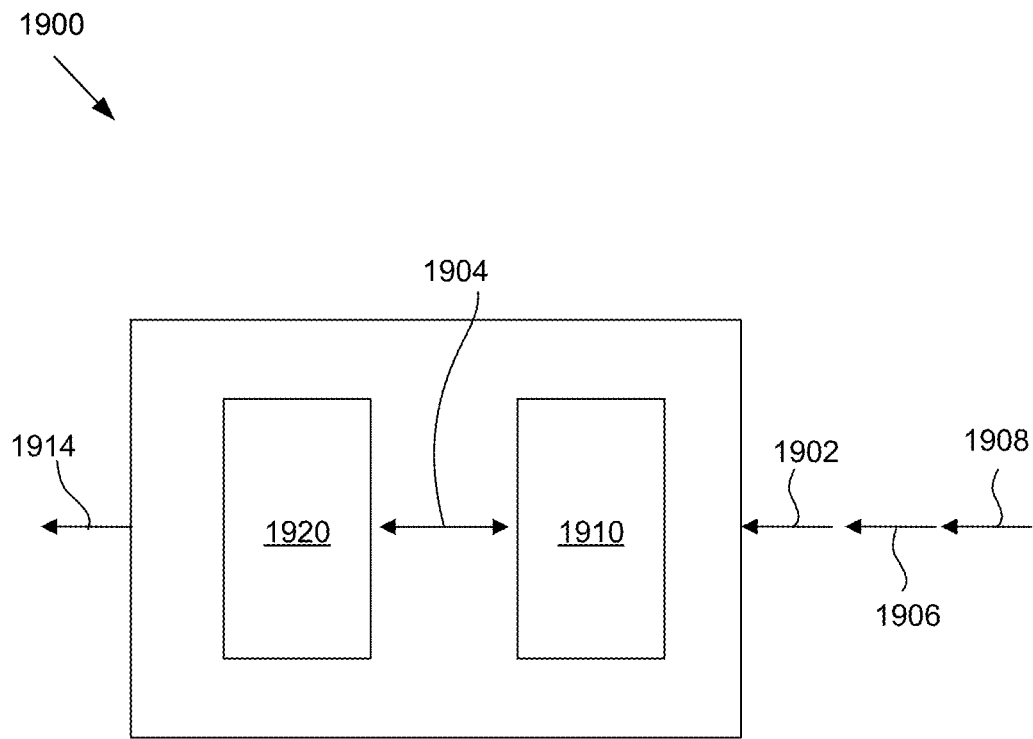
FIG. 19 is a simplified illustration of an exemplary system configured to provide continuous authentication of an individual using facial micromovements consistent with some embodiments of the present disclosure.

FIG. 19 is a simplified block diagram of an exemplary authentication system 1900 for providing identity verification (or authentication) based on an individual's facial skin micromovements. It is to be noted that only elements of authentication system 1900 that are relevant to the discussion below are shown in FIG. 19. Embodiments within the scope of this disclosure may include additional elements or fewer elements. In the depicted embodiment, authentication system 1900 comprises a processor 1910 and a memory 1920. Although only one processor 1910 and one memory 1920 are illustrated in FIG. 19, in some embodiments, processor 1910 may include more than one processor and memory 1920 may include more than one memory device. These multiple processors and memories may each have similar or different constructions and may be electrically connected or disconnected from each other. Although memory 1920 is shown separate from processor 1910 in FIG. 19, in some embodiments, memory 1920 may be integrated with processor 1910. In some embodiments, memory 1920 may be remotely located from system 1900 and may be accessible by system 1900. Memory 1920 may include any device for storing data and/or instructions, such as, for example, a Random Access Memory (RAM), a Read-Only Memory (ROM), a hard disk, an optical disk, a magnetic medium, a flash memory, other permanent, fixed, or volatile memory. In some embodiments, memory 1920 may be a non-transitory computer-readable storage medium that stores instructions that when executed by processor 1910 causes processor 1910 to perform operations for continuous authentication based on facial skin micromovements. In some embodiments, some or all the functionalities of processor 1910 and memory 1920 may be executed by a remote processing device and memory (for example, processing device 400 and memory device 402 of remote processing system 450, see FIG. 4).

Some disclosed embodiments involve receiving during an ongoing electronic transaction, first signals representing coherent light reflections associated with first facial skin micromovements during a first time period. The term "receiving" may include retrieving, acquiring, or otherwise gaining access to, e.g., data. Receiving may include reading data from memory and/or receiving data from a device via a (e.g., wired and/or wireless) communications channel. At least one processor may receive data via a synchronous and/or asynchronous communications protocol, for example by polling a memory buffer for data and/or by receiving data as an interrupt event. The term "signals" or "signal" may refer to information encoded for transmission via a physical medium or wirelessly. Examples of signals may include signals in the electromagnetic radiation spectrum (e.g., AM or FM radio, Wi-Fi, Bluetooth, radar, visible light, lidar, IR, Zigbee, Z-wave, and/or GPS signals), sound or ultrasonic signals, electrical signals (e.g., voltage, current, or electrical charge signals), electronic signals (e.g., as digital data), tactile signals (e.g., touch), and/or any other type of information encoded for transmission between two entities via a physical medium or wirelessly (e.g., via a communications network). In some embodiments, the signals may include, or may be representative of, "speckles," reflection image data, or light reflection analysis data (e.g., speckle analysis, pattern-based analysts, etc.) described elsewhere in this disclosure.

"Coherent light reflections" may refer to reflections that result from coherent light impacting a surface. For example, when coherent light falls on or strikes a surface, the light that reflects or returns from the surface are coherent light reflections. As explained elsewhere in this disclosure, "coherent light" includes light that is highly ordered and exhibits a high degree of spatial and temporal coherence. As also explained in detail elsewhere in this disclosure, when coherent light strikes the facial skin of an individual, some of it is absorbed, some is transmitted, and some is reflected. The amount and type of light that is reflected depends on the properties of the skin and the angle at which the light strikes it. For example, coherent light shining onto a rough, contoured, or textured skin surface may be reflected or scattered in many different directions, resulting in a pattern of bright and dark areas called "speckles." In some embodiments, when coherent light is reflected from the face of an individual, the light reflection analysis performed on the reflected light may include a speckle analysis or any pattern-based analysis to derive information about the skin (e.g., facial skin micromovements) represented in the reflection signals. In some embodiments, a speckle pattern may occur as the result of the interference of coherent light waves added together to give a resultant wave whose intensity varies. In some embodiments, the detected speckle pattern (or any other detected pattern) may be processed to generate reflection image data from which the first signals may be generated.

The first signals may represent coherent light reflections associated with the facial skin micromovements occurring during a first time period. A "time period" may be any length of time (e.g., milliseconds, seconds, minutes, hours, days, or any other measure of time). In some embodiments, a time period may represent the entire length of time that a transaction occurs. In some embodiments, a time period may represent a length of time during which an activity during a transaction occurs. In some embodiments, a time period may be the length of time some facial skin micromovement of the individual occurs. For example, a time period may be the length of time an individual vocalizes or pre-vocalizes a sentence, a word, or a syllable. In some embodiments, a time period may be the length of time that the individual is engaged in a portion of a transaction. For example, in an transaction where an individual is logging into an online account at a financial institution to transfer funds, one time period may be the length of time that the individual takes to log into the account, another time period may be the length of time that the individual is selecting an account to manipulate, yet another time period may be the length of time that the individual takes to select funds, and a further time period may be the length of time that the individual takes to transfer the selected funds. It should be noted that the above described time periods are merely exemplary, and as used herein, a time period may represent any length of time.

The term "transaction" refers to any type of interaction between at least two parties (e.g., the individual and an institution, multiple individuals, or two or more of any other entities). "Electronic transaction" refers to a transaction that, in some manner, utilizes an electronic medium as part of the transaction. For example, two individuals engaged in a conversation via an electronic medium (e.g., over a phone, online, or via any other medium) are engaged in an electronic transaction. An individual logging into an account at an institution using a computer, a smart phone, a PDA, or another device is engaged in an electronic transaction with the institution. As another example, an individual using an ATM to withdraw money is engaged in an electronic transaction. As another example, an individual talking face-to-face with a bank employee who has logged in, or is logging into, the individual's account to conduct a transaction for the individual (e.g., check the account balance, transfer funds, etc.) is engaged in an electronic transaction. As a further example, an individual using an electronic keypad to enter a code and open a locked door is engaged in an electronic transaction. The above-described transactions are merely exemplary, and as explained elsewhere in this disclosure, an electronic transaction includes any transaction that, in some manner, utilizes an electronic medium.

As explained with reference to FIGS. 1-6, speech detection system 100 associated with an individual may detect facial micromovements of the individual. For example, with specific reference to FIGS. 5-7, speech detection system 100 may analyze reflections 300 of coherent light from facial region 108 of the individual to determine facial skin micromovements (e.g., amount of the skin movement, direction of the skin movement, acceleration of the skin movement, speckle pattern, etc.) resulting from recruitment of muscle fiber 520 and output signals representative of the detected facial skin micromovements. Facial skin micromovements that occur during a first time period may be referred to herein as the first skin micromovements. In some embodiments, the first signals may be real-time signals indicative of an individual's facial skin micromovements occurring contemporaneous with the receipt of these signals by the authentication system. For example, the received first signals may correspond to the facial skin micromovements of the individual occurring when the individual is engaged in an electronic transaction. Communication and/or processing latencies may introduce some delays in the time of occurrence of the micromovements and the time when the first signals indicative of these micromovements are received by the system. However, the first signals may be received sufficiently quickly by the system such that the first signals can be considered to be indicative of the individual's facial micromovements at that time.

In some embodiments, the first signals may be generated and sent during the first time period. In some embodiments, the first signals may be generated based on facial skin micromovements occurring when the individual pronounces (e.g., during vocalization or prior to vocalization (e.g., silently speaks)) some word(s), syllable(s), phrases, etc., when engaged in an electronic transaction. In some embodiments, the first time period may be the length of time that it takes the individual to pronounce the selected word(s), syllable(s), phrases, etc. For example, the first signals may correspond to muscle activation that occurs when the individual pronounces the word(s), syllable(s), phrases, etc. As explained elsewhere in this disclosure, as used herein, pronouncing a word refers to when the individual actually utters (or vocalizes) the word or before the individual utters the word (e.g., during silent speech). Speech-related muscle activity occurs prior to vocalization (e.g., when air flow from the lungs is absent but the facial muscles articulate the desired sounds, when some air flows from the lungs but words are articulated in a manner that is not perceptible using an audio sensor, etc.). Thus, in some embodiments of the current disclosure, the first signals may correspond to signals caused by muscle activation that occurs prior to vocalization (e.g., during silent speech) of a word, syllable, phrases, etc. by an individual. However, generating the first signals when an individual pronounces word(s), syllable(s), phrases, etc. is only exemplary. In general, the first signals may be generated based on any movement of facial muscles during the transaction. For example, when an individual smiles, scowls, frowns, grimaces, or expresses another facial expression during an electronic transaction.

In one exemplary embodiment, as illustrated in FIG. 19, system 1900 may receive signals 1902, 1906, 1908, etc. indicative of facial skin micromovements of an individual. These signals may represent coherent light reflections associated with facial skin micromovements of the individual. Signals 1902, 1906, 1908 may be sent from any source. In some embodiments, one or more of these signals may be sent directly from a speech detection system 100 associated with the individual (e.g., see FIGS. 1-4), for example, via a mobile communications device 120 and a communications network 126. In some embodiments, one or more of signals 1902, 1906, 1908 may be sent from an institution (e.g., institution 1800 of FIG. 18) that, for example, engages system 1900 to verify the identity the individual when the individual is engaged in (or attempts to engage in) an electronic transaction with the institution.

Signals 1902, 1906, 1908, etc. may be signals representative of facial skin micromovements of the individual at different time periods. For example, signals 1902 may be representative of facial skin micromovements of the individual at a first time period, signals 1906 may be representative of facial skin micromovements of the individual at a second time period after the first time period, and signals 1908 may be representative of facial skin micromovements of the individual at a third time period after the second time period. These time periods may be contiguous (e.g., sharing a common border) time periods (e.g., 10:45:10 AM to 10:52:45 AM, etc.) or non-contiguous time periods (e.g., 10:45:10 AM to 10:45:55 AM, 10:46:10 AM to 10:48:50 AM, 10:51:20 AM to 10:52:45 AM) spaced apart by any value of time (e.g., seconds, minutes, hours, days, weeks, or another time value). In some embodiments, an authentication service provider may use an authentication system (such as, for example, cloud server 122 of FIG. 18, system 1900 of FIG. 19, remote processing system 450 of FIG. 4, or another computer system) for providing identity verification of the individual based on the individual's facial micromovements.

Consistent with some embodiments, the ongoing electronic transaction is a phone call. For example, two individuals may be engaged in a phone conversation and the system may use facial skin micromovements of one individual to determine if the same individual is on the phone during the entire time (or another selected time period) of the conversation. In another example, the individual may be on the phone with an institution (e.g., a bank) and the institution may use the system to confirm that it is dealing with the same individual throughout the transaction. In another example, a first individual may be physically present at a bank office and talking face-to-face with a second individual (e.g., a bank employee) accessing the first individual's account on a computer using information provided by the first individual. The second employee and/or the institution may use the authentication system to confirm that the first individual is the account holder. Other non-limiting examples of transactions may include, for example, an individual operating a machine, dictation to a computer, an online transaction with a provider such as a bank/restaurant, purchasing of an item (e.g., over the phone, computer, etc.), signing an online document, accessing classified documents/medical records, physically accessing a secure room through a door opened using an electronic keypad, or any other interaction of an individual with another individual or device.

Some disclosed embodiments involve determining, using the first signals, an identity of a specific individual associated with the first facial skin micromovements. The term "identity" of an individual refers to information that assists in understanding who the individual is. In some embodiments, an identity of an individual is information identifying (points out, spots, puts a name to, or links) who the individual is. For example, identity may be, or include, the individual's name, image, account number, and/or other details that someone may use to understand or determine who the individual is. In some embodiments, identity may include information (e.g., fingerprint and/or other biometric data) that may be used by a device to determine who the individual is. The first signals may be indicative of facial skin micromovements of an individual.

The first signals may be used to determine the identity of the individual associated with the first facial skin micromovements in any manner. For example, in some embodiments, the system may maintain, or have access to, a catalog or database of facial skin micromovements of different individual's, and by comparing the received first signals with the facial skin micromovements stored in the catalog, the system may determine the identity of the individual associated with the received facial skin micromovements. In some embodiments, the system may determine the identity of the individual associated with the received facial skin micromovements based on one or more characteristics or features of first signals. For example, by comparing and observing similarities in specific features of the received first signal to corresponding features of the facial skin micromovements stored in catalog, the system may determine the identity of the individual.

In some disclosed embodiments determining the identity of the specific individual includes accessing memory correlating a plurality of reference facial skin micromovements with individuals and determining a match between the first facial skin micromovements and at least one of the plurality of reference facial skin micromovements. "Correlating" (and other constructions of this term such as correlate, correlation, etc.) refers to establishing a mutual relationship or connection between two (or more) things. For example, correlation may be a measure that expresses the extent to which the two things are related. In some embodiments, correlation may be a statistical measure that expresses the extent to which two variables are related. "Reference facial skin micromovements" refer to facial skin micromovements that may be used for reference purposes. For example, similar to a catalog of photographs (fingerprints, DNA, or other biometric markers) of different individuals with their corresponding names stored in a memory (or database), and used to identify individuals by comparing the individual's photograph with the stored catalog of photographs, reference facial skin micromovements of different individuals may be stored in a memory (see, e.g., data structure 124 of FIG. 16) and used to identify individuals by comparing the received facial skin micromovements with the stored reference facial skin micromovements. In some embodiments, the reference facial skin micromovements may be stored in a secure data structure to reduce the possibility of unauthorized access to the data. The stored references may be of various types. For example, individuals may have voice prints, similar to fingerprints, which can be stored for later comparison. Similarly, reflections may correlate to unique biometric data which can be used for comparison. Additionally or alternatively, a dictionary of common spoken words may be stored for an individual and when such words are detected as having been spoken, a lookup of stored associated reflection signals may be compared with the first signals to determine a match or a likely match surpassing a threshold.

For example, as discussed with reference to FIG. 16, reference facial skin micromovements of multiple individuals (e.g., Tom, Amy, Ron, and other customers or account holders of a financial institution) may be collected and stored in a memory (e.g., memory 1920 of FIG. 19) for example, during enrollment and depending on embodiment, on an ongoing basis thereafter. As explained with reference to FIGS. 16-17, the system may securely store correlations of the reference facial skin micromovements with the identity of the different customers in a secure data structure (such as data structure 124) in memory 1920. In some embodiments, the customer's name and/or other identifying information (account number, or other information) that identifies the individual associated with each of the stored reference facial skin micromovements may also be stored in the memory.

In some embodiments, as explained with reference to FIGS. 16-17, the reference facial skin micromovements of an individual stored in memory may be a representation (a summary or a signature) of an individual's facial skin micromovements. In some embodiments, the signature itself may not be stored. Instead, an encrypted version of the signature may be stored. Pretty Good Privacy (PGP) is a known exemplary encryption protocol that provides cryptographic privacy and authentication for data communication. Functionally, the stored reference facial skin micromovement signal of an individual may be stored and communicated using a protocol similar to the PGP protocol or another suitable encryption algorithm. The stored signal may be similar to the individual's encrypted digital signature or reference biometric data and may serve as the individual's unique mark. In some embodiments, the stored reference facial skin micromovements of an individual may be a reduced size version of the individual's facial skin micromovements. In some embodiments, an encrypted version of an individual's facial skin micromovements may be stored in memory as the reference facial skin micromovements of that individual. In some embodiments, a "hash" of an individual's facial skin micromovements may be stored as the reference facial skin micromovements of that individual. A hash may be a unique digital signature generated from an input signal (e.g., facial skin micromovements) using, for example, commercially available algorithms. In some embodiments, an individual's stored reference facial skin micromovements may be, or include, features (or characteristics) extracted from the facial skin micromovements of that individual, using for example, feature extraction algorithms. In some embodiments, the stored reference facial skin micromovements may include information of features (e.g., position and orientation of peaks and/or valleys, spatial and/or temporal gap between peaks and/or valleys) in the facial skin micromovements. Since the stored data (e.g., reference facial skin micromovements) is a representation of the individual's facial micromovements that are affected by that individual's person traits (e.g., muscle fiber structure, blood vessel structure, tissue structure, etc.), the stored data may uniquely identify the individual that the data corresponds to. In some embodiments, as explained with reference to FIG. 16, the stored data may also include the identity (e.g., name, account number, or other identifying information) of the individual that the data is associated with.

The authentication system (e.g., system 1900) may use the stored reference facial skin micromovements in memory 1920 to identify individuals. For example, explained with reference to FIG. 17, when an individual attempts to access a customer's account at a bank (e.g., using an ATM), the bank may request system 1900 to determine the identity of the individual (e.g., to ensure that this individual is the account holder). In conjunction with this request, system 1900 may receive first signals 1902 indicative of facial skin micromovements of the individual at a first time period. System 1900 may then access memory 1920 (e.g., a secure data structure in memory 1920) that includes a correlation of plurality of reference facial skin micromovements (reference signals) with individuals and compare 1904 the received first signals 1902 with the stored reference signals to determine whether the received signals match any of the reference signals. In some embodiments, the received first signals 1902 may be real-time facial skin micromovement signals of the individual when the individual is engaged in the electronic transaction, and the system 1900 may compare 1904 the received first signals 1902 with the stored reference signals to determine whether the individual is a customer. For example, system 1900 may compare the two signals to determine if one or more characteristics of the received signals correspond to, or sufficiently match, characteristics of the stored reference signals to determine if the received signals are associated with a customer authorized to access the account.

In some embodiments, as explained elsewhere in this disclosure (e.g., with reference to FIGS. 16-18), the received first signals 1902 may be compared 1904 with reference facial skin micromovement signals of different individuals stored in memory 1920 to identify the reference facial skin micromovement signals that the received first signal 1902 matches with (or most closely resembles). In some embodiments, the first signals 1902 may be compared with the reference facial skin micromovement signals of everyone stored in memory 1920 to uniquely identify the individual associated with the received signals. In some embodiments, to compare the received first signals 1902 with the stored reference signals, the stored signals may be unencrypted and characteristics of the first signals may be compared with corresponding characteristics of the unencrypted reference signals to determine their similarity (equivalence, correspondence, match, etc.). In embodiments where the possible identity of the individual corresponding to the received first signals 1902 is known (e.g., based on a prior comparison of a previously received signal, based on identifying information received in conjunction with the first signals, or the possible identity of the individual is known in any manner), the first signals 1902 may be compared with the reference signals corresponding to that individual to see if they match (e.g., sufficiently match).

As explained, the first signals 1902 may be compared with the stored reference signals to identify the similarities and/or differences between the two signals. In some embodiments, the comparison of the two signals may include the computation of matching scores based on the similarity and dissimilarity between the two signals. In some embodiments, the determined matching score may be compared to a predefined threshold, and the claimed identity may be accepted if the score is equal to or greater than the threshold value. In general, a "threshold" value or level may include a baseline, a limit (e.g., a maximum or minimum), a tolerance, a starting point, and/or an end point for a measurable quantity. In some embodiments, the threshold value for two signals to be accepted or classified as a match may be user-provided (e.g., provided by institution) and/or predefined, for example, programmed into system 1900.

In some embodiments, the first signals may be considered to be associated with a specific individual if a certainty level or a confidence level of the comparison between the first signals and that specific individual's reference signals exceeds or equals a predefined threshold. Any known technique may be used to compare the received first signals 1902 with the stored reference signals. In some embodiments, known algorithms (e.g., Euclidean distance, support vector machines (SVMs), dynamic time warping (DTW), and hamming distance, Multilayer Perceptron (MLP), Long short-term memory (LSTM), Dynamic Time Warping (DTW), Radial Basis Function Neural Network (RBFNN), k nearest neighbor (KNN), and/or other suitable numerical or analytical techniques) may be used for the comparison.

In some embodiments, comparing the received first signals 1902 with the stored reference signals may include determining a relative degree of similarity between the two signals based on one or more characteristics (e.g., amplitude, phase, frequency, offset DC bias, etc.) of the two signals. In some embodiments, the similarity between the two signals may be determined using a signal analysis technique (e.g., signal spectra using FFT techniques, harmonic contents, distortions, cross-correlation (e.g., in MATLAB), kullback-leibler divergence, cross entropy, Jensen-Shannon divergence, Wasserstein distance, Kolmogorov-Smirnov test, Dynamic Time Warping (DTW), or any other now-known or future-developed method of comparing two electronic/electrical signals). If the determined similarity between the two signals is greater than or equal to a predefined threshold, the individual may be authenticated. In some embodiments, statistical analysis techniques may be used to compare the two signals to determine or estimate a probability that the first signal 1902 matches a reference signal. If the determined probability is greater than or equal to a threshold value, the individual may be authenticated. Since facial skin micromovements are unique characteristics of an individual, using facial skin micromovement signals to identify (or verify the identity of) an individual may enable accurate identification, or validation of the identity of, the individual.

Some disclosed embodiments involve receiving during the ongoing electronic transaction second signals representing coherent light reflections associated with second facial skin micromovements, the second signals being received during a second time period following the first time period. As explained elsewhere in this disclosure, coherent light reflections are reflections that result from coherent light impacting a surface. The second signals may correspond to the facial skin micromovements of the individual occurring during a second time period after the first time period, when the individual is engaged in the same electronic transaction. The second facial skin micromovements may be the skin micromovements occurring in the facial region of the individual in the second time period. In some embodiments, the first and second facial skin micromovements may be obtained from the same facial region (e.g., cheek, etc.) of the individual. In some embodiments, the reflections may be received from precisely the same area or from differing areas. The second time period may extend by any length of time after the first time period ends. In some embodiments, the first and second time periods may be contiguous time periods (e.g., sharing a common border). For example, the first time period may, for example, extend from 10:45:10 AM to 10:46:45 AM and the second time period may extend from 10:46:45 AM to 10.48:04 AM, etc. In some embodiments, the first and second time periods may be non-contiguous time periods. For example, the first time period may, for example, extend from 10:45:10 AM to 10:46:45

AM and the second time period may extend from 10:48:10 AM to 10:49:45 AM, etc. The first and second time periods may be spaced apart by any amount of time (e.g., seconds, minutes, hours, days, weeks, etc. The first time period and the second time period may both have (or represent) the same time duration (e.g., 1 second, 0.1 min, 0.5 min, 1 min, 10 min, etc.) or may represent different lengths of time. In some embodiments, the second signals may be real-time signals indicative of an individual's facial micromovements occurring contemporaneous with the receipt of the second signals.

As illustrated in FIG. 19, system 1900 may receive second signals 1906 during a second time period after the first time period. The second signals 1906 may be similar to the previously received first signals 1902. Similar to the first signals 1902, the second signals 1906 may also be associated with facial skin micromovements of an individual (at a later time than the first signals). In some embodiments, first signals 1902 may correspond to muscle activation that occurs when the individual pronounces (vocalizes or pre-vocalizes) some word(s), syllable(s), phrases, etc. (or "first words") when the individual is engaged in an electronic transaction. And second signals 1906 may correspond to muscle activation that occurs when the individual pronounces some word(s), syllable(s), phrases, etc. (or "second words"), after pronouncing the first words, when the individual is engaged in the same electronic transaction. The second words may be (but do not have to be) the same as the first words. For example, in an exemplary embodiment where an individual is engaged in a telephonic conversation with an institution, the first signals 1902 may be generated when the individual pronounces a word in the first sentence (e.g., the word "hello"), and the second signals 1906 may be generated at a later time when the individual pronounces another word in the second sentence (e.g., "account"). Generating second signals 1906 when the individual pronounces a word is only exemplary. In general, the second signals 1906 may be generated when the individual is engaged in any activity that results in facial skin micromovements (smile, grimace, or any other facial expressions) during the electronic transaction. As will be explained below, system 1900 may use the second signals 1906 to determine whether the second signals 1906 are also associated with the same individual as the first signals 1902.

Some disclosed embodiments involve determining, using the second signals, that the specific individual is also associated with the second facial skin micromovements. For example, in some embodiments, the received second signals may be compared with the pre-stored reference signals (e.g., catalog or database of facial skin micromovements of different individuals, reference facial skin micromovements of FIG. 16, or other stored reference data) of different individuals to determine whether the individual associated with the second signals is the same as the individual associated with the first signals. Additionally or alternatively, in some embodiments, the received second signals may be compared with the stored reference signals of the individual identified using the previously received first signals to determine if the second signals are also associated with the same individual as the first signals. Additionally or alternatively, in some embodiments, the received second signals may be compared with the previously received first signals to determine if both signals are associated with the same individual. The second signals and the pre-stored reference signals (or first signals) may be compared in any manner. For example, the received second signals may be checked against pre-stored signals or data identifying the individual. As explained elsewhere in this disclosure, such pre-stored data may be collected at an inception of an account associated with the individual or at any time thereafter. The entity (company or institution) holding the account may store the information, or the information may be stored by a third party verification service. Additionally or alternatively, the pre-stored data may be augmented over time through additional or ongoing data collection, to improve the identifying information. The first and second signals may additionally or alternatively be compared with each other to identify the similarities and/or differences between the two signals, with differences indicating that a second individual intervened in the communication. As explained elsewhere in this disclosure, in some embodiments, the comparison may include the computation of matching scores (or certainty level, confidence level, relative degree of similarity, or another measure of similarity) based on the similarity and dissimilarity between the two signals. The determined score may be compared to a predefined threshold, and it may be determined that both signals are associated with the same individual if the determined score is equal to greater than the threshold value. In some embodiments, features (or characteristics) of the first and second signals (e.g., position and orientation of peaks and/or valleys, spatial and/or temporal gap between peaks and/or valleys, and/or other signal characteristics) may be extracted (e.g., using feature extraction algorithms) and compared to determine if their similarity exceeds a predetermined threshold.

For example, with reference to FIG. 19, in some embodiments, second signals 1906 may be compared with the stored reference facial skin micromovement signals of the different individuals stored in memory 1920 to determine whether the individual associated with the second signals 1906 is the same as the individual associated with the first signals 1902. Additionally or alternatively, in some embodiments, the second signals 1906 may be compared with the stored reference facial skin micromovement signals of the individual identified using the first signals 1902 to determine if the second signals 1906 are also associated with the same individual as the first signals 1902. Additionally or alternatively, in some embodiments, the second signals 1906 may be compared with the first signals 1902 to determine if both signals are associated with the same individual. As discussed with reference to FIG. 16, in some embodiments, reference facial skin micromovements of multiple individuals may be collected and stored in memory 1920, and system 1900 may compare the first signals 1902 with the stored reference facial skin micromovements to determine the identity of the individual associated with the first signals 1902. In some embodiments, system 1900 may compare the second signals 1906 with the previously identified reference signal to determine if the second signals 1906 also match the reference signal. In some embodiments, system 1900 may also notify, for example, an entity associated with the authentication, whether or not the second signals 1906 are associated with the same individual as the first signals 1902. For example, if it is determined that the first and second signals 1902 and 1906 are associated with the same individual, system 1900 may notify, for example, the entity that requested the authentication that the same user is engaged in the transaction. On the other hand, if it is determined that the first and second signals 1902 and 1906 are not associated with the same individual, the notification may warn the entity that the same user is not engaged in the transaction so that security measures may be initiated. In some embodiments, system 1900 may initiate an action (e.g., stop the electronic transaction, inform security personnel, or another action) if it is determined that the first and second signals are not associated with the same individual.

Consistent with some disclosed embodiments, during the second time period, the operations further include continuously outputting data confirming that the specific individual is associated with the second facial skin micromovements. For example, after comparing the received second signals to the first signals to confirm that the first and second signals are associated with the same individual, a notification indicating that the same individual (e.g., "user is identified," "user is authorized, etc.) is still engaged in the transaction may be issued. In some embodiments, the notification may be issued continuously to the institution or entity who is associated with the transaction. Upon detection of a non-verified user, the system may output a visual and/or audible warning that the speaker is no longer verified. This can occur, for example with a flashing or static indicator on a display, or a verification notation that changes color and/or message, or any other visual or audible indication.

Some disclosed embodiments involve receiving during the ongoing electronic transaction third signals representing coherent light reflections associated with third facial skin micromovements, the third signals being received during a third time period following the second time period. As explained elsewhere in this disclosure, coherent light reflections are reflections that result from coherent light impacting a surface. The third signals may correspond to the facial skin micromovements of the individual occurring during a third time period after the first and second time periods, when the individual is engaged in the same electronic transaction. The third facial skin micromovements may be the skin micromovements occurring in the facial region of the individual in the third time period. In some embodiments, the first, second, and third facial skin micromovements may be obtained from the same facial region (e.g., cheek, etc.) of the individual. In some embodiments, the third signals may be real-time signals indicative of an individual's facial micromovements occurring contemporaneous with the receipt of the third signals. The third time period extend to any length of time after the second time period ends. In some embodiments, the first, second, and third time periods may represent the same interval (e.g., 1 second, 0.1 min, 0.5 min, 1 min, 10 min, etc.). In some embodiments, some or all of the first, second, and third time periods may represent different time intervals. In some embodiments, the first, second, and third time periods may be contiguous time periods (e.g., sharing a common border). For example, the first time period may, for example, extend from 10:45:10 AM to 10:46:45 AM, the second time period may extend from 10:46:45 AM to 10.48:04 AM, and the third time period may extend from 10.48:04 AM to 10:50:00 AM, etc. In some embodiments, the first, second, and third time periods may be non-contiguous spaced-apart time periods. For example, the first time period may, for example, extend from 10:45:10 AM to 10:46:45 AM, the second time period may extend from 10:48:10 AM to 10:49:45 AM, and the third time period may extend from 10:48:00-10:55:12, etc. The first, second, and third time periods may be spaced apart by any duration of time (e.g., seconds, minutes, hours, days, weeks, etc.). It is also contemplated that, in some embodiments, the first and second time periods (or the second and third time periods) may be contiguous time periods, and the second and third time periods (or the first and second time periods) may be non-contiguous time periods.

As described, the first, second, and third time periods are different time periods when the individual is engaged in the same electronic transaction. Although not a requirement, in some embodiments, the first signals may correspond to muscle activation that occurs when the individual pronounces (vocalizes or pre-vocalizes) some word(s), syllable(s), phrases, etc. (or "first words") during the transaction. The second signals may correspond to muscle activation that occurs when the individual pronounces some word(s), syllable(s), phrases, etc. (or "second words"), after pronouncing the first words. And the third signals may correspond to muscle activation that occurs when an individual pronounces some word(s), syllable(s), phrases, etc. (or "third words"), after pronouncing the first and second words. The first, second, and third words may be (but do not have to be) the same word(s), syllable(s), phrases, etc. Generating third signals when an individual pronounces the third words is only exemplary. In general, the third signals may be generated based on any facial expression (e.g., smile, scowl, frown, grimace, or another expression) of the individual that generates facial skin micromovements.

With reference to FIG. 19, system 1900 may receive third signals 1908 after receiving the first and second signals 1902, 1906. In some embodiments, the third signals 1908, that represent the facial skin micromovements at a third time period following the first and second time periods, may be generally similar to the first and second signals 1902, 1906. System 1900 may use the received third signals 1908 to determine whether the facial skin micromovements represented by these signals are associated with the same individual associated with the first and second signals 1902, 1906. For example, if the third signal 1908 is sufficiently similar to the previously received first and/or second signals, system 1900 may determine that the third signal 1908 is associated with the same individual. Instead, if the third signal 1908 is not sufficiently similar, system 1900 may determine that the third signal 1908 is not associated with the same individual. In some embodiments, as discussed, the comparison of the two signals may include the computation of matching scores (or certainty level, confidence level, relative degree of similarity, or another measure of similarity) based on the similarity and dissimilarity between the two signals. The determined score may be compared to a predefined threshold, and it may be determined that both signals are not associated with the same individual if the determined score is less than a threshold value.

Consistent with some disclosed embodiments, the first period of time, the second period of time, and the third period of time are part of a single online activity associated with the ongoing electronic transaction. The term "online activity" may refer to any activity performed using the internet or other computer network. In some embodiments, the first period of time, the second period of time, and the third period of time may be part of one single online activity of the electronic transaction. For example, an individual may have logged into a customer account at a financial institution (e.g., using a computer, a smart phone, a PDA, or another device) and may be interacting with the account to sell some stock, and the first, second, and third periods of time may be different time periods when the individual is in the process of selecting and selling the stock by placing an online order. For example, the first time period may be the time interval when the individual logs into the account, the second time period may be time interval when the individual selects the stock to sell, and the third time period may be the time interval when the sell order is placed. Without limitation, the first, second, and third time periods may be associated with any online activity.

Consistent with some disclosed embodiments, the online activity is at least one of: a financial transaction, a wagering session, an account access session, a gaming session, an exam, a lecture, or an educational session. For example, an individual may be in the process of buying a product from an online retailer, and the first, second, and third periods of time may be different time periods when the individual is in the process of selecting and placing an order for the product. In some embodiments, an individual may be attending an online class and the first, second, and third periods of time may be different time periods when the individual is attending the class. In some embodiments, an individual may be taking an online exam, and the first, second, and third periods of time may be different time periods when the individual is taking the exam. In some embodiments, the individual may be logged into an online betting account and in the process of placing a bet, and the first, second, and third periods of time may be different time periods when the individual is in the process of placing an online betting order.

Consistent with some disclosed embodiments, the online activity includes multiple sessions, and the operations further include using received signals associated with facial skin micromovements to determine that the specific individual participates in each of the multiple sessions. For example, an individual may be attending an online class (or taking an online exam) with multiple sessions having breaks in between the different sessions, and the first, second, and third periods of time may be time periods during different sessions. For example, the first signals may be real-time signals received during a first period of time in the first session of the class, the second signals may be real-time signals received during a second period of time in the second session of the class, and the third signal may be real-time signals received during a third period of time in the third session of the class. The system may compare the facial skin micromovements during the three different time periods to determine whether the same individual attends the different sessions of the class.

Consistent with some disclosed embodiments, the first period of time, the second period of time, and the third period of time are part of a secured session with access to a resource. As used herein, a "resource" may be anything that may satisfy a need of the individual. In some embodiments, resource may be a physical or virtual property. For example, a resource may be a financial account or money (or other security) in a bank account, stocks in a trading account, records or documents stored in a database or computer system, online classes offered by a university, a secure room such as, for example, an access-controlled room, a house, a car, a boat, or other property. A "secured session" may be an online transaction with some type of security for a secure connection. For example, a secure session may be a mechanism for securing network communication (both private and public networks, including the Internet) between parties. In some embodiments, a secured session may be protocol-agnostic and may provide secure end-to-end communication. In some embodiments, a secured session may include encryption and decryption. In some embodiments of a secured session between two parties, when the session is established, a key that is associated with the secure session may be cached and as messages are exchanged during the transaction, an identifier to the cached key may be exchanged for decrypting the message. In some embodiments, a secured session may include a mechanism (e.g., encryption algorithms and scrambling data in transit) for keeping a network connection secure and for safeguarding data exchanged from unauthorized access. Without limitation, any now-known or later developed secured session technology may be used with embodiments of the current disclosure. In some embodiments of the current disclosure, an individual may have signed into a secure database that stores confidential patient medical records in a secured online session, and the first, second, and third periods of time may be different time periods during the same secured session.

Consistent with some disclosed embodiments, the resource is at least one of: a file, a folder, a database, a computer program, a computer code, or computer settings. In general, the resource stored in the secure database may include any digital data, such as, for example, files or folders of confidential data, computer programs or codes, or computer settings. Validating the identity of the individual accessing the database using embodiments of the current disclosure may assist preventing unauthorized access to the database.

Consistent with some disclosed embodiments, the first period of time, the second period of time, and the third period of time are part of a single communication session, and wherein the communication session is at least one of: a phone call, a teleconference, a video conference, or a real-time virtual communication. For example, an individual may be engaged in a real-time communication session (e.g., phone call, messaging session, teleconference, a video conference, a virtual meeting using, e.g., Zoom, Messenger, Teams, or any other virtual communications tool), and the first, second, and third periods of time may be different time periods during the same communications session.

Some disclosed embodiments involve determining, using the third signals, that the third facial skin micromovements are not associated with the specific individual. For example, in a manner similar to verifying that the second signals are associated with the same individual as the first signals, the system may compare the received third signals with the stored reference signals and/or the previously received first and/or second signals to determine whether or not the third signals are associated with the same individual as the first and second signals. For example, the third signals may be compared with pre-stored reference data (e.g., catalog or database of facial skin micromovements of different individuals, reference facial skin micromovements of FIG. 16, or other stored reference data), as indicated elsewhere in this disclosure. In some embodiments, (but not necessarily every embodiment, the third signal may be compared with the first signal and/or the second signal to identify the similarities and/or differences between the signals and determine whether or not the third signals are associated with the same individual as the first and second signals. As explained elsewhere in this disclosure, in some embodiments, comparisons may include the computation of matching scores (or certainty level, confidence level, relative degree of similarity, or another measure of similarity) based on the similarity and dissimilarity between the signals. If the determined score is less than a predefined threshold, the system may determine that the third signals are not associated with the same individual as the previously received first and second signals. In some embodiments, if the determined matching store for a first comparison of the signals (e.g., third signal with pre-stored reference signals) is within or below a predefined threshold, the system may compare the received third signals to other previously received signals (e.g., first signals and/or second signals) to confirm the results of the first comparison and determine the matching score for the second comparison. If the determined score is again less than a predefined threshold, the third signals are not associated with the same individual as the previously received first and second signals.

For example, with reference to FIG. 19, in some embodiments, the third signals 1908 may be compared with the stored reference facial skin micromovement signals of the different individuals stored in memory 1920 to determine whether the individual associated with the third signals 1908 is the same as the individual associated with the first and second signals 1902, 1906. Additionally or alternatively, in some embodiments, the third signals 1908 may be compared with the stored reference facial skin micromovement signals of the individual identified using the first signals 1902 to determine if the third signals 1908 are also associated with the same individual as the first signals 1902. For example, as discussed elsewhere in this disclosure (e.g., with reference to FIG. 16), reference facial skin micromovements of multiple individuals may be collected and stored in memory 1920 as reference signals, and system 1900 may compare the first signals 1902 with the stored reference signals to determine the identity of the individual associated with the first signals 1902. In some embodiments, system 1900 may compare the third signals 1908 with the previously identified reference signals to determine if the third signals 1908 also matches the identified reference signals. If they do not, system 1900 may indicate that the third facial skin micromovements are not associated with the previously identified individual. Additionally or alternatively, in some embodiments, the third signals 1908 may be compared with the previously received second signals 1906 and/or first signals 1902 to determine if the third signals 1908 are associated with the same individual as the first and second signals. In some embodiments, when system 1900 determines that the received third signals 1908 do not match a reference signal stored in memory, the system may store the received third facial skin micromovements signals (or an encrypted hash or signature of these signals as discussed elsewhere in this disclosure, e.g., with reference to FIG. 16) in memory to update reference signals stored in memory.

Some disclosed embodiments involve initiating an action based on the determination that the third facial skin micromovements are not associated with the specific individual. "Initiating" (and other constructions of the word, such as, initiate, etc.) refers to causing an action to begin. In some embodiments, initiating an action means beginning, commencing, starting, or causing the occurrence of an action. The "action" can be anything, for example, in response to determining that the third facial skin micromovements are not associated with the same individual as the first and second facial skin micromovements. The action may be, or include, issuance of a signal, a notification, an alert, and/or a presentation of an audible, textual, or graphical notice. For example, in some embodiments, the institution or another entity associated with the electronic transaction may be notified (audibly, textually, graphically, or by any other technique that is likely to inform the institution/entity) that the individual who is engaged in the transaction is not the individual previously engaged in the transaction. In some embodiments, the action may include sending a query to the individual, for example, seeking clarification (e.g., asking the individual to call the institution to explain and correct the discrepancy). In some embodiments, the action may include blocking the individual from continuing with the transaction.

For example, with reference to FIG. 19, when an individual logs into a customer's account at a financial institution to trade stock from the account, the institution may send a request to the authentication system 1900 to continuously authenticate the individual during the transaction. Associated with this request, system 1900 may receive first signals 1902 indicative of the individual's facial skin micromovements during a first time period when the individual attempts to log into the account. If system 1900 determines, based on the first signals 1902, that the individual is the person associated with the customer account (e.g., an authorized individual), the individual may be permitted to log into the account. System 1900 may then receive second signals 1906 indicative of facial skin micromovements of the individual during a second time period, for example, when the individual attempts to select stock in the account to sell. If system 1900 determines, based on the second signals 1906, that the individual who is engaged in the transaction is still the authorized individual, the individual may be permitted to continue with the transaction. System 1900 may then receive third signals 1908 indicative of facial skin micromovements of the individual during a third time period, for example, when the individual attempts to place a sell order. If system 1900 determines, based on the third signals 1908, that the individual who is attempting to place the sell order is not the same individual who was previously engaged in the transaction (e.g., the authorized individual), system 1900 may initiate an action 1914 in response. Any action 1914 may be taken in response. For example, the action 1914 may include sending a signal to the institution indicating the change in the individual (e.g., "user has changed"). In some embodiments, action 1914 may include blocking or preventing the individual from continuing with the attempted transaction and/or making any further transactions, for example, until the discrepancy is clarified.

Consistent with some disclosed embodiments, the action includes providing an indication that the specific individual is not responsible for the third detected facial skin micromovements. In some embodiments, the institution or another entity associated with the transaction may be notified by sending a signal to the institution of the changed individual (e.g., "user no longer identified," "user changed," or other messages provide an alert or other notification. In some embodiments, the action may include, or result in, a change in the security status of the individual. For example, the secure messages to the institution may trigger an action on the institution's server, for example, blocking the transaction, or another action to prevent unauthorized access.

Consistent with some disclosed embodiments, the action includes executing a process for identifying another individual responsible for the third facial skin micromovements. Any process may be executed to identify the identity of the individual associated with the third facial skin micromovements. In some embodiments, a process similar to that used to determine the identity of the individual associated with the first facial skin micromovements based on the first signals may be used to determine the identity of the individual associated with the third facial skin micromovements from the third signals. For example, as explained with reference to FIGS. 16 and 17, the system may maintain (or have access to) a database of reference facial skin micromovements of different individuals, and by comparing the received third signals with the facial skin micromovements stored in the database, the system may determine the identity of the individual associated with the third facial skin micromovements. For example, a large number of light reflection voice prints or other light reflection prints may be stored in a data structure, and the third signals may be matched with an individual other than the individual responsible for the first and second signals. For example, in some instances, where joint account holders are authorized on a common account, the change from one to the other might not trigger an alert. In such instances, the system may nevertheless provide an indication that although the speaker has changed, verification remains.

Consistent with some disclosed embodiments, the action includes notifying an entity associated with the online activity that an individual other than the specific individual is now participating in the online activity. The term "entity" refers to any legally recognized unit or machine associated with a legally recognized unit, such as an institution, a company, a person, a computer, or any other existing thing associated with legal rights and/or responsibilities. For example, when an individual is engaged in an online transaction (e.g., online financial transaction, online betting, attending an online class, taking an online exam, purchasing a product from an online retainer, or any other online activity), and if by comparing the third signals with the first and/or second signals the system determines that the third facial skin micromovements are not associated with the same individual associated with the first and/or second skin micromovements, the action may include notifying the entity associated with the online session (e.g., a person, computer system, phone, or device associated with the online financial institution, online betting company, online exam center, online university, online retainer, or other online company) that the individual who is engaged in the transaction at the third time period (e.g., currently engaged in the transaction if the third signal is a real-time signal) is not the same person who was previously engaged in the transaction.

Consistent with some embodiments, the action includes preventing participation in the online activity until the identity of specific individual is confirmed. For example, the online transaction may be stopped and the individual may be prevented from continuing with the transactions until the identity of the person engaged in the transaction is confirmed. As another example, in some embodiments, a query may be sent to the individual to call the institution associated with the online transaction and clarify the discrepancy. In some embodiments, the system may attempt to authenticate an individual multiple times before taking an action. For example, the system continue to receive and compare signals indicative of facial skin micromovements of the individual multiple times to determine if the identity of the individual can be confirmed.

Consistent with some disclosed embodiments, the action includes notifying an entity associated with the resource that an individual other than the specific individual gained access to the resource. In some embodiments, in an online transaction with an institution, an individual may have accessed a database with confidential documents stored therein. And when the authentication system determines that the third facial skin micromovements are not associated with the same individual associated with the first and second skin micromovements, it may notify the database administrator (or another entity associated with the database) that an unauthorized individual may have gained access to the database. Consistent with some disclosed embodiments, the action includes terminating the access to the resource. For example, in addition to or alternative to notifying the entity (or taking another action), the system may terminate the individual's access to the database. For example, the online transaction may be terminated when the authentication system determines that the third facial skin micromovements are not associated with the same individual associated with the first and second skin micromovements.

Consistent with some disclosed embodiments, the action includes notifying an entity associated with the communication session that an individual other than the specific individual has joined the communication session. For example, when a first individual is engaged in a communications session (e.g., a real-time virtual communication session such as, for example, teleconference, video conference, a virtual meeting, or another real-time online communication session) with one or more other individuals or entities, when the authentication system determines that the third facial skin micromovements are not associated with the same individual associated with the first and second skin micromovements, it may notify, alert, or warn one or more of the individuals or entities that a different individual has joined the communication session.

Some disclosed embodiments involve determining the first facial skin micromovements, the second facial skin micromovements, and the third facial skin micromovements by analyzing signals indicative of received coherent light reflections to identify temporal and intensity changes of speckles. "Temporal" refers to being related in time as opposed to space. As explained elsewhere in this disclosure, coherent light shining onto a rough, contoured, or textured surface may be reflected or scattered in many different directions, resulting in a pattern of bright and dark areas called "speckles." As also explained elsewhere in this disclosure, e.g., with reference to FIGS. 1-6, speech detection system 100 associated with an individual may analyze reflections 300 of coherent light from facial region 108 of the individual to determine facial skin micromovements (e.g., amount of the skin movement, direction of the skin movement, acceleration of the skin movement, speckle pattern, etc.) of the individual and output signals representative of the detected facial skin micromovements. Such analysis may be performed using a computer (e.g., including a processor) to identify a speckle pattern and derive information about a surface (e.g., facial skin) represented in reflection signals. A speckle pattern may occur as the result of the interference of coherent light waves added together to give a resultant wave whose intensity varies. In some embodiments, the detected speckle pattern may be processed to generate facial skin micromovement signals. In some embodiments, the first facial skin micromovements, the second facial skin micromovements, and the third facial skin micromovements may be determined (e.g., by one or more processors) by analyzing signals indicative of received coherent light reflections to identify temporal and intensity changes of speckles.

Figure 20:
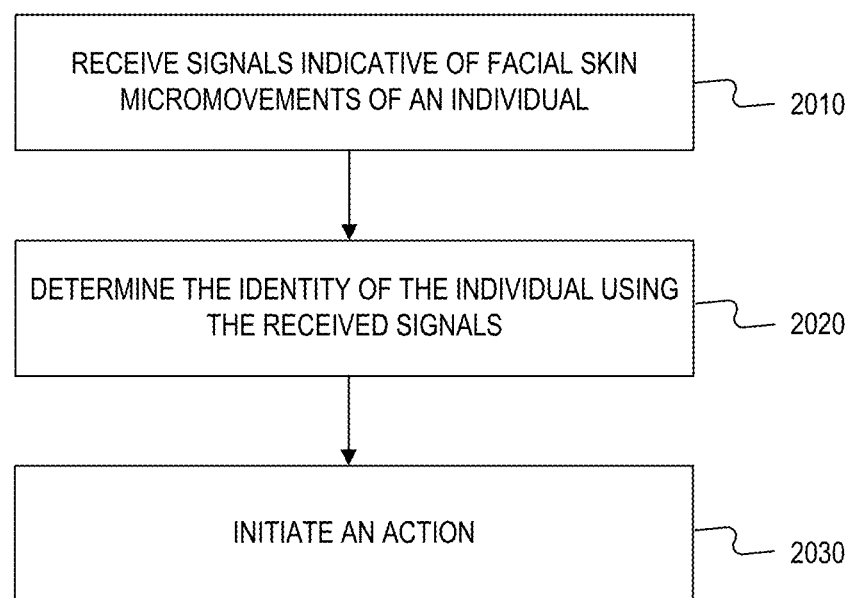
FIG. 20 is a flowchart of an exemplary process for continuous authentication of an individual using facial micromovements consistent with some embodiments of the present disclosure.

FIG. 20 is a flowchart of an exemplary process 2000 that may be used by system 1900 (of FIG. 19) for continuously authenticating an individual using the individual's facial skin micromovements during an electronic transaction. In some embodiments, process 2000 may be performed by at least one processor (e.g., processor 1910 of FIG. 19, processing device 460 of FIG. 4, etc.) to perform the operations or functions described herein. It should be noted that, in some embodiments, some aspects of process 2000 (and other processes disclosed herein) may be implemented as software (e.g., program codes or instructions) stored in a memory (e.g., memory 1920 of FIG. 19, memory device 402 of FIG. 4, etc.) such as, for example, a non-transitory computer readable medium, and some aspects of the process may be implemented as hardware (e.g., a specific-purpose circuit). In some embodiments, process 2000 (and other processes disclosed herein) may be implemented as a combination of software and hardware.

Process 2000 may include receiving signals representative of facial skin micromovements of an individual (step 2010). As explained elsewhere in this disclosure, these signals may be received from any source. These signals may be associated with an individual engaged in an electronic transaction (e.g., talking on phone, engaged in an online activity, logging into an account, doing some activity in the account, attending a class, etc.). In some embodiments, these signals may be real-time signals indicative of facial skin micromovements of the individual engaged in the transaction. As explained elsewhere in this disclosure, real-time signals are indicative of the individual's facial skin micromovements at that time. Process 2000 may also include determining the identity of the individual using the received signals (step 2020). As explained elsewhere in this disclosure (e.g., with reference to system 1900 of FIG. 19), in some embodiments, to determine the identity of the individual, the received signals (in step 2010) may be compared with reference signals (e.g., reference facial skin micromovement signals) of different individuals stored in a database to determine the equivalence, correspondence, similarity, match, etc. between the received signal and the stored reference signals. In some embodiments, the received signals may be compared with all the reference signals (e.g., reference signals of everyone) stored in the database to uniquely identify the individual associated with the received signals (in step 2010). As explained elsewhere in this disclosure, in some embodiments, the received signals may be considered to be associated with a specific individual if a matching score (or certainty level, confidence level, or any other indicator of the extent of the similarity between the two signals) of the comparison (between the received signals and that specific individual's reference signal) exceeds or equals a predefined threshold. In embodiments where the possible identity of the individual corresponding to the received signals (in step 2010) is known or suspected (e.g., based on a prior comparison of a previously received signal, based on identifying information received in conjunction with the signals, etc.), the received signals may be compared with the stored reference signals of that individual to see if there is a match.

Process 2000 may also include initiating an action based on the results of the comparison (step 2030). Any action may be initiated based on the results of the comparison. In general, the action may depend on the application and/or the context. In some embodiments, the institution 1800 (or another entity involved in the transaction), the individual, and/or another authority may be notified (e.g., "user identified," "user not identified," "user no longer identified," etc.) of the results of the comparison. In some embodiments, step 2030 may additionally or alternatively include preventing or blocking the individual from continuing with the transaction. The institution and/or other entities may be notified in any manner (audibly, visually, textually, graphically, etc.). As illustrated in FIG. 20, signals representative of facial skin micromovements of the individual may continue to be received (step 2010) and the received signals may be compared with the reference signal (step 2020) for an extended period of time (for example, for a predetermined period of time, the period of time that the individual is engaged in the transaction, until the system receives a signal to stop authenticating, etc.).

Figure 21:
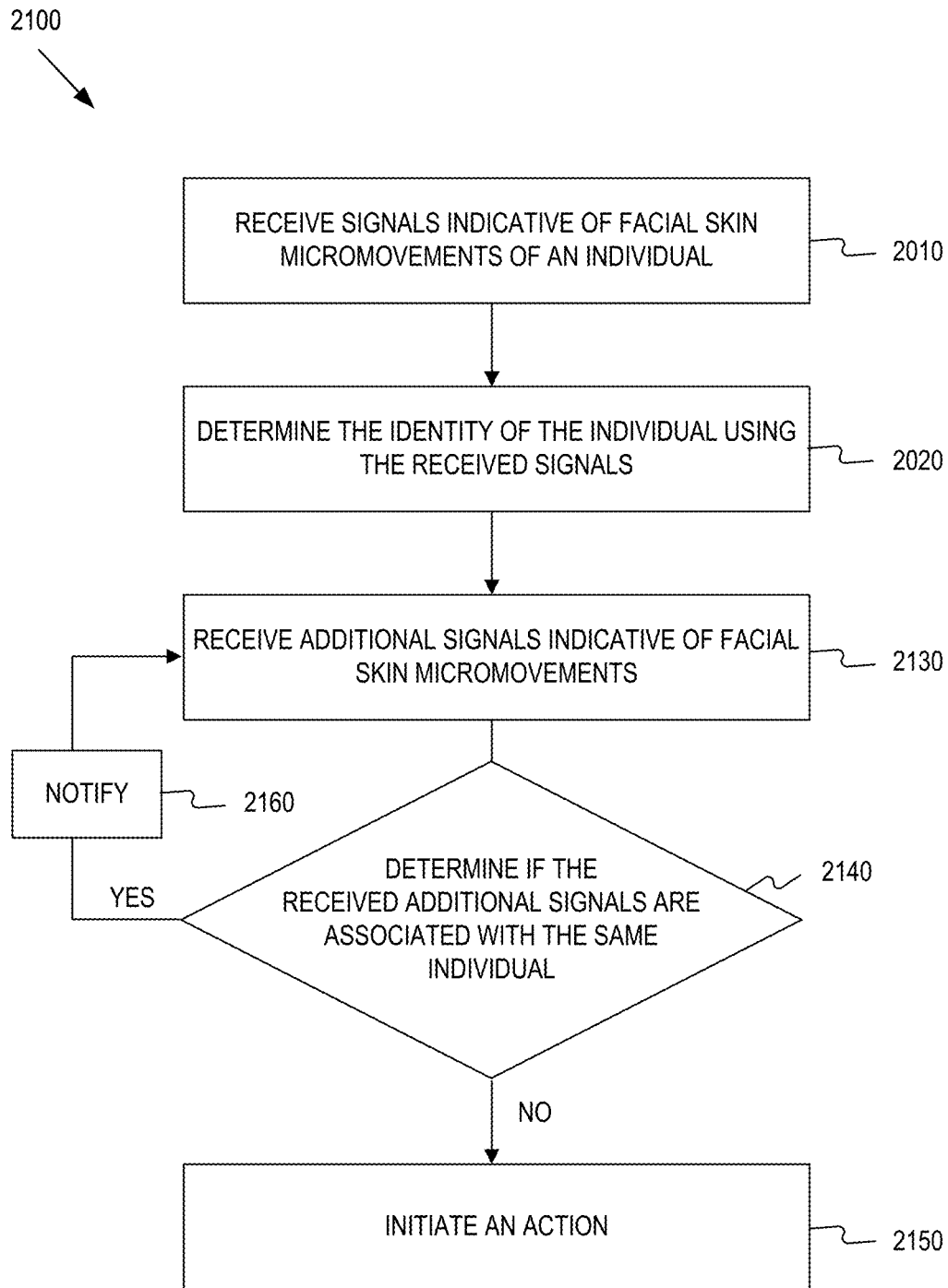
FIG. 21 is a flowchart of another exemplary process for continuous authentication of an individual using facial micromovements consistent with some embodiments of the present disclosure.

FIG. 21 is a flowchart of another exemplary process 2100 that may be used by system 1900 (of FIG. 19) for continuously authenticating an individual using the individual's facial skin micromovements during an electronic transaction. In process 2100, the authentication system (e.g., system 1900) may receive signals representative of facial skin micromovements of an individual (step 2010) and compare the received signals with stored reference signals to identify the individual associated with the signals (step 2020) similar to process 2000 (of FIG. 20). After determining the identity of the individual corresponding to the received signals (in step 2020), the authentication system may continue to receive additional signals indicative of facial skin micromovements (step 2130) for an extended period of time, for example, that the individual is engaged in a transaction. The received additional signals may be compared with the reference signals of the individual previously identified in step 2020 to determine whether the same individual is engaged in the transaction (step 2140). If it is determined that the additional signals received in step 2130 are associated with the same individual identified in step 2020 (e.g., step 440=YES), then the system may continue to receive additional signals and confirm that these signals are associated with the same individual. In some embodiments, the system may also continuously notify 2160 a relevant entity (e.g., the institution 1800 that the individual is conducting a transaction with, a person that the individual is engaged in a transaction with, or another entity associated with the transaction), that the same individual is engaged in the transaction. As in process 2000, the notification may be made in any manner (audibly, textually, visually, etc.). In some embodiments, the notification step 2160 may be eliminated.

If it is determined in step 2140 that the additional signals are not associated with the same individual identified in step 2020 (e.g., step 440=NO), the system may initiate an action (step 2150). In general, any action may be initiated in step 2150. In some embodiments, the institution or person that the individual is engaged in the transaction with may be notified (e.g., "user is no longer identified," etc.). Additionally or alternatively, in some embodiments, security personnel may be notified and/or the system may stop the transaction that the individual is engaged in. In some embodiments, if the system determines in step 2140 that the additional signals are not associated with the same individual that was identified in step 2020, the system may compare the received additional signals (in step 2130) with the stored reference signals (e.g., as in step 2020) to try and identify the individual associated with the additional signals.

Figure 22:
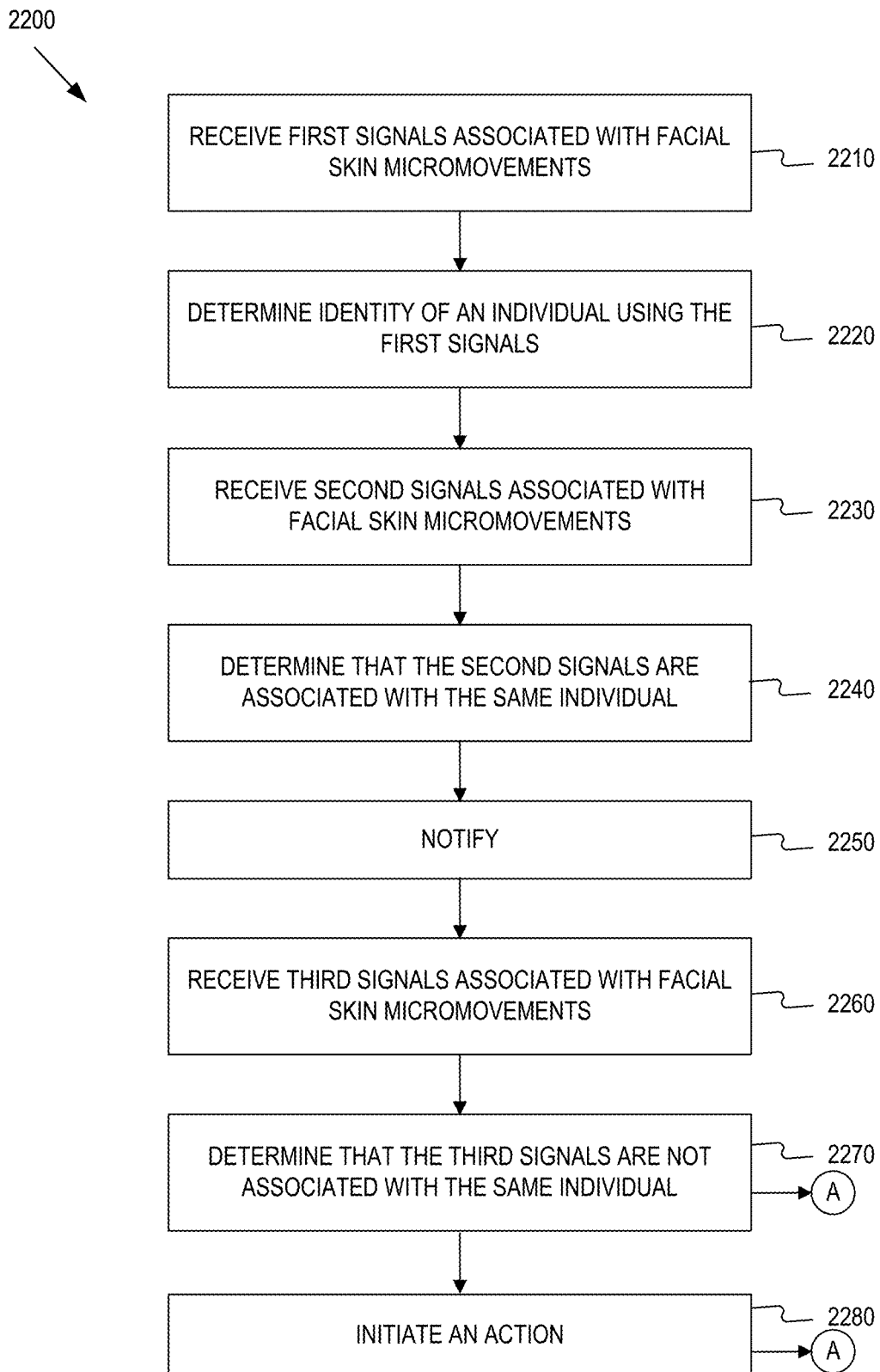
FIG. 22 is a flowchart of another exemplary process for continuous authentication of an individual using facial micromovements consistent with some embodiments of the present disclosure.

FIG. 22 illustrates another exemplary process 2200 that may be performed by an authentication system (e.g., system 1500) for continuous authentication during an electronic transaction based on facial skin micromovements. Process 2200 may include receiving first signals associated with facial skin micromovements (step 2210). The first signals may be real-time signals representative of facial skin micromovements occurring in the facial region of the individual during a first time period of the transaction. System 1900 may determine the identity of the individual using the received first signals (step 2220). The first signals may be used to determine the identity of the individual associated with the facial skin micromovements (represented by the first signals) in the same manner as described with reference to step 2020 (of FIG. 19). For example, the system may maintain (or have access to) a database of representative facial skin micromovements (or representative signals) of different individual's, and the system may determine the identity of the individual by comparing the features of the received first signals and the stored representative signals.

System 1900 may receive second signals representative of the facial skin micromovements of the individual during the electronic transaction (step 2230). The second signals may be real-time signals representative of facial skin micromovements occurring in the facial region of the individual during a second time period following the first time period. The second time period may be contiguous time periods or non-contiguous spaced-apart time periods. System 1900 may determine that the second signals are associated with the same individual that was associated with the previously-received first signals (step 2240). As explained with reference to step 2020, system 1900 may determine that the second signals are associated with the same individual based on the level of similarity between the first and second signals. In some embodiments, system 1900 may notify the institution 1800 (or another entity/person involved in the electronic transaction) that the same individual is engaged in the transaction (step 2250). In some embodiments, as in step 2160 (of FIG. 21), the system may continuously notify 2250 that the same individual is engaged in the transaction. As in processes 2000 and 2100, the notification may be made in any manner (audibly, textually, visually, etc.). In some embodiments, the notification step 2250 may be eliminated.

System 1900 may receive third signals representative of the facial skin micromovements of the individual during a third time period following the first and second time periods while engaged in the electronic transaction (step 2260). The third signals may also be real-time signals indicative of the facial skin micromovements of the individual occurring during that time period. The second and third time periods may be contiguous or non-contiguous time periods. System 1900 may compare the received third signals with the previously received first and/or second signals to determine whether the same individual is still engaged in the transaction. As explained elsewhere in this disclosure, the system may make this determination based on the similarities and differences between the corresponding signals. Based on this comparison, in some embodiments, system 1900 may determine that the third signals are not associated with the same individual associated with the previously-received facial skin micromovement signals (step 2270).

In response to the determination that the same individual is not engaged in the transaction, system 1900 may initiate an action (step 2280). As explained with reference to step 2030 (of FIG. 20) and step 2150 (of FIG. 21), any action may be initiated based on the results of the comparison. For example, in some embodiments, another entity involved in the transaction (e.g., the institution 1800) or another authority (e.g., security personnel) may be notified that the individual engaged in the transaction has changed (e.g., "user not identified," "user no longer identified," etc.). Additionally or alternatively, in some embodiments, the transaction may be stopped, and the individual may be blocked from continuing with the transaction.

Figure 23:
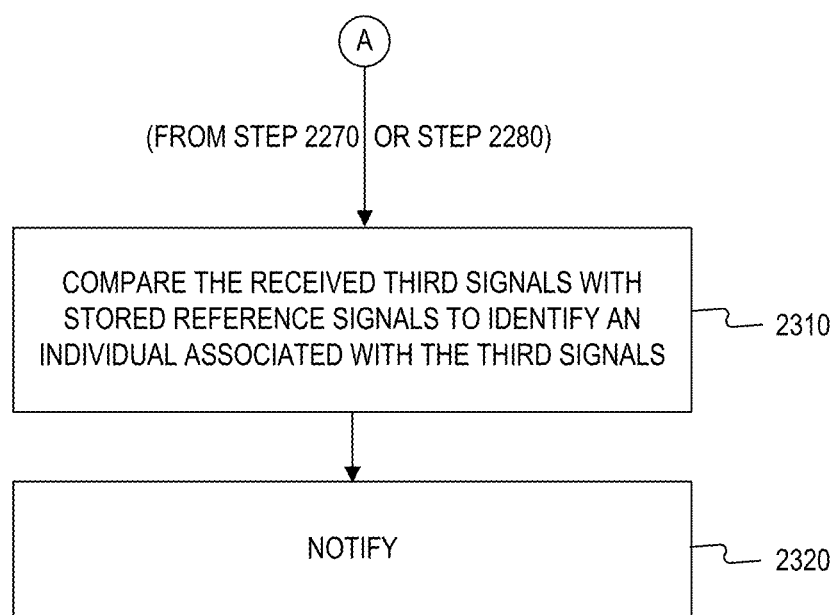
FIG. 23 is a flowchart of another exemplary process for continuous authentication of an individual using facial micromovements consistent with some embodiments of the present disclosure.

In some embodiments, as illustrated in FIG. 23, in addition to, or as an alternative to initiating an action (e.g., step 2280) when it is determined (e.g., based on a comparison of the third signals with the previously received signals) that a different individual is now engaged in the transaction (e.g., in step 2270), system 1900 may determine the identity of the individual associated with the third signals. For example, similar to step 2020 (of FIG. 20), system 1900 may compare the received third signals with the stored reference signals to determine the identity of the individual associated with the third signals (step 2310), and notify the institution and/or another entity associated with the transaction (step 2320).

Continuously authenticating an individual using facial skin micromovements may provide certainty regarding the identity of the individual for an extended period of time during an electronic transaction (e.g., a period of time that the individual is engaged in a transaction). Processes 2000, 2100, and 2200 described above for continuously authenticating an individual are only exemplary and many changes are possible. It should be noted that the steps described with reference to one of the processes 2000, 2100, and 2200 are also applicable to (and/or may be used with) the other processes. In some embodiments, some illustrated steps may be eliminated and/or additional steps added. And in some embodiments, the order of the steps may be changed. Additionally, in some embodiments, processes 2000, 2100, and 2200 may be incorporated into another process or may be part of a larger process.

As described elsewhere in this disclosure, some disclosed embodiments involve providing an approach for detecting prevocalized speech, subvocalized speech and silent speech through the detection of facial skin micromovements to determine words in an absence of perceptible vocalization. Consistent with some disclosed embodiments, a speech detection system may be configured to avoid interpretation of facial micromovements that an individual may not have intended for vocalization or may have been caused for reasons other than intended for vocalization. For example, a user may have prevocalized a profanity that may not have been intended for vocalization. In another example, facial micromovements may change during physical activity such as exercise and the speech detection system may avoid interpretation of facial micromovements during the physical activity. To address such cases where it is advantageous to avoid interpretation of facial micromovements, the speech detection system may be configured with a threshold level of micromovement intensity to trigger interpretation or avoid interpretation of facial micromovements. Micromovements below the threshold may not result in interpretation, while micromovements above the threshold may be interpreted.

By way of a non-limiting example, consistent with disclosed embodiments, a speech detection system may project light towards a facial region of a user and analyze reflected light signals to determine facial micromovements. A light reflection analysis performed on the reflected light may include a comparison with a threshold level based on at least one property or measurement of the reflected light to determine whether to interpret the facial micromovement or to disregard the facial micromovement. By including the threshold level in the light reflection analysis, the speech detection system may add a confidence level to analyzed facial micromovements in cases where comparison with the threshold determines that the facial micromovements should be interpreted and may reduce false detections in cases where the threshold level determines that that the facial micromovements should be disregarded. In some embodiments, thresholds may vary from person to person, and therefore, some embodiments may enable threshold level customization. Further, threshold levels may vary based on environmental conditions, user activity or other factors that may alter pre-vocal facial micromovements versus stable conditions such as an individual at rest. Thus, in some embodiments, a mechanism for enabling the adjustment of threshold levels may be provided.

Some disclosed embodiments involve detecting facial micromovements in an absence of perceptible vocalization associated with the facial micromovements. Facial micromovements (e.g., facial skin micromovements), as described elsewhere herein, may broadly refer to skin motions on the face that may be detectable using a sensor, but which might not be readily detectable to the naked eye. For example, facial micromovements may include nonverbal communication when the muscles in the face, larynx, and mouth articulate the desired sounds or move in a manner enabling interpretation of nonverbal communication while the air flow from the lungs is absent. Facial micromovements may include various types of movements, including involuntary movements caused by muscle recruitments and other types of small-scale skin deformations that fall within the range of micrometers to millimeters and fractions of a second to several seconds in duration. In some examples, facial micromovements may be present during subvocalization, silent speech, speaking soundlessly, during prevocalization muscle recruitments and other types of speech where there may be an absence of perceptible vocalization of the speech. The absence of perceptible vocalization may include no sound being emitted from the mouth, sound emitted from the mouth at a low level such that it may not be perceived by a listener or listening device, prevocalized speech where air flow from the lungs is absent, or any other prevocalization, subvocalization or vocalization where sound may not be perceived.

By way of a non-limiting example, the absence of perceptible vocalization may be associated with facial micromovements of the muscles in the face, larynx, and mouth during the articulation of the desired sounds. For example, absence of perceptible vocalization may include muscle and skin activity such as tongue movement, microbic skin movement, prevocalization muscle recruitment and other detectible activity in the facial region that precedes voice production. Detecting facial micromovements may include the speech detection system sensing the facial micromovements and associating those movements with the absence of perceptible vocalization as described and exemplified elsewhere in this disclosure. For example, facial micromovements may be associated with intent to speak or may be associated with silent speech.

Some disclosed embodiments involve determining an intensity level of the facial micromovements. The term "intensity level" related to facial micromovements broadly refers to the sensed or measured amount of skin or muscle fiber movement. Sensing (e.g., to sense) may include detecting, measuring, and/or receiving a measurement. Intensity level of facial micromovements may be determined (e.g., measured) using a variety of sensors including but not limited to light sensors, optical sensors, image sensors, electromyography (EMG) sensors, motion sensors and any other device that may detect or sense movements in the face region. Typical muscle fiber recruitment may happen at a frequency of 6 Hz to 10 Hz and may have an intensity level (e.g., amplitude or amount of movement of the skin and/or muscle fiber) that depends on the level of intent of the speaker. In one example, an optical sensor, including a light source and light detector, may be used to determine an amount of displacement of one or more locations of the face region (i.e., movement of the skin and muscles in the face) through light reflection analysis of the reflected signals detected from the face region. The reflection signals may be used for performing speckle analysis to analyze pixels, voxels, point cloud, range data, or other parameter of the reflection signals included in the reflection image data corresponding to the face region including displacement of the skin of the face (e.g., intensity level of the movement).

In a second example, an image sensor (e.g., digital camera) may be used to capture image data corresponding to the face region including displacement of the skin of the face. Consistent with the present disclosure, the image data may include pixel data streams, digital images, digital video streams, data derived from captured images, and data that may be used to construct one or more 3D images, a sequence of 3D images, 3D videos, or a virtual 3D representation. From the image data, image processing algorithms may be used to determine an intensity level of facial micromovements and thus may be used to detect facial micromovements in the face region allowing the speech detection system to decipher some subvocalized facial micromovements. In another example, electromyography (EMG) sensors may be used by attaching electrodes to the body surface to capture electrical signals, which may provide information regarding the activation of the user's facial muscles. The speech detection system may use the electrical activity sensed by the electrodes to detect facial micromovements in the face region allowing the speech detection system to decipher some subvocalized facial micromovements. It is to be appreciated that a variety of sensors may be used consistent with disclosed embodiments to detect facial micromovements and/or an intensity level of the facial micromovements.

Consistent with some disclosed embodiments, determining the intensity level includes determining a value associated with a series of micromovements in a time period. A value associated with a series or micromovements may be related to a unit of measure of a parameter associated with reflected light signals or electrical signals, as described above, determined directly or indirectly by the sensing mechanism. In one example, the value may represent an amount of movement measured in micrometers or millimeters. Returning to the example of the optical sensor, the reflection signals may be used to determine range or distance from the optical sensor to a plurality of points in the face region (as shown in FIG. 1 where optical sensing unit 116 may be used measure displacement of a plurality of points in the face region 108). In the example, the value may be determined by analysis of characteristics of light reflection such as by a speckle analysis performed on the light reflected from the face region, by calculating the measured time for the reflected light to return to the receiver (e.g., time of flight), by measuring light intensity, analyzing illumination pattern or analyzing any other optical characteristic that may allow a speech detection system to detect facial micromovements. The value representing the distance of the optical sensor from the skin surface may correspond to the detected displacement of the skin surface.

Consistent with some disclosed embodiments, the value associated with facial micromovements may include measurements of a series of micromovements in a time period. The term "time period" may be broadly defined as a length of time measured in fractions of a second, in seconds, in minutes or in any other length of time in which a measurement of a value associated with facial micromovements may be relevant. The measurements in a time period may include a plurality of discrete sample measurements of a series of micromovements. For example, the optical sensor may make several measurements of the micromovements of the face region over a time period (e.g., samples). It is to be appreciated that the measurements in a time period may occur at any sample rate, scanning frequency, scan rate, duty cycle, sweep frequency or other method of making measurements over time that may be used with disclosed embodiments. Determining the value may include determining a single value obtained from the series of measurements or may include the series of values obtained from the series of measurements.

Some disclosed embodiments involve comparing the determined intensity level with a threshold. The threshold may include a baseline, a limit (e.g., a maximum or minimum), a tolerance, a starting point, and/or an end point for a measurable quantity. In some disclosed embodiments, the measurable quantity related to the threshold level may correspond to the intensity level of facial micromovements. Comparing may involve determining a difference, a ratio, or some other statistical or mathematical value based on the determined intensity level and the threshold. In some embodiments, comparing may involve determining whether the determine intensity level is above, below, or equal to the threshold. In some embodiments, the threshold level may be used to identify when a user does not plan to talk (e.g., thinking to self). It is to be appreciated that different muscles or regions of the face may have different thresholds. For example, a part of the cheek above the mouth may have a different threshold level than a part of the cheek below the mouth. A determined intensity level of a part of the cheek above the mouth may have a different interpretation versus a determined intensity level of a part of the cheek below the mouth therefore they may have different threshold levels to compare to when determining whether to interpret or disregard micromovements in either area of the face.

Consistent with some embodiments, the threshold level may be used to determine if the system should proceed in processing facial micromovements to determine if they are associated with prevocalized or subvocalized speech. The threshold level may provide an indication whether the intensity level of movement dictates further processing. In some embodiments, the threshold level may be crossed during consecutive measurements initiating a trigger to the system to take an action. For example, a determined intensity level below a threshold level may indicate that facial micromovements should be disregarded. On the next measurement, the determined intensity level may transition to above the threshold level indicating that the facial micromovements should be interpreted. In some embodiments, the threshold level may be used to define a speaking session. For example, the threshold level may be relevant to identify the beginning of the speaking session when the determined intensity level transitions above the threshold level. Once in the speaking session, the threshold level may be used, when the signal falls below or transitions below the threshold level, to determine when to disregard detection or when to determine that the speaking session may be ending. It is to be appreciated that more than one threshold level may be implemented with respect to disclosed embodiments. For example, hysteresis may be implemented where two threshold levels may be used, for example dependent on the direction of the change in the measurement, to provide a smooth transition from one mode of operation to another mode of operation (e.g., starting and ending of speaking sessions).

Consistent with some disclosed embodiments, calibration procedures may be employed to set a threshold level for system operation. For example, an audio sensor may be used a part of a calibration procedure, in which an optical sensor detects micromovements of the skin while a user vocalizes certain phonemes or words. The reflection signals may be analyzed to compare the sounds sensed by the audio sensor to calibrate a threshold level for a particular user or for a particular environment in which the system may be used. For example, a calibration procedure may allow the system to be adjusted to identify the beginning and ending of a speaking session by a particular user.

Figure 24:
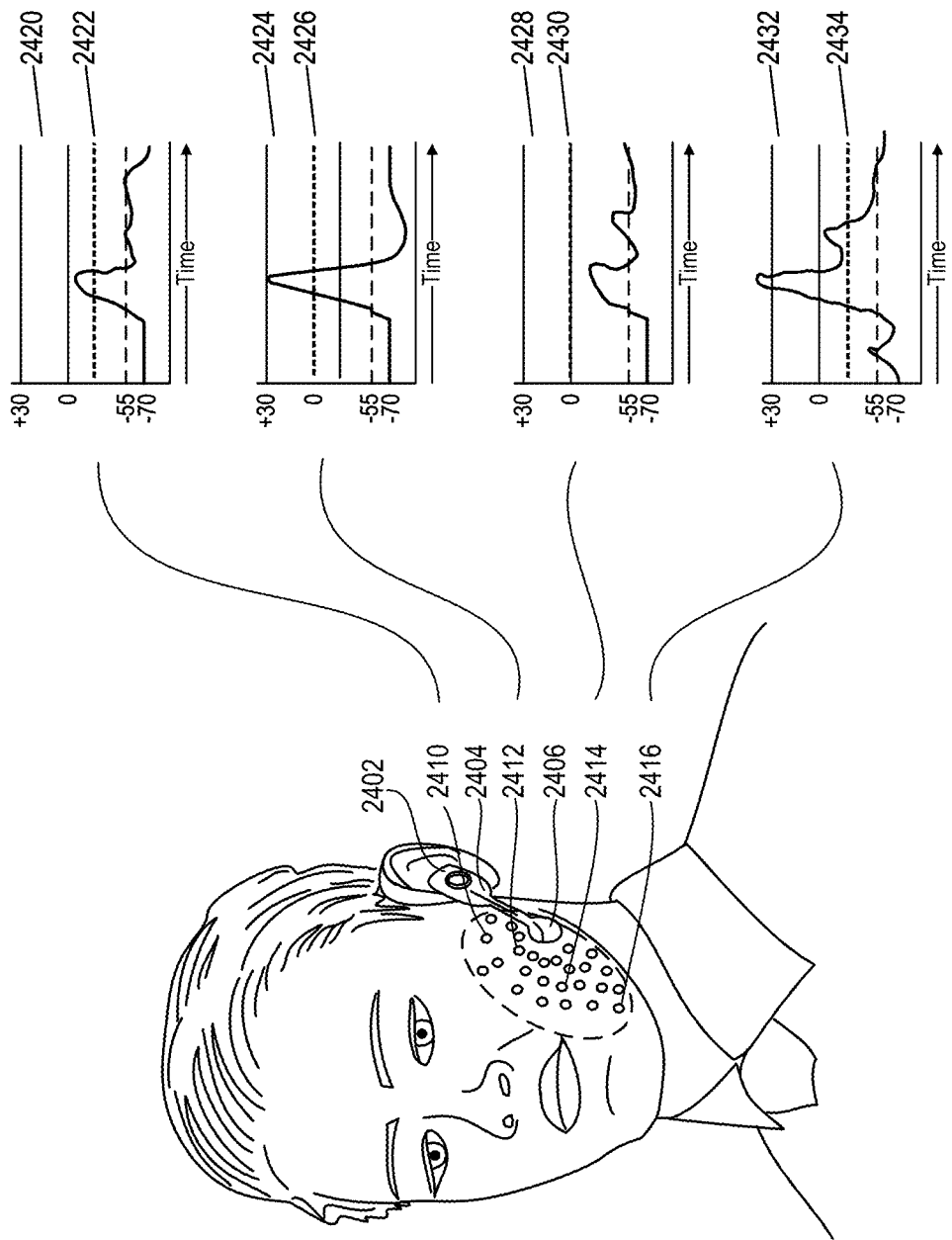
FIG. 24 include a series of displacement versus time charts that include threshold levels associated with a number of facial locations, consistent with some embodiments of the present disclosure.

By way of a non-limiting example, reference is made to FIG. 24 illustrating four locations in facial region showing displacement versus time charts that include threshold levels associated with each location. In FIG. 24, a wearable device 2402 implementing a speech detection system including ear-piece 2404 and optical sensing unit 2406 may be used to detect facial micromovements at a plurality of locations in the facial region depicted by the region within the dotted lines. FIG. 24 shows areas associated with specific muscle recruitments that may cause facial micromovements including a part of the cheek near the ear 2410, a part of the cheek above the mouth 2412, a part of the cheek adjacent to the mouth 2414 and a part of the mid-jaw 2416. It is to be appreciated that such micromovements may occur over a multi-square millimeter facial area. Graph 2420 displays measurements of values associated with determined intensity level (e.g., displacement) for a series of micromovements in a time period for a part of the cheek near the ear 2410. Graph 2420 includes a threshold level 2422. The measured values in graph 2420 may be compared with threshold level 2422 to determine whether to trigger the speech detection system to interpret or cause the speech detection system to disregard movements for that area. In graph 2420, the determined intensity level of series of micromovements in a time period exceeds threshold level 2422. Exceeding the threshold in this manner may provide a trigger to the system to interpret facial micromovements. Similarly, graph 2424 includes measurements of values associated with a determined intensity level for a part of the cheek above the mouth 2412 compared with associated threshold level 2426. It is to be appreciated that different threshold levels may be implemented for different locations or areas of the facial region. Threshold level 2422 and threshold level 2426 are at different levels. Further, it is to be appreciated that facial micromovements may cross thresholds at different times (i.e., threshold level crossings of different regions of the face may be asynchronous). Graph 2428 includes measurements of values associated with a determined intensity level for a part of the cheek adjacent to the mouth 2414 compared with associated threshold level 2430. In this case, the values associated with the determined intensity level for the series of micromovements fall below threshold level 2430 and therefore facial micromovements in this area of the face may be disregarded (i.e., not interpreted). Graph 2432 includes measurements of values associated with a determined intensity level for a part of the mid-jaw 2416 compared with associated threshold level 2434. Note that the determined intensity level crosses the threshold level. Even though a part of the cheek adjacent to the mouth 2414 and a part of the mid-jaw 2416 are in the same area of the face region, one location may have a triggering event based on movement compared to the threshold level and a second location may not have a triggering event because the threshold level may not be crosses.

Figure 25B:
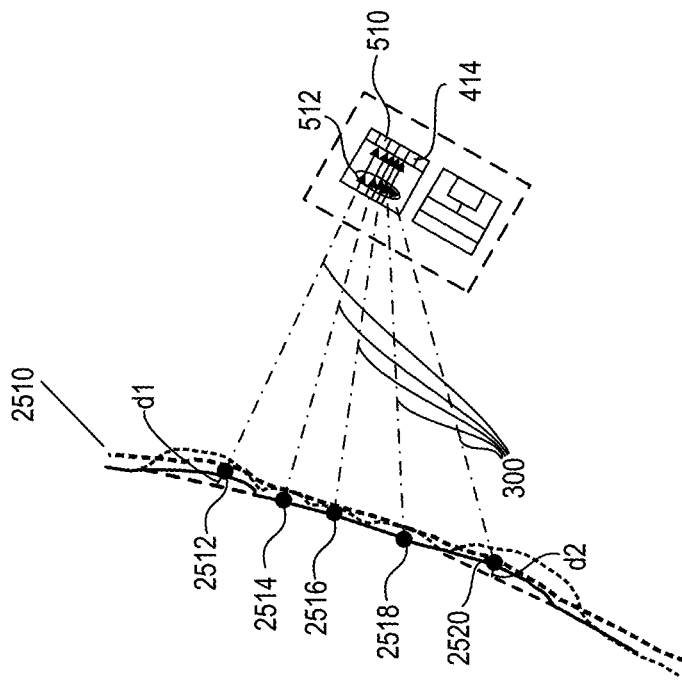
FIGS. 25A and 25B are schematic illustrations of exemplary displacement levels of facial micromovements where a threshold trigger mechanism may be employed, consistent with some embodiments of the present disclosure.
Figure 25A:
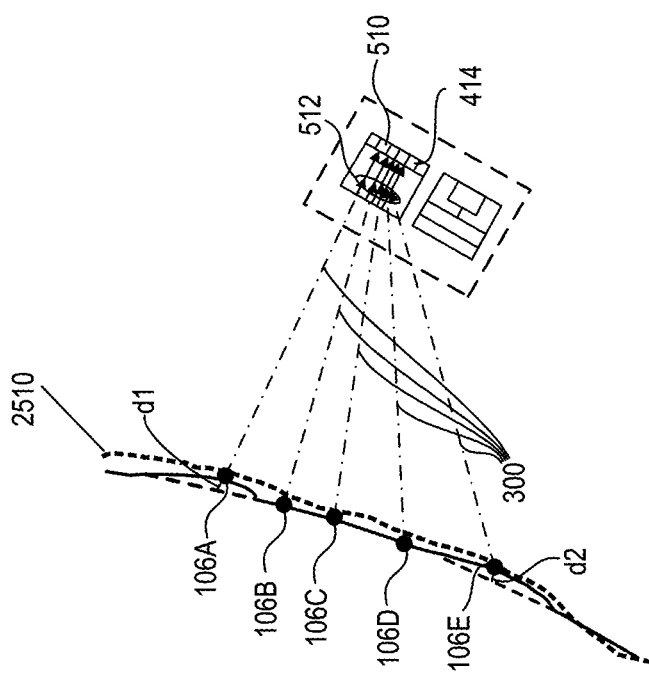

By way of another non-limiting example, reference is made to FIG. 25A and FIG. 25B illustrating an optical sensing unit 116 including illumination source 500 and detection module 502 with light reflections 300 corresponding to two micromovement displacements. FIG. 25A illustrates a position of threshold level 2510 for comparison to the surface of a face region with respective spots 106A-106E in a pattern extending over the facial region. The speech detection system may be configured to process light reflected from a first region of face in proximity to spot 106A to determine an intensity level indicating that the first region moved by a distance d1 and to process light reflected from a second region of face in proximity to spot 106E to determine that the second region moved by a distance d2. Consistent with disclosed embodiments, distances d1 and d2 may be less than 1000 micrometers, less than 100 micrometers, less than 10 micrometers, or less. The speech detection system may compare distances d1 and d2 to threshold level 2510. As shown in FIG. 25A, distances d1 and d2 do not cross threshold level 2510 therefore the silent speech system may disregard the facial micromovements. FIG. 25B illustrates a position of threshold level 2510 for comparison to the surface of a face region with respective spots 2512 to 2520 after one or more facial micromovements. The speech detection system may compare distances d3 and d4 to threshold level 2510. As shown in FIG. 25B, distances d3 and d4 exceed threshold level 2510 and therefore the speech detection system may interpret these facial micromovements.

Some disclosed embodiments involve enabling adjustment of the threshold. Enabling adjustment of the threshold includes an adaption for modifying, changing, or altering a baseline, a limit (e.g., a maximum or minimum), a tolerance, a starting point, and/or an end point for a measurable quantity of the threshold level as compared to the determined intensity level. A threshold may vary from person to person, and therefore, some embodiments may enable threshold level customization for a particular user. In some examples, the user may adjust the threshold level. The adjustment of the threshold level may occur during a calibration process. The user may adjust the threshold level through control settings in a mobile application or via another interface to change the threshold level. Thus, enabling adjustment of the threshold may include providing the one or more control settings in a mobile application or via a control on a wearable. In other examples, the system may adjust the threshold level based on detected conditions. For example, threshold levels may self-adjust based on environmental conditions, user activity or other factors that may alter pre-vocal facial micromovements versus stable conditions such as an individual at rest. Thus, enabling adjustment of the threshold may include providing instruction or code that may be executed by a processor to cause a change in the threshold based on environmental conditions, user activity or other factors that may alter pre-vocal facial micromovements. In some embodiments, a mechanism for enabling the adjustment of threshold levels may be provided. The mechanism may include one or more switches, buttons, levers, knobs, or other widgets in physical form or in the form of icons or widgets on a graphical user interface of a program or application being executed by a computing device (e.g., mobile device of a user).

In some disclosed embodiments, a threshold is variable, depending on environmental conditions. Environmental conditions may include one or more factors associated with the physical space occupied by the user or with factors associated with the user. For example, environmental conditions may include rain, snow, temperature, humidity, background illumination, wind, or presence other speakers, a user physical activity level, breathing, sweating, makeup on the face region, change in the angle of the detector receiving signals, position, background noise, and any other factor that may cause a variation in measurement of the determined intensity level or may affect the threshold value. A speech detection system may include one or more environmental sensors of different types configured to capture data reflective of the environment of user (i.e., environmental conditions). One non-limiting example of an environmental sensor is a microphone for detecting ambient noise. Another non-limiting example is a motion sensor to determine a movement or exercise level. The term variable may refer to the ability to be changed or adapted. With reference to a threshold, the speech detection system may change, adapt, modify, or adjust the threshold level based on environmental conditions. For example, the silent speech system may adjust the threshold to increase the likelihood that the system may disregard facial micromovements under certain environmental conditions. In some embodiments, the threshold may vary based on sensed environmental conditions (e.g., the threshold may be adjusted based on one or more associated, sensed conditions). For example, the threshold may be variable based on the input of a temperature sensor. As the temperature changes over a range from cold to hot, the threshold may be adjusted based on the sensed temperature. In other embodiments, adjustment may be based on a profile for the particular environmental condition. A profile may include a collection of settings and information associated with a user and one or more particular environmental conditions where the settings and information may allow changes to the implementation of the threshold consistent with the operation of the system in response to the one or more particular environmental conditions. In an example in which facial micromovements may be detected using an optical sensor, a user may select a profile that adjusts the threshold based on rain. If the particular environmental condition is rain and the profile for the environmental condition is set for rain, the threshold may change to a lower value to accommodate additional light scattering that may occur, for example, due to refraction of light by water droplets.

Consistent with some disclosed embodiments, the environmental conditions include a background noise level. Background noise level may include extraneous signals received by a sensor or detector that may confound, interfere with, or modify the measurement of the intended received signal. Types of background noise include but are not limited to signal noise, interference, electrical noise, audible noise, random noise, ambient noise, sunlight, white noise and any other environmental signal that may be received by a sensor or detector in addition to the signals associated with facial micromovements that the sensor or detector is configured to receive. By way of a non-limiting example, an optical sensor used in a speech detection system in an outdoor setting may be affected by sunlight as signals associated with sunlight received by a detector may be included with or may cause interference with signals associated with light reflections from the facial region of the user that the optical sensor is configured to receive.

Consistent with some disclosed embodiments, the operations further include receiving data indicative of the background noise level, and determining a value for the threshold based on the received data. Receiving data indicative of background noise level may include configuring a receiver, detector, sensor to take a measurement the environment in the absence of signals associated with facial micromovements to capture a baseline of background noise level. In some embodiments, the baseline of background noise level may be used to determine a value for the threshold based on the received data (e.g., adjust the threshold level). By way of an example, one or more calibration samples may be captured by the receiver or sensor (i.e., received data indicative of the background noise level) wherein an analysis of the one or more calibration samples may allow the system to analyze the sample(s) and estimate background noise level. It is to be appreciated that a plurality of samples may be captured and a statistical measure of the captured sample(s) may be used to estimate background noise level. Based on the calibration, a value for the threshold level may be determined. In other examples, the background noise level may be calculated based on the received data during normal operation (e.g., a separate calibration may not be necessary). The background noise level may be determined based on a statistical analysis of the received input of the sensor. For example, the system may have an expected receiver input based on information about the received data and may be able to extract an estimate of background noise level accordingly. Thus, the system may adjust the threshold based on a determined background noise level during normal operation. By way of a non-limiting example, an optical sensor may detect background noise in an environment where sunlight may be received by the detector in addition to reflected light signals. The detector may be used to capture background noise present in one or more samples received in the absence of reflected light signals. For example, a calibration cycle may be performed in which the detector captures samples intended only to determine background noise level. The background noise level may be determined based on received data indicative of the data received due to sunlight. A value for the threshold may then be determined to take into account the background noise level due to sunlight (i.e., the threshold may be increased to accommodate for the increase in received signal level due to sunlight).

Consistent with some disclosed embodiments, the threshold is variable, depending on at least one physical activity engaged in by an individual associated with the facial micromovements. Physical activity engaged by an individual may include any movement that increases a heart rate and/or breathing of an individual. Examples of physical activity include but is not limited to walking, biking, running, exercising, doing household chores, walking up or down stairs, raking leaves, shoveling snow or any other activity that may cause the heart to pump blood to the body faster and/or increase the breathing rate of the individual. Physical activity may cause a change in the interpretation of facial micromovements of an individual. Consistent with some disclosed embodiments, the threshold may be variable and depending on the at least one physical activity engaged in by the individual, the threshold level may be adjusted such that whether the facial micromovements are interpreted or are disregarded may be at least partially based on the changing condition wherein the individual may be engaged in physical activity. By way of a non-limiting example, an increase in physical activity may cause an increase in neuromuscular activity. For example, running may cause an increase in neuromuscular activity in the face region and as such an increase in the detected intensity level of facial micromovements. Thus, an increased threshold may account for the increase in neuromuscular activity and may allow the speech detection system to disregard movements that may not be indicative of prevocalized speech. The output of a heart rate or respiration sensor may be used to determine an appropriate threshold.

Consistent with some disclosed embodiments, the at least one physical activity includes walking, running, or breathing. Walking and running refer to physical activities that may increase heart rate and breathing of an individual. In some aspects, in addition to increased heart rate and breathing, walking and running may cause an individual to sweat which may affect a sensor detection or system interpretation of facial micromovements. Similarly, the motion in the face region caused by breathing, especially as may be caused by physical activity, may affect sensor detection or system interpretation of facial micromovements. For example, an individual running on a treadmill may have a different set of facial micromovements for detected prevocalization and subvocalization versus an individual at rest (e.g., individual standing at one location or sitting at one location).

Consistent with some disclosed embodiments the operations include receiving data indicative of the of the at least one physical activity in which the individual is engaged, and determining a value for the threshold based on the received data. Receiving data indicative of the of the at least one physical activity may include receiving one or more signals, measurements, or parameters that may have values, variations, or patterns representing physical activity. It is to be appreciated that an environmental sensor may be integrated with the speech detection system to provide data indicative of the at least one physical activity. For example, the speech detection system may be integrated with a heart rate monitor to provide heart rate information. The heart rate information may include values (e.g., beats per minute) or patterns or variations (e.g., rate of increase/decrease of heart rate) that may be indicative of a physical activity (e.g., walking, running, swimming). The speech detection system may receive heart rate data from a heart rate monitor. For example, heart rate values, or patterns (e.g., changes in heart rate over a time period) may be stored in association with one or more physical activities in a memory, database, lookup table, or linked list. Consistent with some disclosed embodiments, a processor may compare the heart rate data and or any variations or patterns in the heart rate data with the stored information to identify a particular physical activity associated with the detected heart rate data. In response, the processor may be configured to determine a value for the threshold based on the receive heart rate data and the identified physical activity. As described and exemplified elsewhere in this disclosure, neuromuscular activity may be increased while running. The level of physical activity may correlate to the level of neuromuscular activity and thus the level of the threshold value. By way of an example, walking may have an increase in neuromuscular activity and jogging may have an increase in neuromuscular activity that is greater than that of walking. Furthermore, running may have an increase in neuromuscular activity that is higher than that of jogging. It is to be appreciated that the value for the threshold may be adjusted based on the level of physical activity. The threshold for running may be higher than the threshold for jogging. The threshold for jogging may be higher than the threshold for walking.

In some embodiments, the threshold is customized to a user. Customized to a user may refer to being built, configured, adjusted, altered or fitted based on the characteristics of the user. In some disclosed embodiments, the characteristics of the user may determine the adjustment to the threshold level pertaining to interpreting or to disregarding facial micromovements. In one example, a trigger adjustment module may perform fine adjustments to the threshold such that it is customized to the user. In this manner, a speech detection system may be ready for deciphering the facial micromovements based on the characteristics of the user, activity of the user or external conditions the user may be experiencing. Consistent with some disclosed embodiments, the user may use a mobile application, voice commands or controls on a wearable device (e.g. buttons, dials etc.) to set or adjust the threshold. In some embodiments, the adjustment may be customized to the user by the system. For example, the system may detect user behavior and set or adjust the threshold based on the detected behavior. A user who speaks softly may have a different level of customization than a user who is animated or speaks loudly. Thus, the threshold for a user speaking softly having lower intensity level of facial micromovements may be lower than for a user speaking loudly that may have higher intensity level of facial micromovements. In another example, artificial intelligence or machine learning, in response to detected characteristics of the user or conditions experienced by the user, may set or adjust the threshold accordingly.

Consistent with some disclosed embodiments, the threshold customized to a user further includes receiving a personalized threshold for a particular individual and storing the personalized threshold in settings associated with the particular individual. Receiving a personalized threshold for a particular individual may include receiving user input via an application, a graphical user interface or other user control interface wherein user input may identify characteristics specific to the particular user including providing the threshold level to be configured for the system used by the particular individual based on those characteristics. The user input may be provided directly from the user, or an interface may be provided to another such as a professional fitter, to provide the user input on the user's behalf. The personalized threshold may be stored in a memory, database, lookup table or other storage medium along with one or more identifiers of the particular individual. Additionally or alternatively, one or more particular settings associated with the particular user may be stored. By way of a non-limiting example, the face region of one individual may be significantly different from another individual (e.g., size, shape, skin type, muscle tone). The threshold may be customized to the face region of a particular individual and the system may receive a personalized threshold based on the particular individual. In another example, one individual may experience one type of environmental conditions such as outdoor conditions on a cold, windy and rainy day versus another individual that may experience indoor conditions at room temperature. Storing the personalized threshold in settings associated with the particular individual may include receiving a personalized threshold and storing that threshold in memory for use by the system for that particular individual. It is to be appreciated that personalized thresholds may be changed based on changing conditions experienced by a particular user.

Some disclosed embodiments involve receiving a plurality of thresholds for a particular individual, each of the plurality of thresholds being associated with a differing condition. Receiving a plurality of thresholds for a particular individual may include receiving via user input a plurality of thresholds to be used by the system under different conditions, each threshold corresponding to one or more conditions. The plurality of thresholds may be stored in the system along with the associated conditions. For example, the plurality of personalized thresholds may be stored in a memory, database, lookup table or other storage medium along with one or more identifiers and/or one or more settings associated with the particular individual. By way of a non-limiting example, one threshold associated with vigorous exercise may be stored, a second threshold associated with mild exercise may be stored and a third threshold associated with the particular user at rest may be stored. It is to be appreciated that any environmental condition, user characteristic or user customized threshold described herein may be used in conjunction with disclosed embodiments. Thresholds may be determined in various ways, and the manner in which the thresholds are determined is not to be considered limiting. In a manual manner, for example, an individual may report a condition, and data related to the associated facial skin micromovements may be stored in an associative manner for later reference. In another example of an automated manner of determining thresholds, one or more other sensors (e.g., an image sensor, pulse sensor, motion sensor, etc.) may derive a condition and that derived condition may be stored as a threshold. In yet another automated example, a dataset trained on persons other than the individual may be employed for threshold purposes (or may be used as a baseline for deriving thresholds).

Consistent with some disclosed embodiments, at least one of the differing conditions includes a physical condition of the particular individual, an emotional condition of the particular individual, or a location of the particular individual. The physical condition of the particular individual may refer to the condition or state of the body or bodily functions, such as a physiological condition or physiological condition of a particular individual. For example, a physiological condition may include good health, illness, diseased state, pathological state or any other physical condition that may affect the body or bodily functions. The emotional condition of the particular individual may refer to the emotions or feelings experienced by a person. For example, the emotional condition of the particular individual may include happiness, sadness, anxiousness, fear, surprise and another other emotion that may be detectable for the particular individual, A location of the particular individual may include the position, geographic location, orientation, situation, or venue where a particular individual is present. Consistent with disclosed embodiments, different conditions may dictate different modes of operation of the speech detection system. For example, an individual that may be crying (i.e., possibly both a physical condition and an emotional condition) may have a customized threshold level for proper operation in that condition for the particular individual. Crying may be indicative of an increase in neuromuscular activity and as such a higher threshold may be set to accommodate a higher intensity level detected from a particular individual when crying versus an emotional state with less neuromuscular activity when not crying.

Some disclosed embodiments involve receiving data indicative of a current condition of the particular individual and selecting one of the plurality of thresholds based on the received data. Receiving data indicative of a current condition of the particular individual may include receiving information associated with the condition a particular individual via a sensor, user input or other means to measure or identify a condition experienced by a particular user that may affect operation of the speech detection system. In response to the received data indicative of a current condition, the system may select one of the plurality of thresholds based on the received data. By way of an example, an Electromyography (EMG) sensor may make measurements to detect facial EMG signals recorded by electrodes attached to a particular individual via a wearable device, the detected signals corresponding to an emotional condition of a particular individual. Based on the detected emotional condition of a particular individual, a threshold level associated with the current condition of the particular individual may be selected from a plurality of thresholds. A determined intensity level may be compared to the selected threshold level to determine whether to interpret or disregard facial micromovements. The selected threshold may be adjusted to take into consideration the changes to facial micromovements related to the emotional condition.

Figure 26:
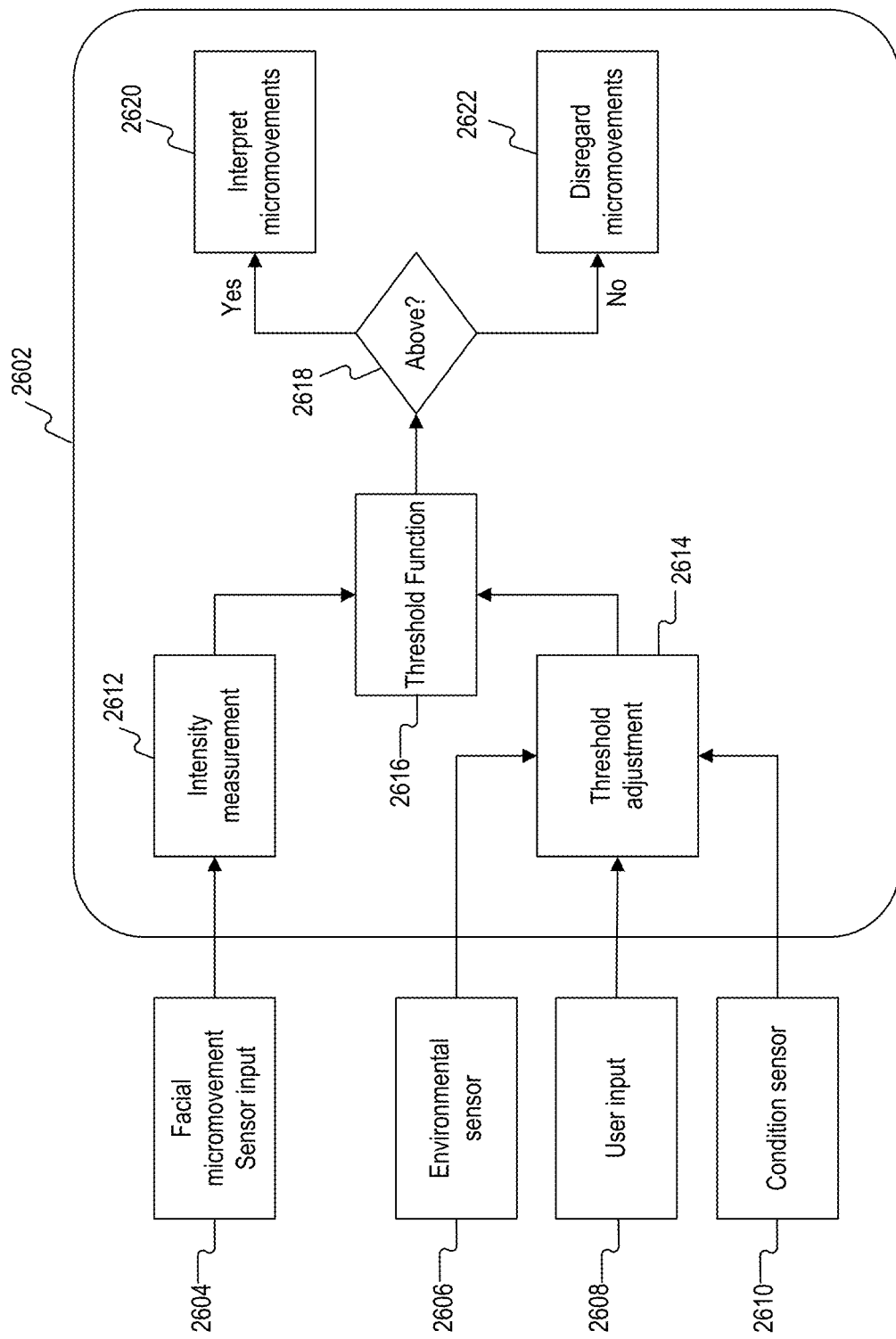
FIG. 26 is a block diagram of an exemplary speech detection system using thresholds and threshold adjustments as a trigger mechanism, consistent with some embodiments of the present disclosure.

By way of a non-limiting example, reference is made to FIG. 26 illustrating a system block diagram implementing threshold levels and threshold adjustment in a speech detection system. It is to be noted that FIG. 26 is a representation of just one embodiment, and it is to be understood that some illustrated elements might be omitted, and others added within the scope of this disclosure. In the depicted embodiment, threshold system 2602 implements an intensity level measurement at block 2612, a threshold function at block 2614, a threshold adjustment at block 2614, a threshold decision at block 2618, interpreting micromovements at block 2620 and disregarding micromovements at block 2622. Intensity level measurement block 2612 may receive input from facial micromovement sensor input 2604. It is to be appreciated that facial micromovements may be provided in various ways including via detection by any sensing mechanism described herein. Threshold adjustment block 2614 may receive input from one or more environmental sensor(s) 2606, user input 2608 and/or condition sensor 2610. During system operation, intensity level measurement 2612 may provide one or more determined intensity levels associated with facial micromovements as an input to threshold function 2616. The determined intensity levels may correspond to a plurality of values associated with a series of micromovements in a time period. The threshold function 2616 may compare the one or more determined intensity levels with one or more thresholds associated with the measurement (e.g., based on the location of the facial region). It is to be appreciated that the threshold function 2616 may have a plurality of stored threshold levels. Further, the stored thresholds may be adjusted over time. Consistent with disclosed embodiments, the threshold function 2616 may further enable adjustment of the threshold levels.

Threshold adjustment block 2614 may provide input to threshold function block 2616 to adjust the threshold levels. Threshold adjustment block 2614 may receive input to implement the adjustment of threshold levels. In some embodiments, threshold adjustment block 2614 may receive input from one or more environmental sensors 2606. Threshold levels may be variable depending on environmental conditions. Thus, based on input from one or more environmental sensors 2606, threshold adjustment block 2614 may adjust thresholds and provide updated threshold values to threshold function block 2616. In some embodiments, the environmental conditions may include a background noise level as may be identified via the facial micromovements sensor input 2604 or via an environmental sensor 2606. It is to be appreciated that the data received from either source may be used to determine a value (e.g., threshold value) for the threshold function block 2616. In some embodiments, a physical activity (e.g., walking, running or breathing) may be detected by one or more condition sensors 2610 and threshold adjustment block 2614 may configure a threshold depending on the physical activity. Consistent with some embodiments, the threshold may be customized to a user. Inputs indicative of different conditions, for example one or more environmental sensors 2606, user input 2608 or condition sensor 2610, may be used to configure the threshold for a particular user based on data received from a source. It is to be appreciated that a plurality of thresholds for a particular user may be stored by the system, each of the plurality of thresholds may be associated with a different condition.

Figure 27:
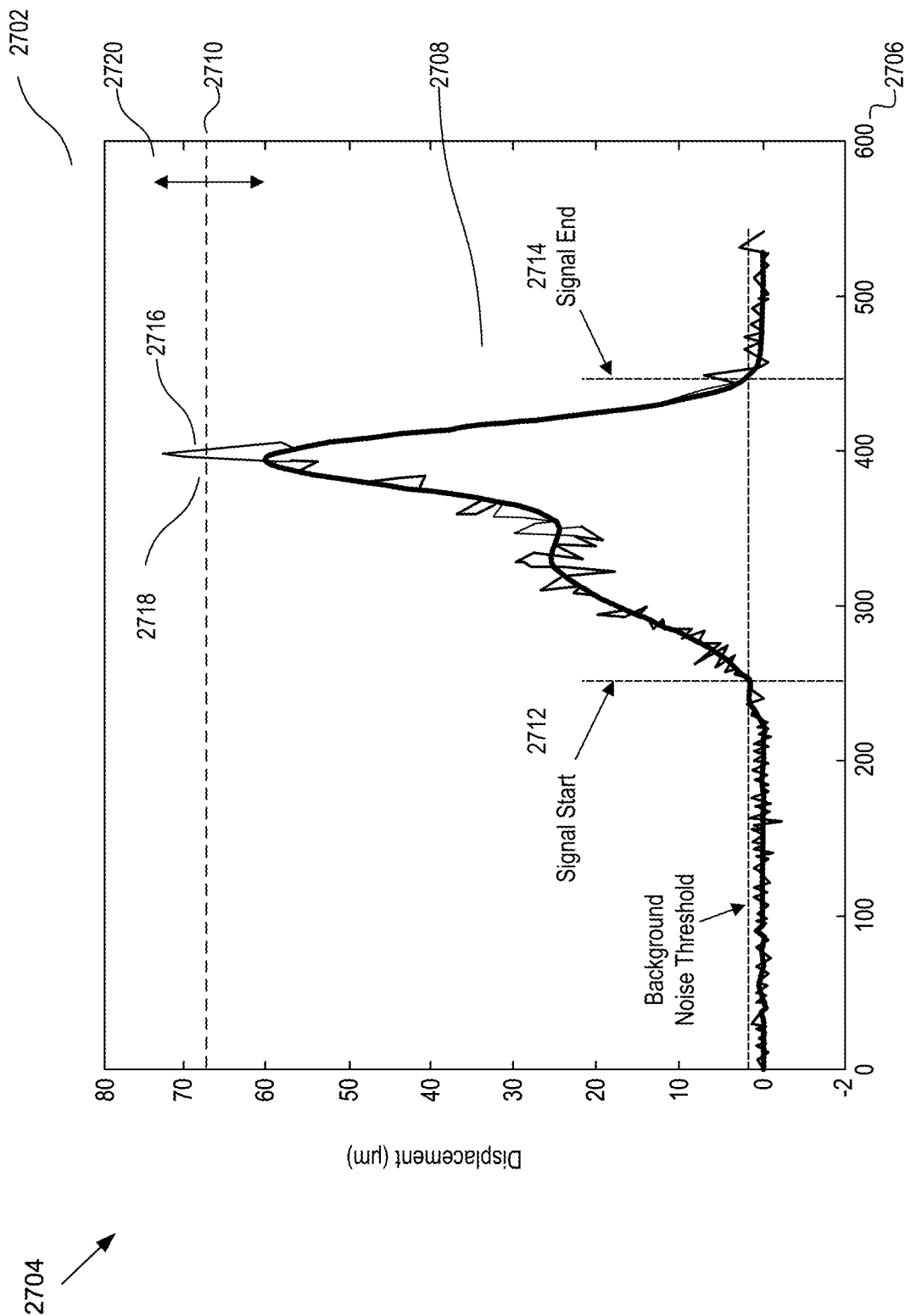
FIG. 27 is a displacement versus time graph including background noise, consistent with some embodiments of the present disclosure.

By way of a non-limiting example, reference is made to FIG. 27 showing a displacement versus time graph 2702 that includes background noise 2716 received by detector during facial micromovement determination where the background noise 2716 may be present in the received signal 2708. As shown, the graph illustrates displacement 2704 of micromovements versus time 2706 with background noise coupled onto the received signals. The background noise 2716 in the received signal 2708 crosses a threshold 2710 at point 2718 causing a false trigger. It is to be appreciated that if the background noise 2716 were not present in the received signal 2708, the threshold would not have been crossed and there would not have been a trigger. Consistent with disclosed embodiments, the background noise 2716 may be determined and the threshold 2710 may be adjusted via a threshold adjustment 2720, for example by adjusting the threshold to interpret or disregard the facial micromovements.

Figure 28B:
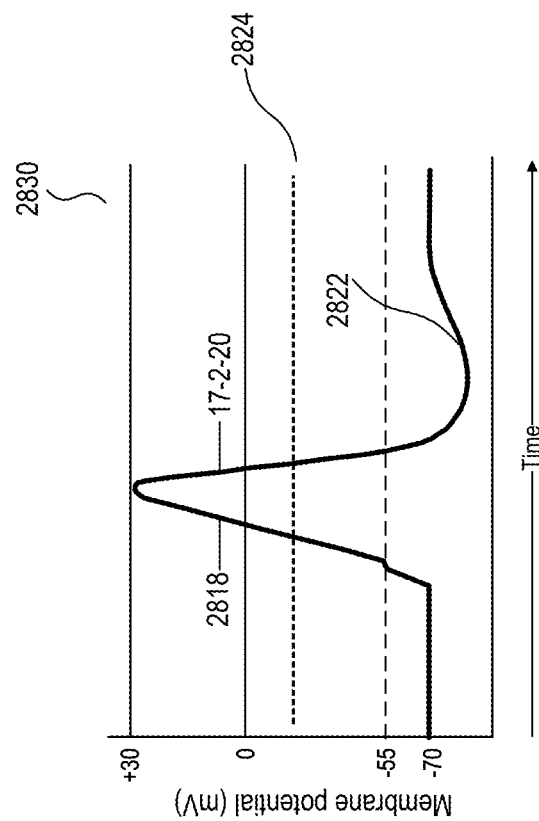
FIGS. 28A and 28B show an example of measuring skin potential difference to determine facial micromovements, consistent with some embodiments of the present disclosure.
Figure 28A:
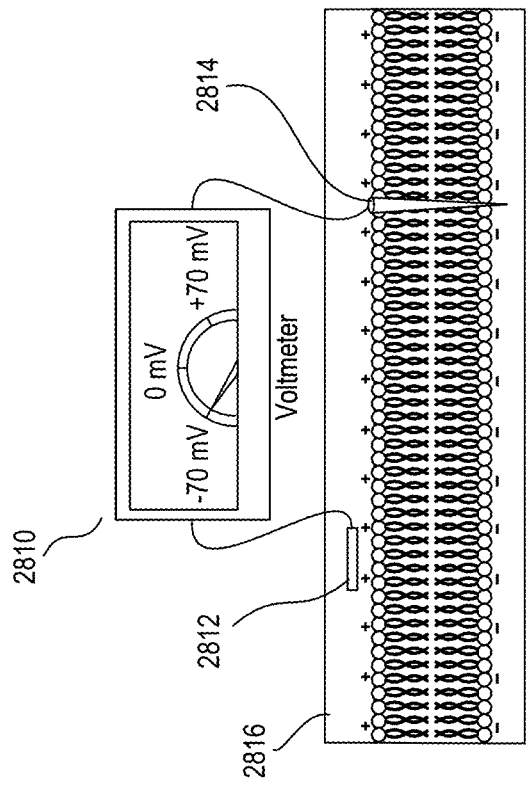

By way of a non-limiting example, reference is made to FIGS. 28A and 28B showing a disclosed embodiment wherein action potential may be used to detect muscle fiber recruitment (e.g., micromovement) in an alternate embodiment. Action potential is a predictable change in potential that occurs due to the changes in voltage on a cell membrane. Detecting the action potential in the face region may allow a speech detection system to detect facial micromovements. As described elsewhere in this disclosure, typical muscle fiber recruitment may happen at a frequency of 6 Hz to 10 Hz and may have an intensity level (e.g., amplitude) that depends on the level of intent of the speaker. In some embodiments, the intensity level may be measured by actual movement and frequency measurement (e.g., measuring the action potential, membrane potential or potential difference measurable across the skin). FIG. 28A illustrates a measurement of a potential difference 2810 measured across a reference electrode 2812 and a recording electrode 2814 of a region of the face 2816. Graph 2830 of an intensity level measurement of a potential difference (e.g., voltage or electrical difference) over time, as shown FIG. 28B may be used to interpret facial micromovements. The intensity level 2822 may be compared to threshold level 2824 to determine whether to interpret or disregard facial micromovements. As shown, the measured intensity level 2822 exceeds the threshold level 2824 at point 2818 and thus may trigger the system to begin interpreting the facial micromovements. Note that while below threshold level 2824, the system may disregard facial micromovements.

Consistent with some disclosed embodiments, when the intensity level is above the threshold, the operations include interpreting the facial micromovements. An intensity level above the threshold may include a measurement of intensity being greater than a baseline, a limit, a tolerance, a starting point, and/or an end point. When the detected intensity level of the facial micromovements exceeds the boundary or limit indicated by the threshold, the system may begin interpreting the facial micromovements. Interpreting the facial micromovements may include analyzing received signals to determine the meaning associated with facial micromovements for a particular individual. As illustrated in FIG. 25B, for example, threshold level 2510 may be used for comparison to the surface of a face region with respective spots 2512 to 2520 after one or more facial micromovements. Distances d3 and d4 are representative of the intensity level of the facial micromovements. As shown in FIG. 25B, distances d3 and d4 are representative of intensity levels above threshold level 2510 and therefore the operations may include interpreting these facial micromovements.

Consistent with some disclosed embodiments, interpreting the facial micromovements includes synthesizing speech associated with the facial micromovements. Synthesizing speech associated with the facial micromovements may include generating the vocalization of words or audio signals determined from the facial skin movements by deciphering subvocalization. For example, the start of a speaking session may be identified when the intensity level of the facial micromovements crosses above the threshold. During the speaking session, the system may interpret prevocalized or subvocalized speech from the user. The determined prevocalized or subvocalized speech may be used to generate synthesized speech. As described and exemplified elsewhere in this disclosure, synthesized speech may be played through an audio speaker, an earpiece and any other method to articulate the silent speech. In the example where a speaking session may be identified, the synthesized speech may be generated from the start of the speaking session through the end of the speaking session. In one example, the synthesized speech or synthesized audio signal may be played back to user via a speaker in output unit. This playback may be useful in giving user feedback with respect to the speech output.

Consistent with some disclosed embodiments, interpreting the facial micromovements includes understanding and executing a command based on the facial micromovements. Understanding and executing a command based on the facial micromovements may include determining the meaning of the facial micromovements, determining a command intended by the individual, and initiating an action based on the command. A command may include a directive or instruction to perform a specific task. Consistent with some disclosed embodiments, executing the command may include following instructions provided to a speech detection system and/or remote device to perform a specific task interpreted based on deciphering facial micromovements. For example, a user may subvocalize a command to retrieve specific information to an earpiece. In response to receiving the command to retrieve specific information, the speech detection system and/or remote device may execute the instructions to cause an audible presentation in the speaker of the earpiece. For example, a processor (e.g., processor of the speech detection system, processor in a remote system, processor in a mobile device or a processor in any other device that may receive a communicated message from the speech detection system that constitutes a command) may execute the command by retrieving the information and generating audio corresponding to the information. Further, the processor may execute the command by playing the generated audio in the earpiece for the user. In another example, detecting prevocalized, subvocalized or silent speech and understanding and executing a command based on the detection, may enable interaction with a virtual personal assistant. For example, a user may cause a command to be sent to a virtual assistant through subvocalization (e.g., cause neuromuscular activity in the facial region without vocalizing words). The unvocalized command may include a request to a virtual personal assistant to gather information and send the information back to the user in a textual presentation on the user's cell phone.

Consistent with some disclosed embodiments, executing the command includes generating a signal for triggering an action. Generating a signal for triggering an action may include interpreting the facial micromovements to initiate sending a signal to begin an action. Generating a signal broadly refers to emitting a command, emitting data, and/or causing any type of electronic device to initiate an action. Consistent with some embodiments, the output may be sound and the sound may be an audible presentation of words associated with silent or prevocalized speech. In one example, the audible presentation of words may include synthesized speech. Triggering an action may refer to causing an activity to occur in response to a command, an input or some other impetus. By way of a non-limiting example, a user may subvocalize command to generate an alert or emergency message requesting help. The command may generate a signal indicating the alert or emergency message that may be sent to a remote location to initiate an action. Consistent with the present disclosure, a speech detection system may be configured to communicate with a remote processing system (e.g., mobile communications device or server).

Consistent with some disclosed embodiments, when the intensity level falls beneath the threshold, the operations include disregarding the facial micromovements. An intensity level falling beneath the threshold may include a measurement of intensity being below or being less than a baseline, a limit, a tolerance, a starting point, and/or an end point. When the intensity level of the facial micromovements is below the boundary or limit indicated by the threshold, the system may disregard the facial micromovements. Disregarding the facial micromovements may include not determining the meaning associated with facial micromovements for a particular individual during a time period while the intensity level is below or falls below the threshold. As illustrated in FIG. 25A, for example, threshold level 2510 may be used for comparison to the surface of a face region with respective spots 106A to 106E after one or more facial micromovements. Distances d1 and d2 are representative of the intensity level of the facial micromovements. As shown in FIG. 25A, distances d1 and d2 are representative of intensity levels below threshold level 2510 and therefore, when the intensity level falls below the baseline established by threshold level 2510, the operations may include disregarding these facial micromovements.

Consistent with some disclosed embodiments, the facial micromovements having an intensity level falling beneath the threshold may be capable of interpretation but are disregarded nevertheless. Capable of interpretation refers to having enough information in the received signals to understand the meaning of facial micromovements even though the intensity level of the facial micromovements may be low. The processor may be capable of interpreting the facial micromovements that have an intensity level that falls beneath the threshold. The facial micromovements may be disregarded nevertheless means that even though the processor can determine meaning from the micromovements, the processor may still disregard the movements. It is to be appreciated that interpretation of low intensity level facial micromovements may lead to an increased failure rate in silent speech detection.

Figure 29:
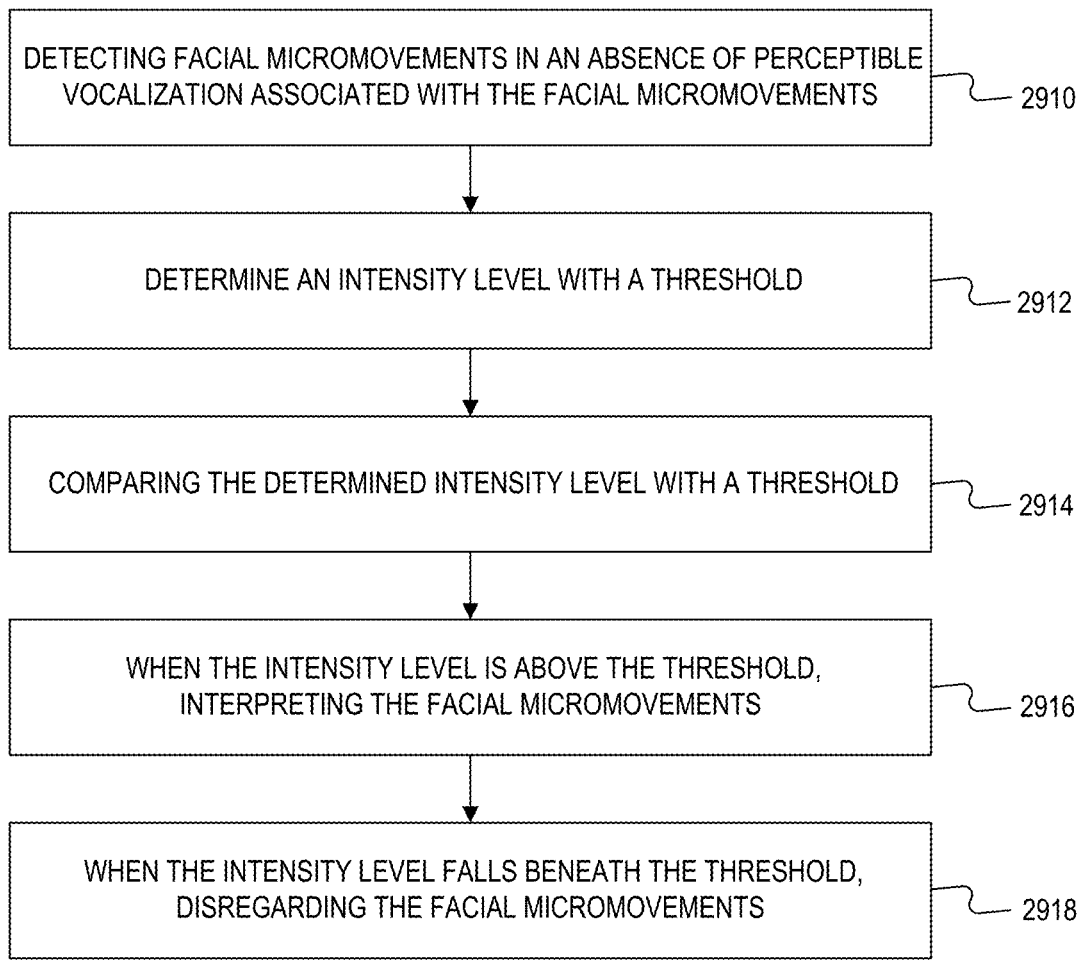
FIG. 29 is a flow chart showing an exemplary method for using a threshold to interpret or disregard facial micromovements, consistent with some embodiments of the present disclosure.

FIG. 29 illustrates a flowchart of an exemplary process 2900 for implementing a threshold to interpret or disregard facial skin micromovements, consistent with embodiments of the present disclosure. Some embodiments involve a method for thresholding interpretation of facial skin micromovements. At step 2910, the method may include detecting facial micromovements in an absence of perceptible vocalization associated with the facial micromovements. At step 2912, the method may include determining an intensity level of the facial micromovements. In some embodiments, determining the intensity level may include measuring a value of intensity level associated with a series of micromovements in a time period. At step 2914, the method may include comparing the determined intensity level with a threshold. In some embodiments, the threshold may be adjustable. In some embodiments, the threshold setting may be variable depending on environmental conditions. The environmental conditions may include a background noise level or may depend on at least one physical activity engaged in by a user. In some embodiments, the threshold may be adjusted based on environmental conditions or based on physical activity detected by the system. The threshold may be customized to the user. In some embodiments, a plurality of thresholds may be employed, each threshold being associated with one or more differing conditions. The differing conditions may include a physical condition, an emotional condition or a location of the user. At step 2916, when the intensity level is above the threshold, the method may include interpreting the facial micromovements. In some embodiments, interpreting the facial micromovements may include synthesizing speech associated with the facial micromovements. In some embodiments, interpreting the facial micromovements may include understanding and executing a command based on the facial micromovements. At step 2918, when the intensity level falls beneath the threshold, the method includes disregarding facial micromovements. In some embodiments, intensity level below or falling below the threshold may cause the system to avoid interpreting facial micromovements.

The embodiments discussed above for performing thresholding operations for interpretation of facial skin micromovements may be implemented through non-transitory computer-readable medium such as software (e.g., as operations executed through code), as methods (e.g., method 2900 shown in FIG. 29), or as a system (e.g., speech detection system 100 shown in FIGS. 1-3). When the embodiments are implemented as a system, the operations may be executed by at least one processor (e.g., processing device 400 or processing device 460, shown in FIG. 4).

In some embodiments, individuals may be able to communicate with each other silently. This may occur, for example, by establishing a wireless communication channel between the users, who can then transmit non-vocalized messages back and forth. The exchanged non-vocalized messages may be presented to the users in any manner. In some embodiments, the exchanged non-vocalized messages may be presented as synthesized speech, for example, through an earbud, headphone, or another audio output device. In some embodiments, the exchanged non-vocalized messages may be transcribed and presented as text or pictorially presented in a display device.

Some disclosed embodiments involve operations for establishing nonvocalized conversations. These operations may occur via a system, computer readable media, or a method. The term "establishing" refers to setting up, conducting, demonstrating, substantiating, managing, regulating, administering, or carrying out. As used herein, the term "nonvocalized conversation" may refer to all forms of communication that do not involve spoken or verbal language. For example, nonvocalized conversation by an individual may include any sort of communications by that individual that do not involve words or sounds being uttered. For example, nonvocalized conversation may include communications using, for example, sign language, gestures or body language, facial expressions, written language, visual aids, symbols and icons, or other ways of communications other than sounding out, or vocalizing, words. In some embodiments, nonvocalized conversation may include the previously described subvocalized, prevocalized, or silent speech. As explained elsewhere in this disclosure, to utter a given phoneme, motor neurons activate muscle groups in the face, larynx, and mouth in preparation for propulsion of air flow out of the lungs, and these muscles continue moving during speech to create words and sentences. Without this air flow from the lungs, no sounds are emitted from the mouth. Silent speech occurs when there is no air flow from the lungs, while the muscles in the face, larynx, and mouth articulate the desired sounds or move in a manner enabling interpretation.

Figure 30:
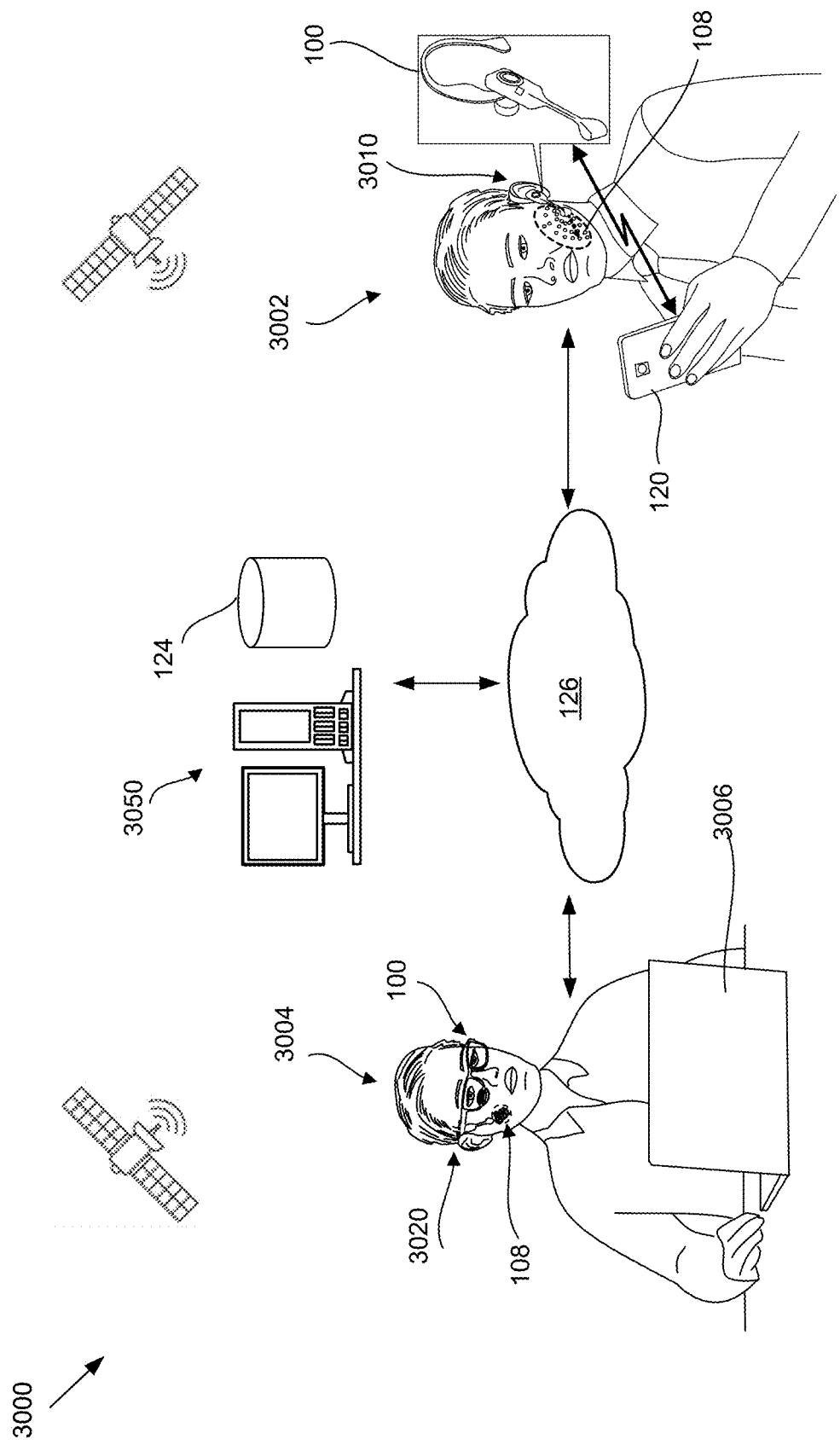
FIG. 30 is a schematic illustration of a system configured to enable nonvocalized conversations between individuals, consistent with some embodiments of the present disclosure.

FIG. 30 illustrates an exemplary device network 3000 configured to enable nonvocalized conversations between individuals, for example, individuals 3002, 3004. In the exemplary embodiment illustrated in FIG. 30, device network 3000 includes a pair of wearable devices 3010, 3020, a mobile communications device 120, a laptop 3006, a cloud server 3050, and a data structure 124 operatively connected together via communications network 126 and configured to enable nonvocalized conversations between individuals 3002 and 3004. It should be noted that the illustrated system is merely exemplary. For example, in some embodiments the system may include fewer devices, and in some embodiments the system may include additional devices (e.g., a desktop computer, a laptop computer, a server, a smart phone, a portable digital assistant (PDA), or a similar devices). Some of these devices may be operatively connected together (e.g., using wires or wirelessly) to share information and/or data.

Some disclosed embodiments involve establishing a wireless communication channel for enabling a nonvocalized conversation via a first wearable device and a second wearable device. A "wireless communication channel" refers to a medium through which wireless signals representative of information or data are transmitted and received between individuals and/or devices. A wireless communication channel may provide a conduit for transferring signals (e.g., representative of information and/or data) between locations without the need for a physical electrical conductor extending all the way between these locations. For example, a wireless communication channel may enable transmission of signals from a first location to a second location wirelessly without requiring wires, cables, or any other electrical conductors extending from the first location all the way to the second location. It should be noted that, when transmitting signals from a first to a second location using a wireless communication channel, in some embodiments, the signals may be transmitted via wires or other electrical conductors in one or more portions between the first and second locations. Examples of wireless communication channels include Radio Frequency (RF) channels that use electromagnetic waves in the radio frequency spectrum to transmit signals wirelessly (e.g., AM/FM radio, Wi-Fi, Bluetooth, and cellular networks (2G, 3G, 4G, 5G)); Infrared (IR) channels that use infrared light to transmit data wirelessly, satellite communication channels that involves transmitting signals to and from satellites orbiting the earth, optical communication channels that use light signals (e.g., laser beams, infrared light, or any other type of light) to transmit data wirelessly, near field communication (NFC) that allows closely positioned devices to communicate, wireless sensor networks (WSN) that use sensors to collect and transmit data, or any other now-known or later developed communication technology which allows signals to be exchanged wirelessly between individuals and/or devices.

In some embodiments, a wireless communication channel may include or use, for example, the Internet, a private data network, a virtual private network using a public network, a Wi-Fi network, a LAN or WAN network, a combination of one or more of the foregoing, and/or other suitable networks to enable information exchange among various components of a communication system. As explained elsewhere in this disclosure, in some embodiments, information exchange between some portions of a wireless communication channel may be via physical links (e.g., wires, cables, optical fiber, or other electrical conductors). A wireless communication channel may use any suitable technology, including, for example, BLUETOOTH™, BLUETOOTH LE™ (BLE), Wi-Fi, near-field communications (NFC), ZigBee, or other suitable communication methods that provide a medium for exchanging data and/or information between entities and/or devices. In some embodiments, as illustrated in FIG. 30, communications network 126 (see also, FIG. 1) may be a wireless communication channel (or part of a wireless communication channel) consistent with the present disclosure.

A "wearable device" refers to any kind of electronic device that is designed or configured to be worn or supported on a user's body. A wearable device may also be known as wearable technology or simply wearables. It some embodiments, a wearable device may be an electronic device that is worn on the user's body as an accessory or incorporated into clothing or other accessories. Wearable devices may, in general, be portable and lightweight and may include electronic circuits, sensors, or other devices to perform a function. Nonlimiting examples of wearable devices include smart watches, fitness trackers, smart glasses, smart rings, smart jewelry, smart clothing, disposable tattoos, or other devices that can be worn by a person. Each of these devices may include sensors and/or electronic circuitry and may be designed to provide various functions and features while being portable. In some exemplary embodiments of the current disclosure, a wearable device may include speech detection system 100 described above, for example, with reference to FIGS. 1-4. As used herein, a "first" wearable device may refer to one wearable device and a "second" wearable device may refer to another wearable device. In other words, the first and second wearable devices may be two distinct wearable devices. Although separate, the two wearable devices may both be the same type of wearable device or different types of wearable devices. For example, in some embodiments, both the first and second wearable devices may be similar to speech detection system 100 illustrated in FIG. 1. Meanwhile, in some embodiments, as illustrated in FIG. 30, the first wearable device 3010 may be similar to speech detection system 100 illustrated in FIG. 1 and the second wearable device 3020 may be similar to speech detection system 100 illustrated in FIG. 2. It should be noted that this is merely exemplary and the first and second wearable devices may be any two distinct wearable devices.

Consistent with some disclosed embodiments, both the first wearable device and the second wearable device each contain a coherent light source and a light detector configured to detect facial skin micromovements from coherent light reflections. As used herein "coherent light source" broadly refers to any device configured to emit "coherent light." The terms "coherent light," "light detector," and "facial skin micromovements" may be interpreted as described and exemplified elsewhere in this disclosure. "Coherent light reflections" refer to reflections that result from coherent light striking or impacting a surface. For example, when coherent light is directed to a surface, the light that reflects or returns from the surface may be coherent light reflections. As explained elsewhere in this disclosure, when coherent light is reflected from the face of an individual, light reflection analysis performed on the reflected light may indicate information indicative of the facial skin micromovements. As discussed above with reference to FIGS. 1-4, speech detection systems 100 of FIGS. 1 and 2, which represent the first and second wearable devices 3010 and 3020 of FIG. 30 includes a coherent light source 410 and a light detector 412 (see FIG. 4) configured to detect reflections from facial region 108 indicative of facial skin movements. For example, with reference to FIG. 30, the coherent light source and light detector of the first wearable device 3010 may be configured to detect facial skin micromovements from coherent light reflections from facial region 108 of individual 3002 and the coherent light source and light detector of the second wearable device 3020 may be configured to detect facial skin micromovements from coherent light reflections from facial region 108 of individual 3004.

Some disclosed embodiments involve detecting by the first wearable device first facial skin micromovements occurring in an absence of perceptible vocalization. The term "perceptible vocalization" refers to a sound that readily able to be understood. For example, perceptible vocalization from an individual may refer to a sound produced through the action of the individual's respiratory system that is capable of being understood. The sound may emanate from the mouth or the vocal chords of the individual. The sound may be speech-related (words, sentences, or other speech-related sounds) or may be non-speech-related (cries, gasps, screeches, whispering, laughing, and other similar sounds that may be used to express an emotion during communication). As explained elsewhere in this disclosure, the normal process of vocalization of a sound uses multiple groups of muscles and nerves, from the chest and abdomen, through the throat, and up through the mouth and face. To utter a given phoneme, motor neurons activate muscle groups in the face, larynx, and mouth in preparation for propulsion of air flow out of the lungs, and these muscles continue moving during speech to create words and sentences. Vocalization, including perceptible vocalization, occurs when air flows out of the lungs. Without this air flow out of the lungs, no sounds are emitted from the mouth, and there is no perceptible vocalization. Instead, as explained elsewhere in this disclosure, silent speech occurs when the air flow from the lungs is absent (or reduced to a level that vocalization is not understandable) and the muscles in the face (e.g., around the mouth) moves in a manner enabling interpretation. It should be noted that even when a small amount of air flows out of the lungs there may be no perceptible vocalization. For example, the sounds emitted by the mouth (if any) as a result of this small air flow may be too faint to be heard or noticed by a person or an audio sensor. In some embodiments of the current disclosure, the first wearable device detects facial skin micromovements that occur when there is no perceptible vocalization.

For example, the first wearable device may detect facial skin micromovements that occur without utterance, before utterance, or during an imperceptible utterance of a sound. The first wearable device may detect facial skin micromovements as described and exemplified elsewhere in this disclosure. In one embodiment, the first wearable device may detect facial skin micromovements that occur during silent speech (i.e., when air flow from the lungs is absent but the facial muscles articulate the desired sounds). In another embodiment, the first wearable device may detect facial skin micromovements that result when an individual is speaking soundlessly (i.e., when some air flow from the lungs, but words are articulated in a manner that is not perceptible using an audio sensor). In yet another embodiment, the first wearable device may detect facial skin micromovements that occur during prevocalization muscle recruitments (i.e., prior to an onset of vocalization). In some cases, the prevocalization facial skin micromovements may be triggered by voluntary muscle recruitments that occur when certain craniofacial muscles start to vocalize words. In other cases, the prevocalization facial skin micromovements may be triggered by involuntary facial muscle recruitments that an individual makes when certain craniofacial muscles prepare to vocalize words. By way of example, the involuntary facial muscle recruitments may occur between 0.1 seconds to 0.5 seconds before the actual vocalization. In some embodiments, the first wearable device may use the detected facial skin micromovement that occur during subvocalization to identify words, syllables, or other sounds that are about to be vocalized.

With reference to FIG. 30, first wearable device 3010 associated with individual 3002 may be capable of detecting facial skin micromovements of individual 3002 without vocalization of speech or utterance of any other speech related sounds by the individual. As explained elsewhere in this disclosure, light detector 412 associated with first wearable device 3010 may include an array of detecting elements capable of imaging facial region 108 of individual 3002 onto the array, and generate signals indicative of the facial skin micromovements occurring in the facial region 108.

Some disclosed embodiments involve transmitting a first communication via the wireless communication channel from the first wearable device to the second wearable device. "Transmitting" refers to causing something (e.g., signals representative of the first communication) to pass from one place or thing to another place or thing (e.g., from first wearable device to second wearable device). In some embodiments, the first communication may be sent from the first wearable device to the second wearable device via the wireless communications channel. The term "communication" may refer to any signals, information, or data. For example, the first communication may include any signals, information, or data that is transmitted from the first wearable device via the wireless communication channel. As will be explained in more detail below, the first communication may be sent from the first wearable device to the second wearable device (via the wireless communications channel) directly or through one or more devices in the signal communication pathway (e.g., in device network 3000).

Consistent with some disclosed embodiments, the first communication contains signals reflective of the first facial skin micromovements. "Reflective of" may refer to relating to or as a consequence of. The term "signals" may refer to information or data encoded for transmission via any medium (e.g., a wireless medium or a physical medium). Examples of signals may include signals in the electromagnetic radiation spectrum (e.g., AM or FM radio, Wi-Fi, Bluetooth, radar, visible light, lidar, IR, Zigbee, Z-wave, and/or GPS signals), sound or ultrasonic signals, electrical signals (e.g., voltage, current, or electrical charge signals), electronic signals (e.g., as digital data), tactile signals (e.g., touch), and/or any other type of information encoded for transmission between two entities. For example, the first communication may include signals related to, or produced as a consequence of, the first facial skin micromovements. In some embodiments, signals reflective of the first facial skin micromovements detected by the first wearable device may be transmitted from the first wearable device to the second wearable device via the wireless communications channel. In some embodiments, the first communication may include the raw data measured (e.g., direction of skin movement, acceleration of the skin movement, and/or any other type of skin movement as a result of voluntary and/or involuntary recruitment of muscle fiber) from the detected facial skin micromovements. In some embodiments, the first communication may include information or data derived from the detected facial skin micromovements. It should be noted that although the first communication is transmitted by the first wearable device to the second wearable device, it is not necessary that the same information or data (e.g., the first communication) be received by the second wearable device. In other words, in some embodiments, the transmitted data may be processed, modified, adjusted, or changed by the first and second wearable devices or by other devices in the wireless communications channel (e.g., in device network 3000).

Consistent with some disclosed embodiments, the wireless communication channel is established directly between the first wearable device and the second wearable device. A direct communication channel is one where two devices communicate without the communication necessarily passing through an intermediate device. In some disclosed embodiments, devices such as wireless access points, modems, routers, and other similar intervening devices may exist in the communication pathway between the first and second wearable devices. Thus, in some embodiments where a wireless communication channel is established between the first and second wearable devices, signals transmitted from the first wearable device to the second wearable device may pass through (e.g., received and transmitted by) these intervening devices. However, in some embodiments, for example when a first wearable device and the second wearable device are in proximity to each other, no intervening devices may be needed, with signals transmitted directly between the first wearable device and the second wearable device (e.g., a via Bluetooth connection). In other words, in some embodiments, first communication may be sent directly from speech detection system 100 of first wearable device to speech detection system 100 of second wearable device via the wireless communications channel.

Consistent with some disclosed embodiments, the wireless communication channel is established from the first wearable device to the second wearable device via at least one intermediate communication device. The term "intermediate communication device" may be interpreted as described and exemplified elsewhere in this disclosure. As explained elsewhere in this disclosure, in some embodiments, first communication may be transmitted from the first wearable device to the second wearable device (via the wireless communications channel) through one or more devices, such as wireless access points, modems, repeaters, routers, cell phones, or other transceivers. For example, the first communication transmitted from the first wearable device may be received by another device (e.g., a smartphone, a tablet, a smartwatch, a personal digital assistant, a desktop computer, a laptop computer, a server, an Internet of Things (IoT) device, a dedicated terminal, a wearable communications device, or any other device configured to receive transmitted signals) which may then retransmit or send the received data (with or without processing or modification of the received data) to another device (e.g., another one or more of the devices listed above) which may then transmit or send the data (with or without processing or modification of the received data) to the second wearable device. Consistent with some disclosed embodiments, the at least one communication device includes at least one of: a first smartphone associated with the wearer of the first wearable device, a second smartphone associated with the wearer of the second wearable device, a router, or a server. For example, in some embodiments, the first wearable device may be operatively coupled to a smartphone of the wearer of the first wearable device, and the first communication transmitted from the first wearable device to the second wearable device may be first received by the smartphone and sent from the smartphone to the second wearable device (directly or through a smartphone or other similar personal devices of the wearer of the second wearable device via the wireless communication channel.

With reference to FIG. 30, first wearable device 3010 associated with individual 3002 may detect facial skin micromovements from coherent light reflections from the facial region 108 of individual 3002 and transmit signals related to the detected facial micromovements to the second wearable device 3020 associated with individual 3004 via communications network 126. In some embodiments, the signals transmitted from the first wearable device 3010 may be received by the second wearable device 3020 directly. In some embodiments, signals (related to the detected facial skin micromovements) may be transmitted from first wearable device 3010 to mobile communications device 120 (e.g., a smart phone or another communications device) associated with individual 3002 which may then transmit the signals (with or without processing the received signals) to second wearable device 3020 directly or via other devices (e.g., a mobile communications device associated with individual 3004, laptop 3006 associated with individual 3004, server 3050, or other devices in device network 3000). In some embodiments, the signals transmitted by first wearable device 3010 may be received by server 3050 directly or through other intervening devices (e.g., mobile communications device 120) in the communications pathway. In some embodiments, one or more of the devices that receives the signals from first wearable device 3010 may process the received signals and transmit the processed signals downstream.

Consistent with some disclosed embodiments, the operations further include interpreting the first facial skin micromovements as words, as described elsewhere in this disclosure. For example, in some embodiments, the first wearable device or another device of the system (e.g., device network 3000) in the communication pathway between the first and second wearable devices may process the received signals before forwarding it to the intended recipient. The processing may include converting (or interpreting) the detected skin micromovements to words. As explained elsewhere in this disclosure, facial skin micromovements of an individual may be converted to words in any manner. For example, a memory device (e.g., memory device 402 of FIG. 4) associated with the first wearable device 3010 may include a data structure that contains correlations of facial skin micromovements with words and a processor (e.g., processing device 400 of FIG. 4) associated with first wearable device 3010 may perform a lookup in the data structure to identify words associated with detected facial skin micromovements. In some embodiments, correlations of particular patterns of facial skin micromovements with words may be stored in the data structure apriori (for example, during training), and when a pattern of facial skin micromovements is observed in the measured data, the processor may perform a lookup in the data structure to identify the words associated with the detected pattern of facial skin micromovements.

Figure 31:
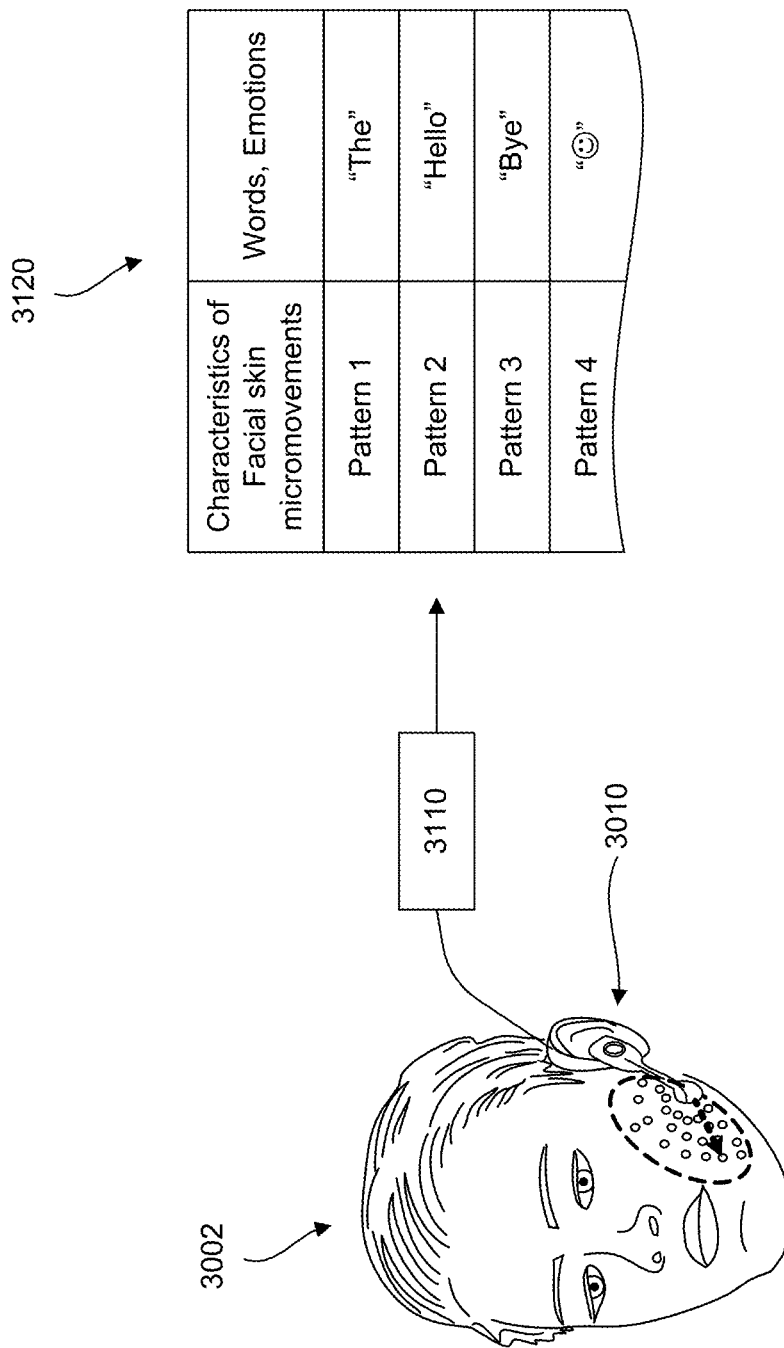
FIG. 31 is a schematic illustration of exemplary processing of detected facial skin micromovements of an individual consistent with some embodiments of the present disclosure.
Figure 32:
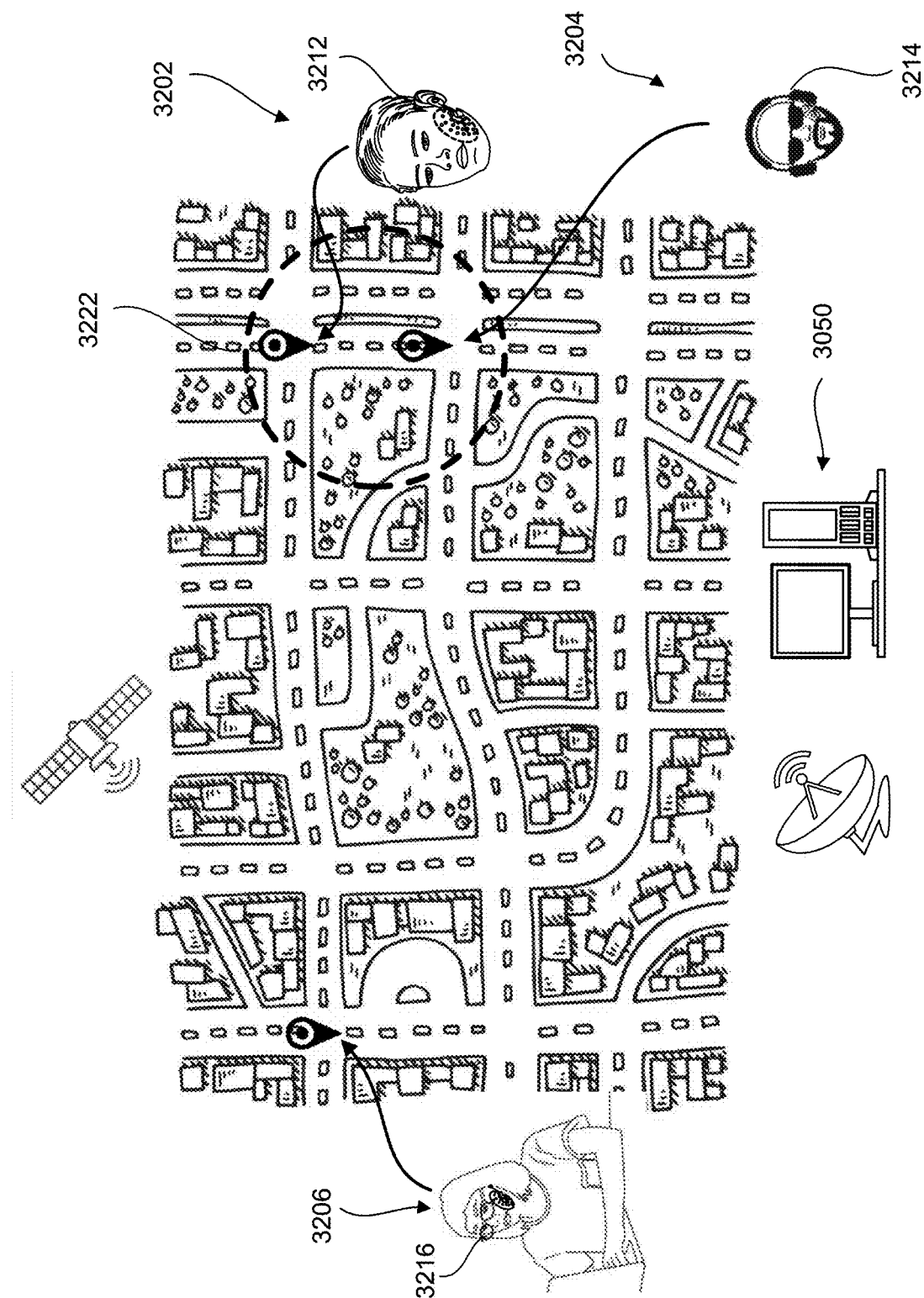
FIG. 32 is a schematic illustration of another system configured to enable nonvocalized conversations between individuals consistent with some embodiments of the present disclosure.

For example, in some embodiments, as illustrated in FIG. 31, a data structure associated with, and accessible by, device network 3000 may store correlations 3120 of characteristics (or patterns) of facial skin micromovements with words, emotions, and/or other speech related facial expressions of individuals (e.g., phonemes, commands, expressions, and/or other biological conditions). And device network 3000 may compare characteristics in the detected facial skin micromovements 3110 of individual 3002 with the stored correlations 3120 to identify the words or emotions corresponding to the detected facial skin micromovements. The correlations 3120 may be stored in any device network 3000 (e.g., first or second wearable device, mobile communications device 120, server 3050, data structure 124, laptop 3006, or any other device of device network 3000).

Consistent with some disclosed embodiments, the first communication includes a transmission of the words. For example, the first communication may include a transmission of the words interpreted from the detected facial skin micromovements, as described elsewhere in this disclosure. The transmission of the words is also to be understood, in the alternative, as including a transmission of signals representing the words, which are ultimately deciphered by the recipient device. In some embodiments, the first wearable device 3010 may process the detected facial skin micromovement data to convert the detected data to words and transmit these words as the first communication. In some embodiments, another device of device network 3000 (e.g., server 3050 and/or mobile communications device 120) may receive signals from first wearable device 3010, process the received signals, and transmit the processed signals downstream. The processing may include determining correlations between the received signals and words. For example, as explained elsewhere in this disclosure, a memory device accessible by the system may contain correlations of facial micromovements with words and a processing device of the system may perform a lookup in the stored correlations to identify words associated with detected facial skin micromovements and transmit the identified words to second wearable device 3020.

Consistent with some disclosed embodiments, the first communication is derived from the first facial skin micromovements and is transmitted for presentation via the second wearable device. "A communication is derived" from a facial skin micromovement when signals associated with the facial skin micromovement are interpreted to ascertain the communication (whether the communication be words, gestures, feelings, expressions, thoughts, etc.) By way of one example as described elsewhere in this disclosure (e.g., with reference to FIG. 5), speech detection system 100 associated with first wearable device 3010 may analyze light reflections to determine facial skin micromovements resulting from recruitment of muscle fiber from facial region 108. For example, the determined facial skin micromovements may include determining, for example, an amount of the skin movement, a direction of the skin movement, an acceleration of the skin movement, and/or any other type of skin movement as a result of voluntary and/or involuntary recruitment of muscle fiber in the facial region. As also explained elsewhere in this disclosure, in some embodiments, a processing device of speech detection system 100 (see, e.g., FIG. 4) may perform analysis (e.g., speckle analysis or another pattern analysis) on the light reflected from a different regions within facial region 108 to determine, for example, the distances that these different regions moved or other related information. In some embodiments, the first communication may include the types of skin movements (e.g., amount, direction, acceleration, or other type of skin movement) and/or the information or results from the pattern analysis of the facial skin micromovements.

The term "presenting" refers to making something known in any manner. For example, presenting information to an individual or entity refers to making that individual aware of the information in any manner. In some embodiments, presenting may include a visual or visible display (e.g., a display of, for example, text, graphics, images, icons, symbols, lights, or other items that can be seen by an individual or entity). In some embodiments, presenting may include an audible presentation (e.g., reading transcribed text or emitting other sounds to make the individual/entity aware). In some embodiments, presenting may include a tactile presentation (e.g., using a display of braille or other characters that be sensed by touch), for example, to a visually-impaired individual. For example, the first communication, derived from the first facial skin micromovements detected by the first wearable device, may be transmitted to the second wearable device for presentation. In some embodiments, the first communication may be transmitted to the second wearable device for presentation via the second wearable device. The term "via" may indicate by way of, through, or by means of. The presentation may be made using the second wearable device in many ways (visual presentation, audio presentation, tactile presentation, or any other manner suitable to alert or an entity). For example, an audio presentation may be made using an earbud (or headphone, or other sound output device) of the second wearable device. As another example, a textual or graphical presentation may be made on a display screen (e.g., a visual display such as a computer monitor, television, mobile communications device, VR or XR glasses, or any other device that enables visual perception) associated with the second wearable device.

With reference to FIG. 30, the signals transmitted by the first wearable device 3010 may be derived from the facial skin micromovements of individual 3002 detected from facial region 108. These signals may be transmitted to second wearable device 3020 for presentation to individual 3004 in some manner (e.g., visible display, audible, tactile, or presenting in any other manner designed to alert individual 3004). In some embodiments, the signals indicative of the detected facial skin micromovements may be transmitted to second wearable device 3020 for presentation to individual 3004 via the second wearable device 3020, e.g., using an output unit (audio, haptic, and/or visual output device) associated with the second wearable device 3020. In some embodiments, the signals indicative of facial skin micromovements may be converted to words by device network 3000 (e.g., by first wearable device 3010, mobile communications device 120, server 3050, or any other device in the communication pathway) and transmitted to the second wearable device 3020 for presentation to individual 3004. In some embodiments, the translated words may be presented to individual 3004 as text in the display screen of laptop 3006 (or any other display screen viewable by individual 3004). In some embodiments, the translated words may be audibly presented to individual 3004 using an audio output device (earbud, headphone, or any other device capable of emitting sound) associated with the second wearable device 3020.

Some disclosed embodiments involve receiving a second communication via the wireless communication channel from the second wearable device. The term "receiving" may include retrieving, acquiring, or otherwise gaining access to, e.g., data. Receiving may include reading data from memory and/or receiving data from a computing device via a communications channel. As explained elsewhere in this disclosure, a "communication" may include any type of signals, information, or data. For example, the second communication may include any signals, information, or data sent or transmitted from the second wearable device via the wireless communications channel. Any device may receive the second communication from the second wearable device directly or indirectly. For example, in some embodiments, the first wearable device may receive (directly or indirectly) the second communication transmitted by the second wearable device via the wireless communication channel. In some embodiments, another system or device may receive this communication. For example, in some embodiments, a mobile communications device or server operatively connected to the second wireless device (e.g., via the wireless communication channel) may receive this communication from the second wearable device.

Consistent with some disclosed embodiments, the second communication is derived from second facial skin micromovements detected by the second wearable device. For example, the second communication may include signals related to, or produced as a consequence of, the second facial skin micromovements detected by the second wearable device. In some embodiments, signals reflective of the second facial skin micromovements may be transmitted via the wireless communications channel as the second communication. In some embodiments, the second communication may include the detected raw data (e.g., direction of skin movement, acceleration of the skin movement, and/or any other type of skin movement) from the facial skin micromovements. In some embodiments, the second communication may include information or data derived from, or obtained using, the detected facial skin micromovements. For example, in some embodiments, the second wearable device or another device operatively connected to the second wearable device (e.g., mobile communication device 120, server 3050, laptop 3006, or another device in the wireless communication channel), may process the detected second facial skin micromovements to convert the detected micromovements data to words, symbols, graphics, audio, or other derived characters. As explained elsewhere in this disclosure, the facial skin micromovements may be converted to such derived characters in any manner (e.g., using stored correlations, algorithms, or by another suitable conversion method). For example, in some embodiments, a memory device associated with the second wearable (or another device of the system) may include a data structure that contains correlations of facial skin micromovements with words and a processing device associated with the second wearable device (or another device of system) may perform a lookup in the data structure to identify words associated with detected facial skin micromovements.

Some disclosed embodiments involve presenting the second communication to a wearer of the first wearable device. As explained elsewhere in this disclosure, the communication may be presented to the wearer of the first wearable device in any manner configured to make the wearer aware of the communication. For example, as explained elsewhere in this disclosure with reference to speech detection system 100 of FIGS. 1-4, the speech detection system may include an output unit (e.g., speaker, earbuds, earplugs, hearing aids, headsets, earmuffs, or other suitable device) configured to present audible and/or vibrational output to the wearer. In some embodiments, the second communication may be presented to the wearer (of the first wearable device) using an output unit of the first wearable device. As also explained elsewhere in this disclosure, in some embodiments, the speech detection system may output information to a display (e.g., a visual display such as a computer monitor, television, mobile communications device, VR or XR glasses, or any other device that enables visual perception) for presentation. In some embodiments, the second communication may be presented to the wearer on a display screen visible to the wearer.

For example, with reference to FIG. 30, data related to facial skin micromovements from the facial region 108 of individual 3004 may be transmitted by second wearable device 3020 via communications network 126. This data may include the detected facial skin micromovements (e.g., direction of skin movement, acceleration of the skin movement, and/or any other type of skin movement) and/or information derived from the detected facial skin micromovements (e.g., words, symbols, graphics, audio, or other characters corresponding to the detected data). The transmitted data may be received by the first wearable device 3010 and/or by another device (e.g., laptop 3006, mobile communication device 120, server 3050) in the communications network 126. The received data may then be presented to individual 3002 in some manner. For example, in some embodiments, the received data may be audibly presented to individual 3002 using a speaker associated with the first wearable device 3010. In some embodiments, a textual and/or graphical display of the received data may be presented to individual 3002 on a display screen of mobile communication device 120.

Consistent with some disclosed embodiments, presenting the second communication to the wearer of the first wearable device includes synthesizing words derived from the second facial skin micromovements. "Synthesizing" refers to producing artificial or electronic sounds. For example, synthesizing may include artificially vocalizing, for example, a character (e.g., word, text, icon, image, cartoon, picture, or some other representation of a character). In some embodiments, a system associated with the wireless communication channel may translate or convert the second facial skin micromovements detected by the second wearable device to sounds of words (or word sounds) represented by the detected micromovements, and present it (e.g., audibly) to the wearer of the first wearable device via a sound output device (e.g., speaker, earbud, or another device configured to emit sound) associated with the first wearable device. The detected facial skin micromovements may be converted or translated to word sounds in any manner. As explained elsewhere in this disclosure, a data structure accessible to the system may include correlations of facial micromovements with words, commands, emotions, expressions, and/or biological conditions, and at least one processor of the system may perform a lookup in the data structure to convert the detected facial skin micromovements to one or more of words, commands, emotions, expressions, or biological conditions. In some embodiments, data structure may also include correlations of facial micromovements (e.g., different patterns in the micromovements) to word sounds and the system may translate the detected micromovements to word sounds based on this database. In some embodiments, the correlation of micromovements to word sounds may be created and stored apriori (e.g., during training) and may be updated over time. In some embodiments, algorithms may be used to convert the micromovements to word sounds. In some embodiments, the system may first convert the detected micromovements to text of words (e.g., using the previously described correlations of micromovements to text of words, or using any other suitable technique) and then synthesize the converted text to word sounds using voice synthesis (or text-speech) software. Any now-known or later developed text-speech software may be used to convert the text to sound. For example, by using voice synthesis software and known techniques. For example, by using deep learning to create voice from text, or to translate the sensor-data directly to voice without first converting to text.

Consistent with some disclosed embodiments, presenting the second communication to the wearer of the first wearable device includes providing textual output reflective of words derived from the second facial skin micromovements. For example, as discussed elsewhere in this disclosure, in some embodiments, the system may convert the detected micromovements to text reflective of words represented by the detected facial skin micromovements (e.g., using stored correlations of facial micromovements to text of words or another suitable technique) and display the text to the wearer of the first wearable device, e.g., on a display screen visible to the wearer. For example, with reference to FIG. 30, the signals representative of the detected facial skin micromovements of individual 3004 may be converted to text (of words corresponding to the detected micromovements) and presented to individual 3002 as text on the display screen of mobile communications device 120. Additionally or alternatively, in some embodiments, as discussed elsewhere in this disclosure, the converted text (or the detected skin micromovements) may be synthesized to word sounds and audibly presented to individual 3002 on a speaker associated with first wearable device 3010 (e.g., earbud, headphone, speaker of mobile communications device 120, or another audio device).

Consistent with some disclosed embodiments, presenting the second communication to the wearer of the first wearable device includes providing a graphical output reflective of at least one facial expression derived from the second facial skin micromovements. As used herein, the term "graphical output" is used to broadly refer to any type of displayed output other than text (e.g., pictures, images, graphs, line drawings, cartoon images, emojis, icons, or any other graphical representation). For example, the second communication derived from the second facial skin micromovements may include signals indicative of one or more facial expressions of the wearer of the second wearable device. Graphical outputs corresponding to these facial expressions may be presented on a display screen such that it is viewable by the wearer of the first wearable device. In some embodiments, the graphical output may be presented in addition to, or in place of, textual or audio output. For example, when the second communication includes signals indicative of both words and facial expressions, the presentation may include a graphical output of the facial expression along with a textual (or audio) output of the accompanying words. In some disclosed embodiments, the graphical output includes at least one emoji. An "emoji" may be an image, symbol, or icon used to express a range of objects and ideas including human emotions, animals, geography, foods, flags, and any other object capable of being depicted as an image. An emoji may be a digital pictogram or image used to express, among other things, the attitude or emotion of an individual. An emoji may be used to convey information succinctly and communicate an electronic message without using words. For example, when the second communication includes signals indicative of a smile (or another facial expression of the individual wearing the second wearable device), the system may present a smiley face emoji (and/or other emojis that convey the emotion or mood of the individual to the wearer) on the display screen. In some embodiments, the second communication may also include signals indicative of words (and/or other expressions) and the system may present the words along with one or more graphical outputs (such as emojis) to convey the individual's facial expressions when the micromovement data was collected. Graphical output reflective of facial expression may be derived from the second facial skin micromovements in any manner. For example, as explained elsewhere in this disclosure, a data structure accessible to the system may include correlations of facial micromovements with, among other things, emotions and expressions. The data structure may also include correlations of emotions and expressions to suitable emojis or other pictorial representations. In some embodiments, the system may convert the detected facial skin micromovements to graphical outputs (such as emojis or other pictorial representations) based on these stored correlations.

Consistent with some disclosed embodiments, the operations further include determining that the second wearable device is located in proximity to the first wearable device. The term "determining" may refer to establishing or arriving at an outcome by some process. For example, a conclusive outcome as a result of a reasoned, learned, calculated or logical process. As used herein, the term "proximity" indicates nearness in spatial distance. For example, one device being located proximate to (or in proximity to) another device may indicate that the spatial distance between the two devices is relatively small or that the two devices are positioned relatively close to each other. The distance between the two devices to be considered proximate to each other may depend on the application. An example, in some embodiments, two wearable device in the same room (or building) may be considered to be proximately positioned. In some embodiments, two wearable device within 0.5 miles (or any other distance) may be considered to be proximately positioned. In some embodiments, this distance may be pre-defined or user-defined (e.g., programmable). For example, during setup of a wearable device (e.g., first wearable device), the wearer (or another user) may be given the option to select or enter this distance. And when another wearable device (e.g., second wearable device) moves to be within the selected distance, the second wearable device may be considered to be proximate to the first wearable device.

In some embodiments, the first and second wearable devices may include global positioning sensors (GPS) and/or other sensors to determine the location of the device. In some embodiments, sensors in one wearable device may determine that there is another wearable device located proximate to it based on the sensor readings. In some embodiments, based on the signals from the sensors in the two wearable devices, the system may determine the location (or track the location) of the two wearable devices and the distance between these devices at any time. The two wearable devices may include the ability to activate and deactivate location tracking in some embodiments. In some embodiments, one of both of the wearable devices may be associated with a mobile communication device (e.g., a smartphone, or another device having GPS capabilities) and the system may track the location of the device by tracking the location of the associated mobile communication device.

Figure 33:
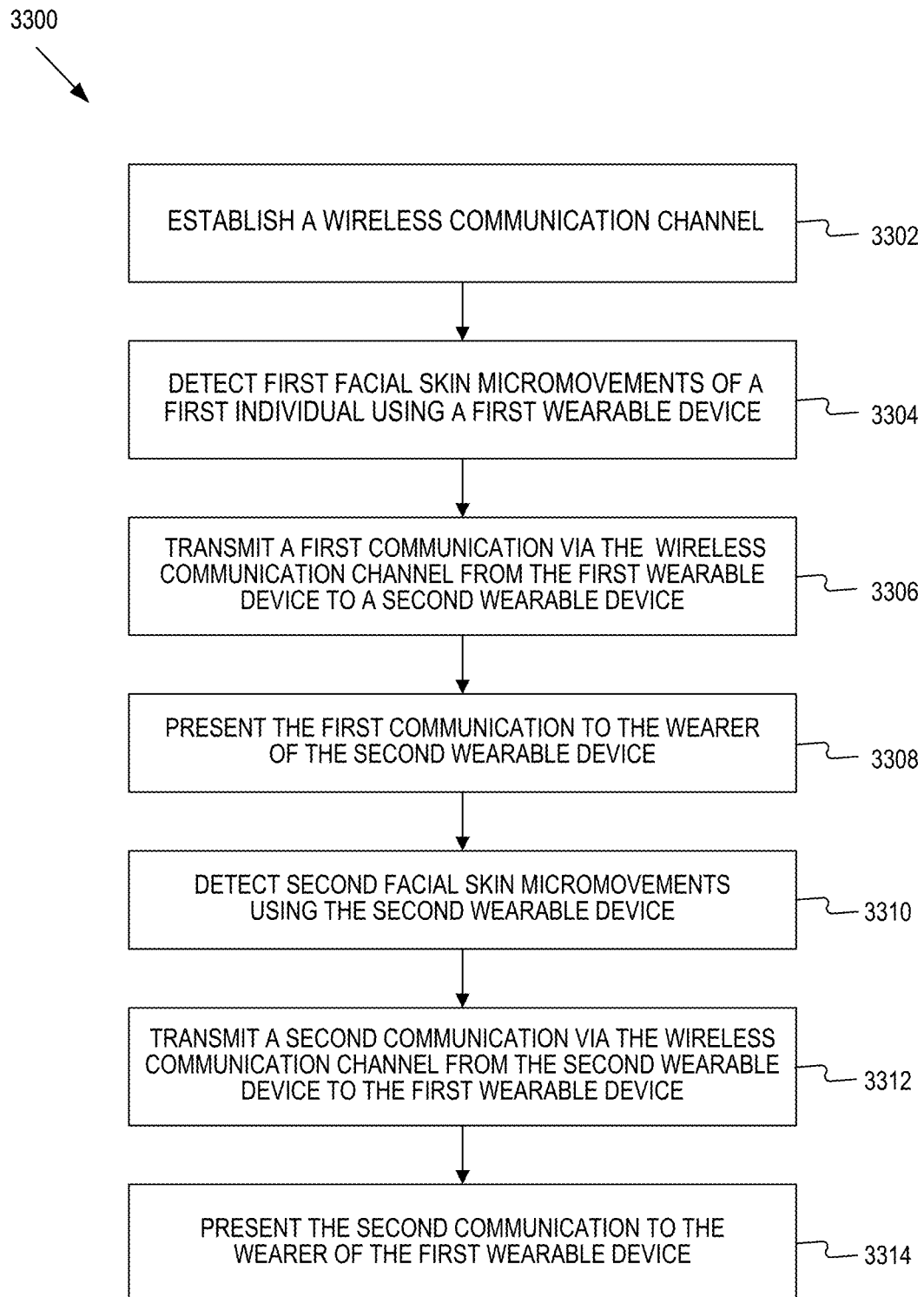
FIG. 33 is a flowchart of an exemplary process for establishing nonvocalized conversations consistent with some embodiments of the present disclosure.

For example, as illustrated in FIG. 33, in some embodiments, wearable devices 3212, 3214, 3216 associated with individuals 3202, 3204, and 3206, respectively, may have GPS sensors (or other location sensors). Based on signals from these location sensors, device network 3000 may track the location of these wearable devices. And based on the detected location of the wearable devices 3212, 3214, 3216, device network 3000 may determine when any one of these devices is located in proximity to another device. For example, during setup of wearable device 3212, individual 3202 may have provided a distance 3222 for proximity determination. And when another wearable device (e.g., wearable device 3214) happens to be located within this preselected distance, device network 3000 may consider it to be proximately positioned to wearable device 3212.

Consistent with some disclosed embodiments, the operations further include automatically establishing the wireless communication channel between the first wearable device and the second wearable device. The term "automatically" may indicate by itself with little or no direct human control. For example, by a device or a process with little or no human intervention. For example, in some embodiments, when it is determined that the first wearable device is located proximately to the second wearable device, a wireless communication channel may be automatically established between the two wearable devices. In some embodiments, based on signals from the location sensors in the two wearable devices, the system may determine that the second wearable device is positioned proximately to the first wearable device and automatically establish a wireless communication channel between the two wearable devices. In some embodiments, the wearers of the wearable devices may be given the option whether or not to automatically establish the wireless communication channel between the two devices. In some embodiments, during setup of a wearable devices, the user of the device may select an option to enable the automatic establishment of a wireless communication channel with another proximately positioned wearable device (e.g., used by a person in the user's contact list).

For example, with reference to FIG. 33, during setup of wearable device 3212, individual 3202 may have selected an option that enables automatic establishment of a wireless communication channel with the wearable device of people in the individual's contact list (e.g., wearable device 3214) if that wearable device is located in proximity to it. And based on this user-selected option, device network 3000 may establish a wireless communication channel between wireless devices 3212 and 3214 when wearable device 3214 is located with the preselected distance 3222 of wearable device 3212.

Some disclosed embodiments involve presenting via the first wearable device a suggestion to establish a nonvocalized conversation with the second wearable device. The term "suggest" (and other constructions of this term) may indicate put forward for consideration. For example, when it is determined that the second wearable device is located proximately to the first wearable device, the wearer of the first wearable device (and in some cases the wearers of both the first and second wearable devices) may be alerted (e.g., audible alert, visual alert, tactile alert) to the presence of the second wearable device proximate to it and given the choice to whether or not automatically establish a wireless communication channel between them. For example, with reference to FIG. 33, when device network 3000 determines that wearable device 3214 is positioned proximately to wearable device 3212, a suggestion may be presented (e.g., audible message, textual message, tactile indication) via wearable device 3212 informing individual 3202 of the presence of wearable device 3214 proximate to it. The suggestion may include an invitation to establish a nonvocalized conversation with individual 3204 using wearable devices 3212, 3214. The suggestion may also give individual 3202 the ability to accept or decline the invitation. In some embodiments, the suggestion may include a pop-up message on the display screen of a mobile communication device associated with individual 3202 (or alerted in another manner) allowing individual 3202 to accept (e.g., by clicking an OK or YES icon) or decline (e.g., by not clicking the OK icon or clicking a NO icon) the invitation. In some embodiments, if individual 3202 accepts the suggestion, a wireless communication channel may be automatically established between wearable devices 3212 and 3214.

Some disclosed embodiments involve determining an intent of the wearer of the first wearable device to initiate a nonvocalized conversation with the wearer of the second wearable device, and automatically establishing the wireless communication channel between the first wearable device and the second wearable device. The wearer's intent may be determined in any manner. In some embodiments, the intent may be determined based on options preselected by the user of a wearable device during setup of the wearable device. For example, the user of a wearable device may have preselected an option to automatically establish a wireless communication channel (to initiate nonvocalized conversations) with wearable devices of, for example, preselected individuals (e.g., people in the user's contact list or other preselected individuals) under certain preselected conditions (e.g., when the wearable devices is positioned proximately to it, if the devices are at a selected location, at preselected times, or other preselected conditions). Intent may additionally or alternatively be determined based on a facing direction of the wearer. For example, if two wearers are facing each other (as captured for example by an image sensor), the system may infer an intent to communicate. In other embodiments, a pick list of nearby wearers may appear on a display, and the selection may be noted by the system such that communication may be automatically established for subsequent interactions. Consistent with some disclosed embodiments, the intent is determined from the first facial skin micromovements. For example, recognition of predetermined keywords (e.g., "connect with" this person, "hey Q," or any other predetermined word or phrase) in the facial skin micromovements detected by the first wearable device may indicate the intent of the wearer. For example, recognition of the phrase "hey Q" may open a window with selectable menu items (e.g., in a mobile communication device or another device associated with the first wearable device) that the wearer may navigate through (e.g., open an application that displays a selectable list of the wearer's contacts) to select a contact that the wearer wishes to connect with. The wearer's intent may also be determined based on some signal not based on facial skin micromovements. In some embodiments, the wearer of the first wearable device may press a button, tap a preselected location, select an icon, or some provide some other machine-recognizable indication (e.g., on the wearable device or on another device associated with the wearable device, e.g., a mobile communication device) to signal to the system that the wearer wishes to take some action, such as, for example, initiate a conversation with the wearer of the second wearable device. And upon receipt of this signal, a wireless communication channel may be automatically established between the first and second wearable devices. For example, the wearer may navigate through menus on a mobile communication device associated with the first wearable device to review a list of contacts and select a contact (e.g., the wearer of the second wearable device) to automatically establish a wireless communication channel with.

Consistent with some disclosed embodiments, the first communication contains signals reflective of first words spoken in a first language and the second communication contains signals reflective of second words spoken in a second language, and wherein presenting the second communication to the wearer of the first wearable device includes translating the second words to the first language. As explained elsewhere in this disclosure, in some embodiments, the first communication from the first wearable device and the second communication from the second wearable device may be processed. The processing may include translating the words in the communication from one language to another. For example, the first communication transmitted from the first wearable device to the second wearable device may include signals indicative of words in one language (e.g., English). The first wearable device, the second wearable device, or another device in the communication pathway between the first and second wearable devices may translate the English words in the first communication to another language (e.g., French) and present them to the wearer of the second wearable device in French. Similarly, the second communication may include signals indicative or words in French and the French words may be translated to English and presented to the wearer of the second wearable device in English. The words may be translated from one language to another using any now known or later developed technique. In some embodiments, suitable algorithms (e.g., deep neural network based algorithms or other translations algorithms) may be used for the translation.

Consistent with some disclosed embodiments, the first communication contains details identifying the wearer of the first wearable device and the second communication contains signals identifying the wearer of the second wearable device. Any detail identifying the wearer may be included in the corresponding communications. For example, in some embodiments, the name, phone number, user ID, nickname, or any other information that identifies the wearer of the wearable device may be included in the corresponding communication. In some embodiments, the entity or organization that the wearer of a wearable device represents may be included in the corresponding communication. For example, when the wearer of the first wearable device is an employee of an organization (e.g., Bank of America) and the wearer of the second wearable device is a customer, the first communication may include the identity of the organization (e.g., you have a call from Bank of America), and the second communication may include the identity of the customer. The identity of the wearer may be determined in any manner. In some embodiments, the detected facial skin micromovements from each wearable device may include words representative of the wearer's identity (e.g., from a salutation such as "hello, this is Bob"). In some embodiments, during setup of a wearable device, the wearer's identity may be programmed into the device (or added in a database associated with the system), and this identity information may be automatically included in communications from the wearable device. In some embodiments, the identity of the wearer of a wearable device may be determined as described elsewhere in this disclosure with reference to, for example, FIGS. 15-17. Consistent with some disclosed embodiments, the first communication contains a time stamp indicating when the first facial skin micromovements were detected. "Time stamp" may refer to an indication of time or to an indication of time and date. In some embodiments, the second communication may also include a time stamp of when the second facial micromovements were detected. The time at which a facial skin micromovement was detected by the first wearable device and the second wearable device may be determined in any manner. For example, in some embodiments, an internal clock or other electronic devices or circuits in a device associated with the system (e.g., in the wearable device, server 3050, or another device) may detect and record the time at which each facial skin micromovement was detected.

FIG. 33 is a flow chart of an exemplary process 3300 that may be used for establishing nonvocalized conversations consistent with some embodiments of the current disclosure. For the sake of brevity, aspects of the different steps in process 3300 that were previously described will not be described again. A wireless communication channel may be established. (Step 3302). The wireless communication channel may be configured to enable nonvocalized conversation via a first wearable device and a second wearable device. The first wearable device and the second wearable device may each contain a coherent light source and a light detector. The light detector on each wearable device may be configured to detect facial skin micromovements from coherent light reflections from a facial region of an individual wearing the wearable device. Process 3300 may include detecting first facial skin micromovements of a first individual using the first wearable device. (Step 3304). In this step, the first wearable device may detect first facial skin micromovements that occur without perceptible vocalization from the first individual. Process 3300 may transmit first communication from the first wearable device to the second wearable device via the wireless communication channel. (Step 3306). The first communication may be derived from the detected first facial skin micromovements and may be transmitted to the second wearable device for presentation to a wearer of the second wearable device. In general, the first communication may contain signals reflective of the first facial skin micromovements. In some embodiments, process 3300 may include interpreting the first facial skin micromovements as words. In some embodiments, process 3300 may also include interpreting facial expressions recorded in the first facial skin micromovements into one or more graphical outputs (e.g., images, emojis, symbols, or another graphical representation). In some embodiments, the first communication may include a transmission of the interpreted words and/or the graphical outputs. The first communication may be transmitted directly to the second wearable device or may be transmitted indirectly (e.g., via one or more devices operatively connected to the two wearable devices by the wireless communication network) to the second wearable device. Process 3300 may present the first communication to the wearer of the second wearable device. (Step 3308). The first communication may be presented in any manner (audibly, textually, graphically, or in any other manner aimed to inform the wearer). In some embodiments, process 3300 may include synthesizing the words that are derived from the second facial skin micromovements and the synthesized words may be presented in step 3308. In some embodiments, the text of the derived words and/or graphical outputs may be presented in a display screen visible to the wearer in step 3308.

Process 3300 may also include detecting second facial skin micromovements using the second wearable device. (Step 3310). In this step, the second wearable device may detect second facial skin micromovements that occur without perceptible vocalization from the second individual. A second communication may be transmitted from the second wearable device to the first wearable device via the wireless communication channel. (Step 3312). As discussed with reference to step 3306, in step 3312, the transmitted second communication may be derived from the detected second facial skin micromovements and may be meant for presentation to a wearer of the first wearable device. In some embodiments, process 3300 may include interpreting the second facial skin micromovements as words and/or graphical outputs representative of facial expressions of the second individual. In some embodiments, the transmitted second communication in step 3312 may include a transmission of the interpreted words and/or graphical outputs. Similar to the first communication, the second communication may be transmitted directly or indirectly to the first wearable device. Process 3300 may present the second communication to the wearer of the first wearable device. (Step 3314). The second communication may be presented in any manner as described with reference to step 3308. In this manner, the first and second individuals may communicate with each other silently.

In some embodiments, process 3300 may include determining a current location of the first and second wearable devices and determining when a wearable device (e.g., the second wearable device) is located in proximity to another wearable device (e.g., the first wearable device). Process 3300 may also include automatically establishing the wireless communication channel in step 3302 between the first wearable device and the second wearable device, for example, when it is determined that the first and second wearable devices are located in proximity to each other. In some embodiments, process 3300 may include presenting a suggestion via a wearable device (e.g., the first wearable device) to establish a nonvocalized conversation with another wearable device (e.g., the second wearable device), for example, when it is determined that the first and second wearable devices are located in proximity to each other. In some embodiments, process 3300 may include determining an intent of the wearer of a wearable device (e.g., the first wearable device) to initiate a nonvocalized conversation with the wearer of another wearable device (e.g., the second wearable device), and automatically establishing the wireless communication channel between the first wearable device and the second wearable device based on the intent. In some embodiments, the intent may be determined from the first facial skin micromovements, for example, based on keywords in the detected facial skin micromovements. In some embodiments, process 3300 may include translating the exchanged communications. For example, the transmitted first communication from the first to second wearable device in step 3306 may be translated from a first language (e.g., English) to a second language (e.g., French) and the transmitted second communication in step 3312 may be translated from the second language to the first language. The translated languages may then be presented in steps 3308 and 3314.

It should be noted that the order of the steps illustrated in FIG. 33 is only exemplary and many variations are possible. For example, the steps may be performed in a different order. As an example, step 3310 may be performed before step 3308. In some embodiments, some of the steps illustrated in FIG. 33 may be omitted, combined, and/or other steps added. For example, in some embodiments, step 3308 may be omitted and one or more of the steps described in the paragraph above may be added. Furthermore, in some embodiments, process 3300 may be incorporated in another process or may be part of a larger process.

The embodiments discussed above for establishing nonvocalized conversations may be implemented through non-transitory computer-readable medium such as software (e.g., as operations executed through code), as methods (e.g., process 3300 shown in FIG. 33), or as a system (e.g., speech detection system 100 shown in FIGS. 1-3). When the embodiments are implemented as a system, the operations may be executed by at least one processor (e.g., processing device 400 or processing device 460, shown in FIG. 4).

During typical use of a language translator in a conference call or meeting, latency may be introduced into a conversation flow as participants wait for a translation to be complete. Similar issues may arise when subtitles are created during live broadcasts. Disclosed embodiments may alleviate such issues by providing an interpretation of a word at substantially the same time as when the word is spoken. Systems, methods, and computer program products are disclosed for determining an interpretation of a word during a time gap between when a word to be spoken is determined and when the word is vocalized, allowing for presentation of the interpretation at substantially the same time that the word is spoken.

Some disclosed embodiments involve initiating content interpretation operations prior to vocalization of content to be interpreted. Content interpretation refers analyzing and making sense of information presented and extracting its underlying message or intent. Initiating content interpretation operations refers to starting or commencing specific activities related to a task. As discussed elsewhere herein, before an individual begins to vocalize words, signals representing facial skin micromovements may be received. At least one word to be spoken prior to vocalization may be determined from the signals (i.e., a derivative of the words to be spoken being the interpretation and the content being the information contained in the signals, in this example). As the at least one word is vocalized, the interpretation of the at least one word may be presented.

By way of a few examples, content may include information encoded and/or formatted according to one or more data types associated with presenting information via an interface of an electronic device. Such data types may include, for example, text, image, audio, video, haptic, electronic signals output from a reflection sensor, olfactory, and any other data type reflective of pre-vocalization information derived from an individual. At least one processor may receive signals from one or more sensors or from intermediate circuitry, and may store received content in long or short term memory. In this example, content interpretation may include analyzing such signals to determine one or more associations and/or mappings to other content, data, and/or information, and thereby attributing to the piece of content one or more of a meaning, a definition, an essence, a general idea, and/or an underlying message. In some embodiments, content interpretation may include identifying one or more underlying assumptions, values, and/or beliefs associated with a piece of content. Content interpretation may be subjective (e.g., based on a particular frame of reference, individual, and/or context) and/or objective (e.g., based on a systematic analysis). In some embodiments, content interpretation may be based on a plurality of frames of reference and/or contexts. Content to be interpreted may include content slated for subsequent interpretation. Vocalization of content may include an audible expression and/or articulation of content. Vocalization of content may include human vocalization of sounds and/or words (e.g., via a human larynx) and/or a synthesized vocalization of content (e.g., via a content synthesizer and speaker). At least one processor may begin interpreting a piece of content before a human begins vocally articulating the piece of content.

By way of a non-limiting example, in FIG. 1, individual 102 donning speech detection system 100 may prepare to vocalize a piece of content to be interpreted. For example, the central nervous system of individual 102 may transmit neural signals to enlist facial muscles needed to articulate the piece of content. Prior to individual 102 articulating the piece of content (e.g., prior to individual 102 emitting any vocal sound relating to the piece of content), at least one processor (e.g., processing device 400 in FIG. 4) may initiate operations to interpret the piece of content, as described in greater detail in this disclosure.

Some disclosed embodiments involve receiving signals representing facial skin micromovements. Receiving may include retrieving, acquiring, or otherwise gaining access to, e.g., data. Receiving may include reading data from memory and/or receiving data from, circuitry, a computing device and/or an output of one or more sensors via a (e.g., wired and/or wireless) communications channel. At least one processor may receive data via a synchronous and/or asynchronous communications protocol, for example by polling a memory buffer for data and/or by receiving data as an interrupt event. Signals represent facial skin micromovements when they convey, characterize, express, or embody the facial skin micromovements. A signal may refer to information encoded for transmission via a physical medium. Examples of signals may include signals in the electromagnetic radiation spectrum (e.g., AM or FM radio, Wi-Fi, Bluetooth, radar, visible light, lidar, IR, Zigbee, Z-wave, and/or GPS signals), sound or ultrasonic signals, electrical signals (e.g., voltage, current, or electrical charge signals), electronic signals (e.g., as digital data), tactile signals (e.g., touch), pressure signals, fluid flow (e.g., air or water) signals, humidity signals, and/or any other type of information encoded for transmission between two entities via a physical medium. Signals representing facial skin micromovements may include signals conveying information characterizing facial skin micromovements that may allow for identification of one or more facial skin micromovements by analyzing the signals. Such signals may include, for example, optical, vibration, temperature, humidity, airflow signals, and/or any other type of signal associated with facial skin micromovements. For example, an optical sensor may capture images of facial skin micromovements. A vibration sensor may capture micro-vibrations associated with facial skin micromovements. A thermometer may sense changes in skin surface temperature due to facial skin micromovements. A humidity sensor and/or a fluid velocity sensor may sense changes in airflow near the facial skin, for example, due to changes in breathing patterns (e.g., changes in breathing rate and/or breathing depth), and/or switching from breathing from the mouth to breathing from the nose, e.g., in preparation for vocalizing content. In some embodiments, signals representing facial skin micromovements may exclude audio signals associated with vocalizing content. For example, at least one processor may receive from an optical sensor, images of facial skin of an individual preparing to speak. The images may be captured over a period of time to indicate micromovements of the facial skin, e.g., based on patterns of reflected light. The at least one processor may analyze the images to identify the facial skin micromovements.

In some disclosed embodiments, the signals representing facial skin micromovements correspond to muscle activation prior to the vocalization of the at least one word. Muscle activation prior to vocalization refers to a time period before an audible presentation of an associated word occurs when one or more muscles are enlisted to expand or contract. (e.g., also referred to as subvocalization elsewhere in this disclosure). The muscle expansion or contraction may generate a force to move a body part, such as overlying facial skin, or facial skin near or connected to the recruited muscle or muscles. A central nervous system may cause muscle activation by transmitting nerve signals via a motor neuron causing targeted muscular fibers to contract and/or expand. Muscle activation may be voluntary or involuntary. Voluntary muscle activation may include a conscious decision to move a body part. Involuntary muscle activation may include automatic triggering of a muscle, without conscious control (e.g., a knee-jerk reflex). In some instances, a bodily activity may involve voluntary and involuntary muscle activation. For example, speaking may involve voluntary and/or involuntary muscle activation in preparation for speaking (e.g., prior to vocalization of at least one word) and voluntary and/or involuntary muscle activation during vocalization of at least one word. Prior to vocalization of at least one word, a central nervous system may transmit nerve signals to recruit and/or prepare one or more targeted facial muscles associated with vocalizing the at least one word. The transmitted nerve signals may cause voluntary and/or involuntary muscle activation of the targeted facial muscles, which may cause facial skin micromovements of a layer of skin covering the targeted facial muscles. An optical sensor may detect light reflected off the facial skin covering the targeted facial muscles, thereby sensing facial skin micromovements corresponding to muscle activation prior to vocalizing at least one word.

In some disclosed embodiments, the muscle activation is associated with at least one specific muscle that includes: a zygomaticus muscle, an orbicularis oris muscle, a risorius muscle, a genioglossus muscle, or a levator labii superioris alaeque nasi muscle. A zygomaticus muscle, an orbicularis oris muscle, a risorius muscle, a genioglossus muscle, or a levator labii superioris alaeque nasi muscle may include facial muscles that may be recruited by a human for vocalization of speech.

By way of a non-limiting example, in FIG. 1, prior to vocalizing at least one word, a central nervous system of individual 102 may transmit nerve signals to enlist facial muscles of individual 102 required to vocalize the at least one word. For instance, in FIG. 5, the targeted facial muscles may be associated with muscle fiber 520 (e.g., part of: a zygomaticus muscle, an orbicularis oris muscle, a risorius muscle, genioglossus muscle, or a levator labii superioris alaeque nasi muscle). The nervous signals may cause the targeted facial muscles of individual 102 to contract, which may cause a layer of facial skin covering the targeted facial muscles (e.g., first facial region 108A) to perform micromovements. Optical sensing unit 116 may capture images of patterns of light reflecting off first facial region 108A of individual 102 during performance of the micromovements and may transmit the images to at least one processor (e.g., processing device 400 of FIG. 4). The at least one processor may receive the images and store the images in a memory (e.g., memory device 402).

Some disclosed embodiments involve determining from the signals at least one word to be spoken prior to vocalization of the at least one word in an origin language. A language may refer to a system of communication including a set of sounds, symbols, and rules used to convey information between individuals or groups via speech, writing, symbols, and/or signs. A language may be characterized by a vocabulary, grammar, and pronunciation patterns, and may be used to express thoughts, feelings, ideas, and/or any other information. Examples of languages include English, Spanish, Chinese, Japanese, French, Hebrew, Arabic, Hindi, German, Russian. An origin language may refer to a source or initial language in which a word, such as a prevocalized word, may be expressed. An origin language may be associated with a user of a speech detection system. For instance, a word for subsequent vocalization by a wearer of a speech detection system may belong to an origin language. A word may refer to a unit of language that carries meaning. A vocalized word may include one or more spoken sounds, phonemes, and/or graphemes representing information. Words may be classified into different categories, for example, nouns, verbs, adjectives, and adverbs, based on their grammatical function and role in a sentence. A noun may be a word that refers to a person, place, thing, or idea. A verb may be a word that describes an action or state of being. A word may have different meanings depending on context and/or on other associated words or expressions. A word may be combined with other words to express an idea and/or an observation, as a phrase or sentence.

A word to be spoken may include a word to be subsequently communicated verbally and/or otherwise articulated audibly. A word to be spoken may be associated with a transmission of a nerve signal by a central nervous system to recruit one or more selected facial muscles required to articulate a sound, a phoneme, and/or a grapheme associated with the word to be spoken. The nerve signal may trigger one or more micro-contractions of the selected facial muscles, which may trigger micromovements of facial skin covering the selected muscles, e.g., prior to activation of the targeted muscles for vocalizing a word to be spoken as described elsewhere in this disclosure. Vocalization of a word may include an audible expression and/or an articulation of a word. Vocalization of a word may involve a central nervous system transmitting signals via motor neurons causing facial muscular fibers to contract concurrently with air being expelled from the lungs and flowing through the larynx. The contraction of the facial muscular fibers may affect a sound produced by air flowing through the larynx and exiting the mouth and may produce a vocalization of a word. A time prior to vocalization of a word may include a time before or preceding vocalization of a word. Determining at least one word from the signals may include making one or more measurements, comparisons, estimations, and/or calculations to arrive at a conclusive outcome based on information contained in signals. The act of determining may occur directly or indirectly. For example, the signals themselves may be interpreted to determine a word or the signals may be interpreted to determine a series of phonemes, and an associated word or group of words may be ascertained from the group. Additionally or alternatively, one or more words may be determined in part from the context of other words in context. A mechanism for mapping signals to one or more words to be spoken is included within the meaning of determining words to be spoken in the context of this disclosure.

For example, one or more specific facial skin micromovements may be associated with a recruitment of one or more specific facial muscles preparing to vocalize a particular word in an origin language. A data structure may store associations between digital representations of a plurality of known facial skin micromovements and a plurality of words in an origin language, e.g., as an index, a linked list, an array, a graph, an AI model, and/or any other data structure for storing relationships. The at least one processor may generate a digital representation of the facial skin micromovements (e.g., as a feature vector and/or one or more tokens) and query the data structure using the digital representation to determine a match with at least one of the known facial skin micromovements (e.g., based on a similarity measurement), to thereby determine the at least one word prior to vocalization in an origin language. For instance, the at least one processor may associate at least one word or group of words with one or more facial skin micromovement attributes. Such attributes may include, for example, a timing, a sequence, a type, a frequency, a degree of movement (e.g., maximal micromovement), a direction of a micromovement, a combination of particular facial micromovements, and/or any other facial skin micromovement attributes. Additionally or alternatively, the at least one processor may associate at least one word in an origin language with a particular facial muscle and/or a combination of particular facial muscles, e.g., associated with facial skin micromovements. Additionally or alternatively, the at least one processor may use a context (e.g., including a history of words vocalized by the user, and/or a history of recorded words heard by the user) to determine at least one word to be spoken in an origin language. Additionally or alternatively, the at least one processor may enlist one or more artificial intelligence algorithms and/or machine learning techniques to determine at least one word using identified facial skin micromovements. For example, the at least one processor may apply a probabilistic function to determine at least one word in an origin language based on a prevalence of the at least one word in the origin language (e.g., for a general population, for the user, and/or for a specific context associated with the user). Additionally or alternatively, the at least one processor may analyze the signals to decipher at least some subvocalization facial skin micromovements to determine at least one word, e.g., using one or more image processing algorithms, light reflection analyses, speech deciphering algorithms, machine learning algorithms, and/or neural networks, as described elsewhere in this disclosure.

By way of a non-limiting example, in FIG. 1, at least one processor (e.g., processing device 400 in FIG. 4) may receive signals from optical sensing unit 116 representing facial skin micromovements. The at least one processor may analyze the signals to determine at least one word to be spoken prior to vocalization of the at least one word in an origin language. The at least one processor may store the at least one word in a memory (e.g., memory device 402).

In some disclosed embodiments, determining from the signals at least one word includes interpreting the facial skin micromovements using speckle analysis. Speckle analysis may be understood as described elsewhere in this disclosure. Prior to a user vocalizing at least one word, but after a central nervous system of the user has transmitted nerve signals to recruit muscles earmarked for vocalizing at least one word, a coherent light source may shine coherent light on a facial region of the user. An image sensor may capture images of coherent light reflecting off the facial region of the user and may transmit the images to at least one processor. The at least one processor may perform a speckle analysis to identify one or more facial skin micromovements, and may determine at least one word using the identified facial skin movements, as described elsewhere in this disclosure.

By way of a non-limiting example, in FIG. 4, light source 410 may shine coherent light on first facial region 108A of individual 102. Light detector 412 may capture images of coherent light reflecting off first facial region 108A and may transmit the images to at least one processor (e.g., processing device 400). The at least one processor may use the images to perform a speckle analysis and identify one or more facial skin micromovements, as described elsewhere in this disclosure.

Some disclosed embodiments involve, prior to the vocalization of the at least one word, instituting an interpretation of the at least one word. Instituting may include initiating, launching, and/or instantiating, e.g., a word interpreter. An interpretation of a word may be understood similarly to content interpretation, as described elsewhere in this disclosure, where interpretation may be applied to a specific word or words. For example, at least one processor may interpret a word by extracting explicit and/or implicit meaning from a word, e.g., by identifying one or more synonyms, antonyms, word associations, contexts, and/or relationships (e.g., semantic, syntactical, grammatical, social, cultural, linguistic, and/or any other type of relationship) with one or more other words in a target language. In some embodiments, interpretation of at least one word may involve using a meaning associated with a cognate, an etymological ancestor, and/or a lexeme of the at least one word. For example, prior to a user vocalizing at least one word, but after the at least one processor has determined at least one word based on received signals representing facial skin micromovements, the at least one processor may identify an association between the determined at least one word and at least one different word (e.g., in the origin language or in a different language). In some embodiments, an interpretation of at least one word may include the at least one word to be spoken.

For example, if a word is prevocalized in Spanish, interpretation of the Spanish word to English may be instituted before the speaker audibly vocalizes the word. Then, simultaneously or near simultaneously with the speaker vocalizing the word in Spanish, the system may audibly and/or textually present the word in English.

By way of a non-limiting example, in FIG. 4, at least one processor (e.g., processing device 400) may institute an interpretation of the at least one word, for example, by querying data structure 422 and/or data structure 464 via network interfaces 420 and 456.

In some disclosed embodiments, the interpretation is a translation of the at least one word from the origin language into at least one target language other than the origin language. A target language may be a language different than an origin language, and may include at least some sounds, symbols, and/or rules for communicating information that are different than at least some sounds, symbols, and/or rules for communicating information in an origin language. A target language may be associated with a dictionary that may allow translation of words from an origin language to the target language. Translation of at least one word from an origin language to a target language may involve transferring a meaning of at least one word in an origin language to at least one word in a target language. Transferring a meaning of a word to a target language may involve, for example, determining a meaning of a word in an origin language (e.g., including nuances, idioms, and/or context), selecting a translation method (e.g., word-for-word, literal, or free translation), and mapping a word from an origin language to one or more words in a target language in a manner that captures the determined meaning of the word in the target language. For example, mapping at least one word from an origin language to a target language may involve searching for the at least one word in a dictionary associated with the origin language and the target language, and/or submitting the at least one word to a machine translator. Transferring a meaning of a word to a target language may additionally involve, for example, considering one or more of grammars, syntax, vocabulary, lexemes, lexical cognates, synonyms, antonyms, nuances, metaphors, idiom, and/or culture associated with the origin language and/or the target language. In some embodiments, transferring a meaning of a word to a target language may additionally involve considering one or more words in a third language, different than the origin language and the target language. For example, the third language may be related to the origin language and/or the target language.

In some disclosed embodiments, the interpretation of the at least one word includes a transcription of the at least one word into text in the at least one target language. Text may refer to a written form of words. Text may represent one or more words (e.g., audible words) as a sequence of symbols (e.g., letters of an alphabet) embodied on a physical medium (e.g., written), where each letter of an alphabet may be associated with a different phoneme and/or grapheme of an audible word. In a digital environment, each letter of an alphabet may be associated with a digitally encoded number (e.g., a series of binary digits) and a corresponding pixel pattern, allowing for storage of each letter as a series of binary digits and for displaying each letter as a corresponding pattern of pixels on an electronic display. Text may be stored as a text file (e.g., TXT, DOC, DOCX, RTF, PDF, and/or any other text file format). Transcription into text may involve converting spoken language into written form, e.g., by storing a digitally encoded word in memory. In some applications, transcription into text may include receiving an audio and/or video recording, identifying one or more audible words in the audio and/or video recording, and/or converting the one or more audible words to written words, e.g., using speech recognition software. In some applications, transcription into text may include converting at least one word to text prior to vocalization (or any other type of audible rendition) of the at least one word. For example, prior to vocalization of at least one word in an origin language, and upon translating the at least one word from the origin language to at least one target language, the at least one processor may store a digitally encoded version of the translated at least one word in the at least one target language in memory (e.g., using an alphabet of the at least one target language), thereby transcribing the at least one word into text in the at least one target language. In some embodiments, the at least one processor may output the text in the at least one target language to an electronic display (e.g., concurrently with a vocalization of the at least one word), allowing an individual to read the at least one word in the at least one target language concurrently with a vocalization of the at least one word in the origin language.

In some disclosed embodiments, the interpretation of the at least one word includes a speech synthetization of the at least one word in the at least one target language. Speech synthetization may involve technology configured to convert written signal representing facial skin micromovements or text (e.g., stored in a memory) into audible words, (e.g., conversion of speech to text). Speech synthetization may involve generating a computerized voice, and using the computerized voice to produce an audible rendering of text stored in memory, e.g., using concatenative speech synthesis and/or parametric speech synthesis. Concatenative speech synthesis may involve using pre-recorded audio segments of human speech, and combining selected segments to generate new words and sentences. Parametric speech synthesis may involve using one or more mathematical models and/or algorithms to generate synthetic speech based on linguistic and acoustic features.

For example, upon determining at least one word in an origin language and translating the at least one word from the origin language to at least one target language (e.g., prior to vocalization of the at least one word in the origin language), the at least one processor may instantiate a speech synthesizer to produce an audible rendition of the at least one word in the at least one target language, to thereby produce a speech synthetization of the at least one word in the at least one target language.

By way of a non-limiting example, in FIG. 4, data structure 422 and/or data structure 464 may store one or more dictionaries allowing translation of at least one word from an origin language to one or more target languages. At least one processor (e.g., processing device 400) may institute an interpretation of the at least one word by querying data structure 422 and/or data structure 464 with the at least one word in an origin language to obtain a translation of the at least one word in one or more target languages. In some embodiments, the at least one processor may transcribe the at least one word in the at least one target language and store the transcription in a memory (e.g., memory device 402). In some embodiments, the at least one processor may enlist a speech synthesizer (e.g., stored in memory device 402) to produce an audio rendition of the at least one word for outputting via a speaker (e.g., speaker 404).

By way of another non-limiting example, in FIG. 34, as individual 102 prepares to speak a word in English (e.g., "Hello"), but before individual 102 vocalizes the word "Hello", at least one processor (e.g., processing device 400 of FIG. 4) of speech detection system 100 may determine the word to be spoken as "Hello", and translate the word "Hello" to French (e.g., "Bonjour"). The at least one processor may encode the translation of the at least one word for transmitting via communications network 126 (see FIG. 1) to a mobile communications device 3400 associated with a different user 3402, causing mobile communications device 3400 to present the translation of the word (e.g., "Bonjour") as individual 102 vocalizes the word "Hello". In some embodiments, the at least one processor may transmit a transcription of "Bonjour" to text, causing the transcribed translated text "Bonjour" to be displayed on a visual display of mobile communications device 3400 at substantially the same time that individual 102 may vocalize the word "Hello" in English. In some embodiments, the at least one processor may invoke output determination module 712 (e.g., see FIG. 7) to synthesize a translation of the word into French (e.g., by synthesizing a vocalization of "Bonjour") and may transmit the synthesized translation to mobile communications device 3400. Mobile communications device 3400 may output the synthesized translated word "Bonjour" via a speaker at substantially the same time that individual 102 may vocalize the word "Hello" in English.

Some disclosed embodiments involve causing the interpretation of the at least one word to be presented as the at least one word is spoken. Causing the interpretation refers to triggering and/or inducing, in the context, the presentation of the at least one spoken word. Such a presentation may include one or more of an audio, video, textual, and/or pictorial rendition of an interpretation of the at least one spoken word via an audio and/or visual output interface. The presentation occurring as the at least one word is spoken refers to the presentation occurring in a timeframe during which the at least one word is vocalized, such that the interpretation of the at least one word is presented substantially concurrently with a human utterance of the at least one word. Upon determining at least one word in an origin language and instituting an interpretation of the at least one word, the at least one processor may time a presentation of the interpretation of the at least one word to be concurrent with a user vocalizing the at least one word. For example, the at least one processor may receive one or more vocalization initiation signals indicating that the user is initiating vocalization of the at least one word. Vocalization initiation signals may include audio signals sensing the user initiating vocalization, optical signals representing facial skin movements associated with vocalization, a (e.g., predicted) time for vocalizing the at least one word after occurrence of associated facial skin micromovements, and/or any other signal (e.g., humidity, air pressure, vibration, head, eye motion, and/or mouth motion) indicating vocalization of the at least one word. In response to the vocalization initiation signals, the at least one processor may cause the interpretation of the at least one word to be presented concurrently with the vocalization of the at least one word by transmitting the interpretation of the at least one word to an output interface.

By way of a non-limiting example, in FIG. 1, the at least one processor (e.g., processing device 400 of FIG. 1) may cause the interpretation of the at least one word to be displayed via mobile communications device 120 as individual 102 vocalizes the at least one word. For example, the at least one processor may display a translation of the at least one word in a target language on mobile communications device 120 as individual 102 vocalizes the at least one word in an origin language.

Some disclosed embodiments involve receiving a selection of the at least one target language. A selection may include a choice, and/or decision. For example, the system may include controls on the user side to select the translation language. Or, a setting or control on a listener side may enable selection of the target translation language. Such controls may be enabled through physical buttons, a touch screen, gesture recognition (e.g., on a pick list presented via smart glasses or smart goggles, via a display such on a mobile communications device, PC, tablet or laptop), voice response, or in any other manner enabling a target language to be selected.

Receiving a selection of a language may include receiving a signal associated with a specific language from a plurality of available languages, e.g., via a user interface of an electronic device. Such a user interface may include, for example, a menu offering a plurality of candidate target languages for selection (e.g., via touch and/or electronic mouse), a text box allowing text entry of a target language (e.g., via a keyboard), a microphone paired with voice recognition software, a camera paired with gesture recognition software, and/or any other type of user interface allowing to select a target language. A signal associated with a selection of a language may be one or more of an audio signal (e.g., of speech detected by a microphone), a touch-based signal (e.g., of a menu item detected by a touch sensor), a visual signal (e.g., of a gesture detected by an optical sensor), a keyboard signal (e.g., of a typed word identifying a language), an image signal of a gesture, and/or any other type of signal associated with a selection of a language. For example, the at least one processor may present a plurality of target languages for selection by a user via an electronic device associated with the user (e.g., a mobile communications device). The user may be associated with vocalizing at least one word in an origin language, and/or a different user associated with receiving a presentation of an interpretation of the at least one word, as the at least one word is spoken in the origin language. Upon receiving a selection of at least one target language, the at least one processor may associate an identifier with each of the selected target languages. For example, the identifier may be used to access a dictionary and/or a translator (e.g., a machine translator) for each of the selected target languages.

In some disclosed embodiments, the selection of the at least one target language includes selections of a plurality of target languages, and wherein causing the interpretation of the at least one word to be presented includes simultaneously causing presentation in the plurality of languages. Selections of a plurality of target languages may involve presenting a plurality of candidate target languages to multiple users, and allowing each user to select a target language, and/or presenting a plurality of candidate target languages to a single user and allowing a single user to select a plurality of target languages (e.g., on behalf of a plurality of users). Simultaneously may refer to substantially concurrently or substantially at the same time, e.g., accounting for processing, communications, and other latencies. Simultaneous presentation in plurality of languages may involve translating at least one word to a plurality of languages and simultaneously presenting the plurality of translations of the at least one word via one or more user interfaces (as described and exemplified elsewhere in this disclosure).

In some embodiments, at least some of the plurality of translations may be presented in a common (e.g., shared) interface, e.g., as text displayed in separate rows of a billboard. In some embodiments, each translation of the at least one word may be presented via a different interface. For example, at least one processor may apply a different speech synthesizer to each translation to produce a plurality of audio renditions corresponding to the plurality of target languages. The at least one processor may concurrently output each audio rendition via a different speaker (e.g., headset) for a different user, such that each different user may hear a different translation of the at least one word in a different target language concurrent with a vocalization of the at least one word in the origin language. As another example, at least one processor may produce a plurality of transcribed texts corresponding to the plurality of languages and output each transcribed text via a plurality of electronic displays, each electronic display associated with a different user. This may allow different users to view a different transcribed translation of the at least one word to a different target language concurrently with a vocalization of the at least one word in the origin language. As a further example, at least one processor may present a plurality of transcribed texts corresponding to a plurality of languages on a single electronic display (e.g., as a billboard).

By way of a non-limiting example, in FIG. 1, the at least one processor (e.g., processing device 400 of FIG. 4) may present a menu listing a plurality of candidate target languages on mobile communications device 120. Individual 102 may select a particular target language (e.g., by touching a touch sensitive screen of mobile communications device 120) from the menu. Mobile communications device 120 may transmit an indication of the selection to the at least one processor. In some embodiments, individual 102 may select a plurality of target languages from the menu, and mobile communications device 120 may transmit a plurality of indications for the plurality of selections to the at least one processor. In response to receiving a plurality of selected target languages, the at least one processor may query data structure 422 and/or data structure 464 with the at least one word in an origin language and receive a plurality of translations in a plurality of target languages. The at least one processor may simultaneously present the plurality of translations via mobile communications device 120.

In some disclosed embodiments, the interpretation of the at least one word includes a transcription of the at least one word into text in the origin language. A transcription may be understood as described elsewhere in this disclosure. Upon determining at least one word to be spoken in an origin language, the at least one processor may convert the at least one word to text in the origin language and store the text in memory. In some embodiments, the at least one processor may output the text to an electronic display (e.g., concurrently with a vocalization of the at least one word), allowing an individual to read the at least one word in the origin language concurrent with a vocalization of the at least one word in the origin language. The word can be presented in the origin language or in a target language. In the context of captioning for those with hearing impairments or for subtitles, textual presentation may occur in the origin language.

For speakers of languages other than the origin language, the spoken words may be presented in their target language of choice.

In some disclosed embodiments, presenting the interpretation of the at least one word includes outputting a textual display of the transcription together with a video of an individual associated with the facial skin micromovements. Outputting a textual display of a transcription may involve storing a digital encoding of each letter of a text in a memory buffer associated with an electronic display to cause a driver of the electronic display to activate pixel patterns corresponding to each letter and graphically depict the text. A video may include a chronological sequence of images (image data) and an associated audio recording (audio data) configured to be presented simultaneously. For example, a video may include image data of an individual vocalizing at least one word and audio data of the vocalization of the at least one word, allowing a user to simultaneously see and hear a vocalization of the at least one word via an electronic medium. A video may be generated by a camera operating concurrently with a microphone. A camera may capture image data associated with an event over a time period as visual electronic signals. Concurrently, a microphone may detect audio data associated with the event over the period of time as audio electronic signals. The camera and microphone may transmit the visual and audio electronic signals, respectively, to at least one processor for storing in memory, e.g., as a MOV, MP3, MP4, WMV, AVI, AVCHD, AVI file and/or in any other type of video file format. An individual associated with facial skin micromovements may include a human donning a speech detection system configured to detect facial skin micromovements of the human prior to the human vocalizing at least one word (e.g. content). A video of an individual associated with the facial skin micromovements may include image data and associated audio data of an individual vocalizing at least one word while donning a speech detection system. For example, during a first time period, a camera associated with a speech detection system may capture facial skin micromovements of an individual prior to vocalizing at least one word. The camera may transmit signals representing the facial skin micromovements to at least one processor. The at least one processor may analyze the signals to determine the at least one word to be spoken and an interpretation thereof. During a second time period immediately following the first time period, the camera and an associated microphone may record a video of the individual vocalizing the at least one word (e.g., determined by the at least one processor prior to vocalization). Outputting a textual display of the transcription together with a video of an individual associated with the facial skin micromovements may include using an electronic display and an associated speaker to present a video of an individual vocalizing at least one word (e.g., as described above), while simultaneously displaying text of a transcription of the at least one word, e.g., using the same or a different electronic display.

For example, the at least one processor may output a textual display of a transcription as subtitles (e.g., displayed in a band at the bottom of an electronic display presenting the video), in a chatbox (e.g., displayed in a separate window than a window used to display the video), as comment bubbles (e.g., overlaid on the video), and/or using any other format or display medium for text accompanying a video.

By way of a non-limiting example, in FIG. 4, at least one processor (e.g., processing device 400 in FIG. 4) may transcribe the at least one word to text and store the text in memory device 402. In some embodiments, the at least one processor may present a video of individual 102 vocalizing the at least one word with a subtitle including a textual display of a transcription of at least one word.

In some disclosed embodiments, receiving signals occurs via at least one detector of coherent light reflections from a facial region of a person vocalizing the at least one word. Coherent light and a facial region may be understood as described elsewhere in this disclosure. A detector of coherent light reflections from a facial region of person vocalizing a word may include a light detector (e.g., as described elsewhere in this disclosure) configured to sense coherent light and positioned in a manner to capture at least some coherent light waves reflecting off a facial region of a person preparing to vocalize at least one word. The detector may detect coherent light waves reflecting off the facial region of the person during performance of facial skin micromovements (e.g., prior to the person vocalizing at least one word) and may transmit signals representing the facial skin micromovements to at least one processor for analysis. In some embodiments, the at least one processor may use the signals to perform a speckle analysis, as described elsewhere in this disclosure.

In some disclosed embodiments, causing the interpretation of the at least one word to be presented occurs concurrently with the at least one word being vocalized by the person. Concurrently may include simultaneously or contemporaneously, e.g., occurring in overlapping time windows. For example, the at least one processor may synchronize a timing for presenting an interpretation of at least one word to coincide with a vocalization of the at least one word by the person. This may allow an observer (e.g., a person other than the person vocalizing the at least one word) to receive a presentation of an interpretation of at least one word at the same time as the person vocalizes the at least one word.

By way of a non-limiting example, in FIG. 1, light source 410 (see FIG. 4) of optical sensing unit 116 may shine coherent light onto first facial region 108A of individual 102. Light detector 412 of optical sensing unit 116 may include a detector of coherent light, and may capture a chronological series of images of coherent light reflecting off first facial region 108A prior to, and during vocalization of at least one word, thereby sensing facial skin micromovements of first facial region 108A prior to and during vocalization. Light detector 412 may provide the chronological series of images (e.g., in real time) to the at least one processor (e.g., processing device 400), e.g., by storing the chronological series of images in memory device 402 in real time. The at least one processor may determine an interpretation of the at least one word as described elsewhere in this disclosure and may present the interpretation of the at least one word via mobile communications device 120 while individual 102 vocalizes the at least one word.

In some disclosed embodiments, causing the interpretation of the at least one word to be presented includes using a wearable speaker to output an audible presentation of the at least one word. A speaker may include an electroacoustic transducer configured to convert an electrical audio signal to an acoustic signal (e.g., sound waves). A wearable speaker may include a speaker connected to an accessory configured to be worn by a user, e.g., as an earpiece, a clip (e.g., a hair clip), a head band, a cap, headphones, earphones, earbuds, and/or any other wearable accessory. Outputting an audible presentation of a word may involve transmitting an electrical audio signal to a speaker to thereby cause the speaker to produce an acoustic signal corresponding to the electrical audio signal.

For example, upon determining and interpreting at least one word (e.g., prior to vocalization of the at least one word), at least one processor may output the at least one word to a wearable speaker. In some embodiments, the at least one processor may time outputting of the at least one word to a wearable speaker to produce an audio rendition of the at least one word such that it is concurrent with a vocalization of the at least one word. This may allow a listener to hear an audio rendition of the at least one word using a wearable speaker at the same time that a person (e.g., associated with facial skin micromovements) vocalizes the at least one word.

By way of a non-limiting example, in FIG. 1, the at least one processor (e.g., processing device 400 of FIG. 4) may output an audible presentation of the at least one word to wearable speaker 404 of speech detection system 100.

In some disclosed embodiments, causing the interpretation of the at least one word to be presented includes transmitting sound signals over a network. Transmitting may include sending, conveying, and/or transporting, e.g., via a communications channel. Sound signals may include data formatted as an audio file (e.g., as a WAV, MP3, MP4, FLAC, or any other format for audio data). Transmitting sound signals over a network may include converting an interpretation of at least one word to an audio file, formatting an audio file for transmission according to one or more communications protocols, and enlisting communications network infrastructure to send an audio file to a remote address.

For example, upon determining an interpretation of at least one word (prior to a vocalization of the at least one word), at least one processor may format the interpretation as an audio file and transmit the audio file to a remote address via a communications network, allowing a user to listen to an audio rendition of the interpretation of the at least one word in a remote location.

Some disclosed embodiments may involve determining at least one prospective word to be spoken following to the at least one word to be spoken, instituting an interpretation of the at least one prospective word prior to vocalization of the at least one word; and causing the interpretation of the at least one prospective word to be presented following presentation of the at least one word as the at least one word is spoken. A prospective word to be spoken following to the at least one word to be spoken may include at least one expected, probable, and/or anticipated word associated with the at least one word, such that concatenating the at least one word to be spoken with the at least one prospective word to be spoken produces a phrase encapsulating an idea or thought, e.g., to implement an auto-complete functionality. At least one processor may determine one or more prospective words expected to follow the at least one word to be spoken using one or more predictive models, artificial intelligence, machine learning, a history, a context, a pattern, and/or any other information that may be used to anticipate at least one word. For example, based on facial skin micromovements (e.g., prior to vocalization), at least one processor may determine that a user is preparing to vocalize the words (e.g., "What time"). The at least one processor may determine at least one prospective word anticipated to follow the at least one word (e.g., "is it now?"), such that concatenating the at least word determined based on facial skin micromovements with the at least one prospective word produces a completed phrase encapsulating an idea (e.g., "What time is it now?), prior to vocalization of any word included in the completed phrase.

Instituting an interpretation of the at least one prospective word and causing the interpretation of the at least one prospective word to be presented following presentation of the at least one word may be understood as described and exemplified elsewhere in this disclosure with respect to the at least one word to be spoken. Returning to the example given earlier, the at least one processor may translate the at least one word determined based on facial skin micromovements (e.g., "What time") and the at least one prospective word (e.g., "is it?") to French (e.g., a target language), thereby translating a completed phrase (e.g., "What time is it?") to a target language (e.g., "Quelle heure est-it?"). The at least one processor may cause the at least one word and the at least one prospective word following the at least one word to be presented at the at least one word is spoken.

In some disclosed embodiments, causing the interpretation of the at least one word to be presented includes transmitting a textual translation of the at least one word over a network. A textual translation of a word may include a transcription of a word in an origin language and/or in a target language. A textual translation of a word may be stored as a text file (e.g., TXT, DOC, DOCX, RTF, PDF, and/or any other text file format). Transmitting a textual translation of at least one word over a network may include converting an interpretation of at least one word to a text file, formatting a text file for transmission according to one or more communications protocols, and enlisting communications network infrastructure to send a text file to a remote address.

For example, upon determining an interpretation of at least one word (prior to a vocalization of the at least one word), at least one processor may convert the interpretation of the at least one word to a text file, and transmit the text file to a remote address via a communications network, allowing a user to read the textual translation of the at least one word in a remote location.

Some disclosed embodiments involve determining from the signals at least one non-verbal interjection, and outputting a representation of the non-verbal interjection. An interjection may include an interruption and/or an abrupt exclamation or gesture that may discontinue a flow of communication. A non-verbal interjection may include a non-verbal expression or gesture than may interrupt a flow of communication. Some examples of non-verbal interjections may include a head motion (e.g., turning sideways, upwards, and/or downwards), eye motion, raised or furled eyebrows, opening of eyes, closing of eyes, non-verbal mouth motion (e.g., opening the mouth in surprise, smiling or frowning), hand or arm motion (e.g., a raised hand or arm), and/or any other bodily gesture that may interrupt a flow of communication. Additional example of non-verbal interjections may include gestures such as a thumbs up, pointing, a high-five, an OK, a V sign, a Vulcan salute, and/or any other bodily gesture that may interrupt a flow of communication. Additional examples of non-verbal interjections may include a sneeze, a cough, a hiccup, a yawn, a sigh, a gasp (e.g., in surprise or shock), laughter, and/or any other non-verbal expression that may interrupt a flow of communication. Some more examples of non-verbal interjections may include a gesture to adjust a microphone, a camera, and/or a setting of an electronic device. At least one processor may determine a non-verbal interjection by analyzing signals representing facial skin micromovements. In some embodiments, a camera capturing facial skin micromovements may also capture movements and/or gestures other than facial skin micromovements. For example, a camera may capture images of an individual performing any of the non-verbal interjections described herein, and may provide the captured images as signals to at least one processor. The at least one processor may analyze the signals to determine at least one non-verbal interjection.

A representation of a non-verbal interjection may include a data item configured to impart a meaning of a non-verbal interjection. Such data items may include, for example, text, a graphic image, a graphic pattern, a sound, and/or any other cue from which a meaning or an identity of a non-verbal interjection may be derived. Examples of text associated with a non-verbal interjection may include one or more of an onomatopoeic word, a text in a popup window, and/or a warning. Examples of graphical images representing a non-verbal interjection may include an emoji, and icon, an image, a Graphics Interchange Format (GIF), and/or a warning symbol. Examples of graphic patterns associated with a non-verbal interjection may include a background and/or foreground pattern and/or color. Example of sounds associated with a non-verbal interjection may include a recording (e.g., from a library) associated with a non-verbal interjection (e.g., a recording of a sneeze representing a real sneeze, or a bell or whistle representing a thumbs up gesture). Outputting a representation of a non-verbal interjection may include transmitting a representation of a non-verbal interjection to an output interface configured to render the representation of the non-verbal interjection to another data type, such as an emoji, a textual description, an audible signal, and/or any other type of.

For example, at least one processor may detect a non-verbal interjection by analyzing signals representing facial skin micromovements. The at least one processor may associate the detected non-verbal interjection with an emoji and output the associated emoji to an electronic display.

By way of a non-limiting example, in FIG. 1, the at least one processor (e.g., processing device 400 of FIG. 4) may transmit sound signals and/or a textual translation of the at least one word over communications network 126. In some embodiments, the at least one processor may determine from the signals a non-verbal interjection (e.g., a smile by individual 102) and may display a smile emoji representing the non-verbal interjection via mobile communications device 120.

Figure 35:
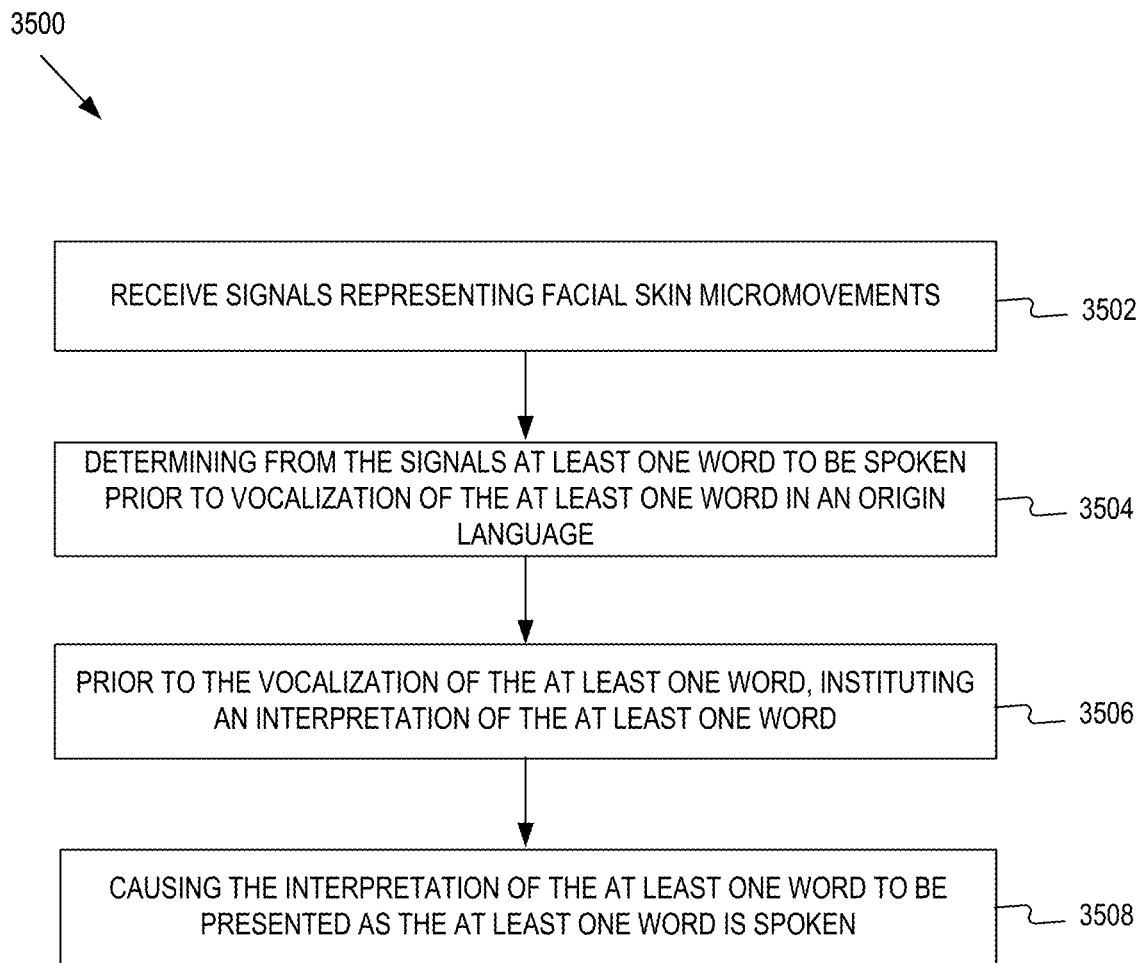
FIG. 35 is a flowchart of an example process for initiating content interpretation prior to vocalization of content to be interpreted, consistent with embodiments of the present disclosure.

FIG. 35 illustrates a flowchart of example process 3500 for enabling user interface display mode toggling, consistent with embodiments of the present disclosure. In some embodiments, process 3500 may be performed by at least one processor (e.g., processing device, 400 shown in FIG. 4) to perform operations or functions described herein. In some embodiments, some aspects of process 3500 may be implemented as software (e.g., program codes or instructions) that are stored in a memory (e.g., memory device 402) or a non-transitory computer readable medium. In some embodiments, some aspects of process 3500 may be implemented as hardware (e.g., a specific-purpose circuit). In some embodiments, process 3500 may be implemented as a combination of software and hardware.

Referring to FIG. 35, process 3500 may include a step 3502 of receiving signals representing facial skin micromovements. By way of a non-limiting example, in FIG. 1, at least one processor (e.g., processing device 400) may receive signals representing facial skin micromovements of first facial region 108a of individual 102.

Process 3500 may include a step 3504 of determining from the signals at least one word to be spoken prior to vocalization of the at least one word in an origin language. By way of a non-limiting example, in FIG. 1, at least one processor (e.g., processing device 400) may determine from the signals at least one word to be spoken prior to individual 102 vocalizing the at least one word in an origin language.

Process 3500 may include a step 3506 of, prior to the vocalization of the at least one word, instituting an interpretation of the at least one word. By way of a non-limiting example, prior to the vocalization of the at least one word, at least one processor (e.g., processing device 400) may institute an interpretation of the at least one word, e.g., by querying data structures 422 and/or 464, and or by enlisting one or more computational nodes 475 of remote processing system 450.

Process 3500 may include a step 3508 of causing the interpretation of the at least one word to be presented as the at least one word is spoken. By way of a non-limiting example, at least one processor (e.g., processing device 400) may cause the interpretation of the at least one word to be presented via mobile communications device 120 as the at least one word is spoken by individual 102.

Some embodiments involve a system for initiating content interpretation prior to vocalization of content to be interpreted, the system comprising: at least one processor configured to: receive signals representing facial skin micromovements; determine from the signals at least one word to be spoken prior to vocalization of the at least one word in an origin language; prior to the vocalization of the at least one word, institute an interpretation of the at least one word; and cause the interpretation of the at least one word to be presented as the at least one word is spoken.

By way of a non-limiting example, in FIG. 1, at least one processor (e.g., processing device 400) may receive signals representing facial skin micromovements of first facial region 108a of individual 102. The at least one processor may determine from the signals at least one word to be spoken prior to individual 102 vocalizing the at least one word in an origin language. Prior to the vocalization of the at least one word, at least one processor may institute an interpretation of the at least one word, e.g., by querying data structures 422 and/or 464, and or by enlisting one or more computational nodes 475 of remote processing system 450. The at least one processor may cause the interpretation of the at least one word to be presented via mobile communications device 120 as the at least one word is spoken by individual 102.

In some disclosed embodiments, the at least one processor may determine from signals representing facial skin micromovements, one or more non-verbal expressions, prior to the user vocalizing the non-verbal vocalization. Examples of non-verbal expressions may include a yawn, a sigh, a sneeze, a smile, a frown, a pursing of lips, a tongue click, a gasp, and/or any other non-verbal expression utilizing facial muscles. The at least one processor may perform any of the procedures described herein relating to determining at least one word based on signals representing facial skin micromovements to one or more non-verbal expressions.

For instance, at least one processor may receive signals representing facial skin micromovements of a user, and determine from the signals at least one non-verbal expression prior to an expression of the at least one non-verbal expression. Prior to the expression of the at least one non-verbal expression, the at least one processor may institute an interpretation of the at least one non-verbal expression. The at least one processor may cause the interpretation of the at least one non-verbal expression to be presented as the at least one non-verbal expression is expressed.

As an example, prior to a user smiling (e.g., expressing a non-verbal expression), the at least one processor may receive signals representing facial micromovements associated with a recruitment of facial muscles associated with smiling. The at least one processor may determine that the user may imminently smile based on the received signals, and may interpret the smile with a smiling emoji. The at least one processor may cause a smiling emoji to be displayed on an electronic display, substantially at the same time that the user smiles.

In some disclosed embodiments, one or more non-verbal expressions may be associated with invoking one or more actions, allowing a user to invoke an action without speaking or using her hands. For instance, at least one processor may associate a non-verbal tongue click expression with playing a recording. Upon receiving signals representing facial skin micromovements, the at least one processor may determine that a user may be preparing to express a non-verbal tongue-click expression, and may interpret the non-verbal tongue-click expression as a command to play a recording. The at least one processor may cause the recording to be played via a speaker of a computing device at substantially the same time that the user may perform the non-verbal tongue-click expression.

Some disclosed embodiments involve an autocomplete functionality based on signals representing facial skin micromovements. An autocomplete functionality may involve determining at least one word based on signals representing facial skin micromovements, determining at least one phrase associated with the at least one word, and causing the at least one phrase to be presented (e.g., as the at least one word is spoken). For example, the at least one phrase may include a continuation, an expansion, an interpretation, an interpolation, a completion, an explanation, and/or any other logical and/or contextual extension of the at least one word. The at least one phrase may be in the same (e.g., origin) language as the at least one word, and/or a translation to a different (e.g., target) language.

For example, a customer may approach a help desk clerk with an inquiry. The help desk clerk may reply to the inquiry with a brief answer (e.g., yes or no). At least one processor may use signals representing facial skin micromovements associated with the short answer to determine a more detailed explanation and cause the more detailed explanation to be presented on a mobile device of the customer, e.g., as the help desk clerk vocalizes the short answer. For instance, in response to a traveler's inquiry to a help desk if a plane is leaving on time, a help desk clerk may answer "no." Based on signals representing facial micromovements for vocalizing the word "no," at least one processor may cause the phrase "The departure of flight A123 from Chicago to New York is being delayed by 30 minutes."

In some disclosed embodiments, an autocomplete functionality may be applied to one or more silently spoken words. At least one processor may receive signals representing facial skin micromovements associated with one or more silently spoken words, and may determine the one or more silently spoken words based on the received signals. The at least one processor may interpret the one or more silently spoken words, e.g., by determining a phrase (e.g., a full sentence) associated therewith. The at least one processor may cause the phrase to be presented (e.g., as a communication accelerator).

In some disclosed embodiments, the at least one processor is configured to translate a phase associated with the one or more silently spoken words and cause the translated phrase to be presented. In some embodiments, at least one processor may determine a substitute phrase associated with at least one silently spoken word. A substitute phrase may depend on a context, and/or a user identity (e.g., an identity of a user expressing a silently spoken word and/or an identity of a user receiving a presentation of a phrase associated with a silently spoken word). For example, a first substitute phrase may be presented in response to determining at least one silently spoken word in a first context, and a second substitute phrase may be presented in response to determining the same at least one silently spoken word in a second context. Examples of contexts for at least one silently spoken word may include private, public, professional, family, leisure, social, religious, urgent (e.g., medical, police, fire safety), espionage, and/or any other setting for communicating.

For instance, in response to an inquiry by a first user "would you like to go to a movie?" a second user may silently answer "no." Based on signals representing facial skin micromovements associated with the second user, at least one processor may determine a first substitute phrase "maybe another time," and present the first substitute phrase on a mobile communications device of the first user. However, in response to a similar inquire by a third user "would you like to go to a movie?" and the second user silently answering "no," at least one processor may determine a second substitute phrase "I have other plans," and present the second substitute phrase on a mobile communications device of the third user. In a similar manner, at least one processor may adapt a translation based on a context and/or a user identity.

Some disclosed embodiments involve performance of private voice assistance operations. Private voice assistance operations refer to actions or aid provided to a particular individual or select group of individuals, as opposed to the general public or an undefined group. The assistance may take a form of any functions or actions that may at least partially be performed digitally e.g., at least in part through the aid of a computer processor, other hardware, software or a combination thereof). Such assistance may, for example, involve using skin micromovements (as described herein), voice recognition, gestures, and/or a synthesis of commands. The assistance may be private because they are provided to a select individual or select group, as discussed elsewhere in this disclosure, or because the request for assistance and/or the assistance provided is either unheard, or otherwise undetectable, by individuals other than the user(s) of the voice assistance system. This is desirable to make requests or commands that a user may not want others to hear, such as those relating to sensitive information like a bank account number, while still in a public setting. In this example, a private voice assistance operation may include a digital assistant, such as a processor, providing only the user with the bank checking account number by recognizing, processing, and synthesizing a command by the user.

Some disclosed embodiments involve receiving signals indicative of specific facial skin micromovements reflective of a private request to an assistant, wherein answering the private request requires an identification of a specific individual associated with the specific facial skin micromovements. Facial skin micromovements may be understood as described and exemplified elsewhere in this disclosure. Receiving signals indicative of specific facial skin micromovements may include obtaining, or accessing any sign or indication that conveys information about the specific facial skin micromovements, such as a time-varying voltage, current, or an electromagnetic wave that may carry information about the specific facial skin micromovements. Such signals may be indicative of a presence or absence of the specific facial skin micromovements. For example, receiving signals indicative of specific facial skin micromovements may include receiving a positive voltage whenever a specific facial skin micromovement is detected. Such signals may also be indicative of one or more characteristics of the specific facial skin micromovements. For example, receiving signals indicative of specific facial skin micromovements may include receiving an electromagnetic waveform indicative of the strength of the specific facial skin micromovements detected. The signals may be received from either a sensor configured to measure those signals or another input of information regarding specific facial skin micromovements. Such signals may reveal movement and/or intensity of particular areas of skin, in combination with movement and/or intensity of other nearby particular areas of skin. From such signals, words and other information may be derived, as described elsewhere herein. As an example, signals indicative of specific facial skin micromovements may be received from a light detector 412, as shown in FIG. 4.

Figure 36:
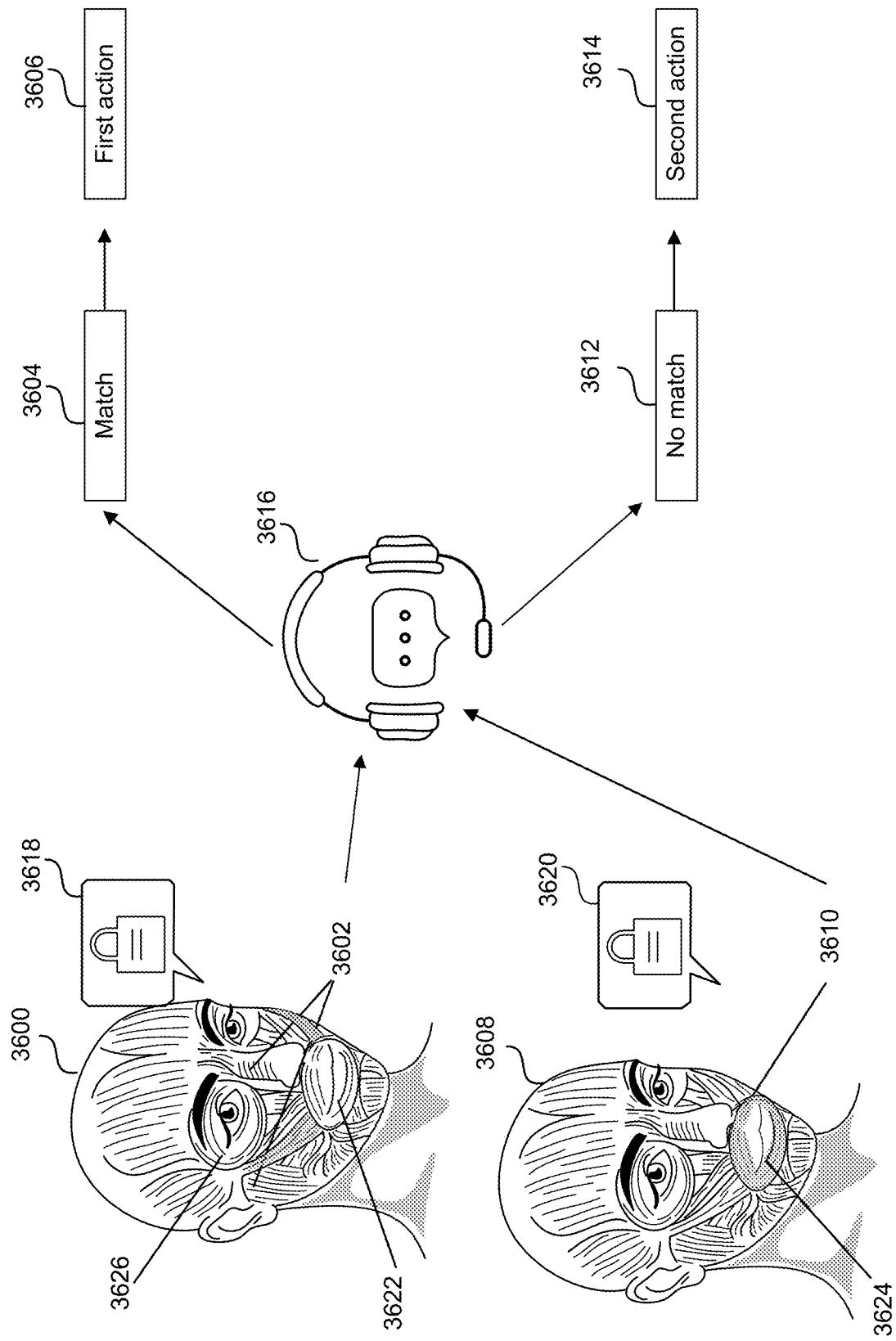
FIG. 36 illustrates an exemplary protocol for performing private voice assistance operations with different facial skin micromovements, consistent with embodiments of the present disclosure.

In some embodiments, virtual private assistance may occur in a completely digital realm, while in other embodiments the digital realm may enable augmented human assistance. Thus, an assistant may include any individual, device, or system that assists or gives aid or support in performing a function. For example, an assistant may include an individual at a call center, who receives requests from a user. In this example, the call center assistant may assist the user in retrieving information or performing certain tasks. As another example, an assistant may include an online help service, such as a website configured to answer a user's questions digitally using tools such as email, social media, live chat, and messaging applications. In this example, a user may chat with the online help service through a live chat program with an automated response generator or an individual on the other end of the program. As another example, an assistant may be a virtual assistant, such software or hardware configured to understand and carry out electronic tasks for a user. For example, a user may speak a command to a virtual assistant, which the virtual assistant receives, recognizes, and synthesizes to carry out a desired task, such as playing music, sending a text message, adding an item to a shopping list, answering a query, or telling a joke. In some examples, a virtual assistant may be implemented as an Artificial Intelligence (AI) assistant, such as an application program that understands natural language voice commands and completes tasks for the user. For example, an AI assistant may be used to understand and carry out multistep requests and perform complex tasks, such as making a plane reservation. FIG. 36 shows an example of an assistant 3616 used to perform private voice assistance operations. Some examples of assistant 3616 include a human operator on the phone, a chat program on a website, or an AI program. The assistant may be configured to receive signals from one or more users. For example, in FIG. 36, assistant 3616 receives first signals indicative of specific facial skin micromovements 3602 from a first individual 3600 and second signals indicative of specific facial skin micromovements 3610 from a second individual 3608.

Specific facial skin micromovements reflective of a private request may include those micromovements that are related to or caused by a private request. Since not all facial skin micromovements may be reflective of a private request, the system may be configured to distinguish between micromovements that are reflective of a private request and those that are not to ensure that an answer is provided when the user makes such micromovements, and not for every micromovement made by the user, such as non-speech related micromovements. One example of receiving signals indicative of specific facial skin micromovements reflective of a private request to an assistant is referring to a data structure that stores a relationship between particular micromovements or signals associated with specific user actions, such as private requests, and other user actions, such as non-private requests or non-speech-related facial movements. In this example, receiving signals reflective of specific facial skin micromovements reflective of a private request may involve only receiving signals that are associated with a private request in that data structure. As another example using an artificial intelligence-based approach, a trained classification engine may be used to receive signals reflective of specific facial skin micromovements, such as one implementing Logistic Regression, Naïve Bayes, K-Nearest Neighbors, Decision Tree, or Support Vector Machines.

A private request to an assistant may include a query for something, such as a request to complete a task, in a nonvocalized, subvocalized, or prevocalized manner, as described and exemplified elsewhere in this disclosure. For example, a private request to an assistant may be a question posed to the assistant where one or more facial muscles in a subvocalized manner. Using private requests to an assistant is desirable for users who seek an answer to a question or completion of a task without others knowing about the request. For example, the request may contain or seek sensitive information, embarrassing details, or otherwise may be undesirable for being shared with others. In such situations, a private request to an assistant may allow a user to acquire the desired information or complete a certain task without the risk of anyone else knowing what the request was, since facial skin micromovements reflective of a private request are not discernable by others. Examples of private request might be, "Please tell me my bank account balance," or "Please share the results of my medical lab tests." These are just examples, and any request for or provision of information that the speaker prefers not to share with other falls within the meaning of a private request.

For example, in FIG. 36, assistant 3616 receives first signals indicative of specific facial skin micromovements 3602 from a first individual 3600 reflective of a first private request 3618. Assistant 3616 also receives second signals indicative of specific facial skin micromovements 3610 from a second individual 3608 reflective of a second private request 3620. In this example, the first signals indicative of specific facial skin micromovements 3602 may be received in response to micromovements by the zygomaticus major muscle of the first individual 3600 reflecting a private question 3618. Similarly, the second signals indicative of specific facial skin micromovements 3610 may be received in response to micromovements by the orbicularis oris muscle of the second individual 3608 reflecting a private command 3620.

Some disclosed embodiments involve operating at least one coherent light source in a manner enabling illuminating a non-lip portion of a face of an individual making the private request, and wherein receiving the signals occurs via at least one detector of coherent light reflections from the non-lip portion of the face. A coherent light source may be understood as described and exemplified elsewhere in this disclosure. Examples of a coherent light source include light source 104 in FIG. 1 and light source 302 in FIG. 3. A non-lip portion of a face may include any portion of the face that does not include a lip of an individual. In some examples, a non-lip portion may include muscles outside the lip 3622 of the individual 3600, such as the zygomaticus major muscle, as shown in FIG. 36 and associated with first signals indicative of specific facial skin micromovements 3602. In other examples, a non-lip portion may include areas outside of a lip 3624, such as the orbicularis oris muscle, as shown in FIG. 36 associated with second signals indicative of specific facial skin micromovements 3610. Operating at least one light source in a manner illuminating a non-lip portion may include locating, moving, placing, or otherwise positioning the at least one light source to illuminate the non-lip portion. In some examples, such operating may be performed manually by the individual making the private request. In other examples, such operating may be performed automatically by one or more components of the private voice assistance operation system, such as the assistant. For example, the assistant may receive data regarding the light source or a face portion, such as position, lighting conditions, or movement via user input or sensor input, and automatically adjust the position of the light source to illuminate a non-lip portion by determining that the received data is not appropriate for a desired illumination, such as by referring to a data structure associating various types of such received data with different illumination conditions. The at least one detector of coherent light reflections may be understood as described and exemplified elsewhere in this disclosure. Examples of at least one detector of coherent light reflections include optical sensing unit 116 in FIG. 1 and a light detector in the mobile communications device 120 of FIG. 3. In the example shown in FIG. 1, receiving the signals via optical sensing unit 116 of coherent light reflections from the non-lip portion (e.g., facial region 108) of the face may involve receiving reflection signals indicative of light patterns (e.g., secondary speckle patterns) that may arise due to reflection of the coherent light from each of spots 106 within a field of view of optical sensing unit 116 from the non-lip portion (e.g., facial region 108).

Consistent with some disclosed embodiments, the at least one processor, the at least one coherent light source, and the at least one detector are integrated in a wearable housing configured to be supported by an ear of the individual. These components are integrated in a wearable, meaning that they assembled, formed, coordinated, or otherwise combined into a whole unit. Some or all components may be housed within a shell, and others may extend from or be connected to the shell. For example, if the wearable housing is an earbud, glasses, goggles or headphones (form factor), some components may be within the casing of the form factor, and other components, such as a portion of the light source may extend from the form factor. As long as there is some form of connection or connect ability, the components are said to be integrated. The wearable housing being configured to be supported by an ear of the individual refers to the wearable housing being braced, lifted up, anchored, or otherwise held up by the ear, such as occurs with an ear bud or with glasses. For example, the wearable housing may be configured to be worn on an ear of the individual. As another example, the wearable housing may be configured to be mounted on an ear of the individual. A wearable housing may be understood as described and exemplified elsewhere in this disclosure. As an example, the processing unit 112, the light source 104, and the optical sensing unit 116 may be integrated in a wearable housing 110 configured to be supported by an ear of the individual 102, as shown in FIG. 1. While the wearable housing is shown as a clip-on headphone in FIG. 1, the wearable housing may be implemented as any other wearable object configured to be supported by an ear of the individual, such as a pair of glasses 200 shown in FIG. 2.

Some disclosed embodiments involve analyzing the received signals to determine prevocalization muscle recruitment, and determining the private request based on the determined prevocalization muscle recruitment. Prevocalization muscle recruitment may be understood as described and exemplified elsewhere in this disclosure. Determining prevocalization muscle recruitment may involve determining any characteristic associated with the activation of motor units in a prevocalization muscle to accomplish an increase in contractile strength of the muscle. For example, determining prevocalization muscle recruitment may include determining an amount of the skin movement, determining a direction of the skin movement, and/or determining an acceleration of the skin movement when certain craniofacial muscles start to vocalize words. In one example, analyzing the received signals to determine prevocalization muscle recruitment may involve performing a speckle analysis on the received signals to determine that a non-lip region moved by a given distance. Determining the private request based on the determined prevocalization muscle recruitment may involve using any characteristic of the determined prevocalization muscle recruitment to identify the private request. Such determination may be performed by any identification technique, such as a matching algorithm that matches a distance moved by the non-lip region to a given private request. In another example, such determination may be performed by rules or data structures that store links between a specific amount, type, or other characteristic of movement of a specific muscle or muscle type and specific private requests. As an example, the assistant may input into an AI matching algorithm, a determination the zygomaticus major muscle, as shown in FIG. 36 associated with first signals indicative of prevocalization micromovements 3602, moved by a given distance. In this example, the AI matching algorithm may match that distance to a private question, such "What is my address?"

Some disclosed embodiments involve, determining the private request in an absence of perceptible vocalization of the private request. An absence of perceptible vocalization may refer to any partial or complete lack, deficiency, or omission of an act or process of producing sounds with voice by an individual that is able to be seen, heard, or otherwise noticed by another individual. For example, an absence of perceptible vocalization may involve an individual mouthing a word without making sound, such that another individual cannot hear it. Another example may involve an individual flexing or extending a facial muscle indicative of a question without making sound, such that another individual cannot hear or see the underlying question. Determining the private request in an absence of such a perceptible vocalization is desirable to ensure that the request remains private such that other individuals do not hear the perceptible vocalization. For example, in public situations, the individual may simply make the prevocalization movements associated with a private request without actually making any sounds, so that others do not know that a request is even being made. In such situations determining the private request in an absence of perceptible vocalization of the private request may involve using any characteristic of the determined prevocalization muscle recruitment to identify the private request that does not rely on a perceptible vocalization, such as a distance moved by the prevocalization muscle. The determining may be performed based on a detection of an absence of such a perceptible vocalization via sensor input (e.g., an audio sensor such as a microphone) or by user input (e.g., a user pressing a button indicating an absence of a perceptible vocalization). For example, an audio sensor, such as audio sensor 414, may be used to capture sounds uttered by individual 102 to determine an absence of a perceptible vocalization by detecting when such sounds are not captured.

Answering the request may include any response, whether supplied by machine or human. The answer may be the provision of requested information, a comment, explanation, feedback, interpretation, report, result, acknowledgement, action, presentation, or other visual, audible, or tactile output. For example, answering the request may involve an audio output device through which an oral answer is provided to a private question. Such a speaker may be embodied in a headphone or earbud. As another example, answering the request may include a display device, such as a screen of a computer or mobile communications device, displaying sensitive information in response to a private query for that information. As another example, answering the request may include sending a text message in response to a private command. Answering the private request may require an identification of a specific individual associated with the specific facial skin micromovements to ensure that the sensitive information in the private request or in an answer to that private request is not divulged to anyone other than an individual with access to that sensitive information. For example, requiring an identification of an individual associated with the specific facial skin micromovements may ensure that personal details of that individual, such as medical information, are not revealed to someone else that uses the assistant.

An identification of a specific individual associated with the specific facial skin micromovements may include a facial skin micromovement print or pattern, some form of an identification of the individual, whether by name, government issued ID number (social security number, driver's license number, passport number, and/or other unique identifier. Additionally or alternatively, the identification may include one or more of a name, biographic data, address, affiliation, occupation, voice print, or other information associated with a specific individual. For example, the identification may involve a determination that the individual making the specific facial skin micromovements is Person A. As another example, the identification may involve a determination that the individual making the specific facial skin micromovements is not Person B. In the example shown in FIG. 36, answering the request 3618 may require an identification of a specific individual 3600 associated with the specific facial skin micromovements 3602. Similarly, answering the request 3620 may require an identification of a specific individual 3608 associated with the specific facial skin micromovements 3610. In the embodiment of FIG. 36, the identification is made, at least in part based on the detected facial skin micromovements of the individual. Like a fingerprint, each person has unique traits associated with their facial skin micromovements. Therefore, for example, an individual may be authenticated after subvocalizing (or vocalizing) one or more words. The facial skin micromovement patterns associated with those words may be compared with facial skin micromovement patterns associated with that individual, maintained in a data structure.

Some disclosed embodiments involve accessing a data structure maintaining correlations between the specific individual and a plurality of facial skin micromovements associated with the specific individual. A data structure may be understood as described and exemplified elsewhere in this disclosure. Correlations between the specific individual and a plurality of facial skin micromovements associated with the specific individual may include one or more of a connection, relationship, link, interaction, mutuality, causation, or other association between the specific individual and a plurality of facial skin micromovements associated with the specific individual. Maintaining correlations between the specific individual and a plurality of facial skin micromovements associated with the specific individual may involve maintaining a linked list, a look-up table, rules, or any other relationship between the specific individual and a plurality of facial skin micromovements associated with the specific individual. Accessing such a data structure may be desirable to provide reusability (i.e., can be accessed again after use) and abstraction (e.g., a mapping between rules and classifications that reduces the computational complexity of the task being considered) while performing the private voice assistance operations. This makes the private voice assistance operations, for example when implemented using AI, more efficient by reducing the time associated with the storage, retrieval, or processing of correlations between the specific individual and a plurality of facial skin micromovements associated with the specific individual, which may be used for identifying the specific individual. At the time an account is established or at some other time, words spoken or subvocalized by an individual may be noted in connection with the associated pattern of facial skin micromovements. Those correlations may be stored in a data structure as discussed elsewhere herein. At a subsequent time of a private request for assistance, a comparison of those same spoken or subvocalized words and their associated facial skin micromovements may be compared with the prestored correlations, as discussed in succeeding paragraphs. Examples of information a data structure may store to maintain these correlations related to micromovements include muscle movements (e.g., flexion, extension), characteristics of muscle movements (e.g., speed, distance moved, frequency of movement), type of muscles being moved (e.g., facial region of muscle, and muscles used for specific movements such as smiling). Examples of information a data structure may store to maintain these correlations related to the specific individual include the individual's identity, organization, location, association with or relationship to other individuals or organizations, and any other characteristics of the individual. Examples of maintaining these correlations include using tables, matrices, coefficients (e.g., correlation coefficient), and other techniques of associating data. For example, the private voice assistance operations may include accessing data structure 124 in FIG. 1 or data structure 422 in FIG. 4, which may be configured to maintain such correlations. As an example, data structure 124 or data structure 422 may include a record (e.g., a table entry) with a specific individual in one field and a specific facial micromovement associated with that individual in another field of the same record.

Some disclosed embodiments involve searching in the data structure for a match indicative of a correlation between a stored identity of the specific individual and the specific facial skin micromovements. Searching in the data structure for a match indicative of a correlation between a stored identity of the specific individual and the specific facial skin micromovements may involve any technique or structure for locating or determining the match. The match need not be precise. For example, the system may set thresholds of similarity, and if the threshold is met, a match is determined. Searching for a match may involve, for example, implementing one or more of a linear (i.e., sequential) search, a binary search, or any other search algorithm to locate a match between the stored identity and the micromovements. When using an AI assistant (or when AI is otherwise implemented in a portion of the voice assistance operations for specific functions), searching may involve any technique or structure for navigating from a starting state to a goal state by transitioning through intermediate states. In some AI implementations, searching may involve performing an uninformed (i.e., blind) search, such as a breadth first search, uniform cost search, depth first search, depth limited search, iterative deepening depth first search, or bidirectional search. In some AI implementations, searching may involve performing an informed (i.e., heuristic) search, such as a best first search, or an A*search. Implementing such iterative search algorithms to search for the match is desirable for improved completeness, optimality, time complexity, and space complexity.

A match indicative of a correlation between a stored identity of the specific individual and the specific facial skin micromovements may include any indication that a stored identity of a specific individual is associated with the specific facial micromovements, such as spatial and temporal statistics that are indicative of the individual, including the type of muscle causing the micromovements, the distance associated with the micromovements, the intensity of the micromovements, the speed of the micromovements, or other attributes of the micromovements. Such an association may include any characteristic linking the individual and the micromovements. For example, a match may include determining a specific individual associated with a first facial skin micromovement from a row of facial skin micromovements associated with that specific individual in a data structure. The match may be determined by analyzing a value, such as a difference, ratio, or other statistical value between signals associated with a detected micromovement and signals associated with stored micromovements. For example, a match may be determined when a cross-correlation between a signal associated with a detected micromovement and a signal associated with stored micromovements is below a predetermined threshold. When the voice assistance operations are implemented using AI, data matching (i.e., the process of finding the matching pieces of information in large sets of data) may be used to search for the match. Such data matching using AI is desirable to provide a powerful matching engine architecture built to leverage the learning capabilities of machine learning algorithms such as natural language processing, image similarity, linear combinators to match data on a deeper level beyond a simple matching of two items in a table. This type of matching may be used to learn a real relationship between the data a user considers a match and the data user does not consider a match, which improves processing efficiency by reducing any tweaking and adjustments that may be required over time. Such AI data matching engines may be trained using training data, such as information regarding various facial micromovements and an identification of those micromovements. In some examples, any data indicating a match between two micromovements may be used to train such AI data matching engines to detect a match.

Some disclosed embodiments involve, in response to a determination of an existence of the match in the data structure, initiating a first action responsive to the request, wherein the first action involves enabling access to information unique to the specific individual. Initiating a first action responsive to the request may involve starting, prompting, or performing a first process or operation for satisfying the request. Examples of initiating a first action responsive to the request may involve one or more of transmitting a signal, presenting a notification, presenting information to an answer, or enabling access. Enabling access may involve granting the specific individual the ability to read, write, modify, communicate, or otherwise make use of information. For example, enabling access may involve presenting previously obscured (or non-presented) information to the specific individual on a display or audibly through an output device such as a speaker in an ear bud or headphone. In some examples, enabling access may refer to cryptographically decrypting content, gaining access to content via password, or otherwise revealing previously hidden or obfuscated data or information, so that the specific individual can view, hear, or otherwise use the information. For example, enabling access may involve presenting a password screen on a display to the user for the user to enter a password and thereby view the information, which may be useful for ensuring data privacy for particularly sensitive information. Information unique to the specific individual may include any information that is distinctive, important, private, belonging to, connected to, or otherwise associated with the specific individual, such as log-in information, legal documents, identity verification, personal notes, bank records, and medical information. Once authentication is established, the private information may be automatically provided (through electronic transmission) to the individual making the private request. In other examples, when an assistant includes a human assistant (an agent) such as a call center operator, initiating a first action may include providing permission to the agent to provide private information. This may occur by presenting a permission notification on a display of the agent, or unlocking information for the agent to share privately.

In FIG. 36, in response to a determination of an existence of a match 3604 in the data structure, the assistant 3616 initiates a first action 3606 responsive to the request 3618, wherein the first action 3606 involves enabling access to information unique to the specific individual 3600. As an example, the first action 3606 may include displaying medical records of the specific individual 3600.

If the match is not identified in the data structure, some disclosed embodiments involve initiating a second action different from the first action. A second action different from the first action may refer to a denial to provide the private information, and/or the provision of information that is not private. The denial may include, for example, any notification (e.g., audible, visual, or tactile), step, movement, or other act that is distinct from the first action in at least one way to convey to the individual that access to the requested information or service is denied. For example, a first action may be the display of a note, while the second action may be the concealment of that note. As another example, a first action may be a visual notification on a phone, while the second action may be a tactile notification, such as a vibration, from a phone, perhaps in combination with transmitted text, that access is denied. In FIG. 36, if assistant 3616 determines no match 3612 in the data structure, assistant 3616 initiates a second action 3614 different from the first action 3606. Continuing from the previous example of the first action 3606 including displaying medical records of the specific individual 3600, the second action 3614 may include concealing those medical records from viewing by the other individual 3608 that is not the specific individual 3600, such as by blurring or blacking out the medical records.

Figure 37:
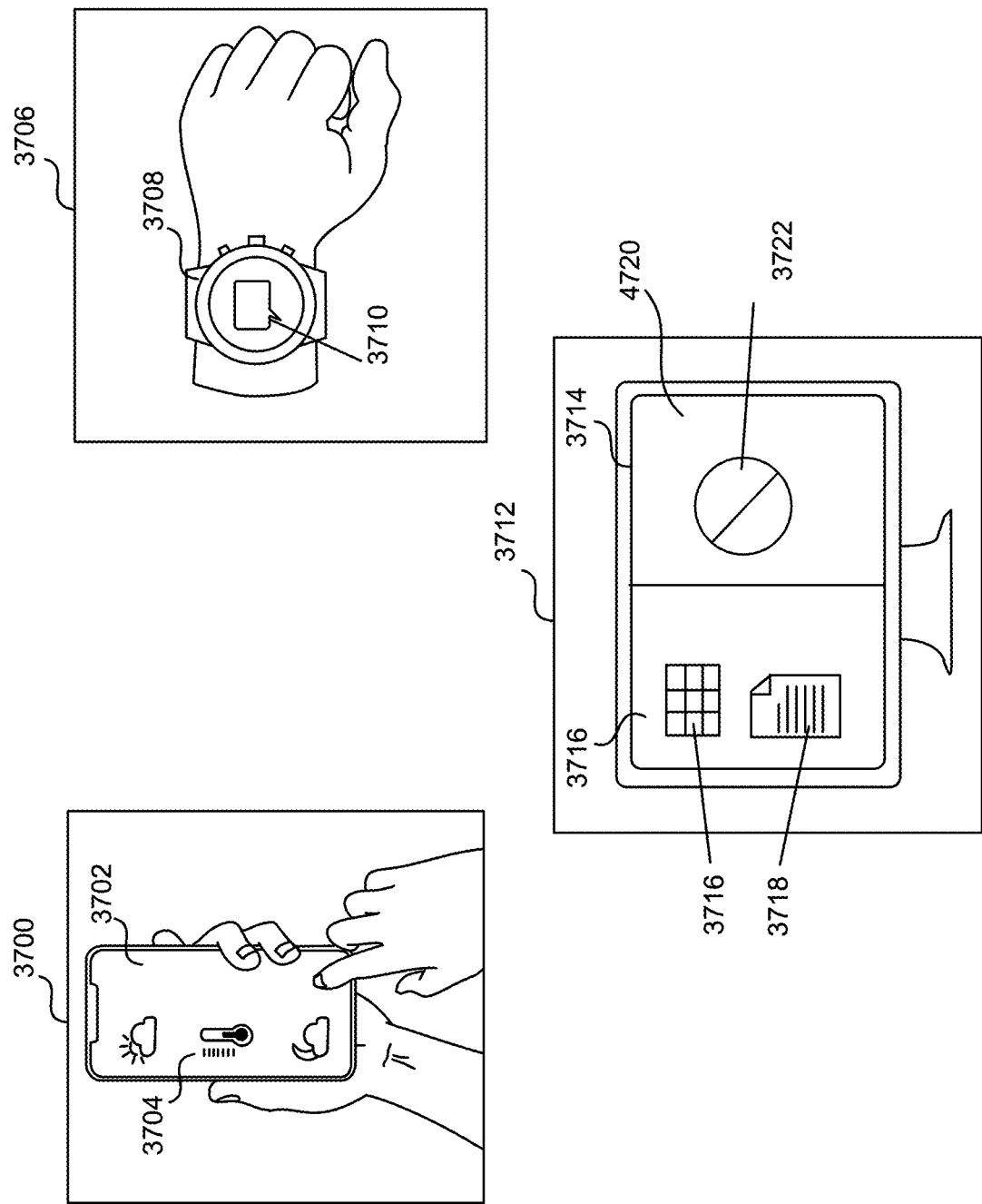
FIG. 37 illustrates examples of second actions initiated if a match is not identified in an exemplary data structure, consistent with embodiments of the present disclosure.

Consistent with some disclosed embodiments, the second action includes providing non-private information. Non-private information may include any information that is public, open, communal, unrestricted, accessible, shared, mutual, non-exclusive, or otherwise not unique or limited to access or modification by a specific individual. Examples of non-private information include news articles, published data, records maintained for public view by the government, census data, tax liens and judgments, criminal records, court records, and property information. One example of non-private information is publicly-accessible information, like the weather 3704 displayed on a phone 3702 shown in the first example 3700 of a second action in FIG. 37. Another example of non-private information is information that a group of individuals has access to. For example, the third example 3712 of a second action in FIG. 37 shows a computer screen 3714 with a non-private portion 33716 that displays a chart 3716 and document 3718 that the individual has access to may be based on the individual's occupation.

Consistent with some disclosed embodiments, the second action includes a notification that access is denied to information unique to the specific individual. A "notification" may include any visual, audible, or tactile indication that the individual is prohibited from access the information. Examples of such a notification include visual displays, sounds, vibrations, and web push notifications. For example, the second example 3706 of a second action in FIG. 37 shows a watch 3708 that displays a visual notification 3710 that access is denied to information unique to the specific individual. In some examples, the notification may be a message indicating that the access is denied. In some examples, the notification may be a graphic that represents a denied access, such as the symbol 3722 shown in private portion 3720 of computer screen 3714 in the third example 3712 of a second action in FIG. 37.

Consistent with some disclosed embodiments, the second action includes blocking access to the information unique to the specific individual. Blocking may involve stopping, pausing, obstructing, barring, deterring, halting, preventing, or otherwise hindering access to the information unique to the specific individual. In one example, the information unique to the specific individual may be displayed on a screen of a computer. In this example, the second action may include stopping the display of that information, such as by closing a document with the information or blacking out the screen. In another example, the second action may include obstructing the information from being viewed, such as by symbol 3722 shown in private portion 3720 of computer screen 3714 in the third example 3712 of a second action in FIG. 37.

Consistent with some disclosed embodiments, the second action includes attempting to authenticate the specific individual using additional data. Authentication may involve any process or action for determining or proving the identity of the specific individual. In some instances, there may be no match because the individual made a mistake while making the facial skin micromovements or signals from the facial skin micromovements were not sufficient to determine a match. In such instances, it may be desirable to attempt to authenticate the individual using additional data to ensure that the individual acquires access to information, such as in urgent situations, even though the match was not initially found. Accordingly, in some examples, authentication may also involve searching in the data structure for a match indicative of a correlation between a stored identity of the specific individual and the additional data. Additional data may include any data in addition to the detected facial skin micromovements. One example of additional data is a secret word, phrase, or sentence, which includes one or more words spoken by the individual without a perceptible vocalization associated with a word, phrase, or sentence that only a specific individual would know. By matching the individual based on the secret word, phrase, or sentence, the assistant may be enabled to perform the authentication with improved accuracy and speed. In some examples, the additional data may be more of the same type of data or other types of data.

Consistent with some disclosed embodiments, the additional data includes additional detected facial skin micromovements. Additional detected facial skin micromovements may include more data from the same muscles or data from other muscles on the face. For example, the detected facial skin micromovements may be from the zygomaticus major muscle. In this example, the additional data may include more detected facial skin micromovements from the same zygomaticus major muscle. Additionally or alternatively, the additional data may include detected facial skin micromovements from the orbicularis oris muscle. These additional facial skin micromovements may be detected in a continuous fashion during the span of the communication by the individual. Such continuous detection is desirable so that the assistant may keep detecting additional data to enable the detection of a match for the access of urgent information. For example, the additional facial skin micromovements may be detected at least once per second. In the example shown in FIG. 36, the additional data may include additional detected facial skin micromovements from an orbicularis oculi muscle 3626 of user 3600.

Consistent with some disclosed embodiments, the additional data includes data other than facial skin micromovements. Data other than facial skin micromovements may include other data from sensors or user input. For example, the additional data may include a user input, such as in the form of pressing a button, that the specific individual should be authenticated, a password or other code, other biometric information such as facial image recognition information or voice data, a fingerprint scan, or any other collected information such as a multifactor authentication. As another example, the additional data may include additional information regarding the activation of the user's facial muscles, such as EMG signals from electrodes 204 and 206 in FIG. 2. As another example, the additional data may include skin movements sensed from other areas of the face, such as eye movements, from optical sensing units 208 in FIG. 2. As another example, the additional data may include data sensed using image sensors, motion sensors, environmental sensors, EMG sensors, resistive sensors, ultrasonic sensors, proximity sensors, biometric sensors, or other sensing devices such as additional sensors 418 in FIG. 4. As another example, the additional data may include the individual making a vocal statement that is different from a statement associated with their subvocal facial skin micromovements. Using such a vocal statement in the authentication is desirable to indicate that the user does not intend to make that statement at that time, such as in situations of duress like being threatened to say that statement.

Some disclosed embodiments involve, when the match is not identified, initiating an additional action for identifying another individual other than the specific individual. Initiating such an additional action in these instances is desirable to provide the individual with an answer to their request when more than one individual has access to the private voice assistance operations or the assistant. For example, a family of different individuals may use the same virtual assistant in their home. In such situations, the assistant may need to initiate different actions for the different family members. For example, when a match is not identified because a first family member is no longer using the assistant, the assistant may initiate an additional action (such as receiving additional information) to identify a second family member in the same family so that the assistant can answer the requests of the second family member. An additional action may include any notification (e.g., audible, visual, or tactile), step, movement, or other act that is configured to aid in identifying another individual other than the specific individual. For example, an additional action may be a request for additional information or a notification that another identification is required. In this example, a request for additional information may be a visual prompt, such as a sentence or question, for more information on a display screen presented to the other individual. The request may include fields for the other individual to type in the requested information, or user interface elements such as buttons and checkboxes to provide the requested information.

In response to an identification of another individual other than the specific individual, some disclosed embodiments involve initiating a third action responsive to the request. A third action may include may refer to any notification (e.g., audible, visual, or tactile), step, movement, or other act associated with the identification of the other individual. The third action may be the same as or different from the first action and the second action. For example, in response to an identification of another individual other than the specific individual, the operations may include continuing the display of information presented to the specific individual in situations where the specific individual and the other individual share access to the displayed information or displaying the information to the other individual on the other individual's device (e.g., phone, computer, watch). As another example, in response to an identification of another individual other than the specific individual, the operations may include closing a document with private information of the specific individual. In an example including banking information, individual A and individual B may both be users of private voice assistance operations. In this example, individual A (who does not have access to individual B's banking information) may privately request a bank balance associated with individual B. The private voice assistance operations may determine that there is no match identified in the data structure indicative of a correlation between individual A's identity and individual B's facial skin micromovements. The private voice assistance operations may then present on individual B's phone, a notification that individual A requests individual B's bank balance. Individual B may make a private request to provide the bank balance and the private voice assistance operations may determine that there is a match identified in the data structure indicative of a correlation between individual A's identity and individual A's facial skin micromovements. In response to this determined match, the private voice assistance operations may display on the phone of individual A or individual B, the requested bank balance.

Consistent with some disclosed embodiments, the third action involves enabling access to information unique to the other individual. Enabling access may be understood as described and exemplified elsewhere in this disclosure. Information unique to the other individual may include any information that is distinctive, important, private, belonging to, connected to, or otherwise associated with the other individual, such as log-in information, legal documents, identity verification, personal notes, bank records, and medical information. For example, the third action may involve playing individual A's private audio recordings from a phone of individual B.

Consistent with some disclosed embodiments, the private request is for activating software code, the first action is activating the software code, and the second action is preventing activation of the software code. Software code may include any instructions, rules, or data that are executable by a computing device or processor. Activating software code may involve initiating, starting, authenticating, or otherwise allowing execution of software code. Preventing activation of the software code may involve blocking, halting, hindering, delaying, inhibiting, prohibiting, restricting, or otherwise stopping the execution of the software code. For example, the private request may be a command to send automatic response to emails, and the first action may be sending the automatic responses to emails, while the second action may be preventing further automatic responses to emails from being sent. As another example, the private request may be a command to execute a smart contract (i.e., one or more programs stored on a blockchain configured to run when predetermined conditions are met), and the first action may be execute the smart contract, while the second action may prevent the smart contract from being executed, such as by not executing the smart contract or by requiring a password for execution of the smart contract. In the example shown in FIG. 37, the private request may be a command to execute smart contract 3718, which may be run in response to a determined match 3604 as the first action 3606.

Consistent with some disclosed embodiments, the private request is for confidential information, and the operations further include determining that the specific individual has permission to access the confidential information. Confidential information may include any information about an individual that is not freely available to the public. By way of example, confidential information may include a social security number, medical records, credit card numbers, or trade secrets. Determining that the specific individual has permission to access the confidential information may involve any technique for associating an identified specific individual with a permission to access the confidential information. For example, the assistant may access a database containing permissions associated with certain individuals to determine whether the specific individual has permission to access the confidential information. As another example, an AI assistant may use a search algorithm to determine whether the specific individual has permission to access the confidential information. In one example, there may be two users, individuals A and B, of the private voice assistance operations, and one of them may make a private request for a blood test report. The operations may determine whether individual A has permission to access the blood test report (e.g., by using an AI search algorithm trained using previous access request results) and provide the report to individual A (e.g., displaying the report on individual A's computer) because A has permission. But if individual B attempts to access the information, the system may determine that B does not have permission and prohibit blood test report from going to B.

Consistent with some disclosed embodiments, receiving, accessing, and searching occur repeatedly during an ongoing session. Receiving, accessing, and searching may be understood as described earlier. An ongoing session may refer to continuous or intermittent period of time in which an individual uses the private voice assistance operations. For example, an ongoing session may be a day, period of continuous minutes, or collection of intermittent hours during which the individual is using the private voice assistance operations, such as by making private requests or by wearing the integrated wearable housing. Performing these functions repeatedly during an ongoing session may involve performing the functions at regular or irregular intervals at least more than once. For example, receiving, accessing, and searching occurring repeatedly during an ongoing session may involve performing these functions every second while the individual is making private requests in a day. As another example, receiving, accessing, and searching occurring repeatedly during an ongoing session may involve performing these functions every ten minutes while the individual is wearing the integrated wearable housing. Whether continuous, regular, or intermittent, the repetition can help to ensure that the authorized individual is the only one receiving the information. If an authenticating ear bud (or other sensing system) is disassociated with authorized individual and associated with an unauthorized individual, the repetitious checking should identify the imposter and cease provision of private information.

Consistent with some disclosed embodiments, in a first time period during the ongoing session the specific individual is identified and the first action is initiated, and wherein in a second time period during the ongoing session, the specific individual is not identified, and any residual first action is terminated in favor of the second action. A first time period refers to any continuous or intermittent length of time during the ongoing session. A second time period refers to any continuous or intermittent length of time during the ongoing session that is different from the first time period, such as a time period after the first time period. For example, a first individual 3600 may use the voice assistance operations via assistant 3616 during an ongoing session of one day, for a first time period of six hours during that day. During the six hours, the first individual 3600 is identified by assistant 3616 as the specific individual through a detected match 3604 and a first action 3606 is initiated, such as the display of private medical records. In this example, the first individual 3600 may stop using the voice assistance operations via assistant 3616 after the first time period of six hours and a second individual 3608 may use the voice assistance operations via assistant 3616 during an ongoing session of one day, for a second time period of four hours during that day following the first time period. During this second time period, the first individual 3600 is no longer identified by assistant 3616 as the specific individual because of no detected match 3612, and any residual first action 3606 is terminated in favor of the second action 3614. Terminating a residual first action in favor of the second action refers to stopping, pausing, hiding, obscuring, obstructing, or otherwise modifying the first action in a manner which allows for the second action to be initiated. Examples of terminating a residual first action in favor of the second action include replacing a notification with another notification, slowing down a first process and introducing a second process, or changing a type of notification (e.g., from a visual notification to an audible notification). Continuing from the previous example, when the first individual 3600 is no longer identified by assistant 3616 as the specific individual because of no detected match 3612, the first action of displaying the private medical records 3606 may be stopped in favor of the second action of displaying a blank screen 3614. As another example, the first action of displaying the private medical records 3606 may be replaced by favor of the second action of displaying public records 3614.

Figure 38:
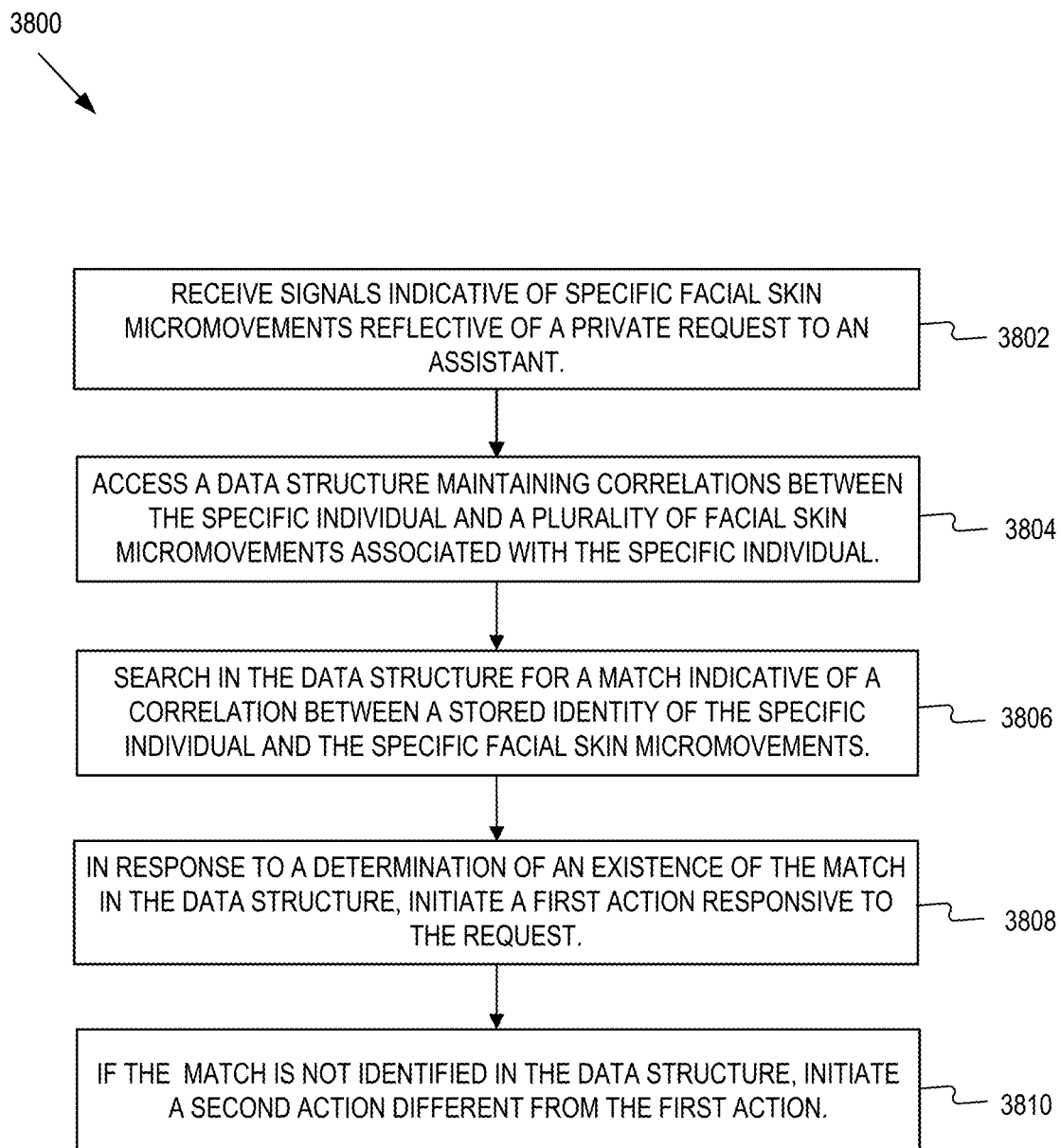
FIG. 38 illustrates a flowchart of an example process for performing private voice assistance operations, consistent with embodiments of the present disclosure.

Some disclosed embodiments involve a method for operating a private voice assistant. FIG. 38 illustrates a flowchart of an exemplary process 3800 for performing private voice assistance operations, consistent with embodiments of the present disclosure. In some embodiments, process 3800 may be performed by at least one processor (e.g., processing unit 112 in FIG. 1, processing device 400 in FIG. 4, or assistant 3616 in FIG. 36) to perform operations or functions described herein. In some embodiments, some aspects of process 3800 may be implemented as software (e.g., program codes or instructions) that are stored in a memory (e.g., data structure 124 in FIG. 1) or a non-transitory computer readable medium. In some embodiments, some aspects of process 3800 may be implemented as hardware (e.g., a specific-purpose circuit). In some embodiments, process 3800 may be implemented as a combination of software and hardware.

Referring to FIG. 38, process 3800 includes a step 3802 of receiving signals indicative of specific facial skin micromovements reflective of a private request to an assistant, wherein answering the private request requires an identification of a specific individual associated with the specific facial skin micromovements. Process 3800 includes a step 3804 of accessing a data structure maintaining correlations between the specific individual and a plurality of facial skin micromovements associated with the specific individual. Process 3800 includes a step 3806 of searching in the data structure for a match indicative of a correlation between a stored identity of the specific individual and the specific facial skin micromovements. Process 3800 includes a step 3808 of in response to a determination of an existence of the match in the data structure, initiating a first action responsive to the request, wherein the first action involves enabling access to information unique to the specific individual. Process 3800 includes a step 3810 of if the match is not identified in the data structure, initiating a second action different from the first action.

Some disclosed embodiments involve a system for operating a private voice assistant, the system comprising: at least one processor configured to: receive signals indicative of specific facial skin micromovements reflective of a private request to an assistant, wherein answering the private request requires an identification of a specific individual associated with the specific facial skin micromovements; access a data structure maintaining correlations between the specific individual and a plurality of facial skin micromovements associated with the specific individual; search in the data structure for a match indicative of a correlation between a stored identity of the specific individual and the specific facial skin micromovements; in response to a determination of an existence of the match in the data structure, initiate a first action responsive to the request, wherein the first action involves enabling access to information unique to the specific individual; and if the match is not identified in the data structure, initiate a second action different from the first action.

The embodiments discussed above for performing private voice assistance operations may be implemented through non-transitory computer-readable medium such as software (e.g., as operations executed through code), as methods (e.g., process 3800 shown in FIG. 38), or as a system (e.g., speech detection system 100 shown in FIGS. 1-3). When the embodiments are implemented as a system, the operations may be executed by at least one processor (e.g., processing device 400 or processing device 460, shown in FIG. 4).

The ability to speak and produce sounds is a uniquely human ability that has evolved over many years, and it is a testament to the remarkable complexity and adaptability of the human vocal system. The process of speaking involves the activation and the coordinated control of dozens of muscles, making it a highly complex and demanding task for the human body. Pronouncing a single phoneme may require a specific combination of facial muscle movements and air flow, and the precise timing and coordination of these movements. For example, when producing the phoneme "oo," the lips are rounded and pushed forward. Specifically, the pronunciation of the phoneme "oo" may involve the contraction of the orbicularis oris muscle, which is the circular muscle around the mouth responsible for puckering the lips; recruitment of the genioglossus muscle, which is the large muscle that runs from the chin to the base of the tongue and responsible for retracting and elevating the tongue; and recruitment of the velum muscle, which is located in the soft palate at the back of the mouth.

As discussed above, facial skin micromovements related to speech-related activity, such as articulating a single phoneme, may be detected during subvocalization (i.e., without utterance of the phoneme, before utterance of the phoneme, or preceding an imperceptible utterance of the phoneme). Consistent with the present disclosure, some disclosed embodiments may be configured to detect facial skin micromovements of an individual from multiple areas of the facial region, and to use the detected facial skin micromovements to determine subvocalized phonemes.

Figure 39:
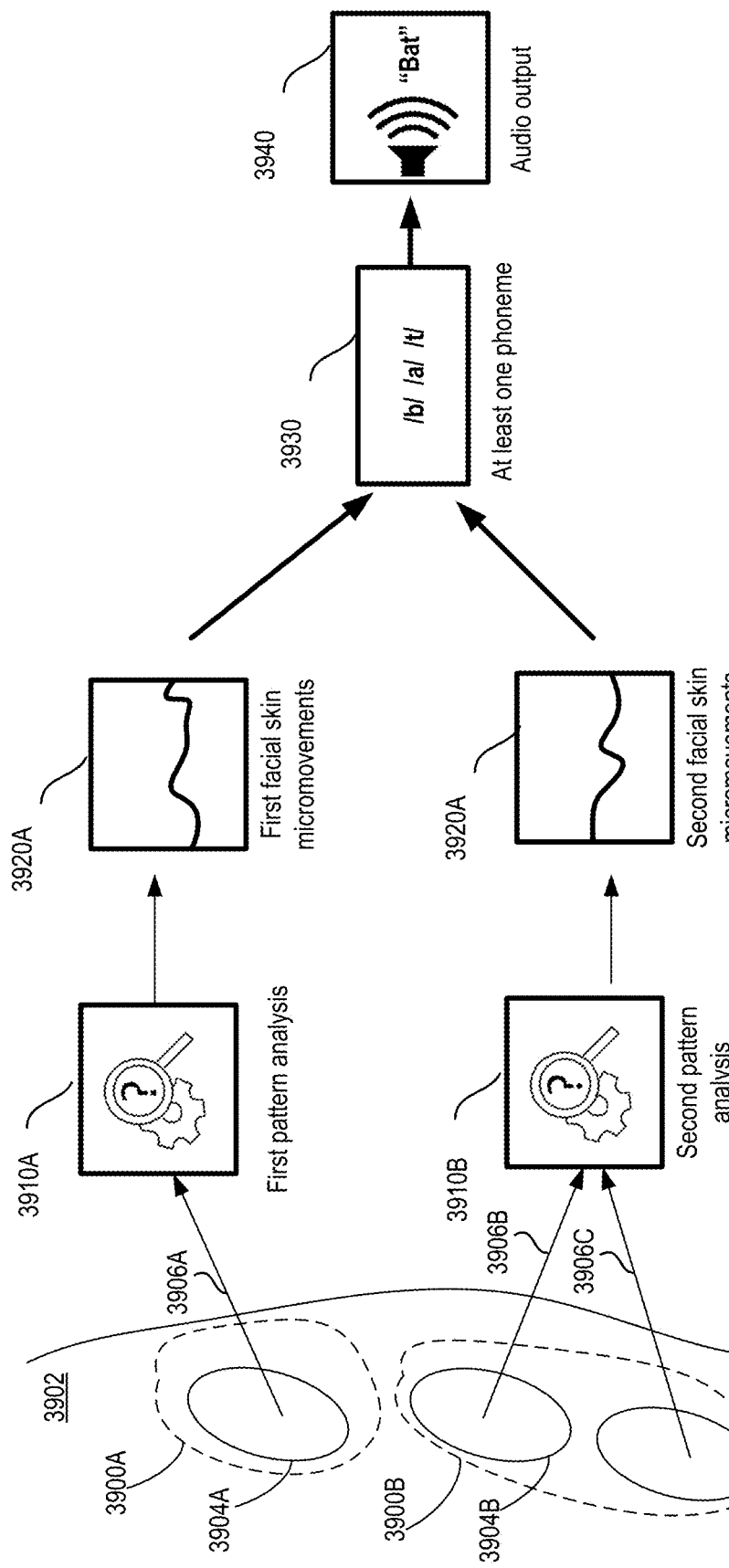
FIG. 39 is an exemplary diagram illustrating how different areas of facial skin are used to detect subvocalized phonemes, consistent with some embodiments of the present disclosure.
Figure 40:
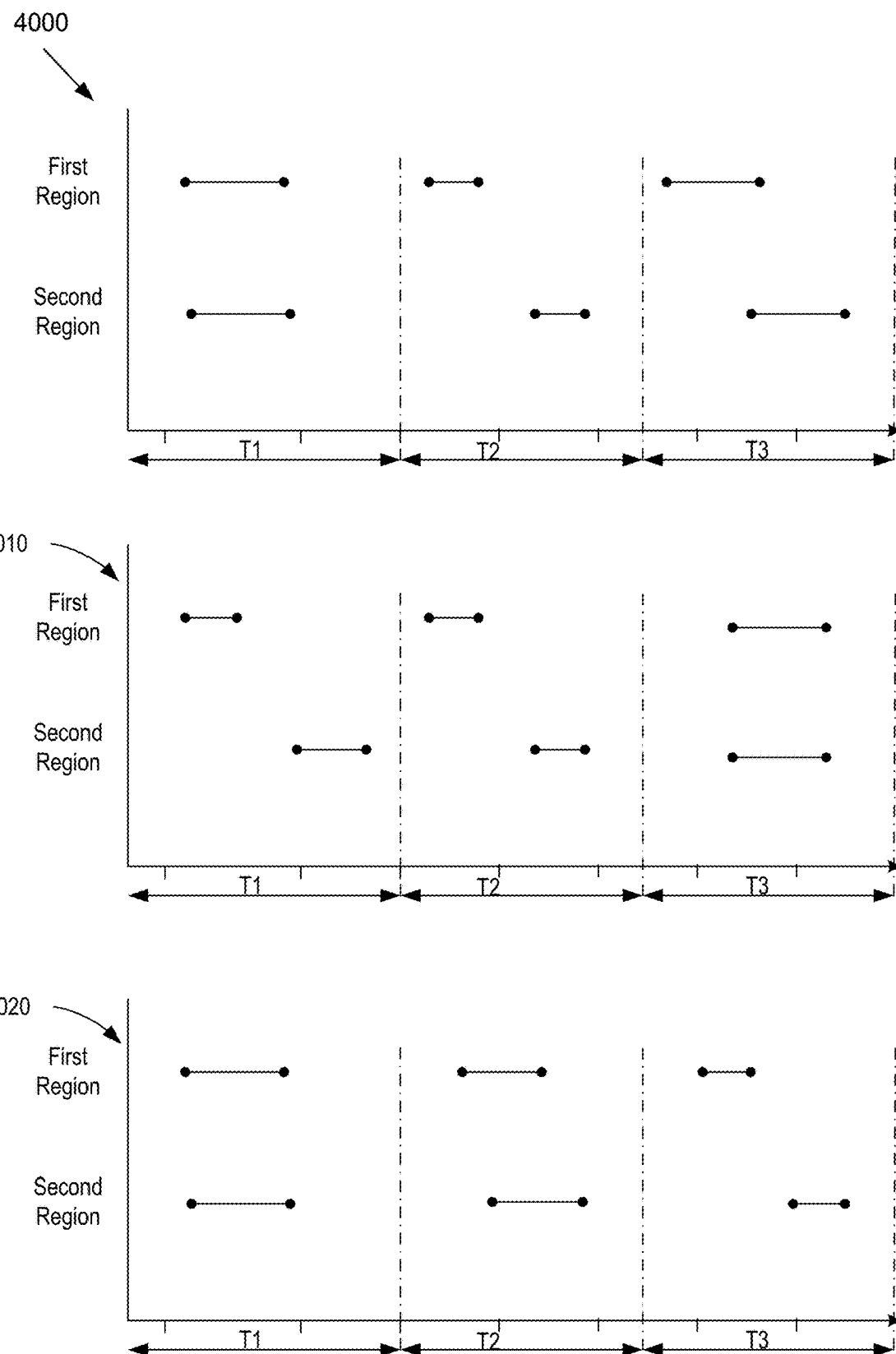
FIG. 40 illustrates three graphs depicting exemplary alternative timings for completing a process that involves detecting subvocalized phonemes, consistent with embodiments of the present disclosure.
Figure 41:
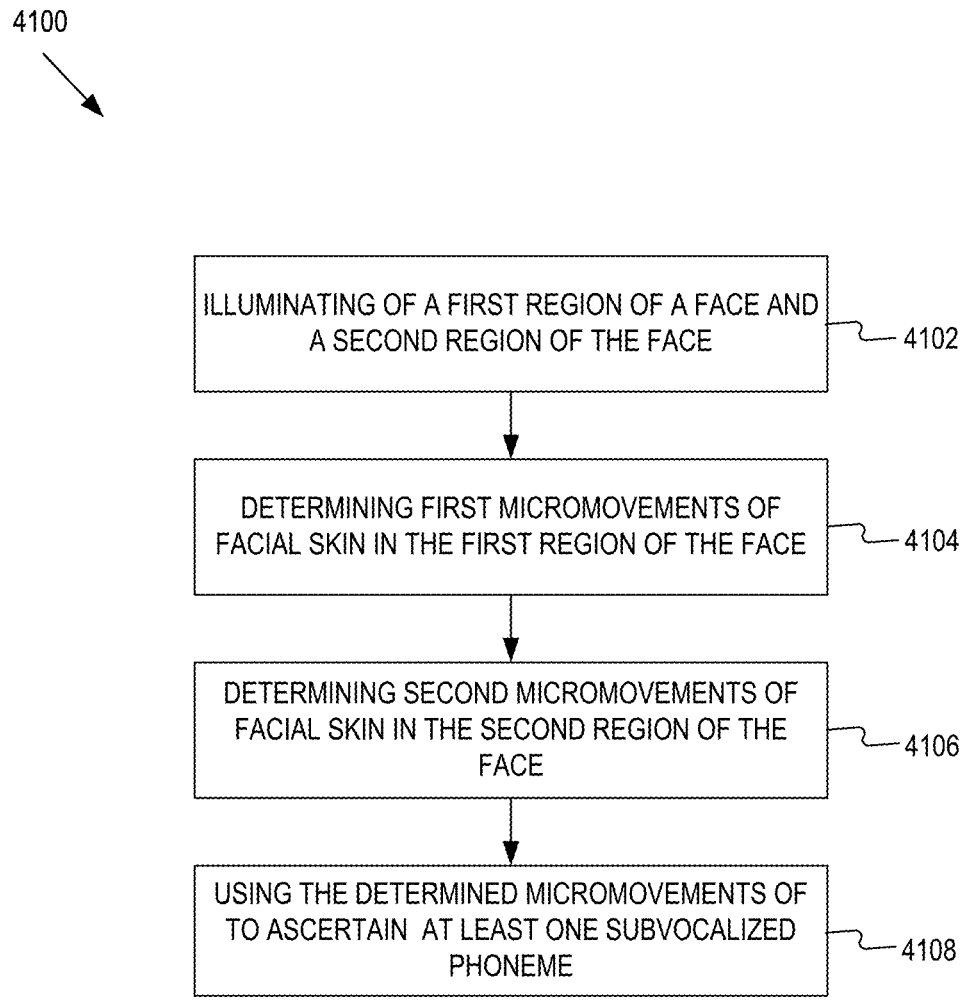
FIG. 41 is a flowchart of an example process determining subvocalized phonemes from facial skin micromovements, consistent with embodiments of the present disclosure.

The description that follows may refer to FIGS. 39 to 41 to illustrate exemplary implementations for determining subvocalized phonemes, consistent with some disclosed embodiments. FIGS. 39 to 41 are intended merely to facilitate conceptualization of exemplary implementations for performing operations to determine subvocalized phonemes and do not intend to limit the disclosure to any particular implementation.

Some disclosed embodiments involve a system, a method and/or a non-transitory computer-readable medium containing instructions that when executed by at least one processor cause the at least one processor to perform operations. The phrases "non-transitory computer-readable medium," "method," "system" and "at least one processor," should be interpreted as discussed elsewhere in this disclosure.

Some disclosed embodiments involve determining subvocalized phonemes from facial skin micromovements. The term "phoneme" refers to a unit of sound within a language distinguishing one element from another. Typically, there are more sounds than there are letters in a given language. For example, in the English alphabet, there are 26 letters and 44 phonemes. The 44 phonemes of the English alphabet can be divided up into two groups: there are 20 vowel sounds (e.g., /a/, /e/, /ai/, /ee/, /ue/) and 24 consonant sounds (e.g., /b/, /f/, /ch/, /ge/, /z/). The term "subvocalized phonemes" refers to a representation of a phoneme (i.e., unit of sound) detected without the phoneme being uttered, before the phoneme is uttered, or preceding an imperceptible utterance of the phoneme. The subvocalized phonemes may be determined by identifying prevocalization facial skin micromovements (i.e., prior to an onset of vocalization of the phoneme). In some cases, the prevocalization facial skin micromovements may be triggered by voluntary or involuntary muscle recruitments that occur when certain craniofacial muscles are instructed to vocalize phonemes. These facial skin micromovements are detectable as described elsewhere in this disclosure.

Some disclosed embodiments involve controlling at least one coherent light source in a manner enabling illumination of a first region of a face and a second region of the face. The term "coherent light source" may be understood as described elsewhere in this disclosure. Controlling at least one coherent light may include regulating, supervising, instructing, allowing, and/or enabling the at least one coherent light source to illuminate at least part of an object. For example, the coherent light source may be controlled to illuminate a region of a face when turned on in response to a trigger. The term "region of a face" refers to a portion or an area of any size or any shape of an anatomical feature of the face, such as: forehead, eyes, cheeks, ears, nose, mouth, chin, and neck. For example, the shape of a region of a face may be round, square, line of any other two- or three-dimensional shape; and the size of the region of the face may be less than 20 $cm^2$, less than 10 $cm^2$, less than 5 $cm^2$, less than 1 $cm^2$, or any other size. Enabling Illumination of a region of a face may include providing at least one coherent light source configured to be aimed at the region of the face. This may occur, for example, through the provision of a device that is configured to be pre-aimed when in use, or that is adjustable for aiming at the region of the face when in use. Consistent with some disclosed embodiments, the first region is spaced apart from the second region. The term "spaced apart" may refer to being non-overlapping or separated by a predetermined distance. Thus spaced apart regions of the face may refer to two or more regions of the face that do not overlap with each other and that are separated from each other by a predetermined distance. For example, stating that the first region is spaced apart from the second region may include distances between the first and second region of less than 1 mm, at least 1 mm, at least 2 mm, at least 3 mm, at least 4 mm, at least, 5 mm, at least 10 mm, at least 15 mm, or any other desired distance. By way of one example, light source 410 in FIG. 4 is employed to illuminate a first region of a face and a second region of the face. As discussed below, FIG. 39 illustrates an example of two spaced apart regions.

In some disclosed embodiments, controlling the at least one coherent light source may include projecting differing light patterns on the first region and the second region. The term "light pattern" may refer to a formation of electromagnetic waves (e.g., in the visible or invisible spectrum) projected from the light source. The formation may have spatial-based structuring associated with geometric shapes. For example, the geometric shapes may include a spot, a line, a circle, an oval, a square, a rectangle, or any other shape, such as strips, spots, or dots. Moreover, the formation may have time-based structuring, such as repetitive illumination pattern. The light pattern may be associated with a combination of various light characteristics of the light illuminating a region of the face. The light characteristic may include, for example, wavelength, color temperatures, intensity, luminance, luminous energy, luminous flux, luminous intensity, number of illuminated areas within a region, or any other light characteristic. Any of these light characteristics may vary across the geometric shape. For example, a light spot may have an intensity that is greater at its center than at its periphery. In some embodiments, one or more variations in light characteristics may aid in determining facial skin micromovements. Projecting differing light patterns may include causing distinct formations of electromagnetic waves to be incident on a surface, e.g., different regions of the facial skin. For example, the distinct formations may include differing types of formation or a same type of formation but at differing locations. In some disclosed embodiments, the differing light patterns may include a plurality of light spots, such that the first region of the face is illuminated by at least a first light spot and the second region of the face is illuminated by at least a second light spot, different from the first light spot. The term "plurality of spots" refers to more than one area of illumination. The number of spots in the plurality of spots may range from two to 64 or more. For example, the plurality of spots may include 4 spots, 8 spots, 16 spots, 32 spots, 64 spots, or any number of spots greater than two. There may be variations in illumination characteristics between spots or within spots, as discussed earlier. In some cases, each of the first region and the second region may be defined by a single light spot. Alternatively, each of the first region and the second region may contain a plurality of spots (e.g., two, three, or more).

By way of one example with reference to FIG. 39, at least one coherent light source (e.g., light source 410—not shown) may illuminate a first region 3900A of a face 3902 and a second region 3900B of face 3902. As shown, first region 3900A is illuminated by a single light spot (i.e., light spot 3904A) while second region 3900B is illuminated by a plurality of light spots (i.e., light spots 3904B and 3904C). In some disclosed embodiments, both first region 3900A and second region 3900B may be part of an area of the face (e.g., the cheek) that is useful in sensing the user's speech. In a first example, both first region 3900A and second region 3900B may be associated with the zygomaticus muscle, which exhibits small movements, with a velocity on the order of one to ten μm/ms, due to silent speech. In a second example, both first region 3900A and second region 3900B may be associated with the risorius muscle which exhibits much larger movements, on the order of 0.5-2 mm, during typical voiced ("loud") speech containing substantial motion. In a third example, first region 3900A may be associated with the zygomaticus muscle, and second region 3900B may be associated with the risorius muscle.

In some disclosed embodiments, controlling the at least one coherent light source includes illuminating the first region and the second region with a common light spot. For example, a single (common) light spot may cover some or all of the first region and the second region. The common light spot may illuminate at least a portion of the first region and the second region. In one example, the common light spot may illuminate 30% of the first region and 10% of the second region. In another example, the common light spot may illuminate 100% of the first region and 100% of the second region. Controlling the at least one coherent light source may include illuminating a continuous area on the face that includes the first region and the second region. By way of one example, as illustrated in FIG. 3 a single spot may illuminate two or more facial regions 108.

Some disclosed embodiments involve performing first pattern analysis on light reflected from the first region of the face to determine first micromovements of facial skin in the first region of the face, and performing second pattern analysis on light reflected from the second region of the face to determine second micromovements of facial skin in the second region of the face. The term "pattern analysis on light reflected" refers to evaluation of light scattered from a surface as described elsewhere in this disclosure. Through the pattern analysis, it is possible to ascertain properties of a surface from which the light is reflected. Depending on implementation, performing a pattern analysis on light reflected from a region of the face may include detecting speckle patterns or any other patterns in reflection signals received via a light detector (e.g., light detector 412) configured to measure light reflected from said region. For example, performing the pattern analysis may include extracting quantitative features indicative of the instantaneous velocity of motion of the skin in the examined region (e.g., the first region of the face and the second region of the face). In some disclosed embodiments, vectors of the extracted quantitative features may be inputted to a neural network in order to determine the micromovements of facial skin in the examined region of the face. For example, one of the features that can be extracted for the purpose of micromovements determination may be speckle contrast. Any suitable measure of contrast may be used for this purpose, for example, the mean square value of the luminance gradient taken over the area of the speckle pattern. The contrast may decrease with increasing velocity of motion. Additionally or alternatively, other features may be extracted from the reflection image and may be processed. Examples of such features may include total brightness of the speckle pattern and/or orientation of the speckle pattern, for instance as computed by a Sobel filter. The result of the pattern analysis may include reflection image data, from which micromovements of facial skin in a region of the face may be determined. The term "micromovements of facial skin" also referred to herein as "facial skin micromovements," is described and exemplified elsewhere in this disclosure. Depending on implementation, separated pattern analyses may be performed for different regions of the face that results in different facial skin micromovements for each region of the face.

In some disclosed embodiments, the determined first micromovements of facial skin in the first region of the face may correspond to recruitment of a first muscle selected from: a zygomaticus muscle, an orbicularis oris muscle, a risorius muscle, or a levator labii superioris alaeque nasi muscle, and the determined second micromovements of facial skin in the second region of the face may correspond to recruitment of a second muscle, different from the first muscle, selected from: the zygomaticus muscle, the orbicularis oris muscle, the risorius muscle, or the levator labii superioris alaeque nasi muscle. In this context, a micromovement of facial skin corresponding to recruitment of a certain muscle may refer to activation of that certain muscle. When the muscle is recruited, it causes a facial skin micromovement. As mentioned above, the first micromovements and the second micromovements may correspond to different muscles. For example, both the first micromovements and the second micromovements may be associated with a same facial muscle or muscle group. As one example, both the first micromovements and the second micromovements may correspond to recruitment of the same muscle (e.g., the orbicularis oris) or recruitment of muscles from the same muscle group (e.g., oral group). Alternatively, the first micromovements and the second micromovements may be associated with recruitment of muscles from differing facial muscles or recruitment of muscles from differing muscle groups. For example, the first micromovements may correspond to recruitment of a first muscle (e.g., the orbicularis oris) or recruitment of muscles from a first muscle group (e.g., the oral group), and the second micromovements may correspond to recruitment of a second muscle (e.g., the buccinator) or recruitment of muscles from a second muscle group (e.g., the nasal group).

By way of one example, with reference to FIG. 39, the at least one processor may perform first pattern analysis 3910A from light reflected from first region 3900A (i.e., light 3906A reflected from light spot 3904A). The result of first pattern analysis 3910A may include reflection image data used to determine first facial skin micromovements 3920A. Additionally, the at least one processor may perform second pattern analysis 3910B from light reflected from second region 3900B (i.e., light 3906B reflected from light spot 3904B and/or light 3906C reflected from light spot 3904C). The result of second pattern analysis 3910B may include reflection image data used to determine second facial skin micromovements 3920B. In some cases, the determination may be that no facial skin micromovements had occurred either in first region 3900A or in second region 3900B.

Consistent with some disclosed embodiments, the performance of the second pattern analysis may occur after performing the first pattern analysis. The term "occur," with regard to the performance of a pattern analysis, implies that the pattern analysis took place or happened at a certain time. For example, it means that at least some the steps involved in the pattern analysis are executed, leading to a determination of the facial micromovements. For example, performance of the second pattern analysis may occur less than 10 milliseconds, less than 5 milliseconds, less than 1 millisecond, or any duration of time after performing the first pattern analysis. Additional details and examples are discussed below with reference to FIG. 40.

In some disclosed embodiments the performance of the second pattern analysis occurs simultaneously with performance of the first pattern analysis. In this context, the term "simultaneously" may refer to the two pattern analyses occurring during coincident or overlapping time periods, either where one begins and ends during the duration of the other, or where a later one starts before the completion of the other. In some cases, simultaneously executing the first and second pattern analysis involve dividing a pattern analysis into sub-tasks that can be executed simultaneously by different parts of the at least one processor or by different processors altogether. In order to perform the second pattern analysis simultaneously with performance of the first pattern analysis, the at least one processor may include a multi-core processor that may allow multiple pattern analysis to be executed concurrently. Alternatively, the at least one processor may include a single processor capable of multi-thread operations with the first and second pattern analysis occurring in different computational threads.

In some disclosed embodiments, the first micromovements of the facial skin and the second micromovements of the facial skin may correspond to concurrent muscle recruitments. In this context, the term "concurrent muscle recruitments" means that the muscle recruitments responsible for first and second micromovements of the facial skin occur during coincident or overlapping time periods, either where one begins and ends during the duration of the other, or where a later one starts before the completion of the other. For example, the first micromovements of the facial skin and the second micromovements of the facial skin may correspond to recruitment of the same muscle at the same time. The micromovements may be different because the facial skin in each region is associated with different location of the muscle. Additional details and examples are discussed below with reference to FIG. 40.

Some disclosed embodiments involve determining both the first micromovements and the second micromovements during a common time period. In this context, the term "common time period" may refer to a shared time frame during which certain activities (e.g., determination of micromovements) take place. For example, the common time period in which both the first micromovements and the second micromovements are determined may be less than a second, less than 100 milliseconds, less than 10 milliseconds, less than 1 millisecond, or any other time period. Additional details and examples are discussed below with reference to FIG. 40.

FIG. 40 illustrates three graphs depicting alternative timings for completing a process for detecting subvocalized phonemes. Each graph includes three time periods. The first time period represents a time period in which the first and the second light reflections are received via the at least one detector. The second time period represents a time period in which the first and the second pattern analysis are performed by the at least one processor. The third time period represents a time period in which the first and the second facial skin micromovements are determined. Consistent with the present disclosure, the third time period may be finished before the at least one phoneme is vocalized. In the first scenario, illustrated in first graph 4000, the first and second light reflections are received together (i.e., the first and second facial skin micromovements occurred at the same time), the performance of the first pattern analysis is completed before the performance of the second pattern analysis starts, and the determination of the first micromovements and the second micromovements occurs concurrently (i.e., the process of determining the second micromovements starts before the process of determining the first micromovements ends). In the second scenario, illustrated in second graph 4010, the first light reflections received before the second light reflections (i.e., the first facial skin micromovements occurred before the second skin micromovements), the performance of the first pattern analysis is completed before the performance of the second pattern analysis starts, and the determination of the first micromovements and the second micromovements occurs at the same time. In the third scenario, illustrated in third graph 4020, the first and second light reflections are received together, the performance of the first pattern analysis and the second pattern analysis occurs concurrently (i.e., the performance of the second pattern analysis starts before the performance of the first pattern analysis ends, and the process of determining the first micromovements ends before the process of determining the second micromovements also occurs. The timings of the performances of the pattern analyses and the determinations of the micromovements by the at least one processor may be determined by a load balancing module (e.g., load balancing module 474) configured to divide the workload among one or more computational nodes of the at least one processor.

Some disclosed embodiments involve using the first micromovements of the facial skin in the first region of the face and the second micromovements of the facial skin in the second region of the face to ascertain at least one subvocalized phoneme. The term "ascertaining" may refer to determining, establishing, or arriving at a conclusive outcome as a result of a reasoned, learned, calculated, or logical process. In this case, the result of the process is a determination of at least one subvocalized phoneme (i.e., the at least one unit of sound that took place during subvocalization). The term "subvocalized phoneme" may be understood as discussed elsewhere in this disclosure. The term "using micromovements to ascertain a subvocalized phoneme" generally means utilizing one or more variables or parameters associated with the micromovements to calculate or determine a particular result. In this case, the result is at least one subvocalized phoneme. For example, the subvocalized phoneme /ch/ may be determined using a first facial skin micromovement that corresponds with a recruitment of the levator labii superioris muscle and a second skin micromovement that corresponds with a recruitment of the orbicularis oris muscle. As disclosed, the process of ascertaining the at least one subvocalized phoneme may involve using the determined micromovements of the facial skin in at least two regions of the face. In a first example use case, the at least one ascertained phoneme may be detected without the phoneme being uttered. This use case relates to an individual engaging in silent speech (i.e., when air flow from the lungs is absent but the facial muscles articulate the desired at least one phoneme). In a second example use case, the at least one ascertained phoneme may be detected before the at least one phoneme is uttered. In this use case, the detected facial skin micromovements are triggered by facial muscle recruitments that occur between, for example, 0.1 seconds to 0.5 seconds before the actual vocalization of the at least one phoneme. In some cases, the at least one processor may use the detected facial skin micromovements that occur during subvocalization to determine the at least one phoneme that is about to be vocalized. In a third example use case, the at least one ascertained phoneme may be detected preceding an imperceptible utterance of the phoneme (i.e., when some air flow from the lungs, but words are articulated in a manner that is not perceptible using an audio sensor).

In some disclosed embodiments, ascertaining the at least one subvocalized phoneme may include ascertaining a sequence of phonemes, and wherein the operations further include extracting meaning from the sequence of phonemes. The term "sequence of phonemes" may include a series of individual speech units that are strung together to create words and/or sentences. For example, the sequence of the three phonemes: /b/ /a/ /t/ forms the word "bat." In one example, each phoneme in the sequence of phonemes may be derived from pattern analysis of at least two regions of the face. For example, the speech detection system may monitor many different regions of the face (e.g., regions A, B, C, D, E, F, G, H, I, and J) and each phoneme in the sequence of phonemes may be derived from analyzing light reflected from the two or more regions. For example, the phoneme /b/ may be derived from light reflected from region A and region B, the phoneme /a/ may be derived from light reflected from region A and region D, and the phoneme /t/ may be derived from light reflected from region F and region G. In some disclosed embodiments, each phoneme in the sequence of phonemes is derived from the first pattern analysis and the second pattern analysis. In other words, phonemes in the sequence of phonemes may be ascertained from light reflected from the first and second regions of the face. For example, the phoneme /b/ may be derived from light reflected from region A and region B, the phoneme /a/ may be derived from light reflected from region A and region B, and the phoneme /t/ may also be derived from light reflected from region A and region B.

By way of example with reference to FIG. 39, the at least one processor may use first facial skin micromovements 3920A and second facial skin micromovements 3920B to ascertain at least one subvocalized phoneme 3930. In the illustrated example, the at least one subvocalized phoneme 3930 is a simple sequence of three phonemes: /b/ /a/It/. The sounds "buh," "ah," and "tuh" can be threaded together to create the word "bat." This sequence includes three individual phonemes, each of which is produced by a specific combination of muscle movements and air flow in the mouth and throat. More complex sequences of phonemes can include entire sentences or phrases.

Some disclosed embodiments involve determining a prosody associated with the sequence of phonemes, and extracting meaning based on the determined prosody. The term "prosody" refers to a wide range of speech characteristics that have domains extending beyond individual phonemes. For example, the speech characteristics may include variations in duration, amplitude, and pitch of the voice, patterns of rhythm, stress, intonation, and timing. Accordingly, the term "determining a prosody" involves the process of analyzing and understanding the speech characteristics. For example, the prosody may be determined by analyzing micromovements. In this context, the term "extracting meaning" refers to the process of identifying and understanding the value, the significance, and/or the implications of the determined prosody associated with the sequence of phonemes. In one example, detecting a change in the volume of speech (as reflected by the movement of the facial skin) may indicate importance of a certain sequence of phoneme. In another example, detecting usage of a fast-paced and upbeat rhythm may indicate excitement associated with a certain sequence of phoneme. The extracted meaning may be stored and/or used to generate a more precise or detailed output.

Some disclosed embodiments involve determining an emotional state of an individual associated with the facial skin micromovements, and extracting meaning from the at least one subvocalized phoneme and the determined emotional state. The term "emotional state" refers to an individual's emotional condition and may be used as an indicator of the individual's behavior, cognition, and overall well-being. Accordingly, the term "determining an emotional state" means the process of analyzing and understanding the individual's emotional condition. The emotional condition may be determined by analyzing micromovements. Examples of emotional states may include happy, sad, excited, disturbed, apprehensive, surprised, and more. In this context, the term "extracting meaning" refers to the process of identifying and understanding the value, the significance, or the implications of the emotional state of the individual. The extracted meaning may be stored and/or used to generate a more precise or detailed output. For example, upon recognizing that the at least one subvocalized phoneme is a part of a message articulated while the individual is in stress, the speech detection system may assign a high urgency indicator to the message.

Some disclosed embodiments involve using a synthesized voice to generate an audio output (e.g., audio output 3940) reflective of the at least one subvocalized phoneme. The term "synthesized voice" refers to an artificial voice that may be generated using computer algorithms and software. In one example, the synthesized voice may be created to mimic the voice of an individual associated with the facial skin micromovements. Some synthesized voices may include a specific human speaker, while others may be designed to be more generic and versatile. Reflective of the at least one subvocalized phoneme means that the utterances vocalized by the synthesized voice convey aspects of the determined at least one subvocalized phoneme. For example, speech detection system 100 may use output determination module 712 to generate a synthesized voice to say the word "bat" upon detecting the subvocalized phonemes /b/, /a/, and/t/.

Some disclosed embodiments involve identifying as private at least one phoneme in the sequence of phonemes and omitting generation of an audio output reflective of the at least one private phoneme. The term "at least one private phoneme" includes any utterance that is not intended to be shared with others. Such utterances may include private information or may be of a type that, if audibly presented aloud, may cause harm, loss, or aggravation or embarrassment to the speaker or a listener. For example, the at least one private phoneme may include harsh, offensive, or strong language not meant to be vocalized. The process of identifying at least one private phoneme (e.g., one or more words) may involve accessing a database or a list of words considered private or sensitive. This database may be created and maintained by speech detection system 100, or it may be sourced from a third-party provider or organization. Then, natural language processing (NLP) techniques may be used to analyze the sequence of phonemes and identify instances of at least one phoneme classified as a private phoneme.

Such private phonemes may refer to, for example, social security numbers, credit card numbers, or other personally identifiable information. Omitting the generation of an audio output reflective of the at least one private phoneme means that the at least one private phoneme is not vocalized by the system or that the audio output for that phoneme is simply not generated. For example, when the at least one private phoneme includes harsh, offensive, or strong language, instead of vocalizing the private phoneme, the system may cause an audible output of an alternative phoneme that may not be harsh, offensive, or may not represent strong language.

Some disclosed embodiments involve identifying at least one extraneous phoneme as part of a filler and omitting generation of an audio output reflective of the extraneous phoneme. The term "extraneous phoneme" refers to a unit of sound that in the context of a word being spoken is considered, non-conventional, unmeaningful, or even inappropriate. Extraneous phonemes can occur for various reasons, such as speech disorders, regional dialects, accents, or individual idiosyncrasies in pronunciation. In some cases, extraneous phonemes may be added unconsciously as a filler and can be influenced by regional accents or individual speech habits. Identifying at least one extraneous phoneme as part of a filler may involve using natural language processing (NLP) techniques to analyze the sequence of phonemes and identify a word intended to be spoken (as described elsewhere in this disclosure) and identifying at least one extraneous phoneme as a filler relative to the identified word. The system may omit generation of an audio output reflective of the extraneous phoneme as described above. For example, filler words or sounds such as "uh," "um," "o.k.," and "like," which may occur as the result of an idiosyncrasy of the vocalizer or sub-vocalizer may be omitted from associated synthesized speech to textual output. In another example, the speech detection system 100 may correct the pronunciation of mispronounced words such that it.

Some disclosed embodiments involve receiving the first light reflections and the second light reflections via at least one detector, wherein the at least one detector and the at least one coherent light source are integrated within a wearable housing. The terms a wearable housing, a light detector, a light source, and receiving light reflections are described and exemplified elsewhere in this disclosure. The term "integrated within a wearable housing" refers to the light detector and the light source being linked, incorporated, affiliated with, connected to, or related to the wearable housing. For example, the light source and/or the light detector may be mounted to the wearable housing using screws or bolts, using adhesives, using plastic clips, using heat and pressure, or any other known way to attach two elements. By way of one example, light source 410 and light detector 412 in FIGS. 5A and 5B may be part of optical sensing unit 116 and may be employed to receive reflections 300.

Some disclosed embodiments involve accessing a default language of an individual associated with the facial skin micromovements, and using the default language to extract meaning from the at least one subvocalized phoneme. The term "extract meaning" may be understood as described elsewhere in this disclosure. The term "accessing" refers to retrieving or examining electronically stored information. This may occur, for example, by communicating with or connecting to electronic devices or components in which data is electronically stored. Accordingly, the term "accessing a default language" means retrieving data associated with a language, which is preset or associated with the wearer. For example, if the wearer is an English speaker, the default language for that speaker should be English, either because the system was designed to set English as the default or the user selected English as the default. Accessing a default language refers to interpretational rules and/or resources associated with the default language. For example, the system may employ or access tools such as a lookup table, dictionary, grammatical rules, sentence structure, verb tenses, plural forms, pronouns, prepositions, and other information that can be used determine meaning in the context of the default language.

FIG. 41 illustrates a flowchart of an exemplary process 4100 for determining subvocalized phonemes from facial skin micromovements, consistent with embodiments of the present disclosure. In some disclosed embodiments, process 4100 may be performed by at least one processor (e.g., processing device 400 or processing device 460, shown in FIG. 4) to perform operations or functions described herein. In some embodiments, some aspects of process 4100 may be implemented as software (e.g., program codes or instructions) that are stored in a memory (e.g., memory device 402 or memory device 466 shown in FIG. 4) or a non-transitory computer-readable medium. In some embodiments, some aspects of process 4100 may be implemented as hardware (e.g., a specific-purpose circuit). In some embodiments, process 4100 may be implemented as a combination of software and hardware.

Referring to FIG. 41, process 4100 includes a step 4102 of illuminating of a first region of a face and a second region of the face. For example, the at least one processor may control at least one coherent light source (e.g., light source 410) in a manner enabling illumination of a first region of a face (e.g., first region 3900A of face 3902) and a second region of the face (e.g., second region 3900B of face 3902). Process 4100 includes steps 4104 and 4106 of determining first micromovements of facial skin in the first region of the face (step 4104) and determining second micromovements of facial skin in the second region of the face (step 4106). For example, the micromovements of facial skin in a region of the face may be determined by performing a pattern analysis, e.g., using light reflections processing module 706 depicted in FIG. 7. For example, first pattern analysis 3910A may be applied to determine first facial skin micromovements 3920A, and second pattern analysis 3910B may be applied to determine second facial skin micromovements 3920B. Process 4100 further includes a step 4108 of using the determined micromovements of to ascertain at least one subvocalized phoneme. Consistent with the present disclosure, the at least one subvocalized phoneme (e.g., the at least one subvocalized phoneme 3930) may be ascertained using the first micromovements of the facial skin in the first region of the face and the second micromovements of the facial skin in the second region of the face. For example, at least one subvocalized phoneme 3930 may be ascertained by using machine learning (ML) algorithms and artificial intelligence (AI) algorithms as described in greater detail with respect to subvocalization deciphering module 708 depicted in FIG. 7.

The embodiments discussed above determining subvocalized phonemes from facial skin micromovements may be implemented through non-transitory computer-readable medium such as software (e.g., as operations executed through code), as methods (e.g., process 4100 shown in FIG. 41), or as a system (e.g., speech detection system 100 shown in FIGS. 1-3). When the embodiments are implemented as a system, the operations may be executed by at least one processor (e.g., processing device 400 or processing device 460, shown in FIG. 4).

Some disclosed embodiments involve systems, methods, and/or a non-transitory computer readable medium containing instructions that when executed by at least one processor cause the at least one processor to perform operations for generating synthesized representations of facial expressions. Non-transitory computer readable medium, instructions, and at least one processor are described and exemplified elsewhere in this disclosure. Facial expression broadly refers to various movements and configurations of the facial muscles that convey emotional states, attitudes, intentions, or reactions. Those movements and configurations may be detected optically or visually via facial skin. Generating broadly refers to emitting a command, emitting data, and/or causing any type of electronic device to initiate an action for creating, producing, originating, or making something. Synthesized may broadly refer to something formed by combining, arranging, blending, or integrating one or more parts or elements. Representation broadly refers to an expression, depiction, portrayal, exhibition, illustration, or designation using a term, character, symbol, image, or icon. Generating synthesized representations of facial expressions may refer to creating, producing, originating, or making a depiction or illustration of a facial expression by combining one or more parameters or features associated with a person's facial region. In some embodiments, the generated synthesized representations may be in the form of a sound, and the sound may be an audible presentation of words associated with silent or prevocalized speech. In one example, the audible presentation of words may include an answer or a question that the user vocalized or prevocalized via one or more facial expressions. In another example, the audible presentation of words may include synthesized speech (e.g., artificial production of human speech). According to other disclosed embodiments, the generated synthesized representations may be directed to a display (e.g., a visual display such as a computer monitor, television, mobile communications device, VR or XR glasses, or any other device that enables visual perception) and the generated synthesized representations may include graphics, images, or textual presentations of words associated with prevocalized or vocalized speech (e.g., subtitles). The textual presentation of the words may be presented at the same time words are vocalized.

Some disclosed embodiments involve controlling at least one coherent light source (as described elsewhere herein) in a manner enabling illumination of a portion of a face (e.g., a portion of a facial region, as described and exemplified elsewhere in this disclosure). Other disclosed embodiments involve controlling at least one non-coherent light source in a manner enabling illumination of a portion of a face. Enabling illumination, as used herein, may refer to the provision of a light source control, such as an on-off switch and/or circuitry and/or software instructions for controlling the switch. When the switch is closed, the light source is caused to illuminate. Such illumination may also be enabled by enabling arrangement of the light source to be directed toward the face. In some embodiments, enabling illumination may also include the provision and/or control of a beam-splitting element (as described elsewhere herein) configured to split an input beam into multiple output beams to illuminate a portion of a face. In an alternative embodiment, enabling illumination may include the provision and/or control of multiple light sources which generate respective groups of output beams, covering different respective sub-areas within a portion of a face. In some embodiments, enabling illumination may include projecting light toward a portion of the face.

Some disclosed embodiments involve projecting a light pattern on a portion of the face. Projecting may refer to shining or directing (as described elsewhere herein). A light pattern may refer to an arrangement, distribution, or sequence of coherent or non-coherent light emitted from a source or reflected off a surface. The light pattern may be a random pattern or may correspond to a specific design, shape, or configuration of projections to manifest a particular visual effect on a portion of the face. In general, the light pattern may refer to any arrangement or distribution of light.

Consistent with some disclosed embodiments, the light pattern includes a plurality of spots. As discussed elsewhere herein, the spots can be manifested in any manner of shapes and intensities. Consistent with some disclosed embodiments, the portion of the face includes cheek skin. A cheek may refer to either of the two fleshy sides of the face below the eyes and between the nose and the ear. Cheek skin may refer to any portion of skin associated with either cheek of the face, including portions of the cheek above the mouth and portions of the cheek below the mouth. Consistent with some disclosed embodiments, the portion of the face excludes lips. Lips may refer to the soft, movable, fleshy structures that form the opening to the mouth of the face, comprised of muscle, connective tissue, and skin.

Some disclosed embodiments involve receiving output signals from a light detector, wherein the output signals correspond to reflections of coherent light from the portion of the face (as discussed elsewhere herein). By receiving output signals from a light detector which correspond to reflections of light from the portion of the face, continuous monitoring (or non-continuous monitoring, in some embodiments) of at least a portion of a user's face may be enabled. In turn, a data stream (e.g., output signals) of the user's facial expressions or skin movements may be generated and transmitted to at least one processor for further processing. In some embodiments, output signals refers to information encoded for transmission via a physical medium. Examples of output signals may include signals in the electromagnetic radiation spectrum (e.g., AM or FM radio, Wi-Fi, Bluetooth, radar, visible light, lidar, IR, Zigbee, Z-wave, and/or GPS signals), sound or ultrasonic signals, electrical signals (e.g., voltage, current, or electrical charge signals), electronic signals (e.g., as digital data), tactile signals (e.g., touch), and/or any other type of information encoded for transmission between two entities via a physical medium.

Consistent with some disclosed embodiments, the output signals from the light detector emanate from a wearable device (as described elsewhere herein). Emanate refers to originating or coming forth from a starting point (e.g., from the light detector). For example, the output signals may originate or come forth from the light detector in the form of energy, light, or a transmission of data or information which corresponds to the reflections of light from the portion of the face that is illuminated. In some embodiments, the wearable device does not obscure the field of view of a user of the wearable device. Obscure may refer to any one or more of hiding, concealing, covering, screening, marking, enveloping, interfering with, or blocking at least a portion of a field of view. Consistent with some disclosed embodiments, the output signals from the light detector emanate from a non-wearable device. In such an instance, light source may not be physically connected to a worn component. For example, the non-wearable light source may be dedicated for use with the wearable detector (or more than one detector)

or might be an ambient source of light the reflections of which are received by a worn detector.

Some disclosed embodiments involve applying speckle analysis (as described elsewhere herein) on the output signals to determine speckle analysis-based facial skin micromovements (as also described elsewhere herein). Consistent with some disclosed embodiments, the determined speckle analysis-based facial skin micromovements are associated with recruitment of at least one of: a zygomaticus muscle, an orbicularis oris muscle, a genioglossus muscle, a risorius muscle, or a levator labii superioris alaeque nasi muscle. Some disclosed embodiments involve using the determined speckle analysis-based facial skin micromovements to identify at least one word prevocalized or vocalized (as described elsewhere herein) during a time period. Using the determined speckle analysis-based facial skin micromovements to identify at least one word may include determining a correlation between the determined speckle analysis and stored data. For example, as discussed elsewhere in this disclosure, a system may be trained to identify words based on detected facial skin micromovements.

A time period may refer to any length of time during which an activity occurs or during which a condition remains. For example, a time period may refer to a number of seconds (or portions thereof) or minutes. More generally, a time period may refer to a range of time during detection in which vocalization or prevocalization occurred. During such a time period, a reflection of light may be detected by the light detector, a change in a reflection of light may be detected at the light detector, a movement of the facial skin may be determined using a processor, or a change in a position of the facial skin may be determined using a processor. The speckle analysis-based facial skin micromovements may be used to identify one or more vocalized or prevocalized words during the time period.

Some disclosed embodiments involve using the determined speckle analysis-based facial skin micromovements to identify at least one change in a facial expression during the time period. Facial expression may refer to any form of signaling or communicating using the movement of one or more muscles of the face. For example, a facial expression may convey an emotion, an attitude, or an intention via the contraction or relaxation of one or more muscles of the face. The contraction or relaxation of one or more muscles of the face may, in turn, create various shapes, positions, or movements of the face. A facial expression may be a conscious expression or an unconscious expression. A facial expression may occur in unison with, or in relation to, a verbal, pre-verbal, or nonverbal act. In some embodiments, a facial expression may be used to communicate non-verbally with others. For example, a facial expression may express an emotion such as, e.g., happiness, sadness, anger, feat, surprise, or disgust. Non-limiting examples of facial expressions may include smiling, frowning, raising eyebrows, rolling eyes, pursing lips, squinting, opening the eyes wide, sticking the tongue out, winking, grimacing, as well as other facial movements which indicate an emotion, attitude, or intention.

A change in a facial expression may refer to a modification of the face (including the skin and/or muscles thereof) based on the movement of one or more muscles of the face. A change in a facial expression may be determined by, e.g., comparing one or more first determined facial skin micromovements with one or more second determined facial skin micromovements. One or more first determined facial skin micromovements may correspond to a first received reflection signal from the light detector, based on a first reflection of light from a portion of the face. One or more second determined facial skin micromovements may correspond to a second received reflection signal from the light detector, based on a second reflection of light from a portion of the face.

Consistent with some disclosed embodiments, the at least one change in the facial expression during the period of time includes speech-related facial expressions and non-speech-related facial expressions. Speech-related facial expressions may refer to facial expressions which are associated with and/or occur in conjunction with one or more vocalized or prevocalized words. Non-limiting examples of speech-related facial expressions may include smiling, frowning, raising one or more eyebrows, nodding, pursing lips, opening the mouth, tilting the head, grimacing, and other facial expressions which may be associated with a word that is spoken or about to be spoken. Non-speech related facial expressions may refer to facial expressions which occur without any associated vocalized or prevocalized words and/or facial expression which are not directly related to speech or language. Non-limiting examples of non-speech-related facial expressions may include smiling, frowning, winking, raising one or more eyebrows, grimacing, eye-rolling, nodding, puckering lips, blinking, smirking, sticking the tongue out, and other facial expressions which do not necessarily relate to (pre)vocalized words or conversation. As indicated at least via the non-limiting examples above, certain facial expressions may be speech-related as well as non-speech-related, based on whether the facial expression is provided in conjunction with one or more vocalized or prevocalized words.

Some disclosed embodiments involve during the time period, outputting data for causing a virtual representation of the face to mimic the at least one change in the facial expression in conjunction with an audio presentation of the at least one word. Outputting may include sending, transmitting, producing, and/or providing. A virtual representation refers to a digital or computer-generated representation that simulates one or more characteristics, properties, or functionalities of the real-world counterpart. For example, the virtual representation may be one dimensional or two dimensional.

As an example, the virtual representation may be rendered based on received input from the light detector and/or the at least one processor. The received input may include reflection data, reflection signals, or any other output provided by the light detector and/or the at least one processor. the virtual representation may be rendered using a process of generating an image or animation from a model representing a virtual representation by, e.g., applying computer graphics algorithms to the model's data. The input received for rendering may come from various sources. In one embodiment, the only source of data may be associated light reflections. In other embodiments the source of data may also include images of a wearer (or other image data associated with the wearer, either pre-captured or captured during the time period of user interaction. Rendering may begin by defining, via at least one processor, a dimensional model (e.g., 2D or 3D model), which includes a mathematical representation of a virtual object (e.g., an avatar, or a face of an avatar). The dimensional model may contain information about the object's shape, texture, and/or lighting properties. Once the model is defined, it may or may not be configured to be placed within a simulated environment. Next, rendering may include receiving input and determining based on the received input, how to display the object in the simulated environment. Such received input may also include a position or an orientation of a sensor capturing data from the real-world environment. Based on the received input, the at least one processor may calculate the camera's position and angle to determine which portion of the simulated environment should be displayed during a given time period. Next, the at least one processor may use algorithms to calculate the appearance of the virtual object. This step may involve calculating how light interacts with the object's surface to create shadows, reflections, and other visual effects. Examples of algorithms that might be used include 3D mesh modeling, texture mapping, facial expression and animation modeling, light and shading models, skin rendering models, wrinkle and detail generation, hair rendering, and/or real time rendering models as known in the art. The at least one processor may also apply textures and materials to the object's surface to make it appear more realistic and/or to cause changes in the appearance of the object over time. Finally, the at least one processor may combine all of the calculated information to create an image or animation of the virtual object. The resulting output may be displayed on a screen or used in a simulated environment.

Figure 42A:
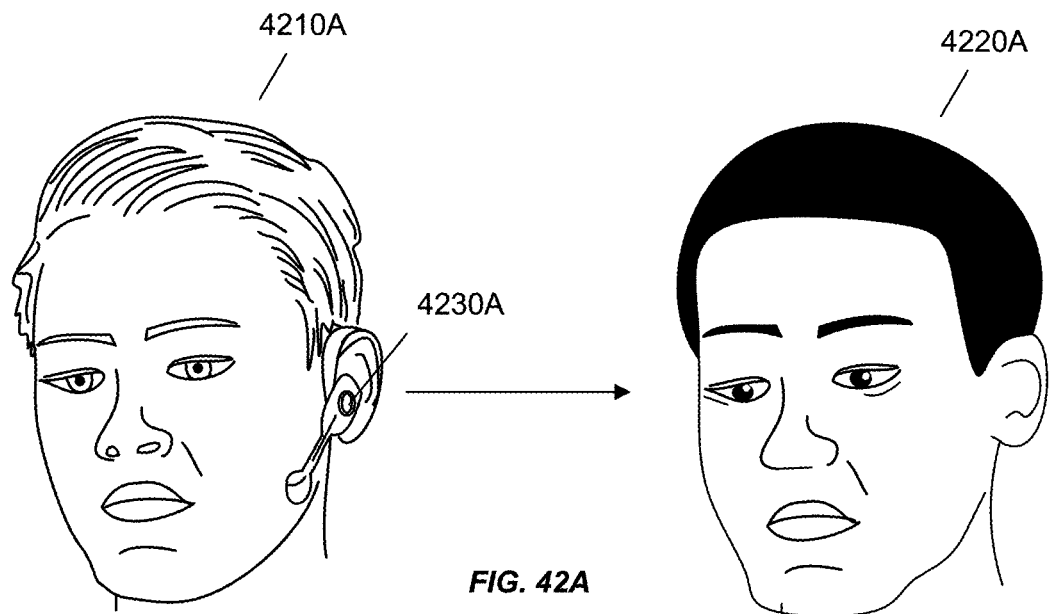
FIG. 42A is one perspective view of a user wearing an example head set and a resulting virtual representation of one facial expression of the user, consistent with some embodiments of the present disclosure.
Figure 42B:
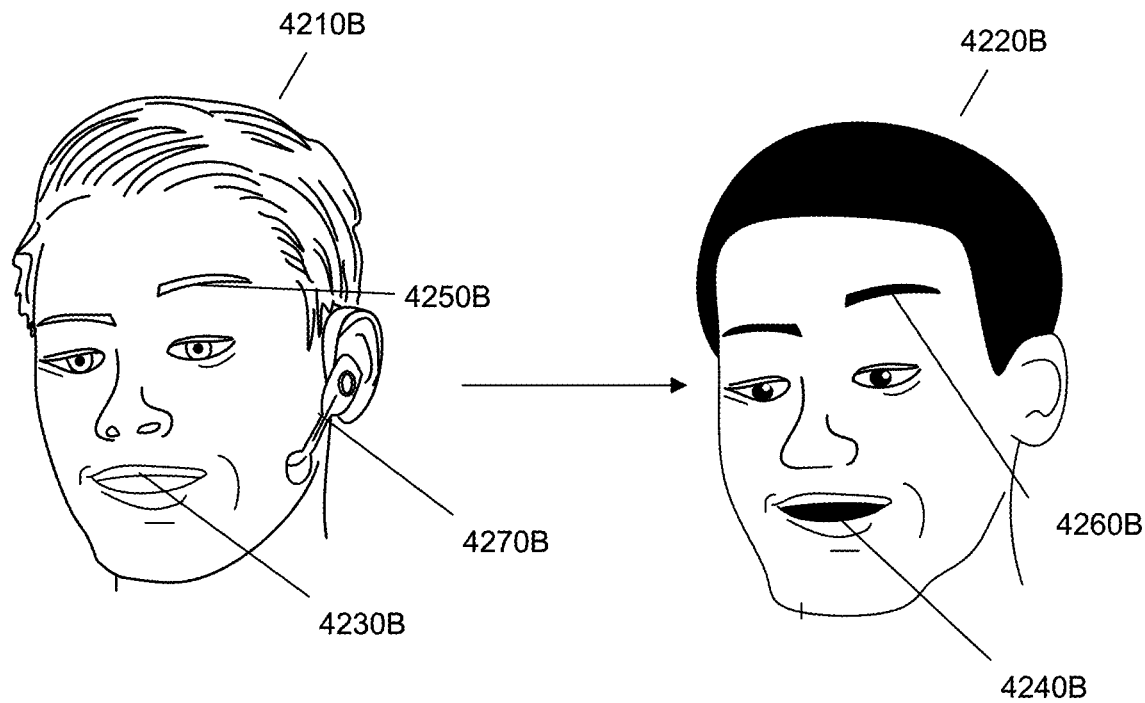
FIG. 42B is another perspective view of a user wearing an example headset and a resulting virtual representation of another facial expression of the user, consistent with some embodiments of the present disclosure.

FIGS. 42A and 42B illustrate examples of virtual representations.

FIG. 42A illustrates one example of a user 4210A wearing a device 4230A including a light source for emitting light on a portion of the face of the user 4210A and a light detector for receiving reflections of light from a portion of the face of the user 4210A. A virtual representation 4220A of at least the face of the user mimics the facial expression of the user 4210A via the processes and components described and exemplified elsewhere in this disclosure. In the example of FIG. 42A, the user 4210A has a neutral facial expression and the virtual representation 4220A mimics the neutral facial expression.

FIG. 42B, illustrates another example of a user 4210B wearing a device 4270B including a light source for emitting light on a portion of the face of the user 4210B and a light detector for receiving reflections of light from a portion of the face of the user 4210B. A virtual representation 4220B of at least the face of the user mimics the facial expression of the user 4210B via the processes and components described and exemplified elsewhere in this disclosure. In the example of FIG. 42B, as compared to the example of FIG. 42A, the user 4210B has a changed facial expression and the virtual representation 4220B mimics the changed facial expression. For instance, the user 4210B has raised an eyebrow 4250B and the virtual representation 4220B mimics the raised eyebrow 4260B. In addition, the user 4210B is smiling 4230B and the virtual representation 4220B mimics the smiling 4240B. The virtual representation 4220B is able to mimic the change in facial expressions of the user 4210B (as well as any words vocalized or prevocalized by, or emotional states of, the user 4210B) based on facial skin micromovements determined by a pattern analysis module and/or at least one processor which receives reflection data (e.g., reflection signals) from device 4270B. The reflection data transmitted by device 4270B is based on reflections of light from a portion of the face of user 4210B as emitted by the light source and as detected by the light detector in device 4270B. Although the mimicking illustrated in FIGS. 42A and 42B appears rather precise, mimicking can occur with much less precision. For example, if an emotional state is determined via light reflections to be sad, the virtual representation is said to mimic the user if the virtual representation conveys a sad virtualization, even if that virtualization does not match the sad expression on the user's face.

A user (e.g., a human or individual associated with the face) may further be enabled to interact with the virtual representation in a real or physical manner through the use of specialized hardware and software (e.g., the detection systems described and exemplified herein). Multiple virtual representations of differing users may be presented in a simulated environment, for various purposes, such as group communication, entertainment, gaming, education, training, therapy, as well as other applications. The simulated environment may also be used across various industries, such as healthcare, education, architecture, engineering, gaming, and other industries.

The virtual representation of the face may be configured to mimic a facial expression. Mimicking refers to an act of copying, simulating, reproducing, or replicating. For example, the output data may cause the virtual representation of the face to simulate the behavior, appearance, physical feature(s), or movements of the face of a user of a detection system, as described herein, in order to create an impression of resemblance or similarity in the simulated environment. As illustrated in FIGS. 42A and 42B, for example, the virtual representations 4220A and 4220B simulate the expressions of the users 4210A and 4210B.

The mimicking may occur in conjunction with an audio presentation of the at least one word in that it may occur at the same or near the same time. For example, as words are vocalized or pre-vocalized by the user and the user's expression changes, that same changes may occur in the virtual representation. Consistent with some disclosed embodiments, the output data may further cause an audio presentation of the at least one word in conjunction with a virtual representation of the face. For example, the output data may cause an audio presentation of the word, "Hello," in conjunction with a virtual representation of the face mimicking a smile as shown on the face in the simulated environment. An audio presentation may refer to information delivered through sound. Sound may refer to spoken words or exclamations, music, sound effects, digital sounds, or any combination thereof. An audio presentation may be pre-recorded or delivered live to the simulated environment, based on the voice of a user.

Consistent with some disclosed embodiments, the virtual representation of the face is associated with an avatar of an individual from whom the output signals are derived. An avatar may refer to a representation of an individual (e.g., a user). The representation of an individual may be a graphical or visual depiction in a digital or virtual realm. An avatar may further be customizable to reflect a user's preferences, personality, movements, and facial expressions. In embodiments that employ a simulated environment with more than one avatar, avatars may interact.

Consistent with some disclosed embodiments, mimicking the at least one change in the facial expression includes causing visual changes to the avatar that reflect at least one of the speech-related facial expressions and the non-speech-related facial expressions. In some embodiments, causing visual changes to the avatar may occur as a result of output data received from the light detector, the output data corresponding to the at least one change in the facial expression as detected by the light detector. Consistent with some disclosed embodiments, the visual changes to the avatar involve changing a color of at least a portion of the avatar. For example, the light detector may receive a reflection of light from a portion of the face and based on the received reflection of light, send reflection data (e.g., one or more reflection signals) to a pattern analysis module and/or at least one processor. Based on the received reflection data, an analysis module and/or at least one processor may determine one or more facial skin micromovements. The analysis module and/or at least one processor may then identify, based on a correlation between the one or more determined facial skin micromovements and stored data relating to various emotional states, that the reflection data received indicates that an individual/user is experiencing an emotion (e.g., an individual is embarrassed, sad, angry, or experiencing another emotion). In turn, the analysis module and/or at least one processor may be configured to emanate a signal (e.g., to a rendering engine for rendering the avatar of the individual in a simulated environment) for causing a change in the facial expression of the avatar (e.g., the avatar's face changes to a pink color to simulate blushing, a blue color to simulate sadness, a red or orange color to simulate anger, or another color to simulate another detected emotion of the individual). Other non-limiting examples of visual changes to the avatar may include altering the shape or size of a facial component (e.g., eyes, ears, mouth, nose) of the avatar, altering the shape or size of a portion of the body of the avatar, changing the skin tone or texture of the avatar, changing the height, weight, or body shape of the avatar, modifying an environment or background in which the avatar is displayed, applying a special effect or animation to the avatar, altering a facial expression and/or gesture of the avatar, changing the style or theme of the avatar (e.g., cartoon, stick figure, realistic), as well as other visual changes to a portion of the avatar or the simulated environment.

Consistent with some disclosed embodiments, the audio presentation of the at least one word is based on a recording of an individual. Recording may refer to audio data captured in a permanent or semi-permanent form. The recording may be created, e.g., by capturing sound waves emitted by an individual associated with the face, converting the sound waves into data in a digital or analog format, and storing the data for playback or editing. Permanent audio data may refer to audio data that is stored using storage methods that can retain data for long periods of time, if power is lost, or if a device is unplugged (e.g., audio data stored on a hard disk drive, a solid state drive, or flash memory or other non-volatile memory). Semi-permanent audio data may refer to audio data that is stored using storage methods than can retain data for a moderate period of time (e.g., audio data stored in random access memory, on a compact disk, DVD, or Blu-ray disc, or on magnetic tape). Various recordings of an individual speaking may be stored and correlated with particular data associated with various reflections detected by the light detector. In turn, when a particular reflection is detected, the output signal from the light detector may be configured to cause the corresponding recording as the audio presentation in the simulated environment. For example, a stored audio sample of a user's voice may be used to simulate prevocalized words later captured based on light reflections from the user's face.

Consistent with some disclosed embodiments, the audio presentation of the at least one word is based on a synthesized voice. A synthesized voice may refer to a computer-generated voice, text-to-speech (TTS) voice, or any other artificial voice created using hardware, software, algorithms, or a combination thereof, configured to convert text or other data into audible speech. The synthesized voices can be generated in real-time or pre-recorded and stored for later use. The synthesized voices may further be customized to different languages, accents, and tones. The synthesized voices may be stored in permanent or semi-permanent form (as described elsewhere in this disclosure).

Consistent with some disclosed embodiments, the synthesized voice corresponds with a voice of an individual from whom the output signals are derived. For example, the synthesized voice may be generated in real-time based on the output signals received from the light detector. Thus, the synthesized voice may be generated based on light reflections received from a face of an individual and the voice may match or be based on the voice of that individual. The synthesized voice may be based on or match the user's voice by accessing a prestored voice data set associated with the individual as a basis for synthesizing the user's voice. As another example, the synthesized voice may be pre-recorded based on various words (or combinations thereof) vocalized or prevocalized by an individual. Various word (or combinations thereof) may, in turn, be correlated with particular reflection data received at the light detector from light signals reflected from the face of that individual. In response to receiving particular reflection data, the light detector may be configured to output data configured to cause an audio presentation including corresponding to speech using the synthesized voice of the individual.

Consistent with some disclosed embodiments, the synthesized voice corresponds with a template voice selected by an individual from whom the output signals are derived. A template voice may refer to a pre-designed or pre-configured set of parameters or characteristics which define a voice for an individual. An individual may select a fully designed template voice from a list of template voices, or an individual may create a custom template voice using a software application or tool, download a custom template from an online source or from the software application or tool, and/or upload a custom template to the list of template voices for selection. Further, reflection data may be received at the light detector from light signals reflected from the face of an individual and the synthesized voice may be generated based on a template voice selected by or generated by that individual.

Consistent with some disclosed embodiments, the operations further include determining an emotional state of an individual from whom the output signals are derived based at least in part on the facial skin micromovements and augmenting the virtual representation of the face to reflect the determined emotional state. An emotional state may refer to a state of an individual's emotional experience or feelings. An emotional state refers to an individual's subjective experience and expression of their emotions at a specific moment or period of time. The state may be temporary and may range from positive emotions (e.g., happiness, excitement, love, surprise, hope, as well as other positive emotions) to negative emotions (e.g., sadness, anger, fear, disgust, guilt, jealousy, envy, pain, embarrassment, shame, as well as other negative emotions), as detected at the light detector based on the reflection data received. An emotional state may also reflect a neutral emotion, or an emotion that is not identified as strongly positive or strongly negative. The intensity and duration of an emotional state may also vary, and the intensity or duration may also be detected at the light detector based on the reflection data received.

Determining an emotional state of an individual may include receiving at least one reflection of light at the light detector, transmitting reflection data to at least one processor, and identifying, via the at least one processor, the emotional state based on a correlation (as described and exemplified elsewhere in this disclosure) between the transmitted and received reflection data and one or more emotional states. The at least one processor may be configured to use the reflection data (e.g., signal) from the light detector and determine the emotional state based on the facial skin micromovements that are detected via an identified correlation between the reflection data and at least one emotional state. Particular facial skin micromovements, as determined, may be correlated with specific emotional states such that a determined facial skin micromovement may indicate a given emotional state. Such correlations may be provided and utilized in a manner similar to correlations between facial skin micromovements and one or more words (as described and exemplified elsewhere in this disclosure).

Augmenting the virtual representation of the face to reflect the determined emotional state may include utilizing computer software and/or hardware to enhance, change, add, or remove at least one property or parameter of the face (or another portion of the avatar) in the simulated environment, based on the emotional state determined from the identified facial skin micromovements. Augmenting may be performed through the use of specialized software tools (including, e.g., machine learning techniques) and/or scripting languages that allow for causing programming changes within simulated virtual environments. For example, at least one property or parameter of the face of the avatar may be augmented to show a smiling expression based on a detected happy emotional state of a corresponding user. Such an augmentation may occur based on a facial skin micromovement correlated with reflection data as detected and transmitted by the light detector to the at least one processor. For example, a facial skin micromovement associated with the movement of the user's cheek in an upward direction may be correlated with a smiling gesture, and based on such a correlation, the at least one processor may associate the detected facial skin micromovement with a smile. In turn, the at least one processor may cause a programming change within the simulated environment (e.g., by adjusting a script associated with the rendering of the mouth of the avatar) to augment the mouth of the avatar from a neutral position to a smiling position.

Figure 43:
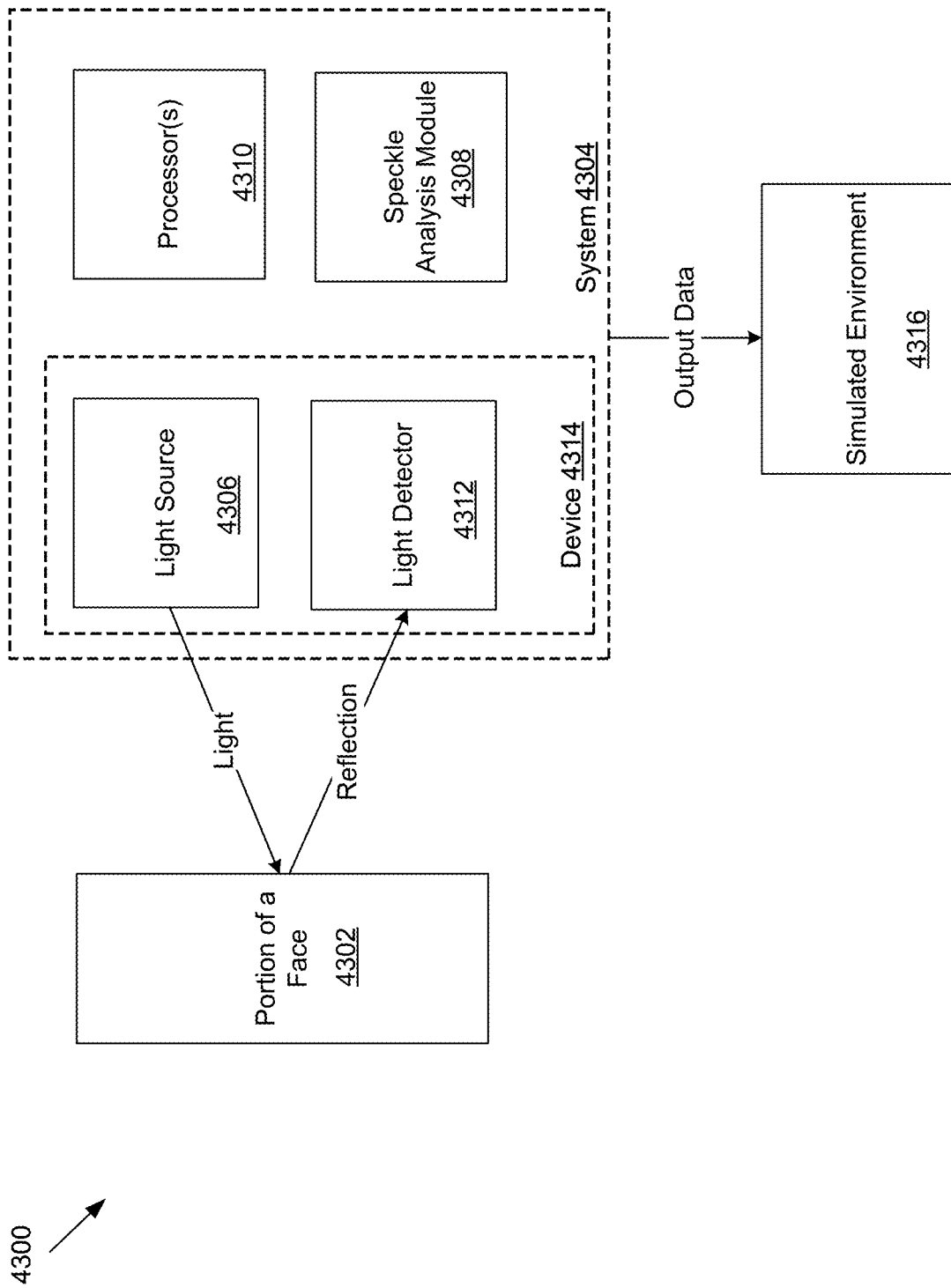
FIG. 43 is a block diagram illustrating an exemplary operating environment for generating synthesized representations of facial expressions, consistent with some embodiments of the present disclosure.

Some disclosed embodiments involve a system for generating synthesized representations of facial expressions, the system comprising at least one processor configured to perform steps consistent with those described above. FIG. 43 illustrates an exemplary operating environment 4300 including a system 4304, the system 4304 including a device 4314, a speckle analysis module 4308, and at least one processor 4310. An exemplary device 4314 includes a light source 4306 which is controlled in a manner enabling illumination of a portion of a face 4302 of a user associated with the device 4314. An exemplary device 4314 further includes a light detector 4312 (or any other type of sensor) configured to receive input in the form of reflections of light from the portion of the face 4302 of the user associated with the device 4314. Based on the input received by the light detector 4312, one or more output signals are emitted from the light detector 4312 or another component of the device 4314. The one or more output signals correspond to the reflections of light from the portion of the face 4302 of the user associated with the device 4314. The speckle analysis module 4308 then receives the one or more output signals and performs speckle analysis on the one or more output signals to determine speckle analysis-based facial skin micromovements. The speckle analysis may be performed via the at least one processor 4310. Subsequently, using the determined speckle analysis-based facial skin micromovements, the speckle analysis module 4308 further identifies at least one word prevocalized or vocalized by the user associated with the device 4314 during a time period. The identification of at least one word vocalized or prevocalized may be performed via the at least one processor 4310. The speckle analysis module 4308 further uses the determined speckle analysis-based facial skin micromovements to identify at least one change in a facial expression of the user associated with the device 4314 during the time period. The identification of at least one change in a facial expression may be performed via the at least one processor 4310. The system 4304 further outputs, during the time period, output data for causing a virtual representation, in a simulated environment 4316, of the face of the user associated with the device 4314. The output data is configured to cause the virtual representation to mimic the at least one change in the facial expression in conjunction with an audio presentation of the at least one word in the simulated environment 4316. The output data is generated via the at least one processor 4310 or via the speckle analysis module 4308.

Figure 44:
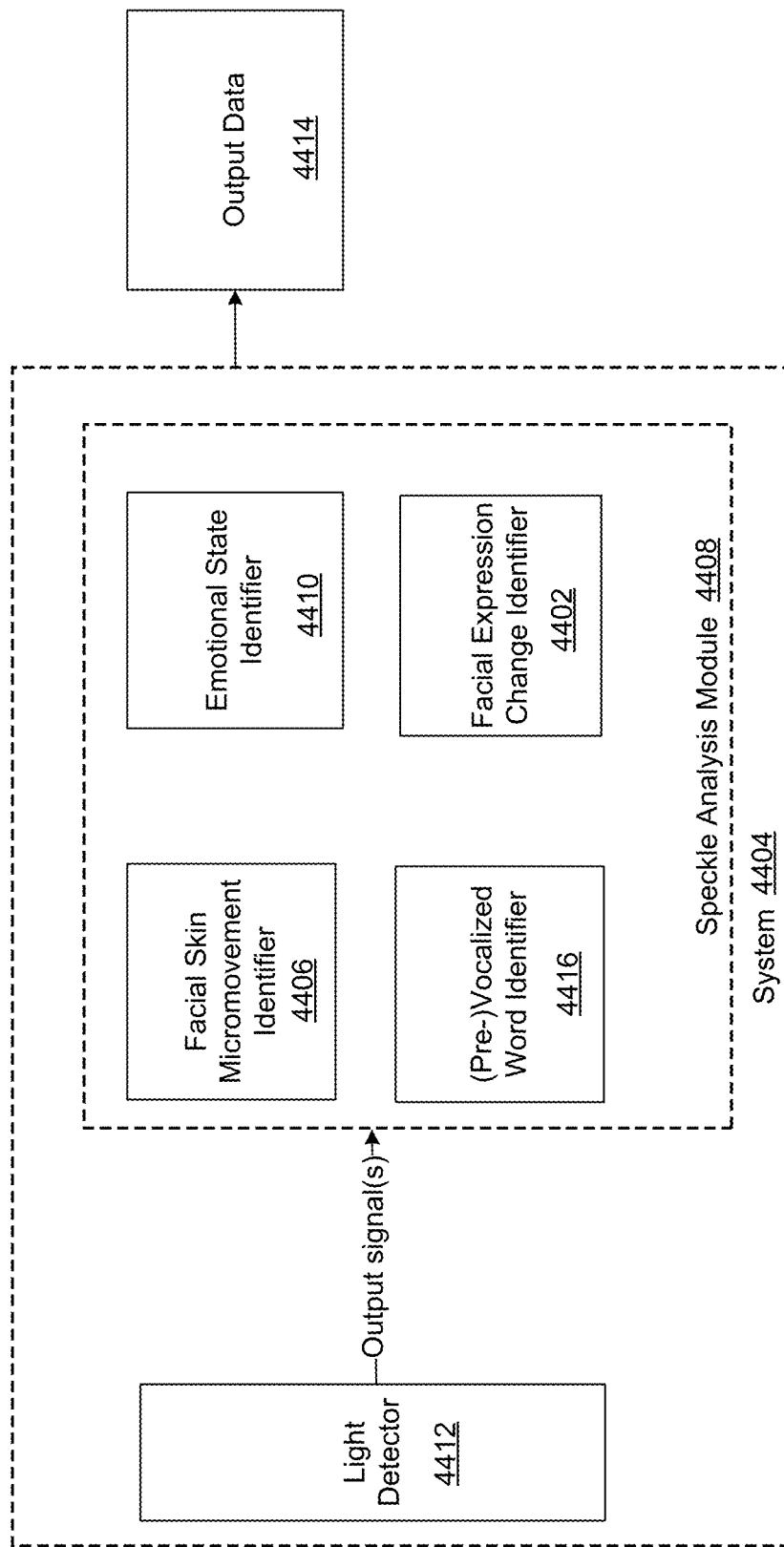
FIG. 44 is a block diagram illustrating an exemplary system for generating synthesized representations of facial expressions and/or for determining spoken phonemes from facial skin micromovements, consistent with some embodiments of the present disclosure.

FIG. 44 illustrates an example of a system 4404 including a speckle analysis module 4408 (or any other pattern analysis module) having a facial skin micromovement identifier 4406, a word identifier 4416, an emotional state identifier 4410, and/or a facial expression change identifier 4402. Although illustrated in separate boxes for ease of illustration, one or more of the identifiers may be combined. Speckle analysis module 4408 receives one or more output signals from a light detector 4412 based on reflections of light from a portion of a face of a user (not shown in FIG. 3). In response to and based on the output signal(s) received by speckle analysis module 4408, one or more of facial skin micromovement identifier 4406, word identifier 4416, emotional state identifier 4410, and/or facial expression change identifier 4402 processes the received output signal(s) and performs speckle analysis on the received output signal(s). For example, in response to receiving one or more output signals, facial skin micromovement identifier 4406 processes the one or more output signals to determine one or more speckle analysis-based facial skin micromovements. As another example, word identifier 4416 processes the one or more output signals (or the identified speckle analysis-based facial skin micromovements) to identify at least one word vocalized or prevocalized during a time period. As yet another example, emotional state identifier 4410 processes the one or more output signals (or the identified speckle analysis-based facial skin micromovements) to identify one or more emotional states during a time period. As another example, facial expression change identifier 4402 processes the one or more output signals (or the identified speckle analysis-based facial skin micromovements) to identify at least one change in the facial expression during the time period. In turn, and based on the processing of the output signal(s), system 4404 provides output data 4414 for causing a virtual representation of the face, rendered in a simulated environment, to mimic the at least one change in the facial expression. In some embodiments, the output data 4414 provided by system 4404 is further configured to cause, in the simulated environment, an audio presentation of the at least one word in conjunction with the virtual representation of the facial expression.

Figure 45:
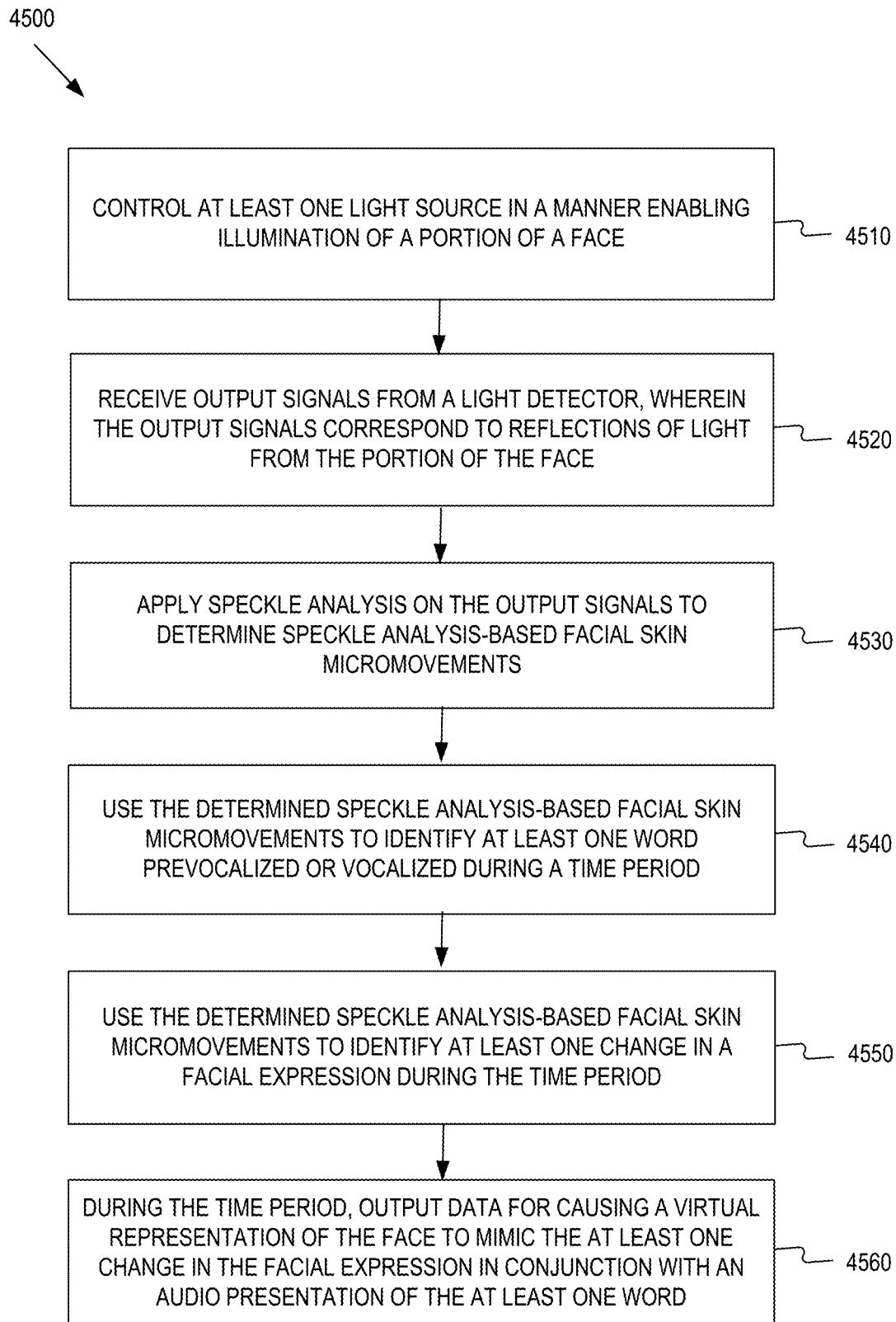
FIG. 45 is a flow chart illustrating an exemplary method for generating synthesized representations of facial expressions and/or for determining spoken phonemes from facial skin micromovements, consistent with some embodiments of the present disclosure.

Some disclosed embodiments involve a method for generating synthesized representations of facial expressions, the method comprising steps consistent with those described above. FIG. 45 is a flow chart of an exemplary method 4500 for generating synthesized representations of facial expressions including step 4510 of controlling at least one light source in a manner enabling illumination of a portion of a face. Exemplary method 4500 further includes step 4520 of receiving output signals (e.g., reflection data or reflection signals) from a light detector, wherein the output signals correspond to reflections of light from the portion of the face. In step 4530, speckle analysis (or any other pattern analysis) is applied to the output signals to determine speckle analysis-based (or pattern analysis-based) facial skin micromovements. In step 4540, the determined speckle analysis-based facial skin micromovements are used to identify at least one word prevocalized or vocalized during a time period. Then, using the determined speckle analysis-based facial skin micromovements in step 4550, at least one change in a facial expression is identified during the time period. In step 4560, data is output during the time period for causing a virtual representation of the face to mimic the at least one change in the facial expression in conjunction with an audio presentation of the at least one word.

Figure 46:
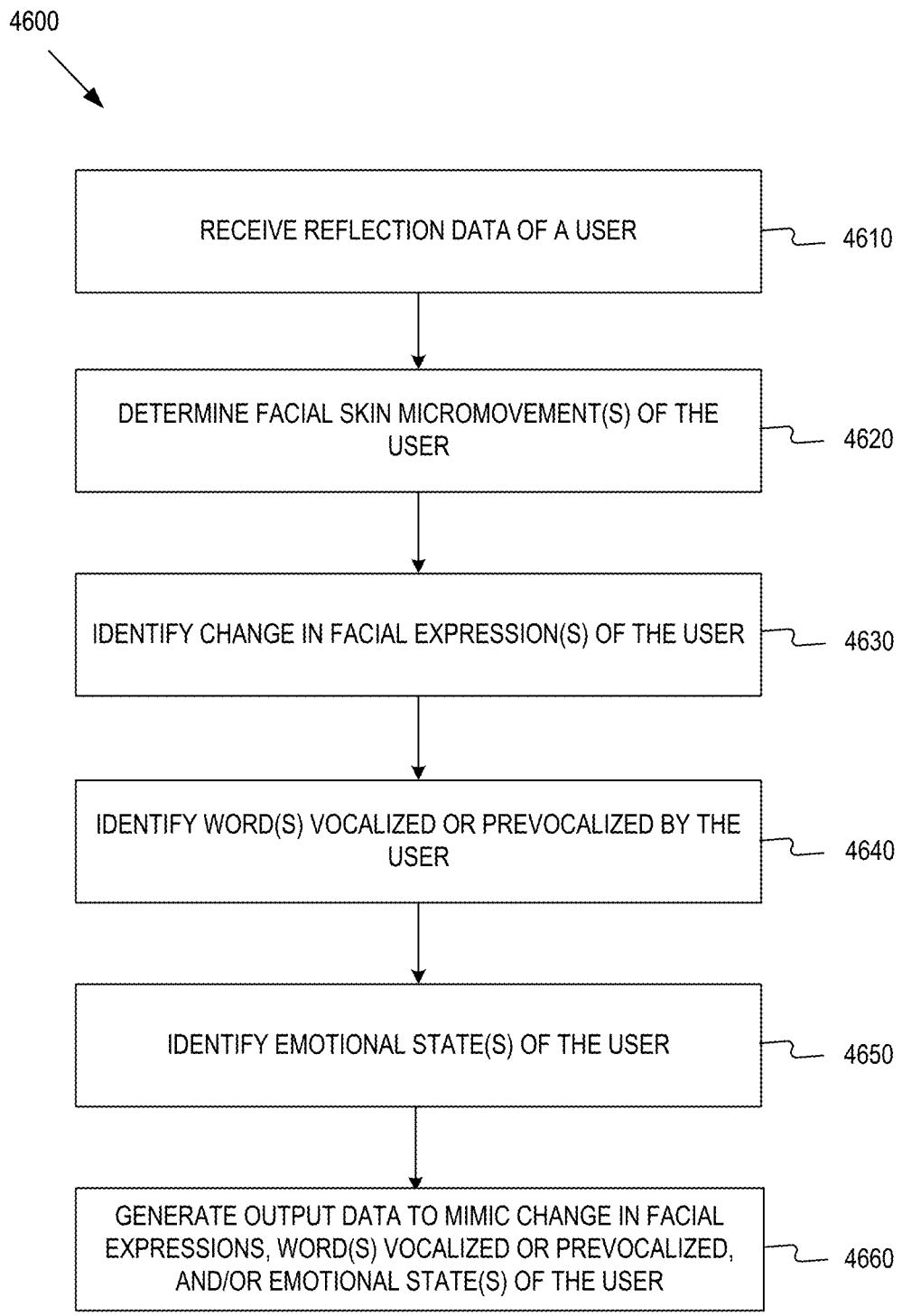
FIG. 46 is a flow chart illustrating another exemplary method for generating synthesized representations of facial expressions and/or for determining spoken phonemes from facial skin micromovements, consistent with some embodiments of the present disclosure.

Consistent with some disclosed embodiments, and with reference to FIG. 46, an exemplary method 4600 for generating output data based on received reflection data includes a step 4610 of receiving reflection data of/from a user. In some disclosed embodiments, the reflection data is transmitted from a light detector which received reflections of light from a face of the user. In some embodiments, the light is coherent light emitted by a coherent light source. In other embodiments, the light is non-coherent light emitted by a non-coherent light source. In some embodiments, a coherent or non-coherent light source illuminates a portion of the face of the user and/or projects a light pattern on the portion of the face of the user. In some embodiments, the light pattern includes a plurality of spots. In some embodiments, the portion of the face includes cheek skin and/or excludes lips. In some embodiments, the reflection data includes output signals emanating from a wearable device. In other embodiments, the reflection data includes output signals emanating from a non-wearable device. Method 4600 may further include a step 4520. In step 4520, facial skin micromovements of the user are determined based on the received reflection data. In some embodiments, the determined facial skin micromovements are associated with the recruitment of at least one of a zygomaticus muscle, an orbicularis oris muscle, a genioglossus muscle, a risorius muscle, or a levator labii superioris alaeque nasi muscle of the face of the user. At step 4530, a change in facial expressions of the user is identified based on the determined facial skin micromovements. In some embodiments, the change in facial expressions of the user is determined for a particular period of time. In some embodiments, the change in facial expressions of the user includes speech-related facial expressions and/or non-speech-related facial expressions. In some embodiments, identifying a change in facial expressions of the user is based on identifying a non-desirable facial expression (e.g., via user selection of the non-desirable facial expression). At step 4540, one or more words vocalized or prevocalized by the user are identified based on the determined facial skin micromovements. At step 4550, one or more emotional states of the user are identified based on the determined facial skin micromovements. Alternatively, identifying one or more emotional states of the user occurs based on a selection of a desired emotional state made by a user. At step 4560, output data is generated to cause a virtual representation of the user to mimic at least one of a change in a facial expression of the user, one or more words vocalized or prevocalized by the user, or one or more emotional states of the user. For example, a virtual representation of the user is caused to mimic the facial expression(s) of the user by causing visual changes to the user's avatar that reflect at least one of speech-related facial expressions and/or non-speech-related facial expressions. As another example, visual changes to the avatar involve changing a color of at least a portion of the avatar. In some embodiments, the generated output data omits data for causing an identified non-desirable facial expression. In some embodiments, in conjunction with a visual change, the generated output data is configured to cause an audio presentation of at least one identified word vocalized or prevocalized by the user. For example, the audio presentation may be based on a recording of an individual. As another example, the audio presentation may be based on a synthesized voice (e.g., a synthesized voice which may correspond with a voice of the individual from whom the output data is derived, or a synthesized voice which may corresponding to a template voice selected by the individual from whom the output data is derived).

The embodiments discussed above for generating synthesized representations of facial expressions may be implemented through non-transitory computer-readable medium such as software (e.g., as operations executed through code), as methods (e.g., method 4500 shown in FIG. 45, method 4600 shown in FIG. 46), or as a system (e.g., speech detection system 100 shown in FIGS. 1-3). When the embodiments are implemented as a system, the operations may be executed by at least one processor (e.g., processing device 400 or processing device 460, as shown in FIG. 4).

Consistent with some disclosed embodiments, the operations further include receiving a selection of a desired emotional state, and augmenting (as described and exemplified elsewhere in this disclosure) the virtual representation of the face to reflect the selected emotional state. Receiving a selection of a desired emotional state may include presenting to a user a list of emotional states and enabling the user to choose at least one of the emotional states from the list (e.g., via checkbox, radio button, selecting from a dropdown menu, slider(s), button(s), or any other method for indicating a user's choice). Receiving a selection may also include receiving a free form input from a user indicating one or more emotional states as one or more desired emotional states. Receiving a selection may also include receiving a non-text input from a user (e.g., receiving a user selected image, detecting a gesture of a user, detecting an eye movement of a user, or detecting any other movement by or of a user which may indicate a selection).

Consistent with some disclosed embodiments, the operations further include identifying a non-desirable facial expression. A non-desirable facial expression may be identified based on receiving a user selection or other user-provided input (e.g., text, audio, video). Non-desirable facial expression may refer to a movement of the face (associated with a reflection of light from the face) which an individual deems unpleasant, unacceptable, unwanted, unappealing, distasteful, reflexive, or non-preferable for any reason. For example, an individual may identify an involuntary movement of the face as an undesirable facial expression (e.g., coughing, sneezing, blinking, blushing, yawning, tick, twitch, nausea, flaring nostrils, or any other unintentional, unappealing, or unwanted, facial movement).

Consistent with some disclosed embodiments, the outputted data for causing the virtual representation omits data for causing the non-desirable facial expression. For example, if an individual prefers that a particular facial expression or movement not be reflected in the simulated environment, the individual may identify the particular facial expression or movement as a non-desirable facial expression. Alternatively, the system may automatically identify non-desirable facial expressions. In turn, that non-desirable facial expression may be overlooked or ignored by the light detector and/or the at least one processor such that the particular movement of the face (or reflection of light from the face) does not cause the processor to send an output signal based on the particular movement of the face which, in turn, may cause a change or augmentation in the virtual representation of the face. In some embodiments, the at least one processor may overlook reflection data corresponding to the non-desirable facial expression received from the light detector. In other embodiments, the light detector may be configured to disregard a reflection of light corresponding to the undesirable facial expression, such that no corresponding reflection data is transmitted to the at least one processor. As a result, the virtual representation of the face and/or the avatar may not be changed or augmented even if the user makes a non-desirable facial expression and/or if an associated facial skin micromovement is detected based on the non-desirable facial expression made by the user, based on the user-provided input and instruction to overlook such a signal or data.

Some disclosed embodiments involve attention-associated interactions based on facial skin micromovements. An "interaction" refers to an exchange of information. When an individual provides an input to a system, for example, that input constitutes an interaction with that system. In some embodiments, a reactive response by the system may also be part of an interaction. An interaction may involve speech, muscle movement, skin movement, limb or extremity movement, or any other activity that conveys information.

"Attention" refers to focusing or providing a greater amount of concentration on one thing or group of things over another thing or group of things. Attention may be manifest, for example, by an act or state of applying the mind, carefully thinking about, or watching some phenomenon, event, occurrence, incident, experience, manifestation, episode, object, signal, and/or wonder to the exclusion of some other stimuli, trigger, cue, signal, provocation, prompt, inducement, and/or influence. Attention may be manifest in the behavior of a person, whether humanly perceptible or perceptible through the aid of a machine or system. Thus, "attention-associated interactions" may include any interactions that are associated with the attention of an individual. In some instances an attention associated interaction may be binary—(the user is providing attention or is not); in other instances attention-associated interactions may be graduated, and assessed by a level, extent, degree, intensity, scope, range, magnitude, of attention of an individual or user.

"Facial skin micromovements" may broadly refer to skin motions on the face that may be detectable using a sensor, but which might not be readily detectable to the naked eye (as described and exemplified elsewhere herein.

Figure 47:
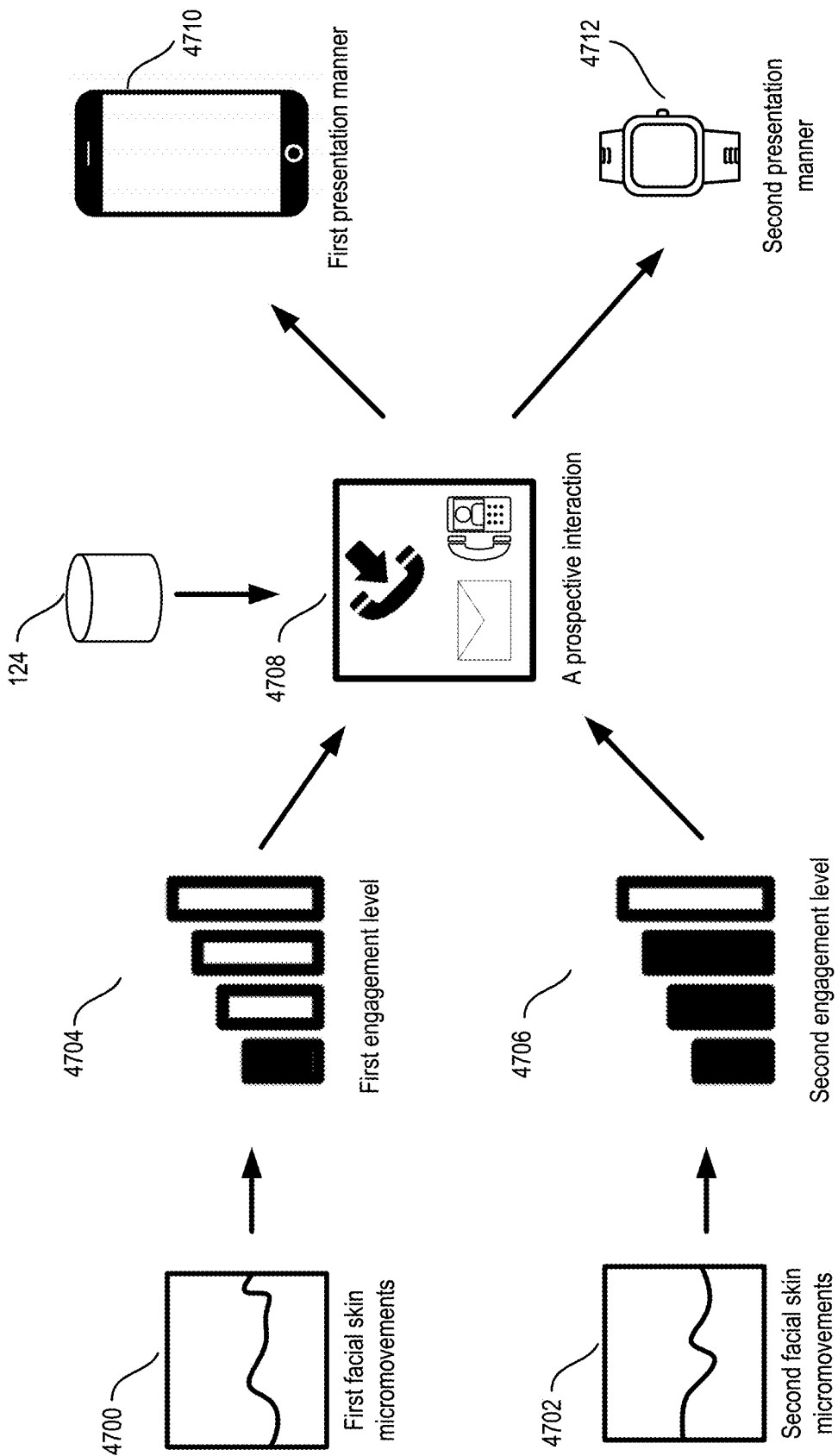
FIG. 47 is a schematic illustration of an example process of ascertaining presentation manners based on facial skin micromovements, consistent with some embodiments of the present disclosure.

By way of a non-limiting example, FIG. 47 illustrates a system 47-100 of attention-associated interactions based on facial skin micromovements, consistent with some embodiments of the present disclosure. As seen in FIG. 47, such a system 47-100 may involve attention association interactions in the form of a first engagement level 4704 and a second engagement level 4706. An engagement level may refer to the attention level of a user as determined based on received facial skin micromovements. Thus, for example, the larger number of solid bars in the second engagement level 4706 indicates that an attention level of the user in the second engagement level 4706 is higher than the attention level of the user in the first engagement level 4704. Furthermore, the first engagement level 4704 may be based on first facial skin micromovements 4700 and the second engagement level 4706 may be based on second facial skin improvements 4702.

Figure 48:
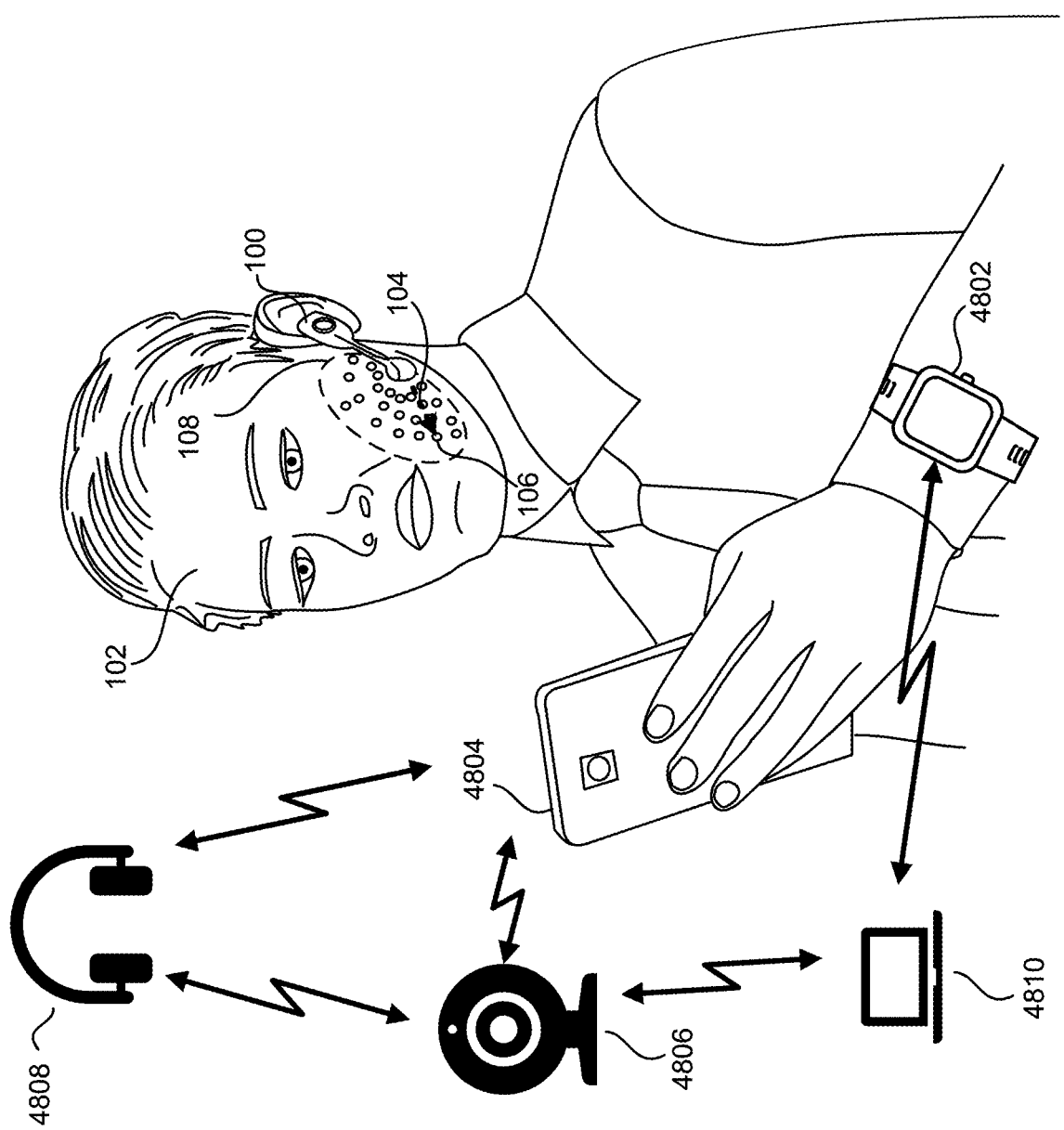
FIG. 48 is a schematic illustration of a user using an exemplary system of attention-associated interactions based on facial skin micromovements, consistent with some embodiments of the present disclosure.

By way of a non-limiting example, FIG. 48 illustrates a user using a system of attention-associated interactions based on facial skin micromovements, consistent with some embodiments of the present disclosure. As seen in FIG. 48, such a system 4820 may include an individual 102 utilizing a speech detection system 100, as describe and exemplified elsewhere in this disclosure. The speech detection system 100 may be configured to direct projected light 104 toward respective location(s) on the face of individual 102, such as the facial region 108, thus creating an array of light spots 106 extending over a facial region 108 of the face of individual 102. Thereafter, the speech detection system 100 may detect attention-associated interactions based on facial skin micromovements of individual 102.

Some disclosed embodiments involve determining facial skin micromovements of an individual based on reflections of coherent light from a facial region of the individual. "Facial skin micromovements" refers to skin motions on the face. As described elsewhere in this disclosure, such motions may occur as the result of movements of one or more muscles underlying the skin. "Determining" or "determine" in this context, refers to ascertaining facial skin micromovements. Thus, determining facial skin micromovements involves ascertaining movements of facial skin. These movements may be ascertained based on reflections of coherent light from a facial region, as described elsewhere herein.

By way of a non-limiting example, FIG. 47 is a schematic illustration of exemplary activities involving attention-associated interactions based on facial skin micromovements. As seen in FIG. 47, first facial skin micromovements 4700 and second facial skin micromovements 4702 are determined. This may occur, for example, using elements of system 4820 as illustrated in FIG. 48, Using such a system 4820, facial skin movements of an individual 102 may be determined based on reflections of coherent light 104 from a facial region 108 of an individual 102.

In some disclosed embodiments the facial skin micromovements are used to determine a specific engagement level of the individual. An "engagement level" refers to a degree or extent to which an individual provides attention or focus. The engagement level may be determined, at least in part with reference to facial skin micromovements. Correlations between attention level and facial skin micromovements may be common across a group of individuals or may be unique to a particular individual. For example, in some instances, a low level of engagement may be ascertained from a lack of facial skin micromovements or from a certain orientation of the facial skin micromovements and a higher level of engagement may be determined from a higher level of facial skin micromovements and/or from a certain orientation of the facial skin micromovements. Additionally or alternatively, the facial skin micromovements may reveal patterns indicative of a level of attention. For example, an attentive or engaged individual may display facial skin micromovements in the form of expressions or micro expressions which indicate attentiveness. For example, a slight raising of the brow, nodding, a wide opening of the eyes, blinking, or any other appropriate expression or micro expression may indicate attentiveness. Alternatively, an individual with lower levels of attention may show less of such expressions or micro expressions. Moreover, an attentive or engaged individual may display facial skin micromovements in the form of micromovements of facial muscle tone and engagement of pre-vocalization muscles which indicate attentiveness. Alternatively, an individual with lower levels of attention may display less changes in the muscle tones and thus less micromovements. Furthermore, any changes in either the aforementioned expressions or micro expressions or in the aforementioned micromovements of facial muscle tone and engagement of pre-vocalization muscles may also indicate a level of attentiveness. Indeed, such changes may be tracked, gathered, measured, and used as training data to interpret the appropriate levels of attention of the user. Additionally or alternatively, the facial skin micromovements may be interpreted as described elsewhere herein to determine silent speech, and that silent speech may be analyzed to determine a correlation to a particular topic or object.

A specific engagement level refers to a particular engagement level. In some embodiments, the particular engagement level may be binary—engaged or disengaged. In other embodiments, the specific level might be based on a gradation such as high, medium, or low. In other embodiments, the gradations may be more topically granular, such as whether or the extent to which a user is engaged with the topic at hand. Engagement levels might also indicate the state of the individual—focused, daydreaming, scattered, divided attention, etc. In yet other embodiments, the engagement level may be a score, such as on a scale of 1-10 or 1-100. Some embodiments may combine two or more of the foregoing factors to determine an engagement level. Any time facial skin micromovements are either collected, analyzed, interpreted, or otherwise employed in determining an engagement level, the facial skin micromovements are "used" to determine the engagement level.

In one example, a specific engagement level may indicate that the user and/or individual is speaking. Another specific engagement level may indicate that the user and/or individual is resting. Still another specific engagement may indicate that the user and/or individual is thinking. In still another example, a specific engagement level may indicate that the user and/or individual is speaking vigorously, speaking softly, whispering, or shouting. In yet another example, the specific engagement level may indicate that the user and/or individual is restless, fidgeting, anxious, agitated, uneasy, tense, nervous, impatient, edgy, and/or unsettled. In still another example, the specific engagement level may indicate that the user and/or individual is resting deeply, relaxing, reclining, unwinding, dozing, and/or sleeping. In still another example, the specific engagement level may indicate that the user and/or individual is thinking deeply, pondering, reflecting, deliberating, ruminating, brooding, musing, and/or contemplating. In yet another example, the specific engagement level may indicate that the user and/or individual is forgetting, overlooking, dismissing, and/or abandoning thoughts. In a further example, the specific engagement level may indicate that the user and/or individual is engaging, connecting, and/or participating at a high figure level (e.g., 9/10), a low figure level (e.g., 1/10), and/or any level in between. In still a further example, the aforementioned levels may have a greater number of graduations and/or be based on a fractional and/or percentage basis. For example, the specific engagement level may indicate that the user and/or individual has an 80% engagement level, an 85% pondering level, and a 50% anxious level. Note such examples are merely exemplary and do not define the specific engagement level to a certain method of evaluation.

Consistent with some disclosed embodiments, the specific engagement level includes a category of engagement. A "category of engagement" may refer to a set, grouping, type, kind, division, genre, bracket, class, and/or classification of different types of user and/or individual engagements that share common characteristics, features, and/or criteria. The examples provided in the forgoing paragraphs may each be characterized as a category of engagement levels. Other examples include interested, disinterested, bored, focused, unfocused, distracted, engaged, unengaged, responsive, unresponsive, motivated, unmotivated, attentive, inattentive, indifferent, apathetic, or any other characterization of engagement.

Consistent with some disclosed embodiments, the specific engagement level may include a magnitude of engagement. A "magnitude of engagement" may refer to the level, extent, degree, or intensity of the engagement. For example, degree such as highly, moderately, or slightly might be associated with each category. Or a numerical value might be associated with a category or an engagement level. For example, the specific engagement level may indicate that the user and/or individual has a magnitude of engagement that points to a 7/10 or a 70% attention level, for example. Note such examples are merely exemplary.

Consistent with some disclosed embodiments, the specific engagement level is reflective of an extent to which the individual is engaged in an activity including at least one of a conversation, thoughts, or rest. A "conversation" may refer to a verbal or nonverbal exchange of ideas, thoughts, information, notions, and/or concepts between two or more people, entities, beings, and/or individuals. A "thought" may refer to a mental process of perceiving, processing, and organization information in the brain. Thoughts may be either conscious or unconscious, rational, or irrational, and/or positive or negative. "Rest" may refer to a state of relaxation of a user, being, and/or entity, when one is not engaging in exertion—wherein such exertion may be either physical or mental exertion. Thus, a specific engagement level reflective of an extent to which an individual is engaged in an activity may refer to any indicator of the level, degree, scope, intensity, or range of an activity being performed by the user.

Some disclosed embodiments involve determining the extent to which the individual is engaged in the activity based on facial skin micromovements that correspond with recruitment of at least one muscle out of a group of muscles including: a zygomaticus muscle, an orbicularis oris muscle, a risorius muscle, or a levator labii superioris alaeque nasi muscle (as described and exemplified elsewhere in this disclosure).

By way of a non-limiting example, in FIG. 47 facial skin micromovements 4700, 4702 are used to determine a specific engagement level 4704, 4706 of the individual. (The bar graphs in FIG. 47 are icons denoting engagement levels for purposes of the figure, and are not intended to suggest that an engagement level is necessarily reflected in a bar graph). Each of the specific engagement levels 4704, 4706 may be reflective of an extent to which the individual is engaged in an activity such as focusing on materials or information being presented to the user. As discussed elsewhere herein, the determination of engagement may be derived from the first facial skin micromovements 4700 and the second facial skin micromovements 4702 corresponding to recruitment of at least one muscle out of a group of muscles including: a zygomaticus muscle, an orbicularis oris muscle, a risorius muscle, or a levator labii superioris alaeque nasi muscle.

By way of a non-limiting example, in FIG. 48 an individual 102 wearing speech detection system 100 exhibits the facial skin micromovements that are manifest in light reflections 104. Those reflections may be analyzed to determine an engagement level of individual 102 in an activity based on muscle movement beneath the skin.

Some disclosed embodiments involve receiving data associated with a prospective interaction with the individual. A "prospective interaction" may include a possible or potential exchange or communication between two or more individuals or entities. Such interactions may include phone calls, video calls, texts, chats, face-to-face, emails, instant messaging, social media interactions, collaboration tool interactions (e.g., Google docs) or any other way one individual might convey information to another or communicate with another. Receiving data associated with a prospective interaction may include detecting a signal reflective of an attempted initiation of the interaction or an initiation of an interaction. For example, if an individual is wearing a connected headset or using a mobile phone, signals (data) may be received indicating an incoming call, email, or other message, or the receipt of information (e.g., a transmitted document or image). The data might be received by intercepting transmission signals transmitted over a network, through analysis of sound, or through an analysis of images. The received data may simply indicate that a communication or exchange is requested (or has initially begun) and/or may also include substantive content. Substantive content may include an identifier of another entity or individual attempting to initiate the interaction, information about the individual, or substance of the attempted interaction. For example, if Bob McDuffy sends an urgent email with an attachment about bird watching, the data associated with the prospective interaction may include 1) the fact that there is a prospective communication in the form of an email; 2) the email is urgent; 3) the email is from Bob McDuffy; 4) the email includes an attachment; and/or 5) the attachment addresses bird watching. Any one or more of the preceding are examples of data associated with a prospective interaction.

Consistent with some disclosed embodiments, the received data associated with the prospective interaction may include an incoming call. An "incoming call" may include any communication event received by a person, individual, being, and/or entity. The incoming call may include a voice call, a video call, a voicemail message, and/or a video message.

Consistent with some disclosure embodiments, the received data associated with the prospective interaction may include an incoming text message. An "incoming text message" may include a communication containing alphanumeric, such as emails, texts, WhatsApp messages, Slack messages, chats, SMS messages or any other textual communication.

Consistent with some disclosed embodiments, the received data associated with the prospective interaction is indicative of an importance level or an urgency level of the prospective interaction. "Indicative" may refer to being suggestive, demonstrative, or representative. An "importance level" may further indicate the extent, degree, scope, range, and/or intensity of relevance, weight, consequence, value, worth, emphasis, seriousness, momentousness, criticality, and/or essentiality assigned to a thing, user, individual, person, being, and/or entity. An "urgency level" may indicate an immediacy of a requested response. "Data indicative of an importance level" may refer to a sign, signal, cue, clue, pointer, manifestation, mark, symbol, evidence, and/or proof in the data that suggests, demonstrates, represents, denotes, connotes, implies, alludes to, or hints at an importance level described above.

For example, an importance level may indicate a prospective interaction as an interaction of either high importance, medium importance, and/or low importance. In such an example, high importance may reflect a matter that requires urgent and immediate attention, medium importance may reflect a matter that requires prompt but not immediate attention, and low importance may reflect a non-urgent issue that requires a resolution and/or solution but does not require either prompt or immediate attention. By way of example, a message may be marked as urgent, indicated an impending deadline, contain text or audio indicating the communication is urgent, or contain information recognized as urgent.

Also, data indicative of an importance level may be, for example, a notification, a voice notification, a video notification, an alert, a message, a text message, a voicemail message, a video message, a vibration, and/or a flashing light that signals the importance level of a matter. For example, the intensity of the voice notification, vibration, and/or flashing light may vary in intensity depending on the importance level of the matter. A matter of high importance may have, for example, a louder voice notification, a louder vibration, and/or a more intensely flashing light than a matter of medium importance. Moreover, a matter of low importance may have a more diminished voice notification, a more diminished vibration, and/or a less intensely flashing light than the matter of medium importance.

By way of non-limiting example, FIG. 49A-C illustrate receipt of a prospective interaction via a device 4904, such as a cell phone. Received data associated with the prospective interaction may be received via the device 4904 and may be indicative of an importance level and/or an urgency level of the prospective interaction. For example, as illustrated in FIG. 49A, a notation of an incoming text message contains a marking "Urgent." In FIG. 49B or 49C, a special ringtone or visual indication may indicate urgency or that an incoming communication is from someone identified as important.

Aspects of the disclosure may further include accessing a data structure correlating information reflective of alternative engagement levels with differing presentation manners. A presentation manner is a way in which information is conveyed. Different manners of presentation may include, for example, textual displays, added color to a display, increased or altered font size, audio presentation or augmentation, a simplified presentation, a graphical presentation, presentation imagery or any other way information can be conveyed. A presentation manner may also refer to a selection of a device on which information is presented. Differing manners of presentation in this context may involve presenting information via one or more of a smartphone, tablet, smart goggles, smart glasses, smartwatch, laptop, PC, or any other mobile or immobile communications device. A data structure may store, for example, templates for differing manners of presentation, correlated to engagement levels. For example, when an engagement level is high, a text message's manner of presentation may be unaltered from its original form. For an engagement level indicative of a user being tired (or straining eyes), the presentation manner may include increasing font size. An engagement level reflecting distraction may correlate to a presentation level that adds color, flash, or other visual enhancements to catch the user's attention. If engagement an engagement level indicates that a user is highly focused on a task, the correlated presentation manner might be to delay the conveyance of information altogether to avoid distraction from the important task at hand. These are just examples. The number and extent of presentation manners may be based on design choice. The data structure, which can be any mechanism for storing correlated information, may be accessed through the performance of a lookup or other comparison of a current engagement level with stored information corresponding to the engagement level. In one example, the correlations may be stored in a form of database, the database being at least part of the associated data structure. In other embodiments, the correlations involve a of a set of rules, and when the rule is met, the correlation is established. In yet other embodiments, the data structure might include an artificial intelligence data set, and an AI engine might be used to identify the correlations. All of the above are examples of a data structure correlating information reflective of alternative engagement levels with differing presentation manners. In each example, the stored information, be it the information in the database, the set of rules, or the AI data set are considered correlating information stored in a data structure.

Consistent with some disclosed embodiments, the associated differing presentation manners include notifying the individual of the incoming call and directing the incoming call to voicemail. Another manner of presentation of a prospective interaction involves redirecting the interaction. For example, a call may be routed to voice mail (e.g., the presentation manner may be redirecting of the call to voicemail to avoid distraction when an engagement level indicates that taking the call is not opportune. Alternatively, a presentation manner may involve providing a notification (notifying) of an incoming call. Notifying refers to informing and directing refers to routing. For example, when an engagement level indicates that a time might not be opportune to take an incoming call, the incoming call might be presented discreetly (e.g., without audible ring). Thereafter, if the call is not accepted by the individual, the presentation manner may involve directing the call to voicemail or playing a predefined message for the caller "Voicemail" refers to a telecommunications service that allows callers to leave recorded voice messages for an unavailable recipient.

Consistent with some disclosure embodiments, the received data associated with the prospective interaction includes an incoming text message and the associated differing presentation manners include presenting the text message to the individual in real time and deferring presentation of the text message to a later time. Similar to other examples, depending on an individual's engagement level, the system may choose presentation manner for a text message that involves either presenting the text message or deferring presentation of the text message. The presenting may occur in real time (i.e., with little or no delay) if the engagement level indicates that the current time is appropriate for presentation (e.g., for displaying, audibly transmitting, or otherwise conveying the substance of the text message). If the engagement level correlates to an inopportune time, presentation of the text message may be deferred until a later time. Deferral refers to delay. For example, the system may continue to monitor the engagement level, and when it reaches an opportune level, the message might then be presented to the individual. In this example, the individual may avoid interruptions when focus is needed, and when focus requirements are no longer as high, messages can be automatically presented. In another example, deferred messages may be archived for the user to access at the user's will.

Processes such as those previously described may be carried out consistent with the flow illustrated in in FIG. 47, where data structure 124 is accessed. The data structure 124 correlates information reflective of alternative engagement levels with presentation manners. In this example, manners of presentation involve differing devices on which information is presented. Based on the detection of a first engagement level 4704, the manner of presentation 4711 involving a cell phone may be employed. Based on detection of a second engagement level 4706, the manner of presentation 4712 presenting information on a smartwatch. By way of example with reference to FIG. 48, an incoming call may be received via smartphone 4804, smartwatch 4802, a device 4810 such as a laptop, desktop, and/or computer, a device 4806, such as a video recorder, and/or a video recording communications device, and/or the device 4808, such as headphones, earphones, and/or speakers.

In some disclosed embodiments based on the specific engagement level and the correlating information, determining a specific presentation manner for the prospective interaction. As described earlier, a data structure containing correlating information is accessed. When a correlation is determined for a specific engagement level (e.g., a current determined engagement level), a specific presentation manner (e.g., the presentation manner correlated to the determined engagement level) is determined based on the correlating information. For example, if a specific engagement level reflects that an individual is highly focused on a matter at hand, the associated presentation manner might be that all calls are diverted to voicemail. In this example, the incoming phone call is the prospective interaction, and the specific presentation manner is the diversion of that phone call to voicemail. Of course, this is just an example, and the prospective interaction, the presentation manner, and the data structure may vary based on implementation. The data in the data structure may be learned from a group or may be specific to an individual user. Some users, for example, might want calls sent to voicemail when they are in a highly focused level of engagement, and others might prefer the distraction, with a presentation manner might include a visual or audio presentation identifying the prospective interaction (in this instance the incoming call). In a rules based approach, the data structure might contain a rule set by the user directing the system to treat prospective interactions in a prescribed manner. In other instances, the system might learn preferred presentation manners from the user's behavioral patterns associated with determined facial skin micromovements. For example, if a user tends to ignore calls when the user is engaged in speaking, the system might learn to divert calls in such situations. If the system learns that regardless of an engagement level, the user always takes calls from a number associated with the user's spouse, an associated rule might be established. Rules can overlap with other forms of correlations. For example, a data structure might store a default correlation, but a user might be permitted to store override correlations, such as in the last example. By way of another example, if an individual has a specific engagement level of "fidgeting" or "restlessness" and the correlating information relays that the individual should be concentrating and/or paying attention, a specific presentation manner may include adjusting a presentation of information to be more engaging. This might include, for example, an audio notification (presentation manner), or an eye catching visual presentation manner.

Consistent with some disclosed embodiments, determining the specific presentation manner for the prospective interaction includes determining how to notify the individual of the prospective interaction. Determining how to notify the individual may include establishing, selecting, or choosing a particular method, way, or technique for notifying the individual and/or user of the prospective interaction. In one example, determining how to notify may include establishing, selecting, or choosing a ringtone, wherein the user and/or individual may be notified of a prospective interaction and/or a call through a ringing tone. The user and/or individual may customize the ringtone to suit preferences. Alternatively, determining how to notify may include establishing, selecting, or choosing vibration of one or more components of a user device, wherein the vibration notifies or alerts the user of an incoming call, incoming video call, incoming message, and/or incoming text message. A vibration notification may be particularly useful when a ringing tone may be disruptive or inappropriate.

In another example, determining how to notify may include establishing, selecting, or choosing a notification sound, wherein the user and/or individual may be notified of a prospective interaction through a notification sound. In effect, the individual and/or user may be notified via a notification sound. Similar to a ringtone, a user and/or individual may also set up a notification sound to notify the user and/or individual of an incoming call, incoming video call, incoming message, and/or incoming text message. This is different from the ringtone, which is specific to incoming calls.

In still another example, determining how to notify may include establishing, selecting, or choosing a light-emitting diode (LED) notification light or other visual presentation on a display, wherein the user and/or individual may be notified of a prospective interaction through such a visual presentation. Many electronic devices, including smartphones, may have a small LED light or a display area that can be set to blink when there is an incoming call, incoming vide call, incoming message, and/or incoming text message. This is particularly useful for a user and/or individual who may not be able to hear the ringing or vibration. The electronic device may also be a tablet, a laptop, a desktop, a computer, and/or smartwatch, among other electronic devices.

In another example, determining how to notify may include establishing, selecting, or choosing a pop-up notification, wherein the user and/or individual may be notified of a prospective interaction through a pop-up notification. A pop-up notification may be displayed on a screen by electronic devices, particularly smartphones, where there is an incoming call, incoming video call, incoming message, and/or incoming text message. The pop-up notification may be useful when the user and/or individual is using and/or utilizing the respective electronic device and may not have noticed the notification or another visual presentation. The electronic device may also be a tablet, a laptop, a desktop, a computer, and/or smartwatch, among other electronic devices.

In another example, determining how to notify may include establishing, selecting, or choosing a lock screen notification, a haptic feedback notification, or a voice notification (real or simulated). Each of these are other examples of presentation manners. Many electronic devices, particularly smartphones, display a notification on the lock screen when there is an incoming call, incoming video call, incoming message, and/or incoming text message.

Haptic feedback may be a slight vibration, movement, interaction, and/or tactile interaction with the user and/or individual that may be felt by the user and/or individual when interacting with the electronic device. The haptic feedback may be used to notify the user and/or individual of an incoming call, incoming video call, incoming message, and/or incoming text message. A voice notification may simulate a human speaking a name of a person seeking to engage.

Consistent with some disclosed embodiments, determining how to notify the individual of the prospective interaction is based least in part on an identification of a plurality of electronic devices currently used by the individual. In some instances, an individual may simultaneously use a number of devices including, for example, all the devices described in connection with FIG. 48. The devices currently used may play a role in the notification of the prospective interaction. Identifying such devices refers the act of recognizing and/or verifying that the device is in use. Once a device is associated with a user, for example, the system may determine through an active pairing or a pinging that the device is available for notifications. Then, the notification manner will take the availability into account. If for example, the user's smart watch is available, a presentation manner may involve sending a notification to the smart watch. But if the smart watch is not available, the presentation manner may differ (e.g., a notification may be sent to the user's smart phone.) In this embodiment, the presentation manners are therefore conditional on the available user devices for receiving notifications.

Consistent with some disclosed embodiments, the specific presentation manner is determined based at least in part on an importance level or an urgency level. "Importance level" and "urgency level" may be understood as described and exemplified elsewhere in this disclosure. Thus, in these exemplary embodiments, the presentation manner is conditional on the importance level or the urgency level of the prospective interaction. A call from a supervisor or a spouse may be assigned an importance level higher than that of a friend. Friends might be routed to voicemail during do not disturb engagement level, while a spouse or supervisor's prospective communication may be announced or presented on a display before being routed to voicemail. Similarly, if the immediacy of a prospective interaction is determined to be high, the interaction may receive an elevated presentation manner.

Consistent with some disclosure embodiments, the specific presentation manner includes deferring presentation of content until a time period of detected low engagement. A time period of low engagement" refers to when an individual is less involved than normal in an activity. The time period can be a matter of design choice. For example, if a low engagement level is detected for a matter of seconds, tens of seconds, a minute or more, deferred content may be automatically presented to the individual. The manner of presentation of the deferred content and the order of presentation may be based on preset rules or may be based on training from past situations that determines what a user deems most important.

Additionally or alternatively, a user might be able to predefine time periods to the user's liking. For example, present deferred text messages on my phone when I have a low engagement level for more than 45 seconds.

By way of other examples, if the specific engagement level of the user indicates that the user is currently speaking vigorously or thinking intensely, the specific presentation manner may be a deferred text message to a smartphone, wherein the text message is delivered after it has been determined that the user has entered a time period of idleness. Also, by way of example, if the specific engagement level of the user indicates that the user is nervous, impatient, and/or unsettled, the specific presentation manner may be a deferred notification to a smartwatch, wherein the notification is delivered after it has been determined that the user has entered a time period of resting and/or relaxation.

Aspects of the disclosure may further include associating the specific presentation manner with the prospective interaction for subsequent engagement with the individual. Associating the specific presentation manner with the prospective interaction refers to the fact that after a presentation manner is determined or correlated to a prospective interaction, that determination or correlation is maintained for further use. In the context of AI, this may occur in a data set trained to provide the specific presentation manner when a similar prospective interaction is encountered in the future under conditions of the same or similar engagement level. In a rules based arrangement, the determination may be reflected in a rule that is adopted, and in a data base embodiment, the determination or correlation may be maintained in a database for future reference.

With reference to the process flow diagram of FIG. 47, the AI dataset, rules, or stored database correlations may be maintained in data structure 124. When a prospective interaction is encountered in combination with a specific detected engagement level, the presentation manner may be selected from data structure 124.

Linkages between devices and/or communications accounts, a data structure, and an engagement level detection system enable the functionality described herein. For example, speech detection system 100 in FIG. 48 may be paired with each of the users devices, such as those illustrated and describe in connection with that figure. The logic operations described herein can be carried out by at least one processor within one or more of the devices illustrated in FIG. 48, or may wholly or partially be carried out in a server associated with data structure 124 (FIG. 47) or by at least one processor associated with data structure 124. Through the linkages (Wi-Fi, Bluetooth, NFC, cellular links, IP or TCP protocols, or other pairings or linking techniques) at least one processor may ascertain prospective communications and the engagement level of the user.

For example, when a prospective interaction is an incoming text message, specific presentation manner may involve display on smartphone 4804 under appropriate engagement level conditions. Thereafter, subsequent text messages may receive similar treatment.

Some disclosed embodiments involve generating an output reflecting the prospective interaction according to the determined specific presentation manner. "Generating an output" refers to an act of producing information. When a presentation manner is determined as previously discussed, information about the prospective interaction may be output in that determined manner. The output reflecting the prospective interaction may include, for example, one or more of an identification of the party initiating the interaction, an importance level, an urgency level, or substance of the prospective interaction. Thus, for example, if it is determined that when an engagement level is low, text messages are to be audibly presented via a speaker (i.e., the presentation manner in this example), an audible output occurs as the presentation manner.

Some disclosed embodiments involve operating at least one coherent light source in a manner enabling illuminating a non-lip portion of a face of the individual, and receiving signals indicative of the reflections of coherent light from the non-lip portion of the face. In some embodiments, speckle analysis is employed. As described elsewhere herein, detecting coherent light reflections from skin (e.g., using speckle analysis) is one way to determine silent speech, audible speech, health conditions, and psychological state. Correlation in all these categories can be determined empirically. The same processes as described herein in these contexts can be similarly applied in the context of using engagement levels for guiding presentation manners.

Some disclosed embodiments involve using the facial skin micromovements to determine that the individual is engaged in a conversation with another individual, determining whether the prospective interaction is relevant for the conversation, and wherein the specific presentation manner is determined based at least in part on a relevancy of the prospective interaction to the conversation. In some embodiments, the operations may further include using the facial skin micromovements to determine a subject of the conversation and wherein determining that the prospective interaction is relevant to the conversation is based on the received data associated with the prospective interaction and subject of the conversation. A conversation refers to a communication between two or more individuals, persons, or entities. Using one or more of the speech detection system described herein or other speech recognition technology, the topic, context, and/or substance of the conversation may be determined. In a similar way, a prospective interaction may be analyzed to determine its topic, context, and/or substance. At least one processor may determine contextual or substantive similarities between the conversation and the prospective interaction. If a similarity is found, the prospective interaction may be deemed "relevant," and that relevancy may impact the presentation manner. There are an infinite number of examples. In one situation, speech recognition analysis may determine that a current conversation involves the whereabouts of Sam Domino. During the conversation which would otherwise be subject to a non-interrupt protocol, a phone call might be incoming from Sam Domino. By comparing the caller ID name with the context of the conversation, at least one processor may determine that the phone call is relevant to the ongoing conversation (they both share a subject). Rather than divert the phone call to voicemail, at least one processor might cause a display on the user's phone that reads, "Incoming call from Sam Domino, do you want to take it?" In another example, a topic of ongoing conversation might be an upcoming conference, during which conversation a text is received from the conference organizer. At least one processor employing speech recognition techniques might identify the text as relevant to the conversation, and escalate the text to a vibration and display on the user's smart watch.

Consistent with some disclosure embodiments, when the prospective interaction is determined to be relevant to the conversation, a first presentation manner is used for the prospective interaction, and when the prospective interaction is determined to be irrelevant to the conversation, a second presentation manner is used for the prospective interaction, wherein the second presentation manner is more preferable to the user than the first presentation manner. As discussed in the previous examples, relevancy determinations resulted in a presentation manner involving presentation of information involving the prospective interaction. When at least one processor comparing the two streams of data (conversation and prospective interaction) determines that the prospective communication is irrelevant to the conversation, a second manner of presentation may be implemented. In the two prior examples, the phone call from Sam Domino might be diverted to voicemail and the text from the conference organizer might be temporarily archived so as not to interfere with the user's attention during the conversation.

Figure 50:
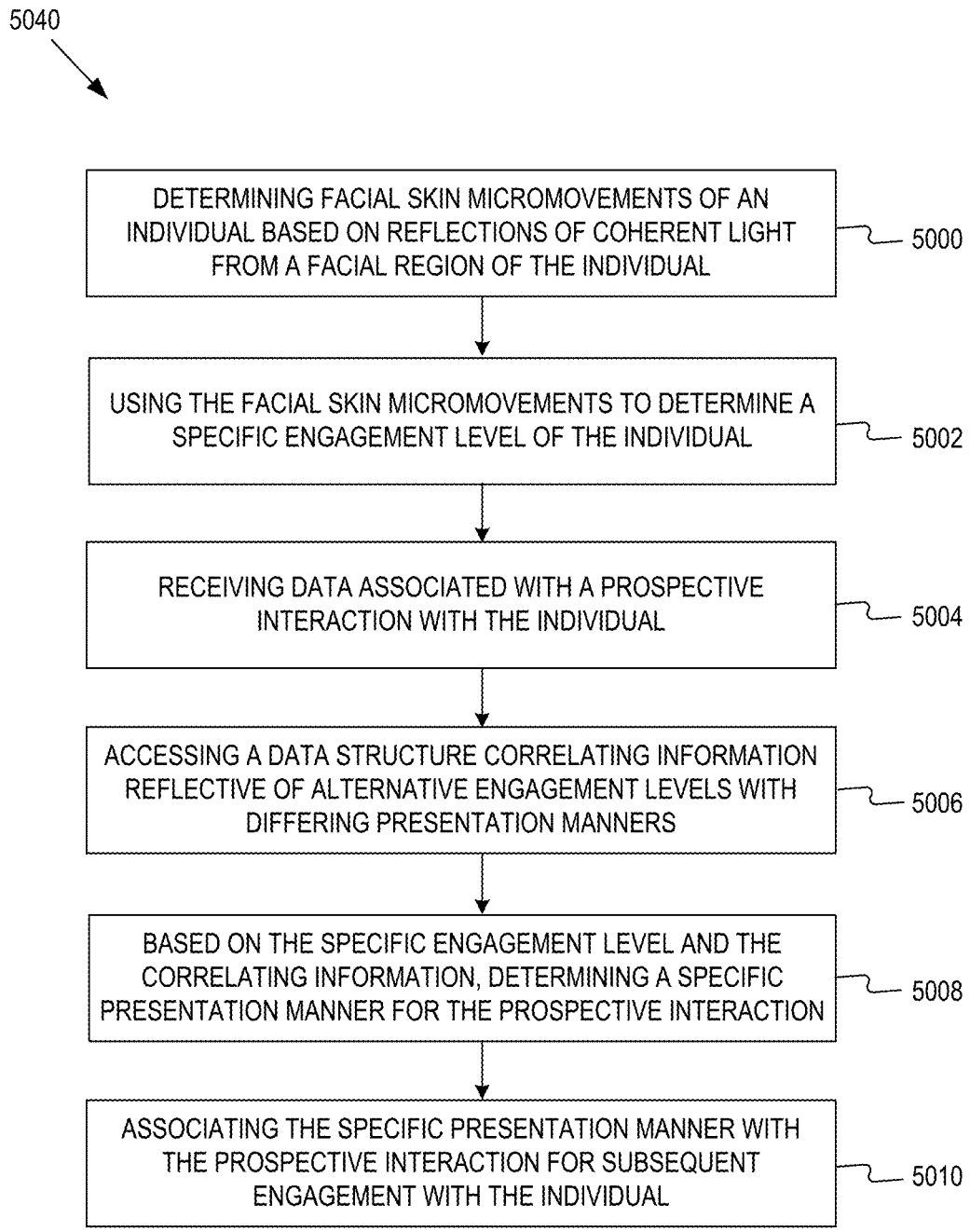
FIG. 50 is a flowchart of an example process of ascertaining presentation manners based on facial skin micromovements, consistent with some embodiments of the present disclosure.

Some disclosed embodiments may be carried out in a manner consistent with process 5040 presented in the flow chart of FIG. 50. In step 5000, facial skin micromovements are of an individual are determined as described earlier based on reflections of coherent light from a facial region of the individual. In step 5002, the facial skin micromovements are used to determine a specific engagement level of the individual, as described earlier. In step 5004, data associated with a prospective interaction with the individual is received as described earlier. In step 5006, a data structure correlating information reflective of alternative engagement levels with differing presentation manners is accessed, as described earlier. In step 5008, based on the specific engagement level and the correlating information, a specific presentation manner for the prospective interaction is determined as described earlier. In step 5010, the specific presentation manner is associated with the prospective interaction for subsequent engagement with the individual, as described earlier.

Different users may be associated with different preferences for consuming synthesized speech. For example, an individual may prefer to receive synthesized speech translated to a familiar language, a person with a hearing disability may prefer to hear synthesized speech at a slower than average pace, and a person in a noisy location may prefer to hear synthesized speech at a higher than average volume. Disclosed embodiments may provide systems, methods and computer program products to synthesize speech from detected facial skin micromovements and customize the synthesized speech to fit the needs of different users.

In some disclosed embodiments, voice synthetization may be based on detected facial micromovements. Particular facial skin micromovements of a first individual communicating with a second individual may be determined based on reflections of light from a facial region of the first individual. A data structure correlating facial micromovements with words may be accessed. A lookup may be performed in the data structure to identify particular words associated with the particular facial skin micromovements. An input associated with a preferred speech consumption characteristic of the second individual may be obtained. The preferred speech consumption characteristic may be adopted. An audible output of the particular words may be synthesized using the adopted preferred speech consumption characteristic.

Some disclosed embodiments involve voice synthetization operations from detected facial skin micromovements. Voice synthetization (e.g., speech synthesis or text-to-speech, TTS) may involve generating artificial, human-like speech using computer algorithms that convert text data to spoken words for outputting via one or more speaker. Voice synthetization may combine linguistic, acoustic, and/or signal processing techniques to create natural-sounding speech. Voice synthetization operations may include at least one processor analyzing text to identify linguistic features such as a language, word boundaries, sentence structure, punctuation, and/or pronunciation rules. Voice synthetization operations may further include at least one processing parsing and transforming text to a phonetic representation (e.g., phonemes and combinations thereof). Additionally, voice synthetization operations may include at least one processor building an acoustic model for a phonetic representation using a phonemes database to capture characteristics, such as duration, pitch, and/or spectral content for each phoneme, and/or converting an acoustic model to a synthetized voice using one or more signal processing techniques (e.g., formant synthesis, concatenative synthesis, or statistical parametric synthesis). In some embodiments, voice synthetization operations may include at least one processor applying one or more post-processing procedures to a synthetized voice, for example prosody adjustment for controlling pitch, stress, and/or rhythm. Detected facial skin micromovements may refer to sensed and/or measured facial skin micromovements (e.g., as described and exemplified elsewhere in this disclosure).

By way of a non-limiting example, in FIG. 1, at least one processor (e.g., processing devices 400 and/or 460 in FIG. 4) may receive from speech detection system 100, signals representing facial skin micromovements performed by individual 102 (e.g., first individual). The at least one processor may use the received signals to perform voice synthetization operations.

Some disclosed embodiments involve determining particular facial skin micromovements of a first individual speaking with a second individual based on reflections of light from a facial region of the first individual. An individual may refer to a human user capable at least of receiving communication from another human user. A first individual speaking with a second individual may refer to a first human user communicating with at least one other human user either through vocalization or through sub-vocalization. This may occur, for example, while wearing a speech detection system, such as those described herein. Reflections of light involve electromagnetic waves bouncing off a surface, where an angle at which a light wave hits a surface (e.g., an angle of incidence) equals an angle at which the light wave reflects off the surface (e.g., an angle of reflection). Reflections of light may include specular reflection and diffuse reflection. Specular reflection may involve light waves bouncing off a smooth surface (e.g., a mirror or still water) in a manner to maintain an original direction and angle of incidence relative to the surface, producing a clear, mirror-like image. Diffuse reflection may involve light waves bouncing off a rough or irregular surface causing reflected light to scatter in multiple directions, producing a diffuse or scattered reflection. Reflections of light from a facial region of an individual may refer to light emitted by an (e.g., controlled) light source to shine onto a facial region of an individual that may reflect off the facial region. The reflected light may be sensed by a light detector, which may provide electronic signals indicative of the reflections of light to at least one processor. For example, a speech detection system may be configured to shine light onto a facial region of a first individual speaking with and/or preparing to speak with a second individual, sense reflections of light bouncing off the facial region of the first individual, and provide electronic signals representing the reflections of light to at least one processor. Particular facial skin micromovements may refer to specific, distinct, and/or identifiable facial skin micromovements (e.g., from a plurality of possible facial skin micromovements). Particular facial skin micromovements may be associated with a preparation for and/or an occurrence of a communication of one or more words and/or (e.g., non-verbal) expressions. For example, at least one processor associated with a speech detection system may receive first signals representing reflections of light from a facial region of a first individual communicating with a second individual at a first instant in time, and receive second signals representing reflections of light from the facial region of the first individual communicating with the second individual at a second instant in time. The at least one processor may compare the first signals with the second signals to detect a discrepancy indicating an occurrence of a facial skin micromovement between the first instant in time and the second instant in time. The at least one processor may analyze the detected facial skin micromovement and/or compare the detected facial skin micromovement to one or more facial skin micromovements stored in memory to identify and/or determine an occurrence of a particular facial skin micromovement of the first individual speaking with the second individual.

By way of a non-limiting example, FIG. 51 illustrates individual 102 (e.g., first individual) wearing speech detection system 100 while speaking with a second individual 5100, consistent with some embodiments of the present disclosure. Second individual 5100 may be associated with a second mobile communications device 5102 configured to communicate with mobile communications device 120 via network 126 (see FIG. 1), and may wear a headset 5104 for consuming synthesized audible output. At least one processor (e.g., processing devices 400 and/or 460 in FIG. 4) may determine particular facial skin micromovements of individual 102 speaking with second individual 5100 based on reflections of light from facial region 108 of individual 102, as described and exemplified elsewhere in this disclosure.

Some disclosed embodiments involve accessing a data structure correlating facial micromovements with words. Accessing a data structure (as described and exemplified elsewhere in this disclosure) may involve establishing a communications channel with a data structure (e.g., via a communications network), gaining an access privilege to read from a data structure, querying a data structure, and/or receiving information from a data structure (e.g., in response to a query). Correlating may involve establishing one or more associations and/or determining one or more relationships between two data items based on commonly identified features. Correlating may additionally involve applying one or more mathematical and/or statistical functions (e.g., cross-correlations, autocorrelations, and/or convolutions) to determine a statistical distance between two or more data items. A data structure correlating facial micromovements with words may be understood as described and exemplified elsewhere in this disclosure. For example, such a data structure may include a searchable index of features or image embeddings capturing visual characteristics of image data, and may associate one or more such features and/or image embeddings with one or more words. At least one processor may query such a data structure with one or more images and/or image embeddings tracking facial micromovements to determine one or more words associated therewith based on a similarity measure. Examples of some similarity measures for correlating facial micromovements with words may include a cosine similarity, Euclidian distance, chi-square distance, and/or any other type of similarity measure.

By way of a non-limiting example, in FIG. 4, at least one processor (e.g., processing devices 400 and/or 460) may access data structure 422 and/or data structure 464 (e.g., via communications network 126 in FIG. 1) correlating facial micromovements with words.

Some disclosed embodiments involve performing a lookup in the data structure of particular words associated with the particular facial skin micromovements. A lookup may include a query, a search, a comparison and/or a request, e.g., for data based on one or more similarity measurements. Performing a lookup in a data structure of particular words associated with the particular facial skin micromovements may involve formulating a query based on particular facial skin micromovements determined based on reflections of light from a facial region of an individual, querying a data structure correlating facial micromovements with words, and/or receiving a response to a query satisfying one or more criterion included in the query, e.g., in accordance with content-based image retrieval (CBIR) techniques. For example, at least one processor may receive image data associated with particular facial skin micromovements from a light detector associated with a speech detection system. The at least one processor may extract features and/or image embeddings (e.g., color histograms, texture descriptors, shape representation, and/or facial movement patterns) from the image data, e.g., using artificial intelligence, deep learning, convolutional neural networks (CNNs), and/or any other feature and/or image embedding extraction methods. The at least one processor may formulate a query by transforming the extracted features and/or image embeddings associated with particular facial skin micromovements to a representation consistent with data stored in a data structure correlating facial micromovements with words, and may submit the generated query to (e.g., a search engine associated with) the data structure. In response to the query, the at least one processor may receive one or more words correlated with features and/or image embeddings represented by the query, e.g., based on one or more similarity measures. In some embodiments, the at least one processor may filter and/or select one or more correlated words based on one or more additional criterion, e.g., a context, a location, environmental factors, a demographic, social, and/or cultural category, other words previously determined based on facial skin micromovements, a language and/or dialect, an identity of a first and/or second individual, user preferences, habits, and/or patterns associated with the first and/or second individual, and/or any other criterion for determining particular words associated with particular facial micromovements. Such additional criteria may be stored in a data structure in association with the first and/or second individual (e.g., indexed using associated unique identifiers), allowing the at least one processor to retrieve additional criteria via query.

By way of a non-limiting example, in FIG. 4, the at least one processor (e.g., processing devices 400 and/or 460) may perform a lookup in data structures 422 and/or data structure 464 (e.g., via communications network 126 in FIG. 1) of particular words associated with the particular facial skin micromovements. For example, the at least one processor may receive information indicating an intention by individual 102 (e.g., first individual) to speak in English, and may base a lookup in data structures 422 and/or data structure 464 based on associating particular facial skin micromovements with particular English words.

Some disclosed embodiments involve obtaining an input associated with a preferred speech consumption characteristic of the second individual. Speech consumption may involve sensing and/or interpreting sound signals to associate words therewith and attribute meaning to the sound signals (e.g., for a particular language, dialect, context, format, medium or interface, and/or timing). Preferred may refer to chosen, elected, and/or favored. Preferred speech consumption characteristic may refer to attributes and/or properties associated with how an individual may prefer to consume speech, e.g., to enable an individual to attribute meaning and comprehension to speech. Some examples of preferred speech consumption characteristics may include sound characteristics, e.g., a preferred volume, speed, pitch, tone, timbre, sound clarity, sound fidelity, dynamic range, and/or frequency response. Some additional examples of preferred speech consumption characteristics may include verbal characteristics, such as enunciation, expression, accent, language, dialect, vocabulary, synonyms (e.g., slang terms), paraphrases, and/or any other verbal characteristic allowing attribution of meaning and comprehension to speech. Some further examples of preferred speech consumption characteristics may include a location, time, and/or date for consuming speech, a medium for consuming speech (e.g., audio, text, and/or image-based), and/or a specific electronic device for receiving speech (e.g., a mobile communications device, a laptop, and/or a headset). For example, an individual with hearing impairment may prefer amplification to consume quietly spoken speech, another individual may prefer a translation to a native tongue to consume speech spoken in a non-native language, and a person with cognitive impairment may prefer a simplified vocabulary to consume sophisticated speech. As another example, when located in a private location, a user may prefer to consume speech audibly, and when located in a public location, a user may prefer to consume speech as readable text. An input may include data provided by a user of an electronic device. An input may include any combination of audio, visual, video, text, gesture, touch input, and/or any other type of user input. Obtaining an input may involve receiving data via a user interface of an electronic device. Such a user interface may include, for example, a menu presenting selectable options, a field allowing for entry of text, a microphone paired with speech recognition software for detecting and analyzing speech, a camera paired with gesture recognition software for detecting and analyzing images, and/or any other user interface technique for receiving an input. In some embodiments, obtaining an input associated with a preferred speech consumption characteristics may include accessing a history of prior speech consumption habits and/or feedback associated therewith.

In some disclosed embodiments, obtaining the input associated with the preferred speech consumption characteristic of the second individual includes receiving the input from the first individual. For example, the first individual may provide an input to at least one processor via a user interface accessible to the first individual. Such a user interface may be associated with a speech detection system worn by the first user and/or with an electronic device (e.g., a mobile communications device) paired to a speech detection system worn by the first user.

By way of a non-limiting example, in FIG. 51, the at least one processor (e.g., processing devices 400 and/or 460) may obtain an input associated with a preferred speech consumption characteristic of second individual 5100 from individual 102 (e.g., first individual) via mobile communications device 120. For example, individual 102 may select a preferred volume by maneuvering a volume widget displayed on mobile communications device 120. Mobile communications device 120 may communicate the selected volume to the at least one processor associated with speech detection system 100 over communications network 126.

In some disclosed embodiments, obtaining the input associated with the preferred speech consumption characteristic of the second individual includes receiving the input from the second individual. For example, the second individual may provide an input to at least one processor via a user interface accessible to the second individual. Such a user interface may be associated with an electronic device (e.g., a mobile communications device and or a speech detection system associated with the second user) in communication with a speech detection system associated with the first user.

By way of a non-limiting example, in FIG. 51, the at least one processor (e.g., processing devices 400 and/or 460) may obtain an input from second individual 5100 via second mobile communications device 5102 indicating a preferred speech consumption characteristic of second individual 5100. For example, second individual 5100 may select French from a menu of candidate languages displayed on second mobile communications device 5102. Second mobile communications device 5102 may communicate the input indicating a preference to consume speech in French to mobile communications device 120 and/or speech detection system 100 via communications network 126 (see FIG. 1).

In some disclosed embodiments, obtaining the input associated with the preferred speech consumption characteristic of the second individual includes retrieving information on the second individual. Information on an individual may include a user profile, default and/or user-defined preferences, one or more recommendations and/or settings, a history, a social, cultural, national, and/or age demographic, a location, a time and/or date, a context, and/or any other information associated with a particular individual (e.g., stored in a data structure in association with a unique identifier for a particular individual), and/or any other information associated with preferred speech consumption characteristics of an individual. Retrieving information on an individual may include querying, searching, mining (e.g., crawling webpages and/or or scraping data via a communications network), and/or reading information from memory, e.g., based on a (e.g., unique) identity of an individual. For example, one or more preferred speech consumption characteristics associated with one or more individuals may be stored in a data structure on a memory device associated with a speech detection system. At least one processor may query the data structure for one or more speech consumption characteristics of a particular individual using a unique identifier for the particular individual.

By way of a non-limiting example, in FIG. 51, at least one processor (e.g., processing devices 400 and/or 460) may store a user profile including one or more preferred speech consumption characteristics for second individual 5100 in data structure 464. The at least one processor may retrieve the user profile associated with second individual 5100 (e.g., based on image data and/or a unique identifier), and determine based on the user profile that second individual 5100 prefers consuming speech in French, thereby obtaining the input associated with the preferred speech consumption characteristic of second individual 5100.

In some disclosed embodiments, obtaining the input associated with the preferred speech consumption characteristic of the second individual includes determining the information based on image data captured by an image sensor worn by the first individual. An image sensor worn by an individual may include any worn device configured to convert light into an electrical signal. Examples of image sensors are discussed elsewhere herein. For example, a light detector (e.g., a camera) included in a speech detection system worn by a first individual may capture one or more images of a second individual speaking with the first individual. At least one processor may receive and analyze the images to identify the second individual and may use the identity of the second individual to query a data structure storing preferred speech consumption characteristics of the second individual. In some embodiments, obtaining the input associated with the preferred speech consumption characteristic of the second individual includes receiving image data captured by a camera associated with a mobile communications device in communication with a speech detection system. The mobile communications device may be associated with the first and/or second individual. For example, at least one processor may analyze image data to determine an age, social, and/or cultural demographic, a spoken language (e.g., based on lip-reading), a location (e.g., indoors or outdoors, public or private), a context, and/or bodily gestures to determine preferred speech consumption characteristics.

In some disclosed embodiments, the input associated with the preferred speech consumption characteristic of the second individual is indicative of an age of the second individual. An age of an individual may refer to an age range (e.g., measured as years) or classification for an individual (e.g., child, adolescent, adult, middle-aged, senior citizen). In some embodiments, an age of an individual may be associated with a social and/or cultural age category (e.g., millennial, generation-Z, generation-X, silent generation). For example, a young adult may be associated with different slang terms, dialects, and/or speech styles than a middle-aged adult, a child may be associated with a simpler vocabulary than an adult, and a senior citizen may be associated with a louder volume and slower speech pace than an adolescent. An input indicative of an age may include at least one age-associated word (e.g., including one or more age-associated slang terms, phases, and/or expressions), a selection of an age category (e.g., from a menu), and/or entry of an age via a user interface (e.g., as text and/or voice entry). An input indicative of an age may include a location, for example a senior residence may be associated with senior citizens, a night club may be associated with youth, and an office may be associated with middle-aged adults. An input indicative of an age may include voice data. For example, at least one processor may analyze voice data of an individual (e.g., voice input) to determine one or more age-related vocal characteristics. For example, a pitch of a voice may change due to aging of a larynx and/or vocal folds (chords). An input indicative of an age may include image data. For example, at least one processor may analyze image data of an individual (e.g., image input) to determine an age of an individual. In some embodiments, adopting a preferred speech consumption characteristic may involve adopting one or more age-associated words, age-related voice characteristics (e.g., a youthful voice versus an elderly voice, a lower volume versus a higher volume, and/or a faster speech pace versus a slower speech pace).

By way of a non-limiting example, in FIG. 51, the at least one processor (e.g., processing devices 400 and/or 460) may receive image data of second individual 5100 from light detector 412 (see FIG. 4) of speech detection system 100 worn by individual 102 (e.g., first individual). The at least one processor may analyze the image data to determine an identity of second individual 5100. The at least one processor may use the identity of second individual 5100 (e.g., using an associated unique identifier) to query data structures 422 and/or 464 for one or more preferred speech consumption characteristics associated with second individual 5100. In some embodiments, the at least one processor may determine the age of second individual 5100 based on the received image data and may adjust a rate of speech based on the determined age. For example, the at least one processor may determine that second individual 5100 is a young adult who may prefer to consume speech at a faster than average pace of speech (e.g., 1.5 times the spoken rate of speech).

In some disclosed embodiments, the input associated with the preferred speech consumption characteristic of the second individual is indicative of environmental conditions associated with the second individual. An environmental condition may include a location, a noise level, an illumination level, a time of day, a time of year, a weather condition, and/or any other environmental factor that may affect a speech consumption capability and/or preference of an individual. Some examples of an environmental condition that may affect a speech consumption capability may include an indoor versus an outdoor location, a high traffic versus low traffic setting, an environment associated with noise restrictions (e.g., a library or hospital), an environment associated with a high level of noise (e.g., a sports stadium, or a windy environment), an environment associated with a content consumption restriction (e.g., a driver of a car who may be restricted from consuming text), and/or any other environmental condition potentially affecting a capability of a user to consume speech. For example, an individual standing outdoors in stormy weather may request to increase a volume for consuming speech, and an individual sitting in a library may request to consume speech silently, e.g., as a transcription to text. As another example, a driver of a car may prefer to consume speech audibly and a passenger of a car may prefer to consume speech as text.

An input indicative of environmental conditions may include audio input, a selection of an environmental condition (e.g., from a menu), and/or entry of an environmental condition via a user interface (e.g., as text and/or voice entry). For example, at least one processor may analyze an audio input associated with an individual to determine a weather condition (e.g., strong wind and/or rain) or background noise (e.g., a train station) associated with a preference to consume speech at an increased volume, or a lack of background noise associated with a preference to consume speech at a decreased volume. An input indicative of environmental conditions may include location data. For example, location data input may indicate a noisy location (e.g., a sports stadium or a night club) associated with a preference to consume speech at an increased volume or a quiet location (e.g., a library or hospital) associated with a preference to consume speech via an ear piece and/or as transcripted text. An input indicative of environmental conditions may include a voice data (e.g., an instruction to increase/decrease a volume and/or to consume speech as transcripted text). An input indicative of environmental conditions may include image data. For example, at least one processor may analyze image data input to determine an environment surrounding an individual and/or a gesture indicative of an environmental condition. For instance, an individual seated on a commuter train may be associated with a preference to consume speech via a headset and/or as transcripted text, and an individual located in a conference room may be associated with a preference to consume speech at a volume audible to other individuals in the conference room.

By way of a non-limiting example, in FIG. 51, the at least one processor (e.g., processing devices 400 and/or 460) may receive location data associated with second individual 5100 from second mobile communications device 5102 indicating a noisy environmental condition (e.g., a sports stadium). The at least one processor may associate the location data indicating a noisy environment with a preference to consume speech at a raised volume, and may cause synthesized speech to be audibly outputted at a maximum volume from headset 5104 paired to second mobile communications device 5102 via communications network 126.

In some disclosed embodiments, the input associated with the preferred speech consumption characteristic of the second individual is indicative of a hearing impairment of the second individual. A hearing impairment may refer to a disability hampering a capability to consume speech. Hearing impairment may be age-related, congenital, and/or environmental or temporal (e.g., while at a rock concert or construction site). For example, an elderly individual suffering from hearing impairment may prefer speech to be spoken louder and/or slower, and an individual located at a construction site may prefer speech to be transcribed to text. An input indicative of a hearing impairment may include at least one vocalized word (e.g., "hearing impaired"), a selection of hearing impairment and/or text entry of a hearing impairment (e.g., via an accessibility user interface). In some embodiments, an input indicative of a hearing impairment may include a signal (e.g., an optical and/or electrical signal) indicative of a hearing aid (e.g., Behind-the-ear (BTE), In-the-ear (ITE), In-the-canal (ITC), and/or Completely-in-the-canal (CIC) hearing aids). For instance, at least one processor may detect a hearing aid based on a Blue-Tooth and/or Wi-Fi connection to another electronic device (e.g., an electronic signal input), and/or based on image data of an individual (e.g., image input). In some embodiments, an input indicative of a hearing impairment may include a voice input of a hearing impaired individual. For example, at least one processor may analyze a voice input to determine one or more vocal distortions associated with hearing impairment (e.g., a flat tone with little modulation or inflection, imprecise articulation, absence of rhythm, and/or an anomalous breathing pattern). In some embodiments, an input indicative of a hearing impairment may include image data capturing a gesture by an individual signaling hearing impairment.

By way of a non-limiting example, in FIG. 51, the at least one processor (e.g., processing devices 400 and/or 460) may receive an input from second individual 5100 via second mobile communications device 5102 indicating a hearing impairment (e.g., via an accessibility user interface displayed on second mobile communications device 5102). The at least one processor may associate the input indicating hearing impairment with a preference to consume speech at a raised volume and a slower pace of speech. Optionally, the at least one processor may cause synthesized speech to be outputted via headset 5104 paired to second mobile communications device 5102.

In some disclosed embodiments, the input associated with the preferred speech consumption characteristic includes a preferred pace of speech. A pace of speech may refer to a rate at which words may be enunciated (e.g., a number of words spoken per minute). Setting a pace of speech may involve determining a duration for expressing one or more syllables of a word, and/or a duration of a silent gap delineating one or more synthesized words. An average pace of speech may range between 140 and 160 words per minute, a slow pace of speech may be less than 140 words per minute, and a fast rate of speech may be greater than 160 words per minute. For example, a child or an elderly individual may prefer a slower pace of speech to enable speech comprehension, and a college student reviewing material for a final exam may prefer a faster pace of speech. As another example, an individual performing a relaxing activity (e.g., yoga or meditation) may prefer slower paced speech, and an individual performing a non-relaxing activity (e.g., active exercise, or a competition) may prefer faster paced speech. An input associated with a preferred pace of speech may include at least one vocalized word (e.g., "slower" or "faster"), a selection of a pace of speech and/or text entry indicating a preferred pace of speech (e.g., via a user interface). In some embodiments, an input associated with a preferred pace of speech may include a physiological activity indicator. For example, at least one processor may detect a slow/fast breathing rate and/or heart rate to determine a preferred slower/faster pace of speech (e.g., to match or counter a physiological indicator). In some embodiments, an input associated with a preferred pace of speech may include a detected pace of speech associated with a voice input of an individual (e.g., such that a preferred pace of speech may match a detected pace of speech). In some embodiments, an input associated with a preferred pace of speech may include a context and/or topic of speech (e.g., a recitation of instructions may be associated with a slower preferred pace of speech and a motivational talk may be associated with a faster preferred pace of speech). In some embodiments, an input associated with a preferred pace of speech may include image data capturing a gesture by an individual signaling a preferred pace of speech.

In some disclosed embodiments, the input associated with the preferred speech consumption characteristic includes a speech volume. A speech volume may refer to loudness and/or intensity of spoken words and may be associated with a sound pressure level produced by a speaking individual. Speech volume may be measured in decibels (dB). Speech volume may range from very soft or whispered speech (e.g., a lower speech volume level of around 30 dB) to normal conversational speech (e.g., around 60 dB) to loud or shouted speech (e.g., a higher speech volume level of around 100 dB). For example, an individual located in a noisy environment may prefer a higher speech volume and an individual located in a quiet environment may prefer a lower speech volume. An input associated with a preferred speech volume may include at least one vocalized word (e.g., "louder" or "quieter"), a selection of a pace of a volume level (e.g., via a volume widget). In some embodimetres, an input associated with a preferred speech volume may include audio data. For example, at least one processor may determine a preferred speech volume to overcome a level of ambient noise and/or to match a volume of vocalized speech by an individual. In some embodiments, an input associated with a preferred speech volume may include image data capturing a gesture by an individual signaling a preferred speech volume. In some embodiments, an input associated with a preferred speech volume may include location data (e.g., a library may be associated with a preference for decreased speech volume and a train station may be associated with a preference for increased speech volume).

In some disclosed embodiments, the input associated with the preferred speech consumption characteristic includes a target language of speech other than a language associated with the particular facial skin micromovements. A target language of speech other than a language associated with a particular facial skin micromovement may refer to a language (e.g., second language) different than a first language associated with a particular facial skin micromovement. For example, a first individual wearing a speech detection system may perform a particular facial skin micromovement in preparation for speaking a word in a first language (e.g., English), and a second individual may prefer to consume the particular word translated to a second language (e.g., French). An input associated with a preferred target language may include at least one vocalized word (e.g., "French"), a selection and/or text entry of a target language (e.g., via a user interface). In some embodiments, an input indicative of a preferred target language may include voice data of an individual speaking in the preferred target language. In some embodiments, an input indicative of a preferred target language may include image data capturing a gesture by an individual signaling a preferred target language.

In some disclosed embodiments, the input associated with the preferred speech consumption characteristic includes a preferred voice. In some embodiments, the preferred voice is at least one of a celebrity voice, an accented voice, or a gender-based voice. A voice refers to a distinguishing audio output, either by a human or a simulation of a human. Voice characteristics that can make a voice distinguishable from another voice may include one or more of a vocal timbre, a tonal quality, a tonal color, a pitch, a loudness factor, and/or any other voice quality distinguishing one voice from another. A celebrity voice may refer to a recognizable voice associated with a well-known person. An accented voice may refer to a pronunciation of one or more words, an enunciation, expression, and/or accent, an emphasis of one or more syllables or phrases, a pitch and/or intonation of one or more vowels and/or consonants that may be distinctive to a particular country, region, cultural and/or ethnic group. A gender-based voice may refer to a vocal pitch and/or timbre characterizing a particular gender (e.g., a woman's voice versus a man's voice). An input associated with a preferred voice refers to any form of information identifying a preferred voice. The input could be for example, text, vocal, subvocal, or a selection from a pick list (e.g., vocalizing, subvocalizing, texting, or selecting the name "Elvis.") via a user interface. For example, at least one processor may receive voice data of an individual and analyze voice data to detect an accent and/or gender associated with the individual. The at least one processor may determine a preferred accent and/or gender to match a detected accent and/or gender of the individual.

By way of a non-limiting example, in FIG. 51, the at least one processor (e.g., processing devices 400 and/or 460) may receive an input from second individual 5100 indicating a preference to consume speech in French using a female voice, at a pace that is 1.5 times a natural pace of speech and at an increased volume. For example, second individual 5100 may provide inputs via a user interface displayed on second mobile communications device 5102 by adjusting a rate of audible output (e.g., via a pace of speech widget), manipulating a volume (e.g., via a volume widget), selecting French (e.g., from a menu offering multiple target languages for consuming speech), and selecting a checkbox indicating a preference for a female voice. Second mobile communications device 5102 may transmit the inputs to the at least one processor via communications network 126.

In some disclosed embodiments, the second individual is one of a plurality of individuals, and wherein the operations further comprise obtaining additional inputs from the plurality of individuals and classifying the plurality of individuals based on the additional inputs. A plurality of individuals may include multiple (e.g., at least two) individuals. Additional inputs may include at least two inputs other than (e.g., following) the received input associated with a preferred speech consumption characteristic of the second individual. For example, each of a plurality of individuals may provide an input via an associated electronic device (e.g., a mobile communications device and/or a speech detection system). The input may include voice data, selections and/or text entries via a user interface, image data (e.g., as gesture inputs), and/or any other type of user inputs. The additional inputs may be associated with one or more preferred speech consumption characteristics and/or one or more attributes allowing at least one processor to classify at least some of a plurality of individuals. Classifying may include categorizing and/or grouping, e.g., based on one or more shared traits and/or attributes. Classifying a plurality of individuals may involve determining a plurality of categories and/or groups and associating each individual of the plurality of individuals to at least one category and/or group (e.g., based on the additional inputs). In some embodiments, classifying a plurality of individuals may involve associating each individual of a plurality of individuals to only one category or group (e.g., exclusively). In some embodiments, at least some individuals may be associated with differing speech consumption characteristics and/or categories, and/or at least some individuals may be associated with the same speech consumption characteristics.

For example, following obtaining of the input associated with the preferred speech consumption characteristic of the second individual, the at least one processor may receive a plurality of additional inputs associated with a plurality of additional individuals. The at least one processor may use the additional inputs to determine a plurality of classifications and may associate each additional individual with at least one classification. For instance, upon receiving an initial input that some (e.g., second) individuals may prefer to consume speech in a foreign language, the at least one processor may receive a first additional inputs from a first subset of individuals indicating a preference to consume speech in French, and second additional inputs from a second subset of individuals indicating a preference to consume speech in Chinese. Based on the additional inputs, the at least one processor may classify the first subset of individuals in a French category, and the second subset of individuals in a Chinese category. The at least one processor may transmit a first synthesized audible output of the particular words translated to French to the first subset of individuals, and transmit a second synthesized audible output of the particular words translated to Chinese to the second subset of individuals based on the classification.

By way of a non-limiting example, in FIG. 51, individual 102 (e.g., first individual) may speak with a second individual 5100 associated with second mobile communications device 5102 and a third individual 5106 associated with a third mobile communications device 5108. The at least one processor (e.g., processing devices 400 and/or 460) may receive a first input from individual 102 indicating a preference of individuals to consume speech in a language other than English. The at least one processor may obtain additional inputs from each of second individual 5100 and third individual 5106 via second and third mobile communications devices 5102 and 5108, respectively. The at least one processor may classify second individual 5100 and third individual 5106 based on the additional inputs. For example, second individual 5100 and third individual 5106 may be positioned in the same location and may be therefore classified in a common environmental condition category (e.g., for determining a recommended volume for audio output). However, the at least one processor may classify second individual 5100 and third individual 5106 in different preferred language categories based on additional inputs, e.g., second individual 5100 may indicate a preference to consume speech in French, and third individual 5106 may indicate a preference to consume speech in Hebrew. Subsequently, upon determining particular English words to be spoken based on facial micromovements by individual 102 (e.g., first individual), the at least one processor may use the classifications to cause a synthesized French version of the particular English words to be audibly outputted at the recommended volume via headset 5104 paired to second mobile communications device 5102 and a synthesized Hebrew version of the particular English words to be audibly outputted at the recommended volume via a headset 5110 paired to third mobile communications device 5108. In some embodiments, the synthesized French version and synthesized Hebrew version of the particular words may be audibly outputted via headsets 5104 and 5110 respectively, substantially concurrently (in real-time) with a vocalization of the particular English words by individual 102 (e.g., first individual).

Some embodiments involve adopting the preferred speech consumption characteristic. Adopting may include using and/or applying one or more traits and/or characteristics, and/or implementing one or more changes or adjustments to take on a trait and/or characteristic. Adopting the preferred speech consumption characteristic may involve implementing one or more adjustments to synthesized speech such that an outputted synthesized speech expresses a preferred speech consumption characteristic. Adopting a preferred speech consumption characteristic may involve adjusting one or more speech characteristic settings (e.g., for a volume, speed, pitch, tone, timbre, sound clarity, sound fidelity, dynamic range, frequency response, enunciation, expression, and/or accent) to match one or more preferred speech characteristic settings. In some embodiments, adopting a preferred speech consumption characteristic may involve selecting a language, a dialect, a vocabulary, a synonym (e.g., a slang term), a paraphrase, and/or any other verbal characterization of a synthesized speech. In some embodiments, adopting a preferred speech consumption characteristic may additionally involve selecting an output medium for speech (e.g., audio and/or text), formatting speech for a selected output medium, and/or rendering speech via an associated output interface and/or electronic device.

By way of a non-limiting example, in FIG. 51, the at least one processor (e.g., processing devices 400 and/or 460 in FIG. 4) may adopt one or more preferred speech consumption characteristics for synthesizing the particular words. For instance, the at least one processor may generate a first synthesized version of the particular words translated to French for second individual 5100 and generate a second synthesized version of the particular words translated to Hebrew for third individual 5106. The at least one processor may classify second individual 5100 and third individual 5106 in a noisy location requiring an increased volume for consuming speech (e.g., based on location data received from second mobile communications device 5102 and third mobile communications device 5108). The at least one processor may adjust a volume for audibly outputting the first and second synthesized versions of the particular words via headset 5104 paired to second mobile communications device 5102 and via headset 5110 paired to third mobile communications device 5108, respectively, based on the classification.

In some disclosed embodiments, adopting the preferred speech consumption characteristic includes pre-setting voice synthesis controls for prospective facial micromovements. Voice synthesis controls may include parameters and/or settings for specifying one or more preferred speech consumption characteristics (as disclosed and exemplified elsewhere in this disclosure). Pre-setting voice synthesis controls may include establishing and/or specifying values for parameters and/or settings for a speech synthesizer in advance, such that subsequently synthesized speech may express a preferred speech consumption characteristic corresponding to the pre-set voice synthesis controls. Prospective facial micromovements may include expected, probable, and/or anticipated facial micromovements (as described and exemplified elsewhere in this disclosure). For example, at least one processor may determine prospective facial micromovements using one or more predictive algorithms (e.g., based on artificial intelligence and/or machine learning). The at least one processor may specify one or more settings for a speech synthesizer in advance, based on the determined prospective facial micromovements such that speech, subsequently synthesized based on detected facial micromovements corresponding to the prospective facial micromovements, may express a preferred speech consumption characteristic. In some embodiments, pre-setting voice synthesis controls for prospective facial micromovements may reduce latency for outputting speech expressing a preferred speech consumption characteristic, allowing to output synthesized speech expressing a preferred speech consumption characteristic and associated with detected facial micromovements in real-time.

For example, at least one processor may identify a repeating phrase by a male speaker and may determine prospective facial micromovement associated with the repeating phrase. The at least one processor may receive an input indicating that a second individual prefers to consume speech expressed using a female voice. The at least one processor may pre-set voice synthesis controls associated with producing a female voice such that a subsequent expression of the repeating phrase (e.g., determined based on detected facial micromovements of the male speaker) may be outputted in a female voice to the second individual using a speech synthesizer substantially in real-time.

By way of a non-limiting example, in FIG. 51, the at least one processor (e.g., processing devices 400 and/or 460 in FIG. 4) may adopt the preferred speech consumption characteristic by pre-setting voice synthesis controls for prospective facial micromovements. For example, the at least one processor may pre-set a voice synthesis control for an audio output for second mobile communications device 5102 associated with second individual 5100 to French, and pre-set a voice synthesis control for an audio output for third mobile communications device 5108 associated with third individual 5106 to Hebrew. Upon subsequently determining particular English words to be spoken based on detected facial skin micromovements by individual 102 (e.g., first individual), the at least one processor may generate synthesized versions of the particular English words translated to French and Hebrew using the pre-set voice synthesis controls.

Some embodiments involve synthesizing, using the adopted preferred speech consumption characteristic, audible output of the particular words. Audible output may include analog and/or digital signals (e.g., encoded in an audio file), that when transmitted to a speaker, may cause the speaker to produce associated sound waves in a frequency and/or volume range perceptible to humans (e.g., 20 Hz to 20 KHz and 0 dB to 130 dB, respectively). Synthesizing audible output of particular words may include performing one or more operations to output an artificial production (e.g., an electronic rendition) of human speech expressing particular words. Such operations may include at least one processor performing a textual analysis of particular words to determine a linguistic structure, meaning and/or context thereof. Such operations may additionally include at least one processor performing preprocessing to handle capitalization, special characters, punctuation, and/or symbols, phonetic conversion of particular words to a phonetic representation (e.g., sounds of human speech). Such operations may additionally include at least one processor performing prosody generation to generate a melody, rhythm, intonation patterns, pitch, duration, and/or emphasis to convey meaning to particular words. Such operations may additionally include at least one processor performing acoustic modeling to generate a speech waveform (e.g., using Fourier synthesis, overlap-add synthesis and/or other signal processing techniques) associated with an expression of particular words, and/or encoding a speech waveform to a digital format stored in an audio file. Synthesizing audible output of particular words may additionally include saving an audio file to memory and/or outputting an audio file to a speaker to produce an electronic rendition of human speech. Synthesizing, using an adopted preferred speech consumption characteristics, audible output of the particular words may involve at least one processor applying one or more preferred speech consumption characteristics to any of the textual analysis, preprocessing, phonetic conversion, prosody generation, acoustic modeling, and/or encoding operations described earlier, to produce an audio file of the particular words, such that outputting the audio file to a speaker produces an audible output expressing the preferred speech consumption characteristics. For example, at least one processor may adjust a volume, a pitch, a tone, an intonation, a rhythm, a duration, a pace, a punctuation, an accent, a language, a paraphrase, a voice, and/or any other speech consumption characteristic to output speech expressing a preferred speech consumption characteristic.

By way of a non-limiting example, in FIG. 4, the at least one processor (e.g., processing devices 400 and/or 460) may synthesize an audible output of particular words (e.g., determined based on facial skin micromovements by individual 102) using the adopted preferred speech consumption characteristic. The at least one processor may store the audible output as an audio file in memory device 402, and/or may transmit the audible output to second mobile communications device 5102 (see FIG. 51).

In some disclosed embodiments, the synthesized audible output of the particular words occurs at the preferred pace of speech. Upon using an input associated with a preferred pace of speech to generate an audio signal, the at least one processor may output the audio signal to a speaker, thereby causing an occurrence of a synthesized audible output of the particular words at the preferred pace of speech. For example, the at least one processor may adjust (e.g., by shortening or lengthening) a duration for one or more word syllables, and/or one or more silent gaps delineating particular words in an audio signal encoding a synthetization of particular words, and transmit the audio signal to a speaker, thereby adopting the preferred pace of speech for a synthesized audible output of the particular words. The audible output from the speaker may include speech having words spoken at the pace of speech specified by the input.

In some disclosed embodiments, the synthesized audible output of the particular words occurs at the preferred speech volume. Upon using an input associated with a preferred speech volume to generate an audio signal, the at least one processor may output the audio signal to a speaker, thereby causing an occurrence of a synthesized audible output of the particular words at the preferred speech volume. For example, the at least one processor may amplify or mute at least a portion of an audio signal encoding a synthetization of particular words, and transmit the audio signal to a speaker, thereby adopting the preferred speech volume for a synthesized audible output of the particular words. The audible output from the speaker may include speech having words spoken at the speech volume specified by the input.

In some disclosed embodiments, the synthesized audible output of the particular words occurs in the target language of speech. Upon using an input associated with a target language of speech to generate an audio signal, the at least one processor may output the audio signal to a speaker, thereby causing an occurrence of a synthesized audible output of the particular words in the target language of speech. For example, the at least one processor may translate particular words spoken by the first individual (e.g., wearing a speech detection system) in a source language to a target language, generate an audio signal encoding a synthetization of the translation of the particular words in the target language, and transmit the audio signal to a speaker, thereby adopting the preferred target language of speech for a synthesized audible output of the particular words. The audible output from the speaker may include speech having words spoken in the target language specified by the input.

In some disclosed embodiments, the synthesized audible output of the particular words occurs in the preferred voice. Upon using an input associated with a preferred voice to generate an audio signal, the at least one processor may output the audio signal to a speaker, thereby causing an occurrence of a synthesized audible output of the particular words in the preferred voice. For example, the at least one processor may apply one or more of a speed, pitch, tone, timbre, sound clarity, sound fidelity, dynamic range, and/or frequency response of a preferred voice to generate an audio signal encoding a synthetization of the particular words in the preferred voice, and transmit the audio signal to a speaker. The audible output from the speaker may include speech having words spoken at the preferred voice specified by the input.

By way of a non-limiting example, in FIG. 51, the at least one processor may cause second mobile communications device 5102 to output the synthesized audible output via headset 5104 at the preferred pace of speech (e.g. 1.5 times the natural pace of speech), at the preferred volume (e.g., the maximum volume), and in the target language of speech (e.g., French) using a female voice.

Some disclosed embodiments may involve presenting at least one of the first individual and the second individual with a user interface for altering the preferred speech consumption characteristic. A user interface may refer to one or more human-machine interfacing layers allowing for interactions between one or more humans and one or more computing systems, software applications, and/or electronic devices. A user interface may include visual and/or interactive elements that enable users to control and communicate with an underlying computer system, to perform tasks, provide input, and receive feedback. Some examples of user interfaces may include graphical user interfaces (GUIs), web-based interfaces, command-line interfaces (CLIs), touch-based interfaces, gesture-based interfaces. A user interface may be associated with one or more input-output (TO) devices, such as a touch-sensitive screen, a keyboard, an electron mouse, a joystick, a camera (e.g., associated with gesture recognition software), a microphone (e.g., associated with speech recognition software), a speaker, a haptic device, and/or any other device configured to receive input from a user and/or provide output to a user. A user interface may be additionally associated with one or more input elements, such as buttons, checkboxes, text fields, forms, sliders, and drop-down menus for receiving input from a user, and/or one or more output elements, such as text, images, videos, audio files, icons, graphs, and notifications. A user interface may include one or more navigational components allowing a user to move between different parts of a system or application, such as menus, tabs, links, and search bars, one or more interactive feature enabling users to performing actions, and manipulate objects, such as drag-and-drop functionality, buttons, gestures, and/or voice commands, and feedback mechanisms providing information regarding a state and/or response of a computer system to one or more user actions. In some embodiments, a user interface may be distributed over a plurality of electronic devices. For example, a user interface for a speech detection system may be configured to receive input from a light detector associated with a wearable electronic device, and output a response to the input via a mobile communications device. Presenting at least one of a first individual and a second individual with a user interface may involve invoking a user interface on at least one electronic device associated with a first individual and/or a second individual. Altering a preferred speech consumption characteristic may include changing, adjusting, and/or modifying at least one preferred speech consumption characteristic (as described and exemplified elsewhere in this disclosure).

For example, at least one processor may receive from the first individual a first input indicating a preference associated with the second individual for an increased pace of speech (e.g., a preferred speech consumption characteristic). The at least one processor may present a user interface on a mobile communications device of the second individual, and the second individual may provide a second input to increase a volume for consuming speech. Upon determining particular facial skin micromovements of the first individual, the at least one processor may generate an audio signal encoding a synthetization of the particular words, and transmit the audio signal to a speaker of the mobile communications device of the second individual. The audible output from the speaker may include speech having words spoken at the increased pace of speech specified by the first input, and at the increased volume specified by the second input, thereby modifying the preferred speech consumption characteristic.

By way of a non-limiting example, in FIG. 51, the at least one processor (e.g., processing devices 400 and/or 460) may present individual 102 (e.g., first individual) and second individual 5100 with a user interface via mobile communications devices 120 and 5102, respectively, for altering one or more preferred speech consumption characteristics. For example, the user interface may include or more controls (e.g., menus, buttons, text boxes, and/forms) for inputting user preferences associated with preferred speech consumption characteristics. Individual 102 may provide a first input via mobile communications device 120 indicating a preference of second individual 5100 to consume speech in French. Second individual 5100 may provide an additional input via second mobile communications device 5102 indicating a preference to consume speech at a slower pace of speech. The at least one processor may transmit an audio signal encoding a synthetization of particular English words translated to French at a slower pace of speech for outputting via headset 5104 paired to second mobile communications device 5102, e.g., in accordance with the first input and the additional input.

Some disclosed embodiments involve presenting a first synthesized version of intended speech based on the facial micromovements and presenting a second synthesized version of speech based on the facial micromovements in combination with the preferred speech consumption characteristic. Intended speech based on facial micromovements may include anticipated and/or predicted speech associated with detected facial micromovements. For example, prior to vocalizing speech, at least one processor may determine intended speech based on facial micromovements detected by a speech detection system (as described and exemplified elsewhere in this disclosure). Presenting a first synthesized version of intended speech based on facial micromovements may involve at least one processor detecting facial micromovements associated with vocalizing at least one word prior to vocalization of the at least one word, determining the at least one word based on the detected facial micromovements, generating an audio file including a synthesized version of the at least one word, and outputting the audio file to a speaker. Presenting a second synthesized version of speech based on the facial micromovements in combination with the preferred speech consumption characteristic may additionally include modifying at least one characteristic of an audio file encoding a synthesized version of at least one word such that an audible rendition of the audio file reflects the preferred speech consumption characteristic, and outputting the modified audio file to a speaker. The at least one processor may present a first synthesized version of intended speech based on the facial micromovements, and a second synthesized version of speech based on the facial micromovements in combination with the preferred speech consumption characteristic sequentially or concurrently.

In some disclosed embodiments, presenting the first synthesized version and the second synthesized version occur sequentially to the first individual. Sequentially may refer to consecutively (e.g., one after the other), and/or successively. For example, at least one processor may receive an input indicating a second individual prefers to consume speech in French. A first individual wearing a speech recognition system may perform facial skin micromovements in preparation for speaking particular words in English. The at least one processor may determine the particular English words based on detection of the facial skin micromovements (e.g., prior to vocalization of the particular English words), and output a first synthesized version of the particular English words to a speaker of an electronic device associated with the first individual. In addition, the at least one processor may translate the particular English words to French, thereby adopting the preferred speech consumption characteristic, and generate a second synthesized version of the particular words translated to French. The at least one processor may output the second synthesized version of the particular words (e.g., in French) to the speaker of the electronic device associated with the first individual, after outputting the first synthesized version of the particular words (e.g., in English). The at least one processor may present the second synthesized version to the first individual prior to, during, or after vocalization of the particular words by the first individual.

By way of a non-limiting example, in FIG. 51, based on facial micromovements performed by individual 102 (e.g., first individual) and detected via speech detection system 100, the at least one processor (e.g., processing devices 400 and/or 460) may determine that individual 102 intends to say, "How do you do?" (e.g., based on detected facial skin micromovements and/or a behavioral pattern associated with individual 102). The at least one processor may cause first mobile communications device 120 to play a synthesized version of "How do you do?" (e.g., prior to vocalization by individual 102). The at least one processor may translate "How do you do?" to French (e.g., "Comment 298 ava?") based on the preferred speech consumption characteristic of second individual 5100 and may cause second mobile communications device 5102 to play a synthesized version of "Comment cava?". In some embodiments, the at least one processor may cause mobile communications device 120 to play the first synthesized version (e.g., "How do you do?") and the second synthesized version (e.g., "Comment ca va?") sequentially.

Figure 52:
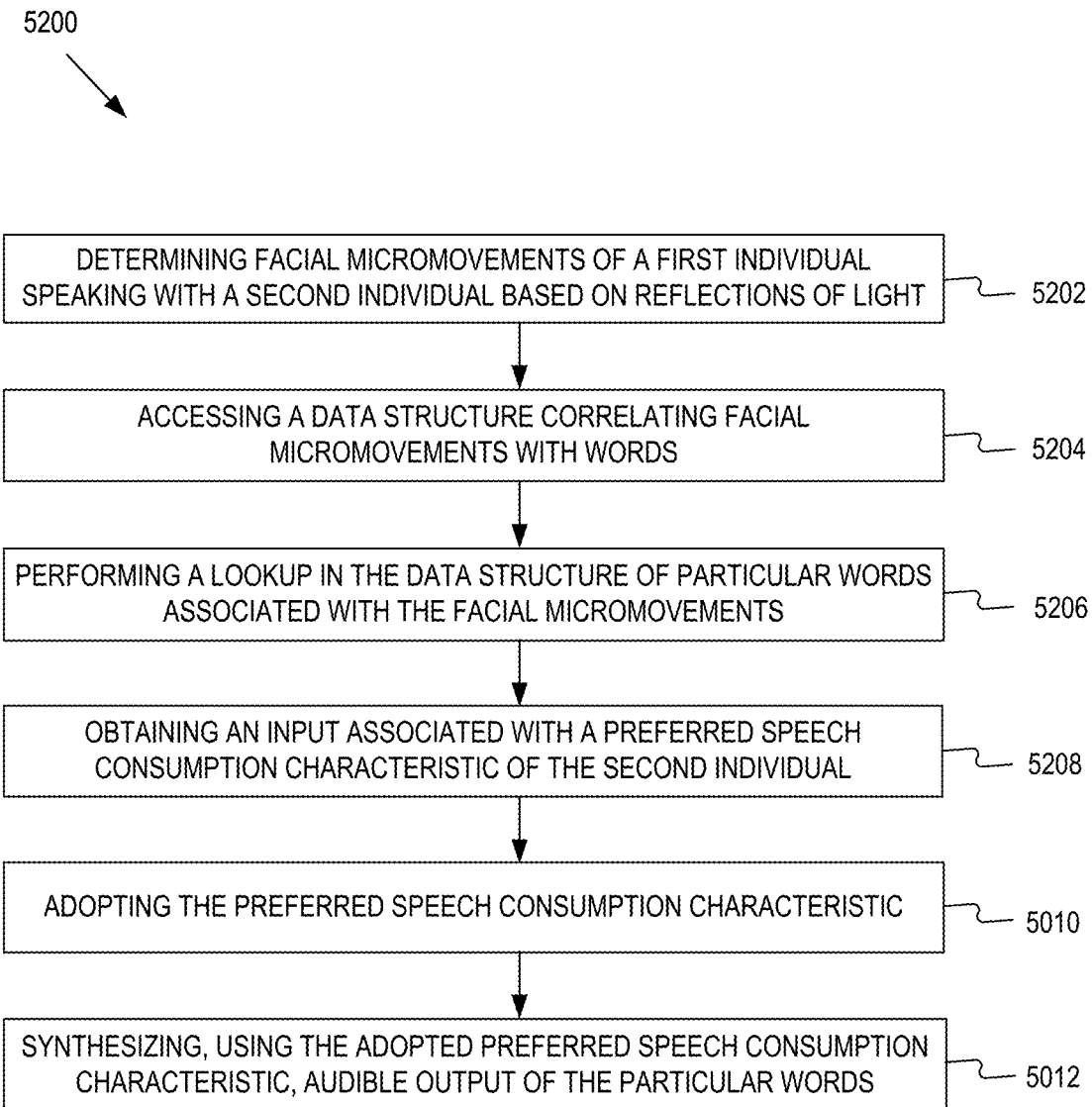
FIG. 52 illustrates a flowchart of an example process for initiating content interpretation prior to vocalization of content to be interpreted, consistent with embodiments of the present disclosure.

FIG. 52 illustrates a flowchart of example process 5200 for performing voice synthetization from detected facial micromovements, consistent with embodiments of the present disclosure. In some embodiments, process 5200 may be performed by at least one processor (e.g., processing device, 400 shown in FIG. 4) to perform operations or functions described herein. In some embodiments, some aspects of process 5200 may be implemented as software (e.g., program codes or instructions) that are stored in a memory (e.g., memory device 402) or a non-transitory computer readable medium. In some embodiments, some aspects of process 5200 may be implemented as hardware (e.g., a specific-purpose circuit). In some embodiments, process 5200 may be implemented as a combination of software and hardware.

Referring to FIG. 52, process 5200 may include a step 5202 of determining particular facial skin micromovements of a first individual speaking with a second individual based on reflections of light from a facial region of the first individual, as described earlier. By way of a non-limiting example, in FIG. 51, at least one processor (e.g., processing devices 400 and/or 460 in FIG. 4) may receive from speech detection system 100, signals representing facial skin micromovements performed by individual 102 (e.g., first individual). The at least one processor may use the received signals to perform voice synthetization operations.

Process 5200 may include a step 5204 of accessing a data structure correlating facial micromovements with words, as described earlier. By way of a non-limiting example, in FIG. 4, at least one processor (e.g., processing devices 400 and/or 460) may access data structure 422 and/or data structure 464 (e.g., via communications network 126 in FIG. 1) correlating facial micromovements with words.

Process 5200 may include a step 5206 of performing a lookup in the data structure of particular words associated with the particular facial skin micromovements, as described earlier. By way of a non-limiting example, in FIG. 4, the at least one processor (e.g., processing devices 400 and/or 460) may perform a lookup in data structures 422 and/or data structure 464 (e.g., via communications network 126 in FIG. 1) of particular words associated with the particular facial skin micromovements.

Process 5200 may include a step 5208 of obtaining an input associated with a preferred speech consumption characteristic of the second individual. as described earlier. By way of a non-limiting example, in FIG. 51, the at least one processor (e.g., processing devices 400 and/or 460) may obtain an input associated with a preferred speech consumption characteristic of second individual 5100 from individual 102 (e.g., first individual) via mobile communications device 120.

Process 5200 may include a step 5010 of adopting the preferred speech consumption characteristic, as described earlier. By way of a non-limiting example, in FIG. 51, the at least one processor (e.g., processing devices 400 and/or 460 in FIG. 4) may adopt one or more preferred speech consumption characteristics for synthesizing the particular words.

Process 5200 may include a step 5012 of synthesizing, using the adopted preferred speech consumption characteristic, audible output of the particular words, as described earlier. By way of a non-limiting example, in FIG. 4, the at least one processor (e.g., processing devices 400 and/or 460) may synthesize an audible output of particular words (e.g., determined based on facial skin micromovements by individual 102) using the adopted preferred speech consumption characteristic. The at least one processor may store the audible output as an audio file in memory device 402, and/or may transmit the audible output to second mobile communications device 5102 (see FIG. 51).

Some embodiments involve a system for the steps discussed above. By way of a non-limiting example, in FIG. 51, at least one processor (e.g., processing devices 400 and/or 460 in FIG. 4) may receive from speech detection system 100, signals representing facial skin micromovements performed by individual 102 (e.g., first individual). The at least one processor may use the received signals to perform voice synthetization operations. In FIG. 4, the at least one processor may access data structure 422 and/or data structure 464 (e.g., via communications network 126 in FIG. 1) correlating facial micromovements with words. The at least one processor may perform a lookup in data structures 422 and/or data structure 464 of particular words associated with the particular facial skin micromovements. The at least one processor may obtain an input associated with a preferred speech consumption characteristic of second individual 5100 from individual 102 (e.g., first individual) via mobile communications device 120. The at least one processor may adopt one or more preferred speech consumption characteristics for synthesizing the particular words. The at least one processor may synthesize an audible output of particular words (e.g., determined based on facial skin micromovements by individual 102) using the adopted preferred speech consumption characteristic. The at least one processor may store the audible output as an audio file in memory device 402, and/or may transmit the audible output to second mobile communications device 5102.

As described elsewhere in this disclosure, some disclosed embodiments involve providing an approach for detecting prevocalized speech, subvocalized speech, and silent speech through the detection of facial skin micromovements to determine words in the absence of vocalization. Some disclosed embodiments involve personal presentation of prevocalization. Personal presentation in this context refers to providing a user with information about what the user is about to speak, before the user audibly projects the speech. Before a person vocalizes words, muscles in the face are recruited and intended speech can be detected from facial micromovements before sound is emitted. Further, when the person is thinking about what they want to say, involuntary muscle movements may be caused that can be detected and deciphered by a speech detection system. Consistent with some disclosed embodiments, a user of a speech detection system may benefit from hearing an audible output or seeing a textual output of their own words before the words are actually spoken. Such a speech detection system may be configured to detect prevocalized speech through the detection of facial micromovements such that the system may be capable of converting prevocalized words into an audible or textual presentation prior to vocalization.

By way of a non-limiting example, a wearable earpiece may be designed with a sensor to detect facial micromovements. Upon detection of one or more facial micromovements, the facial micromovements may be used to access a data structure to lookup words associated with the detected movements. The lookup may happen during prevocalization, and the prevocalized words may be converted to an audible presentation to the user of the wearable earpiece such that the user may hear the words as an audio output at the speaker of the earpiece prior to vocalization. In another example, a sensor may detect facial micromovements, a lookup of words associated with the facial micromovements may be performed referencing a data structure, and the presentation to the user may be a textual presentation allowing the user to read the prevocalized words prior to vocalizing them. To address such cases where it is advantageous to present prevocalized words to a user prior to speaking the words, the speech detection system may be configured with a feedback mechanism to present the prevocalized words prior to vocalization (e.g., audible presentation, textual presentation or other methods to communicate the detected prevocalized words to the user).

There may be several advantages to personal presentation of prevocalized words to a user. By way of a non-limiting example, it may improve articulation of the words for a user to hear or see them prior to vocalizing them. In another example, the system may detect facial micromovements associated with a first language and the system may translate to a second language for audible presentation to the user (i.e., the wearable earpiece) or to another remote device (e.g., a speaker, textual output). In another example, if the user receives the presentation of prevocalized words, the user may be able to change what the user was planning to vocalize or may be able to cease vocalization. In another example, unvocalized words may be detected and the system may generate an audible or textual presentation based on a lookup of facial micromovements associated with the unvocalized words. It is to be appreciated that disclosed embodiments demonstrate examples and are not limited to the identified advantages of a speech detection system capable of personal presentation of provocalization.

By way of example, as illustrated in FIGS. 1 and 4, processor or processing device 400 of speech detection system 100 or processing device 460 of remote processing system 450 may execute one or more instructions stored in memory 402, shared memory module 472, data structures 124, 422, or 464 to perform operations for determining facial skin micromovements. These structures are one non-limiting example of elements that can be used to perform personal presentation of prevocalization.

Some disclosed embodiments involve receiving reflection signals corresponding to light reflected from a facial region of an individual. Consistent with some embodiments, at least one detector may measure any form of reflection or scattering of light from a facial region of an individual. In some disclosed embodiments, the at least one detector may be configured to output reflection signals based on the detected light reflections. As described and exemplified elsewhere in this disclosure, the term reflection signals broadly refers to any form of data retrieved from the at least one light detector in response to the light reflections from the facial region. Receiving reflection signals may refer to detecting an electronic representation of a property determined from the light reflections, or raw measurement signals detected by the at least one light detector. In some disclosed embodiments, the received light may be reflected from a facial region of the individual. For example, receiving reflection signals may include receiving, by a processor, a measurement of voltage or current generated by a light detector, where the magnitude of the voltage or current may be based on the amount of reflected or scattered light received by the light detector. By way of a non-limiting example, a wearable device, such as an earpiece with an integrated optical sensor, may derive information about a surface (e.g., facial skin) represented in reflection signals received by the at least one light detector. Further, the wearable device may include at least one processor that may perform a light reflection analysis of the received light reflections from a facial region of an individual to determine prevocalized words from detected facial skin micromovements from the individual. It is to be appreciated that the at least one light detector configured to receive reflection signals may be integrated with speech detection system consistent with embodiments in the present disclosure. By way of a non-limiting example, as illustrated in FIG. 1, optical sensing unit 116 of speech detection system 100 may receive reflection signals corresponding to reflections of light 104 from facial region 108 of the individual 102.

Consistent with some disclosed embodiments, the light reflected from the facial region of the individual include coherent light reflections. The term "coherent light" may be understood as described and exemplified elsewhere in this disclosure. Coherent light reflections may broadly refer to coherent light reflected from the surface of an object. Consistent with some disclosed embodiments, the at least one detector may be configured to detect coherent light reflections from the one or more portions of the facial region of the individual. The at least one detector may include a plurality of detectors constructed from a plurality of detecting elements. Consistent with some embodiments, the at least one detector may measure any form of reflection and of scattering of light. In some disclosed embodiments, the at least one detector may be configured to output associated reflection signals from the detected coherent light reflections. The output may include reflection signals that include electronic representation of one or more properties determined from the coherent light reflections. By way of a non-limiting example, as illustrated in FIG. 1, optical sensing unit 116 of speech detection system 100 may project coherent light toward the facial region 108 of the individual and receive coherent reflections of light 104 from the individual. It is to be appreciated that coherent light reflections may achieve high-sensitivity optical detection under strong background light conditions therefore using coherent light to detect facial skin micromovements may be advantageous in some disclosed embodiments.

Some disclosed embodiments involve using the received reflections signals to determine particular facial skin micromovements of an individual in an absence of perceptible vocalization associated with the particular facial skin micromovements. Facial skin micromovements, as described and exemplified elsewhere in this disclosure, may broadly refer to skin motions on the face that may be detectable using a sensor, but which might not be readily detectable to the naked eye. Facial micromovements may be present during vocalization, subvocalization, silent speech, speaking soundlessly, during prevocalization muscle recruitments and other types of speech where there may be an absence of perceptible vocalization of the speech. Consistent with some disclosed embodiments, a speech detection system may use received reflection signals to determine particular facial skin micromovements. Particular facial skin micromovements refers to detecting specific movements of the skin and face. The speech detection system may then associate various facial skin micromovements with unvocalized words. For example, a specific neuromuscular activity, detectable using a light detector that may receive reflection signals, may be deciphered to determine particular unvocalized words that a user intended to vocalize. As illustrated in FIG. 1, optical sensing unit 116 of speech detection system 100 (e.g., speech detection system) may project light toward the facial region 108 of the individual and receive reflections of light 104 from the individual that allows the speech detection system 100 to detect particular facial skin micromovements.

The absence of perceptible vocalization may include no sound being emitted from the mouth, sound emitted from the mouth at a low level such that it may not be perceived by a listener or listening device, prevocalized speech where air flow from the lungs is absent, or any other prevocalization, subvocalization or vocalization where sound may not be perceived. By way of a non-limiting example, the absence of perceptible vocalization may be associated with facial micromovements of the muscles in the face, larynx, and mouth during the articulation of the desired sounds. Detecting facial skin micromovements may include the speech detection system sensing the facial micromovements and interpreting those facial micromovements even in the absence of perceptible vocalization. Further, the detected facial skin micromovements may be used by the speech detection system to determine prevocalized and unvocalized words based on the facial skin micromovements in the absence of perceptible vocalization. Consistent with some disclosed embodiments, the speech detection system may then allow an audible presentation of the prevocalized and unvocalized words.

Some disclosed embodiments involve accessing a data structure correlating facial skin micromovements with words. The term "data structure" may be understood as described and exemplified elsewhere in this disclosure, and may include, for example, a database, table, or AI model that can be used for micromovement to meaning correlations. Accessing a data structure refers to querying, gaining entry into, requesting information from, and/or seeking to reference data within a data structure. In some disclosed embodiments, a data structure may contain stored data representing correlations of facial skin micromovements with words or phonemes. In some disclosed embodiments, the particular facial skin micromovements may have been determined for a particular individual, and in other embodiments for a group of individuals or a population. For the individual, the data structure may be populated with entries correlating facial skin micromovements to words or phonemes associated with the facial skin micromovements of the particular individual. The correlation of particular facial skin micromovements and particular words and phonemes may have been captured for the individual at a previous time. For example, at the previous time, a calibration or learning session may occur wherein the particular facial skin micromovements are correlated (e.g., matched) to the particular words and phonemes of the individual. Further, the data structure may be populated with stored data containing the information for system operation. For example, a pointer (e.g., address to a memory location) to a location in the data structure may be the result of a detected particular facial skin micromovement. The at least one processor may have a table containing pointers based on previously determined facial skin micromovements. Upon determining a particular facial skin micromovement, the at least one processor may retrieve the pointer to the data structure then access the data structure to retrieve information associated with one or more words or phonemes. Thus, correlating the particular facial skin micromovement to the words or phonemes happens in the data structure during calibration or training and the record stored in the data structure for a particular facial skin micromovement may contain the information of the associated words or phonemes.

Consistent with disclosed embodiments, during operation of the speech detection system, the at least one processor may initiate a lookup in the data structure to retrieve particular words or phenomes associated with detected facial skin micromovements in response to the light reflection analysis resulting in retrieving a pointer into the data structure associated with the detected facial skin micromovements. It is to be appreciated that in response to detection of particular facial skin micromovements, the at least one processor may convert the result of the light reflection analysis to a lookup into one or more locations in the data structure to retrieve information indicative of particular words or phenomes associated with detected particular facial skin micromovements. The information retrieved from the data structure may have been correlated to the particular facial skin micromovements of an individual and stored in the data structure at a previous time as described above.

By way of one non-limiting example where the data structure may be a component of a wearable earpiece, the wearable earpiece may include a light detector, at least one processor and a data structure (i.e., the data structure may be present in the wearable earpiece consistent with some disclosed embodiments). In other embodiments, the data structure may reside in an electronic component paired with a device that includes the light sensor, and in yet other embodiments the data structure may reside on a remote server or in the cloud. Regardless of where the data structure resides, at least one processor may perform a light reflection analysis of the received light reflections. The light reflection analysis may result in a lookup of one or more locations in the data structure. For example, the light reflection analysis performed by at least one processor may determine that a particular facial skin micromovement may have been detected. The pattern of the particular facial skin micromovement detected by the at least one processor may result in the at least one processor retrieving an address (e.g., pointer, index) to the data structure to retrieve information associated with the facial skin micromovement. The at least one processor may retrieve the data from the data structure corresponding to the facial skin micromovements to associate the facial skin micromovements with one or more words and take an action based on the contents of the retrieved data. For example, the retrieved data may provide an indication that an action should be taken to play the determined words on an audio speaker for the individual using the wearable earpiece.

In another example where the data structure is a component of a mobile communication device, a wearable earpiece may include the light detector, the at least one processor, and a network interface allowing for connection to a communications network over which the speech detection system may be intended to operate. For example, the speech detection system may include a network interface designed to operate over a Bluetooth network to connect to a mobile communications device (e.g., cell phone). In the example, the light reflection analysis performed in the wearable earpiece may result in communication via the network interface to one or more locations in the data structure residing in memory on the mobile communication device. An application on the mobile communication device may perform a lookup in the data structure to retrieve information corresponding to one or more words associated with the detected facial skin micromovements.

In another example, where the data structure is part of a server accessible by the wearable earpiece via the cloud, the wearable earpiece may include the light detector, the at least one processor, and a network interface wherein the speech detection system may be designed to operate over a WiFi network to connect to the cloud via an internet connection. In the example, the light reflection analysis performed in the wearable earpiece may result in communication over the WiFi network (either directly or via a router) to the internet connection communicating to a server in the cloud. In the example, the data structure may be located in memory (e.g., a database) accessible by the server. A lookup may be performed to one or more locations in the data structure by the server to retrieve information corresponding to one or more words associated with the detected the facial skin micromovements.

In an alternate example, the data structure may be a component of a server accessible by the wearable earpiece via a mobile communication device (shown in FIG. 1, consistent with the present disclosure). In the example, the data structure may reside in a database accessible by the server in the cloud however a mobile communication device may provide the connection for the wearable earpiece to the cloud. For example, the wearable earpiece may be connected to the mobile communication device via a Bluetooth network. The mobile communication device may be connected to the internet and provide the communication interface to connect to the server. In such an example, the mobile communication device may have one or more processors that may communicate with the wearable earpiece and may also communicate with the server in the cloud.

Some disclosed embodiments involve performing a lookup in the data structure of particular unvocalized words associated with the particular facial skin micromovements. Performing a lookup in the data structure may include accessing one or more memory storage locations and retrieving data stored in a memory, a database or other storage medium. The lookup may involve artificial intelligence, such as an artificial intelligence model trained on correlations between facial micromovements and meaning. The retrieved data may include, for example, one or more of a plurality of words associated with a plurality of facial skin micromovements, corresponding to a particular individual and a plurality of facial skin micromovements associated with the particular individual, and/or other associations between neuromuscular activity and speech. The correlation between the words and the facial skin micromovements for the particular individual may have been made at a previous time (e.g., during a calibration cycle). At least one processor may have stored the information in the data structure correlating the facial skin micromovements and associated words at the previous time. Further, the at least one processor may have created an address, pointer, vector or other index identifier into the data structure allowing for the retrieval of the record at a future time. For example, at the future time, a light reflection analysis may determine that one or more particular facial skin micromovements may be associated with particular unvocalized words. The at least one processor may retrieve the address, pointer, vector or other index identifier into the data structure indicative of the one or more particular facial micromovements and use the retrieved address, pointer, vector or other index identifier to perform the lookup. One or more lookups (e.g., accesses to memory locations of the data structure) may be performed. The data returned for each access of the data structure may be analyzed by the at least one processor to determine if the particular facial micromovements are associated with any particular unvocalized words (i.e., meaning may be extracted from detected facial skin micromovements). It is to be appreciated that the lookup may or may not result in a retrieved record of previously correlated facial skin micromovements and unvocalized words. For example, the particular facial skin micromovement may be determined by the light reflection analysis and a lookup may be performed retrieving a record identifying particular associated unvocalized words. In another example, a particular facial skin micromovement may be determined by the light reflection analysis and a lookup may be performed however the record may be a null or empty record due to not having recorded a correlation with the particular facial skin micromovements and any unvocalized words at a previous time.

By way of a non-limiting example, returning to FIG. 1 a speech detection system is shown that includes communication to implement data structure lookup based on detected facial micromovement during prevocalization, the data structure lookup retrieving unvocalized words for audible presentation to the user. In FIG. 1, a speech detection system 100 may implement a speech detection system including earpiece (e.g., wearable housing 110) and speaker (e.g., output unit 114) worn by individual 102. The speech detection system 100 may include optical sensing unit 116 which may be used to detect facial micromovements at a plurality of locations in the facial region depicted by the region within the dotted lines. FIG. 1 shows a region of the face associated with specific muscle recruitments that may cause facial micromovements that the optical sensing unit 116 may detect. It is to be appreciated that such micromovements may occur over a multi-square millimeter facial area. FIG. 1 exemplifies the previously described example in which the data structure may be a component of the speech detection system 100. In the example, the speech detection system may be implemented in the speech detection system 100. At least one processor of the speech detection system 100 may perform a light reflection analysis of received light reflections. The data structure may reside in memory storage in the speech detection system 100. The light reflection analysis may be performed by at least one processor (e.g., as illustrated in FIGS. 1 and 4, processor or processing device 400 of speech detection system implemented in speech detection system 100 or processing device 460 of remote processing system 450) and may result in a lookup of one or more locations in the data structure (e.g., to retrieve a record) in the speech detection system 100 that the at least one processor may use to determine one or more words associated with to the facial skin micromovements. Thus, the at least one processor of the speech detection system 100 may use the determined one or more words to cause an audible presentation at the speaker of the wearable earpiece including the one or more words associated with the facial skin micromovements.

As another example, the data structure may be a component of data structure 124 accessible by the speech detection system 100 via the cloud (e.g., communication network 126). The network interface of speech detection system 100 (e.g., WiFi) may communicate via the internet and cloud with server 122. Server 122 may access the data structure located in data structure 124 to lookup particular unvocalized words that may be associated with particular facial micromovements. Server 122 may transmit the particular unvocalized words to speech detection system 100 via cloud.

Some disclosed embodiments involve causing an audible presentation of the particular unvocalized words to the individual prior to vocalization of the particular words by the individual. The term "causing an audible presentation" refers to generating an output of sound, audio, acoustic waves or any other output that may be perceived by human hearing or via a listening device. Generating an output may be accomplished by generating audio signals that when played by a speaker (e.g. headphone or external speaker) may generate sound that may be perceived by a human ear. For example, particular words corresponding to particular facial skin micromovements may be stored in a data structure in a digital audio format. Upon accessing the data structure, the digital audio may be retrieved, converted to analog audio (e.g., using a D/A converter) and the analog audio may be used to drive a speaker to generate sound output. In some embodiments, generating the output may include creating sound (e.g., delivered via a speaker configured to fit in the ear of the user), and the sound may be an audible presentation of particular unvocalized words associated with silent or prevocalized speech. In an example, the audible presentation of words may include synthesized speech (e.g., artificial production of human speech). For example, the synthesized speech may be generated using a text-to-speech algorithm to convert normal language text into speech by assigning a phonetic transcriptions to each text word converting the symbolic linguistic representation into sound. In some examples, a text-to-speech (TTS) system may convert normal language text into speech. Other systems may render symbolic linguistic representations like phonetic transcriptions into speech. In one example, a speaker may be used to generate an audio output based on detected particular unvocalized words through light reflection analysis of the reflected signals detected from the face region.

Consistent with some disclosed embodiments, the audible presentation of the particular unvocalized words may occur prior to vocalization of the particular words by the individual. "Prior to vocalization" may refer to a time before the speech from the individual may be audible. In some disclosed embodiments, the neuromuscular activity may be detectable before the sound is vocalized by the individual. Therefore prior to vocalization may include detecting the neuromuscular activity and determining particular unvocalized or prevocalized words before the sound is generated. Further, the audible presentation of the particular unvocalized words may be made to the individual prior to the individual vocalizing the words. By way of a non-limiting example, the individual giving a speech to an audience may wear an earpiece designed for detecting facial skin micromovements (i.e., a speech detection system) and for making an audible presentation at the earpiece speaker. The speech detection system of the earpiece may detect the facial skin micromovements and cause a lookup in a data structure to determine words associated with the facial skin micromovements. Prior to vocalizing the words, an output may be generated to the speaker of the earpiece including an audible presentation of the unvocalized words. It is to be appreciated that the latency to detect the facial skin micromovements, determine unvocalized words associated with the facial skin micromovements and cause the audible presentation to the speaker in the earpiece may be low enough such that the individual may hear the audible presentation prior to starting or completing vocalization of the words. Further, it is to be appreciated that the audible presentation may provide information to the individual that may be of value to the individual and may cause the individual to change the words they may have vocalized.

Consistent with some disclosed embodiments, the audible presentation of the particular unvocalized words is a synthetization of a selected voice. The term "synthetization of a selected voice" refers generally to generating an audio output of sound waves based on the characteristics of a specific voice including the phonation, pitch, loudness, and rate typical of the speaker associated with the specific voice. A voice may have several characteristics including frequency, harmonic structure, and intensity. The result of vocal cord vibration may be the fundamental tone of the voice, which determines its pitch. The particular unvocalized words detected by the speech detection system may be used to generate an output of a voice different from a voice of the particular individual from whom the unvocalized words were detected. For example, audible presentation of the detected unvocalized words may, through speech synthesis of an audible presentation, generate a different voice for the audio output than the voice of the user of the speech detection system. A selected voice may be a default voice or a voice selected by the user or someone else for use in audible presentation. "For example, the selected voice may be a synthetization of the speaker's (user's) voice. The selected voice may be synthesized by creating a voice output of a particular frequency harmonic structure and intensity to generate the voice to match the selected voice that the user may choose. For example, an application or graphical user interface that may be used to select settings for the speech detection system capable of personal presentation of prevocalization, may allow a user to change the voice output. A user may, for example, select a female voice or a male voice, by setting the selected voice setting in the user interface.

Consistent with some disclosed embodiments, causing the audible presentation may include outputting an audio signal to a personal hearing device configured to be worn by the individual. Outputting an audio signal may include generating an electrical signal, such as an analog, digital or wireless signal, produced by a processor or other electronic device, for converting the electrical signal to sound by a speaker or other sound output device. For example, a processor may generate an electrical signal that may be transformed into sound by the speaker. Consistent with some disclosed embodiments, the processor may access a data structure to determine words associated with facial micromovements and generate the electrical signal to drive to a speaker to produce sound. A personal hearing device may refer generally to headphones, earphones, earbuds, wearable earpieces, headsets, hearing aid devices, bone conducting headphones and other hearing devices with speaker output configured to be worn by the individual. Returning to the example shown in FIG. 1, speech detection system 100 is an example of a personal hearing device configured to be worn by the individual capable of outputting an audio signal to the individual.

Some disclosed embodiments involve operating at least one coherent light source in a manner enabling illumination of the facial region of the individual, wherein the at least one coherent light source is integrated with the personal hearing device. As described elsewhere herein, operating at least one coherent light source may include using an optical sensing unit designed with a light source that may emit coherent light. The coherent light may be projected towards a facial region of the individual enabling illumination of the facial region of the individual. Reflections of light resulting from the illumination may be detected by the optical sensing unit. Consistent with some disclosed embodiments, a personal hearing device may be designed with the optical sensing unit integrated into it. The personal hearing device may be designed into a wearable housing including the optical sensing unit, speaker (e.g., earpiece), microphone and user controls. For example, returning to the example shown in FIG. 1, optical sensing unit 116 may include a coherent light source and a light detector. In a manner enabling illumination of the facial region of the individual may refer designing the coherent light source to allow projecting light onto a portion of the face of the individual. For example, the coherent light source may generate coherent light from optical sensing unit 116 onto the facial region indicated by the oval region in FIG. 1. Within the facial region, there may be several locations where neuromuscular activity may be detected based on the light reflections from the coherent light projected onto the facial region. Integrated with the personal hearing device includes the design of the speech detection system in which the coherent light source (i.e., the light source of optical sensing unit 116) may be designed into the wearable earpiece.

Consistent with some disclosed embodiments, the audible presentation of the particular unvocalized words is provided to the individual at least 20 milliseconds prior to vocalization of the particular words by the individual. At least 20 milliseconds prior to vocalization refers to the difference in time between causing the audible presentation of the particular unvocalized words based on the detection of facial skin micromovements that may be associated with the particular unvocalized words to the vocalization of the particular words by the individual. The audible presentation to the individual may have value when the individual may hear the audible presentation prior to the vocalization by the individual. Consistent with some disclosed embodiments, the audible presentation may be provided to the individual at least 20, 30, 50, 70, 100, 150, 200, 275 or 350 milliseconds prior to vocalization of the particular words by the individual. It is to be appreciated that, consistent with disclosed embodiments, the audible presentation may be provided at any amount of time prior to vocalization. In some embodiments, the audible presentation may be perceived or heard by the individual, enabling the individual to change, alter or stop vocalization based on the content of the audible presentation. Consistent with the present disclosure, the audible presentation may be different than the intended vocalization. For example, the facial skin micromovements for an individual may be detected and an audible presentation may be made to the individual. Based on the audible presentation, the user may cease the vocalization and alter to vocalize something different. It is to be appreciated that the preview of the vocalization may allow the individual to determine if they want to vocalize something different.

Consistent with some embodiments, the selected voice is a synthetization of a voice of the individual. Synthetization of a voice of the individual refers to using the voice of the individual using the speech detection system to generate phonemes or words to create the audible presentation. Some disclosed embodiments may involve using a synthesized voice to generate an audio output reflective of the at least one subvocalized phoneme. The term "synthesized voice" refers to an artificial voice that may be generated using computer algorithms and software. For example, the selected voice for audible presentation may be generated using audio or voice data from historical recordings of the individual associated with the individual's facial skin micromovements. Based on the audio or voice data associated with the facial skin micromovements, the artificial voice may be used to generate the audible presentation. In one example, the synthesized voice may be created to mimic the voice of an individual associated with the facial skin micromovements. Some synthesized voices may include a specific human speaker, while others may be designed to be more generic and versatile. Reflective of the at least one subvocalized phoneme means that the utterances vocalized by the synthesized voice convey aspects of the determined at least one subvocalized phoneme. For example, speech detection system 100 may use output determination module 712 to generate a synthesized voice to say the word "bat" upon detecting the subvocalized phonemes /b/, /a/, and/t/. Consistent with some disclosed embodiments, a calibration or recording process may be performed to associate the particular individual facial skin micromovements with synthetization of the voice of the individual in the audio output. For example, an audio recording may be made of the individual while vocalizing words. While vocalizing the words, a speech detection system used by the individual may detect the facial skin micromovements of the individual associated with the vocalized words. A data structure may be populated using the facial skin micromovements correlated with the vocalized words. Words or phonemes may be stored in the data structure that may be used at a future time in the synthetization of voice of the individual to generate the audible presentation.

In some embodiments, the selected voice may be a synthetization of a voice of another individual other than the individual associated with the facial skin micromovements. Synthetization of a voice of another individual refers to using an artificial voice that may belong to an individual different from the individual using the speech detection system to generate the audible presentation. The phonemes or words in the synthesized voice of another individual may be determined based on the facial skin micromovements of the individual that the facial skin micromovements were detected. The selected voice of another individual may be synthesized using computer algorithms and software. The selected voice may be generated using voice data from recordings of a different individual. Consistent with some disclosed embodiments, the facial skin micromovements of the individual may be correlated with words or phonemes of another individual. The words or phonemes of another individual may be stored in a data structure such that a lookup based on facial skin micromovements of one individual may be used to retrieve words or phonemes of another individual (e.g., selected voice) that may be used to generate an audible presentation in the synthesized voice of another individual to create the audio output. For example, the selected voice may be from a preselected template voice and the words and phonemes of the selected voice of the preselected template voice may be stored in the data structure to be retrieved based on particular facial skin micromovements of the user. As describe elsewhere in this disclosure, a user may select a female voice or a male voice, by setting the selected voice setting in a user interface however it may be possible that there are several female and several male preselected template voices from which to select. In some examples, the selected voice may emulate the voice of a celebrity.

Figure 53B:
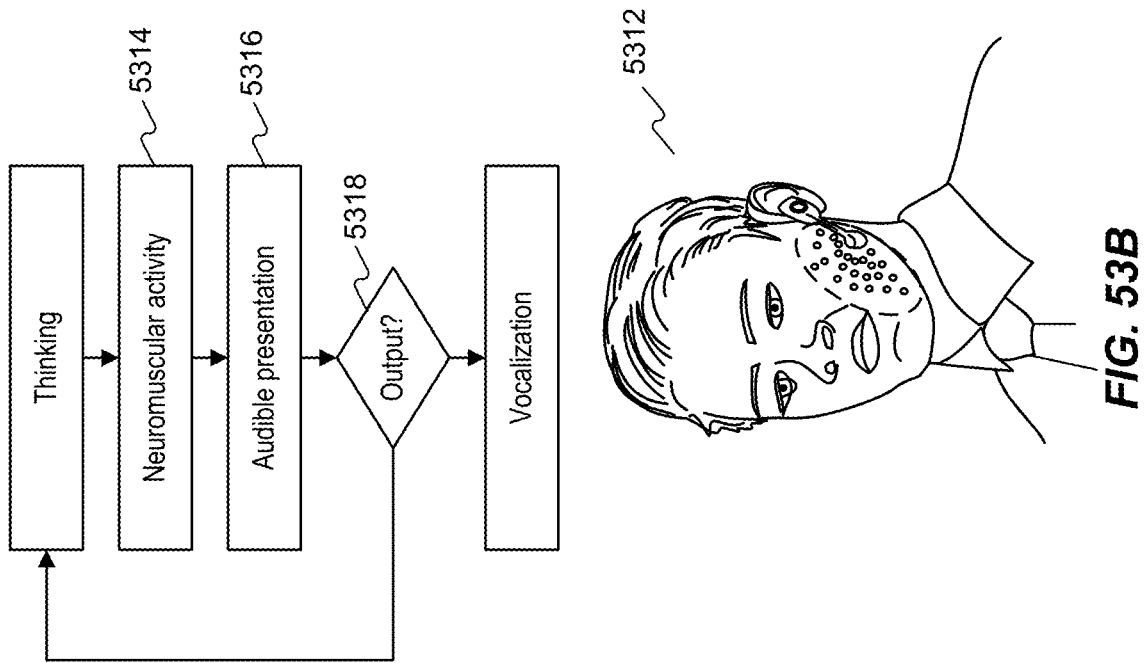
FIGS. 53A and 53B are schematic illustrations of audible presentation of unvocalized words prior to vocalization, consistent with some embodiments of the present disclosure.
Figure 53A:
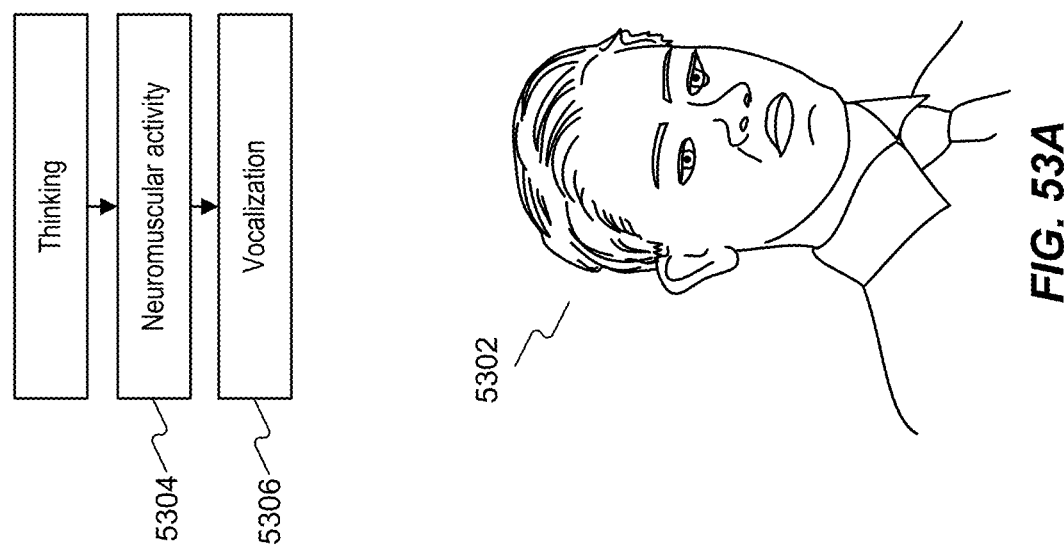

By way of a non-limiting example, reference is made to FIG. 53A and FIG. 53B illustrating neuromuscular activity indicating prevocalized speech that may cause an audible presentation to a user. FIG. 53A shows a flow from user thought to vocalization. As shown, first individual 5302 may think of saying something. As first individual 5302 prepares to speak, the thought of saying something may cause neuromuscular activity 5304. The neuromuscular activity 5304 may precede vocalization 5306. FIG. 53B shows a second individual 5312 that is a user of the speech detection system. Similar to first individual 5302, second individual 5312 may think of saying something. As second individual 5312 prepares to speak, the thought of saying something may cause neuromuscular activity 5304. The speech detection system used by second individual 5312 may detect facial skin micromovements indicative of the neuromuscular activity, perform a lookup in a data structure to associate the facial skin micromovements with one or more particular unvocalized words and generate an audible presentation 5316 to second individual 5312. Based on the audible presentation 5318, second individual 5312 may decide whether to proceed to vocalization of the one or more unvocalized words, proceed to vocalize alternate sounds or words based on the audible presentation 5316 or not vocalize any sounds or words. FIG. 53B provides an example of the difference in the flow of thinking to vocalization when the speech detection system provides feedback based on detected neuromuscular activity 5304 versus, as shown in FIG. 53A, no detection and no feedback.

Figure 54:
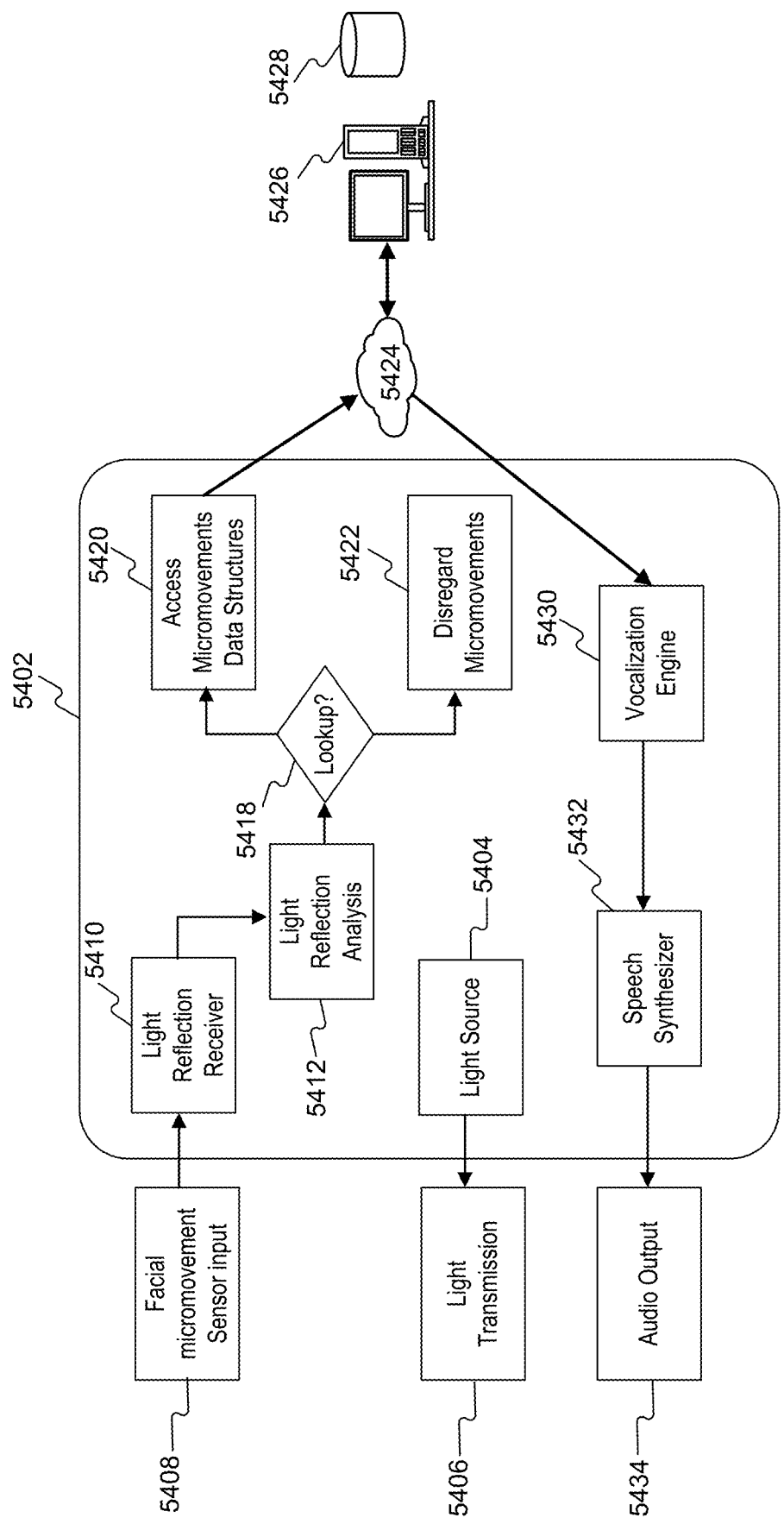
FIG. 54 is a block diagram of an exemplary speech detection system using received reflections to determine unvocalized words from facial micromovement causing an audible presentation, consistent with some embodiments of the present disclosure.

FIG. 54 shows a system block diagram of an exemplary speech detection system that may cause audible presentation to a user based on facial micromovements detected from received reflections. It is to be noted that FIG. 54 is a representation of just one embodiment, and it is to be understood that some illustrated elements might be omitted and others added within the scope of this disclosure. It is to be understood that references in the following discussions to a processing device may refer to processing device 400 of speech detection system 100 and processing device 460 of remote processing system 450 individually or collectively. Accordingly, steps of any of the following processes associated with modules may be performed by one or more processors associated with speech detection system 100. In the depicted embodiment, speech detection system 5402 comprises light source 5404, light reflection receiver 5410, light reflection analysis module 5412, lookup decision block 5414, data structure lookup module 5420, disregard micromovements module 5422, vocalization engine 5430 and speech synthesizer 5432. Light source 5404 may generate a light output (e.g., coherent light output) for transmission 5406 to illuminate a facial region of a user. Light reflection receiver 5410 may receive reflection signals corresponding to light reflected from a facial region of an individual. Using the received reflection signals from facial micromovement sensor input 5408, the system may determine particular facial micromovements of an individual in an absence of perceptible vocalization associated with particular facial skin micromovements. It is to be appreciated that facial micromovements may be sensed by any sensing mechanism described in disclosed embodiments herein.

Light reflection analysis module 5412 may receive input from light reflection receiver 5410 including light reflection data indicative of neuromuscular activity of the user of the speech detection system. Light reflection analysis module 5412 may determine that detected facial skin micromovements may be indicative of one or more particular unvocalized words and cause lookup decision block 5414 to determine whether to initiate action by the disregard micromovements module 5422 (e.g., the facial skin micromovements may not be associated with particular unvocalized words) or to access a data structure correlating facial skin micromovements with words through a lookup initiated by micromovement data structure lookup module 5420. In some disclosed embodiments, the data structure may be accessible at server 5426 in database 5428 via cloud 5424. Server 5426 may perform a lookup in the data structure of particular unvocalized words associated with the particular facial skin micromovements. The result of the lookup may be returned to the speech detection system 5402 via cloud 5424 where vocalization engine 5430 may communicate the result to speech synthesizer 5432 to cause an audible presentation of particular unvocalized words to the individual, for example at audio output 5434, prior to vocalization of the particular words by the individual.

Consistent with some embodiments, speech detection system 5402 may include a personal hearing device configured to be worn by the individual that may generate the audio output 5434. It is to be appreciated that light source 5404 and light reflection receiver 5410 may be integrated into the personal hearing device. For example, at least one coherent light source integrated into the personal hearing device may enable illumination of the facial region of the individual. The light reflection receiver 5410 integrated into the personal hearing device may be configured to receive the coherent light reflections from the facial region of the individual. Consistent with some embodiments, the vocalization engine 5430 and speech synthesizer 5432 may cause the audible presentation a period of time prior to vocalization of the particular words by the individual associated with the facial skin micromovements. It is to be appreciated that the latency from the detection of the facial skin micromovements to the audio output may need to be lower than the amount of time from the facial skin micromovements for the audio output to happen prior to vocalization.

Consistent with some embodiments, the result of the lookup in the data structure may result in the vocalization engine 5430 and speech synthesizer 5432 to cause the audible presentation of the particular unvocalized words in a selected voice (e.g., a particular voice configured in system setup to be played at the audio output 5434). The selected voice may be the voice of the individual using the system. For example, the system may have been trained to the individual by associating a plurality of that individual's facial skin micromovement and associating the movements with particular words spoken by the individual. The data structure may be populated with data indicative of the association and the system may use the particular individual's voice to cause the audible presentation. Consistent with some disclosed embodiments, the selected voice may be the voice other than that of the particular individual using the system. In this case, the individual's facial skin micromovements may be associated with particular words that may be spoken by the individual however the vocalization engine 5430 and speech synthesizer 5432 may generate an audio output of the particular words in a voice different than the particular individual using the system.

Consistent with some disclosed embodiments, the particular unvocalized words correspond to vocalizable words in a first language and the audible presentation includes a synthetization of the vocalizable words in a second language different from the first language. Particular unvocalized words that correspond to vocalizable words in a first language refers to unvocalized words detected from facial skin micromovements being associated with a specific language that may be detected using the neuromuscular activity of the individual using the speech detection system. In some examples, the first language may be the individual's native language. For example, English may be the primary language spoken by the individual and the facial skin micromovements may be associated with English language unvocalized words. In some disclosed embodiments, the first language may be configured based on a user setting. For example, a user may configure the first language to be English, Spanish, Italian, Mandarin or any other language that may be associated with the particular unvocalized words that may be detected from facial skin micromovements for the user of the system. Synthetization of the vocalizable words in a second language refers to generating an audio output in a different language than the first language the individual used during prevocalization. Consistent with some embodiments, the personal presentation of prevocalization system may provide a translation from the first language associated with particular unvocalized words associated with the facial skin micromovements of the individual to an audible presentation or textual presentation to the individual in a second language. The translation may be performed in a lookup of the data structure where the facial skin micromovements detected in the first language may be associated with the particular unvocalized words. The particular unvocalized words in the first language may be associated with particular words in the second language (e.g., the contents of the data structure may contain the information such that the at least one processor may perform the translation from the first language to the second language). By way of a non-limiting example, a speech detection system with translation capabilities may be configured to translate particular unvocalized words for an English speaking user to an audio output for a Spanish speaking listener. The facial skin micromovements may be associated with unvocalized words in English language. The processor may perform a lookup in the data structure based on the facial skin micromovements by determining an index into the data structure then retrieving the record at the location in the data structure. The record in the data structure may contain the information for the corresponding Spanish words. The Spanish words may be presented to the as an audio or text output to the Spanish speaking listener.

The audible presentation to the second language may allow the individual to think or to cause facial skin micromovements in the first language but hear an audible presentation in the second language hence allowing the user a real time translation that they may speak. Consistent with disclosed embodiments, the personal presentation of prevocalization system may help an individual speak in a second language. By way of a non-limiting example, the individual may prevocalize words in Mandarin and receive audio in Italian and thus the system may allow them to vocalize Italian based on facial skin micromovements derived from Mandarin.

Some disclosed embodiments involve associating the particular facial skin micromovements with a plurality of vocalizable words in the second language, and selecting a most appropriate vocalizable word from the plurality of vocalizable words, wherein the audible presentation includes the most appropriate vocalizable word in the second language. A plurality of vocalizable words in the second language refers to two or more words that may be associated with a particular facial micromovement that corresponds with a word in the first language. For example, a particular facial skin micromovement of an English speaker may be associated with the word "crane." A second language of Spanish may have a plurality of vocalizable words that may be associated with "crane," for example, "grulla" in Spanish means a tall bird that lives near water and has a long neck and long legs and "grim" in Spanish means a big machine with a long arm used by builders to lift big objects. The system may select the most appropriate vocalizable word in Spanish. In the example, the system may determine the context in which the English speaker may be using the word "crane." For example, for the English-based sentence "I saw a crane flying above you home," the system may select "grulla" as the most appropriate vocalizable word in Spanish for audible presentation. The most appropriate word may be selected using context determination. Context determination may broadly refer to determining the most appropriate word based by evaluating the surrounding words, facial skin micromovement or other linguistic cues that may allow a determination of the meaning of the word as used. In some disclosed embodiments, context determination may refer to determining the physical or emotional state of the individual during speech. For example, the context determination that allows for the selection of the most appropriate vocalizable word in the second language may be based on facial expressions that may indicate the user level of excitement when saying the word.

Figure 55:
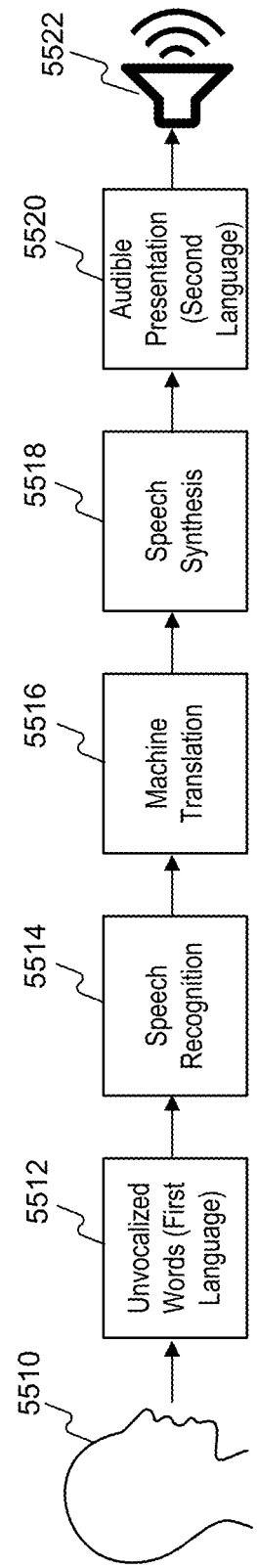
FIG. 55 shows an exemplary schematic illustration of synthesized translation between languages, consistent with some embodiments of the present disclosure.

FIG. 55 illustrates a system capable of synthesized voice translation from a first language to a second language. It is to be noted that FIG. 55 is a representation of just one embodiment, and it is to be understood that some illustrated elements might be omitted and others added within the scope of this disclosure. In the depicted embodiment, a personal presentation of prevocalization system may detect unvocalized words or prevocalization from a user 5510 and cause an audible presentation 5520 for audio output at speaker 5522. The unvocalized words 5512 may be detected in the first language by a speech detection system. Based on the detected words in the first language, the system may recognize speech in speech recognition module 5514. The recognized speech may be translated to the second language via machine translation module 5516. The representation of speech translated to the second language may be synthesized by speech synthesis module 5518 for audible presentation 5520 in the second language. The speaker 5522 may provide audio output. Consistent with some disclosed embodiments, the audio output may be provided to user 5510 (e.g., using a wearable earpiece). Consistent with some embodiments, the audio output may be provided to another individual. For example, facial skin micromovements of user 5510 may be detected as unvocalized words in the first language. The audible presentation 5520 may be provided in the second language to another individual (e.g., translating unvocalized words from a first person in a first language to audio output to a second person in a second language). It is to be appreciated that the audible presentation in the second language may be made to the user 5510, to one or more other individuals, to a recording or to any other audible receiver.

Some disclosed embodiments involve recording data associated with the particular unvocalized words for future use. "Recording" may refer broadly to capturing information and storing the information. For example, a recording may include a capture of audio data, video data, sensor information or any type of information or electronic data. Recording data may include capturing and storing sound, storing audio, capturing and storing video, capturing sensor information and capturing information of any type and storing the information as data. Recording data associated with the particular unvocalized words for future use refers to storing information related to the particular unvocalized words that may be used consistent with some disclosed embodiments. By way of a non-limiting example, the facial skin micromovements may be associated with entries in one or more data structures. The entries in the data structures may contain data related to the particular unvocalized words associated with the facial skin micromovements as described in embodiments herein. In order to create the entries in the data structure, data associated with the particular unvocalized words may be stored in the data structure to make the association (e.g., recorded data associated with the unvocalized words). For example, samples of particular unvocalized words may be recorded and stored indicative of the relationship with particular facial skin micromovements). In future use, for example, a memory address associated with an entry in the data structure may be based on a particular facial skin micromovement. Upon detection of the particular facial skin micromovement, the memory address may be used to lookup in the data structure the previously recorded data associating one or more particular unvocalized words to the particular facial skin micromovement. Thus, the previously recorded data associated with particular unvocalized words may be stored for future use. It is to be appreciated that recording data may occur during a calibration cycle or during normal operation.

Consistent with some disclosed embodiments, the data includes at least one of the audible presentation of the particular unvocalized words or a textual presentation of the particular unvocalized words. The recorded data may be associated with the audible presentation of particular unvocalized words, for example, by capturing information associated with the audio output based on particular unvocalized words. Recorded data of the textual presentation of particular unvocalized words may include storing data representations of graphics, images, or text of words associated with particular unvocalized words. The textual presentation of the words may be data recorded during prevocalization or during vocalization. Data recording may occur as capturing audio or text associated with particular facial skin micromovements. Data including the audible or textual presentation of particular unvocalized words may be associated with particular facial skin micromovements and stored in data structures for future use. The future use may include detecting the particular facial skin micromovements for an individual and retrieving the audible or textual presentation for output. By way of a non-limiting example, a wearable device may be configured for a particular individual using a calibration process. During the calibration process, the data structure may be populated with audible or textual presentation data correlated with facial skin micromovements of the particular individual. For example, while wearing the device, the particular individual may vocalize words into a microphone. The audio of the vocalized words may be recorded as data associated with the unvocalized words and particular facial skin micromovements that may produce the vocalized and unvocalized words. For example, audible or textual presentation may be stored in a data structure based on the calibration. In future use, the audible or textual presentation may be retrieved from the data structure in response to detected unvocalized words.

Consistent with some embodiments, the at least one presentation includes the textual presentation and wherein the operations further include adding punctuation to the textual presentation. Adding punctuation to the textual presentation refers to insertion of standardized marks or symbols used to indicate the structure, organization, and intended meaning of written text. Marks representing punctuation in textual presentation add clarity and precision to textual presentation. By way of a non-limiting example, particular facial skin micromovements may provide information on unvocalized words however the particular facial skin micromovements may not provide information on whether the detected prevocalization includes pauses, stops, emphasis or when a sentence ends, relates to a question or other punctuation. Unvocalized words may indicate the form of the textual presentation. For example, a series of facial skin micromovements forming "Who" "is" "this" may, through context of the three detected unvocalized words together, allow the processor configured to generate the textual presentation to add punctuation of a question mark to the end of the textual presentation. Similarly, the processor may identify locations for commas, periods, exclamation points, or any other punctuation derived, for example, from context. It is to be appreciated that the contextual analysis of words or ideas expressed in a particular sequence may provide information for operations to understand, evaluate or interpret to allow adding punctuation to the textual presentation.

Some disclosed embodiments involve adjusting a speed of the audible presentation of the particular unvocalized words based on input from the individual. "Speed of the audible presentation" may generally refer to the tempo or pace of the audio output. A user interface (audio command, touch screen control, gesture control), for example, may permit the user to select a desired speed of presentation. Consistent with some embodiments, the speed of the audible presentation may include how fast or slow the tempo or pace of the audio output may be. The speed of the audible presentation may be changed to a faster or slower pace. For example, an algorithm may use time stretching to achieve a faster or slower audio playback speed. In one example, the audio playback speed may be decreased by a factor of 0.75× from the original audio speed. In another example, the audio playback speed may be increased by a factor of 1.25× from the original audio speed. It is to be appreciated that decreasing the speed may have an advantage in allowing a listener to consume information more efficiently. Also, increasing the speed may allow a user listening to audio at a higher speed to consume information more quickly. Adjusting the speed refers to altering, modifying, changing, increasing, or decreasing the speed. The operation of a personal presentation of prevocalization system may speed up or slow down audible presentation of the particular unvocalized words based on input from the individual. In some embodiments, a user may prefer to listen to audible presentation at a slower or faster than original speed. By way of a non-limiting example, a user may want to the audio output to be played faster than normal speed to allow them to hear the audible presentation prior to vocalization of the words such that they may have additional time to absorb the information and continue with vocalization, change the vocalization or stop the vocalization. It is to be appreciated that the speed of the audible presentation may be adjusted based on input from the individual using the system. For example, the individual may use a mobile application to configure a speech detection system capable of changing the speed of the audible presentation. For example, a setting in the mobile application on a mobile communication device related to the speech detection system may allow an adjustment of the playback speed (e.g., a slider or a playback rate setting) to fit the preference of the individual. The mobile application may include an interface with widgets like buttons, dials, or sliders that may allow the individual to change the speed of the audible presentation. Based on the input from the individual, the mobile application may communicate a change in the configuration to the processor of the speech detection system to make the adjustment in the speed of the audible presentation based on the input.

Some disclosed embodiments involve adjusting a volume of the audible presentation of the particular unvocalized words based on input from the individual. "Volume" related to audio may generally refer to the intensity of soundwaves or how loud a sound is. Adjusting the volume of the audible presentation refers to changing the sound volume of the audible presentation using the buttons, dials, mobile applications or any other manner of changing the setting of the intensity of sound. Consistent with some embodiments, the audible presentation may be generated based on particular unvocalized words detected by a personal presentation of prevocalization system that operates based on the detection of facial skin micromovements used to determine corresponding unvocalized words through accessing a data structure. The operation of the personal presentation of prevocalization system may allow a user to adjust the volume of particular unvocalized words in the resulting audible presentation based on settings configured via user input. For example, the individual may use a mobile application designed to configure a speech detection system wherein the speech detection system may have controls related to the audible presentation. In some examples, the mobile application may have a setting on a mobile communication device that may allow an adjustment of the volume (e.g., a slider or an explicitly setting a volume level). The mobile application may include an interface with buttons, dials, or sliders that may allow the individual to change the volume of the audio output related to the audible presentation. Based on the input from the individual, the mobile application may communicate with the processor of the speech detection system to make the adjustment of the volume of the audible presentation based on the input.

Some disclosed embodiments involve determining that an intensity of a portion of the particular facial skin micromovements is below a threshold and providing associated feedback to the individual. The term "intensity" related to facial micromovements broadly refers to the sensed or measured amount of skin or muscle fiber movement. Sensing (e.g., to sense) may include detecting, measuring, and/or receiving a measurement. Intensity of facial micromovements may be determined (e.g., measured) using a variety of sensors including but not limited to light sensors, optical sensors, image sensors, electromyography (EMG) sensors, motion sensors and any other device that may detect or sense movements in the face region. A portion of the particular facial skin micromovements may refer to a part of the facial region. As illustrated in FIG. 1, facial region 108 may have a plurality of locations that facial skin micromovements may be detected as depicted by array of light spots 106. The portion of particular facial skin micromovements may refer to a group of the array of light spots 106 that may be a subset of the facial region 108. The threshold may include a baseline, a limit (e.g., a maximum or minimum), a tolerance, a starting point, and/or an end point for a measurable quantity. Consistent with some disclosed embodiments, the measurable quantity related to the threshold may correspond to the intensity of a portion of particular facial skin micromovements. The threshold, as related to intensity of facial skin micromovements, may represent a pre-determined intensity that the system may compare to the measured intensity. For example, intensity below the threshold may involve determining a difference, a ratio, or some other statistical or mathematical value based on the determined intensity level and the threshold where the determined intensity level is lower than or below the threshold. When the intensity may be below a threshold related to intensity, feedback may be provided to the user. Consistent with some disclosed embodiments, the threshold may be used to identify when a user does not plan to talk (e.g., thinking to self). It is to be appreciated that different muscles or regions of the face may have different thresholds. For example, a part of the cheek above the mouth may have a different threshold than a part of the cheek below the mouth. A determined intensity level of a part of the cheek above the mouth may have a different interpretation versus a determined intensity level of a part of the cheek below the mouth therefore they may have different thresholds to compare to when determining whether to interpret or disregard micromovements in either area of the face. Providing associated feedback to the individual may include notifying the individual that the intensity may be below or may be crossing below the threshold.

The feedback may alert the individual that the intensity of the movement of the portion of the facial skin micromovements may be too low for the speech detection system to determine unvocalized words. For example, an individual using a wearable earpiece may receive an audible presentation of an alert sound (e.g., buzz, beep, status words) to indicate that the intensity may be below the threshold. Feedback to the individual may be provided when the individual may start talking indicating that the intensity of the talking and/or facial skin micromovements may be too low. Thus, the feedback may alert the individual to increase their muscle recruitment, for example increase the intensity of their neuromuscular activity. In one example, the individual may increase the intensity of their neuromuscular activity by intentionally becoming more animated or by increasing the volume they are speaking at, to increase the intensity of the particular facial skin micromovements. In one example, the threshold may be used to determine the start and end of a speaking session (i.e., period of time during which the speech detection system may detect unvocalized words and provide audible presentation determined by the detection). The feedback may be one alert sound added to the audible presentation to notify the user that the speaking session has started and a second different alert sound to notify the user when the speaking has ended.

Some disclosed embodiments involve ceasing the audible presentation of the particular unvocalized words in response to a detected trigger. A trigger includes an action that may bring about, cause, generate, produce, prompt, activate, deactivate or provoke a response as result of the action. A measured intensity of facial skin micromovements compared to a threshold or crossing of the threshold may represent a detected trigger that may cause a response by the system. Consistent with some embodiments, the threshold of measured intensity of facial skin micromovements may be crossed during consecutive measurements of the intensity of facial skin micromovements causing a trigger to the system (e.g., detected trigger) to take an action in response. For example, a measured intensity level crossing below a threshold may be configured as a trigger indicating that facial skin micromovements should be disregarded (e.g., that the intensity level is too low and may result in unreliable detection). On the next measurement, the determined intensity level may transition to above the threshold level indicating that the facial micromovements should be interpreted (e.g., that the intensity level is high enough to indicate an intensity consistent with reliable detection). Consistent with some embodiments, when a trigger occurs indicating that the intensity level may be below or may have crossed below a threshold, the system may cease audible presentation of the particular unvocalized words in response. For example, an individual using a wearable earpiece including the speech detection system may stop receiving an audio output to the speaker of the earpiece upon the system detecting a trigger corresponding to the intensity level below the threshold. In the example, the trigger may indicate that the intensity of the facial skin micromovements may be low and detection of unvocalized words may be less reliable therefore the system may cease generating the audible presentation.

Some disclosed embodiments involve detecting the trigger from determined facial skin micromovements of the individual. "Determined facial skin micromovements of the individual" may refer to detected or measured intensity levels of facial skin micromovements for a particular person. Operation of a speech detection system may be based on detected or measured intensity levels of facial skin micromovements for a particular person. Consistent with some disclosed embodiments, the trigger level may be configured based on the specific determined facial skin micromovements of the individual. It is to be appreciated that different individuals may have different facial skin micromovements associated with particular unvocalized words. Thus, in embodiments implementing a threshold, the threshold setting used to determine whether the system may interpret or may disregard facial skin micromovements may be different for a first individual versus a second individual due to differences between the individuals in facial structure, neuromuscular structure and any anatomical differences related to creating unvocalized or vocalized speech. By way of a non-limiting example, the first individual may have a round shaped face and a second individual may have a square shaped face. The trigger generated from comparing an intensity of a portion of the particular facial skin micromovements to a threshold for the first individual with a round shaped face may be different than the trigger generated for the second individual with a square shaped face due to difference in the detected facial skin micromovements based on difference in facial structure. It is to be appreciate that providing associated feedback to the individual based on the trigger may include adjusting the threshold and associated trigger based on the characteristics of the face of the individual (i.e., facial features of the individual).

Figure 56:
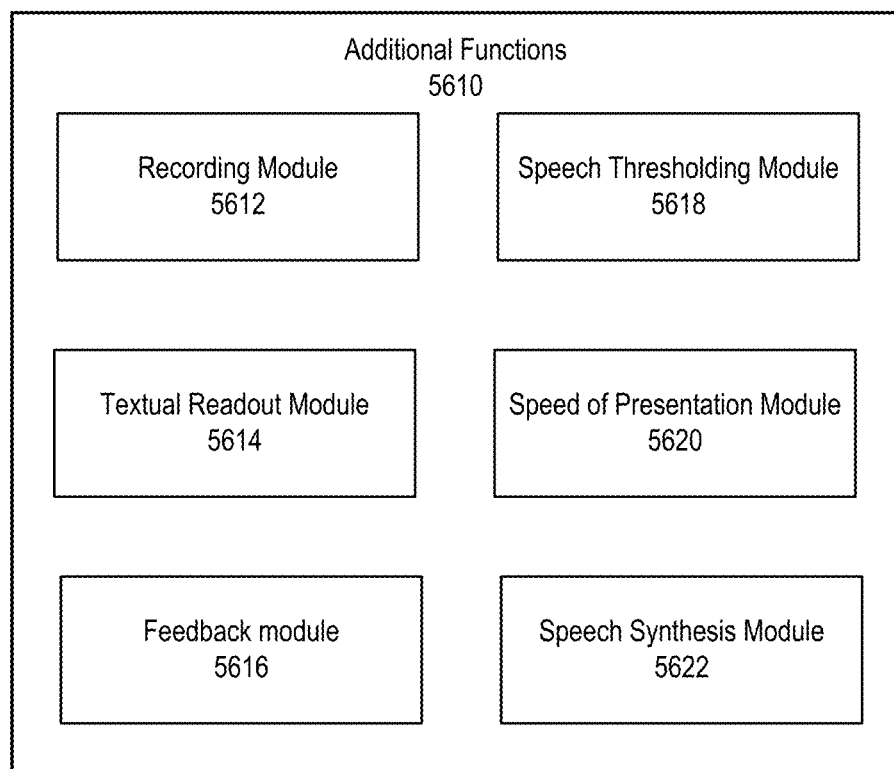
FIG. 56 shows exemplary additional functions of personal presentation of prevocalization, consistent with some embodiments of the present disclosure.

FIG. 56 shows additional functions consistent with disclosed embodiments. Additional functions 5610 may contain software modules execute by one or more processors consistent with the present disclosure. In particular, additional functions 5610 may include a recording module 5612, a textual readout module 5614, a feedback module 5616, a speech thresholding module 5618, a speed of presentation module 5620 and a speech synthesis module 5622. The disclosed embodiments are not limited to any particular configuration. Processing device 400 and/or processing device 460 may execute the instructions stored in memory to implement of modules 5612 to 5622 as described herein. It is to be understood that references in the following discussions to a processing device may refer to processing device 400 of speech detection system 100 and processing device 460 of remote processing system 450 individually or collectively. Accordingly, steps of any of the following processes associated with modules 5612 to 5622 may be performed by one or more processors associated with speech detection system 100.

Consistent with disclosed embodiments, recording module 5612, textual readout module 5614, feedback module 5616, speech thresholding module 5618, speed of presentation module 5620 and speech synthesis module 5622 may cooperate to perform various operations. For example, speed of presentation module 5620 may determine the rate at which speech synthesis module 5622 causes an audible presentation.

Consistent with some disclosed embodiments, the recording module 5612 may capture, record and/or store data associated with particular unvocalized words for future use. For example, recording module 5612 may store one or more particular unvocalized words associated with facial skin micromovements. In the example, the recording module 5612 may implement a process to correlate vocalized words with facial skin micromovements to be able to determine unvocalized words based on those micromovements in future use. The textual readout module 5614 may implement causing a textual presentation of particular unvocalized words in response to particular facial skin micromovements. For example, prevocalized or unvocalized words may be printed on a display in near real time. In one example, a teleprompter may be used to provide a textual presentation to a user in a second language. The user may cause neuromuscular activity in a first language and the detected unvocalized words may be displayed on a teleprompter in the second language such that the user may then vocalize the words in the second language (e.g., a translation function). Feedback module 5616 may provide feedback to a user related to system operation. For example, a threshold may be set such that facial skin micromovements below an intensity level may cause the system to disregard the movements. As such, feedback may be provided to the user to indicate that the intensity of the facial skin micromovement may be too low to reliably detect unvocalized or prevocalized words. It is to be appreciated that a speech thresholding module 5618 may implement a process to set, adjust and compare intensity levels to one or more thresholds consistent with disclosed embodiments.

Consistent with some disclosed embodiments, speed of presentation module 5620 may adjust the rate of playback of audio. Speed of presentation module 5620 may speed up or slow down audible presentation of the particular unvocalized words. A user may prefer to listen to audible presentation slow or faster than the original speed and as such may provide input to speed of presentation module 5620 to adjust the rate of presentation. Consistent with some disclosed embodiments, the speed of presentation module 5620 may implement additional audio processing functions to configure the audio output for a user. For example, an audio speed changer algorithm may implement time stretching to achieve a faster or slower playback without changing the pitch of the sound. Speech synthesis module 5622 may implement any form of speech processing to generate an audible presentation for an audio output. For example, the speech synthesis may decompress stored speech and provide the digital samples to a digital to analog converter at the proper playback rate to produce an audio output to a user.

Figure 57:
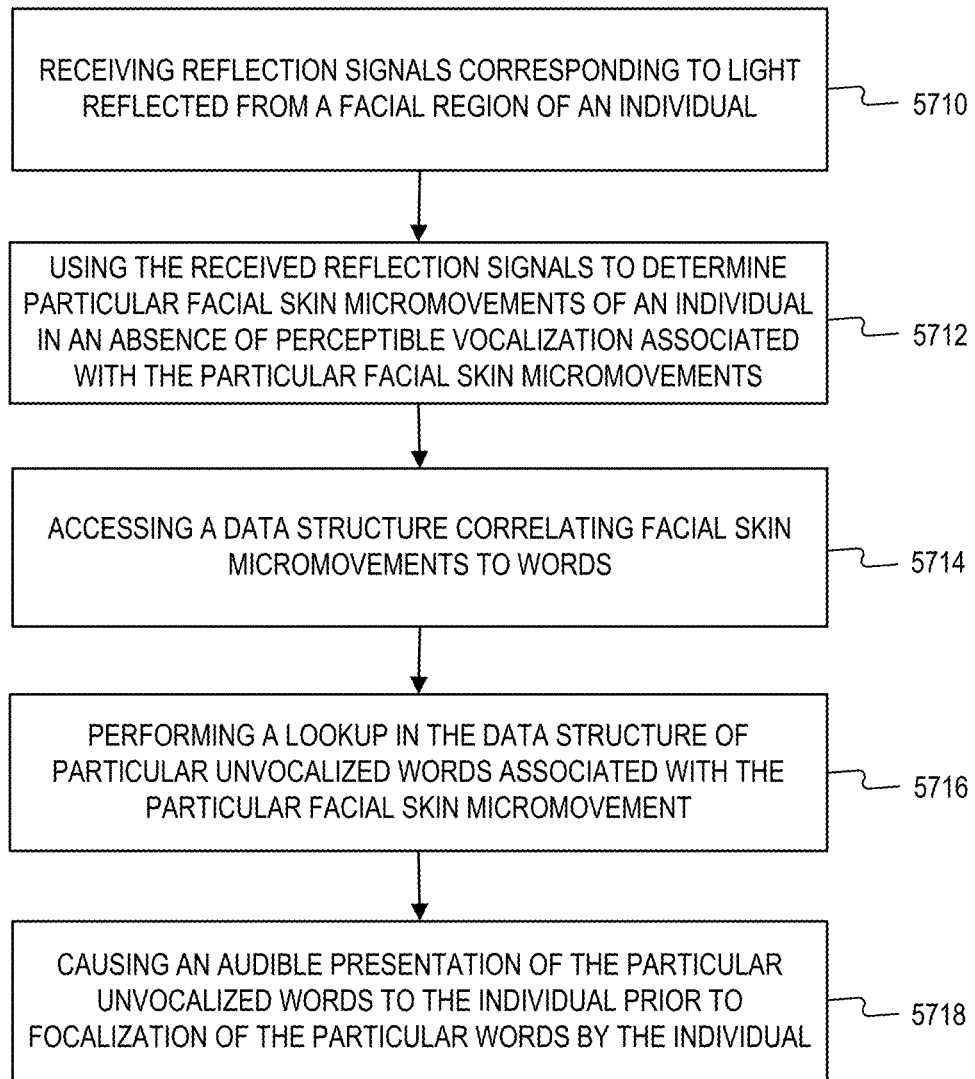
FIG. 57 is a flow chart showing an exemplary method for using received reflections to determine unvocalized words from facial micromovement to cause an audible presentation, consistent with some embodiments of the present disclosure.

FIG. 57 illustrates a flowchart of an exemplary method 5700 for implementing personal presentation of prevocalization for articulation, consistent with embodiments of the present disclosure. Some embodiments involve a method for personal presentation of prevocalization. At step 5710, the method includes receiving reflection signals corresponding to light reflected from a facial region of an individual. In some embodiments, the light reflected from the facial region of the individual may include coherent light reflections. At step 5712, the method includes using the received reflections signals to determine particular facial skin micromovements of an individual in an absence of perceptible vocalization associated with the particular facial skin micromovements. At step 5714, the method includes accessing a data structure correlating facial skin micromovements with words. In some embodiments, the data structure may be stored in memory storage. The lookup may involve accessing the memory. At step 5716, the method includes performing the lookup in the data structure of particular unvocalized words associated with the particular facial skin micromovements. In some embodiments, based on the particular facial skin micromovements, the method may include retrieving words correlating with the micromovements. At step 5718, the method includes causing an audible presentation of the particular unvocalized words to the individual prior to vocalization of the particular words by the individual. Consistent with some disclosed embodiments, the audible presentation may consist of outputting an audio signal to a personal hearing device. Consistent with some disclosed embodiments, the audible presentation may occur some time period prior to vocalization of the particular words by the individual. Consistent with some disclosed embodiments, the audible presentation may be in a different language (e.g., unvocalized words are detected in a first language and the audible presentation may be in a second language). Consistent with some disclosed embodiments, the output may be a textual presentation of particular unvocalized words to the individual.

The embodiments discussed above for personal presentation of prevocalization may be implemented through non-transitory computer-readable medium such as software (e.g., as operations executed through code), as methods (e.g., method 5700 shown in FIG. 57), or as a system (e.g., speech detection system 100 shown in FIGS. 1-3). When the embodiments are implemented as a system, the operations may be executed by at least one processor (e.g., processing device 400 or processing device 460, shown in FIG. 4).

Some disclosed embodiments involve determining facial skin micromovements. By way of example, as illustrated in FIGS. 1 and 4, processor or processing device 400 of speech detection system 100 or processing device 460 of remote processing system 450 may execute one or more instructions stored in memory device 402, shared memory module 472, data structures 124, 422, or 464 to perform operations for determining facial skin micromovements.

Some disclosed embodiments involve controlling at least one coherent light source for projecting a plurality of light spots on a facial region of an individual, wherein the plurality of light spots includes at least a first light spot and a second light spot spaced from the first light spot. The term coherent light source is to be understood as discussed elsewhere in this disclosure. The term projecting includes the light source emitting light, as discussed elsewhere in this disclosure. The term individual includes a person who uses the speech detection system, as described elsewhere in this disclosure. The term facial region includes a portion of the face of the individual, as described elsewhere in this disclosure. By way of example only, the facial region may have an area of at least 1 $cm^2$, at least 2 $cm^2$, at least 4 $cm^2$, at least 6 $cm^2$, or at least 8 $cm^2$.

A light spot includes an area of illumination with a higher intensity, higher luminance, a higher luminous energy, a higher luminous flux, a higher luminous intensity, a higher illuminance, or other measurable light characteristic, than a similar measurable light characteristic of a non-spot area or area adjacent to, near, or in a vicinity of the light spot. The light spot may have any shape, including a line, a circle, an oval, a square, a rectangle, or any other discernable shape such that the measurable light characteristic of light in the light spot is higher than the same measurable light characteristic in another area in a vicinity of the light spot (e.g., a non-spot area or area outside the light spot). As used herein, the phrase "in the vicinity of the light spot" means an area adjacent to the light spot or near the light spot such that to the naked eye, the light spot and (e.g., in a non-spot area) may appear to be a contiguous region or in close proximity to the light spot. A light detector as described elsewhere in this disclosure may be configured to determine the difference between the light spot and another area (e.g., a non-spot area or an area outside the light spot).

Other light in the vicinity of the light spot may include reflected light from an area adjacent to the light spot in any direction or light separated from the light spot by a distance. For example, a light spot may exhibit a luminance that is ten times higher than other light in the vicinity of the light spot. As another example, a light spot may exhibit a luminance that is more than more than five times higher, more than ten times higher or more than 15 times higher than other light in the vicinity of the light spot. As another example, a difference between a light spot and other light in the vicinity of the light spot may be determined by a measurable difference between light characteristics (e.g., luminance, luminous energy, luminous flux, luminous intensity, illuminance, or other measurable light characteristic) of the light spot and the other light in the vicinity of the light spot. A plurality of light spots projected by the coherent light source may be a specific implementation of a non-uniform illumination projected by the light source.

A first light spot may be considered to be "spaced from" a second light spot when there is an intervening area having light characteristics that may be measurably different from the light characteristics of the light in the first spot and the second spot. The intervening area may include a region having any size or any shape and that is located between any two light spots. The area may include some level of light or may be devoid of light. For example, the first light spot may have a first luminance, an area adjacent to the first light spot may have a second luminance lower than the first luminance, and the second light spot may have the first luminance and be adjacent to the area in a different direction from the first light spot. As another example, the second light spot may have a third luminance that is different from the second luminance but is not identical to the first luminance; i.e., the first luminance and the third luminance may be within a predetermined range of each other, for example within 2%, 3%, or 5%.

Consistent with some disclosed embodiments, the plurality of light spots additionally includes a third light spot and a fourth light spot, wherein each of the third light spot and the fourth light spot are spaced from each other and spaced from the first light spot and the second light spot. The third light spot and the fourth light spot may be understood in a similar manner to the first light spot as described above (e.g., having a higher intensity than an area in the vicinity of the spot when measured in a similar manner). The third light spot and the fourth light spot may be considered to be spaced from each other and spaced from the first light spot and the second light spot in a similar manner described above with regard to the first light spot being spaced from the second light spot.

Consistent with some disclosed embodiments, the plurality of light spots includes at least 16 spaced-apart light spots. Each of the light spots may be understood in a similar manner as the first light spot as described above (i.e., having a higher intensity than another area in the vicinity of the spot when measured in a similar manner). The light spots may be spaced-apart from each other in a similar manner described above with regard to first light spot being spaced from the second light spot. Consistent with disclosed embodiments, the number of light spots may vary depending on a number of factors including, but not limited to, properties of the at least one coherent light source, a size and/or shape of each of the light spots, and a size of an area of the individual's face where the light spots are projected (e.g., more light spots may be projected on a larger area than on a smaller area). In some embodiments the number of spaced apart light spots may be 16. It should be understood, however, that any number (e.g., 2, 3, 4, 10, 32, or any other number) of spaced apart light spots are included within the scope of this disclosure.

By way of one example with reference to FIG. 4, the at least one coherent light source may include light source 410 of optical sensing unit 116 of speech detection system 100. By way of another example with reference to FIG. 5, the at least one coherent light source may include illumination module 500 of optical sensing unit 116.

Figure 58:
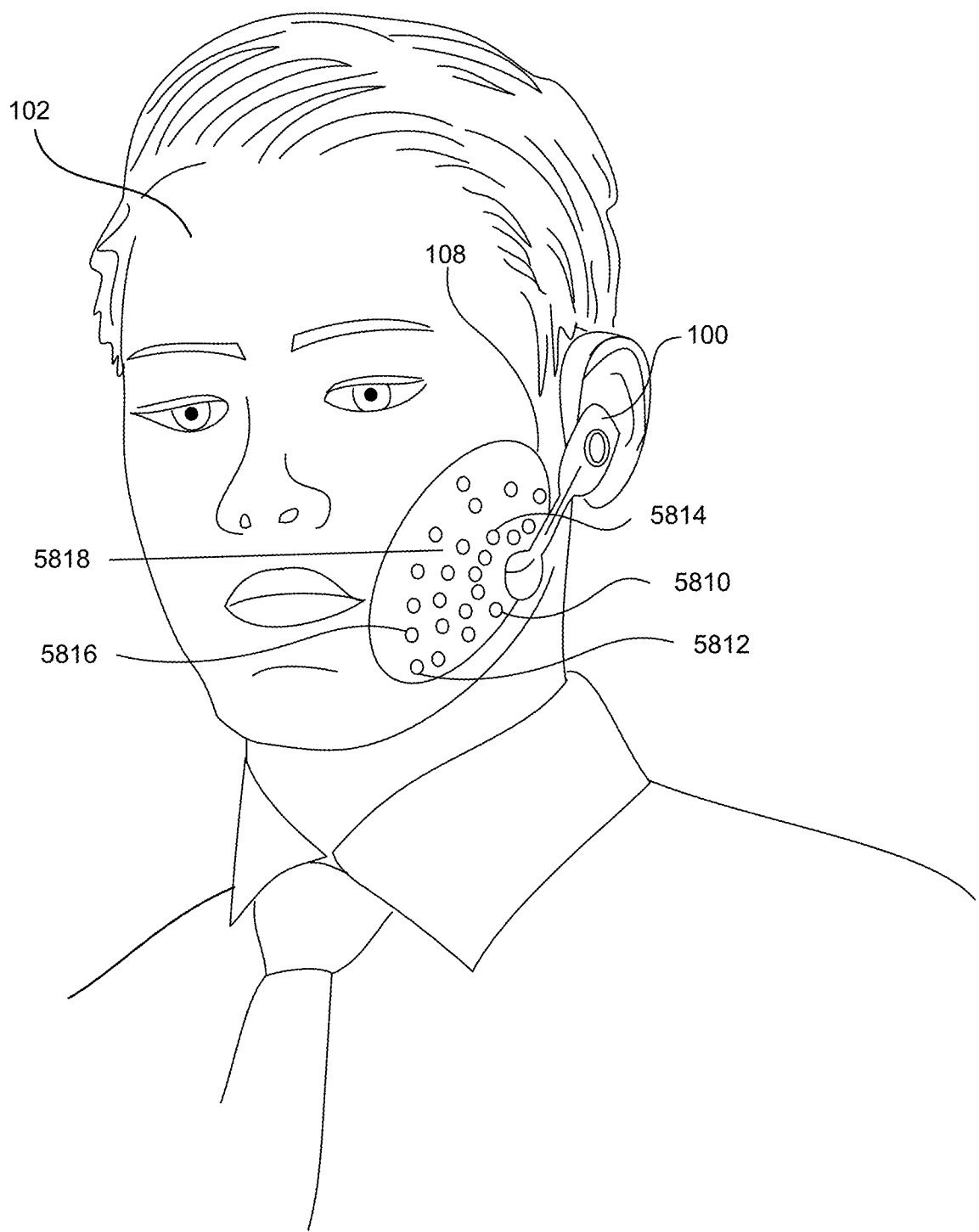
FIG. 58 is a perspective view of an individual using a first example speech detection system, consistent with some embodiments of the present disclosure.

FIG. 58 is a perspective view of an individual 102 using a first example speech detection system 100, consistent with some embodiments of the present disclosure. As shown in FIG. 58, speech detection system 100 projects a plurality of light spots onto facial region 108 of individual 102. For example, speech detection system 100 may project a first light spot 5810, a second light spot 5812, a third light spot 5814, and a fourth light spot 5816 onto facial region 108. It is noted that the light spots as identified in FIG. 58 are arbitrary and that any light spot projected by speech detection system 100 may be designated as the first light spot, the second light spot, the third light spot, or the fourth light spot. Consistent with some disclosed embodiments, the number of projected light spots and the locations of each of the projected light spots may vary without affecting the overall operation of the embodiments described herein.

Each of first light spot 5810, second light spot 5812, third light spot 5814, and fourth light spot 5816 includes an area of light with a higher intensity (e.g., a higher luminance, a higher luminous energy, a higher luminous flux, a higher luminous intensity, a higher illuminance, or other measurable light characteristic) than other light in a vicinity of the light spot. The light spot may include any shape, including a line, a circle, an oval, a square, a rectangle, or any other discernable shape such that the measurable light characteristic of the light spot is higher than the same measurable light characteristic of other light in a vicinity of the light spot. Each of first light spot 5810, second light spot 5812, third light spot 5814, and fourth light spot 5816 may have a same intensity, have a different intensity, have a same shape, or have a different shape, consistent with some disclosed embodiments. Other light in the vicinity of the light spot (e.g., light 5818) may light projected from any source not related to speech detection system 100.

First light spot 5810, second light spot 5812, third light spot 5814, and fourth light spot 5816 may be spaced from each other in a similar manner as described elsewhere in this disclosure. The spacing between first light spot 5810, second light spot 5812, third light spot 5814, and fourth light spot 5816 may be uniform (e.g., a grid or other pattern) or non-uniform (e.g., the distance between any two light spots may be different), consistent with some disclosed embodiments.

Consistent with some disclosed embodiments, the plurality of light spots are projected on a non-lip region of the individual. The light spots may be projected on the individual's face in the orbital, nasal, or oral regions of the face that do not include the lip region. As used in this disclosure, the "lip region" includes a region of the individual's face that includes the orbicularis oris muscle that surrounds the mouth and forms a majority of the lips. As used in this disclosure, the "non-lip region" includes facial skin associated with muscles other than the orbicularis oris muscle. As described elsewhere in this disclosure, facial skin micromovements may be based on the movement of muscles under the skin in regions of the face that correspond to the locations of those muscles. The muscles that cause lip movements may be better measured in parts of the individual's face not including the lips. For example, different muscles or combinations of muscles cause different lip movements. To be able to determine which muscles are activated and causing the lip movements, the muscle movements away from the lip region may be analyzed. By way of one example with reference to FIG. 1, facial region 108 includes a non-lip region of individual 102. As illustrated in FIG. 5, light source 410 may project a plurality of light spots 106A-106E on non-lip region 108 of individual 102.

Some embodiments involve analyzing reflected light from the first light spot to determine changes in first spot reflections. The term light reflection refers to one or more light rays bouncing off a surface (e.g., the individual's face). The terms reflected light and analyzing reflected light are to be understood as discussed elsewhere in this disclosure. The first spot reflections include one or more reflections of the first light spot from the facial region of the user and detected by a light detector. In some embodiments, a measurable light characteristic of the first spot reflection is compared to the same measurable light characteristic of the first light spot to determine if there is a change in the measurable light characteristic. For example, a luminance of the first spot reflection may be determined by using light reflection analysis as described elsewhere in this disclosure. The luminance of the first spot reflection may be compared with the luminance of the first light spot to determine if there is a change in luminance. The change in luminance or change in any other measurable characteristic (e.g., intensity, luminous energy, luminous flux, luminous intensity, or illuminance) of the reflected light from the first spot may be used to determine whether there is a change in the first spot reflection.

For example, a change may be determined if the difference exceeds a threshold difference, either in absolute terms (e.g., greater than 5 candela per square meter (cd/m 2)), a percentage difference (e.g., greater than 5%), an absolute difference (e.g., simple subtraction between two values), a ratio, an absolute value, or any other computed or statistical value. Any of these values may be compared to a threshold. It is noted that the preceding threshold differences are merely exemplary and that other threshold differences may be utilized.

By way of an example with reference to FIG. 5, spot reflections may include reflections 300 of light from light spot 106 of facial region 108 and may be detected by detection module 502. For example as shown in FIG. 5, before muscle recruitment, one output beam 508 may project light spot 106A (e.g., the first light spot). After muscle recruitment, light spot 106A may be reflected (via reflection 300) and detected by detection module 502. The reflection may be used to determine that the facial skin illuminated by light spot 106a moved by a distance d1, as described elsewhere in this disclosure.

Consistent with some disclosed embodiments, the at least one coherent light source is associated with a detector. The term coherent light source is to be understood as described elsewhere in this disclosure. As noted elsewhere in this disclosure, a non-coherent light source may also be used. As described elsewhere in this disclosure, the detector is capable of measuring properties of the projected light and generating an output relating to the measured properties. For example, the detector may measure the luminance of the projected light (e.g., of the first light spot) and may output a value of the measured luminance as a numerical value in candela per square meter (cd/m 2). A coherent light source "associated with" a detector means that the coherent light source and the detector are either contained within a same housing or unit, are located near each other, and/or are configured to cooperate with each other (e.g., the detector receives reflections of light originating from the coherent light source).

Consistent with some disclosed embodiments, the at least one coherent light source and the detector are integrated within a wearable housing. As described elsewhere in this disclosure, the wearable housing may include any structure or enclosure configured to be worn by an individual (such as on a head of the individual). The term "integrated with a wearable housing" indicates that the at least one coherent light source and the detector may be contained within the same wearable housing or may be connected to the same wearable housing. For example, as shown in FIGS. 1 and 4, optical sensing unit 116 of speech detection system 100 may include both the at least one coherent light source (e.g., light source 410) and the detector (e.g., light detector 412).

By way of one example with reference to FIG. 4, the detector may include light detector 412 of optical sensing unit 116 of speech detection system 100. The at least one coherent light source may include light source 410 of optical sensing unit 116. As another example with reference to FIG. 5, illumination module 500 may include the at least one coherent light source and detection module 502 may include a detector. As shown in FIG. 5, illumination module 500 may project light spots 106A-106E onto facial region 108 and detection module 502 may detect reflections 300 of the light from facial region 108. By way of another example with reference to FIG. 1, the wearable housing may include wearable housing 110 and optical sensing unit 116 (including the detector and the light source) may be included with or incorporated with wearable housing 110 as described elsewhere in this disclosure.

Some disclosed embodiments involve analyzing reflected light from the second light spot to determine changes in second spot reflections. The second spot reflections include one or more reflections of the second light spot from the facial region of the user and detected by the light detector. The second spot reflections may be detected and analyzed in a manner similar to the first spot reflections described above.

Consistent with some disclosed embodiments, the changes in the first spot reflections and the changes in the second spot reflections correspond to concurrent muscle recruitments. A muscle recruitment is the activation of at least one muscle fiber by a motor neuron. Recruitment of one or more muscle fibers in turn causes skin micromovements in an area of the skin associated with the recruited muscle fibers. Because the first light spot is spaced from the second light spot, the respective spot reflections may be able to detect concurrent muscle recruitments. A muscle recruitment may be used to determine facial skin micromovements, as described elsewhere in this disclosure. The light reflections may be analyzed to determine facial skin micromovements that result from recruitment of muscle fibers under the skin. The term concurrent means at the same time or at substantially the same time (e.g., fully overlapping in time or partially overlapping in time). By way of one example with reference to FIG. 5, light reflections 300 may be analyzed to determine facial skin micromovements resulting from recruitment of muscle fiber 520, as described elsewhere in this disclosure. For example, reflection 300 from light spot 106A may indicate that the facial skin above muscle 520 moved by a distance d1 while, concurrently, reflection 300 from light spot 106E may indicate that the facial skin above muscle 520 moved by a distance d2, as described elsewhere in this disclosure.

Consistent with some disclosed embodiments, both the first spot reflections and the second spot reflections correspond to recruitment of a single muscle selected from: a zygomaticus muscle, an orbicularis oris muscle, a genioglossus muscle risorius muscle, or a levator labii superioris alaeque nasi muscle. The first light spot and the second light spot may be selected such that both the first light spot and the second light spot are projected on skin associated with a common muscle. Because the locations and the trajectories of the facial muscles are known, it may be possible to select a given facial muscle and to project the first light spot and the second light spot onto different portions of skin associated with the same selected facial muscle. As described elsewhere in this disclosure, the light reflections may be analyzed to determine facial skin micromovements that result from recruitment of muscle fibers under the skin. By projecting light spots onto skin associated with certain muscles, skin micromovements above those muscles may be analyzed. It is noted that the facial muscles identified herein is exemplary and that other facial muscles may be used to determine skin micromovements. To detect prevocalization facial skin micromovements, certain muscles may be preferred to be used and the light spots may be projected onto those preferred muscles to obtain light spot reflections. By way of one example with reference to FIG. 1, these muscles may be located in or at least partially located in facial region 108. By way of another example with reference to FIG. 5, muscle 520 may correspond to any one of these muscles, as described elsewhere in this disclosure.

Consistent with some disclosed embodiments, the first spot reflections correspond to recruitment of a muscle selected from: a zygomaticus muscle, an orbicularis oris muscle, a risorius muscle, a genioglossus muscle, or a levator labii superioris alaeque nasi muscle; and the second spot reflections correspond to recruitment of another muscle selected from: the zygomaticus muscle, the orbicularis oris muscle, the risorius muscle, the genioglossus muscle, or the levator labii superioris alaeque nasi muscle. The first light spot and the second light spot may be selected such that the first light spot is projected onto a region of skin associated with the first muscle and the second light spot is projected onto a region of skin associated with the second muscle, different from the first muscle. Consistent with some embodiments, a desired muscle may be selected and the light spots projected onto skin associated with the selected muscle. By projecting light spots onto skin associated with certain muscles, skin micromovements above or otherwise near those muscles may be analyzed. To detect prevocalization facial skin micromovements, certain muscles may be preferred to be used, and the light spots may be projected onto skin associated with those preferred muscles to obtain light spot reflections. In some disclosed embodiments, projecting the light spots onto areas associated with more than one muscle may enable a finer-grained determination of facial skin micromovements. By way of one example with reference to FIG. 1, these muscles may be located in or at least partially located in facial region 108. By way of another example with reference to FIG. 5, muscle 520 may correspond to any one of these muscles, as described elsewhere in this disclosure.

Some disclosed embodiments involve, based on the determined changes in the first spot reflections and the second spot reflections, determining the facial skin micromovements. The changes in the first spot reflections and the second spot reflections may be used to determine skin micromovements based on the location of the first light spot and the second light spot. As described and exemplified elsewhere in this disclosure, determining skin micromovements may be based on an amount of skin movement, a direction of skin movement, and/or an acceleration of skin movement.

Consistent with some disclosed embodiments, the facial skin micromovements are determined based on the determined changes in the first spot reflections and the second spot reflections, and changes in the third spot reflections and the fourth spot reflections. Determining facial skin micromovements based on changes in the third spot reflections and the fourth spot reflections may be performed in a similar manner as determining facial skin micromovements based on changes in the first spot reflections and the second spot reflections as described elsewhere in this disclosure. In some embodiments, by using more spot reflections (e.g., the third spot reflections and the fourth spot reflections), it may be possible to determine changes that may not be detectable by using fewer spot reflections (e.g., only the first spot reflections and the second spot reflections). For example, some skin micromovements may be more subtle or the recruited muscle fibers may be closer together or spaced farther apart. By using additional light spots and corresponding spot reflections, it may be possible to project the light spots and measure the spot reflections close together in a facial area or farther apart in a facial area. If a particular muscle is targeted (i.e., by projecting light spots onto the facial area corresponding to the particular muscle), it may be known (e.g., by using a lookup table, by applying a predetermined rule, or by using a trained machine learning algorithm) how many light spots and spot reflections may be needed to detect recruitment of the particular muscle. For example, certain muscles may exhibit recruitment in areas close to each other while other muscles may exhibit recruitment in areas spaced farther apart.

Figure 59A:
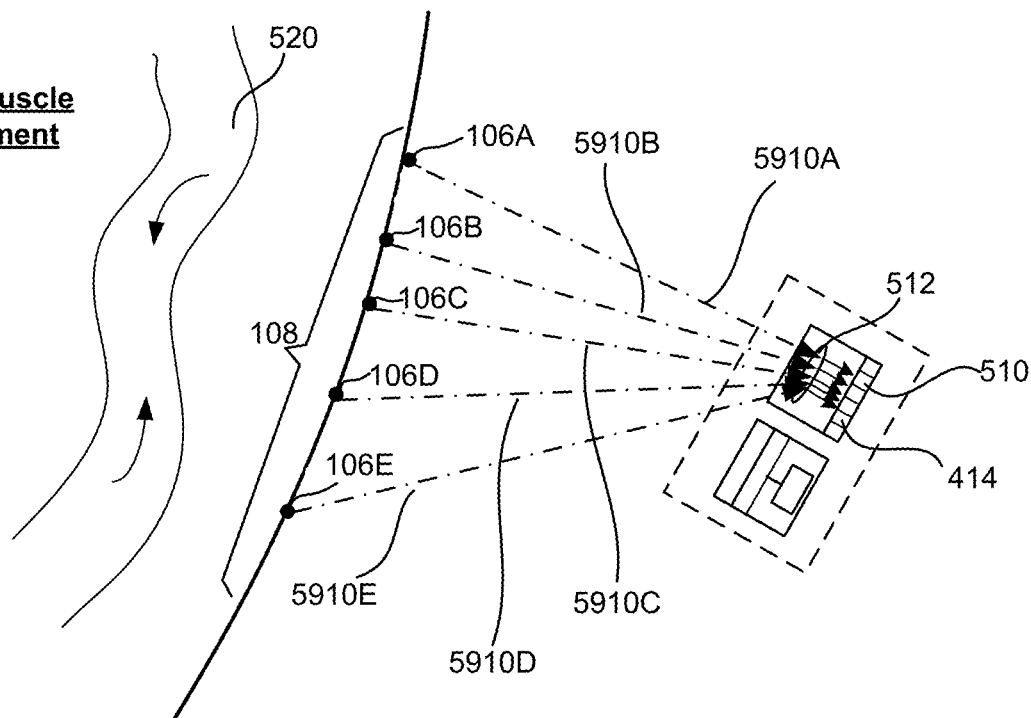
FIGS. 59A and 59B are schematic illustrations of a portion of the speech detection system as it detects facial skin micromovements, consistent with some embodiments of the present disclosure.
Figure 59B:
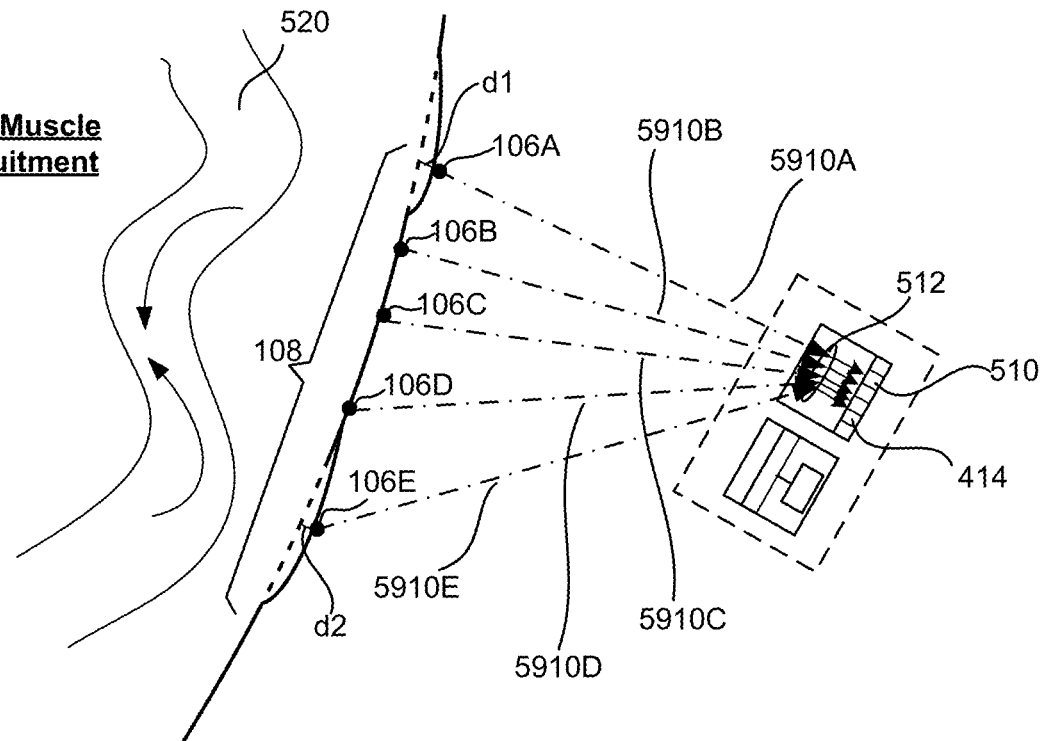

FIGS. 59A and 59B are schematic illustrations of part of the speech detection system as it detects facial skin micromovements, consistent with some embodiments of the present disclosure. FIG. 59A shows light spot reflections 5910A, 5910B, 5910C, 5910D, and 5910E, which correspond respectively to light spots 106A-106E, at a time before muscle recruitment. FIG. 59B shows light spot reflections 5910A-5910E at a time after muscle recruitment. By measuring light spot reflections 5910A-5910E both before muscle recruitment and after muscle recruitment, it may be possible to determine changes in the light spot reflections (e.g., first spot reflections, second spot reflections, third spot reflections, and fourth spot reflections). By determining the changes in the spot reflections, it may be possible to determine facial skin micromovements, as described elsewhere in this disclosure.

Consistent with some disclosed embodiments, determining the facial skin micromovements includes analyzing the changes in the first spot reflections relative to the changes in the second spot reflections. For example, a skin micromovement may be detectable based on a difference in spot reflections in two different locations, such as in locations corresponding to the first spot reflections and the second spot reflections. Changes in the first spot reflections relative to changes in the second spot reflections a change may be determined if a difference between the first spot reflections and the second spot reflections exceeds a threshold difference, for example, a percentage difference (e.g., greater than 5%), an absolute difference (e.g., simple subtraction between two values), a ratio, an absolute value, or any other computed or statistical value. Any of these values may be compared to a threshold. By way of one example and referring to FIGS. 59A and 59B, changes in the first spot reflections (e.g., light spot reflection 5910A) may be analyzed relative to changes in the second spot reflections (e.g., light spot reflection 5910E) to determine facial skin micromovements as shown in FIG. 59B and described elsewhere in this disclosure.

Consistent with some disclosed embodiments, the determined facial skin micromovements in the facial region include micromovements of less than 100 microns. As shown in FIGS. 5A and 5B and described elsewhere in this disclosure, the distance d1 of detectable skin micromovements may be less than 100 microns (micrometers). Consistent with some disclosed embodiments, the micromovements may be less than 1000 micrometers, less than 10 micrometers, or other measurable value.

Some disclosed embodiments involve interpreting the facial skin micromovements derived from analyzing the first spot reflections and analyzing the second spot reflections. As described elsewhere in this disclosure, the facial skin micromovements reflect muscle recruitment indicating prevocalized speech. Consistent with some embodiments, facial skin micromovements may be correlated with particular words. For example, a pattern of facial skin micromovements may be correlated with a specific word or phrase. In some embodiments, the pattern of facial skin micromovements may be stored in a data structure for later recall and comparison with a current pattern of facial skin micromovements to determine currently spoken or prevocalized speech. Interpreting the facial skin micromovements may include extracting meaning from the detected skin micromovements as described elsewhere in this disclosure. For example, the interpreting may include identifying one or more words from the pattern of facial skin micromovements.

As another example, the interpreting may include identifying a facial expression of the individual based on the facial skin micromovements. In a similar manner as determining one or more words based on a pattern of facial skin micromovements, a different pattern of facial skin micromovements may be used to determine a facial expression (e.g., happy, sad, anger, fear, surprise, disgust, contempt, or other emotion) of the individual. A pattern of facial skin micromovements indicating a certain facial expression may be stored in a data structure for later recall and comparison with a current pattern of facial skin micromovements to determine a current facial expression of the individual.

Consistent with some disclosed embodiments, the interpretation includes an emotional state of the individual. For example, the emotional state of the individual may be based on detecting whether the skin micromovements indicate whether a muscle is contracting or relaxing or by detecting a pattern in which the muscle may be contracting or relaxing. For example, the emotional state may include emotions such as happy, sad, anger, fear, surprise, disgust, contempt, or other emotions that may be detected by facial skin micromovements.

Consistent with some disclosed embodiments, the interpretation includes at least one of a heart rate or a respiration rate of the individual. For example, the skin micromovements may correspond to blood flowing through veins or arteries in the individual's face. Consistent with some disclosed embodiments, the interpretation may be performed in a similar manner as with photoplethysmography (i.e., optical blood flow pattern detection). As another example, the skin micromovements may correspond to the respiration rate (also referred to herein as the breathing rate) of the individual. For example, the skin micromovements may detect motion associated with the individual inhaling and exhaling. Consistent with some disclosed embodiments, the heart rate or respiration rate may be determined by correlating the facial skin micromovements to a graph, a table, or a trained machine learning model. For example, a pattern of facial skin micromovements may be used to determine the heart rate or respiration rate. In some embodiments, the pattern may be compared to a previously stored pattern to determine the heart rate or respiration rate. A type of machine learning model used and how the machine learning model is trained may be performed as described elsewhere in this disclosure.

Consistent with some disclosed embodiments, the interpretation includes an identification of the individual. For example, the skin micromovements may be used to assist in determining facial features of the individual, which in turn may be used to identify the individual. Consistent with some disclosed embodiments, a first time the individual wears the speech detection system 100, skin micromovements may be recorded and stored (e.g., in memory device 402 or other storage). At a later point in time, when the individual wears the speech detection system 100, a current pattern of skin micromovements may be obtained and compared to the stored pattern of skin micromovements and the comparison may be used to identify the individual. For example, the comparison may be performed by comparing an image of the stored pattern with an image of the current pattern using a mean squared error or other image comparison algorithm. As another example, the stored pattern and the current pattern may be compared by a statistical comparison or a trained machine learning model as described elsewhere in this disclosure.

Consistent with some disclosed embodiments, the interpretation includes words. The words may include one or more words or phonemes. The one or more words or phonemes may be silently spoken or vocally spoken by the individual. As described elsewhere in this disclosure, the facial skin micromovements reflect muscle recruitment indicating silently spoken or vocally spoken words or phonemes.

Some disclosed embodiments involve generating an output of the interpretation. As described elsewhere in this disclosure, generating the output may include emitting a command, emitting data, and/or causing an electronic device to initiate an action. For example, generating an output of the interpretation may include generating one or more sounds representative of the interpretation (e.g., emotions or words). In some embodiments, generating an output of the interpretation may include displaying the interpretation on a display of a user device (e.g., a display showing the heart rate or the respiration rate or a display showing a transcription of the detected one or more words).

Figure 60:
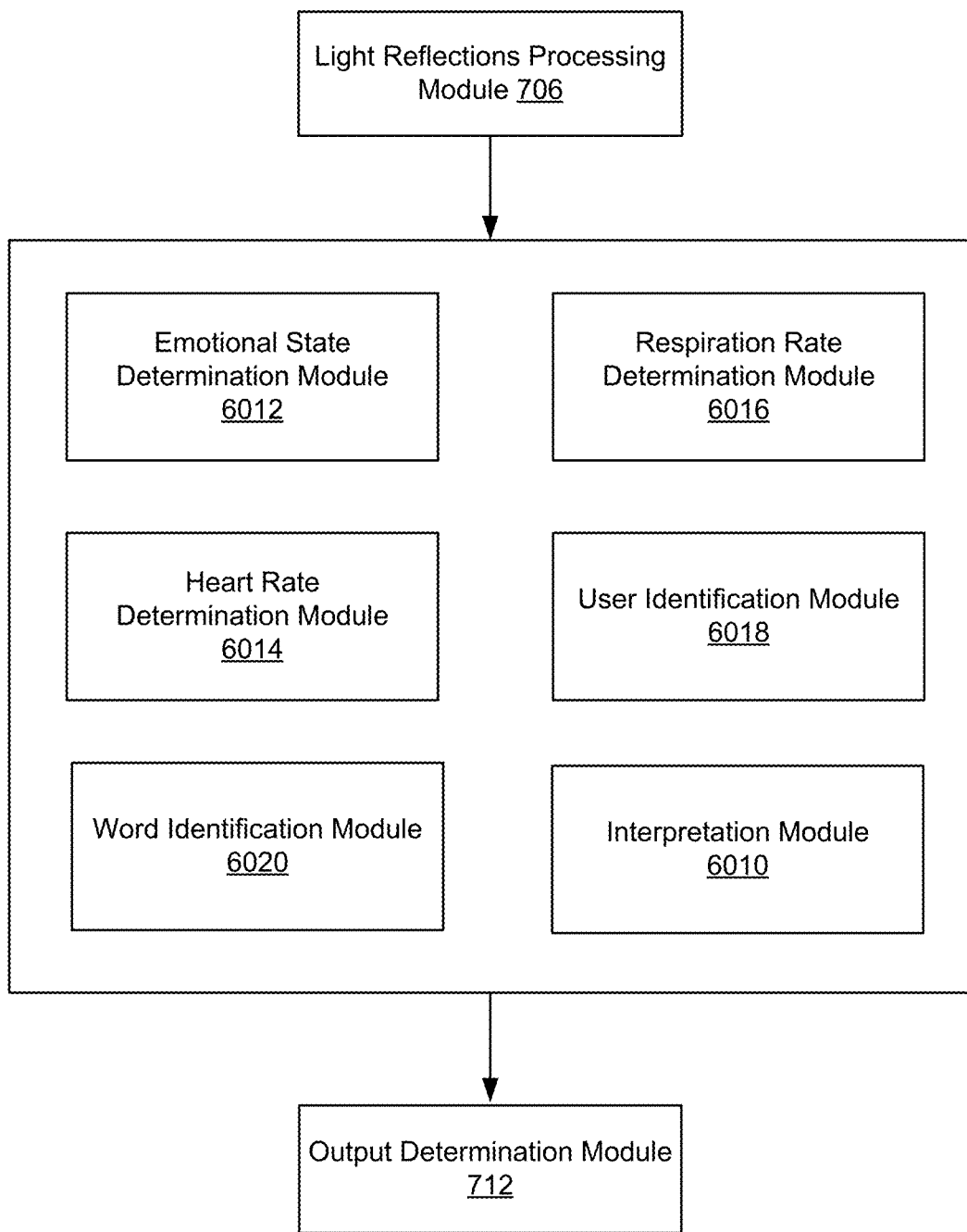
FIG. 60 is a block diagram illustrating exemplary components of the first example of the speech detection system, consistent with some embodiments of the present disclosure.

By way of example, FIG. 60 is a block diagram illustrating exemplary components of the first example of the speech detection system, consistent with some embodiments of the present disclosure. As shown in FIG. 60, light reflections processing module 706 may process reflection signals (e.g., first spot reflections, second spot reflections, third spot reflections, and/or fourth spot reflections) to determine facial skin micromovements, consistent with some disclosed embodiments. Light reflections processing module 706 may provide the determined facial skin micromovements to an interpretation module 6010.

By way of example as illustrated in FIG. 60, interpretation module 6010 may be configured to process the determined facial skin micromovements to determine an emotional state of the individual using speech detection system 100, to determine a heart rate of the individual, to determine a respiration rate of the individual, to identify the individual, or to identify words spoken by the individual, either silently spoken or vocally spoken, consistent with some disclosed embodiments. After completing the processing, interpretation module 6010 may then provide the interpretation to output determination module 712 to generate an output of the interpretation.

For example as illustrated in FIG. 60, interpretation module 6010 may include an emotional state determination module 6012, a heart rate determination module 6014, a respiration rate determination module 6016, a user identification module 6018, and a word identification module 6020. Modules 6010-6020 may be implemented in software, hardware, firmware, a mix of any of those, or the like. While shown in FIG. 60 as separate entities, modules 6010-6020 may be combined into one or more modules. For example, heart rate determination module 6014 and respiration rate determination module 6016 may be combined into a single module.

As one example as illustrated in FIG. 60, emotional state determination module 6012 may be configured to determine an emotional state of the individual and may be based on detecting whether the skin micromovements indicate whether a muscle is contracting or relaxing. For example, the emotional state may include happy, sad, anger, fear, surprise, disgust, contempt, or other emotional state that may be detected by facial skin micromovements.

As another example as illustrated in FIG. 60, heart rate determination module 6014 may be configured to determine a heart rate of the individual. For example, the skin micromovements may correspond to blood flowing through veins or arteries in the individual's face. Consistent with some disclosed embodiments, heart rate determination module 6014 may operate in a similar manner as with photoplethysmography (i.e., optical blood flow pattern detection).

By way of another example as illustrated in FIG. 60, respiration rate determination module 6016 may be configured to determine a respiration rate of the individual. For example, the skin micromovements may correspond to the respiration rate of the individual. For example, the skin micromovements may detect motion associated with the individual inhaling and exhaling.

As another example as illustrated in FIG. 60, user identification module 6018 may be configured to identify the individual wearing speech detection system 100. For example, the skin micromovements may be used to assist in determining facial features of the individual, which in turn may be used to identify the individual. Consistent with some disclosed embodiments, a first time the individual may wear the speech detection system 100, skin micromovements may be recorded and stored (e.g., in memory device 402 or other storage) with a pattern of skin micromovement being used to identify the individual. At a later point in time, when the individual wears the speech detection system 100, current skin micromovements may be obtained and compared to the stored pattern of skin micromovements and the comparison may be used to identify the individual.

By way of example as illustrated in FIG. 60, word identification module 6020 is configured to identify words spoken by the individual, either silently spoken or vocally spoken. The words may include one or more words or phonemes spoken by the individual.

Consistent with some disclosed embodiments, the output includes a textual presentation of the words. The one or more words or phonemes interpreted by the facial skin micromovements may be output as text. For example, the text may be presented to the individual on a display of mobile communications device 120, other communications device associated with the individual, or another display associated with the individual.

Consistent with some disclosed embodiments, the output includes an audible presentation of the words. For example, the audible presentation of the words may include using synthesized speech by the at least one processor converting the words into sounds. For example, the conversion may be performed using a concatenative algorithm, a parametric algorithm, or a trained machine learning model. A type of machine learning model used and how the machine learning model is trained may be performed as described elsewhere in this disclosure. By way of example as illustrated in FIG. 4, the audible presentation may be presented to the individual via output unit 114 of speech detection system 100 (e.g., through speaker 404) or via a speaker or other audio output associated with mobile communications device 120. Consistent with some disclosed embodiments, the output may include both the textual presentation and the audible presentation. For example, the textual presentation of the words may be presented at the same time as the audible presentation of the words.

In some disclosed embodiments, the output includes metadata indicative of facial expressions or prosody associated with words. For example, a facial expression may be determined based on the interpretation of the facial skin micromovements. The metadata may include an indication of the facial expression, such as whether the facial expression is happy, sad, anger, fear, surprise, disgust, contempt, or other facial expression that may be detected by facial skin micromovements. Consistent with some embodiments, the metadata may include a probability associated with one or more facial expressions, as it is possible that the individual may have a complex facial expression (e.g., sad and afraid) or may be attempting to hide their facial expression. For example, the probability associated with a facial expression (i.e., that a particular facial expression is identified by the facial skin micromovements) may be based on an output of a trained machine learning model. A type of machine learning model used and how the machine learning model is trained may be performed as described elsewhere in this disclosure.

As another example, the metadata may be related to prosody associated with the words, whether the words are silent speech or vocalized speech. Prosody relates to properties of syllables, phonemes, or words such as stress (e.g., what syllables are emphasized), rhythm or cadence of the speech, pitch of the speech, length of the sounds, and/or loudness or volume of the speech. Consistent with some embodiments, these speech properties may be measured in terms of frequency (e.g., hertz), duration (e.g., time), and/or intensity (e.g., decibels) and these speech properties may be included in the metadata. Consistent with some disclosed embodiments, the metadata (whether corresponding to prosody associated with the words or other metadata as described herein) may be output by generating one or more sounds representative of the metadata or by displaying the metadata on a display of a user device.

Figure 61:
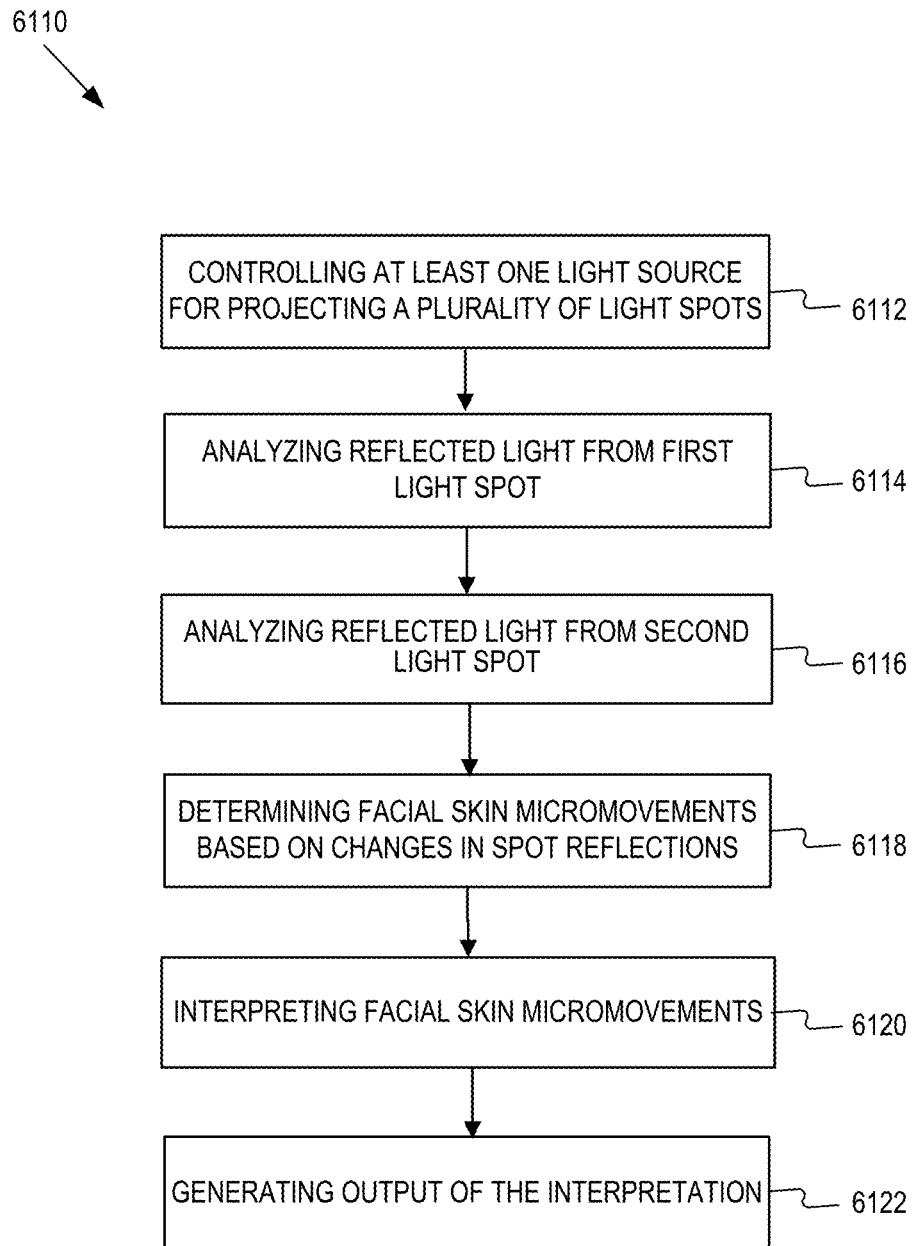
FIG. 61 is a flowchart of an exemplary method for determining facial skin micromovements, consistent with some embodiments of the present disclosure.

FIG. 61 is a flowchart of an exemplary method 6110 for determining facial skin micromovements, consistent with some embodiments of the present disclosure.

Consistent with some disclosed embodiments, method 6110 includes controlling at least one coherent light source for projecting a plurality of light spots on a facial region of an individual (step 6112). The plurality of light spots may include at least a first light spot and a second light spot spaced from the first light spot. In some disclosed embodiments, the light source may be a coherent light source.

A light spot includes an area of light with a higher measurable light characteristic than other light in a vicinity of the light spot. The light spot may include any discernable shape such that the measurable light characteristic of the light spot is higher than the same measurable light characteristic of other light in the vicinity of the light spot. A light detector as described elsewhere in this disclosure is configured to determine the difference between the light spot and the other light. The number of light spots projected and the spacing of the light spots is described elsewhere in this disclosure.

Consistent with some disclosed embodiments, method 6110 includes analyzing reflected light from the first light spot to determine changes in first spot reflections (step 6114). Analyzing the reflected light from the first light spot and determining changes in first spot reflections are performed in a similar manner as described elsewhere in this disclosure.

Consistent with some disclosed embodiments, method 6110 includes analyzing reflected light from the second light spot to determine changes in second spot reflections (step 6116). The second spot reflections include one or more reflections of the second light spot from the facial region of the user and detected by the light detector. The second spot reflections may be detected and analyzed in a manner similar to the first spot reflections described elsewhere in this disclosure.

Consistent with some disclosed embodiments, method 6110 includes determining the facial skin micromovements based on the determined changes in the first spot reflections and the second spot reflections (step 6118). The changes in the first spot reflections and the second spot reflections may be used to determine skin micromovements based on the location of the first light spot and the second light spot. As described elsewhere in this disclosure, determining skin micromovements may be based on an amount of skin movement, a direction of skin movement, and/or an acceleration of skin movement.

Consistent with some disclosed embodiments, method 6110 includes interpreting the facial skin micromovements derived from analyzing the first spot reflections and analyzing the second spot reflections (step 6120). Interpreting the facial skin micromovements may include extracting meaning from the detected skin micromovements. Consistent with some disclosed embodiments, the interpretation may include an emotional state of the individual, a heart rate of the individual, a respiration rate of the individual, an identification of the individual, or words spoken by the individual, either silently spoken or vocally spoken.

Consistent with some disclosed embodiments, method 6110 includes generating an output of the interpretation (step 6122). Consistent with some disclosed embodiments, generating the output may include emitting a command, emitting data, and/or causing an electronic device to initiate an action. Consistent with some disclosed embodiments, the output may include a textual presentation of words or phonemes, an audible presentation of words or phonemes, metadata indicative of facial expressions, or prosody associated with words or phonemes.

The disclosed embodiments discussed above for determining facial skin micromovements may be implemented through a non-transitory computer-readable medium such as software (e.g., as operations executed through code), as methods (e.g., method 6110 shown in FIG. 61), or as a system (e.g., speech detection system 100 shown in FIGS. 1-3). When the disclosed embodiments are implemented as a system, the operations may be executed by at least one processor (e.g., processing device 400 or processing device 460, shown in FIG. 4).

People with speech impairments face huge challenges in their daily lives, since communication is a vital aspect of human interaction. Many speech-impaired individuals have difficulty pronouncing certain sounds or struggle with fluency, which can hinder their ability to express themselves clearly. As a result, speech-impaired individuals often experience misinterpretation, misunderstandings, and even social isolation. The frustration of not being able to convey their thoughts and ideas effectively can have a profound impact on their confidence and overall well-being.

It has been difficult to find a single solution that fits all individuals with speech impairments because each individual's condition is unique and requires a specific approach. However, some disclosed embodiments involve a way to harness AI technology to analyze and understand an individual's specific speech impairment, allowing for personalized intervention and support. By leveraging machine learning, AI systems can learn the unique patterns and characteristics of an individual's speech impairment from facial movement data. Some disclosed embodiments involve receiving signals associated with facial skin movements of an individual having a speech impairment, and generating an output that corrects the speech impairment.

Figure 62:
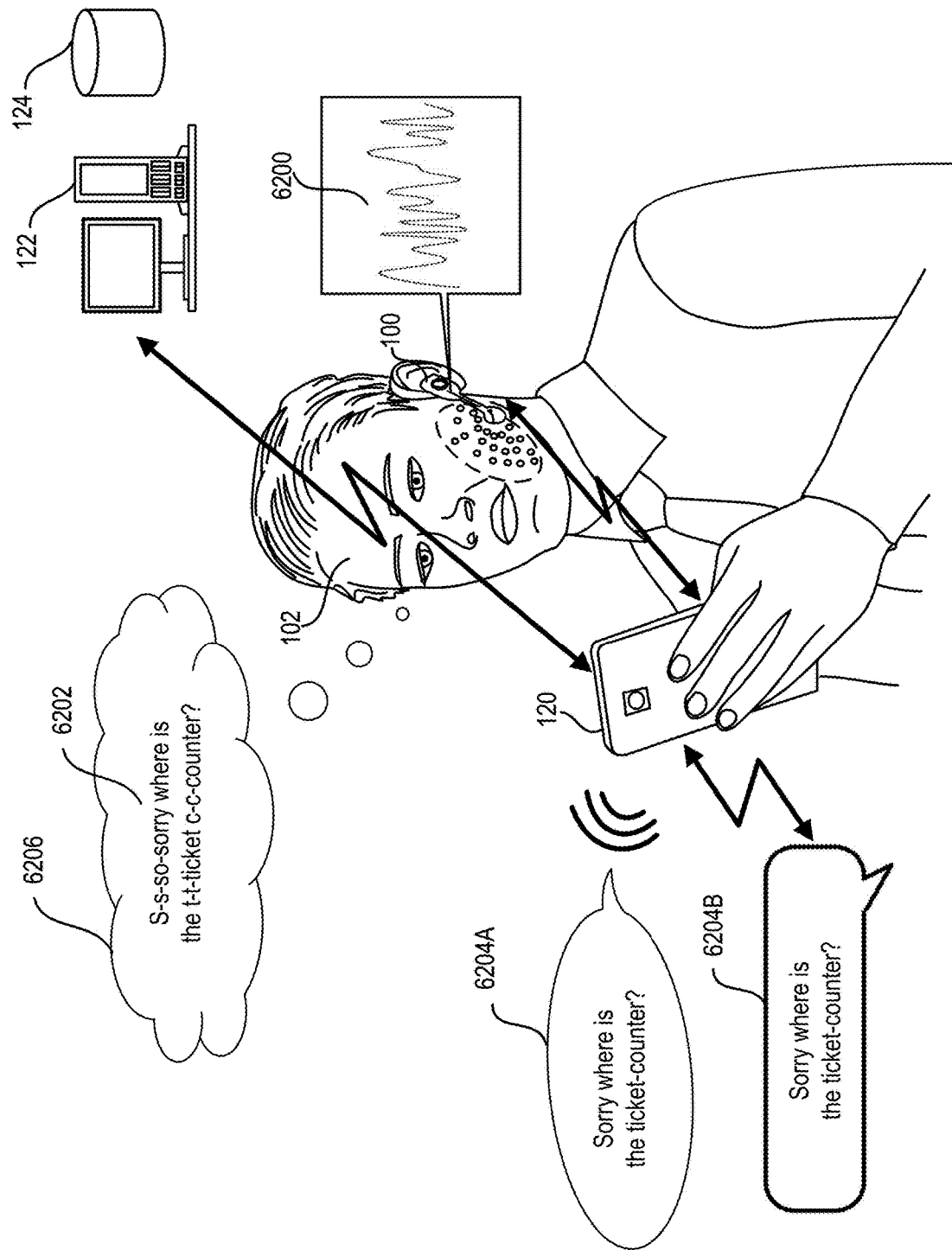
FIG. 62 is an illustration of an example system for correcting speech impairment based on facial movements, consistent with some embodiments of the present disclosure.
Figure 63:
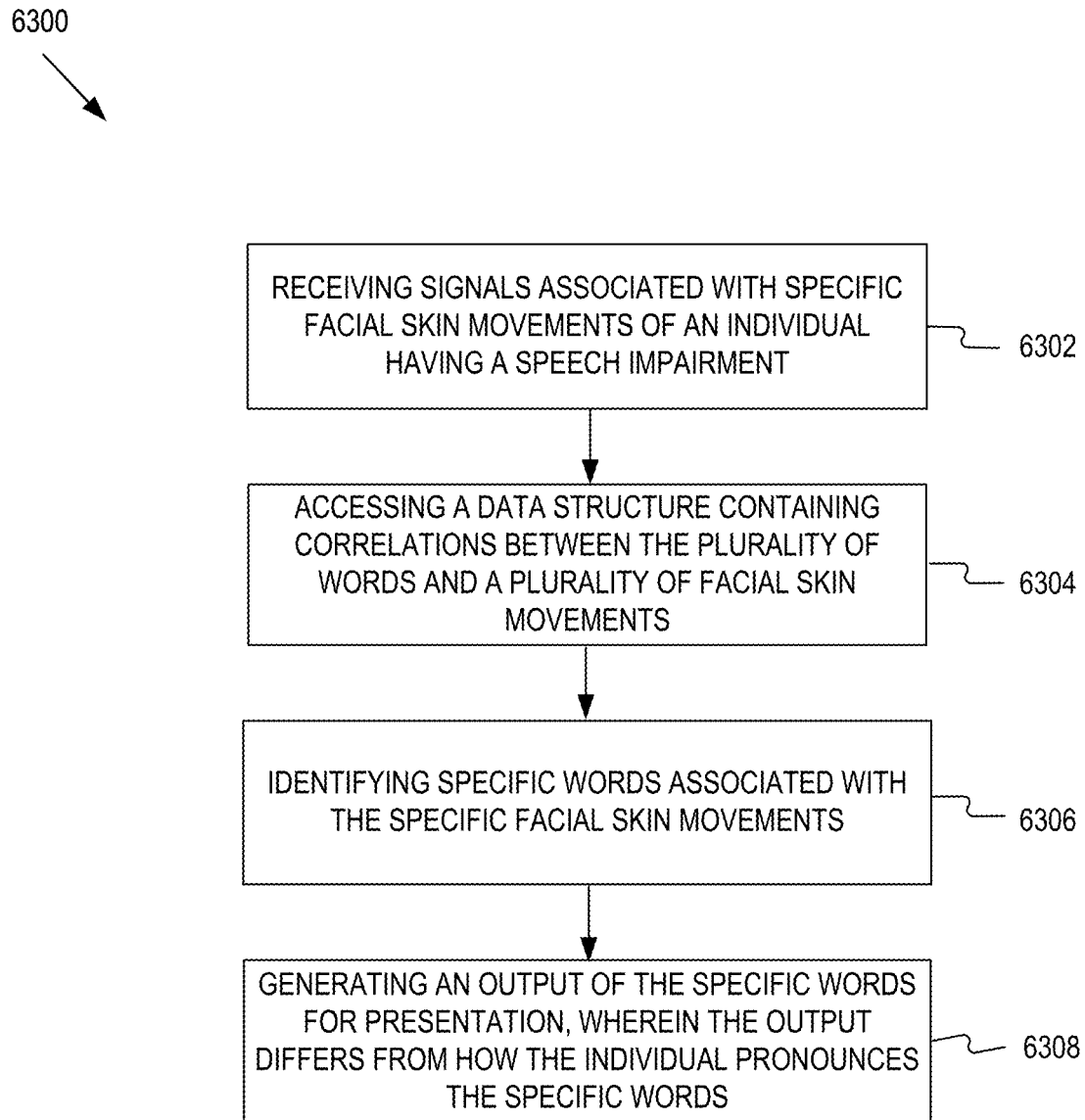
FIG. 63 is a flowchart of an example process for correcting speech impairment based on facial movements, consistent with some embodiments of the present disclosure.

Portions of the description that follows refer to FIGS. 62 and 63 to illustrate exemplary implementations of speech improvement techniques, consistent with some disclosed embodiments. FIG. 62 and FIG. 63 are intended merely to facilitate conceptualization of exemplary implementations for performing operations for speech improvement techniques, such as interpreting impaired speech based on facial movements, and do not limit the disclosure to any particular implementation.

Some disclosed embodiments involve interpreting impaired speech based on facial movements. The term "facial movements" or "facial skin movements" broadly refer to any type of movements prompted by recruitment of underlying facial muscles. As the muscles move, so too does associated facial skin. Consistent with some disclosed embodiments, the facial skin movements are facial skin micromovements, as described and exemplified elsewhere in this disclosure. In another example, the facial skin movements may be larger-scale skin movements generally visible and detectable to the naked eye without the need for magnification. The terms "speech impairment" and "impaired speech" refer to any condition or speech disorder that disrupts the production, clarity, fluency, or quality of spoken language. For example, speech impairment may encompass various difficulties related to speech, including problems with articulating sounds, disruptions in the flow of speech, abnormal voice characteristics, challenges in coordinating speech movements, and even mispronouncing words due to the influence of another language accent. Speech impairments can be caused by developmental delays, neurological conditions, physical limitations, trauma, or the influence of accents from different languages. In the context of this disclosure, mutism may be considered as a specific example of speech impairment because it involves a complete absence or severe limitation of verbal communication. The term "interpreting impaired speech" refers to a process of understanding or determining the meaning of language affected by a speech impairment. For example, interpreting impaired speech includes deciphering nonvocalized words or vocalized words that are difficult to comprehend due to various factors, such as articulation disorders, stuttering, voice disorders, apraxia of speech, dysarthria, or other speech-related challenges. In the disclosed embodiments, the impaired speech may be interpreted based on facial movements. Thus, the meaning of language affected by a speech impairment may be understood or determined by detecting and analyzing the facial movements, as described below.

Some disclosed embodiments involve receiving signals associated with specific facial skin movements of an individual. The term "receiving" may include retrieving, acquiring, or otherwise gaining access to, e.g., data. Receiving may include reading data from memory, receiving signals from a sensor, and/or receiving data from a computing device via a (e.g., wired and/or wireless) communications channel. For example, at least one processor may receive data via a synchronous and/or asynchronous communications protocol, e.g., by polling a memory buffer for data and/or by receiving data as an interrupt event. The term "signals" may refer to information encoded for transmission via a physical medium or wirelessly. Examples of signals may include signals in the electromagnetic radiation spectrum (e.g., AM or FM radio, Wi-Fi, Bluetooth, radar, visible light, lidar, IR, Zigbee, Z-wave, and/or GPS signals), sound or ultrasonic signals, electrical signals (e.g., voltage, current, or electrical charge signals), electronic signals (e.g., as digital data), tactile signals (e.g., touch), and/or any other type of information encoded for transmission between two entities via a physical medium or wirelessly (e.g., via a communications network). In some embodiments, the signals may include, or may be representative of, reflected light, reflection image data, or light analysis data (e.g., data from image analysis, data from speckle analysis, or data from any pattern-based analysis described elsewhere in this disclosure). The phrase "receiving signals associated with specific facial skin movements" may indicate that there is a connection between the received signals and the specific facial skin movements. For example, the signals may be derived from specific facial skin movements, the signals may be indicative of the specific facial skin movements, or the signals may represent the specific facial skin movements. In one implementation, the signals may include encoded data, and at least one processor can determine the specific facial skin movements based on the received signals containing the encoded data. By way of one example, processing device 400 or processing device 460 in FIG. 4 may be employed to process data from, e.g., light detector 412 to determine the specific facial skin movements. In another implementation, the signals may include light reflections, and at least one detector may measure reflections from a facial region in which the specific facial skin movements occurred. By way of one example, light detector 412 in FIGS. 5A and 5B may be employed to receive reflections 300 indicative of facial skin micromovement 522A and facial skin micromovement 522B.

Consistent with some disclosed embodiments, signals are received from a sensor that detects light reflections from a non-lip portion of a face of the individual. The term "sensor" broadly refers to any device, element, or system capable of measuring one or more properties and generating an output relating to the measured properties, as discussed elsewhere in this disclosure. The term "light reflections" should be interpreted as discussed elsewhere in this disclosure, and includes a phenomenon where light waves bounce off a surface and change direction. The term "non-lip portion" includes a facial region (as described elsewhere in this disclosure) is a facial region that does not include the lips of an individual. For example, the facial region may be associated with specific muscles such as the zygomaticus muscle or the risorius muscle. Consistent with some disclosed embodiments, the signals are received from an image sensor (as described elsewhere in this disclosure) configured to measure non-coherent light reflections. The term "non-coherent light reflections" refers to light waves that do not maintain a consistent phase relationship with each other and exhibit randomness in their direction of travel. For example, the sensor that detects light reflections from a non-lip portion of a face of the individual may be an image sensor (e.g., charge-coupled device or an active-pixel sensor) configured to detect light from a non-coherent light source (e.g., incandescent bulbs, LED lamps, sunlight, or any other non-coherent light source). For example, the sensor's bandwidth may be adjusted to encompass the frequency range of the non-coherent signal. In these embodiments, the signals received from the sensor may be used to determine image data (e.g., pixel data streams, digital images, digital video streams, data derived from captured images, and data that may be used to construct one or more 3D images, a sequence of 3D images, 3D videos, or a virtual 3D representation) indicative of facial movements in the non-lip portion of a face of the individual. In other embodiments, the sensor may include a light detector as described elsewhere in this disclosure. In these embodiments, the signals from the sensor may be used to determine reflection image data (as described elsewhere in this disclosure).

Consistent with some disclosed embodiments, received signals may be associated with facial skin micromovements that correspond with recruitment of at least one muscle out of a group of muscles including: a zygomaticus muscle, a genioglossus muscle, an orbicularis oris muscle, a risorius muscle, or a levator labii superioris alaeque nasi muscle. In this context, the term "facial skin micromovements corresponding to recruitment of a certain muscle" refers to an activation of that particular muscle that causes movements of the facial skin that are indetectable to the naked eye. A person might otherwise require magnification to substantively detect the facial skin micromovements. As mentioned above, muscle activation or muscle recruitment is the process of activating motor neurons to produce muscle contraction. As also explained elsewhere in this disclosure, facial skin micromovements include various types of voluntary and involuntary movements (for example, that fall within the range of micrometers to millimeters and a time duration of fractions of a second to several seconds) caused by muscle recruitment or muscle activation. Some muscles, such as the quadriceps (which is a powerful muscle group responsible for displaying force very quickly), have a high ratio of muscle fibers to motor neurons. Other muscles, such as the eye muscles, have much lower ratios as they use more precise, refined movement leading to small-scale skin deformations. As explained elsewhere in this disclosure, the zygomaticus muscle, the orbicularis oris muscle, the risorius muscle, the genioglossus muscle, and the levator labii superioris alaeque nasi muscle may articulate specific points in the individual's cheek above mouth, chin, mid-jaw, cheek below mouth, high cheek, and the back of the cheek.

By way of a non-limiting example, in FIG. 62, as individual 102 silently speaks, at least one processor (e.g., processing device 400 of FIG. 4) of speech detection system 100 may determine specific facial skin movements associated with the specific words that individual 102 articulated silently. Thereafter, the at least one processor of speech detection system 100 may transmit signals 6200 that reflects the specific facial skin movements to mobile communications device 120.

In some disclosed embodiments, the received signals are associated with specific facial skin movements of an individual having a speech impairment that affects the manner in which the individual pronounces a plurality of words. The terms "individual" and "speech impairment" should be interpreted as discussed elsewhere in this disclosure. Accordingly, the phrase "an individual having a speech impairment" means that the individual manifests a condition that affects the manner in which the individual pronounces one or more words. In some cases, the condition may be temporary and may resolve over time. Examples of temporary conditions that may cause speech impairment include post-oral surgery, medication/drug side effects, another language accent, hoarseness, and emotional or psychological event. In other cases, the condition may be persistent but may or may not improve over time using ongoing speech therapy. Examples of persistent conditions that may cause speech impairment include developmental speech disorders (e.g., childhood apraxia of speech) or neurological disorders (e.g., cerebral palsy and Parkinson's disease). The speech impairment may affect the manner in which the individual pronounces one or more words in different ways depending on the individual's condition. For example, some speech impairments (e.g., stuttering) may cause distortions in the production of sounds, cause repetitions of sounds, prolongations of sounds, or blocks on sounds or words. Other speech impairments may impact the ability of the individual to use appropriate prosody and rhythm.

Consistent with some disclosed embodiments, the specific facial skin movements are associated with a vocalization of the specific words, and the vocalization of the specific words is in a non-normative manner. The term "vocalization of the specific words" refers to the act of producing audible sounds or speech that represents the specific words. For example, the vocalization of words encompasses the generation of a combination of various speech sounds, phonemes, and intonation patterns to convey meaning. The term "non-normative manner" means that the way by which the articulation of words is executed deviates from the expected or typical pronunciation of said phonemes or words. For example, a person who stutters may often experience disruptions or interruptions in the flow of their speech, such as repeating sounds, lengthening sounds, adding extra sounds and fillers. Consistent with other embodiments, the specific facial skin movements may be associated with a non-vocalized articulation of the specific words. For example, a non-vocalized articulation of the specific words may happen when the speech impairment is mutism. In these embodiments, the non-vocalized articulation of the specific words may be associated with a non-normative manner. In other words, if speech detection system 100 had vocalized the non-vocalized articulation of the specific words (e.g., using a synthesized voice), it would deviate from the expected or typical pronunciation of said phonemes or words.

Referring to the non-limiting example illustrated in FIG. 62, signals 6200 may be associated with a subvocalized speech that includes the specific words 6202 (i.e., "s-s-so-sorry where is the t-t-to-ticket c-c-counter?"). Specific words 6202 may be determined by performing an analysis of received signals 6200 indicative of the specific facial skin movements of individual 102. In this example, individual 102 may have a speech impairment that causes repetitions and prolongations of sounds such that the question "sorry, where is the ticket counter?" is silently articulated in a non-normative manner.

Some disclosed embodiments involve accessing a data structure containing correlations between the plurality of words and a plurality of facial skin movements. A data structure is described elsewhere in this disclosure. The term "accessing a data structure" refers to retrieving or examining electronically stored information. This may occur, for example, by communicating with or connecting to electronic devices or components in which data is electronically stored. Such data may be organized, for example, in a data structure for the purpose of reading stored data (e.g., acquiring relevant information) or for the purpose of writing new data (e.g., storing additional information). In some cases, the accessed data structure may be part of a speech detection system or part of a remote processing device (e.g., cloud server) that may be accessed by the speech detection system. In some examples, the at least one processor may access the data structure, for example, at startup, at shutdown, at constant intervals, at selected times, in response to queries received from the at least one processor, or at any other determined times. The data structure may store data that correlates a plurality of words with a plurality of facial skin movements. The stored data may be any electronic representation of the facial skin movements, any electronic representation of one or more properties determined from the facial skin movements, or raw measurement signals detected by the at least one light detector and representing the facial skin movements. By way of a non-limiting example, data structure 422 and/or a part of data structure 464 (depicted in FIG. 4) may be accessed by at least one processor.

Consistent with the present disclosure, the term "data structure containing correlations between the plurality of words and a plurality of facial skin movements" means that the data structure is configured to store relationships between facial skin movements and a plurality of words. The data structure may be located locally, remotely such as on a remote server, and/or may otherwise be stored in the cloud. Correlations in a data structure may allow for efficient determination of the plurality of words based on these relationships. For example, the data structure may be associated with a built-in mechanism for linking or associating facial skin movements with the plurality of words. In one example, correlations may be stored between specific phenomes, syllables, words, or phrases and associated facial skin movements corresponding to the manner in which the individual pronounces the plurality of words. In some cases, one or more specific facial skin movements may be associated with a recruitment of one or more specific facial muscles subvocalizing a particular word in the manner in which the speech-impaired individual pronounces the particular word. The data structure may store associations between digital representations of a plurality of known facial skin micromovements associated with impaired speech and a plurality of phenomes, syllables, words, or phrases, e.g., as an index, linked list, array, graph, and/or any other data structure for storing relationships.

Referring to the non-limiting example illustrated in FIG. 62, a processing device of mobile communications device 120 may access data structure 124 containing correlations between a plurality of words and a plurality of facial skin movements associated with individual 102. In alternative embodiments, however, other data structures may be accessed. In one example, a processing device of mobile communications device 120 may access a data structure located in speech detection system 100. In another example, processing device of speech detection system 100 may access a data structure located in mobile communications device 120 or in server 122.

In some disclosed embodiments, the plurality of facial skin movements correspond to the manner in which the individual pronounces the plurality of words. The term "correspond" refers to the degree of similarity, connection, equivalence, match, or connection. For example, the stored facial skin movements may match with manner in which the individual pronounces the plurality of words. Consistent with some disclosed embodiments, the data structure is personalized to unique facial skin movements of the individual. The term "personalized" means that the data structure has been customized or tailored with respect to the manner in which a particular individual pronounces the plurality of words. Thus, the phrase "the data structure is personalized to unique facial skin movements of the individual" means that the stored facial skin movements correspond to the distinct manner in which the particular individual pronounces the plurality of words. For example, the specific individual may have a speech impairment (e.g., lisp) that causes said individual to misarticulate sounds, such as the "s" sound being pronounced as "th." The data structure may store correlation between the word "story" and the unique facial skin movements that corresponds to the articulation of the sounds representing the word "th-tory," as may be presented by the particular individual. In other embodiments, the stored facial skin movements may correspond to a general manner in which individuals with speech impairment may pronounce the plurality of words. By way of a non-limiting example, data structure 124 illustrated in FIG. 62 may be personalized to the unique facial skin movements of individual 102.

Consistent with some disclosed embodiments, the operations further include employing a training model for populating the data structure. The term "training model" refers to a machine learning model that undergoes a process to learn patterns, make predictions, or perform specific tasks. A training model may involve artificial intelligence and may be exposed to a large amount of labeled or unlabeled data, which serves as the input for the model to learn from. For example, the training model may receive training data including, for example, historical signals associated with facial skin movements. The historical signals may (or may not) be associated with labels reflective of specific words corresponding to specific signals. The machine learning algorithm may be trained using the training data, such as information regarding various facial skin micromovements with associated words as articulated by a speech impaired person. In some examples, any data indicating a match between facial skin movements and words as articulated by a speech impaired person may be used to train the machine learning algorithm. Thereafter, the training model may be used to populate the data structure by labeling specific facial skin movements with specific words. in this context, the term "employing" means utilizing or using the training model for a particular purpose which is populating the data structure with data representative of facial skin movements that correspond to the manner in which the individual pronounces the plurality of words. The term "populating the data structure" refers to the process of filling or adding data into a data structure. Thus, a training model may be used to determine new correlations between words and new facial skin movements, and stored the determined correlation in the data structure. By way of example, at least one processor associated with speech detection system 100 may use a training model for personalizing data structure 124 to the unique facial skin movements of individual 102.

Consistent with some disclosed embodiments, the training model may populate the data structure with data from various sources. The sources may include data entries originated from the individual or data entries originated from other individuals having a similar speech impairment. In some disclosed embodiments, the data structure includes data associated with at least one recording of the individual previously pronouncing the specific words. The term "recording" refers to acquired content (e.g., audio, video, or other sensory information) that may be stored for future playback or reference. The recording may be stored as files audio files (e.g., MP3, AAC, WAV), video files (MP4, AVI, WMV, MOV), and any other files that capture how the individual previously pronounced the specific words. In some embodiments the recording may be data associated with light reflections captured based on facial skin micromovements. Such a recording, for example, may be correlated with words. In one example, the at least one recording of the individual may be acquired by an audio sensor (e.g., audio sensor 414). In another example, the at least one recording of the individual may be acquired by an image sensor. In another example, the at least one recording of the individual may be acquired by a light sensor (e.g., light detector 412). The phrase "recording of the individual previously pronouncing the specific words" may indicate that the stored information is indicative to the specific manner the speech-impaired individual articulated the specific words.

Referring to the non-limiting example illustrated in FIG. 62, data structure 124 may be configured to contain correlations between the plurality of words and a plurality of facial skin movements. In some cases, ANN training module 710 (depicted in FIG. 7) may be used to populate data structure 124. For example, ANN training module 710 may use previous recordings of individual 102 to correlate between words and facial skin movements.

Some disclosed embodiments involve, based on the received signals and the correlations, identifying specific words associated with the specific facial skin movements. The term "identifying" refers to the process of recognizing, determining, or establishing the identity of someone or something. For example, specific words may be identified even when the vocalization of the specific words occurs in a non-normative manner or when the non-vocalized articulation of the specific words occurs in a non-normative manner. The process of identifying the specific words may include generating a digital representation of the specific facial skin movements (e.g., as a feature vector and/or one or more tokens) from the received signals. Thereafter, the process may include querying the data structure containing the correlations using the digital representation to determine a match with at least one of the known plurality of facial skin movements that correspond to the manner in which the individual pronounces the plurality of words (e.g., based on a similarity measurement), to thereby determine at least one specific word. For instance, identifying the specific words may include associating at least one specific word with one or more facial skin movement attributes. Such attributes may include, for example, a timing, a sequence, a type, a frequency, a degree of movement (e.g., maximal movement), a direction of a movement, a combination of particular facial movements, and/or any other facial skin movement attributes. Additionally or alternatively, the process of identifying the specific words may include associating at least one specific word with a particular facial muscle and/or a combination of particular facial muscles corresponding to the manner in which the individual having a speech impairment pronounces the at least one specific word.

Additionally or alternatively, the process of identifying the specific words may involve using a context (e.g., including a history of words vocalized by the user, a history of words used by others, and/or a history of recorded words heard by the user) to determine the at least one specific word. Such a process may involve analyzing one or more groups of associated words represented by captured light reflections, and comparing them with groups of associated words in the data structure, in order to ascertain meaning. In this way, even for non-normative speech that may be otherwise difficult to understand, the process may derive an understanding from surrounding words used previously by the subject or others. In a similar manner, a process may involve analyzing groups of phenonomes or syllables to determine a non-normative spoken or subvocalized word. Additionally or alternatively, the process of identifying the specific words may include using one or more artificial intelligence algorithms and/or machine learning techniques to determine at least one specific word based on the received signals and the correlations. For example, the process of identifying the specific words may include applying a probabilistic function to determine specific words based on a prevalence of the at least one word in the daily vocabulary of the individual having a speech impairment.

Consistent with some disclosed embodiments, the identified specific words associated with the specific facial skin movements are nonvocalized or subvocalized. For example, the process of identifying the specific words may include analyzing the received signals to decipher at least some subvocalization facial skin movements to determine at least one specific word spoken in an absence of vocalization (i.e., silent speech). The determination of at least one specific word spoken in an absence of vocalization may involve using one or more image processing algorithms, light reflection analyses, speech deciphering algorithms, machine learning algorithms, and/or neural networks, as described elsewhere in this disclosure, to process received signals associated with the specific facial skin movements of an individual having a speech impairment.

Referring to the non-limiting example illustrated in FIG. 62, a processing device of mobile communications device 120 may identify from signals 6200 and from the correlations stored in data structure 124 that the individual wanted to say "sorry, where is the ticket counter?" Specific words 6202 in thought bubble 6206 are nonvocalized.

Some disclosed embodiments involve generating an output of the specific words for presentation, wherein the output differs from how the individual pronounces the specific words. The term "generating an output" should be interpreted as discussed elsewhere in this disclosure, and includes, for example, producing a response or result. The generated output may be a private presentation or a non-private presentation of the specific words. In some embodiments, the generated output may be an audible presentation of the specific words. For example, the audible presentation of words may include synthesized speech vocalizing the identified words. The term "synthesized speech" refers to an artificial voice that may be generated using computer algorithms and software. In one example, the synthesized voice may be created to mimic the voice of an individual with the speech impairment. Some synthesized voices may include a specific human speaker, while others may be designed to be more generic and versatile. Alternatively, the generated output may be a textual presentation of the specific words. For example, generating the textual presentation of words may include transmitting a message with the identified specific words. In some cases, the textual presentation of the words may be presented at the same time as the audible presentation of the words. The phrase "differs from how the individual pronounces the specific words" means that there are one or more distinctions in characteristics, features, or qualities in the presentation of the identified specific words relative to the manner in which the individual pronounced the specific of words. For example, the generated output may not include the effects of the speech impairment on the specific words. In one instance, the generated output may transform words that were spoken in non-normative manner to be presented in a normative manner.

Referring to the non-limiting example illustrated in FIG. 62, a processing device of mobile communications device 120 may generate a first output 6204A being an audible presentation of the specific words and/or a second output 6204B being a textual presentation of the specific words. The manner in which the words in first output 6204A are pronounced and the manner in which the words in second output 6204B are spelled is different from how individual 102 pronounces specific words 6202. As illustrated, specific words 6202 in thought bubble 6206 form the question "s-s-so-sorry where is the t-t-ticket c-c-counter?" while first output 6204A and second 6204B include the question "sorry, where is the ticket counter?"

Consistent with one disclosed embodiment, the specific facial skin movements are associated with a subvocalization of the specific words, wherein the generated output includes a private audible presentation of the subvocalized words to the individual. The terms "facial skin movements" and "subvocalization" should be interpreted as discussed elsewhere in this disclosure. The term "private audible presentation" refers to a type of output that can be heard only by a specific audience. For example, a private audible presentation may be heard only by the speech-impaired individual. By way of example, as illustrated in FIG. 4, the audible presentation may be presented to individual 102 via output unit 114 of speech detection system 100 (e.g., through speaker 404). This embodiment may be used to alert the individual and thus guide the individual to pronounce the specific word correctly. For example, when the individual mispronounces words due to the influence of another language accent, speech detection system 100 can help the individual to pronounce the specific word correctly by generating an output that only the individual hears a corrected pronunciation of the specific word.

Consistent with some disclosed embodiments, the specific facial skin movements are associated with a subvocalization of the specific words, wherein the generated output includes a non-private audible presentation of the subvocalized words. The term "non-private audible presentation" refers to a type of output that is not to a specific audience. For example, a non-private audible presentation may be heard by more than one individual in physical proximity to the individual. By way of example, as illustrated in FIG. 62, the audible presentation may be presented to one or more individuals in proximity to individual 102 via a speaker or other audio output associated with mobile communications device 120. In some instances, this embodiment may be used by speech-impaired individuals when they communicate with people not accustomed to their impairment. For example, when muted individuals are surrounded by individuals that do not understand sign language, speech detection system 100 can cause an audible presentation (e.g., using a synthesized voice) for enabling them to vocalize their thoughts.

Consistent with the present disclosure, the output of the specific words may be used to correct the speech impairment of the individual. The term "correcting the speech impairment" refers to the process of improving what the speech-impaired individual tried to communicate. In some disclosed embodiments, the output of the specific words is textual. For example, the output may be presented as an instant message, an email, or presented via any other mechanism that allows the content to be read as text. In some cases, the correction of the speech impairment may be fulfilled by adding punctuation to the textual output of the specific words or adding emojis to the textual output of the specific words. Examples of punctuation that may be added include at least one of: a comma, a period, a question mark, an exclamation mark, quotation marks, and/or ellipses. By way of a non-limiting example as illustrated in FIG. 62, output 6204B is textual, and a comma is added after the word "sorry." In some disclosed embodiments, the output of the specific words is audible and used to correct the speech impairment of the individual. When the output of the specific words is audible, the correction of the speech impairment may be fulfilled by generating a synthesized voice (e.g., a voice that may or may not resemble the voice of the individual) for vocalizing a corrected version of what the speech-impaired individual vocally or silently said. If the voice resembling that of the individual is used, the individual's voice may be pre-sampled to develop a model for synthesizing the individual's voice. This may be accomplished via AI techniques. The AI techniques may be used to correct the individual's pronunciation in order to approximate vocalization as the individual might be expected to sound in an absence of a speech impairment. Thus, in some embodiments, the manner of vocalization of the generated output may be a speech-impairment-free form, which means that generated output may not exhibit the impact of the speech impairment. In other embodiments, the manner of vocalization of the generated output may be a near-speech-impairment-free form, which means that generated output may exhibit some of the impact of the speech-impairment, but the severity of impact may be less than the original vocalization of the speech-impaired individual. In a first example, as illustrated in FIG. 62, the speech impairment is stuttering, and correcting includes outputting the specific words spoken in a stutter-free form. In some embodiments, when the speech impairment is stuttering, speech detection system 100 may be used to provide Delayed Auditory Feedback (DAF). DAF involves introducing a time delay between a person's speech and the auditory feedback they receive. In classic DAF, the individual's speech is recorded and played back to them after a short delay, typically ranging from milliseconds to a few seconds. For example, the delay may be between 75 milliseconds and 200 milliseconds. According to the present disclosure, the individual's speech may be detected from facial micromovements and played back to them, e.g., before vocalization. The purpose of using DAF is to disrupt the normal auditory feedback loop during speech production of a person who stutters. By introducing a delay in the auditory feedback, speech detection system 100 can cause disruptions in this feedback loop, leading to changes in speech fluency and rhythm. For example, speech detection system 100 may use DAF to alter of a person's speech rate. When the delayed feedback is introduced, it can cause the person to slow down their speech, as they adjust their speaking rate to compensate for the delayed auditory feedback.

In some disclosed embodiments, the speech impairment is hoarseness, wherein correcting includes outputting the specific words (e.g., using a synthesized voice) in a hoarseness-free form. For example, generated output may not exhibit the impact of the hoarseness. In some disclosed embodiments, the speech impairment is low volume, wherein correcting includes outputting the specific words (e.g., using a synthesized voice) in a volume higher than the specific words were spoken. As another example, the speech impairment is mutism, and correcting includes outputting the specific words not vocalized by the individual. As another example, the speech impairment is due to the influence of another language accent, and correcting includes outputting the specific words without the influence of the another language accent.

FIG. 63 illustrates a flowchart of an exemplary process 6300 for interpreting impaired speech based on facial movements, consistent with embodiments of the present disclosure. In some disclosed embodiments, process 6300 may be performed by at least one processor (e.g., processing device 400 or processing device 460, shown in FIG. 4) to perform operations or functions described herein. In some embodiments, some aspects of process 6300 may be implemented as software (e.g., program codes or instructions) that are stored in a memory (e.g., memory device 402 or memory device 466 shown in FIG. 4) or a non-transitory computer-readable medium. In some embodiments, some aspects of process 6300 may be implemented as hardware (e.g., a specific-purpose circuit). In some embodiments, process 6300 may be implemented as a combination of software and hardware.

Referring to FIG. 63, process 6300 includes a step 6302 of receiving signals associated with specific facial skin movements of an individual having a speech impairment. The speech impairment may affect the manner in which the individual pronounces a plurality of words. For example, the at least one processor may receive signals (e.g., signals 6200) from a light detector (e.g., light detector 412). Process 6300 includes steps 6304 of accessing a data structure containing correlations between the plurality of words and a plurality of facial skin movements. The plurality of facial skin movements may correspond to the manner in which the individual pronounces the plurality of words. For example, the at least one processor may access data structure 422 and/or a part of data structure 464 (depicted in FIG. 4). In some cases, the data structure may be personalized to unique facial skin movements of the individual to account for the specific manner in which the individual pronounces a plurality of words. Process 6300 includes a step 6306 of identifying specific words associated with the specific facial skin movements. The identification of the specific words may be based on the received signals and the correlation. Consistent with the present disclosure, the identification of the specific words may be accomplished by comparing data associated with the received signals with information stored in the data structure. For example, specific words 6202 may be determined by using machine learning (ML) algorithms and artificial intelligence (AI) algorithms as described in greater detail with respect to subvocalization deciphering module 708 depicted in FIG. 7. Process 6300 includes a step 6308 of generating an output of the specific words for presentation, wherein the output differs from how the individual pronounces the specific words. For example, output 6204A and 6204B may be generated by output determination module 712 depicted in FIG. 7.

The embodiments discussed above for interpreting impaired speech based on facial movements may be implemented through a non-transitory computer-readable medium such as software (e.g., as operations executed through code), as methods (e.g., process 6300 shown in FIG. 63), or as a system (e.g., speech detection system 100 shown in FIGS. 1-3). When the embodiments are implemented as a system, the operations may be executed by at least one processor (e.g., processing device 400 or processing device 460, shown in FIG. 4).

As described elsewhere herein, some disclosed embodiments of speech detection systems involve providing an approach for detecting prevocalized speech, subvocalized speech, and silent speech through the detection of facial micromovements (e.g., facial skin micromovements) to determine words in the absence of vocalization. Further, the speech detection system may detect facial micromovements that may be correlated with vocalized speech. The sensing mechanism that detects facial micromovements and determines the vocalized speech associated with those facial micromovements may allow for a determination of the identity of a subject and match the vocalization to the subject. Due to this property, facial micromovements may be used as a biometric identifier when correlated with vocalized speech. Thus, facial micromovements correlated with the vocalized speech may be unique to an individual, much like a fingerprint.

A significant problem exists with deepfake technology such that realistic video of individuals may be created wherein these individuals may appear to be speaking words not actually spoken. Similarly, standalone audio may sound like it emanated from a recognized person, however, the audio could have been simulated. Consistent with some disclosed embodiments, the detection of facial micromovements may be used to identify deepfake video, audio, or other forms of communication derived from human-spoken words by sending a verification data stream. One data stream may include the substance of the communication itself and the verification data stream may serve a checking function derived from facial skin micromovements and which may be used to corroborate that words presented in the communication were actually spoken by the person to whom the speech is attributed. Thus, facial micromovements may be used to verify the authenticity of a communication. For example, a manipulated video may include a change of the facial identity of the subject in the video. A different facial identity may be detected by determining that facial micromovements detected for the subject of the communication do not match the audio communication in the video. This may indicate that the communication may be a deepfake video. In another example, the facial identity may remain the same however the audio communication may be manipulated to deceive the receiver of the communication. An audio communication not matching the video of the subject may indicate a deepfake video. In both examples, sending a second data stream (e.g., verification data stream) may be used to verify the authenticity of the first data stream (i.e., the communication) at the destination to allow the destination to verify the authenticity of the received communication. It is to be appreciated that disclosed embodiments demonstrate but are not limited to the advantages of a speech detection system capable of providing ongoing verification of communication authenticity based on light reflections from facial skin.

By way of a non-limiting example, a wearable earpiece comprising of a speech detection system may be designed including a sensor configured to detect facial micromovements (see, e.g., prior discussion related to FIGS. 1-4). The wearable earpiece may be used in conjunction with a video camera to record audio and video of a subject wearing the earpiece. Further, the wearable earpiece may detect facial micromovements and determine that those facial micromovements match the recorded audio. Upon detection of one or more facial micromovements by the speech detection system, the system may create two data streams, a first data stream associated with the audio and/or video communication intended for a destination and a second data stream associated with the facial micromovements correlated with the communication. At the destination, the recipient may use the second data stream to verify the authenticity of the communication (i.e., verify the first data stream) using facial micromovements unique to the subject detected by the wearable earpiece.

Some disclosed embodiments involve ongoing verification of communication authenticity based on light reflections from facial skin. Ongoing verification of communication authenticity refers to regular, periodic, and/or continuous checking the genuineness or trustworthiness of a communication. Such authentication may occur based on light reflections from facial skin, examples of which are provided elsewhere in this disclosure. By way of example, as illustrated in FIGS. 1 and 4, processor or processing device 400 of speech detection system 100 or processing device 460 of remote processing system 450 may execute one or more instructions stored in memory 402, shared memory module 472, data structures 124, 422, or 464 to perform operations for determining facial skin micromovements.

Some disclosed embodiments involve generating a first data stream representing a communication by a subject, the communication having a duration. A "data stream" refers to a transmission of a sequence of electronic signals to convey information, in this case in the context of a communication. A data stream may include transmitted and received electrical, electromagnetic, or optical signals that carry digital data or digital signals representing various types of information. In one example, a data stream may be transmitted and received as a group of a series of data packets over the internet. In the context of the first data stream referred to in this paragraph, the first data stream conveys the substance of a communication. For example, the first data stream in this context may convey audio, video, text, gestures, expressions, or any other substantive information. The stream itself may be in a digital form that may be understood only after decoding, reading, translating or analysis. In one example, a microphone may be used to capture sound (e.g., audio), the sound may be digitized, packetized, and transmitted as a first data stream to at least one remote device at a destination. In another example, facial micromovements may be detected using an optical sensor, may be digitized, packetized, and may be transmitted as a data stream to at least one remote device at a destination. In this example, when the first data stream includes facial micromovements, they may then be decoded after transmission to ascertain the substantive content of the communication. In another example, the first data stream data derived from detected facial micromovements, e.g., synthesized voice.

A "subject" refers to an entity, individual, person, and/or a group of any of the foregoing. "Communication by a subject" in the context of the first data stream refers to the transmission of substantive information by a subject to another subject or to another place (e.g., a live stream, or a storage location). A communication by the subject may involve, for example, at least one sender, a message, and a recipient wherein the sender includes the subject. A communication may be an audio transmission by the subject. Alternatively, a communication may include a video transmission by the subject, where the video transmission includes both a visual and audio communication. In one example, the video may be sent over the internet as a data stream (e.g., a video call). Thus, the video and audio of the subject may be digitized and packetized by a video camera (e.g., generated) and transmitted as a data stream via a network interface over the internet to one or more recipients at a destination wherein the one or more recipients may have equipment to convert the data stream to video and audio to play the received video on a display and on a speaker. Although a communication may include both a human sender and a human recipient, this need not always be the case. For example, the recipient may be an entity such as an AI agent, a live broadcaster, a server, or another machine or a storage location to which a communication may be directed.

Generating a first data stream representing a communication by a subject involves causing, producing, initiating the formation of the first data stream. For example, in some embodiments, generating may involve converting one format of data into another. For example, a microphone may pick up sound, and the first data stream may be generated when the output of the microphone is adapted for transmission in the form of a sequence of electronic signals to convey information associated with the information communicated via the microphone. This may involve, for example, one or more of analogue to digital conversion, digital signal processing, compression, and/or packetization. In another example, a communication may be derived from light reflections, and the first data stream may be generated when the output of the sensor is adapted for transmission in the form of a sequence of electronic signals to convey information associated with the information associated with the light reflections. Again, the generation of the first data stream in this and other examples might involve one or more of analogue to digital conversion, digital signal processing, compression, and/or packetization. The data stream may have a duration, meaning that it occurs over a period of time. The period of time may be less than a second, multiple seconds, multiple tens of seconds, multiple minutes, or more. The communication may occur for a duration. For example, an audio communication by a first subject, such as a voice call over the internet, may occur for a period of time. The communication may be transmitted over the internet in the form of a data stream to a destination wherein the communication may be interpreted, recorded, stored, analyzed and/or played back. It is to be appreciated that the communication and its duration may include the entire communication or only a portion of the communication. In some examples, the first data stream may include two components, a first component reflecting captured audio and a second component representing captured video. Some disclosed embodiments involve generating a second data stream for corroborating an identity of the subject from facial skin light reflections captured during the duration of the communication. "Corroborating an identity of the subject" refers to confirming that the person involved in the communication is authentic (e.g., that the first data stream did in fact originate from the subject). For example, in a deepfake situation without corroboration, audio and/or video may provide the appearance that a known or visually presented individual is actually communicating, but a viewer may have no way to corroborate the same as true. The video and/or the audio might be altered to mislead. In contrast, in some disclosed embodiments, a second data stream includes information to corroborate that the communication conveyed was actually spoken by the subject. In some disclosed embodiments, the second data stream may be associated with facial skin light reflections captured during the duration of the communication. As a person communicates, facial skin moves in a manner correlated to the speech. In a deepfake situation where video and/or audio is altered, the correlation will necessarily cease to exist. Thus, the second data stream may be used as an indicator of the authenticity of the communication. A communication as referred to herein may be an entire communication or a portion thereof. Thus, light reflections captured during a duration of a communication may, in some instances, include a capture throughout an entire communication, and may, in other instances, include a capture during only a portion of a communication. (In other words, "during a communication" does not necessarily require capture during an entire communication.)

In some embodiments, corroborating an identity of the subject refers only to confirming that the subject portrayed as communicating was the actual source of the communication. In such a situation, if a celebrity look-alike used a system, software, or method of some embodiments, the second stream would correlate to the first stream, assuming the look-alike actually spoke the words, and there would be corroboration. In other embodiments, historical facial skin micromovement data might be used to determine that the celebrity was not the one communicating. The examples provided above with regard to celebrities are not limiting. Regardless of whether a subject is a celebrity, there may be value in confirming that the person portrayed as communicating, either through audible speech, subvocalized speech, other audible output, or non-audible expressions are authentic.

The second data stream may be used in conjunction with the first data stream (i.e., the communication) to verify the authenticity of the communication. By way of a non-limiting example, a person may use a wearable device to capture facial micromovements while vocalizing speech. A video data stream (i.e., first data stream) of a communication by the person wearing the device may be transmitted to a destination. In conjunction with the video data stream of the communication, an optical sensor on the wearable device may detect facial micromovements and generate a second data stream to transmit to the destination. The intent of generating and transmitting the second data stream may include corroborating the identity of the person (i.e., subject) in the communication. (I.e., to corroborate that the source of audio in the communication is the subject portrayed in the video.) It is to be appreciated that the second data stream may provide a method for the receiver at the destination to identify whether a video data stream may be real or may be a deepfake video. A deepfake refers to a manipulated or synthetic video created using deep learning techniques, particularly deep neural networks. Deepfakes use artificial intelligence (AI) to alter or replace the appearance and actions of a person in an existing video with someone else's likeness. By sending a second data stream to verify the authenticity of, for example, a first video/audio data stream, a determination may be made if the video may be a deepfake video.

Consistent with some disclosed embodiments, the first data stream and the second data stream are determined based on signals from a same light detector. In this example, a light detector for detecting facial skin micromovements may serve two purposes, and lead to the generation of two data streams. The light reflections may be interpreted to ascertain substance of a communication, as discussed elsewhere herein. Second, the light reflections can serve as a check function, in a second data stream, to confirm that that the communication in the first data stream is authentic (i.e., that the communication originated with the subject.) Thus, the second data stream may be determined by a light detector for use in authentication of the first data stream. By way of an example, a wearable device including a light detector may be used to determine unvocalized speech by a subject. The light detector may be used to generate a first data stream including content of the subvocalized or unvocalized speech for transmission in a manner to be received as or converted to audio (e.g., synthesized audio) at the destination. The light detector may also be used to generate a second data stream including the authentication information.

In some disclosed embodiments generating the first data stream representing the communication by the subject includes reproducing speech based on the corroborating facial skin light reflections. "Reproducing speech" in this context refers to synthesizing, copying, duplicating, or replicating speech or a speech signal from light reflection data. In this example, the signal uses to corroborate the speech may also be used to reproduce the speech. Thus, the first and second data streams may be the same, may overlap, or may be portions of a common stream or transmission.

Returning to the example of the wearable device, the wearable device including a light detector may be used to determine unvocalized speech by the subject and also corroborate the identity of the subject using facial skin light reflections. In this example, one or more words associated with facial skin light reflections detected by the wearable device may be used to generate a first data stream including digitized data of the one or more words for transmitting to a receiver. At the receiver, the first data stream may be used for reproducing speech including the one or more words for the recipient at the destination. Further, a light detector of the wearable device may be used to generate a second data stream including digitized data that may be used by the destination to corroborate the identity of the subject (i.e., corroborate that the speech in the first data stream emanated from the subject) based on the detected facial skin light reflections.

Some disclosed embodiments involve transmitting the first data stream to a destination. A "destination" in this context refers to a location other than the originating source. Examples of a destination includes one or more computers, servers, individuals, a group of individuals, institutions, entities, or (e.g., or any electronic devices associated with any of the foregoing). The recipient may be the entity that receives the data stream, while the destination may a location where the recipient is located. Alternatively, the recipient and the destination may be considered the same. The destination may be the end of the communication path for the first data stream as described and exemplified herein. For example, a video call between a first person and a second person may consist of a first data stream representing the audio and video of the video call. The first person may use a camera and microphone to create the video that may converted to a first data stream for transmitting over a communication path to a destination. The second person (or electronics associated with the second person) may be the destination for the communication wherein a receiver may receive the first data stream and convert it back to audio and video for consumption by the second person.

In some disclosed embodiments, the first data stream is based on signals associated with sound captured by a microphone during the duration of the communication. Sound captured by a microphone refers to audio received by a device that converts sound waves, which exist as mechanical vibrations that pass through fluids like air or water, into a measurable electrical signal. The electrical signal representative of sound may be further converted to digital form using a device such as an analog-to-digital converters (ADCs), which convert an analog audio signal to digital audio. For example, sound may be captured by a microphone during the duration of a communication by the subject. The captured sound may be represented as a digital audio and the digital audio may be transmitted as a data stream to a destination. As described and exemplified elsewhere in this disclosure, the data stream may be representative of a first data stream wherein the first data stream may be an audio communication by a subject transmitted to a destination. By way of a non-limiting example, a mobile application may be designed to stream audio content captured by the microphone of a mobile device (e.g., cellular phone) over the internet. The microphone integrated into the mobile device may capture sound during the duration of the communication (i.e., streamed audio content). The cellular phone may transmit the captured microphone audio as the first data stream over the internet to a destination. It is to be appreciated the mobile application may also capture facial micromovements with its camera, verify the identity of the subject of the communication and send a second data stream to the destination to verify the identity of the subject of the communication for the destination.

Some disclosed embodiments involve transmitting the second data stream to the destination. Just as the first data stream was described as being transmitted to a destination, in a similar manner the second data stream is transmitted to the destination. In some disclosed embodiments, the second data stream may include check data to enable the authenticity to be checked at the destination. Additionally or alternatively, checking may occur before transmission and the second data stream may contain an authentication signal, message, or notice confirming authenticity. For example, the message may contain a Boolean yes/no data type, yes meaning that the identity of the subject has been verified and no meaning the identity of the subject has not been verified. In other disclosed embodiments, the second data stream may contain a specific identifier corresponding to the subject of the communication. For example, the second data stream may contain the name of the subject, an identification number of the subject, an authentication key, a password or pass phrase or any other form of unique data understood by the transmitter and destination that may be used to confirm a subject's identity. In other disclosed embodiments, the second data stream may include sensor data that may be used by the destination to identify the subject. Consistent with some disclosed embodiments, the second data stream may include indicators facial micromovements containing distinguishing characteristics of the neuromuscular activity of a person that is the subject of the communication. For example, the detected facial skin light reflection may be converted to the second data stream and transmitted to the destination. In another example, one or more words correlated with the facial micromovements may be transmitted to the destination to corroborate the identity of the subject of the communication (e.g., one or more words may be correlated to the content transmitted in the first data stream). It is to be appreciated that the second data stream may repeat or continually re-verify the identity of the subject of the communication throughout the duration of the communication. Thus, a speech detection system may be capable of providing ongoing verification of communication authenticity based on light reflections from facial skin micromovements.

In alternate embodiments, the second data stream may be representative of the identity of the subject based on other biometric sensors. For example, biometric data such as real time image data, retinal scan data, vein pattern data, light reflection data, speech detection data, or fingerprint data may be used to confirm an identity of a subject. For the duration of the communication, the second data stream may be generated based on the biometric data which uniquely identifies the subject of the communication for the duration of the communication.

Consistent with some disclosed embodiments, the second data stream is indicative of a liveliness state of the subject and transmitting the second data stream enables verification of the communication authenticity based on the liveliness state of the subject. "Liveliness" refers to the quality of being active, especially with respect to a person being lively. Detecting liveliness in a subject in a communication may refer to determining that the subject in a communication demonstrates indication of activeness to thereby affirm that the subject in the communication is a real person (as opposed to a fake image or a person that in an unconscious state). Biometric liveliness detection may describe a range of techniques used for authentication to ensure that the person is a true biometric source. For example, biometric liveliness detection may be used to determine that the face of the subject in the communication is a human face rather than a false or recreated image of a face. Further, the biometric liveliness detection may be performed using detected facial micromovements. In some disclosed embodiments, the second data stream used to verify the identity of the subject of the communication transmitted in the first data stream may include an indication of the liveliness state of the subject. For example, detected facial micromovements may provide an indication of liveliness of the subject and may be used to generate a second data stream to a destination verifying the liveliness of the subject. Alternatively, the absence of detected facial micromovements may be indicative of the absence of liveliness of the subject, therefore the second data stream may provide an indication of the absence of liveliness. In some examples, the destination receiving the second data stream indicating an absence of liveliness may determine that the first data stream may not be verifiable as coming from the subject (e.g., the video may be a fake). Thus, the transmitted second data stream may enable verification of the communication authenticity based on the liveliness state of the subject by providing a confirmation of liveliness of the subject or by providing an indication of the absence of liveliness of the subject.

Consistent with some disclosed embodiments, the first data stream is indicative of an expression of the subject and the second data stream enables corroboration of the expression. An "expression of the subject" refers to one or more of the various ways that the facial muscles and features can convey emotions, thoughts, or reactions. It involves the combination of facial movements, such as eyebrow raises, eye widening, lip movements, and changes in the positioning of facial muscles, that collectively communicate a particular emotional or communicative state. The first data stream may be indicative of the expression of the subject by allowing the destination to determine the thoughts or feelings of the subject through interpretation of expressions represented in the first data stream. For example, the first data stream may be a video communication wherein the subject may be laughing and at the destination, the recipient may be able to determine based on the video communication that the subject is laughing. The second data stream may corroborate the expression, by indicating that the expression actually occurred. As with other forms of corroboration, a consumer of the content may be advised by a visual or audible indicator if a lack of authenticity is detected. Additionally or alternatively, a continuous display (such as a check mark) may appear so long as authenticity is detected.

In some disclosed embodiments, recognition of facial expressions of a subject may allow for the identification of the subject. For example, expression may contribute to identity recognition due to the identity and expressions being represented within the same brain regions. Thus, detecting facial micromovements of the subject and determining the expression of the subject may allow for the determination of the identity of the subject. Once the subject has been identified, consistent with some disclosed embodiment, a second data stream may be generated and transmitted to a destination to allow the destination to verify the identity of the subject in the communication received by the destination in the first data stream. By way of a non-limiting example, a video communication between a subject and a receiver at a destination may include a camera and a speech detection system including an optical sensor to detect facial micromovements (e.g., wearable earpiece as described and exemplified herein). The speech detection system may be configured to detect facial micromovements of the subject and may compare the detected facial micromovements to stored data representative of the identity of the subject. The stored data may have been determined based on historical facial micromovements captured that may be unique to the subject. The comparison may allow an identification of the subject. Based on the identification of the subject, the speech detection system may generate and transmit a second data stream in conjunction with the video communication transmitted in the first data stream. The video communication may provide an indication of the expression of the subject in the first data stream. The speech detection system may, based on the detected expression of the subject, provide the second data stream that may enable corroboration of the expression of the subject. In another example, the first data stream may relate to audio communication. At the destination, the recipient may determine through the audio an expression of the subject. For example, the subject may be crying. At the destination, the recipient may hear sound consistent with crying. Separately, a second data stream may verify the expression of the emotional state of the individual (e.g., the subject is crying).

Consistent with some disclosed embodiments, the second data stream is correlated to the first data stream in a manner such that upon receipt at the destination, the second data stream is enabled for use in repeatedly checking during the duration of the communication that the communication originated from the subject. Correlation of the second data stream to the first data stream refers to the establishment or determination of a relationship between the second data stream and the first data stream. A correlation, for example, may be expressed as a measure of the extent to which the two data streams relate to each other. For example, when words are vocalized or subvocalized, the facial skin of the subject moves in a manner correlated to those words. This correlation may be based on historical data derived from the subject, derived from others, or both. Artificial intelligence and/or thresholding of similarities and differences may be used to determine whether the correlation exists. If an extent of correlation surpasses a threshold of similarity, a correlation between the two data streams may be determined to exist. A lack of correlation between the first data stream and the second data stream indicates that the words carried by the first data stream did not originate from the subject. Similarly, if the second data stream is correlated to the first data stream (e.g., by surpassing a threshold of correlation or meeting some other confirming criteria), that correlation indicates that the words carried by the first data stream originated from the subject.

Correlations can be confirmed or established multiple times during a communication to provide repetitive or ongoing authentication. So long as the second data stream carries sufficient information to enable confirmation of such correlation multiple times during a conversation, the second data stream is said to be "correlated to the first data stream in a manner such that upon receipt at the destination, the second data stream is enabled for use in repeatedly checking during the duration of the communication that the communication originated from the subject." In one example, during the duration of the communication, the identity of the subject may be checked periodically, such as multiple times a second, every second, every few seconds, or longer durations, although the longer the duration between checks the more room is left for fraud. In an alternate embodiment, a recipient at the destination may request an update of the verification that the communication originated from the subject. For example, a recipient at the destination may have reason to distrust the communication and may press a button to request subject verification. In response, the origin may respond with an update in the second data stream to verify or not to verify that communication may originate from the subject. It is to be appreciated that during the duration may include constantly throughout the duration, periodically during the duration, at set intervals during the duration and at intervals corresponding to speech patterns during the duration of the communication.

Consistent with some disclosed embodiments, the destination is a social network service the second data stream enables the social network service to publish the communication with an authenticity indicator. A "social network service" (sometimes called a "social networking site") may refer generally to a type of online social media platform which people use to build and maintain social networks or social relationships with other people who share similar personal or career content, interests, activities, backgrounds, or real-life connections. The social network service may feature digital photo and video sharing, diary entries or other messages online, direct messaging, blogging and other forms of information sharing by users related to building or maintaining a social network. Social networking services may allow users to share ideas, digital photos and videos, posts, and to inform others about online or real-world activities and events with people within their social network. In some disclosed embodiments, the destination may be a social network service. A first data stream may be directed to the social network service. For example, a user may post a video to the social network site by uploading a first data stream to the social network site. Further, a second data stream that may be correlated to the communication depicted by the first data stream may be used to corroborate the authenticity of the first data stream.

In some disclosed embodiments, the first data stream may be streaming in real time on the social network site. In other disclosed embodiments, the first data stream may be uploaded to the social network site for viewing at a later time. The second data stream may be used as an authenticity indicator on the social network site. In some disclosed embodiments, the second data stream may enable the social network service to publish the communication depicted by the first data stream with an authenticity indicator. The social network service may specify a format or content for the second data stream that may serve as an authenticity indicator for the first data stream (e.g., posted content). For example, the social network service may provide a feature that a video posted on the social network site that contains a communication by a subject further may contain verification of the identity of the subject provided by facial micromovements. If the verification is authenticated, the social network service may post the communication. In some examples, the post may further contain a positive confirmation for a viewer that the subject in the video in the post may have been verified. The authentication process may reduce misinformation that may spread due to deepfake videos posted on social network sites. It is to be appreciated that in the example, the first data stream may be the video and the second data stream may be the authentication indicator based on identity verification of the subject using facial micromovements. A user of the social network site may use the authentication indicator to confirm that the posted video is not fake.

Consistent with some disclosed embodiments, the destination is an entity engaged in a real-time transaction with the subject and the second data stream enables the entity to verify in real-time the identity of the subject during the duration of the communication. A transaction may include, for example, such activities as an exchange of products or services, the transfer of money or securities, the commitment to exchange goods or services in the future, the establishment of an account, the verification of permissions, or any other interchange for which authentication is desirable. A "real-time transaction" generally refers to a transaction that takes place and may be during a communication. In some disclosed embodiments, the destination may be an entity engaged in real-time transactions. The entity may be a bank, other financial institution, business, website, organization, or any individual or group involved in a transaction. The entity may have incentive to verify the identity of a subject engaged in the real-time transaction. Consistent with disclosed embodiments, the first data stream may include a communication related to the real-time transaction and the second data stream may enable the entity (e.g., destination) to verify in real-time the identity of the subject during the duration of the communication.

Authenticating the subject of the communication may reduce risk during real-time transactions by adding an additional layer of security in verifying the entities involved to the real-time transaction. Consistent with some disclosed embodiments, the second data stream may be generated based on the detection of facial micromovements associated with the communication. Further, the identity of the subject may be transmitted such that the identity may be verified during the duration of the communication. By way of a non-limiting example, a bank transfer may be initiated by a bank customer (i.e., subject). As part of initiating the bank transfer, the bank customer may provide the communication verifying that they wish to proceed with the transaction. Further, the bank customer may use a wearable device configured to detect facial micromovements that may allow the identity of the bank customer to be determined and thus verified by the bank. In the example, the first data stream may be the communication to initiate or confirm the bank transfer and the second data stream may be the verification of the identity of the subject based on the detection of facial micromovements and the determination of the identity of the bank customer using facial micromovements for verification by the bank in completing the real-time transaction.

Consistent with some disclosed embodiments, verifying the identity includes verification of a name of the subject. Verification of the name of the subject may include correlating the identity of the subject of the communication with the name of the subject. For example, facial micromovements may be used to determine the identity of the subject. A data structure may be created based on historical data that correlates the identity of the subject using facial micromovements and the name of the subject. During the real-time transaction, a lookup in the data structure may retrieve the name of the subject and the second data stream may be generated including the name of the subject. The second data stream may be transmitted to the destination (i.e., entity) where the name may be used to verify the identity of the subject. Returning to the example of the bank customer, the name of the bank customer may be retrieved from the data structure during the real-time transaction. The name of the bank customer may be transmitted via the second data stream during the duration of the real-time transaction. It is to be appreciated that other security mechanisms may be added to further secure the transaction such as encrypting the name of the subject in the second data stream.

Consistent with some disclosed embodiments, verifying the identity includes verification at least periodic intervals throughout the communication that the subject spoke words presented in the communication. As described and exemplified elsewhere in this disclosure, verification can occur multiple times during a communication. "Periodic intervals" may refer generally to occurring multiple times, recurring at regular intervals, or occurring repeatedly from time to time either regularly or irregularly. In some disclosed embodiments, the identity of the subject of a communication including spoke words presented in the communication may be verified in at least periodic intervals through the duration of the communication. Further, in some disclosed embodiments, the identity of the subject may be verified using facial micromovements. For example, an audio communication over a voice over IP call may include spoke words via a voice over IP handset. The subject of the communication may be using a speech detection system configured to detect facial micromovements wherein the facial micromovements may be associated with the spoken words (e.g., vocalized words in the communication). For example, the voice over IP handset may include an optical sensor configured to detect facial micromovements. The detected facial micromovements may allow verification of the identity of the subject and that verification may be transmitted at periodic intervals to the destination via the second data stream to allow the destination to regularly authenticate the subject of the spoken words (e.g., the speaker in the audio communication).

Figure 64:
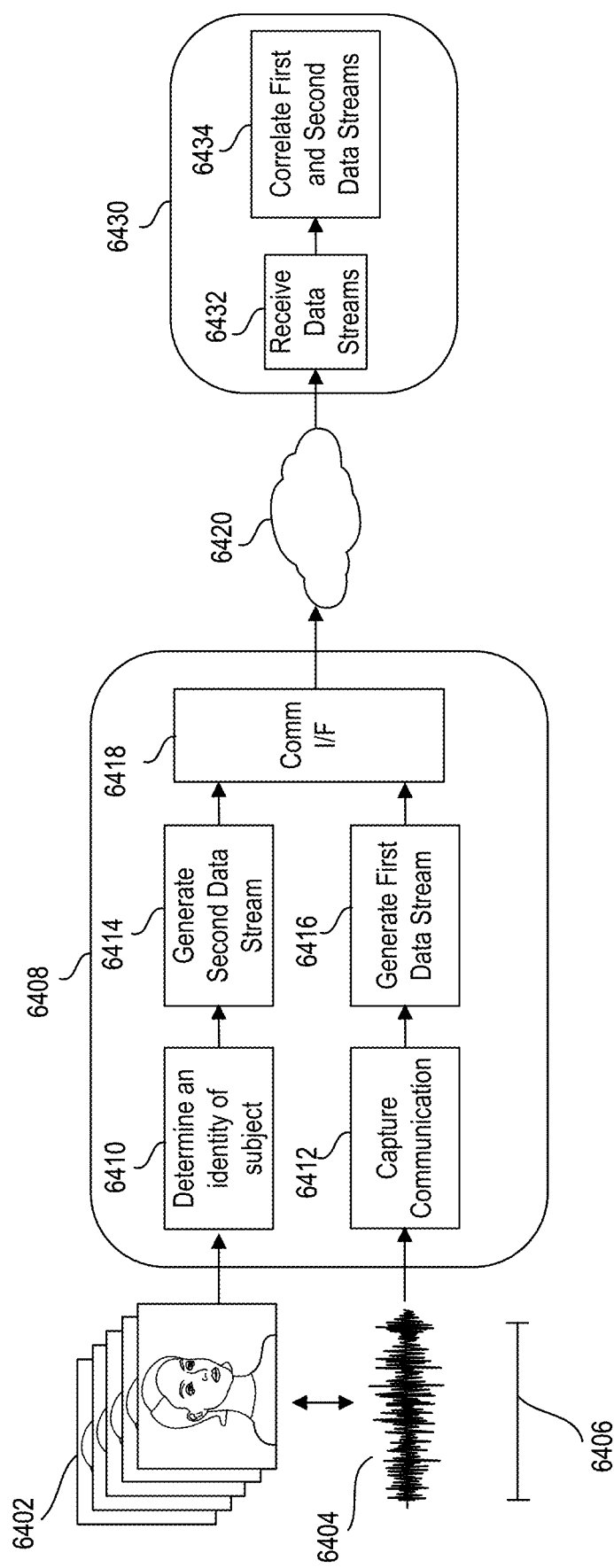
FIG. 64 is a schematic illustration of an exemplary speech detection system that sends two data streams to a destination to verify communication authenticity, consistent with some embodiments of the present disclosure.

By way of a non-limiting example, reference is made to FIG. 64 illustrating a system block diagram for the verification of communication authenticity based on identification of subject using facial micromovements. It is to be noted that FIG. 64 is a representation of just one embodiment, and it is to be understood that some illustrated elements might be omitted, and others added within the scope of this disclosure. In the depicted embodiment, subject 6402 may create a communication 6404 having a duration 6406. The operations 6408 may capture the communication 6412 and generate a first data stream 6416 based on the communication 6412. Further, the operations 6408 may determine the identity of the subject 6410 based on light reflections from facial skin and generate a second data stream 6414 to corroborate the identity of the subject 6402. The first data stream 6416 and the second data stream 6414 may be transmitted via a communication interface 6418 and through the cloud 6420 to a destination 6430. At the destination 6430, the first data stream 6416 may be received 6432 including the communication originating from the subject 6402. Additionally or alternatively at the destination 6430, the second data stream 6414 may be received 6432 including the identity of the subject 6402. At the destination 6430, the second data stream 6414 may be correlated with the first data stream 6416 in a manner such that upon receipt at the destination 6430, the second data stream 6414 may be enabled for use in repeatedly checking, during the duration 6406 of the communication 6404 that the communication 6404 originated with the subject 6402. The second data streams 6414 may allow the recipient of the communication 6404 to verify the authenticity of the communication 6404.

In some examples, the first data stream 6416 and second data stream 6414 may be determined based on signals from the same light detector. For example, the communication 6404 may be derived from facial micromovements. The communication 6404 may be derived from unvocalized words, prevocalized words or silent speech. It is to be appreciated that the first data stream 6416 representing the communication 6404 by the subject 6402 may include reproducing speech at the destination based on corroborating facial skin light reflections determined by the light detector. Further, the second data stream 6414, including information related to the identity of the subject 6402, may be derived from facial micromovements determined based on signals from the same light detector. In some examples, the first data stream 6416 may be based on signals associated with sound captured by a microphone during the duration 6406 of the communication 6404. For example, the microphone may be used in an audio call (i.e., communication 6404) from an originating subject 6402 to a recipient at destination 6430. It is to be appreciated that the destination may convert the first data stream 6416 back to audio to play at a speaker for the recipient. It is to be appreciated that the system may be designed for two way calling in which both ends of the call have a subject 6402 and a recipient such that the communication 6404 may be authenticated in both directions as described and exemplified herein.

In one example of identifying the subject 6402 in the communication 6404, the second data stream 6414 may be indicative of a liveliness state of the subject 6402. The second data stream 6414 may enable verification of the communication authenticity at the destination based on the liveliness state of the subject 6402. For example, a video of the subject 6402 may allow a determination of liveliness in the subject 6402 that may indicate that the video is authentic and not a fake. In another example, the first data stream 6416 may be indicative of an expression of the subject 6402 and the second data stream 6414 may provide verification of the identity of the subject 6402 by enabling corroboration of the expression at the destination. In another example, the destination 6430 may be a social network service. The second data stream 6414 may enable the social network service to authenticate the communication 6404 and therefore, based on the authentication, publish the communication 6404 on the social network service with an authenticity indicator. In another example, the destination 6430 may be an entity engaged in a real-time transaction. The second data stream 6414 may be used to check the identity of the subject 6402 for the duration 6406 of the communication 6404 related to the real-time transaction.

Consistent with some disclosed embodiments, checking that the communication originated from the subject includes verifying that all words in the communication originated from the subject. Verifying that all words in the communication originated from the subject may include detecting all of the spoken words from the subject via a means of sensing that the sounds of all of the words match the neuromuscular activity of the subject to produce the sounds of all of the words. By way of a non-limiting example, the subject may use a speech detection device (e.g., wearable light reflection detector) configured to detect facial micromovements associated with the prevocalized or vocalized words spoken by the subject. The detected prevocalized or vocalized words as determined through detection of facial micromovements may then be compared to the communication originated from the subject (e.g., the words in the communication). In some embodiments, less than all spoken words in a communication (e.g., a group of spoken words) are verified. In other embodiments, all spoken words in a communication are verified. In this way for example, extra words surreptitiously added can be identified as non-authentic.

Consistent with some embodiments, checking that the communication originated from the subject includes verifying at regular time intervals during the duration of the conversation that speech captured at the regular time intervals originated from the subject. Regular intervals refers to a consistent and uniform timing or a pattern. Verifying at regular intervals may include confirming at interval times, that the contents of the data stream generated based on the communication was originated by the subject.

Consistent with some disclosed embodiments, the first data stream and the second data stream are intermingled in a common omnibus data stream. A "common omnibus data stream" refers to a composite data stream including a plurality of data streams combined into a single data stream. The common omnibus data stream may be a combination of a plurality of data streams transmitted via a single communication interface to the destination. The receiver of the common omnibus data stream may extract one or more data streams such that the destination may operate on them separately. In some disclosed embodiments, as described and exemplified in this disclosure, the first data stream (e.g., communication from the subject) and the second data stream (e.g., verification of the identity of the subject) may be intermingled into a common omnibus data stream and transmitted to the destination. At the destination, the first data stream and second data stream may be extracted from the omnibus data stream. Alternatively, extraction may not occur and the omnibus stream and data from the substream may be separately analyzed. The communication may be delivered to the destination and the destination may verify the authenticity of the communication via the second data stream. By way of a non-limiting example, at the origination of a video stream, the source may combine the video stream with identity verification information provided by the detection of facial micromovements into a common omnibus data stream. The common omnibus data stream may be transmitted via a communication interface to the destination. At the destination, the receiver may extract the video stream and verification data stream from the common omnibus data stream. Using the verification data stream, the destination may authenticate the video stream and play the authenticated video stream for the recipient.

Consistent with some disclosed embodiments, the operations further include determining a biometric signature of the subject from light reflections associated with facial skin captured before the communication, and wherein the identity of the subject is determined using the corroborating facial skin light reflections and the biometric signature. A "biometric signature" refers to unique physiological or behavioral characteristics of an individual that can be used for identification or authentication purposes. In this instance, since facial micromovements carry unique identifying information akin to a fingerprint or retinal scan, facial skin light reflections picked up by a sensor can be used to identify a user. This may occur, for example, by storing in advance a biometric signature based on the uniquely identifying information contained in the light reflections. As described and exemplified elsewhere in this disclosure, the identity of the subject may be determined using the facial skin light reflections and the biometric signature. By way of an example, facial micromovements correlated with vocalized speech may be unique to an individual, much like a fingerprint. Thus, facial micromovements may be used as a biometric identifier when correlated with vocalized speech.

Consistent with some disclosed embodiments, the biometric signature is determined based on a micro-veins pattern in the facial skin. "Micro-veins pattern" refers broadly to veins that are tiny blood vessels, called capillaries, which exist under the surface of the skin. The micro-veins pattern may appear as small red lines. Micro-veins pattern in the facial skin may be detectable on the nose, chin, cheek, or any other region of the face. Micro-vein patterns may be unique to an individual person therefore micro-vein patterns may provide a biometric signature for identification of the individual person. For example, the identity of a subject of a communication may be verified through detection of micro-vein patterns in the facial skin. Consistent with some disclosed embodiments, an optical sensor may detect one or more micro-vein patterns in the facial skin of the subject during the duration of a communication. Based on the detected one or more micro-veins patterns, a second data stream may be generated and transmitted to the destination enabling verification of the communication. For example, a subject generating a video communication may provide verification of their identity using the optical sensor to detect one or more micro-vein patterns. Consistent with some disclosed embodiments, the micro-vein pattern may be detected without detecting facial micromovements. Micro-vein pattern detection may provide a biometric signature for identifying the subject.

Consistent with some disclosed embodiments, the biometric signature is determined based on a facial skin micromovement sequence associated with phonemes spoken by the subject. Phonemes spoken by the subject may refer to a sound or a group of different sounds that are the building blocks of words. Phonemes are essentially the smallest unit of sound heard in a word. Consistent with some disclosed embodiments, a facial skin micromovement sequence may be associated with phonemes spoken by a subject. Vocalized or subvocalized phonemes may provide a biometric signature of the subject of the communication. Determination of the biometric signature (e.g., verification of the identity of the subject) may allow a second data stream to be generated to authenticate the subject of the communication received at a destination in the first data stream.

Consistent with some disclosed embodiments, the operations further include storing in a data structure identifying facial skin micromovements of the subject vocalizing or prevocalizing a passphrase, and identifying the subject based on the vocalization or prevocalization of the passphrase. A data structure consistent with the present disclosure may include any collection of data values and relationships among them. By way of example, a data structure may contain correlations of facial micromovements with a subject's vocalized or prevocalized passphrase. For example, if a user sets a passphrase as "Birds fly south in the winter," that phrase will have associated with it a series of associated facial skin movements that occur when the words are vocalized or prevocalized and which can be identified in sensed light reflections. Each person who vocalizes or prevocalizes the phrase will have a unique biosignature incorporated within the associated light reflections, because each person has subtle differences in the way their skin moves when words are articulated. Thus, signals associated with light reflections for passphrases can be used as a biosignature. In some disclosed embodiments, the biosignature may be stored in a data structure in conjunction with an associated password or passphrase identifying the subject. For example, at the beginning of a communication by the subject wearing a speech detection system or in response to a prompt, the subject of the communication may vocalize or prevocalize the passphrase. The speech detection system may identify facial skin micromovements associated with the vocalized or prevocalized words and lookup in a data structure previously stored verification of the identity of the subject based on the association of the detected facial skin micromovements based on the passphrase.

Consistent with some disclosed embodiments, the operations further include storing in a data structure a profile of the subject based on patterns of facial skin micromovements, and identifying the subject based on the patterns. As described and exemplified elsewhere in this disclosure, disclosed embodiments may include and/or a data structure containing stored data indicative of a profile of a subject. The data structure may contain correlations of patterns of facial skin micromovements with a profile identifying the subject. In some disclosed embodiments, identified facial skin micromovements of the patterns of facial skin micromovements may be stored in the data structure. Further, the patterns stored in the data structure may be correlated with the profile identifying the subject. For example, during the duration of a communication by a subject wearing a speech detection system, the speech detection system may identify facial skin micromovements associated with a pattern. The detected pattern may initiate a lookup in the data structure previously stored verifying the identity of the subject based on the association of the detected facial skin micromovements with the profile of the subject. For example, the light reflections associated with common words or phrases, patterns of successive syllables or phenomes, or even silent expressions that are recognized as occurring or occurring in certain order with words or phrases vocalized or prevocalized may be stored. In this way, even in the absence of a defined password or passphrase, a subject's specific identity may be confirmed.

Figure 65:
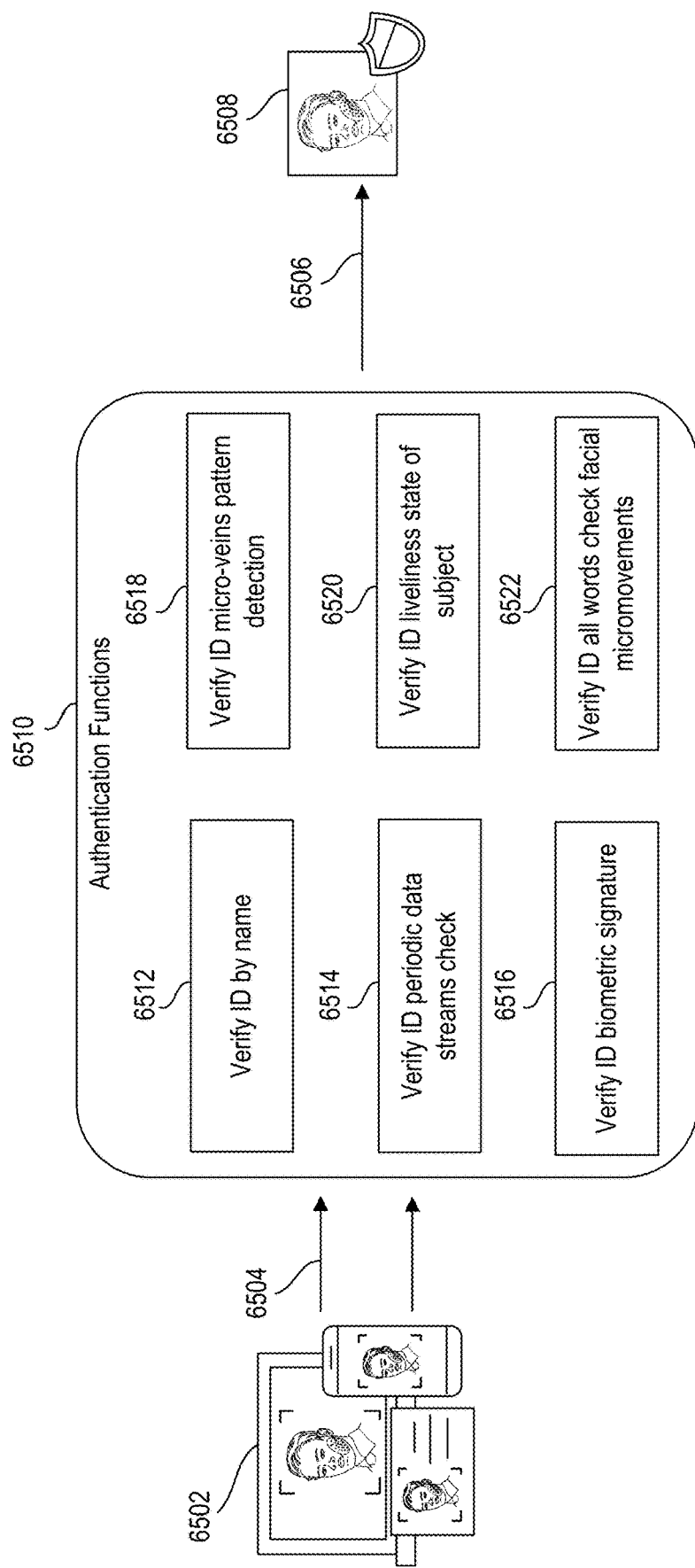
FIG. 65 is a schematic illustration of exemplary functions used to authenticate communication at a destination, consistent with some embodiments of the present disclosure.

By way of a non-limiting example, reference is made to FIG. 65 illustrating a system block diagram for a group of authentication functions 6510 associated with verifying the identity of a subject of a communication. It is to be noted that FIG. 65 is a representation of just one embodiment, and it is to be understood that some illustrated elements might be omitted, and others added within the scope of this disclosure. In the depicted embodiment, communication device 6502 may generate data streams 6504 allowing a destination 6508 to verify the identity of the subject of the communication based on the received data stream 6506. In some disclosed embodiments, the verification of the identity of the subject may be based on name 6512 of the subject. For example, the second data stream may include a representation of the name of the subject (e.g., text string including the name of the subject of the communication). In some disclosed embodiments, the verification of the identity of the subject may be based on periodic check of the data streams 6514. For example, the second data stream may, during the duration of the communication, provide update of the verification of the identity of the subject at regular intervals.

In some disclosed embodiments, verification of the identity of the subject may be done by biometric signature 6516. For example, the biometric signature may be derived from facial micromovements detected based on light reflections from facial skin. In the example, the unique characteristics of a subject's facial micromovements provide the biometric signature to verify the identity of the subject. In some disclosed embodiments, micro-vein pattern detection 6518 may be used to identify the subject to authenticate the communication. Consistent with some disclosed embodiments, the micro-vein pattern may be detected without detecting facial micromovements. Micro-vein pattern detection may provide a biometric signature for identifying the subject. In some disclosed embodiments a liveliness state 6520 may be used to verify the identity of the subject. For example, the destination may be able to determine that a video may be fake based on an absence of liveliness of the subject in the video. In some disclosed embodiments, all of the words in a communication may be checked by detecting facial micromovements 6522 to verify the identity of the subject of the communication. For example, a light detector may be capable of matching all of the words of the communication with detected facial micromovements associated with all of the words of the communication and may transmit, in the second data stream, all of the words as detected by facial micromovements (e.g., text string including all words matching the words in the audio of the communication).

Figure 66:
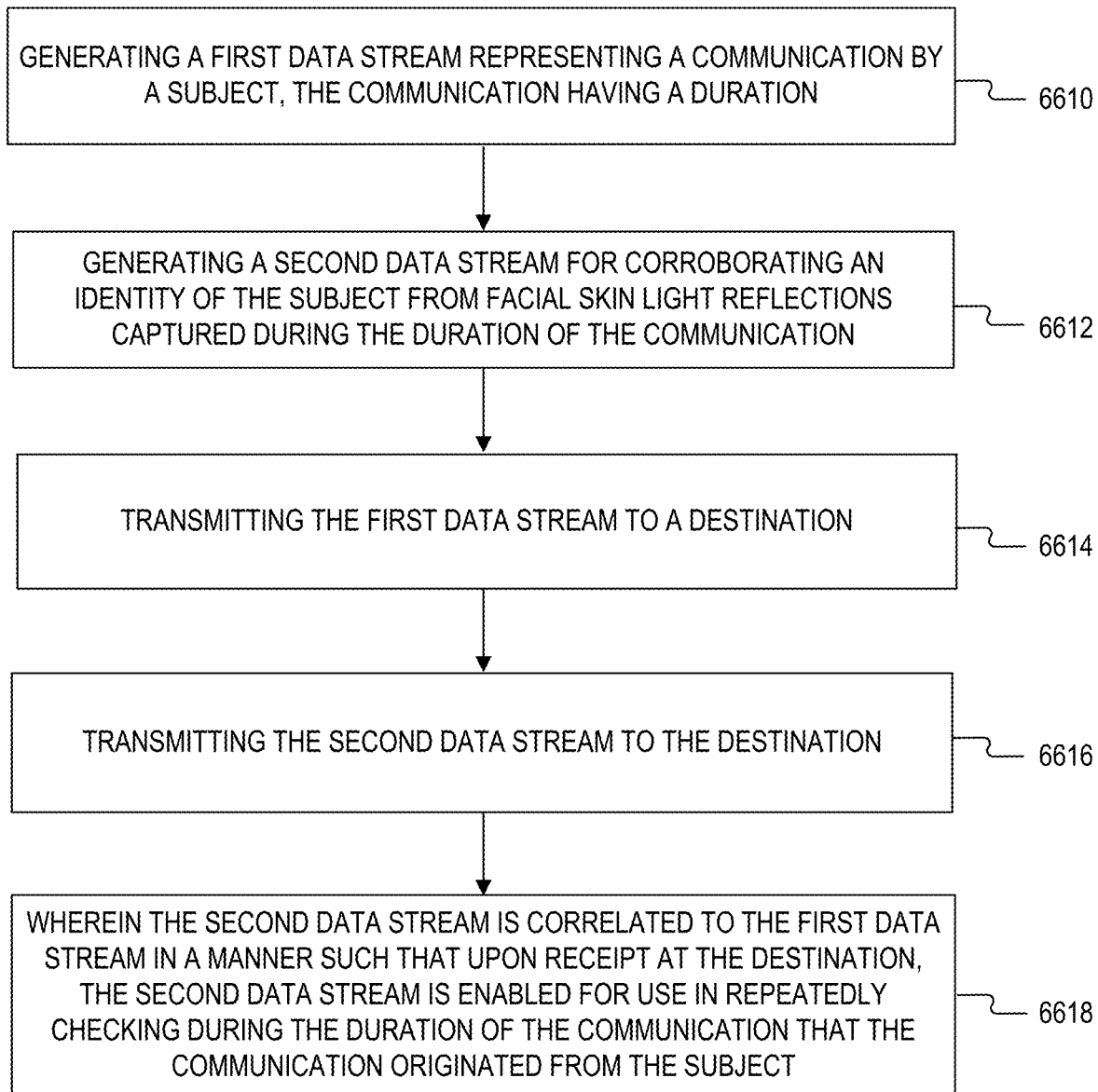
FIG. 66 is a flow chart showing an exemplary method for using received reflections to verify communication authenticity, consistent with some embodiments of the present disclosure.

FIG. 66 illustrates a flowchart of an exemplary process 6600 for using facial micromovements to verify communication authenticity, consistent with embodiments of the present disclosure. Some embodiments disclose a method for verification of communications based on light reflections from facial skin. At step 6610, the method includes generating a first data stream representing a communication by a subject, the communication having a duration, as described elsewhere herein. Consistent with some disclosed embodiments, the communication by the subject may include reproducing speech based on corroborating facial skin light reflections. At step 6612, the method may include generating a second data stream for corroborating an identity of the subject from facial skin light reflections captured during the duration of the communication, as described elsewhere herein. At step 6614, the method may include transmitting the first data stream to a destination, as described elsewhere herein. Consistent with some disclosed embodiments, the first data stream may be based on signals associated with sound captured by a microphone during the duration of the communication. At step 6616, the method may include transmitting the second data stream to the destination, as described elsewhere herein. Consistent with some embodiments, the second data stream may be indicative of a liveliness state of the subject. Consistent with some embodiments, the first data stream may be indicative of an expression of the subject and the second data stream may enable corroboration of the expression. At step 6618, the method may include the second data stream correlated to the first data stream in a manner such that upon receipt at the destination, the second data stream is enabled for use in repeatedly checking during the duration of the communication that the communication originated from the subject. Consistent with some embodiments, the operations may further include determining a biometric signal of the subject associated with facial skin captured before communications. Consistent with some embodiments, the operation may further include storing in a data structure identifying facial skin micromovements of the subject vocalizing or prevocalizing a passphrase. Process 6600 described above is merely exemplary and many changes are possible. In some embodiments, the order of the illustrated steps may be different, and some steps may be eliminated and/or additional steps added. Additionally, in some embodiments, process 6600 may be incorporated into another process or may be part of a larger process.

Some disclosed embodiments involve a system that may differentiate a user's voice from all other voices and noise by correlating facial micromovements with a portion of sensed sound. Knowing the portion of sound attributable to the user, the system may then suppress all other sound. Some disclosed embodiments involve a head mountable system for noise suppression. As described and exemplified elsewhere in this disclosure, a head mountable system may include any arrangement, structure, or other device or combination of devices at least a portion of which is configured to be worn, carried, held, maintained, or otherwise supported by or attached to any portion of a head of a user, such as a user's ear, nose, scalp, or mouth. Examples of a form factor for a head mountable system include an earbud, eyeglasses, goggles, a headset, earphones, headphones, a headband, caps, hat, and mask. In the example shown in FIG. 67, a wearer 6700 wears a head mountable system 6702 for noise suppression on his or her ear in the form of an earpiece, which is inserted into the ear of the wearer 6700 and held in place by the shape of the ear.

Some disclosed embodiments involve a wearable housing configured to be worn on a head of a wearer. A wearable housing configured to be worn on a head of a wearer is described elsewhere herein. In the example shown in FIG. 67, head mountable system 6702 includes a wearable housing 6730 configured to be worn on an ear of the head of wearer 6700. The exemplary wearable housing 6730 may be shaped to fit over the ear of wearer 6700, such as in a curved or bent shape. Although not a requirement, in some embodiments, wearable housing 6730 may be constructed of a malleable material, such as a flexible metal, plastic composite, or thermoplastic elastomers, to conform to a shape of the ear of wearer 6700.

Figure 67:
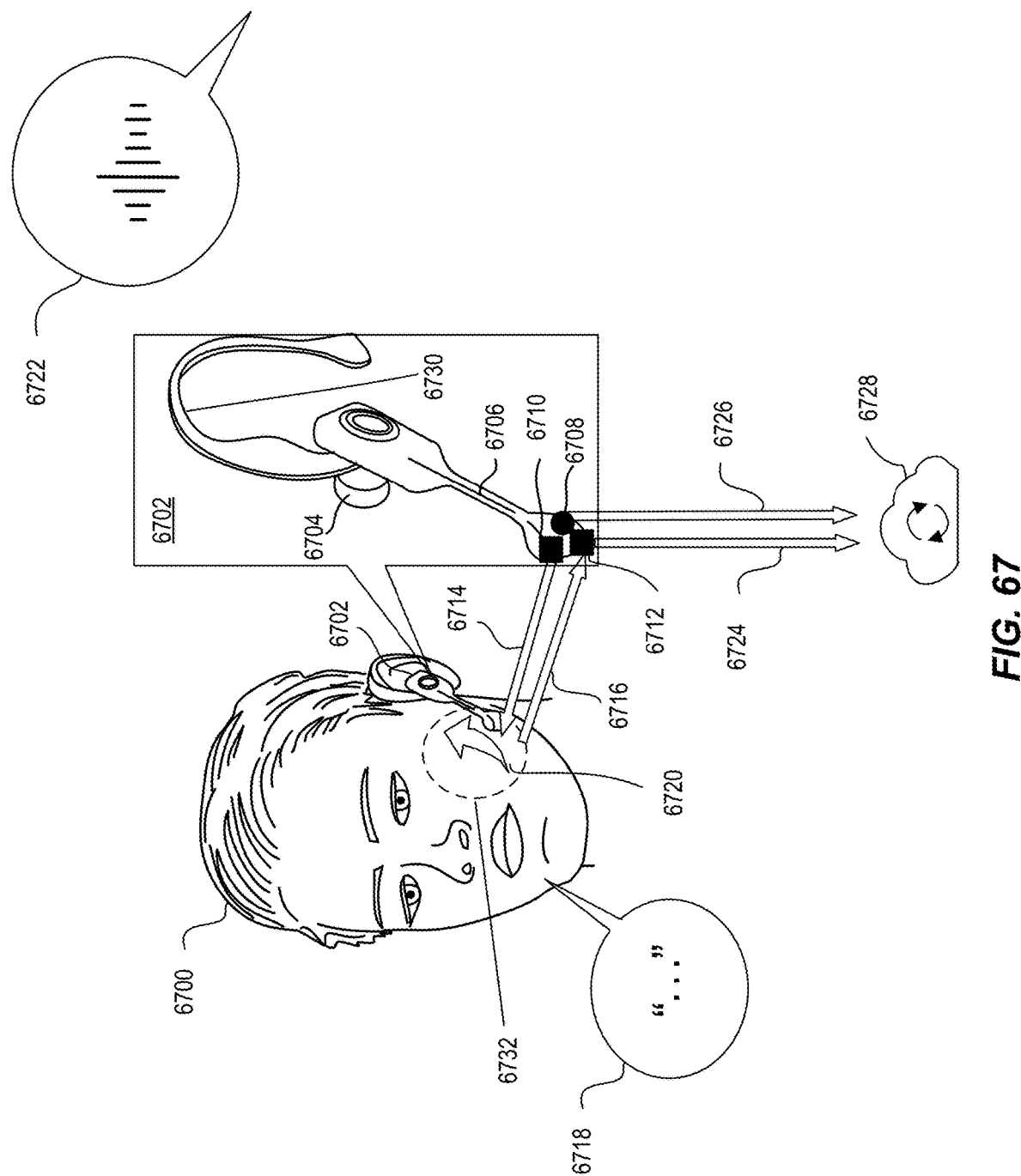
FIG. 67 illustrates an exemplary head mountable system for noise suppression, consistent with some embodiments of the present disclosure.

Some disclosed embodiments involve at least one coherent light source associated with the wearable housing and configured to project light towards a facial region of the head. A coherent light source configured to project light towards a facial region of the head and a facial region of the head are described elsewhere herein. By way of non-limiting example, FIG. 67 shows a coherent light source 6710 of head mountable system 6702 configured to project light 6714 towards a facial region 6732 of the head of wearer 6700. A coherent light source associated with the wearable housing may include a coherent light source (as described elsewhere herein) connecting, communicating, relating, corresponding, linking, coupling, or otherwise having a relationship with the wearable housing. Examples of a coherent light source associated with the wearable housing include a solid-state laser, laser diode, a high-power laser, infrared laser diode, or an alternative light source such as a light emitting diode (LED)-based light source molded with the wearable housing, adhered to the wearable housing with an adhesive, or in wired or wireless communication with the wearable housing, such as through a Bluetooth connection. As used herein, light source "associated" with the wearable housing indicates that the light source is physically or non-physically but operatively connected to the wearable housing. In other words, the light source and the wearable housing may be in a working relationship. For example, FIG. 67 shows a coherent light source 6710 associated with wearable housing 6730 by being connected to wearable housing 6730 so that coherent light source may project light 6714 towards a facial region 6732 of the head of wearer 6700 while wearer 6700 wears the wearable housing 6730 on his ear.

Some disclosed embodiments involve at least one detector associated with the wearable housing and configured to receive coherent light reflections from the facial region associated with facial skin micromovements and to output associated reflection signals. A detector configured to receive coherent light reflections and output associated reflection signals are described elsewhere herein. By way of non-limiting example, in FIG. 67, head mountable system 6702 includes a detector 6712 configured to receive coherent light reflections 6716 and output associated reflection signals 6724. Light reflections from the facial region associated with facial skin micromovements may include any light reflections relating to or indicative of skin motions on the face that may be detectable, for example, using a sensor, but which might not be readily detectable to the naked eye. Examples of light reflections from the facial region associated with facial skin micromovements include secondary speckle patterns, different types of specular reflections, diffuse reflections, speckle interferometry, and any other form of light scattering coming from a muscle, group of muscles, or other region of a face of a user that creates or is related to the creation of micromovements. For example, FIG. 67 shows light reflections 6716 from a cheek 6732 associated with facial skin micromovements 6720, which are received by detector 6712.

Some disclosed embodiments involve analyzing the reflection signals to determine speech timing based on the facial skin micromovements in the facial region. At least one processor may be understood as described and exemplified elsewhere in this disclosure. For example, in FIG. 67, an exemplary processor 6728 is implemented as a virtual server, such as a cloud server. Speech timing may include a placement in occurrence or time associated with one or more aspects of speech, such as sounds, tones, pitch, letters, words, or sentences related to a user's intention to convey information, such as a question. Examples of speech timing include an order of words or sentences, a beginning of speech, an end of speech, a period of speech, and a speed or frequency of speech. For example, a period of time of one hour may be analyzed, and in that hour, a speech timing may include a period of one minute when the user is engaging in movement or activity associated speaking a sentence. Analyzing the reflection signals to determine speech timing based on the facial skin micromovements in the facial region may involve processing, examining, combining, separating, or otherwise studying the reflection signals associated with or caused by facial skin micromovements in the facial region while the user is intending to convey information. Examples of analyzing the reflection signals to determine speech timing include studying the reflection signals using one or more techniques, such as a Hidden Markov Model, Dynamic Time Warping, neural networks, sampling theory, Discrete Fourier Transform, Fast Fourier Transform, cross-correlation, and auto-correlation. For example, analyzing the reflection signals to determine speech timing based on the facial skin micromovements in the facial region may involve analyzing the reflection signals coinciding with a presence of facial skin micromovements in the facial region, such as by a change in the reflection signals caused by the facial skin micromovements. As one example, the analysis may involve manipulating the reflection signals by artifact removal, signal representation, feature extraction, feature compression, and time alignment. In this example, the modified reflection signals may then be used to determine a period of time indicative of speech associated with the facial skin micromovements using feature transformation. As another example, the analysis may involve comparing the reflection signals to signals known to be associated with speech to determine when speech begins and ends.

Some disclosed embodiments involve receiving audio signals from at least one microphone, the audio signals containing sounds of words spoken by the wearer together with ambient sounds. Audio signals may include any representation of sound, typically using either a changing level of electrical voltage for analog signals, or a series of binary numbers for digital signals. Examples of audio signals include waveforms, frequencies, amplitudes, decibels, bits, and pressure levels. For example, an audio signal may include a recording of speech created by a microphone or a sound level as measured by a decibel meter. At least one microphone may include any instrument for converting sound waves into electrical energy variations. The sound waves may then be amplified, transmitted, or recorded. Examples of a microphone include dynamic, condenser, ribbon, carbon, and crystal microphones. The at least one microphone may be physically (e.g., by wires or adhesives) or operationally coupled to the head mountable system (e.g., by wireless connection). For example, FIG. 67 shows an exemplary microphone 6708, which may be a lavalier microphone, attached to the wearable housing 6730. The term "receiving" may include retrieving, acquiring, or otherwise gaining access to, e.g., data. Receiving may include reading data from memory and/or receiving data from a device via a (e.g., wired and/or wireless) communications channel. At least one processor may receive data via a synchronous and/or asynchronous communications protocol, for example by polling a memory buffer for data and/or by receiving data as an interrupt event. For example, receiving the audio signals may refer to capturing or obtaining the acoustic energy of sound waves or the electrical representation of those sound waves and making it available for further use. It may involve any process of capturing or acquiring an audio waveform or electrical representation of sound from a source such that it is detected, acquired, or picked up by a device or system for further processing, amplification, recording, or playback. Examples of receiving the audio signals include capturing the signals using line inputs, wireless systems, or digital interfaces. For example, FIG. 67 shows a microphone 6708 configured to capture sound waves and convert them into electrical signals 6726. In this example, the processor 6728 is configured to receive the electrical signals 6726, making them available for processing, amplification, or recording. Sounds of words spoken by the wearer may include any acoustic characteristics that may contribute to the perception and recognition of speech by the user. Examples of sounds of words spoken by the wearer include phonemes, articulation, vowel sounds, consonant sounds, pitch, intonation, rhythm, tempo, and prosody. For example, in FIG. 67, the audio signals captured by microphone 6708 include sounds 6718 of words spoken by wearer 6700. Ambient sounds may include any auditory elements present in a given environment or space, such as background sounds or environmental sounds. Examples of ambient sounds include nature sounds, background chatter, traffic noise, whispered conversations, and music. For example, in FIG. 67, in FIG. 67, the audio signals captured by microphone 6708 include sounds 6718 of words spoken by wearer 6700 together with ambient sounds 6722, such as background chatter and other noises in a busy office.

Some disclosed embodiments involve at least one processor configured to correlate, based on the speech timing, the reflection signals with the received audio signals to determine portions of the audio signals associated with the words spoken by the wearer. Correlating may involve any process of comparing two or more signals to determine a degree of similarity or relationship between them. Examples of correlating signals may include inspection, cross-correlation, Fourier Transform, statistical analysis, waveform matching, distance measures, and machine learning techniques. Inspection may involve analyzing the signals by a qualitative comparison of the signals to, for example, identify similarities, differences, patterns, or trends. Cross-correlation may involve measuring the similarity between two signals by calculating the correlation at different time lags. The Fourier transform may involve analyzing the frequency content of signals. By converting the signals from the time domain to the frequency domain, it becomes possible to compare their spectral characteristics to determine a similarity or relationship between the signals. Statistical techniques involves comparing signals by assessing their statistical properties. This includes measures such as mean, variance, standard deviation, skewness, kurtosis, or higher-order statistical moments. Statistical tests like t-tests, ANOVA, or regression analysis may be employed to compare the statistical differences or relationships between signals. Techniques such as spectral analysis, power spectrum estimation, or coherence analysis may be applied to compare the frequency components of the signals. Waveform matching involves comparing the waveforms of two signals directly. This may be done by aligning the signals and measuring the differences in amplitude, phase, or shape. Distance measures quantify the dissimilarity between signals by calculating the distance between their feature representations. Examples of distance measures include Euclidean distance, Manhattan distance, Mahalanobis distance, or dynamic time warping (DTW). Machine learning algorithms may be trained to compare and classify signals based on patterns or features. Techniques such as clustering, classification, or similarity matching algorithms may be applied to analyze and compare signals based on their features or learned representations. In one example of using machine learning to correlate the reflection signals with the received audio signals, a model such as a recurrent neural network (RNN), convolutional neural network (CNN), or a combination of both (e.g., an audio-visual fusion network), may be configured to learn to associate the certain features of the reflection signals and the received audio signals. Portions of the audio signals associated with the words spoken by the wearer may include any region, component, piece, section, or segment of the audio signal caused by, preceded by, following, indicating intention of, or otherwise related to the words spoken by the wearer. Examples of portions of the audio signals associated with the words spoken by the wearer include amplitude, frequency, waveforms, duration, harmonics, envelope, and any changes of such portions. For example, an amplitude variation in an audio signal may represent changes in pressure (such as pressure measured by a microphone) corresponding to speech sounds produced by the wearer. In this example, the waveform of the audio signal may start at a relatively low amplitude at the beginning of the wearer's speech. As the wearer continues with the sentence, the amplitude of the waveform may gradually increase to represent speech, and then decrease again toward the end of the sentence. Such an amplitude variation represent a portion of the audio signal in this example that is associated with the words spoken by the wearer. Correlating, based on the speech timing, the reflection signals with the received audio signals to determine portions of the audio signals associated with the words spoken by the wearer may involve aligning, coordinating, regulating, adjusting, or synchronizing the received signals with the reflection signals using the speech timing. Examples of such correlating include cross-correlation, peak alignment, time scaling and resampling, event detection and matching, phase alignment, dynamic time warping, and machine learning-based alignment. For example, event detection may involve detecting prominent amplitude changes or energy bursts in the received audio signals, and matching those events with the reflection signals during a duration of speech based on similarities such as amplitude, frequency content, or temporal structure. Such event-matching may even be combined with machine learning. For example, training data indicative of matched events between an audio signal and a reflection signal may be used to train a machine learning engine configured to perform the correlating.

Some disclosed embodiments involve outputting the determined portions of the audio signals associated with the words spoken by the wearer, while omitting output of other portions of the audio signals not containing the words spoken by the wearer. Outputting may include sending, transmitting, producing, and/or providing. Outputting the determined portions of the audio signals associated with the words spoken by the wearer may involve sending, transmitting, producing, and/or providing any audible, visual, or tactile indication or notification of or related to those determined portions. Accordingly, outputting may involve segment selection of the portions, extracting or copying the corresponding data from the audio signals, format conversion, encoding, compression, playback or processing, associating any relevant metadata such as timestamps, labels, or annotations, and indexing for searchability and later retrieval. Examples of outputting include playback through audio devices such as speakers or earphones, transmission through a telephone line, graphical representation as a waveform on a computer screen or display device, graphical representation on a visual meter or bar graph with an indication of the portion's sound level or volume, converting the portions into corresponding vibrations through devices such as tactile transducers or vibration motors, and haptic feedback. For example, in FIG. 67, the processor 6728 may be configured to output the determined portions of the audio signals 6726 associated with the words spoken 6718 by the wearer 6700 through a speaker of an earphone 6704 incorporated into head mountable system 6702. Omitting output of other portions of the audio signals not containing the words spoken by the wearer may involve preventing, replacing, canceling, reversing, or otherwise prohibiting any audible, visual, or tactile indication or notification of or related to those other portions, including similar steps used for outputting the signal such as segment selection and indexing. Examples of omitting include muting, softening, crossfading, and substituting a sound, graphical representation, or haptic feedback, or providing an audible, visual, or tactile indication or notification that the other portions do not contain the words spoken by the wearer instead of outputting the other portions. For example, in FIG. 67, the audio signals 6726 produced by the microphone 6708 may include sounds not containing words spoken by the user, such as ambient sounds 6722, and the processor 6728 may be configured to mute a playback of the audio signals 6726 containing ambient sounds 6722 in the speaker of earphone 6704. Performing the outputting while performing the omitting may involve performing the outputting and omitting at the same, corresponding, overlapping, or otherwise related times. Examples of performing the outputting while performing the omitting include playing the sound of the words spoken by the wearer and muting other sounds at the same time, playing the sound of the words spoken by the wearer and playing the other sounds at another time, displaying a waveform of the audio signals associated with the words spoken by the wearer and not displaying a waveform of the audio signals associated with ambient sounds, and creating a vibration for a duration of the audio signals associated with the words spoken by the wearer and stopping the vibration for a duration of the audio signals associated with ambient sounds. For example, processor 6728 may be configured to play the sounds of the wearer 6700 speaking 6718 and simultaneously mute ambient sounds 6722 through earphone 6704.

Some disclosed embodiments involve recording the determined portions of the audio signals. Recording the determined portions of the audio signals may involve copying, documenting, marking, registering, cataloging, or otherwise saving the determined portions for later reproduction. Examples of recording the determined portions of the audio signals involve making a copy of the determined portions in their original format in a data structure, converting the determined portions from their original format to another format for storage, and creating a digital representation of a waveform of the determined portions for viewing. For example, in FIG. 67, processor 6728 may be configured to record the determined portions of the audio signals associated with the words 6718 spoken by the wearer 6700 by storing a digital representation of the portions in a data structure.

Some disclosed embodiments involve determining that the other portions of the audio signals are not associated with the words spoken by the wearer. Determining that the other portions of the audio signals are not associated with the words spoken by the wearer may involve detecting, ascertaining, resolving, or otherwise establishing certain portions of the audio signals that are not caused by, arising from, or otherwise related to the words spoken by the wearer. For example, facial skin micromovements may be correlated to spoken words, as described elsewhere herein. Then, audio analogs corresponding to identified spoken words may be isolated in the audio signals. Any extraneous sounds (e.g, sounds that do not match the spoken words determined based on the light reflections) may be determined to be "not associated with words spoken by the wearer." By analyzing the light reflections and subtracting out all words (or other noise) unrelated to the speech associated with the light reflections, other portions of the audio signals not associated with the words spoken by the wearer can be determined.

Other examples of determining that the other portions of the audio signals are not associated with the words spoken by the wearer include detecting ambient noise, speech of at least one person other than the wearer, and sounds other than speech created by the wearer. For example, the processor 6728 may determine specific characteristics or properties that distinguish non-speech sounds from speech sounds in the audio signals, include frequency ranges, spectral patterns, or temporal features associated with non-speech sounds, such as by using a training data set in a machine learning algorithm. In this example, processor 6728 may use the determined characteristics or properties to detect the portions of the audio signal associated with non-speech sounds, such as by using a filter that allows only those non-speech portions to pass through when the audio signals are input into the filter.

Figure 68:
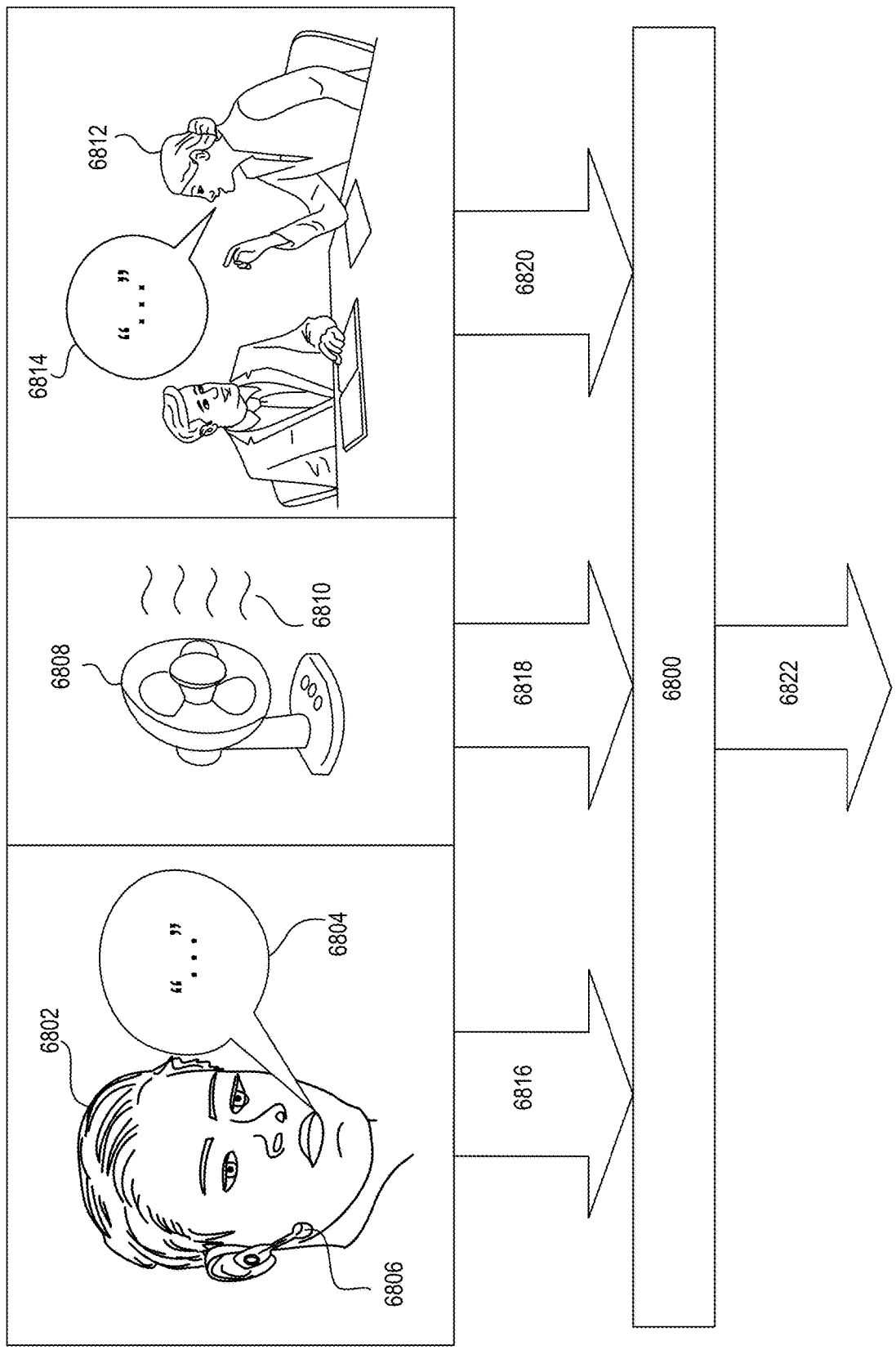
FIG. 68 illustrates examples of audio signal processing for noise suppression, consistent with some embodiments of the present disclosure.

Consistent with some disclosed embodiments, the other portions of the audio signals include ambient noise. Ambient noise may include any auditory elements present in a given environment or space, such as background sounds or environmental sounds. Examples of ambient sounds include nature sounds, background chatter, noise from machines, traffic noise, whispered conversations, music, and non-speech sounds made by at least one person other than the wearer. For example, in FIG. 67, in FIG. 67, the audio signals captured by microphone 6708 include sounds 6718 of words spoken by wearer 6700 together with ambient sounds 6722, such as background chatter and other noises while the wearer is speaking during a phone conversation. As another example, FIG. 68 shows examples of various audio signal portions that may be processed by processor 6800. In this example, the processor 6800 is configured to receive audio signal portions 6816 from a wearable system 6806 associated with words 6804 spoken by user 6802. Because these audio signal portions 6816 are associated with words 6804 spoken by user 6802, the processor is configured to output these portions 6822. In this example, processor 6800 also receives audio signal portions 6818 associated with ambient noise 6810, such as the sound of a fan 6808 spinning in the same room as user 6802. Because these audio signal portions 6818 are associated with ambient noise 6810 and not words 6804 spoken by user 6802, the processor may be configured to omit these portions in its output 6822. As another example, the other portions of the audio signals may include non-speech sounds, such as sneezing, coughing, or laughing, made by at least one person other than the wearer.

Some disclosed embodiments involve determining that the other portions of the audio signals include speech of at least one person other than the wearer. Speech of at least one person other than the wearer may include any verbal communication by an individual other than the wearer used to express that individual's thoughts, ideas, emotions, and other information through the production of spoken sounds. Such speech may include the at least one person's vocal sounds, phonology, prosody, syntax and grammar, semantics, and pragmatics associated with speaking. Examples of such speech include conversational speech, public speaking, phone conversations, broadcasts, news reports, lectures, and presentations by individuals that are not the wearer. The speech of a person other than a wearer may be determined through speech recognition models applied to the audio signals. For example, in FIG. 68, processor 6800 also receives audio signal portions 6820 associated with speech 6814 of at least one person 6812 other than the wearer 6802, such as during a background conversation. Because these audio signal portions 6820 are associated with speech 6814 of at least one person 6812 other than the wearer 6802 and not words 6804 spoken by user 6802, the processor may be configured to omit these portions in its output 6822. Determining that the other portions of the audio signals include speech of at least one person other than the wearer may involve detecting, ascertaining, resolving, or otherwise establishing certain portions of the audio signals that are caused by, arising from, or otherwise related to words spoken by the at least one person other than the wearer. Examples of determining that the other portions of the audio signals include speech of at least one person other than the wearer include energy-based detection, spectral analysis, pattern matching, machine-learning based detection, Hidden Markov Models, and feature extraction and thresholding. For example, the processor may calculate the energy or power of the audio signals over short-time frames using techniques like Short-Time Energy (STE) or Root Mean Square (RMS) analysis, and use sudden increases in energy beyond a certain threshold to indicate a presence of speech of at least one person other than the wearer. As another example, the processor may compare the audio signals with pre-defined patterns or templates of speech by other persons. Such comparison may be implemented using techniques like template matching, cross-correlation, or dynamic time warping. By finding matches or similarities between the signal and known speech patterns of other persons, the processor may determine that the other portions of the audio signals include speech of at least one person other than the wearer.

Some disclosed embodiments involve recording the speech of the at least one person. Recording the speech of the at least one person may involve any manner of creating a record of sounds made by the at least one person which are associated with the at least one person's expression of or the ability to express thoughts and feelings. Examples of recording the speech of the at least one person may involve using the at least one microphone to capture the sound of the at least one person speaking, or using another microphone or other audio capture device to capture that sound. For example, in FIG. 68, the processor 6800 is configured to record the speech 6814 of at least one person 6812 in the form of audio signals 6820.

Some disclosed embodiments involve receiving input indicative of a wearer's desire for outputting the speech of the at least one person, and output portions of the audio signals associated with the speech of the at least one person. Received input may include any information or data provided to the at least one processor to initiate or start a process or operation. Examples of input include sensor inputs such as provided by voice, touch (on a touch screen), facial light reflections indicating a desire for output, or gesture. The input may be received via a microphone, camera, keyboard, trackball, mouse, or a touchpad. The input may be as the result of a rule (upon detection of X, begin recording; when a condition X occurs, begin recording. when a notification X is received, record; when a change in parameter X occurs, begin recording). For example, in FIG. 67, the processor 6728 may receive input in the form of wearer 6700 speaking into the microphone 6708. A wearer's desire for outputting the speech of the at least one person may include any purpose, motivation, objective, or other intent of the wearer to output the speech. Examples of a wearer's desire for outputting the speech of the at least one person may include an intent to listen to the speech of the at least one person through a speaker or microphone, an intent to display visual information associated with the speech of the at least person through a display screen of a device such as a computer, phone, or watch, an intent to generate tactile feedback from a device such as a smartphone or gaming controller, an intent to transmit a communication signal, an intent to display a notification, an intent to provide warning signals, or an intent to control external devices based on the speech of the at least one person. For example, in FIG. 68, user 6802 may desire to hear the speech 6814 of at least one person 6812. Outputting portions of the audio signals associated with the speech of the at least one person may involve producing any audible, visual, or tactile indication or notification of or related to those determined portions. Examples of outputting portions of the audio signals associated with the speech of the at least one person include playback through audio devices such as speakers or earphones, transmission through a telephone line, graphical representation as a waveform on a computer screen or display device, graphical representation on a visual meter or bar graph with an indication of the portion's sound level or volume, converting the portions into corresponding vibrations through devices such as tactile transducers or vibration motors, and haptic feedback. For example, in FIG. 67, the processor 6728 may be configured to output the portions 6820 of the audio signals associated with the speech 6814 of the at least one person 6812 through a speaker of an earphone 6704 incorporated into head mountable system 6702 worn by wearer 6700.

Some disclosed embodiments involve identifying at least one person, determine a relationship of the at least one person to the wearer, and automatically outputting portions of the audio signals associated with the speech of the at least one person based on the determined relationship. Identifying the at least one person may involve any determination of a person's distinct characteristics, qualities, beliefs, values, and other attributes. Identification may occur, for example, through speech recognition or facial recognition. For example, the person's 6812 identity may include their name. Examples of identifying the at least one person include data input, data analysis, pattern recognition, natural language processing, and network analysis. For example, the at least one processor may be configured to receive an input of a name of the at least one person, such as by wearer speaking into microphone. As another example, at least one processor may be configured to receive a sensor input, such as from an image sensor, and process that image data, such as by referencing a data structure containing known identities correlated with images, to identify the at least one person. As another example, the at least one processor may be configured to receive audio signals from the at least one microphone containing the words spoken by the at least one person and reference those audio signals with a database mapping audio signals with identities of various people to identify the at least one person. As another example, the at least one processor may be configured to process various data sources, such as online profiles, social media posts, or public records, to extract information about the at least one person's demographics, interests, affiliations, and activities, to build a profile and identify certain aspects of their identity. As another example, the at least one processor may be configured to train machine learning algorithms on labeled data to recognize patterns that are indicative of specific attributes or identities of the at least one person. As another example, the at least one processor may be configured to use natural language processing to analyze textual data, such as social media posts, emails, or documents, to examine any language used, sentiment, and content to infer aspects of the at least one person's identity, such as beliefs, interests, or cultural background. As another example, the at least one processor may be configured to examine the at least one person's social relationships, online connections, or professional affiliations to determine their social circles, influence, or group memberships. Determining a relationship of the at least one person to the wearer may involve detecting or characterizing a connection, association, or bond between the at least one person and the wearer. The relationship may be determined using the identity of the at least one person. Examples of relationships include an emotional bond, communicative relationship, shared interests and activities, trust, and familial connection. For example, in FIG. 68, person 6812 may be a contact or a favorite contact in a mobile communication device (e.g., phone) of the user 6802. In this example, the at least one processor 6800 may be configured to compare the person's 6812 identity with a contact list in the user's 6802 phone to determine whether the person 6812 is a contact or favorite contact of the user 6802. As another example, in FIG. 68, user 6802 may be related to person 6812 as a family member. Examples of determining the relationship include social network analysis, machine learning, natural language processing, data mining, sentiment analysis, and graph theory. For example, the at least one processor 6800 may be configured to analyze data such as friendship connections, communication patterns, or shared interests from social network analysis using algorithms to determine the strength and nature of a relationship between the at least one person 6812 and the wearer 6802. As another example, the at least one processor 6800 may be configured to implement machine learning to analyze large datasets and identify patterns that indicate a relationship between two people. In this example, by training algorithms on labeled data representing known relationships, the processor may be configured to learn to predict and classify the relationship between the at least one person 6812 and the wearer 6802 based on various features or attributes of the individuals, such as an identity. As another example, the at least one processor 6800 may be configured to use data mining to extract relevant information from various sources such as online profiles, shared activities, or demographic data to identify commonalities or connections that indicate a relationship between the at least one person 6812 and the wearer 6802. As another example, the at least one processor 6800 may be configured to determine the emotional tone or sentiment expressed in forms of communication, such as spoken input by the wearer 6802, and infer the nature and quality of a relationship between the at least one person 6812 and the wearer 6802 based on a positive, negative, or neutral sentiment. As another example, the at least one processor 6800 may apply graph algorithms and metrics, such as nodes representing individuals and edges representing connections or interactions, to determine a strength or structure of a relationship between the at least one person 6812 and the wearer 6802. Automatically outputting portions of the audio signals associated with the speech of the at least one person based on the determined relationship may involve outputting those portions without any intervention. Examples of automatic output include displaying graphical representations of the portions on a screen of a computer without typing any commands, playing the portions on a speaker without requesting that playback, and generating a vibration on a phone without pressing any buttons. For example, the at least one processor 6800 may be configured to play the at least one person's 6812 speech 6814 through wearable system 6806 to wearer 6802 without the wearer 6802 speaking a request to play that speech 6814. Outputting based on the determined relationship may involve determining whether the determined relationship meets a predetermined criteria as a condition for automatically outputting. For example, if the person is determined to be a favorite contact, then portions of the audio signals associated with the speech of the person may be automatically output, while if the person is determined to only be a contact, then portions of the audio signals associated with the speech of the person may not be automatically output.

Some disclosed embodiments involve analyzing the audio signals and the reflection signals to identify non-verbal interjection of the wearer, and omit the non-verbal interjection from the output. Analyzing the audio signals and the reflection signals may involve applying various algorithms, mathematical operations, or signal processing techniques on the signals to gain insights, extract features, or make inferences about the signals. Examples of analyzing the audio signals and the reflection signals include filtering, frequency analysis, time-domain analysis, modulation, demodulation, using machine learning algorithms to train models based on labeled data, enabling the at least one processor to recognize patterns, classify signals, or make predictions based on the learned information, and using pattern recognition algorithms to detect specific patterns or structures in the audio signals and the reflection signals. For example, in FIG. 67, the at least one processor 6728 may be configured to compare the audio signals 6726 to the reflection signals 6724 to identify commonalities or differences between the signals and determine events such as non-verbal interjections. Non-verbal interjection may include any expressions or sounds that convey meanings or emotions without using specific words or language. Examples of non-verbal interjection include sighs, grunts, laughter, hiccups, whimpers, gasps, coughs, giggles, groans, sobs, or any other non-verbal cues. For example, a user may hiccup in the middle of speaking a sentence, which does not convey any verbal information, but may cause a sound. Performing the analysis to identify a non-verbal interjection of the wearer may involve determining a timing, strength, nature, or other characteristic of the non-verbal interjection using the analysis. Examples of identifying a non-verbal interjection based on the analysis include synchronization, feature extraction, event detection, correlation, and alignment. For example, the at least one processor may be configured to identify laughter during speech by the wearer. In this example, the reflection signals may be processed to extract relevant features such as facial expressions and the audio signals may be processed to extract relevant features such as energy, pitch, and spectral content. The at least one processor in this example may be configured to identify sudden peaks in energy or changes in pitch in the audio signals and specific facial expressions like smiling in the reflection signals as potential laughter events. The identified laughter events in the audio signals and reflection signals may be correlated and aligned based on their timing in the respective signals to ensure that the corresponding instances in both signals are matched correctly based on their time of occurrence. As one example, the intensity of laughter may be inferred by analyzing an amplitude of the audio signal and a magnitude of the reflection signals. Based on such characteristics of the correlated laughter events, the at least one processor may be configured to classify the instances into different types of laughter such as genuine laughter, polite laughter, or nervous laughter. As another example, machine learning algorithms or predefined rules may be employed to perform such classification based on the extracted audio signal and reflection signal features. Omitting the non-verbal interjection from the output may involve preventing, replacing, canceling, reversing, or otherwise prohibiting any audible, visual, or tactile indication or notification of or related to the non-verbal interjection. Examples of omitting include muting, softening, crossfading, and substituting a sound, graphical representation, or haptic feedback, or providing an audible, visual, or tactile indication or notification that the corresponding portion contains a non-verbal interjection. For example, in FIG. 67, the audio signals 6726 produced by the microphone 6708 may include a yawn, and the processor 6728 may be configured to mute a playback of the audio signals 6726 containing ambient the yawn in the speaker of earphone 6704.

Consistent with some disclosed embodiments, outputting the determined portions of the audio signals includes synthesizing vocalization of the words spoken by the wearer. Vocalization may include any generation of sounds through the vocal cords, throat, mouth, and other vocal organs. Examples of vocalization include speech, singing, shouting, and whispering. For example, a vocalization may include the sound of the question "Who is she?" Synthesizing vocalization of the words spoken by the wearer may involve any artificial generation or creation of sounds, such as human-like vocal sounds, using a synthesizer or computer-based techniques. Synthesizing vocalization may involve producing speech-like or singing-like sounds that mimic the characteristics and qualities of human voice or other vocal expressions. Examples of synthesizing vocalization include song reproduction, voice emulation, and multilingual speech synthesis. For example, the at least one processor may be configured to synthesize singing using voice samples and vocal modeling techniques. As another example, the at least one processor may be configured to apply deepfake or voice cloning technology or any speech-to-text algorithm to generate speech using the voice of the wearer. As another example, the at least one processor may be configured to output an audio pronunciation of words spoken by the wearer in various languages.

Consistent with some disclosed embodiments, the synthesized vocalization emulates a voice of the wearer. Emulating a voice of the wearer may involve creating an artificial representation of the wearer's vocal characteristic to reproduce their speech patterns, intonation, or other distinctive vocal qualities. Examples of emulating a voice of the wearer may involve reproducing a tone of the wearer, mimicking sarcasm in the speech of the wearer, and copying an accent of the wearer. As one example of emulating a voice of the wearer, the at least one processor may be configured to obtain or recover from a database audio recordings of the wearer. The at least one processor may be configured to analyze the collected audio data to extract various vocal characteristics, such as pitch, timbre, prosody, and phonetic patterns to build a statistical or machine learning model that captures these characteristics, such as Gaussian mixture models, Hidden Markov Models, or deep learning models such as recurrent neural networks or convolutional neural networks. In this example, the at least one processor may be configured to use the words spoken by the wearer as input into the model to generate synthesized speech that emulates the wearer's voice.

Consistent with some disclosed embodiments, the synthesized vocalization emulates a voice of a specific individual other than the wearer. Emulating a voice of a specific individual other than the wearer may involve creating an artificial representation of the vocal characteristic of another individual (either real or imaginary) to reproduce their speech patterns, intonation, or other distinctive vocal qualities, in a manner similar to the earlier description of emulating a voice of the wearer. It may be desirable to emulate in another voice to maintain privacy of the wearer's identity, for improved clarity if the wearer's voice is not easily comprehensible, or for entertainment value. For example, the at least one processor may be configured to refer to a database of vocal characteristics of the specific individual to emulate their voice. A specific individual may be any person, gender, accent, identity, or other characteristic of individuals. The voice of the specific individual may be based on a preselected option set on the head mountable device or the voice of the individual may be modified by user or sensor input. For example, the wearer of the head mountable system may select an option indicating that the synthesized vocalization should be a woman's voice, and the system may output a woman's voice as the synthesized vocalization. As another example, the wearer of the head mountable system may select an option indicating that the synthesized vocalization should be the voice of a celebrity, and the system may output that celebrity's voice as the synthesized vocalization.

Consistent with some disclosed embodiments, the synthesized vocalization includes a translated version of the words spoken by the wearer. A translated version of the words spoken by the wearer may include a conversion of the meaning of the words from one language, such as the spoken language, to another language while preserving the intended message for accurate conveyance. Accordingly, translating the words spoken by the wearer may involve rendering a content, context, tone, and nuances of the original words in a manner that is linguistically and culturally appropriate in the other language. Examples of creating a translated version of the words spoken by the wearer include rule-based machine translation, statistical machine translation, neural machine translation, and example-based machine translation. For example, the at least one processor may be configured to refer to linguistic rules and dictionaries in data structures to perform translation. As another example, the at least one processor may be configured to estimate a likelihood of a translated word by analyzing patterns and statistical associations between words, such as by using n-gram models, phrase-based models, and statistical alignment models. As another example, the at least one processor may be configured to apply encoder-decoder architectures, such as Recurrent Neural Networks or Transformer models, to map spoken words to translated words using training data. As another example, the at least one processor may be configured to refer to a database of translation examples and use those examples to generate translations by comparing the spoken words with the stored examples to find the most similar stored examples. For example, the wearer may speak words in French, and the at least one processor may refer to a database mapping French words and English words to synthesize an English vocalization of the wearer's French spoken words.

Some disclosed embodiments involve analyzing the reflection signals to identify an intent to speak and activate at least one microphone in response to the identified intent. An intent to speak may include any desire or purpose to communicate verbally. Prior to the onset of speech, facial skin micromovements indicate an intent to speak. This intent may be determined by analyzing reflection signals. When the reflections signals indicate that speech is likely to occur, the system can activate the microphone. In this way, for example, the microphone may be activated only when speech is imminent, avoiding the consequences of distracting background noise. For example, a wearer 6700 may have an intent to ask a question while using the head mountable system 6702. Analyzing the reflection signals to identify an intent to speak may involve any observation, interpretation, or examination of the reflection signals to infer the wearer's desire to engage in verbal communication. Examples of analyzing the reflection signals to identify an intent to speak include gesture recognition, emotion detection, pattern recognition, and database matching. As one example, as explained and exemplified elsewhere in this disclosure, the at least one processor may extract facial skin movements from the reflection signals, apply machine learning or pattern recognition algorithms to analyze the extracted facial movements and classify them based on patterns associated with an intent to speak. The at least one processor may perform the classification using a trained model that uses labeled data to learn a relationship between facial movements and the intent to speak. In this example, the classification results may be used to make a decision regarding the presence or likelihood of an intent to speak, such as by using predefined thresholds, confidence scores, or statistical models. At least one microphone may be understood as described and exemplified earlier. For example, the at least one microphone may be a microphone 6708 disposed on the head mountable system 6702. Activating at least one microphone in response to the identified intent may involve turning on, initiating, or otherwise enabling a function of at least one microphone. Activating the microphone in response to the intent to speak may be beneficial for power conservation. Examples of the activating include turning on a microphone when an intent to speak is identified, turning on a microphone when an intent to speak is identified for a predefined period of time, and keeping a microphone for a period of time on based on a determination of an intent to speak for that period of time. As an example, the at least one processor 6728 may, in response to a determination that the wearer 6700 intends to speak, turn on microphone 6708 for the microphone to begin recording sounds, including the wearer's speech 6718 and ambient sounds 6722.

Some disclosed embodiments involve analyzing the reflection signals to identify a pause in the words spoken by the wearer and deactivate at least one microphone during the identified pause. A pause in the words spoken by the wearer may include any interruption or break in a flow of spoken words. Examples of a pause in the words spoken by the wearer include grammatical, reflective, dramatic, hesitation, breath, turn-taking, emotional, and punctuation pauses. For example, the wearer may stop speaking words in a conversation to signal a completion of his or her turn in speaking and allow the other person to respond. Analyzing the reflection signals to identify a pause in the words spoken by the wearer may involve any observation, interpretation, or examination of the reflection signals to infer an interruption or break in a flow of spoken words. When the pause is detected, the microphone may be deactivated, again, avoiding the adverse consequences of background noise. Examples of analyzing the reflection signals to identify a pause in the words spoken by the wearer include matching, classification, and temporal or spectral processing. As one example, the at least one processor may extract facial movements from the reflection signals and monitor a reduction or absence of certain facial movements to detect a pause in the words spoken by the user. As another example, the at least one processor may monitor the facial muscles involved in the words spoken by the wearer to determine pauses in the words spoken by detecting a decrease or absence of muscle activity in those muscles. At least one microphone may be understood as described and exemplified earlier. For example, the at least one microphone may be a microphone 6708 disposed on the head mountable system 6702. Deactivating at least one microphone during the identified pause may involve stopping or pausing a function of at least one microphone for a partial or entire duration of the identified pause. Examples of deactivating at least one microphone include disabling, turning off, shutting down, or powering down the at least one microphone during any portion of the identified pause. As an example, the at least one processor 6728 may, in response to a determination that there is a pause in the wearer's 6700 speech, turn off microphone 6708 such that the microphone 6708 does not record any sounds. In some examples, the deactivation may persist for the entire duration of the pause, or some limited duration, as indicated by user input or predefined settings. For example, the at least one processor 6728 may, in response to a determination that there is, for example, a five-second pause in the wearer's 6700 speech, disable the microphone 6708 for a predefined three seconds such that the microphone 6708 does not record any sounds for only three seconds regardless of the duration of the pause. In some examples, a user of the head mountable system may preset the duration. For example, the preset duration may be one second, five seconds, or one minute, as selectable by the user.

Consistent with some disclosed embodiments, at least one microphone is part of a communications device configured to be wirelessly paired with the head mountable system. A communications device may be understood as described and exemplified earlier. For example, a communications device may be a mobile communication device, such as, for example, mobile communication device 120, as shown in FIG. 1. Wireless pairing may involve establishing or maintaining a connection between two devices to enable communication or data exchange without the need for physical cables or wired connections. Examples of wireless pairing include Wi-Fi, Bluetooth, Near Field Communication, cellular networks, infrared communication, and Zigbee protocol. For example, at least one microphone may be part of a mobile communication device 120 paired via Bluetooth with head mountable system 6702.

Consistent with some disclosed embodiments, at least one microphone is integrated with the wearable housing and the wearable housing is configured such that when worn, the at least one coherent light source assumes an aiming direction for illuminating at least a portion of a cheek of the wearer. At least one microphone being integrated with the wearable housing may involve adhering, mounting, attaching, or otherwise connecting the at least one microphone to at least a portion of the wearable housing. Examples of such integration include connecting at least one microphone to the wearable housing using adhesive, clips, snaps, flexible materials, and threaded mounting. For example, a double-sided adhesive tape may be used to attach microphone 6708 to wearable housing 6730. As another example, microphone 6708 may be connected to wearable housing 6730 using wiring within the wearable housing 6730. An aiming direction for illuminating at least a portion of a cheek of the wearer may include any orientation or course along with the illumination travels to project its light on any region of a cheek of the wearer. Examples of an aiming direction include an angle, line, path, bias, inclination, and trajectory. For example, an aiming direction may be an angle of an extension 6706 of wearable housing 6730 relative to an axis. As another example, an aiming direction may be a tilt of the at least one coherent light source 6710 relative to a plane of cheek region 6732. Configuring the wearable housing such that when worn, the at least one coherent light source assumes an aiming direction for illuminating at least a portion of the cheek of the wearer may involve enabling an automated or manual modification or adjustment of position, orientation, or functionality of the wearable housing such that the at least one coherent light source assumes the aiming direction. Examples of such configuring include moving, twisting, rearranging, sliding, or rotating one or more components of the wearable housing. For example, a wearer 6700 may turn an extension 6706 of wearable housing 6730 about microphone 6708 when wearing wearable housing 6730 on his or her ear to project light 6714 towards cheek region 6732.

Consistent with some disclosed embodiments, a first portion of the wearable housing is configured to be placed in an ear canal of the wearer and second portion is configured to be placed outside the ear canal, and the at least one microphone is included in the second portion. A first portion of the wearable housing configured to be placed in an ear canal of the wearer may include any region, area, or component of the wearable housing that may be inserted or secured inside the ear canal, as opposed to another portion configured to be outside the ear canal. Examples of structures configured for placement in an ear canal include earphones, hearing aids, and earplugs. For example, in FIG. 67, a first portion (e.g., earphone 6704) of the wearable housing 6730 is configured to be placed in an ear canal of wearer 6700. A second portion configured to be placed outside the ear canal may include any region, area, or component of the wearable housing that may be inserted or secured outside the ear canal, such as at any location on a surface of the ear or the wearer's head. Examples of structures configured for placement outside the ear canal include headphones, headsets, headbands, caps, eyeglasses, and visors. For example, in FIG. 67, a second portion (e.g., extension 6706) of the wearable housing 6730 is configured to be placed outside the ear canal of wearer 6700. The at least one microphone being included in the second portion may involve adhering, mounting, or otherwise attaching the at least one microphone to the second portion. Examples of the at least one microphone being included in the second portion include connecting the at least one microphone to the second portion using adhesive, clips, snaps, flexible materials, and threaded mounting. For example, a double-sided adhesive tape may be used to attach microphone 6708 to extension 6706.

Figure 69:
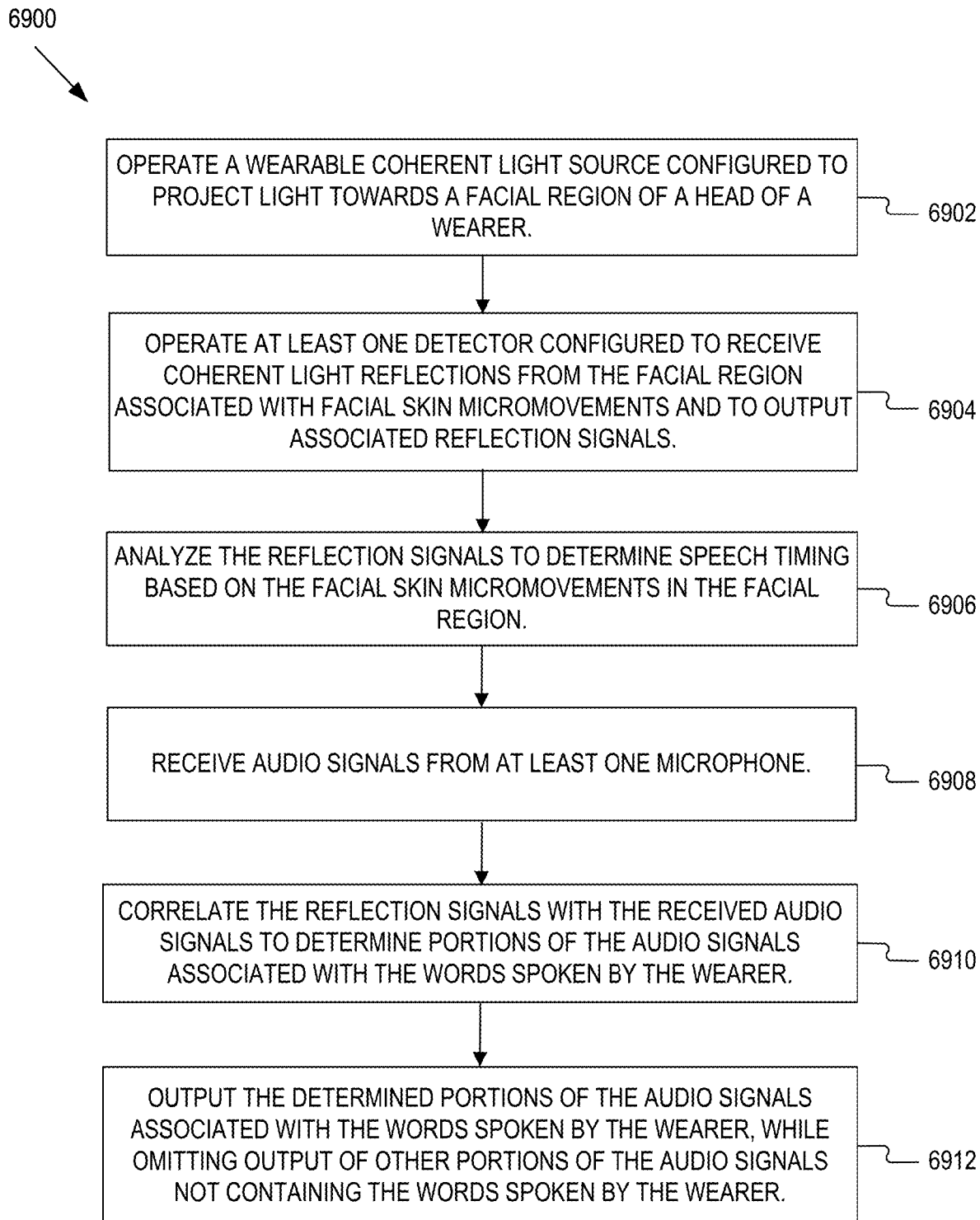
FIG. 69 is a flowchart of an example process for noise suppression, consistent with some embodiments of the present disclosure.

Some disclosed embodiments involve a method for noise suppression using facial skin micromovements. FIG. 69 illustrates a flowchart of an exemplary process 6900 for noise suppression using facial skin micromovements, consistent with embodiments of the present disclosure. Consistent with some disclosed embodiments, process 6900 may be performed by at least one processor (e.g., processing unit 112 in FIG. 1, processing device 400 in FIG. 4) to perform operations or functions described herein. Consistent with some disclosed embodiments, some aspects of process 6900 may be implemented as software (e.g., program codes or instructions) that are stored in a memory (e.g., data structure 124 in FIG. 1) or a non-transitory computer readable medium. Consistent with some disclosed embodiments, some aspects of process 6900 may be implemented as hardware (e.g., a specific-purpose circuit). Consistent with some disclosed embodiments, process 6900 may be implemented as a combination of software and hardware.

Referring to FIG. 69, process 6900 includes a step 6902 of operating a wearable coherent light source configured to project light towards a facial region of a head of a wearer. Process 6900 includes a step 6904 of operating at least one detector configured to receive coherent light reflections from the facial region associated with facial skin micromovements and to output associated reflection signals. Process 6900 includes a step 6906 of analyzing the reflection signals to determine speech timing based on the facial skin micromovements in the facial region. Process 6900 includes a step 6908 of receiving audio signals from at least one microphone, the audio signals containing sounds of words spoken by the wearer together with ambient sounds. Process 6900 includes a step 6910 of correlating, based on the speech timing, the reflection signals with the received audio signals to determine portions of the audio signals associated with the words spoken by the wearer. Process 6900 includes a step 6912 of outputting the determined portions of the audio signals associated with the words spoken by the wearer, while omitting output of other portions of the audio signals not containing the words spoken by the wearer. It should be noted that the order of the steps illustrated in FIG. 69 is only exemplary and many variations are possible. For example, the steps may be performed in a different order, some of the illustrated steps may be omitted, combined, and/or other steps added. Furthermore, in some embodiments, process 6900 may be incorporated in another process or may be part of a larger process.

Some disclosed embodiments involve a non-transitory computer readable medium containing instructions that when executed by at least one processor cause the at least one processor to perform operations for noise suppression using facial skin micromovements. A non-transitory computer-readable medium containing instructions may be understood as described and exemplified elsewhere in this disclosure. At least one processor may include one or more processing devices as previously described and exemplified (e.g., processing unit 112 in FIG. 1 and processing device 400 in FIG. 4). The operations may include operating a wearable coherent light source configured to project light towards a facial region of a head of a wearer; operating at least one detector configured to receive coherent light reflections from the facial region associated with facial skin micromovements and to output associated reflection signals; analyzing the reflection signals to determine speech timing based on the facial skin micromovements in the facial region; receiving audio signals from at least one microphone, the audio signals containing sounds of words spoken by the wearer together with ambient sounds; correlating, based on the speech timing, the reflection signals with the received audio signals to determine portions of the audio signals associated with the words spoken by the wearer; and outputting the determined portions of the audio signals associated with the words spoken by the wearer, while omitting output of other portions of the audio signals not containing the words spoken by the wearer.

The embodiments discussed above for noise suppression using facial skin micromovements may be implemented through non-transitory computer-readable medium such as software (e.g., as operations executed through code), as methods (e.g., process 6900 shown in FIG. 69), or as a system (e.g., speech detection system 100 shown in FIGS. 1-3). When the embodiments are implemented as a system, the operations may be executed by at least one processor (e.g., processing device 400 or processing device 460, shown in FIG. 4).

Some disclosed embodiments involve detecting silent questions and providing private answers. For example, a user may silently inquire as to the name of someone with whom the user is speaking, and may receive a private response to the query, e.g., via earbuds. As used herein, a silent question refers to any subvocalized inquiry, request, query, demand, or other similar statements made by a speaker (e.g., in a nonvocalized manner such as when air flow from the lungs of the speaker is absent or minimal, while facial muscles move in a manner consistent with speech. For example, a silent question may be asked when a speaker prevocalizes a statement, such as "how are you?" without creating a sound through their mouth. Another example of a silent question is a gesture that a system for providing answers recognizes as a question. For example, when a user raises an eyebrow, corresponding facial skin movements may be interpreted as the question, "what?" Silent questions may be useful in situations where a speaker does not want others to hear or otherwise know what the speaker is saying. For example, a speaker may not know or remember the name of an individual in a conversation and may want to determine the individual's name without the individual knowing. In such situations, providing a private answer to a private question about the individual's identity may be helpful. Private answers refers to any response not publicly transmitted. For example, private answers may include any confidential, exclusive, secret, quiet, or otherwise concealed response to a question. A private answer may be provided in any manner maintaining its privacy. For example, providing a private answer may involve providing a response in any manner that is exclusive or directed to one particular person or group of people only. As one example, a private answer may be a visual indication of a response that is only available to a person who has access to the response. As another example, a private answer may be an audible indication of a response that is only available to a person who has access to the response. In other examples, a private answer may be any answer that is at least partially private. For example, a private answer may be a muted audible indication that is intended to be heard by only a person who has access to the response, such as a person close to the source of the audio. In this example, the private answer is private because only that person with access is intended to receive the response, although another person standing close to that person may overhear the response.

Figure 70:
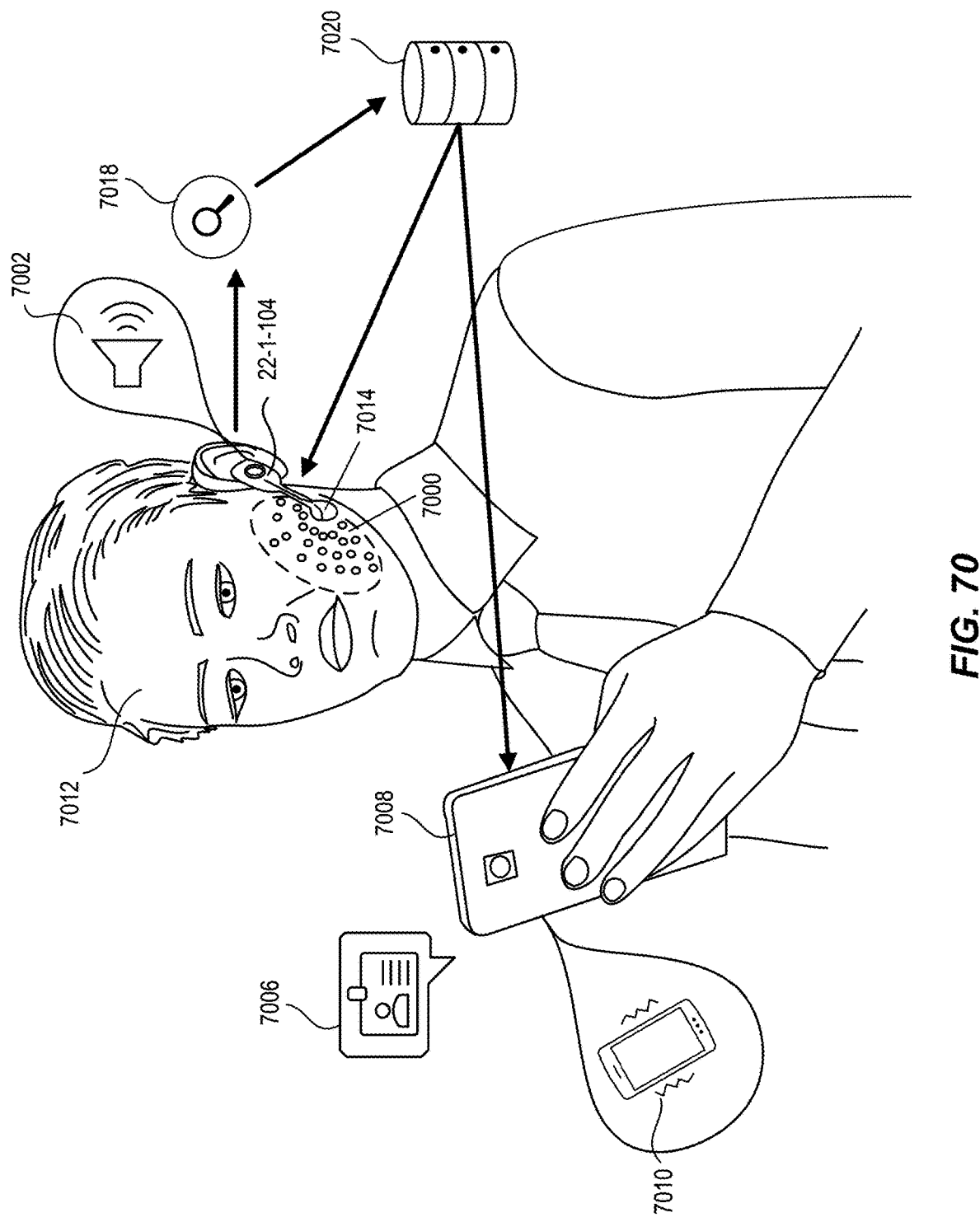
FIG. 70 illustrates an exemplary system for providing private answers to silent questions, consistent with embodiments of the present disclosure.

Some disclosed embodiments involve receiving signals indicative of particular facial micromovements in an absence of perceptible vocalization. Facial skin micromovements may be understood as described and exemplified elsewhere in this disclosure. Facial skin micromovements may be used for providing private answers to silent questions because such movements are readily controllable by a user in a private manner, as opposed to more obvious ways of asking silent questions such as typing a question into a phone or whispering a question into an audio input device, such as a microphone. As shown in FIG. 70, one example of facial skin micromovements includes micromovements of the skin from a cheek region 7000 of a user 7012. Receiving signals indicative of particular facial micromovements may be understood as described and exemplified elsewhere in this disclosure. For example, as explained elsewhere in this disclosure, receiving signals indicative of specific facial skin micromovements may include receiving any sign or indication that conveys information about the specific facial skin micromovements, such as a time-varying voltage, current, or electromagnetic wave that may carry information about the specific facial skin micromovements. For example, as shown in FIG. 70, an optical sensing unit 7014 may be configured to receive reflections of light from micromovements of the skin from a cheek region 7000 and to output associated reflection signals. As an example, the reflection signals may be indicative of light patterns (e.g., secondary speckle patterns) that may arise due to reflection of the coherent light from spots on cheek region 7000 within a field of view of optical sensing unit 7014. These reflection signals may be the received signals indicative of particular facial skin micromovements. An absence of perceptible vocalization may refer to a nonexistence or lack of any sound produced through the action of a user's respiratory system and used in communication. Examples of an absence of perceptible vocalization include situations where a user makes speech vocalizations and nonspeech vocalizations without sound or without sound sufficiently loud to be understood. Speech vocalizations may include consonant and vowel sounds, such as those that make up words and sentences. Nonspeech vocalizations may include other sounds such as cooing, burping, and laughing sounds. As explained elsewhere in this disclosure, the normal process of vocalization of a sound uses multiple groups of muscles and nerves, from the chest and abdomen, through the throat, and up through the mouth and face. To utter a given phoneme, motor neurons activate muscle groups in the face, larynx, and mouth in preparation for propulsion of air flow out of the lungs, and these muscles continue moving during speech to create words and sentences. Vocalization, including perceptible vocalization, occurs when air flows out of the lungs. Without this air flow out of the lungs, no sounds are emitted from the mouth, and there is no perceptible vocalization. Instead, as explained elsewhere in this disclosure, silent speech occurs when the air flow from the lungs is absent and the muscles in the face (e.g., around the mouth) moves in a manner enabling interpretation. It should be noted that even when a small amount of air flows out of the lungs there may be no perceptible vocalization. For example, the sounds emitted by the mouth (if any) as a result of this small air flow may be too faint to be heard or noticed by a person or an audio sensor. One example of receiving signals indicative of particular facial micromovements in an absence of perceptible vocalization is using an optical sensing unit 7014 receive reflections of light from micromovements of the skin from a cheek region 7000 and receive the associated reflection signals when user 7012 mouths a word without making a sound.

Consistent with some disclosed embodiments, the received signals are obtained via a head mountable light detector and derived from skin micromovements of a facial portion other than a mouth. A head mountable light detector may include any light detector (which may be understood as described and exemplified elsewhere in this disclosure) that is configured to be worn on at least a portion of a head of an individual. Examples of a head mountable light detector may include a light detector incorporated into a cap, glasses, goggles, headset, visor, band, or another accessory won on, or supported by, at least a portion of the individual's head. One example of a head mountable light detector may include a light detector incorporated into a wearable housing, as described and exemplified elsewhere in this disclosure. For example, a head mountable light detector may be an optical sensing unit 7014 incorporated into an earbud 7004 worn by user 7012. A facial portion other than a mouth may include any part, region, or area on a face of a user that is not a mouth, such as a cheek, a forehead, a nose, lips, or skin around the mouth. For example, in FIG. 70, the received signals are obtained via an optical sensing unit 7014 and derived from skin micromovements of a facial portion (e.g., cheek region 7000) other than a mouth, which is shown as cheek region 7000.

Consistent with some disclosed embodiments, the head mountable light detector is configured to detect incoherent light reflections from the facial portion. As explained elsewhere herein, incoherent light may be produced by a non-coherent light source such as incandescent bulbs and natural sunlight, which have a broad spectral range and a low degree of monochromaticity. Incoherent light reflections may include any light rays that bounce back upon striking a surface which contain waves whose wavelengths are not in phase with each other and that do not oscillate at the same frequency. Incoherent light reflections may be desirable because sources of incoherent light are less complex and less expensive than sources of coherent light, and the spectral properties of incoherent light reflections can be characterized using sensing devices, such as light detectors, in a continuous manner. Examples of incoherent light reflections include diffuse reflection, Lambertian reflection, and scattering of light caused by light emitted from sources such as incandescent light bulbs, fluorescent lights, LED lights, white noise light sources, and sunlight. For example, the optical sensing unit 7014 may emit incoherent light towards the facial portion (e.g., cheek region 7000) using an LED array and the optical sensing unit 7014 may use a sensor to detect the incoherent light scattering that is reflected from the facial portion (e.g., cheek region 7000).

Consistent with some disclosed embodiments, the operations further include controlling at least one coherent light source in a manner enabling illuminating the facial portion, and wherein the head mountable light detector is configured to detect coherent light reflections from the facial portion. A coherent light source may be understood as described and exemplified elsewhere herein. By way of one non-limiting example with reference to FIG. 70, optical sensing unit 7014 may include a light source and a sensor for illuminating and sensing light reflections from cheek region 7000. Controlling at least one coherent light source in a manner enabling illuminating the facial portion may involve moving, adjusting, or otherwise manipulating the at least one coherent light source to enable the illumination. Examples of controlling at least one coherent light source in a manner enabling illuminating the facial portion refers in one example to activating the light source. In another example, controlling may additionally or alternatively involve changing a property of the at least one coherent light source, such as intensity, propagation direction, frequency, wavelength, or polarization. For example, controlling may involve sensing a distance between the light source and a skin region and emitting a signal to prompt a user to adjust the light source in a manner moving it closer to or further from the skin (e.g., prompting the user to move optical sensing unit 7014 closer to cheek region 7000 to enable illumination of cheek region 7000). As another example, controlling may involve increasing the intensity of the coherent light emitted by optical sensing unit 7014 to enable illumination of cheek region 7000. Detecting coherent light reflections from the facial portion may include measuring any form of reflection and of scattering of light, including secondary speckle patterns, different types of specular reflections, diffuse reflections, speckle interferometry, and any other form of light scattering from the coherent light that is reflected back from the facial portion. Examples of detecting coherent light reflections from the facial portion include using interferometry, holography, laser speckle imaging, coherence length measurement, or other detection techniques. For example, in FIG. 70, the optical sensing unit 7014 may be implemented as a laser speckle sensor configured to detect secondary speckly patterns in coherent light reflected from cheek region 7000.

Consistent with some disclosed embodiments, the facial micromovements correspond with muscle activation of at least one of: a zygomaticus muscle, an orbicularis oris muscle, a risorius muscle, a genioglossus muscle, or a levator labii superioris alaeque nasi muscle. These muscles may be relevant for providing private answers to silent questions because these muscles are typically recruited during vocalization and prevocalization. Additionally, these muscles are desirable for detection of signals indicative of facial micromovements because they are close to the surface of the facial skin and have distinctive locations. In one example, as shown in FIG. 70, the facial micromovements may correspond with muscle activation of muscles used to control a cheek region 7000 of the face, such as a zygomaticus muscle or a risorius muscle.

Some disclosed embodiments involve accessing a data structure correlating facial micromovements with words. A data structure may be understood as described and exemplified elsewhere herein. Correlating facial micromovements with words refers to establishing, identifying, or maintaining one or more of a connection, relationship, link, interaction, mutuality, causation, or other association between facial micromovements and words. Examples of correlating facial micromovements with words may include performing Pearson correlation, scatter plot analysis, cross-tabulation, time series analysis, or regression analysis with facial micromovements and words. For example, correlating facial micromovements with words may involve maintaining a table of rows of facial micromovements associated with columns of words. Accessing the data structure may involve searching, checking, combining, examining, inspecting, probing, scanning, or otherwise using the data structure. Examples of accessing at least one data structure to perform a look up for an answer to the query include using arrays, following references to a desired node in linked lists, retrieving values from stacks, queues, and hash tables, and performing a search algorithm on trees. For example, accessing the data structure may include performing a multiple regression analysis to correlate the words associated with happiness with facial micromovements such as smiling micromovements. Accessing such a data structure may be desirable to provide reusability and abstraction while providing private answers to silent questions. This makes the private answer operations, particularly when implemented using AI, more efficient by reducing the time associated with the storage, retrieval, or processing of correlations between facial micromovements and words. Examples of accessing the data structure include using arrays, following references to a desired node in linked lists, retrieving values from stacks, queues, and hash tables, and performing a search algorithm on trees. For example, the private answer operations may include accessing data structure 124 in FIG. 1 or data structure 422 in FIG. 4, which may be correlate facial micromovements with words. As one example of such a correlation, a micromovement of a given muscle may be associated with a word such as "yes" or "who." In this example, the accessing may include performing a depth-first search in a tree of data structure 124 that compares a facial micromovement (e.g., flexion of the cheek) with a word (e.g., "no").

Some disclosed embodiments involve using the received signals to perform a lookup in the data structure of particular words associated with the particular facial micromovements. A lookup in the data structure may include any action of or a facility for systematic electronic information retrieval, such as a searching function (e.g., linear search, binary search, hash search, and tree search). Examples of performing a lookup in the data structure include performing a key-value lookup, index-based lookup, range lookup, full-text lookup, approximate lookup, external data lookup, and hierarchical lookup. As one example, performing a lookup for information in a data structure may involve using a query-based data retrieval of the information in a web-based data structure implementing HTTP-based remote procedure calls (RPC), such as the Simple Object Access Protocol (SOAP) and Universal Description, Discovery and Integration (UDDI) specification. In another example, the data structure may include an artificial intelligence data set, and the lookup may involve a query of the AI data set. Using the received signals to perform the lookup may include applying, manipulating, managing, or otherwise putting the received signals into action or service in performing the lookup. As one example, using the received signals to perform the lookup may involve using a characteristic of the received signals or determined from the received signals, such as a distance moved by a facial muscle, to search the data structure for information associated with that distance. Particular words associated with the particular facial micromovements may include any words, phrases, or sentences that are connected, linked, correlated, analogous, corresponding, incidental, or otherwise related to specific facial micromovements. Examples of particular words associated with the particular facial micromovements include words made by facial micromovements, words known to be made by facial micromovements, words initiated by facial micromovements, and words ended by facial micromovements. As explained elsewhere herein, facial micromovements may be converted to words in any manner. For example, a memory device (e.g., memory device 402 of FIG. 4) associated with the system may include a data structure that contains correlations of facial micromovements with words and a processor (e.g., processing device 400 of FIG. 4) associated with the system may perform a lookup in the data structure to identify words associated with facial micromovements. In some embodiments, correlations of particular patterns of facial micromovements with words may be stored in the data structure apriori (for example, during training), and when a pattern of facial micromovements is observed, the processor may perform a lookup in the data structure to identify the words associated with the detected pattern. As another example, a given distance moved by a specific facial muscle may be associated with a word such as "who," and the data structure may maintain a correlation of the word "who" with that distance. As shown by example in FIG. 70, the processor may use the signals received by optical sensing unit 7014 to determine a distance moved by a muscle in cheek region 7000, and perform a lookup in the data structure 7018 by searching for a word associated with that distance to find a word, such as "who," associated with the particular facial micromovements causing the muscle to move by that distance.

Some disclosed embodiments involve determining a query from the particular words. A query may refer to a question, inquiry, doubt, poll, interrogation, or any other request or statement seeking a response. For example, a query may be a request for data or information, such as information stored in a data structure, a table, the Internet, an AI agent, or any other source of information. In some examples, a query may be a select query, such as one that retrieves data from a database. For example, a query may be a question such as "who is this?" or "where am I?" In some examples, a query may be an action query, such as one that asks for the performance of an action, such as inserting, updating, deleting or otherwise manipulating data. For example, a query may be a statement such as "what is the sum of these numbers?" Determining a query from the particular words may involve applying, controlling, employing, handling, managing, manipulating, combining, associating, coupling, incorporating, margining, or otherwise using the particular words to form a query. Examples of determining a query from the particular words include combining words together using string manipulation, string concatenation, or template literals, or natural language processing sentence formation, such as by analyzing grammatical structure, identifying parts of speech, and ensuring proper word order. Various tools, including Python, JavaScript, and natural language processing libraries like NLTK (Natural Language Toolkit) in Python or spaCy may be used to determine a query from the particular words. For example, determining a query from the particular words may involve applying natural language processing for positioning each word in the order it was spoken (as determined by the order of the received signals associated with the particular facial micromovements) to form a sentence, such as positioning the words "who," "is," and "this" to form the statement "who is this." In some examples, the processor may be configured to assign a context to the query during the determination based on rules associated with certain words or phrases. For example, the processor may be informed by a rule that statements beginning with words such as "who" and "where" are questions, such that the query in the previous example would be formed as "who is this?" Determining a query may also involve other techniques such as natural language processing applied by artificial intelligence to determine the query based on both the content of the particular words and the context associated with the particular words. For example, such techniques may apply representation learning or deep neural network machine learning techniques to determine a query from the particular words Some disclosed embodiments involve accessing at least one data structure to perform a look up for an answer to the query. The at least one data structure may be any source of data, such as those described elsewhere herein. In the example shown in FIG. 70, the processor may access data structure 7020, which may be implemented in a server, such as a cloud server or other remote server. Accessing at least one data structure to perform a look up for an answer to the query may involve searching, checking, combining, examining, inspecting, probing, scanning, or otherwise using the at least one data structure to determine the answer to the query. Accordingly, the at least one data structure may store information, document, images, or other information associated with the query so that the processor may determine an answer to the query using that information. Examples of accessing at least one data structure to perform a look up for an answer to the query include using arrays, following references to a desired node in linked lists, retrieving values from stacks, queues, and hash tables, and performing a search algorithm on trees. In one example, the processor may match the query to relevant documents stored in the at least one data structure 7020, such as based on associated key words in the documents, to extract an answer from the documents. In this example, the processor may then search through the matched relevant documents in the at least one data structure 7020 to determine an answer. For example, the query may be a question such as "what is the address for Jane Doe?" In this example, the processor may search in the at least one data structure 7020 for documents containing the words "address" and "Jane Doe," and search through those documents to find the address for Jane Doe. Other examples of techniques a processor may use to access at least one data structure to perform a look up for an answer to the query include Information Retrieval (IR)-based factoid questioning, knowledge-based question answering, and using multiple information sources. IR-based factoid questioning may involve answering a query by finding short text segments on the Web or some other collection of documents. In a query-processing phase of this technique, a number of pieces of information from the question are extracted. An answer type may specify the kind of entity the answer consists of (such as a person, location, time). The query may specify the keywords that should be used by the IR system in searching for documents for the answer. Knowledge-based question answering may involve answering a natural language question by mapping it to a query over a structured database The logical form of the question may thus either in the form of a query or may easily be converted into one. In this technique, the at least one data structure may be a full relational database, or simpler structured databases like sets of Resource Description Framework (RDF) triples. When using multiple information sources, the processor may rely on a wide variety of resources in the at least one data structure to answer queries. In a query-processing stage, the processor may run parsing (e.g., entity tagging) and relation extraction to the query. The processor may also extract the focus, the answer type (i.e., the lexical answer type), classify the query, and break the query up into sections. The processor may also extract the focus or goal of the query. The processor may also classify the query by type as a definition question, multiple-choice, puzzle, or fill-in-the-blank. At a candidate answer generation stage, the processor may, according to the query type, combine the processed query with documents and other knowledge sources (e.g., images, videos) in the at least one data structure to suggest many candidate answers. These candidate answers may either be extracted from text documents or from structured knowledge bases in the at least one data structure. The processor may pass these candidate answers through a candidate answer scoring stage, which may use different sources of evidence to score the candidates, such as documents and other information in the at least one data structure. In an answer merging and scoring step, the processor may merge the candidate answers that are equivalent or similar. The merging and ranking may be run iteratively; first the candidates may be ranked by a classifier in the processor, giving a rough first value for each candidate answer. That value may be used to decide which of the variants of an answer the processor may select as the merged answer, and the merged answers may be re-ranked. Through such an iterative process, the processor may look up a final answer to the query in the at least one data structure.

Some disclosed embodiments involve generating a discreet output that includes the answer to the query. A discreet output may include anything produced by a machine or system, such as a visual, audible, or tactile output and configured for presentation in a discreet manner, meaning that it is not publicly broadcast. An output may be discreet, for example, if sent to an earpiece. An output may also be discreet if presented via a personal display device of the wearer (e.g., as text presented via smart glasses or googles, or on a personal display device of the user). By way of another example, a discreet audible output may be one that is muted (e.g., reduced volume). In some embodiments, discreet outputs may take the form of pop-up messages, sound alerts, push notifications, status bar icons, vibrating alerts, LED indicators, text messages, or email notifications that contain an answer to a query, is symbolic of an answer, or directs a user towards the answer. For example, the answer to the query might by "her name is Jane Doe." In this example, the discreet output may be an audio notification that presents "Jane Doe" in a muted volume or in an earpiece. Alternatively, the discreet output may be an audio notification that states "her name is" in full volume and "Jane Doe" in a muted volume.

Consistent with some disclosed embodiments, the discreet output includes an audible output delivered via at least one earbud to a wearer of the head mountable light detector. An audible output may include any notification, warning, alert, communication, message, or report that is perceptible by hearing, such as a sound, an alarm, or a song. An earbud may include any device that produces an audible output, such as a headphone or speaker, that is configured to be worn in, on, or near an ear. Examples of an audible output include a beep, chime, ringtone, jingle, whistle, siren, ticking clock, music playback, voice prompts, speech synthesis, and spoken answers. For example, in FIG. 70, the discreet output includes a sound (e.g., audio notification 7002) delivered via an earbud 7004 to a wearer 7012 of the optical sensing unit 7014. It is desirable to deliver a discreet output as an audible output via an earbud because such an output is less likely to be overheard by a nearby individual, which improves the privacy of the answer.

Consistent with some disclosed embodiments, the discreet output includes a textual output delivered to a wearer of the head mountable light detector. A textual output may include any notification, warning, alert, communication, message, or report that is perceptible by reading. Examples of delivering a textual output to a wearer of the head mountable light detector include text displayed in user interfaces, websites, and applications, messages, results, or logs displayed in console or command line interfaces, printed documents such as reports, invoices, letters, or articles, conversations, notifications, or system-generated messages in chat or messaging applications, records of events, actions, or system activities in logs and audit trails, tabular data, charts, graphs or summaries in reports and analytics, and email, SMS, or push notifications. For example, in FIG. 70, the discreet output includes a text message 7006 delivered to a phone 7008 used by a wearer 7012 of the optical sensing unit 7014. It is desirable to deliver a discreet output as a textual to a wearer of the head mountable light detector because such an output is less likely to be seen by a nearby individual, which improves the privacy of the answer.

Consistent with some disclosed embodiments, the discreet output includes a tactile output delivered to a wearer of the head mountable light detector. A tactile output may include any notification, warning, alert, communication, message, or report that is perceptible by touch. Examples of delivering a tactile output to a wearer of the head mountable light detector include activating devices such as motors in devices such as phone, watches, and computers to create vibrations, pulses, or pressure. For example, in FIG. 70, the discreet output includes a vibration 7010 delivered to a phone 7008 used by a wearer 7012 of the optical sensing unit 7014. It is desirable to deliver a discreet output as a tactile to a wearer of the head mountable light detector because such an output is less likely to be sensed by a nearby individual, which improves the privacy of the answer.

Consistent with some disclosed embodiments, the operations further include receiving image data and wherein the query is determined based on nonvocalized articulation of the particular words and the image data. Image data may be understood as described and exemplified elsewhere herein. For example, as explained elsewhere herein, image data may include pixel data streams, digital images, digital video streams, data derived from captured images, and data that may be used to construct one or more 3D images, a sequence of 3D images, 3D videos, or a virtual 3D representation. As an example, the operations may further include receiving image data such as digital images or digital video streams. Nonvocalized articulation of the particular words may include any speech by a user that does not produce sound, such as the silent speech described earlier. By way of example, an image sensor associated with a wearer may capture an image of an individual or object, and a nonvocalized articulation may include the question, "who is this?" or "what is this?" The system may then understand from context that "this" refers to the captured image (an image in the line of sight of the wearer) and interpret the question in context to supply an answer. Examples of nonvocalized articulation of the particular words include silent reading, whispering, inner speech, speech-related movement such as mouthing or twitching, and movements for speech therapy exercises. For example, nonvocalized articulation may involve subvocalization as described elsewhere herein. The nonvocalized articulation may be determined using the received signals to perform a lookup in the data structure of particular words associated with the particular facial micromovements, as described and exemplified elsewhere herein. For example, the processor may determine a plurality of words using the received signals to synthesize a nonvocalized articulation. Determining the query based on both the nonvocalized articulation of the particular words and the image data may improve accuracy of the operations for providing private answers to silent questions by associating context provided by the image data with the nonvocalized articulation. For example, the query may be determined based on movements associated with a user mouthing a question and a picture of someone or something the user is looking at or speaking with, to provide context for that question.

Figure 71:
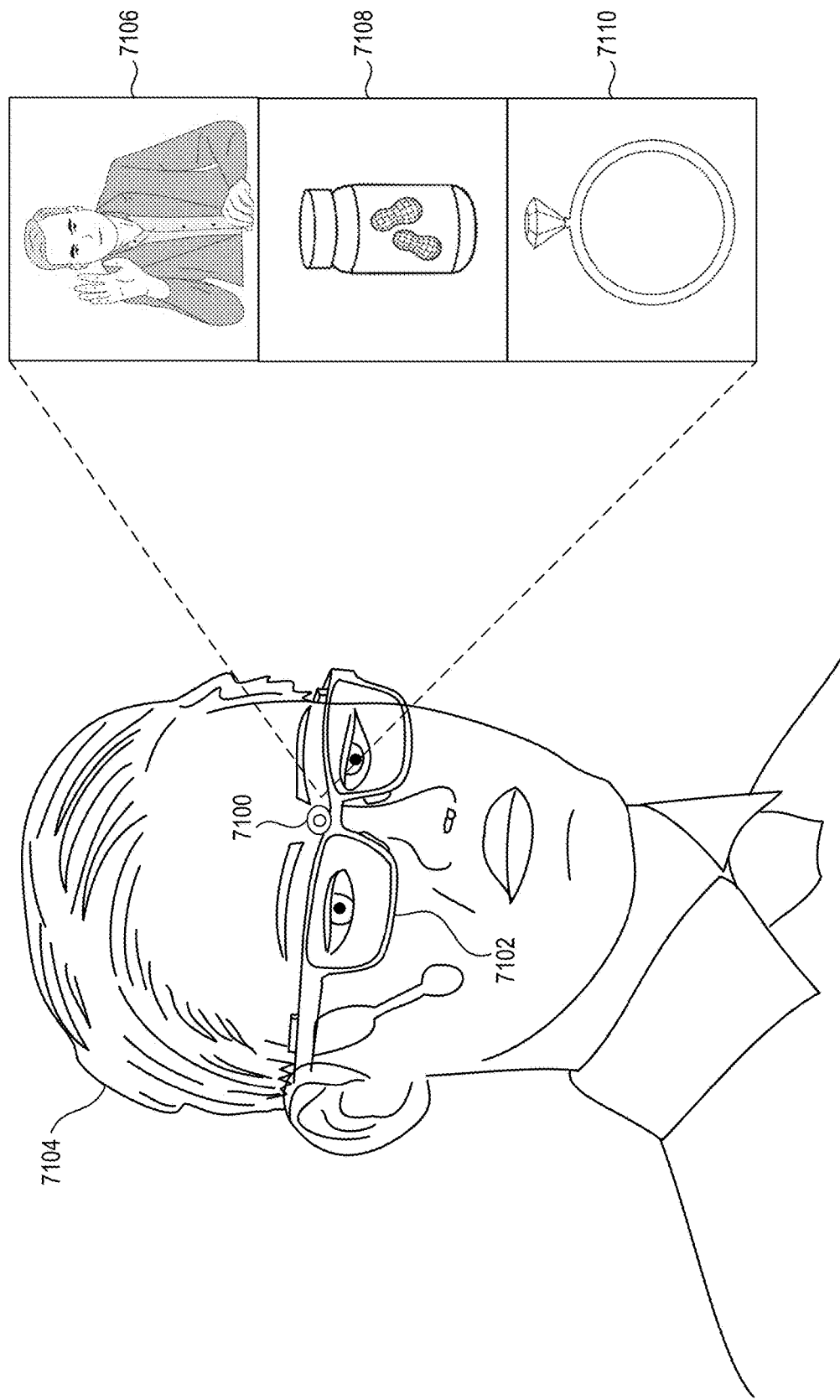
FIG. 71 illustrates examples of image data applications that may be used for providing private answers to silent questions, consistent with embodiments of the present disclosure.

Consistent with some disclosed embodiments, the image data is obtained from a wearable image sensor. An image sensor may be understood as described and exemplified elsewhere herein. A wearable image sensor may include any image sensor that may be worn as an accessory, embedded in clothing, clipped to clothing, implanted in the user's body, strapped to the user, or attached to the user's skin. Examples of a wearable image sensor include an image sensor stitched, sewed, adhered using tape, strips, straps, or Velcro, clipped, clamped, or magnetically mounted to a shirt, vest, garment, glasses, headset, or visor. Obtaining the image data from a wearable image sensor improves the mobility of the user by allowing data collection as the user moves. Examples of obtaining the image data from a wearable image sensor include sensor initialization such as configuring resolution, exposure, or frame rate parameters, triggering the image sensor through a hardware signal or software command, reading the image data from the sensor using a data acquisition interface by reading pixel values from the sensor's pixel array, performing any necessary imaging processing such as demosaicing, white balance adjustment, gamma correction, and noise reduction, saving the image in a file format (e.g., JPEG or RAW), and transmitting the image data over a communication channel (e.g., USB, Ethernet, wireless). For example, in FIG. 71, the image data is obtained wirelessly from a wearable camera 7100 embedded on a pair of glasses 7102 worn by the user 7104.

Consistent with some disclosed embodiments, the image data reflects an identity of a person, the query is for a name of the person, and the discreet output includes the name of the person. An identity may include a name, affiliation, location, height, weight, or any other characteristic of a person. Examples of an identity of a person reflected by image data include gender, nationality, ethnicity, occupation, social role, beliefs and values, personality traits, and life experiences. In one example, the image data may reflect a name of a person using a facial recognition search engine implemented using artificial intelligence. For example, artificial intelligence algorithms may be used to identify specific, distinguishing features on a person's face photographed by a wearable camera 7100. These features, such as the distance between the eyes or the contour of the chin, may then be mathematically represented and compared to data on other faces in a face recognition database to determine the name of the person photographed. In the example shown in FIG. 71, the image data obtained from wearable camera 7100 reflects an identity of a person 7106, the query is for the name of the person 7106, and the discreet output includes the name of the person 7106, which may be displayed on a phone 7008 as a text message 7006.

Consistent with some disclosed embodiments, the image data reflects an identity of an edible product, the query is for a list of allergens included in the edible product, and the discreet output includes the list of allergens. An identity of an edible product may include a name, manufacturer, ingredient, or any other characteristic of an item that may be eaten or consumed. Examples of an identity of an edible product reflected by image data include brand name, product name, ingredients, packaging design, nutrition facts, certification labels, flavors, variants, country of origin, taste, and texture profile. In one example, the image data may reflect an identity of an edible product using image-based food recognition systems (IBFRS). In such examples, the user 7104 takes a photograph of an edible product 7108 with the wearable camera 7100, the image is preprocessed and the different types of food are divided from each other through segmentation techniques, robust and discriminative features are extracted, classification of food items takes place, and the identity of the edible product 7108 is determined by searching databases. In this example, the image data reflects an identity of peanut butter 7108, the user 7104 asks for a list of allergens included in the peanut butter 7108 through nonvocalized articulation, and the discreet output includes the list of allergens, such as peanuts.

Consistent with some disclosed embodiments, the image data reflects an identity of an inanimate object, the query is for details on the inanimate object, and the discreet output includes the requested details on the inanimate object. An inanimate object may include an item that that is not living or that does not move on its own, such as a stone, stapler, hairbrush, or any other non-living object. An identity of an inanimate object may include a name, classification, brand, size, or any other characteristic of an such an object. Examples of an identity of an inanimate object reflected by image data include shape, size, color, texture, design, material composition, purpose or function, branding, manufacturer, features and capabilities, serial number, identification code, historical or cultural significance, packaging or labeling, value or price, and user interaction capabilities. An identity of an inanimate object may be determined using object detection techniques, such as machine learning-based approaches and deep learning-based approaches. In machine learning-based approaches, computer vision techniques may be used to look at various features of an image, such as the color histogram or edges, to identify groups of pixels that may belong to an inanimate object. These features may be fed into a regression model that predicts the location of the object along with its identity. In deep learning-based approaches, convolutional neural networks (CNNs) may be used to perform end-to-end, unsupervised object detection, in which features do not need to be defined and extracted separately, to determine an identity of the inanimate object. For example, the image data obtained from wearable camera 7100 may reflect an identity of a ring 7110, the query may be for the price of the ring 7110, and the discreet output may include the requested price of the ring 7110.

Consistent with some disclosed embodiments, the operations further include using the particular facial micromovements to attempt to authenticate an individual associated with the particular facial micromovements. Authentication may involve any process or action for determining or proving the identity of the individual associated with the particular facial micromovements, as described and exemplified elsewhere in this description. An individual associated with the particular facial micromovements may include any individual making, causing, initiating, or otherwise related to the particular facial micromovements, either concurrently with the operations or at an earlier or later time. For example, the individual may be an individual making nonvocalized articulations that cause the processor to provide private answers to silent questions. As another example, the individual may be an individual that previously used the processor to receive private answers to silent questions. It may be desirable to attempt to authenticate the individual to ensure privacy in instances where private information is being used in or requested for a private answer. Using the particular facial micromovements to attempt to authenticate the individual may involve applying, manipulating, combining, or otherwise handling the facial micromovements or data determined from or using the facial micromovements to perform the authentication. Examples of using the particular facial micromovements to attempt to authenticate the individual include exact matching, fuzzy matching, probabilistic matching, machine learning-based matching, rule-based matching, identity resolution, validation, clustering, and comparative analysis. In one example, using the particular facial micromovements may involve mapping particular facial micromovements to specific individual identities in a data structure and searching the data structure, such as by using a lookup function, to determine a specific individual identity that is mapped to the particular facial micromovements. As another example, an artificial intelligence engine may use a searching algorithm, such as a breadth-first search to determine an identity associated with the particular facial micromovements.

Consistent with some disclosed embodiments, when the individual is authenticated, the operations further include providing a first answer to the query, the first answer including private information; and when the individual is not authenticated, the operations further include providing a second answer to the query, the second answer omitting the private information. Private information may include information that is confidential, exclusive, secret, discreet, or any other information that some individuals may wish to keep hidden from the public. Examples of private information include an individual's name, signature, address, phone number or date of birth, credit card information, employee record information, photographs, internet protocol (IP) addresses, voice print and facial recognition biometrics (because they collect characteristics that make an individual's voice or face unique), location information from a mobile device (because it can reveal user activity patterns and habits), racial or ethnic origin, political opinions or associations, religious or philosophical beliefs, trade union membership or associations, sexual orientation or practices, criminal record, health or genetic information, biometric information and/or any other information that an individual may consider private. For example, in FIG. 70, user 7012 may request private information through a nonvocalized articulation of the question "what is my address?" In this example, the processor may attempt to authenticate the identity of user 7012 using the particular facial micromovements from cheek region 7000 to verify that user 7012 is an individual that has access to this information. Once user 7012 is authenticated, the processor may provide a first answer to the query by displaying on phone 7008 the address 7006 of the user which was requested. Omitting the private information may involve deleting, discarding, disregarding, editing, skipping, withholding, precluding, hiding, concealing, or otherwise leaving out or excluding the private information in the second answer. Examples of omitting the private information include blocking private information, providing a summary to exclude private information, masking, redaction, abbreviation, and providing alternate information. For example, in FIG. 70, user 7012 may request private information through a nonvocalized articulation of the question "what is my bank account number?" In this example, the processor may attempt to authenticate the identity of user 7012 using the particular facial micromovements from cheek region 7000 to verify that user 7012 is an individual that has access to this information. When user 7012 is not authenticated, the processor may provide a second answer to the query by playing an audio notification 7002 in earbud 7004 that the requested information is not available.

Consistent with some disclosed embodiments, the operations further include accessing personal data associated with the individual and using the personal data to generate the discreet output that includes the answer to the query. Personal data may include any data or information that is distinctive, important, private, belonging to, connected to, or otherwise associated with the other individual, such as log-in information, legal documents, identity verification, personal notes, bank records, and medical information. Using the personal data to generate the discreet output that includes the answer to the query may involve applying, manipulating, combining, or otherwise handling the personal data or information determined from or using the personal data to perform the generating. In one example, using the personal data may involve mapping personal data to answers in a data structure and searching the data structure, such as by using a lookup function, to determine a specific answer that is mapped to the personal data. As another example, an artificial intelligence engine may use a searching algorithm, such as an iterative deepening depth first search, to determine an identity associated with the particular facial micromovements.

Consistent with some disclosed embodiments, the personal data includes at least one of: age the individual, gender of the individual, current location of the individual, occupation of the individual, home address of the individual, level of education of the individual, or health condition of the individual. For example, the query may be "what is my log-in information?" and the processor may search for the answer in the user's log-in records using an iterative machine learning algorithm to determine the log-in information before presenting that log-in information as a private answer, such as in a notification 7006 on a phone 7008 of user 7012 in FIG. 70.

Consistent with some disclosed embodiments, the operations further include using the facial micromovements to determine an emotional state of an individual associated with the facial micromovements, and wherein the answer to the query is determined based in part on the determined emotional state. An emotional state of an individual associated with the facial micromovements may refer to the individual's subjective experience of their emotions at a particular moment or over a certain period before, during, or after making the facial micromovements. Some changes occurring throughout the body reflect an emotional state, such as a face turning pale in a state of fear, are visible to an observer and provide information about the affective state. Moreover, some physiological changes during the experience of emotion result in movement. For example, the activation of facial muscles leads to facial movement manifesting as facial expressions. Unlike skeletal muscles in the human body that are generally attached to bones, facial muscles also attach to each other or to the skin of the face. This anatomical set-up allows even slight contractions of facial muscles to pull the facial skin and create a facial expression that is detectable by sensors and can be received as signals indicative of the movements. Thus, the emotional state can provide context to the facial micromovements made by the user, such as if they were made under duress that results in a fearful emotion state. Examples of emotional states associated with facial micromovements include happiness associated with smiling, sadness associated with drooping eyes and a downturned mouth, anger associated with furrowed eyebrows, narrowed eyes, tightened jar, and lips pressed tightly together, surprise associated with widened eyes, raised eyebrows, and an open mouth, fear associated with widened eyes, raised eyebrows, and an open mouth, disgust associated with a wrinkled nose, raised upper lip, and narrowed eyes, contempt associated with one corner of the mouth raised higher than the other, and confusion associated with a furrowed brow and an open mouth. For example, an emotional state of the individual may be calmness associated with relaxed muscles in the cheek region 7000 of user 7012. The emotional state may be determined by a technique capable of associating the micromovements with an emotional state, such as a lookup search in a data structure or a machine learning algorithm. Examples of determining an answer to the query in part based on the determined emotional state include using the determined emotional state in data mining, clustering, classification, and machine learning to output an answer. For example, the operations may use a neural network to input the data associated with the determined emotional state (e.g., the state, time period of the state, frequency of the state) and process it through multiple layers of interconnected neurons, where each neuron performs computations on the data associated with the determined emotional state to adjust the network's weights and biases in determining an answer. In one example, the operations may further include using the facial micromovements to determine that the individual is afraid (e.g., by determining that the facial micromovements are associated with widened eyes, raised eyebrows, and an open mouth), and the answer to the query may conceal confidential information based on that determination, to prevent the divulgement of confidential information under threat.

Figure 72:
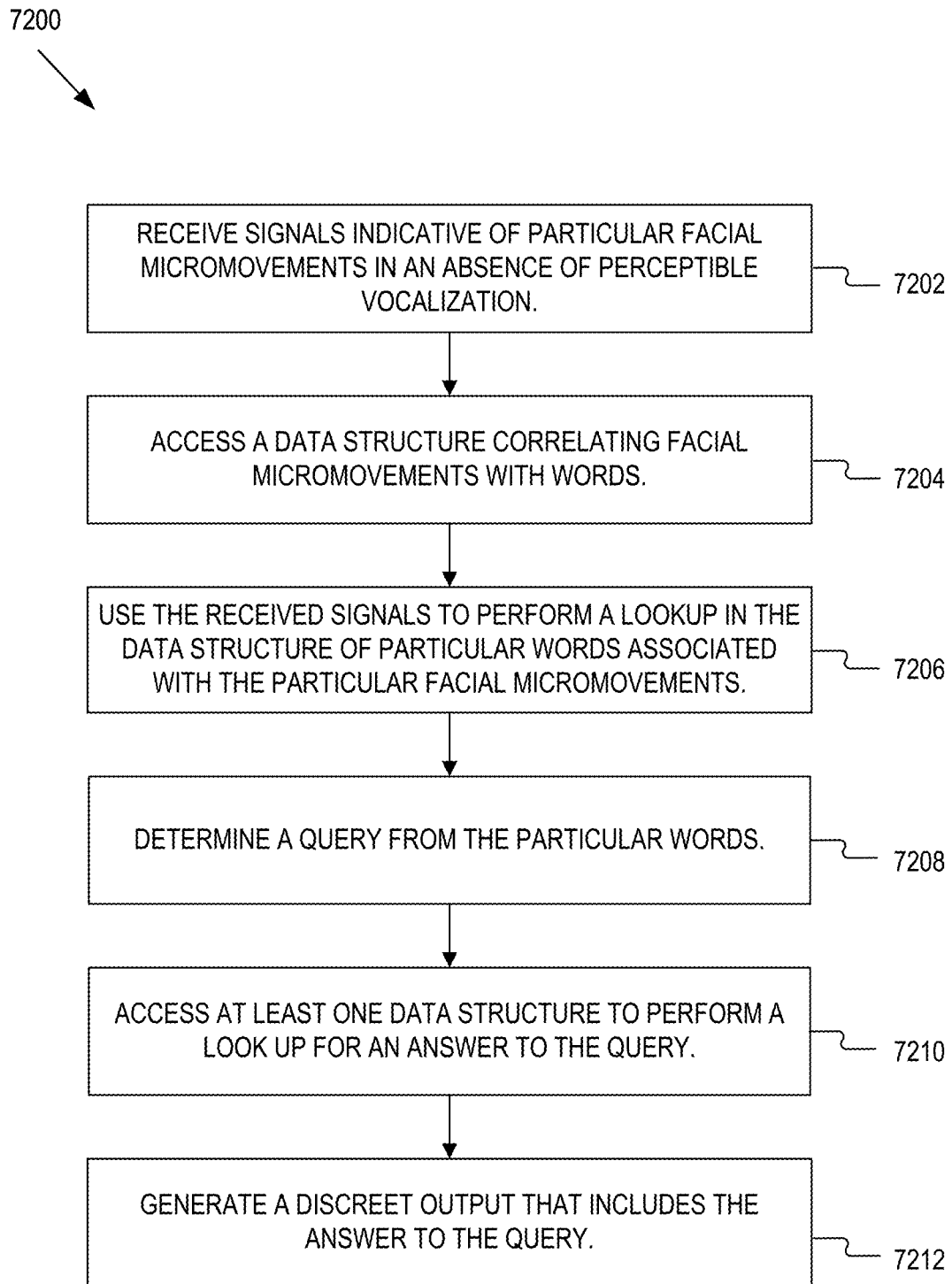
FIG. 72 illustrates a flowchart of an example process for providing private answers to silent questions, consistent with embodiments of the present disclosure.

Some disclosed embodiments involve a method for providing private answers to silent questions. FIG. 72 illustrates a flowchart of an exemplary process 7200 for providing private answers to silent questions, consistent with embodiments of the present disclosure. Consistent with some disclosed embodiments, process 7200 may be performed by at least one processor (e.g., processing unit 112 in FIG. 1, processing device 400 in FIG. 4) to perform operations or functions described herein. Consistent with some disclosed embodiments, some aspects of process 7200 may be implemented as software (e.g., program codes or instructions) that are stored in a memory (e.g., data structure 124 in FIG. 1) or a non-transitory computer readable medium. Consistent with some disclosed embodiments, some aspects of process 7200 may be implemented as hardware (e.g., a specific-purpose circuit). Consistent with some disclosed embodiments, process 7200 may be implemented as a combination of software and hardware.

Referring to FIG. 72, process 7200 includes a step 7202 of receiving signals indicative of particular facial micromovements in an absence of perceptible vocalization. Process 7200 includes a step 7204 of accessing a data structure correlating facial micromovements with words. Process 7200 includes a step 7206 of using the received signals to perform a lookup in the data structure of particular words associated with the particular facial micromovements. Process 7200 includes a step 7208 of determining a query from the particular words. Process 7200 includes a step 7210 of accessing at least one data structure to perform a look up for an answer to the query. Process 7200 includes a step 7212 of generating a discreet output that includes the answer to the query. It should be noted that the order of the steps illustrated in FIG. 72 is only exemplary and many variations are possible. For example, the steps may be performed in a different order, some of the illustrated steps may be omitted, combined, and/or other steps added. Furthermore, in some embodiments, process 7200 may be incorporated in another process or may be part of a larger process.

Some disclosed embodiments involve a system for providing private answers to silent questions, the system comprising: at least one processor configured to: receive signals indicative of particular facial micromovements in an absence of perceptible vocalization; access a data structure correlating facial micromovements with words; use the received signals to perform a lookup in the data structure of particular words associated with the particular facial micromovements; determining a query from the particular words; access at least one data structure to perform a look up for an answer to the query; and generate a discreet output that includes the answer to the query. The terms system and processor may be interpreted as described and exemplified elsewhere in this disclosure.

The embodiments discussed above for providing private answers to silent questions may be implemented through non-transitory computer-readable medium such as software (e.g., as operations executed through code), as methods (e.g., process 7200 shown in FIG. 72), or as a system (e.g., speech detection system 100 shown in FIGS. 1-3). When the embodiments are implemented as a system, the operations may be executed by at least one processor (e.g., processing device 400 or processing device 460, shown in FIG. 4).

Some disclosed embodiments involve performing control commands based on facial skin micromovements. A control command refers to an instruction that is given to control behavior or operation of a program, a device, or a system. For example, a control command may include an instruction provided to software, to a virtual personal assistant, to another electronic device, and/or to a user interface. As described earlier, facial skin micromovements may be interpreted to provide meaning. One example of meaning is a control command. By way of example, a control command may enable an individual, through facial skin micromovements, to press buttons, access fields, cause menus to drop down, check boxes, move sliders, navigate, send messages, open messages, power off, cause displays to appear or disappear, move text or objects, select or enter data, ask for assistance, initiate or accept communications, change audio volume, change presentation settings, control remote devices, programs, or systems, or otherwise initiate any action.

Control commands may affect controls within a device in which the control command is received or in another device or program. For example, with reference to FIG. 73, a control command may control speech detection system 100, a paired mobile communications device 120 (or other paired device), or any other device, system, or program via link 7314 to communications network 126 and/or to server 122. The control command may be initiated, for example, by subvocalized speech, vocalized speech, facial gestures, expressions, or other facial movements. Consistent with some disclosed embodiments, the control command may include one or more words and/or gestures in various combinations. For example, a word command of "volume up" may increase the volume of a speaker of speech detection system 100 or of a media player running on a device paired with speech detection system 100.

Some embodiments involve operating at least one coherent light source in a manner enabling illumination of a non-lip portion of a face. A coherent light source controlled to illuminate a non-lip portion of the face may be understood as discussed elsewhere herein. By way of one example, a light source may be provided in a wearable housing configured to be worn on a head of an individual. The terms "wearable housing," "individual," and "coherent light source" should be interpreted as discussed elsewhere in this disclosure. The term "operating" may include activating or otherwise causing the light source to emit light in a given direction, as discussed elsewhere in this disclosure.

Consistent with some disclosed embodiments, operating the light source may involve activating the light source. In other embodiments, operating the light source may involve deactivating the light source and/or modulating the light source and/or controlling other parameters of the light source. By way of one example, coded instructions may cause the light source to initiate operation in response to an activation signal that is triggered based on environmental factors or in response to an action by a user. For example, the code may activate the light source in response to physical control of a button, a lever, a dial, a switch, or any other mechanical device. By way of another example, the virtual control may include a user interface element such as a button, a toggle, a slider, or other user interface element the interaction with which triggers the code to operate the light source. Similarly, a trigger may include a phrase such as "activate" or one or more predetermined facial gestures.

Consistent with other disclosed embodiments, the light source may be activated when speech detection system 100 is activated or powered on.

By way of an example with reference to FIG. 5, illumination module 500 includes light source 410 configured to generate an input light beam 504. Illumination module 500 further includes beam-splitting element 506 configured to split input beam 504 into multiple output beams 508, which form respective spots 106A-106E in a pattern (e.g., a matrix of locations) enabling illumination of facial region 108.

Consistent with some disclosed embodiments, operating the at least one coherent light source includes determining an intensity or a light pattern for illuminating the non-lip portion of the face. The term "intensity" is described elsewhere in this disclosure. For example, the intensity or light pattern may be determined by a processor based on one of more properties of the light source. By way of example with reference to FIG. 4, light source 410 operating in conjunction with processing unit 112 of speech detection system 100 may determine the intensity or light pattern.

Some embodiments involve receiving specific signals representing coherent light reflections associated with specific non-lip facial skin micromovements. The term "specific signals" may relate to light reflections from facial skin as discussed elsewhere in this disclosure. The signals may be received from the output of a light detector after the reflected light impinges on the light detector. In other words, signals from the output of a light sensor are received. A "specific non-lip facial skin micromovement" refers to movement of facial skin other than skin of the lips. Different sequences of non-lip facial skin micromovements (i.e., one or more non-lip facial skin micromovements that constitute an individual vocalizing, pre-vocalizing, or subvocalizing a word or phrase) may cause different coherent light reflections. For example, the sequence of non-lip facial skin micromovements created when the individual speaks the phrase "end call" may cause coherent light reflections that are different than the sequence of non-lip facial skin micromovements created when the individual speaks the phrase "play movie." The phrase "coherent light reflections" should be interpreted as discussed elsewhere in this disclosure.

For example, the illumination of the non-lip portion of the face may be provided by projecting one or more light spots onto the individual's face. Each light spot may produce a corresponding spot reflection from the facial region of the individual and may be detected (i.e., received) by a light detector. In some embodiments, a measurable light characteristic of a light spot reflection may be compared to the same measurable light characteristic of the light spot to determine if there is a change in the measurable light characteristic. For example, a luminance of the light spot reflection may be determined by using light reflection analysis and the light reflection analysis may be used to determine facial skin micromovements as described elsewhere in this disclosure.

By way of an example with reference to FIG. 5, coherent light reflections may include reflections 300 of light from light spots 106A-106E illuminating facial region 108, such as light projected by light source 410, and may be detected by detection module 502.

In some embodiments, the specific signals are received at a rate of between 50 Hertz (Hz) and 200 Hz. For example, a light detector may detect the reflected light and generate signals representative of the received reflected light. Those signals may then be transmitted to a processor which receives the signals. The number of signals or signal changes over time that the light detector generates and transmits to the processor may be a rate at which signals are received. The rate may depend on the sensitivity, processing speed, and/or any associated time lags between various processes performed by of one or more of the detector and the processor and/or any time lags associated with transmitting the signals from the detector to the processor.

The rate of receiving the signals may correspond to how quickly the reflected light can be processed to determine the corresponding skin micromovements and translate those micromovements into signals. It is noted that the range of 50-200 Hz is exemplary and that other signal rates are possible, including a signal rate of less than 50 Hz or a signal rate of higher than 200 Hz.

In some embodiments the facial skin micromovements correspond to recruitment of at least one specific muscle. As described elsewhere in this disclosure, facial skin micromovements may be based on the movement (i.e., recruitment) of a particular muscle under the skin in regions of the face that correspond to the locations of those muscles. Because the micromovements are based on the recruitment of a particular muscle, those micromovements may be associated with or may correspond to recruitment of that particular muscle.

In some embodiments, the at least one specific muscle includes: a zygomaticus muscle, an orbicularis oris muscle, a risorius muscle, or a levator labii superioris alaeque nasi muscle. As described elsewhere in this disclosure, the determined facial skin micromovements may include voluntary and/or involuntary recruitment of one or more muscle fibers from a selected group of facial muscles. Because the locations and the trajectories of the facial muscles are known, it may be possible to select a given facial muscle to assist in interpreting the control commands, whether the command is vocalized or subvocalized as described elsewhere in this disclosure. It is noted that the facial muscles identified herein are exemplary and that other facial muscles may be used to determine skin micromovements.

In some disclosed embodiments, the facial skin micromovements includes involuntary micromovements. The term "involuntary micromovements" may include facial skin micromovements that occur unconsciously or subconsciously. For example, a user might not consciously make certain facial gestures or move certain facial muscles, however in some contexts, those movements might be the basis for control commands.

In some disclosed embodiments, the involuntary micromovements are triggered by an individual thinking of speaking the specific control command. For example, when the individual is thinking of speaking, this may cause prevocalization muscle recruitments (i.e., prior to an onset of vocalization) and as described elsewhere in this disclosure. In some cases, the prevocalization facial skin micromovements may be triggered by voluntary muscle recruitments that occur when certain craniofacial muscles start to vocalize words. In other cases, the prevocalization facial skin micromovements may be triggered by involuntary facial muscle recruitments that the individual makes when certain craniofacial muscles prepare to vocalize words. For example, if the individual is preparing to speak the phrase "end call," one or more craniofacial muscles will be recruited to speak the phrase. The muscle recruitment in turn may cause non-lip facial skin micromovements.

In some disclosed embodiments, the involuntary micromovements are unnoticeable to a human eye. For example, the facial skin micromovements may not be part of a larger-scale skin movement visible to the naked eye as described elsewhere in this disclosure. While facial skin micromovements may occur over a multi-square millimeter facial area, they may occur in a surface area of the facial skin of less than one square centimeter, less than one square millimeter, less than 0.1 square millimeter, less than 0.01 square millimeter, or an even smaller area. Such small-scale movements may not be visible (i.e., are unnoticeable) to a human eye.

By way of an example with reference to FIG. 5, coherent light reflections may include reflections 300 of light from light spots 106A-106E illuminating facial region 108, such as light projected by light source 410, and may be detected by detection module 502. For example as shown in FIG. 5, before muscle recruitment, one output beam 508 may project light spot 106A (e.g., the first light spot). After muscle recruitment, light spot 106A may be reflected (via reflection 300) and detected by detection module 502. The reflection may be used to determine that the facial skin illuminated by light spot 106a moved by a distance d1, as described elsewhere in this disclosure. The distance d1 may represent an involuntary facial skin micromovement and may be small enough such that it is unnoticeable to a human eye.

Some embodiments involve accessing a data structure associating a plurality of non-lip facial skin micromovements with control commands. The term "data structure" should be interpreted as described elsewhere in this disclosure. For example, a data structure may contain correlations (i.e., associations) of facial skin micromovements with words, phonemes, or gestures which may correspond to one or more control commands.

Some embodiments involve identifying in the data structure a specific control command associated with the specific signals associated with the specific non-lip facial skin micromovements. For example, the at least one processor may perform a lookup in the data structure for one or more control commands associated with the detected specific non-lip facial skin micromovements to identify the specific control command. This lookup may be performed in a manner similar to performing a lookup to locate words or phonemes associated with detected facial skin micromovements as described elsewhere in this disclosure. By way of one example, the data structure may contain correlations of non-lip facial skin micromovements with words or phonemes that may be part of or all of a specific control command. A processor or processing unit may perform a lookup in the data structure to identify the specific control command associated with the specific non-lip facial skin micromovements. A lookup may occur in a conventional database, or in the case of an AI dataset, the lookup may involve querying an AI model.

In some embodiments, the facial skin micromovements includes a sequence of facial skin micromovements from which the specific control command is derived. The term "sequence" includes a series of one or more skin micromovements that, when considered together, may be used to determine a specific control command. For example, if the individual vocalizes or subvocally articulates the phrase "volume up," it may include one or more facial skin micromovements to complete the phrase. As another example, the individual may use other facial movements that correspond to particular commands, including a tongue movement such as left-right to indicate "no," a "tsk" or "nah" vocalization or subvocal articulation to indicate "cancel a prior command," or a "quick" smile (e.g., a very short duration smile or a partial smile) or a kiss-like gesture to indicate "yes" or agreement with respect to a command. A specific control command may be derived from the series of facial skin micromovements by performing a lookup in a data structure, for example, as described elsewhere in this disclosure.

Some embodiments involve executing the specific control command. Executing refers to one or more operations or instructions that initiates the specific control command. The control command may cause a resulting action in any program, device, or system that receives the command. As defined elsewhere in this disclosure, the control command refers to an instruction that is given to control behavior or operation of the program, the device, or the system that receives the control command. By way of one example with reference to FIG. 4, the control command may be executed by processing device 400 of speech detection system 100. Executing the specific control command may include causing an action to be performed by speech detection system 100 or another device in communication with speech detection system 100. For example, the other device may be in communication with speech detection system 100 by wireless communication, such that speech detection system 100 may issue signals or commands to the other device to cause the other device to initiate the action. Executing the specific control command may include issuing one or more instructions to the device that is to perform the control command to perform the action identified by the control command.

Figure 73:
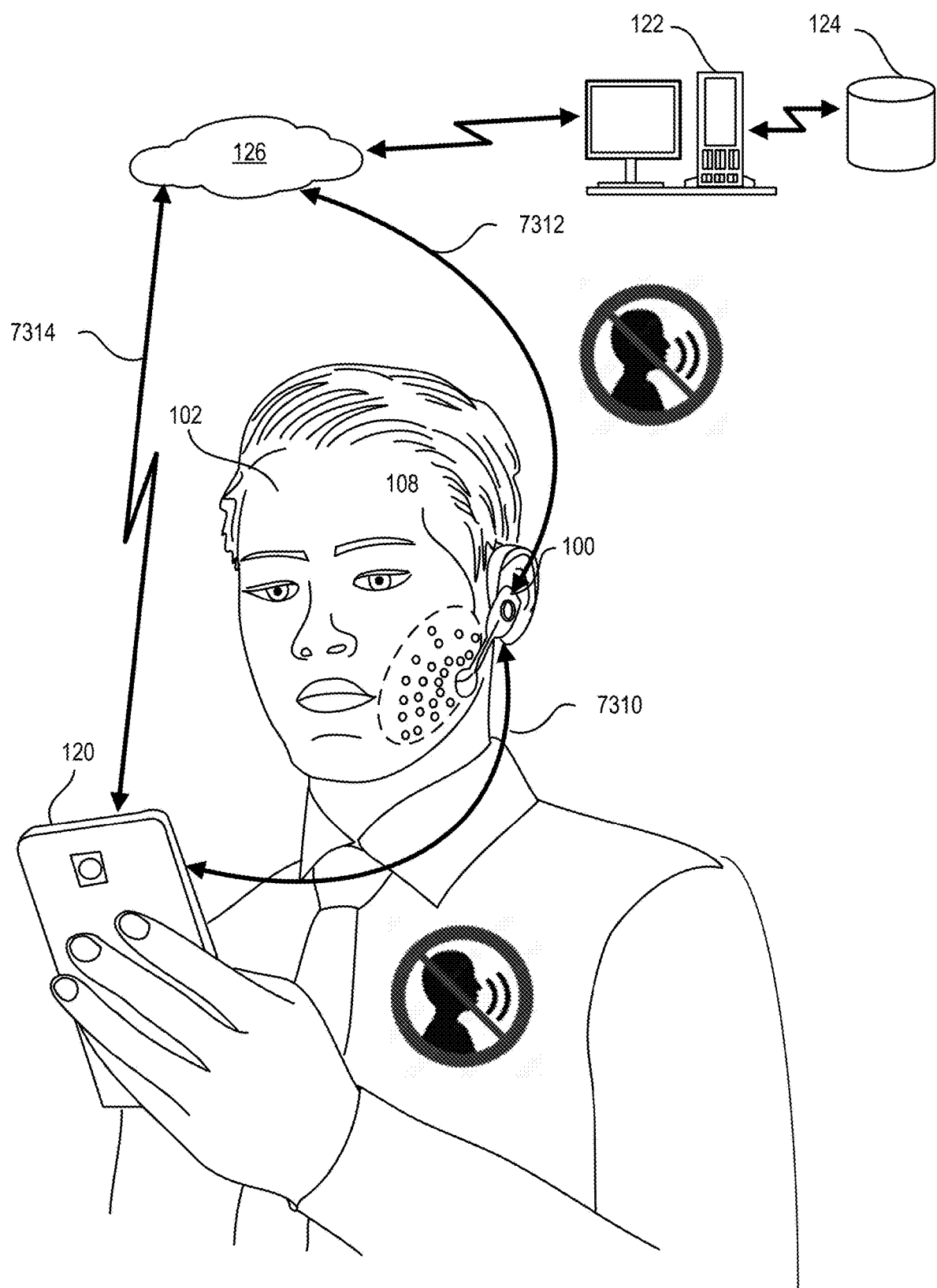
FIG. 73 is a schematic illustration of an individual using a first example speech detection system, consistent with some embodiments of the present disclosure.

FIG. 73 is a schematic illustration of an individual 102 using a first example speech detection system 100, consistent with some embodiments of the present disclosure. In the example shown in FIG. 73, individual 102 may use speech detection system 100 to perform control commands for a program, a device, or a system based on facial skin micromovements.

Speech detection system 100 operates at least one coherent light source to illuminate a non-lip portion of the individual's face, such as facial region 108. As shown in FIG. 73, speech detection system 100 may project light spots (the circles shown inside facial region 108) to illuminate the non-lip portion of the individual's face. Speech detection system 100 receives specific signals representing coherent light reflections associated with specific non-lip facial skin micromovements.

Speech detection system 100 accesses a data structure, such as data structure 124 associating a plurality of non-lip facial skin micromovements with control commands. A specific control command associated with the specific non-lip facial skin micromovements is identified in the data structure and the control command is executed.

For example, individual 102 speaks a control command (either vocally or subvocally), such as "answer call" or "skip song." The control command is identified by speech detection system 100 using the light reflections to determine facial skin micromovements that correspond to the control command. The identified control command may be transmitted (e.g., by wireless communication) to mobile communications device 120 (via link 7310) or to communications network 126 (via link 7312). In some embodiments, the control command may be relayed to communications network 126 from mobile communications device 120 via links 7310 and 7314. The control command may be used to perform one or more operations on mobile communications device 120 or another device, such as server 122, a media player, or a virtual personal assistant, paired with speech detection system 100 and communicating via communications network 126.

In some embodiments, the specific control command is configured to cause an audible translation of words from an origin language into at least one target language other than the origin language. A specific control command may be configured to cause an action by issuing one or more instructions to perform the action identified by the control command. For example, the control command may include the word "translate" or any variation thereof. In response to receiving the control command, the program, device, or system that receives that control command may translate any words following the control command into the at least one target language. By way of one example, the audible translation of words may be presented to the individual via an audio output device, such as a speaker, associated with the disclosed speech detection system such that the audible translation may only be heard by the individual. As another example, the audible translation may be presented to an audio output device such that people other than the individual may also be able to hear the audible translation.

Consistent with some disclosed embodiments, the origin language may be a language spoken by the individual and audio in the origin language may be captured, for example, by an audio sensor of the disclosed speech detection system. For example, the origin language may be a language spoken by the individual and captured via facial skin micromovements as described elsewhere in this disclosure. As another example, the origin language may be a language spoken by another person in proximity to the individual such that audio in the origin language may be captured by an audio sensor of the disclosed speech detection system. As another example, the origin language may be a language spoken by another person on a phone call with the individual or may be a language spoken on an audio portion of a media presentation that the individual is listening to.

Consistent with some disclosed embodiments, the at least one target language may be predetermined by a user setting of the speech detection system or may be selectable by a user interface element of the speech detection system. Consistent with other disclosed embodiments, the at least one target language may be identified as part of the control command. For example, the control command "translate to Spanish" may indicate that any detected speech (vocalized or subvocalized) that follows the control command be translated into Spanish. After the control command is processed, any subsequently detected speech may be translated into Spanish and, for example, displayed to the individual on a display screen of a mobile communications device associated with the disclosed speech detection system and/or audibly presented to the individual.

By way of an example with reference to FIG. 73, individual 102 may speak a control command, such as "translate to Spanish." The control command may be executed by speech detection system 100. After the control command is executed, any subsequent speech detected by speech detection system 100 may be translated into Spanish and sent via link 7310 to be displayed on a display screen of mobile communications device 120 and/or may be audibly presented to individual 102 via speaker 404 of speech detection system 100.

In some embodiments, the specific control command is configured to cause an action in a media player application. For example, the media player application may be configured to play media such as music, a movie, a video, animated images or GIFs, a television program, or any other type of audio-visual content. The control command may provide a signal to the media player application to cause an action, such as "play," "start," "stop," "skip," "skip ahead 10 seconds," "skip song," "next song," "replay song," "shuffle play," "skip scene," "next scene," "change language to Spanish," "volume up," "volume down," or other control command that may cause an action to be performed by the media player application.

By way of an example with reference to FIG. 73, the media player application may be an application running on mobile communications device 120. Individual 102 may speak a control command, such as "next song." The control command may be processed by speech detection system 100 and may be sent via link 7310 to be executed by the media player application on mobile communications device 120 to play the next song, for example, a next song on a playlist in the media player application.

In some embodiments, the specific control command is configured to cause an action associated with an incoming call. An incoming call may include any type of single party or multiparty communication, such as a traditional phone call; an Internet-connected call or meeting, for example, FaceTime®, Teams™, Zoom®; or a call on a similar communications platform or protocol. The control command may provide an instruction to cause an action associated with an incoming call such as "answer," "answer call," "ignore," "decline," or other control command. For example, a mobile communications device associated with the disclosed speech detection system may be configured to receive an incoming call and receive control commands from the speech detection system. The control command may provide an instruction to the mobile communications device to cause an action associated with the incoming call as described herein.

By way of an example with reference to FIG. 73, the incoming call may include a type of call that can be handled by mobile communications device 120, including a traditional phone call, an Internet-connected call, or an Internet-connected meeting. Individual 102 may speak a control command, such as "answer call." The control command is processed by speech detection system 100 and is sent via link 7310 to be executed by mobile communications device 120 to answer the incoming call.

In some embodiments, the specific control command is configured to cause an action associated with an ongoing call. An ongoing call may include any type of single party or multiparty communication, such as a traditional phone call; an Internet-connected call or meeting, for example, FaceTime®, Teams™, Zoom®; or a call on a similar communications platform or protocol. For example, the control command may provide an instruction to cause an action associated with an ongoing call such as "hang up," "disconnect," "volume up," "volume down," "mute," "hold," "conference," or other control command.

By way of an example with reference to FIG. 73, the ongoing call may include a type of call that can be handled by mobile communications device 120, including a traditional phone call, an Internet-connected call, or an Internet-connected meeting. Individual 102 may speak a control command, such as "volume up." The control command may be processed by speech detection system 100 and may be sent via link 7310 to be executed by mobile communications device 120 to increase the volume of the ongoing call, for example, by increasing the volume at speaker 404 of speech detection system 100 or of a speaker of mobile communications device 120.

In some embodiments, the specific control command is configured to cause an action associated with a text message. For example, the text message may be sent or received as part of a text messaging application or other text-based communication application. The control command may provide an instruction to cause an action associated with a text message such as "send message" with the text of the message following the command, "reply to" with the text of the reply following the command, "delete," or other control command associated with a text message. For example, the disclosed speech detection system may be in communication with a device configured to send and receive text messages, such as a mobile communications device (e.g., smartphone, smartwatch, laptop, tablet). The mobile communications device may be configured to receive control commands from the speech detection system. The control command may provide an instruction to the mobile communications device to perform the action, including one or more of the actions identified above.

By way of an example with reference to FIG. 73, mobile communications device 120 may be running a text messaging application. Individual 102 may speak a control command, such as "Send message to Phil. I'll meet you at the park on Saturday at 8:00 for our run." The control command may be processed by speech detection system 100 and may be sent via link 7310 to be executed by mobile communications device 120 to create a text message to be sent to the contact "Phil" with the body of the message including the text "I'll meet you at the park on Saturday at 8:00 for our run."

In some embodiments, the specific control command is configured to cause activation of a virtual personal assistant. A virtual personal assistant may be implemented as an application running on a device and is designed to locate information in response to a question or command spoken by a user of the application. Examples of virtual personal assistant applications include Siri®, Alexa®, or similar applications. The control command may include an activation word or phrase for the virtual personal assistant so that the virtual personal assistant is activated and ready to receive the control command following the activation word or phrase. The control commands may include phrases such as "schedule meeting with Phil on Tuesday at 10 am," "where is the closest coffee shop?" "add milk to my shopping list," or another control command that may cause an action to be performed in response to the control command by the virtual personal assistant.

By way of example with reference to FIG. 1, speech detection system 100 may be in communication with a device that includes a virtual personal assistant, such as mobile communications device 120. Mobile communications device 120 may be configured to receive control commands from speech detection system 100. The control command may provide an instruction to mobile communications device 120 to cause an action to be taken by the virtual personal assistant, such as one of the action identified above.

By way of an example with reference to FIG. 73, the virtual personal assistant may be an application running on mobile communications device 120. Individual 102 may speak a control command, such as "Where is the closest coffee shop?" The control command may be processed by speech detection system 100 and may be sent via link 7310 to be executed by the virtual personal assistant running on mobile communications device 120 to find a coffee shop nearest to the individual's current location (as may be determined by a location of mobile communications device 120) and to display the location of the nearest coffee shop on a map or similar application on a display screen of mobile communications device 120. As another example, audio directions to the nearest coffee shop may be provided to individual 102 through speaker 404 of speech detection system 100 or a speaker of mobile communications device 120.

In some embodiments, the facial skin micromovements correspond to a nonvocalized articulation of at least one word associated with the specific control command. The phrase "facial skin micromovements correspond to a nonvocalized articulation . . . " refers to the fact that some commands may be associated with non-audible series of facial skin micromovements. If such a correlation is maintained in a data structure, when associated facial skin micromovements are detected, the specific control command may be triggered. For example, the control command may be a multiple word command such as "volume up," and the word may be "volume" or "up" received as light reflections of subvocalized words.

Some disclosed embodiments involve analyzing the specific signals to identify temporal and intensity changes of speckles produced by light reflections from the non-lip portion of the face. The terms "speckle," "temporal change," and "intensity change" should be interpreted as described elsewhere in this disclosure. Analyzing the specific signals produced by the light reflections may include light reflection analysis performed by analyzing patterns of light (e.g., speckles) scattered off the surface the skin as described elsewhere in this disclosure.

By way of an example with reference to FIG. 5, light reflections may include reflections 300 of light from light spots 106A-106E of facial region 108 and may be detected by detection module 502. For example as shown in FIG. 5, before muscle recruitment, one output beam 508 may project light spot 106A (e.g., the first light spot). After muscle recruitment, light spot 106A may be reflected (via reflection 300) and detected by detection module 502. The reflection may be used to determine that the facial skin illuminated by light spot 106A moved by a distance d1, as described elsewhere in this disclosure.

Consistent with some disclosed embodiments, a change in the measurable light characteristic between a light spot and a light spot reflection (in an embodiment where light spots are utilized) may be determined over a period of time. For example, the light spot may be measured at a first time, the light spot reflection may be measured a second time later than the first time, the light spot may be measured at a third time later than the second time, and the light spot reflection may be measured at a fourth time later than the third time. For example, a change may be determined if the difference exceeds a threshold difference, either in absolute terms (e.g., greater than 5 candela per square meter (cd/m 2)), or a percentage difference (e.g., greater than 5%), an absolute difference (e.g., simple subtraction between two values), a ratio, an absolute value, or any other computed or statistical value. Any of these values may be compared to a threshold. It is noted that the preceding threshold differences are merely exemplary and that other threshold differences may be utilized.

Some disclosed embodiments involve processing data from at least one sensor to determine context for the specific non-lip facial skin micromovements. The term "sensor" may include any sensor described elsewhere in this disclosure. The data received from the at least one sensor may be used to determine what the individual is doing at a point in time. The "context" is what the individual is doing, where the individual is located, the time of day, the current weather conditions near the individual's location, who or what else is present in the individual's surroundings, the content of a preceding call or meeting, or similar options that may describe the individual's current situation with respect to their surroundings when the data from the at least one sensor is received. For example, an image sensor may determine any people or physical objects in an area surrounding the individual. A motion sensor may determine whether the individual is moving and/or whether people or physical object in the area surrounding the individual are moving. An environmental sensor or weather sensor may determine weather or related conditions in the area surrounding the individual. A proximity sensor may determine whether other people or physical objects are near the individual. A light sensor may be used to assist in determining the current time of day and/or weather conditions. A GPS sensor may determine the individual's current geographic location. An audio sensor may determine the ambient noise in the area surrounding the individual.

By way of one example with reference to FIG. 4, the at least one sensor may include audio sensor 414 of speech detection system 100 or additional sensors 418 of speech detection system 100, such as image sensors, motion sensors, environmental sensors, proximity sensors, or other sensing devices configured to facilitate related functionalities. Data acquired by the at least one sensor may be transmitted by wired or wireless transmission to processing unit 112 or to remote processing system 450, wherein the acquired data may be processed.

For example, the individual may be involved in a phone call or other electronic meeting and the context may be determined to be "phone call" or "meeting." This determination may be based on data received from an audio sensor or another indicator to indicate that the individual is on a phone call or is in an electronic meeting.

As another example, the individual may be in proximity to another person and may be speaking with the other person and the context may be determined to be "in-person conversation." For example, the proximity to another person may be determined by a proximity sensor that detects the presence of the other person within a predetermined distance of the individual. Whether the individual is speaking with the other person may be determined by an audio sensor.

The terms used to describe a particular context may vary and the contexts in which an individual may operate the speech detection system may similarly vary. Any such variations are contemplated to be within the scope of this disclosure. The context may be more complicated than a single determination. For example, if the individual is participating in an ongoing call and there are multiple people near the individual, the context may be "on ongoing call and multiple people detected."

Some disclosed embodiments involve determining an action to initiate based on the specific control command and the determined context. Basing the determination of the action to initiate on the determined context may enable a more accurate interpretation of what the individual has spoken or has silently spoken. For example, if the individual is participating in an ongoing call and there are multiple people near the individual, the context may be determined to be "on ongoing call with multiple people detected." If the individual speaks (vocally or subvocally) the control command "increase volume," an audio sensor may determine the ambient noise in the area surrounding the individual and the volume may be increased. For example, speech detection system 100 may increase the volume of the ongoing call to a level high enough so that the individual may clearly hear the ongoing call over the ambient noise level.

FIG. 74 is a schematic illustration of two individuals (102a, 102b) one of whom is using an example speech detection system 100, consistent with some embodiments of the present disclosure. As described elsewhere in this disclosure, speech detection system 100 projects light onto a facial region 108 of the individual. Speech detection system 100 operates in a similar manner as described elsewhere in this disclosure and may communicate with a communications network 126 via link 7410.

As shown in FIG. 74, individuals 102a and 102b are located near each other but are not speaking to each other. Individual 102a may be participating in an ongoing call. The context for individual 102a may be determined by one or more sensors in speech detection system 100 as described elsewhere in this disclosure, and may be determined to be "on ongoing call and another person is detected." If individual 102a speaks (vocally or subvocally) the control command "increase volume," an audio sensor may determine the ambient noise in the area surrounding individual 102a (the ambient noise may be caused by individual 102b or may be other noise in the area surrounding individual 102a) and speech detection system 100 may then increase the volume of the ongoing call to a level high enough so that individual 102a may clearly hear the ongoing call over the ambient noise level.

Figure 75:
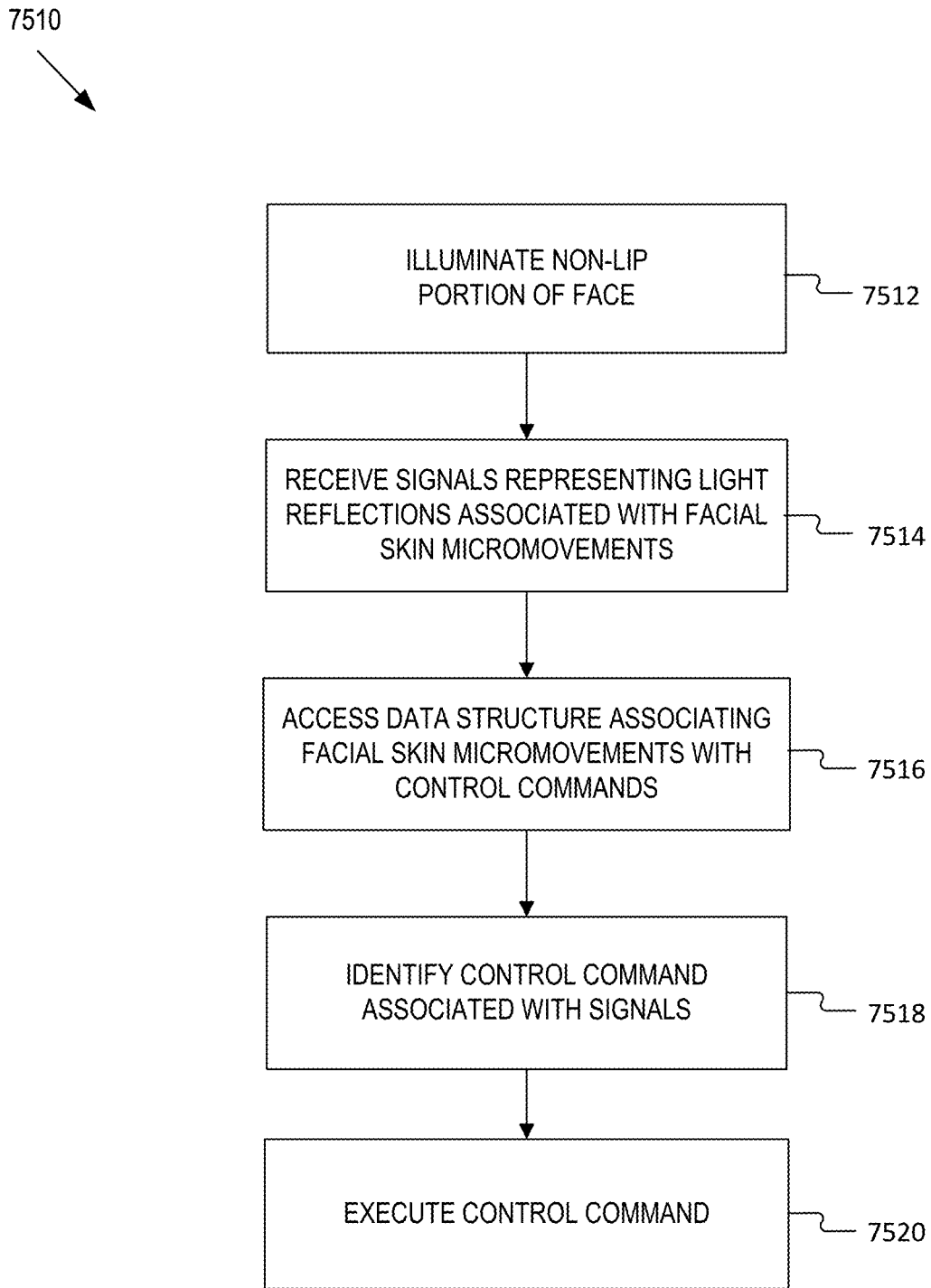
FIG. 75 is a flowchart of an exemplary method for performing silent voice control, consistent with some embodiments of the present disclosure.

FIG. 75 is a flowchart of an exemplary method 7510 for performing silent voice control, consistent with some embodiments of the present disclosure.

Consistent with some embodiments, method 7510 includes operating at least one coherent light source in a manner enabling illumination of a non-lip portion of a face (step 7512). For example, light source 410 of speech detection system 100 may project light onto the face of an individual wearing speech detection system 100 to illuminate a non-lip portion of the individual's face. In some disclosed embodiments, the light source may be a coherent light source.

Consistent with some embodiments, method 7510 includes receiving specific signals representing coherent light reflections associated with specific non-lip facial skin micromovements (step 7514). The signals may include one or more reflection signals, including any form of data retrieved from at least one light detector in response to the light reflections from the facial region. The reflection signals may be based on light reflection analysis, as described elsewhere in this disclosure.

Consistent with some embodiments, method 7510 includes accessing a data structure associating a plurality of non-lip facial skin micromovements with control commands (step 7516). The data structure may include any collection of data values and relationships among them. For example, a data structure may contain correlations (i.e., associations) of facial skin micromovements with words, phonemes, or gestures which may correspond to one or more control commands, as described elsewhere in this disclosure.

Consistent with some embodiments, method 7510 includes identifying in the data structure a specific control command associated with the specific signals associated with the specific non-lip facial skin micromovements (step 7518). For example, a lookup may be performed in the data structure for particular commands associated with the detected facial skin micromovements to identify the specific control command, as described elsewhere in this disclosure.

Consistent with some embodiments, method 7510 includes executing the specific control command (step 7520). For example, the control command may be executed by processing device 400 of speech detection system 100.

The embodiments discussed above for performing control commands based on facial skin micromovements may be implemented through a non-transitory computer-readable medium such as software (e.g., as operations executed through code), as methods (e.g., method 7510 shown in FIG. 75), or as a system (e.g., speech detection system 100 shown in FIGS. 1-3). When the embodiments are implemented as a system, the operations may be executed by at least one processor (e.g., processing device 400 or processing device 460, shown in FIG. 4).

As described elsewhere herein, some disclosed embodiments of a system for detecting neuromuscular activity involve providing an approach for detecting skin micromovements. The detection of skin micromovements may be based on receiving light reflections from the surface of the skin of an individual. In some embodiments, the technology may enable early detection of a medical condition (e.g., Parkinson's disease) through the detection of changes in neuromuscular activity over time. Specifically, some symptoms of the medical condition may be determined from deviation of skin micromovements to determine neuromuscular activity and comparing to a baseline of neuromuscular activity. A system for detecting neuromuscular activity may be configured to detect neuromuscular activity through the detection of skin micromovements such that the system may be capable of determining changes over time that may indicate a possible medical condition.

In some disclosed embodiments, the detection or diagnosis of a condition of a subject may be determined by monitoring or detecting micromovement of facial muscles. The determination may be based on a comparison of detected micromovements. For example, the determination may be based on a comparison between skin micromovements detected for different sides of the face and/or between skin micromovements detected for the same location on the face at different points in time.

In some disclosed embodiments, the extent of disease progression or damage from the medical condition may be determined. For example, a subject's condition may be detected and/or monitored after the subject may have experienced an event such as a stroke, Bell's palsy, or other events which may affect the subject. The event may have an asymmetrical impact on the subject. In such cases, a sensing device may be used for monitoring/detecting muscle micromovements on both sides of the face and comparing said muscle micromovements. The comparison and differences between the facial muscle micromovements of each side of the face may be used to determine the extent of damage, as well as monitor deterioration or improvement in the subject's condition. As a difference in facial muscle micromovements may be determined and may be above a certain threshold, an indication of an illness/condition or episode may be generated. An increase in a detected deviation over a period of time (e.g., difference) may provide an indication of the condition deteriorating, and a decrease in the difference may be an indication of improvement. A decrease in the difference may in certain cases indicate a deterioration when the decrease in the difference may be as a result of the decreasing functionality of the stronger side of the face. In other embodiments, detection may only occur on one side of the face. Even in such a situation, a data structure might store correlations between patterns of muscle movement and indicators of a neuromuscular condition for comparison with detected facial skin micromovements, to thereby identify, predict, or analyze a neuromuscular disorder.

In some disclosed embodiments, the skin micromovements may be detected on other parts of the body. For example, a wearable or non-wearable device may receive light reflections indicative of skin micromovements on the neck, chest, wrist or any other part of the body that may provide information consistent with some disclosed embodiments. It is to be appreciated that the advantages of early detection in determining deviations or trends of changes in neuromuscular activity of any part of the body of a subject related to medical, physical, physiological and other type of conditions experienced by a subject may allow an earlier treatment of the detected condition. Thus, in some embodiments, the detection of medical conditions may occur in parallel with other functionality described herein. For example, while supporting silent speech or any of the other functions described herein, medical condition detection features my operate in the background, checking for signs of a potential neuromuscular condition.

Some disclosed embodiments involve detecting changes in neuromuscular activity over time. Detecting changes in neuromuscular activity over time refers to monitoring and analyzing signals indicative of variations in activity of the muscles and nerves in the body over a period of time. The signals may be detected using various techniques such as optical sensing of skin micromovements, electromyography (EMG) or electroencephalography (EEG). For example, as described and exemplified elsewhere in this disclosure, a wearable device may receive light reflections from the surface of the skin of an individual. Based on the detected light reflections, neuromuscular activity may be detected and monitoring and analyzing a plurality of detected light reflections over time may allow for changes in neuromuscular activity to be detected over time.

Some disclosed embodiments involve establishing a baseline of neuromuscular activity from coherent light reflections associated with historical skin micromovements. A "baseline" refers to a reference point (or range of values) for comparison purposes. For example, a baseline can be determined from historical data of the subject individual, historical data of others, and/or both. A baseline may represent a normative situation. In other words, a baseline of neuromuscular activity may refer to values representing normal neuromuscular activity. The values may be derived by collecting data in the form of signals based on historical light reflections from the subject individual, from others, and/or from both. That baseline can be used for comparison purposes as current signals based on light reflections are received. If current signals stray from the baseline, the deviation may be an indication of a non-normative change in neuromuscular activity. Using historical data from others, abnormal patterns of neuromuscular activity by be associated with one or more medical conditions. Those associations (e.g., correlations) may be stored in a data structure for comparison purposes.) In other disclosed embodiments, a goal may be to identify changes in neuromuscular activity over time, without correlating the changes to a particular disease or abnormality. In such situations, an embodiment may not involve storing correlations in a data structure.

In some disclosed embodiments, establishing a baseline of neuromuscular activity may refer to making one or more initial measurements of skin micromovements associated with neuromuscular activity and determining one or more initial measurement values that may be used for comparison with one or more subsequent measurement values obtained over a period of time to determine if there has been a change. In other embodiments, the baseline may change or refine over time based on data received from the individual and/or others. For example, as people age, there may be normal changes in neuromuscular activity, and if so, the baseline may move accordingly.

Measurements of neuromuscular activity associated with skin micromovements may be made using light reflections to detect movements of the body as described and exemplified elsewhere in this disclosure. As described elsewhere herein, the term light reflections may refer broadly to any form of data retrieved from at least one light detector in response to the light reflections from the surface of an object. In embodiments related to detection of changes in neuromuscular activity, the light reflections may be from the face or any other portion of an individual's body. For example, the reflections may be collected using a head mountable device as described herein, or via any other device that is worn or not worn. For example, a coherent light source may be aimed at one or more skin areas during a diagnostic period (such as a visit to a medical professional) and neuromuscular activity signals may be collected. The medical professional may have access to a data structure correlating light reflections to disorders, and a comparison may be used for diagnostic purposes. In one example, the correlations may vary based on the portion of the body from which the light reflections are collected. The medical professional may collect reflections from various differing areas of the body and the sets of reflections might be collectively used to determine the potential existence of a disorder. In other examples, differing portions of the body may correlate with differing disorders.

Consistent with some embodiments, the at least one light detector may measure any form of reflection and of scattering of light. In some disclosed embodiments, the at least one light detector may be configured to output associated reflection signals determined from detected coherent light reflections. The term "coherent light" may be understood as described and exemplified elsewhere in this disclosure. Coherent light reflections may broadly refer to coherent light reflected from the surface of an object. Consistent with some disclosed embodiments, the at least one detector may be configured to detect coherent light reflections from the one or more portions of the skin of the individual. It is to be appreciated that coherent light reflections may achieve high-sensitivity optical detection under strong background light conditions therefore using coherent light to detect skin micromovements may be advantageous in some disclosed embodiments.

By way of a non-limiting example, a wearable device, such as an earpiece with an integrated optical sensor, may derive information about a surface of the body (e.g., facial skin movements or micromovements) from coherent reflection signals received by the at least one light detector. Further, the wearable device may include at least one processor that may perform a light reflection analysis of the received coherent light reflections. The light reflection analysis may result in the detection of neuromuscular activity (e.g., facial skin micromovements). A baseline of neuromuscular activity may be established based on one or more measurements of skin micromovements made by the wearable device. Thus, the wearable device may store a record of historical facial skin micromovements to establish the baseline of neuromuscular activity.

Some disclosed embodiments involve establishing the baseline from historical signals representing prior coherent light reflections associated with the individual. "Historical signals" may refer broadly to a stored record of previously detected sensor data. In some disclosed embodiments, the historical signals may consist of sensor data from previously detected coherent light reflections. The historical signals may correspond to prior detected coherent light reflections received from the surface of the skin of the individual. In some disclosed embodiments, the historical signals, based on the coherent light reflections, may establish a baseline to be used for comparison over a period of time to look for changes when comparing current detected coherent light reflections to the historical signals. As described and exemplified elsewhere in this disclosure, the coherent light reflections may be used to detect the intensity of skin micromovements from the surface of the skin of the individual. Consistent with disclosed embodiments, the baseline may be established based on the measurements of the skin micromovements of the individual.

By way of a non-limiting example, the individual may use a wearable device to measure coherent light reflections to detect skin micromovements to create a baseline from historical signals. At a future time, the individual may use the wearable device to measure coherent light reflections based on skin movements to capture current signals. A comparison of the signals obtained at the future time to the baseline historical signals of the individual may allow for an analysis over a period of time to detect changes in the condition of the individual. For example, changes to the neuromuscular activity of the individual from the historical signals to the signals obtained at the future time may be indicative of a medical condition detectable due to the change in measurements. In one example, the skin micromovements may be facial skin micromovements and the change in neuromuscular activity may be indicative of the condition of the individual. For example, Bell's palsy may be detected from detecting a change in facial skin micromovements over a period of time.

Consistent with some disclosed embodiments, the operations further include establishing the baseline from historical signals representing prior coherent light reflections associated with persons other than the individual. As discussed elsewhere herein, the baseline may be established based on historical signals representing past measurements of coherent light reflections from coherent light reflections associated with persons other than the individual. The baseline may be established based on the measurements of skin micromovements of a person other than the individual that experienced the medical condition. Thus, a person different than the individual may be used to create the baseline for comparison. For example, the baseline may be established based on historical signals detected for a first person (or group of persons) with a known medical condition, and be used for comparison with a second person to determine if the second person appears to be experiencing the same medical condition. The historical signals associated with the second person may be captured over a period of time before the second person experiences symptoms of the medical condition. Thus, the baseline may enable early detection a medical condition.

By way of a non-limiting example, facial droop may be described as the facial skin not appearing symmetrical wherein one side of the face may be lower than the other side of the face. For example, a person may exhibit facial droop when their eyelids and corners of the mouth appear to be pulled down, and the person may be unable to smile fully. Facial droop may indicate that the facial muscles are not working properly. Based on historical skin micromovements of one person that exhibits facial droop, a baseline may be established. For example, based on coherent light detections from both sides of the face, the position of the neuromuscular structure may be different. Further, neuromuscular activity may be different from one side of the face to the other side of the face. Or a deviant reading from one side of the face may be indicative of a condition affecting the other side of the face, another part of the body, or a global neuro-related issue. A second person may use a device to detect skin micromovements that may allow for a comparison to the historical skin micromovements of the first person or group of persons. Based on the comparison to that baseline, the second person may be diagnosed with facial droop (or may be provided with an indication of a potential disorder, and encouraged to contact a medical professional). Further, an early indication of facial droop may be detected, and subsequently an earlier medical treatment may be initiated based on the early indication. It is to be appreciated that an advantage to using the historical signals from others to diagnosis a condition is that there may not need to be historical signals of the subject individual (second person) on record to make a diagnosis.

Some disclosed embodiments involve receiving current signals representing coherent light reflections associated with current skin micromovements of an individual. Receiving current signals may refer to receiving reflection signals corresponding to light reflected from skin micromovements of an individual. In some disclosed embodiments, the light reflected from the skin of the individual may be received by a light detector which may generate signals representing coherent light reflections. "Current signals" refers to sensor data (or derivatives of sensor data) received after the baseline is established. As described and exemplified elsewhere in this disclosure, at least one detector may be configured to detect light reflections from the one or more portions of the skin of the individual in present time. Consistent with some embodiments, the at least one detector may detect coherent light reflections. The detected coherent light reflections may be detected in at a time different from a time when the initial facial skin micromovements were determined. Further, the detected coherent light reflections may be associated with current skin micromovements of the individual. For example, a light reflection analysis may determine locations and intensity of the skin micromovements in the present time for a region of skin on the body of the individual. The received current skin micromovements may be compared to baseline historical skin micromovements to determine a change in neuromuscular activity of the individual over the time period between measurement of the historical signals and measurement of the current (e.g., present time) signals.

By way of an example, an individual may use a wearable device including an optical sensor that detects coherent light signals from the surface of the skin. The wearable device may include, but is not limited to, an earpiece, a smart watch, a heart rate monitor, a health band, a ring, a headset, a pulse oximeter, a biomedical implant, a skin patch with optical sensing and any other device that includes an optical sensor that may be worn by the individual. The optical sensor included in the wearable device may capture coherent light reflections representing current signals. Historical signals from previously captured coherent light reflections may provide a baseline and based on the comparison of current signals to historical signals, at least one processor may determine changes in neuromuscular activity over time.

Consistent with some disclosed embodiments the historical signals are based on skin micromovements that occurred over a time period of more than a day. "Time period" may broadly refer to length of time during which an activity occurs or a condition remains. The time period may be measured either in seconds, minutes, days, or in many years, depending upon the nature of the activity of condition being considered. A time period of more than a day and refers to a collection period greater than 24 hours. For example, historical signals based on skin micromovements may be detected and recorded over a time period of more than one day prior to the current time. The signals may be collected periodically over the time period (e.g., samples taken every few seconds, minutes, hours or days. Thus the collection may occur continuously, or may occur at periodic times over the time period. Moreover, the historical signals may be collected from more than one individual, and in some instances may be based on populational data.

In one example, a wearable earpiece including an optical sensor may detect facial skin micromovements for an individual and record the historical signals creating a baseline for the individual. It is to be appreciated that the detection of signals, storage of historical signals and establishment of the baseline based on the historical signals may be based on periodic sampling and as such, the baseline may change over time based on the history of captured signals. For example, the baseline of skin micromovements may be set to one day prior and additional skin micromovement samples may be captured once per hour. When a new sample of skin micromovement signals is captured, the baseline may change to reflect the new historical signals that are now one day prior (e.g., the sample taken 24 hours previously). In some examples, the baseline may be based on an average of historical signals of skin micromovements captured more than one day earlier.

By way of a non-limiting example, early detection of a stroke is critical to minimizing the damage caused by the stroke. Symptoms of a stroke may be detectable using the detection of skin micromovements. Symptoms may include numbness or weakness in the face, arm, or leg, especially on one side of the body. Detecting the condition of an individual on two consecutive days may be provided via a method that establishes a baseline based on signals captured on the first day (e.g., historical signals) and compares current signals captured on the second day to the baseline therefore allowing early detection based on a change in neuromuscular activity on the time period of one day. Further, multiple baselines may be created. For example, the current signals may be compared to baselines created each day for 30 consecutive, previous days. An analysis of current signals to multiple baselines for some time period may determine a condition based on the progression of changes in skin micromovements over an extended period of time. In another example, light reflections from skin may be used to monitor a stroke patient's (or any patient's) progress. Thus, a patient in a hospital or at home may use a device to collect skin reflections and those reflections may be conveyed to a medical professional (e.g., via wired or wireless transfer such as over the internet or other network) for analysis by a medical professional.

Consistent with some disclosed embodiments, the historical signals are based on skin micromovements that occurred at least a year before receipt of the current signals. A time period of at least a year may include an interval of time greater than one calendar year. For example, historical signals based on skin micromovements may be detected and recorded over a time period of more than one year prior to the detection of skin micromovements corresponding to the receipt of current signals. Again, the signals need not be collected continuously for a year, but may be collected at periodic intervals over the course of more than a year.

By way of a non-limiting example, an individual may have a physical examination administered by a doctor once every year. A medical device may be used at the physical examination of the individual to capture signals indicative of skin micromovements associated with neuromuscular activity. Over several years, repeated use of the medical device at subsequent physical examinations may allow a baseline of neuromuscular activity to be captured for the individual based on one or more historical signals and may allow current signals to be compared to the baseline. In some examples, changes in neuromuscular activity may be detected from year to year or over the course of several years and the current signals compared to the baseline may allow a diagnosis of a medical condition or allow a determination of changes related to the aging process. For example, prediction of the aging process may allow an assessment of aging-associated diseases. A medical device capable of imaging using coherent light reflections based on skin micromovements may be used to create a set of reliable aging markers over time. The capture of historical signals to be compared with the capture of current signals may allow an assessment of conditions related to the again process.

Figure 76:
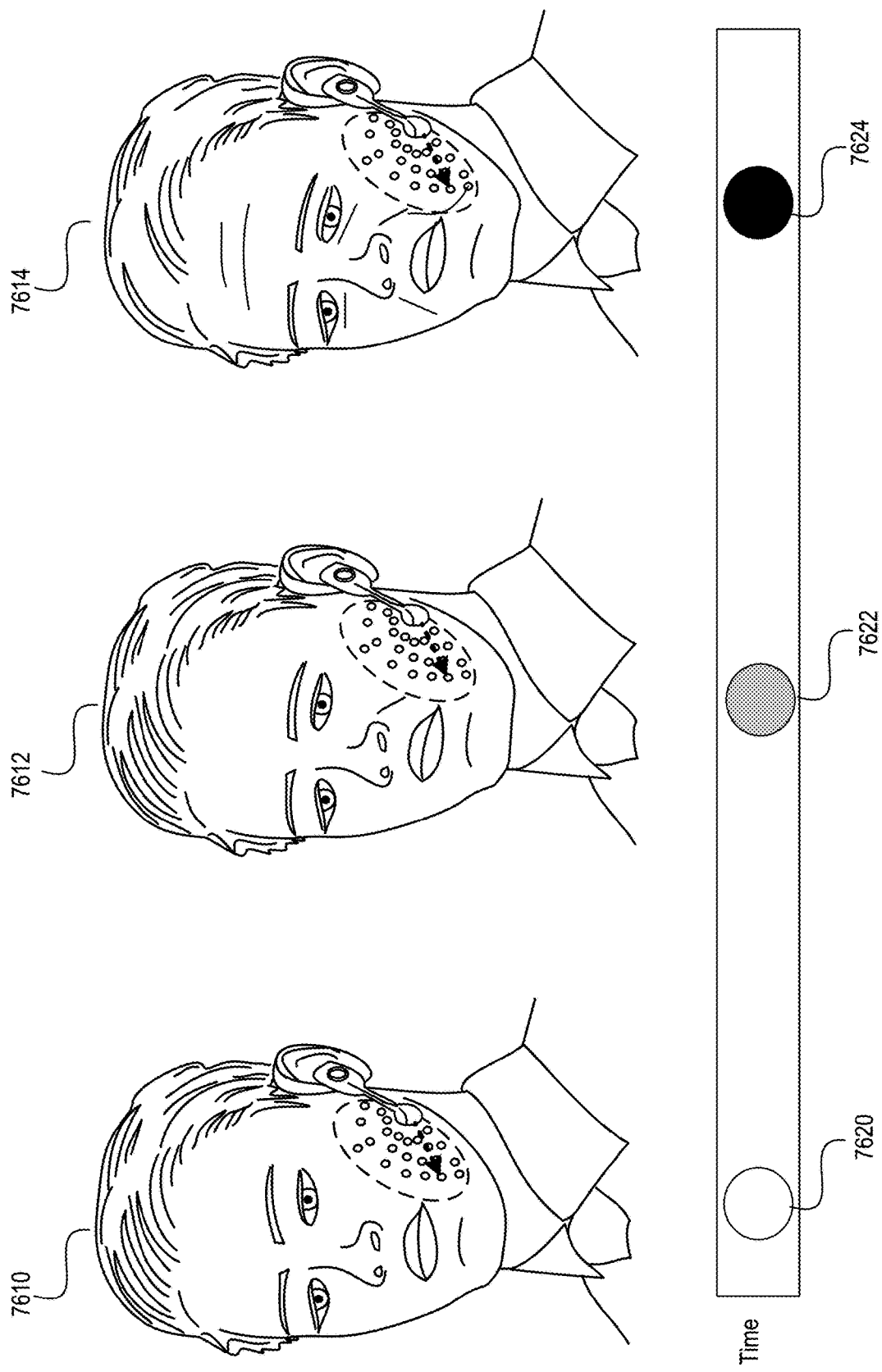
FIG. 76 is a schematic illustration of an exemplary timeline of the progression of a medical condition that may be detectable by measuring skin micromovements over time, consistent with some embodiments of the present disclosure.

FIG. 76 shows a system block diagram of an example of a timeline of changes in neuromuscular activity that may be detected by the system. It is to be noted that FIG. 76 is a representation of just one embodiment, and it is to be understood that some illustrated elements might be omitted and others added within the scope of this disclosure. In the depicted embodiment, individual 7610 may use a wearable device 7616 which may detect a change in facial expression of the individual 7610 over time. For example, at time 7620 on the timeline, the individual 7610 may exhibit a baseline of neuromuscular activity wherein they may not exhibit a detectable condition (e.g., normal neuromuscular activity). At a future point in time 7622, individual 7612 may exhibit a progression of a medical condition in which the individual 7612 may begin to exhibit facial droop. It is to be appreciated that wearable device 7616 may be used to determine a baseline from coherent light reflections used to determine skin micromovements in the facial region. Wearable device 7616 may then be used at time 7622 to detect skin micromovements in the facial region of the individual 7612 that exhibits the change in condition. At a later future point in time 7624, individual 7614 may be further along in the progression of the medical condition as detected by wearable device 7616 via coherent light reflections to detect skin micromovements in the facial region of individual 7614. As shown, individual 7614 may exhibit a later stage of facial droop.

Consistent with some disclosed embodiments, the operations further include receiving the current signals from a wearable light detector while the wearable light detector is worn by the individual. As described and exemplified elsewhere in this disclosure, a current signal (e.g., signal received at a current time) may be detected by a wearable device. In some disclosed embodiments, the wearable device may be a wearable light detector. In real time or near real time as the light detector senses light reflections, associated signals may be sent to a processor. In this way, current signals may be received while the light detector is worn. Wearable light detector may be described broadly as any type of electronic device that may be designed to be worn on the body of an individual that may include at least one light detector to receive light reflections from the surface of the body of the individual. Light reflections received in present time are the current signals. Further, the wearable light detector may include at least one processor to perform a light reflection analysis of the received light reflections. By way of a non-limiting example, a heart rate monitor may be designed as a strap (e.g., chest strap) that includes an optical sensor that may detect heart rate in real time based on skin micromovements detected by a light reflection analysis of received light reflections. In some examples, the optical sensor detecting heart rate may help an individual monitor and control exercise intensity. The strap may be designed such that the optical sensor may be worn in a position to detect heart rate based on skin micromovements caused by the heartbeat of the individual using the wearable light detector. It is to be appreciated that the wearable light detector may have the advantage of higher localization accuracy and tracking when detecting current signals.

Consistent with some disclosed embodiments, the operations further include controlling at least one wearable coherent light source in a manner enabling illumination of a portion of a face of the individual, and wherein the current signals are associated with coherent light reflections from the portion of the face illuminated by the at least one wearable coherent light source. Wearable coherent light source may refer to a body worn light emitter including a coherent light source as described and exemplified elsewhere in this disclosure. The coherent light may be projected from the wearable coherent light source towards the surface of an object (e.g., surface of the body of an individual). In some disclosed embodiments, the wearable coherent light source may be controlled, as described elsewhere in this disclosure, to project light in a manner enabling illumination of a portion of the face of the individual. As described and exemplified elsewhere in this disclosure, a wearable earpiece with an integrated optical sensor, for example, may include a coherent light source and may project coherent light to illuminate a portion of the face of an individual.

Consistent with some disclosed embodiments, the coherent light projected to illuminate the portion of the face of the individual may cause coherent light reflections from the portion of the face of the individual. Current signals (e.g., signals generated or received at a present time) associated with the coherent light reflections may be determined for the portion of the face illuminated by the wearable coherent light source. By way of a non-limiting example, as illustrated in FIG. 1, optical sensing unit 116 of the wearable device depicted by speech detection system 100 may include one or more laser diodes capable of projecting light 104 towards a facial region 108 of individual 102. The projected light 104 may be coherent light and may be projected in a manner to illuminate a portion of the facial region 108 of the individual. The optical sensing unit 116 may receive coherent light reflections from the illuminated portion of the facial region 108. At least one light detector of the speech detection system 100 may determine current signals from the coherent light reflections.

Consistent with some disclosed embodiments, the current skin micromovements correspond to recruitment of at least one of a zygomaticus muscle, an orbicularis oris muscle, a genioglossus muscle, a risorius muscle, or a levator labii superioris alaeque nasi muscle. Current skin micromovements may correspond to locations of interest on the skin from which light reflections may be detected to determine the skin micromovements at those locations. The locations of interest may correspond to anatomical locations associated with recruitment of one or more particular muscles on an individual. The one or more muscles may include muscles in the facial region of the individual. For example, the one or more muscles may include at least one of a zygomaticus muscle, an orbicularis oris muscle, a genioglossus muscle, a risorius muscle, or a levator labii superioris alaeque nasi muscle. The muscles in the facial region of the individual correspond to muscles controlling skin micromovements of the cheek, nose, lips, mouth, tongue or other muscles in the facial structure of the individual. By way of a non-limiting example, facial expression may be a result of muscle recruitment of the risorius and levator labii superioris alaeque nasi muscles. As such, detected facial skin micromovements may be indicative of changes in facial expressions of the individual. By way of a non-limiting example, abnormal facial expressions may be detectable by capturing historical signals to create a baseline. In a present time, facial expressions at the present time may be detected by capturing current signals. A comparison of the current signals with the baseline based on historical signals may allow a determination of whether the individual may be exhibiting abnormal facial expressions at the present time. In some examples, abnormal facial expressions may occur as a result of conditions that damage the nerves to the face, for example Bell's palsy or facial paralysis. Damage to the brain, for example as may be caused by a stroke, may cause impaired movement, including changes in facial expressions. Patients with a number of psychiatric conditions may display abnormal facial expressions. Facial tics, such as those that occur in Tourette syndrome, are one form of abnormal facial expressions. It is to be appreciated that changes that may be determined by detection of current skin micromovements corresponding to recruitment of at least one of the muscles in the facial region of the individual may provide an early predictor of a condition developing in the individual allowing for an earlier medical intervention.

Consistent with some disclosed embodiments, the operations further include receiving the current signals from a non-wearable light detector. A non-wearable light detector may refer to a device that includes a light detector that may not be worn on the body of an individual. Examples of non-wearable light detectors may include an optical body scanner (e.g., 3D body scanner), an optical scanning wand, an entry gate with an optical scanner, a LiDAR sensor and any other type of light sensor not body worn and capable of detecting light reflections from the surface of an object. In some disclosed embodiments, the skin of the body of an individual may be the object. Further, the non-wearable light detector may generate current signals based on light reflections from the body/skin of the individual at the present or current time.

Early detection of Parkinson's Disease may be aided by a non-wearable screening optical sensing device. Traditional diagnosis of Parkinson's Disease may be based on clinical examinations which require several doctor visits by the patient, therefore consuming both time and resources. A non-wearable screening system based on a remote optical sensing device to capture skin micromovements associated with Parkinson's Disease using the non-wearable optical sensors may facilitate the diagnosis of Parkinson's Disease at an early stage. For example, at an entry gate at a doctor's office, a patient may walk through a scanner, similar to a security scanner at the airport. As the patient walks through the scanner current signals detecting skin micromovements, at the present time, may be captured. In some examples, the analysis of the current signals may provide information associated with symptoms of Parkinson's Disease by comparing current signals to historical signals captured for the patient during an earlier visit. In the example, a progression of deteriorating symptoms may be determined over the several patient visits allowing for an earlier intervention with treatment. It is to be appreciated that non-wearable sensors may be less intrusive and may monitor activities in real-life, natural environment of the individual.

Consistent with some disclosed embodiments the coherent light reflections associated with current skin micromovements are received from skin other than facial skin. Received from skin other than facial skin may refer to coherent light reflections received by a light detector from skin on parts of the body of an individual other than the face. As described and exemplified elsewhere in this disclosure, the received coherent light reflections may determine current skin micromovements (e.g., micromovements occurring at the current time). The current skin micromovements may be determined by coherent light reflections detected by a wearable or a non-wearable light detector as described and exemplified herein. By way of an example, a wearable device, such as a smart watch, may detect current skin micromovements on the wrist of the individual. In another example, a non-wearable device, such as a 3D optical scanner that an individual enters similar to an MRI chamber. The 3D optical scanner may project coherent light to the surface of the skin of a body and may receive coherent light reflections associated with current skin micromovements back from the skin on the surface of the body of the individual. In a full body scan, the 3D optical scanner may determine current skin micromovements from a plurality of locations on the body including but not limited to facial skin of the individual.

Consistent with some disclosed embodiments, the skin other than facial skin is from a neck, a wrist, or a chest of the individual. The skin other than facial skin may refer to skin on any area of the body of an individual other than facial skin wherein skin micromovements may be detected, such as the neck, wrist, or chest. The signals may be received from any portion of the body, and may be targeted in some cases to areas of the body appearing to exhibit symptoms of a neuro disorder. In one example, an optical speckle field may be generated by moving red blood cells when the neck may be illuminated with coherent light. In another example, reflections from light spots projected on the neck may be used to detect a disorder. In another example, a user may position their wrist over an optical sensor wherein the optical sensor may detect skin micromovements of the inside of the wrist allowing a determination of some vital signs or allowing a determination of neuromuscular activity of the wrist.

Some disclosed embodiments involve identifying a deviation of the current skin micromovements from the baseline of neuromuscular activity. A "deviation" in this context refers to a departure or divergence from the baseline. For example, the deviation may be from a standard, norm, expectation, or reference point. The deviation may be based on a threshold. For example, some deviations may be considered within a norm, and therefor might not be considered significant. In other examples, an isolated deviation which does not repeat may not be considered significant. In yet other examples, deviations that occur periodically may be considered significant. The deviation may be expressed in any form. For example it can be a difference, ratio, absolute value, root mean square, or may be based on any other statistical or mathematical function determining a relationship between the observed value and the expected value of a quantity. Identifying a deviation of a measurement may refer to making a current measurement, comparing the current measurement to a representation of historical measurements and determining the difference. A representation of historical measurements may be one measurement or a statistical analysis of a plurality of measurements (e.g., mean, median). A baseline may be established based on the representation of historical measurements. For example, the baseline may be based on the average of a plurality of historical measurements. In some disclosed embodiments, the measurements may correspond to skin micromovements. As described and exemplified elsewhere in this disclosure, skin micromovements may be associated with neuromuscular activity. In some disclosed embodiments, a baseline of neuromuscular activity may be determined based on measurements of skin micromovements over a period of time. A measurement of current skin micromovements may determine current neuromuscular activity. The current neuromuscular activity may be compared to a baseline of neuromuscular activity. A deviation may be identified corresponding to a change detected in current neuromuscular activity versus the historic neuromuscular activity of an individual.

In one example, the identified deviation may be symmetrical (e.g., differences detected between two sides of the face). For example, when a patient has a stroke, the differences between the similar muscles on the left and right sides of the face may provide an indication of the extent of damage caused by the stroke Furthermore, the comparison can help determine deterioration or improvement (after following therapy).

Some disclosed embodiments involve outputting an indicator of the deviation. Outputting an indicator refers to generating or producing a signal, symbol, or value that serves as an indicator or representation of the deviation. For example, outputting an indicator may include displaying or sending a signal that may provide information about a deviation. The indicator may be a message presented to the individual or to someone else, such as a medical professional. The indicator may be output for receipt and ultimate presentation via a visual display, audio presenter, or any other type of interface that a user, agent, or computer may perceive. Visual displays may include things like displaying images, videos, graphics, one or symbols, icons, charts and/or text on a display device that may be seen by a user or an individual. Audio outputs may include sounds, sounds representing a text to speech conversion, alerts and/or music that may be played using a speaker, headphone, or other type of audio output device so that the sound may be heard by the user or the individual. Additionally, information associated with outputting an indicator may have various formats, such as analog or digital signals, and may be connected to different types of devices, such as computers, televisions, medical devices, monitors, tablets, mobile phones or other types of devices with user interfaces to receive information. The output may be indicative of a deviation that may represent a change in a measurement over a period of time. Consistent with some disclosed embodiments, the deviation may be indicative of a change in neuromuscular activity of a period of time. For example, one or more historical measurements of neuromuscular activity may be stored in memory. A current measurement of neuromuscular activity may be made and compared to the one or more historical measurements of neuromuscular activity. The deviation determined from the difference in measurements may provide an indication of a change in the condition of the individual that the measurements were taken. An output indicative of the deviation of neuromuscular activity that may correlate to symptoms of a condition of the individual may be output to a medical professional.

By way of a non-limiting example, a medical device designed to detect neuromuscular activity may be used to create a historical record of neuromuscular activity for a patient. The medical device may measure current neuromuscular activity. One or more processors may analyze the deviations detected between current neuromuscular activity and historical neuromuscular activity may identify a condition or predict a condition that may be developing in the patient. Based on the analysis of the deviations, the one or more processors may output an indicator of the deviation. For example, the one or more processors may generate a report identifying the deviations in neuromuscular activity over time that may be indicative of symptoms.

Figure 77:
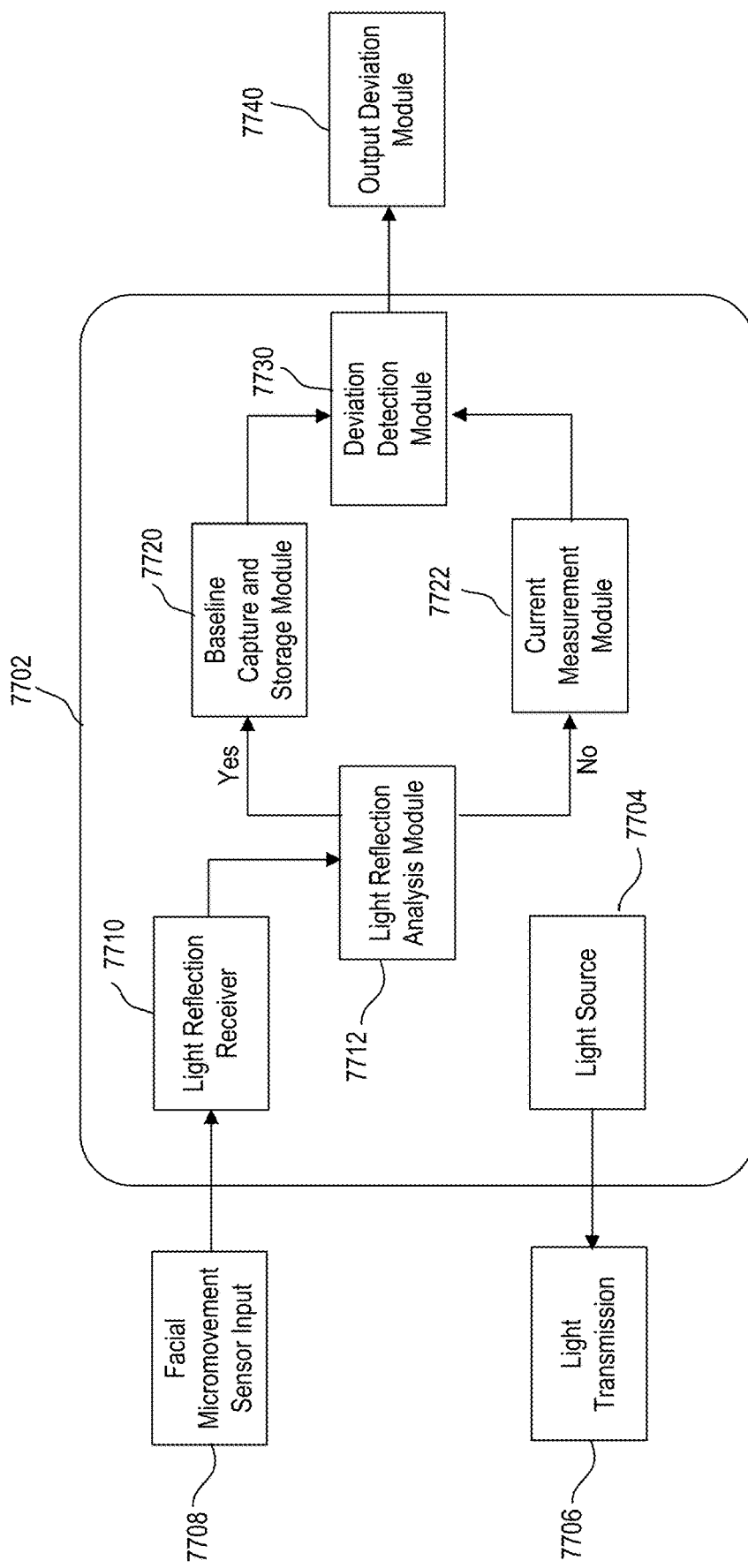
FIG. 77 is a block diagram of an exemplary system capable of detecting changes in neuromuscular activity over time, consistent with some embodiments of the present disclosure.

FIG. 77 shows a system block diagram of an exemplary system capable of detecting changes in neuromuscular activity over time. It is to be noted that FIG. 77 is a representation of just one embodiment, and it is to be understood that some illustrated elements might be omitted and others added within the scope of this disclosure. It is to be understood that references in the following discussions to a processing device may refer to processing device 400 of speech detection system 100 and processing device 460 of remote processing system 450 individually or collectively. Accordingly, steps of any of the following processes associated with modules may be performed by one or more processors associated with speech detection system 100. Further, the following modules and associated processes may be implemented in hardware (e.g., in a special purpose processor, ASIC, FPGA and other types of programmable hardware) in software or in a combination of both. In some disclosed embodiments, each module may be separate from other modules and in other embodiments some or all modules may be combined into an integrated module. Data, messages, signals and any other information may be passed between modules (e.g., as depicted by arrows in FIG. 77) to implement the disclosed embodiments specified herein. In the depicted embodiment, neuromuscular activity detection system 7702 comprises light source 7704, light reflection receiver 7710, light reflection analysis module 7712, baseline capture and storage module 7720, current measurement module 7722 and deviation detection module 7730. Light source 7704 may generate a light output (e.g., coherent light output) for transmission 7706 to illuminate a region of skin on the body of an individual. Transmission 7706 may include light projected toward the region of skin on the surface of the body to illuminate the region and may cause reflections signals from the surface of the body. Light reflection receiver 7710 (e.g., light detector) may receive reflection signals corresponding to light reflected from the of the individual at skin micromovement sensor input 7708. Based on the measured deviation between the current measurement and the baseline determined by historical measurements, the system may output an indication of deviation via the output deviation module 7740. The output deviation module 7740 may identify a deviation of the current skin micromovements versus a baseline of neuromuscular activity that may be based on historical skin micromovements. As described and exemplified in this disclosure, the change in neuromuscular activity over a period of time that may be indicated by the identified deviation, may be indicative of a change in the physical or health condition of an individual. It is to be appreciated that skin micromovements may be sensed by any sensing mechanism described in disclosed embodiments herein.

Light reflection analysis module 7712 may receive input from light reflection receiver 7710 including light reflection data indicative of neuromuscular activity of the individual. Light reflection analysis module 7712 may determine that detected skin micromovements may be associated with neuromuscular activity. Further, neuromuscular activity, based on historical capture of detected skin micromovements, may be used to create a baseline of neuromuscular activity over a period of time. The result of the comparison to the baseline may be to cause an indicator of the deviation to be output to a user, such as an individual, medical professional, storage record or other alert based on the indicator of the deviation. As described and exemplified in this disclosure, the output to the user may be implemented through displaying or sending a signal that may provide information based on the deviation and related one or more conditions through visual displays, audio outputs or any other type of output that a user may perceive.

Consistent with some embodiments, neuromuscular activity detection system 7702 may include establishing the baseline using historical signals via baseline capture and storage module 7720 that may represent prior coherent light reflections associated with the individual or persons other than the individual. The baseline capture and storage module 7720 may create a baseline based on the historical signals and store the baseline for comparison when current signals are received. The baseline capture and storage module 7720 may capture and store historical measurements. The baseline capture and storage module 7720 may perform a statistical analysis of a plurality of historical measurements (e.g., mean, median). A baseline may be established based on the statistical analysis of historical measurements. It is to be appreciated that the historical signals may be based on skin micromovements that may have occurred over a time period of more than a day prior, more than a year prior or any amount of time prior to the collection of current signals that may be consistent with the application. Consistent with some disclosed embodiments, operations may include receiving the current signals from a wearable light detector while the wearable light detector is worn by the individual. For example, a user may wear a smart watch including an optical sensor that may detect skin micromovements on the wrist of the individual. In another example, a wearable coherent light source (e.g., light source 7704) may be controlled in a manner enabling illumination of a portion of a face of the individual and wherein the current signals are associated with coherent light reflections from the portion of the face illuminated by the wearable coherent light source. In some disclosed embodiments, the current skin micromovements detected by light reflection receiver 7710 may correspond to recruitment of at least one of a zygomaticus muscle, an orbicularis oris muscle, a genioglossus muscle, a risorius muscle, or a levator labii superioris alaeque nasi muscle. In some disclosed embodiments, the system may receive the current signals from a non-wearable light detector (e.g., light reflection receiver 7710). In some disclosed embodiments, the coherent light reflections associated with current skin micromovements are received from skin other than facial skin such as from the neck, the wrist of chest of the individual.

Some disclosed embodiments involve receiving additional signals associated with skin micromovements of the individual during a period of time prior to the current skin micromovements, determining a trend of changes in the neuromuscular activity of the individual based on the current signals and the additional signals, and wherein the indicator is indicative of the trend of changes. A "trend" may refer broadly to a general direction (e.g., increase, decrease, or no change) in which something is developing or changing. A trend of changes may refer to the direction that a change of something is developing. For example, an analysis that may indicate a trend of changes may include a quantitative review of data that shows changes in data (e.g., increase, decrease, or no change) over a period of time. In some disclosed embodiments, the trend of changes in neuromuscular activity may refer to measurements of neuromuscular activity over a period of time indicating an improvement, deterioration, or no change in neuromuscular function over the period of time. For example, a trend of changes detected in neuromuscular activity over time may indicate a progression in the medical condition of the individual. The system may capture a data series associated with neuromuscular activity that includes receiving additional signals during a period of time prior to the measurement of current signals. The data series including additional signals and current signals associated with skin micromovements of the individual may be analyzed to evaluate changes in neuromuscular activity over a period of time. The statistical analysis to identify a trend of changes in the data series may include one or more of a simple moving average, an exponential moving average, a moving median, a slope, or any other analysis of the data that allows a determination of a trend (e.g., increase, decrease, no change over time) in the data. Based on the determination of the trend, the indicator may be indicative of the trend of changes. The indicator indicative of the trend may be output as described elsewhere herein.

By way of a non-limiting example, a patient with Parkinson's Disease may have a down or decreasing trend in neuromuscular activity over a period of time. Current signals (e.g., current skin micromovements) may be compared to additional signals collected over a period of time to evaluate the trend and predict the progression of the Parkinson's Disease. In another example, a patient in a trial for a new treatment for Parkinson's Disease may experience an up or increasing trend in some neuromuscular activity in response to the treatment. Determining the trend of changes of neuromuscular activity over time may help determine the effectiveness of the treatment.

Some disclosed embodiments involve determining a likely cause for the deviation of the current skin micromovements from the baseline of neuromuscular activity, and wherein the indicator is indicative of the likely cause. "Likely cause" may generally refer to a probable reason or explanation for a particular event, situation or outcome. Determining the likely cause may refer to analyzing information or data associated with the event, situation, or outcome to identify, detect, derive, or find the most probable reason or explanation for the particular event, situation or outcome. The likely cause may be determined with reference to a data structure storing correlations between signal patterns and particular disorders. When a match is found (e.g., either through a lookup or via an AI analysis) a likely cause may be determined. The likely cause may be expressed as a single likely cause, or may be expressed in the form of a probability. In some embodiments, a likely cause may involve identifications of a number of potential likely causes. In some embodiments where a number of likely causes are identified, the determined likely causes may be ranked in order of likeliness. Consistent with some disclosed embodiments, one or more processors may analyze the current signals and historical signals associated with skin micromovements of an individual to determine one or more most probable reasons or explanations for any deviations and/or changes in the skin micromovements over time. The determinations may be made based on current skin micromovements associated with current neuromuscular activity and comparing the current neuromuscular activity to a baseline of neuromuscular activity. The deviations (e.g., changes) may be compared to stored deviations to determine associated reasons based on historical records of similar deviations of skin micromovements over time. In some embodiments, one or more associated reasons may be determined through multiple matches to historical records. The matching reasons for the deviations may be ranked to find the most probable or most likely cause of the deviations. In some embodiments, a trained machine learning model may be used to determine a matching reason by presenting a vector representing the deviations to the model and determining from the output the likely cause of the deviation. Based on the determination of the likely cause of the deviation, an indicator that may be indicative of the likely cause may be generated. Based on the determination of the likely cause of the deviation, an indicator indicative of the likely cause may be generated, identifying the likely cause and any additional information associated with the likely cause of the deviation. For example, a deviation in skin micromovements may indicate the onset of ALS and additional information may include the amount of change in skin micromovements that may be correlated to the degree of progression of ALS in the individual.

By way of a non-limiting example, a pattern of deviations of skin micromovements indicative of a change in neuromuscular activity for an individual may correlate with a historical record of medical conditions. The pattern of deviations of skin micromovements may be associated with the pattern of change in neuromuscular activity. By matching the pattern of deviations of skin micromovements for the individual to a database of historical records of medical conditions and the progression of changes in neuromuscular activity over a period of time associated with the medical conditions, the likely cause of the deviations may be determined. For example, the likely cause of the deviations may be based on the correlation between the individual and one or more medical conditions exhibited by the skin micromovements matching historical records. As a result, a diagnosis or a report that may include an indicator that is indicative of the likely cause may be generated.

Some disclosed embodiments involve outputting an additional indicator of the likely cause for the deviation. As described and exemplified in this disclosure, outputting an indicator may generally refer to displaying or sending a signal or symbol that may provide information about a particular system or process. In some disclosed embodiments, a first indicator may indicate that the deviation may be indicative that the change occurred. The first indicator may provide a signal that the deviation may be an indicator of a trend of changes. For example, the first indicator may provide an indication that there may be a trend indicating a change in neuromuscular activity of an individual over a period of time. An additional indicator (i.e., second indicator) may indicate or identify the likely cause of the deviation. Thus, based on the determined likely cause of the deviation, the additional indicator may be generated to be displayed or sent as a signal. Returning to the example, the first indicator may provide an indication that a change in neuromuscular activity occurred and the additional indicator may provide an indication of the likely cause of the change in neuromuscular activity.

By way of an example, a stroke may cause a number of symptoms that may be identified by detecting skin micromovements and determining changes in neuromuscular activity (e.g., facial droop). An analysis of a data series including historical skin micromovements and current skin micromovements may determine, based on a deviation in the data, a first indicator that a change in neuromuscular activity may have occurred as detected by current measurements. A further analysis of the data may determine that the trend of change of the neuromuscular activity matches similar trend of changes of individuals that had a stroke. Thus, an additional indicator may be generated identifying that the individual may be having or may have had a stroke. In some examples, data may indicate subsets of individuals that have had a stroke in the past. The severity of the stroke may be identified by comparing the trend of change in neuromuscular activity to previous individuals. For example, based on the trend identified in the data as compared to previous individuals, a mild stroke versus a severe stroke may be diagnosed.

Some disclosed embodiments involve receiving data indicative of at least one environmental condition, and wherein determining the likely cause for the deviation is based on the at least one environmental condition and the identified deviation. Environmental conditions may include rain, snow, temperature, humidity, background illumination, wind, other speakers, an individual's physical activity level, breathing, sweating, makeup on the face region, change in the angle of the detector receiving signals, position, background noise, and any other environmental factor that may cause a variation in measurement. Receiving data indicative of at least one environmental condition may include receiving data from sensors capable of measuring the environmental conditions. The additional received data representing the at least one environmental condition may be used in addition to the deviation in determining the likely cause of the deviation. For example, an elevated ambient temperature measured at the time of the measurement of the skin micromovements may impact the identified deviation. The intensity of the skin micromovements may increase or decrease due to the ambient temperature and thus the determination of the likely cause of the deviation may be based at least partly on the measured ambient temperature level.

By way of a non-limiting example, a sensor may be used to determine the physical activity level of an individual. In some cases, activity level may increase the heart rate of the individual. The increase in heart rate of the individual may influence measurements of skin micromovements. In one example, current skin micromovements may increase in intensity during physical activity and further, detection of the heart rate may have a greater deviation due to the physical activity than if the individual may have at rest. Thus, the change in heart rate should be accounted for in determining the likely cause of the identified deviation.

Some disclosed embodiments involve receiving data indicative of at least one physical condition of the individual, and wherein determining the likely cause for the deviation is based on the at least one physical condition and the identified deviation. The physical condition of the individual may refer to the condition or state of the body or bodily functions, for example a physiological condition of the individual. Types of physical conditions may include but are not limited to conditions related to the health of the individual. Physical conditions related to the health of the individual may include high blood pressure, diabetes, heart disease, arthritis, asthma, good cardiovascular condition, flu, injury, being under the influence, tiredness, stress, and other types of medical conditions that may be detected or determined at a physical exam by a doctor. Receiving data indicative of at least one physical condition of the individual may include obtaining measurements related to the physical condition of the individual using a sensor or similar device that may gather data related to the physical condition of the individual. Examples of types of medical sensors that may detect a physical condition include but are not limited to electrocardiogram (ECG) sensors, blood glucose sensors, blood pressure sensors, pulse oximeters, breathalyzer and temperature sensors. Based on the at least one physical condition and the deviation over a period of time, the likely cause for the deviation may be determined.

For example, a likelihood of heart condition may be determined by a combination of two or more criteria. The first criterion may relate to the physical condition of the individual as may be determined from one or more medical sensors and include the heart rate and blood pressure of the individual. The second criterion may relate to neuromuscular activity of the individual as determined from coherent light reflections associated with current skin micromovements of an individual. Based on the combination of two or more criteria, the system may monitor a progression of heart disease over a period of time and provide a warning to a heart attack.

In some disclosed embodiments the likely cause corresponds to at least one physical condition that includes: being under an influence, tiredness, or stress. The physical condition of the individual may include the physiological state of the individual. The physiological condition of the individual may refer to the condition or state of the individual. Consistent with some disclosed embodiments, the physiological state may include but is not limited to being under the influence, tiredness, stress, illness an emotional condition or any other indicator of the condition of the individual. Tiredness or stress may influence skin micromovements based on changes to neuromuscular activity under those physical conditions. For example, deviations in neuromuscular activity based on tiredness may include decreased muscle strength, slower reaction times, and decreased coordination and therefore an analysis of the detected deviation may be indicative of tiredness. In some examples, the detected deviation may be entirely due to tiredness or stress. In some examples, the detected deviation may be enhanced or reduced due to the level of tiredness or stress experienced by the individual. In some disclosed embodiments, a determination of the likely cause of the at least one physical condition may be made based on data indicative of the physical condition. Further, received data from the detection of skin micromovements may be used to determine a deviation or trend of change of the physical condition of the individual. The data and deviation or trend of change may be further analyzed to determine the likely cause corresponding to the at least one physical condition determined through the analysis of the data and deviation or trend of data. In some embodiments, the determined physical condition may include at least one of being under an influence (e.g., of alcohol, drugs), tiredness or stress.

In some disclosed embodiments the likely cause corresponds to at least one health condition that includes a heart attack, Multiple Sclerosis (MS), Parkinson's Disease, epilepsy, or a stroke. "Health condition" may broadly refer to a state of physical or mental health. In some cases, the health condition of an individual may refer to a medical condition experienced by the individual. Consistent with some disclosed embodiments, the at least one health condition of the individual may relate to a medical condition such as a heart attack, a stroke, epilepsy, flu or other indicator of a change in the health of the individual. Consistent with some embodiments, the health condition of the individual may be indicative of a neurodegenerative disease. Neurodegenerative diseases may include such as conditions/illnesses as amyotrophic lateral sclerosis (ALS), Alzheimer's Disease, Multiple Sclerosis (MS), Parkinson's Disease and other diseases wherein the neuromuscular function may be affected. These neurodegenerative diseases may be characterized in the early stages by mild cognitive impairment (MCI). Early detection of such diseases may be a critical factor for successful treatment and impeding the progression of the disease. Often it may be difficult to detect MCI at the early stages, however changes in speech patterns and reduced vocabulary may be signs of early onset of MCI and such diseases. Hence, the detection of skin micromovements (e.g., facial skin micromovements) indicative of neuromuscular activity and an analysis of trends of change in neuromuscular activity over a period of time may be applied for detecting changes in speech patterns and reduced vocabulary. The deviations may be used to identify the likely cause of the health conditions by storing deviations associated with likely causes in a data structure then upon taking measurements, comparing current signals (e.g., current measurements) with historical signals (e.g., the entries in the data structure) to make a determination of likely causes of health conditions. In some disclosed embodiments, a machine learning model may be used by constructing an input indicative of current signals, inputting to a neural network trained on the machine learning model and evaluating the output to the neural network to determine if a likely cause may have been determined. These changes may be indicators for an individual to submit to testing to determine the causes for the changes. In the event that an underlying medical cause may be diagnosed, the individual may receive early stage treatment.

In some disclosed embodiments, the determining the likely cause of the health condition may further include determining the extent/depth of the state of unconsciousness and changes thereof. In some disclosed embodiments, determining the likely cause of the health condition may further include determining pain and intensity of the health condition. In some disclosed embodiments, changes in breathing patterns may be detected and may be indicative of an array of conditions and pain. In some disclosed embodiments, changes in eye responses (e.g. blinking) may be detected and may be provided as an indicator for changes in physiological and psychophysiological parameters.

Figure 78:
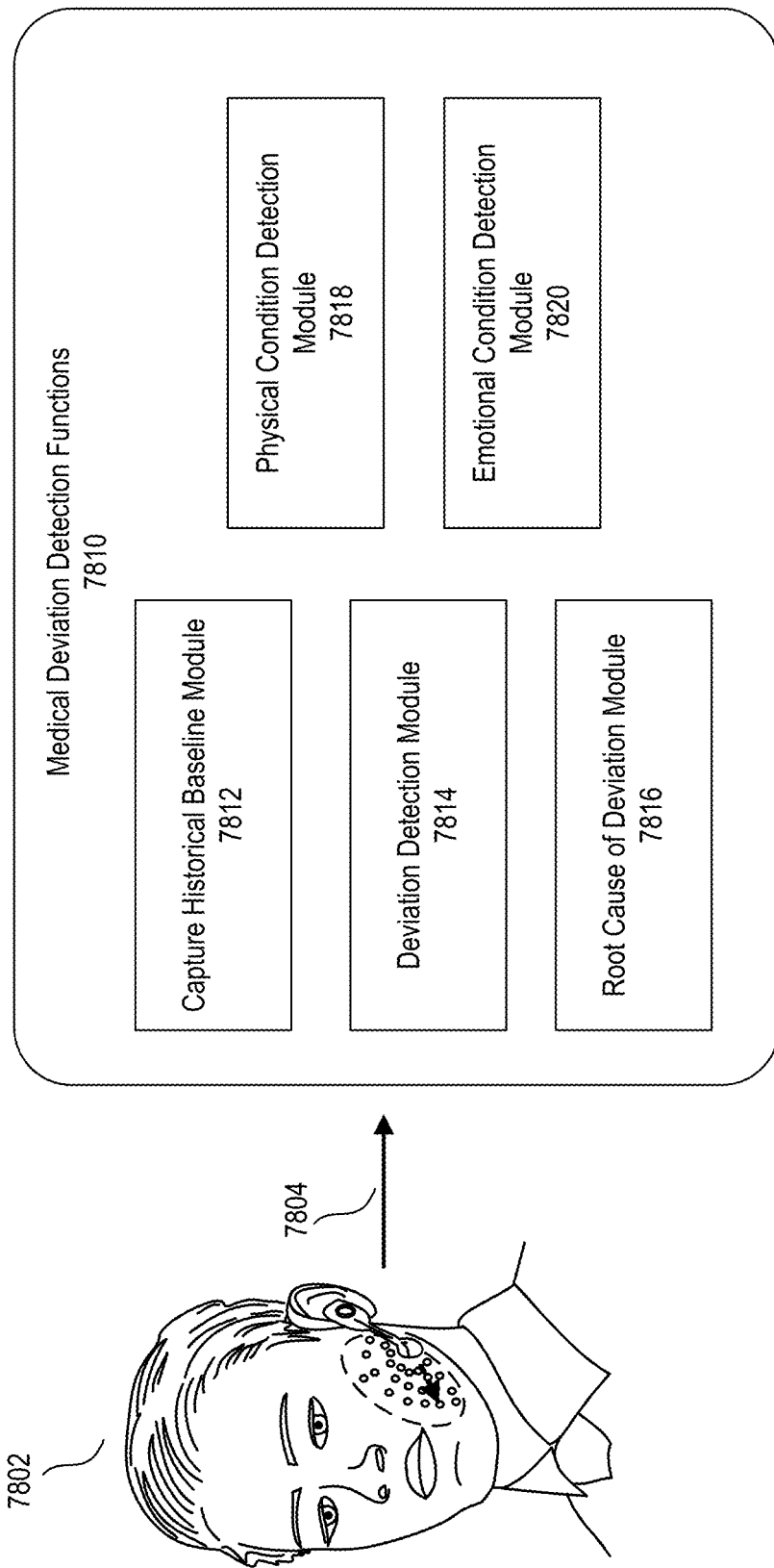
FIG. 78 is a block diagram of exemplary functions for detecting deviation in medical conditions, consistent with some embodiments of the present disclosure.

FIG. 78 shows additional functions consistent with disclosed embodiments. Additional functions 7810 may contain software modules executed by one or more processors consistent with the present disclosure. In particular, additional functions 7810 may include a capture historical baseline module 7812, a deviation detection module 7814, a root cause of deviation module 7816, a physical condition detection module 7818 and an emotional condition detection module 7820. The disclosed embodiments are not limited to any particular configuration. Processing device 400 and/or processing device 460 may execute the instructions stored in memory to implement modules 7812 to 7820 as described herein. It is to be understood that references in the following discussions to a processing device may refer to processing device 400 of speech detection system 100 and processing device 460 of remote processing system 450 individually or collectively. Accordingly, steps of any of the following processes associated with modules 7812 to 7820 may be performed by one or more processors associated with speech detection system 100. Capture historical baseline module 7812 may include logic to establish a baseline based on historical measurements. The baseline based on the historical measurements may be stored for comparison when current measurements are received. Further, the baseline may be captured and stored for future comparison with current measurements particular regions of skin of the body to determine changes in health or physical conditions associated with neuromuscular activity with the specific regions of skin of the body. For example, a scanner that may detect skin micromovements for the check and neck areas may implement the capture historical baseline module 7812 for skin micromovements with a first set of one or more baselines associated with the neck of the individual and a second set of one or more baselines associated with the chest of the individual. Thus, changes in neuromuscular activity may be determined for different areas of the body with one measurement device (e.g., the scanner). Deviation detection module 7814 may determine a deviation or change over a period of time between current measurements and the baseline by comparing current measurements to the baseline. Returning to the example of the scanner, the individual may have several measurements taken over time by the scanner and an analysis of the measurement may determine the deviation or change over time. Root cause of deviation module 7816 may include performing an analysis of the measurement data to determine the likely cause of the deviation over the period of time. Once one or more deviations may be determined, the deviations may be analyzed to determine what the changes may mean regarding changes to the health of the individual. As such, the deviations may be compared against possible health conditions that may have developed in the individual. For example, it may be determined that the likely cause may be a physical condition as determined by the physical condition detection module 7818 or may be an emotional condition as determined by the emotional condition detection module 7820. The physical condition module 7818 may contain a stored set of physical conditions associated with particular changes in neuromuscular activity and may, through a comparison of the measured changes in neuromuscular activity, determine the likely cause of the change in physical conditions. The detected physical conditions may relate to changes in the health of the individual including high blood pressure, diabetes, heart disease, arthritis and other physical conditions as described an exemplified elsewhere in this disclosure. Similarly, the emotional condition detection module 7820 may contain a stored set of emotional conditions associated with particular changes in neuromuscular activity and may, through a comparison of the measured changes in neuromuscular activity, determine the likely cause of the change in emotional conditions. Emotional conditions may include, but is not limited to, anxiety disorders, depression, bipolar disorder, and post-traumatic stress disorder (PTSD). Medical conditions that may be associated with emotional conditions (e.g., affect emotions) may include, but is not limited to, thyroid disorders, neurological conditions like Parkinson's disease, and chronic pain conditions like fibromyalgia.

Figure 79:
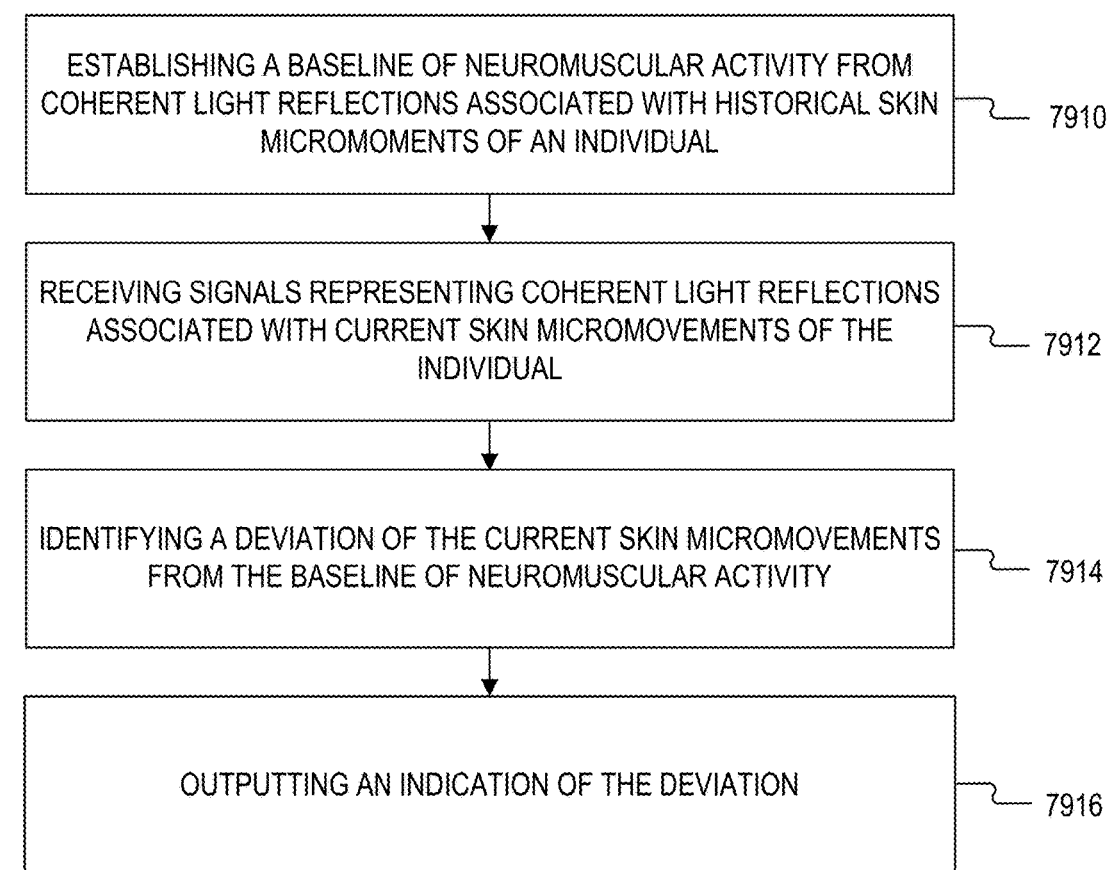
FIG. 79 is a flow chart showing an exemplary method for using received light reflections to detect changes in neuromuscular activity over time, consistent with some embodiments of the present disclosure.

FIG. 79 illustrates a flowchart of an exemplary process 7900 for detecting changes in neuromuscular activity over time, consistent with embodiments of the present disclosure. Some embodiments involve a method for detecting changes in neuromuscular activity over time. At step 7910, the method includes establishing a baseline of neuromuscular activity from coherent light reflections associated with historical skin micromovements of an individual. In some disclosed embodiments, the baseline may be established based on historical signals representing prior coherent light reflection associated with the individual. In some disclosed embodiments, the baseline may be established based on historical signals representing prior coherent light reflection associated with persons other than the individual. In some disclosed embodiments, the method may include determining the historical signals over a period of time that may be more than a day prior or that may be at least one year prior.

At step 7912, the method includes receiving signals representing coherent light reflections associated with current skin micromovements of the individual. In some disclosed embodiments, the method includes receiving current signals from a wearable light detector. In some disclosed embodiments, the method includes receiving current signals from a non-wearable light detector. In some embodiments, the method may include detecting skin micromovements from the face, neck, wrist and/or check of the individual. At step 7914, the method includes identifying a deviation of the current skin micromovements from the baseline of neuromuscular activity. At step 7916, the method includes outputting an indication of the deviation. In some disclosed embodiments, the indication of the deviation may be analyzed to determine a likely cause of the deviation. In some disclosed embodiments, the likely cause of the deviation may be related to an environmental condition or a physical condition of the individual. In some disclosed embodiments, the physical condition of the individual may relate to a health condition of the individual.

The embodiments discussed above for detecting changes in neuromuscular activity over time may be implemented through non-transitory computer-readable medium such as software (e.g., as operations executed through code), as methods (e.g., process 7900 shown in FIG. 79), or as a system (e.g., speech detection system 100 shown in FIGS. 1-3). When the embodiments are implemented as a system, the operations may be executed by at least one processor (e.g., processing device 400 or processing device 460, shown in FIG. 4).

In some embodiments, a wearable device may be used to project a dual-purpose graphic on a wearer's face. The projected graphic may provide information (e.g., in the form of an emoji, logi, icon, text, code, graphic, symbol, or another depiction of information) to a viewer of the projected graphic. The projected graphic may be visible using the viewer's naked eye or may be visible using detectors or sensors (e.g., an IR detector, UV detector, or another device). In addition to providing information to a viewer, the projected graphic may be formed of spots that may be used to detect facial skin micromovements of the wearer (e.g., by speckle analysis or another suitable image analysis). In this way, what appears to viewers as simply a projected graphic may also be used to determine non-verbal speech of the wearer.

Figure 80:
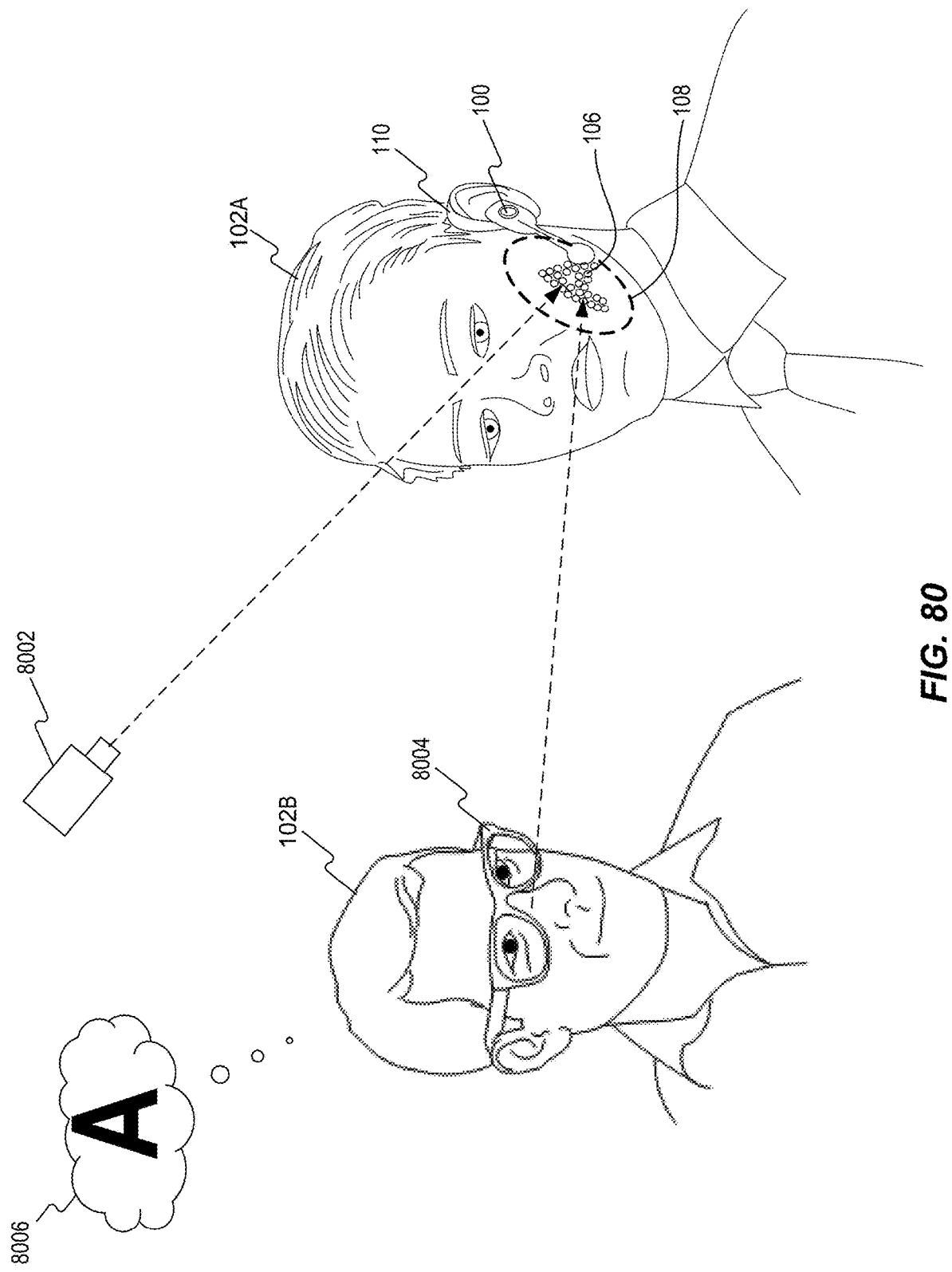
FIG. 80 is a schematic illustration of using a projected graphical pattern to detect non-verbal information from an individual consistent with some embodiments of the present disclosure.

Some disclosed embodiments involve a dual use head mountable system for projecting graphical content and for interpreting non-verbal speech. As explained elsewhere in this document a "head mountable system" includes any mechanism, device, or system (which may be understood as described and exemplified elsewhere herein) at least a portion of which is configured to be worn on, or supported by, at least a portion of an individual's head. Examples of a head mountable system may include a one or more components incorporated into a cap, glasses, headset, visor, goggles, headband, headphone, earphone, earbud, or another accessory configured to be won on or supported by, at least a portion of an individual's head. One example of a head mountable system is illustrated in FIG. 80 which shows a speech detection system 100 (described and exemplified elsewhere herein) with a wearable housing 110 worn on the head of a user 102A. "Dual use" head mountable system indicates that the head mountable system may be used for two purposes. The two purposes may, without limitation, be any two purposes. For example, the two purposes may be different purposes or may be similar or related purposes. The term "graphical content" is used to broadly refer to information, data, images, or any other material. For example, pictures, images, graphs, line drawings, cartoons, emojis, icons, symbols, text, barcode, or any other representation of information may represent graphical content in various embodiments. "Projecting" graphical content refers to causing an image or another representation of the graphical content to be displayed or shown on some medium (e.g., a display screen, wall, skin of an individual or an animal, mirror, or any other medium that an image can be displayed on).

In some embodiments, the displayed image may be visible to the naked human eye (or naked eye), and in some embodiments it may not be visible to the naked eye but may be visible using specialized equipment such as optical sensors or detectors. Visible to the naked eye refers to being able to see something (e.g., the displayed image) without using specialized equipment (e.g., optical sensors, detectors, or other devices configured to see or detect wavelengths of light not normally visible to the human eye). Note that the use of corrective optical glasses or lenses to view something is considered as viewing using the naked eye. In other words, in some embodiments, the displayed image may be visible to the naked eye. In some embodiments, the displayed image may be visible to the naked eye only using specialized equipment (e.g., UV glasses or detectors, IR glasses or detectors, image sensors, photodiodes or phototransistors, or other devices configured to detect the wavelength of light used to project the graphical pattern).

The electromagnetic spectrum refers to the range of all possible wavelengths of electromagnetic radiation. Visible light refers to the portion of the electromagnetic spectrum that can be detected by the human eye without the need for any specialized equipment. It is the range of wavelengths that human eyes are sensitive to and perceive as various colors. Visible light spans approximately 400 to 700 nanometers (nm) in wavelength. The naked eye, without the aid of any sensors or detectors can perceive and distinguish objects that emit or reflect visible light within this range. Radio waves, microwaves, and infrared (IR) radiation are electromagnetic radiation with wavelengths greater than visible light. And ultraviolet (UV) radiation, X-rays, and Gamma rays are electromagnetic radiation with wavelengths smaller than visible light. Although not visible to the naked human eye, there are devices, detectors, and sensors that can detect electromagnetic radiation (or light) at wavelengths above and below the visible spectrum. For example, UV detectors and sensors may detect UV light and IR detectors and sensors may detect IR light.

"Non-verbal speech" (and other constructions of this term, such as, for example, non-verbalization) refers to non-audible communication. For example, non-verbal speech may include communication that does not involve audibly spoken or audibly verbal language. For example, non-verbal speech by an individual may include any sort of communications by that individual that does not involve understandable words or sounds being uttered. For example, non-verbal speech may include communications using gestures or body language, facial expressions, sign language, visual aids, symbols and icons, or other ways of communications other than sounding out, or vocalizing, words. Other examples of non-verbal speech includes the previously described and exemplified nonvocalized, subvocalized, prevocalized, and silent speech manifest in facial skin movements. As explained elsewhere herein, to utter a given phoneme, motor neurons activate muscle groups in the face, larynx, and mouth in preparation for propulsion of air flow out of the lungs, and these muscles continue moving during speech to create words and sentences. Without this air flow from the lungs, no sounds are emitted from the mouth. One form of non-verbal speech may occur when there is no air flow from the lungs, while the muscles in the face, larynx, and mouth articulate the desired sounds or move in a manner enabling interpretation. Another form of non-verbal speech may occur when the facial expression of the individual changes to express an emotion (e.g., grimace, smile, frown, scowl, or any other facial expression). "Interpreting" non-verbal speech refers to translating or converting the non-verbal speech into a form that can be understood by, for example, a person or a device. For example, interpreting non-verbal speech may include converting the non-verbal speech into an understandable form.

Some disclosed embodiments involve a wearable housing configured to be worn on a head of an individual. As explained and exemplified elsewhere herein, the term "wearable housing" broadly includes any structure or enclosure designed for connection to a human body, such as in a manner configured to be worn by a user. For example, the head mountable system in the form of speech detection system 100 of FIG. 80 includes a wearable housing 110 worn on the head of user 102A. Such a wearable housing 110 may be configured to contain or support one or more electronic components or sensors. Although not shown in FIG. 80, in some embodiments, the wearable housing 110 may be attached to a secondary device such as a glasses (sun or corrective vision glasses), a hat, a helmet, a visor, or any other type of head wearable devices.

Some disclosed embodiments involve at least one light source associated with the wearable housing. As explained and exemplified elsewhere herein, as used herein, the term "light source" broadly refers to any device configured to emit light (e.g., visible light, UV light, and/or IR light). The emitted light may be a coherent light or non-coherent light. As explained elsewhere herein, in some examples, coherent light may be produced by a coherent light source, such as lasers and other types of light sources that have a narrow spectral range and a high degree of monochromaticity (i.e., the light consists of a single wavelength). In contrast, incoherent light may be produced by a non-coherent light source such as incandescent bulbs and natural sunlight, which have a broad spectral range and a low degree of monochromaticity. As used herein, light source "associated" with the wearable housing indicates that the light source is physically or non-physically but operatively connected to the wearable housing. In other words, the light source and the wearable housing may be in a working relationship. As explained in detail with reference to FIG. 1, speech detection system 100 may include a light source configured to project light toward a location on the face of user 102A to create an array of light spots 106 extending over a facial region 108. Light source 410 of FIG. 4 and FIGS. 5A and 5B (described in detail elsewhere herein) are non-limiting examples of such a light source that includes one or multiple light sources. As discussed elsewhere herein, light source 410 may be a laser such as a solid-state laser, laser diode, a high-power laser, an infrared laser diode, a light emitting diode (LED) or another light source and may emit light in differing formats, such as light pulses, continuous wave (CW), quasi-CW, and so on.

Consistent with some disclosed embodiments, the at least one light source may be configured to project light in a graphical pattern on a facial region of the individual. As used herein, the term "light" may refer broadly to electromagnetic radiation having a wavelength between about 100 nanometers to about 1 millimeter. In other words, as used herein, light may include ultraviolet (UV) radiation, visible light, and infrared (IR) radiation. Thus, in some embodiments, the projected light may include UV light, visible light, and/or IR light. As explained elsewhere herein, visible light may be light that can be seen or perceived by the naked human eye. Infrared light has wavelength greater than the red end of the visible light spectrum and lower than that of microwave radiation. Infrared light may be detected using an infrared detector or sensor (e.g., infrared glasses or another device configured to detect infrared radiation) but not visible to the naked eye. Ultraviolet light has a wavelength smaller than visible light and may not be visible to the naked eye. UV light may be detected using an ultraviolet detector or sensor. In some embodiments however, the projected light may only include visible light.

Projecting light in a "graphical pattern" refers to a visual representation or image that visually conveys information, data, or an idea. For example, projecting light in a graphical pattern may include projecting light in the pattern of a picture, image, graph, letter, text, sign, drawing, cartoon, emoji, icon, or any other visual representation that conveys information, data, or an idea. "Facial region" refers to any region on the face of an individual. Facial region may have any size and area. As explained elsewhere in this document, in some embodiments, the facial region may have an area of at least 1 $cm^2$, at least 2 $cm^2$, at least 4 $cm^2$, at least 6 $cm^2$, or at least 8 $cm^2$. In some embodiments, the size of facial region may be determined based on the underlying facial muscles in that region. As described and exemplified elsewhere herein, in some embodiments, the facial region may correspond to specific anatomical areas, for example: a part of the cheek above the mouth, a part of the cheek below the mouth, a part of the mid-jaw, a part of the cheek below the eye, a neck, a chin, and other areas associated with specific muscle recruitments that may cause facial skin micromovements. For example, in the exemplary embodiment illustrated in FIG. 80, speech detection system 100 projects light to create a graphical pattern 8006 on facial region 108 on the face of user 102A.

Consistent with some disclosed embodiments, the graphical pattern is constructed of a plurality of spots for use in determining the facial skin micromovements via speckle analysis. As explained and exemplified elsewhere herein, the at least one light source of speech detection system may be configured to project light toward the facial region to create an array of light spots. Each spot may have any shape and size. In some embodiments, each spot may be substantially circular. For example, as shown in FIG. 80, the projected light may create an array of light spots 106 in facial region 108 that together creates the displayed graphical pattern 8006. In general, any number of light beams may be projected to generate the graphical pattern of light spots. For example, in some embodiments, a single light beam may generate all the light spots 106 that create the graphical pattern on facial region 108. In some embodiments, multiple light beams may be projected to create the graphical pattern. It is also contemplated that in some embodiments, the light source may project light in a manner other than an array of spots, such as, for example, facial region 108 may be uniformly or non-uniformly illuminated to create a graphical pattern. As also explained and exemplified elsewhere herein, an optical sensing unit 116 of speech detection system may receive reflections of light from the facial region and perform light reflection analysis, for example, to determine facial skin micromovements. When a coherent light source is used to project the plurality of spots, the light reflection analysis may include speckle analysis or any pattern-based analysis. Coherent light shining onto a rough, contoured, or textured surface may be reflected or scattered in many different directions, resulting in a pattern of bright and dark areas called "speckles." Speckle analysis may be performed using a computer (e.g., including a processor) to identify a speckle pattern and determine the facial skin micromovements represented by the light reflection signals.

Consistent with some disclosed embodiments, the graphical pattern is configured to visibly convey information. As used herein, "convey information" refers to causing the information represented by the graphical pattern to be known or understood by someone or something. "Visibly" convey information indicates that information represented by the graphical pattern may be detected or perceived by someone or something in some manner. For example, the projected graphical pattern may be seen or detected by an individual or a device (e.g., a camera or another device that can record the projected graphical pattern). In some embodiments, the projected graphical pattern may not be discernable using the naked eye of an individual but may be discernable or detectable by a device (e.g., a sensor or another device capable of detecting a display that is not discernable to the naked human eye). For example, with reference to embodiment of FIG. 80, the graphical pattern projected on facial region 108 of user 102A may be seen by individual 102B and recognized.

Consistent with some disclosed embodiments, the projected light is configured to be visible via a human eye to individuals other than the individual. In this instance, the individual is a person donning the wearable housing and the other individuals are individuals viewing the individual donning the wearable housing. As used herein, projected light being "visible via a human eye" indicates that the projected light may be seen by the naked human eye without the aid of sensors or other devices configured to see or detect wavelengths of light not normally visible to the human eye. As explained elsewhere herein, using corrective glasses or lenses is considered to be viewing using the naked eye. The projected light that is visible via the human eye may have a wavelength within the visible light spectrum (e.g., between about 400-700 nanometers). For example, in the embodiment of FIG. 80, the graphical pattern projected on facial region 108 of user 102A may be visible to the eyes of individual 102B without the aid of infrared glasses 8004 or any other device to detect light having a wavelength outside the visible spectrum (light at invisible wavelengths). In some embodiments, the graphical pattern projected on user 102A may not be visible to user 102A. In an exemplary application, a user wearing a disclosed dual use head mountable system may go to a nightclub that permits everyone to attend but only permits people over the age of 21 to purchase alcohol. Upon entry into the club, the user's age may be verified and the light source associated with the head mountable system may be programmed or controlled to project light and display a graphical pattern representing the user's age (e.g., the symbol ☑ to indicate that the user is over 21 and the symbol ☒ to indicate that the user is under 21) on the user's cheek (or another facial region). In some embodiments, the projected light and the displayed symbol may be visible to all other individuals in the nightclub using their naked eyes without the aid of any device to detect light at invisible wavelengths. For example, bartenders and servers at the nightclub may check the displayed symbol before serving alcohol to the user.

Consistent with some disclosed embodiments, the projected light is visible via an infrared sensor. A "sensor" is a device that detects and/or responds to some type of input from the physical environment. The input can be light, heat, motion, moisture, pressure, or any number of other environmental phenomena. For example, a sensor may be a device used to detect and/or record that something is present or that there are changes in something. An "infrared" sensor is any type of sensor that can detect infrared light or radiation. For example, an infrared sensor may be an electronic device or an optoelectronic component that can detect light or energy having a wavelength in the infrared spectrum (e.g., between about 780 nm and 1 mm). For example, in some embodiments, an infrared sensor may be an electronic sensor that detects infrared light radiating from objects in its field of view. In some embodiments, an infrared sensor may be glasses with specially formulated optical filters and/or elements configured to detect infrared radiation from objects in its field of view. With reference to FIG. 80, in some embodiments, the graphical pattern on facial region 108 of user 102A may be invisible or imperceptible to individual 102B without the aid of devices or sensors configured to see or detect wavelengths of light not normally visible to the human eye. For example, in some embodiments, wearing, for example, infrared glasses 8004, individual 102B may see and recognize the graphical pattern projected on facial region 108 of user 102A. Additionally or alternatively, in some embodiments, an infrared sensor 8002 may detect the graphical pattern and convey the information represented by the graphical pattern to individual 102B in some manner (e.g., by transmitting the information to a mobile communication device or a laptop of individual 102B). As another example, in the exemplary nightclub application described above, the projected light and the graphical pattern displayed on the user's cheek (e.g., the symbol ☑ or ☒) may not be visible to the human eye. Instead, it may only be visible or detectable using an infrared sensor that may communicate with or inform the bartenders and servers whether or not the user is allowed to purchase alcohol.

Consistent with some disclosed embodiments, the projected light source includes a laser. A "laser" is a device that stimulates atoms or molecules to emit light at particular wavelengths and amplifies that light, typically producing a narrow beam of radiation that generally covers a limited range of visible, infrared, or ultraviolet wavelengths. For example, a laser may be a device that emits a beam of coherent monochromatic light. As described and exemplified elsewhere herein, in some embodiments, the light source 410 that projects light may include a laser such as, for example, solid-state laser, one or more laser diodes, high-power laser, or one or more infrared laser diodes.

Some disclosed embodiments include a sensor for detecting a portion of the light reflected from the facial region. The term "sensor" may be interpreted as described and exemplified above. For example, a sensor may be any device that detects and/or responds to some type of input (e.g., light, heat, motion, moisture, pressure, or any other environmental phenomena) from the physical environment. As described elsewhere herein, a light source is configured to project light on a facial region. At least some of that light bounces off the facial region (is reflected by the facial region) and impinges on a sensor. As described elsewhere in this disclosure, the sensor detects the light reflections.

By way of one non-limiting example with reference to FIG. 4, optical sensing unit 116 of speech detection system 100 may include light source 410 and a light detector 412. Light source 410 may project coherent light or non-coherent light to facial region 108 and, as discussed above, may include a laser. Meanwhile, light detector 412 may be used to detect reflections from facial region 108 indicative of facial skin movements. In some embodiments, light detector 412 may include an array of detecting elements, for example, a set of a charge-coupled device (CCD) sensors and/or a set of complementary metal-oxide semiconductor (CMOS) sensors, with objective optics for imaging facial region 108 onto the array. Due to the small dimensions of optical sensing unit 116 and its proximity to the skin surface, light detector 412 may have a sufficiently wide field of view to detect spots 106 of facial region 108.

Some disclosed embodiments involve at least one processor configured to receive output signals from the sensor. The term "at least one processor" may be interpreted as described and exemplified elsewhere in this disclosure. The term "receive" (and other constructions of this term, such as, for example, receiving) may include retrieving, acquiring, or otherwise gaining access to, e.g., data output by the sensor. Receiving may include reading data from memory and/or receiving data from the sensor or an associated computing device via a (e.g., wired and/or wireless) communications channel. The at least one processor may receive data via a synchronous and/or asynchronous communications protocol, for example by polling a memory buffer for data and/or by receiving data, e.g., from the sensor, as an interrupt event. As described and exemplified elsewhere herein (e.g., with reference to FIG. 4), light detector 412 of speech detection system 100 may be configured to generate an output relating to the measured properties of the detected light from facial region 108. The output of light detector 412 may include any form of data determined in response to the received light reflections from facial region 108. In some embodiments, the output may include reflection signals that include electronic representation of one or more properties determined from the coherent or non-coherent light reflections. In other embodiments, the output may include raw measurements detected by at least one light detector 412. As also explained and exemplified elsewhere herein, at least one processor associated with the speech detection system may receive the output signals from light detector and analyze the received data (e.g., to identify a speckle pattern and derive information about a surface (e.g., facial skin) represented in reflection signals received from light detector 412).

Consistent with some disclosed embodiments, the at least one processor may be configured to determine from the output signals facial skin micromovements associated with non-verbalization. The term "facial skin micromovements" may be interpreted as described and exemplified elsewhere in this disclosure. As explained elsewhere herein, non-verbalization (and non-verbal speech) may refer to any sort of communication that does not involve words or sounds being uttered, such as, for example, using, gestures or body language, facial expressions, sign language, visual aids, symbols and icons, or other ways of communications other than sounding out, or vocalizing, words. For example, non-verbalization includes the previously described and exemplified nonvocalized, subvocalized, prevocalized, and silent speech. The at least one processor may determine facial skin micromovements associated with non-verbalization from the output signals of light detector 412 as described and exemplified elsewhere in this disclosure. For example, speech detection system 100 may analyze light reflections from facial region 108 to determine facial skin micromovements resulting from recruitment of muscle fiber in facial region 108. This may include determining an amount of the skin movement, determining a direction of the skin movement, and/or determining an acceleration of the skin movement resulting from voluntary and/or involuntary recruitment of muscle fiber. For example, processing device 400 (see FIG. 4) may be configured to perform a first speckle analysis on light reflected from a first region of face in proximity to one spot 106 to determine that the first region moved by a distance d1 (e.g., first facial skin micromovement) and perform a second speckle analysis on light reflected from a second region of face in proximity to another spot 106 to determine that this second region moved by a distance d2 (e.g., second facial skin micromovement), and so on.

Consistent with some disclosed embodiments, the at least one processor may be configured to process the output signals to interpret the facial skin micromovements. "Interpret" facial skin micromovements may refer to translating or converting the determined facial skin micromovements into a form that can be understood by, for example, a person or a device. For example, the determined facial skin micromovements may be converted into a form that may be understood by an individual. The term "process" refers to at least one action by a computer to achieve a particular result or end. In this case, the output signals are processed to interpret the facial skin micromovements (e.g., in any manner described and exemplified elsewhere in this disclosure). Consistent with some disclosed embodiments, processing the output signals to interpret the facial skin micromovements includes determining non-verbalized speech from the facial skin micromovements. For example, as explained and exemplified elsewhere in this disclosure, in some embodiments, a data structure accessible by the system may contain correlations of facial skin micromovements with words, commands, emotions, expressions, and/or biological conditions and the at least one processor may perform a lookup in the data structure to identify the words, meaning of detected facial skin micromovements. In some embodiments, correlations of particular patterns of facial skin micromovements with words, commands, emotions, expressions, and/or biological conditions may be stored in the data structure apriori (for example, during training), and when a pattern of facial skin micromovements is observed, the processor may perform a lookup in the data structure to identify the words or other biological, physiological, or physical conditions associated with the detected pattern of facial skin micromovements. Consistent with some disclosed embodiments, processing the output signals to interpret the facial skin micromovements includes determining an emotional state from the facial skin micromovements. As discussed above, the emotional state of the user may also be determined from the determined facial skin micromovements, for example, by comparing the facial skin micromovements to the stored correlations of facial skin micromovements with, among other things, the attitude or emotion state of an individual. For example, comparing the signals indicative of the detected facial skin micromovements with the stored correlations may indicate that the user is smiling (or expressing another emotional state). Consistent with some disclosed embodiments, the at least one processor is configured to determine the graphical pattern from the determined emotional state. "Determine the graphical pattern" refers to determining any aspect of the projected graphical pattern. For example, determining the size, color, shape, orientation, duration, content, or any other feature of the graphical pattern. One example is determining a graphical pattern that correlates with the emotional state of the user. In some embodiments, a graphical pattern indicative of the determined emotional state may be projected on the user. For example, by comparing the detected facial skin micromovements, the at least one processor may determine that the user is happy and a graphical pattern reflective of the emotional state of the user (e.g., a smiley face emoji) may be projected on the user's facial region.

Consistent with some disclosed embodiments, the at least one processor is further configured to receive a selection of the graphical pattern and to control the at least one light source to project the selected graphical pattern. The at least one processor may control the at least one light source to project the selected graphical pattern in any manner described and exemplified elsewhere in this disclosure. For example, an illumination control module associated with the system may determine light characteristics (e.g., light intensity, pulse frequency, duty cycle, illumination pattern, light flux, or any other optical characteristic for illuminating the facial region) and regulate the operation of light source(s) to project the selected graphical pattern on the facial region. In general, the selection of the graphical pattern may be received by the at least one processor from any source. In other words, the graphical pattern may be selected by any individual or entity. In some embodiments, the user of the head mountable system may select the graphical pattern to be projected on the user's facial region. For example, a user attending, for example, a sporting event between two teams may select a graphical pattern representing the mascot of the team that the user supports to project on the user's facial region. In some embodiments, the user may make a selection of the graphical pattern from a menu of available options from a website or a memory device using, for example, the user's mobile communication device. In some embodiments, another individual or entity (e.g., the institution that the user is visiting) may choose the graphical pattern to project on the user's facial region. For example, when visiting a sporting event, authorities organizing the event may select a graphical pattern to indicate, for example, to a viewer that the user has satisfied some condition (e.g., the user has purchased a ticket, is old enough to purchase alcohol, is authorized to sit in a particular seating area, or any other condition relevant to the particular context). In another example, the wearer may make a selection of a graphical pattern using speech or silent speech. The speech may be detected via either the light reflections or an audio speech recognition system. Such speech may contain a command recognizable by the processor. For example, a wearer at a sporting event may vocally or subvocally command the processor to display the word (or flashing word) "Goal!" when a favored team scores. The user may preconfigure the system with graphics associated with various commands. E.g., when I give a "Happy" command (or when my mood is happy) project a smiley face on my cheek; when I'm focused (or when I give a focused command) display a "Do not disturb" graphic on my cheek. These are just examples; the possibilities are endless.

Consistent with some disclosed embodiments, the at least one processor is configured to alter the graphical pattern over time. The term "alter" refers to change or cause to change in character or composition in some manner. For example, to make different in size, style, color, pattern, or the like. The change may be relatively small or may be significant. The at least one processor may be configured to make some change to the projected graphical pattern over time. For example, with reference to FIG. 81 and the previously described example of a user visiting a sporting event, when the user purchases a ticket for a selected seating area (e.g., bleachers seating) a first graphical pattern 8102 may be projected on the user's facial area. If the user occupies a seat in the appropriate seating area, the graphical pattern 8102 may remain unchanged. However, if the user subsequently moves to a different seating area (e.g., to a more expensive seating area), the graphical pattern on the user's facial region may change to a different graphical pattern 8104 to indicate that the user is not authorized to sit in that area. The graphical pattern may be altered by any individual or entity. For example, in the example above, based on the projected graphical pattern, a sensor may detect that the user has moved into an unauthorized area and cause the at least one processor to alter the projected graphical pattern. As another example, a user have purchased a ticket to stay in a particular area (e.g., a cinema theater) for a certain amount of time (e.g., for one movie). A first graphical pattern (e.g., pattern 8102) may be projected on the user's facial region when the user enters the theater. When the movie is complete, the projected graphical pattern may change (e.g., disappear, change to a different pattern, or some other change in the graphical pattern).

Consistent with some disclosed embodiments, the at least one processor is configured to receive location information and to alter the graphical pattern based on the received location information. "Location information" may be any information that indicates the location of the head mountable system. For example, in some embodiments, the head mountable system may include, or be associated with, a global positioning system (GPS) chip which may indicate the location of the head mountable system at any time. In other embodiments, a sensor (e.g., an infrared sensor) located at a location may detect a graphical pattern, and based on this detection, determine the location of the head mountable system that projected the graphical pattern. With reference to the previously described example of a user visiting a sporting event, when the user purchases a ticket for a first seating area and enters (or sits in) another seating area (e.g., a second seating area), a sensor positioned at the second seating area, or signals from a GPS system, may send the user's location information to the at least one processor and alter the graphical pattern on the user's face, for example, to signal that the user is unauthorized to be in that area.

Consistent with some disclosed embodiments, the graphical pattern includes a scrolling message and the at least one processor is configured to cause the message to scroll. "Scrolling" refers to the action of moving the displayed graphical pattern across on the facial region, for example, to view a different part of it. The graphical pattern may be scrolled in any direction (e.g., up and down, side to side, or in any other direction). In some embodiments, the at least one processor may cause a graphical pattern projected on a user to scroll to produce an effect. For example, when attending a football match, the logo or mascot of the team that the user supports may be projected on the user's facial region as a graphical pattern. When that team scores a goal, the graphical pattern may be scrolled to create a celebratory effect. In another example, when a user visits a secure facility (such as, for example, a defense establishment, a bank, or another access-controlled location), the user's credentials or another information reflective of the user's authorization to be at the location (e.g., identification, badge, authorization pass) may be projected on the user's facial region as a graphical pattern. The at least one processor may cause the projected graphical pattern to scroll, for example, when the pattern is too big.

Consistent with some disclosed embodiments, the at least one processor is further configured to detect a trigger and to cause the graphical pattern to be displayed in response to the trigger. "Trigger" refers to a signal or a condition that causes an event or reaction to happen. For example, a trigger may be something that acts like a switch of a light or a mechanical trigger of a gun that initiates a process or a reaction when the switch or trigger is activated. For example, when a user enters a secure facility, after the user's credentials are confirmed, a signal may be sent to the at least one processor as a trigger to cause a graphical pattern (e.g., a tick mark) to be displayed on the user's facial region. As another example, when a user visits a bank (or another institution) and attempts to operate a customer account (e.g., make enquiries about, attempts to withdraw funds, or conduct any other transaction), based on the user's facial skin micromovements, an authentication system may determine if the user is authorized to operate the account (as described and exemplified elsewhere in this disclosure). In some embodiments, the authentication system may send a signal (e.g., a trigger) to the at least one processor to cause a graphical pattern to displayed on the user's facial region based on the results of the authentication. For example, a ☑ symbol may be displayed if the user is authenticated and a ☒ symbol may be displayed if the user is not authorized.

Consistent with some disclosed embodiments, the at least one processor is configured to determine the graphical pattern from the non-verbalized speech. For example, with reference to the authentication system example described above, the graphical pattern (e.g., ☑ symbol or ☒ symbol) may be determined based the detected facial skin micromovements of the user that is reflective of non-verbalized speech. In another example, a user may have purchased a ticket to an event online and may have received a code (e.g., code word or code number) confirming the purchase. When the user non-verbalizes the received code at the event (e.g., at the ticket counter or entrance), the at least one processor may determine and display a graphical pattern reflective of the code on the user's facial region. The user may be allowed in and seated in the appropriate seating area based on the displayed code.

Consistent with some disclosed embodiments, the at least one processor is configured to identify a trigger and to modify the pattern based on the trigger. "Modify" may refer to making changes. As explained above, a trigger may be a signal or a condition that causes an event or a reaction to happen. For example, with reference to the previously described example of a user visiting a nightclub, a graphical pattern reflective of whether the user is allowed to purchase alcoholic beverages may be projected in the user's facial region. In some embodiments, the graphical pattern may be modified (e.g., the color adjusted, or some other change may be made) when, for example, the lighting at the nightclub changes so that the graphical pattern remains detectable in all lighting conditions. For example, a light sensor associated with the head mountable system may detect the changed lighting and send a signal to the at least one processor to modify the displayed graphical pattern. As another example, when a user prepays for multiple drinks at the nightclub, a first graphical pattern reflective of the number of prepaid drinks (e.g., ❹) may be projected on the user's facial region. After each drink is served, the displayed graphical pattern may be modified to indicate that there is one less drink remaining (e.g., ❸). In some embodiments, a signal from a system associated with the nightclub may trigger the at least one processor to modify the graphical pattern. Consistent with some disclosed embodiments, the at least one processor is configured to analyze the facial skin micromovements to identify the trigger. In some embodiments, the trigger to modify the first graphical pattern may be based on detected facial skin micromovements from the user. For example, the facial skin micromovements associated with the user ordering a drink (and/or consuming the drink) may act as a trigger for the at least one processor to modify the displayed graphical pattern to indicate that there is one less remaining. Consistent with some disclosed embodiments, modifying the pattern includes ceasing the projection of the graphical pattern. "Ceasing" refers to stopping something, or bringing something to, or something coming to, an end. For example, with reference to the example above, after the last prepaid drink is served, the graphical pattern relating to the prepaid drinks may no longer be projected.

Some disclosed embodiments involve an integrated audio output and wherein the at least one processor is configured to initiate an action that involves outputting audio via the audio output. "Audio output" refers to a device or assembly that is configured to output sound or audio. "Integrated" audio output indicates that the head mountable system and the audio output are linked together such that they work together. For example, the head mountable system and the audio output have been assimilated, blended, combined, conformed, or consolidated so that they work together. As used herein, "outputting" may include sending, transmitting, producing, and/or providing. As explained and exemplified elsewhere herein, speech detection system 100 may include a speaker 404 (see FIG. 4) that may be incorporated with a loudspeaker, earbuds, audio headphones, a hearing aid type device, a bone conduction headphone, and any other device capable of converting an electrical audio signal into a corresponding sound. In some embodiments, in addition to displaying a graphical pattern on the facial region of the user, the at least one processor may also output an audio indication (e.g., message, sound, tone) to the user. Any type of audio indication may be output to the user at any time. In some embodiments, the audio indication may provide information to the user regarding the displayed graphical pattern (e.g., type of pattern displayed and/or other details). As an example, when a user purchases a ticket for a first seating area at a sporting event and when a sensor determines that the user has entered a second seating area, in addition to displaying a graphical pattern on the user's facial region, the at least one processor may play and audio message (e.g., via the integrated speaker of the head mountable system) informing the user of the error. As another example, when a user prepays for multiple drinks at the nightclub, in addition to modifying the displayed graphical pattern to indicate the reduced number of drinks remaining, the at least one processor may send an audio message to the user regarding, for example, the number of remaining drinks.

Figure 82:
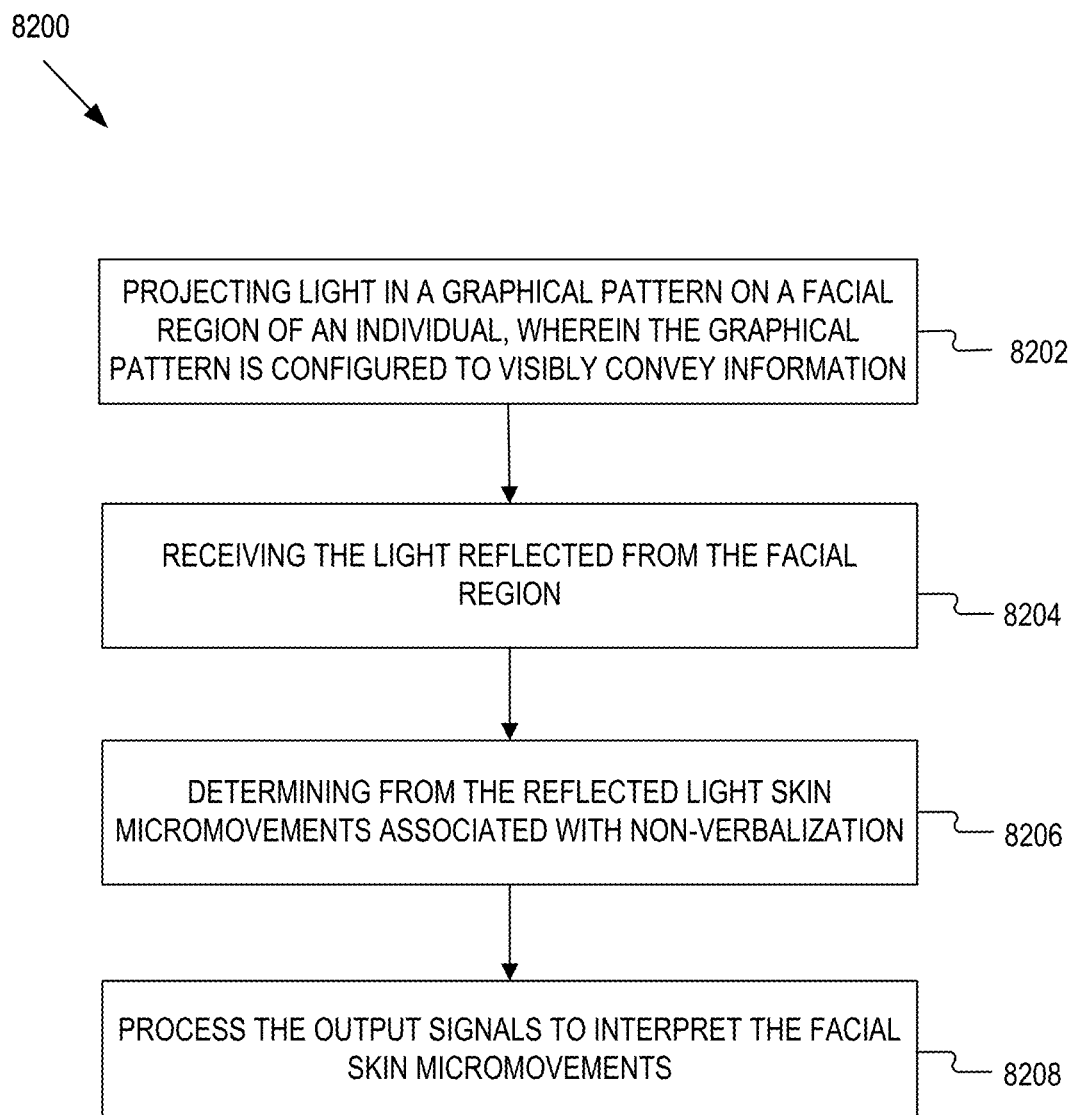
FIG. 82 is a flowchart of an exemplary process of using a projected graphical pattern to detect non-verbal information consistent with some embodiments of the present disclosure.

Some disclosed embodiments involve a method for projecting graphical content and for interpreting non-verbal speech. FIG. 82 is a flow chart of an exemplary method 8200 for projecting graphical content and for interpreting non-verbal speech. Method 8200 may include projecting light in a graphical pattern on a facial region of an individual, wherein the graphical pattern is configured to visibly convey information. (Step 8202). Process may also include receiving the light reflected from the facial region (step 8204), and determining from the reflected light skin micromovements associated with non-verbalization. (Step 8206). Method 8200 may also include processing the output signals to interpret the facial skin micromovements. (Step 8208). It should be noted that the order of the steps illustrated in exemplary method 8200 is only exemplary and many variations are possible. For example, the steps may be performed in a different order or may be part of a larger process.

Consistent with some disclosed embodiments, method 8200 may be performed by at least one processor (e.g., processing unit 112 in FIG. 1, processing device 400 in FIG. 4) to perform operations or functions described herein. Consistent with some disclosed embodiments, some aspects of method 8200 may be implemented as software (e.g., program codes or instructions) that are stored in a memory (e.g., data structure 124 in FIG. 1) or a non-transitory computer readable medium. Consistent with some disclosed embodiments, some aspects of method 8200 may be implemented as hardware (e.g., a specific-purpose circuit). Consistent with some disclosed embodiments, method 8200 may be implemented as a combination of software and hardware.

Some disclosed embodiments involve a non-transitory computer readable medium containing instructions that when executed by at least one processor cause the at least one processor to perform operations for projecting graphical content and for interpreting non-verbal speech. The term non-transitory computer readable medium may be interpreted as described and exemplified elsewhere in this disclosure. The operations may include operating a wearable light source configured to project light in a graphical pattern on a facial region of an individual, wherein the graphical pattern is configured to visibly convey information. The operations may also include receiving from a sensor, output signals corresponding with a portion of the light reflected from the facial region, and determining from the output signals facial skin micromovements associated with non-verbalization. The operations may further include processing the output signals to interpret the facial skin micromovements.

Some disclosed embodiments involve interpreting facial skin micromovements. Interpreting facial skin micromovements may include performing one or operations to translate, understand, construe, read, explain, comprehend, decode, identify, or decipher the facial skin micromovements as vocalized speech, silent speech (e.g., subvocalized, prevocalized, etc., as described elsewhere in this disclosure), facial expressions, or any other form of communication. For example, facial skin micromovements may be associated with certain phonemes, combinations of phonemes, words, combinations of words, or any other speech-related component. For example, interpreting facial skin micromovements may include associating the phrase "Hello, world!" with facial skin micromovements when the phrase "Hello, world!" is vocalized or subvocalized. In another example, interpreting facial skin micromovements may include associating the phrase "Hello, world!" with facial skin micromovements when the phrase "Hello, world!" is said in the absence of vocalization. By way of another example, facial skin micromovements may be associated with facial expressions, such as a smile associated with happiness or a frown associated with sadness, or any other facial expression and the associated emotion or intended communication. Interpreting facial skin micromovements may also include interpreting vocalized sound understood to be communication absent words, such as a grunt, mmmm, mmm-hmmm, a laugh, or a gasp with their associated meaning.

A head mountable system may be used for interpreting facial skin movements and may include any structure or enclosure designed to be connected or attached to a human head, directly or indirectly, such as in a manner configured to be worn by a user. Such a head mountable system may be configured to contain or support one or more of electronic circuitry, components, and/or sensors. In one example, the head mountable system may be configured to be worn directly by the user, e.g., integrated into a pair of glasses, an earbud, headphones, a hat, a necklace, a headband, a monocle, a mask, jewelry, an earring, or any other item could be worn on or near the head of a user. In another example, the head mountable system may be configured to attach, clip, stick (e.g., tape, hook and loop), pin, magnet, clamp, or connect to an item worn on or near the head of a user (e.g., a hat, glasses, necklace, etc.).

Some disclosed embodiments include a housing configured to be worn on a head of a wearer. A housing may be a case, cover, or enclosure to hold, protect, or contain additional components, such as electronics, sensors, lenses, speakers, microphones, wires, transmitters, circuits, processors, buttons, touch pads, or other electrical or mechanical components. The housing may be configured to be worn on a head of a wearer. In one example, the housing may be configured to be worn as or on a pair of glasses. In another example, the housing may be configured to be worn as earbud. In another example, the housing may be configured to be worn as a mask. In another example, the housing may be configured to be worn as a hat or a headband. In another example, the housing may be configured to be worn as a pair of headphones. The housing may have a cross-section that is button-shaped, P-shaped, square, rectangular, rounded rectangular, or any other regular or irregular shape capable of being worn by a user. Such a structure may permit the housing to be worn on, in or around a body part associated with the head, face, or neck of the user (e.g., On the ear, in the ear, over the ear, around the neck, over the mouth, or in any other manner permitting temporary or longer term affixation to an individual). The housing may be made of plastic, metal, composite, a combination of two or more of plastic, metal, and composite, or other suitable material from which a housing may be construction Some disclosed embodiments include at least one detector integrated with the housing. A detector configured to receive light reflections may be a device, instrument, or sensor to identify, sense, pick up, or read information associated with reflected light. The detector may be any mechanism for sensing light. Examples of such detectors include but are not limited to photodiodes, phototransistors, photomultipliers, charge-coupled devices (CCDs), complementary metal-oxide-semiconductor (CMOS) sensors, light dependent resistors, (LDRs), avalanche photodiodes (ADSs), infrared sensors, a thermal imagers, electromyograms, MEMS sensors, wave-meters, spectrometers, spectrophotometers, homodyne detectors, heterodyne detectors, or any other component or element that senses light. In some embodiments, the at least one detector may be configured to detect coherent light reflections, as described elsewhere herein. The detector may be integrated with the housing such that it is connected to the outside of the housing, partially or fully embedded into the housing, or contained within the housing. The detector may be firmly or adjustably affixed to the housing with a wire, pin, pivot, articulating arm, flexible arm, or any other form of rigid or flexible connection. The detector may be affixed to the housing with solder, glue, or tape or molded directly into the housing. In some embodiments, the detector may be wirelessly connected to one or more components within the housing.

In some disclosed embodiments, the detector is configured to receive light reflections from a facial region of the head. Configured to receive light reflections from a facial region refers to the detector being positioned or positionable so that light bouncing off a facial region impinge on the detector. For example, a light detector configured to maintained at an appropriate distance from the face so that reflections may be detected is one example of a detector configured to receive light reflections. Additionally or alternatively, a light detector mounted relative to a light source such that light emitted from the light source bounces off facial skin and impinges on the detector is another example of a detector configured to receive light reflections. Further, a light detector mounted on an adjustable structure that is positionable to receive reflections is yet another example of a light detector configured to receive reflections. The light detector may detect one or more light properties, as described elsewhere in this disclosure. The light reflections may be from the facial region of the head, meaning the front-facing portions of the head that include the structures related to the face. Thus, the facial region may encompass one or more of areas including or surrounding the eyes, nose, mouth, cheek, and/or jaw as described elsewhere in this disclosure.

In some disclosed embodiments, the detector is configured to output associated reflection signals. Reflection signals may be understood as described elsewhere in this disclosure. Outputting associated reflection signals refers to transmitting data and/or providing information, data, or signals to a user, another system, or a device, where the signals relate to the light reflections. For example, the light reflections may be associated with facial skin micromovements, which may be transmitting in a manner characterizing the light reflections and/or the facial skin micromovements. For example, the signals may be output in analog form, digital form, in continuous time, discrete time, periodic time, aperiodic time, and/or as finite, infinite, deterministic, or random data. Output signals may include any electronic representation of a property determined from a measurement, or raw measurement signals detected by a sensor (e.g., data retrieved from a light detector in response to the light reflections from the facial region or data retrieved from a microphone in response to sound). The signals may be transmitted across wires (e.g., copper, fiber, etc.) or wirelessly through long range or short range protocols (e.g., cellular, Bluetooth, W-LAN, etc.). The detector may be a light detector with an associated coherent light source, where the light source emits light on to the region of the face directly below the eye or on the cheek of the user, the light detector reads the light reflections from the facial region of the user and outputs them as a signal representative of the facial skin micromovements to a processor.

Some disclosed embodiments include at least one microphone associated with the housing. A microphone may be understood as any form of audio sensor. For example, a microphone may include one or more unidirectional microphones, bidirectional microphones, cardioid microphones, omnidirectional microphones, onboard microphones, wired microphones, wireless microphones, ribbon microphone, piezoelectric microphone, or any combination of the above. Being associated with the housing may refer to having any physical or wireless connection to the housing or another component associated with the housing. For example, the microphone may be firmly affixed to the exterior or contained within the housing, it may be flexibly or adjustably affixed to the housing with a wire, pin, pivot, articulating arm, flexible arm, or any other form of rigid or flexible connection. A microphone may also be associated with the housing wirelessly. A wirelessly connected microphone may be attached via a separate clip, pin, loop, hook or attachment to a person or their clothing.

In some disclosed embodiments, the microphone is configured to capture sounds produced by the wearer. Capturing sounds produced by the wearer refers to a microphone's function of receiving acoustic energy emitted by a wearer and converting it into an electrical signal that, for example, can be amplified, recorded, or transmitted. The sounds produced by the wearer may be phonemes, syllables, words, sentences, non-linguistic noises such as laughter, cries, grunts, moans, gasps, sighs, sobs, whimpers, sniffs, or any other linguistic or non-linguistic sounds or communication emanating from the nose, mouth, throat, face, or any other region associated with the head of the user. The captured sound may include various details defining the properties of the sound (e.g., tone, volume, pitch, amplitude, duration, frequency).

In some disclosed embodiments, the microphone is configured to output associated audio signals. Audio signals are electrical representations of sound waves, typically in the audible frequency range, that, for example, can be processed, transmitted, or recorded. Outputting associated audio signals refers to transmitting, conveying, or providing such signals. For example, outputting signals may mean transmitting analog, digital, continuous time, discrete time, periodic, aperiodic, finite, infinite, deterministic, or random data. Outputting audio signals may include transmitting any analog or electronic representation of a property of the sound detected by the microphone and as determined from a measurement, or raw measurement (e.g., data retrieved from a microphone in response to sound). The signals may be transmitted across wires (e.g., copper, fiber, etc.) or wirelessly through long range or short range protocols (e.g., wi-fi, cellular, Bluetooth, W-LAN, etc.). For example, the microphone may be a directional microphone attached to the housing and pointed towards the mouth of the user. The user may speak a word or phrase, such as "hello world!" and the microphone may pick up the sounds produced by the wearer and output them as signals readable by a processor.

In some disclosed embodiments, the head mountable system includes at least one light source integrated with the housing. A light source may include a structure capable of producing light. For example, a light source may include a light emitting diode (LED), organic light emitting diode, halogen lamp, florescent lamp, incandescent bulb, chemiluminescent source, laser, or any other form of light source. In some disclosed embodiments, the light source is configured to project coherent light towards the facial region of the head. Coherent light may be understood as described elsewhere in this disclosure. A light source is configured to projecting light towards a facial region if it is arranged such that when powered on, it aims light at a facial region or is capable of being adjusted to aim light at a facial region. Projecting light may involve energizing a light source and allowing it to emit light in a desired direction. Light may be emitted in a specific direction through the use of a reflector, which may be a polished surface in an approximately conical shape around the light source to send light in a specific direction, such as towards a part of the cheek. Alternatively or additionally, a coherent light source may be employed which is designed to emit light in a particular direction. The light source may be configured to repeatedly illuminate the same portion of the facial region of the head. For example, the light source may include an array and only specific light elements may be energized to illuminate the same region of the face. Additionally or alternatively, light elements may be configured to illuminate the entire region of the face or may be connected to an actuator that physically moves the light source to scan a region of the face. Such scanning may be accomplished using one or more mirrors, lenses, prisms, galvanometers, or MEMS devices.

For example, a light source such as an LED may be molded into the housing and configured to direct light onto a small region of the user's cheek. The processor may be configured to activate the light source prior to the onset of vocalization or prior to silent speech in order to illuminate the cheek and produce reflection signals representative of the facial skin micromovements.

Some disclosed embodiments include at least one processor in the housing. A processor may be understood as described elsewhere in this disclosure. The processor may be in the housing meaning that it is contained within a space in the interior of the housing or molded into the structure of housing itself. The processor may be integrated into a motherboard, printed circuit board (PCB), or system on a chip (SOC) that is affixed inside the housing.

Figure 83:
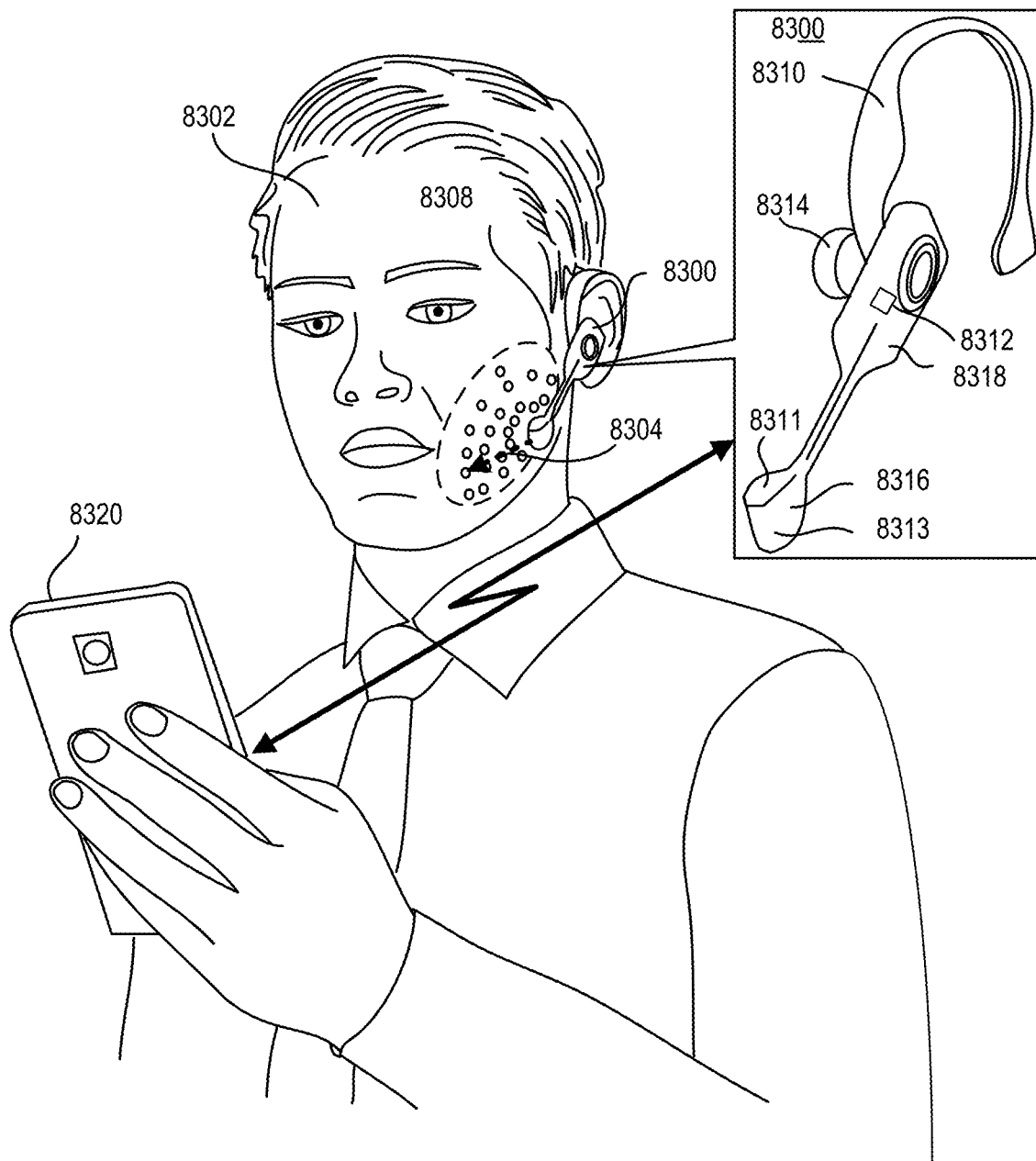
FIG. 83 illustrates an exemplary embodiment of a user wearing the head mountable system for interpreting facial skin micromovements.

By way of nonlimiting example, FIG. 83 provides an example of a disclosed embodiment. User 8302 is showing wearing a head mountable system 8300. The head mountable system 8300 includes a housing 8318, which contains a processor 8312. The housing 8318 is configured to be worn on the head through a clip 8310. The housing 8318 includes an arm which extends down towards an array of sensors which may include a microphone 8311, a detector 8313 for picking up light reflections, and a light source 8316. The housing may also be connected to an output device, which in this example is a speaker 8314 configured to be inserted into the ear of a user 8302. When the user begins the process of speaking, through vocalize or silent speech, the light source 8316 may project light on to the facial region 8308. The detector 8313 receives reflection of light 104 from the facial region 8308. If the user 8302 vocalizes speech, the microphone 8311 would also receive audio signals of the vocalized speech. The microphone 8311 and the detector 8313 may transmit the signals received to the processor 8312 for analysis.

In some disclosed embodiments the processor is configured to use both the reflection signals and the audio signals to generate output that corresponds with words articulated by the wearer. In one example, where neither the reflection signals nor the audio signals alone may be sufficient to generate, with sufficient confidence, the output that corresponds with the words articulated by the wearer, a processor may use both sets of signals (or portions thereof) to derive the words articulated. The words articulated by the wearer may include vocalized speech, silent speech (as described elsewhere in this disclosure), facial muscle recruitment in an absence of audible speech, facial expressions, words spoken, or any other form of communication coming from the wearer. For example, words articulated by the wearer may include single phonemes, combinations of phonemes, words, combinations of words, words in foreign languages, or any other speech-related component. By way of another example, the words articulated by the wearer may include words associated with a facial expression, such as a smile associated with the word happy or a frown associated with the word sad, or any other facial expression and the associated emotion or intended communication. As another example, the words articulated by the wearer may also include vocalized sound understood to be communication absent defined words, such as a grunt, mmmm, mmm-hmmm, a laugh, or a gasp with their associated meaning.

The reflection signals and the audio signals may be used in various ways to generate the output. For example, using the signals may include accessing, interpreting, matching, and/or analyzing the reflection signals and the audio signals to determine the words articulated by the wearer. For example, a processor may receive and process at least portions of both of the signals as input into a trained machine learning model, a trained artificial neural network, an automatic speech recognition tool, or a natural language processing tool. In some embodiments, a lookup may be performed in a database to identify an output correlated to the signals. In other embodiments, using the signals may include processing the signals with a trained machine learning model or algorithm that provides an inferred output (e.g., the words articulated by the wearer) when given the signals as an input. Using the signals may include inputting the signals into a classification neural network that outputs words. For example, the processor may use the reflection signals to perform a lookup in a database that correlates reflection signals to words spoken, where the processor matches the reflection signals to known outputs of words spoken matching those reflection signals, and thus determines the words articulated by the wearer. The process may similarly use the audio signals to perform a lookup in a database that correlates audio signals to words spoken, where the processor matches the audio signals to known outputs of words spoken matching those audio signals, and thus determines the words articulated by the wearer. In another example, the system may use the reflection signals as input into a trained machine learning algorithms that determines the words spoken based on the reflection signals that occur during prevocalization. In another example, the audio signals may be input into an automatic speech recognition algorithm that determines the words articulated by the wearer. Using both the reflection signals and the audio signals may include using the signals together to generate output, using the signals individually to generate output, or using both individually to generate an output simultaneously and compare the results. For example, by interrogating a data structure using both the audio signals and the reflection signals, when one of the audio or reflection signals alone is insufficient to determine words spoken, the other signal might be used to aid in identifying words spoken. Correlations between the two signals, for example, can lead to an identification of the spoken words. Even when one signal appears sufficient to identify the spoken words, the other signal may be used as a check.

Generating output that corresponds with words articulated by the wearer may broadly refer to any audio or visual representation of the words articulated by the user or combination of the two. For example, the output may be audible speech (e.g., audio of language in the structure of a sentence and normal speech, audio of the language as single words or sounds, audio describing a facial expression), text (e.g., written sentences, words, paragraphs, descriptions of expressions or sounds), symbols (e.g. emojis, emoticons), or video (e.g., a recorded or digitally generated face speaking the language, a person signing in American Sign Language). In some embodiments the output may be a combination of both audio and video, for example a video of a face speaking with text subtitles of the language. In some embodiments, the language may be output in the words articulated by the wearer spoken or translated into a different language (e.g., English silently spoken and the output is in English or English silently spoken and the output in Spanish or any other language).

The words articulated by the wearer can be audibly played over a speaker audible to the only one individual, using, for example, headphones or earbuds using a magnetic driver, electrostatic drivers, or bone conduction, or the language can be audibly played over a speaker audible to a plurality of people, such as a television speaker, a computer speaker, a desktop speaker, a floor standing speaker, a public-address (PA) system, or any other speaker. The words articulated by the wearer may be played over a speaker in a head mountable system as described in this embodiment that is being worn by a separate individual.

In some disclosed embodiments, the output includes a textual presentation of the words articulated by the wearer. A textual presentation may include any form of output that can be read as communication, such as text displayed on a screen, projected on to a surface, sent in text message or email, or other form of written communication. The words articulated can be output visually as text on a smartphone screen, a television screen, a computer screen, an AR/VR headset, glasses, projector screen, or any other screen visible to the user.

By way of non-limiting example, FIG. 83 shows a user 8302 wearing the head mountable system 8300. The user 8302 may articulate the words "Hello, world!" where prior to vocalization, the light source 8316 projected light onto facial region 8308 and the detector 8313 received the light reflections from the facial region and output them as reflection signals to the processor 8312. The microphone 8311 would receive audio signals representative the vocalized "Hello, world!" and output them to the processor 8312. The processor 8312 may process both of the signals to produce an output. The output may be displayed as text on the screen of the user's wireless device 8320, which may be wirelessly connected to the head mountable system 8300.

In some disclosed embodiments, the at least one processor is configured to receive a vocalized form of the words Receiving may involve accepting delivery of, acquiring, retrieving, obtaining, or otherwise gaining access to, e.g., information or data by at least one processor. The data may be received via a communications channel, such as a wired channel (e.g., cable, fiber) and/or wireless channel (e.g., radio, cellular, optical, IR). The data may be received as individual packets or as a continuous stream of data. The data may be received synchronously, e.g., by periodically polling a memory buffer, queue or stack, or asynchronously, e.g., via an interrupt event. A vocalized form of the words may broadly refer to any audio conveying the substance of the words. For example, the user may audibly say the phrase "Hello, my name is John Doe!" The microphone may capture the sounds and output the audio signals representing the vocalized words to be received by the processor. Or, the user may subvocalize or prevocalize such a phrase, and a voice synthesizer may output corresponding audio signals.

In some disclosed embodiments, the at least one processor is configured to determine at least one of the words prior to vocalization of the at least one word. Determining the words may include predicting, classifying, describing, identifying, establishing, recognizing, interpreting, translating, construing, or deciphering the words spoken, including any phonemes, combinations of phonemes, syllables, words, combinations of words, or any other speech-related component of the vocalized words. For example, the phrase "Hello, world!" may be identified as the entire phrase (e.g., "Hello, world!") or the single words (e.g., "hello" and "world"). For another examples, the phrase "Hello, world!" may be identified by syllables (e.g., "hel," "lo," "world,"), the phonemes (e.g., "h," "e," "1," etc.), or other speech related component (e.g., "!"). Prior to the vocalization of the word refers to a time prior to the onset of detectable sounds during the normal process of vocalized speech. As discussed elsewhere herein, there is a delay between when muscles are recruited to output speech and an occurrence of audible sound. During that period, the processor may determine the word or words that will be spoken.

Determining at least one of the words prior to vocalization of the at least one word may involve identifying the first word spoken before receiving any signals representing the vocalized form of the words, but after receiving facial reflection signals from the time prior to vocalization. In some disclosed embodiments, determining at least one of the words prior to vocalization of the at least one word may involve determining a word spoken after receiving the first word or beginning of a phrase as the vocalized form of the words, but prior to the vocalization of the rest of the phrase.

By way of non-limiting example, a user may vocalize the phrase "Hello, my name is John Doe!" Prior to receiving the audio signals representing the vocalized phrase "Hello, my name is John Doe!" the processor may use the reflection signals that are measured prior to vocalization to determine that the first word the user will vocalize is "Hello." For example, the processor may use the reflection signals to perform a lookup in a database or it may use the reflection signals as input into a trained machine learning algorithm to determine the vocalized word that corresponds to the prevocalization reflection signals. In some disclosed embodiments, the processor may receive the vocalized words "Hello, my name is" and the reflection signals accompanying the vocalized words. The processor may use the reflection signals to determine the next words prior to their vocalization. The processor may also use the audio signals to determine the next word prior to its vocalization. For example, the processor may use "Hello, my name is . . . " as input into a large language model or a deep learning algorithm such as a transformer to predict that the next words are "John Doe" prior to their vocalization.

In some disclosed embodiments, the words articulated by the wearer include at least one word articulated in a nonvocalized manner. Words articulated in a nonvocalized manner refers to silent, subvocalized, or prevocalized speech as discussed elsewhere herein. Words articulated in a nonvocalized manner may also include words conveyed through facial expressions, eye movement, or any other form of non-audible communication.

The at least one processor is configured to determine the at least one word without using the audio signals. Determining the word may be understood as described above. Without using the audio signals may refer to the processor not having access to the audio signals, for example because they do not exist, or using only the reflection signals to determine the word articulated in a nonvocalized manner, or it may refer to using the reflection signals in addition to any other information the processor has access to regarding reflection signals or the user. For example, the processor may have access to a database that correlates reflection signals to words articulated in the absences of vocalization. It may also have access to a trained machine learning algorithm that infers speech from reflection signals from the facial region of an individual. In another example, the processor may have access to a user profile for the specific individual currently using the head mounted system. A user profile may include a collection of settings (e.g., language, preferred output, etc.) and information associated with a user, and capture certain identifying characteristics about a user (e.g., name, age, payment information, etc.). A user profile may also include specific information associated with the user's voice, facial structure, facial movements, tone, enunciation, accent, speech, words spoken, speech impediments, or any other characteristic regarding the users. For example, the user profile may contain specific information regarding the correlations between reflection signals from the user and words articulated in a vocal or non-vocal manner. The user of the head mountable system may silently speak "hello, my name is John Doe." The detector may pick-up reflection signals from a facial region of the head and output them to the processor. The processor may use a database containing correlations of reflection signals to words articulated to perform a lookup to identify the words associated with the reflection signals. The reflection signals may be compared to the correlations in the database to establish a match by vector distance, similarity, regression, nearest neighbor matching, optimal pair matching, or another method of statistical analysis. The system may determine that the words articulated in a nonvocalized manner by the user were "hello world!"

In some disclosed embodiments, the at least one processor is configured to use the reflection signals to identify one or more words articulated in an absence of perceptible vocalization. Articulated in an absence of perceptible vocalization may be understood similarly as articulated in a nonvocalized manner (e.g., silent, subvocalized, or prevocalized speech). Articulated in an absence of perceptible vocalization may also refer to a scenario in which a user vocalizes speech but the audio signals are unintelligible. For example, this may occur if the user speaks to softly for the microphone to capture the speech, or it may occur if the user is speaking in an extremely loud environment, or during a sudden and unexpectedly loud event (e.g., a car crash). It may also occur, for example, when the microphone fails for any other reason and is unable to capture the vocalization of a user. Using the reflection signals may include accessing, matching, interpreting and/or analyzing the reflection signals. Using the reflection signals to identify one or more words articulated in an absence of perceptible vocalization refers to a reliance, at least in part, on the reflection signals to determine the word articulated in a nonvocalized manner. It may refer to using the reflection signals alone or in addition to any other information to determine words articulated. For example, the processor may have access to a database that correlates reflection signals to words articulated in the absences of vocalization. It may also have access to a trained machine learning algorithm that infers speech from reflection signals from the facial region of an individual. Using the reflection signals may also refer to using the reflection signals associated with a word articulated in an absence of perceptible vocalization in conjunction with the audio signals for words perceptibly vocalized before and/or after the one or more words. For example, a user may state "Hello, my name is John Doe" when a loud crash sounds and obscures the vocalization of the word "name." Here, the processor may receive audio signals for "hello, my is John Doe" and reflection signals for the entire phrase. The processor may use the reflection signals in the absence of the audio signals to identify the word "name." The processor may use the audio signals, for example by inputting them into a natural language processing algorithm or a large language model, to determine the word articulated in the absence of perceptible vocalization was "name."

In some disclosed embodiments, the at least one processor is configured to use the reflection signals to determine particular facial skin micromovements. Facial skin micromovements may be understood as described elsewhere in this disclosure. Using the reflection signals to determine particular facial skin micromovements may include determining how particular light reflections correspond to particular skin movements, to allow interpretation of the facial skin micromovements. For example, determining may include analyzing details defining a surface contour, light reflections, movement, muscle recruitment, skin deformations, scale of movement (e.g., micrometers, millimeters), nerve activity, shape, color, and may include an association with other variables, (e.g., time or audio) and/or any other information required to analyze the particular facial skin micromovements. The particular facial skin micromovements may include prevocalization facial skin micromovements (e.g., movements of the face made prior to vocalizing speech), facial skin micromovements made during vocalization, or facial skin micromovements made during subvocalization or in the absence of vocalization (e.g., when speaking silently). The particular facial skin micromovements may also include the facial skin movements associated with facial expressions, such as a smile or a frown, or any other facial expression and the associated movements. The particular facial skin micromovements may also include the movements associated with vocalized sound understood to be communication absent words, such as a grunt, mmmm, mmm-hmmm, a laugh, or a gasp. For example, if a user says "Hello!" and then smiles, the reflection signals may be used to identify the specific facial skin micromovements associated with prevocalization, vocalization, and post vocalization of "Hello!" and may also identify the movements associated with the smile.

In some disclosed embodiments, the at least one processor is configured to correlate the particular facial skin micromovements with reference skin micromovements that correspond with the words. Reference skin micromovements may refer to the training data used to train a machine learning algorithm or artificial neural network to output speech or other associated characteristics based on skin micromovements or it may refer to skin micromovements contained in a database that are associated with specific phonemes, syllables, words, phrases, other parts of speech, or another property of the user associated with movement of the face (e.g., facial expressions, sounds that are not words, etc.). Alternatively, in a non-AI context, reference skin movements (in the form of signals associated therewith) may be stored in a data structure in association with (e.g., correlated to) corresponding words.

For example, reference skin micromovements that correspond with the words may be included in a database containing any number of specific skin movements associated with particular spoken words. The database could contain example skin movements for particular words for prevocalization facial skin micromovements, during vocalization movements, and post vocalization movements. It may also contain example skin movements for the same word when spoken with various accents (e.g., a French accent or a southern accent) or speech impediments (e.g., a stutter or a lisp). The various reference skin movements may be associated with the words spoken and a processor may be able to perform a lookup in the database for specific words based on the facial skin movements. The references skin micromovements that correspond with the words may be associated with a trained machine learning algorithm, for example, an inference model where the model is trained to determine an output word, phrase, or sentence when provided with facial skin micromovements as an input. Correlating may involve associating, assigning, connecting, matching, or pairing the particular facial skin micromovements with the reference skin micromovements. For example, if the reference skin micromovements are stored in a database, the processor may perform a lookup to identify the reference skin micromovements that most closely match the particular facial skin micromovements by vector distance, similarity, regression, nearest neighbor matching, optimal pair matching, or another method of statistical analysis. The words associated with the identified reference skin micromovements may correspond to the words articulated by the user for the particular facial skin micromovements.

In some disclosed embodiments, the at least one processor is configured to use the audio signals to determine the reference skin micromovements. Using the audio signals may include accessing, matching, interpreting or analyzing the audio signals by the processor. Using the audio signals may refer to the audio signals being the basis for a lookup in a database, entered as input into a machine learning algorithm, analyzed by an artificial neural network, analyzed through automatic speech recognition, or analyzed by another data processing algorithm. Using the audio signals to determine the reference skin micromovements broadly refers to analyzing the audio signals to identify or match reference skin micromovements to the audio signals received when a user articulates words. For example, using the audio signal may involve performing a look up in a database to match the audio signals received by the processor to audio signals in the database associated with reference skin micromovements. The audio signals may be compared to the data in the database to establish a match by vector distance, similarity, regression, nearest neighbor matching, optimal pair matching, or another method of statistical analysis to match the audio signals with reference skin micromovements.

In another example, using the audio signals may involve analyzing the sounds captured by the microphone to identify the words articulated by the wearer, which may include applying one or more sound and/or speech processing techniques (e.g., filters, waveform analysis, spectral analysis, Fourier transforms, wavelet transforms, Cepstral analysis, dynamic time warping, hidden Markov models, phase-aware processing) and/or artificial intelligence techniques (e.g., machine learning, deep learning, neural networks, natural language processing) to extract the information from the signals representing sounds and may include classifying, describing, determining, establishing, recognizing, interpreting, translating, construing, or deciphering the words articulated, including any phonemes, combinations of phonemes, syllables, words, combinations of words, or any other speech-related component of the words spoken. For example, the phrase "Hello, world!" may be identified as the entire phrase (e.g., "Hello, world!") or the single words (e.g., "hello" and "world"). For another examples, the phrase "Hello, world!" may be identified by syllables (e.g., "hel," "lo," "world,"), the phonemes (e.g., "h," "e," "1," etc.), or other speech related component (e.g., "!"). The identified words may be used as input into a database lookup to identify reference facial skin movements associated with the identified words corresponding to the analyzed audio signals.

In some disclosed embodiments, the head mountable system include a speaker integrated with the housing and configured to generate an audio output. A speaker may broadly refer to any device capable of producing sound audible to the user. Generating an audio output broadly refers to energizing a speaker to produce sounds (e.g., the words articulated by the wearer). The speaker may be integrated with the housing such that it is connected to the outside of the housing, partially or fully embedded into the housing, or contained within the housing. For example, as discussed elsewhere herein, the housing may be in the form of a casing of earbuds, goggles, or glasses, and speaker may be included in the associated casing.

In some disclosed embodiments, the output includes an audible presentation of the words articulated by the wearer. An audible presentation of the words may include any form of output that is able to be heard by the user or another individual and understood as single words, phrases, or sentences. For example, the output may be audio recognizable as speech (e.g., audio of language in the structure of a sentence and normal speech, audio of the language as single words or sounds, audio describing a facial expression, audio with a tone that conveys additional meaning, such as an angry, happy, or inquisitive tone). The words can be output over a speaker audible to the only one individual, using, for example, headphones or earbuds using a magnetic driver, electrostatic drivers, or bone conduction, or the words can be audibly played over a speaker audible to a plurality of people, such as a television speaker, a computer speaker, a desktop speaker, a floor standing speaker, a public-address (PA) system, or any other speaker. For example, if a user were to say, "Today is Wednesday?" as a question, the output may be audio that conveys the that the words articulated by the wearer were a question. The output may have an upward inflection at the end of the sentence to indicate a question, or the audio may indicate the words articulated by the wearer was a question by other means, such as output the word question, at the end of the sentence, e.g., "Today is Wednesday, question."

In some disclosed embodiments, the audible presentation includes a synthetization of a voice of an individual other than the wearer. Synthetization of a voice refers to sounds generated using a microprocessor to reproduce, mimic, or simulate sounds created by an individual (whether or not real) when speaking (e.g., tone, inflection, accent, pitch, timber, etc.). Synthetization of a voice may be performed through concatenative synthesis, formant synthesis, or through machine learning, deep learning algorithms, or audio deepfakes. A voice of an individual other than the wearer may refer to a person besides the wearer (e.g., a celebrity, another individual that has used the device, a person with a specific accent, apply a filter to the voice of the wear, or any other individual) or an artificial voice that does not mimic or attempt to mimic a person (e.g., a synthetic voice that sounds like a robot or other artificial entity, a voice that sounds like a fictional character, a voice that is an combination of multiple individual's voices, or a voice of an artificial personal assistant) For example, a user may articulate, "Get to the choppa!" The head mountable system may output those words as speech over a speaker in a television, the system may synthetize the voice of a celebrity, such that the output sounds like the words are being spoken by a famous individual, for example Arnold Schwarzenegger.

In some disclosed embodiments, the audible presentation includes a synthetization of a voice of the wearer. The audible presentation and synthetization of a voice are similar to the descriptions provided above. The voice of the wearer may refer to producing output audio that sounds similar to, attempts to mimic, or is identifiable as the wearer and may be a recording of the voice of the wearer. As discussed elsewhere in this disclosure, a system might be trained to simulate a voice of a wearer. For example, a wearer may vocalize "Hello, my name is John Doe." The microphone of the head mountable system may record the speech of the wearer and output the words articulated by the wear over a speaker, such as a computer speaker such that the speaker plays the words "Hello, my name is John Doe" in the voice of the wearer because it is a recording of the wearer speaking. In another example, the wearer may articulate "Hello, my name is John Doe" without producing sounds that are detectible to the microphone. The system may use the facial skin movement to determine the words articulated and generate output corresponding to those words. The system may use a deep learning or other algorithms that were trained using earlier recordings of the voice of the wearer to reproduce audio that mimics the voice of the wear and play the generated output over a speaker.

In some disclosed embodiments the at least one processor is configured to use the audio signals for determining the voice of the individual for synthetization of words spoken in an absence of perceptible vocalization. Using the signals for determining the voice of an individual may involve comparing the audio signals, as described elsewhere in this disclosure, against known characteristics of the voice of the individual or a voice signature of the individual. Using the signals for determining the voice of an individual may also refer to creating a voice signature defining the voice of the individual for later use. A voice signature may include any information associated with the characteristics of the speech or voice of an individual (e.g., facial skin micromovements, tone, enunciation, accent, language, specific words spoken, specific phonemes spoken, etc.). For example, voice signatures may be associated with certain phenomes, combinations of phonemes, words, combinations of words, or any other speech-related component. For example, if an individual speaks English with a French accent, the voice signature may contain information regarding how a French accent may change facial skin micromovements correlations to specific words spoken. In another example, the user may have a southern drawl, where their speech is slowed or elongated on specific words. A voice signature for that user may contain information that individual's unique speech characteristics. In this disclosed embodiment, synthetization of words spoken in an absence of perceptible vocalization refers to synthesizing speech in a situation where a user does not audibly articulate that speech (either in complete silence or in a way that would be understandable to a listener). In such situations, facial skin micromovements may be interpreted and a voice synthesized as described elsewhere herein.

By way of non-limiting example, FIG. 83 shows a user 8302 wearing the head mountable system 8300. The user 8302 may articulate the words "Hello, my name is John Doe," by vocalizing the word "Hello" and silently speaking the words "my name is John Doe" where prior to vocalization, the light source 8316 projected light onto facial region 8308 and the detector 8313 received the light reflections from the facial region and output them as reflection signals to the processor 8312. The microphone 8311 may receive audio signals representative of the vocalized word "Hello" and output them to the processor 8312. The processor 8312 may process both of the signals to produce an output. The output may be transmitted to wireless device 8320 to be played on the speaker of the wireless device 8320, or the audio may be played through the speaker 8314 of the head mountable system 8300. The processor 8312 may use the audio signals from the microphone 8311 for the vocalize word "hello" to determine the voice of the wearer. The output audio may be produced by synthesizing the voice of the wearer 8302 for the words that were not vocalized, "my name is John Doe."

In some disclosed embodiments, the words articulated by the wearer are in a first language and the generated output may include words spoken in a second language. For example, the first language may refer to English, Hebrew, German, French, Arabic, Bengali, Portuguese, Russian, Spanish, Mandarin, Swahili, emojis, or any other system of communication. The generated output includes words spoken in a second language may mean that at least one of the words articulated by the wearer is output in a language other than the first language. For example, if the wearer articulated a phrase in English (e.g., "Hello, my friend."), the output may present the entire phrase in Spanish (i.e., "Hola, mi amigo."), or a single word of the phrase in Spanish (e.g., "Hola, my friend."). The translation may be performed by a conventional machine translation method, such as a rule based, statistical, or example-based method, or AI based technique, such as an artificial neural network trained to translate between languages.

In some disclosed embodiments the at least one processor is configured to cause a textual presentation of the words to be transmitted over a wireless communication channel to a remote computing device. A textual presentation of the words may be understood as described elsewhere in this disclosure. Transmitted may broadly refer to any method of sending data. For example, transmitted data may be analog, digital, continuous time, discrete time, periodic, aperiodic, finite, infinite, deterministic, or random. Transmitted data may be any electronic representation information, such as a string of text or an audio recording, or a property determined from a measurement, or raw measurement signals detected by a sensor (e.g., data retrieved from a light detector in response to the light reflections from the facial region or data retrieved from a microphone in response to sound). A wireless communication channel may refer to a short range or long-range wireless communication channel. For example, it may refer to Bluetooth, Wi-Fi, wireless LAN, broadcast radio, cellular network, satellite, GSM, LTE, CDMA, 5G, Zigbee, WiMAX, infrared transmission, or any other means of over the air communication. A remote computing device may broadly refer to any processor that is not located in the housing of the head mountable system. For example, a remote computing device may be a server, such as a cloud-based server, a mobile terminal, such as a phone, tablet, PDA, smartwatch, a virtual reality or augmented reality headset, a conventional computer in a separate location, a local server, another head mountable system, a car, or a car infotainment system. By way of non-limiting example, a user may silently articulate the words "Hello, my name is John Doe." The head mountable system may use the reflection signals to generate a textual output of "Hello, my name is John Doe" and transmit that output to a nearby mobile phone, where a message may appear on the screen of the mobile phone that says "Hello, my name is John Doe."

In some disclosed embodiments, the at least one processor is configured to cause the generated output to be transmitted to a remote computing device for executing a control command corresponding to the words articulated by the wearer. Generated output, transmitted, and a remote computing device may be understood similar as described earlier in this disclosure. Executing a control command refers to causing a computing device to perform an action. For example, executing a control command may refer to setting an alarm, turning off the lights, opening a garage door, sending a message, transcribing text, searching the internet, displaying the weather, displaying a score of a game, closing a window, activating GPS map guidance, playing music or other audio, or any other action performed by a remote computing device such as a car, a mobile phone, smartwatch, tablet, or a smart home system. Corresponding to the words articulated by the wearer broadly refers to the executing command closely mimicking the words of the wearer. For example, if the wearer articulates, "Hey digital personal assistant, what is the weather this week?" the remote computing device may display the weather for the next 3 days or 7 days. In another example, the user may articulate "Home assistant, turn on the lights" and the home assistant may turn on the lights in the current room, in the entire house, or in a specific area depending on various factors (e.g., the time of day). In another example, the user may articulate "Hey personal digital assistant, text my wife to tell her I will be home in 15 minutes" and the remote computing device, in this case a mobile phone, may send a text message to the user's wife stating, "be home in 15."

In a non-limiting example, FIG. 83 shows a user 8302 wearing the head mountable system 8300 and holding a remote computing device in the form of a personal wireless device 8320. The user 8302 may articulate the words "Hey digital personal assistant, please set a timer for 5 minutes." The detector 8313 and the microphone 8311 may receive or capture signals from movement of facial region 8304 and vocalization; if vocalization occurred. The processor 8312 may use the signal to generate output, and transmit via a communication module (not pictured) to the wireless device 8320. The wireless device 8320 may execute a command corresponding to the articulated words by setting and starting a timer for 5 minutes.

In some disclosed embodiments, the at least one processor is further configured to analyze the reflection signals to determine facial skin micromovements that correspond to recruitment of at least one specific muscle. Analyzing the reflection signals to determine facial skin micromovements refers to processing the reflection signals and ascertaining the facial skin micromovements that caused the reflections associated with the signals. Analyzing in this context may include, for example, applying one or more processing techniques (e.g., filters, transformations, feature extraction, clustering, pattern recognition, edge detection, fast Fourier Transforms, convolutions, and/or any other type of image processing technique) and/or artificial intelligence (e.g., machine learning, deep learning, neural networks) to extract information from the reflection signals. Analyzing the reflection signals may include identify specific properties of the facial skin micromovements, such as a surface contour, movement, specific muscle recruitment, skin deformations, scale of movement (e.g., micrometers, millimeters), nerve activity, shape, color, or any other property corresponding to the facial skin micromovements. Muscle recruitment may be understood as described elsewhere in this disclosure. Determining facial skin micromovements that correspond to recruitment of at least one specific muscle may involve analyzing the reflection to identify associated skin movements. Since the facial skin micromovements occur as the result of muscle movements, facial skin micromovements necessarily correspond to recruitment of at least one specific muscle. For example, movements of the eyelids may be identified as corresponding to two specific muscles associated with the eye socket. In another example, movements of the nose and skin around it may be identified as corresponding to three specific muscles. In some disclosed embodiments, the at least one specific muscle includes a zygomaticus muscle, an orbicularis oris muscle, a risorius muscle, or a levator labii superioris alaeque nasi muscle. These specific muscles may be understood as described elsewhere in this disclosure.

Figure 84:
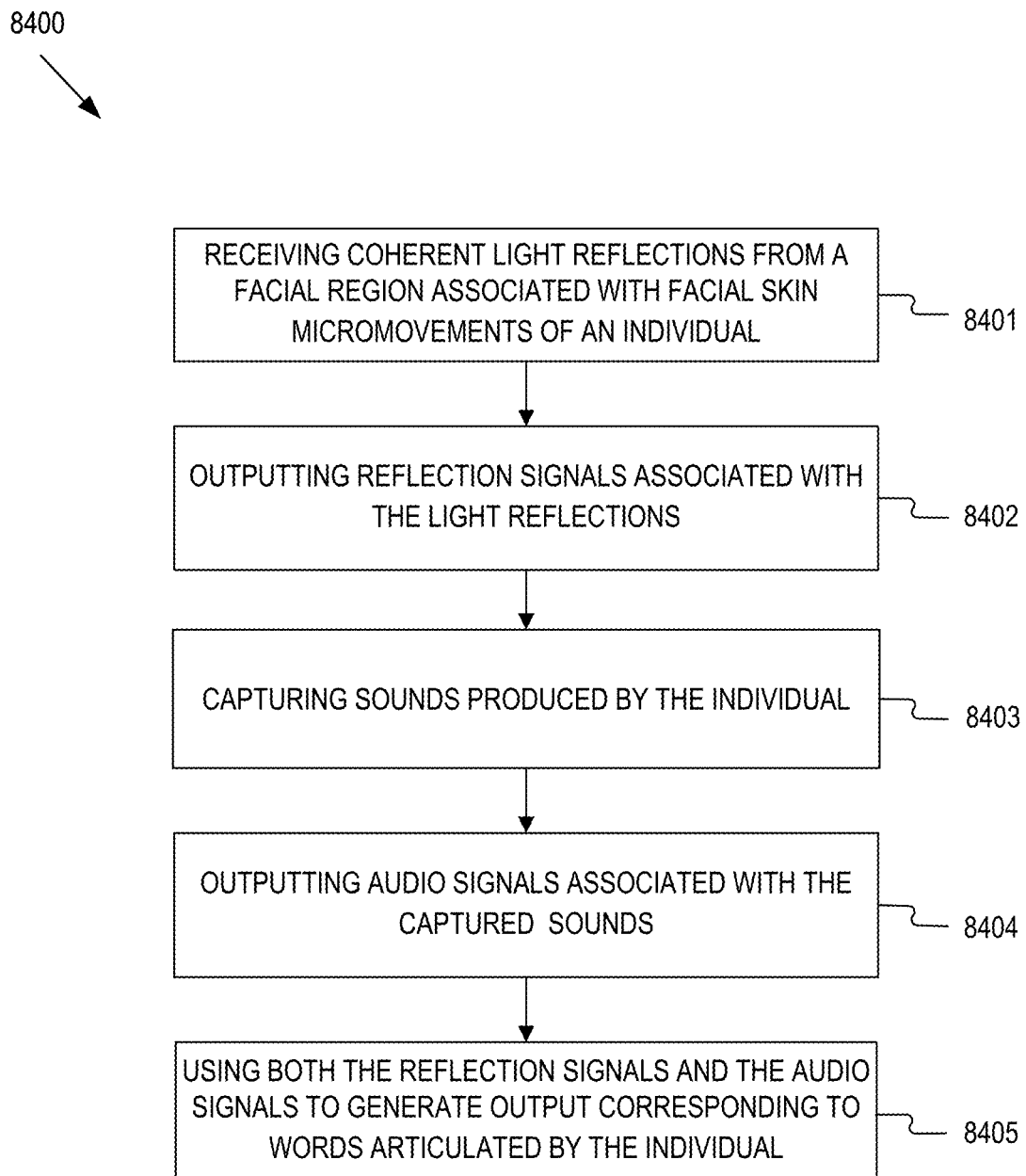
FIG. 84 illustrates a flowchart of an example method for interpreting facial skin micromovements.

FIG. 84 illustrates a flowchart of an exemplary process 34-200 for interpreting facial skin micromovements. Process 8400 includes a step 8401 of receiving coherent light reflections from a facial region associated with facial skin micromovements of an individual. For example, in FIG. 83, detector 8313 may receive light reflections from facial region 8304 when a user 8302 articulates words. Process 8400 includes a step of 8402 of outputting reflection signals associated with the light reflections. For example, in FIG. 83, detector 8313 may output the reflection signals to processor 8312. Process 8400 includes a step of 8403 of capturing sounds produced by the individual. For example in FIG. 83, the user 8302 is wearing head mountable system 8300. The user 8302 may articulate words and vocalize them. Microphone 8311 may capture the sounds produced during the user's 8302 articulation of words. Process 8400 includes a step of 8404 of outputting audio signals associated with the captured sounds. For example, in FIG. 83, microphone 8311, captures the sounds and may output the audio signals to the processor 8312. Process 8400 includes a step of 8405 of using both the reflection signals and the audio signals to generate output corresponding to words articulated by the individual. For example, in FIG. 83, the processor may use the reflection signals received from detector 8313 and the audio signals received from microphone 8311 to generate an output. The processor may display the generated output on a screen, such as the screen of wireless device 8320, if the output is text, or play it on speaker 8314 if the output it audio or any combination thereof.

Some disclosed embodiments involve a non-transitory computer readable medium containing instructions that when executed by at least one processor cause the at least one processor to perform operations for interpreting facial skin micromovements, the operations comprising: receiving coherent light reflections from a facial region associated with facial skin micromovements of an individual, and outputting reflection signals associated with the light reflections; capturing sounds produced by the individual; outputting audio signals associated with the captured sounds; and using both the reflection signals and the audio signals to generate output corresponding to words articulated by the individual.

The embodiments discussed above for interpreting facial skin micromovements may be implemented through non-transitory computer-readable medium such as software (e.g., as operations executed through code), as methods (e.g., process 8400 shown in FIG. 84), or as a system (e.g., head mountable system 100 shown in FIG. 83). When the embodiments are implemented as a system, the operations may be executed by at least one processor (e.g., processing device 400 or processing device 460, shown in FIG. 4)

Figure 85A:
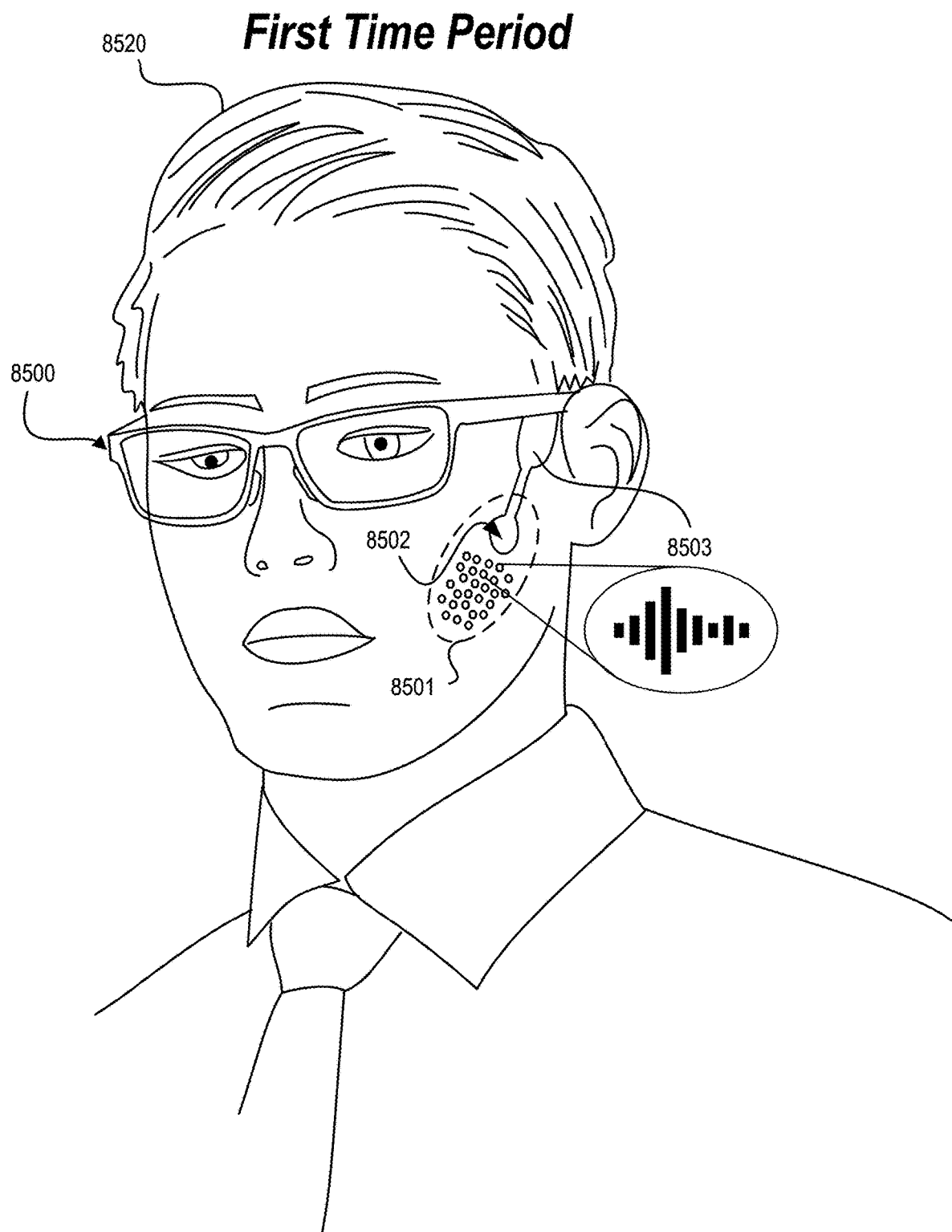
FIG. 85A to 85C illustrate exemplary embodiments of training operations to interpret facial skin micromovements in the first through third time periods, consistent with some disclosed embodiments.
Figure 85B:
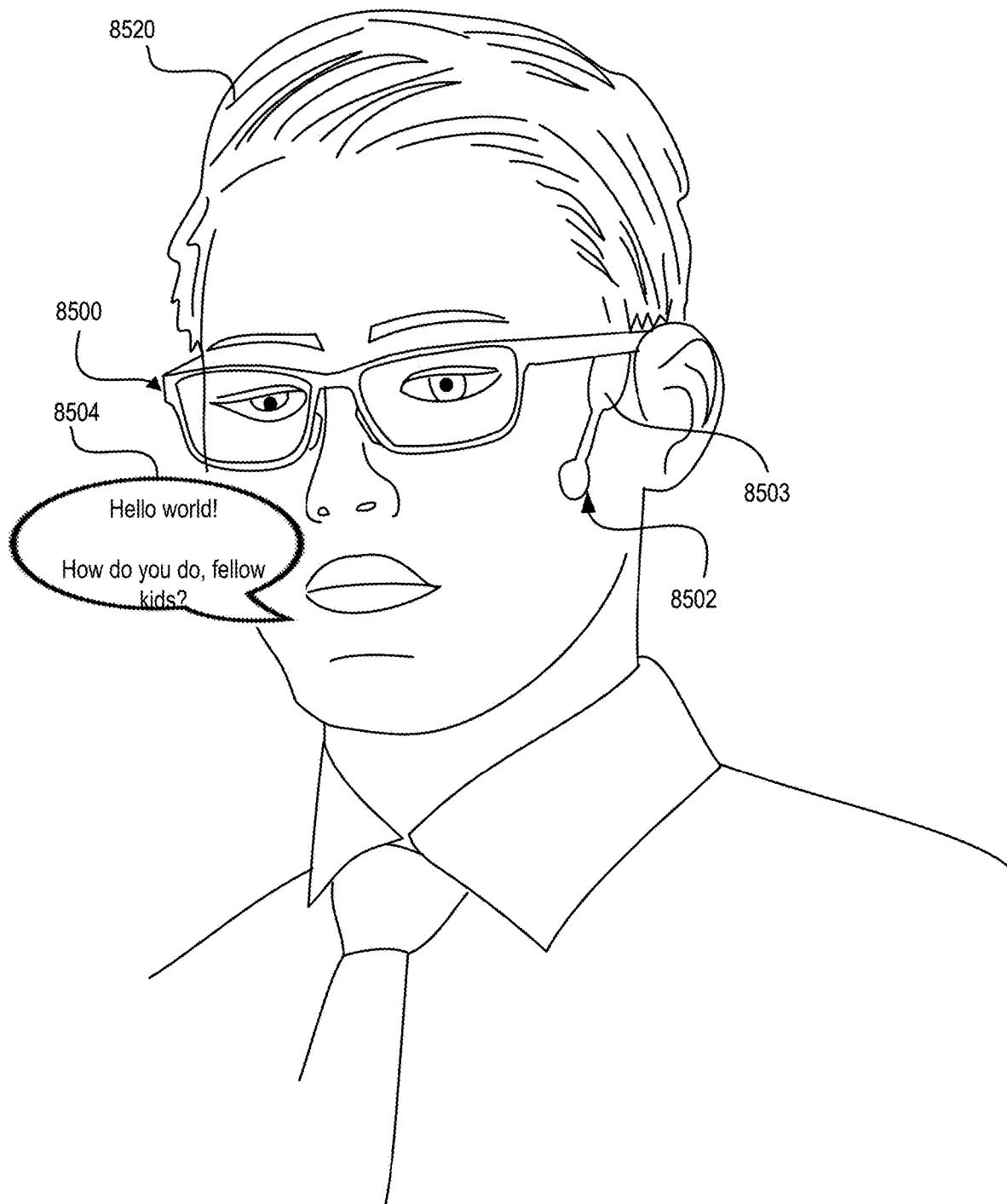
Figure 85C:
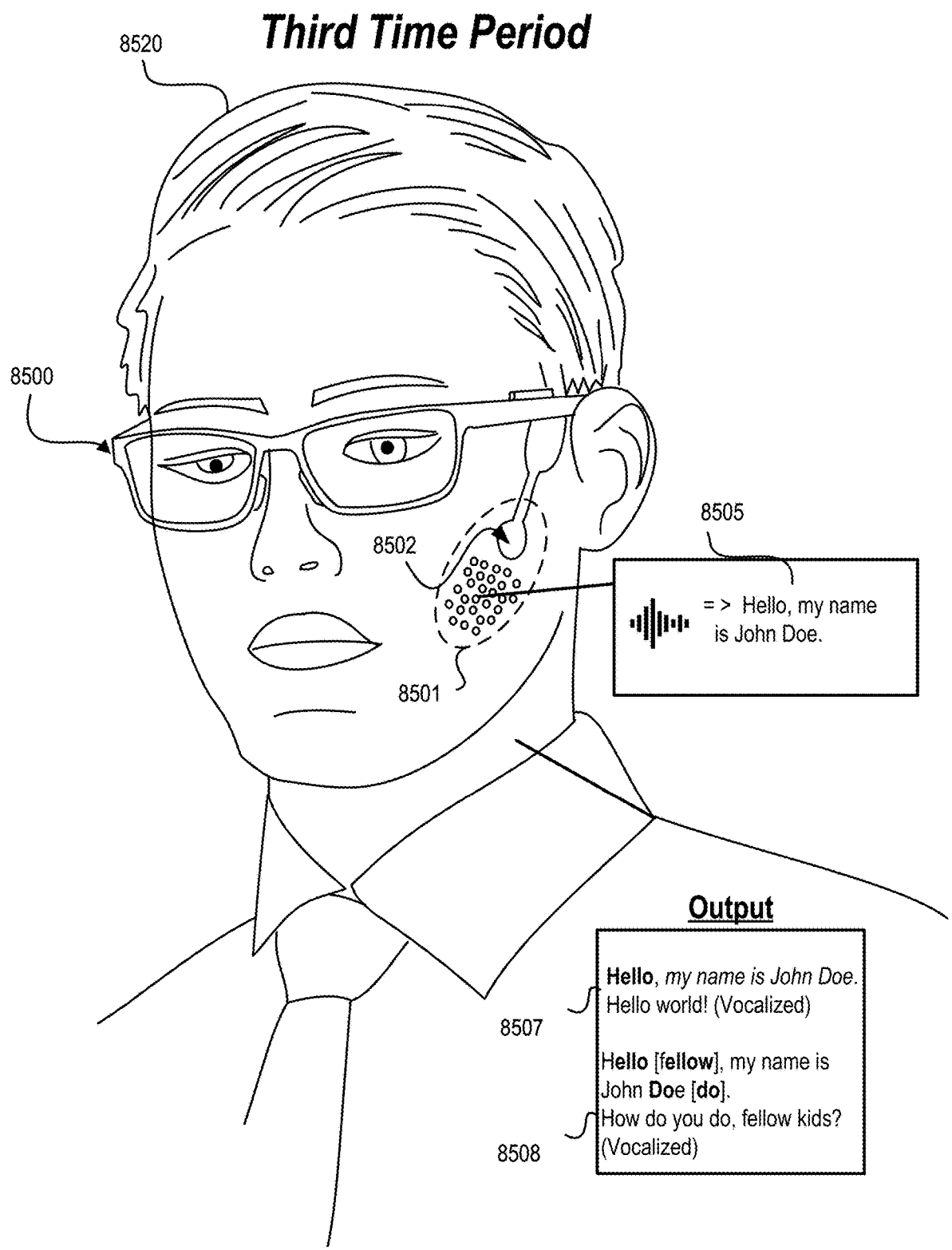
Figure 86:
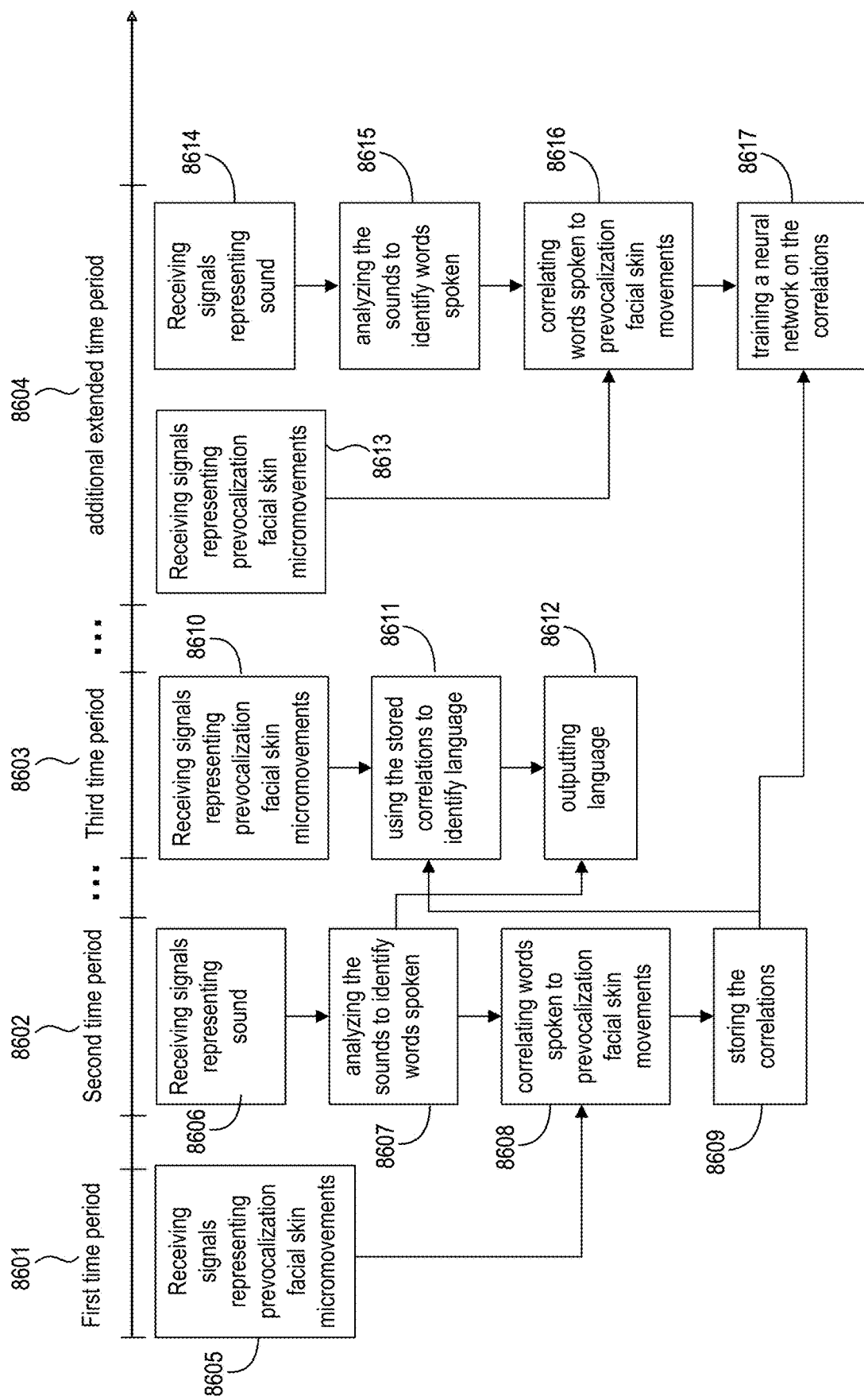
FIG. 86 is a flow diagram of an example of the first through third time periods illustrated in FIG. 85A to 85C with an example additional extended time period, consistent with some disclosed embodiments.
Figure 87:
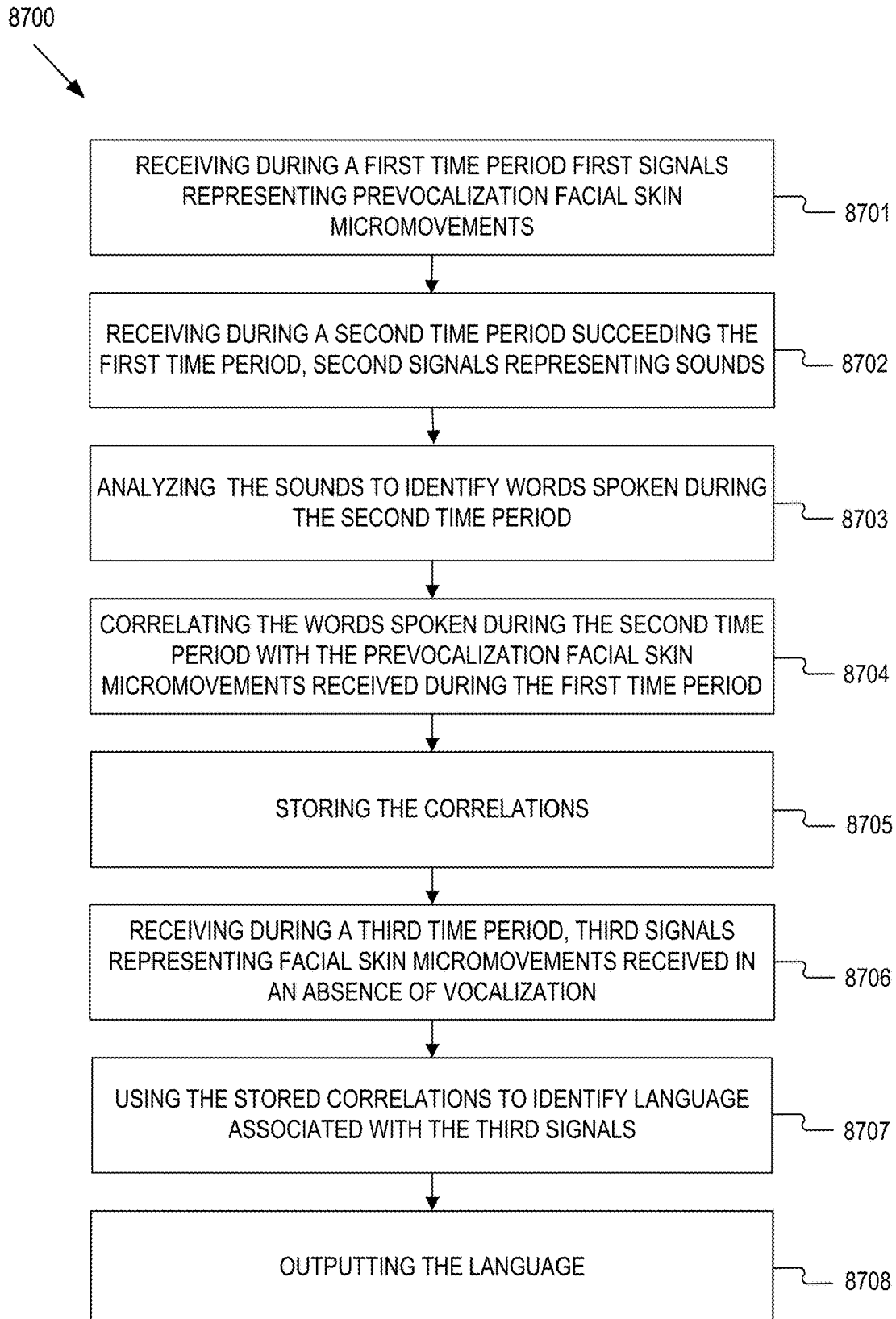
FIG. 87 is a flowchart of an example method for interpreting facial skin micromovements, consistent with some disclosed embodiments.

In some instances, the description that follows may refer to FIGS. 85 to 87, which taken together, illustrate exemplary implementations for managing privacy in an extended reality environment, consistent with some disclosed embodiments. FIGS. 85 to 87 are intended merely to facilitate conceptualization of one exemplary implementation for performing operations for selectively operating a wearable extended reality appliance and do not limit the disclosure to any particular implementation.

Some disclosed embodiments involve training operations to interpret facial skin micromovements. e.g., Facial skin micromovements may be understood as described elsewhere in this disclosure. Training operations may include programing one or more rules, functions, procedures, machine learning algorithms, or neural networks. For example, training operations may include manually programing an inference model, a classification model, or a regression model, or it may involve training a machine learning algorithm. Training a machine learning algorithm may include an algorithm that uses an inference model that when provided with an input generates an inferred output. For example, a training operation may include providing the machine learning algorithm with an input that produces a known output (e.g., input representing facial skin micro movements that immediately preceded vocalized speech and the known output of the vocalized speech). For example, training a machine learning algorithm may include training a classification algorithm, the input may include a sample, and the known output may include a classification of the sample. In another example, training a machine learning algorithm may include training a regression model, the input may include a sample, and the known output may include a known value for the sample. In yet another example, training a machine learning algorithm may include training a clustering model, the input may include a sample, and the known output may include an assignment of the sample to at least one cluster. In an additional example, training a machine learning algorithm may include training a classification algorithm, the input may include an image, and the known output may include a classification of an item depicted in the image. In yet another example, training a machine learning algorithm may include training a regression model, the input may include an image, and the inferred output may include a known value for an item depicted in the image (such as an estimated facial skin motion, and so forth). In an additional example, training a machine learning algorithm may include an image segmentation model, the input may include an image, and the known output may include a segmentation of the image. In yet another example, training a machine learning algorithm may include an object detector, the input may include an image, and the known output may include one or more detected objects in the image and/or one or more locations of objects within the image. In some examples, training a machine learning algorithm may include one or more formulas and/or one or more functions and/or one or more rules and/or one or more procedures, the input may be used as input to the formulas and/or functions and/or rules and/or procedures, and the known output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth).

In the context of AI, a training operation refers to a process of training an artificial intelligence model using a dataset. During training, the model learns to recognize patterns, make predictions, or perform specific tasks based on the input it receives. A training operation typically involves several steps:

Dataset preparation: A training dataset is collected or created, consisting of input data and corresponding labels or target outputs.

Model initialization: An AI model, such as a neural network, is created with an initial set of parameters or weights. These parameters determine how the model initially processes the input data.

Forward propagation: The training dataset is fed into the model, and the input data is processed through the network in a forward direction.

Loss calculation: The output produced by the model is compared to the expected or target output from the dataset. A loss or error metric may be generated to reflect a discrepancy between the predicted and desired outputs.

Backward propagation: The loss may be used to update the model's parameters or weights through a process known as backpropagation. This involves computing the gradients of the loss with respect to the model's parameters and adjusting them with, for example, gradient descent.

Iterative optimization: The forward propagation, loss calculation, and backward propagation steps are repeated multiple times, known as iterations or epochs. Each iteration helps the model refine its parameters and reduce the overall loss, gradually improving its performance.

Model evaluation: Throughout the training process, a separate validation dataset may be used to assess the model's performance on unseen data. This evaluation may help monitor the model's generalization ability and prevent overfitting, where the model becomes too specialized on the training data and performs poorly on new data.

The training operation continues until the model achieves satisfactory performance or meets predefined criteria. Once the training is complete, the trained AI model can be used for inference or making predictions on new, unseen data.

Interpreting facial skin micromovements may include performing one or operations to translate, understand, construe, read, explain, comprehend, decode, identify, or decipher the facial skin micromovements as vocalized speech, silent speech (as described elsewhere in this disclosure), facial expressions, or any other form of communication. For example, facial skin micromovements may be associated with certain phonemes, combinations of phonemes, words, combinations of words, or any other speech-related component. For example, interpreting facial skin micromovements may include associating the phrase "Hello, world!" with facial skin micromovements when the phrase "Hello, world!" is vocalized. In another example, interpreting facial skin micromovements may include associating the phrase "Hello, world!" with facial skin micromovements when the phrase "Hello, world!" is said in the absence of vocalization. By way of another example, facial skin micromovements may be associated with facial expressions, such as a smile associated with happiness or a frown associated with sadness, or any other facial expression and the associated emotion or intended communication. Interpreting facial skin micromovements may also include interpreting vocalized sound understood to be communication absent words, such as a grunt, mmmm, mmm-hmmm, a laugh, or a gasp with their associated meaning.

Some disclosed embodiments involve receiving during a first time period first signals representing prevocalization facial skin micromovements. Receiving may involve accepting delivery of, acquiring, retrieving, obtaining, or otherwise gaining access to, e.g., information or data by at least one processor. The data may be received via a light sensor, electronic circuitry, a communications channel, such as a wired channel (e.g., cable, fiber) and/or a wireless channel (e.g., radio, cellular, optical, IR). The data may be received as individual packets or as a continuous stream of data and may be received synchronously, e.g., by periodically polling a memory buffer, queue, or stack, or asynchronously, e.g., via an interrupt event. A time period may be understood as any fixed or variable length of time. For example, a time period may include a nanosecond, a millisecond, a tenth of a second, a second or any amount of time longer than, shorter than, or in between the identified amounts of time. A time period may also include, for example, a variable amount of time (e.g., the time to speak a single phoneme, syllable, word, sentence, or more).

Signals refer to any form of electrical or electromagnetic variation that carries information or represents data. For example, signals may be analog, digital, continuous time, discrete time, periodic, aperiodic, finite, infinite, deterministic, or random. Signals may be any electronic representation of a property determined from a measurement, or raw measurement signals detected by a sensor (e.g., data retrieved from a light detector in response to the light reflections from the facial region or data retrieved from a microphone in response to sound). Signals representing prevocalization facial skin micromovements may include signals (as defined elsewhere herein) e.g., characterizing facial skin micromovements. For example, the signals may characterize an intensity of light in a reflection, a change in reflection over time, or any other characteristic as described elsewhere herein. These reflection characteristics may correlate to one or more of a surface contour, light an extent of skin movement, muscle recruitment, skin deformations, scale of movement (e.g., micrometers, millimeters), nerve activity, shape, color, and may include an association with other variables, (e.g., time or audio) and/or any other information required to represent the facial skin micromovements. Prevocalization facial skin micromovements may be understood as described elsewhere in this disclosure.

In some disclosed embodiments, the first signals are based on coherent light reflections and the operations further include controlling at least one coherent light source for projecting coherent light on a facial region of an individual from which the light reflections are received. Coherent light, a coherent light source, light reflections, and a facial region may be understood as described elsewhere in this disclosure. The light source may be controlled, as also discussed elsewhere in in this disclosure. For example, in one sense control refers to turning on or off the light source. In another example, controlling may include altering a facial region covered by light spots. In yet another example, controlling may involve changing a characteristic of the projected light.

In some disclosed embodiments, the first signals are received from a light detector. A light detector may be understood as described elsewhere in this disclosure. In some embodiments, the light detector and the coherent light source are part of a wearable assembly. A wearable assembly may include any structure or enclosure designed to be connected or attached to a human body or head, such as in a manner configure to be worn by a user. Such a wearable assembly may be configured to contain or support one or more electronic circuitry, components, and/or sensors. In one example, the wearable assembly is configured for association with a pair of glasses. In another example, the wearable assembly is associated with an earbud. In another example, the wearable assembly is associated with goggles. The wearable assembly may have a cross-section that is button-shaped, P-shaped, square, rectangular, rounded rectangular, or any other regular or irregular shape capable of being worn by a user. Such a structure may permit the wearable housing to be worn on, in or around a body part associated with the head, face, or neck of the user (e.g., on the ear, in the ear, over the ear, around the neck, over the mouth, or in any other manner permitting temporary or longer term affixation to an individual). The wearable assembly may be made of plastic, metal, composite, a combination of two or more of plastic, metal, and composite, or other suitable material from which a housing may be construction.

Thus, for example, a coherent light source may project coherent light on to a facial region of an individual. A light detector may detect coherent light reflected from the facial region of the individual during a particular duration of time (e.g., first time period) and may generate signals representative of micro movements of the facial skin of the individual during the first time period. The signals generated by the light detector may be received by a processor associated with the disclosed system for initiating training operations.

By way of non-limiting example, FIG. 85A illustrates an example of the first time period. A wearable device 8500, consistent with some embodiments of the present disclosure, includes a sensor 8502 for detecting facial skin micromovements, a speaker and microphone array 8503 for recording and outputting audio. A user 8520 is shown wearing the wearable device 8500 and is prevocalizing speech. During a first time period, a processor may initiate a training operation by receiving signals representing prevocalization facial skin micromovements. A light source may project light onto facial region 8501 and a sensor 8502 may detect light reflections from facial region 8501. The sensor 8502 may generate and record signals from the reflected light is that are representative of prevocalization facial skin micromovements and those signals may be received by the processor.

Some disclosed embodiments involve receiving during a second time period succeeding the first time period, second signals representing sounds; Succeeding may refer to a time following, after, or subsequent to a first time period. Succeeding may also involve the second period starting after the start of the first time period, but overlapping with the first time period. Indeed, the time periods may immediately follow one another (e.g., as soon as the first time period ends, the second time period begins), may follow one another after a delay (e.g., the first time period ends, a millisecond passes, and the second time period begins), or may overlap (e.g., the first time period starts, a millisecond passes, and the second time period begins). The amount of time between the start of the first time period and the start of the second time period may be any amount of time (e.g., a nanosecond, a millisecond, a tenth of a second, half a second, a second). In some disclosed embodiments, the second period of time starts less than 350 milliseconds after the first period of time.

The second signals may represent sounds in that they may convey the sounds themselves or convey sound-related information. For example, the second signals may include any information regarding characteristics or parameters of sound waves (e.g., volume, frequency, amplitude), or characteristics or parameters of one or more of sounds from phonemes, sounds from syllables, sounds from words, or sentences spoken, or the sounds from grunts, laughs, or any other non-linguistic sounds or communication. Signals representing sounds may include various details defining the properties of the sound (e.g., tone, volume, pitch, amplitude, duration, frequency). In other embodiments, the second signals may convey the sound itself, either in analog or digital form.

In some disclosed embodiments, the second signals representing sounds are received from a microphone that is part of the wearable assembly. A microphone may be understood as described elsewhere herein (e.g., a device that converts sound waves or acoustic energy into electrical signals). The microphone may be part of the wearable assembly in that it may be physically within or connected to the wearable assembly or may be wirelessly pairable with electronics in the wearable assembly, as discussed elsewhere herein.

By way of a non-limiting example, FIG. 85B illustrates an example of the second time period. A wearable device 8500, consistent with some embodiments of the present disclosure, includes a sensor 8502 for detecting facial skin micromovements, a speaker and microphone array 8503 for recording and outputting audio. During a second time period, a processor may receive signals representing sound. A user 8520 wearing the wearable device 8500 may vocalize speech 8504 (e.g., by saying "Hello world!"). The microphone array 8503 may record the speech and generate signals representative of the sound. The processor may receive these signals representative of sound during the second time period.

Some disclosed embodiments involve analyzing the sounds to identify words spoken during the second time period. Analyzing the sounds may include applying one or more sound and/or speech processing techniques (e.g., filters, waveform analysis, spectral analysis, Fourier transforms, wavelet transforms, Cepstral analysis, dynamic time warping, hidden Markov models, phase-aware processing) and/or artificial intelligence techniques (e.g., machine learning, deep learning, neural networks, natural language processing) to extract the information from the signals representing sounds. Identifying words spoken may include classifying, describing, determining, establishing, recognizing, interpreting, translating, construing, or deciphering the words spoken, including any phonemes, combinations of phonemes, syllables, words, combinations of words, or any other speech-related component of the words spoken. For example, the phrase "Hello, world!" may be identified as the entire phrase (e.g., "Hello, world!") or the single words (e.g., "hello" and "world"). For another examples, the phrase "Hello, world!" may be identified by syllables (e.g., "hel," "lo," "world,"), the phonemes (e.g., "h," "e," "l," etc.), or other speech related component (e.g., "!"). Identifying words spoken may be accomplished through the use of a machine learning model, such as automatic speech recognition algorithm or natural language processing algorithm, or through a database lookup.

By way of non-limiting example, as illustrated in FIG. GD-4, processing unit 112 may receive signals from audio sensor 414. The processing unit 112 may then perform analysis of the audio signals to analyze the sounds by applying any of the processing techniques described above. The processing unit 112 may identify the words spoken through the use of an algorithm (e.g., an automatic speech recognition algorithm) or by perform a lookup for the words spoken in data structure 422 based on the analyzed audio signals.

Some disclosed embodiments involve correlating the words spoken during the second time period with the prevocalization facial skin micromovements received during the first time period. Correlating may involve associating, assigning, connecting, matching, or pairing the words spoken with the facial skin micromovements that preceded articulation of those words. For example, a database may be created where the facial skin micromovements that immediately preceded vocalization of the word "hello" may be matched to the word hello. Correlations for all words spoken during the second time period and the associated facial skin micromovements may be received in a database or other data structure. A relationship between the words spoken and the prevocalization facial skin micromovements may be created and sent to the data structure such that when the data structure is accessed, word spoken may be looked up by data representative of facial skin micromovements and/or facial skin micromovements may be looked up by data representative of words spoken.

Some disclosed embodiments involve storing the correlations. Storing may include saving, archiving, caching, or transferring the data associated with the correlations to local storage (e.g., hard disk drive, solid state drive, flash drive, memory card) or remote storage (e.g., cloud-based storage, private server, public server, network-attached storage). The correlations data may be stored in any type of data structure. In some embodiments, the correlations are stored in a cloud-based data structure. A data structure may be understood as described elsewhere in this disclosure. For example, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database, or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure).

Some embodiments involve receiving during a third time period, third signals representing facial skin micromovements received in an absence of vocalization. Receiving the third signals may be similar to receiving the first and second signals as described above. An absence of vocalization may include a nonexistence, unavailability, omission, lack, exclusion, imperceptibility, or undetectable level of vocalization. For example, the absence of vocalization may include silent speech, prevocalization, or subvocalization as described elsewhere herein. For comparison, prevocalization facial skin micromovements occur prior to the onset of detectable sounds during the normal process of vocalized speech. During the normal process of vocalized speech, multiple groups of muscles and nerves, from the chest and abdomen, through the throat, and up through the mouth and face. To utter a given phoneme, motor neurons activate muscle groups in the face, larynx, and mouth in preparation for propulsion of air flow out of the lungs, and these muscles continue moving during speech to create words and sentences.

A third time period may occur any amount of time succeeding the second time period. For example, the third time period may begin immediately following the second time period or after any length of time after the third time period ended. (e.g., a nanosecond, a second, a minute, an hour, a day, a month, a week, or even a year or more). In some embodiments, the third period of time starts at least a day after the second period of time.

Thus, for example, a coherent light source may project coherent light on to a facial region of an individual. A light detector may detect coherent light reflected from the facial region of the individual during a particular duration of time (e.g., third time period) and may generate signals representative of micro movements of the facial skin of the individual during the third time period. The signals generated by the light detector may be received by a processor associated with the disclosed system for initiating training operations.

By way of non-limiting example, FIG. 85C illustrates an example of the third time period. A wearable device 8500, consistent with some embodiments of the present disclosure, is depicted as attached to or integrated into a pair of glasses on the face of a user 8520. A user 8520, who may be the same or a different user from the first time period, is shown wearing the wearable device 8500 and silently speaking "Hello, my name is John Doe."". During a third time period, a processor may receive signals representing facial skin micromovements in the absence of vocalization. A light source may project light onto facial region 8501 and a sensor 8502 may detect light reflections from facial region 8501. The sensor 8502 may generate and record signals from the reflected light is that is representative of the facial skin micromovements and those signals may be received by the processor.

Some embodiments involve using the stored correlations to identify language associated with the third signals. Using the stored correlations refers to referencing, accessing, matching, or analyzing the stored correlations to identify language associated with the third signals. Identifying may include classifying, describing, determining, establishing, recognizing, interpreting, translating, construing, or deciphering the third signals. Language may include the words spoken or any phonemes, combinations of phonemes, syllables, words, combinations of words, sounds (e.g., grunts, sighs, etc.), or any other speech-related component of the words spoken (e.g., emphasis, exclamation, question, tone) or communication intended (e.g., facial expressions, reflex) from the facial skin micromovements made in the absence of vocalization. For example, the stored correlations may be accessed and the data associated with the first signals representing prevocalization facial skin micromovements may be compared, matched, aligned, or analyzed against the third signals representing facial skin micromovements received during a third time period. The correlations may then be used to match, associate, assign, connect, or pair language to the third signals. For example, the words "hello, my name is John Doe" may be spoken silently during the third time period. The correlations may be used to identify the language "hello, my name is John Doe" from the signals representing the facial skin micromovements during the first and second time periods. For example, if the correlations are stored in a data structure, the processor may perform a lookup to identify the words associated with the facial skin micromovements from the third time period. The third signals may be compared to the correlations in the database to establish a match by vector distance, similarity, regression, nearest neighbor matching, optimal pair matching, or another method of statistical analysis. The lookup may involve identifying the precise combination of words spoken during the third time period, and/or may involve identifying overlapping phonemes, syllables, or words and constructing a meaning of the third signals based on such overlaps. In this way the language of the third signals (e.g., the substance of the communication) may be identified.

Some disclosed embodiments involve outputting the language. Outputting the language refers to any audio or visual representation of the language (e.g., the substance of the communication conveyed by the third signals) or combination of the two. For example, the output may be audible speech (e.g., audio of language in the structure of a sentence and normal speech, audio of the language as single words or sounds, audio describing a facial expression), text (e.g., written sentences, words, paragraphs, descriptions of expressions or sounds), symbols (e.g., emojis, emoticons), or video (e.g., a recorded or digitally generated face speaking the language, a person signing in American Sign Language). In some embodiments the output may be a combination of both audio and video, for example a video of a face speaking with text subtitles of the language. In some embodiments, the language may be output in the language spoken or translated into a different language (e.g., English silently spoken and the output is in English or English silently spoken and the output in Spanish or any other language). In some disclosed embodiments outputting the language includes textually presenting the words associated with the third signals.

The language can be audibly played over a speaker audible to the only one individual, using, for example, headphones or earbuds using a magnetic driver, electrostatic drivers, or bone conduction, or the language can be audibly played over a speaker audible to a plurality of people, such as a television speaker, a computer speaker, a desktop speaker, a floor standing speaker, a public-address (PA) system, or any other speaker. The language can be output visually as text on a smartphone screen, a television screen, a computer screen, an AR/VR headset, glasses, projector screen, or any other screen visible to the user.

By way of non-limiting example, the processing unit GD-112 in FIG. GD-4 may output the language in a variety of ways. Examples of the ways the language may be output can be seen in FIG. GD-1. The language may be output audibly as spoken words directly into the ear of a user through output unit GD-114 or the language may be output visually as text on the screen of mobile communications device GD-120. Or in the embodiment disclosed in FIG. 85C, the language may be output as text by projecting it onto the lenses of the glasses portion of the wearable device 8500.

In some disclosed embodiments, the outputted language includes indications of the words spoken during the second time period. Indications refers to some sign, signal, or piece of information that provides insight, evidence, or a suggestion. For example, if words identified during the second time period overlap with words of the third period, those words might be associated with an indication indicating that the word is precisely recognized. For example, the indications may include one or more of highlighting, bolding, annotating, bracketing, footnoting, signifying in some other way, or outputting separately, the words spoken during the second time period.

For example, if the words spoken during the second time period are "Hello world!" and the output language is the visually displayed text, "Hello, my name is John Doe," the word "hello" overlaps, and may be bolded, highlighted, or annotated in some other way to indicate that it is recognized as having been spoken earlier. In another example, the indication may be performed in audio output during the output of the language from the third time period (e.g., a beep or a ding after words spoken during the second time period) or separately as an additional output (e.g., playing audio of the words spoken during the second time period).

FIG. 85C provides an example output 8507 of the language as text. "Hello world!" was vocalized speech 8504 during the second time period. After silently speaking "Hello, my name is John Doe" the language may be output 8507 textually. In this example, "Hello" silently spoken during the third time period is bolded to indicate that the word hello was also vocalized speech 8504 during the second time period. Alternatively, or in conjunction with the bolding, "Hello world!" may be displayed below the output of the language from the third time period. There may also be a parenthetical indication that the words "Hello world!" were vocalized (e.g., "(Vocalized)").

In some disclosed embodiments, the outputted language includes an indication of at least one word different from the words spoken during the second time period. Different may mean distinct words that are not the same. Different may also mean words that are not the same but are phonetically similar (e.g., tomorrow and sorrow, hello and fellow, night and fight, etc.) This may include indicating words that were not spoken or it may include indicating words that were not spoken but are phonetically similar such as "tomorrow" and "sorrow." This indication may be done by highlight, bolding, italicizing, annotating, bracketing, footnoting, or signifying in some other way that at least one word was different from the words spoken during the second time period. For example, if the words spoken during the second time period were "Tomorrow with be beautiful" and the outputted language is "Bad weather fills me with sorrow," the word "tomorrow" may follow sorrow in brackets (e.g., "Bad weather fills me with sorrow [tomorrow]"). For example, FIG. 85C provides example outputs 8507 and 8508 of the language. In example 8507, the language output indicates words different from those spoken during the second time period by italicizing the different words ("my name is John Doe"). In example 8508, instead of "Hello world!" being vocalized during the second time period, "How do you do, fellow kids?" was vocalized during the second time period. The output 8508, may indicate that fellow and hello and Doe and do are different words by having the word from the second time period in brackets after the output language from the second time period. For example, "Hello [fellow], my name is John Doe [do]."

In some disclosed embodiments, the at least one word includes a phoneme sequence similar to the at least one word spoken during the second time period. Similar phoneme sequences may be two sequences of letters that are the same or produce identical sounds when vocalized. Similar phoneme sequences may also be sequences of letters that are not identical but produce sounds that are close to one another when vocalized. Similar phoneme sequences may also be groups of letters that are not identical but produce identical sounds when vocalized, or groups of letters that are identical and produce different sounds when vocalized. For example, if the word "thesaurus" is spoken during the second time period, and the output language includes the word "thesis." The output may include an indication of the phoneme sequence that is similar. For example, the word the output may include "thesis [thesaurus]" where the matching phoneme sequence "thes" is bolded, highlighted, annotated or signified in some other way as matching. For example, FIG. 85C provides example output 8508. In example 8508, instead of "Hello world!" being vocalized during the second time period, "How do you do, fellow kids?" was vocalized during the second time period. The output 8508, may indicate that fellow and hello and Doe and do are different words but have similar phoneme sequences by having the word from the second time period in brackets after the output language from the second time period and further bolding the similar phoneme sequences (e.g., "ello" and "ellow;" "Do" and "do"). For example, "Hello [fellow], my name is John Doe [do]."

Some disclosed embodiments involve identifying additional correlations of additional words spoken over an additional extended period of time with additional prevocalization facial skin micromovements detected during the additional extended period of time. Additional correlations may be understood as more correlations populate a data structure as described earlier in this disclosure. As additional words are spoken, more data is gleaned and the model becomes more accurate. An additional extended period of time may be any amount of time following the third time period and need not be continuous or have a defined endpoint. The additional extended time period of time may begin immediately following the third time period or after any length of time after the third time period ended. (e.g., a second, a minute, an hour, a day, a month, a week, or even a year or more). For example, an additional extended period of time may be the time period immediately preceding the third time period and continue indefinitely. In other embodiments, it may only be the time periods during which prevocalization facial skin micromovements occur and the speech that follows, or the time period when a user is using or wearing a device. An additional extended period of time may also be a set period of time that recurs each hour, (e.g., the first fifteen minutes of each hour), day (e.g., 9:00 am to 10:00 am everyday), or a set period of time (e.g., 1 second, 10 second, 15 minute, 30 minute, 1 hour, etc.) that is triggered by an event (e.g., facial skin movements, audio, etc.). Some embodiments involve training a neural network using the additional correlations. Training a neural network, as described earlier in this disclosure, may be broadly understood as any method, proceed, procedure, or programming required to feed data to a correlations database, an artificial neural network, convolutional neural network, recurrent neural network, or any other form of neural network or data structure to produce a desired output when provided an input. As applicable to this disclosure, training a neural network may refer to providing the neural network with correlation data, enabling the neural network to process the training data so that when provided data representing facial skin micromovements or data representing spoken words, it can accurately predict the correlated data.

Thus, for example, after the neural network is trained, a coherent light source may project coherent light on to a facial region of an individual while the individual is silently speaking. A light detector may detect coherent light reflected from the facial region of the individual during the time period they are silently speaking and may generate signals representative of micromovements of the facial skin of the individual. The signals generated by the light detector may be received by a processor associated with the disclosed system. The processor may then use the trained ANN to accurately decipher or translate words silently spoken by the individual based on the facial skin micromovements. The processor may then output the words spoken in the form of audible speech through a speaker in an individual's earpiece or text on a display, such as a smartphone.

By way of non-limiting example, FIG. 86 illustrates an example diagram of the operations described above. A first time period 8601 may include operations 8605 of receiving signals representing prevocalization facial skin micromovements. A second time period 8602 succeeding the first time period may include operation 8606 of receiving signals representing sounds, operation 8607 of analyzing the sounds to identify words spoken, operation 8608 of correlating words spoken to prevocalization facial skin movements that were received in the first time period in operation 8605 and operation 8609 of storing the correlations. Operations 8607, 8608, 8609 may be performed in the second time period 8602 or any other time following operation 8606 of receiving signals representing sounds. A third time period 8603 may include operation 8610 of receiving signals representing prevocalization facial skin micromovements, operation 8611 of using the stored correlations to identify language, where the stored correlations are the same correlations that were created and stored in operation 8608 and 8609 during the second time period. The third time period may also include an operation 8612 of outputting language, where the output language may include the words identified during the third time period, but may also include the words identified in operation 8607 during the second time period. Operations 8611 and 8612 may be performed in the third time period 8603 or any other time following operation 8610 of receiving signals representing prevocalization facial skin micromovements. There may also be an additional extended time period 8604, which may include operation 8613 of receiving signals representing prevocalization facial skin micromovements, operation 8614 of receiving signals representing sound, operation 8615 of analyzing the sounds to identify words spoken, operation 8616 of correlating words spoken to prevocalization facial skin movements, and operation 8617 of training a neural network on the correlations. Additionally, training the neural network may be performed using the correlations stored during the second time period in operation 8609 as well as the correlations from operation 8616.

In some disclosed embodiments, the first signals are associated with a first individual and the third signals are associated with a second individual. An individual may include a person who is using the disclosed device/system, such as a person wearing the head-mountable device. For example, a first individual may vocalize speech during a first time period and the first prevocalization micromovements of the first individual may be associated with their speech. A second separate individual, also wearing a head-mountable device, may then silently speak during a third time period. The facial skin micromovements of the second individual may be received by a processor during the third time period. The correlations between the first signals and vocalized speech obtained from the first individual may be used to identify the language of the third individual and output the language associated with the third signals. In another example, the first signals may be associated with any number of individuals (e.g., one, two, ten, one hundred) including, but not limited to, every individual from whom signals representing prevocalization facial skin were received. In another example, the second individual associated with the third signals may be a member of the group of first individuals, or the second individual may have no early correlations associated with them. In another embodiment, the first signals and the third signals are associated with a same individual.

By way of non-limiting example, FIG. 85A and FIG. 85B provide an example of the first and second time period that may be associated with a first individual. A user 8520 may wear the wearable device 8500. During the first time period, a processor may receive signals associated with the first user from facial skin micromovements of prevocalized speech. A light source may project light onto facial region 8501 and a sensor 8502 (e.g., a light detector) may detect light reflections from facial region 8501 during prevocalization. The sensor 8502 may generate and record signals from the reflected light is that is representative of prevocalization facial skin micromovements and those signals may be received by the processor where the signals are associated with a first individual. Similarly, during the second time period, a processor may receive signals representing sound associated with the first individual. A user 8520 (e.g., the first individual) wearing the wearable device 8500 may vocalize speech 8504 (e.g., by saying "Hello world!"). The microphone array 8503 may record the speech and generate signals representative of the sound. The processor may receive these signals representative of sound during the second time period that are associated with the first individual. During the third time period, the processor may receive signals representative of facial skin micromovements in the absence of vocalization. The user 8520 of the wearable device 8500 during the third time period, may be the same first individual from the first and second time periods or it may be a separate individual not associated with the first and second signals. During the third time period, the user 8520 may silently speak "Hello, my name is John Doe," as illustrated in box 8505. During a third time period, a processor may receive signals representing facial skin micromovements in the absence of vocalization. A light source may project light onto facial region 8501 and a sensor 8502 may detect light reflections from facial region 8501 during the silent speech. The sensor 8502 may generate and record signals from the reflected light is that is representative of the facial skin micromovements and those signals which may be associated with the first or second individual.

Some embodiments involve continuously updating, using the correlations, a user profile associated with the individual. Continuously updating refers to regularly or periodically making changes or modifications to bring the profile up to date, to add new information, to revise or replace existing information, features, to provide more recent data. The updating may be continuous in that updates occur over time, such as when the system/device is used by a wearer, or at regular or irregular intervals. In one embodiment, continuously updating may involve updating in real time or near real time every time the device/system is used (e.g., every time the user vocalizes speech and a new correlation is made or when a user speaks in the absence of vocalization and the system used the stored correlations to identify language). In such situations, continuously updating may include updating every second, every minute, every day, or not on a set schedule, such as updating the user profile in a batch when the user removes the wearable device or when the wearable device is charging. A user profile may include specific information on a user's facial skin micromovements and words spoken for their individual facial skin micromovements. In some embodiments a user profile may also include a collection of settings (e.g., language, preferred output, etc.) and information associated with a user, and capture certain identifying characteristics about a user (e.g., name, age, payment information, etc.). A user profile may also include specific information associated with the user's voice, facial structure, facial movements, tone, enunciation, accent, speech, words spoken, speech impediments, or any other characteristic regarding the users. For example, the correlations between the first and second signals from the user's speech may be tied to the user profile for that individual. The user may manually login to their profile or may be automatically logged in (e.g., when they begin vocalizing speech or silently speaking). The user profile may contain all of the correlations created from the user's own use of the wearable device and may be contained on the wearable device locally or remotely in a cloud server. The user profile may be loaded onto the wearable device when the user logs into their user profile, either automatically by putting the device on through a biometric sensor, such as a fingerprint scanner, an iris scanner, or voice recognition software, or manually by typing their username and password into a mobile communication device that is wirelessly connected to the wearable device. The user profile may contain information that the user's preferred output is text displayed on their mobile phone or that it is audio output into their ear through a wireless earbud.

For example, FIG. 1 shows a user wearing speech detection system 100 in wearable housing 110. When output unit 114 is inserted into the ear of the user, the system may automatically log into the user's profile through use of a biometric scanner. The biometric scanner may be a device on speech detection system 100 or within mobile communications device 120. The user may also manually log in to their user profile through a prompt on mobile communication device 120, which is wireless connected to the speech detection system. The user profile may be continuously updated. For example, in FIG. 85B, the user 8520 vocalizes speech 8504 "Hello world!" and/or "How do you do, fellow kids?" The vocalized speech is then correlated to the pre-vocalization facial skin micromovements from the first time period. The correlations from the user in the second time period, may then be used to update their user profile.

Some disclosed embodiments, involve accessing a voice signature of an individual associated with the facial skin micromovements. Accessing may mean obtaining, loading, or retrieving from local or cloud storage for use by the processor. For example, if a user profile is stored on a cloud server, the user may log into their user profile and the processor may retrieve the data specific to the user from the cloud server and store it locally on the wearable device. The data retrieved regarding the individual may include voice signature. A voice signature includes any information associated with the characteristics of the speech or voice of an individual (e.g., facial skin micromovements, tone, enunciation, accent, language, specific words spoken, specific phonemes spoken, etc.). For example, voice signatures may be associated with certain phenomes, combinations of phonemes, words, combinations of words, or any other speech-related component. For example, if an individual speaks English with a French accent, the voice signature may contain information regarding how a French accent may change facial skin micromovements correlations to specific words spoken. In another example, the user may have a southern drawl, where their speech is slowed or elongated on specific words. A voice signature for that user may contain information that individual's unique speech characteristics.

In some disclosed embodiments, analyzing the sounds to identify words spoken during the second time period is based on the voice signature. Analyzing the sounds to identify words spoken based on the voice signature may include analyzing sounds as described elsewhere in this disclosure with the additional information found in the voice signature of the individual to account for unique properties of an individual's vocalized speech, such as accents, speech impediments, tone, unique pronunciation, etc. For example, if a user has a specific characteristic of their speech, such as failing to enunciate the "Ts" in "Atlanta," the analyzed sounds in the absence of a voice signature may identify "Alana" instead of "Atlanta," but with the additional information regarding the user's voice signature, the word identified may be "Atlanta." In another example, a user may be a non-native speaker of a language and have an accent. Analyzing the sounds of the accented speech may use the accent voice signature, (e.g., a French accent on spoken English) to identify the words spoken.

Some disclosed embodiments involve processing additional signals captured during a fourth time period succeeding the third time period to increase the certainty level when a certainty level for identifying the language associated with the third signals is below a threshold. A certainty level may include any form of confidence interval or statistical value to determine the likelihood that the language associated with the third signals was correctly identified. For example, a z-score, t-score, bootstrapping method, Bayesian method, central limit theorem, hypothesis testing, estimating equations, likelihood theory, summary statistics, or any other form of statistical analysis may be used to calculate certainty levels. A threshold may be set at any level necessary to identify the language associated with the third signals. The threshold may be defined as a percentage (e.g., 50%, 60%, 75%, 90%, 95%, 99%) or a specific number of standard deviations away from the mean (e.g., one sigma, two sigma, six sigma, etc.). In some embodiments a threshold may be defined as a limit value or target value associated with the statistical value used to determine the certainty level.

A fourth time period may be any amount of time following the third time period and need not be continuous or have a defined endpoint. A fourth time period may begin immediately following the third time period or after any length of time after the third time period ended. (e.g., a second, a minute, an hour, a day, a month, a week, or even a year or more). The fourth time period may be triggered to begin when the certainty level is below a certain threshold (e.g., 80%, 90%, 95%, etc.) or the fourth time period may run continuously to improve certainty levels of identifying the language. A fourth time period may end when the certainty associated with the language identified using the third signals reaches a certain confidence interval or threshold value. Alternatively, the fourth time period may continue with no defined endpoint to continuously improve the confidence interval of the language identified. For example, a user may silently speak "tomorrow," and the language identified may be "tomorrow" with an 80% certainty level, "borrow" with a 10% certainty level, and another word with a 10% certainty level. In this case, a fourth time period may begin where additional signals representing facial skin micromovements and sound are captured and processed to increases the certainty level of the identified language to a desired threshold (e.g., 90%).

Some disclosed embodiments involve receiving during a fourth time period fourth signals representing additional prevocalization facial skin micromovements, receiving during a fifth time period succeeding the fourth time period, fifth signals representing sounds, and using the fourth signals to identify words spoken in the fifth time period. A fourth time period may be any amount of time following the third time period and need not be continuous or have a defined endpoint. A fourth time period may begin immediately following the third time period or after any length of time after the third time period ended. (e.g., a second, a minute, an hour, a day, a month, a week, or even a year or more). For example, a fourth time period may include the time period immediately preceding the third time period and continue indefinitely. In other embodiments, it may only include the time periods during which prevocalization facial skin micromovements occur and the speech that follows, or the time period when a user is using or wearing a device. A fourth time period may also include a set period of time that recurs each hour, (e.g., the first fifteen minutes of each hour), day (e.g., 9:00 am to 10:00 am everyday), or a set period of time (e.g., 1 second, 10 second, 15 minute, 30 minute, 1 hour, etc.) that is triggered by an event (e.g., facial skin movements, audio, etc.).

A fifth time period succeeding the fourth time period may refer to a time following, after, or subsequent to a fourth time period. For example, the time periods may immediately follow one another (e.g., as soon as the fourth time period end, the fifth time period begins), may follow one another after a delay (e.g., the fourth time period end, a millisecond passes, and the second time period begins), or may overlap (e.g., the fourth time period starts, a millisecond passes, and the fifth time period begins). The amount of time between the start of the fourth time period and the start of the fifth time period may be any amount of time (e.g., a nanosecond, a millisecond, a tenth of a second, half a second, a second, a minute, an hour, or a day).

In some embodiments, the fourth signals may be used to identify words spoken in the fifth time period. The signals representing additional prevocalization facial skin micromovements may be used to identify the subsequently vocalized words. For example, the processor may access the stored correlations to identify words associated with facial skin micromovements, the correlations may be used to identify the words spoken. The system may compare the signals representing sounds to the words identified with the correlations, and update any incorrect correlations. For example, the signals representing facial skin micromovements received during the fourth time period from a user vocalizing the word "tomorrow" may be used to identify the word "tomorrow" as the words associated with the signals representing sounds received during the fifth time period.

FIG. 87 illustrates a flowchart of an exemplary process 33-300 for interpreting facial skin micromovements. Process 8700 includes a step 8701 of receiving during a first time period first signals representing prevocalization facial skin micromovements. For example, in FIG. 85A, sensor 8502, integrated into wearable device 8500, may receive signals representing prevocalization facial skin micromovements. Process 8700 may include a step 8702 of receiving during a second time period succeeding the first time period, second signals representing sounds. For example, as illustrated in FIG. 85B, speaker and microphone array 8503 may receive signals representing the sounds for the vocalized speech 8504. Process 8700 may include a step 8703 of analyzing the sounds to identify words spoken during the second time period. Process 8700 may include a step 8704 of correlating the words spoken during the second time period with the prevocalization facial skin micromovements received during the first time period. Step 8705 of storing the correlations. Process 8700 may include a step 8706 of receiving during a third time period, third signals representing facial skin micromovements received in an absence of vocalization. For example, in FIG. 85C, sensor 8502, integrated into wearable device 8500, may receive signals representing prevocalized facial skin micromovements 8506 associated with silently speaking. Process 8700 may include a step 8707 of using the stored correlations to identify language associated with the third signals. Process 8700 may include a step 8708 of outputting the language.

Some embodiments involve, a system for interpreting facial skin micromovements, the system comprising: at least one processor configured to: receive during a first time period first signals representing prevocalization facial skin micromovements; receive during a second time period succeeding the first time period, second signals representing sounds; analyze the sounds to identify words spoken during the second time period; correlate the words spoken during the second time period with the prevocalization facial skin micromovements received during the first time period; storing the correlations; receive during a third time period, third signals representing facial skin micromovements received in an absence of vocalization; use the stored correlations to identify language associated with the third signals; and output the language.

The embodiments discussed above for interpreting facial skin micromovements may be implemented through non-transitory computer-readable medium such as software (e.g., as operations executed through code), as methods (e.g., process 8700 shown in FIG. 87), or as a system (e.g., speech detection system 100 shown in FIGS. 1-3). When the embodiments are implemented as a system, the operations may be executed by at least one processor (e.g., processing device 400 or processing device 460, shown in FIG. 4).

Some disclosed embodiments involve a multifunctional earpiece with an ear-mountable housing. An "earpiece" refers to an electronic device with at least one component configured to be worn in, over, around, or behind the ear. In some embodiments, an earpiece may be an electronic device that may be used for listening to audio, such as music, phone calls, or any other audio content. An earpiece may include a speaker or a driver (e.g., a bone conduction element) that produces sound or vibration and is configured to be placed near the ear canal or adjacent the ear to deliver audio to the ear. An earpiece may also include other associated components such as a microphone. In some embodiments, an earpiece may feature touch controls including one or more touch-sensitive surfaces or buttons that allows for user customization, such as the adjusting of volume, pausing or playing audio, answering or ending calls, or activation voice assistance. Additionally or alternatively, software associated with the earpiece may enable control or customization via voice command or silent speech (subvocalized or prevocalized) commands. Depending on design choice, an earpiece may also include noise-cancelling technology to reduce ambient noise, voice assistant integration, sweat and water resistance, or a charging case to provide additional battery backup. In some implementations, an earpiece may be connectable to an audio source and may be either wired or wireless. The earpiece may be single sided, to convey sound to one ear, or may be dual-sided, for conveying sound to two ears. Although the term "earpiece" is singular, it is to be understood that an earpiece may include multiple components either physically connected, wirelessly connected, and/or physically detached. An earpiece may also be configured for pairing with other devices, such as smartphones, portable music players, radios, laptops, desktop, or any other suitable communication device.

A "multifunctional earpiece" refers to an earpiece, as mentioned above, that offers at least one feature beyond basic audio listening. In some embodiments, a multifunctional earpiece may serve multiple purposes and provide a plethora of functions, thereby resulting in the integration of various technologies and functionalities into the earpiece. For example, in one embodiment, the multifunctional earpiece may present sound through a speaker, project light toward the skin, and detect received reflections indicative of the prevocalized words.

By way of a non-limiting example, in some, but not necessarily all embodiments, a multifunctional earpiece may also allow for audio playback of music, podcasts, audiobooks, or phone calls with high-quality sound reproduction; allow for wireless connectivity, voice communication, or fitness tracking; and/or incorporate one or more biometric sensors that may track biometric data. For example, in some embodiments, aa multifunctional earpiece may incorporate a heart rate monitor, oxygen saturation sensor, electroencephalogram (EEG) sensor for measuring brain activity, or any other biometric sensor for measuring biometric data. Furthermore, a multifunctional earpiece may be configured to provide translation and language support. For example, such translation and language support may include real-time language translation capabilities, wherein the multifunctional earpiece may translate spoken words from one language to another, thereby allowing users to communicate with people who speak different languages. In some disclosed embodiments, the multifunctional earpiece may allow for smart assistant integration. For example, users may use the multifunctional earpiece to control or actuate various smart devices such as electronic locks, desktops, laptops, electronic wearables, vehicle interfaces (the various functions on a dashboard of a vehicle), IOT devices, appliances, or any other wired or wirelessly connectable device or system. In some disclosed embodiments, the multifunctional earpiece may be integrated with mobile applications. For example, the multifunctional earpiece may have companion mobile applications that provide the user with additional functionality, customization options, or firmware updates for the multifunctional earpiece. Such mobile applications may allow users to use the multifunctional earpiece to fine-tune audio settings, customize controls, or access additional features specific to the multifunctional earpiece, and/or operate/interact with applications that provide varied functionality.

An "ear-mountable housing" may refer to an enclosure or casing configured to be worn on, in, behind, or adjacent an ear. An ear-mountable housing may include an associated headband, ear cup, earbud, or any other structure for securing a sound projecting/conveying device to a head. The ear-mountable housing may be a part of the multifunctional earpiece that holds the various components of the multifunctional earpiece, and may house (e.g., contain) the internal components of the earpiece, such as the speaker driver, microphone, electronic circuitry, or any other components of the earpiece.

In some disclosed embodiments, the ear-mountable housing may further include an attachment mechanism that allows the earpiece to be securely mounted or worn. There are several ways in which the ear-mountable housing can be attached to the ear: In-the-ear (ITE): the ear-mountable housing may be inserted directly into the ear canal and held in place by the shape of the ear. Examples may include earbuds and earplugs. In some cases, the ear-mountable housing may be custom-made to fit the specific shape of an individual's ear and seated in the ear bowl. 2. Behind-the-ear (BTE): the ear-mountable housing may be seated behind the ear and with a small tube that runs to the ear canal. Examples include hearing aids and headsets. 3. Over-the-ear (OTE): the ear-mountable housing may be seated on top of the ear and held in place by a headband or other support. Examples include structures like headphones and earmuffs. 4. Over-the-head (OTH): the ear-mountable housing may be held in place by a headband that goes over the top of the head. In other embodiments, the ear-mountable housing may be attached to a secondary device such as glasses (sunglasses or corrective vision glasses), a hat, a helmet, a visor, or any other type of head wearable device. Housings that do not support an in the ear speaker may be configured for delivering sound through conduction of bone vibration to the skull.

The ear-mountable housing may be ergonomically shaped to conform to the natural structure of the head and/or ear for a secure and comfortable fit and may be compact and lightweight to ensure a comfortable fit while minimizing discomfort during extended use of the multifunctional earpiece. Suitable materials for the housing include plastic, silicone, metal, composites or any combination thereof.

Consistent with some disclosed embodiments, at least a portion of the ear-mountable housing is configured to be placed in an ear canal. A "portion of the ear-mountable housing" may refer to a specific section or part of the ear-mountable housing that may be smaller than the whole of or entirety of the ear-mountable housing and sized to fit within an ear canal. For example, an earbud tip or earbud sleeve may be a portion configured to fit within an ear canal. Such structures are typically a soft, removable portion of the earbud that comes in direct contact with the Consistent with some disclosed embodiments, at least a portion of the ear-mountable housing is configured to be placed over or behind an ear. For example, a cup such as is employed in headphones is one over the ear example. A behind the ear example may adopt a form similar to a behind the ear hearing aid or any other structure configured to arrest at the top of a person's ear, between the ear and the skin of the head. Such structures may include hooks that may go around a rear portion of the ear or that may be flexibly supported by the sides of a person's head adjacent to the rear portion of the individual's ear.

Consistent with some disclosed embodiments, the multifunctional earpiece includes a microphone integrated with the ear-mountable housing for receiving audio indicative of a wearer's speech. A "microphone" refers to a device that receives sound waves and converts the sound waves into electrical signals. The microphone may be an electronic device and may be configured to capture audio or sound and convert it into an electrical representation that may be transmitted, recorded, or processed by various electronic devices. The microphone may be used for recording, communication, broadcasting, or any other suitable audio application. Examples of microphones include dynamic microphones, condenser microphones, electret microphones, ribbon microphones, a lavalier microphone, or any other suitable type of microphone. "Integrated" may refer to being physically or wirelessly connected or linked to. The microphone may be "integrated" with the ear-mountable housing in that it may be incorporated within the ear-mountable housing, may extend from the housing, or may be pairable with electronics in the housing. In some embodiments, the microphone may be connected to the ear-mountable housing via an arm. The microphone may be configured to receive audio in that it is designed to pick up sound, such as sound indicative of a wearer's speech (e.g., the sound that results from a wearer speaking.

Figure 88:
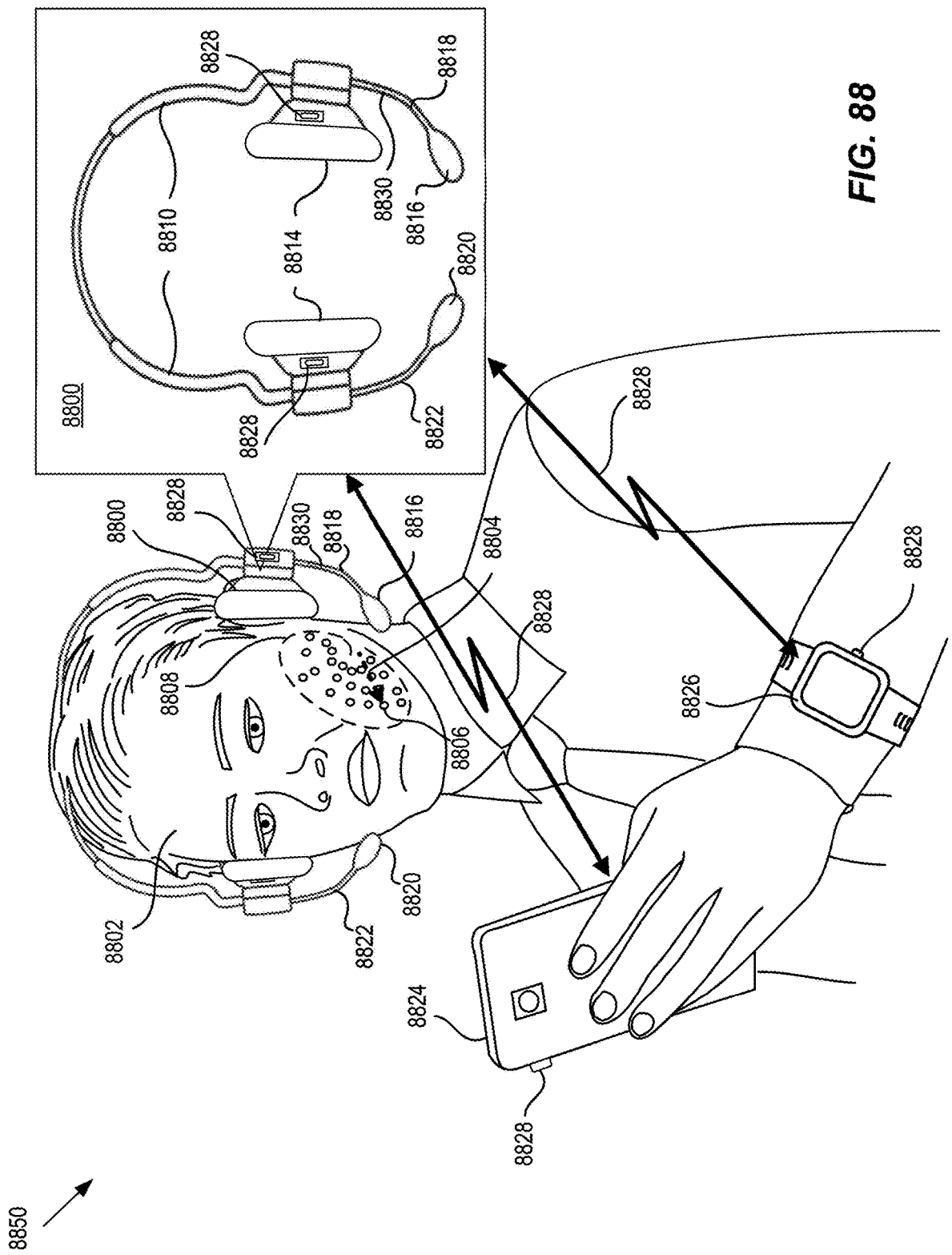
FIG. 88 is a schematic illustration of a user wearing an exemplary headset with added facial micromovement detection capability, consistent with some embodiments of the present disclosure.

By way of a non-limiting example, FIG. 88 illustrates a system 8850 illustrating use of an earbud or earpiece by a user, consistent with some embodiments of the present disclosure. As seen in FIG. 88, the wearer 8802 or wearer 8802 may use or wear a multifunctional earpiece 8800. The multifunctional earpiece 8800 may further comprise an ear-mountable housing 8810. As seen in FIG. 88, at least a portion of the ear-mountable housing 8810 is configured to be placed over the ear of the wearer 8802 or wearer 8802.

Also as seen in FIG. 88, a microphone 8820 may be integrated with the ear-mountable housing 8810 to receive audio indicative of the speech of the wearer 8802. As seen in FIG. 88, the microphone 8820 may be connected to the ear-mountable housing 8810 via an arm 8822.

Figure 91:
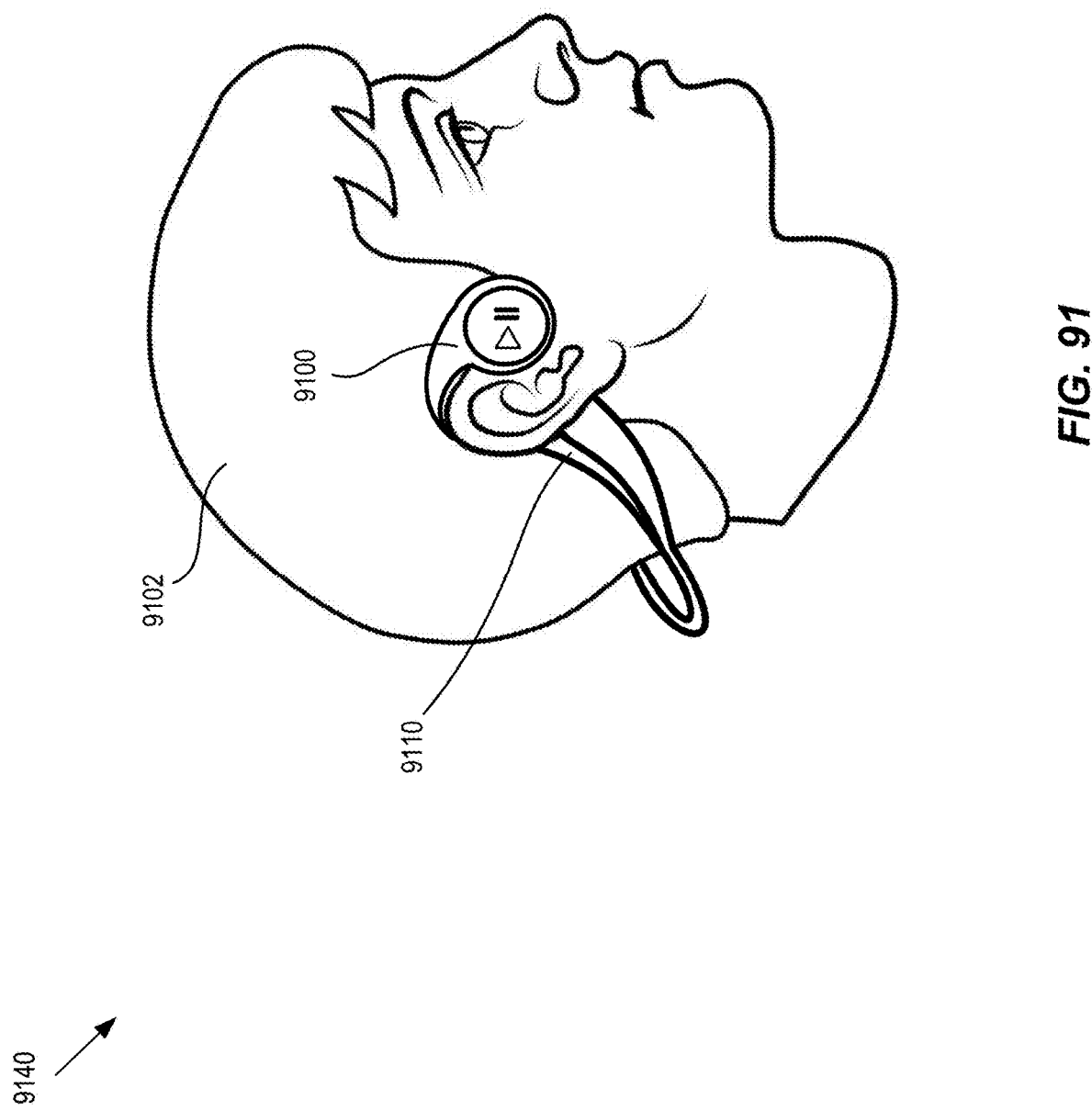
FIG. 91 is a schematic illustration of a user wearing an exemplary headset of an alternative form factor, consistent with some embodiments of the present disclosure.

By way of a non-limiting example, FIG. 91 illustrates a system 9140 that includes an earbud or earpiece that may be used by a user, consistent with some embodiments of the present disclosure. As seen in FIG. 91, user 9102 may use or wear a multifunctional earpiece 9100. The multifunctional earpiece 9100 is substantially similar to multifunctional earpiece 8800, and retains all its elements and features, as discussed above. Moreover, a portion of the ear-mountable housing 9110 may be configured to be placed in front of the ear of the user 9102.

Some disclosed embodiments involve a speaker integrated with the ear-mountable housing for presenting sound. A "speaker" refers to an electronic device that converts electrical signals into sound waves. For example, a speaker may include a driver or transducer, an enclosure, and an amplifier. The speaker may receive electrical signals and the driver of the speaker may convert the electrical signals into sound waves, which may then be emitted in a manner enabling hearing (e.g., by projecting sound). The speaker may be "integrated" with the ear-mountable housing in a manner similar to that described with respect to integration of the microphone with the ear-mountable housing. For example, the speaker may be incorporated within the ear-mountable housing, or attached to or mounted on an appropriate portion of the ear-mountable housing. As another example, the speaker may be housed within the internal structure of the ear-mountable housing. In some disclosed embodiments, the speaker may be connected to the ear-mountable housing via an appropriate structure. It is also contemplated that in some disclosed embodiments the speaker may be integrated with the ear-mountable housing by being connected to one or more components included in the housing via a wired or wireless connection.

By way of a non-limiting example, as seen in FIG. 88, the wearer 8802 or wearer 8802 may use or wear a multifunctional earpiece 8800. Also as seen in FIG. 88, a speaker 8814 may be integrated with the ear-mountable housing 8810 for presenting sound.

Some disclosed embodiments involve a light source integrated with the ear-mountable housing for projecting light toward skin of the wearer's face. A "light source" may be understood as described and exemplified elsewhere in this disclosure. The light source may be "integrated" with the ear-mountable housing in a manner similar to that described above with respect to integration of the microphone and/or speaker with the ear-mountable housing. For example, the light source may be incorporated within the ear-mountable housing or may be integrated with an appropriate portion of the ear-mountable housing. As one example, the light source may be housed within the internal structure of the ear-mountable housing. Alternatively, the light source may be connected to the ear-mountable housing via an appropriate structure. "Projecting light" may be understood as described and exemplified elsewhere in this disclosure. A "wearer" refers to the wearer or user of the multifunctional device and Consistent with some disclosed embodiments, the light source may be configured to project a pattern of coherent light toward the skin of the wearer's face, the pattern including a plurality of spots; or the light source may be configured to project non-coherent light to the face, explanations of both of which are contained elsewhere in this disclosure. By way of a non-limiting example, as seen in FIG. 88, the wearer 8802 or wearer 8802 may use or wear a multifunctional earpiece 8800. Also as seen in FIG. 88, a light source 8830 may be integrated with the ear-mountable housing 8810 for projecting light 8804 toward skin of the wearer's 8802 or the wearer's 8802 face. Moreover, the light source 8830 may be configured to project a pattern of either coherent or noncoherent light toward the skin of the wearer's 8802 face. Furthermore, as seen in FIG. 88, the light source 8830 may be configured to project a pattern of coherent light, wherein the pattern includes a plurality of spots 8806.

Figure 89:
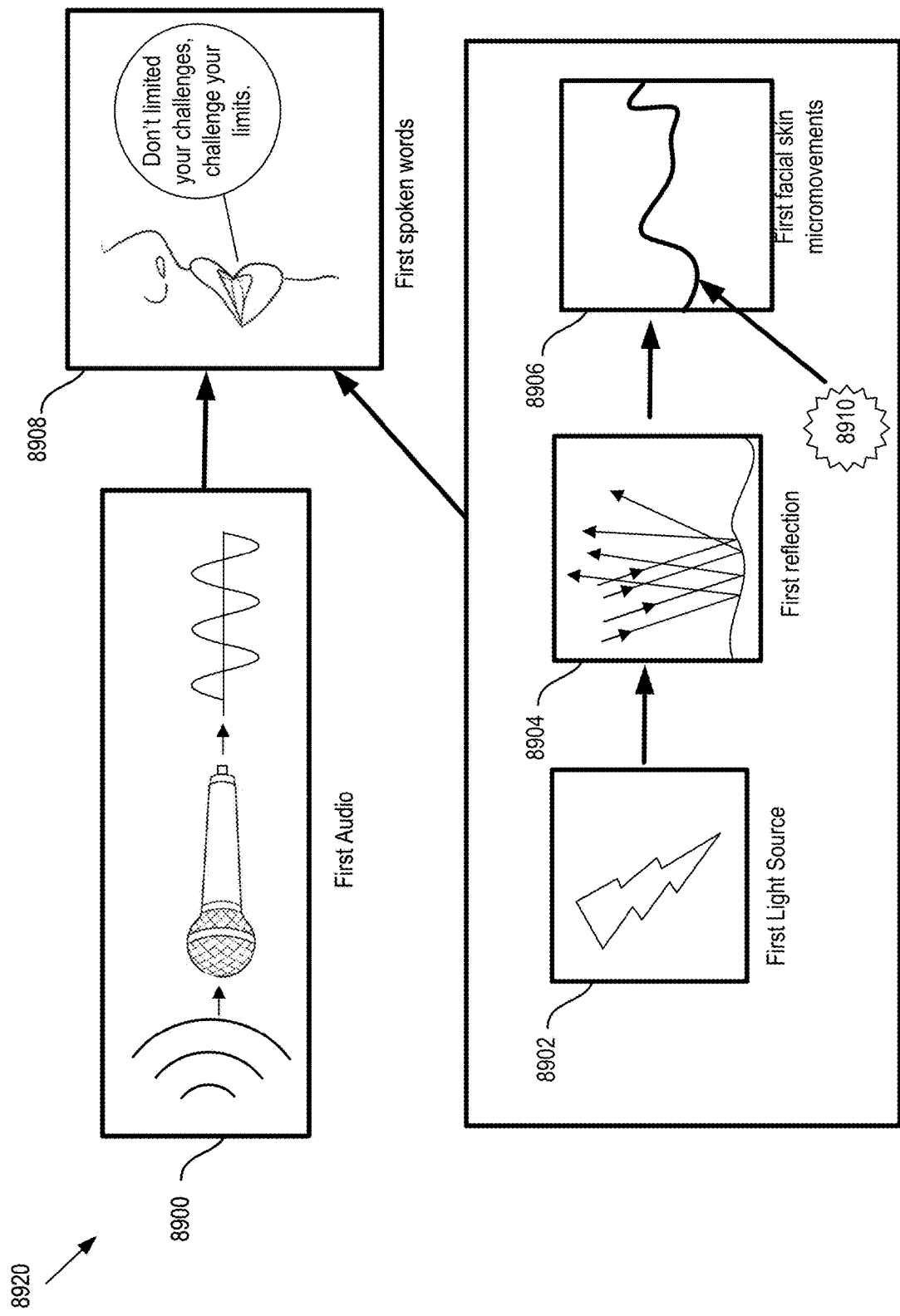
FIG. 89 is a schematic illustration of an exemplary facial micromovement detection process, consistent with some embodiments of the present disclosure.

By a way of a non-limiting example, FIG. 89 illustrates a system 8920 including an earbud with added facial micromovement detection, consistent with some embodiments of the present disclosure. As seen in FIG. 89, the system 8920 may comprise a first light source 8902 integrated with the ear-mountable housing 8810 for projecting light 8804 toward skin of the wearer's 8802 face as shown in FIG. 88.

As described elsewhere in this disclosure, some disclosed embodiments involve a light detector integrated with the ear-mountable housing and configured to receive reflections from the skin corresponding to facial skin micromovements indicative of prevocalized words of the wearer. The light detector may be "integrated" with the ear-mountable housing in a manner similar to that described above with respect to integration of the speaker, the microphone, and the light source as described above.

By way of a non-limiting example, as seen in FIG. 88, the light detector 8816 may be integrated with the ear-mountable housing 8810 and configured to receive reflections from the skin corresponding to facial skin micromovements indicative of prevocalized words of the wearer 8802. As further seen in FIG. 88, the light detector 8816 may be integrated with the ear-mountable housing 8810 via an arm 8818. Also, the light detector 8816 may be configured to receive reflections from skin of the facial region 8808. Thus, the received reflections correspond to facial skin movements indicative of prevocalized words of the wearer 8802.

By a way of a non-limiting example, FIG. 89 illustrates a system 8920 including an earbud with added facial micromovement detection, consistent with some embodiments of the present disclosure. As seen in FIG. 89, the system 8920 may comprise a light detector 8816 (FIG. 88) integrated with the aforementioned ear-mountable housing 8810 and configured to receive a first reflection 8904 from the skin corresponding to first facial skin micromovements 8906 indicative of prevocalized words of the wearer 8802.

In some disclosed embodiments, the multifunctional earpiece is configured to simultaneously present the sound through the speaker, project the light toward the skin, and detect the received reflections indicative of the prevocalized words. "Simultaneously" may refer to the occurrence or execution of multiple actions, events, or processes concurrently, at the same time, or in a same time period. Simultaneous occurrences, for example, may be in in close proximity, physically or temporally, to each other.

As such, the multifunctional earpiece, may be configured, while presenting sound through a speaker, to also project the light the toward the skin, and to detect the received reflections indicative of the prevocalized words. Additionally or alternatively, the multifunctional earpiece may perform each of the above-mentioned actions concurrently, without any noticeable time gap or delay between them. Additionally or alternatively, the multifunctional earpiece may perform each of the above-mentioned actions in close proximity, physically or temporally, to each other.

By way of a non-limiting example, as seen in FIG. 88, the multifunctional earpiece 8800 may be configured to simultaneously present the sound through the speaker 8814, project the light 8804 toward the skin, and detect the received reflections indicative of the prevocalized words. The reflections may be detected via the light detector 8816.

Consistent with some disclosed embodiments, a multifunctional earpiece includes at least one processor configured to output via the speaker an audible simulation of the prevocalized words derived from the reflections. An "audible simulation" refers to a recreation or emulation of sounds or audio. Audible simulation may involve generating synthetic or artificial sounds or audio that resemble real-world sounds or audio. Audible simulation may occur in many differing ways. By way of non-limiting example, an audible simulation may be generated via concatenative synthesis. In concatenative synthesis, small segments of pre-recorded speech are utilized to create new utterances or audible simulation. These segments, known as "units," may be selected and concatenated, such that an algorithm generates the desired audible simulation. Audible simulation may also be generated via format synthesis. In format synthesis, parameters of formats, which are resonant frequencies of the vocal tract, are modeled and manipulated to form the audible speech. This may involve the manipulation of the parameters formants such as pitch, duration, and intensity to produce audible simulation. Audible simulation may also be generated via parametric synthesis. In parametric synthesis, mathematical models and algorithms may be utilized to generate audible simulation. Specifically, these mathematical models and algorithms may define a set of parameters that describe various aspects of the voice, such as pitch, spectral envelope, and timing, to synthesize audible simulation via signal processing techniques. Audible simulation may also be generated via Hidden Markov Model (HMM) synthesis. In HMM synthesis, statistical models known as Hidden Markov Models (HMM) may be trained on a large amount of recorded speech data to capture the relationships between phonemes and their acoustic properties. The HMM model may be used to predict the most likely sequence of acoustic units and thereby generate an audible simulation given an appropriate input, wherein the input may be a text input or any other appropriate data. Additionally or alternatively, audible simulation may be generated via Learning-based synthesis. In Learning-based synthesis, deep leaning techniques such as recurrent neural networks (RNNs) and their variants such as long short-term memory (LSTM) or transformers may be trained on large datasets of speech recordings and text transcriptions to learn the relationships between text inputs and corresponding audio outputs, thereby allowing for the generation of audible simulation. Additionally or alternatively, the audible simulation may be generated via any suitable combination of the aforementioned techniques, thereby leveraging the strengths of different techniques and algorithms to achieve a high-quality and naturally-sounding audible simulation.

Audible simulation may create convincing and immersive auditory experiences that enhance the overall perception and engagement of users. Audible simulation may accurately reproduce or simulate sounds, thereby providing depth, realism, and context to various application, thus contributing to a more immersive, realistic, and enjoyable user experience. Audible simulation may be employed in various domains, including entertainment, training, gaming, education, language learning, stimulation purposes, Virtual Reality (VR) and Augmented Reality (AR), film, or any other appropriate domain that requires or recommends the use of sound or audio.

Prevocalized words may be derived from the reflections "Derived" refers to being deduced from or generated based on the reflections. For example, the reflections can be interpreted or translated to identify the prevocalized words, as described and exemplified elsewhere in this disclosure. By way of example, subvocalization deciphering module 708 may be used to determine the prevocalized words based on the reflections of light received from a user's skin.

Indeed, the at least one processor may be configured to output, via the speaker, an audible simulation of the pre-conceived words derived from the reflections. The audible simulation may be, as defined above, any synthetic or artificial sound or audio of the prevocalized words. The prevocalized words may be derived, as defined above, from the reflections from the skin corresponding to facial skin micromovements. An output determination module 712 may synthesize vocalization of words accordingly, as described and exemplified elsewhere in this disclosure.

Consistent with some disclosed embodiments, the audible simulation of the prevocalized words includes a synthetization of a voice of an individual other than the wearer. "Synthetization of a voice" may refer to voice synthesis or refers to the process of generating artificial sound or audio. Synthetization of a voice may occur via the processes, techniques, or algorithms to generate audible simulation, as described and exemplified elsewhere in this disclosure. In some embodiments, voice characteristics of the wearer may be used to synthesize the voice. In other examples, voice characteristics of an individual other than the wearer may be employed for voice synthesis. The synthesis may be configured to simulate a real or imaginary voice. For example, vocal parameters of a celebrity may be applied during voice synthesis, or a random or preselected set of vocal parameters may be applied to synthesize a voice not correlated to any particular individual.

Voice synthetization may be used in several domains, including accessibility tools for individuals with impairments, automated voice response systems, navigation and guidance systems, e-learning platforms, multimedia content, virtual assistants, wearable devices, or any other domain that recommends or requires the use of voice or sound(s).

The wearer or user may be able to customize or decide the identity of the voice to be synthesized. For example, a wearer or user may customize to have the identity of the voice to be synthesized to be that of a friend, a family member, a famous individual, a trainer, a teacher, a lecturer, or any other suitable individual or group of individuals. By way of non-limiting example, the output determination module 712 may synthesize a vocalization of words determined from the facial skin movements by subvocalization deciphering module 708, wherein the synthesis may emulate a voice of user 102 or emulate a voice of someone other than user 102 (e.g., a voice of a celebrity or preselected template voice), as described and exemplified elsewhere in this disclosure.

Consistent with some disclosed embodiments, the audible simulation of the prevocalized words includes a synthetization of the prevocalized words in a first language other than a second language of the prevocalized words. "Language" may refer to a system of communication that uses a set of symbols, signs, words, or text to convey meaning. Languages may take several forms, including spoken languages, written languages, signed languages, programming languages used in computer science, or other suitable forms of communication. The language in which the prevocalized words are simulated may differ from the language in which they were prevocalized. For example, words subvocalized in English may be audibly simulated in Spanish. In this way, for example, a wearer subvocalizing or prevocalizing in English can hear the words articulated in a different language. This can help users learn languages, or it can help users communicate in other languages. In other embodiments, and additional speaker, such as a loudspeaker or personal speaker of a listener, might be audibly presented with the subvocalized or prevocalized words in the second language. In yet another embodiment, the wearer might vocalize the words in one language, and the light reflections associated with that vocalization may be translated to another language for presentation to the wearer and/or to a listener.

Though the prevocalized words may be derived from the reflections from the skin corresponding to the facial skin micromovements indicative of prevocalized words in the language of the wearer, the synthetization of a voice may be in a language different from the language of the wearer. For example, the wearer or user may be able to customize or decide the language of the voice to be synthesized, such as a language that the wearer or user wishes to learn, a sign language, a programming language, or any other suitable means of communication. By way of non-limiting example, the output determination module 712 may synthesize a vocalization of words determined from the facial skin movements by subvocalization deciphering module 708, wherein the synthesis may emulate a voice of user 102 or emulate a voice of someone other than user 102 (e.g., a voice of a celebrity or a preselected template voice in a different language), as described and exemplified elsewhere in this disclosure.

Consistent with some disclosed embodiments, the light detector is configured to output associated reflection signals indicative of muscle fiber recruitments, and the recruited muscle fibers may include at least one of zygomaticus muscle fibers, orbicularis oris muscle fibers, risorius muscle fibers, or levator labii superioris alaeque nasi muscle fibers (as described and exemplified elsewhere in this disclosure)).

By way of a non-limiting example, FIG. 88 illustrates a system 8850 including the earbud or earpiece with added facial micromovement detection, consistent with some embodiments of the present disclosure. As seen in FIG. 88, the light detector 8816 may be integrated with the ear-mountable housing 8810 and configured to receive reflections from the skin corresponding to facial skin movements indicative of prevocalized words of the wearer 8802. Furthermore, the light detector 8816 may be further configured to output associated reflection signals indicative of muscle fiber recruitments of the facial region 8808 of the wearer 8802. Such recruited muscle fibers may include a zygomaticus muscle, an orbicularis oris muscle, a risorius muscle, or a levator labii superioris alaeque nasi muscle.

Consistent with some disclosed embodiments, at least one processor is configured to analyze the light reflections to determine the facial skin micromovements, which may include speckle analysis (as described and exemplified elsewhere in this disclosure).

By way of a non-limiting example, FIG. 88 illustrates a system 8850 including the earbud or earpiece with added facial micromovement detection, consistent with some embodiments of the present disclosure. As seen in FIG. 88, the light detector 8816 may be integrated with the ear-mountable housing 8810 and configured to receive reflections from the skin corresponding to facial skin micromovements indicative of prevocalized words of the wearer 8802. Moreover, the light detector 8816 may be configured to analyze the light reflections to determine the facial skin micromovements, wherein the analysis may be a speckle analysis.

By a way of a non-limiting example, FIG. 89 illustrates a system 8920 of an earbud with added facial micromovement detection, consistent with some embodiments of the present disclosure. As seen in FIG. 88 and FIG. 89, the system 8920 may comprise a light detector 8816 integrated with the aforementioned ear-mountable housing 8810 and configured to receive a first reflection 8904 from the skin. Thereafter, the light detector 8816 may be configured to analyze the light reflections to determine the first facial skin micromovements 8906, wherein the analysis may be a speckle analysis.

Consistent with some disclosed embodiments, audio received via the microphone and the reflections received via the light detector correlate facial skin micromovements with spoken words for training a neural network to determine subsequent prevocalized words from subsequent facial skin micromovements. "Spoken words" in this context refer to the verbal expression of language through speech, sound, or audio.

A "neural network" in this context refers to a computational model that employs a mathematical framework composed of interconnected nodes, known as artificial neurons or units, organized in layers. Each neuron may receive input signals, perform computations, and produce output signals. Moreover, such computations may involve a weighted sum of the inputs, followed by the application of an activation function that introduces non-linearity to the network, thereby enabling the neural network to model complex relationships between inputs and outputs. The layers may further include an input layer that receives initial input data, an output layer that produces a final output or prediction, and one or more hidden layers between the input layer and the output layer, where complex computations and feature extraction may occur. Also, there may be multiple hidden layers known as deep neural networks. Deep neural networks may allow for learning hierarchical representations and extracting complex features from data, thereby allowing for more powerful and expressive neural networks. Moreover, the neural network may have parameters known as weights and biases, which determine the strength and significance of connections between the aforementioned neurons. These parameters may be adjusted during the training process, allowing the neural network to adapt and optimize its performance.

In some disclosed embodiments, a neural network may be able to receive and learn from inputted data and generalize new inputs based on the received data. A neural network may be utilized in a variety of domains, including machine learning and artificial intelligence, image and speech recognition, natural language processing, autonomous vehicles, recommender systems, and a plethora of other applications. Also, a neural network may be used in machine learning and artificial intelligence to perform tasks such as pattern recognition, classification, regression, and decision-making.

"Training a neural network" refers to the process of teaching the neural network to learn and recognize patterns, relationships, or representations in data. Training a neural network may involve adjusting the aforementioned parameters known as weights and biases based on the input data and the desired output, thereby enabling the neural network to make accurate predictions or classifications. A goal of the training process may be to optimize the neural network's parameters and minimize the difference between predicted and actual outputs.

Training a neural network may involve a multiple step iterative process. Initially, training a neural network may include data preparation, wherein a dataset that includes input data and corresponding target outputs is gathered and prepared. Thereafter, the neural network architecture may be designed and defined such that the neural network architecture includes a number and arrangement of layers, certain types of neurons or units in each respective layer, and connections between them. Additionally, the aforementioned weights and biases parameters may be initialized with random values, wherein such values serve as starting points for the learning process. Subsequently, the training of the neural network may include forward propagation, wherein the input data is passed through the neural network in a forward direction, layer by layer, to obtain the predicted output. At this stage, the training may perform an error calculation by comparing the predicted output with the desired target output and calculate the error or loss, thereby quantifying the discrepancy between the neural network's prediction and the expected output. Thereafter, the training may perform back propagation, wherein a calculated error is utilized to update the neural network's weights and biases parameters. This may be done by propagating the error backward, layer by layer, and adjusting the weights using optimization algorithms such as gradient descent. Doing so may minimize the aforementioned error and may improve the neural network's predictive accuracy. This training process of forward propagation, error calculation, and back propagation may be repeated for multiple iterations, wherein each iteration updates the neural network's weights and biases parameters, thereby gradually improving the neural network's performance and reducing its error. Finally, the performance of the neural network may be evaluated and assessed via the use of separate validation datasets or evaluation metrics to ensure that the neural network functions well with new, unseen data. This step helps determine if the network has learned the desired patterns effectively and if the desired outputs are produced, or if further adjustments may be needed.

In some disclosed embodiments, the at least one processor may be configured to use the audio received via the microphone and the reflections received via the light detector to correlate the facial skin micromovements with spoken words, wherein the spoken words may be any verbal expression of language through speech, sound, or audio. For example, the spoken words may be the aforementioned verbal expression of the wearer or the user. Thereafter, the processor may train a neural network to determine subsequent prevocalized words from subsequent facial skin micromovements.

As described above, the processor may train a neural network with the appropriate datasets to determine subsequent, predicted, or future prevocalized words from subsequent, predicted, or future facial skin micromovements. For example, the processor may utilize the initial data comprising a correlation between certain facial skin micromovements with spoken words as an initial or training dataset to prepare the neural network accordingly. In the training data set the facial skin micro movements may constitute the inputs and the spoken words may constitute the target outputs. Thereafter, the training of the neural network may undergo a series of training steps including, but not limited to, the design of a neural network architecture, data initialization, forward propagation, error calculation, back propagation, iteration, and evaluation and validation. After which, the neural network may determine subsequent, predicted, or future prevocalized words from subsequent, predicted, or future facial skin micromovements. For example, skin micro movements determined based on reflected light received by a light detector may be provided to the trained neural network model as inputs, and the trained neural network model may generate one or more spoken words associated with those skin micromovements as an output.

Some disclosed embodiments involve identifying a trigger in the determined facial skin micromovements for activating the microphone. A "trigger" refers to an event or condition that initiates a predefined action, process, or set of instructions. A trigger may be activated by a specific condition, signal, or input. "Activate" or "activating" may refer to initiating, starting, or putting into action. Activating may involve taking action to activate or enable a device, system, process, function, or state. Activating may involve providing a necessary input, signal, or condition for the device, system, process, function, or state to begin functioning or become operational.

At least one processor may be configured to identify a trigger in the determined facial skin micromovements for activating the microphone. For example, the processor may identify a trigger such as a movement or twitch of facial skin indicating that the wearer or user wishes to speak, and in response may activate the microphone. For example, prevocalization or subvocalization facial skin micromovements correlated to words might serve as a trigger to activate a microphone. Furthermore, the determined facial skin micromovement that acts as a trigger for activating the microphone need not be limited to the wearer's or user's desire to speak.

By way of a non-limiting example, as seen in FIG. 88, the wearer 8802 or wearer 8802 may use or wear a multifunctional earpiece 8800. The multifunctional earpiece 8800 may further comprise an ear-mountable housing 8810, a microphone 8820, and a light detector 8816. As seen in FIG. 88, the microphone 8820 may be integrated with the ear-mountable housing 8810 to receive audio indicative of the speech of the wearer 8802. As further seen in FIG. 88, the light detector 8816 may be configured to receive reflections from skin of the facial region 8808 of the wearer 8802. Thus, the received reflections correspond to facial skin movements indicative of prevocalized words of the wearer 8802.

As such, a processor (e.g., processing device 400 or processing device 460 in FIG. 4, as described and exemplified elsewhere in this disclosure) of the system 8850 may be configured to use audio received via the microphone 8820 and the reflections received via the light detector 8816 to correlate the wearer 8802's facial skin micromovements with the wearer 8802's spoken words. The processor may accordingly train a neural network to determine subsequent prevocalized words from subsequent facial skin micromovements.

By a way of a non-limiting example, FIG. 89 illustrates a system 8920 of an earbud with added facial micromovement detection, consistent with some embodiments of the present disclosure. The system 8920 comprises a microphone 8820 for receiving a first audio 8900. Also, as seen in FIG. 88 and FIG. 89, the system 8920 may comprise a first light source 8902 for projecting light toward skin of the wearer 8902's face. Additionally, the system 8920 may comprise a light detector 8816 configured to receive a first reflection 8904 from the skin corresponding to first facial skin micromovements 8906 indicative of prevocalized words of the wearer 8802.

A processor (e.g., processing device 400 or processing device 460 in FIG. 4, as described and exemplified elsewhere in this disclosure) of the system 8920 may be configured to use the first audio 8900 received via the microphone 8820 and the first reflection 8904 received via the light detector 8816 to correlate the first facial skin micromovements 8906 with spoken words 8908. The processor may accordingly train a neural network to determine subsequent prevocalized words from subsequent facial skin micromovements. In some disclosed embodiments, the processor may be configured to identify a trigger 8910 in the determined first facial skin micromovements 8906 for activating the microphone 8820 that produces the first audio 8900. As seen in FIG. 89, the trigger 8910 identifies a specific valley in the determined first facial skin micromovements 8906 for activating the microphone 8820 that produces the first audio 8900.

Some disclosed embodiments involve a pairing interface for pairing with a communications device, and transmission of an audible simulation of the prevocalized words to the communications device.

A "pairing interface" refers to a component of software and/or hardware that enables connection or communication between two devices. Pairing interfaces may be based on technologies such as Bluetooth, Wi-Fi, and Near Field Communication (NFC) for establishing connections between devices.

A pairing interface may enable the two or more devices to recognize and identify each other, establish a secure communication link, and initiate data transfer or interaction. Additionally, the pairing interface may include mechanisms for device discovery and recognition. For example, two or more devices may use the pairing interface to search and detect compatible and nearby devices with which a connection may be established. This may involve scanning for wireless signals, broadcasting device identifiers, or using other suitable methods to identify available devices.

Furthermore, the pairing interface may incorporate authentication and authorization mechanism to ensure secure and authorized connections. This may involve the use or exchanging of cryptographic keys, passwords, or other security credentials between the devices to verify identity and permission of the devices involved. Also, the pairing interface may provide for a user-friendly interface for users to initiate and manage the pairing process. This may include visual prompts, instructions, or dialogues that guide the user through the necessary steps to establish the pairing connection. The pairing interface may involve selecting devices from a list, entering passcodes, confirming connections, or providing user permissions. Pairing interfaces may be used in a plethora of domains, including Bluetooth devices, wireless peripherals, smart home devices, mobile applications, and IoT (Internet of Things) devices, among other devices and applications.

A "communications device" refers to a hardware or software component that enables the transmission, reception, and exchange of information between two or more devices, entities, appliances, users, or parties. A communications device facilitates communication and the transfer of data over one or more communication networks or channels. Examples of communications devices include telephones, mobile phones, smartphones, smartwatches, tablets, laptops, desktop computers, Augmented Reality (AR) devices, Virtual Reality (VR) devices, extended reality glasses, headset communicators, modems, routers, a satellite communications devices, or any other device for enabling communication.

Some disclosed embodiments involve transmitting a textual presentation of the prevocalized words to the communications device. Similar to the description above of transmitting an audible presentation, a textual presentation may additionally or alternatively be transmitted. A "textual presentation" refers to the representation of information, data, or any suitable content in a written, or printed format (e.g., with visual characters such as numbers and letters as opposed to audio, for example). Textual information is typically conveyed through the use of written words, sentences, paragraphs, or any other textual elements.

By way of a non-limiting example, FIG. 88 illustrates a system 8850 including the earbud or earpiece with added facial micromovement detection, consistent with some embodiments of the present disclosure. As seen in FIG. 88, the wearer 8802 or wearer 8802 may use or wear a multifunctional earpiece 8800. Moreover, the multifunctional earpiece 8800 may comprise a pairing interface 8828 for pairing with a communications device 8824 or communications device 8826. As seen in FIG. 88, the wearer 8802 or wearer 8802 may actuate any one of the buttons 8828 in either the communications device 8824, the communications device 8826, or the multifunctional earpiece 8800 to enabling the pairing.

Furthermore, after pairing with the appropriate communications device 8826 or 8828, the at least one processor is configured to transmit either an audible simulation of the prevocalized words to the communications device 8824 or communications device 8826 or a textual representation of the prevocalized words to the communications device 8824 or communications device 8826.

Figure 90:
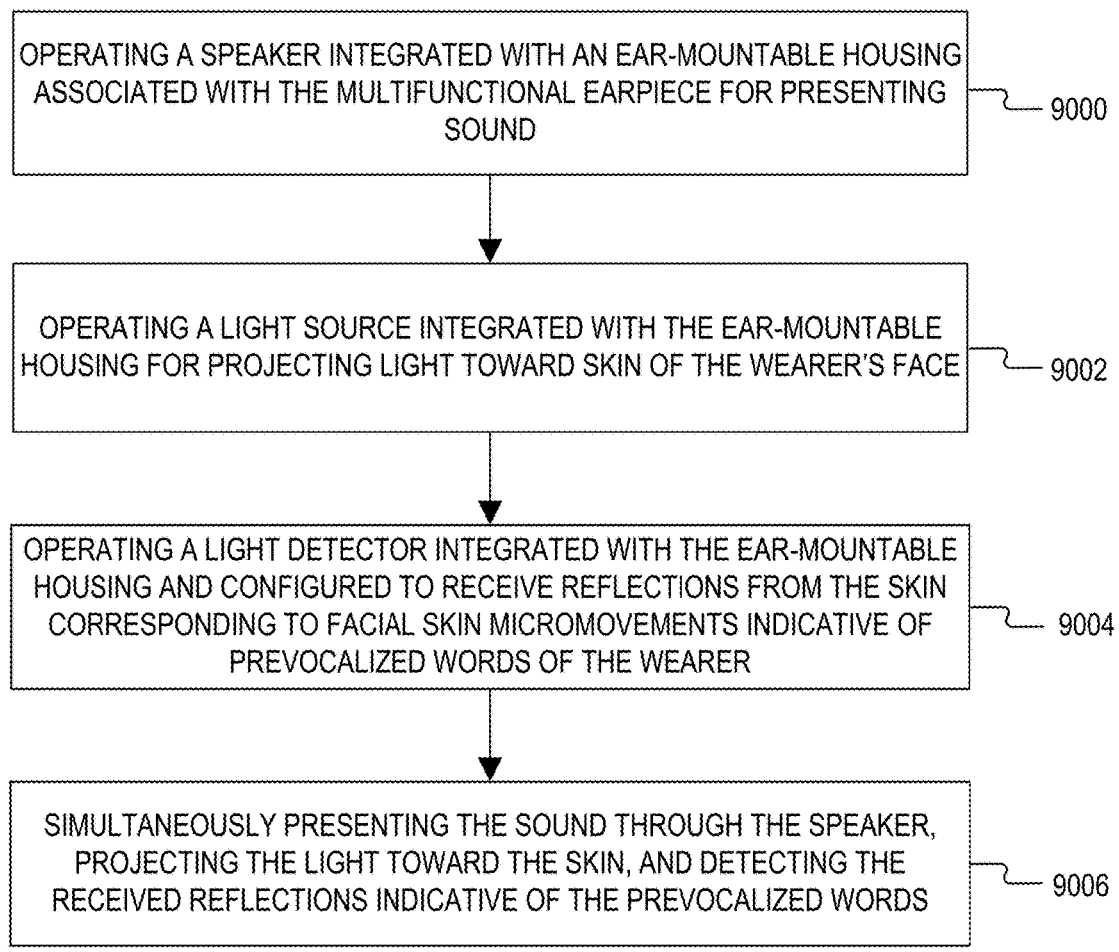
FIG. 90 is a flowchart of an example process of operating a multifunctional earpiece, consistent with some embodiments of the present disclosure.

FIG. 90 illustrates a process 9030 of operating a multifunctional earpiece. Process 9030 includes a step 9000 of operating a speaker integrated with an ear-mountable housing associated with the multifunctional earpiece for presenting sound. By way of example, in FIG. 88, a speaker 8814 is integrated with an ear-mountable housing 8810 associated with the multifunctional earpiece 8800 for presenting sound.

Process 9030 includes a step 9002 of operating a light source integrated with the ear-mountable housing for projecting light toward skin of the wearer's face. By way of example, in FIG. 88, a light source 8830 integrated with the ear-mountable housing 8810 projects light 8804 toward skin of the wearer 8802's face or facial region 8808. Also, by way of example, in FIG. 89, a first light source 8902 integrated with the ear-mountable housing 8810 projects light 8804 toward skin of the wearer 8802's face or facial region 8808.

Process 9030 includes a step 9004 of operating a light detector integrated with the ear-mountable housing and configured to receive reflections from the skin corresponding to facial skin micromovements indicative of prevocalized words of the wearer. By way of example, in FIG. 88, a light detector 8816 may be integrated with the ear-mountable housing 8810 and configured to receive reflections from the skin corresponding to facial skin micromovements indicative of prevocalized words of the wearer 8802. Also, by way of example, in FIG. 89, a light detector 8816 may be integrated with the ear-mountable housing 8810 and configured to receive a first reflection 8904 from the skin corresponding to the first facial skin micromovements 8906 indicative of prevocalized words of the wearer 8802.

Process 9030 includes a step 9006 of simultaneously presenting the sound through the speaker, projecting the light toward the skin, and detecting the received reflections indicative of the prevocalized words. By way of example, in FIG. 88, there is simultaneous presenting of sound through the speaker 8814, projecting of light 8804 toward the skin of the wearer 8802, and the light detector 8816's detection of received reflections indicative of the prevocalized words.

Some embodiments involve a non-transitory computer readable medium containing instructions that when executed by at least one processor cause the at least one processor to perform operations for operating a multifunctional earpiece, the operations comprising: operating a speaker integrated with an ear-mountable housing associated with the multifunctional earpiece for presenting sound; operating a light source integrated with the ear-mountable housing for projecting light toward skin of the wearer's face; operating a light detector integrated with the ear-mountable housing and configured to receive reflections from the skin corresponding to facial skin micromovements indicative of prevocalized words of the wearer; and simultaneously presenting the sound through the speaker, projecting the light toward the skin, and detecting the received reflections indicative of the prevocalized words.

By way of non-limiting example, in FIG. 88, system 8850 includes at least one non-transitory computer readable medium (e.g., one or more memory device 402 of FIG. 4) and least one processor (e.g., one or more processing device 400 or 460 of FIG. 4) that, when executed by at least one processor cause the at least one processor to perform operations for operating a multifunctional earpiece 8800, the operations comprising operating a speaker 8814 integrated with an ear-mountable housing 8810 associated with the multifunctional earpiece 8800 for presenting sound; operating a light source 8830 integrated with the ear-mountable housing 8810 for projecting light 8804 toward skin of the wearer's 8802 face or facial region 8808; operating a light detector 8816 integrated with the ear-mountable housing 8810 and configured to receive reflections from the skin corresponding to facial skin micromovements indicative of prevocalized words of the wearer 8802; and simultaneously presenting the sound through the speaker 8814, projecting the light 8804 toward the skin, and detecting the received reflections indicative of the prevocalized words.

It will be apparent to persons skilled in the art that various modifications and variations can be made to the disclosed structure. While illustrative embodiments have been described herein, the scope of the present disclosure includes any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps and/or inserting or deleting steps, without departing from the principles of the present disclosure. It is intended, therefore, that the specification and examples be considered as exemplary only, with a true scope and spirit of the present disclosure being indicated by the following claims and their full scope of equivalents.

Some aspects of this disclosure involve a driver enabling control of a software program based on neuromuscular activity. The driver may serve as an interface between a neuromuscular detection device and a software program for enabling outputs of the neuromuscular detection device to control at least some aspects of the software program. For example, the driver may enable a neuromuscular detection device to serve as an interface for controlling aspects of the software program. Those aspects might include accessing the software program, initiating commands in the software program, inputting data into the software program, and/or controlling output of the software program.

Some disclosed embodiments involve a driver for integration with a software program. A driver refers to a program, software, or instructions which operate, control, or actuate a device. Drivers may include interfaces to devices such as hardware devices, and drivers may provide electronic communication between hardware and software. In some embodiments, a driver may be a software component which enables communication between an operating system and a device. Integration with a software program refers to including, embedding, or combining with programs, software, or applications. A driver for integration with a software program may refer to a driver, as described herein, capable of being embedded in a software program. Some embodiments may include enabling a neuromuscular detection device to interface with the software program. Enabling a device to interface with the software program may refer to any method of communicating or permitting transfer of data or information between the neuromuscular detection device and the software program. In some embodiments, a driver may include various software components, such as sets of files, which communicate with the operating system of a computer to deliver instructions or commands to one or more devices. A neuromuscular detection device may refer to any system or apparatus for perceiving, sensing, receiving, or processing information from the human body. For example, a neuromuscular detection device may detect signals, data, communication, or information occurring in a human, such as neural activity, skin movements, or muscle activity.

Figure 92:
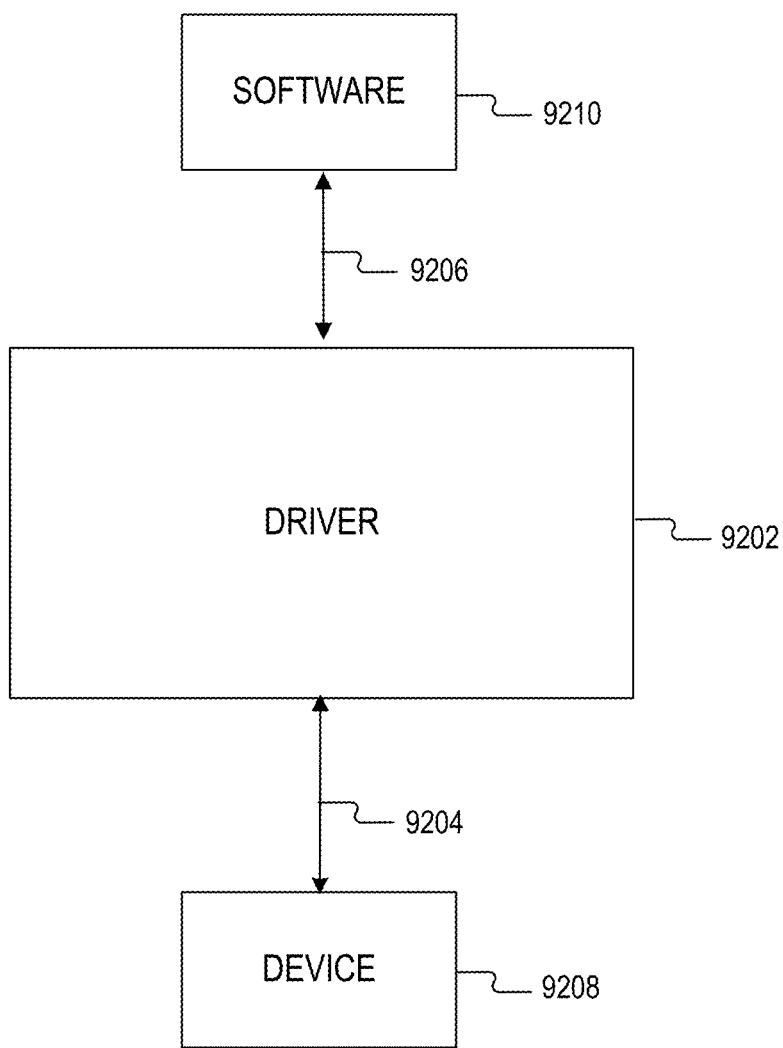
FIG. 92 illustrates a block diagram of an exemplary driver for interfacing with a software program and a device, consistent with disclosed embodiments.

FIG. 92 illustrates a block diagram of an exemplary driver for interfacing with a software program and a device, consistent with disclosed embodiments. Driver 9202 may send electronic communications 9204 to device 9208. Device 9208 may be a neuromuscular detection device. Device 9208 may receive electronic communications 9204 from and may send electronic communications 9204 to driver 9202. Software 9210 may be an application, program, or operating system. Driver 9202 may transmit electronic communications 9206 to software 9210. Driver 9202 may convert or translate signals from device 9208 into data that software 9210 may understand or be able to act on. Driver 9202 may transmit instructions from software 9210 to device 9208 such that device 9208 may execute the instructions. Software 9210, device 9208, and/or driver 9202 may be coupled by any method, as exemplified herein, that permit them to interact with a processor such as processing device 400, as referenced in FIG. 4.

Some disclosed embodiments involve an input handler for receiving non-audible muscle activation signals from the neuromuscular detection device. An input handler includes any component which can receive, sense, or process information, data, events, or signals. Input handlers may include components of hardware or software modules configured for receiving data. In some examples, input handlers may be functions, methods, or routines which perform a particular task. For example, input handlers may focus on controlling or managing entries to the system. Signals, as described and exemplified elsewhere herein, may include any quantity or function conveying information about an event or phenomenon. For example, signals may include data or information captured over a period of time or over a number of events. Muscle activation may involve the triggering or operating of muscles in the body, such as by a contraction of the muscle. Muscle activation may involve recruitment of muscles, as described elsewhere in this disclosure. For example, electrical signals from the brain may trigger motor units to contract the muscle. Non-audible muscle activation signals may involve signals corresponding to silent, subvocalized, or prevocalized speech, as described herein. For example, non-audible muscle activation signals may include signals corresponding to skin micromovements, as discussed elsewhere in this disclosure. In some embodiments, non-audible signals may reflect measurements of signals other than sound. In some embodiments, non-audible muscle activation signals may include recruitment of muscles corresponding to audible activation, or non-audible activation. In some embodiments, non-audible muscle activation signals may include signals received from electromyography (EMG) sensors.

Some disclosed embodiments involve a lookup component for mapping specific ones of the non-audible activation signals to corresponding commands in the software program. A lookup component may include any module, building block, software program, or portion of a software program for mapping or evaluating relationships between values. Lookup components may include dedicated hardware or lines of code or instructions for searching for data within a data structure (as described and exemplified elsewhere herein). In some embodiments, lookup components may include data structures, as described herein. For example, a lookup component may store relationships or associations between data or values, such as a relationship between inputs to the system. As an example, a lookup component may be queried such that an input can be evaluated to determine if any associations exist between the input and values stored in the lookup component. A lookup component may use machine learning to evaluate data contained in the lookup component.

In some embodiments, a lookup component includes an artificial intelligence data structure. Artificial intelligence data structures may include any data structures as described herein used for machine learning or artificial intelligence. For example, artificial intelligence data structures may include arrays, linked lists, stacks, queues, trees, graphs, hash, or any combination thereof. In some embodiments, a lookup component includes a lookup table. A lookup table may include an array or matrix storing values or data. A lookup table may involve inputs or keys which may correspond to certain values or data contained in the lookup table. For example, lookup tables may include array indexing operations, such as direct addressing of values stored in certain slots in the lookup table. Lookup tables may be stored in memory or storage, thereby enabling values to be retrieved from the lookup table faster than performing computations. In some embodiments, a lookup table may map input values to output values.

In some disclosed embodiments, a lookup component maps specific ones of the non-audible activation signals to corresponding commands in the software program. Mapping involves determining or identifying relationships or correspondence between data, elements, or components. Mapping may include linking one or more items or elements, such as identifying a set of values with another set of values. In some embodiments, mapping may involve translating or converting values. In some embodiments, specific ones may include some of the non-audible activation signals. In some embodiments, specific ones may include all of the non-audible activation signals. The software program may involve any software for interacting with hardware, firmware, devices, people, or applications. The software program may include applications, operating systems, or APIs. For example, software programs may include media players, graphical user interfaces, software as a service, messaging apps, data processing apps, communications apps, software components of hardware devices, and webpages. As an example, media players may be capable of storing, playing, or viewing digital media content including audio and/or video. Corresponding commands may involve any order or instruction pertaining to data or inputs. Corresponding commands may include instructions to adjust toggles, switches, or buttons. In some embodiments, corresponding commands may pertain to signals, such as non-audible muscle activation signals. For example, corresponding commands may be associated with non-audible muscle activation signals via relationships demonstrated in the lookup component. As an example, the lookup component may map some non-audible activation signals to the corresponding commands. In some embodiments, an activation signal may be mapped to no commands, one command, or multiple commands. In some embodiments, a command may be mapped to no signals, one signal, or multiple signals. In the example of the media player, the driver might translate facial light reflections corresponding to vocalized, prevocalized, or subvocalized words such as "play," "stop," and "rewind," into corresponding media player commands of "play," "stop," and "rewind." In a messaging app, facial light reflections corresponding to vocalized, prevocalized, or subvocalized words such "write the message, I'm running late. See you at 10:10," might be parsed by the driver into a command to open a message window and into the textual input "I'm running late. See you at 10:10," for presentation in the message window. These are just examples for demonstrative purposes. There are an infinite number of commands that might be recognized in this context, depending on the software application involved.

For example, a specific non-audible muscle activation signal may be mapped to a corresponding command, such as a command to play a certain audio file with speaker 404, as illustrated in FIG. 4. As an example, a corresponding command may be to initiate a vibration with haptic feedback device 408. In one embodiment, the software program may be a media player. In one embodiment, exemplary commands may include play (playing the media file), pause (pausing the currently playing media file), stop (stop the media playback), next (next media file), previous (previous media file), volume up or volume down, and mute or unmute.

Consistent with some disclosed embodiments, the lookup component is configured to map some of the specific ones of the non-audible activation signals to text. Configured to map to text may involve a component being able to associate or determine relationships between activation signals and text. Text, as described herein, may include words, phrases, phonemes, graphemes, alone or in combination. For example, the lookup component may present mappings or relationships between one or more activation signals and one or more words or phrases. The messaging app example described above, is one example of a lookup component configured to map specific non-audible activation signals to text (e.g., where the reflection signals associated with the words "I'm running late. See you at 10:10," is mapped for textual input. In some embodiments, the lookup component or the training module may perform machine learning to determine associations between activation signals and text. In some disclosed embodiments, the text corresponds to subvocalization manifest in the non-audible muscle activation signals. Subvocalization, as discussed and exemplified elsewhere in this disclosure, may involve silent-speech related activity. Subvocalization manifest in the non-audible muscle activation signals may include subvocalization perceived, sensed, or exhibited in the non-audible muscle activation signals. For example, certain non-audible muscle activation signals may include subvocalization or data corresponding to subvocalization.

In some disclosed embodiments, the lookup component is configured to map some of the specific ones of the non-audible muscle activation signals to a command. Configured to map may refer to being capable of mapping, as described elsewhere in this disclosure. For example, the lookup component may map some or all of the activation signals to a command. In some embodiments, the command may be a corresponding command. In some embodiments, the command may be different from a corresponding command. For example, commands may include any initiation of an action on the device, hardware, software, or application. Commands may cause an initiation of actions such as playing a video, displaying a visual output, playing audio, actuating a sensor or light, or activating code. For example, in the messaging app example described earlier, the reflection signals associated with the words, "write the message," is mapped to a command to open a messaging app window. In some embodiments, a command may be for causing at least one of a visual output of the text or an audible synthetization of the text. A visual output of the text may include any picture, video, or other output represented in a format discernable by sight or through the eyes. Visual outputs of text may include graphics, pictures, graphs, printouts, graphical user interfaces, screens, and/or projections that may display text that may be viewed by an individual. In the messaging app example above, the visual output may be a window opened on a display of a smartphone that visually displays the subvocalized message. An audible synthetization may include a combination of audio, including words. Audible synthetization may refer to artificial production of human speech, such as a device or machine emitting sound such as words. The audible synthetization may include converting the text to an audible format, such as using text-to-speech algorithms to convert the text to a sound emitted by a speaker. the device representing the text in an audible format. For example, a command may cause a visual output of the text on the device by displaying the text on a display, and/or causing an audible synthetization by producing or generating a sound representation of the text. As an example, a user may initiate a command which causes a visual output of the text on a display on the device.

In some disclosed embodiments, the lookup component is prepopulated based on training data correlating the non-audible muscle activation signals with the corresponding commands. Prepopulated refers to a lookup component that is initialized or filled with predefined or pre-existing data. Prepopulating may involve adding or inputting data or values to any component capable of storing information, including lookup components, data structures, disk drives, memories, flash memory, or RAM. In some embodiments, prepopulating the lookup component may refer to providing information to the lookup before the lookup component is accessed or used. For example, values may be inputted to the lookup component and the lookup component may contain such values. Training data refers to any data associated with speech, silent speech, words, phonemes, and/or non-audible signals that may be used for training a machine learning model. Correlating muscle activation signals with corresponding commands refers to associating those signals and commands in a data structure. In an AI context, for example, this may involve teaching a machine learning model associations or relationships between activation signals and corresponding commands. For example, machine learning models including neural networks, random forests, regression models, reinforcement models, and classification models may use training data to learn correlations between signals and corresponding commands. For example, a data structure may contain correlations of facial micromovements with words or phonemes, and the at least one processor may perform a lookup in the data structure of particular words or phenomes associated with detected facial skin micromovements. For example, a speech detection system may be configured to correlate facial skin micromovements with words using audio signals concurrently captured with the micromovements. Such training data may be stored in the lookup component. In a database construct, correlating may involve the implementation of a lookup table for associating the muscle activation signals with corresponding commands.

Some disclosed embodiments involve a signal processing module for receiving the non-audible muscle activation signals from the input handler. A signal processing module refers to any software or hardware component designed to act on signals (e.g., to filter, transform, interpret, and/or analyze muscle activation signals as described herein). A signal processing module may handle or manage data, events, or signals. For example, signal processing modules may facilitate communication between different modules or components of software and/or hardware. In some embodiments, signal processing modules may perform various operations on signals, including preparing, compiling, filtering, cleaning, distilling, extracting, or purifying. The signal processing module may receive non-audible muscle activation signals from the input handler. For example, the input handler may provide non-audible muscle activation signals to the signal processing module. Receiving (as described herein) may involve acquiring the non-audible muscle activation signals.

Some disclosed embodiments involve supplying the specific ones of the non-audible muscle activation signals to the lookup component. Supplying may involve providing, transmitting, or delivering. In some embodiments, the signal processing module may supply some of the non-audible muscle activation signals to the lookup component. In some embodiments, the signal processing module may supply all of the non-audible muscle activation signals to the lookup component. Supplying the muscle activation signals may involve processing of the signals. Signal processing may involve reducing or removing noise, extracting features, filtering, compressing, optimizing, or windowing. For example, the signal processing module may apply filtering, including but not limited to low pass, butterworth, high pass, band pass, or notch filter. Filtering may remove noise before the signal is supplied to the lookup component, which may result in a more accurate representation of the signal. Some disclosed embodiments may involve receiving an output as the corresponding commands. An output, as described herein, may involve a command, data, and/or initiation of an action on an electronic device. In some embodiments, the module may include hardware components, such as electronic circuitry. In some embodiments, the module may include software.

Some disclosed embodiments involve a communications module for conveying the corresponding commands to the software program. A communications module may be any hardware and/or software component configured for transmitting, sending, or receiving information or data. A communications module may transmit information internally and/or externally. For example, the communications module may send or receive control code, commands, and/or signals. Some embodiments may involve conveying the corresponding commands to the software program. Conveying may involve transmitting or supplying information, as described herein. For example, the communications module may transmit data or information, such as the corresponding commands, to the software program. Some disclosed embodiments enable control within the software program based on non-audible muscular activity detected by the neuromuscular detection device. Control within the software program may refer to accessing commands, control code, or instructions within the software program. Control within the software program may include accessing, managing, or operating functions, libraries, or outputs generated by the software program. For example, the software program may operate an application or manage an output to a device or other application.

Figure 93:
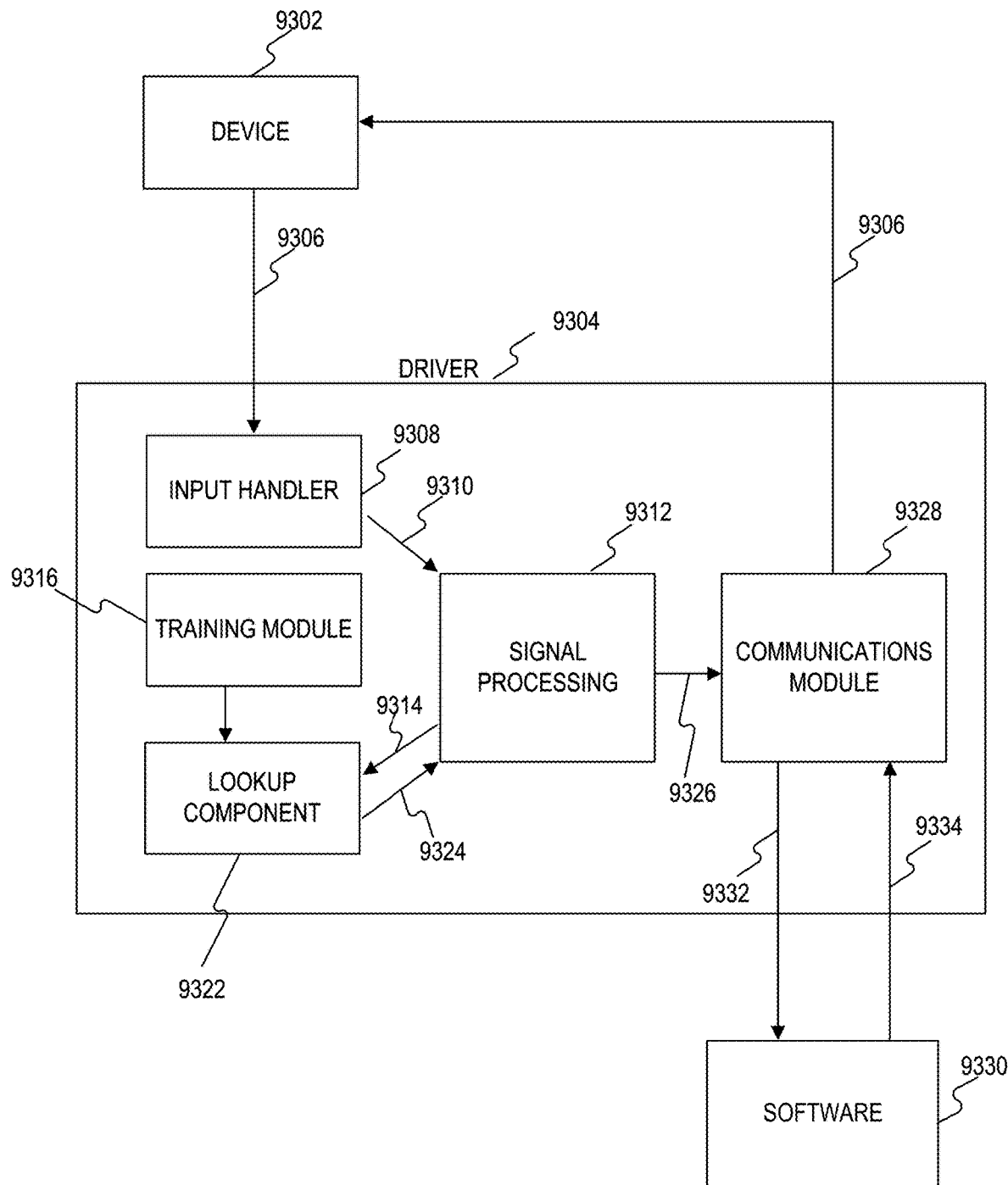
FIG. 93 illustrates a schematic diagram of an exemplary driver for integration with a software program and neuromuscular detection device, consistent with disclosed embodiments.

FIG. 93 illustrates a schematic diagram of a driver for integration with a software program and neuromuscular detection device, consistent with disclosed embodiments. Driver 9304 may include input handler 9308, signal processing module 9312, training module 9316, lookup component 9322, and communications module 93289328. In some embodiments, driver 9304 may receive signals 9306 from device 9302, which may be a neuromuscular detection device. Signals 9306 may be non-audible muscle activation signals. For example, input handler 9308 may receive signals 9306 from device 9302. As an example, signals 9306 may be muscle activation signals, such as signals corresponding to subvocalization. Signal processing module 9312 may receive signals 9310 from input handler 9308. Signal processing module 9312 may supply specific signals 9314 to lookup component 9322. Specific signals 9314 may include some or all of signals 9310. Signal processing module 9312 may apply filtering or noise reduction to specific signals 9314, as described herein. In some embodiments, lookup component 9322 may include a lookup table. In some embodiments, lookup component 9322 may electronically communicate with training module 9316. Lookup component 9322 may map specific signals 9314 to corresponding commands. Signal processing module 9312 may receive corresponding commands 9324 from lookup component 9322. Signal processing module may supply corresponding commands 9326 to communications module 9328. Communications module 9328 may convey corresponding commands 9332 to software 9330.

Some disclosed embodiments involve a training module for determining correlations between the non-audible muscle activation signals with the corresponding commands and for populating the lookup component. A training module may involve any software and/or hardware component for training a machine learning model, as described herein. For example, the training module may include software, hardware, or a programmable chip such as a microprocessor. In some embodiments, the driver may include the training module. In some embodiments, the lookup component may include the training module. In some embodiments, the training module may be separate from the lookup component. Determining correlations may involve evaluating relationships between values or information, or associating data, as described herein. For example, determining correlations may include teaching a machine learning models to learn relationships or correlations between muscle activation signals and corresponding commands. In some embodiments, the training module may populate the lookup component, as described herein. For example, the training module may input into the lookup component a value corresponding to a signal, and also input the correlated value for the corresponding command, as learned by the training module.

For example, as referenced in FIG. 93, lookup component 9322 may be queried or accessed to search for a corresponding command mapped to a non-audible activation signal. The lookup component 9322 may be prepopulated based on training data, such that the lookup component 9322 may store the corresponding command and may identify the command mapped to the given non-audible activation signal, or vice-versa. In some embodiments, training module 9316 may provide the mapping and determine the correlations, such that selecting a given corresponding command in the lookup table maps to a certain activation signal as determined by training module 9316. In some embodiments, upon determining that an activation signal or corresponding command is not present in the lookup component 9322, the activation signal and/or corresponding command may be inputted into training module 9316 as training data.

Some disclosed embodiments include a return path output for transmitting data to the neuromuscular detection device. A return path output may include any information delivered by a component in response to an input. A return path output may be a means or route for data, information, or signals to travel. Transmitting data may involve supplying and/or receiving, as described herein. For example, referring to FIG. 93, return path output 9334 may transmit information from software 9330 to communications module 9328. In some embodiments, return path output 9334 may transmit information from communications module 9328 to device 9302. It will be recognized that such configuration may enable closed loop control of device 9302. For example, such configuration may allow software 9330 to send instructions or commands through driver 9304 to the device 9302. As such, the device may receive signals from the return path output 9334 and the device may act or be controlled by information from software 9330.

In some embodiments, data may be configured to cause at least one of an audio, haptic, or textual output via the neuromuscular detection device. Audio output may include any sound or noise emitted by the device. For example, audio outputs may include phenomes, combinations of phonemes, words, combinations of words, or any other speech-related component emitted by a speaker. Haptic output may include any sensation perceivable by touch and/or proprioception emitted by a device. Haptic outputs may involve tactile sensations such as forces, taps, vibrations, motion, or textures. For example, haptics may include touch feedback. Textual output may include words, phrases, phonemes, or any component of written language emitted from the device. Textual output may include written language on a display, on a graphical user interface, or presented on a device. In some embodiments, haptic outputs, audio outputs, and textual outputs may be transmitted as data to devices such as a remote computing device.

In some embodiments, haptic outputs, audio outputs, and/or textual outputs may include data which may be transmitted to the neuromuscular detection device. For example, return path output 9334 may transmit data causing at least one of a haptics output, audio output, or textual output via device 9302, as referenced in FIG. 93.

Some disclosed embodiments may involve a light source configured to project light toward skin. A light source, as discussed herein, may include any component for emitting light. Light may include electromagnetic radiation such as visible light, ultraviolet light, and/or infrared. Light sources may include light bulbs, lasers, and/or halogens, as exemplified herein. In some embodiments, the light source may be configured to output coherent light, as described elsewhere in this disclosure. Configured to project light toward skin may refer to being adapted for casting, spreading, emitting, or shining light in a direction towards skin. For example, coherent light may be projected towards a facial region of a user. Some embodiments may include a light detector configured to sense reflections of the light from the skin. A light detector, as described and exemplified in this disclosure, may include any image sensor or sensor capable of detecting light reflected from the skin due to one or more movements of the skin. Configured to sense reflections of the light from the skin may include reflections, as discussed herein, from regions of the human skin. For example, light detectors may sense reflections on skin facial regions of the light projected by the light source.

For example, device 9302, as referenced in FIG. 93, may include a light source. Light sources, such as light source 410, may project light toward skin, and light detector 412 may sense reflections of the light from the skin, as referenced in FIG. 4. Some disclosed embodiments involve at least one processor configured to generate the non-audible muscle activation signals based on the sensed light reflections. For example, processing device 400 may generate non-audible muscle activation signals based on the sensed light reflections, as described elsewhere in this disclosure. In some embodiments, the sensed reflections of the light from the skin correspond to micromovements of the skin, as described herein. For example, a sensed reflection may be analyzed to determine amounts of skin movement, direction of skin movement, and/or acceleration of skin movement, as discussed elsewhere in this disclosure. Corresponding to micromovements of the skin may refer to relationships between sensed reflections and micromovements. For example, a sensed reflection may correspond to one or more micromovements, such as one or more movements in different directions. In some embodiments, micromovements of the skin may correspond to muscle activation associated with subvocalization. For example, muscle activation may be associated with at least one anatomical location extracted for light processing. For example, muscle activation may be associated with at least one specific muscle including a zygomaticus muscle, an orbicularis oris muscle, a risorius muscle, a genioglossus muscle, or a levator labii superioris alaeque nasi muscle, as described herein.

In some disclosed embodiments, the at least one processor is configured to generate the non-audible muscle activation signals based on speckle analysis of received reflections of the coherent light. Configured to generate refers to being capable of generating an output, as described herein. For example, the at least one processor may be designed to produce non-audible muscle activation signals. As discussed elsewhere in this disclosure, speckle analysis may involve image processing techniques for detecting, measuring, or analyzing any form of reflection and/or scattering of light. Speckles may include patterns of bright and dark areas, as described herein. For example, speckle analysis may include secondary speckle patterns, different types of specular reflections, diffuse reflections, speckle interferometry, and any other form of light scattering as exemplified elsewhere herein. Speckle analysis of received reflections of the coherent light may involve detection of changes in coherent light patterns, such as changes due to silent speech. For example, a processing device may analyze reflections of coherent light to identify a speckle pattern and derive corresponding micromovements, thereby generating non-audible muscle activation signals based on the speckle analysis.

Figure 94:
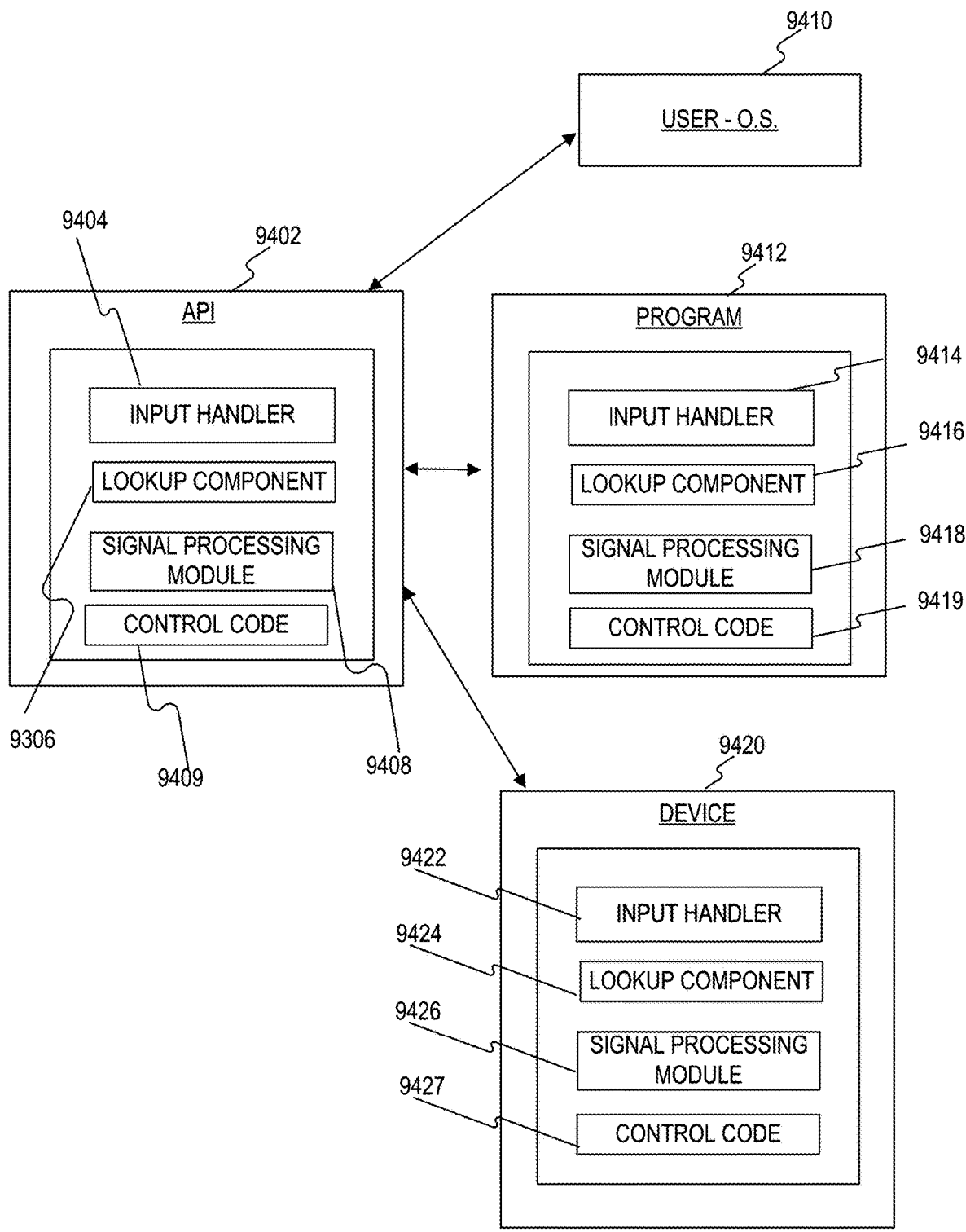
FIG. 94 illustrates a schematic diagram of an exemplary system for integration with a software program and for enabling a device to interface with the software program, consistent with embodiments of the present disclosure.

In some embodiments, the input handler, the lookup component, the signal processing module, and the control code are embedded in the software program. Embedded may refer to being integrated, located, or contained within a component. FIG. 94 illustrates a schematic diagram of a system for integration with a software program and for enabling a device to interface with the software program, consistent with embodiments of the present disclosure. For example, a system may include an API 9402, operating system 9410, software program 9412, and neuromuscular detection device 9420. In some embodiments, at least one of the input handler 9414, the lookup component 9416, the signal processing module 9418, or the control code 9419 may be embedded in the software program 9412. In some embodiments, the input handler, the lookup component, the signal processing module, and the control code are embedded in the neuromuscular detection device. In such embodiments, these components are part of the neuromuscular detection device in hardware and/or software form. For example, at least one of the input handler 9422, lookup component 9424, signal processing module 9426, or the control code 9427 may be embedded in the neuromuscular detection device 9420. In some embodiments, the input handler, the lookup component, the signal processing module, and the control code are embedded in an application programming interface (API). An application programming interface may be located in the cloud. For example, input handler 9404, lookup component 9406, signal processing module 9408, and control code 9409 may be embedded in API 9402.

Some disclosed embodiments involve detection and correction routines to detect and correct errors that occur during data transmission. Detection may include identification, diagnosis, observation, or recognition of issues, problems, or errors. Correction routines may include any function or method for addressing, adjusting, or resolving problems or errors. For example, errors that occur during data transmission may include any problem, issue, bug, or detriment to the operation of the device during sending and/or receiving of data. Errors may include network errors, corruption errors, processing errors, calculation errors, and communication errors. Disclosed embodiments may detect and correct errors through correction routines. For example, detection and correction routines may be included in speech detection system 100 or remote processing system 450. In some embodiments, detection and correction routines may be included in software program 9412, operating system 9410, or device 9420, as referenced in FIG. 94.

Some disclosed embodiments involve configuration management routines for permitting the driver to be configured to applications other than the software program. Configuration management may refer to processes for establishing or maintaining consistency of performance, requirements, or functions of a product. Configuration management may include maintaining updates or requirements of hardware, software, or firmware to desired states or standards. Configuration management routines may include strategies, functions, programs, or plans for executing configuration management. Permitting the driver to be configured to applications may involve ensuring the driver has necessary or sufficient requirements or capabilities for integration or interfacing with applications different from the software program. For example, other applications may include third-party APIs, plug-ins, different hardware devices, or various machine learning models.

Some disclosed embodiments involve context-driven facial micromovement operations. Context refers to circumstances, conditions, and/or environments in which something occurs. As such, context may provide setting information or details which may be helpful for understanding or interpreting a situation, event, or statement. Context may indicate a desired private or public setting through which a communication is made. Context-driven refers to something that is influenced or determined by the specific circumstances, environment, or conditions. For example, it may refer to an approach or methodology dependent on the specific context in which facial skin micromovements are detected, where different situations, environments, and/or factors influence t operations. For example, a context-driven operation may be one including at least a portion that may differ depending on the context. By way of one non-limiting example, if a context involves a setting for a conversation (e.g., where the subject is in a private vs. a public setting, the operations may differ based on the detected setting. (e.g., an output may be made to an earbud in a public setting or a speakerphone in a private setting.

Some disclosed embodiments involve receiving during a first time period, first signals representing first coherent light reflections (as described and exemplified elsewhere) associated with first facial skin micromovements (as described and exemplified elsewhere). Some disclosed embodiments involve receiving during a first time period, first signals representing first non-coherent light reflections (as described and exemplified elsewhere) associated with first facial skin micromovements. A time period may refer to any duration or span of time, such as a defined interval during which events, activities, or processes occur or are considered. A time period may vary in length, ranging from seconds, or a portion of a second, minutes, hours, days, weeks, months, years, or even longer durations. Time periods may be used as units of measurement to track and organize events or to establish a chronological framework (e.g., first time period, second time period, third time period, and so on), thereby providing a temporal context and allowing for the categorization, analysis, or comparison of different occurrences (e.g., different detected facial skin micromovements) within a specific timeframe. Although the terms first, second, third, etc., are used with reference to time periods, it will be understood that such terms do not necessarily refer to sequential time periods. Signals may refer to reflection signals or output signals, as described and exemplified elsewhere. As an example, a wearable device worn by a user may detect light reflections associated with facial skin micromovements as the user vocalizes or pre-vocalizes a plurality of words, and the corresponding detected light reflections may be translated into one or more signals containing data that represents the corresponding detected light reflections. The one or more signals may be received, e.g., at a processor, which may analyze the data within the signals to determine the plurality of words vocalized or pre-vocalized by the user, as described and exemplified elsewhere.

Figure 95:
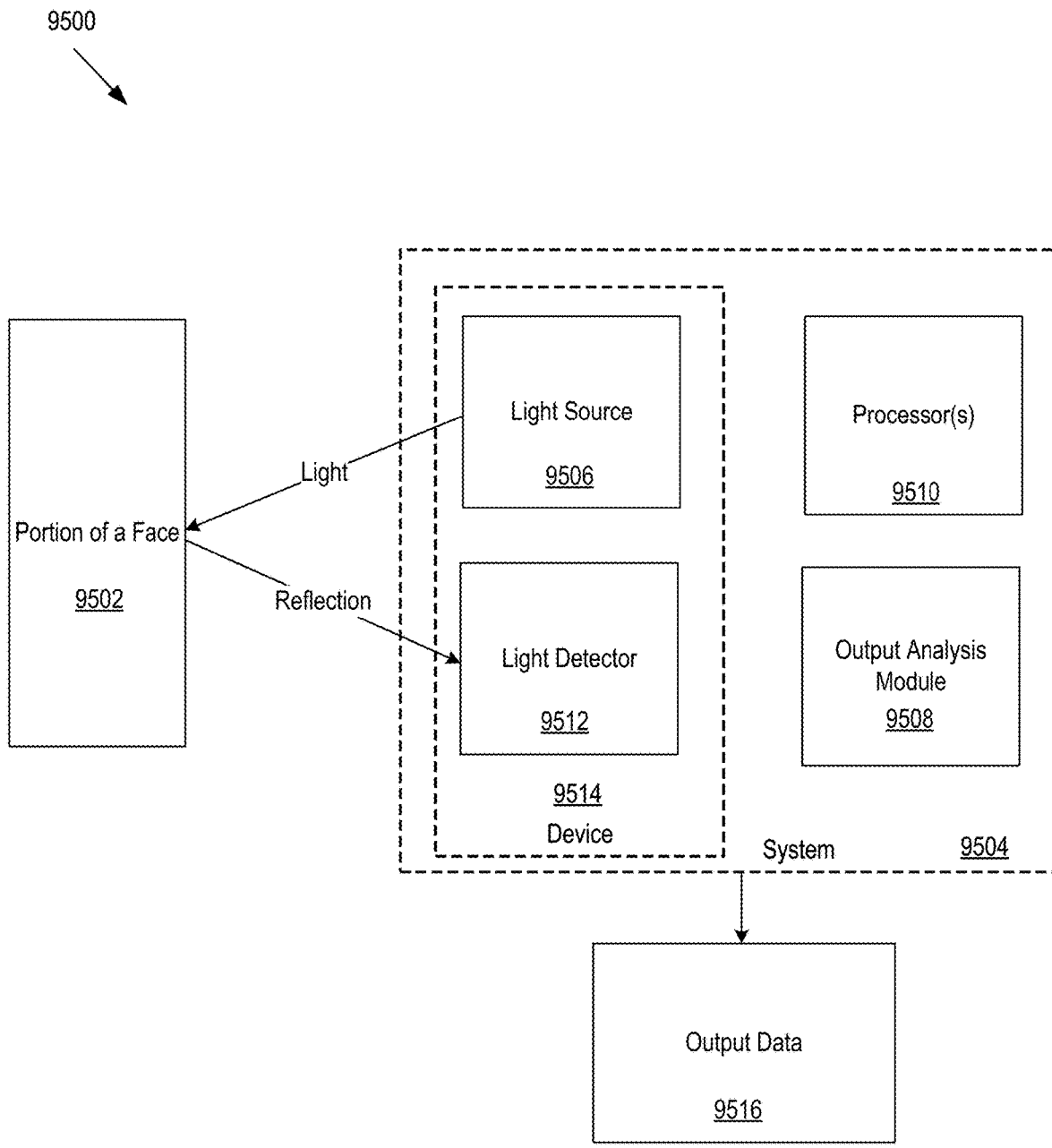
FIG. 95 is a block diagram illustrating an exemplary operating environment for generating context-driven facial micromovement output, consistent with some embodiments of the present disclosure.

As illustrated in FIG. 95, an exemplary device 9514 includes light source 9506 which emits a light onto a portion of a face 9502. Device 9514 further includes light detector 9512 which receives reflection data from the portion of a face 9502. The reflection data includes facial skin micromovement data comprising the first signals representing first coherent (or non-coherent) light reflections associated with first facial skin micromovements. In turn, device 9514 transmits the first signals, based on the first facial skin micromovement data, to processor(s) 9510 and/or output analysis module 9508.

Some disclosed embodiments involve analyzing the first coherent light reflections to determine a first plurality of words associated with the first facial skin micromovements (as described and exemplified elsewhere). Analyzing the first coherent light reflections may involve extracting meaningful information directly from the light reflection signals or from a derivative of the light reflection signals. Such analysis may be similar to analyzing reflected light and/or detected facial skin micromovements, as described and exemplified elsewhere. For example, at least one processor, or another component of the system, may decipher, based on the one or more signals received, that a user wearing the wearable device has vocalized or pre-vocalized a plurality of words based on a combination of detected reflections that are associated with particular facial skin micromovements made during the first time period. For example, at least one processor, or another component of the system (e.g., an output analysis module or a word identifier), may determine that a user wearing the wearable device has asked a question, made a comment, requested confirmation or approval, expressed a feeling, or otherwise communicated or intended to communicate something via a plurality of words. In some disclosed embodiments, determining of the plurality of words may also be performed, e.g., by a word identifier. A word identifier may comprise hardware, software, a combination of hardware and software, or special purpose hardware. In some disclosed embodiments, determining of the plurality of words may also be performed, e.g., by an output analysis module. An output analysis module may comprise hardware, software, a combination of hardware and software, or special purpose hardware.

Figure 96:
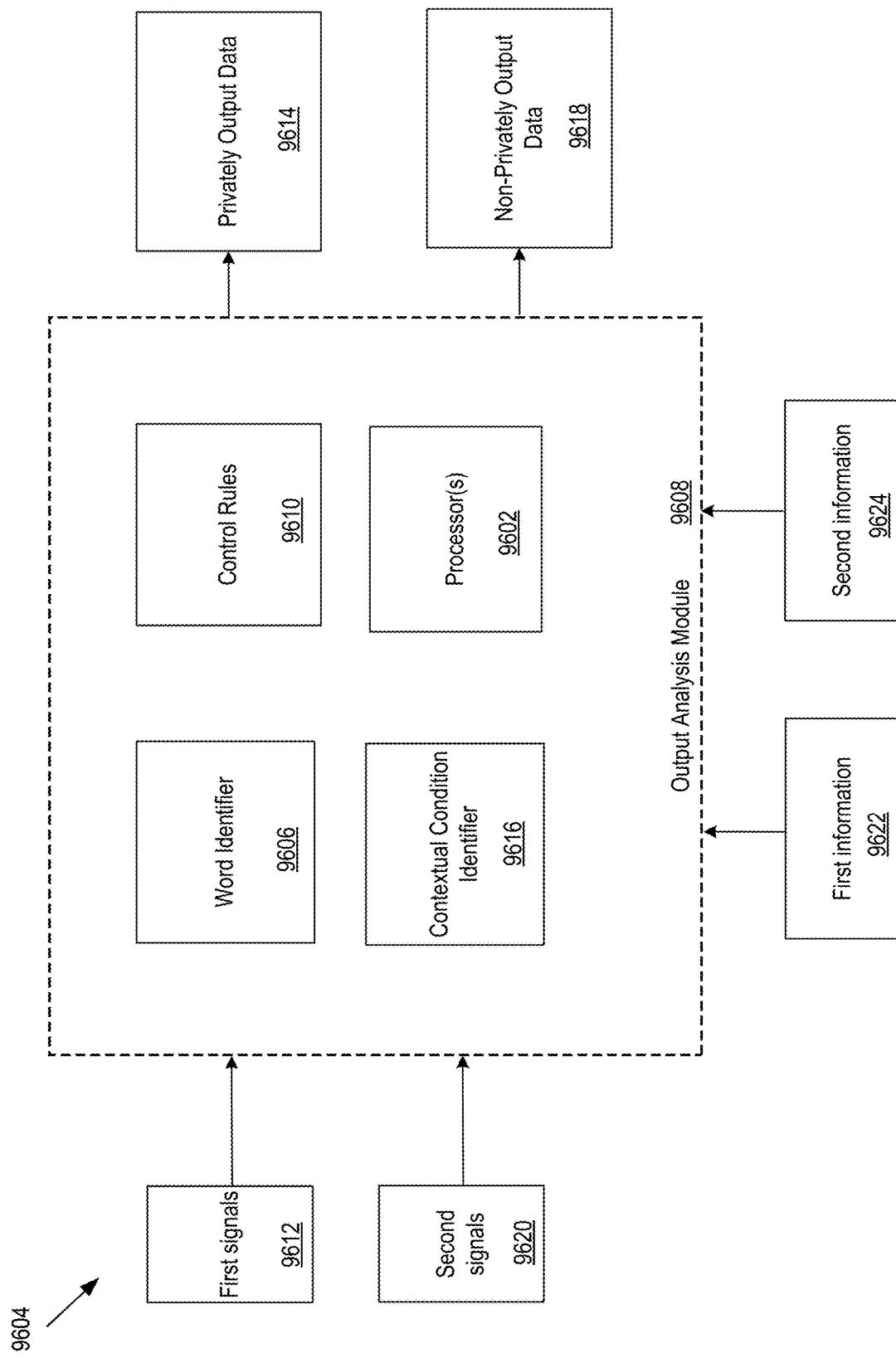
FIG. 96 is a block diagram illustrating an exemplary system for generating context-driven facial micromovement output, consistent with some embodiments of the present disclosure.

As illustrated in FIG. 96, an exemplary operating environment 9604 includes output analysis module 9608, or processor(s) 9602, which receive(s) first signals 9612 which include first coherent (or non-coherent light) reflections of first facial skin micromovements of a user. Word identifier 9606, output analysis module 9608, processor(s) 9602, or a combination thereof then determine(s) a first plurality of words associated with the first facial skin micromovements by analyzing the first coherent (or non-coherent) light reflections, based on the received first signals 9612.

Some disclosed embodiments involve receiving first information indicative of a first contextual condition in which the first facial skin micromovements occurred. A condition refers to a state, a circumstance, and/or situation. A context refers to a background, environment, and/or setting. Thus, a contextual condition refers to a state, circumstance, and/or situation, having to do with a background, environment, and/or setting. By way of non-limiting examples, where an individual is making small talk with another in a bar, the contextual condition may be defined as one or more of loud, public, casual, non-personal, and/or crowded. In a situation where the same individual is having a phone conversation with her financial analyst in a private office, the contextual condition may be defined as quiet, private, business-related, and/or personal. Information indicative of a contextual condition may include any information that identifies the contextual condition. For example, information indicative of a contextual condition may include location data, spatial-related data, image-related data, video-related data, audio-related data, user input-related data, and/or external input data. The first information may constitute one or more of the forgoing or may be a derivative of one or more of any of the forgoing. For example, image data may be receiving reflecting a private situation, and a processor may perform image analysis on the image data and determine from that analysis that the image data reflects a private situation. In this context, the first information may be the output of the analysis that determined the contextual condition as private. In another example, where the user provides an input that the context is private or where location data reflects a private context, analysis of such data may not be required to determine the contextual condition, and therefore the input itself may constitute the first information. Depending on design choice, a definition of a contextual condition may be based on a single factor or multiple factors. Information, such as the first information, may be indicative of a contextual condition in which the first facial skin micromovements occurred. Being indicative refers to some connection between the contextual condition and the facial skin micromovements. For example, when facial skin micromovements occur in a time frame near or overlapping with a time frame of information received on the contextual condition, that information may be said to be indicative of the contextual condition in which the first facial skin micromovements occurred.

Spatial data such as geographic locations or coordinates may be captured by a wearable device via a position sensing device included in the wearable device. As one example, such a position sensing device may include a global positioning system (GPS) sensor although other types of position sensors may also be used. The spatial data may indicate a contextual condition. For example, the geographic coordinates may indicate the user is located in an auditorium, conference room, private office, or any other specific environment. As another example, image or video data may be captured by a device such as camera, sensor, wearable device, smartphone). The image or video data (which could be subject to or the result of image analysis) may indicate a contextual condition. For example, the image or video data may indicate the user is moving in a particular fashion, making a particular gesture, turning in a particular direction, making a facial expression, or performing any other type of movement. Or the absence of other individuals in the image data may provide context. As yet another example, audio data may be captured by a device such as microphone, audio sensor, wearable device, smartphone. The audio data may indicate a contextual condition. For example, the audio data may indicate the user is uttering a predetermined word or plurality of words that indicate(s) specific information or a specific context. Information indicative of contextual conditions, or contextual conditions, may provide background or relevant information to create a framework for evaluating and further transmitting, in a manner desired by the user, a plurality of words associated with the particular facial skin micromovements. Contextual conditions may include, for example, private or semi-private interactions, public interactions, social interactions (e.g., parties, conventions, meetings, conferences, presentations, sporting events, entertainment events), and/or business interactions. For example, a processor may receive spatial data from a GPS sensor or a satellite associated with a wearable device or user. As another example, a processor may receive audio data from a device capturing sounds emitted by the user of a wearable device. As yet another example, a processor may receive image or video data from a device capturing the image or video data, wherein the data provides information indicating a movement made by the user (e.g., positioning of a user's hand over the user's mouth, or any other gesture), and such information may be indicative of either a user-desired private communication or presentation or a user-desired non-private communication or presentation.

Consistent with some disclosed embodiments, the first information indicative of the first contextual condition may include an indication that the first facial skin micromovements are associated with private thought. For example, the first information may include spatial data, image data, video data, audio data, user input data, external data, or other captured data associated with the user of a wearable device. Spatial data, for example, may be captured by a sensor associated with the wearable device and transmitted to a processor. The processor (or a contextual condition identifier) may analyze the spatial data to determine that the user is located in a private office, thereby indicating an association with private thought. Or, a detector may determine that the though is private if there is no audio associated with facial skin micromovements. A contextual condition identifier may include software, hardware, a combination of hardware and software, or special purpose hardware. As another example, image or video data may be captured by a camera associated with the user of a wearable device and transmitted to a processor. The processor may analyze the image or video data to determine that the user is making a gesture (e.g., covering the mouth or face, turning away, performing a predetermined gesture, closing one or more eyes) that indicates an association with private thought. As yet another example, audio data may be captured by a microphone associated with the user of a wearable device and transmitted to a processor. The processor may analyze the audio data to determine that the user is not making a sound (e.g., not saying a predetermined word or phrase) that indicates an association with private thought. A private thought may refer to any internal cognitive process or mental activity that occurs within an individual's mind, which may not be observable (audible) or otherwise accessible to others. Private thought may include, e.g., thoughts, beliefs, perceptions, emotions, memories, and/or imaginations that an individual experiences within their own consciousness. As non-limiting examples, private thoughts may include reflections on personal experiences, decision-making processes (e.g., weighing pros and cons, considering different options, evaluating potential outcomes), problem-solving processes (e.g., engaging in dialogue or exploration), planning (e.g., creating strategies, envisioning scenarios, organizing thoughts), daydreaming (e.g., indulging in imaginative or creative thoughts), emotional processing, memories, visualizations, and/or conceptualizing.

Consistent with some disclosed embodiments, the first information indicative of the first contextual condition may include an indication that the first facial skin micromovements are made in a private situation. For example, the first information may include spatial data, image data, video data, audio data, user input data, external data, or other captured data associated with the user of a wearable device. Spatial data, for example, may be captured by a sensor associated with the wearable device and transmitted to a processor (or to a contextual condition identifier). A private situation may refer to an event, circumstance, or context that is personal and not intended for public consumption or public observation. A private situation may involve aspects of an individual's thoughts or expressions that are typically kept confidential, restricted, or limited to a specific group of people. Non-limiting examples of private situations may include, e.g., an exchange of information relating to, e.g., personal relationships, health or well-being, financial matters, personal space or boundaries, confidential information, personal beliefs or values, secrets or confidences, emotional experiences, personal achievements or aspirations, and/or personal activities. The processor may analyze the spatial data to determine that the user is located in a private office or other private context, thereby indicating that the first facial skin micromovements are made in a private situation. As another example, image or video data may be captured by a camera associated with the user of a wearable device and transmitted to a processor. The processor may analyze the image or video data to determine that the user is making a gesture (e.g., covering the mouth or face, turning away or in a particular direction, performing a predetermined gesture, closing one or more eyes) that indicates that the first facial skin micromovements are made in a private situation. In yet another example, audio data may be captured by a microphone associated with the user of a wearable device and transmitted to a processor. The processor may analyze the audio data in search of predetermined words or phrases, non-vocal sounds, modulation of vocal noise (e.g., whispering) to determine the context of the first facial skin micromovements (by, for example, comparing the audio data with prior audio from other known private contexts) to determine that facial skin micromovements are made in a private situation. As a further example, external data may be collected (e.g., metadata) during the time that the facial micromovements are detected (e.g., during the same time that the first signals are received), wherein the metadata indicates an association with a private situation (e.g., the metadata indicates that the user is connected to a single individual via a phone call or a video conference, or another private and single connection).

Consistent with some disclosed embodiments, the first information indicative of the first contextual condition may include an indication that an individual generating the facial micromovements is looking down. For example, the first information may include spatial data, image data, video data, audio data, user input data, external data, or other captured data associated with the user of a wearable device. Spatial data, for example, may be captured by a sensor associated with the wearable device (e.g., a gravity-based sensor or gyroscope that detects movement of the wearable device) and transmitted to a processor (or to a contextual condition identifier). The processor may analyze the spatial data to determine that the user is looking down. As another example, image or video data may be captured by a camera associated with the user of a wearable device and transmitted to a processor. The image or video data may show the direction in which the user's head is pointed. The processor may analyze the image or video data to determine that the user is looking down. Looking down may refer to any one of the head of an individual pointing or moving downward (e.g., in a downward direction, or toward a lower point, level, or position), one or both eyes of an individual pointing or moving downward, or another downward movement of the face or a part thereof of an individual relative to the ground or relative to a wearable or non-wearable device. As a further example, external data may be collected (e.g., data input by an operator overseeing the user) during the time that the facial micromovements are detected (e.g., during the same time that the first signals are received), wherein the external data indicates that the individual is looking down (e.g., an operator viewing the individual notes that the individual is looking down and sends a signal to the processor). In some embodiments, the first information indicative of the first contextual condition may include an indication that an individual generating the facial micromovements is looking in a different direction (e.g., up, right, left, or in any direction that may indicate a user-desired type of communication or presentation). For example, the first information may contain an indication that an individual generating the facial micromovements is turning to look at another particular individual to whom the first plurality of words, which may be a private thought or question, may be addressed.

As illustrated in FIG. 96, an exemplary operating environment 9604 includes output analysis module 9608, or processor(s) 9602, which receive(s) first information 9622 (e.g., spatial data, image data, video data, audio data, or other data indicative of a contextual condition), the first information 9622 being provided either by a wearable device or another data-capturing device. In turn, output analysis module 9608, processor(s) 9602, contextual condition identifier 9616, or any combination thereof determine(s) a contextual condition (e.g., an association with private thought, an association with a private situation, that the user is looking down or in any particular direction) based on the received first information 9622. Thereafter, upon further analysis (as described below), output analysis module 9608, or processor(s) 9602, determine to output data associated with first signals 9612 as privately output data 9614.

Some disclosed embodiments involve receiving during a second time period, second signals representing second coherent light reflections associated with second facial skin micromovements. Receiving the second signals may occur in a manner similar to receiving the first signals, as described above with respect to the first coherent (or non-coherent) light reflections associated with the first facial skin micromovements. A second time period may refer to any time period other than the first time period. It will further be understood that the second time period need not be consecutive or sequential to the first (or any other) time period. As an example, a wearable device worn by a user may detect light reflections associated with facial skin micromovements as the user vocalizes or pre-vocalizes a plurality of words, and the corresponding detected light reflections may be translated into one or more signals containing data that represents the corresponding detected light reflections. In turn, the one or more signals may be received, e.g., at a processor, output analysis module, or word identifier.

As illustrated in FIG. 95, an exemplary device 9514 includes light source 9506 which emits a light onto a portion of a face 9502. Device 9514 further includes light detector 9512 which receives reflection data from the portion of a face 9502. The reflection data includes facial skin micromovement data comprising the second signals representing second coherent (or non-coherent) light reflections associated with second facial skin micromovements. In turn, device 9514 transmits the second signals, based on the second facial skin micromovement data, to processor(s) 9510 and/or output analysis module 9508.

Some disclosed embodiments involve analyzing the second coherent light reflections to determine a second plurality of words associated with the second facial skin micromovements. Analyzing the second coherent light reflections may be similar to analyzing the first coherent (or non-coherent) light reflections and the determined first plurality of words associated with the first facial skin micromovements. For example, a second plurality of words may have words in common with the first plurality of words and words which are different from the first plurality of words.

As illustrated in FIG. 96, an exemplary operating environment 9604 includes output analysis module 9608, or processor(s) 9602, which receive(s) second signals 9620 which include second coherent (or non-coherent) light reflections of second facial skin micromovements of a user. Output analysis module 9608, processor(s) 9602, word identifier 9606, or a combination thereof then determine(s) a second plurality of words associated with the second facial skin micromovements by analyzing the second coherent (or non-coherent) light reflections, based on the received second signals 9612.

Some disclosed embodiments involve receiving second information indicative of a second contextual condition (as described and exemplified elsewhere) in which the second facial skin micromovements occurred. This receiving step may be performed in a manner similar to the receiving of first information described above. For example, spatial data (e.g., geographic locations or coordinates) may be captured by a wearable device (e.g., a GPS or sensor within the device), wherein the spatial data indicates a second contextual condition (e.g., the geographic coordinates indicate the user is located in a public location). As another example, image or video data captured by a device (e.g., camera, sensor, wearable device, smartphone), wherein the image or video data indicates a second contextual condition (e.g., the image or video data may indicate the user is moving in a particular fashion, making a particular gesture, turning in a particular direction, making a facial expression, or performing any other type of movement that would be associated with an intended non-private communication). As yet another example, audio data may be captured by a device (e.g., microphone, audio sensor, wearable device, smartphone), wherein the audio data indicates a second contextual condition (e.g., the audio data may indicate the user is uttering a predetermined word or plurality of words that indicate(s) specific information or a specific context). As a further example, user input data or external data may be received at the processor(s), output analysis module, or contextual condition identifier, or any combination thereof, wherein the user input data or external data directly indicates a second contextual condition. In any of the given examples, such second information may be indicative of a user-desired non-private communication or presentation.

Consistent with some disclosed embodiments, the second information indicative of the second contextual condition may include an indication that the second facial skin micromovements are made during a phone call. For example, the second information may include external data including connection data or metadata associated with a wearable device or a device connected with the wearable device. Connection data may include, e.g., details related to a phone call being conducted between the user and at least one other individual. A phone call may refer to any form of communication made between two or more individuals using a telephone or a device (e.g., mobile device) equipped with telephone capabilities. A phone call may involve the transmission of audio signals over a telecommunications network, allowing people to have real-time conversations when they are not physically present with each other. For example, the second information may include audio signals or other connection data which represents that the user is making the second facial skin micromovements at the same time that the user is connected via a phone call with at least one other individual.

Consistent with some disclosed embodiments, the second information indicative of the second contextual condition may include an indication that the second facial skin micromovements are made during a video conference. For example, the second information may include external data including connection data or metadata associated with a wearable device or a device connected with the wearable device. Such connection data or metadata may include, e.g., details related to a video conference being conducted between the user and at least one other individual. A video conference may refer to any live and/or real-time communication session that allows individuals or groups of individuals in different or similar locations to see and hear each other using video and audio technology. Video conferences may include interactive meetings, discussions, or presentations without the need for physical presence of all members of the meeting. For example, the second information may include live or real-time communication data, or other connection data, which represents that the user is making the second facial skin micromovements at the same time that the user is presenting (e.g., sharing a screen) via a video conference with at least one other individual.

Consistent with some disclosed embodiments, the second information indicative of the second contextual condition may include an indication that the second facial skin micromovements are made during a social interaction. For example, the second information may include interaction data associated with a wearable device or a device connected with the wearable device. Interaction data may include, e.g., details which are sensed with relation to a real or virtual environment surrounding the user. Interaction data may be collected by, e.g., spatial data sensors, audio sensors, image capturing devices, video capturing devices, or other sensors. A social interaction may refer to any exchange or engagement between individuals or groups of individuals within a communal or societal context. A social interaction may involve the communication, behavior, and/or interplay that occurs when people interact with one another, sharing information, expressing emotions, and/or engaging in reciprocal actions, whether performed face to face or mediated through technology. For example, the second information may include image or video data that shows the user standing in front of a group of individuals, and thereby represents that the user is making the second facial skin micromovements during a social interaction. As another example, the second information may include spatial data that indicates the user is located in an auditorium, and thereby represents that the user is making the second facial skin micromovements during a social interaction. As yet another example, the second information may include data captured by a sensor that indicates the user is surrounded by a group of people, and thereby represents that the user is making the second facial skin micromovements are made during a social interaction.

As illustrated in FIG. 96, an exemplary operating environment 9604 includes output analysis module 9608, processor(s) 9602, or contextual condition identifier 9616, any or all of which receive(s) second information 9624 (e.g., spatial data, image data, video data, audio data, sensor data, connection data, interaction data, user input data, external data, or other data indicative of a second contextual condition), the second information 9624 being provided either by a wearable device or another data-capturing device. In turn, output analysis module 9608, processor(s) 9602, or contextual condition identifier 9616, or any combination thereof determine(s) a second contextual condition (e.g., that the user is speaking to a group of individuals, that the user is on a phone call, that the user is on a video conference, that the user is engaged in a social interaction, or any other contextual condition) based on the received second information 9624. Thereafter, upon further analysis (as described below), output analysis module 9608, or processor(s) 9602, determine to output data associated with first signals 9612 as non-privately output data 9618.

Some disclosed embodiments involve accessing a plurality of control rules correlating a plurality of actions with a plurality of contextual conditions, wherein a first control rule prescribes a form of private presentation based on the first contextual condition, and a second control rule prescribes a form of non-private presentation based on the second contextual condition. Accessing refers to obtaining, receiving, or retrieving data, information, or resources from a source or location. Control rules are instructions or guidelines that govern behavior and/or decision making of system or in a process. Control rules may serve as a framework for establishing standards, constraints, and boundaries within which data output decisions may be made such that a particular action may correspond to a predetermined contextual condition. Control rules correlate actions with contextual condition when, in response to an occurrence of a contextual condition, the control rule causes an action to result. A control rule "prescribes" when it defines, authorizes, recommends, enables, and/or dictates a course of action or behavior based on a condition or input. A form of private presentation may refer to a presentation, communication, or other transmittal of data that is conducted specifically for a limited or exclusive audience (e.g., a single entity, a particular group of entities, or a particular audience excluding at least one entity). A form of non-private presentation may refer to a presentation, communication, or other transmittal of data that is intended for an entire group of entities or the general public (e.g., a full audience without excluding an entity of that audience). Private presentation may provide an opportunity for targeted communication, focused discussions, and/or the exchange of information within a restricted and trusted environment. Private presentation may thus allow for more intimate and tailored interactions as compared to non-private presentation, which may have a broader reach.

For example, a plurality of control rules including a first control rule and a second control rule may be stored in a data structure, wherein the control rules are accessible by a processor such that the processor may determine a particular action based on a specific contextual condition that is indicated by information received by the processor (e.g., the first information or the second information). Each control rule may include a paired combination of a given contextual condition and an associated output type. For example, a control rule may include the following paired combinations: (private thought, private output to one or more specific individuals); (private situation, private output to one or more specific individuals); (user looking down, private output to one or more specific individuals); (user looking in a particular direction, private output to one or more specific individuals in the particular direction); (phone call, non-private output to everyone connected to the phone call); (video conference, non-private output to everyone connected to the video conference); (social interaction, non-private output to a group surrounding the user). Control rules may be predefined and stored, or, for example, in an AI context, the data structure may include a model that determines the control rule (or adjusts a control rule) based one or more factors relating to context. For example, the model may learn that when involved in conversations with particular individuals, a first action is appropriate, but when involved in conversations with other individuals, another action is appropriate.

The processor may, e.g., receive information indicative of a user addressing a specific individual in a private manner (e.g., spatial data, image data, video data, audio data, user data, external data, as described and exemplified elsewhere) and determine a specific contextual condition (e.g., a private thought, a private situation, or an otherwise user-desired privacy) based on the received information. In turn, the processor may then access the database to locate a control rule associated with the determined contextual condition and perform an action that is indicated by the control rule (e.g., presenting a private message, based on the detected facial skin micromovements of the user and based on the determined contextual condition, to a specific individual with whom the user intends to communicate). As another example, the processor may, e.g., receive information indicative of a user making a public announcement (e.g., spatial data, image data, video data, audio data, sensor data, connection data, interaction data, as described and exemplified elsewhere) and determine a specific contextual condition (e.g., a public speech or presentation, a phone call, a video conference, a social interaction, or an otherwise user-desired non-private communication) based on the received information. In turn, the processor may then access the database to locate a control rule associated with the determined contextual condition and perform an action that is indicated by the control rule (e.g., presenting a message, based on the detected facial skin micromovements of the user and based on the determined contextual condition, to a group of individuals or to an entire audience). As a further example, the processor may receive information indicative of other contextual conditions (e.g., social, work-related, entertainment-related, event-related) and determine a specific contextual condition based on the received information. In turn, the processor may then access the database to locate a control rule associated with the determined contextual condition and perform an action that is indicated by the control rule (e.g., presenting a message, based on the detected facial skin micromovements of the user and based on the determined contextual condition, to a specific individual in a private manner, or to a group of individuals or an entire audience in a non-private manner).

As illustrated in FIG. 96, an exemplary operating environment 9604 includes output analysis module 9608 and processor(s) 9602, any or all of which may access control rules 9610 based on the context identified by, e.g., contextual condition identifier 9616. Control rules 9610 comprise paired combinations of information including a given contextual condition and a corresponding data output for that given contextual condition. By accessing control rules 9610, output analysis module 9608 and/or processor(s) 9602 match the contextual condition identified via, e.g., contextual condition identifier 9616 to a specific control rule containing the identified contextual condition. The specific control rule then informs output analysis module 9608 and/or processor(s) 9602 of the corresponding data output based on the paired data within the control rule.

Some disclosed embodiments involve, upon receipt of the first information, implementing the first control rule to privately output the first plurality of words. Receipt of the first information the first information being obtained or acquired. For example, the information may be obtained or acquired in the form of signals received by a processor. Implementing the first control rule refers to putting the control rule into action or carrying out the control rule. For example, implementing the control rule may refer to implementing computer code or instructions to cause an action or result defined by the control rule to occur. In the context of the first control rule, when implemented, the first plurality of words are privately output. This refers to the fact that the first words are presented in a way that is less than fully public. For example, the words may be presented in a completely private way (such as in a text or via audio through an earbud) or may be presented in a semi private way, via an audio speaker with volume reduced). (A private presentation may include audio output, text output, displayed output, or any combination thereof to at least one specific individual or entity while excluding at least one other individual or entity. For example, a processor may implement a first control rule to privately output a first plurality of words as meeting notes, wherein the contextual condition associated with the first control rule is silent speech as determined based on detected facial skin micromovements. In order to determine silent speech as opposed to vocalized speech, a processor may utilize a predefined delay period. If vocalized speech is detected during such a predefined delay period, the processor may determine that the speech corresponding to the detected facial skin micromovements is not silent speech. Alternatively, if vocalized speech is not detected during such a predefined delay period, the processor may determine that the speech corresponding to the detected facial skin micromovements is silent speech. In turn, the processor may privately output the plurality of words associated with the silent speech (e.g., the processor causes the recordation of the silent speech as meeting notes, e.g., via a word processing application, wherein the meeting notes comprise text as deciphered based on the plurality of words determined from detected facial skin micromovements). In some embodiments, if a first word of a plurality of words is associated with silent speech based on the predefined delay period, subsequent words associated with the facial skin micromovements (e.g., those words which follow the first word without a significant delay) may automatically be privately output without requiring the predefined delay period.

Consistent with some disclosed embodiments, privately outputting the first plurality of words may include generating audio output to a personal sound generating device. Audio output may refer to any production or transmission of sound or audio signals from a device or system, including but not limited to mono (e.g., single-channel), stereo (e.g., two-channel), surround sound (e.g., multiple channels), or immersive sound (e.g., three-dimensional sound). Generating audio output may refer to any process of converting digital or analog audio data into audible sound waves that may be heard through a sound generating device. Such digital or analog audio data may be sourced from the individual using a wearable or non-wearable device as described herein. A sound generating device may refer to one or more speakers, headphones, earphones, soundbars, smartphones, televisions, or other audio playback devices that convert electrical/digital signals into audible sound waves, which may be part of a multimedia system, communication device, and/or entertainment equipment, and which may be associated with one or more intended or select recipients (e.g., to the exclusion of at least one other individual or entity). For example, a processor may privately output a plurality of words spoken by a user in a group of people to an earphone worn by one individual within that group of people. As another example, a processor may privately output a plurality of words spoken by a user communicatively connected with a group of people to a speaker accessible by one or more individuals outside of that group of people.

As another example, and consistent with some disclosed embodiments, privately outputting the first plurality of words may include generating textual output to a personal text generating device. Textual output may refer to a presentation or display of text-based information or data generated by a device, system, or software. Textual output may further include output associated with accessibility guidelines for individuals with visual or reading impairments (e.g., screen readers, alternative text, text-to-speech technologies). Generating textual output may involve converting electronic, digital, or coded information into a human-readable format using characters, letters, numbers, symbols, punctuation marks, formatting elements (e.g., font styles, colors), structured elements (e.g., headings, lists), and/or words. A personal text generating device may refer to one or more screens, monitors, programs, applications, mobile devices, digital signs, e-book readers, projection screens, printed papers (e.g., documents, reports, labels, or other printed material), user interfaces, or other media used for rendering a visual representation of textual output to an intended or select individual or group of individuals (e.g., to the exclusion of one or more other entities or individuals). For example, a processor may privately output a plurality of words spoken by a user in a group of people to a screen viewable by only one individual (or only select individuals) within that group of people. As another example, a processor may privately output a plurality of words spoken by a user communicatively connected with a group of people to a program for generating personal notes, wherein the program is accessible to the user and/or to individuals outside of that group of people.

FIG. 96 illustrates an exemplary operating environment 9604 comprising output analysis module 9608, or processor(s) 9602, any or all of which receive(s) first signals 9612 and first information 9622, as well as second signals 9620 and second information 9624. Based on the first information 9622, output analysis module 9608, processor(s) 9602, contextual condition identifier 9616, or any combination thereof determine(s) a contextual condition indicating a user-desired private output of information. Based on the determined contextual condition, output analysis module 9608, or processor(s) 9602, access control rules 9610 which inform the output analysis module 9608 and/or processor(s) 9602 of a data output type (e.g., private, non-private, text, audio, text and audio) associated (e.g., paired) with the determined contextual condition. The output analysis module 9608 and/or processor(s) 9602 then cause(s) an output of privately output data 9614. Based on the second information 9624, output analysis module 9608, or processor(s) 9602, contextual condition identifier 9616, or any combination thereof determine(s) a contextual condition indicating a user-desired non-private output of information. Based on the determined contextual condition, output analysis module 9608, or processor(s) 9602, access control rules 9610 which inform the output analysis module 9608 and/or or processor(s) 9602 of a data output type (e.g., private, non-private, audio, visual, audio and visual) associated with the determined contextual condition. The output analysis module 9608 and/or or processor(s) 9602 then cause(s) an output of non-privately output data 9618.

Some disclosed embodiments involve, upon receipt of the second information, implementing (as described and exemplified elsewhere) the second control rule to non-privately output the second plurality of words. Non-privately output may refer to outputting (as described and exemplified elsewhere) in a form of non-private presentation. A non-private presentation may be an audio output that may be heard by others (e.g., persons in addition to the subject). Non-private presentation may include audio output, text output, displayed output, or any combination thereof to an entire group of individuals or entities without excluding any individual or entity within that group. For example, a processor may non-privately output a plurality of words spoken by a user in a group of people to a screen viewable by the entire group of people. As another example, a processor may non-privately output a plurality of words spoken by a user communicatively connected with a group of people to one or more speakers or earphones that are associated with all individuals within that group of people.

Consistent with some disclosed embodiments, non-privately outputting the second plurality of words may include transmitting audio output to a mobile communication device. Transmitting audio output to a mobile communication device may refer to transmitting (as described and exemplified elsewhere) sound (e.g., the user's voice or a synthesized voice, computer-generated audio, or any other sound resembling a plurality of words) to a mobile communication device such that the mobile communication device may emit the sound via a speaker of the mobile communication device. In some embodiments, output other than audio output may be transmitted to a mobile communication device. For example, visual output (e.g., text, notifications, alerts, emails, text messages, or any other display resembling a plurality of words) may be transmitted to the mobile communication device, either alone or in combination with an audio output. A mobile communication device may refer to a portable electronic device that enables wireless communication and allows users to connect and interact with others remotely. A mobile communication device may include, e.g., a smartphone, tablet, wearable device, non-wearable device, smartwatch, portable gaming device, e-reader, e-book, two-way radio, and/or vehicle communication system. For example, a processor may non-privately output a plurality of words spoken by a user communicatively connected to a group of people to one or more mobile communication devices associated with each individual within that group of people.

Consistent with some disclosed embodiments, non-privately outputting the second plurality of words may include causing textual output to be presented on a shared display. A shared display may refer to one or more screens, monitors, mobile devices, digital signs, e-book readers, projection screens, printed papers (e.g., documents, reports, labels, or other printed material), user interfaces, whiteboards, video walls, large-format displays, or other media used for rendering a visual representation of textual output to multiple individuals or groups of individuals (e.g., simultaneously and without excluding any individual or entity within a group of individuals). For example, a processor may non-privately output a plurality of words spoken by a user communicatively connected to a group of people to one or more shared displays accessible to each individual within that group of people. As another example, a processor may non-privately output a plurality of words spoken by a user to a group of people by displaying the text associated with the spoken words on a large television screen, or projecting the text associated with the spoken words on a wall or screen so that the displayed text is visible to each individual within that group of people. As yet another example, a processor may non-privately output a plurality of words spoken by a user to a group of people by publishing the output on the internet (e.g., on a website, via social media, in a group email, in a blog post, or any other manner of posting content online publicly or to an intended group of individuals).

Figure 99:
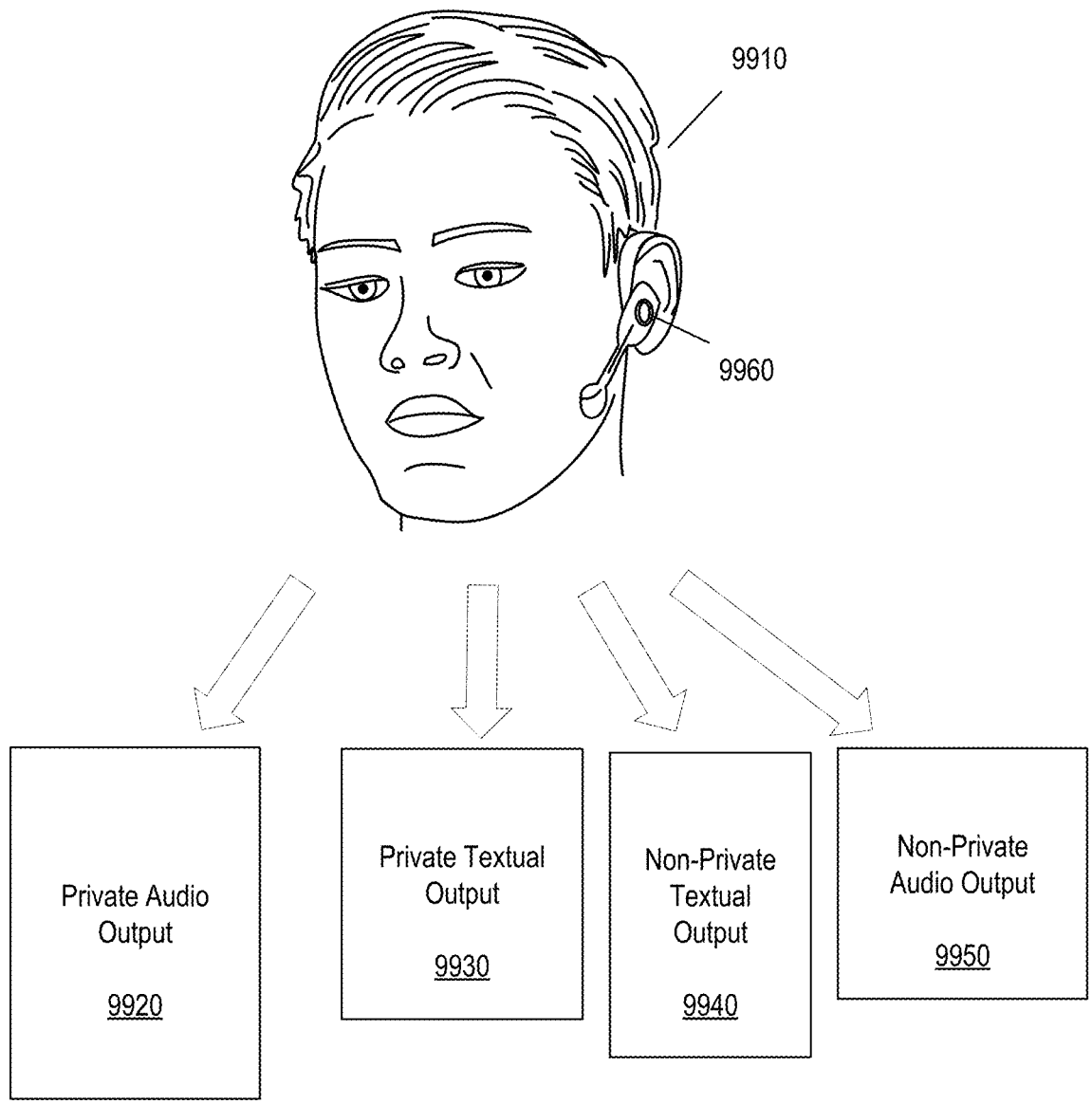
FIG. 99 is a schematic illustration of a user wearing an example head set and resulting context-driven outputs based on facial micromovements, consistent with some embodiments of the present disclosure.

FIG. 99 illustrates examples of private and non-private presentations of output data. FIG. 99 illustrates one example of a user 9910 wearing a device 9560 including a light source 410 for emitting light on a portion of the face of the user 9910 and a light detector 412 for receiving reflections of light from a portion of the face of the user 9910. Pre-vocalized or vocalized speech, as determined via facial skin micromovements detected by the device 9560, is output in various manners based on first or second information received which ultimately indicates a type of output. For example, first information received (as described and exemplified elsewhere) may indicate a contextual condition that is associated with a user-desired private audio output 9520 or private textual output 9530 of the determined pre-vocalized or vocalized speech, wherein the control rules determine the output type based on the contextual condition. As another example, second information received (as described and exemplified elsewhere) may indicate a contextual condition that is associated with a user-desired non-private textual output 9540 or non-private audio output 9550 of the determined pre-vocalized or vocalized speech, and the control rules determine the output type based on the contextual condition. Continued receipt of first and/or second information coupled with newly determined pre-vocalized or vocalized speech allows for switching between types of output as, e.g., the user 9910 continues to present or speak while wearing device 9560.

Consistent with some disclosed embodiments, at least one of the first information and the second information is indicative of an activity of an individual generating the facial micromovements and the operations further include implementing either the first control rule or the second control rule based on the activity. An activity of an individual may refer to any form of action, process, or undertaking that involves physical or mental exertion by the individual, such as engaging in a task, behavior, or event that requires effort, movement, or mental stimulation. Information indicative of an activity of an individual may include, e.g., information relating to speech, vocalization, movement, participation in an event, intended act, or thought. Activities indicated by at least one of the first or second information (as described and exemplified elsewhere) may include, e.g., physical activities (e.g., running, playing a sport, exercising, swimming, hiking, dancing, cycling, or playing a game), creative activities (e.g., drawing, writing, playing an instrument, singing, acting, crafting, photographing, taking videos, cooking, or landscaping), intellectual activities (e.g., reading, answering a question, strategizing, solving, learning, debating, discussing, studying, or exploring), social activities (e.g., meeting, attending a party or social event, participating in a club or organization, attending a social gathering such as a concert, festival, or exhibition, or engaging in a group activity), and leisure or relaxation activities (e.g., watching television, listening to music, walking, relaxing, meditating, travelling, or performing a hobby). The indication of an activity may further lead to the determination of a contextual condition, from which a corresponding control rule may be identified. In turn, the corresponding control rule may be implemented by, e.g., a processor, to cause the output of either privately output data or non-privately output data. By way of example, if the activity is walking on a street, private output may be directed to an earbud. If the activity is standing in secluded space, the private output may be directed to the speaker of a paired smartphone.

Consistent with some disclosed embodiments, at least one of the first information and the second information is indicative of a location of an individual generating the facial micromovements and the operations further include implementing either the first control rule or the second control rule based on the location. A location of an individual may refer to a specific place or position in physical space where the individual is situated or may be found. A location may involve geographical coordinates of the individual, such as latitude and longitude, or a location may relate to a particular landmark, address, position within a room or within a building, or another point of reference. The first or second information indicative of a location may be obtained via spatial data collected from a location-sensing device (e.g., GPS sensor or another satellite navigation system, mobile network location services, wi-fi positioning system, Bluetooth based location tracking, or inertial navigation systems such as those utilizing accelerometers, gyroscopes, or other motion sensors) which may be a part of the wearable device or associated with the wearable device. Different control rules may contain varying paired combinations of contextual conditions with respect to location of an individual generating the facial micromovements and a corresponding output. For example, some control rules may include the following paired combinations: (geographical coordinates associated with a public venue, non-private data output); (geographical coordinates not associated with a public venue, private data output); (location in private office, private data output); (location in conference room, non-private data output). By accessing the control rules, the processor may identify a control rule having a matching contextual condition, identify a corresponding output within that control rule, and implement the control rule by causing the identified corresponding output. For example, if location data indicates that an individual is in a private office, private output may be sent to the speaker of paired smartphone. Yet if the location data indicates that the individual is in a public space, the output may be directed as textual output to a display screen of the same smartphone.

Consistent with some disclosed embodiments, at least one of the first information and the second information is indicative of a type of engagement of an individual generating the facial micromovements with a computing device and the operations further include implementing either the first control rule or the second control rule based on the type of engagement. A type of engagement of an individual may refer to a participation by the individual related to a particular activity associated with the computing device (e.g., communicating with one or more individuals via the device, reading from the device, playing on the device, viewing a screen display of the device, or otherwise engaging with the computing device) as the activity pertains to a given situation, event, scenario, meeting, obligation, communication, or other interaction entered into by the individual and at least one other individual or entity. The first or second information indicative of a type of engagement may be obtained, e.g., via image or video data captured by an imaging device (e.g., a camera) which may be a part of the wearable device or a separate device associated with the wearable device. For example, connection data or metadata associated with a connection between the computing device and the device of at least one other individual may be obtained during the detection of facial skin micromovements. Such connection data or metadata may indicate that the type of engagement is a communication with one or more individuals. It will be understood that a lack of such connection data or metadata may be indicative of other types of engagements, such as the individual reading from, playing on, or viewing a screen display of the device. As another example, connection data or metadata associated with an application or website being accessed by the computing device, in combination with an absence of connection data or metadata associated with a connection between the computing device and another individual's device, obtained during the detected facial skin micromovements, may be indicative of another engagement type (e.g., connection data associated with a newsletter may indicate the engagement type is reading from the device, connection data associated with a gaming application may indicate the engagement type is playing a game using the device, or connection data associated with a streaming application may indicate the engagement type is viewing a screen display of the device). As yet another example, the first or second information indicative of a type of engagement may be obtained via user input or external input (e.g., a selection made by a user or operator and communicated to the processor). For example, the user (or an external operator) may input data directly indicating the type of engagement. Such input data may indicate any type of engagement, based on the selected input. Different control rules may contain varying paired combinations of contextual conditions with respect to each type of engagement of an individual generating the facial micromovements and a corresponding output. For example, some control rules may include the following paired combinations: (communicating with one individual, private data output to that individual); (communicating with more than one individual, non-private data output to all individuals); (reading from the device, private data output); (playing alone using the device, private data output); (playing with others using the device, non-private data output); (viewing a screen display of the device; private data output). By accessing the control rules, the processor may identify a control rule having a matching contextual condition, identify a corresponding output within that control rule, and implement the control rule by causing the identified corresponding output.

As illustrated in FIG. 96, an exemplary operating environment includes output analysis module 9608, contextual condition identifier 9616, and processor(s) 9602, any or all of which receive first information 9622 and second information 9624. As such, at least one of the first information 9622 or second information 9624 may include data that is indicative of specific contextual condition (e.g., activity, location, type of engagement with computing device), as described and exemplified elsewhere. In turn, output analysis module 9608, contextual condition identifier 9616, and/or processor(s) 9602 analyze the received first information 9622 and/or second information 9624 to determine a contextual condition, which may be the activity, location, type of engagement, or a contextual condition that is based on the activity, location, type of engagement, or other data captured and included within the first information 9622 and/or second information 9624.

Some disclosed embodiments involve a method for generating context-driven facial micromovement output, the method involving the steps/activities described above. FIG.

97 illustrates an exemplary method 9700 for generating context-driven facial micromovement output which includes step 9710 of receiving during a first time period, first signals representing first coherent light reflections associated with first facial skin micromovements. At step 9720, the first coherent light reflections are analyzed to determine a first plurality of words associated with the first facial skin micromovements. At step 9730, first information indicative of a first contextual condition in which the first facial skin micromovements occurred is received. At step 9740, during a second time period, second signals representing second coherent light reflections associated with second facial skin micromovements are received. At step 9750, the second coherent light reflections are analyzed to determine a second plurality of words associated with the second facial skin micromovements. At step 9760, second information indicative of a second contextual condition in which the second facial skin micromovements occurred is received. At step 9770, a plurality of control rules correlating a plurality of actions with a plurality of contextual conditions are accessed, wherein a first control rule prescribes a form of private presentation based on the first contextual condition, and wherein a second control rule prescribes a form of non-private presentation based on the second contextual condition. At step 9780, upon receipt of the first information, the first control rule is implemented to privately output the first plurality of words. At step 9790, upon receipt of the second information, the second control rule is implemented to non-privately output the second plurality of words.

Some disclosed embodiments involve a system for generating context-driven facial micromovement output, the system comprising at least one processor configured to perform steps consistent with those described above. FIG. 95 illustrates an exemplary operating environment 9500 including a system 9504, the system 9504 including a device 9514, an output analysis module 9508, and at least one processor 9510. An exemplary device 9514 includes a light source 9506 which is controlled in a manner enabling illumination of a portion of a face 9502 of a user associated with the device 9514. An exemplary device 9514 further includes a light detector 9512 (or any other type of sensor) configured to receive input in the form of reflections of light from the portion of the face 9502 of the user associated with the device 9514. Based on the input received by the light detector 9512, one or more output signals are emitted from the light detector 9512 or another component of the device 9514. The one or more output signals correspond to the reflections of light from the portion of the face 9502 of the user associated with the device 9514. The output analysis module 9508 then receives the one or more output signals and performs, in conjunction with other collected data, output analysis on the one or more output signals to determine a type of output data 9516. The output analysis may be performed via the at least one processor 9510. The output data 9516 is generated via the at least one processor 9510 or via the output analysis module 9508.

FIG. 96 illustrates an output analysis module 9608 of an exemplary system 9604 including a word identifier 9606, a contextual condition identifier 9616, control rules 9610, and/or one or more processors 9602. Although illustrated in separate boxes for ease of illustration, one or more of the identifiers and/or control rules may be combined. Output analysis module 9608 receives, during a first time period, first signals 9612 (e.g., from a light detector, based on reflections of light from a portion of a face of a user) representing first coherent light reflections associated with first facial skin micromovements. In response to and based on the first signals 9612 received by output analysis module 9608, word identifier 9606 processes the received first signals 9612 and analyzes the first coherent light reflections to determine a first plurality of words associated with the first facial skin micromovements. Output analysis module 9608 then receives first information 9622 indicative of a first contextual condition in which the first facial skin micromovements occurred. Based on the received first information 9622, contextual condition identifier 9616 determines the first contextual condition indicated by the first information 9622. Output analysis module 9608 also receives, during a second time period, second signals 9620 (e.g., from the light detector, based on additional reflections of light from a portion of a face of the user) representing second coherent light reflections associated with second facial skin micromovements. In response to and based on the second signals 9620 received by output analysis module 9608, word identifier 9606 processes the received second signals 9620 and analyzes the second coherent light reflections to determine a second plurality of words associated with the second facial skin micromovements. Output analysis module 9608 then receives second information 9624 indicative of a second contextual condition in which the second facial skin micromovements occurred. Based on the received second information 9624, contextual condition identifier 9616 determines the second contextual condition indicated by the second information 9624.

With continued reference to FIG. 96, based on the processing of the first and second signals by word identifier 9606 and contextual condition identifier 9616, output analysis module 9608 accesses a plurality of control rules 9610 correlating a plurality of actions with a plurality of contextual conditions, wherein a first control rule prescribes a form of private presentation based on the first contextual condition, and a second control rule prescribes a form of non-private presentation based on the second contextual condition. In turn, upon receipt of the first information 9622, output analysis module 9608 implements the first control rule to privately output the first plurality of words as privately output data 9614, and upon receipt of the second information 9624, output analysis module 9608 implements the second control rule to non-privately output the second plurality of words as non-privately output data 9618. The output data 9614 and 9618 is generated via the at least one processor 9602 or via the output analysis module 9608.

Consistent with some disclosed embodiments, the operations further include determining a trigger for switching between a private output mode and a non-private output mode. A trigger may refer to an event, condition, or stimulus that initiates or sets off a particular action, response, or sequence of events related to switching between a private output mode and a non-private output mode. A trigger may include, e.g., an external factor in an individual's surroundings or environment, a technological factor, and/or a specific event attended, action performed, or condition exhibited by an individual. For example, a trigger may be provided by a user via a particular word or phrase vocalized or pre-vocalized by the individual and captured by an audio-capturing device (e.g., microphone) associated with the wearable device. A trigger may also be provided via a particular gesture made by the individual and captured by an imaging device (e.g., camera) associated with the wearable device. A trigger may further be provided via a particular selection (e.g., user input, external input) made by the individual (or an external operator) and transmitted to the processor. Upon detection of the particular trigger, a private output mode may be initiated and may persist, e.g., based on a predetermined amount of time or based on another detection of the same or a different trigger. Determining a trigger may refer to receiving a user selection of a trigger. Determining a trigger may also refer to receiving information indicative of a movement or action performed by a user, wherein the user, e.g., desires that movement or action to be the trigger. Determining a trigger may also include detecting a change in surroundings, environment, technological factor, external factor, or event, any or all of which may form a part of the information for determining a contextual condition. A private output mode may refer to a mode of operation wherein all output data is privately output data (as described and exemplified elsewhere). A non-private output mode may refer to a mode of operation wherein all output data is non-privately output data (as described and exemplified elsewhere).

Consistent with some disclosed embodiments, the operations further include receiving third information indicative of a change in contextual conditions and wherein the trigger is determined (as described and exemplified elsewhere) from the third information. Third information may refer to information that is different from either the first or the second information and which indicates a contextual condition (as described and exemplified elsewhere) that is different from either the first or the second contextual condition. It will be understood that the third information may include data types similar to those which the first or second information may include; however, the data itself may be different from that which may be included in the first or second information.

Consistent with some disclosed embodiments, the operations further include determining the trigger based on the first plurality of words or the second plurality of words. Determining the trigger based on the first or second plurality of words may refer to identifying or detecting one or more words within the first or second plurality of words which indicate a user-desired trigger. A user-desired trigger may refer to one or more vocalized or pre-vocalized words, movements, gestures, or actions performed by the user, which the user wants or requests to be the trigger. For example, the first or second plurality of words may comprise a phrase directly indicating a user-desired trigger (e.g., "switch to private output mode" or "switch to non-private output mode"). As another example, the first or second plurality of words may comprise a predefined term or phrase which the processor associates with a trigger and responds accordingly upon identification of the predefined term or phrase. As yet another example, the first plurality of words may be vocalized and therefore be output non-privately, while the second plurality of words may only be pre-vocalized and therefore be output privately (e.g., the absence of vocalization of an identified plurality of words acts as a trigger).

Consistent with some disclosed embodiments, the operations further include receiving an output mode selection from an associated user interface and determining the trigger based on the output mode selection. An output mode may refer to a private presentation, a non-private presentation, audio presentation, visual presentation, audio-visual presentation, as well as muted or unmuted presentation. Receiving an output mode selection from an associated user interface may refer to presenting to a user, via a user interface, a list of output mode options and enabling the user to choose at least one of the output mode options from the list (e.g., via checkbox, radio button, selecting from a dropdown menu, slider(s), button(s), or any other method for indicating a user's choice). Receiving an output mode selection may also include receiving an unstructured or unrestricted text field input from a user indicating one or more output mode selections associated with one or more desired output modes. Receiving an output mode selection may also include receiving a non-text input from a user (e.g., receiving a user selected image, detecting a gesture of a user, detecting an eye movement of a user, or detecting any other movement by or of a user which may indicate a user-desired output mode). Determining the trigger based on the output mode selection may include identifying the trigger directly based on the selection or providing follow up prompts for additional user selection (e.g., via one or more additional options) in order to determine the trigger desired. Determining the trigger based on the output mode selection may also include identifying a series of trigger options based on the output mode selection, and further suggesting or selecting a trigger from the trigger options, or prompting a user or operator to select a desired trigger from the trigger options. For example, an output mode selection may indicate a private output mode or a non-private output mode. In response to the output mode selection, a trigger requiring the user to look down may be determined. Alternatively, in response to the same output mode selection, a menu of trigger options may be displayed for further user selection (e.g., "please select one or more of the following triggers: look down, close eye(s), cover mouth"). As another example, in response to the output mode selection, a list of trigger options may be presented to a user for selection, wherein the trigger options are ranked from most recommended to least recommended. Based on the further selection, the trigger may be determined.

Figure 98:
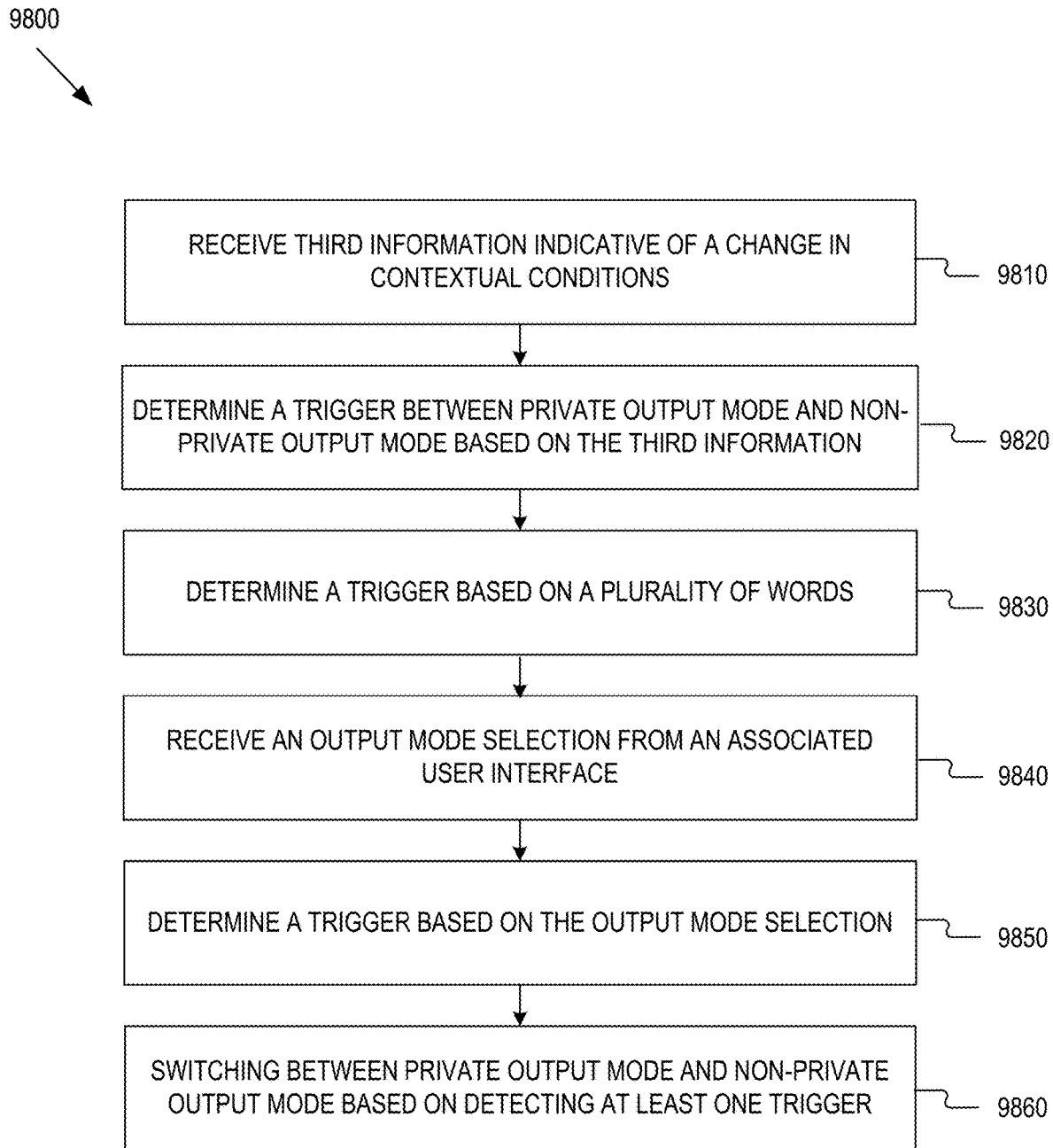
FIG. 98 is a flow chart illustrating another exemplary method for generating context-driven facial micromovement output, consistent with some embodiments of the present disclosure.

FIG. 98 illustrates an exemplary method 9800 for generating context-driven facial micromovement output which includes a step 9810 of receiving third information indicative of a change in contextual conditions. At step 9820, a trigger between private output mode and non-private output mode is determined based on the third information. At step 9830, a trigger based on a plurality of words (e.g., based on the first or second plurality of words) is determined. At step 9840, an output mode selection is received from an associated user interface. At step 9850, a trigger is determined based on the output mode selection. At step 9860, private output mode is switched to non-private output mode, or vice versa, based on detecting at least one of the determined triggers.

Figure 97:
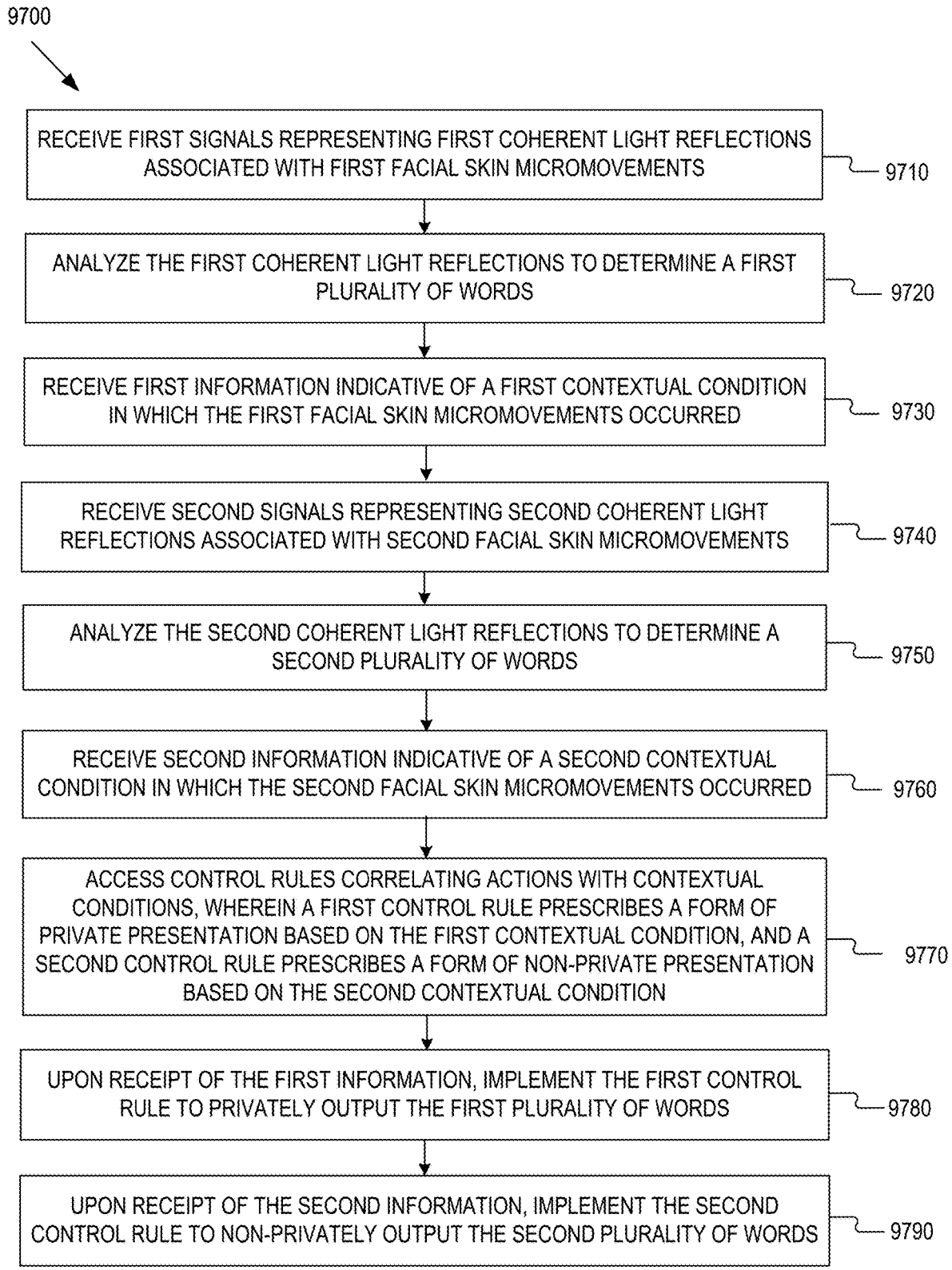
FIG. 97 is a flow chart illustrating an exemplary method for generating context-driven facial micromovement output, consistent with some embodiments of the present disclosure.

The embodiments discussed above for generating context-driven facial micromovement output may be implemented through non-transitory computer-readable media such as software (e.g., as operations executed through code), as methods (e.g., method 9700 shown in FIG. 97, method 9800 shown in FIG. 98), or as a system (e.g., speech detection system 100 shown in FIGS. 1-3). When the embodiments are implemented as a system, the operations may be executed by at least one processor (e.g., processing device 400 or processing device 460, shown in FIG. 4).

Some disclosed embodiments may involve ascertaining reactions to content based on facial skin micromovements. When it comes to consuming content, micro facial expression may reveal users' true reactions towards the consumed content. The subtle and sometimes involuntarily skin micromovements bypass the filters of conscious control and can provide valuable insights into what users really think and feel. Understanding the users' genuine reactions enables a content provider to tailor and personalize content to the users' preferences, leading to higher engagement and satisfaction.

Moreover, an operating system can utilize various forms of user reactions to notices as input. For instance, an operating system may employ interactive elements (e.g., buttons or quick-response options) that allow the operating system to take specific actions automatically based on the user reactions. Head mountable computing systems without a dedicated input device—such as a touch screen, mouse, or keyboard—may utilize facial skin micromovements to determine reactions to system notices or displayed content. By understanding and utilizing these reactions, the operating system can better align with user preferences, provide relevant information, and create a more engaging and user-friendly environment.

Some disclosed embodiments involve operations for extracting reactions to content based on facial skin micromovements. The term "content" may refer to any type of data in a format perceivable to humans. For example, content may include songs, video clips, news articles, social media posts, advertisements, system notifications, and any other combination of data formatted as text, image, audio, video, or virtual objects. In some cases, content may include media formatted according to a distinct specification for presenting the content to an individual via an interface of an electronic device. The term "reactions to content" may include various responses and/or expressions of individuals when they interact with or consume content. For example, the reactions may include a wide range of emotions, opinions, and behaviors displayed by an individual in response to consumed content. In this context, the phrase "extracting reactions to content" refers to the process of identifying, understanding the value, and/or the implications of the individual's reactions to content. In one example, detecting a change in a facial expression may indicate whether the individual is interested or bored by the content. Thereafter, the system may personalize future content to be presented to the individual. In another example, detecting an individual's reaction to a certain advertisement may imply the level of interest of an individual to the advertised product. Thereafter, the system may present to the individual a coupon for the advertised product. In another example, detecting an individual's reaction to a notification of an incoming call, may indicate whether the individual is interested in answering the call. Thereafter, the system may automatically transfer the call to voicemail, for example, when the detected reaction indicates that the individual is not interested in answering the call. Data representing the extracted reactions to content may be stored and/or used to initiate an action. The reactions to the content may be determined by detecting and analyzing facial skin micromovements. The term "facial skin micromovements" is described and exemplified elsewhere in this disclosure.

Figure 100:
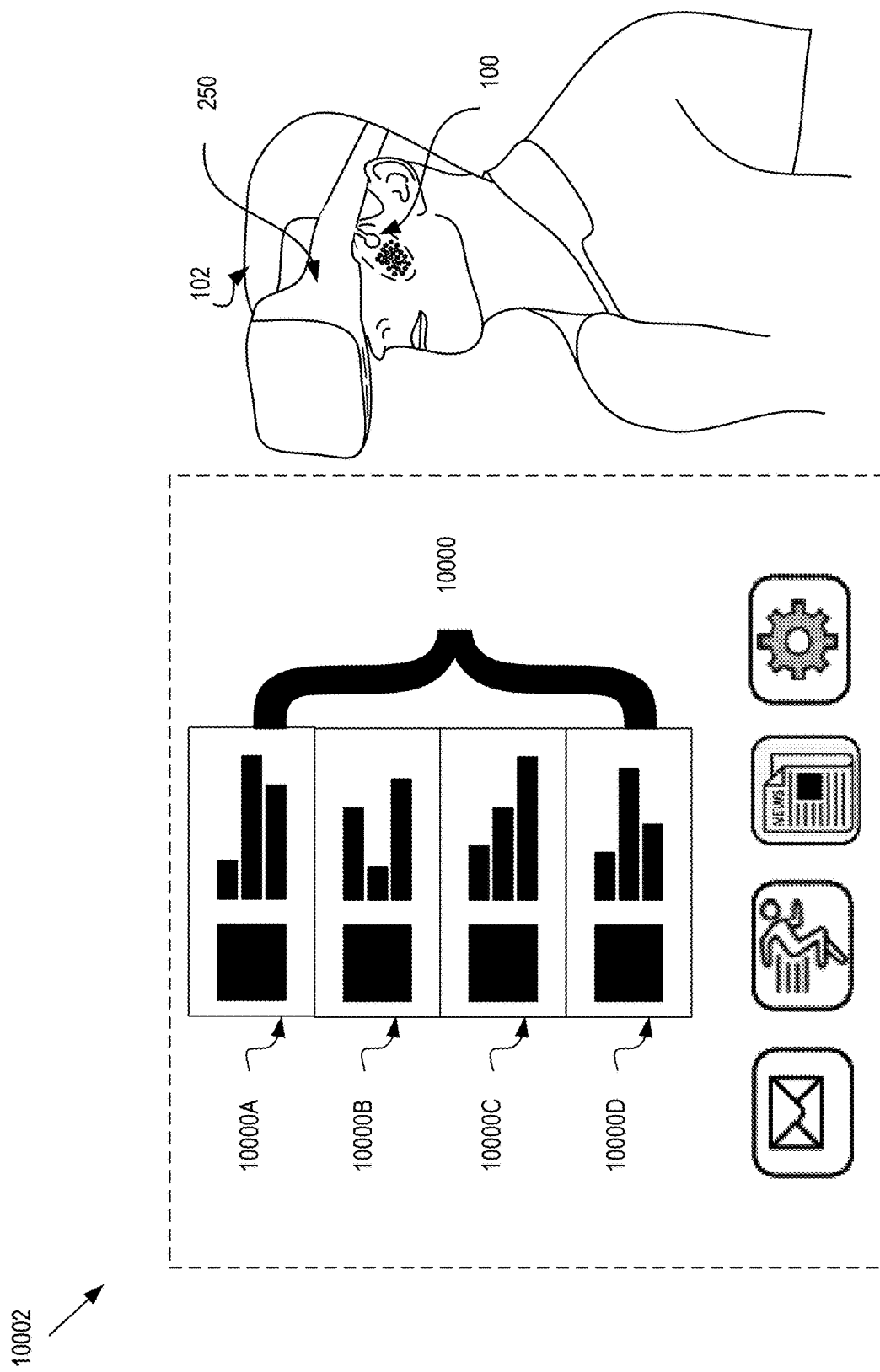
FIG. 100 is a schematic illustration of an example system for extracting reactions to content based on facial skin micromovements, consistent with some embodiments of the present disclosure.

By way of example, FIG. 100 illustrates an implementation of the disclosed embodiment, in which a processing device (e.g., processing device 400 or processing device 460, shown in FIG. 4) associated with speech detection system 100 may determine whether individual 102 is interested or not in the content 10000 being consumed via extended reality appliance 250. The determination as to whether individual 102 is interested or not in the content 10000 presented on virtual display 10002 may be accomplished by detecting and analyzing the individual facial skin micromovements. Thereafter and based on the determination, the processing device may initiate an action.

Some disclosed embodiments involve a time period when an individual is consuming content. The term "time period" may refer to any length of time during which an activity occurs or during which a condition remains. For example, a time period may refer to a number of seconds (or portions thereof), minutes, hours, or any other length of time during which the individual is engaged in a certain activity or activities. In the context of this disclosure, the activity associated with the time period may be consuming content. The term "consuming content" refers to an act of engaging with various forms of data perceivable to humans. For example, consuming content may include viewing a video presented on a virtual display by an extended reality appliance, reading text displayed on a display of a smartphone or in a printed newspaper, listening to music played by an audio device, and/or any other type of user interaction with an electronic device or a medium for perceiving information. In one example, the time period may include a duration in which the individual is listening to a music playlist from his car radio. In another example, the time period may include a duration in which the individual is reviewing a feed of social media on a smartphone. In another example, the time period may include a duration in which the individual is skimming through a printed product catalog. During a time period, some embodiments may involve determining the facial skin micromovements of the individual based on reflections of coherent light from a facial region of the individual. The term "determining" may refer to ascertaining, establishing, or arriving at an outcome by some process, for example, a conclusive outcome as a result of a reasoned, learned, calculated, or logical process. An individual may refer to a human user capable at least of consuming content. Reflections of coherent light involve electromagnetic waves bouncing off a surface and exhibiting a high degree of spatial and temporal coherence, as described elsewhere in this disclosure. Reflections of light from a facial region of an individual may refer to electromagnetic waves that bounced off a facial region, as described elsewhere in this disclosure. The reflected light may be sensed by a light detector, which may provide electronic signals indicative of the reflections of light to at least one processor. Thereafter, the at least one processor may determine the facial skin micromovements of the individual from the received reflections, as described elsewhere in this disclosure.

By way of example, as depicted in FIG. 5, light source 410 of speech detection system 100, which may be part of or incorporated with extended reality appliance 250 (FIG. 100), may be configured to shine light onto a facial region of individual 102 (e.g., while individual 102 is consuming content). Thereafter, light detector 412 may sense reflections 300 bouncing off the facial region of individual 102 and provide electronic signals representing the reflections of light to a processing device associated with extended reality appliance 250. Using the received electronic signals, the processing device may determine facial skin micromovements 522.

In some embodiments, the individual may consume multiple individual pieces of content during a particular time period. For example, when a user listens to a playlist, each song in the playlist may be considered as an individual piece, when a user reads posts in social media each post may be considered as an individual piece, and when a user watches short video clips, each video clip may be considered as an individual piece. Accordingly, some disclosed embodiments may involve determining first facial skin micromovements based on first reflections associated with a first piece of consumed content and determine second facial skin micromovements based on second reflections associated with a second piece of consumed content.

By way of example, as depicted in FIG. 100, content 10000 in FIG. 100 may include a first piece of content 10000A, a second piece of content 10000B, a third piece of content 10000C, and a fourth piece of content 10000D. And, as depicted in FIG. 101, the processing device may use first reflections 10100A (e.g., that may be associated with first piece of content 10000A) to determine first facial skin micromovements 10102A and use second reflections 10100B (e.g., that may be associated with second piece of content 10000B) to determine second facial skin micromovements 10102B.

Some disclosed embodiments involve determining at least one specific micro-expression from the facial skin micromovements. The term "expression" or "facial expression" broadly refers to skin deformations that occur as a result of underlying muscular activity. A "micro-expression" or a "micro-facial-expression" means small-scale skin deformations that fall within the range of micrometers to millimeters and that may last for a time duration of fractions of a second to several seconds. For example, in some embodiments, the at least one specific micro-expression is imperceptible to a human eye. The term "imperceptible to a human eye" means that the skin deformations associated with the micro-expression are so subtle that they cannot be detected or observed by the human eye without the aid of specialized instruments (e.g., optical sensors, EMG sensors, force sensors), or advanced image processing techniques. In some cases, micro-expressions may include involuntary facial expressions that occur as quick flashes of emotion before an individual has a chance to consciously control their facial muscles. This is why micro-expressions are often associated with genuine emotions, as they happen instinctively before conscious thought can regulate facial expressions. For example, when an individual thinks of something funny, their facial muscles may undergo subtle contractions and relaxations, resulting in micro skin deformations in specific areas of the face, such as around the eyes, mouth, or forehead. In some cases, the micro skin deformations can later manifest to a full visible smile. In other cases, however, the micro skin deformations may fade off.

Figure 101:
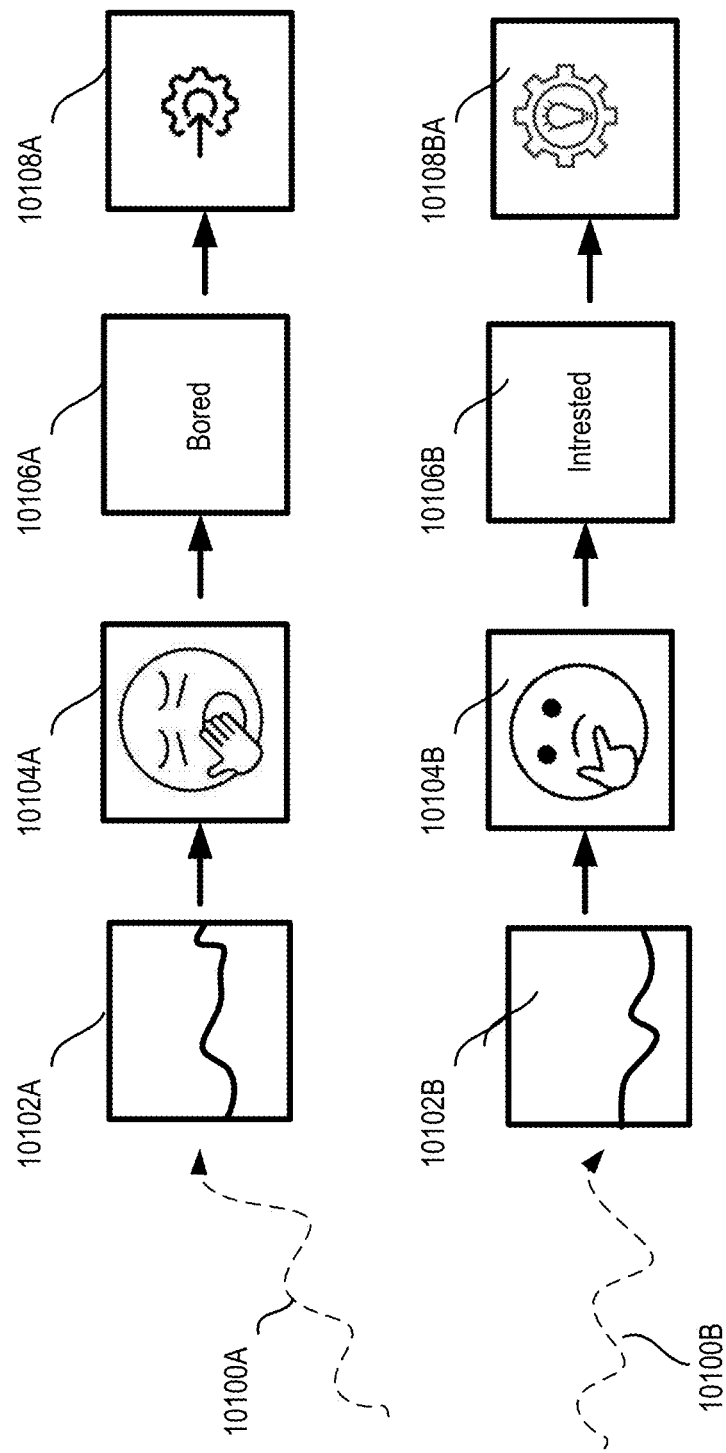
FIG. 101 includes block diagrams of two example use cases for initiating actions based on reactions to content, consistent with some embodiments of the present disclosure.

By way of example, as depicted in FIG. 101, a processing device may determine a first micro-expression 10104A from first facial skin micromovements 10102A and determine a second micro-expression 10104B from second facial skin micromovements 10102B.

Consistent with some disclosed embodiments, the facial skin micromovements used for determining the at least one specific micro-expression correspond to recruitment of at least one muscle from a group of muscles including: a zygomaticus muscle, a genioglossus muscle, an orbicularis oris muscle, a risorius muscle, or a levator labii superioris alaeque nasi muscle. In this context, stating that at least one specific micro-expression corresponds to recruitment of a certain muscle means that the at least one specific micro-expression is associated with or may be caused by activation of that certain muscle. When that muscle is recruited, it causes facial skin micromovements that collectively may be classified as or cause the specific micro-expression. In many cases, a combination of muscles may work together in a coordinated manner to create various facial expressions. For example, the zygomaticus is primarily responsible for the upward movement of the corners of the mouth; the orbicularis responsible for causing the outer corners of the eyes to lift and form "crow's feet" or wrinkles; the levator labii superioris helps elevate the upper lip and contributes to the overall appearance of the smile; and the risorius helps in widening the smile and retracting the lips horizontally. In one example, the processing device may determine the at least one specific micro-expression using data about the recruitment of at least one muscle (or at least two) from a group of muscles including: a zygomaticus muscle, a genioglossus muscle, an orbicularis oris muscle, a risorius muscle, or a levator labii superioris alaeque nasi muscle.

Some disclosed embodiments involve accessing at least one data structure containing correlations between a plurality of micro-expressions and a plurality of non-verbalized perceptions. Accessing at least one data structure, as described and exemplified elsewhere in this disclosure, may involve establishing a communications channel with a data structure, gaining an access privilege to read from a data structure, querying a data structure, and/or receiving information from a data structure (e.g., in response to a query). The at least one data structure may be configured to store correlations between a plurality of micro-expressions and a plurality of non-verbalized perceptions. For example, the at least one data structure may be accessed using a communications network, as described elsewhere in this disclosure. The term "correlations" refers to a relationship between two or more data items. The correlation may be determined using one or more mathematical and/or statistical functions (e.g., cross-correlations, autocorrelations, and/or convolutions) that define a statistical distance between two or more data items. The term "non-verbalized perceptions" refers to the thoughts, feelings, or impressions that an individual may experience and that were not communicated through verbal means, such as spoken or written language. In some disclosed embodiments, the non-verbalized perceptions include an emotional state of the individual. Examples of emotional states associated with non-verbalized perceptions may include discomfort, interest, engagement, anxiety, frustration, happiness, and sadness. In other cases, the non-verbalized perceptions may include an indication of the trustfulness of the individual with respect to certain content (e.g., the content may include a question). In these cases, the indication of the trustfulness can be used to determine if an individual is lying. The fact that that the at least one data structure contains correlations between a plurality of micro-expressions and a plurality of non-verbalized perceptions means that the at least one data structure may include a searchable index of micro-expressions, and may associate one or more such micro-expressions with one or more non-verbalized perceptions. In other embodiments, an index may not exist. For example, an AI data structure encompassed within this disclosure may not employ an index but rather may use an AI model to determine correlations. At least one processor may query such a data structure with one or more micro-expressions to determine one or more non-verbalized perception associated therewith based on a similarity measure. Examples of some similarity measures for correlating facial micromovements with words may include a cosine similarity, Euclidian distance, chi-square distance, and/or any other type of similarity measure.

By way of a non-limiting example, in FIG. 4, at least one processor (e.g., processing devices 400 and/or 460) may access data structure 422 and/or data structure 464 (e.g., via communications network 126 in FIG. 1) configured to store correlations between a plurality of micro-expressions and a plurality of non-verbalized perceptions.

Some disclosed embodiments involve determining a specific non-verbalized perception of the content consumed by the individual based on the at least one specific micro-expression and the correlations in the data structure. "Determining" or "determine," in this context, refers to ascertaining non-verbalized perceptions. Thus, the term "determining a specific non-verbalized perception" may include identifying a match in the at least one data structure between the determined specific micro-expression (as determined from the facial micromovements) and the stored plurality of non-verbalized perceptions. For example, a specific non-verbalized perception may be determined when a cross-correlation between data associated with the detected micro-expression and data associated with stored non-verbalized perceptions is above a predetermined threshold. When the determination of the specific non-verbalized perception is implemented using AI, data matching (i.e., the process of finding the matching pieces of information in large sets of data) may be used to search for making said determination. Such data matching using AI may leverage the learning capabilities of machine learning algorithms such as datasets similarity and linear combinators to match data on a deeper level beyond a simple matching of two items in a table. This type of data matching may be used to learn real relationships between the data a user considers a match and the data user does not consider a match, which improves processing efficiency by reducing any tweaking and adjustments that may be required over time. Such AI data matching engines may be trained using training data, such as information regarding various micro-expressions with associated non-verbalized perception. In some examples, any data indicating a match between micro-expressions and non-verbalized perception may be used to train such AI data matching engines to detect a match.

By way of example, as depicted in FIG. 101, a processing device may determine a first non-verbalized perception 10106A from first micro-expression 10104A and determine a second non-verbalized perception 10106B from a second micro-expression 10104B.

Some disclosed embodiments involve initiating an action associated with the specific non-verbalized perception. The term "initiating" may refer to carrying out, executing, or implementing one or more operative steps. For example, the at least one processor may initiate execution of a program code instructions or cause a message to be sent to another processing device to achieve a targeted (e.g., deterministic) outcome or goal. In this case, an action may be an initiated response to extracted reactions to content based on facial skin micromovements. The term "action" may refer to the performance or execution of an activity or task. For example, performing an action may include executing at least one program code instruction to implement a function or procedure. The action may be user-defined or system-defined (e.g., software and/or hardware), or any combination thereof. At least one processor may determine which action to initiate (e.g., first action or second action) based on the determined non-verbalized perception and based on various criteria. Some disclosed embodiments involve determining an action to initiate based on the consumed content and the specific non-verbalized perception. The term "determining an action to initiate" involves the process of determining an appropriate action to pursue. In some cases, the determination of the action to initiate may include using a rule-based system to select an appropriate action from a predefined list. The action determined might be an optimal action, the first action identified that meets a threshold, or an action that meets one or more criteria. For example, a rule-based system may include a rule to report a content provider every positive reaction to content, or a rule to update a user profile after determining that the individual found certain content boring. In other cases, the determination of the action includes using an AI-powered decision support system to select the most suitable action. In some embodiments, the determination of the action to initiate may also include determining the optimal time to initiate the action. For example, the at least one processor may determine to initiate the action immediately after the reaction is determined, determine to initiate the action the next time the individual will encounter similar content, or determine to initiate the action at a predetermined time. In other embodiments, the determination of the action to initiate may also include determining the manner by which the action is initiated. For example, if the determined action is transmitting a message, the at least one processor may determine the recipient of the message. Consistent with some embodiments of the disclosure, the determination of the action may be based on two parameters: the consumed content and the specific non-verbalized perception. With references to the examples above, the rule-based system and/or the AI-powered decision support system may use, as an input, data associated with the two parameters to determine which action to pursue. In other embodiments, as described below, the determination of the action to initiate may be based on these two parameters and one or more additional parameters.

In some embodiments, the determined action varies based on a type of the consumed content. The term "type of consumed content" or simply "type of content" may be any classification of the consumed content based on any characteristic. Examples of classifications of content may include textual content, audio content, interactive content, video content, social media content, educational content, entertainment content, journalism content, the source of the content, the service that present the content, the subject of the content, the release date of the content, the performer of the content, the context of the content, or any combination thereof. In some cases, each type of content may be classified to a plurality of subclasses. For example, textual content may also be classified to different subclasses, such as, books, poems, fiction, non-fiction, author, and any other known class. Consistent with the present disclosure, the type of the content may be used as an additional parameter to determine which action to initiate. In one example, when the non-verbalized perception is bored and the type of the consumed content is textual journalism (e.g., a news article), the determined action may be providing a summary of the relevant article. But when the non-verbalized perception is bored and the type of the consumed content is audio (e.g., a podcast), the determined action may be to change the speed of a podcast to 1.5 times (or faster). In other cases, the action may be determined based on the subject of consumed content. For example, when the non-verbalized perception is bored and the subject of the consumed content is a safety warning, the determined action may be enlarging the font size of the safety warning. But when the non-verbalized perception is bored and the subject of the consumed content is a weather forecast, the determined action may be to change the consumed content. The action may be initiated by at least one processor associated with the speech detection system, a different local processing device (e.g., associated with a device in proximity to the speech detection system), and/or by a remote processing device (e.g., associated with a cloud server), or any combination thereof. Thus, "initiating an action associated with the specific non-verbalized perception" may include performing or implementing one or more operations in response to a determination of the specific non-verbalized perception of the content consumed by the individual. Examples of actions that may be initiated in response to a determination of the specific non-verbalized perception of the content consumed by the individual may include: storing data about the individual's reaction to a specific content, updating a profile of the individual, providing personalized recommendations, delivering targeted advertisements, providing insights on the content to content providers, determining trends and patterns using data from multiple individuals, generating a notification for the individual, and any commend executable by an operation system associated with the at least one processor.

By way of example, as depicted in FIG. 101, a processing device may initiate a first action 10108A associated with first non-verbalized perception 10106A and initiate a second action 10108B associated with second non-verbalized perception 10106B. The following scenario describes a simplified use case to explain some of the disclosed embodiments. Assuming individual 102 watches short videos on virtual display 10002, first piece of content 1000A includes a first video about a quantum computer and second piece of content 10000B includes a second video about bonsai tree pruning. Using analysis of facial skin micromovements, a processing device may determine that individual 102 found the first video boring but the second video interesting. Thereafter, the processing device may initiate a first action for excluding videos on complex technology from the feed of individual 102 and initiate a second action of adding more videos to the feed on bonsai trees.

In some disclosed embodiments, the at least one data structure includes past non-verbalized perceptions of previously consumed content. The term "past non-verbalized perceptions of previously consumed content" refers to records, data, or information indicative of reactions of the individual and/or others to previously consumed content. For example, the at least one data structure may store information representing the micro-expressions or the micromovements together with data representing the consumed content. One use case is that the least one data structure stores the individual's reactions to tweets. Another use case is that the least one data structure stores the individual's reactions to songs played on the radio. Some disclosed embodiments involve determining a degree of the specific non-verbalized perception relative to the past non-verbalized perceptions, and determining an action to initiate based on the degree of the specific non-verbalized perception. The term "a degree of the specific non-verbalized perception" refers to the intensity of individual's emotional experience or the extent of their reaction in a given situation. In this context, the situation is consuming content. In some instances, the non-verbalized perception may be binary (e.g., the user is providing attention or is not); in other instances, the non-verbalized perceptions may be graduated, and assessed by a level, extent, degree, intensity, scope, range, magnitude, of non-verbalized perceptions of an individual or user. In some cases, the non-verbalized perceptions may be represented by a value on a scale (e.g., a scale of 1 to 100). For example, the individual's reaction to content may be binary—interested or bored. In other embodiments, the specific level might be based on a gradation such as high, medium, or low. Determining the degree of the specific non-verbalized "relative to the past non-verbalized perceptions" means that the level of the specific non-verbalized perception is determined in comparison to the past non-verbalized perceptions. In some examples, the determination of the degree of the specific non-verbalized may include usage of a scoring algorithm and/or Convolutional Neural Networks (CNNs). Such algorithms may compare the determined micro-expression associated with the specific non-verbalized with other micro-expressions associated with past non-verbalized perceptions to ascertain the degree of the specific non-verbalized relative to the past non-verbalized perceptions. For example, if the algorithm determines that a current micro-expression (e.g. a smile) associated with a specific video is greater than past micro-expression associated with other videos, the at least one processor may determine that the individual liked the specific video more than the other videos.

Thereafter and based on the degree of the specific non-verbalized, some embodiments involve determining an action to initiate. Returning to the example above, if the typical level of excitement of the individual from tweets is between 50 to 60, and the determined level of excitement of the individual from a specific tweet is between 90, the processing device may determine based on the parameters described above and predefined settings, to initiate an action to retweet the specific tweet. In other cases, the processing device may determine which user in a video conference is more of interest to the individual and to initiate an action that causes the user of interest to appear in the foreground.

In some disclosed embodiments, the at least one specific micro-expression includes a sequence of micro-expressions associated with the specific non-verbalized perception. The term "sequence of micro-expressions" refers to a series of facial micromovements that occur in succession. For example, the succession may refer to a consecutive manner in which different muscles are activated and cause micro skin deformations. The following example sequence of micro-expressions may be associated with the non-verbalized perception of confusion. The confusion sequence may include first facial skin micromovement caused by activation of the corrugator supercilia muscle (e.g., pulling the eyebrows downward and inward), second facial skin micromovement caused by activation of the *frontalis* muscle (e.g., raising the eyebrows and creating horizontal forehead wrinkles), and third facial skin micromovement caused by activation of the orbicularis oculi muscle (e.g., causing individuals to narrow their eyes slightly or squint as they concentrate or try to understand something). Some disclosed embodiments involve determining a degree of the specific non-verbalized perception based on the sequence of micro-expressions, and determining an action to initiate based on the degree of the specific non-verbalized perception. The term "degree of the specific non-verbalized perception" is described above. In this embodiment, the degree of the specific non-verbalized perception is not relative to the past reaction, but independently ascertained. As described above, the determination of the degree of the specific non-verbalized may include usage of a scoring algorithm and/or Convolutional Neural Networks (CNNs). Such algorithms may compare the determined micro-expression associated with the specific non-verbalized with reference sequences of micro-expressions associated with various non-verbalized perceptions to ascertain the degree of the specific non-verbalize. For example, the specific non-verbalized perception may indicate that the individual's reaction to a certain content points to a 6/10 or a 60% interest level. "Determining an action to initiate based on the degree of the specific non-verbalized perception" means that the determination of the action may be based on the extent of the individual reaction to the consumed content. Upon determining that the individual experiences a great degree of confusion with regards to a specific text that the individual is reading in virtual display 10002, the processing device may cause the virtual display 10002 to show additional content (e.g., figures) to explain the text. But, after determining that the individual experiences a low degree of confusion with regards to a specific text that the individual is reading in virtual display 10002, the processing device may cause the virtual display 10002 to display a notification that checks whether additional explanations are desired.

In some disclosed embodiments, the action initiated includes causing a transmission of a message reflecting a correlation between the specific non-verbalized perception and the consumed content. The term "transmission of a message" refers to a process of conveying information from a first entity to a second entity. The second entity that receives the message reflecting the correlation between the specific non-verbalized perception and the consumed content may be an associated computing device. For example, processing device 400 or processing device 460, shown in FIG. 4 may be considered a first entity and a mobile communications device 120, a cloud server (e.g., server 122), a content provider, a content personalization entity, a data analytic entity, ad server, or any other entity associated with content may be considered a second entity. The transmitted message may be in the form of text, speech, images, data, command, or any other medium that carries meaning. The message may be transmitted via a communication network (e.g., communication network 126 shown in FIG. 1). The term "correlation" is disclosed and explained above. Stating that the message reflecting a correlation between the specific non-verbalized perception and the consumed content means that the message is indicative of a relationship or connection between two the specific non-verbalized perception and the consumed content. In some embodiments, the content of the message describes the correlation. In other embodiments, the content of the message include data determined based on the correlation. For example, upon determining that individual 102 liked a video on bonsai trees, a message may be sent to an ad server that individual 102 is interested in bonsai trees.

In some disclosed embodiments, the action initiated includes storing in memory a correlation between the specific non-verbalized perception and the consumed content. The terms "memory" and "correlation" are described elsewhere in this disclosure. The phrase "storing in memory a correlation" refers to the process of saving the relationship or the connection between two parameters. The relationship or connection may be stored in a data structure, in a linked list, in a correlation table, in an array in a data structure. For example, the relationship between consumed content and non-verbalized perception may be stored in a data structure associated with a system that can detect micro-expression. The memory may be included in an associated computing device (e.g., mobile communications device 120), a cloud server (e.g., server 122), a content provider, a content personalization entity, a data analytic entity, ad server, or any other entity associated with content or the individual.

Consistent with some disclosed embodiments, the action includes determining additional content to be presented to the individual based on the specific non-verbalized perception and the consumed content. The additional content determined to be presented may include any data or information selected for visual display or audible presentation to the individual. The determination of the additional content may be based on the determined reactions of the individual. In some cases, the processing device may determine which additional content to provide from a list of content available to a processing device. For example, using a list of content stored in the data structure. In some embodiments, the additional content may be new content similar to the content for which a reaction was determined. The new content may be similar in the subject or in the type of content. For example, if it was determined that the individual liked a video in which a certain comedian jokes about parenthood, the additional content may be videos of the same comedian or videos of other comedians that include jokes about parenthood. In other embodiments, the additional content may be new content other than the content for which a reaction was determined. For example, if it was determined that the individual disliked a video in which a certain comedian jokes about parenthood, the additional content may be videos on different topics. In some disclosed embodiments, the consumed content is of a first type and the additional content is of a second type differing from the first type. As mentioned above, the term "a type of content" refers to any classification of the consumed content based on one or more of its characteristics. The statement "consumed content is of a first type and the additional content is of a second type differing from the first type" means that the additional content may be classified differently from the original content for which a reaction was determined. In one example, the original content may be a video trailer of movie, the determined non-verbalized perception may be "interested," and the additional content may be a textual review of the movie. In another example, the original content may be a video in YouTube™, the determined non-verbalized perception may be "engaged," and the additional content may be another video content on Netflix™.

In some disclosed embodiments, the action includes selecting an alternative manner for presenting the consumed content. The phrase "selecting an alternative manner for presenting the consumed content" refers to a process of choosing a new format to display the consumed content, which is different from an original format that was used while the reaction of the consumed content was extracted. The format includes the arrangement, design, and appearance parameters used for displaying the content. The alternative format may include additional content or may omit some of the consumed content. Different manners of presentation may include, for example, providing textual displays, adding color to a display, increasing or altering font size, generating audio presentation or augmentation, changing brightness, changing contrast, slowing speed of audio, presenting with closed captioning, providing a simplified presentation, generating a graphical presentation, or any other way information can be conveyed. In some cases, new format may be selected automatically based on previously stored information, or using predefined user preferences. In other cases, the new format may be selected based on a user input, or based on detecting which devices are available and/or based on environmental conditions. A presentation manner may also refer to a selection of a device on which information is presented. Differing manners of presentation in this context may involve presenting information via one or more of a smartphone, tablet, VR headset, smartwatch, laptop, PC, or any other mobile or immobile communications device. For example, when the determined non-verbalized perception is "frustrated," the action may include changing the font of a textual content, increasing the volume of an audio content, changing the brightness of a video content, or changing the size or location of a virtual content.

In some disclosed embodiments, the consumed content is part of a chat with at least one other individual and the action includes generating a visual representation of the specific non-verbalized perception in the chat. The term "chat" refers to a form of communication between two or more individuals using messages (e.g., text messages, audio messages, or video messages). A chat can occur through various platforms, including messaging applications, online chat rooms, instant messaging services, or propriety applications. Examples of online services that support chat session include messaging apps (e.g., WhatsApp, WeChat, Telegram), social media platforms (e.g., Facebook, Twitter, Instagram, and LinkedIn), video conferencing tools (e.g., Zoom, Teams, Google Meet), online chat rooms, customer support chat, and online gaming platforms. In some embodiments, the term "a visual representation of the specific non-verbalized perception" refers to a graphical symbol used to convey emotions, thoughts, feelings, or impressions that individuals experience. Examples of the visual representation include an emoji, an image, a gif, a giphy, an animated gif, a short video, an icon, or a virtual avatar making a facial expression. Accordingly, the phrase "generating a visual representation of the specific non-verbalized perception in the chat" refers to an act of producing or adding a visual representation to an ongoing conversation between the individual and another person or entity. For example, when an individual is determined to be happy in response to a received message in chat, the processing may add a smiling face emoji to the chat.

Some disclosed embodiments involve operating at least one wearable coherent light source in a manner enabling illumination of a non-lip portion of a face of the individual, and receiving signals indicative of coherent light reflections from the non-lip portion of the face. The term "wearable coherent light source" broadly refers to any device, element, or system configured to emit coherent light, as discussed elsewhere in this disclosure. The term "illumination of a non-lip portion" includes projecting light towards a facial region (as described elsewhere herein) that does not include the lips of an individual. For example, the facial region may be associated with specific muscles, such as the zygomaticus muscle or the risorius muscle. The term "receiving signals" may refer to the process of obtaining information encoded for transmission via a physical medium or wirelessly, as discussed elsewhere in this disclosure. The term "indicative of coherent light reflections from the non-lip portion of the face" means that the obtained information is suggestive, demonstrative, or representative of the light reflected from the facial region that does not include the lips of the individual. In some disclosed embodiments, the facial skin micromovements are determined based on speckle analysis of the coherent light reflections. As described elsewhere herein, detecting coherent light reflections from skin and using speckle analysis is one way to determine the facial skin micromovements. The same processes as previously described may be similarly applied in the context of determining facial skin micromovements for extracting reactions to content. In some embodiments, the reflections of coherent light are received by a wearable light detector. The term "wearable light detector" broadly refers to any wearable device, element, or system capable of measuring one or more properties of light and generating an output relating to the measured properties, as discussed elsewhere in this disclosure.

By way of a non-limiting example, in FIG. 100, an individual 102 wearing extended reality appliance 250 exhibits the facial skin micromovements that are manifest in light reflections. Those reflections are detected by a wearable light detector (e.g., light detector 412) and may be analyzed to determine user's reactions to consumed content.

Figure 102:
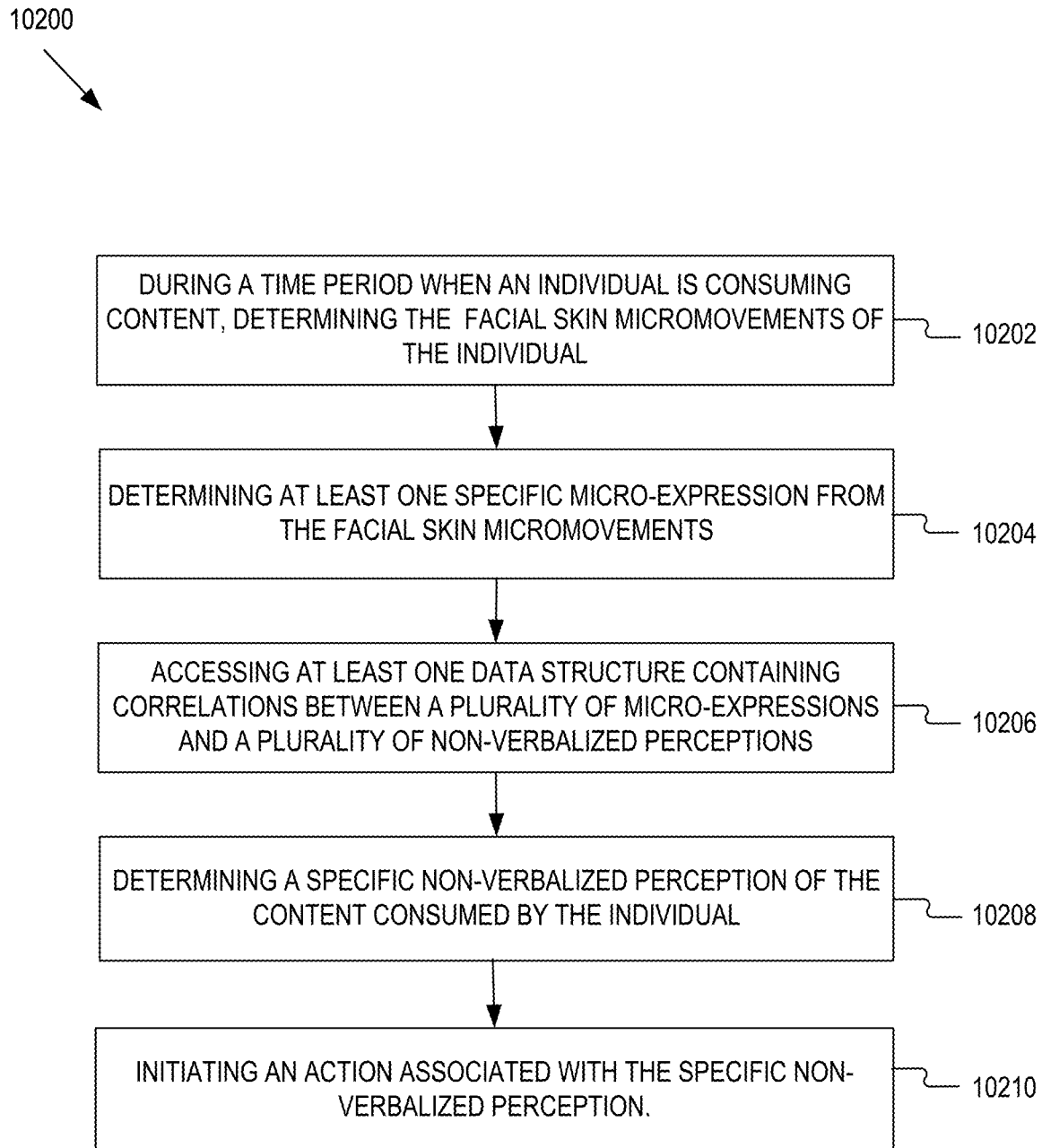
FIG. 102 is a flowchart of an example process for extracting reactions to content based on facial skin micromovements, consistent with some embodiments of the present disclosure.

FIG. 102 illustrates a flowchart of an exemplary process 10200 for extracting reactions to content based on facial skin micromovements, consistent with embodiments of the present disclosure. In some disclosed embodiments, process 10200 may be performed by at least one processor (e.g., processing device 400, processing device 460, or any processor associated with extended reality appliance 250) to perform operations or functions described herein. In some disclosed embodiments, some aspects of process 10200 may be implemented as software (e.g., program codes or instructions) that are stored in a memory (e.g., memory device 402, memory device 466, or any processor associated with a memory device) or a non-transitory computer-readable medium. In some disclosed embodiments, some aspects of process 10200 may be implemented as hardware (e.g., a specific-purpose circuit). In some disclosed embodiments, process 10200 may be implemented as a combination of software and hardware.

Referring to FIG. 102, process 10200 includes a step 10202 of determining the facial skin micromovements of the individual during a time period when an individual is consuming content. For example, the at least one processor may receive light reflections and apply light pattern analysis, e.g., using use light reflections processing module 706 to determine the facial skin micromovements. Process 10200 includes a step 10204 of determining at least one specific micro-expression from the facial skin micromovements. For example, as described above, the at least one processor may use machine learning algorithms to ascertain micro-expression from the facial skin micromovements. Process 10200 includes a step 10206 of accessing at least one data structure containing correlations between a plurality of micro-expressions and a plurality of non-verbalized perceptions. For example, the at least one processor may access data structure 422 and/or a part of data structure 464 (depicted in FIG. 4). Process 10200 includes a step 10208 of determining a specific non-verbalized perception of the content consumed by the individual. As described above, the determination of step 10208 may be based on the at least one specific micro-expression and the correlations in the data structure. Process 10200 includes a step 10210 of initiating an action associated with the specific non-verbalized perception. For example, first action 10108A may be initiated in response to first non-verbalized perception 10106A and second action 10108B may be initiated in response to second non-verbalized perception 10106B.

The embodiments discussed above for extracting reactions to content based on facial skin micromovements may be implemented through a non-transitory computer-readable medium such as software (e.g., as operations executed through code), as methods (e.g., process 10100 shown in FIG. 101), or as a system (e.g., speech detection system 100 shown in FIGS. 1-3 and/or extended reality appliance 250). When the embodiments are implemented as a system, the operations may be executed by at least one processor (e.g., processing device 400 or processing device 460, shown in FIG. 4).

Performance of non-speech-related physical activities may cause facial skin movements in addition to facial skin micromovements associated with prevocalization or subvocalization. For example, impact from running or jumping may cause facial skin to wobble or bounce. Consequently, involvement of an individual in a non-speech-related physical activity while preparing to vocalize one or more words may introduce noise to signals representing light reflections of a face of an individual. Such noise (e.g., measured as a signal to noise ratio, or SNR) may hamper a capability of at least one processor to identify facial skin micromovements associated with prevocalization. For example, an SNR of a signal representing light reflections of a face of an individual may increase between 20% to 50% due to walking (e.g., a non-speech related action) as opposed to sitting (e.g., corresponding to a stationary state). Disclosed embodiments allow for identifying and filtering noise resulting from involvement of a user in a non-speech-related physical activity. In some embodiments, non-speech-related physical activities may include fine motor skills such as breathing, blinking, and tearing, in addition to gross motor skills such as walking, running, and jumping.

In some disclosed embodiments, operations may be performed for removing noise from facial skin micromovement signals. During a time period when an individual is involved in at least one non-speech-related physical activity, a light source may be operated in a manner enabling illumination of a facial skin region of the individual. Signals representing light reflections may be received from the facial skin region. The received signals may be analyzed to identify a first reflection component indicative of prevocalization facial skin micromovements and a second reflection component associated with the at least one non-speech-related physical activity. The second reflection component may be filtered out to enable interpretation of words from the first reflection component indicative of the prevocalization facial skin micromovements.

Some disclosed embodiments involve removing noise from facial skin micromovement signals. Noise may refer to any extraneous, superfluous, unwanted and/or random fluctuations or disturbances that may interfere with a signal, and may interfere with and/or frustrate a capability to extract information from a signal. Noise may be an undesirable component of a signal and may affect quality and/or reliability of a signal during transmission, recording, and/or processing. Noise may arise from various sources, such as electrical interference, thermal effects, atmospheric conditions, motion, vibrations, movement, and/or limitations of the measuring or recording equipment. Such sources may introduce additional signals or disturbances that may mix with an original signal, making it difficult to accurately extract or interpret the desired information from the original signal, leading to errors and/or reduced clarity. The presence of noise in a signal may cause a degradation in signal quality, which may be measured as a signal-to-noise ratio (SNR) comparing a desired signal component (e.g., information) to a noise component of a received signal. A high SNR may indicate that a desired signal component is strong relative to a noise component of a signal, resulting in better signal fidelity and more reliable information extraction. Conversely, a low SNR may indicate that a noise component of a signal may be significant relative to a desired signal component, which may impede a capability to discern and/or utilize information carried in a signal. Some techniques for improving signal quality may include filtering, noise reduction algorithms, shielding, amplification, and/or error correction codes, which may aim to reduce the impact of noise and improve fidelity and accuracy of a desired signal. In some embodiments, performance of a secondary activity simultaneously with performance of a first activity may introduce noise to a signal conveying information associated with the first activity. For example, if a user walks while preparing to vocalize at least one word, vibrations and/or facial skin motion attributable to walking may introduce noise to a signal representing facial skin micromovements associated vocalizing (e.g., and/or preparing to vocalize) at least one word, hampering a capability of at least one processor to interpret at least one word based on the signal. Removing noise from facial skin micromovement signals may involve performance of one or more signal analysis and filtering operations, as described in greater detail herein.

Some disclosed embodiments involve during a time period when an individual is involved in at least one non-speech-related physical activity, operating a light source in a manner enabling illumination of a facial skin region of the individual. A time period may refer to a duration (e.g., a length of time) and/or an interval or gap separating two distinct instances in time. In some embodiments, a time period may distinguish an earlier event (e.g., occurring in a first time period) from a subsequent event (e.g., occurring in a second time period following the first time period). During a time period may include the passage of time in the course of and/or throughout a time period (e.g., between two time instances defining the time period). An individual (as described and exemplified elsewhere in this disclosure) involved in a non-speech-related physical activity may include an individual engaging and/or partaking in a corporeal and/or material action disassociated and/or independent of vocalizing speech, e.g., in a real, non-virtual) environment. Examples of a non-speech-related physical activity may include walking, running, jumping, dancing, bicycle riding, turning of a head, neck and/or torso, rising from a sitting position, sitting from a standing position, reclining, rising from a reclining position, and/or any other material action performed in a real (e.g., non-virtual) environment independently of vocalizing speech. Additional examples of non-speech-related physical activities may include blinking, breathing, crying, coughing, sneezing, gasping, chewing, swallowing, smiling, frowning, squinting, pursing of lips (e.g., to blow a kiss), raising of eyebrows (e.g., in surprise), flaring of nostrils, and/or any other non-speech-related facial gesture. A degree to which facial skin of an individual may move during involvement in a non-speech related physical activity may depend on personal traits, an environment of the individual, a type of activity, and/or any other factor that may affect a degree of facial skin micromovements. For example, an age (e.g., affecting skin elasticity), a weight (e.g., affecting gravitational force on the skin), a shoe type (e.g., affecting cushioning of the skin from impact), a velocity and an acceleration associated with a bodily motion, a type of surface (e.g., soft ground versus a hard floor), a type of activity (e.g., low-impact walking versus high-impact running) may affect a degree to which facial skin of an individual may move during involvement in a non-speech related physical activity. Operating a light source (as described and exemplified elsewhere herein) enabling illumination of a facial skin region of an individual may include controlling, timing, orienting, filtering, focusing, and/or switching a light source on/off to cause light to shine on a specific facial region of an individual in a manner to allow detection of the light reflecting off the specific facial region of the individual. For example, detection of light reflecting off a specific facial region of an individual may allow determining one or more facial skin micromovements, as described elsewhere in this disclosure.

In some embodiments, the light source is a coherent light source, as described and exemplified elsewhere in this disclosure. For example, the coherent light source may include one or more laser diodes. A speech recognition system may include a coherent light detector positioned and/or oriented in a manner to capture reflections of coherent light off a facial region of an individual. At least one processor may use signals representing the reflections of coherent light to perform a speckle analysis and/or a pattern analysis to determine features (e.g., a texture, contour, roughness, and/or smoothness) characterizing the surface of the facial skin, and which may be utilized to determine one or more prevocalization facial skin micromovements. For example, during performance of prevocalization facial skin micromovements, a raised region of skin (e.g., a mole or pimple) may exhibit a larger range of micromovements than an indented region or skin (e.g., a dimple or pit) located in proximity to the raised region of skin. The at least one processor may utilize facial skin texture (e.g., determined based on a speckle analysis) to account for differences in facial skin micromovements in a region of facial skin including the raised region and the indented region to determine the at least one word. In some embodiments, the light source may include a plurality of coherent light sources, e.g., each light source configured to emit coherent light of a differing frequency, as described and exemplified elsewhere in this disclosure.

By way of a non-limiting example, FIG. 103 illustrates individual 102 performing a first non-speech-related activity (e.g., walking) and a second non-speech-related activity (e.g., sitting) while wearing speech detection system 100, consistent with embodiments of the present disclosure. During a first time period when individual 102 is involved in the first non-speech-related physical activity (e.g., walking), at least one processor (e.g., processing device 400 in FIG. 4) may operate light source 410 of optical sensing unit 116 in a manner enabling illumination of facial region 108 of individual 102. During a second time period when individual 102 is involved in the second non-speech-related physical activity (e.g., sitting), the at least one processor may similarly illuminate facial region 108 of individual 102 by operating light source 410 of optical sensing unit 116. For example, light source 410 may include a coherent light source (e.g., a laser) allowing the at least one processor to perform a speckle analysis on image data received from optical sensing unit 116.

Some disclosed embodiments involve receiving signals representing light reflections from the facial skin region, which may be understood as described and exemplified elsewhere herein. For example, at least one processor may receive from a light sensor, a series of images over a period of time capturing a state of the facial skin of an individual prevocalizing or subvocalizing. The at least one processor may analyze the images and compare differing images associated with differing time instances to identify changes in the state and/or position of a facial skin region indicating facial skin micromovements, as described and exemplified herein.

In some embodiments, the signals are received at a rate of between 50 Hz and 200 Hz. A Hz or Hertz may refer to a unit for measuring frequency as a number of cycles per second. Receiving signals at a rate of between 50 Hz and 200 Hz may include receiving signals inside a Super Low Frequency (SLF) band spanning between 30 Hz and 300 Hz. For example, at least one processor of a speech detection system may receive signals from a sensor configured to sense signals representing light reflections from the facial skin region. The sensor may transmit sensed signals to the at least one processor in an SLF band via an antenna. Such a frequency band may be selected to avoid interference with other ambient radio signals. In some embodiments, an overall frequency range may additionally allow for non-uniform sampling. For example, at least one processor may sample two consecutive signals occurring within a small time frame (e.g., close in time) at a sampling frequency of 1 Hz, such that an overall sampling frequency of the system may be low (e.g. 1 Hz), however the at least one processor may sample the two signals at a high frequency, e.g., 1:10,000.

Figure 104:
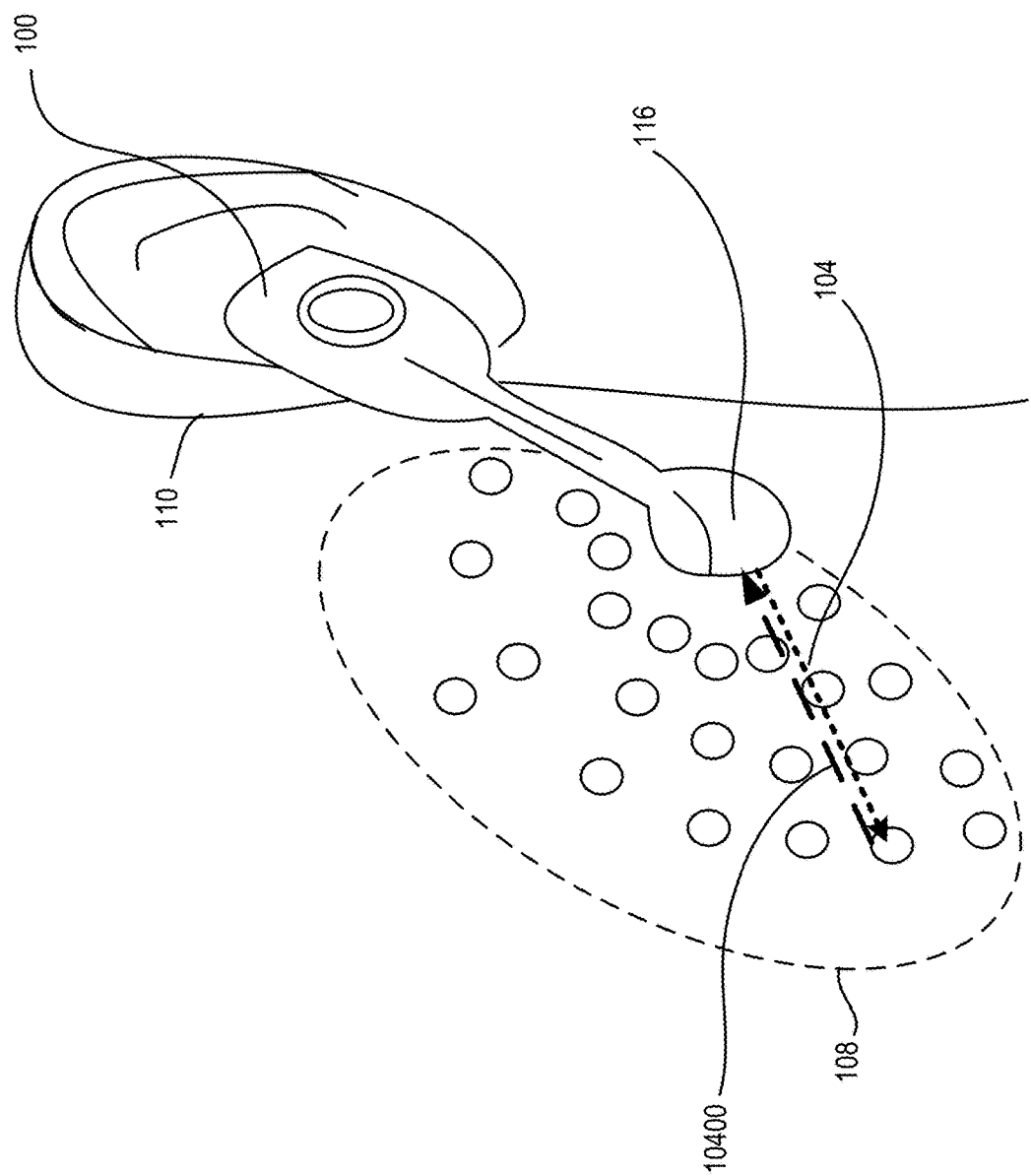
FIG. 104 illustrates an exemplary close-up view of the speech detection system of FIG. 103, consistent with embodiments of the present disclosure.

By way of another non-limiting example, FIG. 104 illustrates an exemplary close-up view of speech detection system 100 of FIG. 103, consistent with embodiments of the present disclosure. Light source 410 (e.g., see FIG. 4) of speech detection system 100 may illuminate facial region 108 of individual 102 with projected light 104 (e.g., see FIG. 1). Projected light 104 may reflect off facial region 108 as reflected light signal 10400. Light detector 412 may detect light signal 10400 reflecting off facial region 108 and may transmit electronic signals representing reflected light signal 10400 to processing device 400. For example, the at least one processor may receive the electronic signals in an SLF band between 50 Hz and 200 Hz.

Some disclosed embodiments involve analyzing the received signals to identify a first reflection component indicative of prevocalization facial skin micromovements and a second reflection component associated with the at least one non-speech-related physical activity. Analyzing a signal may involve performance of one or more measurements, comparison, computations, feature extraction, and/or signal processing techniques on a signal. In some embodiments, analyzing a signal may include deconstructing a signal into a plurality of information components (e.g., features). An information component of a signal may include a portion of a signal representing a particular pattern, order, and/or structure (e.g., measured as a number of bits), and encoded digitally. Some transformation and/or analysis techniques that may be used to deconstruct a signal into multiple information components or features may include a Fourier Transform, a Wavelet Transform, Principal Component Analysis (PCA), Independent Component Analysis (ICA), Singular Value Decomposition (SVD), Time-Frequency Analysis, and/or Empirical Mode Decomposition (EMD). A Fourier transform converts a signal from the time domain to the frequency domain, decomposing the signal into a plurality of sinusoidal components with differing frequencies. A Wavelet transform breaks down a signal into different frequency components over time, allowing identification of localized features in both time and frequency domains. PCA is a statistical technique for transforming a signal into a set of linearly uncorrelated components (principal components), which capture the (e.g., maximum) variance in the signal, allowing for dimensionality reduction and feature extraction. ICA separates a signal into statistically independent subcomponents when an observed signals includes a linear combination of underlying signal sources. SVD decomposes a signal matrix into three matrices (e.g., U, $\Sigma$, and V), enabling dimensionality reduction for feature extraction and/or denoising by retaining higher priority singular values. Time-frequency analysis methods (e.g., spectrograms, Wigner-Ville distribution, or the short-time Fourier transform STFT) provide information about a signal's frequency content and how it evolves over time. EMD may be used for analyzing non-stationary and nonlinear signals by decomposing a signal into a finite number of intrinsic mode functions (IMFs) representing different time scales or oscillatory modes. At least one processor may select a particular transformation or analysis technique depending on the nature of the signal and the information components of interest. Upon identifying one or more information components in a signal (e.g., using a decomposition technique), at least one processor may use the information components to perform one or more computations and/or comparisons to arrive at one or more conclusion, e.g., by feeding one or more of the information components to a classification engine and/or a machine learning engine.

Some additional examples of techniques that may be used to analyze a signal (e.g., for identifying one or more reflection components and/or information components) may include sampling, digital-to-analog conversion, analog-to-digital conversion, frequency and/or time domain transformations such as Fourier Transforms, convolutions, filters (e.g., low-pass, high-pass, and/or band-pass filters), correlations (e.g., auto-correlations, cross-correlation), dithering, harmonic analysis, dividing a signal into multiple windows (e.g., time-frames), time shifting, normalization, dynamic programming (e.g., Viterbi), and/or any other signal processing and/or signal analysis technique. In some embodiments, analyzing a signal may include utilizing one or more artificial intelligence techniques (e.g., including machine learning, deep learning, neural networks, genetic algorithms, graph analysis, tree traversal and/or path discovery in a hidden Markov model) to determine information from a signal.

For example, at least one processor may convert an electronic signal to a digital format via sampling and perform a dithering operation on the digitized signal by adding a measured amount of statistical noise, resulting in cancellation of at least some statistical noise. The at least one processor may perform a Fourier analysis on the at least partially cleaned signal to identify a plurality of information components, each associated with a different frequency or frequencies of differing sinusoidal functions. The at least one processor may feed the plurality of information components to an artificial intelligence engine (e.g., a machine learning and/or classification engine) to arrive at one or more conclusions, e.g., based on discovery of one or more patterns, associations, and/or relationships.

A reflection component may include a portion of reflected light and/or a specific reflected light signal included in an aggregation of multiple reflected light signals (e.g., multiple reflection components). For example, light reflecting off a facial regions of an individual may include a first reflection component associated with skin motion attributable to speech and/or prevocalization and a second reflection component associated with head motion attributable to nodding the head up and down. A reflection component of a signal may include at least one information component and may be associated with one or more frequencies, wavelengths, aberrations (e.g., statistical anomalies), distortions, phase shifts, amplitudes, a timing, a duration, a direction, a polarity, a coherency measure, a light dispersion, light scattering, light diffusion, and/or light absorption factor, and/or any other light signal characteristics. For instance, an image of a person standing in the rain may include a first reflection component indicative of a person and containing information components associated therewith (e.g., an identity, a size, clothing, facial appearance, a gender, an age, and/or a physical state of the person) and a second reflection component indicative of rain and containing information components associated with rain (e.g., a size, a frequency, and/or an intensity of raindrops).

As an example, multiple physical activities performed by an individual simultaneously may affect facial skin of the individual differently, causing differing distortions to light reflected therefrom. Consequently, light reflected off the facial skin region of an individual engaged in multiple physical activities simultaneously may include multiple reflection components, each containing information (e.g., a pattern) attributable to a specific physical activity. For instance, jumping may cause facial skin to oscillate or jiggle and move differently than facial micromovements associated with prevocalization of at least one word. Consequently, a light signal reflected off an individual engaged in jumping while speaking may include a first reflection component representing facial skin movements attributable to jumping (e.g., wobbling at a frequency corresponding to a jumping frequency), and a second reflection component representing facial skin micromovements attributable to prevocalization of at least one word, as described elsewhere herein. The at least one processor may use any of the signal analysis techniques described herein to identify a plurality of reflection components in a signal, where each reflection component may include at least one information component, e.g., the first reflection component may include a first information component associated with prevocalization and a second reflection component may include a second information component associated with jumping.

In some embodiments, one or more substances on a surface of facial skin (e.g., sweat, dirt, makeup, oils, facial hair, sunscreen, moisturizers) may affect one or more reflections components of light reflecting off facial skin, e.g., by affecting light absorption, reflection, scattering, and/or diffusion. Such substances may introduce the same or differing distortions to a first reflection component (e.g., indicative of prevocalization facial skin micromovements) and a second reflection component (e.g., associated with the at least one non-speech-related physical activity). For example, running may cause facial skin to wobble rhythmically and may additionally cause sweat to form on the surface of the facial skin, affecting how light may reflect off the facial skin. Consequently, a light signal reflected off an individual engaged in running during prevocalization of at least one word may include a first reflection component associated with prevocalization (e.g., indicative of facial skin micromovements), a second reflection component attributable to running (e.g., indicative of a first non-speech-related activity), and a third reflection component attributable to sweat accumulation on the skin surface (e.g., indicative of an additional non-speech-related activity), where the third reflection component may affect the information contained in the first and second reflection components substantially equivalently, or differently.

A first reflection component indicative of prevocalization facial skin micromovements (as described and exemplified elsewhere herein) may refer to a portion of a light signal reflecting off a facial region of an individual indicating facial micromovements attributable to a recruitment and/or enlistment of muscles in preparation for (e.g., prior to) vocalizing at least one word (or associated with subvocalization), and containing information associated therewith. At least one processor may analyze and/or process the first reflection component to derive one or more associated information components, which may be used to interpret at least one word to be spoken as described elsewhere in this disclosure (e.g., by feeding the associated information components to an AI engine). A second reflection component associated with the at least one non-speech-related physical activity may refer to a portion of a light signal reflecting off a facial region of an individual indicating facial skin movements attributable to a non-speech-related physical activity as exemplified earlier (e.g., walking, standing up, sitting down, running, breathing, blinking, etc.), and containing information associated therewith. At least one processor may analyze and/or process the second reflection component to derive one or more associated information components, which may be used to determine the at least one non-speech-related physical activity as described elsewhere in this disclosure (e.g., by feeding the associated information components to the same or a different AI engine). For example, a Fourier analysis of a light signal reflecting off a facial region of an individual may produce a first reflective component indicative of prevocalization facial skin micromovements characterized by one or more first frequencies, wavelengths, amplitudes, phases, timing and/or duration, aberrations, anomalies, distortions, direction, and/or polarity, and a second reflective component indicative of a non-speech-related physical activity characterized by one or more second frequencies, wavelengths, amplitudes, phases, timing and/or duration, aberrations, anomalies, distortions, direction, and/or polarity.

Analyzing received signals to identify a first reflection component indicative of prevocalization facial skin micromovements and a second reflection component associated with at least one non-speech-related physical activity may involve at least one processor identifying at least two differing reflection components in signals representing light reflections from a facial skin region, identifying information components included in each reflection component, and/or classifying each information component as belonging to a prevocalization category, a non-speech-related category, or to a different (e.g., unrelated) category. To accomplish this, the at least one processor may perform one or more signal processing, signal analysis, signal decomposition, calculations, comparison, query, and/or matching operations, e.g., using one or more machine learning engines, classification engines, and/or neural networks as described elsewhere herein.

In some embodiments, a memory device may store one or more histories of information components (e.g., as digital representations of facial skin micromovement patterns associated with prevocalization and/or facial skin movement patterns associated with differing non-speech related activities). For example, such a history may be built during a training phase for a speech detection system. The information components may be stored using structured and/or unstructured data schema (e.g., models), tabular and/or non-tabular data schema, relational databases and/or non-relational databases, graphs (e.g., directed graphs), trees, Markov chains (e.g., hidden Markov models), linked lists, tables, matrices, hierarchies, relational models, and/or any other type of data model allowing to store and make comparisons between a plurality of information components.

By way of a non-limiting example, in FIG. 104, at least one processor (e.g., processing device 400 in FIG. 4) may analyze electronic data representing light signals 10400 signal received from light detector 412 to determine a first reflection component indicative of prevocalization facial skin micromovements and a second reflection component associated with at least one non-speech-related physical activity. For example, the at least one processor may deconstruct the electronic signals to identify a plurality of information components, as described herein, and feed the information components to a classification engine.

Figure 105:
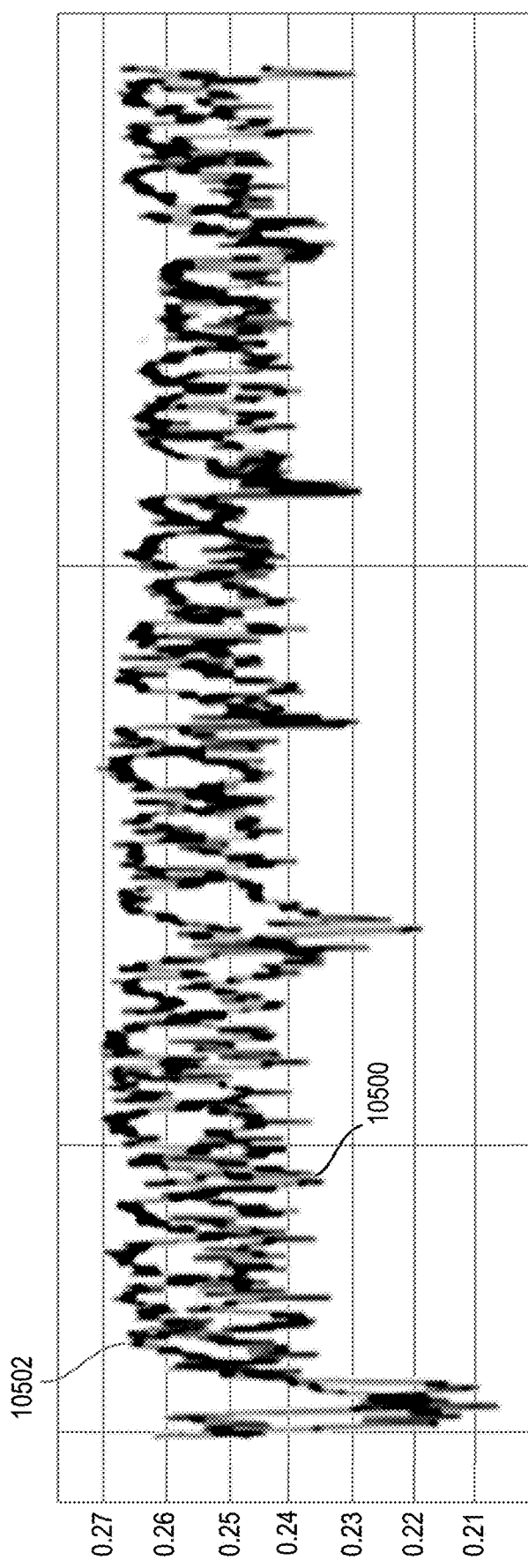
FIG. 105 illustrates an exemplary comparison between a first signal of an individual performing speech-related facial skin movements while walking, and a second signal of the individual performing speech-related facial skin movements while sitting, consistent with embodiments of the present disclosure.

By way of another non-limiting example, FIG. 105 illustrates an exemplary comparison between a first signal 10500 of individual 102 performing speech-related facial skin movements while walking, and a second signal 10502 of individual 102 performing speech-related facial skin movements while sitting, consistent with embodiments of the present disclosure. The speech-related facial skin movements represented by FIG. 105 may include prevocalization facial skin micromovements. Walking may correspond to a non-speech-related activity, and sitting may correspond to a substantially stationary state or nonperformance of a non-speech-related activity. In some embodiments, signals including a reflection component associated with prevocalization while sitting may be used as a control for comparison with signals including a reflection component associated with prevocalization while performing a non-stationary action. Facial movements associated with the non-speech-related activity (walking) may be more pronounced (e.g., more dramatic) than facial movements associated with the second non-speech-related activity (sitting). Consequently, walking may introduce more noise (e.g., interference) to signals indicating speech-related facial skin movements than sitting, and first signal 10500 (e.g., associated with prevocalization while walking) may be lower than second signal 10502 (e.g., associated with prevocalization while sitting), for example, by a factor of 50%. Due to the lower SNR caused by walking, interpreting words from signals including reflection components associated with prevocalization while walking may be more difficult than interpreting words from signals including reflection components associated with prevocalization while sitting.

Figure 106:
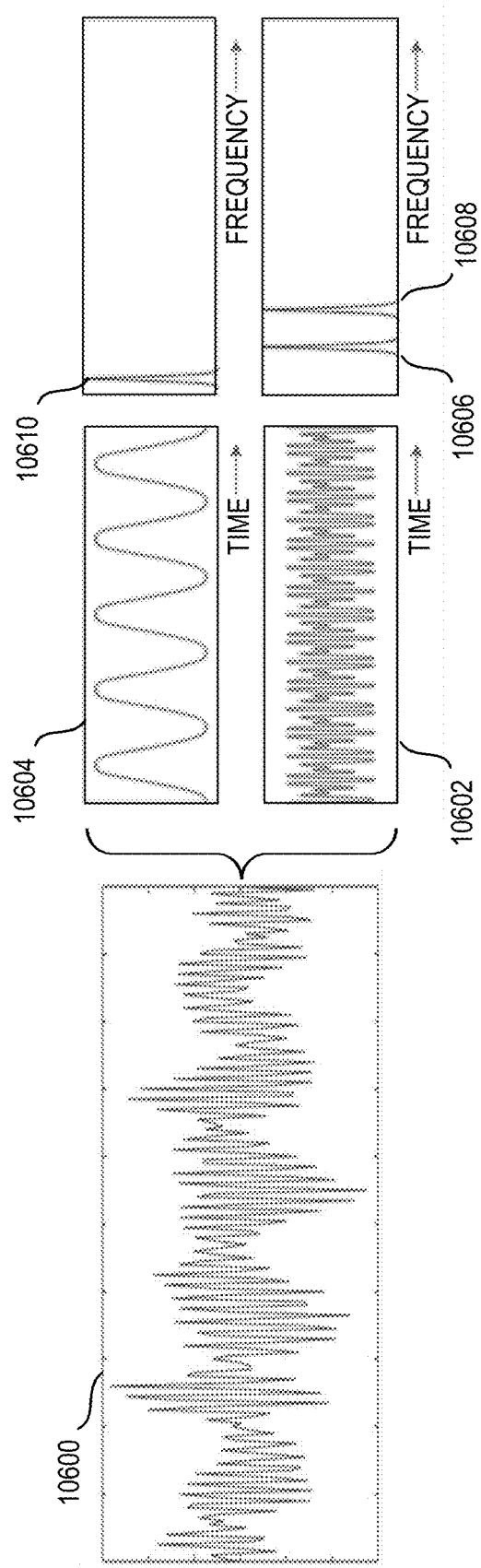
FIG. 106 illustrates an exemplary decomposition and classification of an electronic representation of a light signal into a first reflection component indicative of prevocalization facial skin micromovements and a second reflection component associated with at least one non-speech-related physical activity, consistent with embodiments of the present disclosure.

By way of an additional non-limiting example, FIG. 106 illustrates an exemplary decomposition and classification of an electronic representation 10600 of light signal 10400 (see FIG. 104) into a first reflection component 10602 indicative of prevocalization facial skin micromovements and a second reflection component 10604 associated with at least one non-speech-related physical activity (e.g., walking), consistent with embodiments of the present disclosure. First reflection component 10602 indicative of prevocalization facial skin micromovements may include information components 10606 and 10608 (e.g., frequency components of first reflection component 10602). Second reflection component 10604 associated with walking may include an information component 10608 (e.g., a frequency component of second reflection component 10604).

Figure 109:
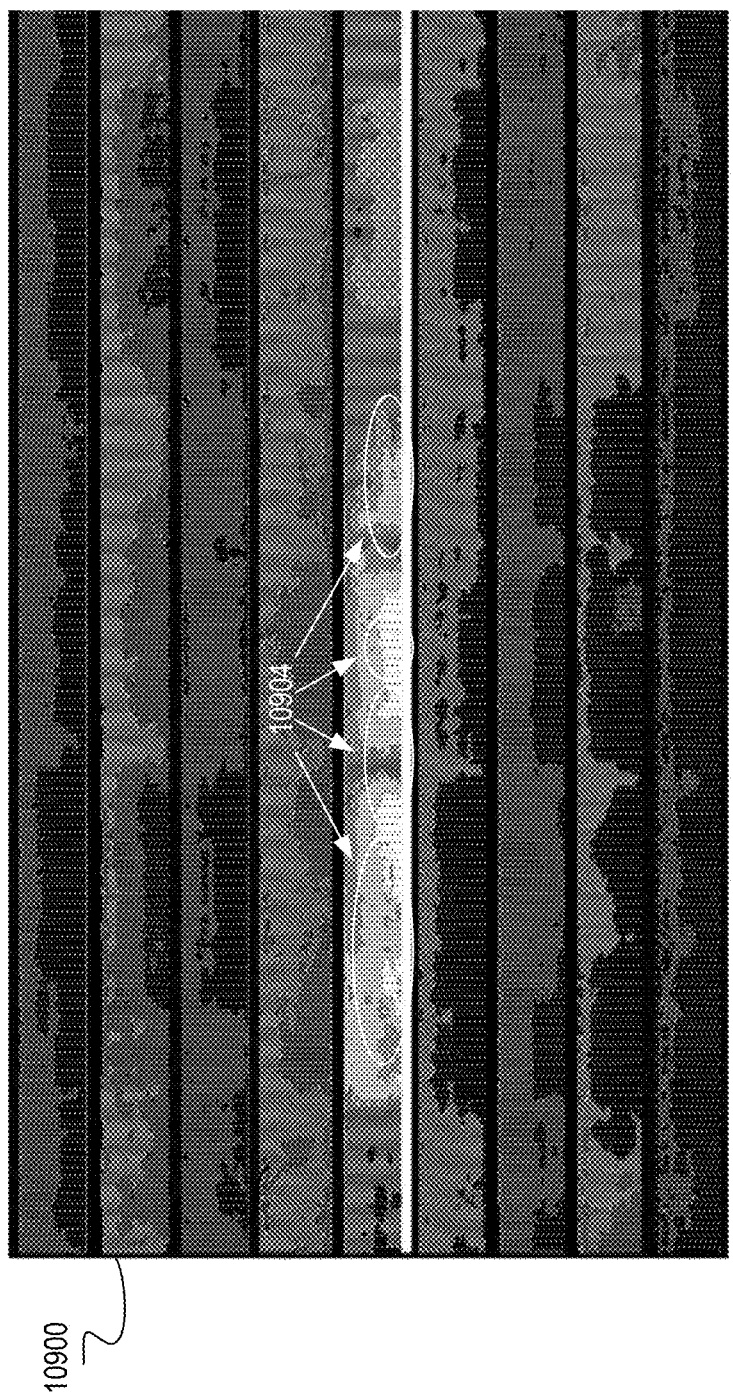
FIG. 109 illustrates another exemplary decomposition and classification of a representation of a light signal to identify a first reflection component indicative of prevocalization facial skin micromovements, consistent with embodiments of the present disclosure.

By way of an additional non-limiting example, FIG. 109 illustrates an exemplary decomposition and classification of a representation 10900 of light signal 10400 (see FIG. 104) to identify a component indicative of prevocalization facial skin micromovements, consistent with embodiments of the present disclosure. Representation 10900 of light signal 10400 includes one or more components indicative of prevocalization facial skin micromovements, as well as multiple noise components 10904 attributable to at least one non-speech-related physical activity (e.g., walking). The at least one processor may analyze representation 10900 of light signal 10400 to identify and filter out (e.g., by subtracting or otherwise removing) all, or at least some of noise components 10904 associated with the at least one non-speech-related physical activity. The at least one processor may classify a remainder of representation 10900 of light signal 10400 (e.g., after filtering out all, or at least some of noise components 10904) as associated with signals indicative of prevocalization facial skin micromovement components.

In some embodiments, the signals are received from a sensor associated with a wearable housing and wherein the instructions further include analyzing the signals to determine the at least one non-speech-related physical activity. A wearable housing may be understood as described and exemplified elsewhere in this disclosure. A sensor (as described and exemplified elsewhere in this disclosure) associated with a wearable housing may include a detector (e.g., at least partially) contained inside and/or otherwise supported by and/or connected to (e.g., electronically, via a communications channel, and/or mechanically) a wearable housing. For example, a light sensor may include a component for detecting light waves and associated electronics for converting a detected light waves to an electronic signal for transmitting to at least one processor for analysis. The component for detecting light waves may be located external to, and support by, a wearable housing and the associated electronics may be located within the wearable housing. Analyzing signals to determine at least one non-speech-related physical activity may involve at least one processor receiving signals from a sensor associated with a wearable housing, performing one or more signal processing techniques on the received signals to extract information from the signals, and/or using the information extracted from the signals to identify at least one non-speech related physical activity, e.g., by querying a database and/or using an AI engine. Such information may allow identifying one or more reflective components indicative of non-speech-related physical activity associated with an introduction of noise into a first reflective component indicative of prevocalization facial skin micromovements. For example, such information may indicate an environment, a circumstance, a context, an action, and/or any other factor introducing reflective components that may introduce noise to a first reflective component indicative of prevocalization facial skin micromovements. For instance, based on image processing performed on received signals, at least one processor may determine that a background of an individual is changing and/or a pose and/or posture of the individual is changing, indicating the individual is in motion which may cause facial skin movements other than prevocalization facial skin micromovements. Based on the changing background and/or changing pose and/or posture, the at least one processor may determine an associated non-speech-related activity, e.g., by querying a database of non-speech-related activities, and/or using an AI classification and/or learning engine, As another example, analyzing the receive signals may allow determining that the sun has emerged from behind a cloud, causing sweat to pool on a facial region of an individual and/or a heart rate to accelerate. The at least one processor may use the extracted information to distinguish a first reflection component indicative of prevocalization facial skin micromovements from other reflective components associated with, for example, motion, sweat beading on a surface of the facial skin, and/or an accelerated heart rate.

In some embodiments, the sensor is an image sensor configured to capture at least one event in an environment of the individual, and wherein the at least one processor is configured to determine that the event is associated with the at least one non-speech-related physical activity. An event in an environment of an individual may include an occurrence of an incident that may change a state of an individual. and/or a situation surrounding an individual, by an individual, and/or associated with an individual. Some examples of an event in an environment of an individual may include a change in background scenery due to motion of the individual, an action by another individual, an object, and/or an animal, a change in environmental conditions surrounding an individual. For instance, an image sensor may capture images of a dog running towards an individual, an onset of rain, and/or a person speaking with an individual. An image sensor (as described and exemplified elsewhere in this disclosure) configured to capture at least one event in an environment of an individual may refer to an image sensor configure to detect a plurality of image frames, that when analyzed by at least one processor, may allow the at least one processor to identify an event in an environment of an individual that may be associated with a non-speech related physical activity. For example, the at least one processor may determine that an onset of rain has caused an individual to run, and may attribute a second reflection component in a received signal to running. As another example, the at least one processor may determine that the individual has bent down to meet a dog and may attribute a second reflection component in a received signal to bending down.

By way of a non-limiting example, in FIG. 104, light signal 10400 may be received from a sensor associated with wearable housing 110, such that light signal 10400 may capture an effect of walking and/or sitting on facial region 108, in addition to an effect of prevocalization. At least one processor (e.g., processing device 400 of FIG. 4) may analyze the electronic representation of light signal 10400 received from light detector 412 to determine the at least one non-speech-related physical activity, e.g., using one or more of the signal processing, analysis, decomposition, matching, and/or classification techniques discussed elsewhere herein.

In some embodiments, the sensor (e.g., light detector 412) includes an image sensor configured to capture at least one event in an environment of individual 102. For example, the event may be associated with a shift in background scenery behind individual 102, indicating that individual is in motion. The at least one processor may determine that the event (e.g., a shifting background) is associated with the at least one non-speech-related physical activity (e.g., walking) by feeding information extracted from an electronic representation of light signal 10400 to a classification engine.

In some embodiments, the prevocalization facial skin micromovements correspond to one or more involuntary muscle fiber recruitments. Involuntary muscle fiber recruitments (e.g., involuntary facial muscle recruitment) may be understood as discussed and exemplified elsewhere in this disclosure. For example, prior to vocalizing at least one word (e.g., 0.1 to 0.5 seconds prior to vocalization), nerve signals may be transmitted automatically (e.g., involuntarily) to enlist one or more muscle fibers in preparation for vocalization. The involuntary nerve signals may cause selected muscles to contract slightly, and/or increase blood flow in the enlisted muscles. Such changes may be detected optically as prevocalization facial skin micromovements based on light reflecting off facial skin covering the recruited muscles. In some embodiments, the involuntary muscle fiber recruitments are a result of an individual thinking of saying the words as occurs during subvocalization. An individual thinking of saying words may involve an individual forming a thought (e.g., translating a thought to words, and/or performing one or more preparatory actions for vocalizing words. Such preparatory actions may include taking air into the lungs, opening the mouth, and/or moving the lips, cheeks, and/or tongue to form a shape such that subsequently, when air exist the lungs through the mouth, a sound may be emitted corresponding to the words. Such preparatory actions may additionally include eye motion (e.g., opening the eyes, blinking, making eye contact with another individual, and/or looking at a text), a bodily gesture (e.g., performing a hand, head, and/or eye motion associated with the words to be spoken, turning a head to face an individual, turning a head down to read a text), and/or any other action indicative of an individual preparing to vocalize words.

In some embodiments, the one or more muscle fiber recruitments include recruitments of at least one of zygomaticus muscle fibers, orbicularis oris muscle fibers, genioglossus muscle fibers, risorius muscle fibers, or levator labii superioris alaeque nasi muscle fibers. Fibers of a zygomaticus muscle, an orbicularis oris muscle, a risorius muscle, a genioglossus muscle, or a levator labii superioris alaeque nasi muscle (e.g., as discussed and exemplified elsewhere in this disclosure) may include muscle cells and/or muscle tissue capable of receiving and reacting to a nerve signal by twitching, contracting, and/or relaxing to thereby control physical motion of a body and/or react to a physical force on a body. In particular, zygomaticus, orbicularis oris, risorius, genioglossus, and/or levator labii superioris alaeque nasi muscle fibers may allow an individual to articular words for speaking, e.g., by controlling a shape of an air channel passing from the lungs, through the larynx and exiting from the mouth during speaking. At least one processor may attribute twitches and/or contractions of zygomaticus, orbicularis oris, risorius, genioglossus, and/or levator labii superioris alaeque nasi muscle fibers as prevocalization facial skin micromovements.

By way of a non-limiting example, in FIG. 104, the at least one processor (e.g., processing device 400 of FIG. 4) may determine that the prevocalization facial skin micromovements may correspond to one or more involuntary muscle fiber recruitments. For example, the involuntary muscle fiber recruitments may be a result of individual 102 thinking of saying words (e.g., omitting vocalization of words). The one or more muscle fiber recruitments may include recruitments of at least one of zygomaticus muscle fibers (e.g., extending diagonally across the cheek of individual 102), orbicularis oris muscle fibers (e.g., surrounding the mouth of individual 102), genioglossus muscle fibers (e.g., associated with the tongue of individual 102), risorius muscle fibers (e.g., associated with the cheek of individual 102), or levator labii superioris alaeque nasi muscle fibers e.g., associated with the nose of individual 102).

Some embodiments involve using a neural network to identify the second reflection component associated with the at least one non-speech-related physical activity. Using a neural network (as described and exemplified elsewhere in this disclosure) to identify a second reflection component associated with the at least one non-speech-related physical activity may include training a neural network with training data of facial skin movements associated with a plurality of non-speech-related physical activities, identifying one or more reflection components included in (e.g., non-training) signals representing light reflections from the facial skin region (e.g., by performing a decomposition on the signals), identifying one or more information components included in each reflection component, formatting each information component to a format consistent with a neural network, and submitting formatted information components to a trained neural network for classification. Based on the classification, at least one processor may determine which information components (e.g., and which associated reflection component) corresponds to a non-speech-related physical activity.

For example, light may reflect off an individual performing a non-speech-related physical activity (e.g., jumping) while performing prevocalization facial skin micromovements in preparation for vocalizing at least one word (e.g., "Hello!"). The jumping activity may cause cheeks of an individual to jiggle (e.g., a non-speech-related facial skin movements) to occur simultaneously with the prevocalization facial skin micromovements associated with saying "Hello!." Consequently, light reflecting off the facial skin of the individual may include at least a first reflection component associated with prevocalization facial skin micromovements for saying "Hello!" and a second reflection component associated with cheek jiggling caused by jumping, and which may introduce noise to the first reflection component. The noise may hamper a capability of at least one processor to identify "Hello!" from the first reflection component indicative of the prevocalization facial skin micromovements.

In some embodiments, the second reflection component is a result of walking. Walking (e.g., a type of non-speech-related physical activity) may refer to advancing a body at a substantially regular pace by alternately lifting and setting down each foot forward, where at any given time instant, at least one foot is on the ground. Walking may cause a head to move, for example, in a rhythmic bobbing (e.g., up and down and/or back and forth) motion due to successively and rhythmically lifting and setting down each foot and advancement of the body. The head motions attributable to walking may be captured in the signals representing light reflections from the facial skin region, e.g., by affecting the position of the facial skin region in each captured image frame, and/or by causing at least some facial skin regions to wobble or bounce due to the impact of each walking step. Such motion and/or movements may occur in addition to facial skin micromovements associated with prevocalization and may hamper a capability of at least one processor to distinguish the prevocalization facial skin micromovements using signals representing light reflections from the facial skin region. Consequently, at least a portion of the second reflection component of the signals may represent the skin movement due to walking. To overcome this, the at least one processor may identify and filter (e.g., remove) a second reflection component associated with walking from signals representing light reflections from the facial skin region, leaving a first reflection component indicating prevocalization facial skin micromovements for analysis (e.g., without interference from the second reflection component).

In some embodiments, an ancillary benefit of identifying, isolating and analyzing a reflection component associated with a non-speech-related physical activity may include use of the reflection component as an indicator of physical motion patterns and/or changes in physical motion patterns. For example, a neural network and/or an AI classification engine may learn characteristics of a gait of an individual (e.g., a gait rhythm, impact, asymmetry, and/or changes thereof) using information extracted from reflection components of light reflected off a facial skin region of an individual, as well as individual characteristics associated with sitting down, standing up, and performance of other non-speech related bodily motions. In some embodiments, at least one processor may use reflection components associated with non-speech related facial skin muscle micromovements to identify non-facial muscle activation patterns, e.g., using artificial intelligence and/or machine learning. For example, at least one processor may collect training data associating non-speech related facial skin muscle movements with known gait characteristics, and provide the training data to a neural network. Once the neural network has been trained, the at least one processor may submit information extracted from subsequently sensed signals representing non-speech related facial skin muscle movements to the neural network to determine a specific type of gait. In some embodiments, at least one processor may learn one or more characterizing physical motion patterns and/or changes in physical motion patterns based on reflection component of light reflected off a facial skin region of the individual. The at least one processor may subsequently use the learned physical motion patterns to analyze a signal representing light reflections from the facial skin and distinguish between the first reflection component indicative of prevocalization facial skin micromovements and the second reflection component associated with the at least one non-speech-related physical activity. For example, during a first time period, at least one processor may use a plurality of signals representing reflections of light off the facial skin of an individual to learn light patterns indicating an asymmetric gait (e.g., a limp) of the individual (e.g., using a neural network and/or AI engine). During a second time period following the first time period (e.g., once the neural network and/or AI engine have been trained), the individual may be walking (e.g., limping) while preparing to vocalize at least one word. The at least one processor may use the learned light patterns indicating an asymmetric gait to analyze a signal representing light reflections from the facial skin and distinguish between a first reflection component indicative of prevocalization facial skin micromovements and a second reflection component associated with the asymmetric gait (e.g., by extracting information from the second reflection component associated with the asymmetric gait and feeding the information to a trained neural network and/or AI engine).

In some embodiments, the second reflection component is a result of running. Running (e.g., a type of non-speech-related physical activity) may refer to advancing at a substantially regular pace by alternately lifting and setting down each foot forward (e.g., at a faster pace than walking), where during each step, there is a time instant during which both feet are off the ground. Running may cause a head to move in a rhythmic bobbing motion that may be more pronounced than walking due to successively and rhythmically lifting the body off the ground (e.g., due to both feet losing contact with the ground) and impact when returning the body to the ground (e.g., due to at least one foot regaining contact with the ground). Gravity combined with the impact from running may cause some facial skin regions to jiggle and/or bounce. Running may also cause breathing to become accelerated and deeper, resulting in additional facial skin movements (e.g., lips opening, nostrils flaring, and/or cheeks swelling). As with walking, the facial skin movements attributable to running may affect the position of the facial skin region in each captured image frame. Such movements may occur in addition to facial skin micromovements associated with prevocalization and may hamper a capability of at least one processor to distinguish the prevocalization facial skin micromovements in signals representing light reflections from the facial skin region. Consequently, at least a portion of the second reflection component of the signals may represent the skin movement due to running. To overcome this, the at least one processor may identify and filter (e.g., remove) a second reflection component associated with running from signals representing light reflections from the facial skin region, leaving a first reflection component indicative of prevocalization facial skin micromovements for analysis (e.g., without interference from the second reflection component).

In some embodiments, the second reflection component is a result of breathing. Breathing may involve an intaking of air into the lungs or expelling of air from the lungs via the nose or mouth. Breathing may cause facial skin to move rhythmically with each breath. For example, lips may open and close, nostrils may widen (e.g., flare) and contract, and/or cheeks may expand and contract, causing facial skin covering the lips, nostrils and/or cheeks to move. Thus, signals representing light reflections from the facial skin region may capture facial skin movements attributable to breathing in addition to facial skin micromovements associated with prevocalization, hampering a capability of at least one processor to distinguish the prevocalization facial skin micromovements. Consequently, at least a portion of the second reflection component of the signals may represent the skin movement due to breathing. To overcome this, the at least one processor may identify and filter (e.g., remove) a second reflection component associated with breathing from signals representing light reflections from the facial skin region, leaving a first reflection component indicative of prevocalization facial skin micromovements for analysis (e.g., without interference from the second reflection component).

In some embodiments, the second reflection component is a result of blinking and is based on neural activation of at least one orbicularis oculi muscle. Blinking (e.g., a type of non-speech-related physical activity) may involve a semi-autonomic rapid closing of the eyelid, and may occur, for example, approximately 15 times per minute. Blinking may protect the eyes from foreign objects, and may moisten the eyes by causing the eyelid to move fluid (e.g., tears) from the lacrimal gland (e.g., tear duct) across the eye. An orbicularis oculi muscle may refer to a facial muscle encircling the eye, and extending (e.g., clockwise when facing a right eye) from the eyebrow to the bridge of the nose, to an upper cheek region, and to the right temple. An orbicularis oculi muscle may close the eyelid for blinking and may assist in pumping fluid from the eye to the nasolacrimal duct system. Blinking may cause periodic (e.g., rhythmic) and rapid facial skin movements of the eyebrow, eyelid, nose bridge, upper cheek region and temple. The facial skin motion attributable to blinking may cause facial skin of the cheek and/or nose to move, in addition to facial skin micromovements indicative of prevocalization. Thus, signals representing light reflections from the facial skin region may capture facial skin movements attributable to blinking and facial skin micromovements associated with prevocalization, hampering a capability of at least one processor to distinguish the prevocalization facial skin micromovements. Consequently, at least a portion of the second reflection component of the signals may represent the skin movement due to blinking. To overcome this, the at least one processor may identify and filter (e.g., remove) a second reflection component associated with blinking from signals representing light reflections from the facial skin region, leaving a first reflection component indicative of prevocalization facial skin micromovements for analysis (e.g., without interference from the second reflection component).

By way of a non-limiting example, in FIG. 4, the at least one processor (e.g., processing device 400) may access remote processing system 450 via communications network 126 to use a neural network to identify second reflection component 10604 (e.g., see FIG. 106) associated with the at least one non-speech-related physical activity. For instance, the at least one processor may classify information component 10610 in association with walking, running, breathing, or blinking, e.g., by querying a database, using a neural network, and/or using an AI classification, matching, and/or learning engine.

Some disclosed embodiments involve filtering out the second reflection component to enable interpretation of words from the first reflection component indicative of the prevocalization facial skin micromovements. Filtering out (e.g., a signal) may include separating, distinguishing, blocking, and/or at least partially suppressing or subtracting a portion of a signal. Filtering may include applying a low-pass filter (e.g., only allowing frequencies below a threshold), a high-pass filter (e.g., only allowing frequencies above a threshold), a band-pass filter (e.g., only allowing a range of frequencies), a Chebyshev filter, a Gaussian filter, a finite and/or infinite impulse response filter, an elliptic filter, a Butterworth filter, and/or any other type of filter. Filtering out a reflection component may be performed optically on a light signal (e.g., using one or more lenses), electronically on an electronic signal representative of a light signal (e.g., using one or more electronic switches), and/or digitally on a digital representation of a light signal (e.g., using at least one processor executing one or more filtering algorithms). Filtering out a reflection component may involve removal of a reflection component from a light signal reflected off a facial region of an individual. Removing a reflection component from a light signal may include applying an optical filter, a digital filter (e.g., to a mathematical representation of a signal), and/or an electronic filter (e.g., to an electronic representation of a signal). For example, upon identifying a first reflection component associated with prevocalization facial skin micromovements and a second reflection component associated with at least one non-speech-related physical activity in signals representing light reflections from the facial skin region, at least one processor may subtract (e.g., a mathematical representation of) the second reflection component from the signals, such that (e.g., a mathematical representation of) the first reflection component (e.g., indicative of prevocalization facial skin micromovements) may remain for analysis (e.g., without interference from the second reflection component). To enable interpretation of words from the first reflection component indicative of prevocalization facial skin micromovements may be understood as discussed and exemplified elsewhere herein, e.g., based on signals representing light reflections from the facial skin region including a first reflection component associated with prevocalization facial skin micromovements, and absent a second reflection component associated with a non-speech-related physical activity.

In some embodiments, the at least one processor may use the remaining first reflection component (e.g., after subtracting the second reflection component) to determine at least one word to be spoken corresponding to the prevocalization facial skin micromovements. For example, the at least one processor may convert signals representing light reflections from the facial skin region of an individual to a digital representation (e.g., by sampling the signals). The at least one processor may analyze the digital representation of the signals (e.g., using Fourier analysis) to determine first and second reflection components, as well as information components (e.g., features) from each reflection component. The at least one processor may use a history of patterns associated with non-speech-related physical activity to attribute at least one of the information components to a specific non-speech-related physical activity (e.g., by querying, comparing, matching, and/or classifying as discussed elsewhere herein). The at least one processor may subtract the information component associated with non-speech-related physical activity from the signals, such that information components included in the first reflection component indicative of prevocalization remain. The at least one processor may analyze the remaining first reflection component (and/or information components included therein) to determine prevocalization facial skin micromovements associated with at least one word to be spoken, as discussed and exemplified elsewhere in this disclosure.

By way of a non-limiting example, in FIG. 106, the at least one processor (e.g., processing device 400 of FIG. 4) may filter out second reflection component 10604 from signal 10600 to enable interpretation of words from first reflection component 10602 indicative of the prevocalization facial skin micromovements. For example, the at least one processor may subtract second reflection component 10604 from signal 10600, such that first reflection component 10602 remains. The at least one processor may interpret words from first reflection component 10602, as described elsewhere herein.

By way of another non-limiting example, in FIG. 109, the at least one processor may filter out the second reflection component (e.g., noise components 10904) from representation 10900 of light signal such that first reflection component, indicative of the prevocalization facial skin micromovements, remains (e.g., representation 10900 of light signal 10400 minus noise components 10904), enabling interpretation of words from the first reflection component.

In some embodiments, when the individual is concurrently involved in a first physical activity and a second physical activity, the operations further include identify a first portion of the second reflection component associated with the first physical activity and a second portion of the second reflection component associated with the second physical activity and filtering out the first portion of the second component and the second portion of the second component from the first component to enable interpretation of words from the prevocalization facial skin micromovements associated with the first component. An individual concurrently involved in a first physical activity and a second physical activity may include an individual performing two different physical activities at the same time (e.g., substantially simultaneously). For example, an individual may walk (e.g., perform a first physical activity) while turning the head (e.g., a second physical activity). Walking may cause the facial skin to perform a first non-speech-related movement, and turning the head may cause the facial skin to perform a second non-speech-related movement. As another example, a person may tear while running, causing a tear drop to fall on a cheek. The sensation of the tear drop on the cheek may cause facial skin covering the cheek to perform a first non-speech-related movement, and running may cause the facial skin to perform a second non-speech-related movement. Identifying a first portion of a second reflection component associated with a first physical activity and a second portion of a second reflection component associated with a second physical activity may involve at least one processing performing an additional classification round on a second reflection component belonging to a non-speech-related classification to identify one or more non-speech-related sub-classifications (e.g., using the same or different classification tool described earlier). The additional classification round may allow the at least one processor to distinguish first and second portions of the second reflection component, each associated with a differing non-speech-related physical activity. For example, a first portion of the second (e.g., non-speech-related) reflection component may be associated with a head turning motion and a second portion of the second reflection component may be associated with walking. As another example, a first portion of the second reflection component may be associated with a response of a cheek to a tear drop, and a second portion of the second reflection component may be associated with running. Filtering out the first portion of the second component and the second portion of the second component from the first component to enable interpretation of words from the prevocalization facial skin micromovements associated with the first component may involve at least one processor removing the first and second portions of the second component from the signals representing light reflections from the facial skin region such that the first reflection component indicative of prevocalization facial skin micromovements remains. For example, at least one processor may convert the received signals to a mathematical representation and perform a decomposition (e.g., a feature extraction) on the mathematical representation to identify the first and second reflection components, and/or information components included therein. The at least one processor may classify each reflection component as described earlier. The at least one processor may perform an additional decomposition and/or feature extraction on the mathematical representation of the second reflection component classified as a non-speech-related physical activity to identify a first portion and a second portion. The at least one processor may sub-classify the first and second portions to associate a first non-speech related physical activity (e.g., walking) with the first portion and a second non-speech related physical activity (e.g., turning the head) with the second portion. The at least one processor may remove the first and second portions of the second reflection component from the signals as described earlier for removing the second reflection component from the received signals. For example, the at least one processor may subtract a mathematical representation of the first and second portions of the second reflection component from a mathematical representation of the received signals, such that a mathematical representation of the first reflection component indicative of prevocalization remains. The at least one processor may analyze the first reflection component (e.g., absent interference from the second reflection component) to enable interpreting words to be spoken.

Figure 107:
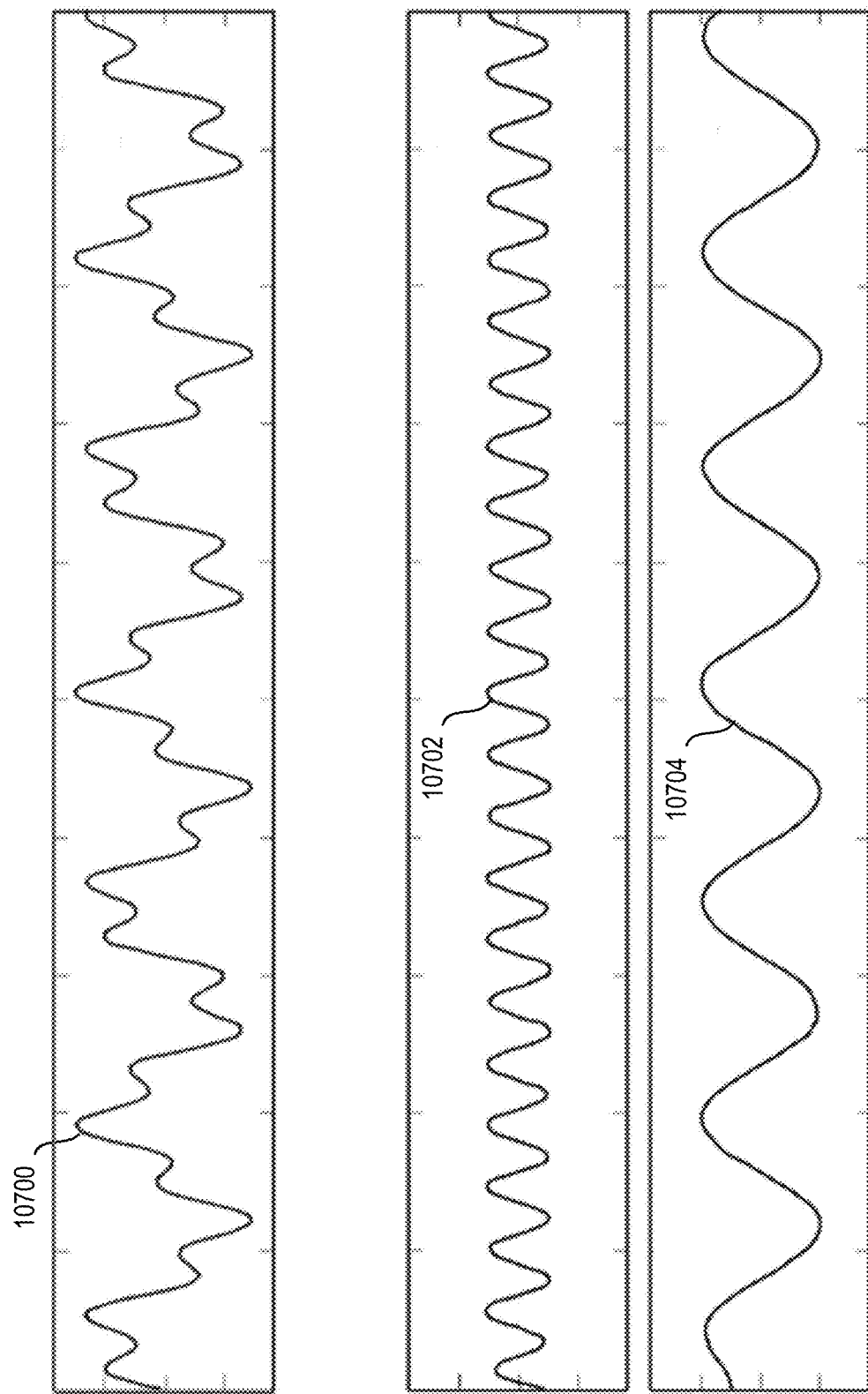
FIG. 107 illustrates an exemplary second reflection component of a light signal reflecting from the facial region of individual concurrently involved in a first physical activity and a second physical activity, consistent with embodiments of the present disclosure.

By way of a non-limiting example, FIG. 107 illustrates an exemplary second reflection component 10700 of light signal 10400 reflecting from facial region 108 of individual 102 concurrently involved in a first physical activity (e.g., walking) and a second physical activity (e.g., turning of the head), consistent with embodiments of the present disclosure. The at least one processor (e.g., processing device 400 of FIG. 4) may identify a first portion 10702 of second reflection component 10700 associated with the first physical activity (e.g., walking) and a second portion 10704 of the second reflection component 10700 associated with the second physical activity (e.g., turning the head). The at least one processor may filter out first portion 10702 of second reflection component 10700 and second portion 10704 of second reflection component 10700 from the first component (e.g., first reflection component 10602 of FIG. 106) to enable interpretation of words from the prevocalization facial skin micromovements associated with first reflection component 10602.

Some embodiments involve receiving data from a mobile communications device, the data being indicative of the at least one non-speech-related physical activity. A mobile communications device may include any electronics equipment that may move with an individual wearing a speech detection system. A mobile communications device may include a mobile phone, a tablet, an electronic notepad, a laptop computer, a smart watch, smart clothing, smart jewelry, a wearable Personal Digital Assistant, a heart monitor, a pacemaker, a hearing aid, and/or any other electronic device configured to communicate via a communications network. Data indicative of at least one non-speech-related physical activity may include location data, tracking data (e.g., data associated with velocity, acceleration, elevation, and/or orientation of an individual), physiological data (e.g., a heart and/or breathing rate, heart and/or blood pressure, body temperature, an amount of sweat generated), voice data (e.g., capturing one or more sounds), image data (e.g., capturing one or more bodily gestures), biometric data, and/or any other type of digitally encoded information indicating a non-speech related activity. For example, at least one processor may associate an elevated heart rate in combination with motion based on tracking data with walking or running (e.g., a non-speech related activity). As another example, at least one processor may associate a change in pose and/or posture of an individual based on image data to determine the person is in the process of sitting (from standing) or in the process of standing (from sitting). As a further example, the at least one processor may receive data associated with a non-speech related physical activity from a software application installed on a mobile communications device for tracking physical activities.

In some embodiments, the data received from the mobile communications device includes at least one of: data indicative of a heart rate of the individual, data indicative of blood pressure of the individual, or data indicative of movement of the individual. Data indicative of a heart rate may include data received from a heart rate monitor (e.g., worn on the chest, around the neck as a necklace, worn on a wrist as a bracelet) and configured to detect a frequency of heart beats (e.g., as a number of heart beats per minute). The heart rate monitor may include an image sensor, with heart rate data derived from a plurality of successive images. Additionally, heart rate data may be derived from a sensor that detects facial skin light reflections. Data indicative of blood pressure may include data received from a digital blood pressure monitor and/or a software application configured to estimate blood pressure. Data indicative of blood pressure may be measured in units of millimeters of mercury (mmHg), and may include a pair of values, with the upper (systolic) value first measuring pressure when the heart muscles contract, followed by the lower (diastolic) value measuring pressure when the heart muscles relax. For example, at least one processor may attribute a higher than average hear rate and/or blood pressure with physical exertion associated with a non-speech-related physical activity. Data indicative of movement of an individual may include tracking data, location data, and/or navigation data.

Receiving data indicative of at least one non-speech-related physical activity from a mobile communications device may involve establishing a connection to a mobile communications device (e.g., a wired and/or wireless connection), and receiving encoded information associated with a non-speech-related physical activity, e.g., as one or more packets and/or a data stream. For example, tracking information indicative of a non-speech related physical activity (e.g., a movement of an individual) may be received from an inertial measurement unit of a mobile communications device, and/or from a software application (e.g., a navigation application like Google Maps®, and/or a tracking application such as Strava®). As another example, location data indicative of a non-speech related physical activity (e.g., a movement of an individual) may be received from a mobile (e.g., cellular) communications network and/or from a satellite network (e.g. Global Positioning System). As a further example, physiological data (e.g., a heart rate and/or blood pressure) may be received from a heart rate monitor and/or an electronic blood pressure monitor paired to a speech detection system. Additionally or alternatively, at least one processor may receive data indicative of a non-speech related physical activity from a social media account accessible via the mobile communications device, as user-generated data (e.g., image, voice, and/or text data), and/or any other type of encoded information. For instance, an individual may post on a social media account an image of the individual climbing a mountain and at least one processor may analyze the image with an associated timestamp to determine that the individual is currently engaged in mountain climbing.

In some embodiments, the mobile communications device lacks a light sensor for detecting the light reflections. Lacking a light sensor may refer to an absence of a light sensor, such that (e.g., visible) light signals may not be detectable by the mobile communications device. A mobile communications device lacking a light sensor for detecting the light reflections may refer to a mobile communications device that does not have a light sensor, and/or a mobile communications device including a light sensor located and/or oriented in a manner preventing detection of light reflecting off a face of an individual. For example, a mobile device may be located in the individual's pocket, and/or worn under clothing. Consequently, data received from a mobile communications device indicative of the at least one non-speech-related physical activity may include data other that does not include data associated with light reflecting off the face of the individual.

By way of a non-limiting example, in FIG. 103, the at least one processor (e.g., processing device 400 of FIG. 4) may receive data from mobile communications device 120, the data being indicative of the at least one non-speech-related physical activity. The data received from the mobile communications device 120 may include at least one of: data indicative of a heart rate of individual 102, data indicative of blood pressure of individual 102, or data indicative of movement of individual 102. In some embodiments, mobile communications device 120 may lack a light sensor for detecting light signals 10400 reflecting from facial region 108 of individual 102 (e.g., see FIG. 104).

Some embodiments involve presenting the words in a synthesized voice. Presenting words may include displaying words on an electronic display (e.g., as text, images, and/or video) and/or playing an audible rendition of words via a speaker. Presenting words in a synthesized voice may be understood as speech synthetization of the at least one word, as described and exemplified elsewhere in this disclosure. For example, upon interpreting words from the first reflection component indicative of the prevocalization facial skin micromovements, the at least one processor may invoke a speech synthesizer to produce an audible rendition of the words, and transmit the audible rendition to a speaker for presenting audibly to one or more individuals.

By way of a non-limiting example, in FIG. 103, at least one processor (e.g., processing device 400 of FIG. 1) may present the words in a synthesized voice via a speaker of mobile communications device 120.

Figure 108:
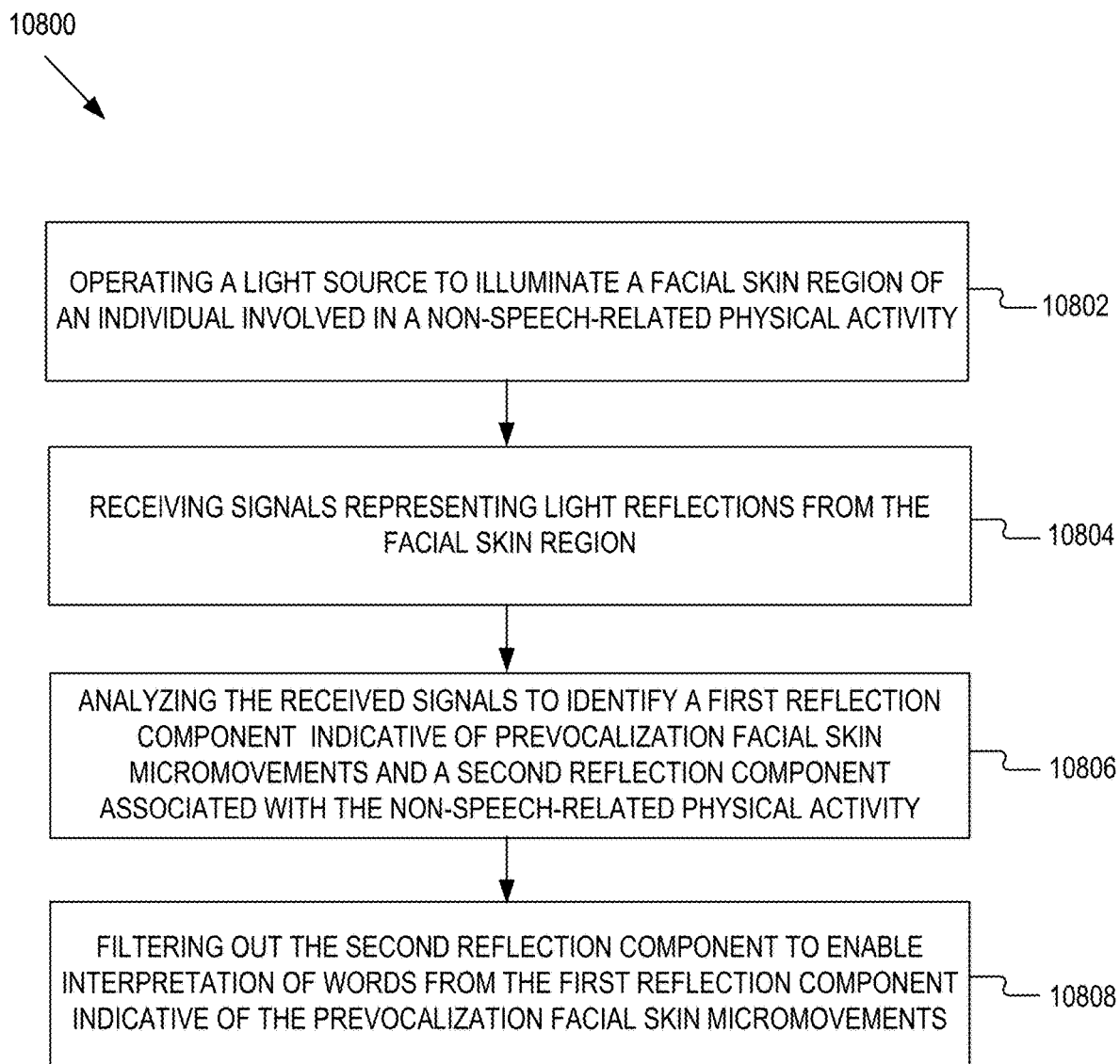
FIG. 108 illustrates a flowchart of example process for removing noise from facial skin micromovement signals, consistent with embodiments of the present disclosure.

FIG. 108 illustrates a flowchart of example process 10800 for removing noise from facial skin micromovement signals, consistent with embodiments of the present disclosure. In some embodiments, process 10800 may be performed by at least one processor (e.g., processing device, 400 shown in FIG. 4) to perform operations or functions described herein. In some embodiments, some aspects of process 10800 may be implemented as software (e.g., program codes or instructions) that are stored in a memory (e.g., memory device 402) or a non-transitory computer readable medium. In some embodiments, some aspects of process 10800 may be implemented as hardware (e.g., a specific-purpose circuit). In some embodiments, process 10800 may be implemented as a combination of software and hardware.

Referring to FIG. 108, process 10800 may include a step 10802 of operating a light source in a manner enabling illumination of a facial skin region of an individual during a time period when the individual is involved in at least one non-speech-related physical activity, as described earlier. By way of a non-limiting example, in FIG. 103, at least one processor (e.g., processing device 400 of FIG. 4) may operate light source 410 of optical sensing unit 116 in a manner enabling illumination of facial region 108 of individual 102 while individual 102 is walking.

Process 10800 may include a step 10804 of receiving signals representing light reflections from the facial skin region, as described earlier. By way of a non-limiting example, in FIG. 104, light detector 412 (e.g., see FIG. 4) may detect light signal 10400 reflecting off facial region 108 and may transmit electronic signals representing reflected light signal 10400 to at least one processor (e.g., processing device 400).

Process 10800 may include a step 10806 of analyzing the received signals to identify a first reflection component indicative of prevocalization facial skin micromovements and a second reflection component associated with the at least one non-speech-related physical activity, as described earlier. By way of a non-limiting example, in FIG. 106, at least one processor (e.g., processing device 400 of FIG. 4) may analyze an electronic representation 10600 of light signal 10400 to identify first reflection component 10602 indicative of prevocalization facial skin micromovements and second reflection component 10604 associated with the at least one non-speech-related physical activity (e.g., walking).

Process 10800 may include a step 10808 of filtering out the second reflection component to enable interpretation of words from the first reflection component indicative of the prevocalization facial skin micromovements, as described earlier. By way of a non-limiting example, in FIG. 106, at least one processor (e.g., processing device 400 of FIG. 4) may filter out second reflection component 10604 to enable interpretation of words from first reflection component 10602 indicative of the prevocalization facial skin micromovements.

Some embodiments involve a system for the steps discussed above. By way of a non-limiting example, in FIG. 103, at least one processor (e.g., processing device 400 of FIG. 4) may operate light source 410 of optical sensing unit 116 in a manner enabling illumination of facial region 108 of individual 102 while individual 102 is walking. In FIG. 104, light detector 412 may detect light signal 10400 reflecting off facial region 108 and may transmit electronic signals representing reflected light signal 10400 to the at least one processor. In FIG. 106, the at least one processor may analyze electronic representation 10600 of light signal 10400 to identify first reflection component 10602 indicative of prevocalization facial skin micromovements and second reflection component 10604 associated with the at least one non-speech-related physical activity (e.g., walking). The at least one processor may filter out second reflection component 10604 to enable interpretation of words from first reflection component 10602 indicative of the prevocalization facial skin micromovements.

Various example embodiments of speech detection technology are articulated below in the form of clauses. It is to be understood the term "technology" refers equally to systems, methods, and non-transitory computer readable media:

Clause 1. A speech detection technology for identifying individuals using facial skin micromovements, the technology comprising: a wearable housing configured to be worn on a head of an individual; at least one coherent light source associated with the wearable housing and configured to project light towards a facial region of the head; at least one detector associated with the wearable housing and configured to receive coherent light reflections from the facial region and to output associated reflection signals; at least one processor configured to: analyze the reflection signals to determine specific facial skin micromovements of the individual; access memory correlating a plurality of facial skin micromovements with the individual; search for a match between the determined specific facial skin micromovements and at least one of the plurality of facial skin micromovements in the memory; if a match is identified, initiate a first action; and if a match is not identified, initiate a second action different from the first action.

Clause 2. The technology of clause 1, wherein the first action institutes at least one predetermined setting associated with the individual.

Clause 3. The technology of each preceding clause, wherein the first action unlocks a computing device, and the second action includes presentation of a message indicating that the computing device remains locked.

Clause 4. The technology of each preceding clause, wherein the first action provides personal information, and the second action provides public information.

Clause 5. The technology of each preceding clause, wherein the first action authorizes a transaction, and the second action provides information indicating that the transaction is not authorized.

Clause 6. The technology of each preceding clause, wherein the first action permits access to an application, and the second action prevents access to the application.

Clause 7. The technology of each preceding clause, wherein at least some of the specific facial skin micromovements in the facial region are micromovements of less than 100 microns.

Clause 8. The technology of each preceding clause, wherein the specific facial skin micromovements correspond to prevocalization muscle recruitment.

Clause 9. The technology of each preceding clause, wherein the specific facial skin micromovements correspond to muscle recruitment during pronunciation of at least one word.

Clause 10. The technology of each preceding clause, wherein the at least one word corresponds to a password.

Clause 11. The technology of each preceding clause, wherein the memory is configured to correlate a plurality of facial skin movements with a plurality of individuals, and wherein the at least one processor is configured to distinguish the plurality of individuals from each other based on reflection signals unique to each of the plurality of individuals.

Clause 12. The technology of each preceding clause, further include an integrated audio output and wherein at least one of the first action or at least one of the second action includes outputting audio via the audio output.

Clause 13. The technology of each preceding clause, wherein the match is identified upon determination by the at least one processor of a certainty level.

Clause 14. The technology of each preceding clause, wherein when the certainty level is initially not reached, the at least one processor is configured to analyze additional reflection signals to determine additional facial skin micromovements, and to arrive at the certainty level based at least in part on analysis of the additional reflection signals.

Clause 15. The technology of each preceding clause, wherein the at least one processor is further configured to continuously compare new facial skin micromovements with the plurality of facial skin micromovements in the memory to determine an instantaneous level of certainty.

Clause 16. The technology of each preceding clause, wherein, after initiating the first action, when the instantaneous certainty level is below a threshold, the at least one processor is configured to stop the first action.

Clause 17. The technology of each preceding clause, wherein, when the instantaneous certainty level is below a threshold, the at least one processor is configured to initiate an associated action.

Clause 18. The technology of each preceding clause, wherein initiating the first action is associated with an event, and the at least one processor is configured to continuously compare the new facial skin micromovements during the event.

Clause 19. Speech detection technology for interpreting facial skin movements as set forth in this clause alone, and/or in combination with each preceding clause, further comprising: projecting light on a plurality of facial region areas of an individual, wherein the plurality of areas includes at least a first area and a second area, the first area being closer to at least one of a zygomaticus muscle or a risorius muscle than the second area; receiving reflections from the plurality of areas; detecting first facial skin movements corresponding to reflections from the first area and second facial skin movements corresponding to reflections from the second area; determining, based on differences between the first facial skin movements and the second facial skin movements, that the reflections from the first area closer to the at least one of a zygomaticus muscle or a risorius muscle are a stronger indicator of communication than the reflections from the second area; based on the determination that the reflections from the first area are a stronger indicator of communication, processing the reflections from the first area to ascertain the communication, and ignoring the reflections from the second area.

Clause 20. The technology of each preceding clause, wherein the first area and the second area are spaced apart.

Clause 21. The technology of each preceding clause, wherein the communication ascertained from the reflections from the first area includes words articulated by the individual.

Clause 22. The technology of each preceding clause, wherein the communication ascertained from the reflections from the first area includes non-verbal cues of the individual.

Clause 23. The technology of each preceding clause, further include operating a coherent light source located within a wearable housing in a manner enabling illumination of the plurality of facial region areas.

Clause 24. The technology of each preceding clause, further include operating a coherent light source located remote from a wearable housing in a manner enabling illumination of the plurality of facial region areas.

Clause 25. The technology of each preceding clause, further include illuminating at least a portion of the first area and at least a portion of the second area with a common light spot.

Clause 26. The technology of each preceding clause, further include illuminating the first area with a first group of spots and illuminating the second area with a second group of spots distinct from the first group of spots.

Clause 27. The technology of each preceding clause, further include operating a coherent light source in a manner enabling bi-mode illumination of the plurality of facial region areas, analyzing reflections associated with a first mode of illumination to identify one or more light spots associated with the first area, and analyzing reflections associated with a second mode of illumination to ascertain the communication.

Clause 28. The technology of each preceding clause, wherein a first light intensity of the first mode of illumination differs from a second light intensity of the second mode of illumination.

Clause 29. The technology of each preceding clause, wherein a first illumination pattern of the first mode of illumination differs from a second illumination pattern of the second mode of illumination.

Clause 30. The technology of each preceding clause, further include determining, based on differences between the first facial skin movements and the second facial skin movements, that the first area is closer than the second area to the subcutaneous tissue associated with cranial nerve V or with cranial nerve VII.

Clause 31. The technology of each preceding clause, wherein the first area is closer than the second area to the zygomaticus muscle, and the plurality of light areas further includes a third area closer to the risorius muscle than each of the first area and the second area.

Clause 32. The technology of each preceding clause, further include analyzing reflected light from the first area when speech is generated with perceptible vocalization and analyzing reflected light from the third area when speech is generated in an absence of perceptible vocalization.

Clause 33. The technology of each preceding clause, wherein the differences between the first facial skin movements and the second facial skin movements include differences of less than 100 microns, and the determination that the reflections from the first area are a stronger indicator of communication than the reflections from the second area is based on the differences of less than 100 microns.

Clause 34. The technology of each preceding clause, wherein ignoring the reflections from the second area includes omitting use of the reflections from the second area to ascertain the communication.

Clause 35. The technology of each preceding clause, wherein detecting the first facial skin movements involves performing a first speckle analysis on light reflected from the first area, and wherein detecting the second facial skin movements involves performing a second speckle analysis on light reflected from the second area.

Clause 36. The technology of each preceding clause, wherein the first speckle analysis and the second speckle analysis occur concurrently by the at least one processor.

Clause 37. Speech detection technology for performing identity verification operations based on facial micromovements as set forth in this clause alone, and/or in combination with each preceding clause, further comprising: receiving in a trusted manner, reference signals for verifying correspondence between a particular individual and an account at an institution, the reference signals being derived based on reference facial micromovements detected using first coherent light reflected from a face of the particular individual; storing in a secure data structure, a correlation between an identity of the particular individual and the reference signals reflecting the facial micromovements; following storing, receiving via the institution, a request to authenticate the particular individual; receiving real-time signals indicative of second coherent light reflections being derived from second facial micromovements of the particular individual; comparing the real-time signals with the reference signals stored in the secure data structure to thereby authenticate the particular individual; and upon authentication, notifying the institution that the particular individual is authenticated.

Clause 38. The technology of each preceding clause, wherein the authentication is associated with a financial transaction at the institution.

Clause 39. The technology of each preceding clause, wherein the financial transaction includes at least one of: a transfer of funds, a purchase of stocks, a sale of stocks, an access to financial data, or access to an account of the particular individual.

Clause 40. The technology of each preceding clause, wherein receiving the real-time signals and comparing the real-time signals occur multiple times during a transaction, and further include: reporting a mismatch if a subsequent difference is detected following the notifying.

Clause 41. The technology of each preceding clause, further include determining a certainty level that an individual associated with the real-time signals is the particular individual.

Clause 42. The technology of each preceding clause, wherein, when the certainty level is below a threshold, further include terminating the transaction.

Clause 43. The technology of each preceding clause, wherein the transaction is a financial transaction that includes providing access to the particular individual's account, and when a certainty level is below a threshold, further include blocking the individual associated with the real-times signals from the particular individual's account.

Clause 44. The technology of each preceding clause, wherein the reference signals for authentication correspond to muscle activation during pronunciation of at least one word.

Clause 45. The technology of each preceding clause, wherein the muscle activation is associated with at least one specific muscle that includes: a zygomaticus muscle, an orbicularis oris muscle, a risorius muscle, a genioglossus muscle, or a levator labii superioris alaeque nasi muscle.

Clause 46. The technology of each preceding clause, wherein the at least one word is a password.

Clause 47. The technology of each preceding clause, further include presenting the at least one word to the particular individual for pronunciation.

Clause 48. The technology of each preceding clause, wherein presenting the at least one word to the particular individual for pronunciation includes audibly presenting the at least one word.

Clause 49. The technology of each preceding clause, wherein presenting the at least one word to the particular individual for pronunciation includes textually presenting the at least one word.

Clause 50. The technology of each preceding clause, wherein the reference signals for authentication correspond to muscle activation during pronunciation of one or more syllables.

Clause 51. The technology of each preceding clause, wherein the institution is associated with an online activity, and upon authentication, the particular individual is provided access to perform the online activity.

Clause 52. The technology of each preceding clause, wherein the online activity is at least one of: a financial transaction, a wagering session, an account access session, a gaming session, an exam, a lecture, or an educational session.

Clause 53. The technology of each preceding clause, wherein the institution is associated with a resource, and upon authentication, the particular individual is provided access to the resource.

Clause 54. The technology of each preceding clause, wherein the resource is at least one of: a file, a folder, a data structure, a computer program, computer code, or computer settings.

Clause 55. Speech detection technology for providing identity verification based on facial micromovements as set forth in this clause alone, and/or in combination with each preceding clause, further comprising: receiving during an ongoing electronic transaction, first signals representing coherent light reflections associated with first facial skin micromovements during a first time period; determining, using the first signals, an identity of a specific individual associated with the first facial skin micromovements; receiving during the ongoing electronic transaction second signals representing coherent light reflections associated with second facial skin micromovements, the second signals being received during a second time period following the first time period; determining, using the second signals, that the specific individual is also associated with the second facial skin micromovements; receiving during the ongoing electronic transaction third signals representing coherent light reflections associated with third facial skin micromovements, the third signals being received during a third time period following the second time period; determining, using the third signals, that the third facial skin micromovements are not associated with the specific individual; and initiating an action based on the determination that the third facial skin micromovements are not associated with the specific individual.

Clause 56. The technology of each preceding clause, wherein the ongoing electronic transaction is a phone call.

Clause 57. The technology of each preceding clause, wherein during the second time period, further include continuously outputting data confirming that the specific individual is associated with the second facial skin micromovements.

Clause 58. The technology of each preceding clause, wherein the action includes providing an indication that the specific individual is not responsible for the third detected facial skin micromovements.

Clause 59. The technology of each preceding clause, wherein the action includes executing a process for identifying another individual responsible for the third facial skin micromovements.

Clause 60. The technology of each preceding clause, wherein the first period of time, the second period of time, and the third period of time are part of a single online activity associated with the ongoing electronic transaction.

Clause 61. The technology of each preceding clause, wherein the online activity is at least one of: a financial transaction, a wagering session, an account access session, a gaming session, an exam, a lecture, or an educational session.

Clause 62. The technology of each preceding clause, wherein the online activity includes multiple sessions, further include using received signals associate with facial skin micromovements to determine that the specific individual participates in each of the multiple sessions.

Clause 63. The technology of each preceding clause, wherein the action includes notifying an entity associated with the online activity that an individual other than the specific individual is now participating in the online activity.

Clause 64. The technology of each preceding clause, wherein the action includes preventing participation in the online activity until the identity of specific individual is confirmed.

Clause 65. The technology of each preceding clause, wherein the first period of time, the second period of time, and the third period of time are part of a secured session with access to a resource.

Clause 66. The technology of each preceding clause, wherein the resource is at least one of: a file, a folder, a database, a computer program, a computer code, or computer settings.

Clause 67. The technology of each preceding clause, wherein the action includes notifying an entity associated with the resource that an individual other than the specific individual gained access to the resource.

Clause 68. The technology of each preceding clause, wherein the action includes terminating the access to the resource.

Clause 69. The technology of each preceding clause, wherein the first period of time, the second period of time, and the third period of time are part of a single communication session, and wherein the communication session is at least one of: a phone call, a teleconference, a video conference, or a real-time virtual communication.

Clause 70. The technology of each preceding clause, wherein the action includes notifying an entity associated with the communication session that an individual other than the specific individual has joined the communication session.

Clause 71. The technology of each preceding clause, wherein determining the identity of the specific individual includes accessing memory correlating a plurality of reference facial skin micromovements with individuals and determining a match between the first facial skin micromovements and at least one of the plurality of reference facial skin micromovements.

Clause 72. The technology of each preceding clause, further include determining the first facial skin micromovements, the second facial skin micromovements, and the third facial skin micromovements by analyzing signals indicative of received coherent light reflections to identify temporal and intensity changes of speckles.

Clause 73. Speech detection technology for performing thresholding operations for interpretation of facial skin micromovements as set forth in this clause alone, and/or in combination with each preceding clause, further comprising: detecting facial micromovements in an absence of perceptible vocalization associated with the facial micromovements; determining an intensity level of the facial micromovements; comparing the determined intensity level with a threshold; when the intensity level is above the threshold, interpreting the facial micromovements; and when the intensity level falls beneath the threshold, disregarding the facial micromovements.

Clause 74. The technology of each preceding clause, further include enabling adjustment of the threshold.

Clause 75. The technology of each preceding clause, wherein the threshold is variable, depending on environmental conditions.

Clause 76. The technology of each preceding clause, wherein the environmental conditions include a background noise level.

Clause 77. The technology of each preceding clause, further include receiving data indicative of the background noise level, and determining a value for the threshold based on the received data.

Clause 78. The technology of each preceding clause, wherein the threshold is variable, depending on at least one physical activity engaged in by an individual associated with the facial micromovements.

Clause 79. The technology of each preceding clause, wherein the at least one physical activity includes walking, running, or breathing.

Clause 80. The technology of each preceding clause, further include receiving data indicative of the of the at least one physical activity in which the individual is engaged, and determining a value for the threshold based on the received data.

Clause 81. The technology of each preceding clause, wherein the threshold is customized to a user.

Clause 82. The technology of each preceding clause, further include receiving a personalized threshold for a particular individual and storing the personalized threshold in settings associated with the particular individual.

Clause 83. The technology of each preceding clause, further include receiving a plurality of thresholds for a particular individual, each of the plurality of thresholds being associated with a differing condition.

Clause 84. The technology of each preceding clause, wherein at least one of the differing conditions includes a physical condition of the particular individual, an emotional condition of the particular individual, or a location of the particular individual.

Clause 85. The technology of each preceding clause, further include receiving data indicative of a current condition of the particular individual, and selecting one of the plurality of thresholds based on the received data.

Clause 86. The technology of each preceding clause, wherein interpreting the facial micromovements includes synthesizing speech associated with the facial micromovements.

Clause 87. The technology of each preceding clause, wherein interpreting the facial micromovements includes understanding and executing a command based on the facial micromovements.

Clause 88. The technology of each preceding clause, wherein executing the command includes generating a signal for triggering an action.

Clause 89. The technology of each preceding clause, wherein determining the intensity level includes determining a value associated with a series of micromovements in a time period.

Clause 90. The technology of each preceding clause, wherein the facial micromovements having an intensity level falling beneath the threshold are capable of interpretation but are disregarded nevertheless.

Clause 91. Speech detection technology for establishing nonvocalized conversations as set forth in this clause alone, and/or in combination with each preceding clause, further comprising: establishing a wireless communication channel for enabling a nonvocalized conversation via a first wearable device and a second wearable device, wherein both the first wearable device and the second wearable device each contain a coherent light source and a light detector configured to detect facial skin micromovements from coherent light reflections; detecting by the first wearable device first facial skin micromovements occurring in an absence of perceptible vocalization; transmitting a first communication via the wireless communication channel from the first wearable device to the second wearable device, wherein the first communication is derived from the first facial skin micromovements and is transmitted for presentation via the second wearable device; receiving a second communication via the wireless communication channel from the second wearable device, wherein the second communication is derived from second facial skin micromovements detected by the second wearable device; and presenting the second communication to a wearer of the first wearable device.

Clause 92. The technology of each preceding clause, wherein the first communication contains signals reflective of the first facial skin micromovements.

Clause 93. The technology of each preceding clause, further include interpreting the first facial skin micromovements as words, and wherein the first communication includes a transmission of the words.

Clause 94. The technology of each preceding clause, wherein presenting the second communication to the wearer of the first wearable device includes synthesizing words derived from the second facial skin micromovements.

Clause 95. The technology of each preceding clause, wherein presenting the second communication to the wearer of the first wearable device includes providing textual output reflective of words derived from the second facial skin micromovements.

Clause 96. The technology of each preceding clause, wherein presenting the second communication to the wearer of the first wearable device includes providing a graphical output reflective of at least one facial expression derived from the second facial skin micromovements.

Clause 97. The technology of each preceding clause: wherein the graphical output includes at least one emoji.

Clause 98. The technology of each preceding clause, further include: determining that the second wearable device is located in proximity to the first wearable device.

Clause 99. The technology of each preceding clause, further include: automatically establishing the wireless communication channel between the first wearable device and the second wearable device.

Clause 100. The technology of each preceding clause, further include: presenting via the first wearable device a suggestion to establish a nonvocalized conversation with the second wearable device.

Clause 101. The technology of each preceding clause, further include determining an intent of the wearer of the first wearable device to initiate a nonvocalized conversation with the wearer of the second wearable device, and automatically establishing the wireless communication channel between the first wearable device and the second wearable device.

Clause 102. The technology of each preceding clause, wherein the intent is determined from the first facial skin micromovements.

Clause 103. The technology of each preceding clause, wherein the wireless communication channel is established directly between the first wearable device and the second wearable device.

Clause 104. The technology of each preceding clause, wherein the wireless communication channel is established from the first wearable device to the second wearable device via at least one intermediate communication device.

Clause 105. The technology of each preceding clause, wherein the at least one communication device includes at least one of: a first smartphone associated with the wearer of the first wearable device, a second smartphone associated with the wearer of the second wearable device, a router, or a server.

Clause 106. The technology of each preceding clause, wherein the first communication contains signals reflective of first words spoken in a first language and the second communication contains signals reflective of second words spoken in a second language, and wherein presenting the second communication to the wearer of the first wearable device includes translating the second words to the first language.

Clause 107. The technology of each preceding clause, the first communication contains details identifying the wearer of the first wearable device and the second communication contains signals identifying the wearer of the second wearable device.

Clause 108. The technology of each preceding clause, wherein the first communication contains a time stamp indicating when the first facial skin micromovements were detected.

Clause 109. Speech detection technology for initiating content interpretation operations prior to vocalization of content to be interpreted as set forth in this clause alone, and/or in combination with each preceding clause, further comprising: determining from the signals at least one word to be spoken prior to vocalization of the at least one word in an origin language; prior to the vocalization of the at least one word, instituting an interpretation of the at least one word; and causing the interpretation of the at least one word to be presented as the at least one word is spoken.

Clause 110. The technology of each preceding clause, wherein the interpretation is a translation of the at least one word from the origin language into at least one target language other than the origin language.

Clause 111. The technology of each preceding clause, wherein the interpretation of the at least one word includes a transcription of the at least one word into text in the at least one target language.

Clause 112. The technology of each preceding clause, the interpretation of the at least one word includes a speech synthetization of the at least one word in the at least one target language.

Clause 113. The technology of each preceding clause, further include receiving a selection of the at least one target language.

Clause 114. The technology of each preceding clause, wherein the selection of the at least one target language includes selections of a plurality of target languages, and wherein causing the interpretation of the at least one word to be presented includes simultaneously causing presentation in the plurality of languages.

Clause 115. The technology of each preceding clause, wherein the interpretation of the at least one word includes a transcription of the at least one word into text in the origin language.

Clause 116. The technology of each preceding clause, wherein presenting the interpretation of the at least one word includes outputting a textual display of the transcription together with a video of an individual associated with the facial skin micromovements.

Clause 117. The technology of each preceding clause, wherein receiving signals occurs via at least one detector of coherent light reflections from a facial region of a person vocalizing the at least one word.

Clause 118. The technology of each preceding clause, wherein causing the interpretation of the at least one word to be presented occurs concurrently with the at least one word being vocalized by the person.

Clause 119. The technology of each preceding clause, wherein causing the interpretation of the at least one word to be presented includes using a wearable speaker to output an audible presentation of the at least one word.

Clause 120. The technology of each preceding clause, wherein causing the interpretation of the at least one word to be presented includes transmitting sound signals over a network.

Clause 121. The technology of each preceding clause, further include: determining at least one prospective word to be spoken following to the at least one word to be spoken, instituting an interpretation of the at least one prospective word prior to vocalization of the at least one word; and causing the interpretation of the at least one prospective word to be presented following presentation of the at least one word as the at least one word is spoken.

Clause 122. The technology of each preceding clause, wherein causing the interpretation of the at least one word to be presented includes transmitting a textual translation of the at least one word over a network.

Clause 123. The technology of each preceding clause, further include: determining from the signals at least one non-verbal interjection, and outputting a representation of the non-verbal interjection.

Clause 124. The technology of each preceding clause, wherein determining from the signals at least one word includes interpreting the facial skin micromovements using speckle analysis.

Clause 125. The technology of each preceding clause, wherein the signals representing facial skin micromovements correspond to muscle activation prior to the vocalization of the at least one word.

Clause 126. The technology of each preceding clause, wherein the muscle activation is associated with at least one specific muscle that includes: a zygomaticus muscle, an orbicularis oris muscle, a risorius muscle, a genioglossus muscle, or a levator labii superioris alaeque nasi muscle.

Clause 127. Speech detection technology for performing private voice assistance operations as set forth in this clause alone, and/or in combination with each preceding clause, further comprising: receiving signals indicative of specific facial skin micromovements reflective of a private request to an assistant, wherein answering the private request requires an identification of a specific individual associated with the specific facial skin micromovements; accessing a data structure maintaining correlations between the specific individual and a plurality of facial skin micromovements associated with the specific individual; searching in the data structure for a match indicative of a correlation between a stored identity of the specific individual and the specific facial skin micromovements; in response to a determination of an existence of the match in the data structure, initiating a first action responsive to the request, wherein the first action involves enabling access to information unique to the specific individual; and if the match is not identified in the data structure, initiating a second action different from the first action.

Clause 128. The technology of each preceding clause, wherein the second action includes providing non-private information.

Clause 129. The technology of each preceding clause, wherein the second action includes a notification that access is denied to information unique to the specific individual.

Clause 130. The technology of each preceding clause, wherein the second action includes blocking access to the information unique to the specific individual.

Clause 131. The technology of each preceding clause, wherein the second action includes attempting to authenticate the specific individual using additional data.

Clause 132. The technology of each preceding clause, wherein the additional data includes additional detected facial skin micromovements.

Clause 133. The technology of each preceding clause, wherein the additional data includes data other than facial skin micromovements.

Clause 134. The technology of each preceding clause, wherein when the match is not identified, further including initiating an additional action for identifying another individual other than the specific individual.

Clause 135. The technology of each preceding clause, wherein, in response to an identification of another individual other than the specific individual, further include initiating a third action responsive to the request.

Clause 136. The technology of each preceding clause, wherein the third action involves enabling access to information unique to the other individual.

Clause 137. The technology of each preceding clause, wherein the private request is for activating software code, the first action is activating the software code, and the second action is preventing activation of the software code.

Clause 138. The technology of each preceding clause, wherein the private request is for confidential information, and further include determining that the specific individual has permission to access the confidential information.

Clause 139. The technology of each preceding clause, wherein receiving, accessing, and searching occur repeatedly during an ongoing session.

Clause 140. The technology of each preceding clause, wherein in a first time period during the ongoing session the specific individual is identified and the first action is initiated, and wherein in a second time period during the ongoing session, the specific individual is not identified, and any residual first action is terminated in favor of the second action.

Clause 141. The technology of each preceding clause, further include operating at least one coherent light source in a manner enabling illuminating a non-lip portion of a face of an individual making the private request, and wherein receiving the signals occurs via at least one detector of coherent light reflections from the non-lip portion of the face.

Clause 142. The technology of each preceding clause, wherein the at least one processor, the at least one coherent light source, and the at least one detector are integrated in a wearable housing configured to be supported by an ear of the individual.

Clause 143. The technology of each preceding clause, further include analyzing the received signals to determine prevocalization muscle recruitment, and determining the private request based on the determined prevocalization muscle recruitment.

Clause 144. The technology of each preceding clause, further include determining the private request in an absence of perceptible vocalization of the private request.

Clause 145. Speech detection technology for determining subvocalized phonemes from facial skin micromovements as set forth in this clause alone, and/or in combination with each preceding clause, further comprising: controlling at least one coherent light source in a manner enabling illumination of a first region of a face and a second region of the face; performing first pattern analysis on light reflected from the first region of the face to determine first micromovements of facial skin in the first region of the face; performing second pattern analysis on light reflected from the second region of the face to determine second micromovements of facial skin in the second region of the face; and using the first micromovements of the facial skin in the first region of the face and the second micromovements of the facial skin in the second region of the face to ascertain at least one subvocalized phoneme.

Clause 146. The technology of each preceding clause, wherein performance of the second pattern analysis occurs after performing the first pattern analysis.

Clause 147. The technology of each preceding clause, wherein performance of the second pattern analysis occurs simultaneously with performance of the first pattern analysis.

Clause 148. The technology of each preceding clause, wherein the first region is spaced apart from the second region.

Clause 149. The technology of each preceding clause, wherein ascertaining the at least one subvocalized phoneme includes ascertaining a sequence of phonemes, further include extracting meaning from the sequence of phonemes.

Clause 150. The technology of each preceding clause, wherein each phoneme in the sequence of phonemes is derived from the first pattern analysis and the second pattern analysis.

Clause 151. The technology of each preceding clause, further include identifying as private at least one phoneme in the sequence of phonemes and omitting generation of an audio output reflective of the at least one private phoneme.

Clause 152. The technology of each preceding clause, further include determining both the first micromovements and the second micromovements during a common time period.

Clause 153. The technology of each preceding clause, further include receiving the first light reflections and the second light reflections via at least one detector, wherein the at least one detector and the at least one coherent light source are integrated within a wearable housing.

Clause 154. The technology of each preceding clause, wherein controlling the at least one coherent light source includes projecting differing light patterns on the first region and the second region.

Clause 155. The technology of each preceding clause, wherein the differing light patterns include a plurality of light spots, such that the first region of the face is illuminated by at least a first light spot and the second region of the face is illuminated by at least a second light spot, different from the first light spot.

Clause 156. The technology of each preceding clause, wherein controlling the at least one coherent light source includes illuminating the first region and the second region with a common light spot.

Clause 157. The technology of each preceding clause, wherein the first micromovements of the facial skin and the second micromovements of the facial skin correspond to concurrent muscle recruitments, wherein the determined first micromovements of facial skin in the first region of the face correspond to recruitment of a first muscle selected from: a zygomaticus muscle, an orbicularis oris muscle, a risorius muscle, or a levator labii superioris alaeque nasi muscle, and the determined second micromovements of facial skin in the second region of the face corresponds to recruitment of a second muscle, different from the first muscle, selected from: the zygomaticus muscle, the orbicularis oris muscle, the risorius muscle, or the levator labii superioris alaeque nasi muscle.

Clause 158. The technology of each preceding clause, further include accessing a default language of an individual associated with the facial skin micromovements, and using the default language to extract meaning from the at least one subvocalized phoneme.

Clause 159. The technology of each preceding clause, further include using a synthesized voice to generate an audio output reflective of the at least one subvocalized phoneme.

Clause 160. The technology of each preceding clause, wherein the at least one phoneme includes a sequence of phonemes, further include determining a prosody associated with the sequence of phonemes, and extracting meaning based on the determined prosody.

Clause 161. The technology of each preceding clause, further include determining an emotional state of an individual associated with the facial skin micromovements, and extracting meaning from the at least one subvocalized phoneme and the determined emotional state.

Clause 162. The technology of each preceding clause, further include identifying at least one extraneous phoneme as part of a filler and omitting generation of an audio output reflective of the extraneous phoneme.

Clause 163. Speech detection technology for generating synthesized representations of facial expressions as set forth in this clause alone, and/or in combination with each preceding clause, further comprising: controlling at least one coherent light source in a manner enabling illumination of a portion of a face; receiving output signals from a light detector, wherein the output signals correspond to reflections of coherent light from the portion of the face; applying speckle analysis on the output signals to determine speckle analysis-based facial skin micromovements; using the determined speckle analysis-based facial skin micromovements to identify at least one word prevocalized or vocalized during a time period; using the determined speckle analysis-based facial skin micromovements to identify at least one change in a facial expression during the time period; and during the time period, outputting data for causing a virtual representation of the face to mimic the at least one change in the facial expression in conjunction with an audio presentation of the at least one word.

Clause 164. The technology of each preceding clause, wherein controlling the at least one coherent light source in a manner enabling illumination of the portion of the face includes projecting a light pattern on the portion of the face.

Clause 165. The technology of each preceding clause, wherein the light pattern includes a plurality of spots.

Clause 166. The technology of each preceding clause, wherein the portion of the face includes cheek skin.

Clause 167. The technology of each preceding clause, wherein the portion of the face excludes lips.

Clause 168. The technology of each preceding clause, wherein the output signals from the light detector emanate from a wearable device.

Clause 169. The technology of each preceding clause, wherein the output signals from the light detector emanate from a non-wearable device.

Clause 170. The technology of each preceding clause, wherein the determined speckle analysis-based facial skin micromovements are associated with recruitment of at least one of: a zygomaticus muscle, an orbicularis oris muscle, a genioglossus muscle, a risorius muscle, or a levator labii superioris alaeque nasi muscle.

Clause 171. The technology of each preceding clause, wherein the at least one change in the facial expression during the period of time includes speech-related facial expressions and non-speech-related facial expressions.

Clause 172. The technology of each preceding clause, wherein the virtual representation of the face is associated with an avatar of an individual from whom the output signals are derived, and wherein mimicking the at least one change in the facial expression includes causing visual changes to the avatar that reflect at least one of the speech-related facial expressions and the non-speech-related facial expressions.

Clause 173. The technology of each preceding clause, wherein the visual changes to the avatar involve changing a color of at least a portion of the avatar.

Clause 174. The technology of each preceding clause, wherein the audio presentation of the at least one word is based on a recording of an individual.

Clause 175. The technology of each preceding clause, wherein the audio presentation of the at least one word is based on a synthesized voice.

Clause 176. The technology of each preceding clause, wherein the synthesized voice corresponds with a voice of an individual from whom the output signals are derived.

Clause 177. The technology of each preceding clause, wherein the synthesized voice corresponds with template voice selected by an individual from whom the output signals are derived.

Clause 178. The technology of each preceding clause, further include: determining an emotional state of an individual from whom the output signals are derived based at least in part on the facial skin micromovements and augmenting the virtual representation of the face to reflect the determined emotional state.

Clause 179. The technology of each preceding clause, further include: receiving a selection of a desired emotional state, and augmenting the virtual representation of the face to reflect the selected emotional state.

Clause 180. The technology of each preceding clause, further include: identifying a non-desirable facial expression, and wherein the outputted data for causing the virtual representation omits data for causing the non-desirable facial expression.

Clause 181. Speech detection technology for attention-associated interactions based on facial skin micromovements as set forth in this clause alone, and/or in combination with each preceding clause, further comprising: determining facial skin micromovements of an individual based on reflections of coherent light from a facial region of the individual; using the facial skin micromovements to determine a specific engagement level of the individual; receiving data associated with a prospective interaction with the individual; accessing a data structure correlating information reflective of alternative engagement levels with differing presentation manners; based on the specific engagement level and the correlating information, determining a specific presentation manner for the prospective interaction; and associating the specific presentation manner with the prospective interaction for subsequent engagement with the individual.

Clause 182. The technology of each preceding clause, further include generating an output reflecting the prospective interaction according to the determined specific presentation manner.

Clause 183. The technology of each preceding clause, further include: operating at least one coherent light source in a manner enabling illuminating a non-lip portion of a face of the individual, and receiving signals indicative of the reflections of coherent light from the non-lip portion of the face.

Clause 184. The technology of each preceding clause, further include performing a speckle analysis on the coherent light reflections from the non-lip portion of the face to determine the facial skin micromovements.

Clause 185. The technology of each preceding clause, wherein the specific engagement level is a category of engagement.

Clause 186. The technology of each preceding clause, wherein the specific engagement level includes a magnitude of engagement.

Clause 187. The technology of each preceding clause, wherein the specific engagement level is reflective of an extent to which the individual is engaged in an activity including at least one of a conversation, thoughts, or rest.

Clause 188. The technology of each preceding clause, further include determining the extent to which the individual is engaged in the activity based on facial skin micromovements that correspond with recruitment of at least one muscle out of a group of muscles including: a zygomaticus muscle, an orbicularis oris muscle, a risorius muscle, or a levator labii superioris alaeque nasi muscle.

Clause 189. The technology of each preceding clause, wherein the received data associated with the prospective interaction includes an incoming call, and wherein the associated differing presentation manners include notifying the individual of the incoming call, and directing the incoming call to voicemail.

Clause 190. The technology of each preceding clause, wherein the received data associated with the prospective interaction includes an incoming text message, and wherein the associated differing presentation manners include presenting the text message to the individual in real time and deferring presentation of the text message to a later time.

Clause 191. The technology of each preceding clause, wherein determining the specific presentation manner for the prospective interaction includes determining how to notify the individual of the prospective interaction.

Clause 192. The technology of each preceding clause, wherein determining how to notify the individual of the prospective interaction is based least in part on an identification of a plurality of electronic devices currently used by the individual.

Clause 193. The technology of each preceding clause, wherein the received data associated with the prospective interaction is indicative of an importance level of the prospective interaction, and wherein the specific presentation manner is determined based at least in part on the importance level.

Clause 194. The technology of each preceding clause, wherein the received data associated with the prospective interaction is indicative of an urgency level of the prospective interaction, and wherein the specific presentation manner is determined based at least in part on the specific urgency level.

Clause 195. The technology of each preceding clause, wherein the specific presentation manner includes deferring presentation of content until a time period of detected low engagement and further include: detecting low engagement at a subsequent time and presenting the content at the subsequent time.

Clause 196. The technology of each preceding clause, further include using the facial skin micromovements to determine that the individual is engaged in a conversation with another individual, determining whether the prospective interaction is relevant for the conversation, and wherein the specific presentation manner is determined based at least in part on a relevancy of the prospective interaction to the conversation.

Clause 197. The technology of each preceding clause, further include using the facial skin micromovements to determine a subject of the conversation and wherein determining that the prospective interaction is relevant to the conversation is based on the received data associated with the prospective interaction and subject of the conversation.

Clause 198. The technology of each preceding clause, wherein when the prospective interaction is determined to be relevant to the conversation, a first presentation manner is used for the prospective interaction, and when the prospective interaction is determined to be irrelevant to the conversation, a second presentation manner is used for the prospective interaction.

Clause 199. Speech detection technology for performing voice synthetization operations from detected facial skin micromovements as set forth in this clause alone, and/or in combination with each preceding clause, further comprising: determining particular facial skin micromovements of a first individual speaking with a second individual based on reflections of light from a facial region of the first individual; accessing a data structure correlating facial micromovements with words; performing a lookup in the data structure of particular words associated with the particular facial skin micromovements; obtaining an input associated with a preferred speech consumption characteristic of the second individual; adopting the preferred speech consumption characteristic; and synthesizing, using the adopted preferred speech consumption characteristic, audible output of the particular words.

Clause 200. The technology of each preceding clause, further include presenting at least one of the first individual and the second individual with a user interface for altering the preferred speech consumption characteristic.

Clause 201. The technology of each preceding clause, wherein obtaining the input associated with the preferred speech consumption characteristic of the second individual includes receiving the input from the first individual.

Clause 202. The technology of each preceding clause, wherein obtaining the input associated with the preferred speech consumption characteristic of the second individual includes receiving the input from the second individual.

Clause 203. The technology of each preceding clause, wherein obtaining the input associated with the preferred speech consumption characteristic of the second individual includes retrieving information on the second individual.

Clause 204. The technology of each preceding clause, wherein obtaining the input associated with the preferred speech consumption characteristic of the second individual includes determining the information based on image data captured by an image sensor worn by the first individual.

Clause 205. The technology of each preceding clause, wherein the input associated with the preferred speech consumption characteristic of the second individual is indicative of an age of the second individual.

Clause 206. The technology of each preceding clause, wherein the input associated with the preferred speech consumption characteristic of the second individual is indicative of environmental conditions associated with the second individual.

Clause 207. The technology of each preceding clause, wherein the input associated with the preferred speech consumption characteristic of the second individual is indicative of a hearing impairment of the second individual.

Clause 208. The technology of each preceding clause, wherein the second individual is one of a plurality of individuals, obtaining additional inputs from the plurality of individuals and classifying the plurality of individuals based on the additional inputs.

Clause 209. The technology of each preceding clause, wherein adopting the preferred speech consumption characteristic includes pre-setting voice synthesis controls for prospective facial micromovements.

Clause 210. The technology of each preceding clause, wherein the input associated with the preferred speech consumption characteristic includes a preferred pace of speech, and wherein the synthesized audible output of the particular words occurs at the preferred pace of speech.

Clause 211. The technology of each preceding clause, wherein the input associated with the preferred speech consumption characteristic includes a speech volume, and wherein the synthesized audible output of the particular words occurs at the preferred speech volume.

Clause 212. The technology of each preceding clause, wherein the input associated with the preferred speech consumption characteristic includes a target language of speech other than a language associated with the particular facial skin micromovements, and wherein the synthesized audible output of the particular words occurs in the target language of speech.

Clause 213. The technology of each preceding clause, wherein the input associated with the preferred speech consumption characteristic includes a preferred voice, and wherein the synthesized audible output of the particular words occurs in the preferred voice.

Clause 214. The technology of each preceding clause, wherein the preferred voice is at least one of a celebrity voice, an accented voice, or a gender-based voice.

Clause 215. The technology of each preceding clause, further include presenting a first synthesized version of intended speech based on the facial micromovements and presenting a second synthesized version of speech based on the facial micromovements in combination with the preferred speech consumption characteristic.

Clause 216. The technology of each preceding clause, wherein presenting the first synthesized version and the second synthesized version occur sequentially to the first individual.

Clause 217. Speech detection technology for personal presentation of prevocalization as set forth in this clause alone, and/or in combination with each preceding clause, further comprising: receiving reflection signals corresponding to light reflected from a facial region of an individual; using the received reflections signals to determine particular facial skin micromovements of an individual in an absence of perceptible vocalization associated with the particular facial skin micromovements; accessing a data structure correlating facial skin micromovements with words; performing a lookup in the data structure of particular unvocalized words associated with the particular facial skin micromovements; and causing an audible presentation of the particular unvocalized words to the individual prior to vocalization of the particular words by the individual.

Clause 218. The technology of each preceding clause, further include recording data associated with the particular unvocalized words for future use.

Clause 219. The technology of each preceding clause, wherein the data includes at least one of the audible presentation of the particular unvocalized words or a textual presentation of the particular unvocalized words.

Clause 220. The technology of each preceding clause, wherein the light reflected from the facial region of the individual include coherent light reflections.

Clause 221. The technology of each preceding clause, further include adding punctuation to the textual presentation.

Clause 222. The technology of each preceding clause, further include adjusting a speed of the audible presentation of the particular unvocalized words based on input from the individual.

Clause 223. The technology of each preceding clause, further include adjusting a volume of the audible presentation of the particular unvocalized words based on input from the individual.

Clause 224. The technology of each preceding clause, wherein causing the audible presentation includes outputting an audio signal to a personal hearing device configured to be worn by the individual.

Clause 225. The technology of each preceding clause, further include operating at least one coherent light source in a manner enabling illumination of the facial region of the individual, wherein the at least one coherent light source is integrated with the personal hearing device.

Clause 226. The technology of each preceding clause, wherein the audible presentation of the particular unvocalized words is a synthetization of a selected voice.

Clause 227. The technology of each preceding clause, wherein the selected voice is a synthetization of a voice of the individual.

Clause 228. The technology of each preceding clause, wherein the selected voice is a synthetization of a voice of another individual other than the individual associated with the facial skin micromovements.

Clause 229. The technology of each preceding clause, wherein the particular unvocalized words correspond to vocalizable words in a first language and the audible presentation includes a synthetization of the vocalizable words in a second language different from the first language.

Clause 230. The technology of each preceding clause, further include associating the particular facial skin micromovements with a plurality of vocalizable words in the second language, and selecting a most appropriate vocalizable word from the plurality of vocalizable words, wherein the audible presentation includes the most appropriate vocalizable word in the second language.

Clause 231. The technology of each preceding clause, include determining that an intensity of a portion of the particular facial skin micromovements is below a threshold and providing associated feedback to the individual.

Clause 232. The technology of each preceding clause, wherein the audible presentation of the particular unvocalized words is provided to the individual at least 20 milliseconds prior to vocalization of the particular words by the individual.

Clause 233. The technology of each preceding clause, further include ceasing the audible presentation of the particular unvocalized words in response to a detected trigger.

Clause 234. The technology of each preceding clause, further include detecting the trigger from determined facial skin micromovements of the individual.

Clause 235. Speech detection technology for determining facial skin micromovements as set forth in this clause alone, and/or in combination with each preceding clause, further comprising: controlling at least one coherent light source for projecting a plurality of light spots on a facial region of an individual, wherein the plurality of light spots includes at least a first light spot and a second light spot spaced from the first light spot; analyzing reflected light from the first light spot to determine changes in first spot reflections; analyzing reflected light from the second light spot to determine changes in second spot reflections; based on the determined changes in the first spot reflections and the second spot reflections, determining the facial skin micromovements; interpreting the facial skin micromovements derived from analyzing the first spot reflections and analyzing the second spot reflections; and generating an output of the interpretation.

Clause 236. The technology of each preceding clause, wherein the plurality of light spots additionally includes a third light spot and a fourth light spot, wherein each of the third light spot and the fourth light spot are spaced from each other and spaced from the first light spot and the second light spot.

Clause 237. The technology of each preceding clause, wherein the facial skin micromovements are determined based on the determined changes in the first spot reflections and the second spot reflections, and changes in the third spot reflections and the fourth spot reflections.

Clause 238. The technology of each preceding clause, wherein the plurality of light spots includes at least 16 spaced-apart light spots.

Clause 239. The technology of each preceding clause, wherein the plurality of light spots are projected on a non-lip region of the individual.

Clause 240. The technology of each preceding clause, wherein the changes in the first spot reflections and the changes in the second spot reflections correspond to concurrent muscle recruitments.

Clause 241. The technology of each preceding clause, wherein both the first spot reflections and the second spot reflections correspond to recruitment of a single muscle selected from: a zygomaticus muscle, an orbicularis oris muscle, a genioglossus muscle risorius muscle, or a levator labii superioris alaeque nasi muscle.

Clause 242. The technology of each preceding clause, wherein the first spot reflections correspond to recruitment of a muscle selected from: a zygomaticus muscle, an orbicularis oris muscle, a risorius muscle, a genioglossus muscle, or a levator labii superioris alaeque nasi muscle; and the second spot reflections correspond to recruitment of another muscle selected from: the zygomaticus muscle, the orbicularis oris muscle, the risorius muscle, the genioglossus muscle, or the levator labii superioris alaeque nasi muscle.

Clause 243. The technology of each preceding clause, wherein the at least one coherent light source is associated with a detector, and wherein the at least one coherent light source and the detector are integrated within a wearable housing.

Clause 244. The technology of each preceding clause, wherein determining the facial skin micromovements includes analyzing the changes in the first spot reflections relative to the changes in the second spot reflections.

Clause 245. The technology of each preceding clause, wherein the determined facial skin micromovements in the facial region include micromovements of less than 100 microns.

Clause 246. The technology of each preceding clause, wherein the interpretation includes an emotional state of the individual.

Clause 247. The technology of each preceding clause, wherein the interpretation includes at least one of a heart rate or a respiration rate of the individual.

Clause 248. The technology of each preceding clause, wherein the interpretation includes an identification of the individual.

Clause 249. The technology of each preceding clause, wherein the interpretation includes words.

Clause 250. The technology of each preceding clause, wherein the output includes a textual presentation of the words.

Clause 251. The technology of each preceding clause, wherein the output includes an audible presentation of the words.

Clause 252. The technology of each preceding clause, wherein the output includes metadata indicative of facial expressions or prosody associated with words.

Clause 253. Speech detection technology for interpreting impaired speech based on facial movements as set forth in this clause alone, and/or in combination with each preceding clause, further comprising: receiving signals associated with specific facial skin movements of an individual having a speech impairment that affects a manner in which the individual pronounces a plurality of words; accessing a data structure containing correlations between the plurality of words and a plurality of facial skin movements corresponding to the manner in which the individual pronounces the plurality of words; based on the received signals and the correlations, identifying specific words associated with the specific facial skin movements; and generating an output of the specific words for presentation, wherein the output differs from how the individual pronounces the specific words.

Clause 254. The technology of each preceding clause, wherein the facial skin movements are facial skin micromovements.

Clause 255. The technology of each preceding clause, wherein the signals are received from a sensor that detects light reflections from a non-lip portion of a face of the individual.

Clause 256. The technology of each preceding clause, wherein the facial skin micromovements correspond with recruitment of at least one muscle out of a group of muscles including: a zygomaticus muscle, a genioglossus muscle, an orbicularis oris muscle, a risorius muscle, or a levator labii superioris alaeque nasi muscle.

Clause 257. The technology of each preceding clause, wherein the signals are received from an image sensor configured to measure non-coherent light reflections.

Clause 258. The technology of each preceding clause, wherein the data structure is personalized to unique facial skin movements of the individual.

Clause 259. The technology of each preceding clause, further include employing a training model for populating the data structure.

Clause 260. The technology of each preceding clause, wherein the specific facial skin movements are associated with a vocalization of the specific words, and wherein the vocalization of the specific words is in a non-normative manner.

Clause 261. The technology of each preceding clause, wherein the output of the specific words is audible and used to correct the speech impairment of the individual.

Clause 262. The technology of each preceding clause, wherein the speech impairment is stuttering and wherein correcting includes outputting the specific words spoken in a stutter-free form.

Clause 263. The technology of each preceding clause, wherein the speech impairment is hoarseness, and wherein correcting includes outputting the specific words in a hoarseness-free form.

Clause 264. The technology of each preceding clause, wherein the speech impairment is low volume, and wherein correcting includes outputting the specific words in a volume higher than the specific words were spoken.

Clause 265. The technology of each preceding clause, wherein the output of the specific words is textual.

Clause 266. The technology of each preceding clause, further include adding punctuation to the textual output of the specific words.

Clause 267. The technology of each preceding clause, wherein the data structure includes data associated with at least one recording of the individual previously pronouncing the specific words.

Clause 268. The technology of each preceding clause, wherein the identified specific words associated with the specific facial skin movements are nonvocalized.

Clause 269. The technology of each preceding clause, wherein the specific facial skin movements are associated with a subvocalization of the specific words, and wherein the generated output includes a private audible presentation of the subvocalized words to the individual.

Clause 270. The technology of each preceding clause, wherein the specific facial skin movements are associated with a subvocalization of the specific words, and wherein the generated output includes a non-private audible presentation of the subvocalized words.

Clause 271. Speech detection technology for ongoing verification of communication authenticity based on light reflections from facial skin as set forth in this clause alone, and/or in combination with each preceding clause, further comprising: generating a first data stream representing a communication by a subject, the communication having a duration; generating a second data stream for corroborating an identity of the subject from facial skin light reflections captured during the duration of the communication; transmitting the first data stream to a destination; transmitting the second data stream to the destination; and wherein the second data stream is correlated to the first data stream in a manner such that upon receipt at the destination, the second data stream is enabled for use in repeatedly checking during the duration of the communication that the communication originated from the subject.

Clause 272. The technology of each preceding clause, wherein checking that the communication originated from the subject includes verifying that all words in the communication originated from the subject.

Clause 273. The technology of each preceding clause, wherein checking that the communication originated from the subject incudes verifying at regular time intervals during the duration of the conversation that speech captured at the regular time intervals originated from the subject.

Clause 274. The technology of each preceding clause, wherein the first data stream and the second data stream are intermingled in a common omnibus data stream.

Clause 275. The technology of each preceding clause, wherein the destination is a social network service the second data stream enables the social network service to publish the communication with an authenticity indicator.

Clause 276. The technology of each preceding clause, wherein the destination is an entity engaged in a real-time transaction with the subject and the second data stream enables the entity to verify in real-time the identity of the subject during the duration of the communication.

Clause 277. The technology of each preceding clause, wherein verifying the identity includes verification of a name of the subject.

Clause 278. The technology of each preceding clause, wherein verifying the identity includes verification at least periodic intervals throughout the communication that the subject spoke words presented in the communication.

Clause 279. The technology of each preceding clause, further include determining a biometric signature of the subject from light reflections associated with facial skin captured before the communication, and wherein the identity of the subject is determined using the corroborating facial skin light reflections and the biometric signature.

Clause 280. The technology of each preceding clause, wherein the biometric signature is determined based on a micro-veins pattern in the facial skin.

Clause 281. The technology of each preceding clause, wherein the biometric signature is determined based on a facial skin micromovement sequence associated with phenomes spoken by the subject.

Clause 282. The technology of each preceding clause, wherein the second data stream is indicative of a liveliness state of the subject and transmitting the second data stream enables verification of the communication authenticity based on the liveliness state of the subject.

Clause 283. The technology of each preceding clause, wherein the first data stream is indicative of an expression of the subject and the second data stream enables corroboration of the expression.

Clause 284. The technology of each preceding clause, further include storing in a data structure identifying facial skin micromovements of the subject vocalizing or prevocalizing a passphrase, and identifying the subject based on the vocalization or prevocalization of the passphrase.

Clause 285. The technology of each preceding clause, further include storing in a data structure a profile of the subject based on patterns of facial skin micromovements, and identifying the subject based on the patterns.

Clause 286. The technology of each preceding clause, wherein the first data stream is based on signals associated with sound captured by a microphone during the duration of the communication.

Clause 287. The technology of each preceding clause, wherein the first data stream and the second data stream are determined based on signals from a same light detector.

Clause 288. The technology of each preceding clause, wherein generating the first data stream representing the communication by the subject includes reproducing speech based on the corroborating facial skin light reflections.

Clause 289. Speech detection technology for noise suppression as set forth in this clause alone, and/or in combination with each preceding clause, further comprising: a wearable housing configured to be worn on a head of a wearer; at least one coherent light source associated with the wearable housing and configured to project light towards a facial region of the head; at least one detector associated with the wearable housing and configured to receive coherent light reflections from the facial region associated with facial skin micromovements and to output associated reflection signals; at least one processor configured to: analyze the reflection signals to determine speech timing based on the facial skin micromovements in the facial region; receive audio signals from at least one microphone, the audio signals containing sounds of words spoken by the wearer together with ambient sounds; correlate, based on the speech timing, the reflection signals with the received audio signals to determine portions of the audio signals associated with the words spoken by the wearer; and output the determined portions of the audio signals associated with the words spoken by the wearer, while omitting output of other portions of the audio signals not containing the words spoken by the wearer.

Clause 290. The technology of each preceding clause, wherein the at least one processor is further configured to record the determined portions of the audio signals.

Clause 291. The technology of each preceding clause, wherein the at least one processor is further configured to determine that the other portions of the audio signals are not associated with the words spoken by the wearer.

Clause 292. The technology of each preceding clause, wherein the other portions of the audio signals include ambient noise.

Clause 293. The technology of each preceding clause, wherein the at least one processor is further configured to determine that the other portions of the audio signals include speech of at least one person other than the wearer.

Clause 294. The technology of each preceding clause, wherein the at least one processor is further configured to record the speech of the at least one person.

Clause 295. The technology of each preceding clause, wherein the at least one processor is further configured to receive input indicative of a wearer's desire for outputting the speech of the at least one person, and output portions of the audio signals associated with the speech of the at least one person.

Clause 296. The technology of each preceding clause, wherein the at least one processor is further configured to identify the at least one person, determine relationship of the at least one person to the wearer, and automatically output portions of the audio signals associated with the speech of the at least one person based on the determined relationship.

Clause 297. The technology of each preceding clause, wherein the at least one processor is further configured to analyze the audio signals and the reflection signals to identify non-verbal interjection of the wearer, and omit the non-verbal interjection from the output.

Clause 298. The technology of each preceding clause, wherein outputting the determined portions of the audio signals includes synthesizing vocalization of the words spoken by the wearer.

Clause 299. The technology of each preceding clause, wherein the synthesized vocalization emulates a voice of the wearer.

Clause 300. The technology of each preceding clause, wherein the synthesized vocalization emulates a voice of a specific individual other than the wearer.

Clause 301. The technology of each preceding clause, wherein the synthesized vocalization includes a translated version of the words spoken by the wearer.

Clause 302. The technology of each preceding clause, wherein the at least one processor is further configured to analyze the reflection signals to identify an intent to speak and activate at least one microphone in response to the identified intent.

Clause 303. The technology of each preceding clause, wherein the at least one processor is further configured to analyze the reflection signals to identify a pause in the words spoken by the wearer and deactivate at least one microphone during the identified pause.

Clause 304. The technology of each preceding clause, wherein at least one microphone is part of a communications device configured to be wirelessly paired with the head mountable system.

Clause 305. The technology of each preceding clause, wherein at least one microphone is integrated with the wearable housing and the wearable housing is configured such that when worn, the at least one coherent light source assumes an aiming direction for illuminating at least a portion of a cheek of the wearer.

Clause 306. The technology of each preceding clause, wherein a first portion of the wearable housing is configured to be placed in an ear canal of the wearer and second portion is configured to be placed outside the ear canal, and the at least one microphone is included in the second portion.

Clause 307. Speech detection technology for providing private answers to silent questions as set forth in this clause alone, and/or in combination with each preceding clause, further comprising: receiving signals indicative of particular facial micromovements in an absence of perceptible vocalization; accessing a data structure correlating facial micromovements with words; using the received signals to perform a lookup in the data structure of particular words associated with the particular facial micromovements; determining a query from the particular words; accessing at least one data structure to perform a look up for an answer to the query; and generating a discreet output that includes the answer to the query.

Clause 308. The technology of each preceding clause, wherein the received signals are obtained via a head mountable light detector and derived from skin micromovements of a facial portion other than a mouth.

Clause 309. The technology of each preceding clause, wherein the head mountable light detector is configured to detect incoherent light reflections from the facial portion.

Clause 310. The technology of each preceding clause, wherein the operations further include controlling at least one coherent light source in a manner enabling illuminating the facial portion, and wherein the head mountable light detector is configured to detect coherent light reflections from the facial portion.

Clause 311. The technology of each preceding clause, wherein the discreet output includes an audible output delivered via at least one earbud to a wearer of the head mountable light detector.

Clause 312. The technology of each preceding clause, wherein the discreet output includes a textual output delivered to a wearer of the head mountable light detector.

Clause 313. The technology of each preceding clause, wherein the discreet output includes a tactile output delivered to a wearer of the head mountable light detector.

Clause 314. The technology of each preceding clause, wherein the facial micromovements correspond with muscle activation of at least one of: a zygomaticus muscle, an orbicularis oris muscle, a risorius muscle, a genioglossus muscle, or a levator labii superioris alaeque nasi muscle.

Clause 315. The technology of each preceding clause, further include receiving image data and wherein the query is determined based on nonvocalized articulation of the particular words and the image data.

Clause 316. The technology of each preceding clause, wherein the image data is obtained from a wearable image sensor.

Clause 317. The technology of each preceding clause, wherein the image data reflects an identity of a person, the query is for a name of the person, and the discreet output includes the name of the person.

Clause 318. The technology of each preceding clause, wherein the image data reflects an identity of an edible product, the query is for a list of allergens included in the edible product, and the discreet output includes the list of allergens.

Clause 319. The technology of each preceding clause, wherein the image data reflects an identity of an inanimate object, the query is for details on the inanimate object, and the discreet output includes the requested details on the inanimate object.

Clause 320. The technology of each preceding clause, further include using the particular facial micromovements to attempt to authenticate an individual associated with the particular facial micromovements.

Clause 321. The technology of each preceding clause, when the individual is authenticated, further include providing a first answer to the query, the first answer including private information; and when the individual is not authenticated, further include providing a second answer to the query, the second answer omitting the private information.

Clause 322. The technology of each preceding clause, further include accessing personal data associated with the individual and using the personal data to generate the discreet output that includes the answer to the query.

Clause 323. The technology of each preceding clause, the personal data includes at least one of: age the individual, gender of the individual, current location of the individual, occupation of the individual, home address of the individual, level of education of the individual, or health condition of the individual.

Clause 324. The technology of each preceding clause, further include using the facial micromovements to determine an emotional state of an individual associated with the facial micromovements, and wherein the answer to the query is determined based in part on the determined emotional state.

Clause 325. Speech detection technology for performing control commands based on facial skin micromovements as set forth in this clause alone, and/or in combination with each preceding clause, further comprising: operating at least one coherent light source in a manner enabling illumination of a non-lip portion of a face; receiving specific signals representing coherent light reflections associated with specific non-lip facial skin micromovements; accessing a data structure associating a plurality of non-lip facial skin micromovements with control commands; identifying in the data structure a specific control command associated with the specific signals associated with the specific non-lip facial skin micromovements; and executing the specific control command.

Clause 326. The technology of each preceding clause, wherein the facial skin micromovements correspond to a nonvocalized articulation of at least one word associated with the specific control command.

Clause 327. The technology of each preceding clause, wherein the facial skin micromovements correspond to recruitment of at least one specific muscle.

Clause 328. The technology of each preceding clause, wherein the at least one specific muscle includes: a zygomaticus muscle, an orbicularis oris muscle, a risorius muscle, or a levator labii superioris alaeque nasi muscle.

Clause 329. The technology of each preceding clause, wherein the facial skin micromovements includes a sequence of facial skin micromovements from which the specific control command is derived.

Clause 330. The technology of each preceding clause, wherein the facial skin micromovements includes involuntary micromovements.

Clause 331. The technology of each preceding clause, wherein the involuntary micromovements are triggered by an individual thinking of speaking the specific control command.

Clause 332. The technology of each preceding clause, wherein the involuntary micromovements are unnoticeable to a human eye.

Clause 333. The technology of each preceding clause, operating the at least one coherent light source includes determining an intensity or a light pattern for illuminating the non-lip portion of the face.

Clause 334. The technology of each preceding clause, wherein the specific signals are received at a rate of between 50 Hz and 200 Hz.

Clause 335. The technology of each preceding clause, further include analyzing the specific signals to identify temporal and intensity changes of speckles produced by light reflections from the non-lip portion of the face.

Clause 336. The technology of each preceding clause, further include processing data from at least one sensor to determine context for the specific non-lip facial skin micromovements, and determining an action to initiate based on the specific control command and the determined context.

Clause 337. The technology of each preceding clause, wherein the specific control command is configured to cause an audible translation of words from an origin language into at least one target language other than the origin language.

Clause 338. The technology of each preceding clause, wherein the specific control command is configured to cause an action in media player application.

Clause 339. The technology of each preceding clause, wherein the specific control command is configured to cause an action associated with an incoming call.

Clause 340. The technology of each preceding clause, wherein the specific control command is configured to cause an action associated with an ongoing call.

Clause 341. The technology of each preceding clause, wherein the specific control command is configured to cause an action associated with a text message.

Clause 342. The technology of each preceding clause, wherein the specific control command is configured to cause activation of a virtual personal assistant.

Clause 343. Speech detection technology for detecting changes in neuromuscular activity over time as set forth in this clause alone, and/or in combination with each preceding clause, further comprising: establishing a baseline of neuromuscular activity from coherent light reflections associated with historical skin micromovements; receiving current signals representing coherent light reflections associated with current skin micromovements of an individual; identifying a deviation of the current skin micromovements from the baseline of neuromuscular activity; and outputting an indicator of the deviation.

Clause 344. The technology of each preceding clause, include establishing the baseline from historical signals representing prior coherent light reflections associated with persons other than the individual.

Clause 345. The technology of each preceding clause, include establishing the baseline from historical signals representing prior coherent light reflections associated with the individual.

Clause 346. The technology of each preceding clause, wherein the historical signals are based on skin micromovements that occurred over a time period of more than a day.

Clause 347. The technology of each preceding clause, wherein the historical signals are based on skin micromovements that occurred at least a year before receipt of the current signals.

Clause 348. The technology of each preceding clause, further include receiving the current signals from a wearable light detector while the wearable light detector is worn by the individual.

Clause 349. The technology of each preceding clause, further include controlling at least one wearable coherent light source in a manner enabling illumination of a portion of a face of the individual, and wherein the current signals are associated with coherent light reflections from the portion of the face illuminated by the at least one wearable coherent light source.

Clause 350. The technology of each preceding clause, wherein the current skin micromovements correspond to recruitment of at least one of a zygomaticus muscle, an orbicularis oris muscle, a genioglossus muscle, a risorius muscle, or a levator labii superioris alaeque nasi muscle.

Clause 351. The technology of each preceding clause, further include receiving the current signals from a non-wearable light detector.

Clause 352. The technology of each preceding clause, wherein the coherent light reflections associated with current skin micromovements are received from skin other than facial skin.

Clause 353. The technology of each preceding clause, wherein the skin other than facial skin is from a neck, a wrist, or a chest of the individual.

Clause 354. The technology of each preceding clause, include receiving additional signals associated with skin micromovements of the individual during a period of time prior to the current skin micromovements, determining a trend of changes in the neuromuscular activity of the individual based on the current signals and the additional signals, and wherein the indicator is indicative of the trend of changes.

Clause 355. The technology of each preceding clause, further include determining a likely cause for the deviation of the current skin micromovements from the baseline of neuromuscular activity, and wherein the indicator is indicative of the likely cause.

Clause 356. The technology of each preceding clause, further include outputting an additional indicator of the likely cause for the deviation.

Clause 357. The technology of each preceding clause, further include receiving data indicative of at least one environmental condition, and wherein determining the likely cause for the deviation is based on the at least one environmental condition and the identified deviation.

Clause 358. The technology of each preceding clause, further include receiving data indicative of at least one physical condition of the individual, and wherein determining the likely cause for the deviation is based on the at least one physical condition and the identified deviation.

Clause 359. The technology of each preceding clause, wherein the likely cause corresponds to at least one physical condition that includes: being under an influence, tiredness, or stress.

Clause 360. The technology of each preceding clause, wherein the likely cause corresponds to at least one health condition that includes a heart attack, Multiple Sclerosis (MS), Parkinson's Disease, epilepsy, or a stroke.

Clause 361. Speech detection technology for projecting graphical content as set forth in this clause alone, and/or in combination with each preceding clause, further comprising: a wearable housing configured to be worn on a head of an individual; at least one light source associated with the wearable housing and configured to project light in a graphical pattern on a facial region of the individual, wherein the graphical pattern is configured to visibly convey information; a sensor for detecting a portion of the light reflected from the facial region; at least one processor configured to: receive output signals from the sensor; determine from the output signals facial skin micromovements associated with non-verbalization; and process the output signals to interpret the facial skin micromovements.

Clause 362. The technology of each preceding clause, wherein the at least one processor is further configured to receive a selection of the graphical pattern and to control the at least one light source to project the selected graphical pattern.

Clause 363. The technology of each preceding clause, wherein the graphical pattern is constructed of a plurality of spots for use in determining the facial skin micromovements via speckle analysis.

Clause 364. The technology of each preceding clause, wherein the projected light is configured to be visible via a human eye to individuals other than the individual.

Clause 365. The technology of each preceding clause, wherein the projected light is visible via an infrared sensor.

Clause 366. The technology of each preceding clause, the projected light source includes a laser.

Clause 367. The technology of each preceding clause, wherein the at least one processor is configured to alter the graphical pattern over time.

Clause 368. The technology of each preceding clause, wherein the at least one processor is configured to receive location information and to alter the graphical pattern based on the received location information.

Clause 369. The technology of each preceding clause, wherein the graphical pattern includes a scrolling message and the at least one processor is configured to cause the message to scroll.

Clause 370. The technology of each preceding clause, wherein the at least one processor is further configured to detect a trigger and to cause the graphical pattern to be displayed in response to the trigger.

Clause 371. The technology of each preceding clause, wherein processing the output signals to interpret the facial skin micromovements includes determining non-verbalized speech from the facial skin micromovements.

Clause 372. The technology of each preceding clause, wherein the at least one processor is configured to determine the graphical pattern from the non-verbalized speech.

Clause 373. The technology of each preceding clause, wherein processing the output signals to interpret the facial skin micromovements includes determining an emotional state from the facial skin micromovements.

Clause 374. The technology of each preceding clause, wherein the at least one processor is configured to determine the graphical pattern from the determined emotional state.

Clause 375. The technology of each preceding clause, further include an integrated audio output and wherein the at least one processor is configured to initiate an action that involves outputting audio via the audio output.

Clause 376. The technology of each preceding clause, wherein the at least one processor is configured to identify a trigger and to modify the pattern based on the trigger.

Clause 377. The technology of each preceding clause, wherein the at least one processor is configured to analyze the facial skin micromovements to identify the trigger.

Clause 378. The technology of each preceding clause, wherein modifying the pattern includes ceasing the projection of the graphical pattern.

Clause 379. Speech detection technology including a head mountable system for interpreting facial skin micromovements as set forth in this clause alone, and/or in combination with each preceding clause, further comprising: a housing configured to be worn on a head of a wearer; at least one detector integrated with the housing and configured to receive light reflections from a facial region of the head and to output associated reflection signals; at least one microphone associated with the housing and configured to capture sounds produced by the wearer and to output associated audio signals; and at least one processor in the housing, configured to use both the reflection signals and the audio signals to generate output that corresponds with words articulated by the wearer.

Clause 380. The technology of each preceding clause, further include at least one light source integrated with the housing and configured to project coherent light towards the facial region of the head.

Clause 381. The technology of each preceding clause, wherein the at least one processor is configured to receive a vocalized form of the words and to determine at least one of the words prior to vocalization of the at least one word.

Clause 382. The technology of each preceding clause, wherein the words articulated by the wearer include at least one word articulated in a nonvocalized manner, and the at least one processor is configured to determine the at least one word without using the audio signals.

Clause 383. The technology of each preceding clause, wherein the at least one processor is configured to use the reflection signals to identify one or more words articulated in an absence of perceptible vocalization.

Clause 384. The technology of each preceding clause, wherein the at least one processor is configured to use the reflection signals to determine particular facial skin micromovements, and to correlate the particular facial skin micromovements with reference skin micromovements that correspond with the words.

Clause 385. The technology of each preceding clause, wherein the at least one processor is configured to use the audio signals to determine the reference skin micromovements.

Clause 386. The technology of each preceding clause, further include a speaker integrated with the housing and configured to generate an audio output.

Clause 387. The technology of each preceding clause, wherein the output includes an audible presentation of the words articulated by the wearer.

Clause 388. The technology of each preceding clause, further include: wherein the audible presentation includes a synthetization of a voice of an individual other than the wearer.

Clause 389. The technology of each preceding clause, wherein the audible presentation includes a synthetization of a voice of the wearer.

Clause 390. The technology of each preceding clause, wherein the words articulated by the wearer are in a first language and the generated output includes words spoken in a second language.

Clause 391. The technology of each preceding clause, wherein the at least one processor is configured to use the audio signals for determining the voice of the individual for synthetization of words spoken in an absence of perceptible vocalization.

Clause 392. The technology of each preceding clause, wherein the output includes a textual presentation of the words articulated by the wearer.

Clause 393. The technology of each preceding clause, wherein the at least one processor is configured to cause a textual presentation of the words to be transmitted over a wireless communication channel to a remote computing device.

Clause 394. The technology of each preceding clause, wherein the at least one processor is configured to cause the generated output to be transmitted to a remote computing device for executing a control command corresponding to the words articulated by the wearer.

Clause 395. The technology of each preceding clause, wherein the at least one processor is further configured to analyze the reflection signals to determine facial skin micromovements that correspond to recruitment of at least one specific muscle.

Clause 396. The technology of each preceding clause, wherein the at least one specific muscle includes a zygomaticus muscle, an orbicularis oris muscle, a risorius muscle, or a levator labii superioris alaeque nasi muscle.

Clause 397. Speech detection technology for interpreting facial skin micromovements as set forth in this clause alone, and/or in combination with each preceding clause, further comprising: receiving during a first time period first signals representing prevocalization facial skin micromovements; receiving during a second time period succeeding the first time period, second signals representing sounds; analyzing the sounds to identify words spoken during the second time period; correlating the words spoken during the second time period with the prevocalization facial skin micromovements received during the first time period; storing the correlations; receiving during a third time period, third signals representing facial skin micromovements received in an absence of vocalization; using the stored correlations to identify language associated with the third signals; and outputting the language.

Clause 398. The technology of each preceding clause, further include identifying additional correlations of additional words spoken over an additional extended period of time with additional prevocalization facial skin micromovements detected during the additional extended period of time, and training a neural network using the additional correlations.

Clause 399. The technology of each preceding clause, wherein the outputted language includes indications of the words spoken during the second time period.

Clause 400. The technology of each preceding clause, wherein the outputted language includes an indication of at least one word different from the words spoken during the second time period.

Clause 401. The technology of each preceding clause, wherein the at least one word includes a phoneme sequence similar to the at least one word spoken during the second time period.

Clause 402. The technology of each preceding clause, wherein the first signals are associated with a first individual and the third signals are associated with a second individual.

Clause 403. The technology of each preceding clause, wherein first signals and the third signals are associated with a same individual.

Clause 404. The technology of each preceding clause, further include continuously updating, using the correlations, a user profile associated with the individual.

Clause 405. The technology of each preceding clause, wherein the correlations are stored in a cloud-based data structure.

Clause 406. The technology of each preceding clause, further include accessing a voice signature of an individual associated with the facial skin micromovements and wherein analyzing the sounds to identify words spoken during the second time period is based on the voice signature.

Clause 407. The technology of each preceding clause, wherein the second period of time starts less than 350 milliseconds after the first period of time.

Clause 408. The technology of each preceding clause, wherein the third period of time starts at least a day after the second period of time.

Clause 409. The technology of each preceding clause, wherein the first signals are based on coherent light reflections and wherein the operations further include controlling at least one coherent light source for projecting coherent light on a facial region of an individual from which the light reflections are received.

Clause 410. The technology of each preceding clause, wherein the first signals are received from a light detector, and wherein the light detector and the coherent light source are part of a wearable assembly.

Clause 411. The technology of each preceding clause, wherein the second signals representing sounds are received from a microphone that is part of the wearable assembly.

Clause 412. The technology of each preceding clause, wherein outputting the language includes textually presenting the words associated with the third signals.

Clause 413. The technology of each preceding clause, further include, when a certainty level for identifying the language associated with the third signals is below a threshold, processing additional signals captured during a fourth time period succeeding the third time period to increase the certainty level.

Clause 414. The technology of each preceding clause, further include receiving during a fourth time period fourth signals representing additional prevocalization facial skin micromovements, receiving during a fifth time period succeeding the fourth time period, fifth signals representing sounds, and using the fourth signals to identify words spoken in the fifth time period.

Clause 415. Speech detection technology for operating a multifunctional earpiece as set forth in this clause alone, and/or in combination with each preceding clause, further comprising: an ear-mountable housing; a speaker integrated with the ear-mountable housing for presenting sound; a light source integrated with the ear-mountable housing for projecting light toward skin of the wearer's face; a light detector integrated with the ear-mountable housing and configured to receive reflections from the skin corresponding to facial skin micromovements indicative of prevocalized words of the wearer; and wherein the multifunctional earpiece is configured to simultaneously present the sound through the speaker, project the light toward the skin, and detect the received reflections indicative of the prevocalized words.

Clause 416. The technology of each preceding clause, wherein at least a portion of the ear-mountable housing is configured to be placed in an ear canal.

Clause 417. The technology of each preceding clause, wherein at least a portion of the ear-mountable housing is configured to be placed over or behind an ear.

Clause 418. The technology of each preceding clause, further include at least one processor configured to output via the speaker an audible simulation of the prevocalized words derived from the reflections.

Clause 419. The technology of each preceding clause, wherein the audible simulation of the prevocalized words includes a synthetization of a voice of an individual other than the wearer.

Clause 420. The technology of each preceding clause, wherein the audible simulation of the prevocalized words includes a synthetization of the prevocalized words in a first language other than a second language of the prevocalized words.

Clause 421. The technology of each preceding clause, further include a microphone integrated with the ear-mountable housing for receiving audio indicative of a wearer's speech.

Clause 422. The technology of each preceding clause, wherein the light source is configured to project a pattern of coherent light toward the skin of the wearer's face, the pattern including a plurality of spots.

Clause 423. The technology of each preceding clause, wherein the light detector is configured to output associated reflection signals indicative of muscle fiber recruitments.

Clause 424. The technology of each preceding clause, wherein the recruited muscle fibers include further include: at least one of zygomaticus muscle fibers, orbicularis oris muscle fibers, risorius muscle fibers, or levator labii superioris alaeque nasi muscle fibers.

Clause 425. The technology of each preceding clause, further include at least one processor configured to analyze the light reflections to determine the facial skin micromovements.

Clause 426. The technology of each preceding clause, wherein the analysis includes speckle analysis.

Clause 427. The technology of each preceding clause, further include a microphone integrated with the ear-mountable housing for receiving audio indicative of a wearer's speech, and wherein the at least one processor is configured to use the audio received via the microphone and the reflections received via the light detector to correlate facial skin micromovements with spoken words and to train a neural network to determine subsequent prevocalized words from subsequent facial skin micromovements.

Clause 428. The technology of each preceding clause, wherein the at least one processor is configured to identify a trigger in the determined facial skin micromovements for activating the microphone.

Clause 429. The technology of each preceding clause, further include a pairing interface for pairing with a communications device, and wherein the at least one processor is configured to transmit an audible simulation of the prevocalized words to the communications device.

Clause 430. The technology of each preceding clause, further include a pairing interface for pairing with a communications device, and wherein the at least one processor is configured to transmit a textual presentation of the prevocalized words to the communications device.

Clause 431. The technology of each preceding clause, wherein the light source is configured to project coherent light toward the skin of the wearer's face.

Clause 432. The technology of each preceding clause, wherein the light source is configured to project a noncoherent light toward the skin of the wearer's face.

Clause 433. Speech detection technology for enabling a neuromuscular detection device to interface with the software program as set forth in this clause alone, and/or in combination with each preceding clause, further comprising: an input handler for receiving non-audible muscle activation signals from the neuromuscular detection device; a lookup component for mapping specific ones of the non-audible activation signals to corresponding commands in the software program; a signal processing module for receiving the non-audible muscle activation signals from the input handler, supplying the specific ones of the non-audible muscle activation signals to the lookup component, and receiving an output as the corresponding commands; and a communications module for conveying the corresponding commands to the software program, to thereby enable control within the software program based on non-audible muscular activity detected by the neuromuscular detection device.

Clause 434. The technology of each preceding clause, wherein the input handler, the lookup component, the signal processing module, and the control code are embedded in the software program.

Clause 435. The technology of each preceding clause wherein the input handler, the lookup component, the signal processing module, and the control code are embedded in the neuromuscular detection device.

Clause 436. The technology of each preceding clause wherein the input handler, the lookup component, the signal processing module, and the control code are embedded in an application programming interface (API).

Clause 437. The technology of each preceding clause wherein the neuromuscular detection device includes a light source configured to project light toward skin, a light detector configured to sense reflections of the light from the skin, and at least one processor configured to generate the non-audible muscle activation signals based on the sensed light reflections.

Clause 438. The technology of each preceding clause, wherein the sensed reflections of the light from the skin correspond to micromovements of the skin.

Clause 439. The technology of each preceding clause wherein the lookup component is prepopulated based on training data correlating the non-audible muscle activation signals with the corresponding commands.

Clause 440. The technology of each preceding clause, further include a training module for determining correlations between the non-audible muscle activation signals with the corresponding commands and for populating the lookup component.

Clause 441. The technology of each preceding clause, wherein the lookup component includes a lookup table, wherein the lookup component includes an artificial intelligence data structure.

Clause 442. The technology of each preceding clause, wherein the neuromuscular detection device includes a light source for projecting light toward skin, a light detector configured to sense reflections of the light from the skin, and at least one processor configured to generate, based on the sensed light reflections, the non-audible muscle activation signals.

Clause 443. The technology of each preceding clause, wherein the at least one processor is configured to generate the non-audible muscle activation signals based on speckle analysis of received reflections of the coherent light.

Clause 444. The technology of each preceding clause, wherein the lookup component is further configured to map some of the specific ones of the non-audible activation signals to text.

Clause 445. The technology of each preceding clause, wherein the text corresponds to subvocalization manifest in the non-audible muscle activation signals.

Clause 446. The technology of each preceding clause, wherein the lookup component is further configured to map some of the specific ones of the non-audible muscle activation signals to a command for causing at least one of a visual output of the text or an audible synthetization of the text.

Clause 447. The technology of each preceding clause, further include a return path output for transmitting data to the neuromuscular detection device.

Clause 448. The technology of each preceding clause, wherein the data is configured to cause at least one of an audio, haptic, or textual output via the neuromuscular detection device.

Clause 449. The technology of each preceding clause, further include detection and correction routines to detect and correct errors that occur during data transmission.

Clause 450. The technology of each preceding clause, further include configuration management routines for permitting the driver to be configured to applications other than the software program.

Clause 451. Speech detection technology for performing context-driven facial micromovement operations as set forth in this clause alone, and/or in combination with each preceding clause, further comprising: receiving during a first time period, first signals representing first coherent light reflections associated with first facial skin micromovements; analyzing the first coherent light reflections to determine a first plurality of words associated with the first facial skin micromovements; receiving first information indicative of a first contextual condition in which the first facial skin micromovements occurred; receiving during a second time period, second signals representing second coherent light reflections associated with second facial skin micromovements; analyzing the second coherent light reflections to determine a second plurality of words associated with the second facial skin micromovements; receiving second information indicative of a second contextual condition in which the second facial skin micromovements occurred; accessing a plurality of control rules correlating a plurality of actions with a plurality of contextual conditions, wherein a first control rule prescribes a form of private presentation based on the first contextual condition, and a second control rule prescribes a form of non-private presentation based on the second contextual condition; upon receipt of the first information, implementing the first control rule to privately output the first plurality of words; and upon receipt of the second information, implementing the second control rule to non-privately output the second plurality of words.

Clause 452. The technology of each preceding clause, wherein the first information indicative of the first contextual condition includes an indication that the first facial skin micromovements are associated with private thought.

Clause 453. The technology of each preceding clause, wherein the first information indicative of the first contextual condition includes an indication that the first facial skin micromovements are made in a private situation.

Clause 454. The technology of each preceding clause, wherein the first information indicative of the first contextual condition includes an indication that an individual generating the facial micromovements is looking down.

Clause 455. The technology of each preceding clause, wherein the second information indicative of the second contextual condition includes an indication that the second facial skin micromovements are made during a phone call.

Clause 456. The technology of each preceding clause, wherein the second information indicative of the second contextual condition includes an indication that the second facial skin micromovements are made during a video conference.

Clause 457. The technology of each preceding clause, wherein the second information indicative of the second contextual condition includes an indication that the second facial skin micromovements are made during a social interaction.

Clause 458. The technology of each preceding clause, wherein at least one of the first information and the second information is indicative of an activity of an individual generating the facial micromovements and the operations further include implementing either the first control rule or the second control rule based on the activity.

Clause 459. The technology of each preceding clause, wherein at least one of the first information and the second information is indicative of a location of an individual generating the facial micromovements and the operations further include implementing either the first control rule or the second control rule based on the location.

Clause 460. The technology of each preceding clause, wherein at least one of the first information and the second information is indicative of a type of engagement of an individual generating the facial micromovements with a computing device and the operations further include implementing either the first control rule or the second control rule based on the type of engagement.

Clause 461. The technology of each preceding clause, wherein privately outputting the first plurality of words includes generating audio output to a personal sound generating device.

Clause 462. The technology of each preceding clause, wherein privately outputting the first plurality of words includes generating textual output to a personal text generating device.

Clause 463. The technology of each preceding clause, wherein non-privately outputting the second plurality of words includes transmitting audio output to a mobile communication device.

Clause 464. The technology of each preceding clause, wherein non-privately outputting the second plurality of words includes causing textual output to be presented on a shared display.

Clause 465. The technology of each preceding clause, wherein the operations further include determining a trigger for switching between a private output mode and a non-private output mode.

Clause 466. The technology of each preceding clause, further include receiving third information indicative of a change in contextual conditions and wherein the trigger is determined from the third information.

Clause 467. The technology of each preceding clause, include determining the trigger based on the first plurality of words or the second plurality of words.

Clause 468. The technology of each preceding clause, further include receiving an output mode selection from an associated user interface and determining the trigger based on the output mode selection.

Clause 469. Speech detection technology for extracting reactions to content based on facial skin micromovements as set forth in this clause alone, and/or in combination with each preceding clause, further comprising: during a time period when an individual is consuming content, determining the facial skin micromovements of the individual based on reflections of coherent light from a facial region of the individual; determining at least one specific micro-expression from the facial skin micromovements; accessing at least one data structure containing correlations between a plurality of micro-expressions and a plurality of non-verbalized perceptions; based on the at least one specific micro-expression and the correlations in the data structure, determining a specific non-verbalized perception of the content consumed by the individual; and initiating an action associated with the specific non-verbalized perception.

Clause 470. The technology of each preceding clause, wherein the at least one specific micro-expression is imperceptible to a human eye.

Clause 471. The technology of each preceding clause, wherein the facial skin micromovements used for determining the at least one specific micro-expression correspond to recruitment of at least one muscle from a group of muscles including: a zygomaticus muscle, a genioglossus muscle, an orbicularis oris muscle, a risorius muscle, or a levator labii superioris alaeque nasi muscle.

Clause 472. The technology of each preceding clause, wherein the at least one specific micro-expression includes a sequence of micro-expressions associated with the specific non-verbalized perception.

Clause 473. The technology of each preceding clause, further include determining a degree of the specific non-verbalized perception based on the sequence of micro-expressions, and determining an action to initiate based on the degree of the specific non-verbalized perception.

Clause 474. The technology of each preceding clause, wherein the at least one data structure includes past non-verbalized perceptions of previously consumed content, and wherein the operations further comprise determining a degree of the specific non-verbalized perception relative to the past non-verbalized perceptions, and determining an action to initiate based on the degree of the specific non-verbalized perception.

Clause 475. The technology of each preceding clause, wherein the non-verbalized perceptions include an emotional state of the individual.

Clause 476. The technology of each preceding clause, wherein the operations further include determining an action to initiate based on the consumed content and the specific non-verbalized perception.

Clause 477. The technology of each preceding clause, wherein the action initiated includes causing a transmission of a message reflecting a correlation between the specific non-verbalized perception and the consumed content.

Clause 478. The technology of each preceding clause, wherein the action initiated includes storing in memory a correlation between the specific non-verbalized perception and the consumed content.

Clause 479. The technology of each preceding clause, wherein the action includes determining additional content to be presented to the individual based on the specific non-verbalized perception and the consumed content.

Clause 480. The technology of each preceding clause, wherein the consumed content is of a first type and the additional content is of a second type differing from the first type.

Clause 481. The technology of each preceding clause, wherein the consumed content is part of a chat with at least one other individual and the action includes generating a visual representation of the specific non-verbalized perception in the chat.

Clause 482. The technology of each preceding clause, wherein the action includes selecting an alternative manner for presenting the consumed content.

Clause 483. The technology of each preceding clause, wherein the action varies based on a type of the consumed content.

Clause 484. The technology of each preceding clause, further include operating at least one wearable coherent light source in a manner enabling illumination of a non-lip portion of a face of the individual, and receiving signals indicative of coherent light reflections from the non-lip portion of the face.

Clause 485. The technology of each preceding clause, wherein the facial skin micromovements are determined based on speckle analysis of the coherent light reflections.

Clause 486. The technology of each preceding clause, wherein the reflections of coherent light are received by a wearable light detector.

Clause 487. Speech detection technology for removing noise from facial skin micromovement signals as set forth in this clause alone, and/or in combination with each preceding clause, further comprising: during a time period when an individual is involved in at least one non-speech-related physical activity, operating a light source in a manner enabling illumination of a facial skin region of the individual; receiving signals representing light reflections from the facial skin region: analyzing the received signals to identify a first reflection component indicative of prevocalization facial skin micromovements and a second reflection component associated with the at least one non-speech-related physical activity; and filtering out the second reflection component to enable interpretation of words from the first reflection component indicative of the prevocalization facial skin micromovements.

Clause 488. The technology of each preceding clause, wherein the light source is a coherent light source.

Clause 489. The technology of each preceding clause, wherein the second reflection component is a result of walking.

Clause 490. The technology of each preceding clause, wherein the second reflection component is a result of running.

Clause 491. The technology of each preceding clause, wherein the second reflection component is a result of breathing.

Clause 492. The technology of each preceding clause, wherein the second reflection component is a result of blinking and is based on neural activation of at least one orbicularis oculi muscle.

Clause 493. The technology of each preceding clause, wherein, when the individual is concurrently involved in a first physical activity and a second physical activity, the operations further include identify a first portion of the second reflection component associated with the first physical activity and a second portion of the second reflection component associated with the second physical activity and filtering out the first portion of the second component and the second portion of the second component from the first component to enable interpretation of words from the prevocalization facial skin micromovements associated with the first component.

Clause 494. The technology of each preceding clause, wherein the operations further include receiving data from a mobile communications device, the data being indicative of the at least one non-speech-related physical activity.

Clause 495. The technology of each preceding clause, wherein the mobile communications device lacks a light sensor for detecting the light reflections.

Clause 496. The technology of each preceding clause wherein the data received from the mobile communications device includes at least one of: data indicative of a heart rate of the individual, data indicative of blood pressure of the individual, or data indicative of movement of the individual.

Clause 497. The technology of each preceding clause, further include presenting the words in a synthesized voice Clause 498. The technology of each preceding clause, wherein the signals are received from a sensor associated with a wearable housing and wherein the instructions further include analyzing the signals to determine the at least one non-speech-related physical activity.

Clause 499. The technology of each preceding clause, wherein the sensor is an image sensor configured to capture at least one event in an environment of the individual, and wherein the at least one processor is configured to determine that the event is associated with the at least one non-speech-related physical activity.

Clause 500. The technology of each preceding clause, further include using a neural network to identify the second reflection component associated with the at least one non-speech-related physical activity.

Clause 501. The technology of each preceding clause, wherein the prevocalization facial skin micromovements correspond to one or more involuntary muscle fiber recruitments.

Clause 502. The technology of each preceding clause, wherein the involuntary muscle fiber recruitments are a result of an individual thinking of saying the words.

Clause 503. The technology of each preceding clause, wherein the one or more muscle fiber recruitments include recruitments of: at least one of zygomaticus muscle fibers, orbicularis oris muscle fibers, genioglossus muscle fibers, risorius muscle fibers, or levator labii superioris alaeque nasi muscle fibers.

Clause 504. The technology of each preceding clause, wherein the signals are received at a rate of between 50 Hz and 200 Hz.

Disclosed embodiments may include any one of the following bullet-pointed features alone or in combination with one or more other bullet-pointed features, whether implemented as a system and/or method, by at least one processor or circuitry, and/or stored as executable instructions on non-transitory computer readable media or computer readable media.

- a head mountable system.
- identifying individuals using facial skin micromovements.
- a wearable housing configured to be worn on a head of an individual.
- at least one coherent light source associated with the wearable housing and configured to project light towards a facial region of the head.
- at least one detector associated with the wearable housing and configured to receive coherent light reflections from the facial region and to output associated reflection signals.
- at least one processor configured to.
- analyzing the reflection signals to determine specific facial skin micromovements of the individual.
- accessing memory correlating a plurality of facial skin micromovements with the individual.
- search for a match between the determined specific facial skin micromovements and at least one of the plurality of facial skin micromovements in the memory.
- if a match is identified, initiate a first action.
- if a match is not identified, initiate a second action different from the first action.
- the first action institutes at least one predetermined setting associated with the individual.
- the first action unlocks a computing device.
- the second action includes presentation of a message indicating that the computing device remains locked.
- the first action provides personal information.
- the second action provides public information.
- the first action authorizes a transaction.
- the second action provides information indicating that the transaction is not authorized.
- the first action permits access to an application.
- the second action prevents access to the application.
- at least some of the specific facial skin micromovements in the facial region are micromovements of less than 100 microns.
- the specific facial skin micromovements correspond to prevocalization muscle recruitment.
- the specific facial skin micromovements correspond to muscle recruitment during pronunciation of at least one word.
- the at least one word corresponds to a password.
- the memory is configured to correlate a plurality of facial skin movements with a plurality of individuals.
- distinguishing the plurality of individuals from each other based on reflection signals unique to each of the plurality of individuals.
- comprising an integrated audio output and wherein at least one of the first action or at least one of the second action includes outputting audio via the audio output.
- the match is identified upon determination by the at least one processor of a certainty level.
- when the certainty level is initially not reached, the at least one processor is configured to analyze additional reflection signals to determine additional facial skin micromovements, and to arrive at the certainty level based at least in part on analysis of the additional reflection signals.

continuously compare new facial skin micromovements with the plurality of facial skin micromovements in the memory to determine an instantaneous level of certainty.

after initiating the first action, when the instantaneous certainty level is below a threshold, the at least one processor is configured to stop the first action.

when the instantaneous certainty level is below a threshold, the at least one processor is configured to initiate an associated action.

initiating the first action is associated with an event, and the at least one processor is configured to continuously compare the new facial skin micromovements during the event.

interpreting facial skin movements.

projecting light on a plurality of facial region areas of an individual.

the plurality of areas includes at least a first area and a second area, the first area being closer to at least one of a zygomaticus muscle or a risorius muscle than the second area.

receiving reflections from the plurality of areas.

detecting first facial skin movements corresponding to reflections from the first area and second facial skin movements corresponding to reflections from the second area.

determining, based on differences between the first facial skin movements and the second facial skin movements, that the reflections from the first area closer to the at least one of a zygomaticus muscle or a risorius muscle are a stronger indicator of communication than the reflections from the second area.

based on the determination that the reflections from the first area are a stronger indicator of communication, processing the reflections from the first area to ascertain the communication, and ignoring the reflections from the second area.

the first area and the second area are spaced apart.

the communication ascertained from the reflections from the first area includes words articulated by the individual.

the communication ascertained from the reflections from the first area includes non-verbal cues of the individual.

operating a coherent light source located within a wearable housing in a manner enabling illumination of the plurality of facial region areas.

operating a coherent light source located remote from a wearable housing in a manner enabling illumination of the plurality of facial region areas.

illuminating at least a portion of the first area and at least a portion of the second area with a common light spot.

illuminating the first area with a first group of spots and illuminating the second area with a second group of spots distinct from the first group of spots.

operating a coherent light source in a manner enabling bi-mode illumination of the plurality of facial region areas.

analyzing reflections associated with a first mode of illumination to identify one or more light spots associated with the first area.

a first light intensity of the first mode of illumination differs from a second light intensity of the second mode of illumination.

analyzing reflections associated with a second mode of illumination to ascertain the communication.

a first illumination pattern of the first mode of illumination differs from a second illumination pattern of the second mode of illumination.

determining, based on differences between the first facial skin movements and the second facial skin movements.

that the first area is closer than the second area to the subcutaneous tissue associated with cranial nerve V or with cranial nerve VII.

the first area is closer than the second area to the zygomaticus muscle, and the plurality of light areas further includes a third area closer to the risorius muscle than each of the first area and the second area.

analyzing reflected light from the first area when speech is generated with perceptible vocalization.

analyzing reflected light from the third area when speech is generated in an absence of perceptible vocalization.

the differences between the first facial skin movements and the second facial skin movements include differences of less than 100 microns, and the determination that the reflections from the first area are a stronger indicator of communication than the reflections from the second area is based on the differences of less than 100 microns.

ignoring the reflections from the second area includes omitting use of the reflections from the second area to ascertain the communication.

detecting the first facial skin movements involves performing a first speckle analysis on light reflected from the first area, and wherein detecting the second facial skin movements involves performing a second speckle analysis on light reflected from the second area.

the first speckle analysis and the second speckle analysis occur concurrently by the at least one processor.

performing identity verification operations based on facial micromovements.

receiving in a trusted manner, reference signals for verifying correspondence between a particular individual and an account at an institution.

the reference signals being derived based on reference facial micromovements detected using first coherent light reflected from a face of the particular individual.

storing in a secure data structure, a correlation between an identity of the particular individual and the reference signals reflecting the facial micromovements.

following storing, receiving via the institution, a request to authenticate the particular individual.

receiving real-time signals indicative of second coherent light reflections being derived from second facial micromovements of the particular individual.

comparing the real-time signals with the reference signals stored in the secure data structure to thereby authenticate the particular individual.

upon authentication, notifying the institution that the particular individual is authenticated.

the authentication is associated with a financial transaction at the institution.

the financial transaction includes at least one of: a transfer of funds, a purchase of stocks, a sale of stocks, an access to financial data, or access to an account of the particular individual.

receiving the real-time signals and comparing the real-time signals occur multiple times during a transaction.

reporting a mismatch if a subsequent difference is detected following the notifying.

determining a certainty level that an individual associated with the real-time signals is the particular individual.

when the certainty level is below a threshold, the operations further include terminating the transaction.

the transaction is a financial transaction that includes providing access to the particular individual's account.

when a certainty level is below a threshold, the operations further include blocking the individual associated with the real-times signals from the particular individual's account.

the reference signals for authentication correspond to muscle activation during pronunciation of at least one word.

the muscle activation is associated with at least one specific muscle that includes: a zygomaticus muscle, an orbicularis oris muscle, a risorius muscle, a genioglossus muscle, or a levator labii superioris alaeque nasi muscle.

the at least one word is a password.

presenting the at least one word to the particular individual for pronunciation.

presenting the at least one word to the particular individual for pronunciation includes audibly presenting the at least one word.

presenting the at least one word to the particular individual for pronunciation includes textually presenting the at least one word.

the reference signals for authentication correspond to muscle activation during pronunciation of one or more syllables.

the institution is associated with an online activity, and upon authentication, the particular individual is provided access to perform the online activity.

the online activity is at least one of: a financial transaction, a wagering session, an account access session, a gaming session, an exam, a lecture, or an educational session.

the institution is associated with a resource, and upon authentication, the particular individual is provided access to the resource.

the resource is at least one of: a file, a folder, a data structure, a computer program, computer code, or computer settings.

continuous authentication based on facial skin micromovements.

receiving during an ongoing electronic transaction.

first signals representing coherent light reflections associated with first facial skin micromovements during a first time period.

determining, using the first signals, an identity of a specific individual associated with the first facial skin micromovements.

receiving during the ongoing electronic transaction second signals representing coherent light reflections associated with second facial skin micromovements.

the second signals being received during a second time period following the first time period.

determining, using the second signals, that the specific individual is also associated with the second facial skin micromovements.

receiving during the ongoing electronic transaction third signals representing coherent light reflections associated with third facial skin micromovements.

the third signals being received during a third time period following the second time period.

determining, using the third signals, that the third facial skin micromovements are not associated with the specific individual.

initiating an action based on the determination that the third facial skin micromovements are not associated with the specific individual.

the ongoing electronic transaction is a phone call.

continuously outputting data confirming that the specific individual is associated with the second facial skin micromovements.

the action includes providing an indication that the specific individual is not responsible for the third detected facial skin micromovements.

the action includes executing a process for identifying another individual responsible for the third facial skin micromovements.

the first period of time, the second period of time, and the third period of time are part of a single online activity associated with the ongoing electronic transaction.

the online activity includes multiple sessions, and using received signals associate with facial skin micromovements to determine that the specific individual participates in each of the multiple sessions.

the action includes notifying an entity associated with the online activity that an individual other than the specific individual is now participating in the online activity.

the action includes preventing participation in the online activity until the identity of specific individual is confirmed.

the first period of time, the second period of time, and the third period of time are part of a secured session with access to a resource.

the resource is at least one of: a file, a folder, a database, a computer program, a computer code, or computer settings.

the action includes notifying an entity associated with the resource that an individual other than the specific individual gained access to the resource.

the action includes terminating the access to the resource.

the first period of time, the second period of time, and the third period of time are part of a single communication session, and wherein the communication session is at least one of: a phone call, a teleconference, a video conference, or a real-time virtual communication.

the action includes notifying an entity associated with the communication session that an individual other than the specific individual has joined the communication session.

determining the identity of the specific individual includes accessing memory correlating a plurality of reference facial skin micromovements with individuals and determining a match between the first facial skin micromovements and at least one of the plurality of reference facial skin micromovements.

determining the first facial skin micromovements, the second facial skin micromovements, and the third facial skin micromovements by analyzing signals indicative of received coherent light reflections to identify temporal and intensity changes of speckles.

performing thresholding operations for interpretation of facial skin micromovements.

detecting facial micromovements in an absence of perceptible vocalization associated with the facial micromovements.

determining an intensity level of the facial micromovements.

comparing the determined intensity level with a threshold.

when the intensity level is above the threshold, interpreting the facial micromovements.

when the intensity level falls beneath the threshold, disregarding the facial micromovements.

enabling adjustment of the threshold.

the threshold is variable, depending on environmental conditions.

the environmental conditions include a background noise level.

receiving data indicative of the background noise level, and determining a value for the threshold based on the received data.

the threshold is variable, depending on at least one physical activity engaged in by an individual associated with the facial micromovements.

the at least one physical activity includes walking, running, or breathing.

receiving data indicative of the of the at least one physical activity in which the individual is engaged, and determining a value for the threshold based on the received data.

the threshold is customized to a user.

receiving a personalized threshold for a particular individual and storing the personalized threshold in settings associated with the particular individual.

receiving a plurality of thresholds for a particular individual, each of the plurality of thresholds being associated with a differing condition.

at least one of the differing conditions includes a physical condition of the particular individual, an emotional condition of the particular individual, or a location of the particular individual.

receiving data indicative of a current condition of the particular individual, and selecting one of the plurality of thresholds based on the received data.

interpreting the facial micromovements includes synthesizing speech associated with the facial micromovements.

interpreting the facial micromovements includes understanding and executing a command based on the facial micromovements.

executing the command includes generating a signal for triggering an action.

determining the intensity level includes determining a value associated with a series of micromovements in a time period.

the facial micromovements having an intensity level falling beneath the threshold are capable of interpretation but are disregarded nevertheless.

establishing nonvocalized conversations.

both the first wearable device and the second wearable device each contain a coherent light source and a light detector configured to detect facial skin micromovements from coherent light reflections.

establishing a wireless communication channel for enabling a nonvocalized conversation via a first wearable device and a second wearable device.

detecting by the first wearable device first facial skin micromovements occurring in an absence of perceptible vocalization.

transmitting a first communication via the wireless communication channel from the first wearable device to the second wearable device.

wherein the first communication is derived from the first facial skin micromovements and is transmitted for presentation via the second wearable device.

receiving a second communication via the wireless communication channel from the second wearable device, wherein the second communication is derived from second facial skin micromovements detected by the second wearable device.

presenting the second communication to a wearer of the first wearable device.

the first communication contains signals reflective of the first facial skin micromovements.

interpreting the first facial skin micromovements as words, and wherein the first communication includes a transmission of the words.

presenting the second communication to the wearer of the first wearable device includes synthesizing words derived from the second facial skin micromovements.

presenting the second communication to the wearer of the first wearable device includes providing textual output reflective of words derived from the second facial skin micromovements.

presenting the second communication to the wearer of the first wearable device includes providing a graphical output reflective of at least one facial expression derived from the second facial skin micromovements.

the graphical output includes at least one emoji.

determining that the second wearable device is located in proximity to the first wearable device.

automatically establishing the wireless communication channel between the first wearable device and the second wearable device.

presenting via the first wearable device a suggestion to establish a nonvocalized conversation with the second wearable device.

determining an intent of the wearer of the first wearable device to initiate a nonvocalized conversation with the wearer of the second wearable device.

the intent is determined from the first facial skin micromovements.

the wireless communication channel is established directly between the first wearable device and the second wearable device.

the wireless communication channel is established from the first wearable device to the second wearable device via at least one intermediate communication device.

the at least one communication device includes at least one of: a first smartphone associated with the wearer of the first wearable device, a second smartphone associated with the wearer of the second wearable device, a router, or a server.

the first communication contains signals reflective of first words spoken in a first language and the second communication contains signals reflective of second words spoken in a second language, and wherein presenting the second communication to the wearer of the first wearable device includes translating the second words to the first language.

the first communication contains details identifying the wearer of the first wearable device and the second communication contains signals identifying the wearer of the second wearable device.

the first communication contains a time stamp indicating when the first facial skin micromovements were detected.

initiate content interpretation operations prior to vocalization of content to be interpreted.

receiving signals representing facial skin micromovements.

determining from the signals at least one word to be spoken prior to vocalization of the at least one word in an origin language.

prior to the vocalization of the at least one word, instituting an interpretation of the at least one word.

causing the interpretation of the at least one word to be presented as the at least one word is spoken.

the interpretation is a translation of the at least one word from the origin language into at least one target language other than the origin language.

the interpretation of the at least one word includes a transcription of the at least one word into text in the at least one target language.

the interpretation of the at least one word includes a speech synthetization of the at least one word in the at least one target language.

receiving a selection of the at least one target language.

the selection of the at least one target language includes selections of a plurality of target languages.

the interpretation of the at least one word to be presented includes simultaneously causing presentation in the plurality of languages.

the interpretation of the at least one word includes a transcription of the at least one word into text in the origin language.

presenting the interpretation of the at least one word includes outputting a textual display of the transcription together with a video of an individual associated with the facial skin micromovements.

receiving signals occurs via at least one detector of coherent light reflections from a facial region of a person vocalizing the at least one word.

causing the interpretation of the at least one word to be presented occurs concurrently with the at least one word being vocalized by the person.

causing the interpretation of the at least one word to be presented includes using a wearable speaker to output an audible presentation of the at least one word.

causing the interpretation of the at least one word to be presented includes transmitting sound signals over a network.

determining at least one prospective word to be spoken following to the at least one word to be spoken, instituting an interpretation of the at least one prospective word prior to vocalization of the at least one word; and causing the interpretation of the at least one prospective word to be presented following presentation of the at least one word as the at least one word is spoken.

causing the interpretation of the at least one word to be presented includes transmitting a textual translation of the at least one word over a network.

determining from the signals at least one non-verbal interjection, and outputting a representation of the non-verbal interjection.

determining from the signals at least one word includes interpreting the facial skin micromovements using speckle analysis.

the signals representing facial skin micromovements correspond to muscle activation prior to the vocalization of the at least one word.

performing private voice assistance operations.

receive signals representing facial skin micromovements.

prior to the vocalization of the at least one word, institute an interpretation of the at least one word.

cause the interpretation of the at least one word to be presented as the at least one word is spoken.

the second action includes providing non-private information.

determine from the signals at least one word to be spoken prior to vocalization of the at least one word in an origin language.

the second action includes a notification that access is denied to information unique to the specific individual.

the second action includes blocking access to the information unique to the specific individual.

the second action includes attempting to authenticate the specific individual using additional data.

the additional data includes additional detected facial skin micromovements.

the additional data includes data other than facial skin micromovements.

when the match is not identified, the operations further comprise initiating an additional action for identifying another individual other than the specific individual.

in response to an identification of another individual other than the specific individual, initiating a third action responsive to the request.

the third action involves enabling access to information unique to the other individual.

the private request is for activating software code, the first action is activating the software code, and the second action is preventing activation of the software code.

the private request is for confidential information, and the operations further include determining that the specific individual has permission to access the confidential information.

wherein receiving, accessing, and searching occur repeatedly during an ongoing session.

in a first time period during the ongoing session the specific individual is identified and the first action is initiated, and wherein in a second time period during the ongoing session, the specific individual is not identified, and any residual first action is terminated in favor of the second action.

operating at least one coherent light source in a manner enabling illuminating a non-lip portion of a face of an individual making the private request, and wherein receiving the signals occurs via at least one detector of coherent light reflections from the non-lip portion of the face.

the at least one processor, the at least one coherent light source, and the at least one detector are integrated in a wearable housing configured to be supported by an ear of the individual.

analyzing the received signals to determine prevocalization muscle recruitment, and determining the private request based on the determined prevocalization muscle recruitment.

determining the private request in an absence of perceptible vocalization of the private request.

determining subvocalized phonemes from facial skin micromovements.

controlling at least one coherent light source in a manner enabling illumination of a first region of a face and a second region of the face.

performing first pattern analysis on light reflected from the first region of the face to determine first micromovements of facial skin in the first region of the face.

performing second pattern analysis on light reflected from the second region of the face to determine second micromovements of facial skin in the second region of the face.

using the first micromovements of the facial skin in the first region of the face and the second micromovements of the facial skin in the second region of the face to ascertain at least one subvocalized phoneme.

performance of the second pattern analysis occurs after performing the first pattern analysis.

performance of the second pattern analysis occurs simultaneously with performance of the first pattern analysis.

wherein the first region is spaced apart from the second region.

wherein ascertaining the at least one subvocalized phoneme includes ascertaining a sequence of phonemes, and.

wherein the operations further include extracting meaning from the sequence of phonemes.

wherein each phoneme in the sequence of phonemes is derived from the first pattern analysis and the second pattern analysis.

identifying as private at least one phoneme in the sequence of phonemes.

omitting generation of an audio output reflective of the at least one private phoneme.

determining both the first micromovements and the second micromovements during a common time period.

receiving the first light reflections and the second light reflections via at least one detector.

wherein the at least one detector and the at least one coherent light source are integrated within a wearable housing.

wherein controlling the at least one coherent light source includes projecting differing light patterns on the first region and the second region.

the differing light patterns include a plurality of light spots, such that the first region of the face is illuminated by at least a first light spot and the second region of the face is illuminated by at least a second light spot, different from the first light spot.

wherein controlling the at least one coherent light source includes illuminating the first region and the second region with a common light spot.

wherein the first micromovements of the facial skin and the second micromovements of the facial skin correspond to concurrent muscle recruitments.

wherein the determined first micromovements of facial skin in the first region of the face correspond to recruitment of a first muscle selected from: a zygomaticus muscle, an orbicularis oris muscle, a risorius muscle, or a levator labii superioris alaeque nasi muscle.

wherein the determined second micromovements of facial skin in the second region of the face corresponds to recruitment of a second muscle, different from the first muscle, selected from: the zygomaticus muscle, the orbicularis oris muscle, the risorius muscle, or the levator labii superioris alaeque nasi muscle.

accessing a default language of an individual associated with the facial skin micromovements.

using the default language to extract meaning from the at least one subvocalized phoneme.

using a synthesized voice to generate an audio output reflective of the at least one subvocalized phoneme.

wherein the at least one phoneme includes a sequence of phonemes.

determining a prosody associated with the sequence of phonemes, and extracting meaning based on the determined prosody.

determining an emotional state of an individual associated with the facial skin micromovements.

extracting meaning from the at least one subvocalized phoneme and the determined emotional state.

identifying at least one extraneous phoneme as part of a filler and omitting generation of an audio output reflective of the extraneous phoneme.

generating synthesized representations of facial expressions.

controlling at least one coherent light source in a manner enabling illumination of a portion of a face.

receiving output signals from a light detector, wherein the output signals correspond to reflections of coherent light from the portion of the face.

applying speckle analysis on the output signals to determine speckle analysis-based facial skin micromovements.

using the determined speckle analysis-based facial skin micromovements to identify at least one word prevocalized or vocalized during a time period.

using the determined speckle analysis-based facial skin micromovements to identify at least one change in a facial expression during the time period.

during the time period, outputting data for causing a virtual representation of the face to mimic the at least one change in the facial expression in conjunction with an audio presentation of the at least one word.

wherein controlling the at least one coherent light source in a manner enabling illumination of the portion of the face includes projecting a light pattern on the portion of the face.

wherein the light pattern includes a plurality of spots.

wherein the portion of the face includes cheek skin.

wherein the portion of the face excludes lips.

wherein the output signals from the light detector emanate from a wearable device.

wherein the output signals from the light detector emanate from a non-wearable device.

wherein the determined speckle analysis-based facial skin micromovements are associated with recruitment of at least one of: a zygomaticus muscle, an orbicularis oris muscle, a genioglossus muscle, a risorius muscle, or a levator labii superioris alaeque nasi muscle.

wherein the at least one change in the facial expression during the period of time includes speech-related facial expressions and non-speech-related facial expressions.

wherein the virtual representation of the face is associated with an avatar of an individual from whom the output signals are derived.

wherein mimicking the at least one change in the facial expression includes causing visual changes to the avatar that reflect at least one of the speech-related facial expressions and the non-speech-related facial expressions.

the visual changes to the avatar involve changing a color of at least a portion of the avatar.

wherein the audio presentation of the at least one word is based on a recording of an individual.

wherein the audio presentation of the at least one word is based on a synthesized voice.

wherein the synthesized voice corresponds with a voice of an individual from whom the output signals are derived.

wherein the synthesized voice corresponds with template voice selected by an individual from whom the output signals are derived.

determining an emotional state of an individual from whom the output signals are derived based at least in part on the facial skin micromovements and.

augmenting the virtual representation of the face to reflect the determined emotional state.

receiving a selection of a desired emotional state, and augmenting the virtual representation of the face to reflect the selected emotional state.

identifying a non-desirable facial expression, and wherein the outputted data for causing the virtual representation omits data for causing the non-desirable facial expression.

attention-associated interactions based on facial skin micromovements.

determining facial skin micromovements of an individual based on reflections of coherent light from a facial region of the individual.

using the facial skin micromovements to determine a specific engagement level of the individual.

receiving data associated with a prospective interaction with the individual.

accessing a data structure correlating information reflective of alternative engagement levels with differing presentation manners.

based on the specific engagement level and the correlating information, determining a specific presentation manner for the prospective interaction.

associating the specific presentation manner with the prospective interaction for subsequent engagement with the individual.

generating an output reflecting the prospective interaction according to the determined specific presentation manner.

operating at least one coherent light source in a manner enabling illuminating a non-lip portion of a face of the individual.

receiving signals indicative of the reflections of coherent light from the non-lip portion of the face.

performing a speckle analysis on the coherent light reflections from the non-lip portion of the face to determine the facial skin micromovements.

wherein the specific engagement level is a category of engagement.

wherein the specific engagement level includes a magnitude of engagement.

wherein the specific engagement level is reflective of an extent to which the individual is engaged in an activity including at least one of a conversation, thoughts, or rest.

determining the extent to which the individual is engaged in the activity based on facial skin micromovements that correspond with recruitment of at least one muscle out of a group of muscles including: a zygomaticus muscle, an orbicularis oris muscle, a risorius muscle, or a levator labii superioris alaeque nasi muscle.

wherein the received data associated with the prospective interaction includes an incoming call.

wherein the associated differing presentation manners include notifying the individual of the incoming call, and directing the incoming call to voicemail.

wherein the received data associated with the prospective interaction includes an incoming text message.

wherein the associated differing presentation manners include presenting the text message to the individual in real time and deferring presentation of the text message to a later time.

wherein determining the specific presentation manner for the prospective interaction includes determining how to notify the individual of the prospective interaction.

wherein determining how to notify the individual of the prospective interaction is based least in part on an identification of a plurality of electronic devices currently used by the individual.

wherein the received data associated with the prospective interaction is indicative of an importance level of the prospective interaction.

wherein the specific presentation manner is determined based at least in part on the importance level.

wherein the received data associated with the prospective interaction is indicative of an urgency level of the prospective interaction.

wherein the specific presentation manner is determined based at least in part on the specific urgency level.

wherein the specific presentation manner includes deferring presentation of content until a time period of detected low engagement and.

wherein the operations further include detecting low engagement at a subsequent time and presenting the content at the subsequent time.

using the facial skin micromovements to determine that the individual is engaged in a conversation with another individual, determining whether the prospective interaction is relevant for the conversation.

wherein the specific presentation manner is determined based at least in part on a relevancy of the prospective interaction to the conversation.

using the facial skin micromovements to determine a subject of the conversation and.

wherein determining that the prospective interaction is relevant to the conversation is based on the received data associated with the prospective interaction and subject of the conversation.

wherein when the prospective interaction is determined to be relevant to the conversation, a first presentation manner is used for the prospective interaction.

wherein when the prospective interaction is determined to be irrelevant to the conversation, a second presentation manner is used for the prospective interaction.

performing voice synthetization operations from detected facial skin micromovements.

determining particular facial skin micromovements of a first individual speaking with a second individual based on reflections of light from a facial region of the first individual.

accessing a data structure correlating facial micromovements with words.

performing a lookup in the data structure of particular words associated with the particular facial skin micromovements.

obtaining an input associated with a preferred speech consumption characteristic of the second individual.

adopting the preferred speech consumption characteristic.

synthesizing, using the adopted preferred speech consumption characteristic, audible output of the particular words.

presenting at least one of the first individual and the second individual with a user interface for altering the preferred speech consumption characteristic.

wherein obtaining the input associated with the preferred speech consumption characteristic of the second individual includes receiving the input from the first individual.

wherein obtaining the input associated with the preferred speech consumption characteristic of the second individual includes receiving the input from the second individual.

wherein obtaining the input associated with the preferred speech consumption characteristic of the second individual includes retrieving information on the second individual.
wherein obtaining the input associated with the preferred speech consumption characteristic of the second individual includes determining the information based on image data captured by an image sensor worn by the first individual.
wherein the input associated with the preferred speech consumption characteristic of the second individual is indicative of an age of the second individual.
wherein the input associated with the preferred speech consumption characteristic of the second individual is indicative of environmental conditions associated with the second individual.
wherein the input associated with the preferred speech consumption characteristic of the second individual is indicative of a hearing impairment of the second individual.
wherein the second individual is one of a plurality of individuals.
obtaining additional inputs from the plurality of individuals and classifying the plurality of individuals based on the additional inputs.
wherein adopting the preferred speech consumption characteristic includes pre-setting voice synthesis controls for prospective facial micromovements.
wherein the input associated with the preferred speech consumption characteristic includes a preferred pace of speech.
wherein the synthesized audible output of the particular words occurs at the preferred pace of speech.
wherein the input associated with the preferred speech consumption characteristic includes a speech volume.
wherein the synthesized audible output of the particular words occurs at the preferred speech volume.
wherein the input associated with the preferred speech consumption characteristic includes a target language of speech other than a language associated with the particular facial skin micromovements.
wherein the synthesized audible output of the particular words occurs in the target language of speech.
wherein the input associated with the preferred speech consumption characteristic includes a preferred voice.
wherein the synthesized audible output of the particular words occurs in the preferred voice.
wherein the preferred voice is at least one of a celebrity voice, an accented voice, or a gender-based voice.
presenting a first synthesized version of intended speech based on the facial micromovements and.
presenting a second synthesized version of speech based on the facial micromovements in combination with the preferred speech consumption characteristic.
presenting the first synthesized version and the second synthesized version occur sequentially to the first individual.
operations for personal presentation of prevocalization.
receiving reflection signals corresponding to light reflected from a facial region of an individual.
using the received reflections signals to determine particular facial skin micromovements of an individual in an absence of perceptible vocalization associated with the particular facial skin micromovements.
accessing a data structure correlating facial skin micromovements with words.
performing a lookup in the data structure of particular unvocalized words associated with the particular facial skin micromovements.
causing an audible presentation of the particular unvocalized words to the individual prior to vocalization of the particular words by the individual.
recording data associated with the particular unvocalized words for future use.
wherein the data includes at least one of the audible presentation of the particular unvocalized words or a textual presentation of the particular unvocalized words.
wherein the light reflected from the facial region of the individual include coherent light reflections.
adding punctuation to the textual presentation.
receiving reflection signals corresponding to light reflected from a facial region of an individual.
adjusting a speed of the audible presentation of the particular unvocalized words based on input from the individual.
using the received reflections signals to determine particular facial skin micromovements of an individual in an absence of perceptible vocalization associated with the particular facial skin micromovements.
adjusting a volume of the audible presentation of the particular unvocalized words based on input from the individual.
accessing a data structure correlating facial skin micromovements with words.
causing the audible presentation includes outputting an audio signal to a personal hearing device configured to be worn by the individual.
performing a lookup in the data structure of particular unvocalized words associated with the particular facial skin micromovements.
operating at least one coherent light source in a manner enabling illumination of the facial region of the individual.
wherein the at least one coherent light source is integrated with the personal hearing device.
wherein the audible presentation of the particular unvocalized words is a synthetization of a selected voice.
wherein the selected voice is a synthetization of a voice of the individual.
wherein the selected voice is a synthetization of a voice of another individual other than the individual associated with the facial skin micromovements.
wherein the particular unvocalized words correspond to vocalizable words in a first language and the audible presentation includes a synthetization of the vocalizable words in a second language different from the first language.
associating the particular facial skin micromovements with a plurality of vocalizable words in the second language.
selecting a most appropriate vocalizable word from the plurality of vocalizable words, wherein the audible presentation includes the most appropriate vocalizable word in the second language.
determining that an intensity of a portion of the particular facial skin micromovements is below a threshold and providing associated feedback to the individual.
wherein the audible presentation of the particular unvocalized words is provided to the individual at least 20 milliseconds prior to vocalization of the particular words by the individual.

ceasing the audible presentation of the particular unvocalized words in response to a detected trigger.
detecting the trigger from determined facial skin micromovements of the individual.
determining facial skin micromovements.
controlling at least one coherent light source for projecting a plurality of light spots on a facial region of an individual.
wherein the plurality of light spots includes at least a first light spot and a second light spot spaced from the first light spot.
analyzing reflected light from the first light spot to determine changes in first spot reflections.
analyzing reflected light from the second light spot to determine changes in second spot reflections.
based on the determined changes in the first spot reflections and the second spot reflections, determining the facial skin micromovements.
interpreting the facial skin micromovements derived from analyzing the first spot reflections and analyzing the second spot reflections.
generating an output of the interpretation.
wherein the plurality of light spots additionally includes a third light spot and a fourth light spot, wherein each of the third light spot and the fourth light spot are spaced from each other and spaced from the first light spot and the second light spot.
wherein the facial skin micromovements are determined based on the determined changes in the first spot reflections and the second spot reflections, and changes in the third spot reflections and the fourth spot reflections.
wherein the plurality of light spots includes at least 16 spaced-apart light spots.
wherein the plurality of light spots are projected on a non-lip region of the individual.
wherein the changes in the first spot reflections and the changes in the second spot reflections correspond to concurrent muscle recruitments.
wherein both the first spot reflections and the second spot reflections correspond to recruitment of a single muscle selected from: a zygomaticus muscle, an orbicularis oris muscle, a genioglossus muscle risorius muscle, or a levator labii superioris alaeque nasi muscle.
wherein the first spot reflections correspond to recruitment of a muscle selected from: a zygomaticus muscle, an orbicularis oris muscle, a risorius muscle, a genioglossus muscle, or a levator labii superioris alaeque nasi muscle.
wherein the second spot reflections correspond to recruitment of another muscle selected from: the zygomaticus muscle, the orbicularis oris muscle, the risorius muscle, the genioglossus muscle, or the levator labii superioris alaeque nasi muscle.
wherein the at least one coherent light source is associated with a detector.
wherein the at least one coherent light source and the detector are integrated within a wearable housing.
wherein determining the facial skin micromovements includes analyzing the changes in the first spot reflections relative to the changes in the second spot reflections.
wherein the determined facial skin micromovements in the facial region include micromovements of less than 100 microns.
wherein the interpretation includes an emotional state of the individual.
wherein the interpretation includes at least one of a heart rate or a respiration rate of the individual.
wherein the interpretation includes an identification of the individual.
wherein the interpretation includes words.
wherein the output includes a textual presentation of the words.
wherein the output includes an audible presentation of the words.
wherein the output includes metadata indicative of facial expressions or prosody associated with words.
performing operations for interpreting impaired speech based on facial movements.
receiving signals associated with specific facial skin movements of an individual having a speech impairment that affects a manner in which the individual pronounces a plurality of words.
accessing a data structure containing correlations between the plurality of words and a plurality of facial skin movements corresponding to the manner in which the individual pronounces the plurality of words.
based on the received signals and the correlations, identifying specific words associated with the specific facial skin movements.
generating an output of the specific words for presentation, wherein the output differs from how the individual pronounces the specific words.
wherein the facial skin movements are facial skin micromovements.
wherein the signals are received from a sensor that detects light reflections from a non-lip portion of a face of the individual.
wherein the facial skin micromovements correspond with recruitment of at least one muscle out of a group of muscles including: a zygomaticus muscle, a genioglossus muscle, an orbicularis oris muscle, a risorius muscle, or a levator labii superioris alaeque nasi muscle.
wherein the signals are received from an image sensor configured to measure non-coherent light reflections.
wherein the data structure is personalized to unique facial skin movements of the individual.
wherein the operations further include employing a training model for populating the data structure.
wherein the specific facial skin movements are associated with a vocalization of the specific words, and wherein the vocalization of the specific words is in a non-normative manner.
wherein the output of the specific words is audible and used to correct the speech impairment of the individual.
wherein the speech impairment is stuttering and wherein correcting includes outputting the specific words spoken in a stutter-free form.
wherein the speech impairment is hoarseness, and wherein correcting includes outputting the specific words in a hoarseness-free form.
wherein the speech impairment is low volume, and wherein correcting includes outputting the specific words in a volume higher than the specific words were spoken.
wherein the output of the specific words is textual.
wherein the operations further include adding punctuation to the textual output of the specific words.
wherein the data structure includes data associated with at least one recording of the individual previously pronouncing the specific words.

wherein the identified specific words associated with the specific facial skin movements are nonvocalized.

wherein the specific facial skin movements are associated with a subvocalization of the specific words.

wherein the generated output includes a private audible presentation of the subvocalized words to the individual.

wherein the generated output includes a non-private audible presentation of the subvocalized words.

performing operations for ongoing verification of communication authenticity based on light reflections from facial skin.

generating a first data stream representing a communication by a subject, the communication having a duration.

generating a second data stream for corroborating an identity of the subject from facial skin light reflections captured during the duration of the communication.

transmitting the first data stream to a destination.

transmitting the second data stream to the destination.

wherein the second data stream is correlated to the first data stream in a manner such that upon receipt at the destination, the second data stream is enabled for use in repeatedly checking during the duration of the communication that the communication originated from the subject.

wherein checking that the communication originated from the subject includes verifying that all words in the communication originated from the subject.

wherein checking that the communication originated from the subject incudes verifying at regular time intervals during the duration of the conversation that speech captured at the regular time intervals originated from the subject.

wherein the first data stream and the second data stream are intermingled in a common omnibus data stream.

wherein the destination is a social network service the second data stream enables the social network service to publish the communication with an authenticity indicator.

wherein the destination is an entity engaged in a real-time transaction with the subject and the second data stream enables the entity to verify in real-time the identity of the subject during the duration of the communication.

wherein verifying the identity includes verification of a name of the subject.

wherein verifying the identity includes verification at least periodic intervals throughout the communication that the subject spoke words presented in the communication.

wherein the operations further include determining a biometric signature of the subject from light reflections associated with facial skin captured before the communication.

wherein the identity of the subject is determined using the corroborating facial skin light reflections and the biometric signature.

wherein the biometric signature is determined based on a micro-veins pattern in the facial skin.

wherein the biometric signature is determined based on a facial skin micromovement sequence associated with phenomes spoken by the subject.

wherein the second data stream is indicative of a liveliness state of the subject and transmitting the second data stream enables verification of the communication authenticity based on the liveliness state of the subject.

wherein the first data stream is indicative of an expression of the subject and the second data stream enables corroboration of the expression.

storing in a data structure identifying facial skin micromovements of the subject vocalizing or pre-vocalizing a passphrase, and identifying the subject based on the vocalization or prevocalization of the passphrase.

storing in a data structure a profile of the subject based on patterns of facial skin micromovements, and identifying the subject based on the patterns.

wherein the first data stream is based on signals associated with sound captured by a microphone during the duration of the communication.

wherein the first data stream and the second data stream are determined based on signals from a same light detector.

wherein generating the first data stream representing the communication by the subject includes reproducing speech based on the corroborating facial skin light reflections.

a head mountable system for noise suppression.

a wearable housing configured to be worn on a head of a wearer.

at least one detector associated with the wearable housing and configured to receive coherent light reflections from the facial region associated with facial skin micromovements and to output associated reflection signals.

analyzing the reflection signals to determine speech timing based on the facial skin micromovements in the facial region.

receiving audio signals from at least one microphone, the audio signals containing sounds of words spoken by the wearer together with ambient sounds.

correlating, based on the speech timing, the reflection signals with the received audio signals to determine portions of the audio signals associated with the words spoken by the wearer.

outputting the determined portions of the audio signals associated with the words spoken by the wearer, while omitting output of other portions of the audio signals not containing the words spoken by the wearer.

wherein the at least one processor is further configured to record the determined portions of the audio signals.

wherein the at least one processor is further configured to determine that the other portions of the audio signals are not associated with the words spoken by the wearer.

wherein the other portions of the audio signals include ambient noise.

determining that the other portions of the audio signals include speech of at least one person other than the wearer.

recording the speech of the at least one person.

receiving input indicative of a wearer's desire for outputting the speech of the at least one person, and output portions of the audio signals associated with the speech of the at least one person.

identifying the at least one person, determine relationship of the at least one person to the wearer, and automatically output portions of the audio signals associated with the speech of the at least one person based on the determined relationship.

analyzing the audio signals and the reflection signals to identify non-verbal interjection of the wearer, and omit the non-verbal interjection from the output.

wherein outputting the determined portions of the audio signals includes synthesizing vocalization of the words spoken by the wearer.

wherein the synthesized vocalization emulates a voice of the wearer.

wherein the synthesized vocalization emulates a voice of a specific individual other than the wearer.

wherein the synthesized vocalization includes a translated version of the words spoken by the wearer.

wherein the at least one processor is further configured to analyze the reflection signals to identify an intent to speak and activate at least one microphone in response to the identified intent.

wherein the at least one processor is further configured to analyze the reflection signals to identify a pause in the words spoken by the wearer and deactivate at least one microphone during the identified pause.

wherein at least one microphone is part of a communications device configured to be wirelessly paired with the head mountable system.

wherein at least one microphone is integrated with the wearable housing and the wearable housing is configured such that when worn, the at least one coherent light source assumes an aiming direction for illuminating at least a portion of a cheek of the wearer.

wherein a first portion of the wearable housing is configured to be placed in an ear canal of the wearer and second portion is configured to be placed outside the ear canal, and the at least one microphone is included in the second portion.

performing operations for providing private answers to silent questions.

receiving signals indicative of particular facial micromovements in an absence of perceptible vocalization.

using the received signals to perform a lookup in the data structure of particular words associated with the particular facial micromovements.

determining a query from the particular words.

accessing at least one data structure to perform a look up for an answer to the query.

generating a discreet output that includes the answer to the query.

wherein the received signals are obtained via a head mountable light detector and derived from skin micromovements of a facial portion other than a mouth.

wherein the head mountable light detector is configured to detect incoherent light reflections from the facial portion.

controlling at least one coherent light source in a manner enabling illuminating the facial portion.

wherein the head mountable light detector is configured to detect coherent light reflections from the facial portion.

wherein the discreet output includes an audible output delivered via at least one earbud to a wearer of the head mountable light detector.

wherein the discreet output includes a textual output delivered to a wearer of the head mountable light detector.

wherein the discreet output includes a tactile output delivered to a wearer of the head mountable light detector.

wherein the facial micromovements correspond with muscle activation of at least one of: a zygomaticus muscle, an orbicularis oris muscle, a risorius muscle, a genioglossus muscle, or a levator labii superioris alaeque nasi muscle.

receiving image data and wherein the query is determined based on nonvocalized articulation of the particular words and the image data.

wherein the image data is obtained from a wearable image sensor.

wherein the image data reflects an identity of a person, the query is for a name of the person, and the discreet output includes the name of the person.

wherein the image data reflects an identity of an edible product, the query is for a list of allergens included in the edible product, and the discreet output includes the list of allergens.

wherein the image data reflects an identity of an inanimate object, the query is for details on the inanimate object, and the discreet output includes the requested details on the inanimate object.

using the particular facial micromovements to attempt to authenticate an individual associated with the particular facial micromovements.

when the individual is authenticated, the operations further include providing a first answer to the query, the first answer including private information.

when the individual is not authenticated, the operations further include providing a second answer to the query, the second answer omitting the private information.

accessing personal data associated with the individual and using the personal data to generate the discreet output that includes the answer to the query.

wherein the personal data includes at least one of: age the individual, gender of the individual, current location of the individual, occupation of the individual, home address of the individual, level of education of the individual, or health condition of the individual.

using the facial micromovements to determine an emotional state of an individual associated with the facial micromovements, and wherein the answer to the query is determined based in part on the determined emotional state.

performing control commands based on facial skin micromovements.

operating at least one coherent light source in a manner enabling illumination of a non-lip portion of a face.

receiving specific signals representing coherent light reflections associated with specific non-lip facial skin micromovements.

accessing a data structure associating a plurality of non-lip facial skin micromovements with control commands.

identifying in the data structure a specific control command associated with the specific signals associated with the specific non-lip facial skin micromovements.

executing the specific control command.

wherein the facial skin micromovements correspond to a nonvocalized articulation of at least one word associated with the specific control command.

wherein the facial skin micromovements correspond to recruitment of at least one specific muscle.

wherein the at least one specific muscle includes: a zygomaticus muscle, an orbicularis oris muscle, a risorius muscle, or a levator labii superioris alaeque nasi muscle.

wherein the facial skin micromovements includes a sequence of facial skin micromovements from which the specific control command is derived.

wherein the facial skin micromovements includes involuntary micromovements.

wherein the involuntary micromovements are triggered by an individual thinking of speaking the specific control command.

wherein the involuntary micromovements are unnoticeable to a human eye.

wherein operating the at least one coherent light source includes determining an intensity or a light pattern for illuminating the non-lip portion of the face.

wherein the specific signals are received at a rate of between 50 Hz and 200 Hz. analyzing the specific signals to identify temporal and intensity changes of speckles produced by light reflections from the non-lip portion of the face.

processing data from at least one sensor to determine context for the specific non-lip facial skin micromovements.

determining an action to initiate based on the specific control command and the determined context.

wherein the specific control command is configured to cause an audible translation of words from an origin language into at least one target language other than the origin language.

wherein the specific control command is configured to cause an action in media player application.

wherein the specific control command is configured to cause an action associated with an incoming call.

wherein the specific control command is configured to cause an action associated with an ongoing call.

wherein the specific control command is configured to cause an action associated with a text message.

wherein the specific control command is configured to cause activation of a virtual personal assistant.

performing operations for detecting changes in neuromuscular activity over time.

establishing a baseline of neuromuscular activity from coherent light reflections associated with historical skin micromovements.

receiving current signals representing coherent light reflections associated with current skin micromovements of an individual.

identifying a deviation of the current skin micromovements from the baseline of neuromuscular activity.

outputting an indicator of the deviation.

establishing the baseline from historical signals representing prior coherent light reflections associated with persons other than the individual.

establishing the baseline from historical signals representing prior coherent light reflections associated with the individual.

wherein the historical signals are based on skin micromovements that occurred over a time period of more than a day.

wherein the historical signals are based on skin micromovements that occurred at least a year before receipt of the current signals.

wherein the operations further include receiving the current signals from a wearable light detector while the wearable light detector is worn by the individual.

controlling at least one wearable coherent light source in a manner enabling illumination of a portion of a face of the individual.

wherein the current signals are associated with coherent light reflections from the portion of the face illuminated by the at least one wearable coherent light source.

wherein the current skin micromovements correspond to recruitment of at least one of a zygomaticus muscle, an orbicularis oris muscle, a genioglossus muscle, a risorius muscle, or a levator labii superioris alaeque nasi muscle.

receiving the current signals from a non-wearable light detector.

wherein the coherent light reflections associated with current skin micromovements are received from skin other than facial skin.

wherein the skin other than facial skin is from a neck, a wrist, or a chest of the individual.

receiving additional signals associated with skin micromovements of the individual during a period of time prior to the current skin micromovements.

determining a trend of changes in the neuromuscular activity of the individual based on the current signals and the additional signals, and wherein the indicator is indicative of the trend of changes.

determining a likely cause for the deviation of the current skin micromovements from the baseline of neuromuscular activity, and wherein the indicator is indicative of the likely cause.

outputting an additional indicator of the likely cause for the deviation.

receiving data indicative of at least one environmental condition, and wherein determining the likely cause for the deviation is based on the at least one environmental condition and the identified deviation.

receiving data indicative of at least one physical condition of the individual.

wherein determining the likely cause for the deviation is based on the at least one physical condition and the identified deviation.

wherein the likely cause corresponds to at least one physical condition that includes: being under an influence, tiredness, or stress.

wherein the likely cause corresponds to at least one health condition that includes a heart attack, Multiple Sclerosis (MS), Parkinson's Disease, epilepsy, or a stroke.

a dual use head mountable system for projecting graphical content and for interpreting non-verbal speech.

at least one light source associated with the wearable housing and configured to project light in a graphical pattern on a facial region of the individual, wherein the graphical pattern is configured to visibly convey information.

a sensor for detecting a portion of the light reflected from the facial region.

receive output signals from the sensor.

determine from the output signals facial skin micromovements associated with non-verbalization.

process the output signals to interpret the facial skin micromovements.

receiving a selection of the graphical pattern and to control the at least one light source to project the selected graphical pattern.

wherein the graphical pattern is constructed of a plurality of spots for use in determining the facial skin micromovements via speckle analysis.

wherein the projected light is configured to be visible via a human eye to individuals other than the individual.

wherein the projected light is visible via an infrared sensor.

wherein the projected light source includes a laser.

wherein the at least one processor is configured to alter the graphical pattern over time.

wherein the at least one processor is configured to receive location information and to alter the graphical pattern based on the received location information.

wherein the graphical pattern includes a scrolling message and the at least one processor is configured to cause the message to scroll.
wherein the at least one processor is further configured to detect a trigger and to cause the graphical pattern to be displayed in response to the trigger.
wherein processing the output signals to interpret the facial skin micromovements includes determining non-verbalized speech from the facial skin micromovements.
wherein the at least one processor is configured to determine the graphical pattern from the non-verbalized speech.
wherein processing the output signals to interpret the facial skin micromovements includes determining an emotional state from the facial skin micromovements.
wherein the at least one processor is configured to determine the graphical pattern from the determined emotional state.
further comprising an integrated audio output and wherein the at least one processor is configured to initiate an action that involves outputting audio via the audio output.
wherein the at least one processor is configured to identify a trigger and to modify the pattern based on the trigger.
wherein the at least one processor is configured to analyze the facial skin micromovements to identify the trigger.
wherein modifying the pattern includes ceasing the projection of the graphical pattern.
a head mountable system for interpreting facial skin micromovements.
a housing configured to be worn on a head of a wearer.
at least one detector integrated with the housing and configured to receive light reflections from a facial region of the head and to output associated reflection signals.
at least one microphone associated with the housing and configured to capture sounds produced by the wearer and to output associated audio signals.
at least one processor in the housing, configured to use both the reflection signals and the audio signals to generate output that corresponds with words articulated by the wearer.
further comprising at least one light source integrated with the housing and configured to project coherent light towards the facial region of the head.
receiving a vocalized form of the words and to determine at least one of the words prior to vocalization of the at least one word.
wherein the words articulated by the wearer include at least one word articulated in a nonvocalized manner, and the at least one processor is configured to determine the at least one word without using the audio signals.
wherein the at least one processor is configured to use the reflection signals to identify one or more words articulated in an absence of perceptible vocalization.
using the reflection signals to determine particular facial skin micromovements, and to correlate the particular facial skin micromovements with reference skin micromovements that correspond with the words.
using the audio signals to determine the reference skin micromovements.
comprising a speaker integrated with the housing and configured to generate an audio output.
wherein the output includes an audible presentation of the words articulated by the wearer.
wherein the audible presentation includes a synthetization of a voice of an individual other than the wearer.
wherein the audible presentation includes a synthetization of a voice of the wearer.
wherein the words articulated by the wearer are in a first language and the generated output includes words spoken in a second language.
wherein the at least one processor is configured to use the audio signals for determining the voice of the individual for synthetization of words spoken in an absence of perceptible vocalization.
wherein the output includes a textual presentation of the words articulated by the wearer.
causing a textual presentation of the words to be transmitted over a wireless communication channel to a remote computing device.
causing the generated output to be transmitted to a remote computing device for executing a control command corresponding to the words articulated by the wearer.
analyzing the reflection signals to determine facial skin micromovements that correspond to recruitment of at least one specific muscle.
wherein the at least one specific muscle includes a zygomaticus muscle, an orbicularis oris muscle, a risorius muscle, or a levator labii superioris alaeque nasi muscle.
initiate training operations to interpret facial skin micromovements.
receiving during a first time period first signals representing prevocalization facial skin micromovements.
receiving during a second time period succeeding the first time period, second signals representing sounds.
analyzing the sounds to identify words spoken during the second time period.
correlating the words spoken during the second time period with the prevocalization facial skin micromovements received during the first time period.
storing the correlations.
receiving during a third time period, third signals representing facial skin micromovements received in an absence of vocalization.
using the stored correlations to identify language associated with the third signals.
outputting the language.
identifying additional correlations of additional words spoken over an additional extended period of time with additional prevocalization facial skin micromovements detected during the additional extended period of time, and training a neural network using the additional correlations.
wherein the outputted language includes indications of the words spoken during the second time period.
wherein the outputted language includes an indication of at least one word different from the words spoken during the second time period.
wherein the at least one word includes a phoneme sequence similar to the at least one word spoken during the second time period.
wherein the first signals are associated with a first individual and the third signals are associated with a second individual.
wherein first signals and the third signals are associated with a same individual.
continuously updating, using the correlations, a user profile associated with the individual.
wherein the correlations are stored in a cloud-based data structure.

accessing a voice signature of an individual associated with the facial skin micromovements and.

wherein analyzing the sounds to identify words spoken during the second time period is based on the voice signature.

wherein the second period of time starts less than 350 milliseconds after the first period of time.

wherein the third period of time starts at least a day after the second period of time.

the first signals are based on coherent light reflections and.

controlling at least one coherent light source for projecting coherent light on a facial region of an individual from which the light reflections are received.

wherein the first signals are received from a light detector, and wherein the light detector and the coherent light source are part of a wearable assembly.

wherein the second signals representing sounds are received from a microphone that is part of the wearable assembly.

wherein outputting the language includes textually presenting the words associated with the third signals.

when a certainty level for identifying the language associated with the third signals is below a threshold, processing additional signals captured during a fourth time period succeeding the third time period to increase the certainty level.

receiving during a fourth time period fourth signals representing additional prevocalization facial skin micromovements, receiving during a fifth time period succeeding the fourth time period, fifth signals representing sounds, and using the fourth signals to identify words spoken in the fifth time period.

a multifunctional earpiece.

an ear-mountable housing.

a speaker integrated with the ear-mountable housing for presenting sound.

a light source integrated with the ear-mountable housing for projecting light toward skin of the wearer's face.

a light detector integrated with the ear-mountable housing and configured to receive reflections from the skin corresponding to facial skin micromovements indicative of prevocalized words of the wearer.

wherein the multifunctional earpiece is configured to simultaneously present the sound through the speaker, project the light toward the skin, and detect the received reflections indicative of the prevocalized words.

wherein at least a portion of the ear-mountable housing is configured to be placed in an ear canal.

wherein at least a portion of the ear-mountable housing is configured to be placed over or behind an ear.

outputting via the speaker an audible simulation of the prevocalized words derived from the reflections.

wherein the audible simulation of the prevocalized words includes a synthetization of a voice of an individual other than the wearer.

wherein the audible simulation of the prevocalized words includes a synthetization of the prevocalized words in a first language other than a second language of the prevocalized words.

further comprising a microphone integrated with the ear-mountable housing for receiving audio indicative of a wearer's speech.

wherein the light source is configured to project a pattern of coherent light toward the skin of the wearer's face, the pattern including a plurality of spots.

wherein the light detector is configured to output associated reflection signals indicative of muscle fiber recruitments.

wherein the recruited muscle fibers include at least one of zygomaticus muscle fibers, orbicularis oris muscle fibers, risorius muscle fibers, or levator labii superioris alaeque nasi muscle fibers.

further comprising at least one processor configured to analyze the light reflections to determine the facial skin micromovements.

wherein the analysis includes speckle analysis.

further comprising a microphone integrated with the ear-mountable housing for receiving audio indicative of a wearer's speech.

using the audio received via the microphone and the reflections received via the light detector to correlate facial skin micromovements with spoken words and to train a neural network to determine subsequent prevocalized words from subsequent facial skin micromovements.

identifying a trigger in the determined facial skin micromovements for activating the microphone.

further comprising a pairing interface for pairing with a communications device, and wherein the at least one processor is configured to transmit an audible simulation of the prevocalized words to the communications device.

further comprising a pairing interface for pairing with a communications device, and wherein the at least one processor is configured to transmit a textual presentation of the prevocalized words to the communications device.

wherein the light source is configured to project coherent light toward the skin of the wearer's face.

wherein the light source is configured to project a non-coherent light toward the skin of the wearer's face.

a driver for integration with a software program and for enabling a neuromuscular detection device to interface with the software program.

an input handler for receiving non-audible muscle activation signals from the neuromuscular detection device.

a lookup component for mapping specific ones of the non-audible activation signals to corresponding commands in the software program.

a signal processing module for receiving the non-audible muscle activation signals from the input handler, supplying the specific ones of the non-audible muscle activation signals to the lookup component, and receiving an output as the corresponding commands.

a communications module for conveying the corresponding commands to the software program, to thereby enable control within the software program based on non-audible muscular activity detected by the neuromuscular detection device.

wherein the input handler, the lookup component, the signal processing module, and the control code are embedded in the software program.

wherein the input handler, the lookup component, the signal processing module, and the control code are embedded in the neuromuscular detection device.

wherein the input handler, the lookup component, the signal processing module, and the control code are embedded in an application programming interface (API).

wherein the neuromuscular detection device includes a light source configured to project light toward skin, a light detector configured to sense reflections of the light from the skin.

generating the non-audible muscle activation signals based on the sensed light reflections.

wherein the sensed reflections of the light from the skin correspond to micromovements of the skin.

wherein the lookup component is prepopulated based on training data correlating the non-audible muscle activation signals with the corresponding commands.

comprising a training module for determining correlations between the non-audible muscle activation signals with the corresponding commands and for populating the lookup component.

wherein the lookup component includes a lookup table.

wherein the lookup component includes an artificial intelligence data structure.

wherein the neuromuscular detection device includes a light source for projecting light toward skin, a light detector configured to sense reflections of the light from the skin, and at least one processor configured to generate, based on the sensed light reflections, the non-audible muscle activation signals.

wherein the light source is configured to output coherent light.

wherein the at least one processor is configured to generate the non-audible muscle activation signals based on speckle analysis of received reflections of the coherent light.

wherein the lookup component is further configured to map some of the specific ones of the non-audible activation signals to text.

wherein the text corresponds to subvocalization manifest in the non-audible muscle activation signals.

wherein the lookup component is further configured to map some of the specific ones of the non-audible muscle activation signals to a command for causing at least one of a visual output of the text or an audible synthetization of the text.

further comprising a return path output for transmitting data to the neuromuscular detection device.

wherein the data is configured to cause at least one of an audio, haptic, or textual output via the neuromuscular detection device.

further comprising detection and correction routines to detect and correct errors that occur during data transmission.

further comprising configuration management routines for permitting the driver to be configured to applications other than the software program.

performing context-driven facial micromovement operations.

receiving during a first time period, first signals representing first coherent light reflections associated with first facial skin micromovements.

analyzing the first coherent light reflections to determine a first plurality of words associated with the first facial skin micromovements.

receiving first information indicative of a first contextual condition in which the first facial skin micromovements occurred.

receiving during a second time period, second signals representing second coherent light reflections associated with second facial skin micromovements.

analyzing the second coherent light reflections to determine a second plurality of words associated with the second facial skin micromovements.

receiving second information indicative of a second contextual condition in which the second facial skin micromovements occurred.

accessing a plurality of control rules correlating a plurality of actions with a plurality of contextual conditions.

wherein a first control rule prescribes a form of private presentation based on the first contextual condition, and a second control rule prescribes a form of non-private presentation based on the second contextual condition.

upon receipt of the first information, implementing the first control rule to privately output the first plurality of words.

upon receipt of the second information, implementing the second control rule to non-privately output the second plurality of words.

wherein the first information indicative of the first contextual condition includes an indication that the first facial skin micromovements are associated with private thought.

wherein the first information indicative of the first contextual condition includes an indication that the first facial skin micromovements are made in a private situation.

wherein the first information indicative of the first contextual condition includes an indication that an individual generating the facial micromovements is looking down.

wherein the second information indicative of the second contextual condition includes an indication that the second facial skin micromovements are made during a phone call.

wherein the second information indicative of the second contextual condition includes an indication that the second facial skin micromovements are made during a video conference.

wherein the second information indicative of the second contextual condition includes an indication that the second facial skin micromovements are made during a social interaction.

wherein at least one of the first information and the second information is indicative of an activity of an individual generating the facial micromovements.

implementing either the first control rule or the second control rule based on the activity.

wherein at least one of the first information and the second information is indicative of a location of an individual generating the facial micromovements and.

implementing either the first control rule or the second control rule based on the location.

wherein at least one of the first information and the second information is indicative of a type of engagement of an individual generating the facial micromovements with a computing device.

implementing either the first control rule or the second control rule based on the type of engagement.

wherein privately outputting the first plurality of words includes generating audio output to a personal sound generating device.

wherein privately outputting the first plurality of words includes generating textual output to a personal text generating device.

wherein non-privately outputting the second plurality of words includes transmitting audio output to a mobile communication device.

wherein non-privately outputting the second plurality of words includes causing textual output to be presented on a shared display.

wherein the operations further include determining a trigger for switching between a private output mode and a non-private output mode.

receiving third information indicative of a change in contextual conditions and wherein the trigger is determined from the third information.

wherein the operations further include determining the trigger based on the first plurality of words or the second plurality of words.

wherein the operations further include receiving an output mode selection from an associated user interface and determining the trigger based on the output mode selection.

performing operations for extracting reactions to content based on facial skin micromovements.

during a time period when an individual is consuming content, determining the facial skin micromovements of the individual based on reflections of coherent light from a facial region of the individual.

determining at least one specific micro-expression from the facial skin micromovements.

accessing at least one data structure containing correlations between a plurality of micro-expressions and a plurality of non-verbalized perceptions.

based on the at least one specific micro-expression and the correlations in the data structure, determining a specific non-verbalized perception of the content consumed by the individual.

initiating an action associated with the specific non-verbalized perception.

wherein the at least one specific micro-expression is imperceptible to a human eye.

wherein the facial skin micromovements used for determining the at least one specific micro-expression correspond to recruitment of at least one muscle from a group of muscles including: a zygomaticus muscle, a genioglossus muscle, an orbicularis oris muscle, a risorius muscle, or a levator labii superioris alaeque nasi muscle.

wherein the at least one specific micro-expression includes a sequence of micro-expressions associated with the specific non-verbalized perception.

wherein the operations further include determining a degree of the specific non-verbalized perception based on the sequence of micro-expressions.

determining an action to initiate based on the degree of the specific non-verbalized perception.

wherein the at least one data structure includes past non-verbalized perceptions of previously consumed content.

determining a degree of the specific non-verbalized perception relative to the past non-verbalized perceptions.

determining an action to initiate based on the degree of the specific non-verbalized perception.

wherein the non-verbalized perceptions include an emotional state of the individual.

wherein the operations further include determining an action to initiate based on the consumed content and the specific non-verbalized perception.

wherein the action initiated includes causing a transmission of a message reflecting a correlation between the specific non-verbalized perception and the consumed content.

wherein the action initiated includes storing in memory a correlation between the specific non-verbalized perception and the consumed content.

wherein the action includes determining additional content to be presented to the individual based on the specific non-verbalized perception and the consumed content.

wherein the consumed content is of a first type and the additional content is of a second type differing from the first type.

wherein the consumed content is part of a chat with at least one other individual and the action includes generating a visual representation of the specific non-verbalized perception in the chat.

wherein the action includes selecting an alternative manner for presenting the consumed content.

wherein the action varies based on a type of the consumed content.

wherein the operations further include operating at least one wearable coherent light source in a manner enabling illumination of a non-lip portion of a face of the individual.

receiving signals indicative of coherent light reflections from the non-lip portion of the face.

wherein the facial skin micromovements are determined based on speckle analysis of the coherent light reflections.

wherein the reflections of coherent light are received by a wearable light detector.

performing operations for removing noise from facial skin micromovement signals.

during a time period when an individual is involved in at least one non-speech-related physical activity, operating a light source in a manner enabling illumination of a facial skin region of the individual.

receiving signals representing light reflections from the facial skin region.

analyzing the received signals to identify a first reflection component indicative of prevocalization facial skin micromovements and a second reflection component associated with the at least one non-speech-related physical activity.

filtering out the second reflection component to enable interpretation of words from the first reflection component indicative of the prevocalization facial skin micromovements.

wherein the light source is a coherent light source.

wherein the second reflection component is a result of walking.

wherein the second reflection component is a result of running.

wherein the second reflection component is a result of breathing.

wherein the second reflection component is a result of blinking and is based on neural activation of at least one orbicularis oculi muscle.

wherein, when the individual is concurrently involved in a first physical activity and a second physical activity.

identifying a first portion of the second reflection component associated with the first physical activity and a second portion of the second reflection component associated with the second physical activity and filtering out the first portion of the second component and the second portion of the second component from the first component to enable interpretation of words from the prevocalization facial skin micromovements associated with the first component.

receiving data from a mobile communications device, the data being indicative of the at least one non-speech-related physical activity.

wherein the mobile communications device lacks a light sensor for detecting the light reflections.

wherein the data received from the mobile communications device includes at least one of: data indicative of a heart rate of the individual, data indicative of blood pressure of the individual, or data indicative of movement of the individual.

presenting the words in a synthesized voice.

wherein the signals are received from a sensor associated with a wearable housing and wherein the instructions further include analyzing the signals to determine the at least one non-speech-related physical activity.

wherein the sensor is an image sensor configured to capture at least one event in an environment of the individual.

determining that the event is associated with the at least one non-speech-related physical activity.

using a neural network to identify the second reflection component associated with the at least one non-speech-related physical activity.

wherein the prevocalization facial skin micromovements correspond to one or more involuntary muscle fiber recruitments.

wherein the involuntary muscle fiber recruitments are a result of an individual thinking of saying the words.

wherein the one or more muscle fiber recruitments include recruitments of at least one of zygomaticus muscle fibers, orbicularis oris muscle fibers, genioglossus muscle fibers, risorius muscle fibers, or levator labii superioris alaeque nasi muscle fibers.

wherein the signals are received at a rate of between 50 Hz and 200 Hz.

Implementation of the method and system of the present disclosure may involve performing or completing certain selected tasks or steps manually, automatically, or a combination thereof. Moreover, according to actual instrumentation and equipment of preferred embodiments of the method and system of the present disclosure, several selected steps may be implemented by hardware (HW) or by software (SW) on any operating system of any firmware, or by a combination thereof. For example, as hardware, selected steps of the disclosure could be implemented as a chip or a circuit. As software or algorithm, selected steps of the disclosure could be implemented as a plurality of software instructions being executed by a computer using any suitable operating system. In any case, selected steps of the method and system of the disclosure could be described as being performed by a data processor, such as a computing device for executing a plurality of instructions.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet. The computing system can include clients and servers. A client and server are generally remote from each other and typically interact through a communication network. The relationship of client and server arises by virtue of computer programs running on the respective computers and having a client-server relationship to each other.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware and software, but systems and methods consistent with the present disclosure may be implemented as hardware alone.

It is appreciated that the above-described embodiments can be implemented by hardware, or software (program codes), or a combination of hardware and software. If implemented by software, it can be stored in the above-described computer-readable media. The software, when executed by the processor can perform the disclosed methods. The computing units and other functional units described in the present disclosure can be implemented by hardware, or software, or a combination of hardware and software. One of ordinary skill in the art will also understand that multiple ones of the above-described modules/units can be combined as one module or unit, and each of the above-described modules/units can be further divided into a plurality of sub-modules or sub-units.

The block diagrams in the figures illustrate the architecture, functionality, and operation of possible implementations of systems, methods, and computer hardware or software products according to various example embodiments of the present disclosure. In this regard, each block in a flowchart or block diagram may represent a module, segment, or portion of code, which includes one or more executable instructions for implementing the specified logical functions. It should be understood that in some alternative implementations, functions indicated in a block may occur out of order noted in the figures. For example, two blocks shown in succession may be executed or implemented substantially concurrently, or two blocks may sometimes be executed in reverse order, depending upon the functionality involved. Some blocks may also be omitted. It should also be understood that each block of the block diagrams, and combination of the blocks, may be implemented by special purpose hardware-based systems that perform the specified functions or acts, or by combinations of special purpose hardware and computer instructions.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the invention disclosed herein. It is intended that the specification and examples be considered as example only, with a true scope and spirit of the invention being indicated by the following claims. It is also intended that the sequence of steps shown in figures are only for illustrative purposes and are not intended to be limited to any particular sequence of steps. As such, those skilled in the art can appreciate that these steps can be performed in a different order while implementing the same method.

It will be appreciated that the embodiments of the present disclosure are not limited to the exact construction that has been described above and illustrated in the accompanying drawings, and that various modifications and changes may be made without departing from the scope thereof. And other embodiments will be apparent to those skilled in the art from consideration of the specification and practice of the disclosed embodiments disclosed herein. It is intended that the specification and examples be considered as exemplary only, with a true scope and spirit of the disclosed embodiments being indicated by the following claims.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application. These examples are to be construed as non-exclusive. Further, the steps of the disclosed methods can be modified in any manner, including by reordering steps or inserting or deleting steps. It is intended, therefore, that the specification and examples be considered as exemplary only, with a true scope and spirit being indicated by the following claims and their full scope of equivalents.

The invention claimed is:

1. A non-transitory computer readable medium containing instructions that when executed by at least one processor cause the at least one processor to initiate content interpretation operations prior to vocalization of content to be interpreted, the operations comprising:
receiving signals representing facial skin micromovements;
determining from the signals at least one word to be spoken prior to vocalization of the at least one word in an origin language;
prior to the vocalization of the at least one word, instituting an interpretation of the at least one word; and
causing the interpretation of the at least one word to be presented as the at least one word is spoken.

2. The non-transitory computer readable medium of claim 1, wherein the interpretation is a translation of the at least one word from the origin language into at least one target language other than the origin language.

3. The non-transitory computer readable medium of claim 2, wherein the interpretation of the at least one word includes a transcription of the at least one word into text in the at least one target language.

4. The non-transitory computer readable medium of claim 2, wherein the interpretation of the at least one word includes a speech synthetization of the at least one word in the at least one target language.

5. The non-transitory computer readable medium of claim 2, further comprising receiving a selection of the at least one target language.

6. The non-transitory computer readable medium of claim 5, wherein the selection of the at least one target language includes selections of a plurality of target languages, and wherein causing the interpretation of the at least one word to be presented includes simultaneously causing presentation in the plurality of languages.

7. The non-transitory computer readable medium of claim 1, wherein the interpretation of the at least one word includes a transcription of the at least one word into text in the origin language.

8. The non-transitory computer readable medium of claim 7, wherein presenting the interpretation of the at least one word includes outputting a textual display of the transcription together with a video of an individual associated with the facial skin micromovements.

9. The non-transitory computer readable medium of claim 1, wherein receiving signals occurs via at least one detector of coherent light reflections from a facial region of a person vocalizing the at least one word.

10. The non-transitory computer readable medium of claim 9, wherein causing the interpretation of the at least one word to be presented occurs concurrently with the at least one word being vocalized by the person.

11. The non-transitory computer readable medium of claim 1, wherein causing the interpretation of the at least one word to be presented includes using a wearable speaker to output an audible presentation of the at least one word.

12. The non-transitory computer readable medium of claim 1, wherein causing the interpretation of the at least one word to be presented includes transmitting sound signals over a network.

13. The non-transitory computer readable medium of claim 1, further comprising determining at least one prospective word to be spoken following to the at least one word to be spoken, instituting an interpretation of the at least one prospective word prior to vocalization of the at least one word; and causing the interpretation of the at least one prospective word to be presented following presentation of the at least one word as the at least one word is spoken.

14. The non-transitory computer readable medium of claim 1, wherein causing the interpretation of the at least one word to be presented includes transmitting a textual translation of the at least one word over a network.

15. The non-transitory computer readable medium of claim 1, wherein the operations further include determining from the signals at least one non-verbal interjection, and outputting a representation of the non-verbal interjection.

16. The non-transitory computer readable medium of claim 1, wherein determining from the signals at least one word includes interpreting the facial skin micromovements using speckle analysis.

17. The non-transitory computer readable medium of claim 1, wherein the signals representing facial skin micromovements correspond to muscle activation prior to the vocalization of the at least one word.

18. The non-transitory computer readable medium of claim 17, wherein the muscle activation is associated with at least one specific muscle that includes: a zygomaticus muscle, an orbicularis oris muscle, a risorius muscle, a genioglossus muscle, or a levator labii superioris alaeque nasi muscle.

19. A method for initiating content interpretation prior to vocalization of content to be interpreted, the method comprising:
   receiving signals representing facial skin micromovements;
   determining from the signals at least one word to be spoken prior to vocalization of the at least one word in an origin language;
   prior to the vocalization of the at least one word, instituting an interpretation of the at least one word; and
   causing the interpretation of the at least one word to be presented as the at least one word is spoken.

20. A system for initiating content interpretation prior to vocalization of content to be interpreted, the system comprising:
   at least one processor configured to:
      receive signals representing facial skin micromovements;
      determine from the signals at least one word to be spoken prior to vocalization of the at least one word in an origin language;
      prior to the vocalization of the at least one word, institute an interpretation of the at least one word; and
      cause the interpretation of the at least one word to be presented as the at least one word is spoken.

* * * * *